(12) United States Patent
Mita et al.

(10) Patent No.: US 8,022,089 B2
(45) Date of Patent: Sep. 20, 2011

(54) ISOXAZOLINE-SUBSTITUTED BENZAMIDE COMPOUND AND PESTICIDE

(75) Inventors: Takeshi Mita, Funabashi (JP);
Takamasa Kikuchi, Funabashi (JP);
Takashi Mizukoshi, Funabashi (JP);
Manabu Yaosaka, Funabashi (JP);
Mitsuaki Komoda, Minamisaitama-gun (JP)

(73) Assignee: Nissan Chemical Industries, Ltd., Tokyo (JP)

(*) Notice: Subject to any disclaimer, the term of this patent is extended or adjusted under 35 U.S.C. 154(b) by 0 days.

(21) Appl. No.: 12/509,859

(22) Filed: Jul. 27, 2009

(65) Prior Publication Data
US 2009/0312330 A1  Dec. 17, 2009

Related U.S. Application Data

(60) Division of application No. 11/514,921, filed on Sep. 5, 2006, now Pat. No. 7,662,972, which is a continuation-in-part of application No. PCT/JP2005/004268, filed on Mar. 4, 2005.

(30) Foreign Application Priority Data

Mar. 5, 2004 (JP) ................. 2004-061749
Jul. 7, 2004 (JP) ................. 2004-200119

(51) Int. Cl.
*A61K 31/42* (2006.01)
(52) U.S. Cl. .................................. 514/378
(58) Field of Classification Search ............... 514/378
See application file for complete search history.

(56) References Cited

U.S. PATENT DOCUMENTS

| | | | |
|---|---|---|---|
| 4,018,801 A | 4/1977 | Ozretich | |
| 4,629,492 A | 12/1986 | Pews | |
| 5,154,749 A | 10/1992 | Dorman et al. | |
| 5,716,967 A | 2/1998 | Kleinman | |
| 5,814,627 A | 9/1998 | Schwab et al. | |
| 2002/0049213 A1 | 4/2002 | Weidner-Wells et al. | |
| 2005/0250822 A1 | 11/2005 | Mita et al. | |
| 2005/0250826 A1 | 11/2005 | Sielecki-Dzurdz et al. | |
| 2008/0113997 A1 | 5/2008 | Sielecki-Dzurdz et al. | |

FOREIGN PATENT DOCUMENTS

| | | |
|---|---|---|
| CS | 265 658 B1 | 11/1989 |
| EP | 0 455 052 A1 | 11/1991 |
| JP | A-50-148525 | 11/1975 |
| JP | A-60-092281 | 5/1985 |
| WO | WO 95/14683 A1 | 6/1995 |
| WO | WO 95/19773 A1 | 7/1995 |
| WO | WO 95/24398 A1 | 9/1995 |
| WO | WO 96/38426 A1 | 12/1996 |
| WO | WO 97/00853 A1 | 1/1997 |
| WO | WO 97/23212 A1 | 7/1997 |
| WO | WO 97/48395 A1 | 12/1997 |
| WO | WO 98/57937 A2 | 12/1998 |
| WO | WO 99/14210 A1 | 3/1999 |
| WO | WO 00/66558 A1 | 11/2000 |
| WO | WO 01/70673 A2 | 9/2001 |
| WO | WO 02/100332 | 12/2002 |
| WO | WO 2004/018410 A1 | 3/2004 |

OTHER PUBLICATIONS

J. Patrick Parkman. Pest Management Strategic Plan for Beef Cattle in Tennessee and Kentucky. Summary of Workshops held in Jan. 2005 Princeton, KY and Nashville, TN (2005).*
Chagas disease [online], {retrieved from the Internet on Apr. 9, 2008}, URL: http://en.wikipedia.org/wiki/Chagas_disease.*
Cryptosporidium parvum [online], {retrieved from the Internet on Apr. 9, 2008} URL: http:llvm.cfsan.fda.govl-mowlchap24.html.*
Trypanosoma [online], {retrieved from the Internet on Apr. 9, 2008} URL: http://en.wikipedia.org/wiki/Trypanosoma.*
Masami Kawase et al.; "Chemistry of Amine-Boranes. Part 5. Reduction of Oximes, O-Acyl-oximes, and O-Alkyl-oximes with Pyridine-Borane in Acid;" *J. Chem. Soc.*; Perkin Transactions 1: Organic and Bio-Organic Chem.; No. 3; pp. 643-645; 1979.
Sung Hee Hwang et al.; "Solid-Phase Synthesis of an Isoxazolinopyrrole Library;" *J. Comb. Chem.*; vol. 6, No. 1; pp. 142-148; 2004.
Matthew J. Walters et al.; "The Preparation of 5-Aryl-5-methyl-4,5-dihydroisoxazoles from Dilithiated C($\alpha$),O-Oximes and Select Acetyl Ketones;" *Synthetic Communications*; vol. 33, No. 23; pp. 4163-4171; 2003.
Robert K. Norris et al; "The Effect of Steric Hindrance on Radical and Ionic Substitution Reactions of Nucleophiles with Some $\alpha$-Alkyl-p-Nitrobenzyl Chlorides;" *Aust. J. Chem.*; vol. 32; pp. 1487-1509; 1979.
Anica Markovac et al.; "The Synthesis of Oximes. III. Iodine-Dimethyl Sulfoxide Reaction with Methylpyridines;" *J. Org. Chem.*; vol. 35, No. 3; pp. 841-843; 1970.

(Continued)

*Primary Examiner* — Shawquia Young
(74) *Attorney, Agent, or Firm* — Oliff & Berridge, PLC

(57) ABSTRACT

An isoxazoline-substituted benzamide compound of formula (1) or a salt thereof:

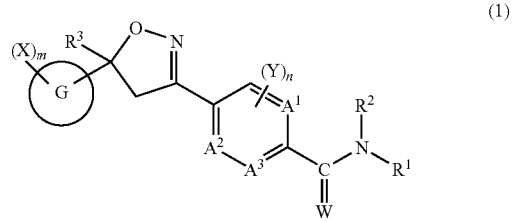

(1)

wherein $A^1$, $A^2$ and $A^3$ independently of one another are carbon atom or nitrogen atom, G is benzene ring, etc., X is halogen atom, $C_1$-$C_6$haloalkyl, etc., Y is halogen atm, $C_1$-$C_6$alkyl, etc., $R^1$ is $C_1$-$C_{12}$alkyl arbitrarily substituted with $R^{16}$, $C_3$-$C_{12}$alkenyl, arbitrarily substituted with $R^{16}$ is oxygen atom or sulfur atom, —N($R^{20}$)$R^{19}$, etc., $R^2$ is hydrogen atom, $C_1$-$C_4$alkoxy $C_1$-$C_6$alkyl, etc., $R^3$ is $C_1$-$C_6$haloalkyl, etc., $R^{16}$ is halogen atom, cyano, phenyl substituted with $(Z)_{p1}$, D-1 to D-60, E-1 to E-49, etc., $R^{19}$ is phenyl, phenyl substituted with $(Z)_{p1}$, etc., $R^{20}$ is hydrogen atom, $C_1$-$C_6$alkyl, etc., Z is halogen atom, nitro, $C_1$-$C_4$alkoxy, etc., D-1 to D-60 are 5- or 6-membered aromatic heterocyclic rings, E-1 to E-49 are 5- or 6-membered saturated heterocyclic rings, m is an integer of 0 to 5, n is an integer of 0 to 4, p1 is an integer of 1 to 5. The pesticide containing these compounds.

17 Claims, No Drawings

OTHER PUBLICATIONS

Paul Tarrant et al.; "Fluoroolefins. VI. The Synthesis of Some a-Trifluoromethylstyrenes;" *J. Org. Chem.*; vol. 24; pp. 238-239; 1959.

K. M. Koshy et al.; "Substituent Effects of the Trifluoromethyl Group on Electrophilic Additions to Alkenes. Solvolysis of the Trifluoromethyl Group. Protonation of Alkenes Less Basic Than Ethylene, *p*+ Values of Deactivated Styrenes, and Reactivity-Selectivity Effects"; *J. Am. Chem. Soc.*; vol. 101, No. 2; pp. 357-363; 1979.

Masaaki Mishima et al.; "Gas-Phase Substituent Effects in Highly Electron-Deficient Systems. I. Intrinsic Stabilities of 1-Aryl-1-(trifluoromethyl)ethyl Cations;" *Bull. Chem. Soc. Jpn.*; vol. 69; pp. 3273-3280; 1996.

U.S. Appl. No. 11/742,978 to Sielecki-Dzurdz et al. filed May 1, 2007.

* cited by examiner

ISOXAZOLINE-SUBSTITUTED BENZAMIDE COMPOUND AND PESTICIDE This is a Division of application Ser. No. 11/514,921, filed Sep. 5, 2006, which in turn is a Continuation-in-part of International Application No. PCT/JP05/04268, filed, Mar. 4, 2005, which claims priority to Japanese Patent Applications Nos. 2004-200119, filed Jul. 7, 2004, and 2004-061749, filed Mar. 5, 2004. The disclosure of the prior applications are hereby incorporated by reference herein in their entirety.

TECHNICAL FIELD

The present invention relates to a novel isoxazoline-substituted benzamide compound and the salt thereof, and a pesticide characterized by containing the compound as an active ingredient. The pesticide in the present invention means a pest controlling agent applied for harmful arthropods in agricultural and horticultural field or livestock farming and hygienic field (endo-parasiticides and ecto-parasiticides for mammals or birds as domestic animals or pets, or hygienic pest- or unpleasant pest-controlling agents for domestic or business use). In addition, agricultural chemicals in the present invention mean insecticides, acaricides (miticides), nematicides, herbicides and fungicides, and the like.

BACKGROUND ART

Conventionally, as to isoxazoline-substituted benzoic acid amide compounds, the followings are known: a report of synthesis by use of solid phase synthesis of 4-(5-methyl-5-substituted pyrrolyl-4,5-dihydroisoxazole-3-yl)benzoic acid amide derivatives (see, Non-patent Document 1); 4-(5-pyridyl-4,5-dihydroisoxazole-3-yl)benzoic acid amide derivatives have matrix metalloprotease and TNF-α inhibition activity, or the like, and can be used as an anti-inflammatory agent or a chondro-protective agent (see, Patent Document 1); 4-(5-substituted carbamoylmethyl-4,5-dihydroisoxazole-3-yl)benzoic acid amide derivatives, 3-(5-substituted carbamoylmethyl-5-substituted alkyl-4,5-dihydroisoxazole-3-yl) benzoic acid amide derivatives and 4-(5-substituted carbamoylmethyl-4,5-dihydroisoxazole-3-yl)benzamidine derivatives have platelet glycoprotein IIb/IIIa fibrinogen receptor complex competitive activity or factor Xa inhibition activity or the like, and can be used as a thrombolysis agent or a therapeutic agent of thronbo-embolic disorder (see, for example Patent Documents 2-5), etc. In addition, it is known that other specific substituted isoxazoline compound can be used as a production intermediate of HIV protease inhibitors, or production intermediate of insecticides (see, for example Patent Documents 6 and 7). However, there is no disclosure on 4-(5-substituted-5-substituted aryl-4,5-dihydroisoxazole-3-yl)benzoic acid amide compounds according to the present invention, and further the usefulness thereof as a pesticide is not known at all.

On the other hand, as to 3-(4-substituted phenyl)-4,5-dihydroisoxazole derivatives, 5-substituted alkyl-3,5-bis substituted phenyl-4,5-dihydroisoxazole derivatives (see, Patent Document 7), 3-alkoxyphenyl-5-substituted-5-phenyl-4,5-dihydroisoxazole derivatives (see, Patent Document 8), 3-alkoxyphenyl-5-substituted alkyl-5-substituted carbamoyl-4,5-dihydroisoxazole derivatives (see, Patent Document 9), 3-(4-halophenyl)-5-substituted-5-substituted phenyl-4,5-dihydroisoxazole derivatives (see, Patent Documents 10 and Non-patent Document 2), and 3-(4-nitrophenyl)-5-substituted-5-substituted phenyl-4,5-dihydroisoxazole derivatives (see, patent Document 11 and Non-patent Document 3), etc. are known. However, 5-substituted alkyl-3,5-bis substituted phenyl-4,5-dihydroisoxazole derivatives that can be used as a production intermediate of the pesticides according to the present invention are not described in any documents and thus novel compounds.

Further, as to 4-hydroxyiminomethyl benzoic acid amide derivatives, 4-hydroxyiminomethyl-N,N-dimethyl benzoic acid amide (see, Non-patent Document 4), 4-hydroxyiminomethyl benzoyl piperidine derivatives (see, Patent Documents 12 and 13), 4-hydroxyiminomethyl-N-bicycloalkyl benzoic acid amide derivatives (see, Patent Document 14), and 6-(hydroxyiminomethyl)pyridine-2-carboxamide derivatives (see, Non-patent Document 5), etc. are known. However, 4-hydroxyiminomethyl benzoic acid amide derivatives that can be used as a production intermediate of the pesticides according to the present invention are not described in any documents and thus novel compounds.

In addition, as to haloalkenylbenzene derivatives, substituted 3,3,3-trifluoro-2-propenylbenzene derivatives (see, Non-patent Documents 6-8), etc. are known. However, specific substituted haloalkenylbenzene derivatives that can be used as a production intermediate of the pesticides according to the present invention are not described in any documents and thus novel compounds.

Patent Document 1: WO 01/070673 Pamphlet
Patent Document 2: WO 96/038426 Pamphlet
Patent Document 3: WO 97/023212 Pamphlet
Patent Document 4: WO 95/014683 Pamphlet
Patent Document 5: WO 97/048395 Pamphlet
Patent Document 6: WO 99/014210 Pamphlet
Patent Document 7: WO 04/018410 Pamphlet
Patent Document 8: WO 95/024398 Pamphlet
Patent Document 9: WO 98/057937 Pamphlet
Patent Document 10: EP 0455052 A1 (1991)
Patent Document 11: WO 2004/018410 Pamphlet
Patent Document 12: WO 95/019773 Pamphlet
Patent Document 13: WO 00/066558 Pamphlet
Patent Document 14: WO 97/000853 Pamphlet
Non-patent Document 1: J. Comb. Chem., vol. 6, p. 142 (2004)
Non-patent Document 2: Synth. Commun., vol. 33, p. 4163 (2003)
Non-patent Document 3: Australian J. Chem., vol. 32, p. 1487 (1979)
Non-patent Document 4: J. Chem. Soc. Perkin Trans, 1, p. 643 (1979)
Non-patent Document 5: J. Org. Chem., vol. 35, p. 841 (1970)
Non-patent Document 6: J. Org. Chem., vol. 24, p. 238 (1959)
Non-patent Document 7: J. Am. Chem. Soc., vol. 101, p. 357 (1979)
Non-patent Document 8: Bull. Chem. Soc. Jpn., vol. 69, p. 3273 (1996)

DISCLOSURE OF INVENTION

Problems to be Solved by the Invention

Recently, pests acquire resistance by the use of pesticides such as insecticides or fungicides over long term, and thus control by the insecticides or fungicides that have been conventionally used becomes difficult. In addition, a part of known pesticides has a high toxicity, or some of them start to disturb native ecosystems due to long-term persistency. Under the circumstances, it is expected all the time to develop a novel pesticide having a low toxicity and a low persistency.

Means for Solving the Problems

The inventors have eagerly investigated in order to solve the above-mentioned problems, and as a result of it, they found that novel isoxazoline-substituted benzamide compounds of formula (I) are extremely useful compounds having excellent pest controlling activity, particularly insecticidal activity and acaricidal activity, and having little adverse affect on non-targeted beings such as mammals, fishes and useful insects, etc. Thus, the present invention has been accomplished.

That is, the present invention relates to the following aspects (1) to (15):

(1) An isoxazoline-substituted benzamide compound of formula (1) or a salt thereof:

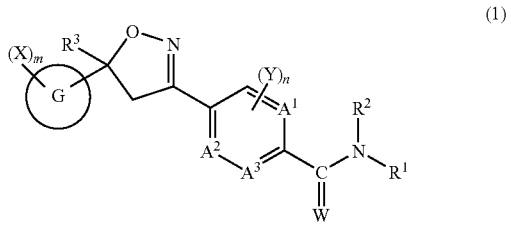

(1)

wherein $A^1$, $A^2$ and $A^3$ independently of one another are carbon atom or nitrogen atom, G is benzene ring, nitrogen-containing 6-membered aromatic heterocyclic ring, furan ring, thiophene ring, or 5-membered aromatic heterocyclic ring containing two or more hetero atoms selected from oxygen atom, sulfur atom and nitrogen atom, W is oxygen atom or sulfur atom, X is halogen atom, cyano, nitro, azido, —SCN, —SF$_5$, C$_1$-C$_6$alkyl, C$_1$-C$_6$alkyl arbitrarily substituted with R$^4$, C$_3$-C$_8$cycloalkyl, C$_3$-C$_8$cycloalkyl arbitrarily substituted with R$^4$, C$_2$-C$_6$alkenyl, C$_2$-C$_6$alkenyl arbitrarily substituted with R$^4$, C$_3$-C$_8$cycloalkenyl, C$_3$-C$_8$halocycloalkenyl, C$_2$-C$_6$alkynyl, C$_2$-C$_6$alkynyl arbitrarily substituted with R$^4$, —OH, —OR$^5$, —OSO$_2$R$^5$, —SH, —S(O)$_r$R$^5$, —N=CHOR$^8$, —N=C(R$^9$)OR$^8$, —CHO, —C(O)R$^9$, —C(O)OR$^9$, —C(O)SR$^9$, —C(O)NHR$^{10}$, —C(O)N(R$^{10}$)R$^9$, —C(S)OR$^9$, —C(S)SR$^9$, —C(S)NHR$^{10}$, —C(S)N(R$^{10}$)R$^9$, —CH=NOR$^{11}$, —C(R$^9$)=NOR$^{11}$, —S(O)$_2$OR$^9$, —S(O)$_2$NHR$^{10}$, —S(O)$_2$N(R$^{10}$)R$^9$, —Si(R$^{13}$)(R$^{14}$)R$^{12}$, phenyl, phenyl substituted with (Z)$_{p1}$, D-1 to D-65 or E-1 to E-49, when m is 2, 3, 4 or 5, each X may be identical with or different from each other, further, when two Xs are adjacent, the adjacent two Xs may form 5-membered or 6-membered ring together with carbon atoms to which the two Xs are bonded by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N(R$^{15}$)—, —CH$_2$N(R$^{15}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N(R$^{15}$)CH=CH—, —OCH=N—, —SCH=N—, —N(R$^{15}$)CH=N—, —N(R$^{15}$)N=CH—, —CH=CHCH=CH—, —OCH$_2$CH=CH—, —N=CHCH=CH—, —N=CHCH=N— or —N=CHN=CH—, in this case, hydrogen atoms bonded to each carbon atom forming the ring may be arbitrarily substituted with Z, further when the hydrogen atoms are substituted with two or more Zs at the same time, each Z may be identical with or different from each other, Y is halogen atom, cyano, nitro, azido, —SCN, —SF$_5$, C$_1$-C$_6$alkyl, C$_1$-C$_6$alkyl arbitrarily substituted with R$^4$, C$_3$-C$_8$cycloalkyl, C$_3$-C$_8$cycloalkyl arbitrarily substituted with R$^4$, C$_2$-C$_6$alkynyl, C$_2$-C$_6$alkynyl arbitrarily substituted with R$^4$, —OH, —OR$^5$, —OSO$_2$R$^5$, —SH, —S(O)$_r$R$^5$, —NHR$^7$, —N(R$^7$)R$^6$, —N=CHOR$^8$, —N=C(R$^9$)OR$^8$, —C(O)NHR$^{10}$, —C(O)N(R$^{10}$)R$^9$, —C(S)NHR$^{10}$, —C(S)N(R$^{10}$)R$^9$, —Si(R$^{13}$)(R$^{14}$)R$^{12}$, phenyl, phenyl substituted with (Z)$_{p1}$, D-1 to D-65 or E-1 to E-49, when n is 2, 3 or 4, each Y may be identical with or different from each other, further, when two Ys are adjacent, the adjacent two Ys may form 5-membered or 6-membered ring together with carbon atoms to which the two Ys are bonded by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH=N— or —SCH=N—, in this case, hydrogen atoms bonded to each carbon atom forming the ring may be arbitrarily substituted with Z, further when the hydrogen atoms are substituted with two or more Zs at the same time, each Z may be identical with or different from each other, R$^1$ and R$^2$ independently of each other are hydrogen atom, cyano, C$_1$-C$_{12}$alkyl, C$_1$-C$_{12}$alkyl arbitrarily substituted with R$^{16}$, C$_3$-C$_{12}$cycloalkyl, C$_3$-C$_{12}$cycloalkyl arbitrarily substituted with R$^{16}$, C$_2$-C$_{12}$alkenyl, C$_2$-C$_{12}$alkenyl arbitrarily substituted with R$^{16}$, C$_3$-C$_{12}$cycloalkenyl, C$_3$-C$_{12}$halocycloalkenyl, C$_3$-C$_{12}$alkynyl, C$_3$-C$_{12}$alkynyl arbitrarily substituted with R$^{16}$, —SR$^9$, —S(O)$_2$R$^9$, —SN(R$^{18}$)R$^{17}$, —S(O)$_2$N(R$^{10}$)R$^9$, —OR$^{19}$, —N(R$^{20}$)R$^{19}$, N=CHR$^{19b}$, —N=C(R$^{19b}$)R$^{19a}$, —CHO, —C(O)R$^9$, —C(O)OR$^9$, —C(O)SR$^9$, —C(O)N(R$^{10}$)R$^9$, —C(S)OR$^9$, —C(S)SR$^9$, —C(S)N(R$^{10}$)R$^9$, —C(=NR$^{11}$)OR$^9$, —C(=NR$^{11}$)SR$^9$, —C(=NR$^{11}$)N(R$^{10}$)R$^9$, phenyl, phenyl substituted with (Z)$_{p1}$, D-1 to D-63, D-65, E-3 to E-9, E17, E-23 to E-31, E-33, E-34 or E-45, or R$^1$ and R$^2$ together form =C(R$^{2a}$)R$^{1a}$, or R$^1$ and R$^2$ together may form 3- to 8-membered ring together with the nitrogen atom bonding them by forming C$_2$-C$_7$ alkylene chain, in this case, the alkylene chain may contain one oxygen atom, sulfur atom or nitrogen atom, and may be arbitrarily substituted with halogen atom, C$_1$-C$_6$alkyl, C$_1$-C$_6$haloalkyl, C$_1$-C$_6$alkoxy(C$_1$-C$_6$)alkyl, C$_1$-C$_6$alkoxy, formyl, C$_1$-C$_6$alkylcarbonyl, C$_1$-C$_6$haloalkylcarbonyl, C$_1$-C$_6$alkoxycarbonyl, C$_1$-C$_6$haloalkoxycarbonyl, C$_1$-C$_6$alkylaminocarbonyl, C$_1$-C$_6$haloalkylaminocarbonyl, phenyl, phenyl substituted with (Z)$_{p1}$, D-47, D-50, D-51, D-53 or 54, or in case where substituent Y is present at the adjacent position, R$^2$ together with Y may form 5- or 6-membered ring together with the atom bonding them by forming —CH$_2$—, —CH$_2$CH$_2$—, —CH$_2$O—, —CH$_2$S—, —CH$_2$N(R$^6$)—, —CH=CH— or —CH=N—, in this case, hydrogen atoms bonded to each carbon atom forming the ring may be arbitrarily substituted with halogen atom, C$_1$-C$_6$alkyl, C$_1$-C$_6$haloalkyl, C$_1$-C$_6$alkylidene, C$_1$-C$_6$haloalkylidene, oxo or thioxo, R$^{1a}$ and R$^{2a}$ together may form 5- or 6-membered ring together with the carbon atom bonding them by forming C$_4$-C$_5$ alkylene chain or C$_4$-C$_5$ alkenylene chain, in this case, the alkylene chain and the alkenylene chain may contain one to three oxygen atoms, sulfur atoms or nitrogen atoms, and may be arbitrarily substituted with halogen atom, C$_1$-C$_6$alkyl, C$_1$-C$_6$haloalkyl, C$_1$-C$_6$alkoxy, C$_1$-C$_6$haloalkoxy, C$_1$-C$_6$alkylthio or C$_1$-C$_6$haloalkylthio, R$^3$ is halogen atom, cyano, C$_1$-C$_6$alkyl, C$_1$-C$_6$alkyl arbitrarily substituted with R$^4$, C$_3$-C$_8$cycloalkyl, C$_3$-C$_8$cycloalkyl arbitrarily substituted with R$^4$, C$_3$-C$_6$alkenyl, C$_2$-C$_6$alkenyl arbitrarily substituted with R$^4$, C$_3$-C$_6$alkynyl, C$_2$-C$_6$alkynyl arbitrarily substituted with R$^4$, —OR$^5$, —S(O)$_r$R$^5$, —N(R$^{10}$)R$^9$, —CHO, —C(O)R⁹, —C(O)OR⁹, —C(O)SR⁹, —C(O)NHR¹⁰, —C(O)N(R¹⁰)R⁹, —C(S)OR⁹, —C(S)SR⁹, —C(S)NHR¹⁰, —C(S)N(R¹⁰)R⁹,
—CH=NOR¹¹, —C(R⁹)=NOR¹¹, —Si(R¹³)(R¹⁴)R¹², —P(O)(OR²¹)₂, phenyl, phenyl substituted with $(Z)_{p1}$, D-1 to D-65 or E-1 to E-49,
D-1 to D-65 are aromatic heterocyclic rings of the following formulae, respectively
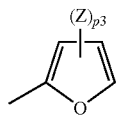
D-1
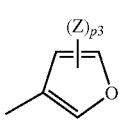
D-2
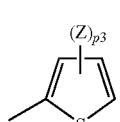
D-3
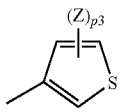
D-4
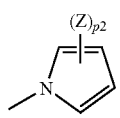
D-5
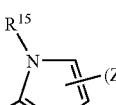
D-6
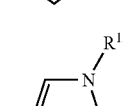
D-7
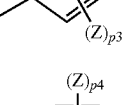
D-8
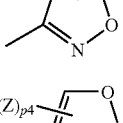
D-9
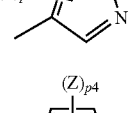
D-10
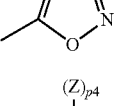
D-11
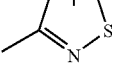
-continued
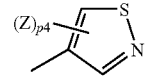
D-12
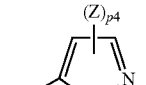
D-13
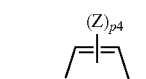
D-14
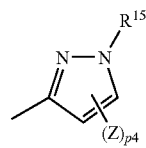
D-15
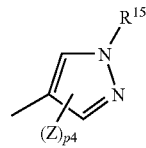
D-16
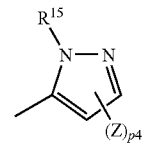
D-17
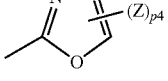
D-18
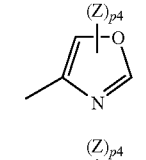
D-19
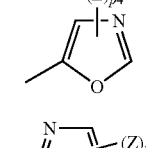
D-20
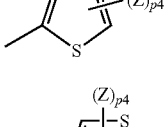
D-21
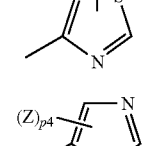
D-22
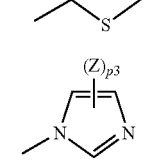
D-23
D-24

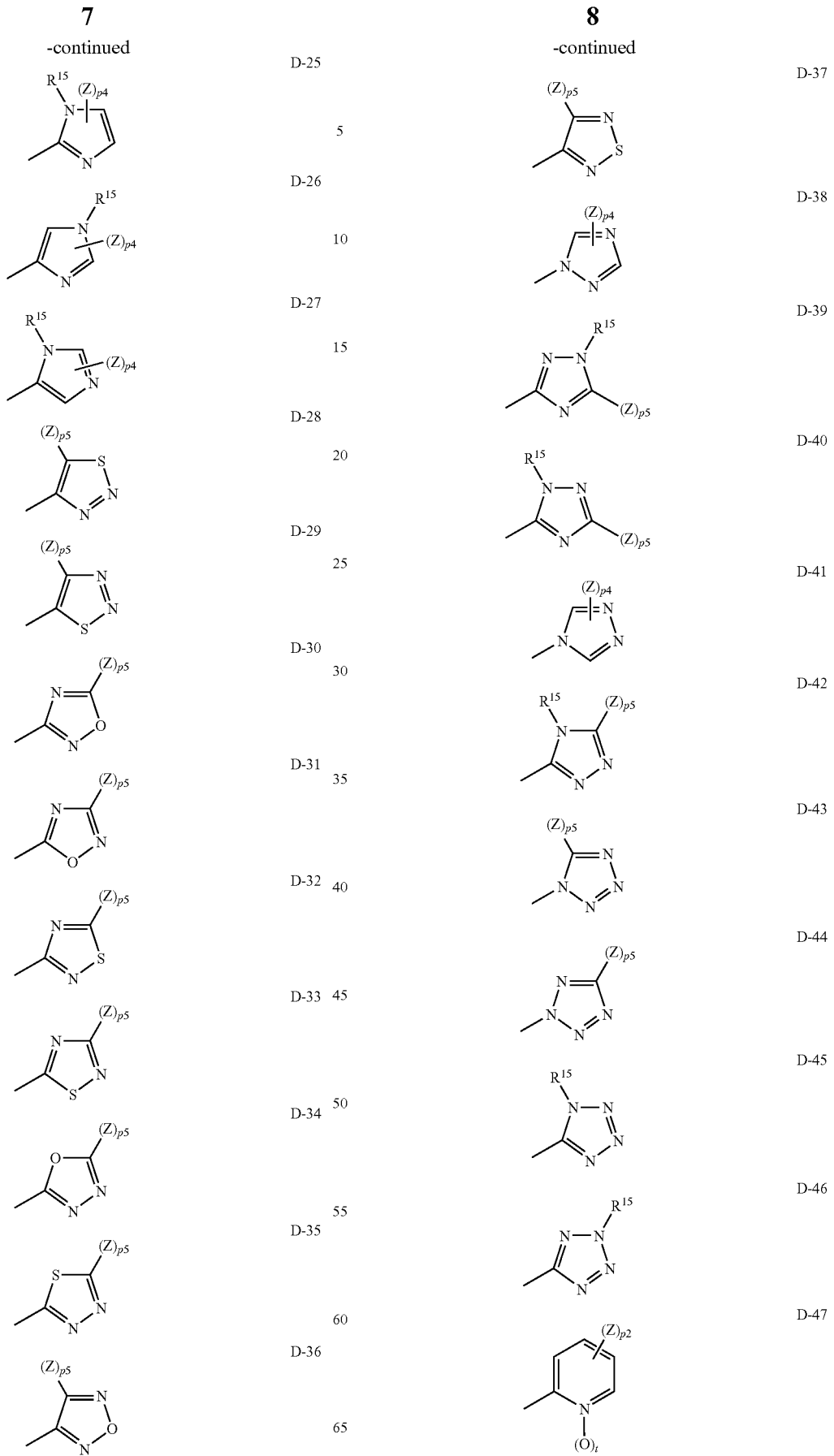

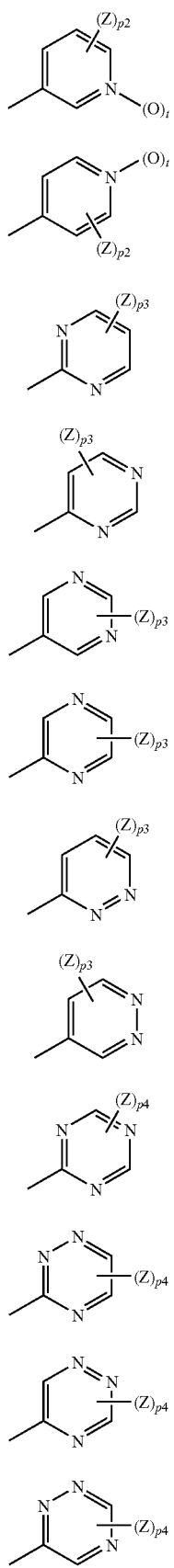
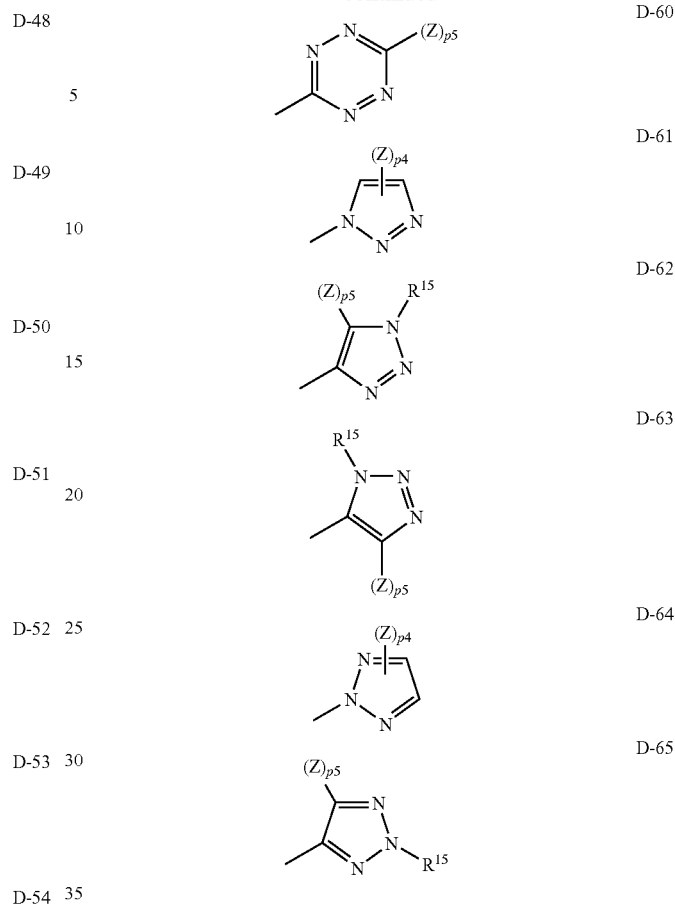

Z is halogen atom, cyano, nitro, $C_1$-$C_6$alkyl, $C_1$-$C_6$haloalkyl, $C_1$-$C_4$alkoxy $C_1$-$C_4$alkyl, $C_1$-$C_4$haloalkoxy $C_1$-$C_4$alkyl, $C_1$-$C_4$alkylthio $C_1$-$C_4$alkyl, $C_1$-$C_4$haloalkylthio $C_1$-$C_4$alkyl, $C_1$-$C_4$alkylsulfinyl $C_1$-$C_4$alkyl, $C_1$-$C_4$haloalkylsulfinyl $C_1$-$C_4$alkyl, $C_1$-$C_4$alkylsulfonyl $C_1$-$C_4$alkyl, $C_1$-$C_4$haloalkylsulfonyl $C_1$-$C_4$alkyl, $C_3$-$C_6$cycloalkyl, $C_3$-$C_6$halocycloalkyl, —OH, $C_1$-$C_6$alkoxy, $C_1$-$C_6$haloalkoxy, $C_1$-$C_6$alkylsulfonyloxy, $C_1$-$C_6$haloalkylsulfonyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, —$NH_2$, $C_1$-$C_6$alkylamino, di($C_1$-$C_6$alkyl)amino, $C_1$-$C_6$alkoxycarbonyl, $C_1$-$C_6$haloalkoxycarbonyl, —C(O)$NH_2$, $C_1$-$C_6$alkylaminocarbonyl, $C_1$-$C_6$haloalkylaminocarbonyl, di($C_1$-$C_6$alkyl)aminocarbonyl, —C(S)$NH_2$, —S(O)$_2NH_2$, $C_1$-$C_6$alkylaminosulfonyl, di($C_1$-$C_6$alkyl)aminosulfonyl, phenyl or phenyl arbitrarily substituted with halogen atom, when p1, p2, p3 or p4 is an integer of 2 or more, each Z may be identical with or different from each other, further, when two Zs are adjacent, the adjacent two Zs may form 5-membered or 6-membered ring together with carbon atoms to which the two Zs are bonded by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, in this case, hydrogen atoms bonded to each carbon atom forming the ring may be arbitrarily substituted with halogen atom, cyano, nitro, $C_1$-$C_4$alkyl, $C_1$-$C_4$haloalkyl, $C_1$-$C_4$alkoxy or $C_1$-$C_4$alkylthio,
E-1 to E-49 are saturated heterocyclic rings of the following formulae, respectively
E-1
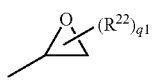
E-2
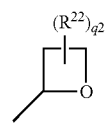
E-3
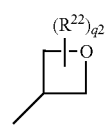
E-4
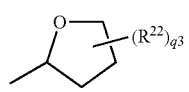
E-5
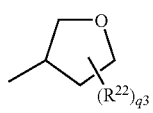
E-6
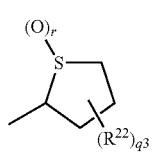
E-7
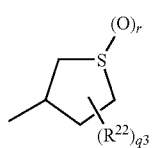
E-8
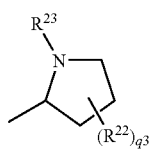
E-9
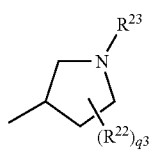
E-10
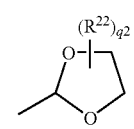
E-11
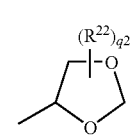
E-12
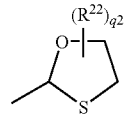
E-13
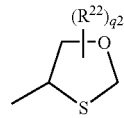
E-14
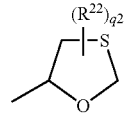
E-15
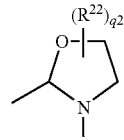
E-16
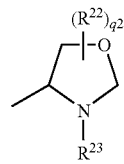
E-17
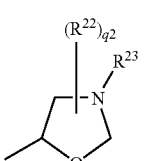
E-18
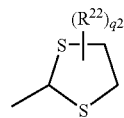
E-19
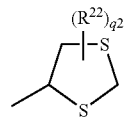
E-20
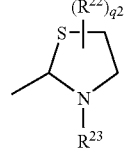
E-21
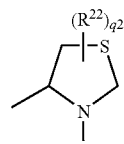

| | | |
|---|---|---|
| 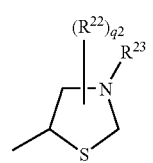 | E-22 | 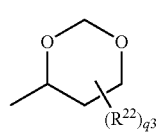 E-33 |
| 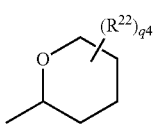 | E-23 | 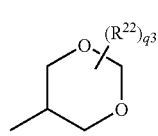 E-34 |
| 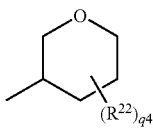 | E-24 | 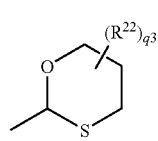 E-35 |
| 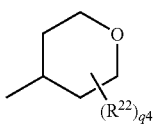 | E-25 | 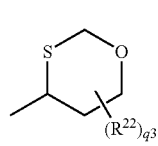 E-36 |
| 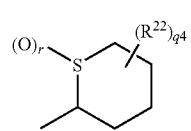 | E-26 | 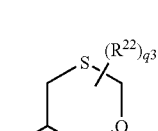 E-37 |
| 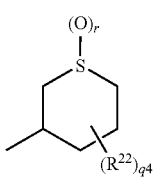 | E-27 | 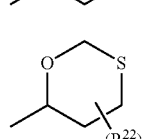 E-38 |
| 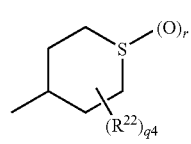 | E-28 | 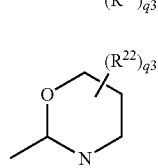 E-39 |
| 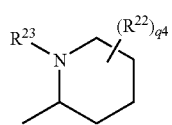 | E-29 | 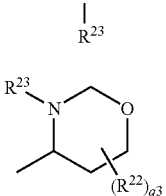 E-40 |
| 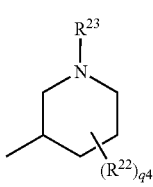 | E-30 | 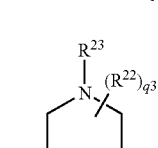 E-41 |
| 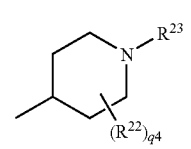 | E-31 | 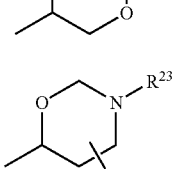 E-42 |
| 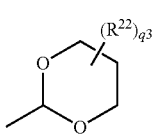 | E-32 | 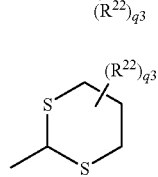 E-43 |

-continued

E-44
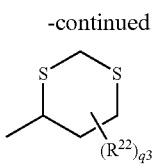

E-45
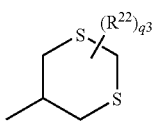

E-46
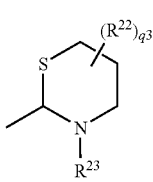

E-47
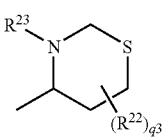

E-48
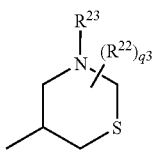

E-49
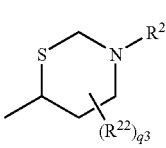

$R^4$ is halogen atom, cyano, $C_3$-$C_8$cycloalkyl, $C_3$-$C_8$halocycloalkyl, —OH, —$OR^5$, —SH, —S(O)$_r$$R^5$, —N($R^{10}$)$R^9$, —N($R^{10}$)CHO, —N($R^{10}$)C(O)$R^9$, —N($R^{10}$)C(O)$OR^9$, —N($R^{10}$)C(O)$SR^9$, —N($R^{10}$)C(S)$OR^9$, —N($R^{10}$)C(S)$SR^9$, —N($R^{10}$)S(O)$_2$$R^9$, —C(O)$OR^9$, —C(O)N($R^{10}$)$R^9$, —Si($R^{13}$)($R^{14}$)$R^{12}$, phenyl, phenyl substituted with $(Z)_{p1}$, D-1 to D-65 or E-1 to E-49, $R^5$ is $C_1$-$C_6$alkyl, $C_1$-$C_6$alkyl arbitrarily substituted with $R^{24}$, $C_3$-$C_8$cycloalkyl, $C_3$-$C_8$cycloalkyl arbitrarily substituted with $R^{24}$, $C_2$-$C_6$alkenyl, $C_2$-$C_6$alkenyl arbitrarily substituted with $R^{24}$, $C_3$-$C_8$cycloalkenyl, $C_3$-$C_8$halocycloalkenyl, $C_3$-$C_6$alkynyl, $C_3$-$C_6$alkynyl arbitrarily substituted with $R^{24}$, $C_1$-$C_6$alkylcarbonyl, $C_1$-$C_6$alkoxycarbonyl, phenyl, phenyl substituted with $(Z)_{p1}$, D-1 to D-4, D-6 to D-13, D-15 to D-23, D-25 to D-37, D-39, D-40, D-42, D-45 to D-60, D-62, D-63, D-65, E-3 to E-9, E-23 to E-31, E-34 or E-45, $R^6$ is $C_1$-$C_6$alkyl, $C_1$-$C_6$alkyl arbitrarily substituted with $R^{24}$, $C_3$-$C_6$cycloalkyl, $C_3$-$C_8$halocycloalkyl, $C_3$-$C_6$alkenyl, $C_3$-$C_6$haloalkenyl, $C_3$-$C_6$alkynyl, $C_3$-$C_6$haloalkynyl, —OH, $C_1$-$C_6$alkylcarbonyloxy, $C_1$-$C_6$alkylthio, $C_1$-$C_6$haloalkylthio, phenylthio, phenylthio substituted with $(Z)_{p1}$, —SN($R^{18}$)$R^{17}$, —S(O)$_r$$R^9$, —S(O)$_2$N($R^{10}$)$R^9$, —CHO, —C(O)$R^9$, —C(O)$OR^9$, —C(O)$SR^9$, —C(O)NH$R^{10}$, —C(O)N($R^{10}$)$R^9$, —C(S)$OR^9$, —C(S)$SR^9$, —C(S)NH$R^{10}$, —C(S)N($R^{10}$)$R^9$, —C(O)C(O)$R^9$, —C(O)C(O)$OR^9$, —P(O)(O$R^{21}$)$_2$ or —P(S)(O$R^{21}$)$_2$, $R^7$ is hydrogen atom, $C_1$-$C_6$alkyl, $C_1$-$C_6$haloalkyl, $C_3$-$C_8$cycloalkyl $C_1$-$C_6$alkyl, $C_1$-$C_4$alkoxy $C_1$-$C_4$alkyl, $C_1$-$C_4$alkylthio $C_1$-$C_4$alkyl, $C_3$-$C_8$cycloalkyl, $C_3$-$C_6$alkenyl, $C_3$-$C_6$haloalkenyl, $C_3$-$C_6$alkynyl, $C_3$-$C_6$haloalkynyl, —CHO, $C_1$-$C_6$alkylcarbonyl, $C_1$-$C_6$haloalkylcarbonyl or $C_1$-$C_6$alkoxycarbonyl, or $R^7$ together with $R^6$ may form 3- to 7-membered ring with the bonding nitrogen atom by forming $C_2$-$C_6$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$haloalkyl, oxo or thioxo, $R^8$ is $C_1$-$C_6$alkyl, $C_1$-$C_6$haloalkyl, $C_3$-$C_6$alkenyl, phenyl or phenyl substituted with $(Z)_{p1}$, $R^9$ is $C_1$-$C_6$alkyl, $C_1$-$C_6$alkyl arbitrarily substituted with $R^{24}$, $C_3$-$C_8$cycloalkyl, $C_3$-$C_8$halocycloalkyl, $C_2$-$C_6$alkenyl, $C_2$-$C_6$haloalkenyl, $C_2$-$C_6$alkynyl, $C_2$-$C_6$haloalkynyl, phenyl, phenyl substituted with $(Z)_{p1}$, D-1 to D-65 or E-1 to E-49, $R^{10}$ is hydrogen atom, $C_1$-$C_6$alkyl, $C_1$-$C_6$haloalkyl, $C_3$-$C_6$cycloalkyl $C_1$-$C_4$alkyl, $C_1$-$C_6$alkoxy $C_1$-$C_4$alkyl, $C_1$-$C_6$alkylthio $C_1$-$C_4$alkyl, cyano $C_1$-$C_6$alkyl, $C_3$-$C_6$alkenyl or $C_3$-$C_6$alkynyl, $R^{10}$ together with $R^9$ may form 3- to 7-membered ring with the atom bonding them by forming $C_2$-$C_6$alkylene chain, in this case, the alkylene chain may contain one oxygen atom, sulfur atom or nitrogen atom, and may be arbitrarily substituted with halogen atom, $C_1$-$C_6$alkyl or $C_1$-$C_6$haloalkoxy, formyl, $C_1$-$C_6$alkylcarbonyl or $C_1$-$C_6$alkoxycarbonyl, $R^{11}$ is hydrogen atom, $C_1$-$C_6$alkyl, $C_1$-$C_6$haloalkyl, phenyl $C_1$-$C_4$alkyl, phenyl $C_1$-$C_4$alkyl substituted with $(Z)_{p1}$, $C_3$-$C_6$alkenyl, $C_3$-$C_6$haloalkenyl, $C_3$-$C_6$alkynyl, $C_3$-$C_6$haloalkynyl, phenyl or phenyl that may be substituted with $(Z)_{p1}$, $R^{11}$ together with $R^9$ may form 5- to 7-membered ring with the atom bonding them by forming $C_2$-$C_4$alkylene chain, in this case, the alkylene chain may contain one oxygen atom, sulfur atom or nitrogen atom, and may be arbitrarily substituted with halogen atom, $C_1$-$C_6$alkyl or $C_1$-$C_6$haloalkyl, $R^{12}$ is $C_1$-$C_6$alkyl, $C_1$-$C_6$haloalkyl, phenyl or phenyl substituted with $(Z)_{p1}$, $R^{13}$ and $R^{14}$ independently of each other are $C_1$-$C_6$alkyl or $C_1$-$C_6$haloalkyl, $R^{15}$ is hydrogen atom, $C_1$-$C_6$alkyl, $C_1$-$C_6$haloalkyl, $C_1$-$C_6$alkoxycarbonyl $C_1$-$C_4$alkyl, $C_1$-$C_6$haloalkoxycarbonyl $C_1$-$C_4$alkyl, phenyl $C_1$-$C_4$alkyl, phenyl $C_1$-$C_4$alkyl substituted with $(Z)_{p1}$, $C_3$-$C_6$alkenyl, $C_3$-$C_6$haloalkenyl, $C_3$-$C_6$alkynyl, $C_3$-$C_6$haloalkynyl, $C_1$-$C_6$alkoxy, $C_1$-$C_6$alkoxycarbonyl, $C_1$-$C_6$haloalkoxycarbonyl, phenyl or phenyl substituted with $(Z)_{p1}$, further, in case where Z is present in an adjacent position of $R^{15}$, the adjacent $R^{15}$ and Z may form 6-membered ring together with the atom bonding them by forming —CH$_2$CH$_2$CH$_2$CH$_2$—, —CH=CH—CH=CH—, —N=CH—CH=CH—, —CH=N—CH=CH—, —CH=CH—N=CH— or —CH=CH—CH=N—, in this case, hydrogen atoms bonded to each carbon atom forming the ring may be arbitrarily substituted with halogen atom, $C_1$-$C_4$alkyl or $C_1$-$C_4$haloalkyl, $R^{16}$ is halogen atom, cyano, nitro, $C_3$-$C_8$cycloalkyl, $C_3$-$C_8$halocycloalkyl, hydroxy $C_3$-$C_6$cycloalkyl, $C_1$-$C_4$alkoxy $C_3$-$C_6$cycloalkyl, $C_5$-$C_6$cycloalkenyl, —$OR^{25}$, —N($R^{26}$)$R^{25}$, —SH, —S(O)$_r$$R^{27}$, —SO$_2$OH, —SO$_2$NHR$^{29}$, —SO$_2$N($R^{29}$)$R^{28}$, —CHO, —C(O)$R^{28}$, —C(O)OH, —C(O)$OR^{28}$, —C(O)$SR^{28}$, —C(O)NH$R^{29}$, —C(O)N($R^{29}$)$R^{28}$, —C(O)N($R^{29}$)$OR^{28}$, —C(O)N($R^{29}$)N($R^{28a}$)$R^{28}$, C(S)$OR^{28}$, —C(S)$SR^{28}$, —C(S)NH$R^{29}$, —C(S)N($R^{29}$)$R^{28}$, —C(O)C(O)$R^{28}$, —C($R^{31}$)=NOH, —C($R^{31}$)=NO$R^{30}$, —C(=N$R^{31}$)$OR^{30}$, —C(=N$R^{31}$)$SR^{30}$, —C(=N$R^{31}$)N($R^{29}$)$R^{30}$, —C(=NO$R^{31}$)NHR$^{29}$, —C(=NO$R^{31}$)N($R^{29}$)$R^{30}$, —Si($R^{13}$)($R^{14}$)$R^{12}$, —P(O)(O$R^{21}$)$_2$, —P(S)(O$R^{21}$)$_2$, —P(phenyl)$_2$, —P(O)(phenyl)$_2$, phenyl, phenyl substituted with (Z)$_{p1}$, naphthyl, D-1 to D-65, E-1 to E-49 or M-1 to M-22,
M-1 to M-22 are partially saturated heterocyclic rings of the following formulae, respectively
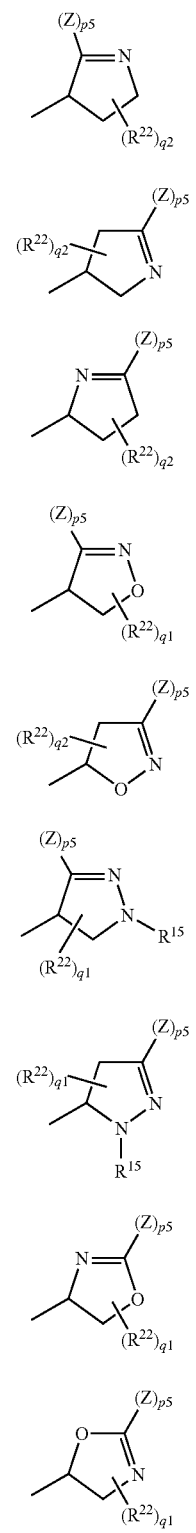
M-1
M-2
M-3
M-4
M-5
M-6
M-7
M-8
M-9
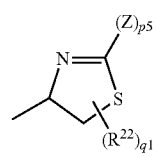
M-10
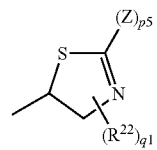
M-11
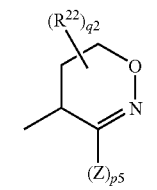
M-12
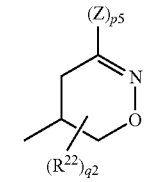
M-13
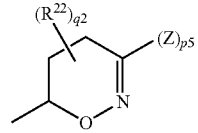
M-14
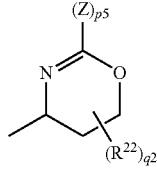
M-15
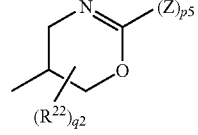
M-16
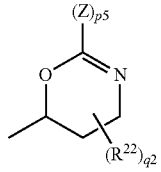
M-17
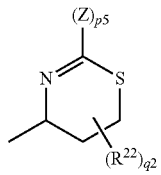
M-18

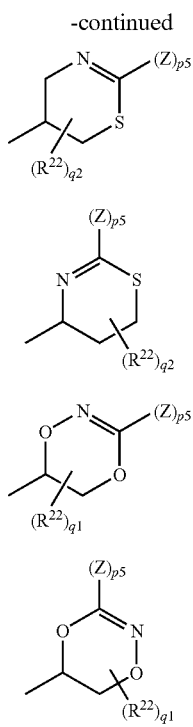

M-19

M-20

M-21

M-22

$R^{17}$ is $C_1$-$C_{12}$alkyl, $C_1$-$C_{12}$haloalkyl, $C_1$-$C_{12}$alkoxy $C_1$-$C_{12}$alkyl, cyano $C_1$-$C_{12}$alkyl, $C_1$-$C_{12}$alkoxycarbonyl $C_1$-$C_{12}$alkyl, phenyl $C_1$-$C_4$alkyl, phenyl $C_1$-$C_4$alkyl substituted with $(Z)_{p1}$, $C_3$-$C_{12}$alkenyl, $C_3$-$C_{12}$haloalkenyl, $C_3$-$C_{12}$alkynyl, $C_3$-$C_{12}$haloalkynyl, $C_1$-$C_{12}$alkylcarbonyl, $C_1$-$C_{12}$alkoxycarbonyl, —C(O)ON=C(CH$_3$)SCH$_3$, —C(O)ON=C(SCH$_3$)C(O)N(CH$_3$)$_2$, phenyl or phenyl substituted with $(Z)_{p1}$, $R^{18}$ is $C_1$-$C_{12}$alkyl, $C_1$-$C_{12}$haloalkyl, $C_1$-$C_{12}$alkoxy $C_1$-$C_{12}$alkyl, cyano $C_1$-$C_{12}$alkyl, $C_1$-$C_{12}$alkoxycarbonyl $C_1$-$C_{12}$alkyl, phenyl $C_1$-$C_4$alkyl, phenyl $C_1$-$C_4$alkyl substituted with $(Z)_{p1}$, $C_3$-$C_{12}$alkenyl, $C_3$-$C_{12}$haloalkenyl, $C_3$-$C_{12}$alkynyl, $C_3$-$C_{12}$haloalkynyl, phenyl or phenyl substituted with $(Z)_{p1}$, or $R^{18}$ together with $R^{17}$ may form 5- to 8-membered ring with the nitrogen atom bonding them by forming $C_4$-$C_7$alkylene chain, in this case, the alkylene chain may contain one oxygen atom or sulfur atom, and may be arbitrarily substituted with $C_1$-$C_4$alkyl or $C_1$-$C_4$alkoxy, $R^{19}$ is hydrogen atom, $C_1$-$C_6$alkyl, $C_1$-$C_6$alkyl arbitrarily substituted with $R^{16}$, $C_3$-$C_8$cycloalkyl, $C_3$-$C_8$halocycloalkyl, $C_3$-$C_6$alkenyl, $C_3$-$C_6$haloalkenyl, $C_3$-$C_6$alkynyl, $C_3$-$C_6$haloalkynyl, —CHO, —C(O)R$^{28}$, —C(O)OR$^{28}$, —C(O)SR$^{28}$, —C(O)NHR$^{29}$, —C(O)N(R$^{29}$)R$^{28}$, C(S)OR$^{28}$, C(S)SR$^{28}$, —C(S)NHR$^{29}$, —C(S)N(R$^{29}$)R$^{28}$, —S(O)$_2$R$^{28}$, —S(O)$_2$NHR$^{29}$, —S(O)$_2$N(R$^{29}$)R$^{28}$, —P(O)(OR$^{21}$)$_2$, —P(S)(OR$^{21}$)$_2$, phenyl, phenyl substituted with $(Z)_{p1}$, D-1 to D-13, D-15 to D-25, D-30 to D-37, D-39, D-40, D-42, D-45 to D-60, E-5, E-7, E-9, E-24, E-25, E-27, E-28, E-30 or E-31, $R^{19a}$ is hydrogen atom, $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_1$-$C_4$alkylsulfonyl $C_1$-$C_4$alkyl, $C_1$-$C_4$alkoxycarbonyl $C_1$-$C_4$alkyl, phenyl $C_1$-$C_4$alkyl, phenyl $C_1$-$C_4$alkyl substituted with $(Z)_{p1}$, $C_3$-$C_6$cycloalkyl, phenyl $C_2$-$C_4$alkenyl, di($C_1$-$C_6$alkyl)amino, phenyl, phenyl substituted with $(Z)_{p1}$, D-1 to D-65 or E-1 to E-49, $R^{19b}$ is hydrogen atom, $C_1$-$C_6$alkyl, $C_1$-$C_6$alkoxy, $C_1$-$C_6$alkylthio or di($C_1$-$C_6$alkyl)amino, or $R^{19a}$ together with $R^{19b}$ may form 4- to 6-membered ring with the carbon atom bonding them by forming $C_3$-$C_5$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$haloalkyl, formyl, $C_1$-$C_6$alkylcarbonyl or $C_1$-$C_6$alkoxycarbonyl, $R^{20}$ is hydrogen atom, $C_1$-$C_6$alkyl, $C_1$-$C_6$haloalkyl, $C_1$-$C_4$alkoxy $C_1$-$C_4$alkyl, $C_1$-$C_4$haloalkoxy $C_1$-$C_4$alkyl, $C_1$-$C_4$alkylthio $C_1$-$C_4$alkyl, $C_1$-$C_4$haloalkylthio $C_1$-$C_4$alkyl, $C_1$-$C_4$alkylsulfonyl $C_1$-$C_4$alkyl, $C_1$-$C_4$haloalkylsulfonyl $C_1$-$C_4$alkyl, cyano $C_1$-$C_6$alkyl, $C_1$-$C_4$alkoxycarbonyl $C_1$-$C_4$alkyl, phenyl $C_1$-$C_4$alkyl, $C_2$-$C_6$alkenyl, $C_2$-$C_6$haloalkenyl, $C_3$-$C_6$alkynyl, $C_3$-$C_6$haloalkynyl, —CHO, —C(O)R$^9$, —C(O)OR$^9$, —C(O)SR$^9$, —C(S)OR$^9$, —C(S)SR$^9$, $C_1$-$C_6$alkylsulfonyl or $C_1$-$C_6$haloalkylsulfonyl, or $R^{20}$ together with $R^{19}$ may form 5- to 6-membered ring with the nitrogen atom bonding them by forming $C_4$-$C_5$alkylene chain, in this case, the alkylene chain may contain one oxygen atom, sulfur atom or nitrogen atom, and may be arbitrarily substituted with $C_1$-$C_6$alkyl, $C_1$-$C_6$alkoxy $C_1$-$C_6$alkyl, —CHO, $C_1$-$C_6$alkylcarbonyl or $C_1$-$C_6$alkoxycarbonyl, $R^{21}$ is $C_1$-$C_6$alkyl or $C_1$-$C_6$haloalkyl, $R^{22}$ is halogen atom, cyano, $C_1$-$C_6$alkyl, $C_1$-$C_6$haloalkyl, hydroxy $C_1$-$C_6$alkyl, $C_1$-$C_4$alkoxy $C_1$-$C_4$alkyl, $C_1$-$C_4$alkoxycarbonyl $C_1$-$C_4$alkyl, $C_1$-$C_6$alkoxy, $C_1$-$C_6$alkylthio, $C_1$-$C_6$alkylamino, di($C_1$-$C_4$alkyl)amino, $C_1$-$C_6$alkoxycarbonyl, phenyl or phenyl substituted with $(Z)_{p1}$, when q1, q2, q3 or q4 is an integer of 2 or more, each $R^{22}$ may be identical with or different from each other, further in case where two $R^{22}$s are present on the same carbon atom, the two $R^{22}$s together may form oxo, thioxo, imino, $C_1$-$C_6$alkylimino, $C_1$-$C_6$alkoxyimino or $C_1$-$C_6$alkylidene, $R^{23}$ is hydrogen atom, $C_1$-$C_6$alkyl, $C_1$-$C_6$alkyl substituted with $R^{32}$, $C_3$-$C_6$cycloalkyl, $C_3$-$C_6$alkenyl, $C_3$-$C_6$haloalkenyl, $C_3$-$C_6$alkynyl, —OH, benzyloxy, —CHO, —C(O)R$^{33}$, —C(O)OR$^{33}$, —C(O)SR$^{33}$, —C(O)NHR$^{34}$, —C(O)N(R$^{34}$)R$^{33}$, —C(S)NHR$^{34}$, —C(S)N(R$^{34}$)R$^{33}$, —S(O)$_2$R$^{33}$, —P(O)(OR$^{21}$)$_2$, —P(S)(OR$^{21}$)$_2$, phenyl, phenyl substituted with $(Z)_{p1}$ or D-5, $R^{24}$ is halogen atom, cyano, $C_3$-$C_8$cycloalkyl, $C_3$-$C_8$halocycloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkylamino, di($C_1$-$C_6$alkyl)amino, —CHO, $C_1$-$C_6$alkylcarbonyl, $C_1$-$C_6$haloalkylcarbonyl, $C_1$-$C_6$alkoxycarbonyl, $C_1$-$C_6$haloalkoxycarbonyl, $C_1$-$C_6$alkylaminocarbonyl, di($C_1$-$C_6$alkyl)aminocarbonyl, phenyl, phenyl substituted with $(Z)_{p1}$, D-1 to D-65 or E-1 to E-49, $R^{25}$ is hydrogen atom, $C_1$-$C_8$alkyl, $C_1$-$C_8$alkyl arbitrarily substituted with $R^{32}$, $C_3$-$C_8$cycloalkyl, $C_3$-$C_8$cycloalkyl arbitrarily substituted with $R^{32}$, $C_3$-$C_8$alkenyl, $C_3$-$C_8$alkenyl arbitrarily substituted with $R^{32}$, $C_3$-$C_8$alkynyl, $C_3$-$C_8$alkynyl arbitrarily substituted with $R^{32}$, —CHO, —C(O)R$^{33}$, —C(O)OR$^{33}$, —C(O)SR$^{33}$, —C(O)NHR$^{34}$, —C(O)N(R$^{34}$)R$^{33}$, —C(O)C(O)R$^{33}$, —C(O)C(O)OR$^{33}$, —C(S)R$^{33}$, —C(S)OR$^{33}$, —C(S)SR$^{33}$, —C(S)NHR$^{34}$, —C(S)N(R$^{34}$)R$^{33}$, —S(O)$_2$R$^{33}$, —S(O)$_2$N(R$^{34}$)R$^{33}$, —Si(R$^{13}$)(R$^{14}$)R$^{12}$, —P(O)(OR$^{21}$)$_2$, —P(S)(OR$^{21}$)$_2$, phenyl, phenyl substituted with $(Z)_{p1}$, D-1 to D-4, D-6 to D-13, D-15 to D-23, D-25 to D-37, D-39, D-40, D-42, D-45 to D-60, D-62, D-63, D-65, E-3 to E-9, E-23 to E-31, E-34 or E-45, $R^{26}$ is hydrogen atom, $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_3$-$C_6$cycloalkyl, $C_3$-$C_6$alkenyl, $C_3$-$C_6$alkynyl, $C_1$-$C_6$alkoxy, phenyl or phenyl substituted with $(Z)_{p1}$, or $R^{26}$ together with $R^{25}$ may form 3- to 6-membered ring with the nitrogen atom bonding them by forming $C_2$-$C_5$alkylene chain, in this case, the alkylene chain may contain one oxygen atom, sulfur atom or nitrogen atom, and may be substituted with halogen atom, $C_1$-$C_6$alkyl, $C_1$-$C_6$haloalkyl, $C_1$-$C_6$alkoxy, phenyl, phenyl substituted with $(Z)_{p1}$, oxo or thioxo, $R^{27}$ is $C_1$-$C_8$alkyl, $C_1$-$C_8$alkyl arbitrarily substituted with $R^{32}$, $C_3$-$C_8$cycloalkyl, $C_3$-$C_8$cycloalkyl arbitrarily substituted with $R^{32}$, $C_3$-$C_8$alkenyl, $C_3$-$C_8$alkenyl arbitrarily substituted with $R^{32}$, $C_3$-$C_8$alkynyl, $C_3$-$C_8$alkynyl arbitrarily substituted with $R^{32}$, —SH, $C_1$-$C_6$alkylthio, $C_1$-$C_6$haloalkylthio, phenylthio, phenylthio substituted with $(Z)_{p1}$, —CHO, —C(O)$R^{33}$, —C(O)O$R^{33}$, —C(O)S$R^{33}$, —C(O)NH$R^{34}$—C(O)N($R^{34}$)$R^{33}$, —C(O)C(O)$R^{33}$, —C(O)C(O)O$R^{33}$, —C(S)$R^{33}$, —C(S)O$R^{33}$—C(S)S$R^{33}$, —C(S)NH$R^{34}$, —C(S)N($R^{34}$)$R^{33}$, —P(O)(O$R^{21}$)$_2$, —P(S)(O$R^{21}$)$_2$, phenyl, phenyl substituted with $(Z)_{p1}$, D-18, D-21, D-25, D-30 to D-35, D-47, D-50, D-51, E-3 to E-9, E-23 to E-31, E-34 or E-45, $R^{28}$ is $C_1$-$C_6$alkyl, $C_1$-$C_6$alkyl arbitrarily substituted with $R^{32}$, $C_3$-$C_8$cycloalkyl, $C_3$-$C_8$cycloalkyl arbitrarily substituted with $R^{32}$, $C_2$-$C_6$alkenyl $C_3$-$C_8$cycloalkyl, $C_2$-$C_6$haloalkenyl $C_3$-$C_8$cycloalkyl, $C_2$-$C_8$alkenyl, $C_2$-$C_8$alkenyl arbitrarily substituted with $R^{32}$, $C_2$-$C_8$alkynyl, $C_2$-$C_8$alkynyl arbitrarily substituted with $R^{32}$, phenyl, phenyl substituted with $(Z)_{p1}$, D-1 to D-65 or E-1 to E-49, $R^{28a}$ is hydrogen atom or $C_1$-$C_6$alkyl, $R^{29}$ is hydrogen atom, $C_1$-$C_6$alkyl, $C_1$-$C_6$alkyl arbitrarily substituted with $R^{32}$, $C_3$-$C_6$alkenyl, $C_3$-$C_6$haloalkenyl, $C_3$-$C_6$alkynyl, $C_3$-$C_6$haloalkynyl, phenyl or phenyl substituted with $(Z)_{p1}$, or $R^{29}$ together with $R^{28}$ may form 3- to 6-membered ring with the nitrogen atom bonding them by forming $C_2$-$C_5$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$alkoxy, formyl, $C_1$-$C_6$alkylcarbonyl, $C_1$-$C_6$alkoxycarbonyl, phenyl or phenyl substituted with $(Z)_{p1}$, $R^{30}$ is $C_1$-$C_8$alkyl, $C_1$-$C_8$alkyl arbitrarily substituted with $R^{32}$, $C_3$-$C_8$cycloalkyl, $C_3$-$C_8$alkenyl, $C_3$-$C_8$alkenyl arbitrarily substituted with $R^{32}$, $C_3$-$C_8$alkynyl, $C_3$-$C_8$alkynyl arbitrarily substituted with $R^{32}$, $R^{31}$ is hydrogen atom, $C_1$-$C_6$alkyl, $C_1$-$C_6$haloalkyl, $C_3$-$C_6$cycloalkyl $C_1$-$C_4$alkyl, $C_1$-$C_6$alkoxy $C_1$-$C_4$alkyl, $C_1$-$C_6$haloalkoxy $C_1$-$C_4$alkyl, $C_1$-$C_6$alkylthio $C_1$-$C_4$alkyl, $C_1$-$C_6$haloalkylthio $C_1$-$C_4$alkyl, $C_1$-$C_6$alkylsulfonyl $C_1$-$C_4$alkyl, $C_1$-$C_6$haloalkylsulfonyl $C_1$-$C_4$alkyl, phenyl $C_1$-$C_4$alkyl, phenyl $C_1$-$C_4$alkyl substituted with $(Z)_{p1}$, $C_3$-$C_6$cycloalkyl, phenyl or phenyl substituted with $(Z)_{p1}$, or $R^{31}$ together with $R^{30}$ may form 5- to 7-membered ring with the atom bonding them by forming $C_2$-$C_4$alkylene chain, in this case, the alkylene chain may contain one oxygen atom, sulfur atom or nitrogen atom, and may be arbitrarily substituted with halogen atom, $C_1$-$C_6$alkyl or $C_1$-$C_6$haloalkyl, $R^{32}$ is halogen atom, cyano, nitro, $C_3$-$C_8$cycloalkyl, $C_3$-$C_8$halocycloalkyl, —OH, —O$R^{33}$, —OC(O)$R^{33}$, —OC(O)O$R^{33}$, —OC(O)NH$R^{34}$, —OC(O)N($R^{34}$)$R^{33}$, —OC(S)NH$R^{34}$, —OC(S)N($R^{34}$)$R^{33}$, —SH, —S(O)$_r$$R^{33}$, —SC(O)$R^{33}$, —SC(O)O$R^{33}$, —SC(O)NH$R^{33}$, —SC(O)N($R^{34}$)$R^{33}$, —SC(S)NH$R^{34}$, —SC(S)N($R^{34}$)$R^{33}$, —NH$R^{34}$, —N($R^{34}$)$R^{33}$, —N($R^{34}$)CHO, —N($R^{34}$)C(O)$R^{33}$, —N($R^{34}$)C(O)O$R^{33}$, —N($R^{34}$)C(O)NH$R^{34}$, —N($R^{34}$)C(O)N($R^{34}$)$R^{33}$, —N($R^{34}$)C(S)NH$R^{34}$, —N($R^{34}$)C(S)N($R^{34}$)$R^{33}$, —CHO, —C(O)$R^{33}$, —C(O)O$R^{33}$, —C(O)S$R^{33}$, —C(O)NH$R^{34}$, —C(O)N($R^{34}$)$R^{33}$, —C(O)C(O)O$R^{33}$, —Si($R^{13}$)($R^{14}$)$R^{12}$, —P(O)(O$R^{21}$)$_2$, —P(S)(O$R^{21}$)$_2$, —P(phenyl)$_2$, —P(O)(phenyl)$_2$, phenyl, phenyl substituted with $(Z)_{p1}$, D-1 to D-65 or E-4 to E-7, E10 to E-14, E-18, E-19, E-23 to E-28, E-32 to E-38, E-43, E-44 or E-45, $R^{33}$ is $C_1$-$C_6$alkyl, $C_1$-$C_6$haloalkyl, $C_1$-$C_4$alkyl arbitrarily substituted with $R^{35}$, $C_3$-$C_6$cycloalkyl, $C_3$-$C_6$halocycloalkyl, $C_2$-$C_6$alkenyl $C_3$-$C_8$cycloalkyl, $C_2$-$C_6$haloalkenyl $C_3$-$C_8$cycloalkyl, $C_2$-$C_8$alkenyl, $C_2$-$C_8$haloalkenyl, $C_3$-$C_8$cycloalkenyl, $C_3$-$C_8$halocycloalkenyl, $C_2$-$C_8$alkynyl, $C_2$-$C_8$haloalkynyl, phenyl, phenyl substituted with $(Z)_{p1}$, D-1 to D-65, E-4 to E-7, E-23 to E-27 or E-28, $R^{34}$ is hydrogen atom, $C_1$-$C_6$alkyl, $C_1$-$C_6$haloalkyl, $C_3$-$C_8$cycloalkyl, $C_3$-$C_6$alkenyl, $C_3$-$C_6$alkynyl, $C_1$-$C_6$alkylcarbonyl, $C_1$-$C_6$haloalkylcarbonyl, $C_1$-$C_6$alkoxycarbonyl, $C_1$-$C_6$haloalkoxycarbonyl, phenoxycarbonyl, phenoxycarbonyl substituted with $(Z)_{p1}$, phenylcarbonyl, phenylcarbonyl substituted with $(Z)_{p1}$, $C_1$-$C_6$alkylsulfonyl, $C_1$-$C_6$haloalkylsulfonyl, phenyl, phenyl substituted with $(Z)_{p1}$, D-1 to D-4, D-6 to D-13, D-15 to D-23, D-25 to D-37, D-39, D-40, D-42, D-45 to D-60, D-62, D-63 or D-65, or $R^{34}$ together with $R^{33}$ may form 3- to 6-membered ring with the nitrogen atom bonding them by forming $C_2$-$C_5$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$alkoxy, formyl, $C_1$-$C_6$alkylcarbonyl, $C_1$-$C_6$alkoxycarbonyl, phenyl or phenyl substituted with $(Z)_{p1}$, $R^{35}$ is cyano, $C_3$-$C_6$cycloalkyl, $C_3$-$C_6$halocylcoalkyl, E-4 to E-7, E-23 to E-28, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfonyl, $C_1$-$C_4$haloalkylsulfonyl, $C_1$-$C_6$alkylcarbonyl, $C_1$-$C_6$haloalkylcarbonyl, $C_1$-$C_6$alkoxycarbonyl, di($C_1$-$C_6$alkyl)aminocarbonyl, tri($C_1$-$C_6$alkyl)silyl, phenyl, phenyl substituted with $(Z)_{p1}$ or D-1 to D-65, m is an integer of 0 to 5,
n is an integer of 0 to 4,
p1 is an integer of 1 to 5,
p2 is an integer of 0 to 4,
p3 is an integer of 0 to 3,
p4 is an integer of 0 to 2,
p5 is an integer of 0 or 1,
q1 is an integer of 0 to 3,
q2 is an integer of 0 to 5,
q3 is an integer of 0 to 7,
q4 is an integer of 0 to 9,
r is an integer of 0 to 2, and
t is an integer of 0 or 1.

(2) The isoxazoline-substituted benzamide compound or the salt thereof as set forth in (1), wherein
G is an aromatic 6-membered ring shown in any one of G-1 to G-10 or an aromatic 5-membered ring shown in any one of G-11 to G-25

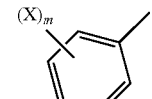

G-1

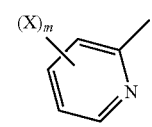

G-2

-continued
G-3 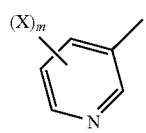
G-4 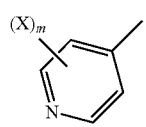
G-5 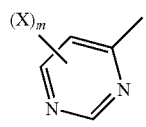
G-6 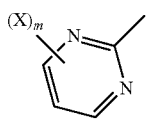
G-7 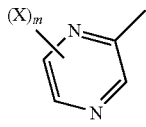
G-8 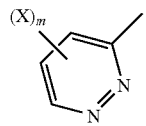
G-9 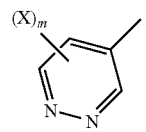
G-10 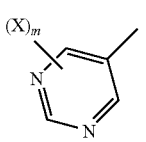
G-11 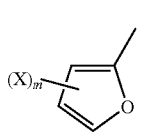
G-12 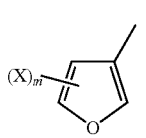
G-13 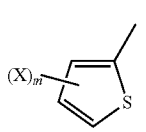
G-14 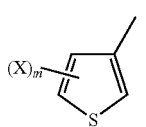
-continued
G-15 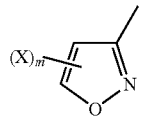
G-16 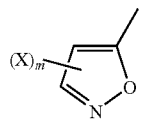
G-17 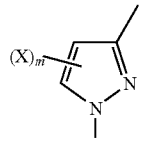
G-18 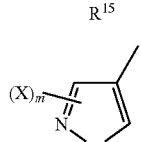
G-19 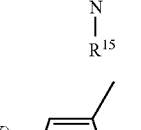
G-20 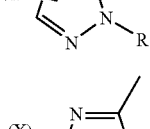
G-21 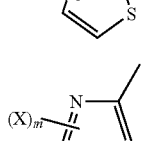
G-22 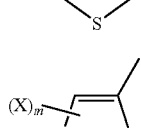
G-23 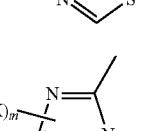
G-24 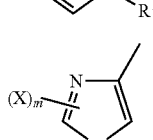
G-25 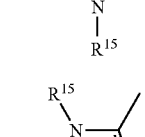
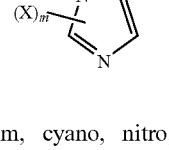
X is halogen atom, cyano, nitro, —SF$_5$, C$_1$-C$_6$alkyl, C$_1$-C$_6$alkyl arbitrarily substituted with R$^4$, C$_3$-C$_8$cycloalkyl, C$_3$-C$_8$cycloalkyl arbitrarily substituted with R$^4$, $C_2$-$C_6$alkenyl, $C_2$-$C_6$alkenyl arbitrarily substituted with $R^4$, $C_2$-$C_6$alkynyl, $C_2$-$C_6$alkynyl arbitrarily substituted with $R^4$, —OH, —OR$^5$, —OSO$_2$R$^5$, —S(O)$_r$R$^5$, —C(O)OR$^9$, —C(O)SR$^9$,
—C(O)NHR$^{10}$, —C(O)N(R$^{10}$)R$^9$, —C(S)OR$^9$, —C(S)SR$^9$, —C(S)NHR$^{10}$, —C(S)N(R$^{10}$)R$^9$, —CH=NOR$^{11}$, —C(R$^9$)=NOR$^{11}$, —S(O)$_2$NHR$^{10}$, —S(O)$_2$N(R$^{10}$)R$^9$, —Si(R$^{13}$)(R$^{14}$)R$^{12}$, phenyl, phenyl substituted with $(Z)_{p1}$, D-1 to D-60 or E-1 to E-49, when m is an integer of 2 or more, each X may be identical with or different from each other, further, when two Xs are adjacent, the adjacent two Xs may form 5-membered or 6-membered ring together with carbon atoms to which the two Xs are bonded by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S— or —CH=CHCH=CH—, in this case, hydrogen atoms bonded to each carbon atom forming the ring may be arbitrarily substituted with halogen atom, $C_1$-$C_4$alkyl or $C_1$-$C_4$haloalkyl, Y is halogen atom, cyano, nitro, $C_1$-$C_6$alkyl, $C_1$-$C_6$alkyl arbitrarily substituted with $R^4$, —OR$^5$, —OSO$_2$R$^5$, —S(O)$_r$R$^5$—NHR$^7$, —N(R$^7$)R$^6$, —N=CHOR$^8$, —N=C(R$^9$)OR$^8$, —C(O)NHR$^{10}$,
—C(O)N(R$^{10}$)R$^9$, —C(S)NHR$^{10}$, —C(S)N(R$^{10}$)R$^9$, phenyl, phenyl substituted with $(Z)_{p1}$, D-1 to D-24, D-30 to D-38, D-43 to D-52 or D-53, when n is an integer of 2 or more, each Y may be identical with or different from each other, further, when two Ys are adjacent, the adjacent two Ys may form 5-membered or 6-membered ring together with carbon atoms to which the two Ys are bonded by forming —CH$_2$CH$_2$CH$_2$—, —CH$_2$CH$_2$O—, —CH$_2$OCH$_2$—, —OCH$_2$O—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH=N— or —SCH=N—, in this case, hydrogen atoms bonded to each carbon atom forming the ring may be arbitrarily substituted with halogen atom, $C_1$-$C_4$alkyl or $C_1$-$C_4$haloalkyl, $R^1$ is $C_1$-$C_8$alkyl, $C_1$-$C_8$alkyl arbitrarily substituted with $R^{16}$, $C_3$-$C_8$cycloalkyl, $C_3$-$C_8$halocycloalkyl, $C_3$-$C_8$alkenyl, $C_3$-$C_8$haloalkenyl, phenyl $C_3$-$C_6$alkenyl, phenyl $C_3$-$C_6$alkenyl substituted with $(Z)_{p1}$, $C_3$-$C_8$alkynyl, $C_3$-$C_8$alkynyl, phenyl $C_3$-$C_6$alkynyl, phenyl $C_3$-$C_6$alkynyl substituted with $(Z)_{p1}$, $C_1$-$C_6$alkoxy, —N(R$^{20}$)R$^{19}$, —N=CHR$^{19b}$,
—N=C(R$^{19b}$)R$^{19a}$, —C(O)N(R$^{10}$)R$^9$, —C(S)N(R$^{10}$)R$^9$, —C(=NR$^{11}$)OR$^9$, —C(=NR$^{11}$)SR$^9$, —C(=NR$^{11}$)N(R$^{10}$)R$^9$, phenyl, phenyl substituted with $(Z)_{p1}$, D-1 to D-4, D-6 to D-18, D-21 to D-24, D-26 to D-40, D-42, D-45 to D-58, E-4 to E-9, E-23 to E-28, E-30, E-31, E-34 or E-45, $R^2$ is hydrogen atom, $C_1$-$C_6$alkyl, $C_1$-$C_6$haloalkyl, $C_3$-$C_6$cycloalkyl $C_1$-$C_4$alkyl, $C_1$-$C_4$alkoxy $C_1$-$C_4$alkyl, $C_1$-$C_4$haloalkoxy $C_1$-$C_4$alkyl, benzyloxy $C_1$-$C_4$alkyl, $C_1$-$C_4$alkylthio $C_1$-$C_4$alkyl, $C_1$-$C_4$haloalkylthio $C_1$-$C_4$alkyl, $C_1$-$C_4$alkylsulfonyl $C_1$-$C_4$alkyl, $C_1$-$C_4$haloalkylsulfonyl $C_1$-$C_4$alkyl, phenylthio $C_1$-$C_4$alkyl, phenylthio $C_1$-$C_4$alkyl substituted with $(Z)_{p1}$, cyano $C_1$-$C_6$alkyl, nitro $C_1$-$C_6$alkyl, $C_1$-$C_4$alkylcarbonyl $C_1$-$C_4$alkyl, $C_1$-$C_4$alkoxycarbony $C_1$-$C_4$alkyl, $C_3$-$C_6$cycloalkyl, $C_3$-$C_6$alkenyl, $C_3$-$C_6$haloalkenyl, $C_3$-$C_6$alkynyl, —SR$^9$, —S(O)$_2$R$^9$, —SN(R$^{18}$)R$^{17}$, —OH, —OR$^{19}$, —NHR$^{20}$, N(R$^{20}$)R$^{19}$, —N=CHR$^{19b}$, —N=C(R$^{19b}$)R$^{19a}$, —C(O)R$^9$, —C(O)OR$^9$, —C(O)SR$^9$, —C(S)OR$^9$ or —C(S)SR$^9$,
or $R^1$ and $R^2$ together form =C(R$^{2a}$)R$^{1a}$, and further $R^1$ and $R^2$ together may form 3- to 7-membered ring together with the nitrogen atom bonding them by forming $C_2$ to $C_6$ alkylene chain, in this case, the alkylene chain may contain one oxygen atom, sulfur atom or nitrogen atom, and may be arbitrarily substituted with $C_1$-$C_6$alkyl, formyl, $C_1$-$C_6$alkylcarbonyl or $C_1$-$C_6$alkoxycarbonyl, $R^{1a}$ and $R^{2a}$ together may form 5- or 6-membered ring together with the carbon atom bonding them by forming $C_4$ or $C_5$ alkylene chain or $C_4$ or $C_5$ alkenylene chain, in this case, the alkylene chain and the alkenylene chain may contain one to three oxygen atoms, sulfur atoms or nitrogen atoms, and may be arbitrarily substituted with halogen atom or $C_1$-$C_6$alkyl, $R^3$ is cyano, $C_1$-$C_6$alkyl, $C_1$-$C_6$alkyl arbitrarily substituted with $R^4$, $C_3$-$C_8$cycloalkyl, $C_3$-$C_8$halocycloalkyl, $C_3$-$C_6$alkenyl, $C_3$-$C_6$haloalkenyl, $C_3$-$C_6$alkynyl, $C_3$-$C_6$haloalkynyl, —OR$^5$, —S(O)$_r$R$^5$—N(R$^{10}$)R$^9$, —C(O)OR$^9$, —C(O)SR$^9$, —C(O)NHR$^{10}$,
—C(O)N(R$^{10}$)R$^9$, —C(S)OR$^9$, —C(S)SR$^9$, —C(S)NHR$^{10}$, —C(S)N(R$^{10}$)R$^9$, —CH=NOR$^{11}$, —C(R$^9$)=NOR$^{11}$, —Si(R$^{13}$)(R$^{14}$)R$^{12}$, phenyl, phenyl substituted with $(Z)_{p1}$, D-1 to D-4, D8- to D-13, D-15 to D-23, D-25 to D-37, D-39, D-40, D-42, D-45 to D-60 or E-4 to E-7, E-23 to E27 or E-28, $R^4$ is halogen atom, cyano, $C_3$-$C_6$cycloalkyl, $C_3$-$C_6$halocycloalkyl, —OH, —OR$^5$, —S(O)$_r$R$^5$, —N(R$^{10}$)R$^9$, —N(R$^{10}$)C(O)R$^9$, —N(R$^{10}$)C(O)OR$^9$, —N(R$^{10}$)C(O)SR$^9$,
—N(R$^{10}$)C(S)OR$^9$, —N(R$^{10}$)C(S)SR$^9$, —N(R$^{10}$)S(O)$_2$R$^9$, —Si(R$^{13}$)(R$^{14}$)R$^{12}$, phenyl, phenyl substituted with $(Z)_{p1}$, D-1 to D-5, D-8 to D-38, D-41, D-43, D-44, D-47 to D-52 or D-53, $R^5$ is $C_1$-$C_6$alkyl, $C_1$-$C_6$haloalkyl, $C_1$-$C_3$haloalkoxy $C_1$-$C_3$haloalkyl, $C_3$-$C_8$cycloalkyl, $C_3$-$C_8$halocycloalkyl, $C_2$-$C_6$alkenyl, $C_2$-$C_6$haloalkenyl, $C_3$-$C_6$alkynyl, $C_3$-$C_6$haloalkynyl, phenyl, phenyl substituted with $(Z)_{p1}$, D-1 to D-4, D-7, D-9, D-15 to D-23, D-30 to D-35, D-47 to D-53, E-3 to E-9, E-23 to E-27 or E-28, $R^6$ is $C_1$-$C_6$alkyl, $C_1$-$C_6$haloalkyl, $C_3$-$C_6$cycloalkyl $C_1$-$C_4$alkyl, $C_1$-$C_4$alkoxy $C_1$-$C_4$alkyl, $C_1$-$C_4$alkylthio $C_1$-$C_4$alkyl, —S(O)$_2$R$^9$, —CHO, —C(O)R$^9$, —C(O)OR$^9$, —C(O)SR$^9$, —C(S)OR$^9$ or —C(S)SR$^9$, $R^7$ is hydrogen atom, $C_1$-$C_6$alkyl, $C_1$-$C_6$haloalkyl, $C_3$-$C_6$alkenyl or $C_3$-$C_6$alkynyl, $R^8$ is $C_1$-$C_6$alkyl, $R^9$ is $C_1$-$C_6$alkyl, $C_1$-$C_6$haloalkyl, $C_3$-$C_6$cycloalkyl $C_1$-$C_4$alkyl, $C_1$-$C_4$alkoxy $C_1$-$C_4$alkyl, $C_1$-$C_4$alkylthio $C_1$-$C_4$alkyl, cyano $C_1$-$C_6$alkyl, phenyl $C_1$-$C_4$alkyl, phenyl $C_1$-$C_4$alkyl substituted with $(Z)_{p1}$, $C_3$-$C_8$cycloalkyl, $C_3$-$C_8$halocycloalkyl, $C_3$-$C_6$alkenyl, $C_3$-$C_6$haloalkenyl, $C_3$-$C_6$alkynyl, $C_3$-$C_6$haloalkynyl, phenyl, phenyl substituted with $(Z)_{p1}$, D-1 to D-4, D-6 to D-35, D-38, D-47 to D-54 or D-55, $R^{10}$ is hydrogen atom or $C_1$-$C_6$alkyl, or $R^{10}$ together with $R^9$ may form 5- to 7-membered ring with the nitrogen atom bonding them by forming $C_4$-$C_6$alkylene chain, in this case, the alkylene chain may contain one oxygen atom or sulfur atom, $R^{11}$ is $C_1$-$C_6$alkyl, $C_1$-$C_6$haloalkyl, phenyl $C_1$-$C_4$alkyl, phenyl $C_1$-$C_4$alkyl substituted with $(Z)_{p1}$, phenyl or phenyl substituted with $(Z)_{p1}$, or $R^{11}$ together with $R^9$ may form 5- or 6-membered ring with the atom bonding them by forming $C_2$-$C_3$alkylene chain, in this case, the alkylene chain may be arbitrarily substituted with $C_1$-$C_6$alkyl, $R^{12}$ is $C_1$-$C_6$alkyl, phenyl or phenyl substituted with $(Z)_{p1}$, $R^{13}$ and $R^{14}$ independently of each other are $C_1$-$C_6$alkyl, $R^{15}$ is $C_1$-$C_6$alkyl, $C_1$-$C_6$haloalkyl, phenyl $C_1$-$C_4$alkyl, phenyl $C_1$-$C_4$alkyl substituted with $(Z)_{p1}$, phenyl or phenyl substituted with $(Z)_{p1}$, $R^{16}$ is halogen atom, cyano, $C_3$-$C_6$cycloalkyl, $C_3$-$C_6$halocycloalkyl, —$OR^{25}$, —$N(R^{26})R^{25}$, —SH, —$S(O)_r$ $R^{27}$, —$SO_2NHR^{29}$, —$SO_2N(R^{29})R^{28}$, —CHO, —$C(O)R^{28}$, —$C(O)OR^{28}$, —$C(O)NHR^{29}$,
—$C(O)N(R^{29})R^{28}$, —$C(O)N(R^{29})OR^{28}$, —$C(S)NHR^{29}$, —$C(S)N(R^{29})R^{28}$, —$C(R^{31})$=NOH, —$C(R^{31})$=$NOR^{30}$, —$C(=NR^{31})OR^{30}$, —$C(=NR^{31})SR^{30}$, —$C(=NR^{31})N(R^{29})R^{30}$, —$C(=NOR^{31})NHR^{29}$, —$C(=NOR^{31})N(R^{29})R^{30}$, —$Si(R^{13})(R^{14})R^{12}$, phenyl, phenyl substituted with $(Z)_{p1}$, D-1 to D-60, E-1 to E-49 or M-1 to M-22, $R^{17}$ is $C_1$-$C_6$alkyl, $C_1$-$C_4$alkoxy $C_1$-$C_4$alkyl, $C_1$-$C_6$alkoxycarbonyl $C_1$-$C_4$alkyl, phenyl $C_1$-$C_4$alkyl, phenyl $C_1$-$C_4$alkyl substituted with $(Z)_{p1}$ or $C_1$-$C_6$alkoxycarbonyl, $R^{18}$ is $C_1$-$C_6$alkyl, phenyl $C_1$-$C_4$alkyl or phenyl $C_1$-$C_4$alkyl substituted with $(Z)_{p1}$, or $R^{18}$ together with $R^{17}$ may form 5- or 6-membered ring with the nitrogen atom bonding them by forming $C_4$-$C_5$alkylene chain, in this case, the alkylene chain may contain one oxygen atom or sulfur atom, and may be arbitrarily substituted with methyl or methoxy, $R^{19}$ is $C_1$-$C_6$alkyl, $C_1$-$C_6$alkyl arbitrarily substituted with $R^{16}$, $C_3$-$C_6$cycloalkyl, $C_3$-$C_6$halocycloalkyl, $C_3$-$C_6$alkenyl, $C_3$-$C_6$haloalkenyl, $C_3$-$C_6$alkynyl, —CHO, —$C(O)R^{28}$, —$C(O)OR^{28}$, —$C(O)NHR^{29}$, —$C(O)N(R^{29})R^{28}$, —$C(S)NHR^{29}$, —$C(S)N(R^{29})R^{28}$, —$S(O)_rR^{28}$, —$S(O)_2NHR^{29}$, —$S(O)_2N(R^{29})R^{28}$, phenyl, phenyl substituted with $(Z)_{p1}$, D-1 to D-13, D-15 to D-25, D-30 to D-37, D-39, D-40, D-42, D-45 to D-60, E-5, E-7, E-9, E-24, E-25, E-27, E-28, E-30 or E-31, $R^{19a}$ is $C_1$-$C_6$alkyl, $C_1$-$C_6$haloalkyl, $C_3$-$C_6$cycloalkyl, phenyl, phenyl substituted with $(Z)_{p1}$, D-1 to D-4, D-8 to D-10, D-15 to D-23, D-47 to D-55, E-4 to E-7, E-23 to E-27 or E-28, $R^{19b}$ is hydrogen atom or $C_1$-$C_6$alkyl, or $R^{19a}$ together with $R^{19b}$ may form 5- or 6-membered ring with the carbon atom bonding them by forming $C_4$-$C_5$alkylene chain, in this case, the alkylene chain may contain one oxygen atom or sulfur atom, $R^{20}$ is hydrogen atom, $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, cyano $C_1$-$C_6$alkyl, $C_1$-$C_4$alkoxycarbonyl $C_1$-$C_4$alkyl, $C_2$-$C_6$alkenyl, $C_3$-$C_6$alkynyl, —CHO, —$C(O)R^9$, —$C(O)OR^9$, —$C(O)SR^9$, —$C(S)OR^9$, —$C(S)SR^9$ or $C_1$-$C_6$alkylsulfonyl, $R^{22}$ is halogen atom, cyano, $C_1$-$C_6$alkyl, $C_1$-$C_6$haloalkyl, $C_1$-$C_6$alkoxy, $C_1$-$C_6$alkoxycarbonyl,
—$C(O)NH_2$ or —$C(S)NH_2$, when q1, q2, q3 or q4 is an integer of 2 or more, each $R^{22}$ may be identical with or different from each other, further in case where two $R^{22}$s are present on the same carbon atom, the two $R^{22}$s together may form oxo, thioxo, imino, $C_1$-$C_6$alkylimino, $C_1$-$C_6$alkoxyimino or $C_1$-$C_6$alkylidene, $R^{23}$ is hydrogen atom, $C_1$-$C_6$alkyl, $C_1$-$C_6$alkyl arbitrarily substituted with $R^{32}$, $C_3$-$C_6$cycloalkyl, $C_3$-$C_6$alkenyl, $C_3$-$C_6$alkynyl, —OH, benzyloxy, —CHO, —$C(O)R^{33}$, —$C(O)OR^{33}$, —$C(O)SR^{33}$, —$C(O)NHR^{34}$, —$C(O)N(R^{34})R^{33}$, —$S(O)_2R^{33}$, phenyl, phenyl substituted with $(Z)_{p1}$ or D-5, $R^{25}$ is hydrogen atom, $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, cyano $C_1$-$C_6$alkyl, phenyl $C_1$-$C_4$alkyl, phenyl $C_1$-$C_4$alkyl substituted with $(Z)_{p1}$, $C_3$-$C_6$alkenyl, $C_3$-$C_6$alkynyl, —CHO, —$C(O)R^{33}$, —$C(O)OR^{33}$, —$C(O)SR^{33}$, —$C(O)NHR^{34}$, —$C(O)N(R^{34})R^{33}$, —$C(S)R^{33}$, —$C(S)OR^{33}$, —$C(S)SR^{33}$, —$C(S)NHR^{34}$, —$C(S)N(R^{34})R^{33}$, —$S(O)_2R^{33}$, —$S(O)_2N(R^{34})R^{33}$, di($C_1$-$C_6$alkyl)phosphoryl, di($C_1$-$C_6$alkyl)thiophosphoryl, tri($C_1$-$C_4$alkyl)silyl, phenyl or phenyl substituted with $(Z)_{p1}$, $R^{26}$ is hydrogen atom, $C_1$-$C_6$alkyl, $C_3$-$C_6$alkenyl, $C_3$-$C_6$alkynyl or $C_1$-$C_6$alkoxy, or $R^{26}$ together with $R^{25}$ may form 4- to 6-membered ring with the nitrogen atom bonding them by forming $C_3$-$C_5$alkylene chain, in this case, the alkylene chain may contain one oxygen atom, sulfur atom or nitrogen atom, and may substituted with $C_1$-$C_6$alkyl, oxo or thioxo, $R^{27}$ is $C_1$-$C_6$alkyl, $C_1$-$C_6$haloalkyl, hydroxy $C_1$-$C_6$alkyl, $C_1$-$C_4$alkoxy $C_1$-$C_4$alkyl, $C_1$-$C_4$alkylthio $C_1$-$C_4$alkyl, $C_1$-$C_4$alkylcarbonyl $C_1$-$C_4$alkyl, $C_1$-$C_4$alkoxycarbonyl $C_1$-$C_4$alkyl, di($C_1$-$C_4$alkyl)aminocarbonyl $C_1$-$C_4$alkyl, tri($C_1$-$C_4$alkyl)silyl $C_1$-$C_4$alkyl, phenyl $C_1$-$C_4$alkyl, phenyl $C_1$-$C_4$alkyl substituted with $(Z)_{p1}$, $C_3$-$C_6$alkenyl, $C_3$-$C_6$alkynyl, $C_1$-$C_6$alkylcarbonyl, $C_1$-$C_6$alkylthio, phenylthio, phenylthio substituted with $(Z)_{p1}$,
—$C(O)NHR^{34}$, —$C(O)N(R^{34})R^{33}$, —$C(S)NHR^{34}$, —$C(S)N(R^{34})R^{33}$, phenyl, phenyl substituted with $(Z)_{p1}$, D-21, D-35, D-47 or D-50, $R^{28}$ is $C_1$-$C_6$alkyl, $C_1$-$C_6$alkyl arbitrarily substituted with $R^{32}$, $C_3$-$C_6$cycloalkyl, $C_3$-$C_6$halocycloalkyl, $C_3$-$C_6$alkenyl, $C_3$-$C_6$haloalkenyl, $C_3$-$C_6$alkynyl, $C_3$-$C_6$haloalkynyl, phenyl, phenyl substituted with $(Z)_{p1}$, D-1 to D-60 or E-1 to E-49, $R^{29}$ is hydrogen atom, $C_1$-$C_6$alkyl, $C_1$-$C_4$alkoxy $C_1$-$C_4$alkyl, $C_1$-$C_4$alkylthio $C_1$-$C_4$alkyl, cyano $C_1$-$C_6$alkyl, $C_3$-$C_6$alkenyl or $C_3$-$C_6$alkynyl, or $R^{29}$ together with $R^{28}$ may form 3- to 6-membered ring with the nitrogen atom bonding them by forming $C_2$-$C_5$alkylene chain, in this case, the alkylene chain may contain one oxygen atom or sulfur atom, $R^{30}$ is $C_1$-$C_6$alkyl, $C_1$-$C_4$alkoxy $C_1$-$C_4$alkyl, $C_1$-$C_4$alkylthio $C_1$-$C_4$alkyl, $C_3$-$C_6$cycloalkyl $C_1$-$C_4$alkyl, tri($C_1$-$C_6$alkyl)silyl $C_1$-$C_4$alkyl, phenyl $C_1$-$C_4$alkyl, phenyl $C_1$-$C_4$alkyl substituted with $(Z)_{p1}$, $C_3$-$C_8$alkenyl, $C_3$-$C_8$haloalkenyl, $C_3$-$C_8$alkynyl or $C_3$-$C_8$haloalkynyl, $R^{31}$ is hydrogen atom, $C_1$-$C_6$alkyl, $C_1$-$C_6$haloalkyl or $C_3$-$C_6$cycloalkyl, or $R^{31}$ together with $R^{30}$ may form 5- or 6-membered ring with the atom bonding them by forming $C_2$-$C_3$alkylene chain, in this case, the alkylene chain may be arbitrarily substituted with $C_1$-$C_6$alkyl, $R^{32}$ is halogen atom, cyano, $C_3$-$C_8$cycloalkyl, $C_3$-$C_8$halocycloalkyl, —$OR^{33}$, —$OC(O)R^{33}$,
—$OC(O)NHR^{33}$, —$OC(O)N(R^{34})R^{33}$, —$S(O)_rR^{33}$, —$SC(O)R^{33}$, —$SC(O)NHR^{33}$, —$SC(O)N(R^{34})R^{33}$, —$N(R^{34})$CHO, —$N(R^{34})C(O)R^{33}$, —$N(R^{34})C(O)OR^{33}$, —$C(O)OR^{33}$, —$C(O)NHR^{34}$, —$C(O)N(R^{34})R^{33}$, phenyl, phenyl substituted with $(Z)_{p1}$, D-1 to D-60 or E-1 to E-49, $R^{33}$ is $C_1$-$C_6$alkyl, $C_1$-$C_6$haloalkyl, $C_3$-$C_6$cycloalkyl $C_1$-$C_4$alkyl, $C_1$-$C_4$alkoxy $C_1$-$C_4$alkyl, $C_1$-$C_4$haloalkoxy $C_1$-$C_4$alkyl, $C_1$-$C_4$alkylthio $C_1$-$C_4$alkyl, $C_1$-$C_4$haloalkylthio $C_1$-$C_4$alkyl, $C_1$-$C_4$alkylsulfonyl $C_1$-$C_4$alkyl, $C_1$-$C_4$haloalkylsulfonyl $C_1$-$C_4$alkyl, cyano $C_1$-$C_6$alkyl, phenyl $C_1$-$C_4$alkyl, phenyl $C_1$-$C_4$alkyl substituted with $(Z)_{p1}$, $C_3$-$C_6$cycloalkyl, $C_3$-$C_6$halocycloalkyl, $C_3$-$C_6$alkenyl, $C_3$-$C_6$haloalkenyl, $C_3$-$C_6$alkynyl, phenyl, phenyl substituted with $(Z)_{p1}$, D-1 to D-4, D-8 to D-13, D-15 to D-18, D-21, D-29 to D-37, D-47 to D-55, E-5, E-7, E-9, E-24, E-25, E-27, E-28, E-30, E-31 or E-34, $R^{34}$ is hydrogen atom, $C_1$-$C_6$alkyl, $C_1$-$C_6$haloalkyl, $C_3$-$C_6$alkenyl or $C_3$-$C_6$alkynyl, or
$R^{34}$ together with $R^{33}$ may form 3- to 6-membered ring with the nitrogen atom bonding them by forming $C_2$-$C_5$alkylene chain, in this case, the alkylene chain may contain one oxygen atom or sulfur atom.

(3) The isoxazoline-substituted benzamide compound or the salt thereof as set forth in (2), wherein
G is G-1, G-3, G-4, G-13, G-14, G-17, G-18, G-20, G-21 or G-22,
X is halogen atom, cyano, nitro, $—SF_5$, $C_1$-$C_6$alkyl, $C_1$-$C_6$alkyl arbitrarily substituted with $R^4$, $C_3$-$C_8$cycloalkyl, $C_3$-$C_8$halocycloalkyl, $C_2$-$C_6$alkenyl, $C_2$-$C_6$haloalkenyl, $C_2$-$C_6$alkynyl, $C_2$-$C_6$haloalkynyl, $—OR^5$, $—OSO_2R^5$, $—S(O)_rR^5$, $—C(O)OR^9$, $—C(O)SR^9$, $—C(S)OR^9$, $—C(S)SR^9$, $—C(S)NHR^{10}$, $—C(S)N(R^{10})R^9$, $—CH=NOR^{11}$, $—C(R^9)=NOR^{11}$, $—Si(R^{13})(R^{14})R^{12}$, E-10, E-12, E-18, E-32, E-35 or E-43, when m is 2 or 3, each X may be identical with or different from each other,
further, when two Xs are adjacent, the adjacent two Xs may form 5-membered or 6-membered ring together with carbon atoms to which the two Xs are bonded by forming $—CF_2OCF_2—$, $—OCF_2O—$, $—CF_2OCF_2O—$ or $—OCF_2CF_2O—$,
Y is halogen atom, cyano, nitro, $C_1$-$C_6$alkyl, $C_1$-$C_6$alkyl arbitrarily substituted with $R^4$, $—OR^5$, $—OSO_2R^5$, $—S(O)_rR^5$, $—NHR^7$, $—N(R^7)R^6$, $—N=C(R^9)OR^8$, $—C(O)NH_2$ or $—C(S)NH_2$, when n is 2 or 3, each Y may be identical with or different from each other,
$R^1$ is $C_1$-$C_8$alkyl, $C_1$-$C_8$alkyl arbitrarily substituted with $R^{16}$, $C_3$-$C_8$cycloalkyl, $C_3$-$C_8$halocycloalkyl, $C_3$-$C_8$alkenyl, $C_3$-$C_8$haloalkenyl, $C_3$-$C_8$alkynyl, $C_3$-$C_8$haloalkynyl, $—N(R^{20})R^{19}$, $—C(O)N(R^{10})R^9$, $—C(S)N(R^{10})R^9$, phenyl substituted with $(Z)_{p1}$, D-8 to D-18, D-21 to D-24, D-26 to D-40, D-42, D-45 to D-58, E-4, E-5, E-7, E-8, E-9, E-23 to E-25, E-27, E-28, E-30, E-31 or E-34,
$R^2$ is hydrogen atom, $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, cyano $C_1$-$C_6$alkyl, $C_3$-$C_6$cycloalkyl, $C_3$-$C_6$alkenyl, $C_3$-$C_6$alkynyl, $—OH$, $C_1$-$C_6$alkoxy, $C_1$-$C_6$alkylcarbonyloxy, $C_1$-$C_6$alkoxycarbonyloxy, $C_1$-$C_6$alkylsulfonyloxy, $C_1$-$C_6$haloalkylthio, phenylthio, phenylthio substituted with $(Z)_{p1}$, $C_1$-$C_6$alkylsulfonyl, $—SN(R^{18})R^{17}$, $—NHR^{20}$, $—N=CHR^{19b}$, $—N=C(R^{19b})R^{19a}$, $—C(O)R^9$, $—C(O)OR^9$, $—C(O)SR^9$, $—C(S)OR^9$ or $—C(S)SR^9$, or $R^2$ together with $R^1$ may form 3- to 7-membered ring with the nitrogen atom bonding them by forming $C_2$-$C_6$alkylene chain, in this case, the alkylene chain may contain one oxygen atom or sulfur atom,
$R^3$ is $C_1$-$C_6$alkyl, $C_1$-$C_6$haloalkyl, $C_3$-$C_6$cycloalkyl $C_1$-$C_4$alkyl, $C_3$-$C_6$halocycloalkyl $C_1$-$C_4$alkyl, $C_1$-$C_4$alkoxy $C_1$-$C_4$alkyl, $C_1$-$C_4$haloalkoxy $C_1$-$C_4$alkyl, $C_1$-$C_4$alkylthio $C_1$-$C_4$alkyl, $C_1$-$C_4$alkylsulfinyl $C_1$-$C_4$alkyl, $C_1$-$C_4$alkylsulfonyl $C_1$-$C_4$alkyl, $C_1$-$C_4$haloalkylthio $C_1$-$C_4$alkyl, $C_1$-$C_4$haloalkylsulfinyl $C_1$-$C_4$alkyl, $C_1$-$C_4$haloalkylsulfonyl $C_1$-$C_4$alkyl, cyano $C_1$-$C_6$alkyl, $C_1$-$C_4$alkoxy $C_1$-$C_4$haloalkyl, $C_1$-$C_4$haloalkoxy $C_1$-$C_4$haloalkyl, $C_1$-$C_4$alkylthio $C_1$-$C_4$haloalkyl, $C_1$-$C_4$alkylsulfinyl $C_1$-$C_4$haloalkyl, $C_1$-$C_4$alkylsulfonyl $C_1$-$C_4$haloalkyl, $C_1$-$C_4$haloalkylthio $C_1$-$C_4$haloalkyl, $C_1$-$C_4$haloalkylsulfinyl $C_1$-$C_4$haloalkyl, $C_1$-$C_4$haloalkylsulfonyl $C_1$-$C_4$haloalkyl, cyano $C_1$-$C_6$haloalkyl, $C_3$-$C_8$cycloalkyl, $C_3$-$C_8$halocycloalkyl, E-4 to E-7, E-23 to E-27 or E-28,
$R^4$ is halogen atom, cyano, $—OH$, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl or tri($C_1$-$C_6$alkyl)silyl,
$R^5$ is $C_1$-$C_6$alkyl, $C_1$-$C_6$haloalkyl, $C_1$-$C_3$haloalkoxy $C_1$-$C_3$haloalkyl, $C_3$-$C_8$cycloalkyl, $C_3$-$C_8$halocycloalkyl, $C_2$-$C_6$alkenyl, $C_2$-$C_6$haloalkenyl, $C_3$-$C_6$alkynyl, $C_3$-$C_6$haloalkynyl, E-4 to E-9, E-23 to E-27 or E-28, $R^6$ is $C_1$-$C_6$alkyl, $C_1$-$C_6$haloalkyl, $—S(O)_2R^9$, $—CHO$, $—C(O)R^9$, $—C(O)OR^9$, $—C(O)SR^9$, $—C(S)OR^9$ or $—C(S)SR^9$,
$R^7$ is hydrogen atom, $C_1$-$C_6$alkyl or $C_1$-$C_6$haloalkyl,
$R^9$ is $C_1$-$C_6$alkyl, $C_1$-$C_6$haloalkyl, $C_3$-$C_6$cycloalkyl $C_1$-$C_4$alkyl, $C_1$-$C_6$alkoxy $C_1$-$C_4$alkyl, $C_1$-$C_6$alkylthio $C_1$-$C_4$alkyl, cyano $C_1$-$C_6$alkyl, phenyl $C_1$-$C_4$alkyl, $C_3$-$C_8$cycloalkyl, $C_3$-$C_8$halocycloalkyl, $C_3$-$C_6$alkenyl or $C_3$-$C_6$alkynyl,
$R^{10}$ is hydrogen atom or $C_1$-$C_6$alkyl, or $R^{10}$ together with $R^9$ may form 5- or 6-membered ring with the nitrogen atom bonding them by forming $C_4$ or $C_5$alkylene chain, in this case, the alkylene chain may contain one oxygen atom or sulfur atom,
$R^{11}$ is $C_1$-$C_6$alkyl or $C_1$-$C_6$haloalkyl, or $R^{11}$ together with $R^9$ may form 5- or 6-membered ring with the atom bonding them by forming $C_2$ or $C_3$alkylene chain, in this case, the alkylene chain may be arbitrarily substituted with $C_1$-$C_6$alkyl,
$R^{15}$ is $C_1$-$C_6$alkyl or $C_1$-$C_6$haloalkyl,
$R^{16}$ is halogen atom, cyano, $C_3$-$C_6$cycloalkyl, $C_3$-$C_6$halocycloalkyl, $—OR^{25}$, $—N(R^{26})R^{25}$, $—S(O)_rR^{27}$, $—SO_2NHR^{29}$, $—SO_2N(R^{29})R^{28}$, $—CHO$, $—C(O)R^{28}$, $—C(O)OR^{28}$, $—C(O)NHR^{29}$, $—C(O)N(R^{29})R^{28}$, $—C(O)N(R^{29})OR^{28}$, $—C(S)NHR^{29}$, $—C(S)N(R^{29})R^{28}$, $—C(R^{31})=NOH$, $—C(R^{31})=NOR^{30}$, $—C(=NR^{31})OR^{30}$, $—C(=NR^{31})SR^{30}$, $—C(=NR^{31})N(R^{29})R^{30}$, $—C(=NOR^{31})NHR^{29}$, $—C(=NOR^{31})N(R^{29})R^{30}$, phenyl, phenyl substituted with $(Z)_{p1}$, D-1 to D-4, D-8 to D-42, D-47 to D-55, E-4 to E-12, E-14, E-16 to E-19, E-21 to E-23, E-26 to E-35, E-40 to E-45, E-48, M-2, M-3, M-5, M-8 to M-10, M-14, M-15 or M-16,
$R^{17}$ is $C_1$-$C_6$alkyl, $C_1$-$C_6$alkoxycarbonyl $C_1$-$C_4$alkyl or $C_1$-$C_6$alkoxycarbonyl,
$R^{18}$ is $C_1$-$C_6$alkyl or benzyl,
$R^{19}$ is $C_1$-$C_6$alkyl, $C_1$-$C_6$haloalkyl, $C_3$-$C_6$cycloalkyl $C_1$-$C_6$alkyl, phenyl $C_1$-$C_6$alkyl, phenyl $C_1$-$C_6$alkyl substituted with $(Z)_{p1}$, $C_3$-$C_6$cycloalkyl, $C_3$-$C_6$alkenyl, $C_3$-$C_6$haloalkenyl, $C_3$-$C_6$alkynyl, $—C(O)R^{28}$, $—C(O)OR^{28}$, $—C(O)NH R^{29}$, $—C(O)N(R^{29})R^{28}$, $—C(S)NHR^{29}$, $—C(S)N(R^{29})R^{28}$, $C_2$-$C_6$alkylsulfonyl, $C_1$-$C_6$haloalkylsulfonyl, phenylsulfonyl, phenylsulfonyl substituted with $(Z)_{p1}$, phenyl, phenyl substituted with $(Z)_{p1}$, D-1 to D-4, D-18, D-21, D-25, D-30 to D-35, D-47 to D-55 or D-56,
$R^{19a}$ is $C_1$-$C_6$alkyl,
$R^{19b}$ is hydrogen atom or $C_1$-$C_6$alkyl,
$R^{20}$ is hydrogen atom, $C_1$-$C_6$alkyl, $C_1$-$C_4$alkoxy $C_1$-$C_4$alkyl, $C_1$-$C_4$alkylthio $C_1$-$C_4$alkyl, cyano $C_1$-$C_6$alkyl, $C_3$-$C_6$alkenyl, $C_3$-$C_6$alkynyl, $—CHO$, $C_1$-$C_6$alkylcarbonyl, $C_1$-$C_6$haloalkylcarbonyl, $C_1$-$C_6$alkoxycarbonyl, $C_1$-$C_6$haloalkoxycarbonyl or $C_1$-$C_6$alkylsulfonyl,
$R^{22}$ is $C_1$-$C_4$alkyl or $C_1$-$C_4$haloalkyl, or two $R^{22}$s present on the same carbon atom may together form oxo, or thioxo,
$R^{23}$ is hydrogen atom, $C_1$-$C_6$alkyl, $—CHO$, $C_1$-$C_6$alkylcarbonyl, $C_1$-$C_6$haloalkylcarbonyl, $C_1$-$C_6$alkoxycarbonyl, $C_1$-$C_6$alkylsulfonyl or $C_1$-$C_6$haloalkylsulfonyl,
$R^{25}$ is hydrogen atom, $C_1$-$C_6$alkyl, $C_1$-$C_6$haloalkyl, $—C(O)R^{33}$, $—C(O)OR^{33}$, $—C(O)SR^{33}$, $—C(O)NHR^{34}$, $—C(O)N(R^{34})R^{33}$, $—C(S)R^{33}$, $—C(S)OR^{33}$, $—C(S)SR^{33}$, $—C(S)NHR^{34}$, $—C(S)N(R^{34})R^{33}$, $—S(O)_2R^{33}$, $—S(O)_2N(R^{34})R^{33}$, di($C_1$-$C_6$alkyl)thiophosphoryl, phenyl or phenyl substituted with $(Z)_{p1}$,
$R^{26}$ is hydrogen atom or $C_1$-$C_6$alkyl, or $R^{26}$ together with $R^{25}$ may form 4- to 6-membered ring with the nitrogen atom bonding them by forming $C_3$-$C_5$alkylene chain, in this case, the alkylene chain may contain one oxygen atom, sulfur atom or nitrogen atom, and may be substituted with $C_1$-$C_6$alkyl, oxo or thioxo, $R^{27}$ is $C_1$-$C_6$alkyl, $C_1$-$C_6$haloalkyl, tri($C_1$-$C_4$alkyl)silyl $C_1$-$C_4$alkyl, $C_1$-$C_6$alkylthio, —C(O)NHR$^{34}$, —C(O)N(R$^{34}$) R$^{33}$, —C(S)NHR$^{34}$, —C(S)N(R$^{34}$)R$^{33}$, phenyl, phenyl substituted with $(Z)_{p1}$, D-47 or D-50, $R^{28}$ is $C_1$-$C_6$alkyl, $C_1$-$C_6$alkyl arbitrarily substituted with $R^{32}$, $C_3$-$C_6$cycloalkyl, $C_3$-$C_6$halocycloalkyl, $C_3$-$C_6$alkenyl, $C_3$-$C_6$haloalkenyl, $C_3$-$C_6$alkynyl, $C_3$-$C_6$haloalkynyl, phenyl or phenyl substituted with $(Z)_{p1}$, $R^{29}$ is hydrogen atom, $C_1$-$C_6$alkyl, $C_3$-$C_6$alkenyl or $C_3$-$C_6$alkynyl, or $R^{29}$ together with $R^{28}$ may form 3- to 6-membered ring with the nitrogen atom bonding them by forming $C_2$-$C_5$alkylene chain, in this case, the alkylene chain may contain one oxygen atom or sulfur atom, $R^{30}$ is $C_1$-$C_6$alkyl, $C_3$-$C_6$cycloalkyl $C_1$-$C_4$alkyl, phenyl $C_1$-$C_4$alkyl, phenyl $C_1$-$C_4$alkyl substituted with $(Z)_{p1}$, $C_3$-$C_8$alkenyl or $C_3$-$C_8$alkynyl, $R^{31}$ is hydrogen atom or $C_1$-$C_6$alkyl, or $R^{31}$ together with $R^{30}$ may form 5- or 6-membered ring with the atom bonding them by forming $C_2$ or $C_3$alkylene chain, in this case, the alkylene chain may be arbitrarily substituted with $C_1$-$C_6$alkyl, $R^{32}$ is halogen atom, cyano, $C_3$-$C_6$cycloalkyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkoxycarbonyl, —C(O)NH$_2$, $C_1$-$C_4$alkylaminocarbonyl, di($C_1$-$C_4$alkyl)aminocarbonyl, phenyl or phenyl substituted with $(Z)_{p1}$, $R^{33}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_1$-$C_4$alkylsulfonyl $C_1$-$C_4$alkyl, phenyl $C_1$-$C_4$alkyl, phenyl $C_1$-$C_4$alkyl substituted with $(Z)_{p1}$, $C_3$-$C_6$cycloalkyl, $C_3$-$C_6$halocycloalkyl, $C_3$-$C_6$alkenyl, $C_3$-$C_6$alkynyl, phenyl or phenyl substituted with $(Z)_{p1}$, $R^{34}$ is hydrogen atom or $C_1$-$C_6$alkyl, m is an integer of 1 to 3, n is an integer of 0 to 2, q1 is 0, q2 is an integer of 0 to 3, q3 is an integer of 0 to 2, and q4 is an integer of 0 to 2.

(4) The isoxazoline-substituted benzamide compound or the salt thereof as set forth in (3), wherein $A^1$ is carbon atom or nitrogen atom, $A^2$ and $A^3$ are carbon atom, G is G-1, X is halogen atom, cyano, nitro, —SF$_5$, $C_1$-$C_6$alkyl, $C_1$-$C_6$alkyl arbitrarily substituted with $R^4$, $C_3$-$C_8$cycloalkyl, $C_3$-$C_8$halocycloalkyl, $C_2$-$C_6$alkenyl, $C_2$-$C_6$haloalkenyl, $C_2$-$C_6$alkynyl, $C_2$-$C_6$haloalkynyl, —OR$^5$, —OSO$_2$R$^5$, —S(O)$_n$R$^5$ or tri($C_1$-$C_6$alkyl)silyl, when m is 2 or 3, each X may be identical with or different from each other, further, when two Xs are adjacent, the adjacent two Xs may form 5-membered or 6-membered ring together with carbon atoms to which the two Xs are bonded by forming
—CF$_2$OCF$_2$—, —OCF$_2$O—, —CF$_2$OCF$_2$O— or —OCF$_2$CF$_2$O—, Y is halogen atom, cyano, nitro, $C_1$-$C_6$alkyl, $C_1$-$C_6$alkyl arbitrarily substituted with $R^4$, —OR$^5$, —OSO$_2$R$^5$, —S(O)$_n$R$^5$, —NHR$^7$, —N(R$^7$)R$^6$, —C(O)NH$_2$ or —C(S)NH$_2$, when n is 2 or 3, each Y may be identical with or different from each other, $R^1$ is $C_1$-$C_6$alkyl, $C_1$-$C_6$alkyl arbitrarily substituted with $R^{16}$, $C_3$-$C_6$cycloalkyl, $C_3$-$C_6$halocycloalkyl, $C_3$-$C_6$alkenyl, $C_3$-$C_6$haloalkenyl, $C_3$-$C_6$alkynyl, $C_3$-$C_6$haloalkynyl, —N(R$^{20}$)R$^{19}$, —C(O)N(R$^{10}$)R$^9$, —C(S)N(R$^{10}$)R$^9$, phenyl substituted with $(Z)_{p1}$, D-8, D-10, D-11, D-13 to D-15, D-17, D-18, D-21 to D-23, D-26 to D-37, D-39, D-40, D-42, D-45, D-47 to D-54, D-56, D-58, E-4, E-5, E-7 or E-9, $R^2$ is hydrogen atom, $C_1$-$C_6$alkyl, $C_1$-$C_4$alkoxy $C_1$-$C_4$alkyl, $C_1$-$C_4$alkylthio $C_1$-$C_4$alkyl, cyano $C_1$-$C_6$alkyl, $C_3$-$C_6$cycloalkyl, $C_3$-$C_6$alkenyl, $C_3$-$C_6$alkynyl, —OH, $C_1$-$C_6$alkylcarbonyloxy, $C_1$-$C_6$alkylsulfonyloxy, —NH$_2$, —C(O)R$^9$, —C(O)OR$^9$, —C(O)SR$^9$, —C(S)OR$^9$ or —C(S)SR$^9$, $R^3$ is $C_1$-$C_6$haloalkyl, $C_1$-$C_4$alkoxy $C_1$-$C_4$haloalkyl, $C_1$-$C_4$haloalkoxy $C_1$-$C_4$haloalkyl, $C_1$-$C_4$alkylthio $C_1$-$C_4$haloalkyl, $C_1$-$C_4$haloalkylthio $C_1$-$C_4$haloalkyl, cyano $C_1$-$C_6$haloalkyl or $C_3$-$C_8$halocycloalkyl, $R^4$ is halogen atom, cyano, —OH, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl or tri($C_1$-$C_6$alkyl)silyl, $R^5$ is $C_1$-$C_6$alkyl, $C_1$-$C_6$haloalkyl, $C_1$-$C_3$haloalkoxy $C_1$-$C_3$haloalkyl, $C_3$-$C_8$cycloalkyl, $C_3$-$C_8$halocycloalkyl, $C_2$-$C_6$alkenyl, $C_2$-$C_6$haloalkenyl, $C_3$-$C_6$alkynyl or $C_3$-$C_6$haloalkynyl, $R^6$ is $C_1$-$C_6$alkyl, $C_1$-$C_6$haloalkyl, —CHO, $C_1$-$C_6$alkylcarbonyl, $C_1$-$C_6$haloalkylcarbonyl, $C_3$-$C_6$cycloalkylcarbonyl, $C_3$-$C_6$halocycloalkylcarbonyl, $C_1$-$C_6$alkoxycarbonyl, $C_1$-$C_6$haloalkoxycarbonyl, $C_1$-$C_6$alkylthiocarbonyl, $C_1$-$C_6$alkoxythiocarbonyl, $C_1$-$C_6$alkyldithiocarbonyl, $C_1$-$C_6$alkylsulfonyl or $C_1$-$C_6$haloalkylsulfonyl, $R^7$ is hydrogen atom or $C_1$-$C_6$alkyl, $R^9$ is $C_1$-$C_6$alkyl, $C_1$-$C_6$haloalkyl, $C_3$-$C_6$cycloalkyl $C_1$-$C_4$alkyl, $C_1$-$C_6$alkoxy $C_1$-$C_4$alkyl, $C_1$-$C_6$alkylthio $C_1$-$C_4$alkyl, cyano $C_1$-$C_6$alkyl, $C_3$-$C_8$cycloalkyl, $C_3$-$C_6$alkenyl or $C_3$-$C_6$alkynyl, $R^{16}$ is halogen atom, cyano, $C_3$-$C_6$cycloalkyl, $C_3$-$C_6$halocycloalkyl, —OR$^{25}$, —N(R$^{26}$)R$^{25}$, —S(O)$_r$R$^{27}$, —SO$_2$NHR$^{29}$, —SO$_2$N(R$^{29}$)R$^{28}$, —C(O)R$^{28}$, —C(O)OR$^{28}$, —C(O)NHR$^{29}$, —C(O)N(R$^{29}$)R$^{28}$, —C(O)N(R$^{29}$)OR$^{28}$, —C(S)NHR$^{29}$, —C(S)N(R$^{29}$)R$^{28}$, —C(R$^{31}$)=NOH, —C(R$^{31}$)=NOR$^{30}$, —C(=NR$^{31}$)OR$^{30}$, —C(=NR$^{31}$)SR$^{30}$, phenyl, phenyl substituted with $(Z)_{p1}$, D-1 to D-4, D-8 to D-38, D-47 to D-55, E-4 to E-12, E-18, E-19, E-32, E-35, E-43, M-2, M-3, M-5, M-8, M-9 or M-10, $R^{19}$ is $C_1$-$C_6$haloalkyl, $C_3$-$C_6$cycloalkyl, —C(O)R$^{28}$, —C(O)OR$^{28}$, —C(O)NHR$^{29}$, —C(O)N(R$^{29}$)R$^{28}$, —C(S)NHR$^{29}$, —C(S)N(R$^{29}$)R$^{28}$, phenyl, phenyl substituted with $(Z)_{p1}$, D-3, D-4, D-21, D-47, D-50, D-51, D-53 or D-54, $R^{20}$ is hydrogen atom, $C_1$-$C_6$alkyl, $C_1$-$C_4$alkoxy $C_1$-$C_4$alkyl, $C_1$-$C_4$alkylthio $C_1$-$C_4$alkyl, cyano $C_1$-$C_6$alkyl, $C_3$-$C_6$alkenyl, $C_3$-$C_6$alkynyl, —CHO, $C_1$-$C_6$alkylcarbonyl, $C_1$-$C_6$alkoxycarbonyl or $C_1$-$C_6$alkylsulfonyl, $R^{25}$ is $C_1$-$C_6$alkyl, $C_1$-$C_6$haloalkyl, $C_1$-$C_6$alkylcarbonyl, $C_1$-$C_6$alkoxycarbonyl, $C_1$-$C_6$alkylaminocarbonyl, di($C_1$-$C_6$alkyl)aminocarbonyl or $C_1$-$C_6$alkylsulfonyl, $R^{26}$ is hydrogen atom or $C_1$-$C_6$alkyl, $R^{27}$ is $C_1$-$C_6$alkyl, $C_1$-$C_6$haloalkyl or tri($C_1$-$C_4$alkyl)silyl $C_1$-$C_4$alkyl, $R^{28}$ is $C_1$-$C_6$alkyl, $C_1$-$C_6$haloalkyl, $C_3$-$C_6$cycloalkyl $C_1$-$C_4$alkyl, $C_1$-$C_4$alkoxy $C_1$-$C_4$alkyl, $C_1$-$C_4$alkylthio $C_1$-$C_4$alkyl, cyano $C_1$-$C_6$alkyl, phenyl $C_1$-$C_4$alkyl, phenyl $C_1$-$C_4$alkyl substituted with $(Z)_{p1}$, $C_3$-$C_6$cycloalkyl, $C_3$-$C_6$alkenyl, $C_3$-$C_6$haloalkenyl, $C_3$-$C_6$alkynyl, phenyl or phenyl substituted with $(Z)_{p1}$, $R^{29}$ is hydrogen atom, $C_1$-$C_6$alkyl, $C_3$-$C_6$alkenyl or $C_3$-$C_6$alkynyl, $R^{30}$ is $C_1$-$C_6$alkyl or $C_3$-$C_6$cycloalkyl $C_1$-$C_4$alkyl, $R^{31}$ is hydrogen atom or $C_1$-$C_6$alkyl, or $R^{31}$ together with $R^{30}$ may form 5- or 6-membered ring with the atom bonding them by forming $C_2$ or $C_3$alkylene chain.

(5) The isoxazoline-substituted benzamide compound or the salt thereof as set forth in (4), wherein
X is halogen atom, cyano, nitro, —SF$_5$, $C_1$-$C_6$alkyl, $C_1$-$C_6$haloalkyl, hydroxy $C_1$-$C_6$haloalkyl, $C_1$-$C_6$alkoxy $C_1$-$C_6$haloalkyl, $C_1$-$C_6$haloalkoxy $C_1$-$C_6$haloalkyl, $C_3$-$C_8$halocycloalkyl, —OR$^5$, —OSO$_2$R$^5$ or —S(O)$_r$R$^5$, when m is 2 or 3, each X may be identical with or different from each other,
Y is halogen atom, cyano, nitro, $C_1$-$C_4$alkyl, $C_1$-$C_4$haloalkyl, $C_1$-$C_4$alkoxy, $C_1$-$C_4$haloalkoxy, $C_1$-$C_6$alkylthio, $C_1$-$C_6$haloalkylthio, $C_1$-$C_6$alkylsulfonyl, $C_1$-$C_6$haloalkylsulfonyl, —NHR$^7$ or —N(R$^7$)R$^6$,
$R^1$ is $C_1$-$C_6$alkyl, $C_1$-$C_6$alkyl arbitrarily substituted with R$^{16}$, $C_3$-$C_6$cycloalkyl, E-4, E-5, $C_3$-$C_6$alkenyl, $C_3$-$C_6$haloalkenyl, $C_3$-$C_6$alkynyl, —N(R$^{20}$)R$^{19}$, D-8, D-10, D-13 to D-15, D-18, D-21, D-34, D-35, D-47, D-48, D-50 to D-53 or D-54,
$R^2$ is hydrogen atom, $C_1$-$C_6$alkyl, $C_1$-$C_4$alkoxy $C_1$-$C_4$alkyl, cyano $C_1$-$C_6$alkyl, $C_3$-$C_6$alkynyl, —C(O)R$^9$ or —C(O)OR$^9$,
$R^3$ is $C_1$-$C_6$haloalkyl or $C_3$-$C_8$halocycloalkyl,
$R^5$ is $C_1$-$C_6$alkyl, $C_1$-$C_6$haloalkyl or $C_1$-$C_3$haloalkoxy $C_1$-$C_3$haloalkyl,
$R^6$ is $C_1$-$C_6$alkyl, —CHO, $C_1$-$C_6$alkylcarbonyl, $C_1$-$C_6$haloalkylcarbonyl, $C_1$-$C_6$alkoxycarbonyl, $C_1$-$C_6$alkylthiocarbonyl, $C_1$-$C_6$alkoxythiocarbonyl, $C_1$-$C_6$alkyldithiocarbonyl, $C_1$-$C_6$alkylsulfonyl or $C_1$-$C_6$haloalkylsulfonyl,
$R^9$ is $C_1$-$C_6$alkyl, $C_1$-$C_6$alkoxy $C_1$-$C_4$alkyl, $C_1$-$C_6$alkylthio $C_1$-$C_4$alkyl, $C_3$-$C_8$cycloalkyl, $C_3$-$C_6$alkenyl or $C_3$-$C_6$alkynyl,
$R^{16}$ is halogen atom, cyano, $C_3$-$C_6$cycloalkyl, $C_3$-$C_6$halocycloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_1$-$C_6$alkylcarbonyl, —C(O)OR$^{28}$, —C(O)NHR$^{29}$, —C(O)N(R$^{29}$)R$^{28}$, —C(S)NH$_2$, —C(R$^{31}$)=NOH, —C(R$^{31}$)=NOR$^{30}$, phenyl, phenyl substituted with (Z)$_{p1}$, D-1 to D-4, D-8 to D-38, D-47 to D-55, E-4 to E-7, E-10, E-11 or E-32,
$R^{19}$ is $C_1$-$C_6$haloalkyl, —C(O)R$^{28}$, —C(O)OR$^{28}$, phenyl, phenyl substituted with (Z)$_{p1}$, D-3, D-4, D-21, D-47, D-50, D-51, D-53 or D-54,
$R^{20}$ is hydrogen atom or $C_1$-$C_6$alkyl,
$R^{28}$ is $C_1$-$C_6$alkyl, $C_1$-$C_6$haloalkyl, $C_3$-$C_6$cycloalkyl $C_1$-$C_4$alkyl, $C_3$-$C_6$cycloalkyl, $C_3$-$C_6$alkenyl or $C_3$-$C_6$alkynyl,
$R^{29}$ is hydrogen atom or $C_1$-$C_6$alkyl,
$R^{30}$ is $C_1$-$C_6$alkyl,
$R^{31}$ is hydrogen atom or $C_1$-$C_6$alkyl, and
n is an integer of 0 or 1.

(6) 3,5-Bis (substituted aryl) substituted isoxazoline compound of formula (2) or a salt thereof:

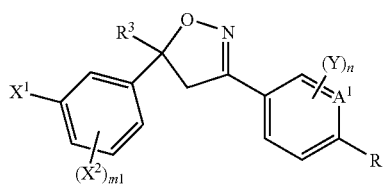

(2)

wherein
$A^1$ is carbon atom or nitrogen atom,
$X^1$ is halogen atom, —SF$_5$, $C_1$-$C_6$haloalkyl, hydroxy $C_1$-$C_6$haloalkyl, $C_1$-$C_6$alkoxy $C_1$-$C_6$haloalkyl, $C_1$-$C_6$haloalkoxy $C_1$-$C_6$haloalkyl, $C_3$-$C_8$halocycloalkyl, $C_1$-$C_6$haloalkoxy, $C_1$-$C_3$haloalkoxy $C_1$-$C_3$haloalkoxy, $C_1$-$C_6$haloalkylthio, $C_1$-$C_6$haloalkylsulfinyl or $C_1$-$C_6$haloalkylsulfonyl,
$X^2$ is halogen atom, cyano, nitro, $C_1$-$C_6$alkyl, $C_1$-$C_6$haloalkyl, —OR$^5$, —OSO$_2$R$^5$ or —S(O)$_r$R$^5$, when m1 is 2, each $X^2$ may be identical with or different from each other,
Y is halogen atom, cyano, nitro, $C_1$-$C_4$alkyl, $C_1$-$C_4$haloalkyl, $C_1$-$C_4$alkoxy, $C_1$-$C_4$haloalkoxy, $C_1$-$C_6$alkylthio, $C_1$-$C_6$haloalkylthio, $C_1$-$C_6$alkylsulfonyl, $C_1$-$C_6$haloalkylsulfonyl, —NHR$^7$ or —N(R$^7$)R$^6$,
$R^3$ is $C_1$-$C_6$haloalkyl or $C_3$-$C_8$halocycloalkyl,
$R^5$ is $C_1$-$C_6$alkyl or $C_1$-$C_6$haloalkyl,
$R^6$ is $C_1$-$C_6$alkyl, —CHO, $C_1$-$C_6$alkylcarbonyl, $C_1$-$C_6$haloalkylcarbonyl, $C_1$-$C_6$alkoxycarbonyl, $C_1$-$C_6$alkylthiocarbonyl, $C_1$-$C_6$alkoxythiocarbonyl, $C_1$-$C_6$alkyldithiocarbonyl, $C_1$-$C_6$alkylsulfonyl or $C_1$-$C_6$haloalkylsulfonyl,
$R^7$ is hydrogen atom or $C_1$-$C_6$alkyl,
R is halogen atom, cyano, nitro, —NH$_2$, halosulfonyloxy, $C_1$-$C_6$alkylsulfonyloxy, $C_1$-$C_6$haloalkylsulfonyloxy, phenylsulfonyloxy, phenylsulfonyloxy substituted with (Z)$_{p1}$ or —C(O)R$^a$,
$R^a$ is halogen atom, —OH, $C_1$-$C_6$alkoxy, 1-pyrazolyl, 1-imidazolyl or 1-triazolyl,
Z is halogen atom, $C_1$-$C_6$alkyl or $C_1$-$C_6$haloalkyl, when p1 is an integer of 2 or more,
each Z may be identical with or different from each other,
m1 is an integer of 0 to 2,
n is an integer of 0 or 1,
p1 is an integer of 1 or 5, and
r is an integer of 0 to 2.

(7) 3,5-Bis (substituted aryl) substituted isoxazoline compound or the salt thereof as set forth in (6), wherein
(a) in case where R is halosulfonyloxy, $C_1$-$C_6$haloalkylsulfonyloxy, phenylsulfonyloxy or phenylsulfonyloxy substituted with (Z)$_{p1}$, Y is halogen atom, cyano, nitro, $C_1$-$C_6$alkyl, $C_1$-$C_4$haloalkyl, $C_1$-$C_4$alkoxy, $C_1$-$C_4$haloalkoxy, $C_1$-$C_6$alkylthio, $C_1$-$C_6$haloalkylthio, $C_1$-$C_6$alkylsulfonyl or $C_1$-$C_6$haloalkylsulfonyl,
(b) in case where R is —C(O)R$^a$, Y is cyano, nitro, $C_1$-$C_6$alkyl, $C_1$-$C_4$haloalkyl, $C_1$-$C_6$haloalkylthio or $C_1$-$C_6$haloalkylsulfonyl,
(c) in case where, R is halogen atom, cyano, nitro or —NH$_2$, Y is cyano, $C_1$-$C_6$alkyl, $C_1$-$C_6$haloalkyl, $C_1$-$C_6$haloalkylthio or $C_1$-$C_6$haloalkylsulfonyl.

(8) 4-Hydroxyiminomethyl substituted benzamide compound of formula (3) or a salt thereof:

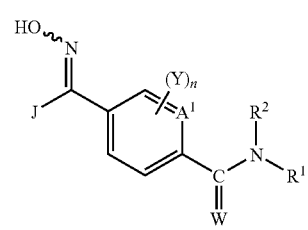

(3)

wherein
$A^1$ is carbon atom or nitrogen atom,
J is hydrogen atom or halogen atom,
W is oxygen atom or sulfur atom, Y is halogen atom, cyano, nitro, $C_1$-$C_4$alkyl, $C_1$-$C_4$haloalkyl, $C_1$-$C_4$alkoxy, $C_1$-$C_4$haloalkoxy, $C_1$-$C_6$alkylsulfonyl, $C_1$-$C_6$haloalkylsulfonyl or —N($R^7$)$R^6$, $R^1$ is $C_1$-$C_6$alkyl, $C_1$-$C_6$alkyl arbitrarily substituted with $R^{16}$, $C_3$-$C_6$cycloalkyl, E-4, E-5, $C_3$-$C_6$alkenyl, $C_3$-$C_6$haloalkenyl, $C_3$-$C_6$alkynyl, —N($R^{20}$)$R^{19}$, phenyl substituted with $(Z)_{p1}$, D-8, D-10, D-13 to D-15, D-18, D-21, D-34, D-35, D-47, D-48, D-50 to D-53 or D-54, $R^2$ is hydrogen atom, $C_1$-$C_6$alkyl, $C_1$-$C_4$alkoxy $C_1$-$C_4$alkyl, cyano $C_1$-$C_6$alkyl, $C_3$-$C_6$alkynyl, —C(O)$R^9$ or —C(O)O$R^9$, $R^6$ is —CHO, $C_1$-$C_6$alkylcarbonyl, $C_1$-$C_6$haloalkylcarbonyl, $C_1$-$C_6$alkoxycarbonyl, $C_1$-$C_6$alkylthiocarbonyl, $C_1$-$C_6$alkoxythiocarbonyl, $C_1$-$C_6$alkyldithiocarbonyl, $C_1$-$C_6$alkylsulfonyl or $C_1$-$C_6$haloalkylsulfonyl, $R^7$ is hydrogen atom or $C_1$-$C_6$alkyl, $R^9$ is $C_1$-$C_6$alkyl, $C_1$-$C_6$alkoxy $C_1$-$C_4$alkyl, $C_1$-$C_6$alkylthio $C_1$-$C_4$alkyl, $C_3$-$C_8$cycloalkyl, $C_3$-$C_6$alkenyl or $C_3$-$C_6$alkynyl, $R^{16}$ is halogen atom, cyano, $C_3$-$C_6$cycloalkyl, $C_3$-$C_6$halocycloalkyl, $C_1$-$C_6$alkoxy, $C_1$-$C_6$haloalkoxy, $C_1$-$C_6$alkylsulfonyl, $C_1$-$C_6$haloalkylsulfonyl, $C_1$-$C_6$alkylcarbonyl, —C(O)O$R^{28}$, —C(O)NH$R^{29}$, —C(O)N($R^{29}$)$R^{28}$, —C(S)NH$_2$, —C($R^{31}$)=NOH, —C($R^{31}$)=NO$R^{30}$, phenyl, phenyl substituted with $(Z)_{p1}$, D-1 to D-4, D-8 to D-38, D-47 to D-55, E-4 to E-7, E-10, E-11 or E-32, D-1 to D-4, D-8 to D-38, D-47 to D-54 and D-55 are aromatic heterocyclic rings of the following formulae, respectively,

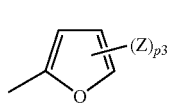
D-1

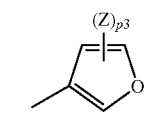
D-2

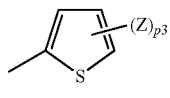
D-3

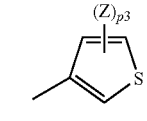
D-4

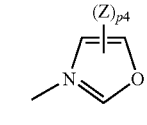
D-8

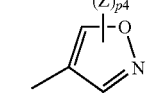
D-9

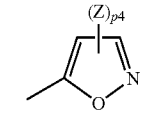
D-10

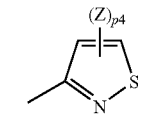
D-11

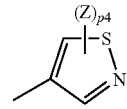
D-12

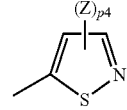
D-13

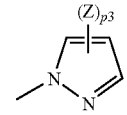
D-14

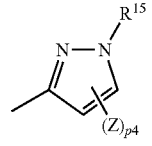
D-15

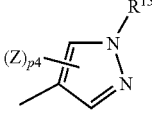
D-16

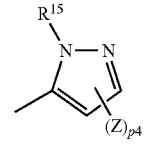
D-17

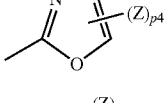
D-18

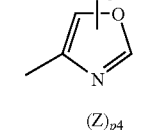
D-19

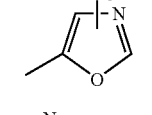
D-20

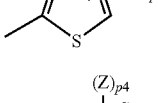
D-21

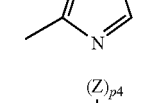
D-22

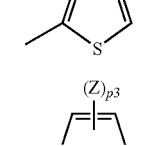
D-23

D-24

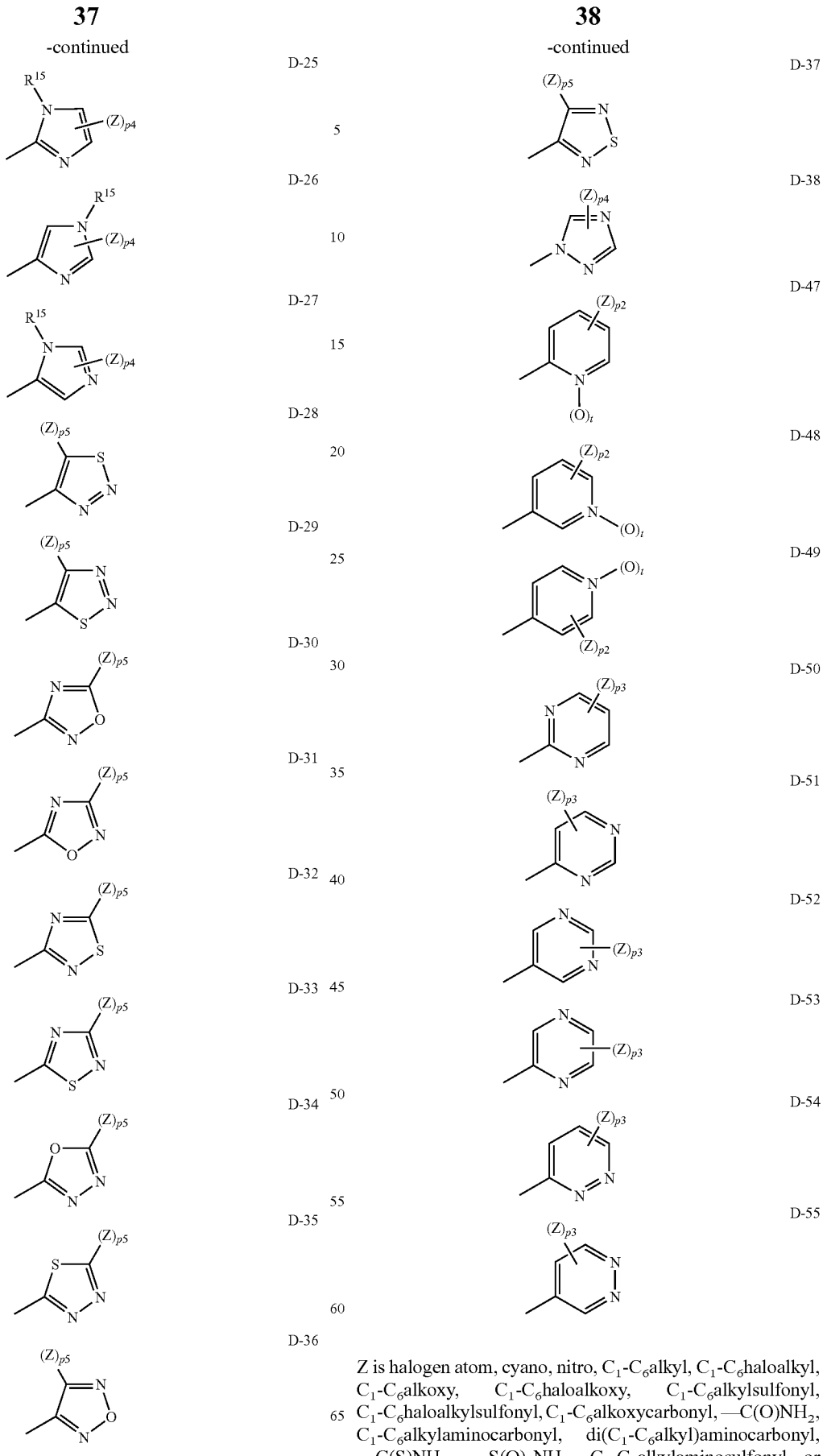
Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylsulfonyl, $C_1$-$C_6$haloalkylsulfonyl, $C_1$-$C_6$alkoxycarbonyl, —C(O)NH$_2$, $C_1$-$C_6$alkylaminocarbonyl, di($C_1$-$C_6$alkyl)aminocarbonyl, —C(S)NH$_2$, —S(O)$_2$NH$_2$, $C_1$-$C_6$alkylaminosulfonyl or di($C_1$-$C_6$alkyl)aminosulfonyl, when p1, p2, p3 or p4 is an integer of 2 or more, each Z may be identical with or different from each other, $R^{15}$ is $C_1$-$C_6$alkyl, phenyl or phenyl substituted with $(Z)_{p1}$, E-4, E-5, E-10, E-11 or E-32 is a saturated heterocyclic ring of the following formulae, respectively

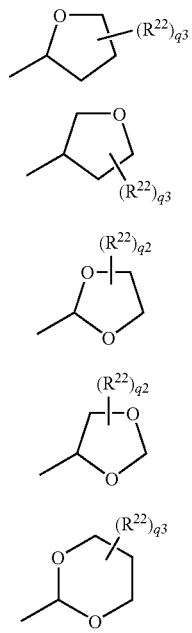

$R^{19}$ is $C_1$-$C_6$haloalkyl, —C(O)$R^{28}$, —C(O)O$R^{28}$, phenyl, phenyl substituted with $(Z)_{p1}$, D-3, D-4, D-21, D-47, D-50, D-51, D-53 or D-54, $R^{20}$ is hydrogen atom or $C_1$-$C_6$alkyl, $R^{22}$ is $C_1$-$C_4$alkyl, $R^{28}$ is $C_1$-$C_6$alkyl, $C_1$-$C_6$haloalkyl, $C_3$-$C_6$cycloalkyl $C_1$-$C_4$alkyl, $C_3$-$C_6$cycloalkyl, $C_3$-$C_6$alkenyl or $C_3$-$C_6$alkynyl, $R^{29}$ is hydrogen atom or $C_1$-$C_6$alkyl, $R^{30}$ is $C_1$-$C_6$alkyl, $R^{31}$ is $C_1$-$C_6$alkyl, n is an integer of 0 or 1, with a proviso that n is 1 when $R^1$ and $R^2$ are methyl at the same time, p1 is an integer of 1 to 5, p2 is an integer of 0 to 4, p3 is an integer of 0 to 3, p4 is an integer of 0 to 2, p5 is an integer of 0 or 1, q2 is an integer of 0 to 3, and q3 is an integer of 0 to 2

(9) 4-Hydroxyiminomethyl substituted benzamide compound or the salt thereof as set forth in (8), wherein $A^1$ is carbon atom, W is oxygen atom, Y is halogen atom, $C_1$-$C_6$alkyl or $C_1$-$C_6$haloalkyl, $R^1$ is $C_1$-$C_6$alkyl arbitrarily substituted with $R^{16}$, $C_3$-$C_6$cycloalkyl, E-4, E-5, $C_3$-$C_6$alkenyl, $C_3$-$C_6$haloalkenyl, $C_3$-$C_6$alkynyl, D-13 to D-15, D-21, D-47, D-48, D-50 to D-53 or D-54, $R^{16}$ is halogen atom, cyano, $C_3$-$C_6$cycloalkyl, E-4, E-5, E-10, $C_1$-$C_6$alkoxy, $C_1$-$C_6$haloalkoxy, $C_1$-$C_6$alkylsulfonyl, $C_1$-$C_6$haloalkylsulfonyl, —C(O)N($R^{29}$)$R^{28}$, D-1, D-8, D-15 to D-17, D-21, D-22, D-28, D-29, D-34, D-35, D-38, D-47, D-50, D-51 or D-53.

(10) Substituted alkenylbenzene compound of formula (4):

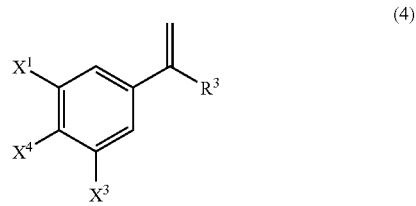

wherein $X^1$ is halogen atom, —$SF_5$, $C_1$-$C_6$haloalkyl, hydroxy $C_1$-$C_6$haloalkyl, $C_1$-$C_6$alkoxy $C_1$-$C_6$haloalkyl, $C_3$-$C_8$halocycloalkyl, $C_1$-$C_6$haloalkoxy, $C_1$-$C_3$haloalkoxy $C_1$-$C_3$haloalkoxy, $C_1$-$C_6$haloalkylthio, $C_1$-$C_6$haloalkylsulfinyl or $C_1$-$C_6$haloalkylsulfonyl, $X^3$ is hydrogen atom, halogen atom, cyano, nitro, $C_1$-$C_6$alkyl, $C_1$-$C_6$haloalkyl, $C_1$-$C_6$alkoxy or $C_1$-$C_6$alkylthio, $X^4$ is hydrogen atom, halogen atom, cyano, $C_1$-$C_4$alkyl, $C_1$-$C_4$alkoxy or $C_1$-$C_4$haloalkoxy, $R^3$ is —C($R^{3a}$)($R^{3b}$)$R^{3c}$, $R^{3a}$ and $R^{3b}$ independently of each other are halogen atom, or $R^{3a}$ and $R^{3b}$ together may form 3- to 6-membered ring together with the carbon atom bonding them by forming $C_2$-$C_5$haloalkylene chain, $R^{3c}$ is hydrogen atom, halogen atom, $C_1$-$C_5$alkyl, $C_1$-$C_5$haloalkyl, $C_1$-$C_4$haloalkoxy or $C_1$-$C_4$haloalkylthio, with a proviso that in case where $X^1$ is fluorine atom, chlorine atom or trifluoromethyl and both $X^2$ and $X^3$ are hydrogen atom, in case where both $X^1$ and $X^2$ are fluorine atom and $X^3$ is hydrogen atom, and in case where both $X^1$ and $X^2$ are trifluoromethyl and $X^3$ is hydrogen atom, $R^{3c}$ is hydrogen atom, chlorine atom, bromine atom, iodine atom, $C_1$-$C_5$alkyl, $C_1$-$C_5$haloalkyl, $C_1$-$C_4$haloalkoxy or $C_1$-$C_4$haloalkylthio.

(11) The substituted alkenylbenzene compound as set forth in (10), wherein $X^1$ is halogen atom, —$SF_5$, $C_1$-$C_6$haloalkyl, $C_1$-$C_6$haloalkoxy or $C_1$-$C_6$haloalkylthio, $X^3$ is hydrogen atom, halogen atom, cyano, nitro, $C_1$-$C_6$alkyl, $C_1$-$C_6$haloalkyl or $C_1$-$C_6$alkoxy, $X^4$ is hydrogen atom or halogen atom, $R^{3a}$ and $R^{3b}$ are flourine atom, $R^{3c}$ is hydrogen atom, fluorine atom, chlorine atom, bromine atom or trifluoromethyl, with a proviso that in case where $X^1$ is fluorine atom, chlorine atom or trifluoromethyl and both $X^3$ and $X^4$ are hydrogen atom, in case where both $X^1$ and $X^3$ are fluorine atom and $X^4$ is hydrogen atom, and in case where both $X^1$ and $X^3$ are trifluoromethyl and $X^4$ is hydrogen atom, $R^{3c}$ is hydrogen atom, chlorine atom, bromine atom or trifluoromethyl.

(12) A pesticide containing as an active ingredient one or more selected from isoxazoline-substituted benzamide compound and the salt thereof as set forth in (1) to (5).

(13) An agrochemical containing as an active ingredient one or more selected from isoxazoline-substituted benzamide compound and the salt thereof as set forth in (1) to (5).

(14) An endo- or ecto-parasiticide for mammals or birds containing as an active ingredient one or more selected from isoxazoline-substituted benzamide compound and the salt thereof as set forth in (1) to (5).

(15) An insecticide or acaricide containing as an active ingredient one or more selected from isoxazoline-substituted benzamide compound and the salt thereof as set forth in (1) to (5).

Effect of the Invention

The compound according to the present invention has an excellent insecticidal and acaricidal activity for many agricultural insect pests, spider mites, endo- or ecto-parasiticide for mammals or birds, and exerts a control effect sufficient for pest insects that acquire resistance against exiting insecticides. Further, the compound has little adverse affect on mammals, fishes and beneficial insects, and has a low persistency and a low impact on the environment. Therefore, the present invention can provide a useful and novel pesticide.

BEST MODE FOR CARRYING OUT THE INVENTION

Active compounds used as the pesticide in the present invention are generally the compounds of formulae (1) to (5) mentioned above, and the compounds of formulae (6) to (11) mentioned above are novel production intermediates used for the production of these active compounds. These intermediates contain specific compounds themselves having control activity against specific pests that can be used as a control agent for the pest.

In the compounds included in the present invention, some compounds have geometrical isomers of E-form and Z-form depending on the kind of substituents. The present invention includes these E-forms, Z-forms and mixtures containing E-form and Z-form in an arbitrary proportion. In addition, the compounds included in the present invention have optically active forms resulting from the presence of 1 or more asymmetric carbon atoms, and the present invention includes all optically active forms or racemates. Further, in the compounds of formula (1) according to the present invention, some compounds wherein $R^2$ is hydrogen atom are present in tautomer, and the present invention includes these structures, Hereinafter, concrete examples of each substituent shown in the specification are described. In the specification, "n-" means normal, "i-" means iso, "s-" means secondary, and "t-" means tertiary, and "Ph" means phenyl.

Halogen atom in the compounds of the present invention includes fluorine atom, chlorine atom, bromine atom and iodine atom. In the interim, the indication of "halo" in the specification also means these halogen atoms.

In the specification, the indication of "$C_a$-$C_b$alkyl" means straight-chain or branched-chain hydrocarbon groups having carbon atom number of a to b, and includes for example methyl, ethyl, n-propyl, i-propyl, n-butyl, s-butyl, i-butyl, t-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl, 1-ethyl-2-methylpropyl, heptyl, 5-methylhexyl, 2-ethylpentyl, octyl, 2-ethylhexyl, nonyl, 2-methyloctyl, decyl, 2-methylnonyl, undecyl, 2-methyldecyl, dodecyl and the like. It is selected from the scope of the indicated carbon atom number.

In the specification, the indication of "$C_a$-$C_b$haloalkyl" means straight-chain or branched-chain hydrocarbon groups having carbon atom number of a to b that a hydrogen atom (hydrogen atoms) bonded to carbon atom is (are) arbitrarily substituted with a halogen atom (halogen atoms). In this case, if it is substituted with two or more halogen atoms, these halogen atoms may be identical with or different from each other. Concrete examples thereof are for example fluoromethyl, chloromethyl, difluoromethyl, dichloromethyl, trifluoromethyl, chlorodifluoromethyl, trichloromethyl, bromodif-

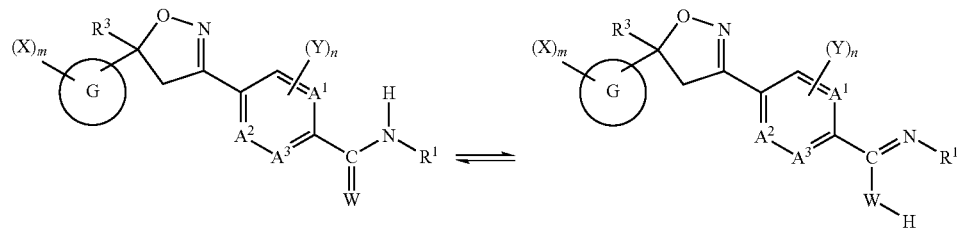

The compounds included in the present invention can be converted to acid addition salts for example salts of hydrohalide acid such as hydrofluoric acid, hydrochloric acid, hydrobromic acid, hydriodic acid or the like, salts of inorganic acids such as nitric acid, sulfuric acid, phosphoric acid, chloric acid, perchloric acid or the like, salts of sulfonic acid such as methansulfonic acid, ethanesulfonic acid, trufluoromethansulfonic acid, benzene sulfonic acid, p-toluene sulfonic acid or the like, salts of carboxylic acid such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid, citric acid or the like, or salts of amino acid such as glutamic acid, aspartic acid or the like, according to a conventional method.

The compounds included in the present invention can be converted to metal salts for example salts of alkali metal such as lithium, sodium, potassium, salts of alkaline earth metal such as calcium, barium, magnesium, or salts of aluminum, according to a conventional method.

luoromethyl, 2-fluoroethyl, 2-chloroethyl, 2-bromoethyl, 2,2-difluoroethyl, 2-chloro-2-fluoroethyl, 2,2-dichloroethyl, 2-bromo-2-fluoroethyl, 2-bromo-2-chloroethyl, 2,2,2-trifluoroethyl, 2-chloro-2,2-difluoroethyl, 2,2-dichloro-2-fluoroethyl, 2,2,2-trichloroethyl, 2-bromo-2,2-difluoroethyl, 2-bromo-2-chloro-2-fluoroethyl, 2-bromo-2,2-dichloroethyl, pentafluoroethyl, 2-fluoropropyl, 2-chloropropyl, 2-bromopropyl, 2,3-dichloropropyl, 2,3-dibromopropyl, 3,3,3-trifluoropropyl, 3-bromo-3,3-difluoropropyl, 2,2,3,3-tetrafluoropropyl, 2-chloro-3,3,3-trifluoropropyl, 2,2,3,3,3-pentafluoropropyl, 2,2,2-trifluoro-1-trifluoromethylethyl, heptafluoropropyl, 1,2,2,2-tetrafluoro-1-trifluoromethylethyl, 2,2,3,3,4,4-hexafluorobutyl, 2,2,3,4,4,4-hexafluorobutyl, 2,2,3,3,4,4,4-heptafluorobutyl, nonafluorobutyl, 5-chloro-2,2,3,4,4,5,5-heptafluoropentyl, and the like. It is selected from the scope of the indicated carbon atom number.

In the specification, the indication of "cyano $C_a$-$C_b$alkyl" means straight-chain or branched-chain alkyl groups having carbon atom number of a to b that a hydrogen atom (hydrogen atoms) bonded to carbon atom is (are) arbitrarily substituted with a cyano group (cyano groups). Concrete examples thereof are for example cyanomethyl, 1-cyanoethyl, 2-cyanoethyl, 2-cyanopropyl, 3-cyanopropyl, 2-cyanobutyl, and the like. It is selected from the scope of the indicated carbon atom number.

In the specification, the indication of "$C_a$-$C_b$cycloalkyl" means cyclic hydrocarbon groups having carbon atom number of a to b, and can form 3-membered to 6-membered single ring or conjugated ring structure. In addition, each ring may be arbitrarily substituted alkyl group in the scope of the indicated carbon atom number. Concrete examples thereof are for example cyclopropyl, 1-methylcyclopropyl, 2-methylcyclopropyl, 2,2-dimethylcyclopropyl, 2,2,3,3-tetramethylcyclopropyl, cyclobutyl, cyclopentyl, 2-methylcyclopentyl, 3-methylcyclopentyl, cyclohexyl, 2-methylcyclohexyl, 3-methylcyclohexyl, 4-methylcyclohexyl, bicyclo[2.2.1]heptan-2-yl and the like. It is selected from the scope of the indicated carbon atom number.

In the specification, the indication of "$C_a$-$C_b$halocycloalkyl" means cyclic hydrocarbon groups having carbon atom number of a to b that a hydrogen atom (hydrogen atoms) bonded to carbon atom is (are) arbitrarily substituted with a halogen atom (halogen atoms), and can form 3-membered to 6-membered single ring or conjugated ring structure. In addition, each ring may be arbitrarily substituted alkyl group in the scope of the indicated carbon atom number. The substitution for halogen atom may be in the ring structure moiety, the side chain moiety or both of them. Further, if it is substituted with two or more halogen atoms, these halogen atoms may be identical with or different from each other. Concrete examples thereof are for example 2,2-dichlorocyclopropyl, 2,2-dibromocyclopropyl, 2,2-difluoro-1-methylcyclopropyl, 2,2-dichloro-1-methylcyclopropyl, 2,2-dibromo-1-methylcyclopropyl, 2,2-dichloro-3,3-dimethylcyclopropyl, 2,2,3,3-tetrafluorocyclobutyl, 2-trifluoromethylcyclohexyl, 3-trifluoromethylcyclohexyl, 4-trifluoromethylcyclohexyl and the like. It is selected from the scope of the indicated carbon atom number.

In the specification, the indication of "$C_a$-$C_b$alkenyl" means straight-chain or branched-chain unsaturated hydrocarbon groups having carbon atom number of a to b and having 1 or more double bonds. Concrete examples thereof are for example vinyl, 1-propenyl, 1-methylethenyl, 2-propenyl, 2-butenyl, 1-methyl-2-propenyl, 2-methyl-2-propenyl, 2-methyl-2-butenyl, 3-methyl-2-butenyl, 2-hexenyl, 2-methyl-2-pentenyl, 2,4-dimethyl-2,6-heptadienyl, 3,7-dimethyl-2,6-octadienyl, and the like. It is selected from the scope of the indicated carbon atom number.

In the specification, the indication of "$C_a$-$C_b$halolkenyl" means straight-chain or branched-chain unsaturated hydrocarbon groups having carbon atom number of a to b and having 1 or more double bonds, which a hydrogen atom (hydrogen atoms) bonded to carbon atom is (are) arbitrarily substituted with a halogen atom (halogen atoms). In this case, if it is substituted with two or more halogen atoms, these halogen atoms may be identical with or different from each other. Concrete examples thereof are for example 2,2-dichlorovinyl, 2-fluoro-2-propenyl, 2-chloro-2-propenyl, 2-bromo-2-propenyl, 3-bromo-2-propenyl, 3,3-difluoro-2-propenyl, 2,3-dichloro-2-propenyl, 3,3-dichloro-2-propenyl, 2,3-dibromo-2-propenyl, 2,3,3-trifluoro-2-propenyl, 1-trifluoromethylvinyl, 2,3,3-trichloro-2-propenyl, 2-bromo-2-butenyl, 3-bromo-2-methyl-2-propenyl, 4,4-difluoro-3-butenyl, 3,4,4-trifluoro-3-butenyl, 3-chloro-4,4,4-trifluoro-2-butenyl, and the like. It is selected from the scope of the indicated carbon atom number.

In the specification, the indication of "$C_a$-$C_b$cycloalkenyl" means cyclic unsaturated hydrocarbon groups having carbon atom number of a to b and having 1 or more double bonds, and can form 3-membered to 6-membered single ring or conjugated ring structure. In addition, each ring may be arbitrarily substituted alkyl group in the scope of the indicated carbon atom number, and further the double bond may be either endo- or exo-form. Concrete examples thereof are for example 2-cyclopenten-1-yl, 3-cyclopenten-1-yl, 2-cyclohexen-1-yl, 3-cyclohexen-1-yl, bicyclo[2.2.1]-5-hepten-2-yl and the like. It is selected from the scope of the indicated carbon atom number.

In the specification, the indication of "$C_a$-$C_b$haloycloalkenyl" means cyclic unsaturated hydrocarbon groups having carbon atom number of a to b and having 1 or more double bonds, which a hydrogen atom (hydrogen atoms) bonded to carbon atom is (are) arbitrarily substituted with a halogen atom (halogen atoms), and can form 3-membered to 6-membered single ring or conjugated ring structure. In addition, each ring may be arbitrarily substituted alkyl group in the scope of the indicated carbon atom number, and further the double bond may be either endo- or exo-form. The substitution for halogen atom may be in the ring structure moiety, the side chain moiety or both of them. Further, if it is substituted with two or more halogen atoms, these halogen atoms may be identical with or different from each other. Concrete examples thereof are for example 2-chlorobicyclo[2.2.1]-5-hepten-2-yl and the like. It is selected from the scope of the indicated carbon atom number.

In the specification, the indication of "$C_a$-$C_b$alkynyl" means straight-chain or branched-chain unsaturated hydrocarbon groups having carbon atom number of a to b and having 1 or more triple bonds. Concrete examples thereof are for example ethynyl, 1-propynyl, 2-propynyl, 1-methyl-2-propynyl, 2-butynyl, 2-pentynyl, 1-methyl-2-butynyl, 2-hexynyl, and the like. It is selected from the scope of the indicated carbon atom number.

In the specification, the indication of "$C_a$-$C_b$halolkynyl" means straight-chain or branched-chain unsaturated hydrocarbon groups having carbon atom number of a to b and having 1 or more triple bonds, which a hydrogen atom (hydrogen atoms) bonded to carbon atom is (are) arbitrarily substituted with a halogen atom (halogen atoms). In this case, if it is substituted with two or more halogen atoms, these halogen atoms may be identical with or different from each other. Concrete examples thereof are for example 2-chloroethynyl, 2-bromoethynyl, 2-iodoethynyl, 3-chloro-2-propynyl, 3-bromo-2-propynyl, 3-iodo-2-propynyl, and the like. It is selected from the scope of the indicated carbon atom number.

In the specification, the indication of "$C_a$-$C_b$alkoxy" means alkyl-O— groups wherein the alkyl has carbon atom number of a to b, and includes for example methoxy, ethoxy, n-propyloxy, i-propyloxy, n-butyloxy, s-butyloxy, i-butyloxy, t-butyloxy, n-pentyloxy, n-hexyloxy and the like. It is selected from the scope of the indicated carbon atom number.

In the specification, the indication of "$C_a$-$C_b$haloalkoxy" means haloalkyl-O— groups wherein the haloalkyl has carbon atom number of a to b, and includes for example difluoromethoxy, trifluoromethoxy, chlorodifluoromethoxy, bromodifluoromethoxy, 2-fluoroethoxy, 2-chloroethoxy, 2,2,2-trifluoroethoxy, 1,1,2,2-tetrafluoroethoxy, 2-chloro-1,1,2-trifluoroethoxy, 2-bromo-1,1,2-trifluoroethoxy, 2,2-dichloro-1,1,2-trifluoroethoxy, pentafluoroethoxy, 2,2,2-trichloro-1,1-difluoroethoxy, 2-bromo-1,1,2,2-tetrafluoroethoxy, 2,2,3,3-tetrafluoropropyloxy, 1,1,2,3,3,3-hexafluoropropyloxy, 2,2,2-trifluoro-1-trifluoromethylethoxy, heptafluoropropyloxy, 2-bromo-1,1, 2,3,3,3-hexafluoropropyloxy, and the like. It is selected from the scope of the indicated carbon atom number.

In the specification, the indication of "$C_a$-$C_b$alkylthio" means alkyl-S— groups wherein the alkyl has carbon atom number of a to b, and includes for example methylthio, ethylthio, n-propylthio, i-propylthio, n-butylthio, s-butylthio, i-butylthio, t-butylthio, n-pentylthio, n-hexylthio and the like. It is selected from the scope of the indicated carbon atom number.

In the specification, the indication of "$C_a$-$C_b$haloalkylthio" means haloalkyl-S— groups wherein the haloalkyl has carbon atom number of a to b, and includes for example difluoromethylthio, trifluoromethylthio, bromodifluoromethylthio, 2,2,2-trifluoroethylthio, 1,1,2,2-tetrafluoroethylthio, 1,1,2-trifluoro-2-chloroethylthio, pentafluoroethylthio, 2-bromo-1,1,2,2-tetrafluoroethylthio, heptafluoropropylthio, 1,2,2,2-tetrafluoro-1-trifluoromethylthio, 1,2,2,2-tetrafluoro-1-trifluoroethylthio, nonafluorobutylthio, and the like. It is selected from the scope of the indicated carbon atom number.

In the specification, the indication of "$C_a$-$C_b$alkylsulfinyl" means alkyl-S(O)— groups wherein the alkyl has carbon atom number of a to b, and includes for example methylsulfinyl, ethylsulfinyl, n-propylsulfinyl, i-propylsulfinyl, n-butylsulfinyl, s-butylsulfinyl, i-butylsulfinyl, t-butylsulfinyl, and the like. It is selected from the scope of the indicated carbon atom number.

In the specification, the indication of "$C_a$-$C_b$haloalkylsulfinyl" means haloalkyl-S(O)— groups wherein the haloalkyl has carbon atom number of a to b, and includes for example difluoromethylsulfinyl, trifluoromethylsulfinyl, bromodifluoromethylsulfinyl, 2,2,2-trifluoroethylsulfinyl, 2-bromo-1,1,2,2-tetrafluoroethylsulfinyl, 1,2,2,2-tetrafluoro-1-trifluoromethylethylsulfinyl, nonafluorobutylsulfinyl, and the like. It is selected from the scope of the indicated carbon atom number.

In the specification, the indication of "$C_a$-$C_b$alkylsulfonyl" means alkyl-$SO_2$— groups wherein the alkyl has carbon atom number of a to b, and includes for example methanesulfonyl, ethanesulfonyl, n-propylsulfonyl, i-propylsulfonyl, n-butylsulfonyl, s-butylsulfonyl, i-butylsulfonyl, t-butylsulfonyl, n-pentylsulfonyl, n-hexylsulfonyl, and the like. It is selected from the scope of the indicated carbon atom number.

In the specification, the indication of "$C_a$-$C_b$haloalkylsulfonyl" means haloalkyl-$SO_2$— groups wherein the haloalkyl has carbon atom number of a to b, and includes for example difluoromethanesulfonyl, trifluoromethanesulfonyl, chlorodifluoromethanesulfonyl, bromodifluoromethanesulfonyl, 2,2,2-trifluoroethanesulfonyl, 1,1,2,2-tetrafluoroethanesulfonyl, 1,1,2-trifluoro-2-chloroethanesulfonyl, and the like. It is selected from the scope of the indicated carbon atom number.

In the specification, the indication of "$C_a$-$C_b$alkylamino" means amino groups, which either hydrogen atom is substituted with the above-mentioned alkyl group having carbon atom number of a to b, and includes for example methylamino, ethylamino, n-propylamino, i-propylamino, n-butylamino, i-butylamino, t-butylamino, and the like. It is selected from the scope of the indicated carbon atom number.

In the specification, the indication of "di($C_a$-$C_b$alkyl)amino" means amino groups, which both hydrogen atoms are substituted with the above-mentioned alkyl groups having carbon atom number of a to b that may be identical with or different from each other, and includes for example dimethylamino, ethyl(methyl)amino, diethylamino, n-propyl(methyl)amino, i-propyl(methyl)amino, di(n-propyl)amino, n-butyl(methyl)amino, i-butyl(methyl)amino, t-butyl(methyl)amino, and the like. It is selected from the scope of the indicated carbon atom number.

In the specification, the indication of "$C_a$-$C_b$alkylcarbonyl" means alkyl-C(O)— groups wherein the alkyl has carbon atom number of a to b, and includes for example $CH_3C(O)$—, $CH_3CH_2C(O)$—, $CH_3CH_2CH_2C(O)$—, $(CH_3)_2CHC(O)$—, $CH_3(CH_2)_3C(O)$—, $(CH_3)_2CHCH_2C(O)$—, $CH_3CH_2CH(CH_3)C(O)$—, $(CH_3)_3CC(O)$—, $CH_3(CH_2)_4C(O)$—, $CH_3(CH_2)_5C(O)$—, and the like. It is selected from the scope of the indicated carbon atom number.

In the specification, the indication of "$C_a$-$C_b$haloalkylcarbonyl" means haloalkyl-C(O)— groups wherein the haloalkyl has carbon atom number of a to b, and includes for example $FCH_2C(O)$—, $ClCH_2C(O)$—, $F_2CHC(O)$—, $Cl_2CHC(O)$—, $CF_3C(O)$—, $ClCF_2C(O)$—, $BrCF_2C(O)$—, $CCl_3C(O)$—, $CF_3CF_2C(O)$—, $ClCH_2CH_2C(O)$—, $CF_3CF_2CF_2C(O)$—, $ClCH_2C(CH_3)_2C(O)$—, and the like. It is selected from the scope of the indicated carbon atom number.

In the specification, the indication of "$C_a$-$C_b$alkoxycarbonyl" means alkyl-O—C(O)— groups wherein the alkyl has carbon atom number of a to b, and includes for example $CH_3OC(O)$—, $CH_3CH_2OC(O)$—, $CH_3CH_2CH_2OC(O)$—, $(CH_3)_2CHOC(O)$—, $CH_3(CH_2)_3OC(O)$—, $(CH_3)_2CHCH_2OC(O)$—, $(CH_3)_3COC(O)$—, and the like. It is selected from the scope of the indicated carbon atom number.

In the specification, the indication of "$C_a$-$C_b$haloalkoxycarbonyl" means haloalkyl-O—C(O)— groups wherein the haloalkyl has carbon atom number of a to b, and includes for example $ClCH_2CH_2OC(O)$—, $CF_3CH_2OC(O)$—, and the like. It is selected from the scope of the indicated carbon atom number.

In the specification, the indication of "$C_a$-$C_b$alkylaminocarbonyl" means carbamoyl groups, which either hydrogen atom is substituted with the above-mentioned alkyl group having carbon atom number of a to b, and includes for example $CH_3NHC(O)$—, $CH_3CH_2NHC(O)$—, $CH_3CH_2CH_2NHC(O)$—, $(CH_3)_2CHNHC(O)$—, $CH_3(CH_2)_3NHC(O)$—, $(CH_3)_2CHCH_2NHC(O)$—, $CH_3CH_2CH(CH_3)NHC(O)$—, $(CH_3)_3CNHC(O)$—, and the like. It is selected from the scope of the indicated carbon atom number.

In the specification, the indication of "$C_a$-$C_b$haloalkylaminocarbonyl" means carbamoyl groups, which either hydrogen atom is substituted with the above-mentioned haloalkyl group having carbon atom number of a to b, and includes for example 2-fluoroethylcarbamoyl, 2-chloroethylcarbamoyl, 2,2-difluorocarbamoyl, 2,2,2-trifluoroethylcarbamoyl, and the like. It is selected from the scope of the indicated carbon atom number.

In the specification, the indication of "di($C_a$-$C_b$alkyl)aminocarbonyl" means carbamoyl groups, which both hydrogen atoms are substituted with the above-mentioned alkyl group having carbon atom number of a to b that may be identical with or different from each other, and includes for example $(CH_3)_2NC(O)$—, $CH_3CH_2N(CH_3)C(O)$—, $(CH_3CH_2)_2NC(O)$—, $(CH_3CH_2CH_2)_2NC(O)$—, $(CH_3CH_2CH_2CH_2)_2NC(O)$—, and the like. It is selected from the scope of the indicated carbon atom number.

In the specification, the indication of "$C_a$-$C_b$alkylaminosulfonyl" means sulfamoyl groups, which either hydrogen atom is substituted with the above-mentioned alkyl group having carbon atom number of a to b, and includes for example $CH_3NHSO_2$—, $CH_3CH_2NHSO_2$—, $CH_3CH_2CH_2NHSO_2$—, $(CH_3)_2CHNHSO_2$—, $CH_3(CH_2)_3NHSO_2$—, $(CH_3)_2CHCH_2NHSO_2$—, $CH_3CH_2CH(CH_3)NHSO_2$—, $(CH_3)_3CNHSO_2$, and the like. It is selected from the scope of the indicated carbon atom number.

In the specification, the indication of "di($C_a$-$C_b$alkyl)aminosulfonyl" means sulfamoyl groups, which both hydrogen atoms are substituted with the above-mentioned alkyl group having carbon atom number of a to b that may be identical with or different from each other, and includes for example $(CH_3)_2NSO_2$—, $CH_3CH_2N(CH_3)SO_2$—, $(CH_3CH_2)_2NSO_2$—, $(CH_3CH_2CH_2)_2NSO_2$—, $(CH_3CH_2CH_2CH_2)_2NSO_2$—, and the like. It is selected from the scope of the indicated carbon atom number.

In the specification, the indication of "tri($C_a$-$C_b$alkyl)silyl" means silyl groups substituted with the above-mentioned alkyl group having carbon atom number of a to b that may be identical with or different from each other, and includes for example trimethylsilyl, triethylsilyl, tri(n-propyl)silyl, ethyldimethylsilyl, n-propyldimethylsilyl, n-butyldimethylsilyl, i-butyldimethylsilyl, t-butyldimethylsilyl, and the like. It is selected from the scope of the indicated carbon atom number.

In the specification, the indication of "$C_a$-$C_b$alkylcarbonyloxy" means alkylcarbonyl-O— groups wherein the alkyl has carbon atom number of a to b, and includes for example $CH_3C(O)$—O—, $CH_3CH_2C(O)$—O—, $CH_3CH_2CH_2C(O)$—O—, $(CH_3)_2CHC(O)$—O—, $CH_3(CH_2)_3C(O)$—O—, $(CH_3)_2CHCH_2C(O)$—O—, $CH_3CH_2CH(CH_3)C(O)$—O—, $(CH_3)_3CC(O)$—O—, and the like. It is selected from the scope of the indicated carbon atom number.

In the specification, the indication of "$C_a$-$C_b$alkylsulfonyloxy" means alkylsulfonyl-O— groups wherein the alkyl has carbon atom number of a to b, and includes for example $CH_3SO_2$—O—, $CH_3CH_2SO_2$—O—, $CH_3CH_2CH_2SO_2$—O—, $(CH_3)_2CHSO_2$—O—, and the like. It is selected from the scope of the indicated carbon atom number.

In the specification, the indication of "$C_a$-$C_b$haloalkylsulfonyloxy" means haloalkylsulfonyl-O— groups wherein the haloalkyl has carbon atom number of a to b, and includes for example difluoromethanesulfonyl-O—, trifluoromethanesulfonyl-O—, chlorodifluoromethanesulfonyl-O—, bromodifluoromethanesulfonyl-O—, and the like. It is selected from the scope of the indicated carbon atom number.

In the specification, the indication of "$C_a$-$C_b$cycloalkyl $C_d$-$C_e$alkyl", "$C_a$-$C_b$halocycloalkyl $C_d$-$C_e$alkyl", "$C_a$-$C_b$alkoxy $C_d$-$C_e$alkyl", "$C_a$-$C_b$haloalkoxy $C_d$-$C_e$alkyl", "$C_a$-$C_b$alkylthio $C_d$-$C_e$alkyl", "$C_a$-$C_b$haloalkylthio $C_d$-$C_e$alkyl", "$C_a$-$C_b$alkylsulfinyl $C_d$-$C_e$alkyl", "$C_a$-$C_b$haloalkylsulfinyl $C_d$-$C_e$alkyl", "$C_a$-$C_b$alkylsulfonyl $C_d$-$C_e$alkyl", "$C_a$-$C_b$haloalkylsulfonyl $C_d$-$C_e$alkyl", "$C_a$-$C_b$alkoxycarbonyl $C_d$-$C_e$alkyl", "phenyl $C_d$-$C_e$alkyl" or "phenyl $C_d$-$C_e$alkyl substituted with $(Z)_{p1}$" means straight-chain or branched-chain hydrocarbon groups having carbon atom number of d to e, which a hydrogen atom (hydrogen atoms) bonded to carbon atom is (are) arbitrarily substituted with the $C_a$-$C_b$cycloalkyl, $C_a$-$C_b$halocycloalkyl, $C_a$-$C_b$alkoxy, $C_a$-$C_b$haloalkoxy, $C_a$-$C_b$alkylthio, $C_a$-$C_b$haloalkylthio, $C_a$-$C_b$alkylsulfinyl, $C_a$-$C_b$haloalkylsulfinyl, $C_a$-$C_b$alkylsulfonyl, $C_a$-$C_b$haloalkylsulfonyl, $C_a$-$C_b$alkoxycarbonyl, phenyl or phenyl substituted with $(Z)_{p1}$ that has the meaning mentioned above, respectively. It is selected from the scope of the indicated carbon atom number.

In the specification, the indication of "$C_a$-$C_b$alkyl arbitrarily substituted with $R^4$", "$C_a$-$C_b$alkyl arbitrarily substituted with $R^{16}$", "$C_a$-$C_b$alkyl arbitrarily substituted with $R^{24}$", "$C_a$-$C_b$alkyl arbitrarily substituted with $R^{32}$", or "$C_a$-$C_b$alkyl arbitrarily substituted with $R^{35}$" means straight-chain or branched-chain hydrocarbon groups having carbon atom number of d to e, which a hydrogen atom (hydrogen atoms) bonded to carbon atom is (are) arbitrarily substituted with $R^4$, $R^{16}$, $R^{24}$, $R^{32}$ or $R^{35}$. It is selected from the scope of the indicated carbon atom number.

In this case, when two or more substituents $R^4$, $R^{16}$, $R^{24}$, $R^{32}$ or $R^{35}$ are present on the $C_a$-$C_b$alkyl, respective $R^4$, $R^{16}$, $R^{24}$, $R^{32}$ or $R^{35}$ may be identical with or different from each other.

In the specification, the indication of "hydroxy $C_d$-$C_e$cycloalkyl", "$C_a$-$C_b$alkoxy $C_d$-$C_e$cycloalkyl", "$C_a$-$C_b$alkenyl $C_d$-$C_e$cycloalkyl" or "$C_a$-$C_b$haloalkenyl $C_d$-$C_e$cycloalkyl" means the cycloalkyl having carbon atom number of d to e, which a hydrogen atom (hydrogen atoms) bonded to carbon atom is (are) arbitrarily substituted with $C_a$-$C_b$alkoxy, $C_a$-$C_b$alkenyl, $C_a$-$C_b$haloalkenyl or hydroxy. It is selected from the scope of the indicated carbon atom number.

In the specification, the indication of "$C_a$-$C_b$cycloalkyl arbitrarily substituted with $R^4$", "$C_a$-$C_b$cycloalkyl arbitrarily substituted with $R^{16}$", "$C_a$-$C_b$cycloalkyl arbitrarily substituted with $R^{24}$" or "$C_a$-$C_b$cycloalkyl arbitrarily substituted with $R^{32}$" means the cycloalkyl groups having carbon atom number of a to b, which a hydrogen atom (hydrogen atoms) bonded to carbon atom is (are) arbitrarily substituted with $R^4$, $R^{16}$, $R^{24}$ or $R^{32}$. The substitution for $R^4$, $R^{16}$, $R^{24}$ or $R^{32}$ may be in the ring structure moiety, the side chain moiety or both of them. In this case, when two or more substituents $R^4$, $R^{16}$, $R^{24}$ or $R^{32}$ are present on the $C_a$-$C_b$cycloalkyl, respective $R^4$, $R^{16}$, $R^{24}$ or $R^{32}$ may be identical with or different from each other.

In the specification, the indication of "phenyl $C_a$-$C_b$alkenyl" or "phenyl $C_a$-$C_b$alkenyl substituted with $(Z)_{p1}$" means the alkenyl having carbon atom number of a to b, which a hydrogen atom (hydrogen atoms) bonded to carbon atom is (are) arbitrarily substituted phenyl or phenyl substituted with $(Z)_{p1}$. It is selected from the scope of the indicated carbon atom number.

In the specification, the indication of "$C_a$-$C_b$alkenyl arbitrarily substituted with $R^4$", "$C_a$-$C_b$alkenyl arbitrarily substituted with $R^{16}$", "$C_a$-$C_b$alkenyl arbitrarily substituted with $R^{24}$" or "$C_a$-$C_b$alkenyl arbitrarily substituted with $R^{32}$" means the alkenyl groups having carbon atom number of a to b, which a hydrogen atom (hydrogen atoms) bonded to carbon atom is (are) arbitrarily substituted with $R^4$, $R^{16}$, $R^{24}$ or $R^{32}$. It is selected from the scope of the indicated carbon atom number. In this case, when two or more substituents $R^4$, $R^{16}$, $R^{24}$ or $R^{32}$ are present on the $C_a$-$C_b$alkenyl, respective $R^4$, $R^{16}$, $R^{24}$ or $R^{32}$ may be identical with or different from each other.

In the specification, the indication of "phenyl $C_a$-$C_b$alkynyl" or "phenyl $C_a$-$C_b$alkynyl substituted with $(Z)_{p1}$" means the alkynyl having carbon atom number of a to b, which a hydrogen atom (hydrogen atoms) bonded to carbon atom is (are) arbitrarily substituted phenyl or phenyl substituted with $(Z)_{p1}$. It is selected from the scope of the indicated carbon atom number.

In the specification, the indication of "$C_a$-$C_b$alkynyl arbitrarily substituted with $R^4$", "$C_a$-$C_b$alkynyl arbitrarily substituted with $R^{16}$", "$C_a$-$C_b$alkynyl arbitrarily substituted with $R^{24}$" or "$C_a$-$C_b$alkynyl arbitrarily substituted with $R^{32}$" means the alkynyl groups having carbon atom number of a to b, which a hydrogen atom (hydrogen atoms) bonded to carbon atom is (are) arbitrarily substituted with $R^4$, $R^{16}$, $R^{24}$ or $R^{32}$. It is selected from the scope of the indicated carbon atom number. In this case, when two or more substituents $R^4$, $R^{16}$, $R^{24}$ or $R^{32}$ are present on the $C_a$-$C_b$alkenyl, respective $R^4$, $R^{16}$, $R^{24}$ or $R^{32}$ may be identical with or different from each other.

In the specification, concrete examples of the indication of "$R^1$ and $R^2$ together may form 3- to 8-membered ring together with the nitrogen atom bonding them by forming $C_2$ to $C_7$ alkylene chain, in this case, the alkylene chain may contain one oxygen atom, sulfur atom or nitrogen atom", "$R^{10}$ together with $R^9$ may form 3- to 7-membered ring with the nitrogen atom bonding them by forming $C_2$-$C_6$alkylene chain, in this case, the alkylene chain may contain one oxygen atom, sulfur atom or nitrogen atom", "$R^{18}$ together with $R^{17}$ may form 5- to 8-membered ring with the nitrogen atom bonding them by forming $C_4$-$C_7$alkylene chain, in this case, the alkylene chain may contain one oxygen atom or sulfur atom", "$R^{26}$ together with $R^{25}$ may form 3- to 6-membered ring with the nitrogen atom bonding them by forming $C_2$-$C_5$alkylene chain, in this case, the alkylene chain may contain one oxygen atom or sulfur atom", "$R^{29}$ together with $R^{28}$ may form 3- to 6-membered ring with the nitrogen atom bonding them by forming $C_2$-$C_5$alkylene chain, in this case, the alkylene chain may contain one oxygen atom, sulfur atom or nitrogen atom", "$R^{34}$ together with $R^{33}$ may form 3- to 6-membered ring with the nitrogen atom bonding them by forming $C_2$-$C_5$alkylene chain, in this case, the alkylene chain may contain one oxygen atom or sulfur atom", are for example aziridine, azetidine, pyrrolidine, oxazolidine, thiazoridine, imidazolidine, piperidine, morpholine, thiomorpholine, piperazine, homopiperidine, heptamethyleneimine, and the like. It is selected from the scope of the indicated carbon atom number.

In the specification, concrete examples of the indication of "$R^7$ together with $R^6$ may form 3- to 7-membered ring with the nitrogen atom bonding them by forming $C_2$-$C_6$alkylene chain, in this case, the alkylene chain may contain one oxygen atom, sulfur atom or nitrogen atom" are for example aziridine, azetidine, azetidin-2-one, pyrrolidine, pyrrolidin-2-one, oxazolidine, oxazolidin-2-one, thiazoridine, thiazoridin-2-one, imidazolidine, imidazolidin-2-one, piperidine, piperidin-2-one, morpholine, tetrahydro-1,3-oxadin-2-one, thiomorpholine, tetrahydro-1,3-thiazin-2-one, piperazine, tetrahydropyrimidin-2-one, homopiperidine, homopiperidin-2-one, and the like. It is selected from the scope of the indicated carbon atom number.

In the specification, concrete examples of the indication of "$R^{11}$ together with $R^9$ may form 5- to 7-membered ring with the atom bonding them by forming $C_2$-$C_4$alkylene chain, in this case, the alkylene chain may contain one oxygen atom, sulfur atom or nitrogen atom" are for example isoxazoline, oxazoline, thiazoline, imidazoline, 1,4,2-dioxazoline, 1,4,2-oxathiazoline, 1,2,4-oxadiazoline, dihydro-1,2-oxadine, dihydro-1,3-oxadine, dihydro-1,3-thiazine, 3,4,5,6-tetrahydropyrimidine, dihydro-1,4,2-dioxadine, dihydro-1,4,2-oxathiazine, dihydro-4H-1,2,4-oxadiazine, tetrahydro-1,2-oxazepine, and the like. It is selected from the scope of the indicated carbon atom number.

In the specification, concrete examples of the indication of "$R^{31}$ together with $R^{30}$ may form 5- to 7-membered ring with the atom bonding them by forming $C_2$-$C_4$alkylene chain, in this case, the alkylene chain may contain one oxygen atom, sulfur atom or nitrogen atom" are for example oxazoline, thiazoline, imidazoline, dihydro-1,3-oxazine, dihydro-1,3-thiazine, 3,4,5,6-tetrahydropyrimidine, dihydro-1,4,2-dioxadine, and the like. It is selected from the scope of the indicated carbon atom number.

In the compounds included in the present invention, the combination of the atoms of $A^1$, $A^2$ and $A^3$ includes for example the following groups.

That is, A-I: $A^1$, $A^2$ and $A^3$ are carbon atoms.
A-II: $A^1$ is nitrogen atom, $A^2$ and $A^3$ are carbon atoms.
A-III: $A^2$ is nitrogen atom, $A^1$ and $A^3$ are carbon atoms.
A-IV: $A^1$ and $A^3$ are nitrogen atom, $A^2$ is carbon atom.
A-V: $A^2$ and $A^3$ are nitrogen atom, $A^1$ is carbon atom.

In the compounds included in the present invention, the substituent G includes for example aromatic 6-membered rings shown in any one of G-1 to G-10 and aromatic 5-membered rings shown in any one of G-11 to G-25. Among them, aromatic 6-membered rings shown in G-1, G-3 and G-4 and aromatic 5-membered rings shown in any one of G-13, G-14, G-17, G-18, G-20, G-21 and G-22 are preferable, and aromatic 6-membered ring shown in G-1 is particularly preferable.

In the compounds included in the present invention, the substituent W includes for example oxygen atom or sulfur atom.

In the compounds included in the present invention, the substituent X includes for example the following groups. In each case mentioned below, when m is an integer of 2 or more, Xs may be identical with or different from each other.

That is, X-I: halogen atom and $C_1$-$C_6$haloalkyl.
X-II: halogen atom, $C_1$-$C_6$alkyl, $C_1$-$C_6$haloalkyl, $C_1$-$C_6$alkoxy, $C_1$-$C_6$alkylsulfonyloxy, $C_1$-$C_6$alkylthio, $C_1$-$C_6$alkylsulfinyl and $C_1$-$C_6$alkylsulfonyl.
X-III: halogen atom, $C_1$-$C_6$haloalkyl, $C_1$-$C_6$haloalkoxy, $C_1$-$C_3$haloalkoxy, $C_1$-$C_3$haloalkoxy, $C_1$-$C_6$haloalkylsulfonyloxy, $C_1$-$C_6$haloalkylthio, $C_1$-$C_6$haloalkylsulfinyl and $C_1$-$C_6$haloalkylsulfonyl.
X-IV: halogen atom, $C_1$-$C_6$haloalkyl, cyano, nitro, —$SF_5$ and —$Si(R^{13})(R^{14})R^{12}$ wherein $R^{12}$ is $C_1$-$C_6$alkyl, phenyl or phenyl substituted with $(Z)_{p1}$, $R^{13}$ and $R^{14}$ independently of each other are $C_1$-$C_6$alkyl.
X-V: halogen atom and $C_1$-$C_6$alkyl arbitrarily substituted with $R^4$ wherein $R^4$ is halogen atom, cyano, —OH, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl or tri($C_1$-$C_6$alkyl)silyl.
X-VI: halogen atom, $C_1$-$C_6$haloalkyl, $C_3$-$C_8$cycloalkyl, $C_3$-$C_8$halocycloalkyl, $C_2$-$C_6$alkenyl, $C_2$-$C_6$haloalkenyl, $C_2$-$C_6$alkynyl, $C_2$-$C_6$haloalkynyl, E-10, E-12, E-18, E-32, E-35 and E-43.
X-VII: halogen atom, $C_1$-$C_6$haloalkyl, —$OR^5$, —$OSO_2R^5$ and —$S(O)_rR^5$ wherein $R^5$ is $C_1$-$C_6$alkyl, $C_1$-$C_6$haloalkyl, $C_1$-$C_3$haloalkoxy, $C_1$-$C_3$haloalkyl, $C_3$-$C_8$cycloalkyl, $C_3$-$C_8$halocycloalkyl, $C_2$-$C_6$alkenyl, $C_2$-$C_6$haloalkenyl, $C_3$-$C_6$alkynyl, $C_3$-$C_6$haloalkynyl, E-4 to E-9, E-23 to E-27 or E-28, r is an integer of 0 to 2.
X-VIII: halogen atom, $C_1$-$C_6$haloalkyl, —C(O)$OR^9$, —C(O)$SR^9$, —C(S)$OR^9$, —C(S)$SR^9$, —C(S)$NHR^{10}$, —C(S)N($R^{10}$)$R^9$, —CH=$NOR^{11}$ and —C($R^9$)=$NOR^{11}$ wherein $R^9$ is $C_1$-$C_6$alkyl, $C_1$-$C_6$haloalkyl, $C_3$-$C_8$cycloalkyl or $C_3$-$C_8$halocycloalkyl, $R^{10}$ is hydrogen atom or $C_1$-$C_6$alkyl, or $R^{10}$ together with $R^9$ may form 5- or 6-membered ring with the nitrogen atom bonding them by forming $C_4$-$C_5$alkylene chain, in this case, the alkylene chain may contain one oxygen atom or sulfur atom, $R^{11}$ is $C_1$-$C_6$alkyl or $C_1$-$C_6$haloalkyl, or $R^{11}$ together with $R^9$ may form 5- or 6-membered ring with the atom bonding them by forming $C_2$-$C_3$alkylene chain, in this case, the alkylene chain may be arbitrarily substituted with $C_1$-$C_6$alkyl.
X-IX: m is 2, two adjacent Xs form 5- or 6-membered ring with the carbon atom bonding them by forming —$CF_2OCF_2$—, —$OCF_2O$—, —$CF_2OCF_2O$— or —$OCF_2CF_2O$—.

In the compounds included in the present invention, m indicating the number of substituent X is an integer of 0 to 5. Among them, m is preferably 1, 2 and 3.

In the compounds included in the present invention, the substituent Y includes for example the following groups. In each case mentioned below, when n is an integer of 2 or more, Ys may be identical with or different from each other.

That is, Y-I: halogen atom, $C_1$-$C_6$alkyl and $C_1$-$C_6$haloalkyl.

Y-II: halogen atom, $C_1$-$C_6$alkyl, cyano, nitro, —C(O)NH$_2$ and —C(S)NH$_2$.

Y-III: halogen atom, $C_1$-$C_6$alkyl and $C_1$-$C_6$alkyl arbitrarily substituted with $C_1$-$C_6$alkyl and $R^4$ wherein $R^4$ is halogen atom, cyano, —OH, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl or tri($C_1$-$C_6$alkyl)silyl.

Y-IV: halogen atom, $C_1$-$C_6$alkyl, —OR$^5$, —OSO$_2$R$^5$ and —S(O)$_r$R$^5$ wherein $R^5$ is $C_1$-$C_6$alkyl, $C_1$-$C_6$haloalkyl, $C_1$-$C_3$haloalkoxy $C_1$-$C_3$haloalkyl, $C_3$-$C_8$cycloalkyl, $C_3$-$C_8$halocycloalkyl, $C_2$-$C_6$alkenyl, $C_2$-$C_6$haloalkenyl, $C_3$-$C_6$alkynyl, $C_3$-$C_6$haloalkynyl, E-4 to E-9, E-23 to E-27 or E-28, r is an integer of 0 to 2.

Y-V: halogen atom, $C_1$-$C_6$alkyl, —NHR$^7$, —N(R$^7$)R$^6$ wherein $R^6$ is $C_1$-$C_6$alkyl, $C_1$-$C_6$haloalkyl, —S(O)$_2$R$^9$, —CHO, —C(O)R$^9$, —C(O)OR$^9$, —C(O)SR$^9$, —C(S)OR$^9$ or —C(S)SR$^9$, $R^7$ is hydrogen atom, $C_1$-$C_6$alkyl or $C_1$-$C_6$haloalkyl, $R^9$ is $C_1$-$C_6$alkyl, $C_1$-$C_6$haloalkyl, $C_3$-$C_8$cycloalkyl or $C_3$-$C_8$halocycloalkyl and —N=C(R$^9$)OR$^8$ wherein $R^8$ is $C_1$-$C_6$alkyl, $R^9$ is $C_1$-$C_6$alkyl or $C_1$-$C_6$haloalkyl.

Y-VI: halogen atom, nitro, $C_1$-$C_6$alkyl, $C_1$-$C_6$haloalkyl, $C_1$-$C_6$alkylthio, $C_1$-$C_6$alkylamino and di($C_1$-$C_6$alkyl)amino.

In the compounds included in the present invention, n indicating the number of substituent Y is an integer of 0 to 4. Among them, n is preferably 0 and 1.

In the compounds included in the present invention, the substituent $R^1$ includes for example the following groups.

That is, $R^1$-I: $C_1$-$C_6$alkyl, $C_1$-$C_6$alkyl arbitrarily substituted with $R^{16}$ (wherein $R^{16}$ is halogen atom, $C_3$-$C_6$cycloalkyl, $C_3$-$C_6$halocycloalkyl, phenyl, phenyl substituted with (Z)$_{p1}$, D-1 to D-4, D-8 to D-38, D-47 to D-55, E-4 to E-12, E-18, E-19, E-32, E-35, E-43, M-2, M-3, M-5, M-8, M-9 or M-10), $C_3$-$C_8$cycloalkyl and $C_3$-$C_8$halocycloalkyl.

$R^1$-II: $C_1$-$C_6$alkyl arbitrarily substituted with —OR$^{25}$ wherein $R^{25}$ is $C_1$-$C_6$alkyl, $C_1$-$C_6$haloalkyl, $C_1$-$C_6$alkylcarbonyl, $C_1$-$C_6$alkoxycarbonyl, $C_1$-$C_6$alkylaminocarbonyl, di($C_1$-$C_6$alkyl)aminocarbonyl or $C_1$-$C_6$alkylsulfonyl.

$R^1$-III: $C_1$-$C_6$alkyl arbitrarily substituted with —N(R$^{26}$)R$^{25}$ wherein $R^{25}$ is $C_1$-$C_6$alkyl, $C_1$-$C_6$haloalkyl, $C_1$-$C_6$alkylcarbonyl, $C_1$-$C_6$alkoxycarbonyl, $C_1$-$C_6$alkylaminocarbonyl, di($C_1$-$C_6$alkyl)aminocarbonyl or $C_1$-$C_6$alkylsulfonyl, $R^{26}$ is hydrogen or $C_1$-$C_6$alkyl.

$R^1$-IV: $C_1$-$C_6$alkyl arbitrarily substituted with —S(O)$_r$R$^{27}$ wherein $R^{27}$ is $C_1$-$C_6$alkyl, $C_1$-$C_6$haloalkyl or tri($C_1$-$C_4$alkyl) silyl $C_1$-$C_4$alkyl, r is an integer of 0 to 2.

$R^1$-V: $C_1$-$C_6$alkyl arbitrarily substituted with $R^{16}$ wherein $R^{16}$ is cyano, —C(O)R$^{28}$, —C(O)OR$^{28}$, —C(O)NHR$^{29}$, —C(O)N(R$^{29}$)R$^{28}$, —C(O)N(R$^{29}$)OR$^{28}$, —C(S)NHR$^{29}$, —C(S)N(R$^{29}$)R$^{28}$, —SO$_2$NHR$^{29}$, —SO$_2$N(R$^{29}$)R$^{28}$, —C(R$^{31}$)=NOH, —C(R$^{31}$)=NOR$^{30}$, —C(=NR$^{31}$)OR$^{30}$ or —C(=NR$^{31}$)SR$^{30}$, $R^{28}$ is $C_1$-$C_6$alkyl, $C_1$-$C_6$haloalkyl, $C_3$-$C_6$cycloalkyl $C_1$-$C_4$alkyl, $C_1$-$C_6$alkoxy $C_1$-$C_4$alkyl, $C_1$-$C_6$alkylthio $C_1$-$C_4$alkyl, cyano $C_1$-$C_6$alkyl, phenyl $C_1$-$C_4$alkyl, phenyl $C_1$-$C_4$alkyl substituted with (Z)$_{p1}$, $C_3$-$C_6$cycloalkyl, $C_3$-$C_6$alkenyl, $C_3$-$C_6$haloalkenyl, $C_3$-$C_6$alkynyl, phenyl or phenyl substituted with (Z)$_{p1}$, $R^{29}$ is hydrogen atom, $C_1$-$C_6$alkyl, $C_3$-$C_6$alkenyl or $C_3$-$C_6$alkynyl, $R^{30}$ is $C_1$-$C_6$alkyl or $C_3$-$C_6$cycloalkyl $C_1$-$C_4$alkyl, $R^{31}$ is hydrogen atom or $C_1$-$C_6$alkyl, or $R^{31}$ together with $R^{30}$ may for 5- or 6-membered ring with the atom bonding them by forming $C_2$-$C_3$alkylene chain.

$R^1$-VI: $C_3$-$C_6$alkenyl, $C_3$-$C_6$haloalkenyl, $C_3$-$C_6$alkynyl, $C_3$-$C_6$haloalkynyl, phenyl substituted with (Z)$_{p1}$, D-8, D-10, D-11, D-13 to D-15, D-17, D-18, D-21 to D-23, D-26 to D-37, D-39, D-40, D-42, D-45, D-47 to D-54, D-56, D-58, E-4, E-5, E-7 and E-9.

$R^1$-VII: —N(R$^{20}$)R$^{19}$ wherein $R^{19}$ is $C_1$-$C_6$haloalkyl, $C_3$-$C_6$cycloalkyl, —C(O)R$^{28}$, —C(O)OR$^{28}$, —C(O)NHR$^{29}$, —C(O)N(R$^{29}$)R$^{28}$, —C(S)NHR$^{29}$, —C(S)N(R$^{29}$)R$^{28}$, phenyl, phenyl substituted with (Z)$_{p1}$, D-3, D-4, D-21, D-47, D-50, D-51, D-53 or D-54, $R^{20}$ is hydrogen atom, $C_1$-$C_6$alkyl, $C_1$-$C_4$alkoxy $C_1$-$C_4$alkyl, $C_1$-$C_4$alkylthio $C_1$-$C_4$alkyl, cyano $C_1$-$C_6$alkyl, $C_3$-$C_6$alkenyl, $C_3$-$C_6$alkynyl, —CHO, $C_1$-$C_6$alkylcarbonyl, $C_1$-$C_6$alkoxycarbonyl or $C_1$-$C_6$alkylsulfonyl, $R^{28}$ is $C_1$-$C_6$alkyl, $C_1$-$C_6$haloalkyl, $C_3$-$C_6$cycloalkyl $C_1$-$C_4$alkyl, $C_1$-$C_6$alkoxy $C_1$-$C_4$alkyl, $C_1$-$C_6$alkylthio $C_1$-$C_4$alkyl, cyano $C_1$-$C_6$alkyl, phenyl $C_1$-$C_4$alkyl, phenyl $C_1$-$C_4$alkyl substituted with (Z)$_{p1}$, $C_3$-$C_6$cycloalkyl, $C_3$-$C_6$alkenyl, $C_3$-$C_6$haloalkenyl, $C_3$-$C_6$alkynyl, phenyl or phenyl substituted with (Z)$_{p1}$, $R^{29}$ is hydrogen atom, $C_1$-$C_6$alkyl, $C_3$-$C_6$alkenyl or $C_3$-$C_6$alkynyl.

$R^1$-VIII: $C_1$-$C_6$alkyl, $C_1$-$C_6$haloalkyl, $C_1$-$C_6$alkyl arbitrarily substituted with $R^{16}$ (wherein $R^{16}$ is cyano, $C_3$-$C_6$cycloalkyl, $C_3$-$C_6$halocycloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_1$-$C_6$alkylcarbonyl, —C(O)OR$^{28}$, —C(O)NHR$^{29}$, —C(O)N(R$^{29}$)R$^{28}$, —C(S)NH$_2$, —C(R$^{31}$)=NOH, —C(R$^{31}$)=NOR$^{30}$, phenyl, phenyl substituted with (Z)$_{p1}$, D-1 to D-4, D-8 to D-38, D-47 to D-55, E-4 to E-7, E-10, E-11 or E-32, $R^{28}$ is $C_1$-$C_6$alkyl, $C_1$-$C_6$haloalkyl, $C_3$-$C_6$cycloalkyl $C_1$-$C_4$alkyl, $C_3$-$C_6$cycloalkyl, $C_3$-$C_8$alkenyl or $C_3$-$C_8$alkynyl, $R^{29}$ is hydrogen atom or $C_1$-$C_6$alkyl, $R^{30}$ is $C_1$-$C_6$alkyl, $R^{31}$ is hydrogen or $C_1$-$C_6$alkyl), $C_3$-$C_6$cycloalkyl, E-4, E-5, $C_3$-$C_6$alkenyl, $C_3$-$C_6$haloalkenyl, $C_3$-$C_6$alkynyl, —N(R$^{20}$)R$^{19}$ (wherein $R^{19}$ is $C_1$-$C_6$haloalkyl, —C(O)R$^{28}$, —C(O)OR$^{28}$, phenyl, phenyl substituted with (Z)$_{p1}$, D-3, D-4, D-21, D-47, D-50, D-51, D-53 or D-54, $R^{20}$ is hydrogen atom or $C_1$-$C_6$alkyl, $R^{28}$ is $C_1$-$C_6$alkyl, $C_1$-$C_6$haloalkyl, $C_3$-$C_6$cycloalkyl $C_1$-$C_4$alkyl, $C_3$-$C_6$cycloalkyl, $C_3$-$C_8$alkenyl or $C_3$-$C_8$alkynyl), phenyl substituted with (Z)$_{p1}$, D-8, D-10, D-13 to D-15, D-18, D-21, D-34, D-35, D-47, D-48, D-50 to D-53 and D-54.

$R^1$-IX: $C_1$-$C_6$haloalkyl, $C_1$-$C_6$alkyl arbitrarily substituted with $R^{16}$ (wherein $R^{16}$ is cyano, $C_3$-$C_6$cycloalkyl, $C_3$-$C_6$halocycloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_1$-$C_6$alkylcarbonyl, —C(O)OR$^{28}$, —C(O)NHR$^{29}$, —C(O)N(R$^{29}$)R$^{28}$, —C(S)NH$_2$, —C(R$^{31}$) =NOH, —C(R$^{31}$)=NOR$^{30}$, phenyl substituted with (Z)$_{p1}$, D-1 to D-4, D-8 to D-38, D-47 to D-55, E-4 to E-7, E-10, E-11 or E-32, $R^{28}$ is $C_1$-$C_6$alkyl, $C_1$-$C_6$haloalkyl, $C_3$-$C_6$cycloalkyl $C_1$-$C_4$alkyl, $C_3$-$C_6$cycloalkyl, $C_3$-$C_8$alkenyl or $C_3$-$C_8$alkynyl, $R^{29}$ is hydrogen atom or $C_1$-$C_6$alkyl, $R^{30}$ is $C_1$-$C_6$alkyl, $R^{31}$ is hydrogen or $C_1$-$C_6$alkyl), $C_3$-$C_6$cycloalkyl, E-4, E-5, $C_3$-$C_6$alkenyl, $C_3$-$C_6$haloalkenyl, $C_3$-$C_6$alkynyl, —N(R$^{20}$) R$^{19}$ (wherein $R^{19}$ is $C_1$-$C_6$haloalkyl, —C(O)R$^{28}$, —C(O) OR$^{28}$, phenyl, phenyl substituted with (Z)$_{p1}$, D-3, D-4, D-21, D-47, D-50, D-51, D-53 or D-54, $R^{20}$ is hydrogen atom or $C_1$-$C_6$alkyl, $R^{28}$ is $C_1$-$C_6$alkyl, $C_1$-$C_6$haloalkyl, $C_3$-$C_6$cycloalkyl $C_1$-$C_4$alkyl, $C_3$-$C_6$cycloalkyl, $C_3$-$C_8$alkenyl or $C_3$-$C_8$alkynyl), phenyl substituted with (Z)$_{p1}$, D-8, D-10, D-13 to D-15, D-18, D-21, D-34, D-35, D-47, D-48, D-50 to D-53 and D-54.

R$^1$-X: C$_1$-C$_8$haloalkyl, C$_1$-C$_6$alkyl arbitrarily substituted with R$^{16}$ (wherein R$^{16}$ is C$_3$-C$_6$cycloalkyl, C$_1$-C$_6$alkoxy, C$_1$-C$_6$alkylthio, C$_1$-C$_6$alkylsulfinyl, C$_1$-C$_6$alkylsulfonyl, —C(O)NH$_2$, —C(O)NHR$^{28}$, —C(S)NH$_2$, —C(R$^{31}$)=NOH, —C(R$^{31}$)=NOR$^{30}$, D-1 to D-4, D-8 to D-38, D-47 to D-54, E-4 to E-7, E-10, E-11 or E-32, R$^{28}$ is C$_1$-C$_6$alkyl, C$_1$-C$_6$haloalkyl, C$_3$-C$_6$cycloalkyl, C$_3$-C$_8$alkenyl or C$_3$-C$_8$alkynyl, R$^{30}$ is C$_1$-C$_6$alkyl, R$^{31}$ is hydrogen or C$_1$-C$_6$alkyl), C$_3$-C$_6$cycloalkyl, E-4, E-5, C$_3$-C$_8$alkenyl, C$_3$-C$_8$haloalkenyl, C$_3$-C$_8$alkynyl, —N(R$^{20}$)R$^{19}$ (wherein R$^{19}$ is C$_1$-C$_6$haloalkyl, —C(O)R$^{28}$, —C(O)OR$^{28}$, phenyl, D-3, D-4, D-21, D-47, D-50, D-51, D-53 or D-54, R$^{20}$ is hydrogen atom or C$_1$-C$_6$alkyl, R$^{28}$ is C$_1$-C$_6$alkyl, C$_1$-C$_6$haloalkyl, C$_3$-C$_6$cycloalkyl C$_1$-C$_4$alkyl, C$_3$-C$_6$cycloalkyl, C$_3$-C$_8$alkenyl or C$_3$-C$_8$alkynyl), D-8, D-10, D-13 to D-15, D-18, D-21, D-34, D-35, D-47, D-48, D-50 to D-53 and D-54.

R$^1$-XI: C$_1$-C$_6$alkyl and phenyl C$_1$-C$_6$alkyl.

R$^1$-XII: C$_1$-C$_8$alkyl, C$_1$-C$_8$alkyl arbitrarily substituted with R$^{16}$ (wherein R$^{16}$ is halogen atom, C$_3$-C$_6$cycloalkyl, C$_3$-C$_6$halocycloalkyl, phenyl, phenyl substituted with (Z)$_{p1}$, D-1 to D-4, D-8 to D-42, D-47 to D-55, E-4 to E-12, E-14, E-16 to E-19, E-21 to E-23, E-26 to E-35, E-40 to E-45, E-48, M-2, M-3, M-5, M-8 to M-10, M-14, M-15 or M-16), C$_3$-C$_8$cycloalkyl and C$_3$-C$_8$halocycloalkyl.

R$^1$-XIII: C$_1$-C$_8$alkyl arbitrarily substituted with —OR$^{25}$ wherein R$^{25}$ is hydrogen atom, C$_1$-C$_6$alkyl, C$_1$-C$_6$haloalkyl, —C(O)R$^{33}$, —C(O)OR$^{33}$, —C(O)NHR$^{34}$, —C(O)N(R$^{34}$)R$^{33}$, —C(S)NHR$^{34}$, —C(S)N(R$^{34}$)R$^{33}$, —S(O)$_2$R$^{33}$, —S(O)$_2$N(R$^{34}$)R$^{33}$, di(C$_1$-C$_6$alkyl)thiophosphoryl, phenyl or phenyl substituted with (Z)$_{p1}$, R$^{33}$ is C$_1$-C$_6$alkyl, C$_1$-C$_6$haloalkyl, C$_3$-C$_6$cycloalkyl, C$_3$-C$_6$halocycloalkyl, phenyl C$_1$-C$_4$alkyl, phenyl C$_1$-C$_4$alkyl substituted with (Z)$_{p1}$, C$_3$-C$_6$alkenyl, C$_3$-C$_6$alkynyl, phenyl or phenyl substituted with (Z)$_{p1}$, R$^{34}$ is hydrogen atom or C$_1$-C$_6$alkyl.

R$^1$-XIV: C$_1$-C$_8$alkyl arbitrarily substituted with —N(R$^{26}$)R$^{25}$ wherein R$^{25}$ is C$_1$-C$_6$alkyl, C$_1$-C$_6$haloalkyl, —C(O)R$^{33}$, —C(O)OR$^{33}$, —C(O)SR$^{33}$, —C(O)NHR$^{34}$, —C(O)N(R$^{34}$)R$^{33}$, —C(S)R$^{33}$, —C(S)OR$^{33}$, —C(S)SR$^{33}$, —C(S)NHR$^{34}$, —C(S)N(R$^{34}$)R$^{33}$, —S(O)$_2$R$^{33}$ or —S(O)$_2$N(R$^{34}$)R$^{33}$, R$^{26}$ is hydrogen atom or C$_1$-C$_6$alkyl, or R$^{26}$ together with R$^{25}$ may form 4- to 6-membered ring with the nitrogen atom bonding them by forming C$_3$-C$_5$alkylene chain, in this case, the alkylene chain may contain one oxygen atom, sulfur atom or nitrogen atom, and may be substituted with C$_1$-C$_6$alkyl, oxo or thioxo, R$^{33}$ is C$_1$-C$_6$alkyl, C$_1$-C$_6$haloalkyl, C$_3$-C$_6$cycloalkyl, C$_3$-C$_6$halocycloalkyl, phenyl C$_1$-C$_4$alkyl, phenyl C$_1$-C$_4$alkyl substituted with (Z)$_{p1}$, C$_3$-C$_6$alkenyl, C$_3$-C$_6$alkynyl, phenyl or phenyl substituted with (Z)$_{p1}$, R$^{34}$ is hydrogen atom or C$_1$-C$_6$alkyl.

R$^1$-XV: C$_1$-C$_8$alkyl arbitrarily substituted with —S(O)$_r$R$^{27}$ wherein R$^{27}$ is C$_1$-C$_6$alkyl, C$_1$-C$_6$haloalkyl, tri(C$_1$-C$_4$alkyl)silyl C$_1$-C$_4$alkyl, C$_1$-C$_6$alkylthio, —C(O)NHR$^{34}$, —C(O)N(R$^{34}$)R$^{33}$, —C(S)NHR$^{34}$, —C(S)N(R$^{34}$)R$^{33}$, phenyl, phenyl substituted with (Z)$_{p1}$, D-47 or D-50, R$^{33}$ is C$_1$-C$_6$alkyl, C$_1$-C$_6$haloalkyl, C$_3$-C$_6$cycloalkyl, C$_3$-C$_6$halocycloalkyl, phenyl C$_1$-C$_4$alkyl, phenyl C$_1$-C$_4$alkyl substituted with (Z)$_{p1}$, C$_3$-C$_6$alkenyl, C$_3$-C$_6$alkynyl, phenyl or phenyl substituted with (Z)$_{p1}$, R$^{34}$ is hydrogen atom or C$_1$-C$_6$alkyl, r is an integer of 0 to 2.

R$^1$-XVI: C$_1$-C$_8$alkyl arbitrarily substituted with R$^{16}$ wherein R$^{16}$ is cyano, —SO$_2$NHR$^{29}$, —SO$_2$N(R$^{29}$)R$^{28}$, —CHO, —C(O)R$^{28}$, —C(O)OR$^{28}$, —C(O)NHR$^{29}$, —C(O)N(R$^{29}$)R$^{28}$, C(S)NHR$^{29}$, —C(S)N(R$^{29}$)R$^{28}$, —C(R$^{31}$)=NOH, —C(R$^{31}$)=NOR$^{30}$, —C(=NR$^{31}$)OR$^{30}$, —C(=NR$^{31}$)SR$^{30}$, —C(=NR$^{31}$)N(R$^{30}$)R$^{29}$, —C(=NOR$^{31}$)NHR$^{29}$ or —C(=NOR$^{31}$)N(R$^{30}$)R$^{29}$, R$^{28}$ is C$_1$-C$_6$alkyl, C$_1$-C$_6$alkyl arbitrarily substituted with R$^{32}$, C$_3$-C$_6$cycloalkyl, C$_3$-C$_6$halocycloalkyl, C$_3$-C$_6$alkenyl, C$_3$-C$_6$haloalkenyl, C$_3$-C$_6$alkynyl, C$_3$-C$_6$haloalkenyl, phenyl or phenyl substituted with (Z)$_{p1}$, R$^{29}$ is hydrogen atom, C$_1$-C$_6$alkyl, C$_3$-C$_6$alkenyl or C$_3$-C$_6$alkynyl, or R$^{29}$ together with R$^{28}$ may form 3- to 6-membered ring with the nitrogen atom bonding them by forming C$_2$-C$_5$alkylene chain, in this case, the alkylene chain may contain one oxygen atom or sulfur atom, R$^{30}$ is C$_1$-C$_6$alkyl, C$_3$-C$_6$cycloalkyl C$_1$-C$_4$alkyl, phenyl C$_1$-C$_4$alkyl, phenyl C$_1$-C$_4$alkyl substituted with (Z)$_{p1}$, C$_3$-C$_8$alkenyl or C$_3$-C$_8$alkynyl, R$^{31}$ is hydrogen atom or C$_1$-C$_6$alkyl, or R$^{31}$ together with R$^{30}$ may form 5- or 6-membered ring with the atom bonding them by forming C$_2$-C$_3$alkylene chain, in this case, the alkylene chain may be arbitrarily substituted with C$_1$-C$_6$alkyl, R$^{32}$ is halogen atom, cyano, C$_3$-C$_6$cycloalkyl, C$_3$-C$_6$halocycloalkyl, C$_1$-C$_4$alkoxy, C$_1$-C$_4$haloalkoxy, C$_1$-C$_4$alkylthio, C$_1$-C$_4$haloalkylthio, C$_1$-C$_4$alkoxycarbonyl, —C(O)NH$_2$, C$_1$-C$_4$alkylaminocarbonyl, di(C$_1$-C$_4$alkyl)aminocarbonyl, phenyl or phenyl substituted with (Z)$_{p1}$.

R$^1$-XVII: C$_3$-C$_8$alkenyl, C$_3$-C$_8$haloalkenyl, C$_3$-C$_8$alkynyl, C$_3$-C$_8$haloalkynyl, phenyl substituted with (Z)$_{p1}$, D-8 to D-18, D-21 to D-24, D-26 to D-40, D-42, D-45 to D-58, E-4, E-5, E-7, E-9, E-23 to E-25, E-27, E-28, E-30, E-31 and E-34.

R$^1$-XVIII: —N(R$^{20}$)R$^{19}$ wherein R$^{19}$ is C$_1$-C$_6$alkyl, C$_1$-C$_6$haloalkyl, C$_3$-C$_6$cycloalkyl C$_1$-C$_6$alkyl, phenyl C$_1$-C$_6$alkyl, phenyl C$_1$-C$_6$alkyl substituted with (Z)$_{p1}$, C$_3$-C$_6$cycloalkyl, C$_3$-C$_6$alkenyl, C$_3$-C$_6$haloalkenyl, C$_3$-C$_6$alkynyl, —C(O)R$^{28}$, —C(O)OR$^{28}$, —C(O)NHR$^{29}$, —C(O)N(R$^{29}$)R$^{28}$, —C(S)NHR$^{29}$, —C(S)N(R$^{29}$)R$^{28}$, C$_1$-C$_6$alkylsulfonyl, C$_1$-C$_6$haloalkylsulfonyl, phenylsulfonyl, phenylsulfonyl substituted with (Z)$_{p1}$, phenyl, phenyl substituted with (Z)$_{p1}$, D-1 to D-4, D-18, D-21, D-25, D-30 to D-35, D-47 to D-55 or D-56, R$^{20}$ is hydrogen atom, C$_1$-C$_6$alkyl, C$_1$-C$_4$alkoxy C$_1$-C$_4$alkyl, C$_1$-C$_4$alkylthio C$_1$-C$_4$alkyl, cyano C$_1$-C$_4$alkyl, C$_3$-C$_6$alkenyl, C$_3$-C$_6$alkynyl, —CHO, C$_1$-C$_6$alkylcarbonyl, C$_1$-C$_6$haloalkylcarbonyl, C$_1$-C$_6$alkoxycarbonyl, C$_1$-C$_6$haloalkoxycarbonyl or C$_1$-C$_6$alkylsulfonyl, R$^{28}$ is C$_1$-C$_6$alkyl, C$_1$-C$_6$alkyl arbitrarily substituted with R$^{32}$, C$_3$-C$_6$cycloalkyl, C$_3$-C$_6$halocycloalkyl, C$_3$-C$_6$alkenyl, C$_3$-C$_6$haloalkenyl, C$_3$-C$_6$alkynyl, C$_3$-C$_6$haloalkynyl, phenyl or phenyl substituted with (Z)$_{p1}$, R$^{29}$ is hydrogen atom, C$_1$-C$_6$alkyl, C$_3$-C$_6$alkenyl or C$_3$-C$_6$alkynyl, R$^{29}$ together with R$^{28}$ may form 3- to 6-membered ring with the nitrogen atom bonding them by forming C$_2$-C$_5$alkylene chain, in this case, the alkylene chain may contain one oxygen atom or sulfur atom, R$^{32}$ is hydrogen atom, cyano, C$_3$-C$_6$cycloalkyl, C$_3$-C$_6$halocycloalkyl, C$_1$-C$_4$alkoxy, C$_1$-C$_4$haloalkoxy, C$_1$-C$_4$alkylthio, C$_1$-C$_4$haloalkylthio, C$_1$-C$_4$alkoxycarbonyl, —C(O)NH$_2$, C$_1$-C$_4$alkylaminocarbonyl, di(C$_1$-C$_4$alkyl)aminocarbonyl, phenyl or phenyl substituted with (Z)$_{p1}$.

In the compounds included in the present invention, the substituent R$^2$ includes for example the following groups. That is, R$^2$-I: hydrogen atom.

R$^2$-II: C$_1$-C$_6$alkyl, C$_1$-C$_6$haloalkyl and C$_3$-C$_6$cycloalkyl.

R$^2$-III: C$_1$-C$_4$alkoxy C$_1$-C$_4$alkyl, C$_1$-C$_4$alkylthio C$_1$-C$_4$alkyl and cyano C$_1$-C$_6$alkyl.

R$^2$-IV: C$_3$-C$_6$alkenyl and C$_3$-C$_6$alkynyl.

R$^2$-V: —OH, C$_1$-C$_6$alkoxy, C$_1$-C$_6$alkylcarbonyloxy, C$_1$-C$_6$alkoxycarbonyloxy and C$_1$-C$_6$alkylsulfonyloxy.

R$^2$-VI: C$_1$-C$_6$haloalkylthio, phenylthio, phenylthio substituted with (Z)$_{p1}$ and —SN(R$^{18}$)R$^{17}$ wherein R$^{17}$ is C$_1$-C$_6$alkyl, C$_1$-C$_6$alkoxycarbonyl C$_1$-C$_4$alkyl or C$_1$-C$_6$alkoxycarbonyl, R$^{18}$ is C$_1$-C$_6$alkyl or benzyl.

R$^2$-VII: —NHR$^{20}$ (wherein R$^{20}$ is hydrogen atom, C$_1$-C$_6$alkyl, —CHO, C$_1$-C$_6$alkylcarbonyl, C$_1$-C$_6$alkoxycarbonyl or C$_1$-C$_6$alkylsulfonyl), —N=CHR$^{19b}$ and —N=C(R$^{19b}$)R$^{19a}$ wherein R$^{19a}$ is C$_1$-C$_6$alkyl, R$^{19b}$ is hydrogen atom or C$_1$-C$_6$alkyl.

R$^2$-VIII: —C(O)R$^9$, —C(O)OR$^9$, —C(O)SR$^9$, —C(S)OR$^9$, —C(S)SR$^9$ (wherein R$^9$ is C$_1$-C$_6$alkyl, C$_1$-C$_6$haloalkyl, C$_3$-C$_6$cycloalkyl C$_1$-C$_4$alkyl, C$_1$-C$_6$alkoxy C$_1$-C$_4$alkyl, C$_1$-C$_6$alkylthio C$_1$-C$_4$alkyl, cyano C$_1$-C$_6$alkyl, phenyl C$_1$-C$_4$alkyl, C$_3$-C$_8$cycloalkyl, C$_3$-C$_8$halocycloalkyl, C$_3$-C$_6$alkenyl or C$_3$-C$_6$alkynyl) and C$_1$-C$_6$alkylsulfonyl.

R$^2$-IX: 3- to 7-membered ring that R$^2$ forms together with R$^1$ is aziridine, azetidine, pyrrolidine, oxazolidine, thiazoridine, piperidine, morpholine, thiomorpholine and homopiperidine.

R$^2$-X: hydrogen atom, C$_1$-C$_6$alkyl, C$_1$-C$_4$alkoxy C$_1$-C$_4$alkyl, C$_1$-C$_4$alkylthio C$_1$-C$_4$alkyl, cyano C$_1$-C$_6$alkyl, C$_3$-C$_6$cycloalkyl, C$_3$-C$_6$alkenyl, C$_3$-C$_6$alkynyl, —OH, C$_1$-C$_6$alkylcarbonyloxy, C$_1$-C$_6$alkylsulfonyloxy, —NH$_2$, —C(O)R$^9$, —C(O)OR$^9$, —C(O)SR$^9$, —C(S)OR$^9$ and —C(S)SR$^9$ wherein R$^9$ is C$_1$-C$_6$alkyl, C$_1$-C$_6$haloalkyl, C$_3$-C$_6$cycloalkyl C$_1$-C$_4$alkyl, C$_1$-C$_6$alkoxy C$_1$-C$_4$alkyl, C$_1$-C$_6$alkylthio C$_1$-C$_4$alkyl, cyano C$_1$-C$_6$alkyl, C$_3$-C$_8$cycloalkyl, C$_3$-C$_6$alkenyl or C$_3$-C$_6$alkynyl.

R$^2$-XI: hydrogen atom, C$_1$-C$_6$alkyl, C$_1$-C$_4$alkoxy C$_1$-C$_4$alkyl, cyano C$_1$-C$_6$alkyl, C$_3$-C$_6$alkynyl, —C(O)R$^9$ and —C(O)OR$^9$ wherein R$^9$ is C$_1$-C$_6$alkyl, C$_1$-C$_6$alkoxy C$_1$-C$_4$alkyl, C$_1$-C$_6$alkylthio C$_1$-C$_4$alkyl, C$_3$-C$_8$cycloalkyl, C$_3$-C$_6$alkenyl or C$_3$-C$_6$alkynyl.

In the compounds included in the present invention, the substituent R$^3$ includes for example the following groups. That is, R$^3$-I: C$_1$-C$_6$haloalkyl and C$_3$-C$_8$halocycloalkyl.

R$^3$-II: C$_1$-C$_6$alkyl, C$_3$-C$_8$cycloalkyl, E-4 to E-7, E-23 to E-27 and E-28.

R$^3$-III: C$_1$-C$_4$alkoxy C$_1$-C$_4$haloalkyl, C$_1$-C$_4$haloalkoxy C$_1$-C$_4$haloalkyl, C$_1$-C$_4$alkylthio C$_1$-C$_4$haloalkyl, C$_1$-C$_4$alkylsulfinyl C$_1$-C$_4$haloalkyl, C$_1$-C$_4$alkylsulfonyl C$_1$-C$_4$haloalkyl, C$_1$-C$_4$haloalkylthio C$_1$-C$_4$haloalkyl, C$_1$-C$_4$haloalkylsulfinyl C$_1$-C$_4$haloalkyl, C$_1$-C$_4$haloalkylsulfonyl C$_1$-C$_4$haloalkyl and cyano C$_1$-C$_6$haloalkyl.

R$^3$-IV: C$_3$-C$_6$cycloalkyl C$_1$-C$_4$alkyl, C$_3$-C$_6$halocycloalkyl C$_1$-C$_4$alkyl, C$_1$-C$_4$alkoxy C$_1$-C$_4$alkyl, C$_1$-C$_4$haloalkoxy C$_1$-C$_4$alkyl, C$_1$-C$_4$alkylthio C$_1$-C$_4$alkyl, C$_1$-C$_4$alkylsulfinyl C$_1$-C$_4$alkyl, C$_1$-C$_4$alkylsulfonyl C$_1$-C$_4$alkyl, C$_1$-C$_4$haloalkylthio C$_1$-C$_4$alkyl, C$_1$-C$_4$haloalkylsulfinyl C$_1$-C$_4$alkyl, C$_1$-C$_4$haloalkylsulfonyl C$_1$-C$_4$alkyl and cyano C$_1$-C$_6$alkyl.

R$^3$-V: C$_1$-C$_6$haloalkyl, C$_1$-C$_4$alkoxy C$_1$-C$_4$haloalkyl, C$_1$-C$_4$haloalkoxy C$_1$-C$_4$haloalkyl, C$_1$-C$_4$alkylthio C$_1$-C$_4$haloalkyl, C$_1$-C$_4$haloalkylthio C$_1$-C$_4$haloalkyl, cyano C$_1$-C$_6$haloalkyl and C$_3$-C$_8$halocycloalkyl.

R$^3$-VI: C$_1$-C$_6$haloalkyl.

R$^3$-VII: C$_1$-C$_6$alkyl arbitrarily substituted with two or more arbitrary halogen atoms.

Each group showing the scope of each substituent in the compounds included in the present invention can be arbitrarily combined one another, and all combination thereof falls within the scope of the present invention. Examples of the combination of the scope of X, Y and R$^1$ include for example the combination shown in Table 1. In the meantime, the combination of Table 1 is for illustrative purposes, and the present invention is not limited thereto.

TABLE 1

| X | Y | R$^1$ |
| --- | --- | --- |
| X-I | Y-I | R$^1$-I |
| X-I | Y-I | R$^1$-II |
| X-I | Y-I | R$^1$-III |
| X-I | Y-I | R$^1$-IV |
| X-I | Y-I | R$^1$-V |
| X-I | Y-I | R$^1$-VI |
| X-I | Y-I | R$^1$-VII |
| X-I | Y-I | R$^1$-VIII |
| X-I | Y-I | R$^1$-IX |
| X-I | Y-I | R$^1$-X |
| X-I | Y-I | R$^1$-XI |
| X-I | Y-II | R$^1$-I |
| X-I | Y-II | R$^1$-II |
| X-I | Y-II | R$^1$-III |
| X-I | Y-II | R$^1$-IV |
| X-I | Y-II | R$^1$-V |
| X-I | Y-II | R$^1$-VI |
| X-I | Y-II | R$^1$-VII |
| X-I | Y-II | R$^1$-VIII |
| X-I | Y-II | R$^1$-IX |
| X-I | Y-II | R$^1$-X |
| X-I | Y-II | R$^1$-XI |
| X-I | Y-III | R$^1$-I |
| X-I | Y-III | R$^1$-VII |
| X-I | Y-III | R$^1$-VIII |
| X-I | Y-III | R$^1$-IX |
| X-I | Y-III | R$^1$-X |
| X-I | Y-IV | R$^1$-I |
| X-I | Y-IV | R$^1$-II |
| X-I | Y-IV | R$^1$-III |
| X-I | Y-IV | R$^1$-IV |
| X-I | Y-IV | R$^1$-V |
| X-I | Y-IV | R$^1$-VI |
| X-I | Y-IV | R$^1$-VII |
| X-I | Y-IV | R$^1$-VIII |
| X-I | Y-IV | R$^1$-IX |
| X-I | Y-IV | R$^1$-X |
| X-I | Y-IV | R$^1$-XI |
| X-I | Y-V | R$^1$-I |
| X-I | Y-V | R$^1$-II |
| X-I | Y-V | R$^1$-III |
| X-I | Y-V | R$^1$-IV |
| X-I | Y-V | R$^1$-V |
| X-I | Y-V | R$^1$-VI |
| X-I | Y-V | R$^1$-VII |
| X-I | Y-V | R$^1$-VIII |
| X-I | Y-V | R$^1$-IX |
| X-I | Y-V | R$^1$-X |
| X-I | Y-V | R$^1$-XI |
| X-I | Y-VI | R$^1$-I |
| X-I | Y-VI | R$^1$-II |
| X-I | Y-VI | R$^1$-III |
| X-I | Y-VI | R$^1$-IV |
| X-I | Y-VI | R$^1$-V |
| X-I | Y-VI | R$^1$-VI |
| X-I | Y-VI | R$^1$-VII |
| X-I | Y-VI | R$^1$-VIII |
| X-I | Y-VI | R$^1$-IX |
| X-I | Y-VI | R$^1$-X |
| X-I | Y-VI | R$^1$-XI |
| X-II | Y-I | R$^1$-I |
| X-II | Y-I | R$^1$-II |
| X-II | Y-I | R$^1$-III |
| X-II | Y-I | R$^1$-IV |
| X-II | Y-I | R$^1$-V |
| X-II | Y-I | R$^1$-VI |
| X-II | Y-I | R$^1$-VII |
| X-II | Y-I | R$^1$-VIII |
| X-II | Y-I | R$^1$-IX |
| X-II | Y-I | R$^1$-X |
| X-II | Y-II | R$^1$-X |
| X-II | Y-III | R$^1$-X |
| X-II | Y-IV | R$^1$-X |
| X-II | Y-V | R$^1$-X |
| X-II | Y-VI | R$^1$-I |
| X-II | Y-VI | R$^1$-II |
| X-II | Y-VI | R$^1$-III |
| X-II | Y-VI | R$^1$-IV |
| X-II | Y-VI | R$^1$-V |
| X-II | Y-VI | R$^1$-VI |
| X-II | Y-VI | R$^1$-VII |

TABLE 1-continued

| X | Y | R¹ |
|---|---|---|
| X-II | Y-VI | R¹-VIII |
| X-II | Y-VI | R¹-IX |
| X-II | Y-VI | R¹-X |
| X-III | Y-I | R¹-I |
| X-III | Y-I | R¹-II |
| X-III | Y-I | R¹-III |
| X-III | Y-I | R¹-IV |
| X-III | Y-I | R¹-V |
| X-III | Y-I | R¹-VI |
| X-III | Y-I | R¹-VII |
| X-III | Y-I | R¹-VIII |
| X-III | Y-I | R¹-IX |
| X-III | Y-I | R¹-X |
| X-III | Y-I | R¹-XI |
| X-III | Y-II | R¹-X |
| X-III | Y-III | R¹-X |
| X-III | Y-IV | R¹-X |
| X-III | Y-V | R¹-X |
| X-III | Y-VI | R¹-I |
| X-I | Y-I | R¹-XII |
| X-I | Y-I | R¹-XIII |
| X-I | Y-I | R¹-XIV |
| X-I | Y-I | R¹-XV |
| X-I | Y-I | R¹-XVI |
| X-I | Y-I | R¹-XVII |
| X-I | Y-I | R¹-XVIII |
| X-III | Y-I | R¹-XII |
| X-III | Y-I | R¹-XIII |
| X-III | Y-I | R¹-XIV |
| X-III | Y-I | R¹-XV |
| X-III | Y-I | R¹-XVI |
| X-III | Y-I | R¹-XVII |
| X-III | Y-I | R¹-XVIII |
| X-III | Y-VI | R¹-II |
| X-III | Y-VI | R¹-III |
| X-III | Y-VI | R¹-IV |
| X-III | Y-VI | R¹-V |
| X-III | Y-VI | R¹-VI |
| X-III | Y-VI | R¹-VII |
| X-III | Y-VI | R¹-VIII |
| X-III | Y-VI | R¹-IX |
| X-III | Y-VI | R¹-X |
| X-III | Y-VI | R¹-XI |
| X-IV | Y-I | R¹-I |
| X-IV | Y-I | R¹-II |
| X-IV | Y-I | R¹-III |
| X-IV | Y-I | R¹-IV |
| X-IV | Y-I | R¹-V |
| X-IV | Y-I | R¹-VI |
| X-IV | Y-I | R¹-VII |
| X-IV | Y-I | R¹-VIII |
| X-IV | Y-I | R¹-IX |
| X-IV | Y-I | R¹-X |
| X-IV | Y-I | R¹-XI |
| X-IV | Y-II | R¹-X |
| X-IV | Y-III | R¹-X |
| X-IV | Y-IV | R¹-X |
| X-IV | Y-V | R¹-X |
| X-IV | Y-VI | R¹-I |
| X-IV | Y-VI | R¹-II |
| X-IV | Y-VI | R¹-III |
| X-IV | Y-VI | R¹-IV |
| X-IV | Y-VI | R¹-V |
| X-IV | Y-VI | R¹-VI |
| X-IV | Y-VI | R¹-VII |
| X-IV | Y-VI | R¹-VIII |
| X-IV | Y-VI | R¹-IX |
| X-IV | Y-VI | R¹-X |
| X-IV | Y-VI | R¹-XI |
| X-V | Y-I | R¹-I |
| X-V | Y-I | R¹-VII |
| X-V | Y-I | R¹-IX |
| X-V | Y-I | R¹-X |
| X-V | Y-II | R¹-X |
| X-V | Y-III | R¹-X |
| X-V | Y-IV | R¹-X |
| X-V | Y-V | R¹-X |
| X-V | Y-VI | R¹-I |
| X-V | Y-VI | R¹-VII |
| X-V | Y-VI | R¹-IX |
| X-V | Y-VI | R¹-X |
| X-VI | Y-I | R¹-I |
| X-VI | Y-I | R¹-II |
| X-VI | Y-I | R¹-III |
| X-VI | Y-I | R¹-IV |
| X-VI | Y-I | R¹-V |
| X-VI | Y-I | R¹-VI |
| X-VI | Y-I | R¹-VII |
| X-VI | Y-I | R¹-VIII |
| X-VI | Y-I | R¹-IX |
| X-VI | Y-I | R¹-X |
| X-VI | Y-II | R¹-X |
| X-VI | Y-III | R¹-X |
| X-VI | Y-IV | R¹-X |
| X-VI | Y-V | R¹-X |
| X-VI | Y-VI | R¹-I |
| X-VI | Y-VI | R¹-II |
| X-VI | Y-VI | R¹-III |
| X-VI | Y-VI | R¹-IV |
| X-VI | Y-VI | R¹-V |
| X-VI | Y-VI | R¹-VI |
| X-VI | Y-VI | R¹-VII |
| X-VI | Y-VI | R¹-VIII |
| X-VI | Y-VI | R¹-IX |
| X-VI | Y-VI | R¹-X |
| X-VII | Y-I | R¹-I |
| X-VII | Y-I | R¹-II |
| X-VII | Y-I | R¹-III |
| X-VII | Y-I | R¹-IV |
| X-VII | Y-I | R¹-V |
| X-VII | Y-I | R¹-VI |
| X-VII | Y-I | R¹-VII |
| X-VII | Y-I | R¹-VIII |
| X-VII | Y-I | R¹-IX |
| X-VII | Y-I | R¹-X |
| X-VII | Y-II | R¹-X |
| X-VII | Y-III | R¹-X |
| X-VII | Y-IV | R¹-X |
| X-VII | Y-V | R¹-X |
| X-VII | Y-VI | R¹-I |
| X-VII | Y-VI | R¹-II |
| X-VII | Y-VI | R¹-III |
| X-VII | Y-VI | R¹-IV |
| X-VII | Y-VI | R¹-V |
| X-VII | Y-VI | R¹-VI |
| X-VII | Y-VI | R¹-VII |
| X-VII | Y-VI | R¹-VIII |
| X-VII | Y-VI | R¹-IX |
| X-VII | Y-VI | R¹-X |
| X-VIII | Y-I | R¹-X |
| X-VIII | Y-VI | R¹-X |
| X-IX | Y-I | R¹-X |
| X-IX | Y-VI | R¹-X |
| X-I | Y-VI | R¹-XII |
| X-I | Y-VI | R¹-XIII |
| X-I | Y-VI | R¹-XIV |
| X-I | Y-VI | R¹-XV |
| X-I | Y-VI | R¹-XVI |
| X-I | Y-VI | R¹-XVII |
| X-I | Y-VI | R¹-XVIII |
| X-III | Y-VI | R¹-XII |
| X-III | Y-VI | R¹-XIII |
| X-III | Y-VI | R¹-XIV |
| X-III | Y-VI | R¹-XV |
| X-III | Y-VI | R¹-XVI |
| X-III | Y-VI | R¹-XVII |
| X-III | Y-VI | R¹-XVIII |

The compounds of the present invention can be produced for example according to the methods mentioned below.

Production Method A

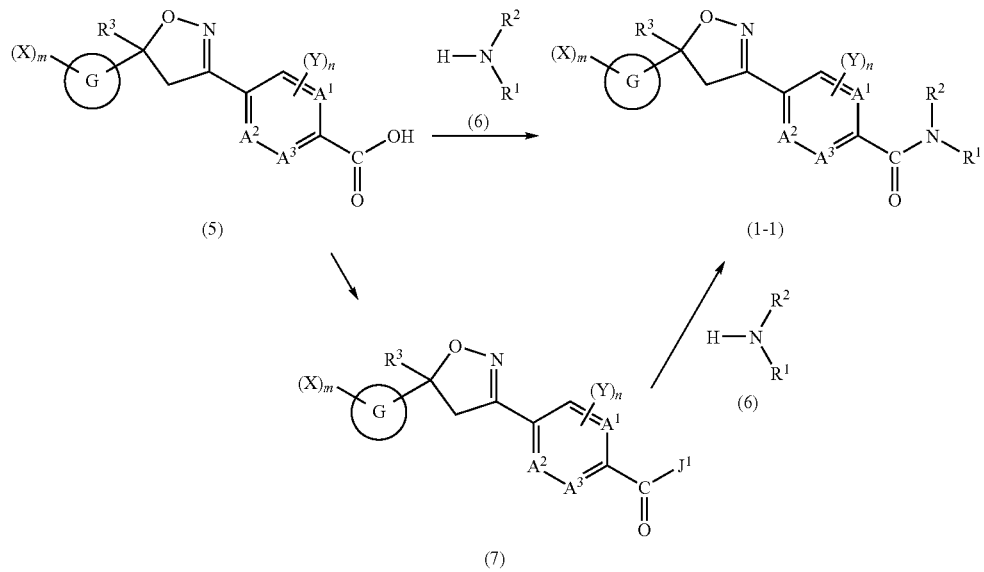

The compound of formula (I-1) wherein $A^1$, $A^2$, $A^3$, G, X, Y, $R^1$, $R^2$, $R^3$, m and n are as defined above that is the compound of formula (1) wherein W is oxygen atom can be obtained by reacting the compound of formula (5) wherein $A^1$, $A^2$, $A^3$, G, X, Y, $R^3$, m and n are as defined above with the compound of formula (6) wherein $R^1$ and $R^2$ are as defined above by use of a condensation agent, optionally by using a solvent inactive for the reaction, optionally in the presence of a base.

The reaction substrates can be used in an amount of 1 to 100 equivalents of the compound of formula (6) based on 1 equivalent of the compound of formula (5).

The condensation agent is not specifically limited if it is a compound used for ordinary amide synthesis, but it is for example Mukaiyama agent (2-chloro-N-methylpyridinium iodide), DCC (1,3-dicyclohexyl carbodiimide), WSC (1-ethyl-3-(3-dimethylaminopropyl)-carbodiimide hydrochloride), CDI (carbonyl diimidazole), dimethylpropynyl sulfonium bromide, propagyl triphenyl phosphonium bromide, DEPC (diethyl phosphorocyanidate) or the like, and can be used in an amount of 1 to 4 equivalents based on the compound of formula (5).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrolidone or the like, amines such as triethyl amine, tributyl amine, N,N-dimethyl aniline or the like, pyridines such as pyridine, picoline or the like, acetonitrile and dimethyl sulfoxide, and the like. These solvents may be used alone or in a mixture of two or more.

The addition of a base is not necessarily required. However, when the base is used, alkali metal hydroxides such as sodium hydroxide, potassium hydroxide or the like, alkali metal carbonates such as sodium carbonate, potassium carbonate or the like, alkali metal bicarbonates such as sodium hydrogen carbonate, potassium hydrogen carbonate or the like, organic bases such as triethylamine, tributylamine, N,N-dimethylaniline, pyridine, 4-(dimethylamino)pyridine, imidazole, 1,8-diazabicyclo[5.4.0]-7-undecene, and the like can be used in an amount of 1 to 4 equivalents based on the compound of formula (5).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 20 equivalents of the compound of formula (6) and 1 to 4 equivalent of the condensation agent such as WSC (1-ethyl-3-(3-dimethylaminopropyl)-carbodiimide hydrochloride), CDI (carbonyl diimidazole) or the like based on 1 equivalent of the compound of formula (5), optionally in the presence of 1 to 4 equivalents of a base such as potassium carbonate, triethylamine, pyridine, 4-(dimethylamino)pyridine or the like, without solvent or in a solvent such as dichloromethane, chloroform, diethyl ether, tetrahydrofurane, 1,4-dioxane or the like, at a temperature ranging from 0° C. to the reflux temperature of these solvents for 10 minutes to 24 hours.

In addition, the compound of formula (1-1) according to the present invention can be also synthesized by reacting the compound of formula (7) wherein $A^1$, $A^2$, $A^3$, G, X, Y, $R^3$, m and n are as defined above, $J^1$ is chlorine atom, bromine atom, $C_1$-$C_4$alkylcarbonyloxy (for example pivaloyloxy), $C_1$-$C_4$alkoxycarbonyloxy (for example isobutyloxycarbonyloxy) or azolyl (for example imidazol-1-yl) that can be synthesized according to a known method disclosed in documents from the compound of formula (5), for example a method by reacting with a chlorinating agent such as thionyl chloride, phosphorus pentachloride or oxalyl chloride, a method by reacting with a organic acid halide such as pivaloyl chloride or isobutyl chloroformate, etc. optionally in the presence of a base, or a method by reacting with carbonyl diimidazole or sulfonyl diimidazole, etc., with the compound of formula (6), optionally by using a solvent inactive for the reaction, optionally in the presence of a base.

The reaction substrates can be used in an amount of 1 to 50 equivalents of the compound of formula (6) based on 1 equivalent of the compound of formula (7).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrolidone or the like, amines such as triethyl amine, tributyl amine, N,N-dimethyl aniline or the like, pyridines such as pyridine, picoline or the like, acetonitrile and water, and the like. These solvents may be used alone or in a mixture of two or more.

The addition of a base is not necessarily required. However, when the base is used, alkali metal hydroxides such as sodium hydroxide, potassium hydroxide or the like, alkali metal carbonates such as sodium carbonate, potassium carbonate or the like, alkali metal bicarbonates such as sodium hydrogen carbonate, potassium hydrogen carbonate or the like, organic bases such as triethylamine, tributylamine, N,N-dimethylaniline, pyridine, 4-(dimethylamino)pyridine, imidazole, 1,8-diazabicyclo[5.4.0]-7-undecene, and the like can be used in an amount of 1 to 4 equivalents based on the compound of formula (7).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 10 equivalents of the compound of formula (6) based on 1 equivalent of the compound of formula (7), optionally in the presence of 1 to 2 equivalents of a base such as potassium carbonate, triethylamine, pyridine, 4-(dimethylamino)pyridine or the like, without solvent or in a solvent such as dichloromethane, chloroform, diethyl ether, tetrahydrofurane, 1,4-dioxane, ethyl acetate, acetonitrile or the like, at a temperature ranging from 0° C. to the reflux temperature of these solvents for 10 minutes to 24 hours.

Production Method B

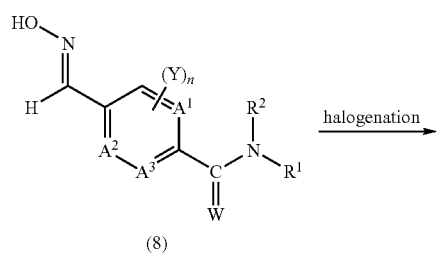

(8)

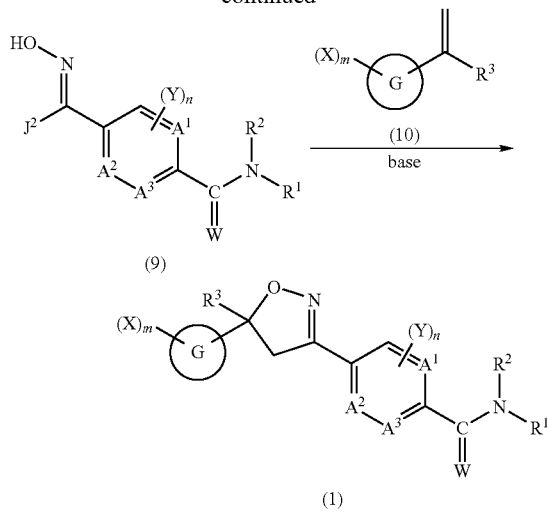

Hydroxamic chloride of formula (9) wherein $A^1$, $A^2$, $A^3$, W, Y, $R^1$, $R^2$ and n are as defined above, $J^2$ means halogen atom such as chlorine atom and bromine atom can be obtained by halogenating the compound of formula (8) wherein $A^1$, $A^2$, $A^3$, W, Y, $R^1$, $R^2$ and n are as defined above using a halogenating reagent optionally by using a solvent inactive for the reaction, optionally in the presence of a base.

Halogenating agents include for example N-halosuccinimides such as N-chlorosuccinimide, N-bromosuccinimide or the like, hypohalogenous acid alkali metal salts such as sodium hypochlorite or the like, hypohalogenous acid esters such as hypochlorous acid-t-butyl ester or the like, simple substance halogens such as chlorine gas or the like, and it can be used in an amount of 1 to 10 equivalents based on the compound of formula (8).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrolidone or the like, alcohols such as methanol, ethanol, ethylene glycol or the like, carboxylic acids such as acetic acid, propionic acid or the like, acetonitrile and water, and the like. These solvents may be used alone or in a mixture of two or more.

The reaction temperature may be an arbitrary temperature ranging from −60° C. to the reflux temperature of a reaction mixture, and the reaction time may be an arbitrary time ranging from 5 minutes to 24 hours although it varies depending on the concentration of the reaction substrates or the reaction temperature.

The compounds of formula (1) wherein $A^1$, $A^2$, $A^3$, G, W, X, Y, $R^1$, $R^2$, $R^3$, m and n are as defined above according to the present invention can be obtained by reacting the compound of formula (9) with the compound of formula (10) wherein G, X, $R^3$ and m are as defined above in the presence of a base optionally by use of a solvent inactive for the reaction.

The reaction substrates can be used in an amount of 1 to 5 equivalents of the compound of formula (10) based on 1 equivalent of the compound of formula (9).

The used base includes for example alkali metal hydroxides such as sodium hydroxide, potassium hydroxide or the like, alkali metal carbonates such as sodium carbonate, potassium carbonate or the like, alkali metal bicarbonates such as sodium hydrogen carbonate, potassium hydrogen carbonate or the like, organic bases such as triethylamine, tributylamine, N,N-dimethylaniline, pyridine, 4-(dimethylamino)pyridine, imidazole, 1,8-diazabicyclo[5.4.0]-7-undecene, and the like can be used in an amount of 1 to 5 equivalents based on the compound of formula (9).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrolidone or the like, and acetonitrile, and the like. These solvents may be used alone or in a mixture of two or more.

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, the compound of formula (9) can be obtained for example by carrying out the reaction by using 1 to 2 equivalents of a halogenating agent such as N-chlorosuccinimide, sodium hypochlorite aqueous solution, hypochlorous acid-t-butyl ester, chlorine gas or the like based on 1 equivalent of the compound of formula (8) in a solvent such as dichloromethane, chloroform, 1,2-dimethoxyethane, tetrahydrofurane, 1,4-dioxane, N,N-dimethylformamide or the like, at a temperature ranging from 0° C. to the reflux temperature of these solvents for 10 minutes to 2 hours. Then, preferably without the isolation of the compound of formula (9), 1 to 2 equivalents of the compound of formula (10) and 1 to 2 equivalents of a base such as sodium carbonate, sodium hydrogen carbonate, triethyl amine or the like are added, and the reaction is carried out at a temperature ranging from 0° C. to the reflux temperature of these solvents for 10 minutes to 24 hours.

Production Method C

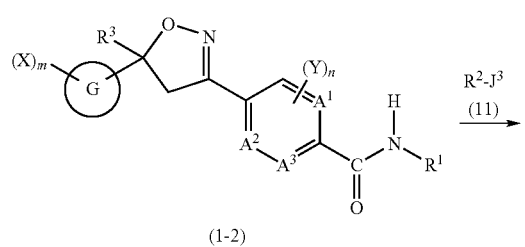

(1-2)

-continued

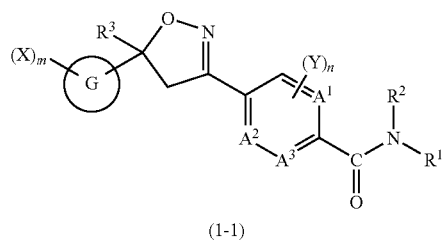

(1-1)

The compound of formula (1-1) wherein $A^1$, $A^2$, $A^3$, G, X, Y, $R^1$, $R^3$, m and n are as defined above and $R^2$ has the same meaning defined above excluding hydrogen atom according to the present invention that is the compound of formula (1) wherein W is oxygen atom can be obtained by reacting the compound of formula (1-2) wherein $A^1$, $A^2$, $A^3$, G, X, Y, $R^1$, $R^3$, m and n are as defined above that is the compound of formula (1) wherein W is oxygen atom and $R^2$ is hydrogen atom with the compound of formula (11) wherein $R^2$ has the same meaning defined above excluding hydrogen atom, $J^3$ is a good leaving group such as chlorine atom, bromine atom, iodine atom, $C_1$-$C_4$alkylcarbonyloxy (for example pivaloyloxy), $C_1$-$C_4$alkylsulfonate (for example methane sulfonyloxy), $C_1$-$C_4$haloalkylsulfonate (for example trifluoromethane sulfonyloxy), arylsulfonate (for example benzene sulfonyloxy, p-toluene sulfonyloxy) or azolyl (for example imidazol-1-yl), optionally in the presence of a base, optionally by using a solvent inactive for the reaction.

The reaction substrates can be used in an amount of 1 to 50 equivalents of the compound of formula (11) based on 1 equivalent of the compound of formula (1-2).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrolidone or the like, amines such as triethyl amine, tributyl amine, N,N-dimethyl aniline or the like, pyridines such as pyridine, picoline or the like, alcohols such as methanol, ethanol, ethylene glycol or the like, acetonitrile, dimethylsulfoxide, sulfolane, 1,3-dimethyl-2-imidazolidinone and water, and the like. These solvents may be used alone or in a mixture of two or more.

When the base is used, alkali metal hydride such as sodium hydride, potassium hydride or the like, alkali metal hydroxides such as sodium hydroxide, potassium hydroxide or the like, alkali metal alkoxides such as sodium ethoxide, potassium t-butoxide or the like, alkali metal amides such as lithium diisopropylamide, lithium hexamethyl disilazane, sodium amide or the like, organic metal compounds such as t-butyl lithium or the like, alkali metal carbonates such as sodium carbonate, potassium carbonate, sodium hydrogen carbonate or the like, organic bases such as triethylamine, tributylamine, N,N-dimethylaniline, pyridine, 4-(dimethylamino)pyridine, imidazole, 1,8-diazabicyclo[5.4.0]-7-undecene, and the like can be used in an amount of 1 to 4 equivalents based on the compound of formula (1-2).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 10 equivalents of the compound of formula (11) based on 1 equivalent of the compound of formula (1-2), in a polar solvent such as tetrahydrofurane, 1,4-dioxane, acetonitrile, N,N-dimethylformamide or the like, optionally in the presence of 1 to 3 equivalents of a base such as sodium hydride, potassium t-butoxide, potassium hydroxide, potassium carbonate, triethylamine, pyridine or the like, based on 1 equivalent of the compound of formula (1-2), at a temperature ranging from 0 to 90° C. for 10 minutes to 24 hours.

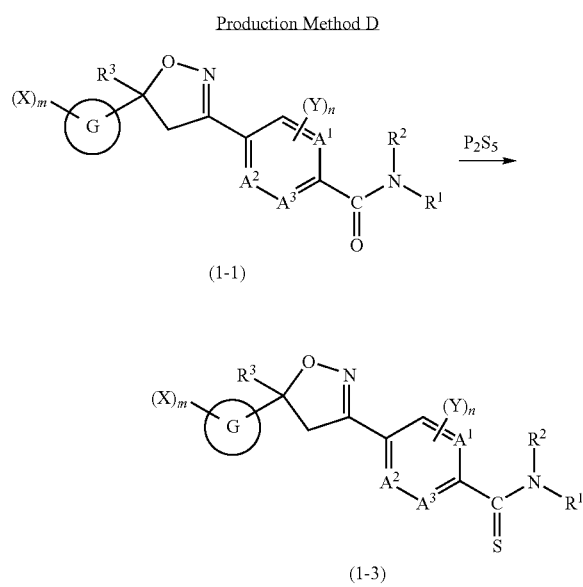

Production Method D (1-1)

(1-3)

The compound of formula (1-3) wherein $A^1$, $A^2$, $A^3$, G, X, Y, $R^1$, $R^2$, $R^3$, m and n are as defined above according to the present invention that is the compound of formula (1) wherein W is sulfur atom can be obtained by reacting the compound of formula (1-1) wherein $A^1$, $A^2$, $A^3$, G, X, Y, $R^1$, $R^2$, $R^3$, m and n are as defined above according to the present invention that is the compound of formula (1) wherein W is oxygen atom with a sulfurizing agent such as diphosphorus pentasulfide, diphosphorus pentasulfide-HMDO (hexamethyldisiloxane), Lawesson's Reagent (2,4-bis(4-methoxyphenyl)-1,3,2,4-dithiadiphosphetane-2,4-disulfide), optionally by using a solvent inactive for the reaction, optionally in the presence of a base.

The reaction substrates can be used in an amount of 1 to 50 equivalents of the sulfurizing agent based on 1 equivalent of the compound of formula (1-1).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, 1,2-dimethoxyethane, tetrahydrofuran, 1,4-dioxane or the like, amines such as triethyl amine, tributyl amine, N,N-dimethyl aniline or the like, pyridines such as pyridine, picoline or the like, and HMPA (hexamethylphosphoric triamide), and the like. These solvents may be used alone or in a mixture of two or more.

The addition of a base is not necessarily required. However, when the base is used, alkali metal carbonates such as sodium carbonate, potassium carbonate, sodium hydrogen carbonate or the like, organic bases such as triethylamine, tributylamine, N,N-dimethylaniline, pyridine, 4-(dimethylamino)pyridine, imidazole, 1,8-diazabicyclo[5.4.0]-7-undecene, and the like can be used in an amount of 1 to 10 equivalents based on the compound of formula (1-1).

The reaction temperature may be an arbitrary temperature ranging from 0° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 10 equivalents of a sulfurizing agent such as diphosphorus pentasulfide, diphosphorus pentasulfide-HMDO, Lawesson's Reagent or the like, based on 1 equivalent of the compound of formula (1-1), optionally in the presence of 1 to 4 equivalents of a base such as sodium hydrogen carbonate, triethylamine, pyridine or the like, in a solvent such as benzene, toluene, chlorobenzene, dichloromethane, chloroform, 1,2-dimethoxyethane, tetrahydrofurane, 1,4-dioxane, HMPA or the like, at a temperature ranging from room temperature to the reflux temperature of the reaction mixture for 10 minutes to 50 hours, or in a solvent amount of pyridine at a temperature of 80° C. to the reflux temperature of the reaction mixture for 1 to 3 hours.

In Production Method A to Production Method D, the aimed compound of the present invention can be obtained by subjecting the reaction mixture after the completion of the reaction to ordinary post-treatment such as a direct concentration, or a concentration after dissolving in an organic solvent and washing with water or a concentration after placing in ice water and extracting with an organic solvent. In addition, when a purification is required, it can be separated and purified by an arbitrary purification process such as recrystallization, column chromatograph, thin layer chromatograph, liquid chromatograph collection or the like.

The compound of formula (5) used in Production Method A can be synthesized as follows, for example.

Reaction Scheme 1

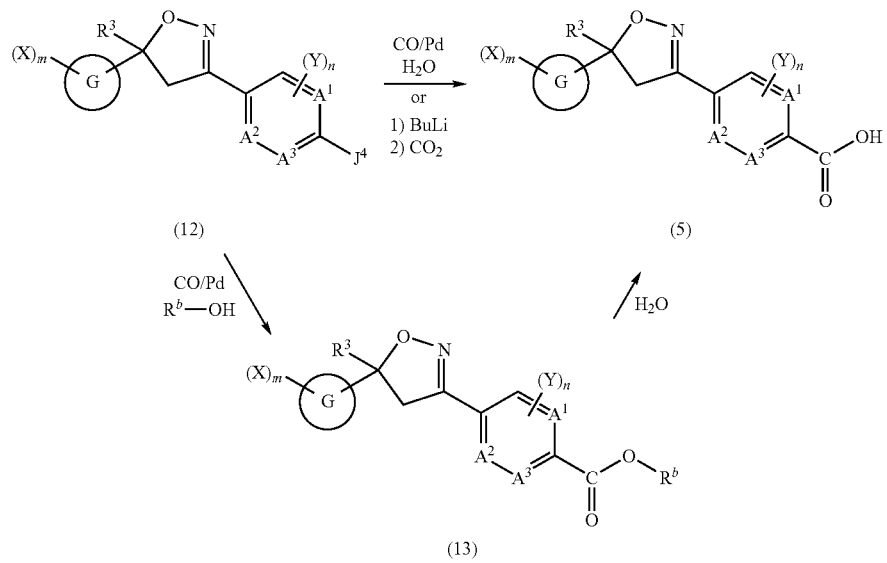

That is, the compound of formula (5) wherein $A^1$, $A^2$, $A^3$, G, X, Y, $R^3$, m and n are as defined above can be obtained by reacting the compound of formula (12) wherein $A^1$, $A^2$, $A^3$, G, X, Y, $R^3$, m and n are as defined above, $J^4$ is bromine atom, iodine atom, halosulfonyloxy (for example fluorosulfonyloxy), $C_1$-$C_4$haloalkylsulfonyloxy (for example trifluoromethane sulfonyloxy) or arylsulfonyloxy (for example benzenesulfonyloxy) according to a known method disclosed in documents, for example by CO insertion reaction by use of a transition metal catalyst such as palladium or the like stated in J. Org. Chem., 1999, vol. 64, p. 6921 or the like, or by a process by lithiation and then reaction with carbonic acid gas stated in Chem. Rev., 1990, vol. 90, p. 879.

In addition, the compound of formula (5) can be obtained by subjecting the compound of formula (12) to a reaction according to a reaction condition for CO insertion reaction by use of a transition metal catalyst such as palladium or the like stated in J. Org. Chem., 1974, vol. 39, p. 3318 or the like to convert the compound of formula (13) wherein $A^1$, $A^2$, $A^3$, G, X, Y, $R^3$, m and n are as defined above, $R^b$ is $C_1$-$C_6$alkyl such as methyl, ethyl or the like, and then hydrolizing according to an ordinary ester hydrolysis disclosed in documents, for example a reaction condition stated in Angew. Chem., 1951, vol. 63, p. 329, J. Am. Chem. Soc., 1929, vol. 51, p. 1865 or the like.

Some of the compounds of formula (6) used in Production Method A are known compounds, and a part thereof is commercially available. Also, the compounds other than the above-mentioned compounds can be synthesized according to methods stated in for example Justus Liebigs Ann. Chem., 1979, p. 920, U.S. Pat. No. 5,990,323, WO 96/11200 or the like, and general synthetic methods for primary or secondary alkyl amines disclosed in documents.

The compounds of formula (8) used in Production Method B can be synthesized as follows, for example.

Reaction Scheme 2

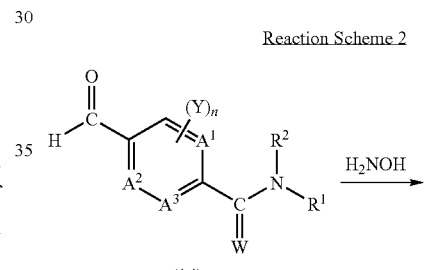

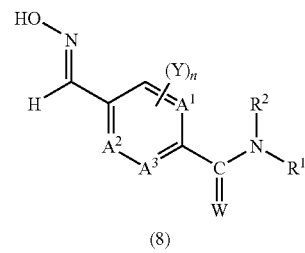

That is, the compound of formula (8) wherein $A^1$, $A^2$, $A^3$, W, Y, $R^1$, $R^2$ and n are as defined above can be easily synthesized by reacting the compound of formula (14) wherein $A^1$, $A^2$, $A^3$, W, Y, $R^1$, $R^2$ and n are as defined above with hydroxyamine or the salt thereof according to known methods disclosed in documents, for example the method stated in J. Med. Chem., 2001, vol. 44, p. 2308 or the like.

The compounds of formula (10) used in Production Method B can be synthesized as follows, for example.

Reaction Scheme 3

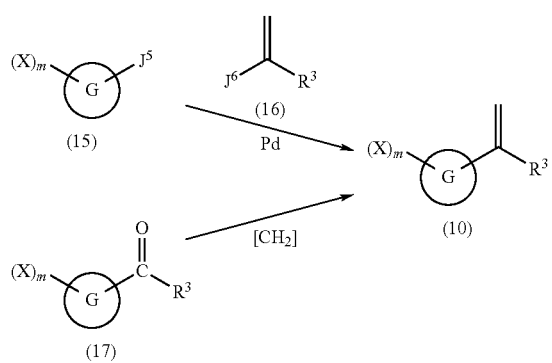

Reaction Scheme 4

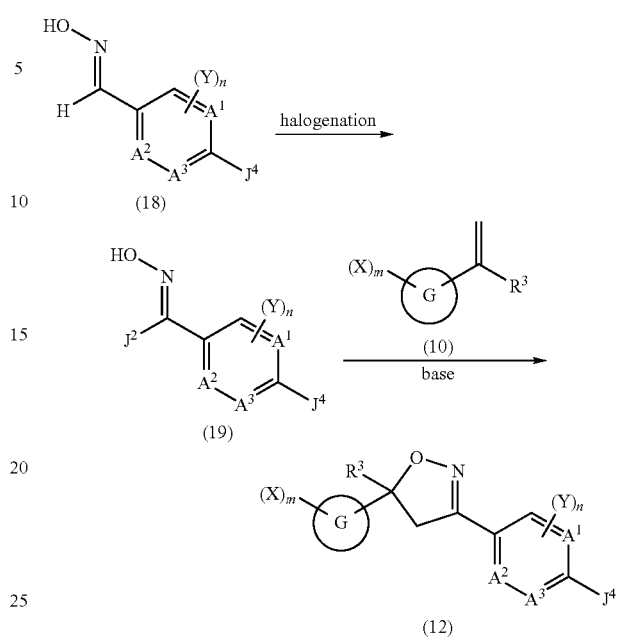

That is, the compound of formula (10) wherein G, X, R³ and m are as defined above can be obtained by reacting the known compound of formula (15) wherein G, X and m are as defined above, $J^5$ is bromine atom, iodine atom, $C_1$-$C_4$haloalkylsulfonyloxy (for example trifluoromethanesulfonyloxy), —B(OH)₂, 4,4,5,5-tetramethyl-1,3,2-dioxaborolan-2-yl, —Si(OEt)₃, —ZnCl, —ZnBr or —ZnI, etc. with the compound of formula (16) wherein R³ is as defined above, $J^6$ is halogen atom such as bromine atom, iodine atom or the like, or —B(OH)₂ according to an ordinary crosscoupling reaction by use of a transition metal catalyst such as palladium or the like disclosed in documents, for example a reaction condition stated in J. Org. Chem., 1991, vol. 56, p. 7336, Tetrahedron Lett., 2001, vol. 42, p. 4083, or the like.

Some of the compounds of formula (16) used in the abovementioned process are known compounds, and a part thereof is commercially available. Also, the compounds other than the above-mentioned compounds can be synthesized according to methods disclosed in documents, for example a method stated in J. Am. Chem. Soc., 1971, vol. 93, p. 1925, Tetrahedron Lett., 1990, vol. 31, p. 1919 and 2001, vol. 42, p. 4083 or the like.

In addition, the compounds of formula (10) can be obtained by reacting the compound of formula (17) wherein G, X, R³ and m are as defined above according to a reaction of converting carbonyl to olefine disclosed in documents, for example a reaction condition stated in J. Org. Chem., 1986, vol. 51, p. 5252 and 1994, vol. 59, p. 2898, Synthesis, 1991, p. 29, Tetrahedron Lett., 1985, vol. 26, p. 5579 or the like.

Some of the compounds of formula (11) used in Production method C are known compounds, and a part thereof is commercially available. Also, the compounds other than the above-mentioned compounds can be easily synthesized according to methods disclosed in documents, for example a method stated in Chem. Lett., 1976, p. 373, J. Am. Chem. Soc., 1964, vol. 86, p. 4383, J. Org. Chem., 1976, vol. 41, p. 4028 and 1978, vol. 43, p. 3244, Org. Synth., 1988, Corrective vol. 6, p. 101, Tetrahedron Lett., 1972, p. 4339, GB 2,161,802, EP 0,051,273 or the like.

The compounds of formula (12) can be synthesized as follows, for example.

That is, the compounds of formula (12) wherein A¹, A², A³, G, X, Y, R³, m, n and $J^4$ are as defined above can be obtained by halogenating the compound of formula (18) wherein A¹, A², A³, Y, n and $J^4$ are as defined above under a condition similar to that of Production Method B to obtain the compound of formula (19) wherein A¹, A², A³, Y, n, $J^3$ and $J^4$ are as defined above, and then reacting it with the compound of formula (10) wherein G, X, R³ and m are as defined above.

The compound of formula (18) can be easily synthesized by use of the corresponding known substituted aromatic aldehyde similarly to the process described in Reaction Scheme 2.

The compound of formula (14) can be synthesized for example according to Reaction Scheme 5 or Reaction Scheme 6.

Reaction Scheme 5

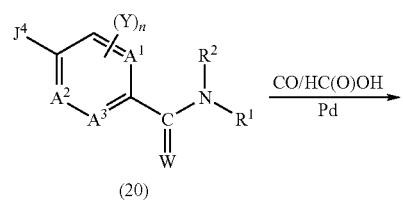

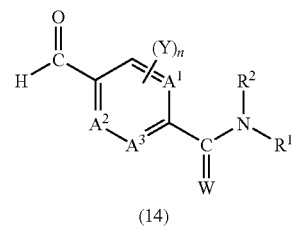

The compounds of formula (14) wherein A¹, A², A³, W, Y, R¹, R² and n are as defined above can be obtained by subjecting the compound of formula (20) wherein A¹, A², A³, W, Y, R¹, R², n and $J^4$ are as defined above to CO insertion reaction according to known methods disclosed in documents, for example the reaction by use of a transition metal catalyst such as palladium or the like in the presence of hydride source such as formic acid or the like stated in Bull. Chem. Soc. Jpn., 1994, vol. 67, p. 2329, J. Am. Chem. Soc., 1986, vol. 108, p. 452, or the like.

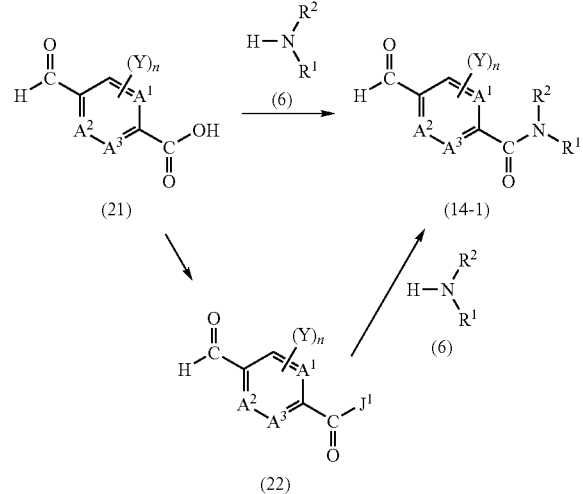

Reaction Scheme 6

The compounds of formula (14-1) wherein $A^1$, $A^2$, $A^3$, Y, $R^1$, $R^2$ and n are as defined above that are the compounds of formula (14) wherein W is oxygen atom can be synthesized by reacting the known compound of formula (21) wherein $A^1$, $A^2$, $A^3$, Y and n are as defined above with the compound of formula (6) wherein $R^1$ and $R^2$ are as defined above by use of the method similar to Production Method A.

The compounds of formula (17) can be synthesized as follows, for example.

That is, the compounds of formula (17) wherein X, $R^3$ and m are as defined above, G is benzene ring can be obtained by reacting the known compound of formula (23) wherein X and m are as defined above, G is benzene ring with the known compound of formula (24) wherein $R^3$ is as defined above, $J^7$ is a leaving group such as halogen atom, trifluoromethanesulfonyloxy, 2-pyridyloxy or the like, or the known compound of formula (25) wherein $R^3$ is as defined above according to a general acylating reaction of aromatic ring disclosed in documents, for example a method stated in Chem. Lett., 1990, p. 783, J. Org. Chem., 1991, vol. 56, p. 1963 or the like.

In addition, the compound of formula (17) wherein G, X, $R^3$ and m are as defined above can be obtained according to general methods disclosed in documents for example by a method stated in J. Am. Chem. Soc., 1955, vol. 77, p. 3657, Tetrahedron Lett., 1980, vol. 21, p. 2129 and 1991, vol. 32, p. 2003, U.S. Pat. No. 5,514,816 in which the compound of formula (26) wherein G, X and m are as defined above, $J^8$ is bromine atom or iodine atom is lithiated and the resulting compound is reacted with the known compound of formula (27) wherein $R^3$ is as defined above, $J^9$ is halogen atom, hydroxy, metal salt (for example, —OLi, —ONa), $C_1$-$C_4$alkoxy (for example, methoxy, ethoxy), di($C_1$-$C_4$alkyl)amino (for example, diethylamino), $C_1$-$C_4$alkoxy $C_1$-$C_4$alkyl amino(for example O,N-dimethylhydroxyamino) or cyclic amino (for example, piperidin-1-yl, morpholin-4-yl, 4-methylpiperidin-1-yl), or the known compound of formula (25), or by a method stated in Heterocycles, 1987, vol. 25, p. 221, Synth. Commun., 1985, vol. 15, p. 1291 and 1990, vol. 20, p. 1469, DE 19727042, or the like in which a Grignard reagent is formed and then it is reacted with the compound of formula (27) or the compound of formula (25).

The compounds of formula (20) can be synthesized according to for example Reaction Scheme 8 or Reaction Scheme 9.

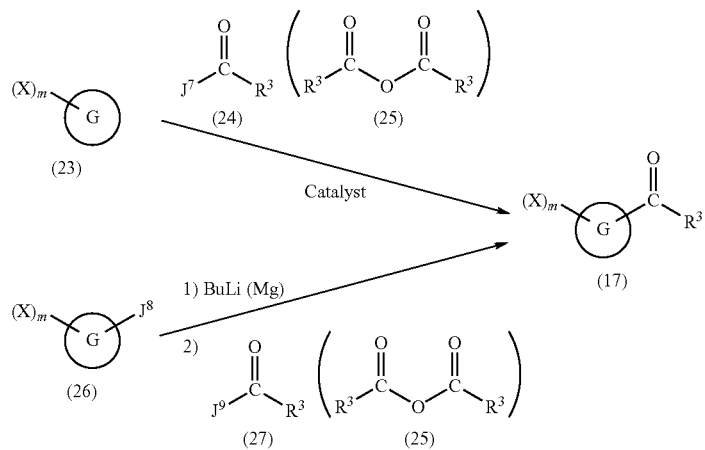

Reaction Scheme 7

Reaction Scheme 8

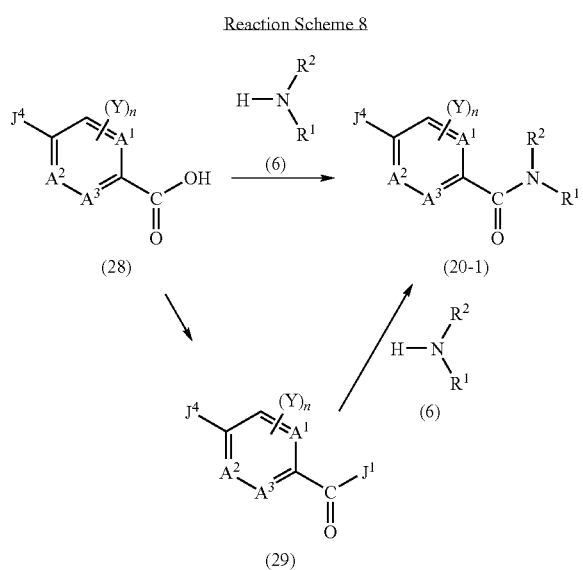

The compounds of formula (20-1) wherein $A^1$, $A^2$, $A^3$, Y, $R^1$, $R^2$, n and $J^4$ are as defined above that are the compounds of formula (20) wherein W is oxygen atom can be obtained by reacting the known compound of formula (28) wherein $A^1$, $A^2$, $A^3$, Y, n and $J^4$ are as defined above with the compound of formula (6) wherein $R^1$ and $R^2$ are as defined above by use of the method similar to Production Method A.

Reaction Scheme 9

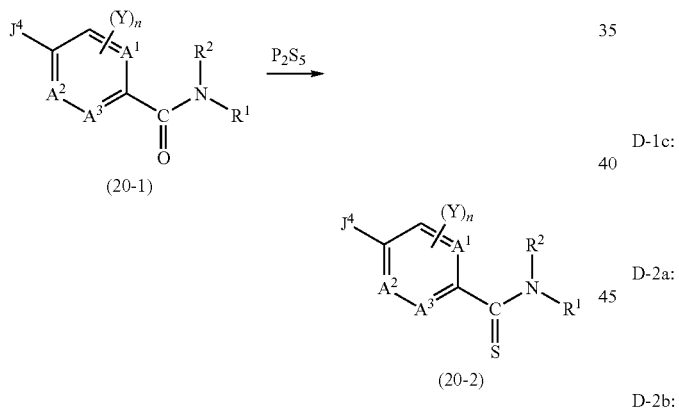

The compounds of formula (20-2) wherein $A^1$, $A^2$, $A^3$, Y, $R^1$, $R^2$, n and $J^5$ are as defined above that are the compounds of formula (20) wherein W is sulfur atom can be obtained by reacting the compound of formula (20-1) wherein $A^1$, $A^2$, $A^3$, Y, $R^1$, $R^2$, n and $J^4$ are as defined above that are the compounds of formula (20) wherein W is oxygen atom with a sulfurizing agent such as diphosphorus pentasulfide, diphosphorus pentasulfide-HMDO (hexamethyldisiloxane), Lawesson's Reagent (2,4-bis(4-methoxyphenyl)-1,3,2,4-dithiadiphosphetane-2,4-disulfide) under a condition similar to that of Production Method D.

In each reaction, after the completion of the reaction, each production intermediate that is a starting compound in Production Method A to Production Method C can be obtained by carrying out normal post-treatments.

In addition, each production intermediate produced by the above-mentioned methods can be used for the following reaction step as such without isolation or purification.

The active compounds included in the present invention concretely include for example the compounds shown in Tables 2 and 3. The compounds that can be used as novel production intermediates for producing the active compounds included in the present invention concretely include for example the compounds shown in Tables 4 to 6. In the interim, the compounds shown in Tables 2 to 6 are for purposes of illustration and the present invention is not limited thereto.

In the meantime, in Tables, the indication "Et" means ethyl, hereinafter similarly thereto, "n-Pr" and "Pr-n" mean normal propyl, "i-Pr" and "Pr-i" mean isopropyl, "c-Pr" and "Pr-c" mean cyclopropyl, "n-Bu" and "Bu-n" mean normal butyl, "s-Bu" and "Bu-s" mean secondary butyl, "i-Bu" and "Bu-i" mean isobutyl, "t-Bu" and "Bu-t" mean tertiary butyl, "c-Bu" and "Bu-c" mean cyclobutyl, "n-Pen" and "Pen-n" mean normal pentyl, "c-Pen" and "Pen-c" mean cyclopentyl, "n-Hex" and "Hex-n" mean normal hexyl, "c-Hex" and "Hex-c" mean cyclohexyl, "Hept" means heptyl, "Oct" means octyl, "Ph" means phenyl, "1-Naph" means 1-naphthyl, "2-Naph" means 2-naphthyl, and in Tables, aromatic heterocyclic rings of D-1a to D-65a are the following structures, respectively D-1a:

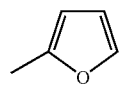

D-1b:

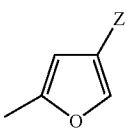

D-1c:

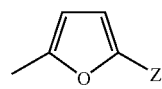

D-2a:

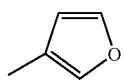

D-2b:

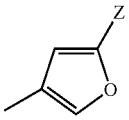

D-3a:

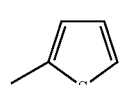

D-3b:

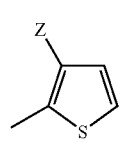

-continued
D-3c: 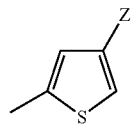
D-3d: 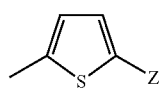
D-4a: 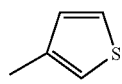
D-4b: 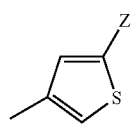
D-5a: 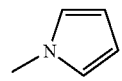
D-6a: 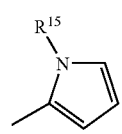
D-6b: 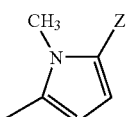
D-6c: 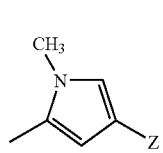
D-8a: 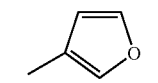
D-8b: 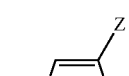
D-9a: 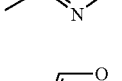
D-9b: 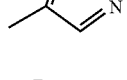
-continued
D-10a: 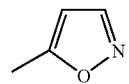
D-10b: 
D-11a: 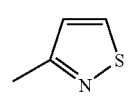
D-11b: 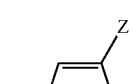
D-12a: 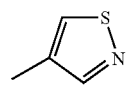
D-12b: 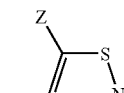
D-13a: 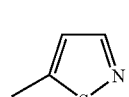
D-13b: 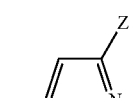
D-14a: 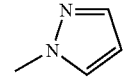
D-14b: 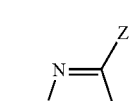
D-14c: 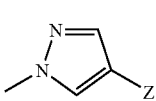
D-15a: 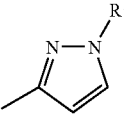

-continued

D-15b:
D-15c:
D-16a:
D-16b:
D-16c:
D-17a:
D-17b:
D-18a:
D-18b:
D-18c:

-continued

D-19a:
D-19b:
D-20a:
D-20b:
D-21a:
D-21b:
D-21c:
D-22a:
D-22b:
D-23a:
D-23b:
D-23c:
D-24a:

-continued

D-25a:
D-25b:
D-25c:
D-26a:
D-27a:
D-27b:
D-28a:
D-29a:
D-29b:
D-30a:
D-30b:

-continued

D-31a:
D-31b:
D-32a:
D-33a:
D-33b:
D-34a:
D-34b:
D-35a:
D-35b:
D-36a:
D-36b:
D-37a:

-continued

D-37b: [structure with Z, N, S, N]

D-38a: [triazole structure]

D-38b: [triazole with Z]

D-39a: [triazole with R¹⁵]

D-39b: [triazole with Z, CH₃]

D-40a: [triazole with R¹⁵]

D-40b: [triazole with CH₃, Z]

D-41a: [triazole structure]

D-42a: [triazole with R¹⁵]

D-42b: [triazole with CH₃, Z]

D-43a: [tetrazole structure]

D-43b: [tetrazole with Z]

D-44a: [tetrazole structure]

D-44b: [tetrazole with Z]

D-45a: [tetrazole with R¹⁵]

D-46a: [tetrazole with R¹⁵]

D-47a: [pyridine structure]

D-47b: [pyridine with Z]

D-47c: [pyridine with Z]

D-47d: [pyridazine with Z]

D-47e: [pyridazine with Z]

D-47f: [pyridine with Z¹, Z²]

-continued
D-47g: 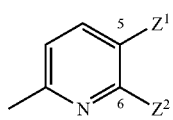
D-47h: 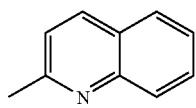
D-47i: 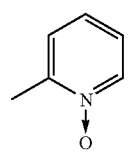
D-48a: 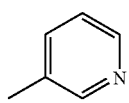
D-48b: 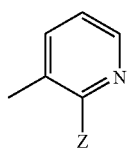
D-48c: 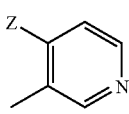
D-48d: 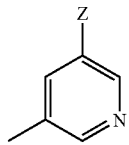
D-48e: 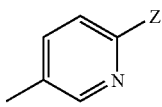
D-48f: 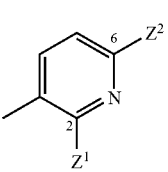
D-48g: 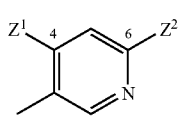
-continued
D-48h: 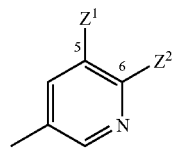
D-49a: 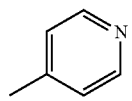
D-49b: 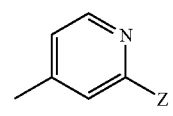
D-49c: 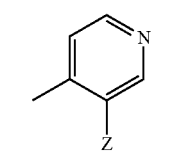
D-49d: 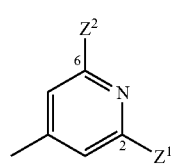
D-49e: 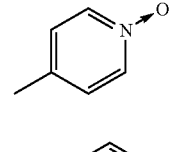
D-50a: 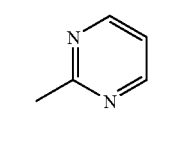
D-50b: 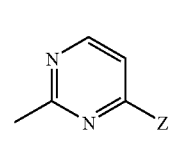
D-50c: 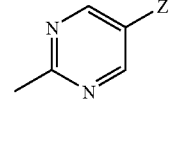
D-51a: 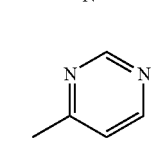
D-51b: 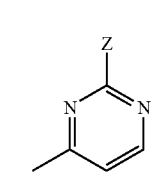

D-51c: 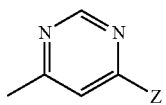
D-51d: 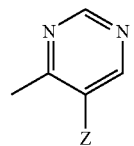
D-52a: 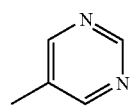
D-52b: 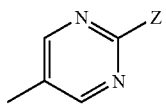
D-52c: 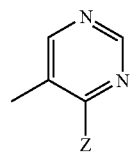
D-53a: 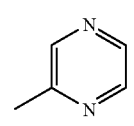
D-53b: 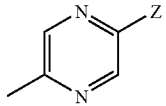
D-53c: 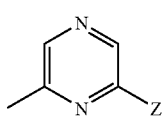
D-53d: 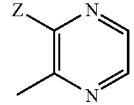
D-54a: 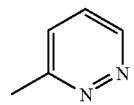
D-54b: 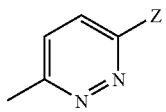
D-55a: 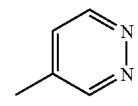
D-56a: 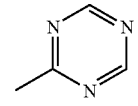
D-56b: 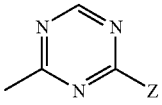
D-57a: 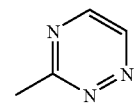
D-57b: 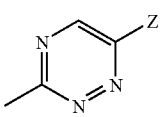
D-58a: 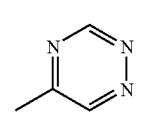
D-58b: 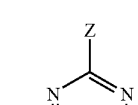
D-59a: 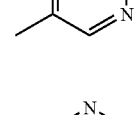
D-60b: 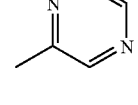
D-61a: 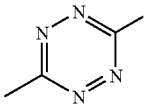
D-62a: 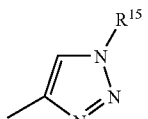

D-63a:
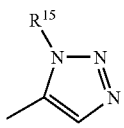
D-64a:
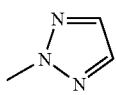
D-65a:
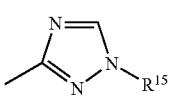
For example, the indication "[CH$_2$(D-17a)CH$_3$]" means 1-methylpyrazol-5-yl methyl, the indication "[CH$_2$(D-22b)CH$_3$]" means 2-methylthiazol-4-yl methyl.
In addition, aliphatic heterocyclic rings of E-4a to E-43b are the following structures, respectively
E-4a:
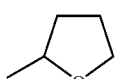
E-4b:
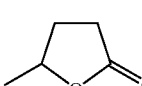
E-5a:
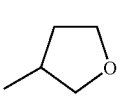
E-5b:
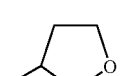
E-5c:
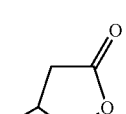
E-6a:
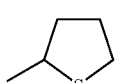
E-7a:
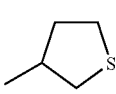
E-7b:
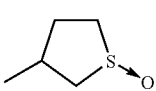
E-7c:
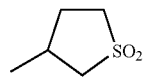
E-7d:
E-8a:
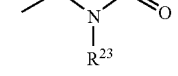
E-8b:
E-9a:
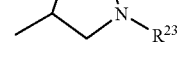
E-9b:
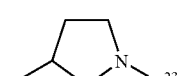
E-10a:
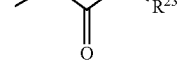
E-10b:
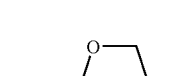
E-11a:
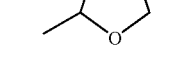
E-11b:
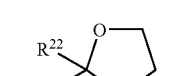
E-11c:
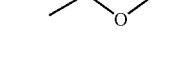
E-12a:

E-12b: 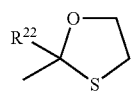
E-14a: 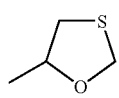
E-14b: 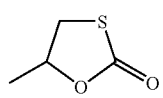
E-14c: 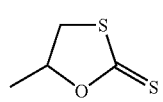
E-16a: 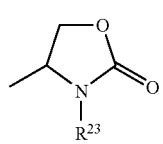
E-16b: 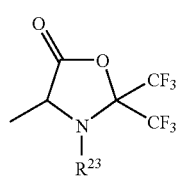
E-17a: 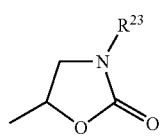
E-18a: 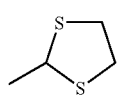
E-18b: 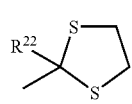
E-21a: 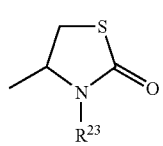
E-21b: 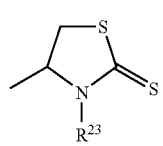
E-22a: 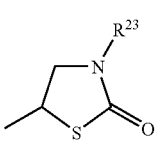
E-22b: 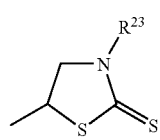
E-23a: 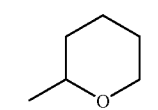
E-24a: 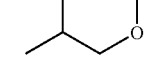
E-25a: 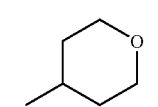
E-25b: 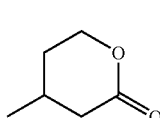
E-26a: 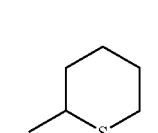
E-27a: 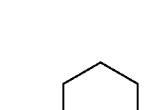
E-27b: 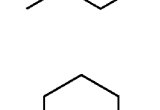
E-27c: 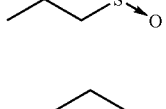
E-28a: 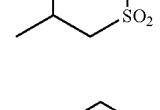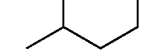

E-29a: 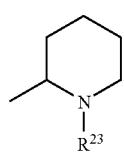
E-29b: 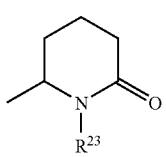
E-30a: 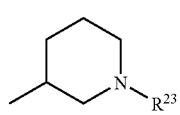
E-30b: 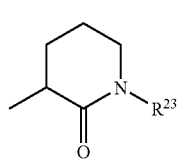
E-30c: 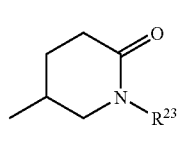
E-31a: 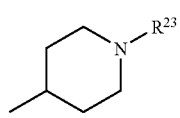
E-31b: 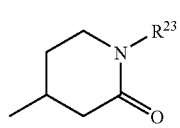
E-32a: 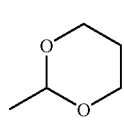
E-32b: 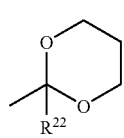
E-33a: 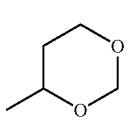
E-34a: 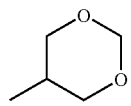
E-35a: 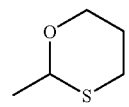
E-35b: 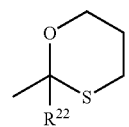
E-40a: 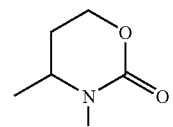
E-41a: 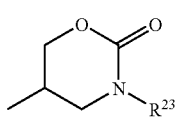
E-42a: 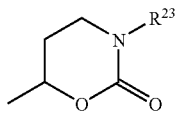
E-42b: 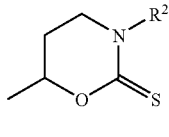
E-43a: 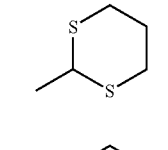
E-43b: 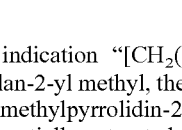
For example, the indication "[CH$_2$(E-10b)CH$_3$]" means 2-methyl-1,3-dioxolan-2-yl methyl, the indication "[CH$_2$(E-8a)CH$_3$]" means N-methylpyrrolidin-2-yl methyl.
Further, in Tables, partially saturated heterocyclic rings of M-2a to M-16a are the following structures, respectively
M-2a: 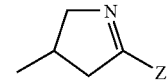

M-3a: 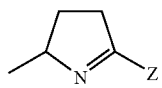
M-5a: 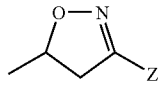
M-8a: 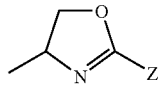
M-9a: 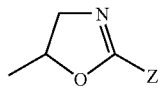
M-10a: 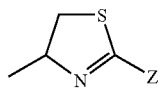
M-14a: 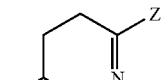
M-15a: 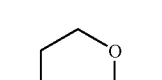
M-16a: 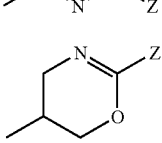
For example, the indication "[CH$_2$(M-5a)CH$_3$]" means 3-methyl-4,5-dihydroisoxazole-5-yl methyl.
Further, in Tables, T-1 to T-49 are the following structures, respectively
T-1: 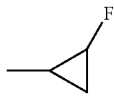
T-2: 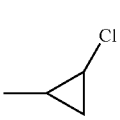
T-3: 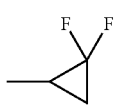
T-4: 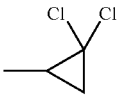
T-5: 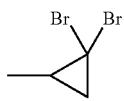
T-6: 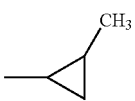
T-7: 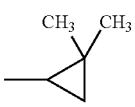
T-8: 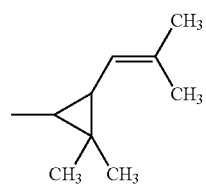
T-9: 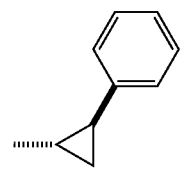
T-10: 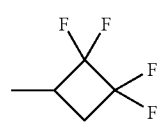
T-11: 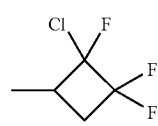
T-12: 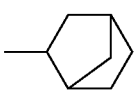
T-13: 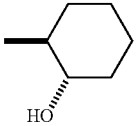
T-14: 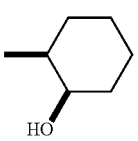

-continued
T-15: 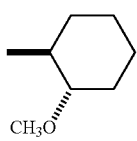
T-16: 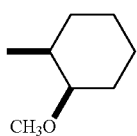
T-17: 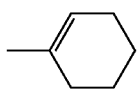
T-18: 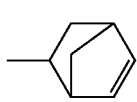
T-19: 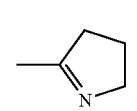
T-20: 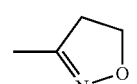
T-21: 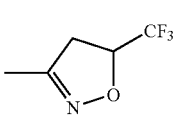
T-22: 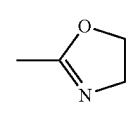
T-23: 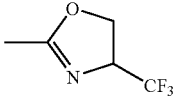
T-24: 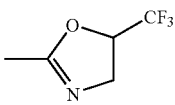
T-25: 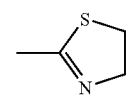
T-26: 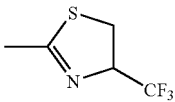
-continued
T-27: 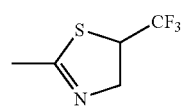
T-28: 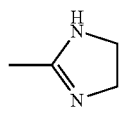
T-29: 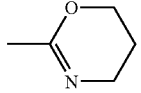
T-30: 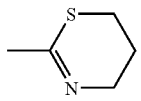
T-31: 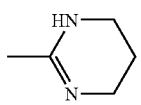
T-32: 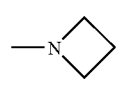
T-33: 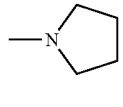
T-34: 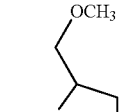
T-35: 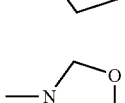
T-36: 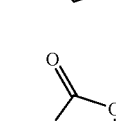
T-37: 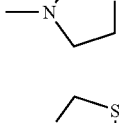
T-38: 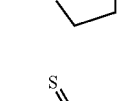
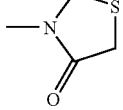

T-39: 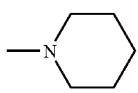
T-40: 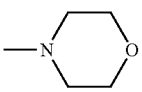
T-41: 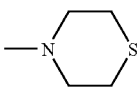
T-42: 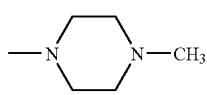
T-43: 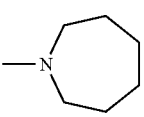
T-44: 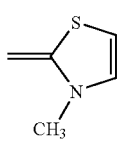
T-45: 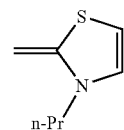
n-Pr
T-46: 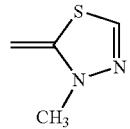
T-47: 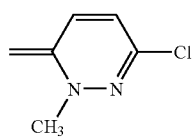
T-48: 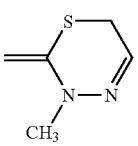
T-49: 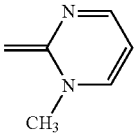
TABLE 2
In the table, the number showing the substitution position of substituent $(X)_m$ corresponds to the position number indicated in the following structural formulae. The indication "—" means no-substitution.
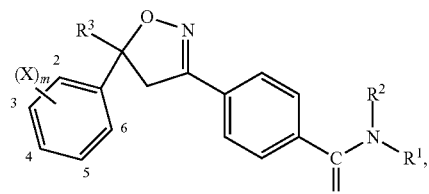
[1] - 1
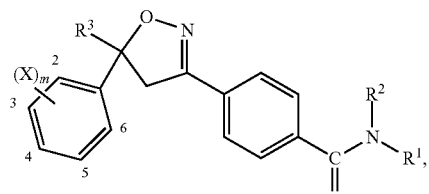
[1] - 2
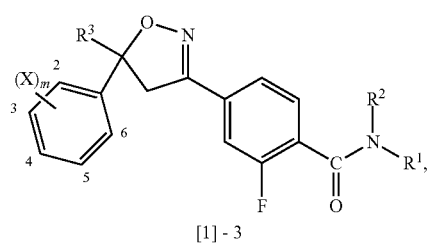
[1] - 3
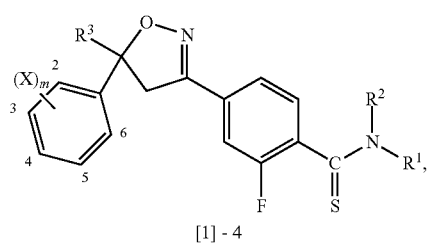
[1] - 4

TABLE 2-continued
In the table, the number showing the substitution position of substituent (X)$_m$ corresponds to the position number indicated in the following structural formulae. The indication "—" means no-substitution.
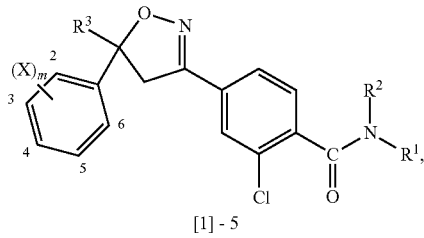
[1] - 5
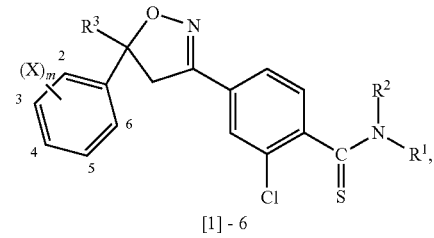
[1] - 6
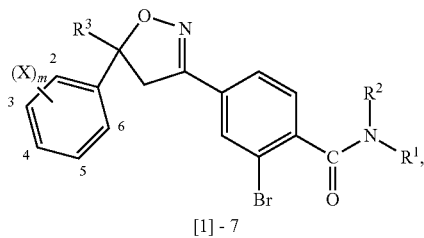
[1] - 7
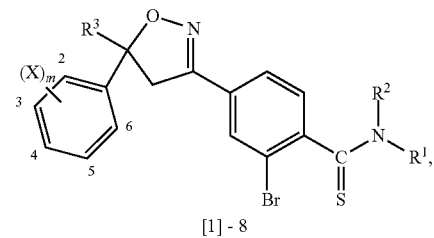
[1] - 8
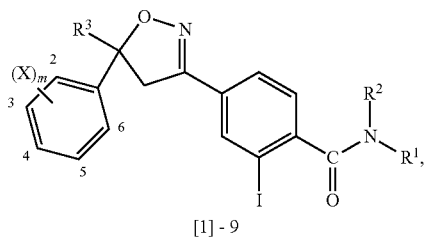
[1] - 9
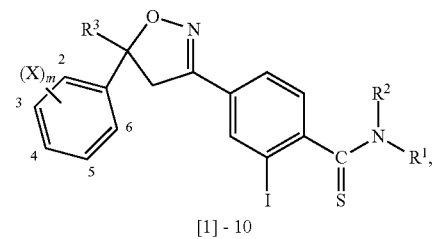
[1] - 10
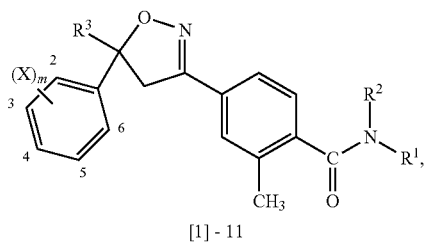
[1] - 11
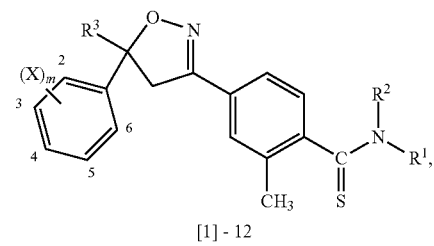
[1] - 12
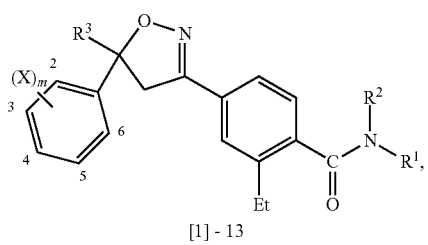
[1] - 13
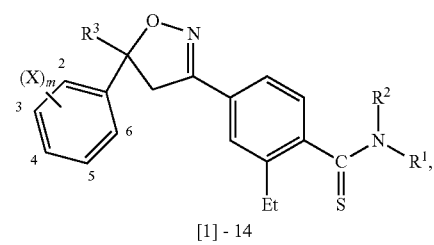
[1] - 14
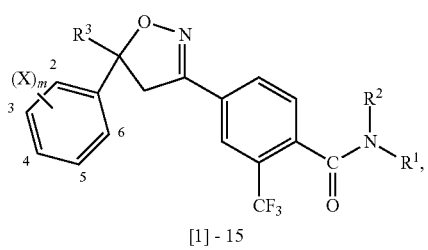
[1] - 15
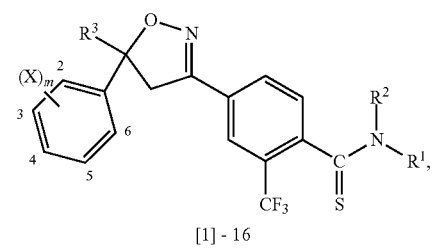
[1] - 16

TABLE 2-continued
In the table, the number showing the substitution position of substituent $(X)_m$ corresponds to the position number indicated in the following structural formulae. The indication "—" means no-substitution.
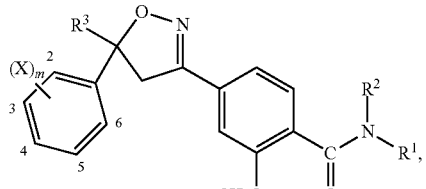
[1]-17
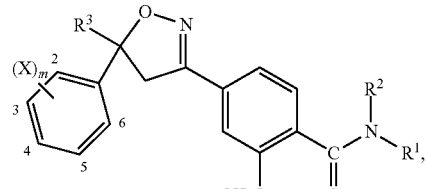
[1]-18
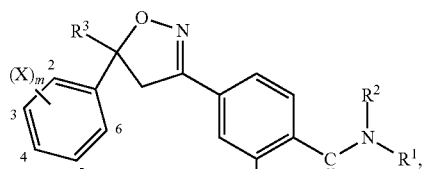
[1]-19
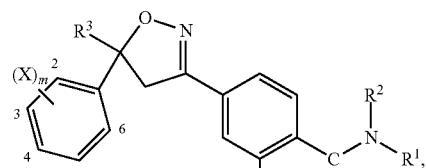
[1]-20
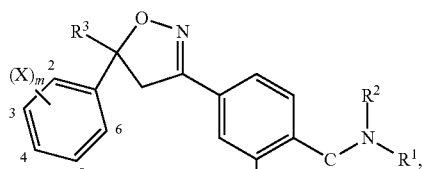
[1]-21
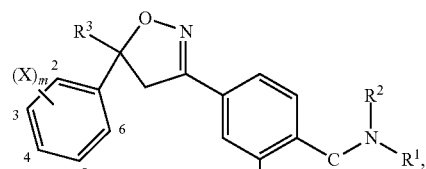
[1]-22
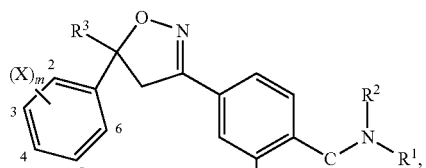
[1]-23
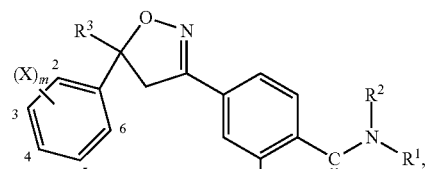
[1]-24
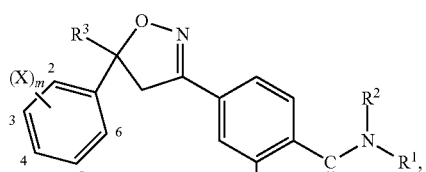
[1]-25
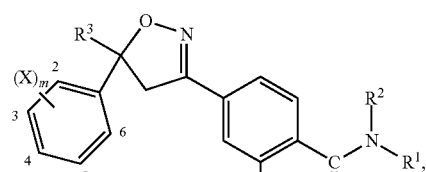
[1]-26
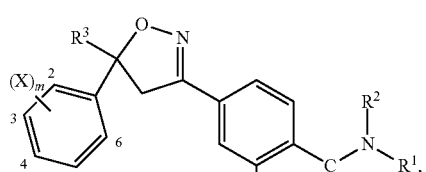
[1]-27
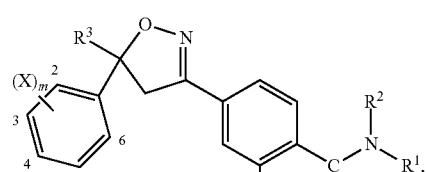
[1]-28

TABLE 2-continued
In the table, the number showing the substitution position of substituent $(X)_m$ corresponds to the position number indicated in the following structural formulae. The indication "—" means no-substitution.
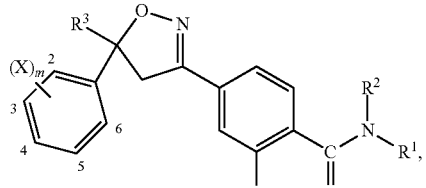
[1] - 29
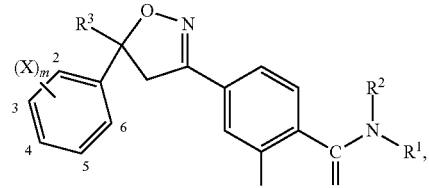
[1] - 30
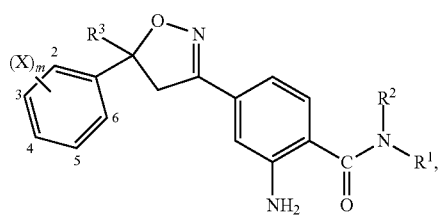
[1] - 31
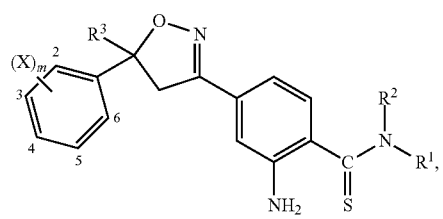
[1] - 32
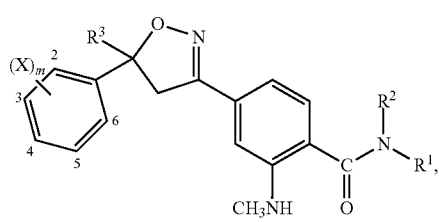
[1] - 33
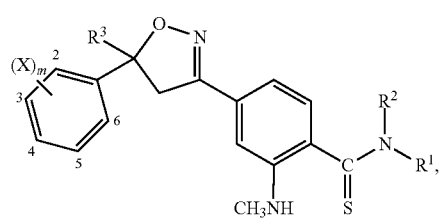
[1] - 34
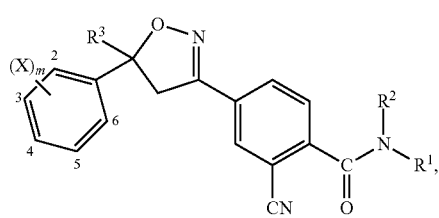
[1] - 35
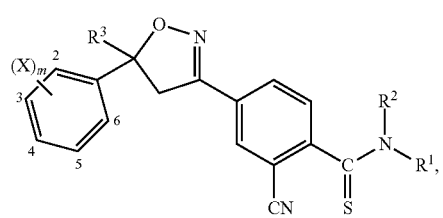
[1] - 36
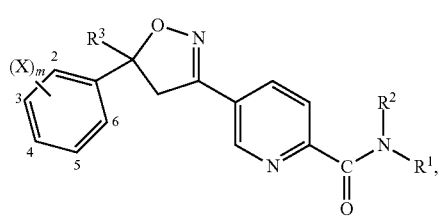
[1] - 37
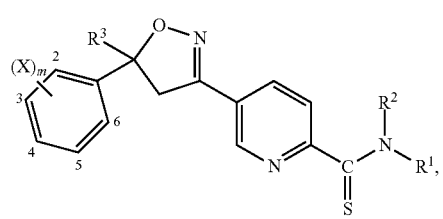
[1] - 38
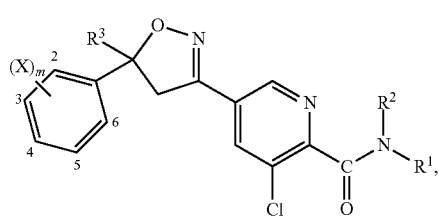
[1] - 39
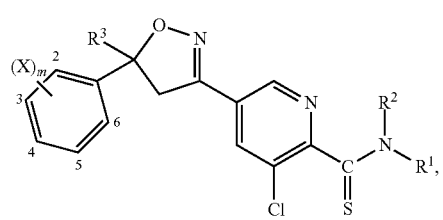
[1] - 40

TABLE 2-continued
In the table, the number showing the substitution position of substituent $(X)_m$ corresponds to the position number indicated in the following structural formulae. The indication "—" means no-substitution.
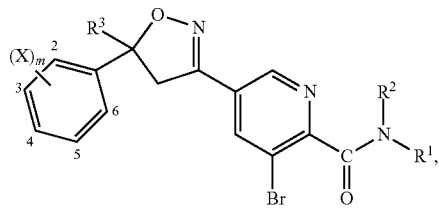
[1]-41
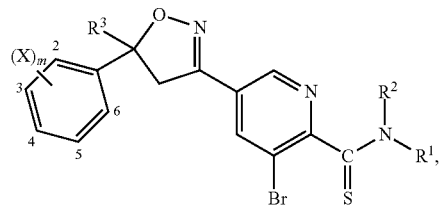
[1]-42
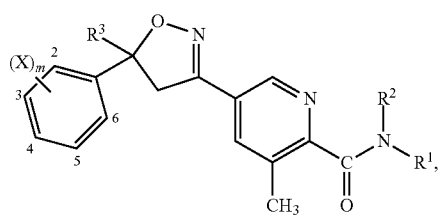
[1]-43
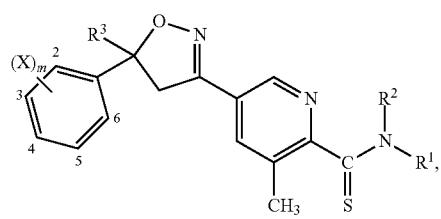
[1]-44
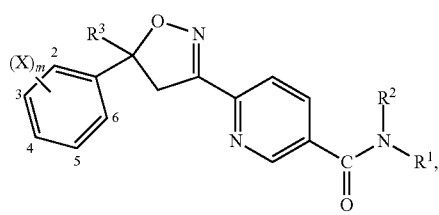
[1]-45
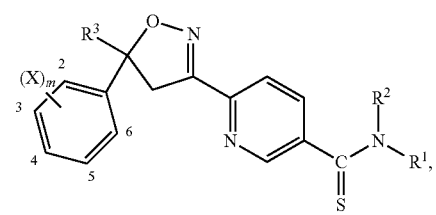
[1]-46
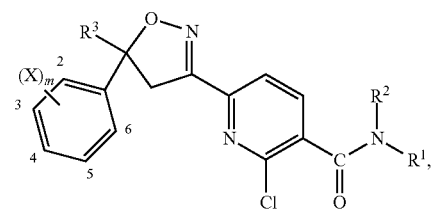
[1]-47
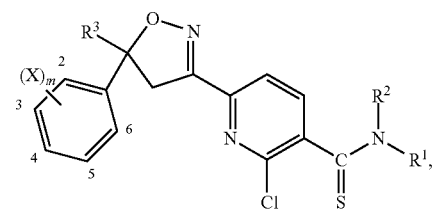
[1]-48
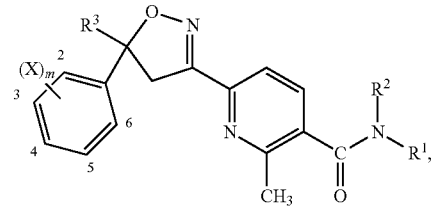
[1]-49
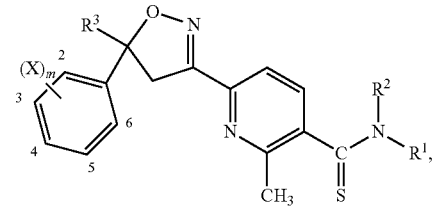
[1]-50
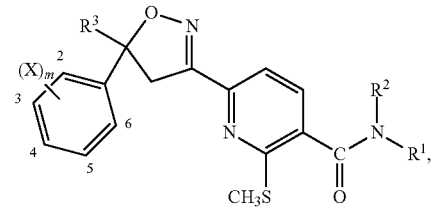
[1]-51
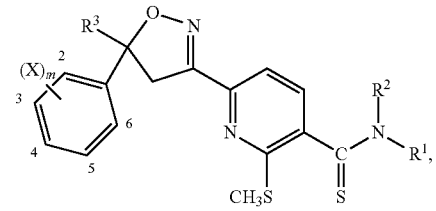
[1]-52

TABLE 2-continued

In the table, the number showing the substitution position of substituent $(X)_m$ corresponds to the position number indicated in the following structural formulae. The indication "—" means no-substitution.

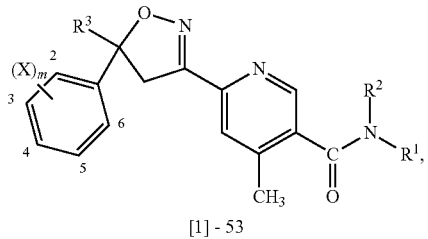

[1] - 53

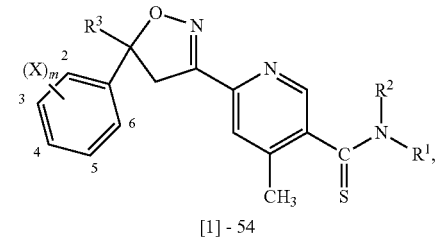

[1] - 54

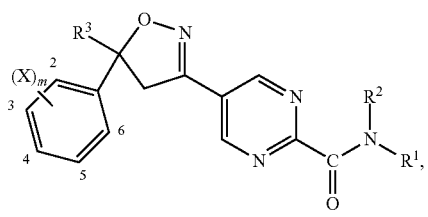

[1] - 55

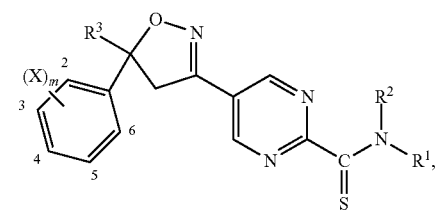

[1] - 56

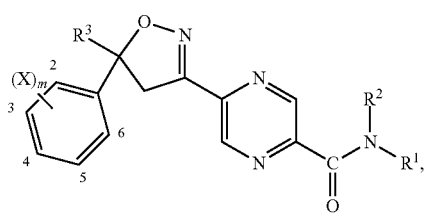

[1] - 57

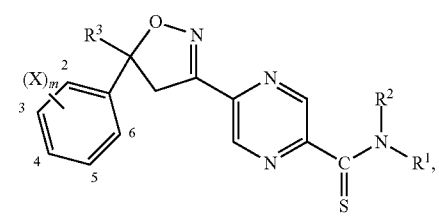

[1] - 58

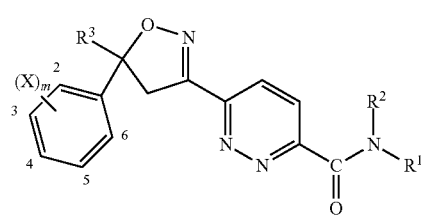

[1] - 59

または

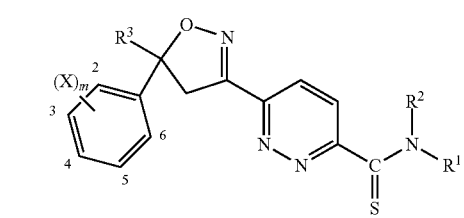

[1] - 60

| $(X)_m$ | $R^3$ | $R^2$ | $R^1$ |
|---|---|---|---|
| — | $CF_3$ | H | $CH_2CF_3$ |
| 2-F | $CF_3$ | H | $CH_2OCH_2CF_3$ |
| 3-F | $CF_3$ | H | $CH_2CF_3$ |
| 3-F | $CF_3$ | H | $CH_2OCH_2CF_3$ |
| 3-F | $CF_3$ | H | E-4a |
| 3-F | $CF_3$ | H | $CH_2C(O)NHCH_2CF_3$ |
| 3-F | $CF_3$ | H | $CH(CH_3)C(O)NHCH_2CF_3(D)$ |
| 3-F | $CF_3$ | H | $CH_2(D-22a)$ |
| 3-F | $CF_3$ | H | $CH_2(D-47a)$ |
| 3-F | $CF_3$ | $C(O)OCH_3$ | $CH_2(D-47a)$ |
| 3-F | $CF_3$ | H | $N(CH_3)Ph$ |
| 3-F | $CF_3$ | H | (D-50c)Cl |
| 4-F | $CF_3$ | H | E-4a |
| 2-Cl | $CF_3$ | H | $CH_2C(O)NHCH_2CF_3$ |
| 3-Cl | $CF_3$ | H | $CH_2CF_3$ |
| 3-Cl | $CF_3$ | $C(O)CH_3$ | $CH_2CF_3$ |
| 3-Cl | $CF_3$ | H | $CH_2OCH_2CF_3$ |
| 3-Cl | $CF_3$ | H | E-4a |
| 3-Cl | $CF_3$ | H | $CH_2C(O)NHCH_2CF_3$ |
| 3-Cl | $CF_3$ | H | $CH(CH_3)C(O)NHCH_2CF_3(D)$ |
| 3-Cl | $CF_3$ | H | $CH(CH_3)Ph(R)$ |
| 3-Cl | $CF_3$ | H | $CH_2(D-22a)$ |
| 3-Cl | $CF_3$ | H | $CH_2(D-47a)$ |
| 3-Cl | $CF_3$ | $CH_2CN$ | $CH_2(D-47a)$ |
| 3-Cl | $CF_3$ | $C(O)Et$ | $CH_2(D-47a)$ |
| 3-Cl | $CF_3$ | $C(O)OCH_3$ | $CH_2(D-47a)$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl | CF$_3$ | H | N(CH$_3$)Ph |
| 3-Cl | CF$_3$ | H | (D-50c)Cl |
| 3-Cl | CF$_3$ | H | D-52a |
| 3-Cl | CF$_2$Cl | H | CH$_2$CF$_3$ |
| 3-Cl | CF$_2$Cl | H | E-4a |
| 3-Cl | CF$_2$Cl | H | CH$_2$C(O)NHCH$_2$CF$_3$ |
| 3-Cl | CF$_2$Cl | H | CH$_2$(D-22a) |
| 3-Cl | CF$_2$Cl | H | CH$_2$(D-47a) |
| 3-Cl | CF$_2$Cl | H | (D-50c)Cl |
| 4-Cl | CF$_3$ | H | CH$_2$CF$_3$ |
| 4-Cl | CF$_3$ | H | CH$_2$(D-22a) |
| 2-Br | CF$_3$ | H | CH$_2$(D-47a) |
| 3-Br | CF$_3$ | H | c-Bu |
| 3-Br | CF$_3$ | H | CH$_2$CF$_3$ |
| 3-Br | CF$_3$ | H | CH$_2$OEt |
| 3-Br | CF$_3$ | H | CH$_2$OCH$_2$CF$_3$ |
| 3-Br | CF$_3$ | C(O)CH$_3$ | CH$_2$OCH$_2$CF$_3$ |
| 3-Br | CF$_3$ | H | CH$_2$CH$_2$OCH$_3$ |
| 3-Br | CF$_3$ | H | CH$_2$(E-10a) |
| 3-Br | CF$_3$ | H | E-4a |
| 3-Br | CF$_3$ | H | CH$_2$C(O)NHCH$_2$CH$_2$Cl |
| 3-Br | CF$_3$ | H | CH$_2$C(O)NHCH$_2$CF$_3$ |
| 3-Br | CF$_3$ | H | CH(CH$_3$)C(O)NHCH$_2$CF$_3$ |
| 3-Br | CF$_3$ | H | CH(CH$_3$)C(O)NHCH$_2$CF$_3$(D) |
| 3-Br | CF$_3$ | H | CH(CH$_3$)Ph(R) |
| 3-Br | CF$_3$ | H | CH$_2$(D-22a) |
| 3-Br | CF$_3$ | C(O)CH$_3$ | CH$_2$(D-22a) |
| 3-Br | CF$_3$ | C(O)Et | CH$_2$(D-22a) |
| 3-Br | CF$_3$ | H | CH$_2$(D-47a) |
| 3-Br | CF$_3$ | CH$_2$OCH$_3$ | CH$_2$(D-47a) |
| 3-Br | CF$_3$ | CH$_2$CN | CH$_2$(D-47a) |
| 3-Br | CF$_3$ | C(O)CH$_3$ | CH$_2$(D-47a) |
| 3-Br | CF$_3$ | C(O)Et | CH$_2$(D-47a) |
| 3-Br | CF$_3$ | C(O)OCH$_3$ | CH$_2$(D-47a) |
| 3-Br | CF$_3$ | H | N(CH$_3$)Ph |
| 3-Br | CF$_3$ | H | N(CH$_3$)(D-50a) |
| 3-Br | CF$_3$ | H | C(O)NHCH$_2$CF$_3$ |
| 3-Br | CF$_3$ | H | Ph-2,4-F$_2$ |
| 3-Br | CF$_3$ | H | (D-50c)Cl |
| 3-Br | CF$_3$ | H | D-52a |
| 3-Br | CF$_2$Cl | H | CH$_2$CF$_3$ |
| 3-Br | CF$_2$Cl | H | CH$_2$OCH$_2$CF$_3$ |
| 3-Br | CF$_2$Cl | H | E-4a |
| 3-Br | CF$_2$Cl | H | CH$_2$C(O)NHCH$_2$CF$_3$ |
| 3-Br | CF$_2$Cl | H | CH(CH$_3$)C(O)NHCH$_2$CF$_3$(D) |
| 3-Br | CF$_2$Cl | H | CH$_2$(D-22a) |
| 3-Br | CF$_2$Cl | H | CH$_2$(D-47a) |
| 3-Br | CF$_2$Cl | C(O)OCH$_3$ | CH$_2$(D-47a) |
| 3-Br | CF$_2$Cl | H | N(CH$_3$)Ph |
| 3-Br | CF$_2$Cl | H | (D-50c)Cl |
| 4-Br | CF$_3$ | H | CH$_2$CF$_3$ |
| 4-Br | CF$_3$ | C(O)OCH$_3$ | CH$_2$(D-47a) |
| 2-I | CF$_3$ | H | N(CH$_3$)Ph |
| 3-I | CHF$_2$ | H | (D-50c)Cl |
| 3-I | CF$_3$ | H | c-Pr |
| 3-I | CF$_3$ | H | CH$_2$Pr-c |
| 3-I | CF$_3$ | H | c-Bu |
| 3-I | CF$_3$ | H | CH$_2$CF$_3$ |
| 3-I | CF$_3$ | C(O)CH$_3$ | CH$_2$CF$_3$ |
| 3-I | CF$_3$ | H | CH$_2$CH$_2$CF$_3$ |
| 3-I | CF$_3$ | H | CH$_2$OCH$_3$ |
| 3-I | CF$_3$ | H | CH$_2$OEt |
| 3-I | CF$_3$ | C(O)CH$_3$ | CH$_2$OEt |
| 3-I | CF$_3$ | H | CH$_2$OCH$_2$CF$_3$ |
| 3-I | CF$_3$ | C(O)CH$_3$ | CH$_2$OCH$_2$CF$_3$ |
| 3-I | CF$_3$ | H | CH$_2$CH$_2$OCH$_3$ |
| 3-I | CF$_3$ | H | CH$_2$(E-10a) |
| 3-I | CF$_3$ | H | E-4a |
| 3-I | CF$_3$ | H | E-5a(R) |
| 3-I | CF$_3$ | H | CH$_2$CH=NOCH$_3$ |
| 3-I | CF$_3$ | H | CH$_2$C(O)NHCH$_2$CH$_2$Cl |
| 3-I | CF$_3$ | H | CH$_2$C(O)NHCH$_2$CF$_3$ |
| 3-I | CF$_3$ | H | CH(CH$_3$)C(O)NHEt |
| 3-I | CF$_3$ | H | CH(CH$_3$)C(O)NHCH$_2$CF$_3$ |
| 3-I | CF$_3$ | H | CH(CH$_3$)C(O)NHCH$_2$CF$_3$(D) |
| 3-I | CF$_3$ | H | CH$_2$CH=CH$_2$ |
| 3-I | CF$_3$ | H | CH$_2$CCl=CH$_2$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-I | CF$_3$ | H | CH(CH$_3$)Ph(R) |
| 3-I | CF$_3$ | H | CH$_2$(Ph-4-NO$_2$) |
| 3-I | CF$_3$ | H | CH$_2$(Ph-4-CN) |
| 3-I | CF$_3$ | H | CH$_2$(D-17b)Cl |
| 3-I | CF$_3$ | H | CH$_2$(D-21a) |
| 3-I | CF$_3$ | H | CH$_2$(D-22a) |
| 3-I | CF$_3$ | C(O)CH$_3$ | CH$_2$(D-22a) |
| 3-I | CF$_3$ | C(O)Et | CH$_2$(D-22a) |
| 3-I | CF$_3$ | H | CH$_2$(D-47a) |
| 3-I | CF$_3$ | CH$_2$OCH$_3$ | CH$_2$(D-47a) |
| 3-I | CF$_3$ | CH$_2$CN | CH$_2$(D-47a) |
| 3-I | CF$_3$ | C(O)CH$_3$ | CH$_2$(D-47a) |
| 3-I | CF$_3$ | C(O)Et | CH$_2$(D-47a) |
| 3-I | CF$_3$ | C(O)Pr-c | CH$_2$(D-47a) |
| 3-I | CF$_3$ | C(O)OCH$_3$ | CH$_2$(D-47a) |
| 3-I | CF$_3$ | H | CH(CH$_3$)(D-47a) |
| 3-I | CF$_3$ | H | CH$_2$(D-50a) |
| 3-I | CF$_3$ | H | N(CH$_3$)Ph |
| 3-I | CF$_3$ | H | N(CH$_3$)(D-50a) |
| 3-I | CF$_3$ | C(O)OCH$_3$ | C(O)N(CH$_3$)$_2$ |
| 3-I | CF$_3$ | H | C(O)NHEt |
| 3-I | CF$_3$ | CH$_3$ | C(O)NHEt |
| 3-I | CF$_3$ | H | C(O)NHCH$_2$CH$_2$Cl |
| 3-I | CF$_3$ | H | C(O)NHCH$_2$(Ph-4-F) |
| 3-I | CF$_3$ | H | Ph-4-CN |
| 3-I | CF$_3$ | H | Ph-2,4-F$_2$ |
| 3-I | CF$_3$ | H | (D-15a)CH$_3$ |
| 3-I | CF$_3$ | H | (D-47d)CN |
| 3-I | CF$_3$ | H | (D-47e)Br |
| 3-I | CF$_3$ | H | D-50a |
| 3-I | CF$_3$ | H | (D-50c)Cl |
| 3-I | CF$_3$ | H | (D-50c)Br |
| 3-I | CF$_3$ | H | D-52a |
| 3-I | CF$_3$ | H | D-53a |
| 3-I | CF$_2$Cl | H | CH$_2$CF$_3$ |
| 3-I | CF$_2$Cl | C(O)CH$_3$ | CH$_2$CF$_3$ |
| 3-I | CF$_2$Cl | H | CH$_2$OCH$_2$CF$_3$ |
| 3-I | CF$_2$Cl | H | E-4a |
| 3-I | CF$_2$Cl | H | CH$_2$C(O)NHCH$_2$CF$_3$ |
| 3-I | CF$_2$Cl | H | CH(CH$_3$)C(O)NHCH$_2$CF$_3$(D) |
| 3-I | CF$_2$Cl | H | CH(CH$_3$)Ph(R) |
| 3-I | CF$_2$Cl | H | CH$_2$(D-22a) |
| 3-I | CF$_2$Cl | H | CH$_2$(D-47a) |
| 3-I | CF$_2$Cl | CH$_2$CN | CH$_2$(D-47a) |
| 3-I | CF$_2$Cl | C(O)Et | CH$_2$(D-47a) |
| 3-I | CF$_2$Cl | C(O)OCH$_3$ | CH$_2$(D-47a) |
| 3-I | CF$_2$Cl | H | N(CH$_3$)Ph |
| 3-I | CF$_2$Cl | H | (D-50c)Cl |
| 3-I | CF$_2$Cl | H | D-52a |
| 3-I | CF$_2$Br | H | CH$_2$CF$_3$ |
| 3-I | CF$_2$CHF$_2$ | H | CH$_2$OCH$_2$CF$_3$ |
| 4-I | CF$_3$ | H | CH$_2$CF$_3$ |
| 4-I | CF$_3$ | H | E-4a |
| 4-I | CF$_3$ | H | CH$_2$(D-47a) |
| 2-CH$_3$ | CF$_3$ | H | CH$_2$C(O)NHCH$_2$CF$_3$ |
| 3-CH$_3$ | CF$_3$ | H | CH$_2$(D-22a) |
| 4-CH$_3$ | CF$_3$ | H | CH$_2$(D-47a) |
| 2-Et | CF$_3$ | C(O)OCH$_3$ | CH$_2$(D-47a) |
| 3-Et | CF$_3$ | H | N(CH$_3$)Ph |
| 3-n-Pr | CF$_3$ | H | (D-50c)Cl |
| 3-i-Pr | CF$_3$ | H | CH$_2$CF$_3$ |
| 3-n-Bu | CF$_3$ | H | CH$_2$OCH$_2$CF$_3$ |
| 3-i-Bu | CF$_3$ | H | E-4a |
| 3-t-Bu | CF$_3$ | H | CH$_2$C(O)NHCH$_2$CF$_3$ |
| 4-t-Bu | CF$_3$ | H | CH$_2$(D-22a) |
| 2-CF$_3$ | CF$_3$ | H | CH$_2$(D-47a) |
| 3-CF$_3$ | CHF$_2$ | C(O)OCH$_3$ | CH$_2$(D-47a) |
| 3-CF$_3$ | CF$_3$ | H | c-Pr |
| 3-CF$_3$ | CF$_3$ | H | CH$_2$Pr-c |
| 3-CF$_3$ | CF$_3$ | H | c-Bu |
| 3-CF$_3$ | CF$_3$ | H | CH$_2$CF$_3$ |
| 3-CF$_3$ | CF$_3$ | C(O)CH$_3$ | CH$_2$CF$_3$ |
| 3-CF$_3$ | CF$_3$ | H | CH$_2$CH$_2$CF$_3$ |
| 3-CF$_3$ | CF$_3$ | H | CH$_2$OCH$_3$ |
| 3-CF$_3$ | CF$_3$ | H | CH$_2$OEt |
| 3-CF$_3$ | CF$_3$ | C(O)CH$_3$ | CH$_2$OEt |
| 3-CF$_3$ | CF$_3$ | H | CH$_2$OCH$_2$CF$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CF$_3$ | CF$_3$ | C(O)CH$_3$ | CH$_2$OCH$_2$CF$_3$ |
| 3-CF$_3$ | CF$_3$ | H | CH$_2$CH$_2$OCH$_3$ |
| 3-CF$_3$ | CF$_3$ | H | CH$_2$(E-10a) |
| 3-CF$_3$ | CF$_3$ | H | E-4a |
| 3-CF$_3$ | CF$_3$ | H | E-5a(R) |
| 3-CF$_3$ | CF$_3$ | H | CH$_2$CH=NOCH$_3$ |
| 3-CF$_3$ | CF$_3$ | H | CH$_2$C(O)NHCH$_2$CH$_2$Cl |
| 3-CF$_3$ | CF$_3$ | H | CH$_2$C(O)NHCH$_2$CF$_3$ |
| 3-CF$_3$ | CF$_3$ | H | CH(CH$_3$)C(O)NHEt |
| 3-CF$_3$ | CF$_3$ | H | CH(CH$_3$)C(O)NHCH$_2$CF$_3$ |
| 3-CF$_3$ | CF$_3$ | H | CH(CH$_3$)C(O)NHCH$_2$CF$_3$(D) |
| 3-CF$_3$ | CF$_3$ | H | CH$_2$CH=CH$_2$ |
| 3-CF$_3$ | CF$_3$ | H | CH$_2$CCl=CH$_2$ |
| 3-CF$_3$ | CF$_3$ | H | CH(CH$_3$)Ph(R) |
| 3-CF$_3$ | CF$_3$ | H | CH$_2$(Ph-4-NO$_2$) |
| 3-CF$_3$ | CF$_3$ | H | CH$_2$(Ph-4-CN) |
| 3-CF$_3$ | CF$_3$ | H | CH$_2$(D-17b)Cl |
| 3-CF$_3$ | CF$_3$ | H | CH$_2$(D-21a) |
| 3-CF$_3$ | CF$_3$ | H | CH$_2$(D-22a) |
| 3-CF$_3$ | CF$_3$ | C(O)CH$_3$ | CH$_2$(D-22a) |
| 3-CF$_3$ | CF$_3$ | C(O)Et | CH$_2$(D-22a) |
| 3-CF$_3$ | CF$_3$ | H | CH$_2$(D-47a) |
| 3-CF$_3$ | CF$_3$ | CH$_2$OCH$_3$ | CH$_2$(D-47a) |
| 3-CF$_3$ | CF$_3$ | CH$_2$CN | CH$_2$(D-47a) |
| 3-CF$_3$ | CF$_3$ | C(O)CH$_3$ | CH$_2$(D-47a) |
| 3-CF$_3$ | CF$_3$ | C(O)Et | CH$_2$(D-47a) |
| 3-CF$_3$ | CF$_3$ | C(O)Pr-c | CH$_2$(D-47a) |
| 3-CF$_3$ | CF$_3$ | C(O)OCH$_3$ | CH$_2$(D-47a) |
| 3-CF$_3$ | CF$_3$ | H | CH(CH$_3$)(D-47a) |
| 3-CF$_3$ | CF$_3$ | H | CH$_2$(D-50a) |
| 3-CF$_3$ | CF$_3$ | H | N(CH$_3$)Ph |
| 3-CF$_3$ | CF$_3$ | H | N(CH$_3$)(D-50a) |
| 3-CF$_3$ | CF$_3$ | C(O)OCH$_3$ | C(O)N(CH$_3$)$_2$ |
| 3-CF$_3$ | CF$_3$ | H | C(O)NHEt |
| 3-CF$_3$ | CF$_3$ | CH$_3$ | C(O)NHEt |
| 3-CF$_3$ | CF$_3$ | H | C(O)NHCH$_2$CH$_2$Cl |
| 3-CF$_3$ | CF$_3$ | H | C(O)NHCH$_2$(Ph-4-F) |
| 3-CF$_3$ | CF$_3$ | H | Ph-4-CN |
| 3-CF$_3$ | CF$_3$ | H | Ph-2,4-F$_2$ |
| 3-CF$_3$ | CF$_3$ | H | (D-15a)CH$_3$ |
| 3-CF$_3$ | CF$_3$ | H | (D-47d)CN |
| 3-CF$_3$ | CF$_3$ | H | (D-47e)Br |
| 3-CF$_3$ | CF$_3$ | H | D-50a |
| 3-CF$_3$ | CF$_3$ | H | (D-50c)Cl |
| 3-CF$_3$ | CF$_3$ | H | (D-50c)Br |
| 3-CF$_3$ | CF$_3$ | H | D-52a |
| 3-CF$_3$ | CF$_3$ | H | D-53a |
| 3-CF$_3$ | CF$_2$Cl | H | CH$_2$CF$_3$ |
| 3-CF$_3$ | CF$_2$Cl | C(O)CH$_3$ | CH$_2$CF$_3$ |
| 3-CF$_3$ | CF$_2$Cl | H | CH$_2$OCH$_2$CF$_3$ |
| 3-CF$_3$ | CF$_2$Cl | H | E-4a |
| 3-CF$_3$ | CF$_2$Cl | H | CH$_2$C(O)NHCH$_2$CF$_3$ |
| 3-CF$_3$ | CF$_2$Cl | H | CH(CH$_3$)C(O)NHCH$_2$CF$_3$(D) |
| 3-CF$_3$ | CF$_2$Cl | H | CH(CH$_3$)Ph(R) |
| 3-CF$_3$ | CF$_2$Cl | H | CH$_2$(D-22a) |
| 3-CF$_3$ | CF$_2$Cl | H | CH$_2$(D-47a) |
| 3-CF$_3$ | CF$_2$Cl | CH$_2$CN | CH$_2$(D-47a) |
| 3-CF$_3$ | CF$_2$Cl | C(O)Et | CH$_2$(D-47a) |
| 3-CF$_3$ | CF$_2$Cl | C(O)OCH$_3$ | CH$_2$(D-47a) |
| 3-CF$_3$ | CF$_2$Cl | H | N(CH$_3$)Ph |
| 3-CF$_3$ | CF$_2$Cl | H | (D-50c)Cl |
| 3-CF$_3$ | CF$_2$Cl | H | D-52a |
| 3-CF$_3$ | CF$_2$Br | H | N(CH$_3$)Ph |
| 3-CF$_3$ | CF$_2$CHF$_2$ | H | (D-50c)Cl |
| 4-CF$_3$ | CF$_3$ | H | CH$_2$CF$_3$ |
| 3-CF$_2$CF$_3$ | CHF$_2$ | H | CH$_2$OCH$_2$CF$_3$ |
| 3-CF$_2$CF$_3$ | CF$_3$ | H | c-Pr |
| 3-CF$_2$CF$_3$ | CF$_3$ | H | CH$_2$Pr-c |
| 3-CF$_2$CF$_3$ | CF$_3$ | H | c-Bu |
| 3-CF$_2$CF$_3$ | CF$_3$ | H | CH$_2$CF$_3$ |
| 3-CF$_2$CF$_3$ | CF$_3$ | C(O)CH$_3$ | CH$_2$CF$_3$ |
| 3-CF$_2$CF$_3$ | CF$_3$ | H | CH$_2$CH$_2$CF$_3$ |
| 3-CF$_2$CF$_3$ | CF$_3$ | H | CH$_2$OCH$_3$ |
| 3-CF$_2$CF$_3$ | CF$_3$ | H | CH$_2$OEt |
| 3-CF$_2$CF$_3$ | CF$_3$ | C(O)CH$_3$ | CH$_2$OEt |
| 3-CF$_2$CF$_3$ | CF$_3$ | H | CH$_2$OCH$_2$CF$_3$ |
| 3-CF$_2$CF$_3$ | CF$_3$ | C(O)CH$_3$ | CH$_2$OCH$_2$CF$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CF$_2$CF$_3$ | CF$_3$ | H | CH$_2$CH$_2$OCH$_3$ |
| 3-CF$_2$CF$_3$ | CF$_3$ | H | CH$_2$(E-10a) |
| 3-CF$_2$CF$_3$ | CF$_3$ | H | E-4a |
| 3-CF$_2$CF$_3$ | CF$_3$ | H | E-5a(R) |
| 3-CF$_2$CF$_3$ | CF$_3$ | H | CH$_2$CH=NOCH$_3$ |
| 3-CF$_2$CF$_3$ | CF$_3$ | H | CH$_2$C(O)NHCH$_2$CH$_2$Cl |
| 3-CF$_2$CF$_3$ | CF$_3$ | H | CH$_2$C(O)NHCH$_2$CF$_3$ |
| 3-CF$_2$CF$_3$ | CF$_3$ | H | CH(CH$_3$)C(O)NHEt |
| 3-CF$_2$CF$_3$ | CF$_3$ | H | CH(CH$_3$)C(O)NHCH$_2$CF$_3$ |
| 3-CF$_2$CF$_3$ | CF$_3$ | H | CH(CH$_3$)C(O)NHCH$_2$CF$_3$(D) |
| 3-CF$_2$CF$_3$ | CF$_3$ | H | CH$_2$CH=CH$_2$ |
| 3-CF$_2$CF$_3$ | CF$_3$ | H | CH$_2$CCl=CH$_2$ |
| 3-CF$_2$CF$_3$ | CF$_3$ | H | CH(CH$_3$)Ph(R) |
| 3-CF$_2$CF$_3$ | CF$_3$ | H | CH$_2$(Ph-4-NO$_2$) |
| 3-CF$_2$CF$_3$ | CF$_3$ | H | CH$_2$(Ph-4-CN) |
| 3-CF$_2$CF$_3$ | CF$_3$ | H | CH$_2$(D-17b)Cl |
| 3-CF$_2$CF$_3$ | CF$_3$ | H | CH$_2$(D-21a) |
| 3-CF$_2$CF$_3$ | CF$_3$ | H | CH$_2$(D-22a) |
| 3-CF$_2$CF$_3$ | CF$_3$ | C(O)CH$_3$ | CH$_2$(D-22a) |
| 3-CF$_2$CF$_3$ | CF$_3$ | C(O)Et | CH$_2$(D-22a) |
| 3-CF$_2$CF$_3$ | CF$_3$ | H | CH$_2$(D-47a) |
| 3-CF$_2$CF$_3$ | CF$_3$ | CH$_2$OCH$_3$ | CH$_2$(D-47a) |
| 3-CF$_2$CF$_3$ | CF$_3$ | CH$_2$CN | CH$_2$(D-47a) |
| 3-CF$_2$CF$_3$ | CF$_3$ | C(O)CH$_3$ | CH$_2$(D-47a) |
| 3-CF$_2$CF$_3$ | CF$_3$ | C(O)Et | CH$_2$(D-47a) |
| 3-CF$_2$CF$_3$ | CF$_3$ | C(O)Pr-c | CH$_2$(D-47a) |
| 3-CF$_2$CF$_3$ | CF$_3$ | C(O)OCH$_3$ | CH$_2$(D-47a) |
| 3-CF$_2$CF$_3$ | CF$_3$ | H | CH(CH$_3$)(D-47a) |
| 3-CF$_2$CF$_3$ | CF$_3$ | H | CH$_2$(D-50a) |
| 3-CF$_2$CF$_3$ | CF$_3$ | H | N(CH$_3$)Ph |
| 3-CF$_2$CF$_3$ | CF$_3$ | H | N(CH$_3$)(D-50a) |
| 3-CF$_2$CF$_3$ | CF$_3$ | C(O)OCH$_3$ | C(O)N(CH$_3$)$_2$ |
| 3-CF$_2$CF$_3$ | CF$_3$ | H | C(O)NHEt |
| 3-CF$_2$CF$_3$ | CF$_3$ | CH$_3$ | C(O)NHEt |
| 3-CF$_2$CF$_3$ | CF$_3$ | H | C(O)NHCH$_2$CH$_2$Cl |
| 3-CF$_2$CF$_3$ | CF$_3$ | H | C(O)NHCH$_2$(Ph-4-F) |
| 3-CF$_2$CF$_3$ | CF$_3$ | H | Ph-4-CN |
| 3-CF$_2$CF$_3$ | CF$_3$ | H | Ph-2,4-F$_2$ |
| 3-CF$_2$CF$_3$ | CF$_3$ | H | (D-15a)CH$_3$ |
| 3-CF$_2$CF$_3$ | CF$_3$ | H | (D-47d)CN |
| 3-CF$_2$CF$_3$ | CF$_3$ | H | (D-47e)Br |
| 3-CF$_2$CF$_3$ | CF$_3$ | H | D-50a |
| 3-CF$_2$CF$_3$ | CF$_3$ | H | (D-50c)Cl |
| 3-CF$_2$CF$_3$ | CF$_3$ | H | (D-50c)Br |
| 3-CF$_2$CF$_3$ | CF$_3$ | H | D-52a |
| 3-CF$_2$CF$_3$ | CF$_3$ | H | D-53a |
| 3-CF$_2$CF$_3$ | CF$_2$Cl | H | CH$_2$CF$_3$ |
| 3-CF$_2$CF$_3$ | CF$_2$Cl | C(O)CH$_3$ | CH$_2$CF$_3$ |
| 3-CF$_2$CF$_3$ | CF$_2$Cl | H | CH$_2$OCH$_2$CF$_3$ |
| 3-CF$_2$CF$_3$ | CF$_2$Cl | H | E-4a |
| 3-CF$_2$CF$_3$ | CF$_2$Cl | H | CH$_2$C(O)NHCH$_2$CF$_3$ |
| 3-CF$_2$CF$_3$ | CF$_2$Cl | H | CH(CH$_3$)C(O)NHCH$_2$CF$_3$(D) |
| 3-CF$_2$CF$_3$ | CF$_2$Cl | H | CH(CH$_3$)Ph(R) |
| 3-CF$_2$CF$_3$ | CF$_2$Cl | H | CH$_2$(D-22a) |
| 3-CF$_2$CF$_3$ | CF$_2$Cl | H | CH$_2$(D-47a) |
| 3-CF$_2$CF$_3$ | CF$_2$Cl | CH$_2$CN | CH$_2$(D-47a) |
| 3-CF$_2$CF$_3$ | CF$_2$Cl | C(O)Et | CH$_2$(D-47a) |
| 3-CF$_2$CF$_3$ | CF$_2$Cl | C(O)OCH$_3$ | CH$_2$(D-47a) |
| 3-CF$_2$CF$_3$ | CF$_2$Cl | H | N(CH$_3$)Ph |
| 3-CF$_2$CF$_3$ | CF$_2$Cl | H | (D-50c)Cl |
| 3-CF$_2$CF$_3$ | CF$_2$Cl | H | D-52a |
| 3-CF$_2$CF$_3$ | CF$_2$Br | H | E-4a |
| 3-CF$_2$CF$_3$ | CF$_2$CHF$_2$ | H | CH$_2$C(O)NHCH$_2$CF$_3$ |
| 3-CF$_2$CF$_2$CF$_3$ | CF$_3$ | H | c-Bu |
| 3-CF$_2$CF$_2$CF$_3$ | CF$_3$ | H | CH$_2$CF$_3$ |
| 3-CF$_2$CF$_2$CF$_3$ | CF$_3$ | H | CH$_2$OEt |
| 3-CF$_2$CF$_2$CF$_3$ | CF$_3$ | H | CH$_2$OCH$_2$CF$_3$ |
| 3-CF$_2$CF$_2$CF$_3$ | CF$_3$ | C(O)CH$_3$ | CH$_2$OCH$_2$CF$_3$ |
| 3-CF$_2$CF$_2$CF$_3$ | CF$_3$ | H | CH$_2$CH$_2$OCH$_3$ |
| 3-CF$_2$CF$_2$CF$_3$ | CF$_3$ | H | CH$_2$(E-10a) |
| 3-CF$_2$CF$_2$CF$_3$ | CF$_3$ | H | E-4a |
| 3-CF$_2$CF$_2$CF$_3$ | CF$_3$ | H | CH$_2$C(O)NHCH$_2$CH$_2$Cl |
| 3-CF$_2$CF$_2$CF$_3$ | CF$_3$ | H | CH$_2$C(O)NHCH$_2$CF$_3$ |
| 3-CF$_2$CF$_2$CF$_3$ | CF$_3$ | H | CH(CH$_3$)C(O)NHCH$_2$CF$_3$ |
| 3-CF$_2$CF$_2$CF$_3$ | CF$_3$ | H | CH(CH$_3$)C(O)NHCH$_2$CF$_3$(D) |
| 3-CF$_2$CF$_2$CF$_3$ | CF$_3$ | H | CH(CH$_3$)Ph(R) |
| 3-CF$_2$CF$_2$CF$_3$ | CF$_3$ | H | CH$_2$(D-22a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-$CF_2CF_2CF_3$ | $CF_3$ | $C(O)CH_3$ | $CH_2$(D-22a) |
| 3-$CF_2CF_2CF_3$ | $CF_3$ | $C(O)Et$ | $CH_2$(D-22a) |
| 3-$CF_2CF_2CF_3$ | $CF_3$ | H | $CH_2$(D-47a) |
| 3-$CF_2CF_2CF_3$ | $CF_3$ | $CH_2OCH_3$ | $CH_2$(D-47a) |
| 3-$CF_2CF_2CF_3$ | $CF_3$ | $CH_2CN$ | $CH_2$(D-47a) |
| 3-$CF_2CF_2CF_3$ | $CF_3$ | $C(O)CH_3$ | $CH_2$(D-47a) |
| 3-$CF_2CF_2CF_3$ | $CF_3$ | $C(O)Et$ | $CH_2$(D-47a) |
| 3-$CF_2CF_2CF_3$ | $CF_3$ | $C(O)OCH_3$ | $CH_2$(D-47a) |
| 3-$CF_2CF_2CF_3$ | $CF_3$ | H | $N(CH_3)Ph$ |
| 3-$CF_2CF_2CF_3$ | $CF_3$ | H | $N(CH_3)$(D-50a) |
| 3-$CF_2CF_2CF_3$ | $CF_3$ | H | $C(O)NHCH_2CF_3$ |
| 3-$CF_2CF_2CF_3$ | $CF_3$ | H | Ph-2,4-$F_2$ |
| 3-$CF_2CF_2CF_3$ | $CF_3$ | H | (D-50c)Cl |
| 3-$CF_2CF_2CF_3$ | $CF_3$ | H | D-52a |
| 3-$CF_2CF_2CF_3$ | $CF_2Cl$ | H | $CH_2CF_3$ |
| 3-$CF_2CF_2CF_3$ | $CF_2Cl$ | H | $CH_2OCH_2CF_3$ |
| 3-$CF_2CF_2CF_3$ | $CF_2Cl$ | H | E-4a |
| 3-$CF_2CF_2CF_3$ | $CF_2Cl$ | H | $CH_2C(O)NHCH_2CF_3$ |
| 3-$CF_2CF_2CF_3$ | $CF_2Cl$ | H | $CH(CH_3)C(O)NHCH_2CF_3(D)$ |
| 3-$CF_2CF_2CF_3$ | $CF_2Cl$ | H | $CH_2$(D-22a) |
| 3-$CF_2CF_2CF_3$ | $CF_2Cl$ | H | $CH_2$(D-47a) |
| 3-$CF_2CF_2CF_3$ | $CF_2Cl$ | $C(O)OCH_3$ | $CH_2$(D-47a) |
| 3-$CF_2CF_2CF_3$ | $CF_2Cl$ | H | $N(CH_3)Ph$ |
| 3-$CF_2CF_2CF_3$ | $CF_2Cl$ | H | (D-50c)Cl |
| 3-$CF(CF_3)_2$ | $CF_3$ | H | c-Bu |
| 3-$CF(CF_3)_2$ | $CF_3$ | H | $CH_2CF_3$ |
| 3-$CF(CF_3)_2$ | $CF_3$ | H | $CH_2OEt$ |
| 3-$CF(CF_3)_2$ | $CF_3$ | H | $CH_2OCH_2CF_3$ |
| 3-$CF(CF_3)_2$ | $CF_3$ | $C(O)CH_3$ | $CH_2OCH_2CF_3$ |
| 3-$CF(CF_3)_2$ | $CF_3$ | H | $CH_2CH_2OCH_3$ |
| 3-$CF(CF_3)_2$ | $CF_3$ | H | $CH_2$(E-10a) |
| 3-$CF(CF_3)_2$ | $CF_3$ | H | E-4a |
| 3-$CF(CF_3)_2$ | $CF_3$ | H | $CH_2C(O)NHCH_2CH_2Cl$ |
| 3-$CF(CF_3)_2$ | $CF_3$ | H | $CH_2C(O)NHCH_2CF_3$ |
| 3-$CF(CF_3)_2$ | $CF_3$ | H | $CH(CH_3)C(O)NHCH_2CF_3$ |
| 3-$CF(CF_3)_2$ | $CF_3$ | H | $CH(CH_3)C(O)NHCH_2CF_3(D)$ |
| 3-$CF(CF_3)_2$ | $CF_3$ | H | $CH(CH_3)Ph(R)$ |
| 3-$CF(CF_3)_2$ | $CF_3$ | H | $CH_2$(D-22a) |
| 3-$CF(CF_3)_2$ | $CF_3$ | $C(O)CH_3$ | $CH_2$(D-22a) |
| 3-$CF(CF_3)_2$ | $CF_3$ | $C(O)Et$ | $CH_2$(D-22a) |
| 3-$CF(CF_3)_2$ | $CF_3$ | H | $CH_2$(D-47a) |
| 3-$CF(CF_3)_2$ | $CF_3$ | $CH_2OCH_3$ | $CH_2$(D-47a) |
| 3-$CF(CF_3)_2$ | $CF_3$ | $CH_2CN$ | $CH_2$(D-47a) |
| 3-$CF(CF_3)_2$ | $CF_3$ | $C(O)CH_3$ | $CH_2$(D-47a) |
| 3-$CF(CF_3)_2$ | $CF_3$ | $C(O)Et$ | $CH_2$(D-47a) |
| 3-$CF(CF_3)_2$ | $CF_3$ | $C(O)OCH_3$ | $CH_2$(D-47a) |
| 3-$CF(CF_3)_2$ | $CF_3$ | H | $N(CH_3)Ph$ |
| 3-$CF(CF_3)_2$ | $CF_3$ | H | $N(CH_3)$(D-50a) |
| 3-$CF(CF_3)_2$ | $CF_3$ | H | $C(O)NHCH_2CF_3$ |
| 3-$CF(CF_3)_2$ | $CF_3$ | H | Ph-2,4-$F_2$ |
| 3-$CF(CF_3)_2$ | $CF_3$ | H | (D-50c)Cl |
| 3-$CF(CF_3)_2$ | $CF_3$ | H | D-52a |
| 3-$CF(CF_3)_2$ | $CF_2Cl$ | H | $CH_2CF_3$ |
| 3-$CF(CF_3)_2$ | $CF_2Cl$ | H | $CH_2OCH_2CF_3$ |
| 3-$CF(CF_3)_2$ | $CF_2Cl$ | H | E-4a |
| 3-$CF(CF_3)_2$ | $CF_2Cl$ | H | $CH_2C(O)NHCH_2CF_3$ |
| 3-$CF(CF_3)_2$ | $CF_2Cl$ | H | $CH(CH_3)C(O)NHCH_2CF_3(D)$ |
| 3-$CF(CF_3)_2$ | $CF_2Cl$ | H | $CH_2$(D-22a) |
| 3-$CF(CF_3)_2$ | $CF_2Cl$ | H | $CH_2$(D-47a) |
| 3-$CF(CF_3)_2$ | $CF_2Cl$ | $C(O)OCH_3$ | $CH_2$(D-47a) |
| 3-$CF(CF_3)_2$ | $CF_2Cl$ | H | $N(CH_3)Ph$ |
| 3-$CF(CF_3)_2$ | $CF_2Cl$ | H | (D-50c)Cl |
| 3-$CF_2CF_2CF_2CF_3$ | $CF_3$ | H | $CH_2CF_3$ |
| 3-$CF_2CF_2CF_2CF_3$ | $CF_3$ | $C(O)CH_3$ | $CH_2CF_3$ |
| 3-$CF_2CF_2CF_2CF_3$ | $CF_3$ | H | $CH_2OCH_2CF_3$ |
| 3-$CF_2CF_2CF_2CF_3$ | $CF_3$ | H | E-4a |
| 3-$CF_2CF_2CF_2CF_3$ | $CF_3$ | H | $CH_2C(O)NHCH_2CF_3$ |
| 3-$CF_2CF_2CF_2CF_3$ | $CF_3$ | H | $CH(CH_3)C(O)NHCH_2CF_3(D)$ |
| 3-$CF_2CF_2CF_2CF_3$ | $CF_3$ | H | $CH(CH_3)Ph(R)$ |
| 3-$CF_2CF_2CF_2CF_3$ | $CF_3$ | H | $CH_2$(D-22a) |
| 3-$CF_2CF_2CF_2CF_3$ | $CF_3$ | H | $CH_2$(D-47a) |
| 3-$CF_2CF_2CF_2CF_3$ | $CF_3$ | $CH_2CN$ | $CH_2$(D-47a) |
| 3-$CF_2CF_2CF_2CF_3$ | $CF_3$ | $C(O)Et$ | $CH_2$(D-47a) |
| 3-$CF_2CF_2CF_2CF_3$ | $CF_3$ | $C(O)OCH_3$ | $CH_2$(D-47a) |
| 3-$CF_2CF_2CF_2CF_3$ | $CF_3$ | H | $N(CH_3)Ph$ |
| 3-$CF_2CF_2CF_2CF_3$ | $CF_3$ | H | (D-50c)Cl |
| 3-$CF_2CF_2CF_2CF_3$ | $CF_3$ | H | D-52a |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CF$_2$CF$_2$CF$_2$CF$_3$ | CF$_2$Cl | H | CH$_2$(D-22a) |
| 3-CH$_2$OCH$_3$ | CF$_3$ | H | CH$_2$(D-47a) |
| 3-CH$_2$OCH$_2$CF$_3$ | CF$_3$ | C(O)OCH$_3$ | CH$_2$(D-47a) |
| 3-C(CF$_3$)$_2$OH | CF$_3$ | H | CH$_2$CF$_3$ |
| 3-C(CF$_3$)$_2$OH | CF$_3$ | C(O)CH$_3$ | CH$_2$CF$_3$ |
| 3-C(CF$_3$)$_2$OH | CF$_3$ | H | CH$_2$OCH$_2$CF$_3$ |
| 3-C(CF$_3$)$_2$OH | CF$_3$ | H | E-4a |
| 3-C(CF$_3$)$_2$OH | CF$_3$ | H | CH$_2$C(O)NHCH$_2$CF$_3$ |
| 3-C(CF$_3$)$_2$OH | CF$_3$ | H | CH(CH$_3$)C(O)NHCH$_2$CF$_3$(D) |
| 3-C(CF$_3$)$_2$OH | CF$_3$ | H | CH(CH$_3$)Ph(R) |
| 3-C(CF$_3$)$_2$OH | CF$_3$ | H | CH$_2$(D-22a) |
| 3-C(CF$_3$)$_2$OH | CF$_3$ | H | CH$_2$(D-47a) |
| 3-C(CF$_3$)$_2$OH | CF$_3$ | CH$_2$CN | CH$_2$(D-47a) |
| 3-C(CF$_3$)$_2$OH | CF$_3$ | C(O)Et | CH$_2$(D-47a) |
| 3-C(CF$_3$)$_2$OH | CF$_3$ | C(O)OCH$_3$ | CH$_2$(D-47a) |
| 3-C(CF$_3$)$_2$OH | CF$_3$ | H | N(CH$_3$)Ph |
| 3-C(CF$_3$)$_2$OH | CF$_3$ | H | (D-50c)Cl |
| 3-C(CF$_3$)$_2$OH | CF$_3$ | H | D-52a |
| 3-C(CF$_3$)$_2$OH | CF$_2$Cl | H | N(CH$_3$)Ph |
| 3-C(CF$_3$)$_2$OCH$_3$ | CF$_3$ | H | CH$_2$CF$_3$ |
| 3-C(CF$_3$)$_2$OCH$_3$ | CF$_3$ | C(O)CH$_3$ | CH$_2$CF$_3$ |
| 3-C(CF$_3$)$_2$OCH$_3$ | CF$_3$ | H | CH$_2$OCH$_2$CF$_3$ |
| 3-C(CF$_3$)$_2$OCH$_3$ | CF$_3$ | H | E-4a |
| 3-C(CF$_3$)$_2$OCH$_3$ | CF$_3$ | H | CH$_2$C(O)NHCH$_2$CF$_3$ |
| 3-C(CF$_3$)$_2$OCH$_3$ | CF$_3$ | H | CH(CH$_3$)C(O)NHCH$_2$CF$_3$(D) |
| 3-C(CF$_3$)$_2$OCH$_3$ | CF$_3$ | H | CH(CH$_3$)Ph(R) |
| 3-C(CF$_3$)$_2$OCH$_3$ | CF$_3$ | H | CH$_2$(D-22a) |
| 3-C(CF$_3$)$_2$OCH$_3$ | CF$_3$ | H | CH$_2$(D-47a) |
| 3-C(CF$_3$)$_2$OCH$_3$ | CF$_3$ | CH$_2$CN | CH$_2$(D-47a) |
| 3-C(CF$_3$)$_2$OCH$_3$ | CF$_3$ | C(O)Et | CH$_2$(D-47a) |
| 3-C(CF$_3$)$_2$OCH$_3$ | CF$_3$ | C(O)OCH$_3$ | CH$_2$(D-47a) |
| 3-C(CF$_3$)$_2$OCH$_3$ | CF$_3$ | H | N(CH$_3$)Ph |
| 3-C(CF$_3$)$_2$OCH$_3$ | CF$_3$ | H | (D-50c)Cl |
| 3-C(CF$_3$)$_2$OCH$_3$ | CF$_3$ | H | D-52a |
| 3-C(CF$_3$)$_2$OCH$_3$ | CF$_2$Cl | H | (D-50c)Cl |
| 3-CH$_2$SCH$_3$ | CF$_3$ | H | CH$_2$CF$_3$ |
| 3-CH$_2$S(O)CH$_3$ | CF$_3$ | H | CH$_2$OCH$_2$CF$_3$ |
| 3-CH$_2$SO$_2$CH$_3$ | CF$_3$ | H | E-4a |
| 3-CH$_2$SEt | CF$_3$ | H | CH$_2$C(O)NHCH$_2$CF$_3$ |
| 3-CH$_2$S(O)Et | CF$_3$ | H | CH$_2$(D-22a) |
| 3-CH$_2$SO$_2$Et | CF$_3$ | H | CH$_2$(D-47a) |
| 3-CH$_2$SPr-n | CF$_3$ | C(O)OCH$_3$ | CH$_2$(D-47a) |
| 3-CH$_2$SO$_2$Pr-n | CF$_3$ | H | N(CH$_3$)Ph |
| 3-CH$_2$SPr-i | CF$_3$ | H | (D-50c)Cl |
| 3-CH$_2$SO$_2$Pr-i | CF$_3$ | H | CH$_2$CF$_3$ |
| 3-CH$_2$SPr-c | CF$_3$ | H | CH$_2$OCH$_2$CF$_3$ |
| 3-CH$_2$SO$_2$Pr-c | CF$_3$ | H | E-4a |
| 3-CH$_2$SBu-n | CF$_3$ | H | CH$_2$C(O)NHCH$_2$CF$_3$ |
| 3-CH$_2$SO$_2$Bu-n | CF$_3$ | H | CH$_2$(D-22a) |
| 3-CH$_2$SCF$_3$ | CF$_3$ | H | CH$_2$(D-47a) |
| 3-CH$_2$S(O)CF$_3$ | CF$_3$ | C(O)OCH$_3$ | CH$_2$(D-47a) |
| 3-CH$_2$SO$_2$CF$_3$ | CF$_3$ | H | N(CH$_3$)Ph |
| 3-CH$_2$SCH$_2$CF$_3$ | CF$_3$ | H | (D-50c)Cl |
| 3-(T-3) | CF$_3$ | H | CH$_2$CF$_3$ |
| 3-(T-3) | CF$_3$ | H | E-4a |
| 3-(T-3) | CF$_3$ | H | CH$_2$C(O)NHCH$_2$CF$_3$ |
| 3-(T-3) | CF$_3$ | H | CH$_2$(D-22a) |
| 3-(T-3) | CF$_3$ | H | CH$_2$(D-47a) |
| 3-(T-3) | CF$_3$ | H | (D-50c)Cl |
| 3-(T-4) | CF$_3$ | H | CH$_2$CF$_3$ |
| 3-(T-4) | CF$_3$ | H | E-4a |
| 3-(T-4) | CF$_3$ | H | CH$_2$C(O)NHCH$_2$CF$_3$ |
| 3-(T-4) | CF$_3$ | H | CH$_2$(D-22a) |
| 3-(T-4) | CF$_3$ | H | CH$_2$(D-47a) |
| 3-(T-4) | CF$_3$ | H | (D-50c)Cl |
| 3-(T-5) | CF$_3$ | H | CH$_2$CF$_3$ |
| 3-(T-5) | CF$_3$ | H | E-4a |
| 3-(T-5) | CF$_3$ | H | CH$_2$C(O)NHCH$_2$CF$_3$ |
| 3-(T-5) | CF$_3$ | H | CH$_2$(D-22a) |
| 3-(T-5) | CF$_3$ | H | CH$_2$(D-47a) |
| 3-(T-5) | CF$_3$ | H | (D-50c)Cl |
| 2-OH | CF$_3$ | H | CH$_2$CF$_3$ |
| 3-OH | CF$_3$ | H | CH$_2$OCH$_2$CF$_3$ |
| 4-OH | CF$_3$ | H | E-4a |
| 2-OCH$_3$ | CF$_3$ | H | CH$_2$C(O)NHCH$_2$CF$_3$ |
| 3-OCH$_3$ | CF$_3$ | H | CH$_2$(D-22a) |
| 4-OCH$_3$ | CF$_3$ | H | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-OEt | $CF_3$ | $C(O)OCH_3$ | $CH_2(D-47a)$ |
| 3-OPr-n | $CF_3$ | H | $N(CH_3)Ph$ |
| 3-OPr-i | $CF_3$ | H | $(D-50c)Cl$ |
| 3-OBu-n | $CF_3$ | H | $CH_2CF_3$ |
| 3-OBu-t | $CF_3$ | H | $CH_2OCH_2CF_3$ |
| 2-$OCHF_2$ | $CF_3$ | H | E-4a |
| 3-$OCHF_2$ | $CF_3$ | H | $CH_2C(O)NHCH_2CF_3$ |
| 4-$OCHF_2$ | $CF_3$ | H | $CH_2(D-22a)$ |
| 2-$OCF_3$ | $CF_3$ | H | $CH_2(D-47a)$ |
| 3-$OCF_3$ | $CF_3$ | H | $CH_2CF_3$ |
| 3-$OCF_3$ | $CF_3$ | $C(O)CH_3$ | $CH_2CF_3$ |
| 3-$OCF_3$ | $CF_3$ | H | $CH_2OCH_2CF_3$ |
| 3-$OCF_3$ | $CF_3$ | H | E-4a |
| 3-$OCF_3$ | $CF_3$ | H | $CH_2C(O)NHCH_2CF_3$ |
| 3-$OCF_3$ | $CF_3$ | H | $CH(CH_3)C(O)NHCH_2CF_3(D)$ |
| 3-$OCF_3$ | $CF_3$ | H | $CH(CH_3)Ph(R)$ |
| 3-$OCF_3$ | $CF_3$ | H | $CH_2(D-22a)$ |
| 3-$OCF_3$ | $CF_3$ | H | $CH_2(D-47a)$ |
| 3-$OCF_3$ | $CF_3$ | $CH_2CN$ | $CH_2(D-47a)$ |
| 3-$OCF_3$ | $CF_3$ | $C(O)Et$ | $CH_2(D-47a)$ |
| 3-$OCF_3$ | $CF_3$ | $C(O)OCH_3$ | $CH_2(D-47a)$ |
| 3-$OCF_3$ | $CF_3$ | H | $N(CH_3)Ph$ |
| 3-$OCF_3$ | $CF_3$ | H | $(D-50c)Cl$ |
| 3-$OCF_3$ | $CF_3$ | H | D-52a |
| 3-$OCF_3$ | $CF_2Cl$ | H | $CH_2CF_3$ |
| 3-$OCF_3$ | $CF_2Cl$ | H | E-4a |
| 3-$OCF_3$ | $CF_2Cl$ | H | $CH_2C(O)NHCH_2CF_3$ |
| 3-$OCF_3$ | $CF_2Cl$ | H | $CH_2(D-22a)$ |
| 3-$OCF_3$ | $CF_2Cl$ | H | $CH_2(D-47a)$ |
| 3-$OCF_3$ | $CF_2Cl$ | H | $(D-50c)Cl$ |
| 4-$OCF_3$ | $CF_3$ | $C(O)OCH_3$ | $CH_2(D-47a)$ |
| 3-$OCF_2Br$ | $CF_3$ | H | $CH_2CF_3$ |
| 3-$OCF_2Br$ | $CF_3$ | $C(O)CH_3$ | $CH_2CF_3$ |
| 3-$OCF_2Br$ | $CF_3$ | H | $CH_2OCH_2CF_3$ |
| 3-$OCF_2Br$ | $CF_3$ | H | E-4a |
| 3-$OCF_2Br$ | $CF_3$ | H | $CH_2C(O)NHCH_2CF_3$ |
| 3-$OCF_2Br$ | $CF_3$ | H | $CH(CH_3)C(O)NHCH_2CF_3(D)$ |
| 3-$OCF_2Br$ | $CF_3$ | H | $CH(CH_3)Ph(R)$ |
| 3-$OCF_2Br$ | $CF_3$ | H | $CH_2(D-22a)$ |
| 3-$OCF_2Br$ | $CF_3$ | H | $CH_2(D-47a)$ |
| 3-$OCF_2Br$ | $CF_3$ | $CH_2CN$ | $CH_2(D-47a)$ |
| 3-$OCF_2Br$ | $CF_3$ | $C(O)Et$ | $CH_2(D-47a)$ |
| 3-$OCF_2Br$ | $CF_3$ | $C(O)OCH_3$ | $CH_2(D-47a)$ |
| 3-$OCF_2Br$ | $CF_3$ | H | $N(CH_3)Ph$ |
| 3-$OCF_2Br$ | $CF_3$ | H | $(D-50c)Cl$ |
| 3-$OCF_2Br$ | $CF_3$ | H | D-52a |
| 3-$OCF_2Br$ | $CF_2Cl$ | H | $CH_2CF_3$ |
| 3-$OCF_2Br$ | $CF_2Cl$ | H | E-4a |
| 3-$OCF_2Br$ | $CF_2Cl$ | H | $CH_2C(O)NHCH_2CF_3$ |
| 3-$OCF_2Br$ | $CF_2Cl$ | H | $CH_2(D-22a)$ |
| 3-$OCF_2Br$ | $CF_2Cl$ | H | $CH_2(D-47a)$ |
| 3-$OCF_2Br$ | $CF_2Cl$ | H | $(D-50c)Cl$ |
| 3-$OCH_2CH_2Cl$ | $CF_3$ | H | $N(CH_3)Ph$ |
| 3-$OCH_2CF_3$ | $CF_3$ | H | $(D-50c)Cl$ |
| 3-$OCF_2CHF_2$ | $CF_3$ | H | $CH_2CF_3$ |
| 3-$OCF_2CHF_2$ | $CF_3$ | $C(O)CH_3$ | $CH_2CF_3$ |
| 3-$OCF_2CHF_2$ | $CF_3$ | H | $CH_2OCH_2CF_3$ |
| 3-$OCF_2CHF_2$ | $CF_3$ | H | E-4a |
| 3-$OCF_2CHF_2$ | $CF_3$ | H | $CH_2C(O)NHCH_2CF_3$ |
| 3-$OCF_2CHF_2$ | $CF_3$ | H | $CH(CH_3)C(O)NHCH_2CF_3(D)$ |
| 3-$OCF_2CHF_2$ | $CF_3$ | H | $CH(CH_3)Ph(R)$ |
| 3-$OCF_2CHF_2$ | $CF_3$ | H | $CH_2(D-22a)$ |
| 3-$OCF_2CHF_2$ | $CF_3$ | H | $CH_2(D-47a)$ |
| 3-$OCF_2CHF_2$ | $CF_3$ | $CH_2CN$ | $CH_2(D-47a)$ |
| 3-$OCF_2CHF_2$ | $CF_3$ | $C(O)Et$ | $CH_2(D-47a)$ |
| 3-$OCF_2CHF_2$ | $CF_3$ | $C(O)OCH_3$ | $CH_2(D-47a)$ |
| 3-$OCF_2CHF_2$ | $CF_3$ | H | $N(CH_3)Ph$ |
| 3-$OCF_2CHF_2$ | $CF_3$ | H | $(D-50c)Cl$ |
| 3-$OCF_2CHF_2$ | $CF_3$ | H | D-52a |
| 3-$OCF_2CHF_2$ | $CF_2Cl$ | H | $CH_2CF_3$ |
| 3-$OCF_2CHFCl$ | $CF_3$ | H | $CH_2CF_3$ |
| 3-$OCF_2CHFCl$ | $CF_3$ | $C(O)CH_3$ | $CH_2CF_3$ |
| 3-$OCF_2CHFCl$ | $CF_3$ | H | $CH_2OCH_2CF_3$ |
| 3-$OCF_2CHFCl$ | $CF_3$ | H | E-4a |
| 3-$OCF_2CHFCl$ | $CF_3$ | H | $CH_2C(O)NHCH_2CF_3$ |
| 3-$OCF_2CHFCl$ | $CF_3$ | H | $CH(CH_3)C(O)NHCH_2CF_3(D)$ |
| 3-$OCF_2CHFCl$ | $CF_3$ | H | $CH(CH_3)Ph(R)$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-OCF$_2$CHFCl | CF$_3$ | H | CH$_2$(D-22a) |
| 3-OCF$_2$CHFCl | CF$_3$ | H | CH$_2$(D-47a) |
| 3-OCF$_2$CHFCl | CF$_3$ | CH$_2$CN | CH$_2$(D-47a) |
| 3-OCF$_2$CHFCl | CF$_3$ | C(O)Et | CH$_2$(D-47a) |
| 3-OCF$_2$CHFCl | CF$_3$ | C(O)OCH$_3$ | CH$_2$(D-47a) |
| 3-OCF$_2$CHFCl | CF$_3$ | H | N(CH$_3$)Ph |
| 3-OCF$_2$CHFCl | CF$_3$ | H | (D-50c)Cl |
| 3-OCF$_2$CHFCl | CF$_3$ | H | D-52a |
| 3-OCF$_2$CHFCl | CF$_2$Cl | H | CH$_2$OCH$_2$CF$_3$ |
| 3-OCF$_2$CHFBr | CF$_3$ | H | E-4a |
| 3-OCF$_2$CF$_2$Br | CF$_3$ | H | CH$_2$C(O)NHCH$_2$CF$_3$ |
| 3-OCF$_2$CFCl$_2$ | CF$_3$ | H | CH$_2$(D-22a) |
| 3-OCF$_2$CCl$_3$ | CF$_3$ | H | CH$_2$(D-47a) |
| 3-OCH$_2$CF$_2$CHF$_2$ | CF$_3$ | C(O)OCH$_3$ | CH$_2$(D-47a) |
| 3-OCF$_2$CHFCF$_3$ | CF$_3$ | H | CH$_2$CF$_3$ |
| 3-OCF$_2$CHFCF$_3$ | CF$_3$ | C(O)CH$_3$ | CH$_2$CF$_3$ |
| 3-OCF$_2$CHFCF$_3$ | CF$_3$ | H | CH$_2$OCH$_2$CF$_3$ |
| 3-OCF$_2$CHFCF$_3$ | CF$_3$ | H | E-4a |
| 3-OCF$_2$CHFCF$_3$ | CF$_3$ | H | CH$_2$C(O)NHCH$_2$CF$_3$ |
| 3-OCF$_2$CHFCF$_3$ | CF$_3$ | H | CH(CH$_3$)C(O)NHCH$_2$CF$_3$(D) |
| 3-OCF$_2$CHFCF$_3$ | CF$_3$ | H | CH(CH$_3$)Ph(R) |
| 3-OCF$_2$CHFCF$_3$ | CF$_3$ | H | CH$_2$(D-22a) |
| 3-OCF$_2$CHFCF$_3$ | CF$_3$ | H | CH$_2$(D-47a) |
| 3-OCF$_2$CHFCF$_3$ | CF$_3$ | CH$_2$CN | CH$_2$(D-47a) |
| 3-OCF$_2$CHFCF$_3$ | CF$_3$ | C(O)Et | CH$_2$(D-47a) |
| 3-OCF$_2$CHFCF$_3$ | CF$_3$ | C(O)OCH$_3$ | CH$_2$(D-47a) |
| 3-OCF$_2$CHFCF$_3$ | CF$_3$ | H | N(CH$_3$)Ph |
| 3-OCF$_2$CHFCF$_3$ | CF$_3$ | H | (D-50c)Cl |
| 3-OCF$_2$CHFCF$_3$ | CF$_3$ | H | D-52a |
| 3-OCF$_2$CHFCF$_3$ | CF$_2$Cl | H | N(CH$_3$)Ph |
| 3-OCH(CF$_3$)$_2$ | CF$_3$ | H | (D-50c)Cl |
| 3-OCF$_2$CFBrCF$_3$ | CF$_3$ | H | CH$_2$CF$_3$ |
| 3-OCF$_2$CHFOCF$_3$ | CF$_3$ | H | CH$_2$CF$_3$ |
| 3-OCF$_2$CHFOCF$_3$ | CF$_3$ | C(O)CH$_3$ | CH$_2$CF$_3$ |
| 3-OCF$_2$CHFOCF$_3$ | CF$_3$ | H | CH$_2$OCH$_2$CF$_3$ |
| 3-OCF$_2$CHFOCF$_3$ | CF$_3$ | H | E-4a |
| 3-OCF$_2$CHFOCF$_3$ | CF$_3$ | H | CH$_2$C(O)NHCH$_2$CF$_3$ |
| 3-OCF$_2$CHFOCF$_3$ | CF$_3$ | H | CH(CH$_3$)C(O)NHCH$_2$CF$_3$(D) |
| 3-OCF$_2$CHFOCF$_3$ | CF$_3$ | H | CH(CH$_3$)Ph(R) |
| 3-OCF$_2$CHFOCF$_3$ | CF$_3$ | H | CH$_2$(D-22a) |
| 3-OCF$_2$CHFOCF$_3$ | CF$_3$ | H | CH$_2$(D-47a) |
| 3-OCF$_2$CHFOCF$_3$ | CF$_3$ | CH$_2$CN | CH$_2$(D-47a) |
| 3-OCF$_2$CHFOCF$_3$ | CF$_3$ | C(O)Et | CH$_2$(D-47a) |
| 3-OCF$_2$CHFOCF$_3$ | CF$_3$ | C(O)OCH$_3$ | CH$_2$(D-47a) |
| 3-OCF$_2$CHFOCF$_3$ | CF$_3$ | H | N(CH$_3$)Ph |
| 3-OCF$_2$CHFOCF$_3$ | CF$_3$ | H | (D-50c)Cl |
| 3-OCF$_2$CHFOCF$_3$ | CF$_3$ | H | D-52a |
| 3-OCF$_2$CHFOCF$_3$ | CF$_2$Cl | H | CH$_2$OCH$_2$CF$_3$ |
| 3-OCF$_2$CHFOCF$_2$CF$_2$CF$_3$ | CF$_3$ | H | CH$_2$CF$_3$ |
| 3-OCF$_2$CHFOCF$_2$CF$_2$CF$_3$ | CF$_3$ | H | E-4a |
| 3-OCF$_2$CHFOCF$_2$CF$_2$CF$_3$ | CF$_3$ | H | CH$_2$C(O)NHCH$_2$CF$_3$ |
| 3-OCF$_2$CHFOCF$_2$CF$_2$CF$_3$ | CF$_3$ | H | CH$_2$(D-22a) |
| 3-OCF$_2$CHFOCF$_2$CF$_2$CF$_3$ | CF$_3$ | H | CH$_2$(D-47a) |
| 3-OCF$_2$CHFOCF$_2$CF$_2$CF$_3$ | CF$_3$ | H | (D-50c)Cl |
| 3-OCH$_2$CH=CH$_2$ | CF$_3$ | H | E-4a |
| 3-OCH$_2$CH=CF$_2$ | CF$_3$ | H | CH$_2$C(O)NHCH$_2$CF$_3$ |
| 3-OCH$_2$CF=CF$_2$ | CF$_3$ | H | CH$_2$(D-22a) |
| 3-OCH$_2$CH=CCl$_2$ | CF$_3$ | H | CH$_2$(D-47a) |
| 3-OCH$_2$CCl=CCl$_2$ | CF$_3$ | C(O)OCH$_3$ | CH$_2$(D-47a) |
| 2-OCH$_2$Ph | CF$_3$ | H | N(CH$_3$)Ph |
| 3-OCH$_2$Ph | CF$_3$ | H | (D-50c)Cl |
| 4-OCH$_2$Ph | CF$_3$ | H | CH$_2$CF$_3$ |
| 3-OCH$_2$(Ph-2-Cl) | CF$_3$ | H | CH$_2$OCH$_2$CF$_3$ |
| 3-OCH$_2$(Ph-3-Cl) | CF$_3$ | H | E-4a |
| 3-OCH$_2$(Ph-4-Cl) | CF$_3$ | H | CH$_2$C(O)NHCH$_2$CF$_3$ |
| 3-OSO$_2$CH$_3$ | CF$_3$ | H | CH$_2$(D-22a) |
| 3-OSO$_2$Et | CF$_3$ | H | CH$_2$(D-47a) |
| 3-OSO$_2$Pr-n | CF$_3$ | C(O)OCH$_3$ | CH$_2$(D-47a) |
| 3-OSO$_2$Pr-i | CF$_3$ | H | N(CH$_3$)Ph |
| 3-OSO$_2$Pr-c | CF$_3$ | H | (D-50c)Cl |
| 3-OSO$_2$Bu-n | CF$_3$ | H | CH$_2$CF$_3$ |
| 3-OSO$_2$CHCl$_2$ | CF$_3$ | H | CH$_2$OCH$_2$CF$_3$ |
| 3-OSO$_2$CF$_3$ | CF$_3$ | H | E-4a |
| 3-OSO$_2$CH$_2$CF$_3$ | CF$_3$ | H | CH$_2$C(O)NHCH$_2$CF$_3$ |
| 2-OPh | CF$_3$ | H | CH$_2$(D-22a) |
| 3-OPh | CF$_3$ | H | CH$_2$(D-47a) |
| 4-OPh | CF$_3$ | C(O)OCH$_3$ | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-O(Ph-2-Cl) | CF$_3$ | H | N(CH$_3$)Ph |
| 3-O(Ph-3-Cl) | CF$_3$ | H | (D-50c)Cl |
| 3-O(Ph-4-Cl) | CF$_3$ | H | CH$_2$CF$_3$ |
| 3-O(Ph-4-Br) | CF$_3$ | H | CH$_2$OCH$_2$CF$_3$ |
| 3-O(Ph-2-CF$_3$) | CF$_3$ | H | E-4a |
| 3-O(Ph-3-CF$_3$) | CF$_3$ | H | CH$_2$C(O)NHCH$_2$CF$_3$ |
| 3-O(Ph-4-CF$_3$) | CF$_3$ | H | CH$_2$(D-22a) |
| 3-O(Ph-2-Cl-4-CF$_3$) | CF$_3$ | H | CH$_2$(D-47a) |
| 3-O(D-21c)Br | CF$_3$ | C(O)OCH$_3$ | CH$_2$(D-47a) |
| 3-O(D-21c)CF$_3$ | CF$_3$ | H | N(CH$_3$)Ph |
| 3-O(D-47d)Br | CF$_3$ | H | (D-50c)Cl |
| 3-O(D-47d)CF$_3$ | CF$_3$ | H | CH$_2$CF$_3$ |
| 2-O[(D-47f)-3-Cl-5-CF$_3$] | CF$_3$ | H | CH$_2$OCH$_2$CF$_3$ |
| 3-O[(D-47f)-3-Cl-5-CF$_3$] | CF$_3$ | H | CH$_2$CF$_3$ |
| 3-O[(D-47f)-3-Cl-5-CF$_3$] | CF$_3$ | H | E-4a |
| 3-O[(D-52f)-3-Cl-5-CF$_3$] | CF$_3$ | H | CH$_2$(D-47a) |
| 3-O(D-50c)Br | CF$_3$ | H | CH$_2$C(O)NHCH$_2$CF$_3$ |
| 2-SCH$_3$ | CF$_3$ | H | CH$_2$(D-22a) |
| 2-S(O)CH$_3$ | CF$_3$ | H | CH$_2$(D-47a) |
| 2-SO$_2$CH$_3$ | CF$_3$ | C(O)OCH$_3$ | CH$_2$(D-47a) |
| 3-SCH$_3$ | CF$_3$ | H | N(CH$_3$)Ph |
| 3-S(O)CH$_3$ | CF$_3$ | H | (D-50c)Cl |
| 3-SO$_2$CH$_3$ | CF$_3$ | H | CH$_2$CF$_3$ |
| 4-SCH$_3$ | CF$_3$ | H | CH$_2$CF$_3$ |
| 4-SCH$_3$ | CF$_3$ | H | CH$_2$OCH$_2$CF$_3$ |
| 4-S(O)CH$_3$ | CF$_3$ | H | E-4a |
| 4-SO$_2$CH$_3$ | CF$_3$ | H | CH$_2$C(O)NHCH$_2$CF$_3$ |
| 3-SEt | CF$_3$ | H | CH$_2$(D-22a) |
| 3-S(O)Et | CF$_3$ | H | CH$_2$(D-47a) |
| 3-SO$_2$Et | CF$_3$ | C(O)OCH$_3$ | CH$_2$(D-47a) |
| 3-SPr-n | CF$_3$ | H | N(CH$_3$)Ph |
| 3-S(O)Pr-n | CF$_3$ | H | (D-50c)Cl |
| 3-SO$_2$Pr-n | CF$_3$ | H | CH$_2$CF$_3$ |
| 3-SPr-i | CF$_3$ | H | CH$_2$OCH$_2$CF$_3$ |
| 3-S(O)Pr-i | CF$_3$ | H | E-4a |
| 3-SO$_2$Pr-i | CF$_3$ | H | CH$_2$C(O)NHCH$_2$CF$_3$ |
| 3-SBu-n | CF$_3$ | H | CH$_2$(D-22a) |
| 3-S(O)Bu-n | CF$_3$ | H | CH$_2$(D-47a) |
| 3-SO$_2$Bu-n | CF$_3$ | C(O)OCH$_3$ | CH$_2$(D-47a) |
| 2-SBu-t | CF$_3$ | H | N(CH$_3$)Ph |
| 3-SBu-t | CF$_3$ | H | (D-50c)Cl |
| 3-S(O)Bu-t | CF$_3$ | H | CH$_2$CF$_3$ |
| 3-SO$_2$Bu-t | CF$_3$ | H | CH$_2$OCH$_2$CF$_3$ |
| 3-SCH$_2$F | CF$_3$ | H | E-4a |
| 3-S(O)CH$_2$F | CF$_3$ | H | CH$_2$C(O)NHCH$_2$CF$_3$ |
| 3-SO$_2$CH$_2$F | CF$_3$ | H | CH$_2$(D-22a) |
| 2-SCHF$_2$ | CF$_3$ | H | CH$_2$(D-47a) |
| 2-S(O)CHF$_2$ | CF$_3$ | C(O)OCH$_3$ | CH$_2$(D-47a) |
| 2-SO$_2$CHF$_2$ | CF$_3$ | H | N(CH$_3$)Ph |
| 3-SCHF$_2$ | CF$_3$ | H | (D-50c)Cl |
| 3-S(O)CHF$_2$ | CF$_3$ | H | CH$_2$CF$_3$ |
| 3-SO$_2$CHF$_2$ | CF$_3$ | H | CH$_2$OCH$_2$CF$_3$ |
| 4-SCHF$_2$ | CF$_3$ | H | E-4a |
| 4-S(O)CHF$_2$ | CF$_3$ | H | CH$_2$C(O)NHCH$_2$CF$_3$ |
| 4-SO$_2$CHF$_2$ | CF$_3$ | H | CH$_2$(D-22a) |
| 2-SCF$_3$ | CF$_3$ | H | CH$_2$(D-47a) |
| 2-S(O)CF$_3$ | CF$_3$ | C(O)OCH$_3$ | CH$_2$(D-47a) |
| 2-SO$_2$CF$_3$ | CF$_3$ | H | N(CH$_3$)Ph |
| 3-SCF$_3$ | CF$_3$ | H | c-Bu |
| 3-SCF$_3$ | CF$_3$ | H | CH$_2$CF$_3$ |
| 3-SCF$_3$ | CF$_3$ | H | CH$_2$OEt |
| 3-SCF$_3$ | CF$_3$ | H | CH$_2$OCH$_2$CF$_3$ |
| 3-SCF$_3$ | CF$_3$ | C(O)CH$_3$ | CH$_2$OCH$_2$CF$_3$ |
| 3-SCF$_3$ | CF$_3$ | H | CH$_2$CH$_2$OCH$_3$ |
| 3-SCF$_3$ | CF$_3$ | H | CH$_2$(E-10a) |
| 3-SCF$_3$ | CF$_3$ | H | E-4a |
| 3-SCF$_3$ | CF$_3$ | H | CH$_2$C(O)NHCH$_2$CH$_2$Cl |
| 3-SCF$_3$ | CF$_3$ | H | CH$_2$C(O)NHCH$_2$CF$_3$ |
| 3-SCF$_3$ | CF$_3$ | H | CH(CH$_3$)C(O)NHCH$_2$CF$_3$ |
| 3-SCF$_3$ | CF$_3$ | H | CH(CH$_3$)C(O)NHCH$_2$CF$_3$(D) |
| 3-SCF$_3$ | CF$_3$ | H | CH(CH$_3$)Ph(R) |
| 3-SCF$_3$ | CF$_3$ | H | CH$_2$(D-22a) |
| 3-SCF$_3$ | CF$_3$ | C(O)CH$_3$ | CH$_2$(D-22a) |
| 3-SCF$_3$ | CF$_3$ | C(O)Et | CH$_2$(D-22a) |
| 3-SCF$_3$ | CF$_3$ | H | CH$_2$(D-47a) |
| 3-SCF$_3$ | CF$_3$ | CH$_2$OCH$_3$ | CH$_2$(D-47a) |
| 3-SCF$_3$ | CF$_3$ | CH$_2$CN | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-SCF$_3$ | CF$_3$ | C(O)CH$_3$ | CH$_2$(D-47a) |
| 3-SCF$_3$ | CF$_3$ | C(O)Et | CH$_2$(D-47a) |
| 3-SCF$_3$ | CF$_3$ | C(O)OCH$_3$ | CH$_2$(D-47a) |
| 3-SCF$_3$ | CF$_3$ | H | N(CH$_3$)Ph |
| 3-SCF$_3$ | CF$_3$ | H | N(CH$_3$)(D-50a) |
| 3-SCF$_3$ | CF$_3$ | H | C(O)NHCH$_2$CF$_3$ |
| 3-SCF$_3$ | CF$_3$ | H | Ph-2,4-F$_2$ |
| 3-SCF$_3$ | CF$_3$ | H | (D-50c)Cl |
| 3-SCF$_3$ | CF$_3$ | H | D-52a |
| 3-SCF$_3$ | CF$_2$Cl | H | CH$_2$CF$_3$ |
| 3-SCF$_3$ | CF$_2$Cl | H | CH$_2$OCH$_2$CF$_3$ |
| 3-SCF$_3$ | CF$_2$Cl | H | E-4a |
| 3-SCF$_3$ | CF$_2$Cl | H | CH$_2$C(O)NHCH$_2$CF$_3$ |
| 3-SCF$_3$ | CF$_2$Cl | H | CH(CH$_3$)C(O)NHCH$_2$CF$_3$(D) |
| 3-SCF$_3$ | CF$_2$Cl | H | CH$_2$(D-22a) |
| 3-SCF$_3$ | CF$_2$Cl | H | CH$_2$(D-47a) |
| 3-SCF$_3$ | CF$_2$Cl | C(O)OCH$_3$ | CH$_2$(D-47a) |
| 3-SCF$_3$ | CF$_2$Cl | H | N(CH$_3$)Ph |
| 3-SCF$_3$ | CF$_2$Cl | H | (D-50c)Cl |
| 3-S(O)CF$_3$ | CF$_3$ | H | CH$_2$CF$_3$ |
| 3-S(O)CF$_3$ | CF$_3$ | H | E-4a |
| 3-S(O)CF$_3$ | CF$_3$ | H | CH$_2$C(O)NHCH$_2$CF$_3$ |
| 3-S(O)CF$_3$ | CF$_3$ | H | CH$_2$(D-22a) |
| 3-S(O)CF$_3$ | CF$_3$ | H | CH$_2$(D-47a) |
| 3-S(O)CF$_3$ | CF$_3$ | H | (D-50c)Cl |
| 3-SO$_2$CF$_3$ | CF$_3$ | H | CH$_2$CF$_3$ |
| 3-SO$_2$CF$_3$ | CF$_3$ | H | E-4a |
| 3-SO$_2$CF$_3$ | CF$_3$ | H | CH$_2$C(O)NHCH$_2$CF$_3$ |
| 3-SO$_2$CF$_3$ | CF$_3$ | H | CH$_2$(D-22a) |
| 3-SO$_2$CF$_3$ | CF$_3$ | H | CH$_2$(D-47a) |
| 3-SO$_2$CF$_3$ | CF$_3$ | H | (D-50c)Cl |
| 4-SCF$_3$ | CF$_3$ | H | (D-50c)Cl |
| 4-S(O)CF$_3$ | CF$_3$ | H | CH$_2$CF$_3$ |
| 4-SO$_2$CF$_3$ | CF$_3$ | H | CH$_2$OCH$_2$CF$_3$ |
| 3-SCF$_2$Cl | CF$_3$ | H | c-Bu |
| 3-SCF$_2$Cl | CF$_3$ | H | CH$_2$CF$_3$ |
| 3-SCF$_2$Cl | CF$_3$ | H | CH$_2$OEt |
| 3-SCF$_2$Cl | CF$_3$ | H | CH$_2$OCH$_2$CF$_3$ |
| 3-SCF$_2$Cl | CF$_3$ | C(O)CH$_3$ | CH$_2$OCH$_2$CF$_3$ |
| 3-SCF$_2$Cl | CF$_3$ | H | CH$_2$CH$_2$OCH$_3$ |
| 3-SCF$_2$Cl | CF$_3$ | H | CH$_2$(E-10a) |
| 3-SCF$_2$Cl | CF$_3$ | H | E-4a |
| 3-SCF$_2$Cl | CF$_3$ | H | CH$_2$C(O)NHCH$_2$CH$_2$Cl |
| 3-SCF$_2$Cl | CF$_3$ | H | CH$_2$C(O)NHCH$_2$CF$_3$ |
| 3-SCF$_2$Cl | CF$_3$ | H | CH(CH$_3$)C(O)NHCH$_2$CF$_3$ |
| 3-SCF$_2$Cl | CF$_3$ | H | CH(CH$_3$)C(O)NHCH$_2$CF$_3$(D) |
| 3-SCF$_2$Cl | CF$_3$ | H | CH(CH$_3$)Ph(R) |
| 3-SCF$_2$Cl | CF$_3$ | H | CH$_2$(D-22a) |
| 3-SCF$_2$Cl | CF$_3$ | C(O)CH$_3$ | CH$_2$(D-22a) |
| 3-SCF$_2$Cl | CF$_3$ | C(O)Et | CH$_2$(D-22a) |
| 3-SCF$_2$Cl | CF$_3$ | H | CH$_2$(D-47a) |
| 3-SCF$_2$Cl | CF$_3$ | CH$_2$OCH$_3$ | CH$_2$(D-47a) |
| 3-SCF$_2$Cl | CF$_3$ | CH$_2$CN | CH$_2$(D-47a) |
| 3-SCF$_2$Cl | CF$_3$ | C(O)CH$_3$ | CH$_2$(D-47a) |
| 3-SCF$_2$Cl | CF$_3$ | C(O)Et | CH$_2$(D-47a) |
| 3-SCF$_2$Cl | CF$_3$ | C(O)OCH$_3$ | CH$_2$(D-47a) |
| 3-SCF$_2$Cl | CF$_3$ | H | N(CH$_3$)Ph |
| 3-SCF$_2$Cl | CF$_3$ | H | N(CH$_3$)(D-50a) |
| 3-SCF$_2$Cl | CF$_3$ | H | C(O)NHCH$_2$CF$_3$ |
| 3-SCF$_2$Cl | CF$_3$ | H | Ph-2,4-F$_2$ |
| 3-SCF$_2$Cl | CF$_3$ | H | (D-50c)Cl |
| 3-SCF$_2$Cl | CF$_3$ | H | D-52a |
| 3-SCF$_2$Cl | CF$_2$Cl | H | CH$_2$CF$_3$ |
| 3-SCF$_2$Cl | CF$_2$Cl | H | CH$_2$OCH$_2$CF$_3$ |
| 3-SCF$_2$Cl | CF$_2$Cl | H | E-4a |
| 3-SCF$_2$Cl | CF$_2$Cl | H | CH$_2$C(O)NHCH$_2$CF$_3$ |
| 3-SCF$_2$Cl | CF$_2$Cl | H | CH(CH$_3$)C(O)NHCH$_2$CF$_3$(D) |
| 3-SCF$_2$Cl | CF$_2$Cl | H | CH$_2$(D-22a) |
| 3-SCF$_2$Cl | CF$_2$Cl | H | CH$_2$(D-47a) |
| 3-SCF$_2$Cl | CF$_2$Cl | C(O)OCH$_3$ | CH$_2$(D-47a) |
| 3-SCF$_2$Cl | CF$_2$Cl | H | N(CH$_3$)Ph |
| 3-SCF$_2$Cl | CF$_2$Cl | H | (D-50c)Cl |
| 3-S(O)CF$_2$Cl | CF$_3$ | H | E-4a |
| 3-SO$_2$CF$_2$Cl | CF$_3$ | H | CH$_2$C(O)NHCH$_2$CF$_3$ |
| 3-SCF$_2$Br | CF$_3$ | H | c-Bu |
| 3-SCF$_2$Br | CF$_3$ | H | CH$_2$CF$_3$ |
| 3-SCF$_2$Br | CF$_3$ | H | CH$_2$OEt |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-SCF$_2$Br | CF$_3$ | H | CH$_2$OCH$_2$CF$_3$ |
| 3-SCF$_2$Br | CF$_3$ | C(O)CH$_3$ | CH$_2$OCH$_2$CF$_3$ |
| 3-SCF$_2$Br | CF$_3$ | H | CH$_2$CH$_2$OCH$_3$ |
| 3-SCF$_2$Br | CF$_3$ | H | CH$_2$(E-10a) |
| 3-SCF$_2$Br | CF$_3$ | H | E-4a |
| 3-SCF$_2$Br | CF$_3$ | H | CH$_2$C(O)NHCH$_2$CH$_2$Cl |
| 3-SCF$_2$Br | CF$_3$ | H | CH$_2$C(O)NHCH$_2$CF$_3$ |
| 3-SCF$_2$Br | CF$_3$ | H | CH(CH$_3$)C(O)NHCH$_2$CF$_3$ |
| 3-SCF$_2$Br | CF$_3$ | H | CH(CH$_3$)C(O)NHCH$_2$CF$_3$(D) |
| 3-SCF$_2$Br | CF$_3$ | H | CH(CH$_3$)Ph(R) |
| 3-SCF$_2$Br | CF$_3$ | H | CH$_2$(D-22a) |
| 3-SCF$_2$Br | CF$_3$ | C(O)CH$_3$ | CH$_2$(D-22a) |
| 3-SCF$_2$Br | CF$_3$ | C(O)Et | CH$_2$(D-22a) |
| 3-SCF$_2$Br | CF$_3$ | H | CH$_2$(D-47a) |
| 3-SCF$_2$Br | CF$_3$ | CH$_2$OCH$_3$ | CH$_2$(D-47a) |
| 3-SCF$_2$Br | CF$_3$ | CH$_2$CN | CH$_2$(D-47a) |
| 3-SCF$_2$Br | CF$_3$ | C(O)CH$_3$ | CH$_2$(D-47a) |
| 3-SCF$_2$Br | CF$_3$ | C(O)Et | CH$_2$(D-47a) |
| 3-SCF$_2$Br | CF$_3$ | C(O)OCH$_3$ | CH$_2$(D-47a) |
| 3-SCF$_2$Br | CF$_3$ | H | N(CH$_3$)Ph |
| 3-SCF$_2$Br | CF$_3$ | H | N(CH$_3$)(D-50a) |
| 3-SCF$_2$Br | CF$_3$ | H | C(O)NHCH$_2$CF$_3$ |
| 3-SCF$_2$Br | CF$_3$ | H | Ph-2,4-F$_2$ |
| 3-SCF$_2$Br | CF$_3$ | H | (D-50c)Cl |
| 3-SCF$_2$Br | CF$_3$ | H | D-52a |
| 3-SCF$_2$Br | CF$_2$Cl | H | CH$_2$CF$_3$ |
| 3-SCF$_2$Br | CF$_2$Cl | H | CH$_2$OCH$_2$CF$_3$ |
| 3-SCF$_2$Br | CF$_2$Cl | H | E-4a |
| 3-SCF$_2$Br | CF$_2$Cl | H | CH$_2$C(O)NHCH$_2$CF$_3$ |
| 3-SCF$_2$Br | CF$_2$Cl | H | CH(CH$_3$)C(O)NHCH$_2$CF$_3$(D) |
| 3-SCF$_2$Br | CF$_2$Cl | H | CH$_2$(D-22a) |
| 3-SCF$_2$Br | CF$_2$Cl | H | CH$_2$(D-47a) |
| 3-SCF$_2$Br | CF$_2$Cl | C(O)OCH$_3$ | CH$_2$(D-47a) |
| 3-SCF$_2$Br | CF$_2$Cl | H | N(CH$_3$)Ph |
| 3-SCF$_2$Br | CF$_2$Cl | H | (D-50c)Cl |
| 3-S(O)CF$_2$Br | CF$_3$ | H | CH$_2$(D-22a) |
| 3-SO$_2$CF$_2$Br | CF$_3$ | H | CH$_2$(D-47a) |
| 3-SCH$_2$CF$_3$ | CF$_3$ | C(O)OCH$_3$ | CH$_2$(D-47a) |
| 3-SCF$_2$CHF$_2$ | CF$_3$ | H | N(CH$_3$)Ph |
| 3-SCF$_2$CHFCl | CF$_3$ | H | (D-50c)Cl |
| 3-SCF$_2$CF$_3$ | CF$_3$ | H | CH$_2$CF$_3$ |
| 3-SCF$_2$CF$_2$Br | CF$_3$ | H | CH$_2$OCH$_2$CF$_3$ |
| 3-SCF$_2$CHFCF$_3$ | CF$_3$ | H | E-4a |
| 3-SCF$_2$CF$_2$CF$_3$ | CF$_3$ | H | CH$_2$C(O)NHCH$_2$CF$_3$ |
| 3-S(Ph-4-Cl) | CF$_3$ | H | CH$_2$(D-22a) |
| 3-S(Ph-4-Br) | CF$_3$ | H | CH$_2$(D-47a) |
| 3-S(Ph-4-CF$_3$) | CF$_3$ | C(O)OCH$_3$ | CH$_2$(D-47a) |
| 3-S(D-21c)Br | CF$_3$ | H | N(CH$_3$)Ph |
| 3-S(D-21c)CF$_3$ | CF$_3$ | H | (D-50c)Cl |
| 3-S(D-47d)Br | CF$_3$ | H | CH$_2$CF$_3$ |
| 3-S(D-47d)CF$_3$ | CF$_3$ | H | CH$_2$OCH$_2$CF$_3$ |
| 3-S[(D-47f)-3-Cl-5-CF$_3$] | CF$_3$ | H | E-4a |
| 3-S(D-50c)Br | CF$_3$ | H | CH$_2$C(O)NHCH$_2$CF$_3$ |
| 3-SF$_5$ | CHF$_2$ | H | CH$_2$(D-22a) |
| 3-SF$_5$ | CF$_3$ | H | c-Pr |
| 3-SF$_5$ | CF$_3$ | H | CH$_2$Pr-c |
| 3-SF$_5$ | CF$_3$ | H | c-Bu |
| 3-SF$_5$ | CF$_3$ | H | CH$_2$CF$_3$ |
| 3-SF$_5$ | CF$_3$ | C(O)CH$_3$ | CH$_2$CF$_3$ |
| 3-SF$_5$ | CF$_3$ | H | CH$_2$CH$_2$CF$_3$ |
| 3-SF$_5$ | CF$_3$ | H | CH$_2$OCH$_3$ |
| 3-SF$_5$ | CF$_3$ | H | CH$_2$OEt |
| 3-SF$_5$ | CF$_3$ | C(O)CH$_3$ | CH$_2$OEt |
| 3-SF$_5$ | CF$_3$ | H | CH$_2$OCH$_2$CF$_3$ |
| 3-SF$_5$ | CF$_3$ | C(O)CH$_3$ | CH$_2$OCH$_2$CF$_3$ |
| 3-SF$_5$ | CF$_3$ | H | CH$_2$CH$_2$OCH$_3$ |
| 3-SF$_5$ | CF$_3$ | H | CH$_2$(E-10a) |
| 3-SF$_5$ | CF$_3$ | H | E-4a |
| 3-SF$_5$ | CF$_3$ | H | E-5a(R) |
| 3-SF$_5$ | CF$_3$ | H | CH$_2$CH=NOCH$_3$ |
| 3-SF$_5$ | CF$_3$ | H | CH$_2$C(O)NHCH$_2$CH$_2$Cl |
| 3-SF$_5$ | CF$_3$ | H | CH$_2$C(O)NHCH$_2$CF$_3$ |
| 3-SF$_5$ | CF$_3$ | H | CH(CH$_3$)C(O)NHEt |
| 3-SF$_5$ | CF$_3$ | H | CH(CH$_3$)C(O)NHCH$_2$CF$_3$ |
| 3-SF$_5$ | CF$_3$ | H | CH(CH$_3$)C(O)NHCH$_2$CF$_3$(D) |
| 3-SF$_5$ | CF$_3$ | H | CH$_2$CH=CH$_2$ |
| 3-SF$_5$ | CF$_3$ | H | CH$_2$CCl=CH$_2$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-SF$_5$ | CF$_3$ | H | CH(CH$_3$)Ph(R) |
| 3-SF$_5$ | CF$_3$ | H | CH$_2$(Ph-4-NO$_2$) |
| 3-SF$_5$ | CF$_3$ | H | CH$_2$(Ph-4-CN) |
| 3-SF$_5$ | CF$_3$ | H | CH$_2$(D-17b)Cl |
| 3-SF$_5$ | CF$_3$ | H | CH$_2$(D-21a) |
| 3-SF$_5$ | CF$_3$ | H | CH$_2$(D-22a) |
| 3-SF$_5$ | CF$_3$ | C(O)CH$_3$ | CH$_2$(D-22a) |
| 3-SF$_5$ | CF$_3$ | C(O)Et | CH$_2$(D-22a) |
| 3-SF$_5$ | CF$_3$ | H | CH$_2$(D-47a) |
| 3-SF$_5$ | CF$_3$ | CH$_2$OCH$_3$ | CH$_2$(D-47a) |
| 3-SF$_5$ | CF$_3$ | CH$_2$CN | CH$_2$(D-47a) |
| 3-SF$_5$ | CF$_3$ | C(O)CH$_3$ | CH$_2$(D-47a) |
| 3-SF$_5$ | CF$_3$ | C(O)Et | CH$_2$(D-47a) |
| 3-SF$_5$ | CF$_3$ | C(O)Pr-c | CH$_2$(D-47a) |
| 3-SF$_5$ | CF$_3$ | C(O)OCH$_3$ | CH$_2$(D-47a) |
| 3-SF$_5$ | CF$_3$ | H | CH(CH$_3$)(D-47a) |
| 3-SF$_5$ | CF$_3$ | H | CH$_2$(D-50a) |
| 3-SF$_5$ | CF$_3$ | H | N(CH$_3$)Ph |
| 3-SF$_5$ | CF$_3$ | H | N(CH$_3$)(D-50a) |
| 3-SF$_5$ | CF$_3$ | C(O)OCH$_3$ | C(O)N(CH$_3$)$_2$ |
| 3-SF$_5$ | CF$_3$ | H | C(O)NHEt |
| 3-SF$_5$ | CF$_3$ | CH$_3$ | C(O)NHEt |
| 3-SF$_5$ | CF$_3$ | H | C(O)NHCH$_2$CH$_2$Cl |
| 3-SF$_5$ | CF$_3$ | H | C(O)NHCH$_2$(Ph-4-F) |
| 3-SF$_5$ | CF$_3$ | H | Ph-4-CN |
| 3-SF$_5$ | CF$_3$ | H | Ph-2,4-F$_2$ |
| 3-SF$_5$ | CF$_3$ | H | (D-15a)CH$_3$ |
| 3-SF$_5$ | CF$_3$ | H | (D-47d)CN |
| 3-SF$_5$ | CF$_3$ | H | (D-47e)Br |
| 3-SF$_5$ | CF$_3$ | H | D-50a |
| 3-SF$_5$ | CF$_3$ | H | (D-50c)Cl |
| 3-SF$_5$ | CF$_3$ | H | (D-50c)Br |
| 3-SF$_5$ | CF$_3$ | H | D-52a |
| 3-SF$_5$ | CF$_3$ | H | D-53a |
| 3-SF$_5$ | CF$_2$Cl | H | CH$_2$CF$_3$ |
| 3-SF$_5$ | CF$_2$Cl | C(O)CH$_3$ | CH$_2$CF$_3$ |
| 3-SF$_5$ | CF$_2$Cl | H | CH$_2$OCH$_2$CF$_3$ |
| 3-SF$_5$ | CF$_2$Cl | H | E-4a |
| 3-SF$_5$ | CF$_2$Cl | H | CH$_2$C(O)NHCH$_2$CF$_3$ |
| 3-SF$_5$ | CF$_2$Cl | H | CH(CH$_3$)C(O)NHCH$_2$CF$_3$(D) |
| 3-SF$_5$ | CF$_2$Cl | H | CH(CH$_3$)Ph(R) |
| 3-SF$_5$ | CF$_2$Cl | H | CH$_2$(D-22a) |
| 3-SF$_5$ | CF$_2$Cl | H | CH$_2$(D-47a) |
| 3-SF$_5$ | CF$_2$Cl | CH$_2$CN | CH$_2$(D-47a) |
| 3-SF$_5$ | CF$_2$Cl | C(O)Et | CH$_2$(D-47a) |
| 3-SF$_5$ | CF$_2$Cl | C(O)OCH$_3$ | CH$_2$(D-47a) |
| 3-SF$_5$ | CF$_2$Cl | H | N(CH$_3$)Ph |
| 3-SF$_5$ | CF$_2$Cl | H | (D-50c)Cl |
| 3-SF$_5$ | CF$_2$Cl | H | D-52a |
| 3-SF$_5$ | CF$_2$Br | H | CH$_2$(D-47a) |
| 3-SF$_5$ | CF$_2$CHF$_2$ | C(O)OCH$_3$ | CH$_2$(D-47a) |
| 3-NO$_2$ | CF$_3$ | H | CH$_2$CF$_3$ |
| 3-NO$_2$ | CF$_3$ | H | CH$_2$Ph |
| 3-NO$_2$ | CF$_3$ | H | N(CH$_3$)Ph |
| 3-N(CH$_3$)$_2$ | CF$_3$ | H | (D-50c)Cl |
| 3-N(Et)$_2$ | CF$_3$ | H | CH$_2$CF$_3$ |
| 3-NHC(O)CH$_3$ | CF$_3$ | H | CH$_2$OCH$_2$CF$_3$ |
| 4-NHC(O)CH$_3$ | CF$_3$ | H | E-4a |
| 3-NHC(O)CF$_3$ | CF$_3$ | H | CH$_2$C(O)NHCH$_2$CF$_3$ |
| 3-NHSO$_2$CF$_3$ | CF$_3$ | H | CH$_2$(D-22a) |
| 3-N(CH$_3$)C(O)CF$_3$ | CF$_3$ | H | CH$_2$(D-47a) |
| 3-N(Et)C(O)CF$_3$ | CF$_3$ | C(O)OCH$_3$ | CH$_2$(D-47a) |
| 3-N(CH$_3$)C(O)CF$_2$Cl | CF$_3$ | H | N(CH$_3$)Ph |
| 3-N(Et)C(O)CF$_2$Cl | CF$_3$ | H | (D-50c)Cl |
| 3-N(CH$_3$)C(O)CF$_2$Br | CF$_3$ | H | CH$_2$CF$_3$ |
| 3-N(Et)C(O)CF$_2$Br | CF$_3$ | H | CH$_2$OCH$_2$CF$_3$ |
| 3-N(CH$_3$)SO$_2$CF$_3$ | CF$_3$ | H | E-4a |
| 3-N(Et)SO$_2$CF$_3$ | CF$_3$ | H | CH$_2$C(O)NHCH$_2$CF$_3$ |
| 3-(T-33) | CF$_3$ | H | CH$_2$(D-22a) |
| 2-CN | CF$_3$ | H | CH$_2$(D-47a) |
| 3-CN | CF$_3$ | H | CH$_2$CF$_3$ |
| 3-CN | CF$_3$ | C(O)OCH$_3$ | CH$_2$(D-47a) |
| 4-CN | CF$_3$ | H | N(CH$_3$)Ph |
| 3-CHO | CF$_3$ | H | (D-50c)Cl |
| 3-C(O)CH$_3$ | CF$_3$ | H | CH$_2$CF$_3$ |
| 4-C(O)CH$_3$ | CF$_3$ | H | CH$_2$OCH$_2$CF$_3$ |
| 3-CH=NOH | CF$_3$ | H | E-4a |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CH=NOCH$_3$ | CF$_3$ | H | CH$_2$C(O)NHCH$_2$CF$_3$ |
| 3-C(CH$_3$)=NOCH$_3$(E) | CF$_3$ | H | CH$_2$(D-22a) |
| 3-C(CH$_3$)=NOCH$_3$(Z) | CF$_3$ | H | CH$_2$(D-47a) |
| 3-C(O)OCH$_3$ | CF$_3$ | C(O)OCH$_3$ | CH$_2$(D-47a) |
| 3-C(O)OEt | CF$_3$ | H | N(CH$_3$)Ph |
| 3-C(O)NH$_2$ | CF$_3$ | H | (D-50c)Cl |
| 3-C(O)NHCH$_3$ | CF$_3$ | H | CH$_2$CF$_3$ |
| 3-C(O)NHEt | CF$_3$ | H | CH$_2$OCH$_2$CF$_3$ |
| 3-C(O)N(CH$_3$)$_2$ | CF$_3$ | H | E-4a |
| 3-C(S)NH$_2$ | CF$_3$ | H | CH$_2$C(O)NHCH$_2$CF$_3$ |
| 3-SO$_2$NHCH$_3$ | CF$_3$ | H | CH$_2$(D-22a) |
| 3-SO$_2$N(CH$_3$)$_2$ | CF$_3$ | H | CH$_2$(D-47a) |
| 3-Si(CH$_3$)$_3$ | CF$_3$ | C(O)OCH$_3$ | CH$_2$(D-47a) |
| 3-Ph | CF$_3$ | H | N(CH$_3$)Ph |
| 4-Ph | CF$_3$ | H | (D-50c)Cl |
| 3-(D-5a) | CF$_3$ | H | CH$_2$CF$_3$ |
| 3-(D-14a) | CF$_3$ | H | CH$_2$OCH$_2$CF$_3$ |
| 3-(D-24a) | CF$_3$ | H | E-4a |
| 3-(D-38a) | CF$_3$ | H | CH$_2$C(O)NHCH$_2$CF$_3$ |
| 2,3-F$_2$ | CF$_3$ | H | CH$_2$(D-22a) |
| 2,4-F$_2$ | CF$_3$ | H | CH$_2$(D-47a) |
| 2,5-F$_2$ | CF$_3$ | C(O)OCH$_3$ | CH$_2$(D-47a) |
| 2,6-F$_2$ | CF$_3$ | H | N(CH$_3$)Ph |
| 3,4-F$_2$ | CF$_3$ | H | CH$_2$Pr-c |
| 3,4-F$_2$ | CF$_3$ | H | CH$_2$CF$_3$ |
| 3,4-F$_2$ | CF$_3$ | H | CH$_2$OCH$_2$CF$_3$ |
| 3,4-F$_2$ | CF$_3$ | H | E-4a |
| 3,4-F$_2$ | CF$_3$ | H | CH$_2$C(O)NHCH$_2$CF$_3$ |
| 3,4-F$_2$ | CF$_3$ | H | CH(CH$_3$)C(O)NHCH$_2$CF$_3$(D) |
| 3,4-F$_2$ | CF$_3$ | CH$_3$ | CH$_2$Ph |
| 3,4-F$_2$ | CF$_3$ | H | CH$_2$(D-22a) |
| 3,4-F$_2$ | CF$_3$ | H | CH$_2$(D-47a) |
| 3,4-F$_2$ | CF$_3$ | C(O)OCH$_3$ | CH$_2$(D-47a) |
| 3,4-F$_2$ | CF$_3$ | H | N(CH$_3$)Ph |
| 3,4-F$_2$ | CF$_3$ | H | (D-50c)Cl |
| 3,5-F$_2$ | CF$_3$ | H | CH$_2$CF$_3$ |
| 3,5-F$_2$ | CF$_3$ | H | CH$_2$OCH$_2$CF$_3$ |
| 3,5-F$_2$ | CF$_3$ | H | E-4a |
| 3,5-F$_2$ | CF$_3$ | H | CH$_2$C(O)NHCH$_2$CF$_3$ |
| 3,5-F$_2$ | CF$_3$ | H | CH(CH$_3$)C(O)NHCH$_2$CF$_3$(D) |
| 3,5-F$_2$ | CF$_3$ | H | CH$_2$Ph |
| 3,5-F$_2$ | CF$_3$ | H | CH$_2$(D-22a) |
| 3,5-F$_2$ | CF$_3$ | H | CH$_2$(D-47a) |
| 3,5-F$_2$ | CF$_3$ | C(O)OCH$_3$ | CH$_2$(D-47a) |
| 3,5-F$_2$ | CF$_3$ | H | N(CH$_3$)Ph |
| 3,5-F$_2$ | CF$_3$ | H | (D-50c)Cl |
| 2-Cl-4-F | CF$_3$ | H | (D-50c)Cl |
| 2-F-3-Cl | CF$_3$ | H | CH$_2$CF$_3$ |
| 3-Cl-4-F | CHF$_2$ | H | CH$_2$OCH$_2$CF$_3$ |
| 3-Cl-4-F | CF$_3$ | H | c-Pr |
| 3-Cl-4-F | CF$_3$ | H | CH$_2$Pr-c |
| 3-Cl-4-F | CF$_3$ | H | c-Bu |
| 3-Cl-4-F | CF$_3$ | H | CH$_2$CF$_3$ |
| 3-Cl-4-F | CF$_3$ | C(O)CH$_3$ | CH$_2$CF$_3$ |
| 3-Cl-4-F | CF$_3$ | H | CH$_2$CH$_2$CF$_3$ |
| 3-Cl-4-F | CF$_3$ | H | CH$_2$OCH$_3$ |
| 3-Cl-4-F | CF$_3$ | H | CH$_2$OEt |
| 3-Cl-4-F | CF$_3$ | C(O)CH$_3$ | CH$_2$OEt |
| 3-Cl-4-F | CF$_3$ | H | CH$_2$OCH$_2$CF$_3$ |
| 3-Cl-4-F | CF$_3$ | C(O)CH$_3$ | CH$_2$OCH$_2$CF$_3$ |
| 3-Cl-4-F | CF$_3$ | H | CH$_2$CH$_2$OCH$_3$ |
| 3-Cl-4-F | CF$_3$ | H | CH$_2$(E-10a) |
| 3-Cl-4-F | CF$_3$ | H | E-4a |
| 3-Cl-4-F | CF$_3$ | H | E-5a(R) |
| 3-Cl-4-F | CF$_3$ | H | CH$_2$CH=NOCH$_3$ |
| 3-Cl-4-F | CF$_3$ | H | CH$_2$C(O)NHCH$_2$CH$_2$Cl |
| 3-Cl-4-F | CF$_3$ | H | CH$_2$C(O)NHCH$_2$CF$_3$ |
| 3-Cl-4-F | CF$_3$ | H | CH(CH$_3$)C(O)NHEt |
| 3-Cl-4-F | CF$_3$ | H | CH(CH$_3$)C(O)NHCH$_2$CF$_3$ |
| 3-Cl-4-F | CF$_3$ | H | CH(CH$_3$)C(O)NHCH$_2$CF$_3$(D) |
| 3-Cl-4-F | CF$_3$ | H | CH$_2$CH=CH$_2$ |
| 3-Cl-4-F | CF$_3$ | H | CH$_2$CCl=CH$_2$ |
| 3-Cl-4-F | CF$_3$ | H | CH$_2$Ph |
| 3-Cl-4-F | CF$_3$ | H | CH(CH$_3$)Ph(R) |
| 3-Cl-4-F | CF$_3$ | H | CH$_2$(Ph-4-NO$_2$) |
| 3-Cl-4-F | CF$_3$ | H | CH$_2$(Ph-4-CN) |
| 3-Cl-4-F | CF$_3$ | H | CH$_2$(D-17b)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-4-F | $CF_3$ | H | $CH_2$(D-21a) |
| 3-Cl-4-F | $CF_3$ | H | $CH_2$(D-22a) |
| 3-Cl-4-F | $CF_3$ | $C(O)CH_3$ | $CH_2$(D-22a) |
| 3-Cl-4-F | $CF_3$ | C(O)Et | $CH_2$(D-22a) |
| 3-Cl-4-F | $CF_3$ | H | $CH_2$(D-47a) |
| 3-Cl-4-F | $CF_3$ | $CH_2OCH_3$ | $CH_2$(D-47a) |
| 3-Cl-4-F | $CF_3$ | $CH_2CN$ | $CH_2$(D-47a) |
| 3-Cl-4-F | $CF_3$ | $C(O)CH_3$ | $CH_2$(D-47a) |
| 3-Cl-4-F | $CF_3$ | C(O)Et | $CH_2$(D-47a) |
| 3-Cl-4-F | $CF_3$ | C(O)Pr-c | $CH_2$(D-47a) |
| 3-Cl-4-F | $CF_3$ | $C(O)OCH_3$ | $CH_2$(D-47a) |
| 3-Cl-4-F | $CF_3$ | H | $CH(CH_3)$(D-47a) |
| 3-Cl-4-F | $CF_3$ | H | $CH_2$(D-50a) |
| 3-Cl-4-F | $CF_3$ | H | $N(CH_3)$Ph |
| 3-Cl-4-F | $CF_3$ | H | $N(CH_3)$(D-50a) |
| 3-Cl-4-F | $CF_3$ | $C(O)OCH_3$ | $C(O)N(CH_3)_2$ |
| 3-Cl-4-F | $CF_3$ | H | C(O)NHEt |
| 3-Cl-4-F | $CF_3$ | $CH_3$ | C(O)NHEt |
| 3-Cl-4-F | $CF_3$ | H | $C(O)NHCH_2CH_2Cl$ |
| 3-Cl-4-F | $CF_3$ | H | $C(O)NHCH_2$(Ph-4-F) |
| 3-Cl-4-F | $CF_3$ | H | Ph-4-CN |
| 3-Cl-4-F | $CF_3$ | H | Ph-2,4-$F_2$ |
| 3-Cl-4-F | $CF_3$ | H | (D-15a)$CH_3$ |
| 3-Cl-4-F | $CF_3$ | H | (D-47d)CN |
| 3-Cl-4-F | $CF_3$ | H | (D-47e)Br |
| 3-Cl-4-F | $CF_3$ | H | D-50a |
| 3-Cl-4-F | $CF_3$ | H | (D-50c)Cl |
| 3-Cl-4-F | $CF_3$ | H | (D-50c)Br |
| 3-Cl-4-F | $CF_3$ | H | D-52a |
| 3-Cl-4-F | $CF_3$ | H | D-53a |
| 3-Cl-4-F | $CF_2Cl$ | H | $CH_2CF_3$ |
| 3-Cl-4-F | $CF_2Cl$ | $C(O)CH_3$ | $CH_2CF_3$ |
| 3-Cl-4-F | $CF_2Cl$ | H | $CH_2OCH_2CF_3$ |
| 3-Cl-4-F | $CF_2Cl$ | H | E-4a |
| 3-Cl-4-F | $CF_2Cl$ | H | $CH_2C(O)NHCH_2CF_3$ |
| 3-Cl-4-F | $CF_2Cl$ | H | $CH(CH_3)C(O)NHCH_2CF_3$(D) |
| 3-Cl-4-F | $CF_2Cl$ | H | $CH(CH_3)$Ph(R) |
| 3-Cl-4-F | $CF_2Cl$ | H | $CH_2$(D-22a) |
| 3-Cl-4-F | $CF_2Cl$ | H | $CH_2$(D-47a) |
| 3-Cl-4-F | $CF_2Cl$ | $CH_2CN$ | $CH_2$(D-47a) |
| 3-Cl-4-F | $CF_2Cl$ | C(O)Et | $CH_2$(D-47a) |
| 3-Cl-4-F | $CF_2Cl$ | $C(O)OCH_3$ | $CH_2$(D-47a) |
| 3-Cl-4-F | $CF_2Cl$ | H | $N(CH_3)$Ph |
| 3-Cl-4-F | $CF_2Cl$ | H | (D-50c)Cl |
| 3-Cl-4-F | $CF_2Cl$ | H | D-52a |
| 3-Cl-4-F | $CF_2Br$ | H | E-4a |
| 3-Cl-4-F | $CF_2CHF_2$ | H | $CH_2C(O)NHCH_2CF_3$ |
| 2-F-4-Cl | $CF_3$ | H | $CH_2$(D-22a) |
| 3-F-4-Cl | $CF_3$ | H | $CH_2$(D-47a) |
| 3-F-5-Cl | $CHF_2$ | $C(O)OCH_3$ | $CH_2$(D-47a) |
| 3-F-5-Cl | $CF_3$ | H | c-Pr |
| 3-F-5-Cl | $CF_3$ | H | $CH_2$Pr-c |
| 3-F-5-Cl | $CF_3$ | H | c-Bu |
| 3-F-5-Cl | $CF_3$ | H | $CH_2CF_3$ |
| 3-F-5-Cl | $CF_3$ | $C(O)CH_3$ | $CH_2CF_3$ |
| 3-F-5-Cl | $CF_3$ | H | $CH_2CH_2CF_3$ |
| 3-F-5-Cl | $CF_3$ | H | $CH_2OCH_3$ |
| 3-F-5-Cl | $CF_3$ | H | $CH_2OEt$ |
| 3-F-5-Cl | $CF_3$ | $C(O)CH_3$ | $CH_2OEt$ |
| 3-F-5-Cl | $CF_3$ | H | $CH_2OCH_2CF_3$ |
| 3-F-5-Cl | $CF_3$ | $C(O)CH_3$ | $CH_2OCH_2CF_3$ |
| 3-F-5-Cl | $CF_3$ | H | $CH_2CH_2OCH_3$ |
| 3-F-5-Cl | $CF_3$ | H | $CH_2$(E-10a) |
| 3-F-5-Cl | $CF_3$ | H | E-4a |
| 3-F-5-Cl | $CF_3$ | H | E-5a(R) |
| 3-F-5-Cl | $CF_3$ | H | $CH_2CH$=$NOCH_3$ |
| 3-F-5-Cl | $CF_3$ | H | $CH_2C(O)NHCH_2CH_2Cl$ |
| 3-F-5-Cl | $CF_3$ | H | $CH_2C(O)NHCH_2CF_3$ |
| 3-F-5-Cl | $CF_3$ | H | $CH(CH_3)C(O)NHEt$ |
| 3-F-5-Cl | $CF_3$ | H | $CH(CH_3)C(O)NHCH_2CF_3$ |
| 3-F-5-Cl | $CF_3$ | H | $CH(CH_3)C(O)NHCH_2CF_3$(D) |
| 3-F-5-Cl | $CF_3$ | H | $CH_2CH$=$CH_2$ |
| 3-F-5-Cl | $CF_3$ | H | $CH_2CCl$=$CH_2$ |
| 3-F-5-Cl | $CF_3$ | H | $CH(CH_3)$Ph(R) |
| 3-F-5-Cl | $CF_3$ | H | $CH_2$(Ph-4-$NO_2$) |
| 3-F-5-Cl | $CF_3$ | H | $CH_2$(Ph-4-CN) |
| 3-F-5-Cl | $CF_3$ | H | $CH_2$(D-17b)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-F-5-Cl | CF$_3$ | H | CH$_2$(D-21a) |
| 3-F-5-Cl | CF$_3$ | H | CH$_2$(D-22a) |
| 3-F-5-Cl | CF$_3$ | C(O)CH$_3$ | CH$_2$(D-22a) |
| 3-F-5-Cl | CF$_3$ | C(O)Et | CH$_2$(D-22a) |
| 3-F-5-Cl | CF$_3$ | H | CH$_2$(D-47a) |
| 3-F-5-Cl | CF$_3$ | CH$_2$OCH$_3$ | CH$_2$(D-47a) |
| 3-F-5-Cl | CF$_3$ | CH$_2$CN | CH$_2$(D-47a) |
| 3-F-5-Cl | CF$_3$ | C(O)CH$_3$ | CH$_2$(D-47a) |
| 3-F-5-Cl | CF$_3$ | C(O)Et | CH$_2$(D-47a) |
| 3-F-5-Cl | CF$_3$ | C(O)Pr-c | CH$_2$(D-47a) |
| 3-F-5-Cl | CF$_3$ | C(O)OCH$_3$ | CH$_2$(D-47a) |
| 3-F-5-Cl | CF$_3$ | H | CH(CH$_3$)(D-47a) |
| 3-F-5-Cl | CF$_3$ | H | CH$_2$(D-50a) |
| 3-F-5-Cl | CF$_3$ | H | N(CH$_3$)Ph |
| 3-F-5-Cl | CF$_3$ | H | N(CH$_3$)(D-50a) |
| 3-F-5-Cl | CF$_3$ | C(O)OCH$_3$ | C(O)N(CH$_3$)$_2$ |
| 3-F-5-Cl | CF$_3$ | H | C(O)NHEt |
| 3-F-5-Cl | CF$_3$ | CH$_3$ | C(O)NHEt |
| 3-F-5-Cl | CF$_3$ | H | C(O)NHCH$_2$CH$_2$Cl |
| 3-F-5-Cl | CF$_3$ | H | C(O)NHCH$_2$(Ph-4-F) |
| 3-F-5-Cl | CF$_3$ | H | Ph-4-CN |
| 3-F-5-Cl | CF$_3$ | H | Ph-2,4-F$_2$ |
| 3-F-5-Cl | CF$_3$ | H | (D-15a)CH$_3$ |
| 3-F-5-Cl | CF$_3$ | H | (D-47d)CN |
| 3-F-5-Cl | CF$_3$ | H | (D-47e)Br |
| 3-F-5-Cl | CF$_3$ | H | D-50a |
| 3-F-5-Cl | CF$_3$ | H | (D-50c)Cl |
| 3-F-5-Cl | CF$_3$ | H | (D-50c)Br |
| 3-F-5-Cl | CF$_3$ | H | D-52a |
| 3-F-5-Cl | CF$_3$ | H | D-53a |
| 3-F-5-Cl | CF$_2$Cl | H | CH$_2$CF$_3$ |
| 3-F-5-Cl | CF$_2$Cl | C(O)CH$_3$ | CH$_2$CF$_3$ |
| 3-F-5-Cl | CF$_2$Cl | H | CH$_2$OCH$_2$CF$_3$ |
| 3-F-5-Cl | CF$_2$Cl | H | E-4a |
| 3-F-5-Cl | CF$_2$Cl | H | CH$_2$C(O)NHCH$_2$CF$_3$ |
| 3-F-5-Cl | CF$_2$Cl | H | CH(CH$_3$)C(O)NHCH$_2$CF$_3$(D) |
| 3-F-5-Cl | CF$_2$Cl | H | CH(CH$_3$)Ph(R) |
| 3-F-5-Cl | CF$_2$Cl | H | CH$_2$(D-22a) |
| 3-F-5-Cl | CF$_2$Cl | H | CH$_2$(D-47a) |
| 3-F-5-Cl | CF$_2$Cl | CH$_2$CN | CH$_2$(D-47a) |
| 3-F-5-Cl | CF$_2$Cl | C(O)Et | CH$_2$(D-47a) |
| 3-F-5-Cl | CF$_2$Cl | C(O)OCH$_3$ | CH$_2$(D-47a) |
| 3-F-5-Cl | CF$_2$Cl | H | N(CH$_3$)Ph |
| 3-F-5-Cl | CF$_2$Cl | H | (D-50c)Cl |
| 3-F-5-Cl | CF$_2$Cl | H | D-52a |
| 3-F-5-Cl | CF$_2$Br | H | N(CH$_3$)Ph |
| 3-F-5-Cl | CF$_2$CHF$_2$ | H | (D-50c)Cl |
| 2-F-6-Cl | CF$_3$ | H | CH$_2$CF$_3$ |
| 2,3-Cl$_2$ | CF$_3$ | H | CH$_2$OCH$_2$CF$_3$ |
| 2,4-Cl$_2$ | CF$_3$ | H | E-4a |
| 2,5-Cl$_2$ | CF$_3$ | H | CH$_2$C(O)NHCH$_2$CF$_3$ |
| 2,6-Cl$_2$ | CF$_3$ | H | CH$_2$(D-22a) |
| 3,4-Cl$_2$ | CHF$_2$ | H | CH$_2$(D-47a) |
| 3,4-Cl$_2$ | CF$_3$ | H | CH$_3$ |
| 3,4-Cl$_2$ | CF$_3$ | CH$_3$ | CH$_3$ |
| 3,4-Cl$_2$ | CF$_3$ | H | Et |
| 3,4-Cl$_2$ | CF$_3$ | Et | Et |
| 3,4-Cl$_2$ | CF$_3$ | H | n-Pr |
| 3,4-Cl$_2$ | CF$_3$ | H | i-Pr |
| 3,4-Cl$_2$ | CF$_3$ | H | c-Pr |
| 3,4-Cl$_2$ | CF$_3$ | H | n-Bu |
| 3,4-Cl$_2$ | CF$_3$ | CH$_3$ | n-Bu |
| 3,4-Cl$_2$ | CF$_3$ | H | i-Bu |
| 3,4-Cl$_2$ | CF$_3$ | CH$_3$ | i-Bu |
| 3,4-Cl$_2$ | CF$_3$ | H | CH$_2$Pr-c |
| 3,4-Cl$_2$ | CF$_3$ | H | s-Bu |
| 3,4-Cl$_2$ | CF$_3$ | H | c-Bu |
| 3,4-Cl$_2$ | CF$_3$ | H | t-Bu |
| 3,4-Cl$_2$ | CF$_3$ | H | n-Pen |
| 3,4-Cl$_2$ | CF$_3$ | H | CH$_2$Bu-s |
| 3,4-Cl$_2$ | CF$_3$ | H | CH$_2$Bu-c |
| 3,4-Cl$_2$ | CF$_3$ | H | CH$_2$Bu-t |
| 3,4-Cl$_2$ | CF$_3$ | H | CH(CH$_3$)Pr-n |
| 3,4-Cl$_2$ | CF$_3$ | H | c-Pen |
| 3,4-Cl$_2$ | CF$_3$ | H | c-Hex |
| 3,4-Cl$_2$ | CF$_3$ | H | CH$_2$Hex-c |
| 3,4-Cl$_2$ | CF$_3$ | | —CH$_2$CH$_2$CH$_2$CH$_2$CH$_2$CH$_2$— |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4-Cl$_2$ | CF$_3$ | H | CH$_2$CH$_2$Cl |
| 3,4-Cl$_2$ | CF$_3$ | H | CH$_2$CF$_3$ |
| 3,4-Cl$_2$ | CF$_3$ | C(O)CH$_3$ | CH$_2$CF$_3$ |
| 3,4-Cl$_2$ | CF$_3$ | H | CH$_2$CH$_2$CF$_3$ |
| 3,4-Cl$_2$ | CF$_3$ | H | CH$_2$CF$_2$CF$_3$ |
| 3,4-Cl$_2$ | CF$_3$ | H | CH$_2$CF$_2$CF$_2$CF$_3$ |
| 3,4-Cl$_2$ | CF$_3$ | H | CH$_2$OCH$_3$ |
| 3,4-Cl$_2$ | CF$_3$ | H | CH$_2$OEt |
| 3,4-Cl$_2$ | CF$_3$ | C(O)CH$_3$ | CH$_2$OEt |
| 3,4-Cl$_2$ | CF$_3$ | H | CH$_2$OCH$_2$CF$_3$ |
| 3,4-Cl$_2$ | CF$_3$ | C(O)CH$_3$ | CH$_2$OCH$_2$CF$_3$ |
| 3,4-Cl$_2$ | CF$_3$ | H | CH$_2$CH$_2$OCH$_3$ |
| 3,4-Cl$_2$ | CF$_3$ | H | CH$_2$CH(CH$_3$)OH(R) |
| 3,4-Cl$_2$ | CF$_3$ | H | CH$_2$CH(CH$_3$)OH(S) |
| 3,4-Cl$_2$ | CF$_3$ | H | CH$_2$CH(CH$_3$)OC(O)NHEt(S) |
| 3,4-Cl$_2$ | CF$_3$ | H | CH(CH$_3$)CH$_2$OCH$_3$ |
| 3,4-Cl$_2$ | CF$_3$ | H | CH$_2$CH(Et)OH |
| 3,4-Cl$_2$ | CF$_3$ | H | CH(Et)CH$_2$OCH$_3$ |
| 3,4-Cl$_2$ | CF$_3$ | H | CH$_2$CH(OCH$_3$)$_2$ |
| 3,4-Cl$_2$ | CF$_3$ | H | CH$_2$CH$_2$CH$_2$OH |
| 3,4-Cl$_2$ | CF$_3$ | H | CH$_2$CH$_2$CH$_2$OCH$_3$ |
| 3,4-Cl$_2$ | CF$_3$ | H | CH$_2$(T-13) |
| 3,4-Cl$_2$ | CF$_3$ | H | CH$_2$(E-4a) |
| 3,4-Cl$_2$ | CF$_3$ | H | CH$_2$(E-10a) |
| 3,4-Cl$_2$ | CF$_3$ | H | CH$_2$(E-11c) |
| 3,4-Cl$_2$ | CF$_3$ | H | E-4a |
| 3,4-Cl$_2$ | CF$_3$ | H | E-5a(R) |
| 3,4-Cl$_2$ | CF$_3$ | | —CH$_2$CH$_2$OCH$_2$CH$_2$— |
| 3,4-Cl$_2$ | CF$_3$ | | —CH$_2$CH(CH$_3$)OCH(CH$_3$)CH$_2$— |
| 3,4-Cl$_2$ | CF$_3$ | H | CH$_2$CH$_2$SCH$_3$ |
| 3,4-Cl$_2$ | CF$_3$ | H | CH$_2$CH$_2$SBu-t |
| 3,4-Cl$_2$ | CF$_3$ | H | CH(CH$_3$)CH$_2$SCH$_3$ |
| 3,4-Cl$_2$ | CF$_3$ | H | C(CH$_3$)$_2$CH$_2$SCH$_3$ |
| 3,4-Cl$_2$ | CF$_3$ | H | C(CH$_3$)$_2$CH$_2$S(O)CH$_3$ |
| 3,4-Cl$_2$ | CF$_3$ | H | C(CH$_3$)$_2$CH$_2$SO$_2$CH$_3$ |
| 3,4-Cl$_2$ | CF$_3$ | H | CH$_2$CH$_2$CH$_2$SCH$_3$ |
| 3,4-Cl$_2$ | CF$_3$ | | —CH$_2$CH$_2$SCH$_2$CH$_2$— |
| 3,4-Cl$_2$ | CF$_3$ | H | CH$_2$CH$_2$NHC(O)OBu-t |
| 3,4-Cl$_2$ | CF$_3$ | | —CH$_2$CH$_2$N(CHO)CH$_2$CH$_2$— |
| 3,4-Cl$_2$ | CF$_3$ | H | CH$_2$CH$_2$CH$_2$Si(CH$_3$)(OEt)$_2$ |
| 3,4-Cl$_2$ | CF$_3$ | H | CH$_2$C(O)(Ph-4-OCH$_3$) |
| 3,4-Cl$_2$ | CF$_3$ | H | CH$_2$CH=NOCH$_3$ |
| 3,4-Cl$_2$ | CF$_3$ | H | CH$_2$C(O)NH$_2$ |
| 3,4-Cl$_2$ | CF$_3$ | H | CH$_2$C(O)NHCH$_2$CH$_2$Cl |
| 3,4-Cl$_2$ | CF$_3$ | H | CH$_2$C(O)NHCH$_2$CF$_3$ |
| 3,4-Cl$_2$ | CF$_3$ | H | CH(CH$_3$)C(O)NHEt |
| 3,4-Cl$_2$ | CF$_3$ | H | CH(CH$_3$)C(O)NHCH$_2$CF$_3$ |
| 3,4-Cl$_2$ | CF$_3$ | H | CH(CH$_3$)C(O)NHCH$_2$CF$_3$(D) |
| 3,4-Cl$_2$ | CF$_3$ | H | CH$_2$CH=CH$_2$ |
| 3,4-Cl$_2$ | CF$_3$ | CH$_3$ | CH$_2$CH=CH$_2$ |
| 3,4-Cl$_2$ | CF$_3$ | CH$_2$CH=CH$_2$ | CH$_2$CH=CH$_2$ |
| 3,4-Cl$_2$ | CF$_3$ | H | CH$_2$CCl=CH$_2$ |
| 3,4-Cl$_2$ | CF$_3$ | H | CH$_2$C≡CH |
| 3,4-Cl$_2$ | CF$_3$ | CH$_3$ | CH$_2$C≡CH |
| 3,4-Cl$_2$ | CF$_3$ | H | CH$_2$Ph |
| 3,4-Cl$_2$ | CF$_3$ | CH$_3$ | CH$_2$Ph |
| 3,4-Cl$_2$ | CF$_3$ | H | CH(CH$_3$)Ph(R) |
| 3,4-Cl$_2$ | CF$_3$ | H | C(CH$_3$)$_2$Ph |
| 3,4-Cl$_2$ | CF$_3$ | H | CH$_2$(Ph-2-F) |
| 3,4-Cl$_2$ | CF$_3$ | H | CH$_2$(Ph-3-F) |
| 3,4-Cl$_2$ | CF$_3$ | H | CH$_2$(Ph-4-F) |
| 3,4-Cl$_2$ | CF$_3$ | H | CH$_2$(Ph-2-Cl) |
| 3,4-Cl$_2$ | CF$_3$ | H | CH$_2$(Ph-3-Cl) |
| 3,4-Cl$_2$ | CF$_3$ | H | CH(CH$_3$)(Ph-3-Cl) |
| 3,4-Cl$_2$ | CF$_3$ | H | CH$_2$(Ph-4-Cl) |
| 3,4-Cl$_2$ | CF$_3$ | H | CH$_2$(Ph-2-CH$_3$) |
| 3,4-Cl$_2$ | CF$_3$ | H | CH$_2$(Ph-2-CF$_3$) |
| 3,4-Cl$_2$ | CF$_3$ | H | CH$_2$(Ph-3-CF$_3$) |
| 3,4-Cl$_2$ | CF$_3$ | H | CH$_2$(Ph-2-OCH$_3$) |
| 3,4-Cl$_2$ | CF$_3$ | H | CH$_2$(Ph-3-OCH$_3$) |
| 3,4-Cl$_2$ | CF$_3$ | H | CH$_2$(Ph-4-OCH$_3$) |
| 3,4-Cl$_2$ | CF$_3$ | H | CH$_2$(Ph-3-OCF$_3$) |
| 3,4-Cl$_2$ | CF$_3$ | H | CH$_2$(Ph-4-SO$_2$CH$_3$) |
| 3,4-Cl$_2$ | CF$_3$ | H | CH$_2$(Ph-3-NO$_2$) |
| 3,4-Cl$_2$ | CF$_3$ | H | CH$_2$(Ph-4-NO$_2$) |
| 3,4-Cl$_2$ | CF$_3$ | H | CH$_2$[Ph-4-N(CH$_3$)$_2$] |
| 3,4-Cl$_2$ | CF$_3$ | H | CH$_2$(Ph-4-CN) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4-Cl$_2$ | CF$_3$ | H | CH$_2$[Ph-4-C(O)OCH$_3$] |
| 3,4-Cl$_2$ | CF$_3$ | H | CH$_2$(Ph-2,5-F$_2$) |
| 3,4-Cl$_2$ | CF$_3$ | H | CH$_2$(Ph-2,6-F$_2$) |
| 3,4-Cl$_2$ | CF$_3$ | H | CH$_2$(Ph-3,5-F$_2$) |
| 3,4-Cl$_2$ | CF$_3$ | H | CH$_2$(Ph-3-Cl-4-F) |
| 3,4-Cl$_2$ | CF$_3$ | H | CH$_2$(Ph-2,3-Cl$_2$) |
| 3,4-Cl$_2$ | CF$_3$ | H | CH$_2$(Ph-2,4-Cl$_2$) |
| 3,4-Cl$_2$ | CF$_3$ | H | CH$_2$(Ph-2,5-Cl$_2$) |
| 3,4-Cl$_2$ | CF$_3$ | H | CH$_2$(Ph-2,6-Cl$_2$) |
| 3,4-Cl$_2$ | CF$_3$ | H | CH$_2$(Ph-3,4-Cl$_2$) |
| 3,4-Cl$_2$ | CF$_3$ | H | CH$_2$(Ph-3,5-Cl$_2$) |
| 3,4-Cl$_2$ | CF$_3$ | H | CH$_2$(Ph-3-CF$_3$-4-F) |
| 3,4-Cl$_2$ | CF$_3$ | H | CH$_2$[Ph-3,4-(OCH$_3$)$_2$] |
| 3,4-Cl$_2$ | CF$_3$ | H | CH$_2$(Ph-3-OCH$_2$O-4) |
| 3,4-Cl$_2$ | CF$_3$ | H | CH$_2$(1-Naph) |
| 3,4-Cl$_2$ | CF$_3$ | H | CH(CH$_3$)CH$_2$(Ph-4-Cl) |
| 3,4-Cl$_2$ | CF$_3$ | H | T-9 |
| 3,4-Cl$_2$ | CF$_3$ | H | CH$_2$CH$_2$CH$_2$Ph |
| 3,4-Cl$_2$ | CF$_3$ | H | CH$_2$(D-1a) |
| 3,4-Cl$_2$ | CF$_3$ | H | CH$_2$(D-1c)CH$_3$ |
| 3,4-Cl$_2$ | CF$_3$ | H | CH$_2$(D-3a) |
| 3,4-Cl$_2$ | CF$_3$ | H | CH$_2$(D-3b)CH$_3$ |
| 3,4-Cl$_2$ | CF$_3$ | H | CH$_2$(D-17b)Cl |
| 3,4-Cl$_2$ | CF$_3$ | H | CH$_2$(D-21a) |
| 3,4-Cl$_2$ | CF$_3$ | H | CH$_2$(D-22a) |
| 3,4-Cl$_2$ | CF$_3$ | C(O)CH$_3$ | CH$_2$(D-22a) |
| 3,4-Cl$_2$ | CF$_3$ | C(O)Et | CH$_2$(D-22a) |
| 3,4-Cl$_2$ | CF$_3$ | H | CH$_2$(D-47a) |
| 3,4-Cl$_2$ | CF$_3$ | CH$_2$OCH$_3$ | CH$_2$(D-47a) |
| 3,4-Cl$_2$ | CF$_3$ | CH$_2$CN | CH$_2$(D-47a) |
| 3,4-Cl$_2$ | CF$_3$ | C(O)CH$_3$ | CH$_2$(D-47a) |
| 3,4-Cl$_2$ | CF$_3$ | C(O)Et | CH$_2$(D-47a) |
| 3,4-Cl$_2$ | CF$_3$ | C(O)Pr-c | CH$_2$(D-47a) |
| 3,4-Cl$_2$ | CF$_3$ | C(O)OCH$_3$ | CH$_2$(D-47a) |
| 3,4-Cl$_2$ | CF$_3$ | H | CH(CH$_3$)(D-47a) |
| 3,4-Cl$_2$ | CF$_3$ | H | CH$_2$[(D-47f)-3-Cl-5-CF$_3$] |
| 3,4-Cl$_2$ | CF$_3$ | H | CH$_2$(D-48a) |
| 3,4-Cl$_2$ | CF$_3$ | H | CH$_2$(D-48e)Cl |
| 3,4-Cl$_2$ | CF$_3$ | Et | CH$_2$(D-48e)Cl |
| 3,4-Cl$_2$ | CF$_3$ | H | CH$_2$(D-49a) |
| 3,4-Cl$_2$ | CF$_3$ | H | CH$_2$(D-50a) |
| 3,4-Cl$_2$ | CF$_3$ | H | CH$_2$(D-53b)CH$_3$ |
| 3,4-Cl$_2$ | CF$_3$ | H | CH$_2$CH$_2$(D-47a) |
| 3,4-Cl$_2$ | CF$_3$ | H | CH$_2$CH$_2$(D-48a) |
| 3,4-Cl$_2$ | CF$_3$ | H | CH$_2$CH$_2$(D-49a) |
| 3,4-Cl$_2$ | CF$_3$ | H | CH$_2$CH$_2$CH$_2$(D-24a) |
| 3,4-Cl$_2$ | CF$_3$ | H | NHPh |
| 3,4-Cl$_2$ | CF$_3$ | H | N(CH$_3$)Ph |
| 3,4-Cl$_2$ | CF$_3$ | H | N(CH$_3$)(D-50a) |
| 3,4-Cl$_2$ | CF$_3$ | C(O)OCH$_3$ | C(O)N(CH$_3$)$_2$ |
| 3,4-Cl$_2$ | CF$_3$ | H | C(O)NHEt |
| 3,4-Cl$_2$ | CF$_3$ | CH$_3$ | C(O)NHEt |
| 3,4-Cl$_2$ | CF$_3$ | H | C(O)NHCH$_2$CH$_2$Cl |
| 3,4-Cl$_2$ | CF$_3$ | H | C(O)NHCH$_2$(Ph-4-F) |
| 3,4-Cl$_2$ | CF$_3$ | H | Ph-4-CN |
| 3,4-Cl$_2$ | CF$_3$ | H | Ph-2,4-F$_2$ |
| 3,4-Cl$_2$ | CF$_3$ | H | (D-15a)CH$_3$ |
| 3,4-Cl$_2$ | CF$_3$ | H | D-21a |
| 3,4-Cl$_2$ | CF$_3$ | H | (D-21b)CH$_3$ |
| 3,4-Cl$_2$ | CF$_3$ | H | (D-21c)CH$_3$ |
| 3,4-Cl$_2$ | CF$_3$ | H | D-35a |
| 3,4-Cl$_2$ | CF$_3$ | H | (D-47d)CN |
| 3,4-Cl$_2$ | CF$_3$ | H | (D-47e)Br |
| 3,4-Cl$_2$ | CF$_3$ | H | D-48a |
| 3,4-Cl$_2$ | CF$_3$ | H | D-49a |
| 3,4-Cl$_2$ | CF$_3$ | H | D-50a |
| 3,4-Cl$_2$ | CF$_3$ | H | (D-50c)Cl |
| 3,4-Cl$_2$ | CF$_3$ | H | (D-50c)Br |
| 3,4-Cl$_2$ | CF$_3$ | H | D-52a |
| 3,4-Cl$_2$ | CF$_3$ | H | D-53a |
| 3,4-Cl$_2$ | CF$_2$Cl | H | CH$_2$CF$_3$ |
| 3,4-Cl$_2$ | CF$_2$Cl | C(O)CH$_3$ | CH$_2$CF$_3$ |
| 3,4-Cl$_2$ | CF$_2$Cl | H | CH$_2$OCH$_2$CF$_3$ |
| 3,4-Cl$_2$ | CF$_2$Cl | H | E-4a |
| 3,4-Cl$_2$ | CF$_2$Cl | H | CH$_2$C(O)NHCH$_2$CF$_3$ |
| 3,4-Cl$_2$ | CF$_2$Cl | H | CH(CH$_3$)C(O)NHCH$_2$CF$_3$(D) |
| 3,4-Cl$_2$ | CF$_2$Cl | H | CH(CH$_3$)Ph(R) |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,4-Cl$_2$ | CF$_2$Cl | H | CH$_2$(D-22a) |
| 3,4-Cl$_2$ | CF$_2$Cl | H | CH$_2$(D-47a) |
| 3,4-Cl$_2$ | CF$_2$Cl | CH$_2$CN | CH$_2$(D-47a) |
| 3,4-Cl$_2$ | CF$_2$Cl | C(O)Et | CH$_2$(D-47a) |
| 3,4-Cl$_2$ | CF$_2$Cl | C(O)OCH$_3$ | CH$_2$(D-47a) |
| 3,4-Cl$_2$ | CF$_2$Cl | H | N(CH$_3$)Ph |
| 3,4-Cl$_2$ | CF$_2$Cl | H | (D-50c)Cl |
| 3,4-Cl$_2$ | CF$_2$Cl | H | D-52a |
| 3,4-Cl$_2$ | CF$_2$Br | C(O)OCH$_3$ | CH$_2$(D-47a) |
| 3,4-Cl$_2$ | CF$_2$CHF$_2$ | H | N(CH$_3$)Ph |
| 3,4-Cl$_2$ | Ph | H | CH$_2$Ph |
| 3,5-Cl$_2$ | CH$_3$ | H | CH$_2$CF$_3$ |
| 3,5-Cl$_2$ | CH$_3$ | H | (D-50c)Cl |
| 3,5-Cl$_2$ | Et | H | CH$_2$CF$_3$ |
| 3,5-Cl$_2$ | n-Pr | H | CH$_2$OCH$_2$CF$_3$ |
| 3,5-Cl$_2$ | i-Pr | H | CH$_2$CF$_3$ |
| 3,5-Cl$_2$ | i-Pr | H | E-4a |
| 3,5-Cl$_2$ | c-Pr | H | CH$_2$CF$_3$ |
| 3,5-Cl$_2$ | c-Pr | H | CH$_2$C(O)NHCH$_2$CF$_3$ |
| 3,5-Cl$_2$ | c-Pr | H | CH$_2$(D-47a) |
| 3,5-Cl$_2$ | n-Bu | H | CH$_2$(D-22a) |
| 3,5-Cl$_2$ | i-Bu | H | CH$_2$(D-47a) |
| 3,5-Cl$_2$ | s-Bu | C(O)OCH$_3$ | CH$_2$(D-47a) |
| 3,5-Cl$_2$ | c-Bu | H | N(CH$_3$)Ph |
| 3,5-Cl$_2$ | c-Pen | H | (D-50c)Cl |
| 3,5-Cl$_2$ | n-Hex | H | CH$_2$CF$_3$ |
| 3,5-Cl$_2$ | c-Hex | H | CH$_2$OCH$_2$CF$_3$ |
| 3,5-Cl$_2$ | CH$_2$F | H | E-4a |
| 3,5-Cl$_2$ | CH$_2$Cl | H | CH$_2$CF$_3$ |
| 3,5-Cl$_2$ | CH$_2$Cl | H | CH$_2$C(O)NHCH$_2$CF$_3$ |
| 3,5-Cl$_2$ | CH$_2$Cl | H | CH$_2$(D-47a) |
| 3,5-Cl$_2$ | CH$_2$Br | H | CH$_2$(D-22a) |
| 3,5-Cl$_2$ | CH$_2$I | H | CH$_2$(D-47a) |
| 3,5-Cl$_2$ | CHF$_2$ | H | CH$_2$CF$_3$ |
| 3,5-Cl$_2$ | CHF$_2$ | C(O)CH$_3$ | CH$_2$CF$_3$ |
| 3,5-Cl$_2$ | CHF$_2$ | H | CH$_2$OCH$_2$CF$_3$ |
| 3,5-Cl$_2$ | CHF$_2$ | H | E-4a |
| 3,5-Cl$_2$ | CHF$_2$ | H | CH$_2$C(O)NHCH$_2$CF$_3$ |
| 3,5-Cl$_2$ | CHF$_2$ | H | CH(CH$_3$)C(O)NHCH$_2$CF$_3$(D) |
| 3,5-Cl$_2$ | CHF$_2$ | H | CH(CH$_3$)Ph(R) |
| 3,5-Cl$_2$ | CHF$_2$ | H | CH$_2$(D-22a) |
| 3,5-Cl$_2$ | CHF$_2$ | H | CH$_2$(D-47a) |
| 3,5-Cl$_2$ | CHF$_2$ | CH$_2$CN | CH$_2$(D-47a) |
| 3,5-Cl$_2$ | CHF$_2$ | C(O)Et | CH$_2$(D-47a) |
| 3,5-Cl$_2$ | CHF$_2$ | C(O)OCH$_3$ | CH$_2$(D-47a) |
| 3,5-Cl$_2$ | CHF$_2$ | H | N(CH$_3$)Ph |
| 3,5-Cl$_2$ | CHF$_2$ | H | (D-50c)Cl |
| 3,5-Cl$_2$ | CHF$_2$ | H | D-52a |
| 3,5-Cl$_2$ | CHFCl | H | CH$_2$CF$_3$ |
| 3,5-Cl$_2$ | CHFCl | H | CH$_2$OCH$_2$CF$_3$ |
| 3,5-Cl$_2$ | CHFCl | H | E-4a |
| 3,5-Cl$_2$ | CHFCl | H | CH$_2$C(O)NHCH$_2$CF$_3$ |
| 3,5-Cl$_2$ | CHFCl | H | CH(CH$_3$)C(O)NHCH$_2$CF$_3$(D) |
| 3,5-Cl$_2$ | CHFCl | H | CH$_2$(D-22a) |
| 3,5-Cl$_2$ | CHFCl | H | CH$_2$(D-47a) |
| 3,5-Cl$_2$ | CHFCl | C(O)OCH$_3$ | CH$_2$(D-47a) |
| 3,5-Cl$_2$ | CHFCl | H | N(CH$_3$)Ph |
| 3,5-Cl$_2$ | CHFCl | H | (D-50c)Cl |
| 3,5-Cl$_2$ | CHCl$_2$ | H | CH$_2$CF$_3$ |
| 3,5-Cl$_2$ | CHCl$_2$ | H | CH$_2$OCH$_2$CF$_3$ |
| 3,5-Cl$_2$ | CHCl$_2$ | H | E-4a |
| 3,5-Cl$_2$ | CHCl$_2$ | H | CH$_2$C(O)NHCH$_2$CF$_3$ |
| 3,5-Cl$_2$ | CHCl$_2$ | H | CH(CH$_3$)C(O)NHCH$_2$CF$_3$(D) |
| 3,5-Cl$_2$ | CHCl$_2$ | H | CH$_2$(D-22a) |
| 3,5-Cl$_2$ | CHCl$_2$ | H | CH$_2$(D-47a) |
| 3,5-Cl$_2$ | CHCl$_2$ | C(O)OCH$_3$ | CH$_2$(D-47a) |
| 3,5-Cl$_2$ | CHCl$_2$ | H | N(CH$_3$)Ph |
| 3,5-Cl$_2$ | CHCl$_2$ | H | (D-50c)Cl |
| 3,5-Cl$_2$ | CHFBr | H | CH$_2$CF$_3$ |
| 3,5-Cl$_2$ | CHFBr | H | CH$_2$OCH$_2$CF$_3$ |
| 3,5-Cl$_2$ | CHFBr | H | E-4a |
| 3,5-Cl$_2$ | CHFBr | H | CH$_2$C(O)NHCH$_2$CF$_3$ |
| 3,5-Cl$_2$ | CHFBr | H | CH(CH$_3$)C(O)NHCH$_2$CF$_3$(D) |
| 3,5-Cl$_2$ | CHFBr | H | CH$_2$(D-22a) |
| 3,5-Cl$_2$ | CHFBr | H | CH$_2$(D-47a) |
| 3,5-Cl$_2$ | CHFBr | C(O)OCH$_3$ | CH$_2$(D-47a) |
| 3,5-Cl$_2$ | CHFBr | H | N(CH$_3$)Ph |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CHFBr | H | (D-50c)Cl |
| 3,5-Cl$_2$ | CF$_3$ | H | H |
| 3,5-Cl$_2$ | CF$_3$ | H | CH$_3$ |
| 3,5-Cl$_2$ | CF$_3$ | CH$_3$ | CH$_3$ |
| 3,5-Cl$_2$ | CF$_3$ | C(O)Et | CH$_3$ |
| 3,5-Cl$_2$ | CF$_3$ | C(O)CF$_3$ | CH$_3$ |
| 3,5-Cl$_2$ | CF$_3$ | C(O)OCH$_2$Cl | CH$_3$ |
| 3,5-Cl$_2$ | CF$_3$ | C(O)OCH$_2$CH$_2$F | CH$_3$ |
| 3,5-Cl$_2$ | CF$_3$ | C(O)OCH$_2$CH$_2$CF$_3$ | CH$_3$ |
| 3,5-Cl$_2$ | CF$_3$ | C(O)OCH$_2$C(CF$_3$)$_2$CH$_3$ | CH$_3$ |
| 3,5-Cl$_2$ | CF$_3$ | OCH$_3$ | CH$_3$ |
| 3,5-Cl$_2$ | CF$_3$ | NH$_2$ | CH$_3$ |
| 3,5-Cl$_2$ | CF$_3$ | H | Et |
| 3,5-Cl$_2$ | CF$_3$ | CH$_3$ | Et |
| 3,5-Cl$_2$ | CF$_3$ | Et | Et |
| 3,5-Cl$_2$ | CF$_3$ | C(O)CH$_3$ | Et |
| 3,5-Cl$_2$ | CF$_3$ | C(O)Et | Et |
| 3,5-Cl$_2$ | CF$_3$ | C(O)OCH$_2$Cl | Et |
| 3,5-Cl$_2$ | CF$_3$ | C(O)OCH$_2$CH$_2$F | Et |
| 3,5-Cl$_2$ | CF$_3$ | C(O)OCH$_2$CH$_2$CF$_3$ | Et |
| 3,5-Cl$_2$ | CF$_3$ | C(O)OCH$_2$C(CF$_3$)$_2$CH$_3$ | Et |
| 3,5-Cl$_2$ | CF$_3$ | NH$_2$ | Et |
| 3,5-Cl$_2$ | CF$_3$ | NHC(O)CH$_3$ | Et |
| 3,5-Cl$_2$ | CF$_3$ | N=C(CH$_3$)$_2$ | Et |
| 3,5-Cl$_2$ | CF$_3$ | H | n-Pr |
| 3,5-Cl$_2$ | CF$_3$ | H | i-Pr |
| 3,5-Cl$_2$ | CF$_3$ | CH$_2$CN | i-Pr |
| 3,5-Cl$_2$ | CF$_3$ | H | c-Pr |
| 3,5-Cl$_2$ | CF$_3$ | CH$_3$ | c-Pr |
| 3,5-Cl$_2$ | CF$_3$ | CH$_2$OCH$_3$ | c-Pr |
| 3,5-Cl$_2$ | CF$_3$ | CH$_2$OCH$_2$CF$_3$ | c-Pr |
| 3,5-Cl$_2$ | CF$_3$ | CH$_2$OC(O)CH$_3$ | c-Pr |
| 3,5-Cl$_2$ | CF$_3$ | CH$_2$CN | c-Pr |
| 3,5-Cl$_2$ | CF$_3$ | CH$_2$C≡CH | c-Pr |
| 3,5-Cl$_2$ | CF$_3$ | C(O)CH$_3$ | c-Pr |
| 3,5-Cl$_2$ | CF$_3$ | C(O)Et | c-Pr |
| 3,5-Cl$_2$ | CF$_3$ | C(O)OCH$_3$ | c-Pr |
| 3,5-Cl$_2$ | CF$_3$ | CH$_2$CN | n-Bu |
| 3,5-Cl$_2$ | CF$_3$ | H | i-Bu |
| 3,5-Cl$_2$ | CF$_3$ | H | CH$_2$Pr-c |
| 3,5-Cl$_2$ | CF$_3$ | CH$_3$ | CH$_2$Pr-c |
| 3,5-Cl$_2$ | CF$_3$ | CH$_2$OCH$_3$ | CH$_2$Pr-c |
| 3,5-Cl$_2$ | CF$_3$ | CH$_2$OCH$_2$CF$_3$ | CH$_2$Pr-c |
| 3,5-Cl$_2$ | CF$_3$ | CH$_2$OC(O)CH$_3$ | CH$_2$Pr-c |
| 3,5-Cl$_2$ | CF$_3$ | CH$_2$CN | CH$_2$Pr-c |
| 3,5-Cl$_2$ | CF$_3$ | CH$_2$C≡CH | CH$_2$Pr-c |
| 3,5-Cl$_2$ | CF$_3$ | C(O)CH$_3$ | CH$_2$Pr-c |
| 3,5-Cl$_2$ | CF$_3$ | C(O)Et | CH$_2$Pr-c |
| 3,5-Cl$_2$ | CF$_3$ | C(O)OCH$_3$ | CH$_2$Pr-c |
| 3,5-Cl$_2$ | CF$_3$ | H | c-Bu |
| 3,5-Cl$_2$ | CF$_3$ | CH$_3$ | c-Bu |
| 3,5-Cl$_2$ | CF$_3$ | CH$_2$OCH$_3$ | c-Bu |
| 3,5-Cl$_2$ | CF$_3$ | CH$_2$OEt | c-Bu |
| 3,5-Cl$_2$ | CF$_3$ | CH$_2$OCH$_2$CF$_3$ | c-Bu |
| 3,5-Cl$_2$ | CF$_3$ | CH$_2$OC(O)CH$_3$ | c-Bu |
| 3,5-Cl$_2$ | CF$_3$ | CH$_2$CN | c-Bu |
| 3,5-Cl$_2$ | CF$_3$ | CH$_2$C≡CH | c-Bu |
| 3,5-Cl$_2$ | CF$_3$ | C(O)CH$_3$ | c-Bu |
| 3,5-Cl$_2$ | CF$_3$ | C(O)Et | c-Bu |
| 3,5-Cl$_2$ | CF$_3$ | C(O)OCH$_3$ | c-Bu |
| 3,5-Cl$_2$ | CF$_3$ | H | CH$_2$Bu-i |
| 3,5-Cl$_2$ | CF$_3$ | H | CH$_2$Bu-c |
| 3,5-Cl$_2$ | CF$_3$ | H | CH$_2$(T-6) |
| 3,5-Cl$_2$ | CF$_3$ | H | CH(Et)$_2$ |
| 3,5-Cl$_2$ | CF$_3$ | H | C(CH$_3$)$_2$Et |
| 3,5-Cl$_2$ | CF$_3$ | H | c-Pen |
| 3,5-Cl$_2$ | CF$_3$ | H | n-Hex |
| 3,5-Cl$_2$ | CF$_3$ | H | CH$_2$(T-7) |
| 3,5-Cl$_2$ | CF$_3$ | H | CH(CH$_3$)Bu-i |
| 3,5-Cl$_2$ | CF$_3$ | H | C(CH$_3$)$_2$Pr-n |
| 3,5-Cl$_2$ | CF$_3$ | H | Hept |
| 3,5-Cl$_2$ | CF$_3$ | H | Oct |
| 3,5-Cl$_2$ | CF$_3$ | H | CH$_2$(T-12) |
| 3,5-Cl$_2$ | CF$_3$ | —CH$_2$CH$_2$CH$_2$— | |
| 3,5-Cl$_2$ | CF$_3$ | —CH$_2$CH$_2$CH$_2$CH$_2$— | |
| 3,5-Cl$_2$ | CF$_3$ | —CH$_2$CH$_2$CH$_2$CH$_2$CH$_2$— | |
| 3,5-Cl$_2$ | CF$_3$ | H | CH$_2$Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$CH$_2$F |
| 3,5-Cl$_2$ | CF$_3$ | H | CH$_2$CH$_2$Cl |
| 3,5-Cl$_2$ | CF$_3$ | H | CH$_2$CH$_2$Br |
| 3,5-Cl$_2$ | CF$_3$ | H | CH$_2$CHF$_2$ |
| 3,5-Cl$_2$ | CF$_3$ | H | CH$_2$CHFCl |
| 3,5-Cl$_2$ | CF$_3$ | H | CH$_2$CHCl$_2$ |
| 3,5-Cl$_2$ | CF$_3$ | H | CH$_2$CHFBr |
| 3,5-Cl$_2$ | CF$_3$ | H | CH$_2$CF$_3$ |
| 3,5-Cl$_2$ | CF$_3$ | CH$_3$ | CH$_2$CF$_3$ |
| 3,5-Cl$_2$ | CF$_3$ | Et | CH$_2$CF$_3$ |
| 3,5-Cl$_2$ | CF$_3$ | n-Pr | CH$_2$CF$_3$ |
| 3,5-Cl$_2$ | CF$_3$ | i-Pr | CH$_2$CF$_3$ |
| 3,5-Cl$_2$ | CF$_3$ | CH$_2$OCH$_3$ | CH$_2$CF$_3$ |
| 3,5-Cl$_2$ | CF$_3$ | CH$_2$OEt | CH$_2$CF$_3$ |
| 3,5-Cl$_2$ | CF$_3$ | CH$_2$OCH$_2$CH$_2$Cl | CH$_2$CF$_3$ |
| 3,5-Cl$_2$ | CF$_3$ | CH$_2$OCH$_2$CF$_3$ | CH$_2$CF$_3$ |
| 3,5-Cl$_2$ | CF$_3$ | CH$_2$OCH$_2$CH$_2$OCH$_3$ | CH$_2$CF$_3$ |
| 3,5-Cl$_2$ | CF$_3$ | CH$_2$OCH$_2$Ph | CH$_2$CF$_3$ |
| 3,5-Cl$_2$ | CF$_3$ | CH$_2$OC(O)CH$_3$ | CH$_2$CF$_3$ |
| 3,5-Cl$_2$ | CF$_3$ | CH$_2$OC(O)Et | CH$_2$CF$_3$ |
| 3,5-Cl$_2$ | CF$_3$ | CH$_2$OC(O)Pr-n | CH$_2$CF$_3$ |
| 3,5-Cl$_2$ | CF$_3$ | CH$_2$OC(O)Pr-i | CH$_2$CF$_3$ |
| 3,5-Cl$_2$ | CF$_3$ | CH$_2$OC(O)Pr-c | CH$_2$CF$_3$ |
| 3,5-Cl$_2$ | CF$_3$ | CH$_2$OC(O)Bu-t | CH$_2$CF$_3$ |
| 3,5-Cl$_2$ | CF$_3$ | CH$_2$OC(O)CH$_2$Ph | CH$_2$CF$_3$ |
| 3,5-Cl$_2$ | CF$_3$ | CH$_2$OC(O)Ph | CH$_2$CF$_3$ |
| 3,5-Cl$_2$ | CF$_3$ | CH$_2$OC(O)OCH$_3$ | CH$_2$CF$_3$ |
| 3,5-Cl$_2$ | CF$_3$ | CH$_2$OC(O)OEt | CH$_2$CF$_3$ |
| 3,5-Cl$_2$ | CF$_3$ | CH$_2$OC(O)OPh | CH$_2$CF$_3$ |
| 3,5-Cl$_2$ | CF$_3$ | CH$_2$OC(O)NHPh | CH$_2$CF$_3$ |
| 3,5-Cl$_2$ | CF$_3$ | CH$_2$OPh | CH$_2$CF$_3$ |
| 3,5-Cl$_2$ | CF$_3$ | CH(CH$_3$)OC(O)CH$_3$ | CH$_2$CF$_3$ |
| 3,5-Cl$_2$ | CF$_3$ | CH(CH$_3$)OC(O)Bu-t | CH$_2$CF$_3$ |
| 3,5-Cl$_2$ | CF$_3$ | CH(CH$_3$)OC(O)OCH$_3$ | CH$_2$CF$_3$ |
| 3,5-Cl$_2$ | CF$_3$ | CH(CH$_3$)OC(O)SCH$_3$ | CH$_2$CF$_3$ |
| 3,5-Cl$_2$ | CF$_3$ | CH$_2$CH$_2$OCH$_3$ | CH$_2$CF$_3$ |
| 3,5-Cl$_2$ | CF$_3$ | CH$_2$SCH$_3$ | CH$_2$CF$_3$ |
| 3,5-Cl$_2$ | CF$_3$ | CH$_2$SO$_2$CH$_3$ | CH$_2$CF$_3$ |
| 3,5-Cl$_2$ | CF$_3$ | CH$_2$SCF$_3$ | CH$_2$CF$_3$ |
| 3,5-Cl$_2$ | CF$_3$ | CH$_2$SC(O)CH$_3$ | CH$_2$CF$_3$ |
| 3,5-Cl$_2$ | CF$_3$ | CH$_2$SC(O)Et | CH$_2$CF$_3$ |
| 3,5-Cl$_2$ | CF$_3$ | CH$_2$SC(O)Ph | CH$_2$CF$_3$ |
| 3,5-Cl$_2$ | CF$_3$ | CH$_2$SC(S)OCH$_3$ | CH$_2$CF$_3$ |
| 3,5-Cl$_2$ | CF$_3$ | CH$_2$SC(S)OEt | CH$_2$CF$_3$ |
| 3,5-Cl$_2$ | CF$_3$ | CH$_2$SC(S)OPr-n | CH$_2$CF$_3$ |
| 3,5-Cl$_2$ | CF$_3$ | CH$_2$SC(S)OPr-i | CH$_2$CF$_3$ |
| 3,5-Cl$_2$ | CF$_3$ | CH$_2$SC(S)N(CH$_3$)$_2$ | CH$_2$CF$_3$ |
| 3,5-Cl$_2$ | CF$_3$ | CH$_2$SC(S)(T-33) | CH$_2$CF$_3$ |
| 3,5-Cl$_2$ | CF$_3$ | CH$_2$SPh | CH$_2$CF$_3$ |
| 3,5-Cl$_2$ | CF$_3$ | CH$_2$N(CH$_3$)$_2$ | CH$_2$CF$_3$ |
| 3,5-Cl$_2$ | CF$_3$ | CH$_2$N(CH$_3$)C(O)CH$_3$ | CH$_2$CF$_3$ |
| 3,5-Cl$_2$ | CF$_3$ | CH$_2$NHC(O)OCH$_3$ | CH$_2$CF$_3$ |
| 3,5-Cl$_2$ | CF$_3$ | CH$_2$N(CH$_3$)C(O)OCH$_3$ | CH$_2$CF$_3$ |
| 3,5-Cl$_2$ | CF$_3$ | CH$_2$N(CH$_3$)SO$_2$CH$_3$ | CH$_2$CF$_3$ |
| 3,5-Cl$_2$ | CF$_3$ | CH$_2$CN | CH$_2$CF$_3$ |
| 3,5-Cl$_2$ | CF$_3$ | CH$_2$CH=CH$_2$ | CH$_2$CF$_3$ |
| 3,5-Cl$_2$ | CF$_3$ | CH$_2$C≡CH | CH$_2$CF$_3$ |
| 3,5-Cl$_2$ | CF$_3$ | C(O)CH$_3$ | CH$_2$CF$_3$ |
| 3,5-Cl$_2$ | CF$_3$ | C(O)Et | CH$_2$CF$_3$ |
| 3,5-Cl$_2$ | CF$_3$ | C(O)Pr-n | CH$_2$CF$_3$ |
| 3,5-Cl$_2$ | CF$_3$ | C(O)Pr-i | CH$_2$CF$_3$ |
| 3,5-Cl$_2$ | CF$_3$ | C(O)Pr-c | CH$_2$CF$_3$ |
| 3,5-Cl$_2$ | CF$_3$ | C(O)Bu-t | CH$_2$CF$_3$ |
| 3,5-Cl$_2$ | CF$_3$ | C(O)CH$_2$OCH$_3$ | CH$_2$CF$_3$ |
| 3,5-Cl$_2$ | CF$_3$ | C(O)CH$_2$SCH$_3$ | CH$_2$CF$_3$ |
| 3,5-Cl$_2$ | CF$_3$ | C(O)CH=CH$_2$ | CH$_2$CF$_3$ |
| 3,5-Cl$_2$ | CF$_3$ | C(O)OCH$_3$ | CH$_2$CF$_3$ |
| 3,5-Cl$_2$ | CF$_3$ | C(O)OEt | CH$_2$CF$_3$ |
| 3,5-Cl$_2$ | CF$_3$ | C(O)OPr-n | CH$_2$CF$_3$ |
| 3,5-Cl$_2$ | CF$_3$ | C(O)OPr-i | CH$_2$CF$_3$ |
| 3,5-Cl$_2$ | CF$_3$ | C(O)OPr-c | CH$_2$CF$_3$ |
| 3,5-Cl$_2$ | CF$_3$ | C(O)OCH$_2$Cl | CH$_2$CF$_3$ |
| 3,5-Cl$_2$ | CF$_3$ | C(O)OCH$_2$CH$_2$Cl | CH$_2$CF$_3$ |
| 3,5-Cl$_2$ | CF$_3$ | C(O)OCH$_2$CH$_2$OCH$_3$ | CH$_2$CF$_3$ |
| 3,5-Cl$_2$ | CF$_3$ | C(O)OCH$_2$CH$_2$SO$_2$CH$_3$ | CH$_2$CF$_3$ |
| 3,5-Cl$_2$ | CF$_3$ | C(O)OCH$_2$CH=CH$_2$ | CH$_2$CF$_3$ |
| 3,5-Cl$_2$ | CF$_3$ | C(O)OCH$_2$C≡CH | CH$_2$CF$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | C(O)SCH$_3$ | CH$_2$CF$_3$ |
| 3,5-Cl$_2$ | CF$_3$ | C(S)OCH$_3$ | CH$_2$CF$_3$ |
| 3,5-Cl$_2$ | CF$_3$ | C(S)SCH$_3$ | CH$_2$CF$_3$ |
| 3,5-Cl$_2$ | CF$_3$ | SCH$_3$ | CH$_2$CF$_3$ |
| 3,5-Cl$_2$ | CF$_3$ | SCCl$_3$ | CH$_2$CF$_3$ |
| 3,5-Cl$_2$ | CF$_3$ | SPh | CH$_2$CF$_3$ |
| 3,5-Cl$_2$ | CF$_3$ | SN(Et)$_2$ | CH$_2$CF$_3$ |
| 3,5-Cl$_2$ | CF$_3$ | SN(Pr-i)$_2$ | CH$_2$CF$_3$ |
| 3,5-Cl$_2$ | CF$_3$ | SN(Bu-n)$_2$ | CH$_2$CF$_3$ |
| 3,5-Cl$_2$ | CF$_3$ | S(T-40) | CH$_2$CF$_3$ |
| 3,5-Cl$_2$ | CF$_3$ | SN(CH$_3$)CH$_2$CH$_2$C(O)OEt | CH$_2$CF$_3$ |
| 3,5-Cl$_2$ | CF$_3$ | SN(Et)CH$_2$CH$_2$C(O)OEt | CH$_2$CF$_3$ |
| 3,5-Cl$_2$ | CF$_3$ | SN(Pr-i)CH$_2$CH$_2$C(O)OEt | CH$_2$CF$_3$ |
| 3,5-Cl$_2$ | CF$_3$ | SN(CH$_2$Ph)CH$_2$CH$_2$C(O)OEt | CH$_2$CF$_3$ |
| 3,5-Cl$_2$ | CF$_3$ | SN(CH$_3$)C(O)OEt | CH$_2$CF$_3$ |
| 3,5-Cl$_2$ | CF$_3$ | SN(CH$_3$)C(O)OPr-n | CH$_2$CF$_3$ |
| 3,5-Cl$_2$ | CF$_3$ | SN(CH$_3$)C(O)OBu-n | CH$_2$CF$_3$ |
| 3,5-Cl$_2$ | CF$_3$ | SN(CH$_3$)C(O)OHex-n | CH$_2$CF$_3$ |
| 3,5-Cl$_2$ | CF$_3$ | SN(Et)C(O)OEt | CH$_2$CF$_3$ |
| 3,5-Cl$_2$ | CF$_3$ | SN(Et)C(O)OPr-n | CH$_2$CF$_3$ |
| 3,5-Cl$_2$ | CF$_3$ | SN(Et)C(O)OBu-n | CH$_2$CF$_3$ |
| 3,5-Cl$_2$ | CF$_3$ | SN(Pr-i)C(O)OEt | CH$_2$CF$_3$ |
| 3,5-Cl$_2$ | CF$_3$ | SN(Pr-i)C(O)OPr-n | CH$_2$CF$_3$ |
| 3,5-Cl$_2$ | CF$_3$ | SN(Pr-i)C(O)OBu-n | CH$_2$CF$_3$ |
| 3,5-Cl$_2$ | CF$_3$ | SO$_2$CH$_3$ | CH$_2$CF$_3$ |
| 3,5-Cl$_2$ | CF$_3$ | SO$_2$Et | CH$_2$CF$_3$ |
| 3,5-Cl$_2$ | CF$_3$ | NH$_2$ | CH$_2$CF$_3$ |
| 3,5-Cl$_2$ | CF$_3$ | NHCH$_3$ | CH$_2$CF$_3$ |
| 3,5-Cl$_2$ | CF$_3$ | NHCHO | CH$_2$CF$_3$ |
| 3,5-Cl$_2$ | CF$_3$ | NHC(O)CH$_3$ | CH$_2$CF$_3$ |
| 3,5-Cl$_2$ | CF$_3$ | NHC(O)CF$_3$ | CH$_2$CF$_3$ |
| 3,5-Cl$_2$ | CF$_3$ | NHC(O)OCH$_3$ | CH$_2$CF$_3$ |
| 3,5-Cl$_2$ | CF$_3$ | NHC(O)NHCH$_3$ | CH$_2$CF$_3$ |
| 3,5-Cl$_2$ | CF$_3$ | N=C(CH$_3$)$_2$ | CH$_2$CF$_3$ |
| 3,5-Cl$_2$ | CF$_3$ | N=CHPh | CH$_2$CF$_3$ |
| 3,5-Cl$_2$ | CF$_3$ | H | CH$_2$CF$_2$Cl |
| 3,5-Cl$_2$ | CF$_3$ | H | CH$_2$CFCl$_2$ |
| 3,5-Cl$_2$ | CF$_3$ | H | CH$_2$CCl$_3$ |
| 3,5-Cl$_2$ | CF$_3$ | H | CH$_2$CF$_2$Br |
| 3,5-Cl$_2$ | CF$_3$ | H | CH$_2$CFClBr |
| 3,5-Cl$_2$ | CF$_3$ | H | CH$_2$CCl$_2$Br |
| 3,5-Cl$_2$ | CF$_3$ | H | CF$_2$CF$_3$ |
| 3,5-Cl$_2$ | CF$_3$ | H | CH(CH$_3$)CH$_2$F |
| 3,5-Cl$_2$ | CF$_3$ | H | CH(CH$_3$)CH$_2$F(R) |
| 3,5-Cl$_2$ | CF$_3$ | H | CH(CH$_3$)CH$_2$F(S) |
| 3,5-Cl$_2$ | CF$_3$ | H | CH(CH$_3$)CH$_2$Cl |
| 3,5-Cl$_2$ | CF$_3$ | H | CH(CH$_3$)CH$_2$Br |
| 3,5-Cl$_2$ | CF$_3$ | H | CH(CH$_3$)CH$_2$Br(R) |
| 3,5-Cl$_2$ | CF$_3$ | H | CH(CH$_3$)CH$_2$Br(S) |
| 3,5-Cl$_2$ | CF$_3$ | H | CH$_2$CHFCH$_3$ |
| 3,5-Cl$_2$ | CF$_3$ | H | CH$_2$CHClCH$_3$ |
| 3,5-Cl$_2$ | CF$_3$ | H | CH$_2$CHClCH$_3$(R) |
| 3,5-Cl$_2$ | CF$_3$ | H | CH$_2$CHClCH$_3$(S) |
| 3,5-Cl$_2$ | CF$_3$ | H | CH$_2$CHBrCH$_3$ |
| 3,5-Cl$_2$ | CF$_3$ | H | CH$_2$CFClCH$_3$ |
| 3,5-Cl$_2$ | CF$_3$ | H | CH$_2$CHClCH$_2$Cl |
| 3,5-Cl$_2$ | CF$_3$ | H | CH$_2$CHBrCH$_2$F |
| 3,5-Cl$_2$ | CF$_3$ | H | CH$_2$CHClCH$_2$Br |
| 3,5-Cl$_2$ | CF$_3$ | H | CH$_2$CHBrCH$_2$Cl |
| 3,5-Cl$_2$ | CF$_3$ | H | CH$_2$CClBrCH$_3$ |
| 3,5-Cl$_2$ | CF$_3$ | H | CH$_2$CHBrCH$_2$Br |
| 3,5-Cl$_2$ | CF$_3$ | H | CH(CH$_3$)CF$_3$ |
| 3,5-Cl$_2$ | CF$_3$ | H | CH$_2$CH$_2$CF$_3$ |
| 3,5-Cl$_2$ | CF$_3$ | CH$_2$OCH$_3$ | CH$_2$CH$_2$CF$_3$ |
| 3,5-Cl$_2$ | CF$_3$ | CH$_2$OC(O)CH$_3$ | CH$_2$CH$_2$CF$_3$ |
| 3,5-Cl$_2$ | CF$_3$ | CH$_2$CN | CH$_2$CH$_2$CF$_3$ |
| 3,5-Cl$_2$ | CF$_3$ | C(O)CH$_3$ | CH$_2$CH$_2$CF$_3$ |
| 3,5-Cl$_2$ | CF$_3$ | C(O)Et | CH$_2$CH$_2$CF$_3$ |
| 3,5-Cl$_2$ | CF$_3$ | C(O)OCH$_3$ | CH$_2$CH$_2$CF$_3$ |
| 3,5-Cl$_2$ | CF$_3$ | H | CH$_2$CH$_2$CF$_2$Br |
| 3,5-Cl$_2$ | CF$_3$ | H | CH$_2$CClBrCH$_2$Cl |
| 3,5-Cl$_2$ | CF$_3$ | H | CH$_2$CF$_2$CHF$_2$ |
| 3,5-Cl$_2$ | CF$_3$ | H | CH$_2$CHClCF$_3$ |
| 3,5-Cl$_2$ | CF$_3$ | H | CH$_2$CF$_2$CF$_3$ |
| 3,5-Cl$_2$ | CF$_3$ | H | CH(CF$_3$)$_2$ |
| 3,5-Cl$_2$ | CF$_3$ | H | CH$_2$CF(CH$_3$)$_2$ |
| 3,5-Cl$_2$ | CF$_3$ | H | CH$_2$CHFCH$_2$CH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$CHClCH$_2$CH$_3$ |
| 3,5-Cl$_2$ | CF$_3$ | H | CH$_2$CF$_2$CHFCF$_3$ |
| 3,5-Cl$_2$ | CF$_3$ | H | CH$_2$CF$_2$CF$_2$CHF$_2$ |
| 3,5-Cl$_2$ | CF$_3$ | H | CH$_2$CF$_2$CF$_2$CF$_3$ |
| 3,5-Cl$_2$ | CF$_3$ | H | C(CH$_3$)$_2$CH$_2$Cl |
| 3,5-Cl$_2$ | CF$_3$ | H | C(CH$_3$)$_2$CH$_2$Br |
| 3,5-Cl$_2$ | CF$_3$ | H | CH$_2$(T-1) |
| 3,5-Cl$_2$ | CF$_3$ | H | CH$_2$(T-2) |
| 3,5-Cl$_2$ | CF$_3$ | H | CH$_2$(T-3) |
| 3,5-Cl$_2$ | CF$_3$ | H | CH$_2$(T-4) |
| 3,5-Cl$_2$ | CF$_3$ | H | CH$_2$(T-5) |
| 3,5-Cl$_2$ | CF$_3$ | H | C(CH$_3$)$_2$CHBrCH$_2$Br |
| 3,5-Cl$_2$ | CF$_3$ | H | CH$_2$(T-10) |
| 3,5-Cl$_2$ | CF$_3$ | H | CH$_2$(T-11) |
| 3,5-Cl$_2$ | CF$_3$ | H | CH$_2$OH |
| 3,5-Cl$_2$ | CF$_3$ | H | CH$_2$OCH$_3$ |
| 3,5-Cl$_2$ | CF$_3$ | CH$_3$ | CH$_2$OCH$_3$ |
| 3,5-Cl$_2$ | CF$_3$ | Et | CH$_2$OCH$_3$ |
| 3,5-Cl$_2$ | CF$_3$ | CH$_2$OCH$_3$ | CH$_2$OCH$_3$ |
| 3,5-Cl$_2$ | CF$_3$ | C(O)CH$_3$ | CH$_2$OCH$_3$ |
| 3,5-Cl$_2$ | CF$_3$ | C(O)Et | CH$_2$OCH$_3$ |
| 3,5-Cl$_2$ | CF$_3$ | C(O)OCH$_2$Cl | CH$_2$OCH$_3$ |
| 3,5-Cl$_2$ | CF$_3$ | C(O)OCH$_2$CH$_2$F | CH$_2$OCH$_3$ |
| 3,5-Cl$_2$ | CF$_3$ | C(O)OCH$_2$CH$_2$CF$_3$ | CH$_2$OCH$_3$ |
| 3,5-Cl$_2$ | CF$_3$ | C(O)OCH$_2$C(CF$_3$)$_2$CH$_3$ | CH$_2$OCH$_3$ |
| 3,5-Cl$_2$ | CF$_3$ | H | CH$_2$OEt |
| 3,5-Cl$_2$ | CF$_3$ | CH$_3$ | CH$_2$OEt |
| 3,5-Cl$_2$ | CF$_3$ | CH$_2$OCH$_3$ | CH$_2$OEt |
| 3,5-Cl$_2$ | CF$_3$ | CH$_2$OEt | CH$_2$OEt |
| 3,5-Cl$_2$ | CF$_3$ | CH$_2$OC(O)CH$_3$ | CH$_2$OEt |
| 3,5-Cl$_2$ | CF$_3$ | C(O)CH$_3$ | CH$_2$OEt |
| 3,5-Cl$_2$ | CF$_3$ | C(O)Et | CH$_2$OEt |
| 3,5-Cl$_2$ | CF$_3$ | C(O)OCH$_2$Cl | CH$_2$OEt |
| 3,5-Cl$_2$ | CF$_3$ | C(O)OCH$_2$CH$_2$F | CH$_2$OEt |
| 3,5-Cl$_2$ | CF$_3$ | C(O)OCH$_2$CH$_2$CF$_3$ | CH$_2$OEt |
| 3,5-Cl$_2$ | CF$_3$ | C(O)OCH$_2$C(CF$_3$)$_2$CH$_3$ | CH$_2$OEt |
| 3,5-Cl$_2$ | CF$_3$ | H | CH$_2$OPr-n |
| 3,5-Cl$_2$ | CF$_3$ | H | CH$_2$OPr-i |
| 3,5-Cl$_2$ | CF$_3$ | CH$_3$ | CH$_2$OPr-i |
| 3,5-Cl$_2$ | CF$_3$ | Et | CH$_2$OPr-i |
| 3,5-Cl$_2$ | CF$_3$ | CH$_2$OCH$_3$ | CH$_2$OPr-i |
| 3,5-Cl$_2$ | CF$_3$ | CH$_2$OEt | CH$_2$OPr-i |
| 3,5-Cl$_2$ | CF$_3$ | CH$_2$OPr-i | CH$_2$OPr-i |
| 3,5-Cl$_2$ | CF$_3$ | C(O)CH$_3$ | CH$_2$OPr-i |
| 3,5-Cl$_2$ | CF$_3$ | C(O)Et | CH$_2$OPr-i |
| 3,5-Cl$_2$ | CF$_3$ | H | CH$_2$OBu-i |
| 3,5-Cl$_2$ | CF$_3$ | H | CH$_2$OCH$_2$Pr-c |
| 3,5-Cl$_2$ | CF$_3$ | H | CH$_2$OBu-s |
| 3,5-Cl$_2$ | CF$_3$ | H | CH$_2$OBu-t |
| 3,5-Cl$_2$ | CF$_3$ | H | CH$_2$OPen-c |
| 3,5-Cl$_2$ | CF$_3$ | H | CH$_2$OCH$_2$CH$_2$F |
| 3,5-Cl$_2$ | CF$_3$ | H | CH$_2$OCH$_2$CH$_2$Cl |
| 3,5-Cl$_2$ | CF$_3$ | H | CH$_2$OCH$_2$CH$_2$Br |
| 3,5-Cl$_2$ | CF$_3$ | H | CH$_2$OCH$_2$CHF$_2$ |
| 3,5-Cl$_2$ | CF$_3$ | CH$_3$ | CH$_2$OCH$_2$CHF$_2$ |
| 3,5-Cl$_2$ | CF$_3$ | Et | CH$_2$OCH$_2$CHF$_2$ |
| 3,5-Cl$_2$ | CF$_3$ | CH$_2$OCH$_3$ | CH$_2$OCH$_2$CHF$_2$ |
| 3,5-Cl$_2$ | CF$_3$ | CH$_2$OEt | CH$_2$OCH$_2$CHF$_2$ |
| 3,5-Cl$_2$ | CF$_3$ | CH$_2$OPr-i | CH$_2$OCH$_2$CHF$_2$ |
| 3,5-Cl$_2$ | CF$_3$ | CH$_2$OCH$_2$CHF$_2$ | CH$_2$OCH$_2$CHF$_2$ |
| 3,5-Cl$_2$ | CF$_3$ | C(O)CH$_3$ | CH$_2$OCH$_2$CHF$_2$ |
| 3,5-Cl$_2$ | CF$_3$ | C(O)Et | CH$_2$OCH$_2$CHF$_2$ |
| 3,5-Cl$_2$ | CF$_3$ | H | CH$_2$OCH$_2$CHCl$_2$ |
| 3,5-Cl$_2$ | CF$_3$ | H | CH$_2$OCH$_2$CF$_3$ |
| 3,5-Cl$_2$ | CF$_3$ | CH$_3$ | CH$_2$OCH$_2$CF$_3$ |
| 3,5-Cl$_2$ | CF$_3$ | CH$_2$OCH$_3$ | CH$_2$OCH$_2$CF$_3$ |
| 3,5-Cl$_2$ | CF$_3$ | CH$_2$OEt | CH$_2$OCH$_2$CF$_3$ |
| 3,5-Cl$_2$ | CF$_3$ | CH$_2$OPr-i | CH$_2$OCH$_2$CF$_3$ |
| 3,5-Cl$_2$ | CF$_3$ | CH$_2$OCH$_2$CHF$_2$ | CH$_2$OCH$_2$CF$_3$ |
| 3,5-Cl$_2$ | CF$_3$ | CH$_2$OCH$_2$CF$_3$ | CH$_2$OCH$_2$CF$_3$ |
| 3,5-Cl$_2$ | CF$_3$ | CH$_2$OC(O)CH$_3$ | CH$_2$OCH$_2$CF$_3$ |
| 3,5-Cl$_2$ | CF$_3$ | C(O)CH$_3$ | CH$_2$OCH$_2$CF$_3$ |
| 3,5-Cl$_2$ | CF$_3$ | C(O)Et | CH$_2$OCH$_2$CF$_3$ |
| 3,5-Cl$_2$ | CF$_3$ | C(O)Pr-n | CH$_2$OCH$_2$CF$_3$ |
| 3,5-Cl$_2$ | CF$_3$ | C(O)Pr-i | CH$_2$OCH$_2$CF$_3$ |
| 3,5-Cl$_2$ | CF$_3$ | C(O)Pr-c | CH$_2$OCH$_2$CF$_3$ |
| 3,5-Cl$_2$ | CF$_3$ | C(O)Bu-t | CH$_2$OCH$_2$CF$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | C(O)OCH$_2$Cl | CH$_2$OCH$_2$CF$_3$ |
| 3,5-Cl$_2$ | CF$_3$ | C(O)OCH$_2$CH$_2$F | CH$_2$OCH$_2$CF$_3$ |
| 3,5-Cl$_2$ | CF$_3$ | C(O)OCH$_2$CH$_2$CF$_3$ | CH$_2$OCH$_2$CF$_3$ |
| 3,5-Cl$_2$ | CF$_3$ | C(O)OCH$_2$C(CF$_3$)$_2$CH$_3$ | CH$_2$OCH$_2$CF$_3$ |
| 3,5-Cl$_2$ | CF$_3$ | H | CH$_2$OCH$_2$CF$_2$Cl |
| 3,5-Cl$_2$ | CF$_3$ | H | CH$_2$OCH$_2$CCl$_3$ |
| 3,5-Cl$_2$ | CF$_3$ | H | CH$_2$OCH$_2$CF$_2$CHF$_2$ |
| 3,5-Cl$_2$ | CF$_3$ | H | CH$_2$OCH$_2$CF$_2$CF$_3$ |
| 3,5-Cl$_2$ | CF$_3$ | H | CH$_2$OCH$_2$CH$_2$OCH$_3$ |
| 3,5-Cl$_2$ | CF$_3$ | H | CH$_2$OCH$_2$CH$_2$OCH$_2$CF$_3$ |
| 3,5-Cl$_2$ | CF$_3$ | H | CH$_2$OCH$_2$CH$_2$OCH$_2$CH$_2$OCH$_3$ |
| 3,5-Cl$_2$ | CF$_3$ | H | CH$_2$OCH$_2$CF$_2$OCF$_2$CF$_2$OCF$_3$ |
| 3,5-Cl$_2$ | CF$_3$ | H | CH$_2$OCH$_2$CH$_2$OPh |
| 3,5-Cl$_2$ | CF$_3$ | H | CH$_2$OCH$_2$CH$_2$SCH$_3$ |
| 3,5-Cl$_2$ | CF$_3$ | H | CH$_2$OCH$_2$CH$_2$SO$_2$CH$_3$ |
| 3,5-Cl$_2$ | CF$_3$ | H | CH$_2$OCH$_2$CH$_2$SCH$_2$CF$_3$ |
| 3,5-Cl$_2$ | CF$_3$ | H | CH$_2$OCH$_2$CN |
| 3,5-Cl$_2$ | CF$_3$ | H | CH$_2$OCH$_2$CH$_2$CN |
| 3,5-Cl$_2$ | CF$_3$ | H | CH$_2$OCH$_2$C(O)NH$_2$ |
| 3,5-Cl$_2$ | CF$_3$ | H | CH$_2$OCH$_2$C(O)N(Et)$_2$ |
| 3,5-Cl$_2$ | CF$_3$ | H | CH$_2$OCH$_2$CH=CH$_2$ |
| 3,5-Cl$_2$ | CF$_3$ | H | CH$_2$OCH$_2$CCl=CH$_2$ |
| 3,5-Cl$_2$ | CF$_3$ | H | CH$_2$OCH$_2$C≡CH |
| 3,5-Cl$_2$ | CF$_3$ | H | CH$_2$OCH$_2$Ph |
| 3,5-Cl$_2$ | CF$_3$ | H | CH$_2$OCH$_2$(D-1a) |
| 3,5-Cl$_2$ | CF$_3$ | H | CH$_2$OCH$_2$(D-3a) |
| 3,5-Cl$_2$ | CF$_3$ | H | CH$_2$OCH$_2$(D-47a) |
| 3,5-Cl$_2$ | CF$_3$ | H | CH$_2$OC(O)CH$_3$ |
| 3,5-Cl$_2$ | CF$_3$ | H | CH$_2$OC(O)Bu-t |
| 3,5-Cl$_2$ | CF$_3$ | H | CH$_2$OC(O)Ph |
| 3,5-Cl$_2$ | CF$_3$ | H | CH$_2$OC(O)OCH$_3$ |
| 3,5-Cl$_2$ | CF$_3$ | H | CH$_2$OC(O)OEt |
| 3,5-Cl$_2$ | CF$_3$ | H | CH$_2$OC(O)SCH$_3$ |
| 3,5-Cl$_2$ | CF$_3$ | H | CH$_2$OC(O)NHCH$_3$ |
| 3,5-Cl$_2$ | CF$_3$ | H | CH$_2$OC(O)NHEt |
| 3,5-Cl$_2$ | CF$_3$ | H | CH$_2$OC(O)N(Et)$_2$ |
| 3,5-Cl$_2$ | CF$_3$ | H | CH$_2$OC(O)NHCH$_2$CF$_3$ |
| 3,5-Cl$_2$ | CF$_3$ | H | CH$_2$OPh |
| 3,5-Cl$_2$ | CF$_3$ | H | CH(CH$_3$)OH |
| 3,5-Cl$_2$ | CF$_3$ | H | CH(CH$_3$)OCH$_3$ |
| 3,5-Cl$_2$ | CF$_3$ | H | CH(CH$_3$)OPr-i |
| 3,5-Cl$_2$ | CF$_3$ | H | CH(CH$_3$)OCH$_2$CH$_2$Cl |
| 3,5-Cl$_2$ | CF$_3$ | H | CH(CH$_3$)OCH$_2$CHF$_2$ |
| 3,5-Cl$_2$ | CF$_3$ | H | CH(CH$_3$)OCH$_2$CF$_3$ |
| 3,5-Cl$_2$ | CF$_3$ | CH$_2$OCH$_3$ | CH(CH$_3$)OCH$_2$CF$_3$ |
| 3,5-Cl$_2$ | CF$_3$ | CH$_2$OC(O)CH$_3$ | CH(CH$_3$)OCH$_2$CF$_3$ |
| 3,5-Cl$_2$ | CF$_3$ | CH$_2$CN | CH(CH$_3$)OCH$_2$CF$_3$ |
| 3,5-Cl$_2$ | CF$_3$ | C(O)CH$_3$ | CH(CH$_3$)OCH$_2$CF$_3$ |
| 3,5-Cl$_2$ | CF$_3$ | C(O)Et | CH(CH$_3$)OCH$_2$CF$_3$ |
| 3,5-Cl$_2$ | CF$_3$ | H | CH(CH$_3$)OCH$_2$CF$_2$Cl |
| 3,5-Cl$_2$ | CF$_3$ | H | CH(CH$_3$)OC(O)CH$_3$ |
| 3,5-Cl$_2$ | CF$_3$ | H | CH(CH$_3$)OC(O)Bu-t |
| 3,5-Cl$_2$ | CF$_3$ | H | CH(CH$_3$)OC(O)Ph |
| 3,5-Cl$_2$ | CF$_3$ | H | CH(CH$_3$)OC(O)OCH$_3$ |
| 3,5-Cl$_2$ | CF$_3$ | H | CH(CH$_3$)OC(O)OEt |
| 3,5-Cl$_2$ | CF$_3$ | H | CH(CH$_3$)OC(O)SCH$_3$ |
| 3,5-Cl$_2$ | CF$_3$ | H | CH(CH$_3$)OC(O)NHCH$_3$ |
| 3,5-Cl$_2$ | CF$_3$ | H | CH(CH$_3$)OC(O)NHEt |
| 3,5-Cl$_2$ | CF$_3$ | H | CH(CH$_3$)OC(O)N(Et)$_2$ |
| 3,5-Cl$_2$ | CF$_3$ | H | CH(CH$_3$)OC(O)NHCH$_2$CF$_3$ |
| 3,5-Cl$_2$ | CF$_3$ | H | CH(CH$_3$)OC(S)NHCH$_2$CF$_3$ |
| 3,5-Cl$_2$ | CF$_3$ | H | CH(Et)OCH$_3$ |
| 3,5-Cl$_2$ | CF$_3$ | H | CH(Pr-i)OCH$_3$ |
| 3,5-Cl$_2$ | CF$_3$ | H | CH(CF$_3$)OH |
| 3,5-Cl$_2$ | CF$_3$ | H | CH(CF$_3$)OCH$_3$ |
| 3,5-Cl$_2$ | CF$_3$ | H | CH(CF$_3$)OEt |
| 3,5-Cl$_2$ | CF$_3$ | H | CH(CF$_3$)OPr-n |
| 3,5-Cl$_2$ | CF$_3$ | H | CH(CF$_3$)OPr-i |
| 3,5-Cl$_2$ | CF$_3$ | H | CH(CF$_3$)OPr-c |
| 3,5-Cl$_2$ | CF$_3$ | H | CH(CF$_3$)OCH$_2$CF$_3$ |
| 3,5-Cl$_2$ | CF$_3$ | H | CH(CF$_3$)OCH$_2$CH=CH$_2$ |
| 3,5-Cl$_2$ | CF$_3$ | H | CH(CF$_3$)OCH$_2$C≡CH |
| 3,5-Cl$_2$ | CF$_3$ | H | CH$_2$CH$_2$OH |
| 3,5-Cl$_2$ | CF$_3$ | H | CH$_2$CH$_2$OCH$_3$ |
| 3,5-Cl$_2$ | CF$_3$ | CH$_3$ | CH$_2$CH$_2$OCH$_3$ |
| 3,5-Cl$_2$ | CF$_3$ | CH$_2$OCH$_3$ | CH$_2$CH$_2$OCH$_3$ |
| 3,5-Cl$_2$ | CF$_3$ | CH$_2$OEt | CH$_2$CH$_2$OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | CH$_2$OCH$_2$CF$_3$ | CH$_2$CH$_2$OCH$_3$ |
| 3,5-Cl$_2$ | CF$_3$ | CH$_2$OC(O)CH$_3$ | CH$_2$CH$_2$OCH$_3$ |
| 3,5-Cl$_2$ | CF$_3$ | CH$_2$CH$_2$OCH$_3$ | CH$_2$CH$_2$OCH$_3$ |
| 3,5-Cl$_2$ | CF$_3$ | CH$_2$CN | CH$_2$CH$_2$OCH$_3$ |
| 3,5-Cl$_2$ | CF$_3$ | CH$_2$C≡CH | CH$_2$CH$_2$OCH$_3$ |
| 3,5-Cl$_2$ | CF$_3$ | C(O)CH$_3$ | CH$_2$CH$_2$OCH$_3$ |
| 3,5-Cl$_2$ | CF$_3$ | C(O)Et | CH$_2$CH$_2$OCH$_3$ |
| 3,5-Cl$_2$ | CF$_3$ | C(O)OCH$_3$ | CH$_2$CH$_2$OCH$_3$ |
| 3,5-Cl$_2$ | CF$_3$ | H | CH$_2$CH$_2$OEt |
| 3,5-Cl$_2$ | CF$_3$ | H | CH$_2$CH$_2$OPr-n |
| 3,5-Cl$_2$ | CF$_3$ | H | CH$_2$CH$_2$OPr-i |
| 3,5-Cl$_2$ | CF$_3$ | H | CH$_2$CH$_2$OBu-i |
| 3,5-Cl$_2$ | CF$_3$ | H | CH$_2$CH$_2$OCH$_2$CH$_2$Cl |
| 3,5-Cl$_2$ | CF$_3$ | H | CH$_2$CH$_2$OCH$_2$CF$_3$ |
| 3,5-Cl$_2$ | CF$_3$ | H | CH$_2$CH$_2$OCH$_2$CH$_2$OH |
| 3,5-Cl$_2$ | CF$_3$ | H | CH$_2$CH$_2$OCH$_2$CH$_2$OCH$_3$ |
| 3,5-Cl$_2$ | CF$_3$ | H | CH$_2$CH$_2$OCH$_2$CH$_2$OCH$_2$CH$_2$OCH$_3$ |
| 3,5-Cl$_2$ | CF$_3$ | H | CH$_2$CH$_2$OCH$_2$CH$_2$SCH$_3$ |
| 3,5-Cl$_2$ | CF$_3$ | H | CH$_2$CH$_2$OCH$_2$CH$_2$SEt |
| 3,5-Cl$_2$ | CF$_3$ | H | CH$_2$CH$_2$OCH$_2$Ph |
| 3,5-Cl$_2$ | CF$_3$ | H | CH$_2$CH$_2$OC(O)CH$_3$ |
| 3,5-Cl$_2$ | CF$_3$ | H | CH$_2$CH$_2$OC(O)NHCH$_3$ |
| 3,5-Cl$_2$ | CF$_3$ | H | CH$_2$CH$_2$OC(O)N(CH$_3$)$_2$ |
| 3,5-Cl$_2$ | CF$_3$ | H | CH$_2$CH$_2$OC(O)NHEt |
| 3,5-Cl$_2$ | CF$_3$ | H | CH$_2$CH$_2$OC(O)NHPh |
| 3,5-Cl$_2$ | CF$_3$ | H | CH$_2$CH$_2$OPh |
| 3,5-Cl$_2$ | CF$_3$ | H | CH$_2$CH$_2$O(Ph-2-F) |
| 3,5-Cl$_2$ | CF$_3$ | H | CH$_2$CH$_2$O(Ph-3-F) |
| 3,5-Cl$_2$ | CF$_3$ | H | CH$_2$CH$_2$O(Ph-4-F) |
| 3,5-Cl$_2$ | CF$_3$ | H | CH$_2$CH(CH$_3$)OH |
| 3,5-Cl$_2$ | CF$_3$ | H | CH$_2$CH(CH$_3$)OCH$_3$ |
| 3,5-Cl$_2$ | CF$_3$ | H | CH$_2$CH(CH$_3$)OCH$_3$(R) |
| 3,5-Cl$_2$ | CF$_3$ | H | CH$_2$CH(CH$_3$)OCH$_3$(S) |
| 3,5-Cl$_2$ | CF$_3$ | H | CH$_2$CH(CH$_3$)OC(O)NHCH$_3$ |
| 3,5-Cl$_2$ | CF$_3$ | H | CH$_2$CH(CH$_3$)OC(O)N(CH$_3$)$_2$ |
| 3,5-Cl$_2$ | CF$_3$ | H | CH$_2$CH(CH$_3$)OC(O)NHEt |
| 3,5-Cl$_2$ | CF$_3$ | H | CH$_2$CH(CH$_3$)OC(O)NH(Ph-4-F) |
| 3,5-Cl$_2$ | CF$_3$ | H | CH$_2$CH(Et)OCH$_3$ |
| 3,5-Cl$_2$ | CF$_3$ | H | CH$_2$CH(OCH$_3$)$_2$ |
| 3,5-Cl$_2$ | CF$_3$ | CH$_3$ | CH$_2$CH(OCH$_3$)$_2$ |
| 3,5-Cl$_2$ | CF$_3$ | CH$_2$OCH$_3$ | CH$_2$CH(OCH$_3$)$_2$ |
| 3,5-Cl$_2$ | CF$_3$ | CH$_2$OC(O)CH$_3$ | CH$_2$CH(OCH$_3$)$_2$ |
| 3,5-Cl$_2$ | CF$_3$ | CH$_2$CN | CH$_2$CH(OCH$_3$)$_2$ |
| 3,5-Cl$_2$ | CF$_3$ | C(O)CH$_3$ | CH$_2$CH(OCH$_3$)$_2$ |
| 3,5-Cl$_2$ | CF$_3$ | C(O)Et | CH$_2$CH(OCH$_3$)$_2$ |
| 3,5-Cl$_2$ | CF$_3$ | C(O)OCH$_3$ | CH$_2$CH(OCH$_3$)$_2$ |
| 3,5-Cl$_2$ | CF$_3$ | H | CH$_2$CH(OEt)$_2$ |
| 3,5-Cl$_2$ | CF$_3$ | H | CH$_2$CF(CF$_3$)OCF$_2$CF$_2$CF$_3$ |
| 3,5-Cl$_2$ | CF$_3$ | H | CH$_2$C(CH$_3$)$_2$OSi(CH$_3$)$_3$ |
| 3,5-Cl$_2$ | CF$_3$ | H | CH(CH$_3$)CH$_2$OH |
| 3,5-Cl$_2$ | CF$_3$ | H | CH(CH$_3$)CH$_2$OCH$_3$ |
| 3,5-Cl$_2$ | CF$_3$ | H | CH(CH$_3$)CH$_2$OCH$_3$(R) |
| 3,5-Cl$_2$ | CF$_3$ | H | CH(CH$_3$)CH$_2$OCH$_3$(S) |
| 3,5-Cl$_2$ | CF$_3$ | H | CH(CH$_3$)CH$_2$OEt |
| 3,5-Cl$_2$ | CF$_3$ | H | CH(CH$_3$)CH$_2$OC(O)CH$_3$ |
| 3,5-Cl$_2$ | CF$_3$ | H | CH(CH$_3$)CH$_2$OC(O)CF$_3$ |
| 3,5-Cl$_2$ | CF$_3$ | H | CH(CH$_3$)CH$_2$OC(O)NHCH$_3$ |
| 3,5-Cl$_2$ | CF$_3$ | H | CH(CH$_3$)CH$_2$OC(O)N(CH$_3$)$_2$ |
| 3,5-Cl$_2$ | CF$_3$ | H | CH(CH$_3$)CH$_2$OC(O)NHEt |
| 3,5-Cl$_2$ | CF$_3$ | H | CH(CH$_3$)CH$_2$OC(O)N(Et)$_2$ |
| 3,5-Cl$_2$ | CF$_3$ | H | CH(CH$_3$)CH$_2$OC(O)NHPr-n |
| 3,5-Cl$_2$ | CF$_3$ | H | CH(CH$_3$)CH$_2$OC(O)NHPr-i |
| 3,5-Cl$_2$ | CF$_3$ | H | CH(CH$_3$)CH$_2$OC(O)N(Pr-i)$_2$ |
| 3,5-Cl$_2$ | CF$_3$ | H | CH(CH$_3$)CH$_2$OC(O)NHPr-c |
| 3,5-Cl$_2$ | CF$_3$ | H | CH(CH$_3$)CH$_2$OC(O)NHBu-t |
| 3,5-Cl$_2$ | CF$_3$ | H | CH(CH$_3$)CH$_2$OC(O)NHCH$_2$CH$_2$Cl |
| 3,5-Cl$_2$ | CF$_3$ | H | CH(CH$_3$)CH$_2$OC(O)NHCH$_2$CF$_3$ |
| 3,5-Cl$_2$ | CF$_3$ | H | CH(CH$_3$)CH$_2$OC(O)NHCH$_2$CH$_2$OCH$_3$ |
| 3,5-Cl$_2$ | CF$_3$ | H | CH(CH$_3$)CH$_2$OC(O)NHCH$_2$CH$_2$SCH$_3$ |
| 3,5-Cl$_2$ | CF$_3$ | H | CH(CH$_3$)CH$_2$OC(O)NHCH$_2$CH$_2$SCH$_3$ |
| 3,5-Cl$_2$ | CF$_3$ | H | CH(CH$_3$)CH$_2$OC(O)NHCH$_2$CH=CH$_2$ |
| 3,5-Cl$_2$ | CF$_3$ | H | CH(CH$_3$)CH$_2$OC(O)NHCH$_2$Ph |
| 3,5-Cl$_2$ | CF$_3$ | H | CH(CH$_3$)CH$_2$OC(O)NHCH$_2$(D-47a) |
| 3,5-Cl$_2$ | CF$_3$ | H | CH(CH$_3$)CH$_2$OC(O)NHCH$_2$(D-48a) |
| 3,5-Cl$_2$ | CF$_3$ | H | CH(CH$_3$)CH$_2$OC(O)NHCH$_2$(D-49a) |
| 3,5-Cl$_2$ | CF$_3$ | H | CH(CH$_3$)CH$_2$OC(O)NHPh |
| 3,5-Cl$_2$ | CF$_3$ | H | CH(CH$_3$)CH$_2$OC(O)N(CH$_3$)Ph |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH(CH$_3$)CH$_2$OC(O)(T-33) |
| 3,5-Cl$_2$ | CF$_3$ | H | CH(CH$_3$)CH$_2$OC(O)(T-39) |
| 3,5-Cl$_2$ | CF$_3$ | H | CH(CH$_3$)CH$_2$OC(O)(T-40) |
| 3,5-Cl$_2$ | CF$_3$ | H | CH(CH$_3$)CH$_2$OC(O)(T-41) |
| 3,5-Cl$_2$ | CF$_3$ | H | CH(CH$_3$)CH$_2$OC(S)NHCH$_3$ |
| 3,5-Cl$_2$ | CF$_3$ | H | CH(CH$_3$)CH$_2$OC(S)N(CH$_3$)$_2$ |
| 3,5-Cl$_2$ | CF$_3$ | H | CH(CH$_3$)CH$_2$OC(S)NHEt |
| 3,5-Cl$_2$ | CF$_3$ | H | CH(CH$_3$)CH$_2$OP(O)(OEt)$_2$ |
| 3,5-Cl$_2$ | CF$_3$ | H | CH(CH$_3$)CH$_2$OP(S)(OCH$_3$)$_2$ |
| 3,5-Cl$_2$ | CF$_3$ | H | CH(CH$_3$)CH$_2$OP(S)(OEt)$_2$ |
| 3,5-Cl$_2$ | CF$_3$ | H | CH(CH$_3$)CH$_2$OPh |
| 3,5-Cl$_2$ | CF$_3$ | H | CH(Et)CH$_2$OH |
| 3,5-Cl$_2$ | CF$_3$ | H | C(CH$_3$)$_2$CH$_2$OH |
| 3,5-Cl$_2$ | CF$_3$ | H | C(CH$_3$)$_2$CH$_2$OCH$_3$ |
| 3,5-Cl$_2$ | CF$_3$ | H | CH$_2$CH$_2$CH$_2$OEt |
| 3,5-Cl$_2$ | CF$_3$ | H | CH$_2$CH$_2$CH$_2$OPr-i |
| 3,5-Cl$_2$ | CF$_3$ | H | CH$_2$CH$_2$CH$_2$CH$_2$OC(O)NHEt |
| 3,5-Cl$_2$ | CF$_3$ | H | CH$_2$CH$_2$CH$_2$CH$_2$OC(O)NHPr-i |
| 3,5-Cl$_2$ | CF$_3$ | H | CH$_2$CH$_2$CH$_2$CH$_2$CH$_2$OC(O)NHEt |
| 3,5-Cl$_2$ | CF$_3$ | H | CH$_2$(T-14) |
| 3,5-Cl$_2$ | CF$_3$ | H | CH$_2$(T-15) |
| 3,5-Cl$_2$ | CF$_3$ | H | CH$_2$(T-16) |
| 3,5-Cl$_2$ | CF$_3$ | H | CH$_2$CH(OH)CH$_2$OH |
| 3,5-Cl$_2$ | CF$_3$ | H | CH$_2$(E-4a) |
| 3,5-Cl$_2$ | CF$_3$ | CH$_3$ | CH$_2$(E-4a) |
| 3,5-Cl$_2$ | CF$_3$ | CH$_2$OCH$_3$ | CH$_2$(E-4a) |
| 3,5-Cl$_2$ | CF$_3$ | CH$_2$OC(O)CH$_3$ | CH$_2$(E-4a) |
| 3,5-Cl$_2$ | CF$_3$ | CH$_2$CN | CH$_2$(E-4a) |
| 3,5-Cl$_2$ | CF$_3$ | C(O)CH$_3$ | CH$_2$(E-4a) |
| 3,5-Cl$_2$ | CF$_3$ | C(O)Et | CH$_2$(E-4a) |
| 3,5-Cl$_2$ | CF$_3$ | C(O)OCH$_3$ | CH$_2$(E-4a) |
| 3,5-Cl$_2$ | CF$_3$ | H | CH$_2$(E-5a) |
| 3,5-Cl$_2$ | CF$_3$ | CH$_2$OCH$_3$ | CH$_2$(E-5a) |
| 3,5-Cl$_2$ | CF$_3$ | CH$_2$OC(O)CH$_3$ | CH$_2$(E-5a) |
| 3,5-Cl$_2$ | CF$_3$ | CH$_2$CN | CH$_2$(E-5a) |
| 3,5-Cl$_2$ | CF$_3$ | C(O)CH$_3$ | CH$_2$(E-5a) |
| 3,5-Cl$_2$ | CF$_3$ | C(O)Et | CH$_2$(E-5a) |
| 3,5-Cl$_2$ | CF$_3$ | C(O)OCH$_3$ | CH$_2$(E-5a) |
| 3,5-Cl$_2$ | CF$_3$ | H | CH$_2$(E-10a) |
| 3,5-Cl$_2$ | CF$_3$ | CH$_3$ | CH$_2$(E-10a) |
| 3,5-Cl$_2$ | CF$_3$ | CH$_2$OCH$_3$ | CH$_2$(E-10a) |
| 3,5-Cl$_2$ | CF$_3$ | CH$_2$OEt | CH$_2$(E-10a) |
| 3,5-Cl$_2$ | CF$_3$ | CH$_2$OCH$_2$CF$_3$ | CH$_2$(E-10a) |
| 3,5-Cl$_2$ | CF$_3$ | CH$_2$OC(O)CH$_3$ | CH$_2$(E-10a) |
| 3,5-Cl$_2$ | CF$_3$ | CH$_2$CN | CH$_2$(E-10a) |
| 3,5-Cl$_2$ | CF$_3$ | CH$_2$C≡CH | CH$_2$(E-10a) |
| 3,5-Cl$_2$ | CF$_3$ | C(O)CH$_3$ | CH$_2$(E-10a) |
| 3,5-Cl$_2$ | CF$_3$ | C(O)Et | CH$_2$(E-10a) |
| 3,5-Cl$_2$ | CF$_3$ | C(O)OCH$_3$ | CH$_2$(E-10a) |
| 3,5-Cl$_2$ | CF$_3$ | C(O)NH$_2$ | CH$_2$(E-10a) |
| 3,5-Cl$_2$ | CF$_3$ | C(S)NH$_2$ | CH$_2$(E-10a) |
| 3,5-Cl$_2$ | CF$_3$ | H | CH$_2$(E-10b)CH$_3$ |
| 3,5-Cl$_2$ | CF$_3$ | CH$_2$OCH$_3$ | CH$_2$(E-10b)CH$_3$ |
| 3,5-Cl$_2$ | CF$_3$ | CH$_2$OC(O)CH$_3$ | CH$_2$(E-10b)CH$_3$ |
| 3,5-Cl$_2$ | CF$_3$ | CH$_2$CN | CH$_2$(E-10b)CH$_3$ |
| 3,5-Cl$_2$ | CF$_3$ | C(O)CH$_3$ | CH$_2$(E-10b)CH$_3$ |
| 3,5-Cl$_2$ | CF$_3$ | C(O)Et | CH$_2$(E-10b)CH$_3$ |
| 3,5-Cl$_2$ | CF$_3$ | C(O)OCH$_3$ | CH$_2$(E-10b)CH$_3$ |
| 3,5-Cl$_2$ | CF$_3$ | H | CH$_2$(E-11a) |
| 3,5-Cl$_2$ | CF$_3$ | H | CH$_2$(E-11b)CH$_3$ |
| 3,5-Cl$_2$ | CF$_3$ | H | CH$_2$(E-23a) |
| 3,5-Cl$_2$ | CF$_3$ | H | CH$_2$(E-24a) |
| 3,5-Cl$_2$ | CF$_3$ | H | CH$_2$(E-25a) |
| 3,5-Cl$_2$ | CF$_3$ | H | CH$_2$(E-32a) |
| 3,5-Cl$_2$ | CF$_3$ | H | CH$_2$(E-32b)CH$_3$ |
| 3,5-Cl$_2$ | CF$_3$ | H | CH$_2$(E-14b) |
| 3,5-Cl$_2$ | CF$_3$ | H | CH$_2$(E-14c) |
| 3,5-Cl$_2$ | CF$_3$ | H | CH$_2$(E-17a)H |
| 3,5-Cl$_2$ | CF$_3$ | H | CH$_2$(E-17a)CH$_3$ |
| 3,5-Cl$_2$ | CF$_3$ | H | CH$_2$(E-41a)CH$_3$ |
| 3,5-Cl$_2$ | CF$_3$ | H | CH$_2$(E-42a)H |
| 3,5-Cl$_2$ | CF$_3$ | H | CH$_2$(E-42b)H |
| 3,5-Cl$_2$ | CF$_3$ | H | CH$_2$CH$_2$(E-10a) |
| 3,5-Cl$_2$ | CF$_3$ | H | E-4a |
| 3,5-Cl$_2$ | CF$_3$ | CH$_3$ | E-4a |
| 3,5-Cl$_2$ | CF$_3$ | CH$_2$OCH$_3$ | E-4a |
| 3,5-Cl$_2$ | CF$_3$ | CH$_2$OEt | E-4a |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | CH$_2$OCH$_2$CF$_3$ | E-4a |
| 3,5-Cl$_2$ | CF$_3$ | CH$_2$OC(O)CH$_3$ | E-4a |
| 3,5-Cl$_2$ | CF$_3$ | CH$_2$CN | E-4a |
| 3,5-Cl$_2$ | CF$_3$ | CH$_2$C≡CH | E-4a |
| 3,5-Cl$_2$ | CF$_3$ | C(O)CH$_3$ | E-4a |
| 3,5-Cl$_2$ | CF$_3$ | C(O)Et | E-4a |
| 3,5-Cl$_2$ | CF$_3$ | C(O)Pr-i | E-4a |
| 3,5-Cl$_2$ | CF$_3$ | H | E-5a |
| 3,5-Cl$_2$ | CF$_3$ | H | E-5a(R) |
| 3,5-Cl$_2$ | CF$_3$ | CH$_2$OCH$_3$ | E-5a(R) |
| 3,5-Cl$_2$ | CF$_3$ | CH$_2$OC(O)CH$_3$ | E-5a(R) |
| 3,5-Cl$_2$ | CF$_3$ | CH$_2$CN | E-5a(R) |
| 3,5-Cl$_2$ | CF$_3$ | C(O)CH$_3$ | E-5a(R) |
| 3,5-Cl$_2$ | CF$_3$ | C(O)Et | E-5a(R) |
| 3,5-Cl$_2$ | CF$_3$ | C(O)Pr-i | E-5a(R) |
| 3,5-Cl$_2$ | CF$_3$ | C(O)OCH$_3$ | E-5a(R) |
| 3,5-Cl$_2$ | CF$_3$ | H | E-5a(S) |
| 3,5-Cl$_2$ | CF$_3$ | H | E-23a |
| 3,5-Cl$_2$ | CF$_3$ | H | (E-23b)OCH$_3$ |
| 3,5-Cl$_2$ | CF$_3$ | H | E-24a |
| 3,5-Cl$_2$ | CF$_3$ | H | E-25a |
| 3,5-Cl$_2$ | CF$_3$ | H | E-33a |
| 3,5-Cl$_2$ | CF$_3$ | H | E-34a |
| 3,5-Cl$_2$ | CF$_3$ | | —CH$_2$OCH$_2$C(CH$_3$)$_2$— |
| 3,5-Cl$_2$ | CF$_3$ | | —CH(Et)OCH$_2$CH$_2$— |
| 3,5-Cl$_2$ | CF$_3$ | | —CH$_2$CH$_2$OCH$_2$CH$_2$— |
| 3,5-Cl$_2$ | CF$_3$ | H | CH$_2$SCH$_3$ |
| 3,5-Cl$_2$ | CF$_3$ | H | CH$_2$S(O)CH$_3$ |
| 3,5-Cl$_2$ | CF$_3$ | H | CH$_2$SO$_2$CH$_3$ |
| 3,5-Cl$_2$ | CF$_3$ | H | CH$_2$SCH$_2$CF$_3$ |
| 3,5-Cl$_2$ | CF$_3$ | H | CH$_2$S(O)CH$_2$CF$_3$ |
| 3,5-Cl$_2$ | CF$_3$ | H | CH$_2$SO$_2$CH$_2$CF$_3$ |
| 3,5-Cl$_2$ | CF$_3$ | H | CH$_2$SCH$_2$CH$_2$OCH$_2$CF$_3$ |
| 3,5-Cl$_2$ | CF$_3$ | H | CH$_2$S(O)CH$_2$CH$_2$OCH$_2$CF$_3$ |
| 3,5-Cl$_2$ | CF$_3$ | H | CH$_2$SO$_2$CH$_2$CH$_2$OCH$_2$CF |
| 3,5-Cl$_2$ | CF$_3$ | H | CH$_2$SCH$_2$CH$_2$SCH$_2$CF$_3$ |
| 3,5-Cl$_2$ | CF$_3$ | H | CH$_2$SCH$_2$C(O)NHCH$_2$CF$_3$ |
| 3,5-Cl$_2$ | CF$_3$ | H | CH$_2$S(O)CH$_2$C(O)NHCH$_2$CF$_3$ |
| 3,5-Cl$_2$ | CF$_3$ | H | CH$_2$SO$_2$CH$_2$C(O)NHCH$_2$CF$_3$ |
| 3,5-Cl$_2$ | CF$_3$ | H | CH$_2$SC(O)CH$_3$ |
| 3,5-Cl$_2$ | CF$_3$ | H | CH$_2$SC(O)NHCH$_2$CF$_3$ |
| 3,5-Cl$_2$ | CF$_3$ | H | CH$_2$SC(O)Ph |
| 3,5-Cl$_2$ | CF$_3$ | H | CH$_2$SC(S)OCH$_3$ |
| 3,5-Cl$_2$ | CF$_3$ | H | CH$_2$SC(S)OEt |
| 3,5-Cl$_2$ | CF$_3$ | H | CH$_2$SC(S)NHCH$_2$CF$_3$ |
| 3,5-Cl$_2$ | CF$_3$ | H | CH$_2$SC(S)(T-33) |
| 3,5-Cl$_2$ | CF$_3$ | H | CH(CH$_3$)SCH$_2$CF$_3$ |
| 3,5-Cl$_2$ | CF$_3$ | H | CH(CH$_3$)S(O)CH$_2$CF$_3$ |
| 3,5-Cl$_2$ | CF$_3$ | H | CH(CH$_3$)SO$_2$CH$_2$CF$_3$ |
| 3,5-Cl$_2$ | CF$_3$ | H | CH(CF$_3$)SCH$_3$ |
| 3,5-Cl$_2$ | CF$_3$ | H | CH(CF$_3$)SEt |
| 3,5-Cl$_2$ | CF$_3$ | H | CH$_2$CH$_2$SCH$_3$ |
| 3,5-Cl$_2$ | CF$_3$ | H | CH$_2$CH$_2$S(O)CH$_3$ |
| 3,5-Cl$_2$ | CF$_3$ | H | CH$_2$CH$_2$SO$_2$CH$_3$ |
| 3,5-Cl$_2$ | CF$_3$ | H | CH$_2$CH$_2$SEt |
| 3,5-Cl$_2$ | CF$_3$ | H | CH$_2$CH$_2$S(O)Et |
| 3,5-Cl$_2$ | CF$_3$ | H | CH$_2$CH$_2$SO$_2$Et |
| 3,5-Cl$_2$ | CF$_3$ | H | CH$_2$CH$_2$SPr-n |
| 3,5-Cl$_2$ | CF$_3$ | H | CH$_2$CH$_2$S(O)Pr-n |
| 3,5-Cl$_2$ | CF$_3$ | H | CH$_2$CH$_2$SO$_2$Pr-n |
| 3,5-Cl$_2$ | CF$_3$ | H | CH$_2$CH$_2$SPr-i |
| 3,5-Cl$_2$ | CF$_3$ | H | CH$_2$CH$_2$S(O)Pr-i |
| 3,5-Cl$_2$ | CF$_3$ | H | CH$_2$CH$_2$SO$_2$Pr-i |
| 3,5-Cl$_2$ | CF$_3$ | H | CH$_2$CH$_2$SBu-n |
| 3,5-Cl$_2$ | CF$_3$ | H | CH$_2$CH$_2$SBu-i |
| 3,5-Cl$_2$ | CF$_3$ | H | CH$_2$CH$_2$SBu-s |
| 3,5-Cl$_2$ | CF$_3$ | H | CH$_2$CH$_2$S(O)Bu-t |
| 3,5-Cl$_2$ | CF$_3$ | H | CH$_2$CH$_2$SO$_2$Bu-t |
| 3,5-Cl$_2$ | CF$_3$ | H | CH$_2$CH$_2$SHex-n |
| 3,5-Cl$_2$ | CF$_3$ | H | CH$_2$CH$_2$SHex-c |
| 3,5-Cl$_2$ | CF$_3$ | H | CH$_2$CH$_2$SCH$_2$CF$_3$ |
| 3,5-Cl$_2$ | CF$_3$ | H | CH$_2$CH$_2$S(O)CH$_2$CF$_3$ |
| 3,5-Cl$_2$ | CF$_3$ | H | CH$_2$CH$_2$SO$_2$CH$_2$CF$_3$ |
| 3,5-Cl$_2$ | CF$_3$ | H | CH$_2$CH$_2$SCH$_2$CH$_2$OH |
| 3,5-Cl$_2$ | CF$_3$ | H | CH$_2$CH$_2$SCH$_2$CH$_2$OCH$_3$ |
| 3,5-Cl$_2$ | CF$_3$ | H | CH$_2$CH$_2$S(O)CH$_2$CH$_2$OCH$_3$ |
| 3,5-Cl$_2$ | CF$_3$ | H | CH$_2$CH$_2$SO$_2$CH$_2$CH$_2$OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$CH$_2$SCH$_2$CH$_2$OEt |
| 3,5-Cl$_2$ | CF$_3$ | H | CH$_2$CH$_2$S(O)CH$_2$CH$_2$OEt |
| 3,5-Cl$_2$ | CF$_3$ | H | CH$_2$CH$_2$SO$_2$CH$_2$CH$_2$OEt |
| 3,5-Cl$_2$ | CF$_3$ | H | CH$_2$CH$_2$SCH$_2$CH$_2$OC(O)CF$_3$ |
| 3,5-Cl$_2$ | CF$_3$ | H | CH$_2$CH$_2$SCH$_2$CH$_2$SCH$_3$ |
| 3,5-Cl$_2$ | CF$_3$ | H | CH$_2$CH$_2$SCH$_2$CH$_2$Si(CH$_3$)$_3$ |
| 3,5-Cl$_2$ | CF$_3$ | H | CH$_2$CH$_2$SCH$_2$C(O)CH$_3$ |
| 3,5-Cl$_2$ | CF$_3$ | H | CH$_2$CH$_2$SCH$_2$CH$_2$C(O)OCH$_3$ |
| 3,5-Cl$_2$ | CF$_3$ | H | CH$_2$CH$_2$S(O)CH$_2$CH$_2$C(O)OCH$_3$ |
| 3,5-Cl$_2$ | CF$_3$ | H | CH$_2$CH$_2$SO$_2$CH$_2$CH$_2$C(O)OCH$_3$ |
| 3,5-Cl$_2$ | CF$_3$ | H | CH$_2$CH$_2$SCH$_2$C(O)N(Et)$_2$ |
| 3,5-Cl$_2$ | CF$_3$ | H | CH$_2$CH$_2$S(O)CH$_2$C(O)N(Et)$_2$ |
| 3,5-Cl$_2$ | CF$_3$ | H | CH$_2$CH$_2$SO$_2$CH$_2$C(O)N(Et)$_2$ |
| 3,5-Cl$_2$ | CF$_3$ | H | CH$_2$CH$_2$SCH$_2$CH=CH$_2$ |
| 3,5-Cl$_2$ | CF$_3$ | H | CH$_2$CH$_2$SCH$_2$C≡CH |
| 3,5-Cl$_2$ | CF$_3$ | H | CH$_2$CH$_2$SCH$_2$Ph |
| 3,5-Cl$_2$ | CF$_3$ | H | CH$_2$CH$_2$S(O)CH$_2$Ph |
| 3,5-Cl$_2$ | CF$_3$ | H | CH$_2$CH$_2$SO$_2$CH$_2$Ph |
| 3,5-Cl$_2$ | CF$_3$ | H | CH$_2$CH$_2$SCH$_2$(Ph-2-F) |
| 3,5-Cl$_2$ | CF$_3$ | H | CH$_2$CH$_2$SCH$_2$(Ph-3-F) |
| 3,5-Cl$_2$ | CF$_3$ | H | CH$_2$CH$_2$SCH$_2$(Ph-4-F) |
| 3,5-Cl$_2$ | CF$_3$ | H | CH$_2$CH$_2$SCH$_2$(D-1a) |
| 3,5-Cl$_2$ | CF$_3$ | H | CH$_2$CH$_2$SO$_2$CH$_2$(D-1a) |
| 3,5-Cl$_2$ | CF$_3$ | H | CH$_2$CH$_2$SC(O)CH$_3$ |
| 3,5-Cl$_2$ | CF$_3$ | H | CH$_2$CH$_2$SC(O)N(CH$_3$)$_2$ |
| 3,5-Cl$_2$ | CF$_3$ | H | CH$_2$CH$_2$SC(O)NHEt |
| 3,5-Cl$_2$ | CF$_3$ | H | CH$_2$CH$_2$SC(O)N(Et)$_2$ |
| 3,5-Cl$_2$ | CF$_3$ | H | CH$_2$CH$_2$SC(O)NH(Ph-4-F) |
| 3,5-Cl$_2$ | CF$_3$ | H | CH$_2$CH$_2$SC(S)NHCH$_3$ |
| 3,5-Cl$_2$ | CF$_3$ | H | CH$_2$CH$_2$SC(S)N(CH$_3$)$_2$ |
| 3,5-Cl$_2$ | CF$_3$ | H | CH$_2$CH$_2$SC(S)NHEt |
| 3,5-Cl$_2$ | CF$_3$ | H | CH$_2$CH$_2$SPh |
| 3,5-Cl$_2$ | CF$_3$ | H | CH$_2$CH$_2$S(O)Ph |
| 3,5-Cl$_2$ | CF$_3$ | H | CH$_2$CH$_2$SO$_2$Ph |
| 3,5-Cl$_2$ | CF$_3$ | H | CH$_2$CH$_2$S(D-21a) |
| 3,5-Cl$_2$ | CF$_3$ | H | CH$_2$CH$_2$SO$_2$(D-21a) |
| 3,5-Cl$_2$ | CF$_3$ | H | CH$_2$CH$_2$S(D-47a) |
| 3,5-Cl$_2$ | CF$_3$ | H | CH$_2$CH$_2$S(O)(D-47a) |
| 3,5-Cl$_2$ | CF$_3$ | H | CH$_2$CH$_2$SO$_2$(D-47a) |
| 3,5-Cl$_2$ | CF$_3$ | H | CH$_2$CH$_2$S(D-50a) |
| 3,5-Cl$_2$ | CF$_3$ | H | CH$_2$CH$_2$S(O)(D-50a) |
| 3,5-Cl$_2$ | CF$_3$ | H | CH$_2$CH$_2$SO$_2$(D-50a) |
| 3,5-Cl$_2$ | CF$_3$ | H | CH$_2$CH$_2$SSCH$_3$ |
| 3,5-Cl$_2$ | CF$_3$ | H | CH$_2$CH$_2$SS(Ph-2-NO$_2$) |
| 3,5-Cl$_2$ | CF$_3$ | H | CH$_2$CH(CH$_3$)SCH$_3$ |
| 3,5-Cl$_2$ | CF$_3$ | H | CH$_2$CH(CH$_3$)SCH$_3$(R) |
| 3,5-Cl$_2$ | CF$_3$ | H | CH$_2$CH(CH$_3$)SCH$_3$(S) |
| 3,5-Cl$_2$ | CF$_3$ | H | CH$_2$CH(CH$_3$)S(O)CH$_3$ |
| 3,5-Cl$_2$ | CF$_3$ | H | CH$_2$CH(CH$_3$)SO$_2$CH$_3$ |
| 3,5-Cl$_2$ | CF$_3$ | H | CH$_2$CH(CH$_3$)SEt |
| 3,5-Cl$_2$ | CF$_3$ | H | CH$_2$CH(CH$_3$)SEt(R) |
| 3,5-Cl$_2$ | CF$_3$ | H | CH$_2$CH(CH$_3$)SEt(S) |
| 3,5-Cl$_2$ | CF$_3$ | H | CH$_2$CH(CH$_3$)S(O)Et |
| 3,5-Cl$_2$ | CF$_3$ | H | CH$_2$CH(CH$_3$)SO$_2$Et |
| 3,5-Cl$_2$ | CF$_3$ | H | CH$_2$CH(Et)SCH$_3$ |
| 3,5-Cl$_2$ | CF$_3$ | H | CH$_2$CH(Et)S(O)CH$_3$ |
| 3,5-Cl$_2$ | CF$_3$ | H | CH$_2$CH(Et)SO$_2$CH$_3$ |
| 3,5-Cl$_2$ | CF$_3$ | H | CH$_2$CH(Pr-n)SCH$_3$ |
| 3,5-Cl$_2$ | CF$_3$ | H | CH$_2$CH(Pr-i)SCH$_3$ |
| 3,5-Cl$_2$ | CF$_3$ | H | CH$_2$CH(Ph)SCH$_3$ |
| 3,5-Cl$_2$ | CF$_3$ | H | CH$_2$CH(SEt)$_2$ |
| 3,5-Cl$_2$ | CF$_3$ | H | CH(CH$_3$)CH$_2$SH |
| 3,5-Cl$_2$ | CF$_3$ | H | CH(CH$_3$)CH$_2$SCH$_3$ |
| 3,5-Cl$_2$ | CF$_3$ | H | CH(CH$_3$)CH$_2$SCH$_3$(R) |
| 3,5-Cl$_2$ | CF$_3$ | H | CH(CH$_3$)CH$_2$SCH$_3$(S) |
| 3,5-Cl$_2$ | CF$_3$ | H | CH(CH$_3$)CH$_2$S(O)CH$_3$ |
| 3,5-Cl$_2$ | CF$_3$ | H | CH(CH$_3$)CH$_2$SO$_2$CH$_3$ |
| 3,5-Cl$_2$ | CF$_3$ | H | CH(CH$_3$)CH$_2$SEt |
| 3,5-Cl$_2$ | CF$_3$ | H | CH(CH$_3$)CH$_2$SEt(R) |
| 3,5-Cl$_2$ | CF$_3$ | H | CH(CH$_3$)CH$_2$SEt(S) |
| 3,5-Cl$_2$ | CF$_3$ | H | CH(CH$_3$)CH$_2$S(O)Et |
| 3,5-Cl$_2$ | CF$_3$ | H | CH(CH$_3$)CH$_2$SO$_2$Et |
| 3,5-Cl$_2$ | CF$_3$ | H | CH(CH$_3$)CH$_2$SPr-n |
| 3,5-Cl$_2$ | CF$_3$ | H | CH(CH$_3$)CH$_2$S(O)Pr-n |
| 3,5-Cl$_2$ | CF$_3$ | H | CH(CH$_3$)CH$_2$SO$_2$Pr-n |
| 3,5-Cl$_2$ | CF$_3$ | H | CH(CH$_3$)CH$_2$SPr-i |
| 3,5-Cl$_2$ | CF$_3$ | H | CH(CH$_3$)CH$_2$S(O)Pr-i |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH(CH$_3$)CH$_2$SO$_2$Pr-i |
| 3,5-Cl$_2$ | CF$_3$ | H | CH(CH$_3$)CH$_2$SBu-t |
| 3,5-Cl$_2$ | CF$_3$ | H | CH(CH$_3$)CH$_2$S(O)Bu-t |
| 3,5-Cl$_2$ | CF$_3$ | H | CH(CH$_3$)CH$_2$SO$_2$Bu-t |
| 3,5-Cl$_2$ | CF$_3$ | H | CH(CH$_3$)CH$_2$SCH$_2$Ph |
| 3,5-Cl$_2$ | CF$_3$ | H | CH(CH$_3$)CH$_2$S(O)CH$_2$Ph |
| 3,5-Cl$_2$ | CF$_3$ | H | CH(CH$_3$)CH$_2$SO$_2$CH$_2$Ph |
| 3,5-Cl$_2$ | CF$_3$ | H | CH(CH$_2$SCH$_3$)$_2$ |
| 3,5-Cl$_2$ | CF$_3$ | H | CH(Ph)CH$_2$SCH$_3$ |
| 3,5-Cl$_2$ | CF$_3$ | H | CH(Ph)CH$_2$S(O)CH$_3$ |
| 3,5-Cl$_2$ | CF$_3$ | H | CH(Ph)CH$_2$SO$_2$CH$_3$ |
| 3,5-Cl$_2$ | CF$_3$ | H | CH(CH$_3$)CH(CH$_3$)SCH$_3$ |
| 3,5-Cl$_2$ | CF$_3$ | H | CH(CH$_3$)CH(CH$_3$)SO$_2$CH$_3$ |
| 3,5-Cl$_2$ | CF$_3$ | H | C(CH$_3$)$_2$CH$_2$SCH$_3$ |
| 3,5-Cl$_2$ | CF$_3$ | H | C(CH$_3$)$_2$CH$_2$S(O)CH$_3$ |
| 3,5-Cl$_2$ | CF$_3$ | H | C(CH$_3$)$_2$CH$_2$S(O)CH$_3$(−) |
| 3,5-Cl$_2$ | CF$_3$ | H | C(CH$_3$)$_2$CH$_2$S(O)CH$_3$(+) |
| 3,5-Cl$_2$ | CF$_3$ | H | C(CH$_3$)$_2$CH$_2$SO$_2$CH$_3$ |
| 3,5-Cl$_2$ | CF$_3$ | H | CH$_2$CH$_2$CH(CH$_3$)SCH$_3$ |
| 3,5-Cl$_2$ | CF$_3$ | H | CH$_2$CH$_2$CH(CH$_3$)S(O)CH$_3$ |
| 3,5-Cl$_2$ | CF$_3$ | H | CH$_2$CH$_2$CH(CH$_3$)SO$_2$CH$_3$ |
| 3,5-Cl$_2$ | CF$_3$ | H | CH$_2$CH(CH$_3$)CH$_2$SCH$_3$ |
| 3,5-Cl$_2$ | CF$_3$ | H | CH$_2$CH(CH$_3$)CH$_2$S(O)CH$_3$ |
| 3,5-Cl$_2$ | CF$_3$ | H | CH$_2$CH(CH$_3$)CH$_2$SO$_2$CH$_3$ |
| 3,5-Cl$_2$ | CF$_3$ | H | CH$_2$CH(CH$_3$)CH$_2$SEt |
| 3,5-Cl$_2$ | CF$_3$ | H | CH$_2$CH(CH$_3$)CH$_2$S(O)Et |
| 3,5-Cl$_2$ | CF$_3$ | H | CH$_2$CH(CH$_3$)CH$_2$SO$_2$Et |
| 3,5-Cl$_2$ | CF$_3$ | H | CH(CH$_3$)CH$_2$CH$_2$SCH$_3$ |
| 3,5-Cl$_2$ | CF$_3$ | H | CH(CH$_3$)CH$_2$CH$_2$S(O)CH$_3$ |
| 3,5-Cl$_2$ | CF$_3$ | H | CH(CH$_3$)CH$_2$CH$_2$SO$_2$CH$_3$ |
| 3,5-Cl$_2$ | CF$_3$ | H | CH(Et)CH$_2$CH$_2$SCH$_3$ |
| 3,5-Cl$_2$ | CF$_3$ | H | CH(CH$_2$OH)CH$_2$CH$_2$SCH$_3$ |
| 3,5-Cl$_2$ | CF$_3$ | H | C(CH$_3$)$_2$CH$_2$CH$_2$SCH$_3$ |
| 3,5-Cl$_2$ | CF$_3$ | H | C(CH$_3$)$_2$CH$_2$CH$_2$SEt |
| 3,5-Cl$_2$ | CF$_3$ | H | CH(CH$_3$)(CH$_2$)$_3$SCH$_3$ |
| 3,5-Cl$_2$ | CF$_3$ | H | CH(CH$_3$)(CH$_2$)$_3$S(O)CH$_3$ |
| 3,5-Cl$_2$ | CF$_3$ | H | CH(CH$_3$)(CH$_2$)$_3$SO$_2$CH$_3$ |
| 3,5-Cl$_2$ | CF$_3$ | H | C(CH$_3$)2(CH$_2$)$_3$SCH$_3$ |
| 3,5-Cl$_2$ | CF$_3$ | H | CH(CH$_3$)(CH$_2$)$_4$SCH$_3$ |
| 3,5-Cl$_2$ | CF$_3$ | H | CH(CH$_3$)(CH$_2$)$_4$SO$_2$CH$_3$ |
| 3,5-Cl$_2$ | CF$_3$ | H | CH$_2$(E-6a) |
| 3,5-Cl$_2$ | CF$_3$ | H | CH$_2$(E-7a) |
| 3,5-Cl$_2$ | CF$_3$ | H | CH$_2$(E-7b) |
| 3,5-Cl$_2$ | CF$_3$ | H | CH$_2$(E-7c) |
| 3,5-Cl$_2$ | CF$_3$ | H | CH$_2$(E-12a) |
| 3,5-Cl$_2$ | CF$_3$ | H | CH$_2$(E-12b)CH$_3$ |
| 3,5-Cl$_2$ | CF$_3$ | H | CH$_2$(E-14a) |
| 3,5-Cl$_2$ | CF$_3$ | H | CH$_2$(E-18a) |
| 3,5-Cl$_2$ | CF$_3$ | H | CH$_2$(E-18b)CH$_3$ |
| 3,5-Cl$_2$ | CF$_3$ | H | CH$_2$(E-26a) |
| 3,5-Cl$_2$ | CF$_3$ | H | CH$_2$(E-27a) |
| 3,5-Cl$_2$ | CF$_3$ | H | CH$_2$(E-28a) |
| 3,5-Cl$_2$ | CF$_3$ | H | CH$_2$(E-35a) |
| 3,5-Cl$_2$ | CF$_3$ | H | CH$_2$(E-35b)CH$_3$ |
| 3,5-Cl$_2$ | CF$_3$ | H | CH$_2$(E-43a) |
| 3,5-Cl$_2$ | CF$_3$ | H | CH$_2$(E-43b)CH$_3$ |
| 3,5-Cl$_2$ | CF$_3$ | H | CH$_2$(E-22a)Ph |
| 3,5-Cl$_2$ | CF$_3$ | H | CH$_2$(E-22b)H |
| 3,5-Cl$_2$ | CF$_3$ | H | E-6a |
| 3,5-Cl$_2$ | CF$_3$ | CH$_3$ | E-6a |
| 3,5-Cl$_2$ | CF$_3$ | CH$_2$OCH$_3$ | E-6a |
| 3,5-Cl$_2$ | CF$_3$ | CH$_2$OEt | E-6a |
| 3,5-Cl$_2$ | CF$_3$ | CH$_2$OCH$_2$CF$_3$ | E-6a |
| 3,5-Cl$_2$ | CF$_3$ | CH$_2$OC(O)CH$_3$ | E-6a |
| 3,5-Cl$_2$ | CF$_3$ | CH$_2$CN | E-6a |
| 3,5-Cl$_2$ | CF$_3$ | CH$_2$C≡CH | E-6a |
| 3,5-Cl$_2$ | CF$_3$ | C(O)CH$_3$ | E-6a |
| 3,5-Cl$_2$ | CF$_3$ | C(O)Et | E-6a |
| 3,5-Cl$_2$ | CF$_3$ | H | E-7a |
| 3,5-Cl$_2$ | CF$_3$ | CH$_2$OCH$_3$ | E-7a |
| 3,5-Cl$_2$ | CF$_3$ | CH$_2$OC(O)CH$_3$ | E-7a |
| 3,5-Cl$_2$ | CF$_3$ | CH$_2$CN | E-7a |
| 3,5-Cl$_2$ | CF$_3$ | C(O)CH$_3$ | E-7a |
| 3,5-Cl$_2$ | CF$_3$ | C(O)Et | E-7a |
| 3,5-Cl$_2$ | CF$_3$ | C(O)OCH$_3$ | E-7a |
| 3,5-Cl$_2$ | CF$_3$ | H | E-7b |
| 3,5-Cl$_2$ | CF$_3$ | H | E-7c |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | CH$_2$OCH$_3$ | E-7c |
| 3,5-Cl$_2$ | CF$_3$ | CH$_2$OC(O)CH$_3$ | E-7c |
| 3,5-Cl$_2$ | CF$_3$ | CH$_2$CN | E-7c |
| 3,5-Cl$_2$ | CF$_3$ | C(O)CH$_3$ | E-7c |
| 3,5-Cl$_2$ | CF$_3$ | C(O)Et | E-7c |
| 3,5-Cl$_2$ | CF$_3$ | C(O)OCH$_3$ | E-7c |
| 3,5-Cl$_2$ | CF$_3$ | H | E-27a |
| 3,5-Cl$_2$ | CF$_3$ | H | E-27b |
| 3,5-Cl$_2$ | CF$_3$ | H | E-27c |
| 3,5-Cl$_2$ | CF$_3$ | H | E-28a |
| 3,5-Cl$_2$ | CF$_3$ | | —CH$_2$SCH$_2$CH$_2$— |
| 3,5-Cl$_2$ | CF$_3$ | | —CH$_2$S(O)CH$_2$CH$_2$— |
| 3,5-Cl$_2$ | CF$_3$ | | —CH$_2$SO$_2$CH$_2$CH$_2$— |
| 3,5-Cl$_2$ | CF$_3$ | | —C(CH$_3$)$_2$SCH$_2$CH$_2$— |
| 3,5-Cl$_2$ | CF$_3$ | | —CH$_2$CH$_2$SCH$_2$CH$_2$— |
| 3,5-Cl$_2$ | CF$_3$ | H | CH$_2$NH$_2$ |
| 3,5-Cl$_2$ | CF$_3$ | H | CH$_2$NHCH$_3$ |
| 3,5-Cl$_2$ | CF$_3$ | H | CH$_2$N(CH$_3$)$_2$ |
| 3,5-Cl$_2$ | CF$_3$ | CH$_3$ | CH$_2$N(CH$_3$)$_2$ |
| 3,5-Cl$_2$ | CF$_3$ | H | CH$_2$NHEt |
| 3,5-Cl$_2$ | CF$_3$ | H | CH$_2$NHCH$_2$CF$_3$ |
| 3,5-Cl$_2$ | CF$_3$ | H | CH$_2$NHC(O)CH$_3$ |
| 3,5-Cl$_2$ | CF$_3$ | H | CH$_2$N(CH$_3$)C(O)CH$_3$ |
| 3,5-Cl$_2$ | CF$_3$ | H | CH$_2$N(CH$_2$CF$_3$)C(O)CH$_3$ |
| 3,5-Cl$_2$ | CF$_3$ | H | CH$_2$NHC(O)Et |
| 3,5-Cl$_2$ | CF$_3$ | H | CH$_2$NHC(O)Pr-n |
| 3,5-Cl$_2$ | CF$_3$ | H | CH$_2$NHC(O)Pr-i |
| 3,5-Cl$_2$ | CF$_3$ | H | CH$_2$NHC(O)Bu-t |
| 3,5-Cl$_2$ | CF$_3$ | H | CH$_2$NHC(O)CF$_3$ |
| 3,5-Cl$_2$ | CF$_3$ | H | CH$_2$NHC(O)CF$_2$Cl |
| 3,5-Cl$_2$ | CF$_3$ | CH$_3$ | CH$_2$NHC(O)CCl$_3$ |
| 3,5-Cl$_2$ | CF$_3$ | H | CH$_2$NHC(O)CH$_2$CHFBr |
| 3,5-Cl$_2$ | CF$_3$ | H | CH$_2$NHC(O)CH$_2$CF$_3$ |
| 3,5-Cl$_2$ | CF$_3$ | H | CH$_2$N(CH$_3$)C(O)CH$_2$CF$_3$ |
| 3,5-Cl$_2$ | CF$_3$ | H | CH$_2$NHC(O)CH$_2$CF$_2$CF$_3$ |
| 3,5-Cl$_2$ | CF$_3$ | H | CH$_2$NHC(O)CH$_2$CF$_2$CF$_2$Cl |
| 3,5-Cl$_2$ | CF$_3$ | H | CH$_2$NHC(O)CH$_2$CFClCF$_2$Cl |
| 3,5-Cl$_2$ | CF$_3$ | H | CH$_2$NHC(O)OCH$_3$ |
| 3,5-Cl$_2$ | CF$_3$ | H | CH$_2$N(CH$_2$CF$_3$)C(O)OCH$_3$ |
| 3,5-Cl$_2$ | CF$_3$ | H | CH$_2$NHC(O)OEt |
| 3,5-Cl$_2$ | CF$_3$ | H | CH$_2$NHC(O)OPr-n |
| 3,5-Cl$_2$ | CF$_3$ | H | CH$_2$NHC(O)OPr-i |
| 3,5-Cl$_2$ | CF$_3$ | H | CH$_2$NHC(O)OPr-c |
| 3,5-Cl$_2$ | CF$_3$ | H | CH$_2$NHC(O)OBu-t |
| 3,5-Cl$_2$ | CF$_3$ | H | CH$_2$NHC(O)OCH$_2$CF$_3$ |
| 3,5-Cl$_2$ | CF$_3$ | H | CH$_2$NHC(O)OPh |
| 3,5-Cl$_2$ | CF$_3$ | H | CH$_2$NHC(O)SCH$_3$ |
| 3,5-Cl$_2$ | CF$_3$ | H | CH$_2$NHC(O)NHEt |
| 3,5-Cl$_2$ | CF$_3$ | H | CH$_2$NHC(O)NHCH$_2$CF$_3$ |
| 3,5-Cl$_2$ | CF$_3$ | H | CH$_2$NHC(O)Ph |
| 3,5-Cl$_2$ | CF$_3$ | H | CH$_2$NHC(O)(D-17a)CH$_3$ |
| 3,5-Cl$_2$ | CF$_3$ | H | CH$_2$NHC(O)(D-17b)Cl |
| 3,5-Cl$_2$ | CF$_3$ | H | CH$_2$NHC(O)(D-21a) |
| 3,5-Cl$_2$ | CF$_3$ | H | CH$_2$NHC(O)(D-22a) |
| 3,5-Cl$_2$ | CF$_3$ | H | CH$_2$NHC(O)(D-23a) |
| 3,5-Cl$_2$ | CF$_3$ | H | CH$_2$NHC(O)(D-47a) |
| 3,5-Cl$_2$ | CF$_3$ | H | CH$_2$NHC(O)(D-48a) |
| 3,5-Cl$_2$ | CF$_3$ | H | CH$_2$NHC(O)(D-49a) |
| 3,5-Cl$_2$ | CF$_3$ | H | CH$_2$NHC(S)OCH$_3$ |
| 3,5-Cl$_2$ | CF$_3$ | H | CH$_2$NHC(S)OCH$_2$CF$_3$ |
| 3,5-Cl$_2$ | CF$_3$ | H | CH$_2$NHC(S)SCH$_3$ |
| 3,5-Cl$_2$ | CF$_3$ | H | CH$_2$NHC(S)NHCH$_2$CF$_3$ |
| 3,5-Cl$_2$ | CF$_3$ | H | CH$_2$NHSO$_2$CH$_3$ |
| 3,5-Cl$_2$ | CF$_3$ | H | CH$_2$N(CH$_3$)SO$_2$CH$_3$ |
| 3,5-Cl$_2$ | CF$_3$ | H | CH$_2$NHSO$_2$CF$_3$ |
| 3,5-Cl$_2$ | CF$_3$ | H | CH$_2$NHSO$_2$Ph |
| 3,5-Cl$_2$ | CF$_3$ | H | CH$_2$N(Ph)SO$_2$CH$_3$ |
| 3,5-Cl$_2$ | CF$_3$ | H | CH(CH$_3$)NHCH$_2$CF$_3$ |
| 3,5-Cl$_2$ | CF$_3$ | H | CH(CH$_3$)NHC(O)CH$_3$ |
| 3,5-Cl$_2$ | CF$_3$ | H | CH(CH$_3$)NHC(O)Et |
| 3,5-Cl$_2$ | CF$_3$ | H | CH(CH$_3$)NHC(O)Pr-n |
| 3,5-Cl$_2$ | CF$_3$ | H | CH(CH$_3$)NHC(O)Pr-i |
| 3,5-Cl$_2$ | CF$_3$ | H | CH(CH$_3$)NHC(O)Bu-t |
| 3,5-Cl$_2$ | CF$_3$ | H | CH(CH$_3$)NHC(O)CF$_3$ |
| 3,5-Cl$_2$ | CF$_3$ | H | CH(CH$_3$)NHC(O)CF$_2$Cl |
| 3,5-Cl$_2$ | CF$_3$ | H | CH(CH$_3$)NHC(O)CH$_2$CF$_3$ |
| 3,5-Cl$_2$ | CF$_3$ | H | CH(CH$_3$)NHC(O)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH(CH$_3$)NHC(O)OCH$_3$ |
| 3,5-Cl$_2$ | CF$_3$ | H | CH(CH$_3$)NHC(O)OEt |
| 3,5-Cl$_2$ | CF$_3$ | H | CH(CH$_3$)NHC(O)OPr-n |
| 3,5-Cl$_2$ | CF$_3$ | H | CH(CH$_3$)NHC(O)OPr-i |
| 3,5-Cl$_2$ | CF$_3$ | H | CH(CH$_3$)NHC(O)OPr-c |
| 3,5-Cl$_2$ | CF$_3$ | H | CH(CH$_3$)NHC(O)OBu-t |
| 3,5-Cl$_2$ | CF$_3$ | H | CH(CH$_3$)NHC(O)OCH$_2$CF$_3$ |
| 3,5-Cl$_2$ | CF$_3$ | H | CH(CH$_3$)NHC(O)OPh |
| 3,5-Cl$_2$ | CF$_3$ | H | CH(CH$_3$)NHC(O)SCH$_3$ |
| 3,5-Cl$_2$ | CF$_3$ | H | CH(CH$_3$)NHC(O)N(CH$_3$)$_2$ |
| 3,5-Cl$_2$ | CF$_3$ | H | CH(CH$_3$)NHC(O)NHCH$_2$CF$_3$ |
| 3,5-Cl$_2$ | CF$_3$ | H | CH(CH$_3$)NHC(O)Ph |
| 3,5-Cl$_2$ | CF$_3$ | H | CH(CH$_3$)NHC(O)(D-17a)CH$_3$ |
| 3,5-Cl$_2$ | CF$_3$ | H | CH(CH$_3$)NHC(O)(D-17b)Cl |
| 3,5-Cl$_2$ | CF$_3$ | H | CH(CH$_3$)NHC(O)(D-21a) |
| 3,5-Cl$_2$ | CF$_3$ | H | CH(CH$_3$)NHC(O)(D-22a) |
| 3,5-Cl$_2$ | CF$_3$ | H | CH(CH$_3$)NHC(O)(D-23a) |
| 3,5-Cl$_2$ | CF$_3$ | H | CH(CH$_3$)NHC(O)(D-47a) |
| 3,5-Cl$_2$ | CF$_3$ | H | CH(CH$_3$)NHC(O)(D-48a) |
| 3,5-Cl$_2$ | CF$_3$ | H | CH(CH$_3$)NHC(O)(D-49a) |
| 3,5-Cl$_2$ | CF$_3$ | H | CH(CH$_3$)NHC(S)OCH$_3$ |
| 3,5-Cl$_2$ | CF$_3$ | H | CH(CH$_3$)NHC(S)SCH$_3$ |
| 3,5-Cl$_2$ | CF$_3$ | H | CH(CH$_3$)NHSO$_2$CH$_3$ |
| 3,5-Cl$_2$ | CF$_3$ | H | CH(CH$_3$)NHSO$_2$Ph |
| 3,5-Cl$_2$ | CF$_3$ | H | CH$_2$CH$_2$N(CH$_3$)$_2$ |
| 3,5-Cl$_2$ | CF$_3$ | H | CH$_2$CH$_2$(T-33) |
| 3,5-Cl$_2$ | CF$_3$ | H | CH$_2$CH$_2$(T-39) |
| 3,5-Cl$_2$ | CF$_3$ | H | CH$_2$CH$_2$NHC(O)CH$_3$ |
| 3,5-Cl$_2$ | CF$_3$ | H | CH$_2$CH$_2$N(CH$_3$)C(O)CH$_3$ |
| 3,5-Cl$_2$ | CF$_3$ | H | CH$_2$CH$_2$NHC(O)Et |
| 3,5-Cl$_2$ | CF$_3$ | H | CH$_2$CH$_2$NHC(O)Pr-n |
| 3,5-Cl$_2$ | CF$_3$ | H | CH$_2$CH$_2$NHC(O)Pr-i |
| 3,5-Cl$_2$ | CF$_3$ | H | CH$_2$CH$_2$NHC(O)Pr-c |
| 3,5-Cl$_2$ | CF$_3$ | H | CH$_2$CH$_2$NHC(O)Bu-n |
| 3,5-Cl$_2$ | CF$_3$ | H | CH$_2$CH$_2$NHC(O)Bu-i |
| 3,5-Cl$_2$ | CF$_3$ | H | CH$_2$CH$_2$NHC(O)Bu-s |
| 3,5-Cl$_2$ | CF$_3$ | H | CH$_2$CH$_2$NHC(O)Bu-t |
| 3,5-Cl$_2$ | CF$_3$ | H | CH$_2$CH$_2$NHC(O)CF$_3$ |
| 3,5-Cl$_2$ | CF$_3$ | H | CH$_2$CH$_2$N(CH$_3$)C(O)CF$_3$ |
| 3,5-Cl$_2$ | CF$_3$ | H | CH$_2$CH$_2$NHC(O)CF$_2$Cl |
| 3,5-Cl$_2$ | CF$_3$ | H | CH$_2$CH$_2$NHC(O)CH$_2$CF$_3$ |
| 3,5-Cl$_2$ | CF$_3$ | H | CH$_2$CH$_2$NHC(O)Ph |
| 3,5-Cl$_2$ | CF$_3$ | H | CH$_2$CH$_2$NHC(O)(D-17a)CH$_3$ |
| 3,5-Cl$_2$ | CF$_3$ | H | CH$_2$CH$_2$NHC(O)(D-17b)Cl |
| 3,5-Cl$_2$ | CF$_3$ | H | CH$_2$CH$_2$NHC(O)(D-21a) |
| 3,5-Cl$_2$ | CF$_3$ | H | CH$_2$CH$_2$NHC(O)(D-22a) |
| 3,5-Cl$_2$ | CF$_3$ | H | CH$_2$CH$_2$NHC(O)(D-23a) |
| 3,5-Cl$_2$ | CF$_3$ | H | CH$_2$CH$_2$NHC(O)(D-47a) |
| 3,5-Cl$_2$ | CF$_3$ | H | CH$_2$CH$_2$NHC(O)(D-48a) |
| 3,5-Cl$_2$ | CF$_3$ | H | CH$_2$CH$_2$NHC(O)(D-49a) |
| 3,5-Cl$_2$ | CF$_3$ | H | CH$_2$CH$_2$NHC(O)OCH$_3$ |
| 3,5-Cl$_2$ | CF$_3$ | H | CH$_2$CH$_2$NHC(O)OEt |
| 3,5-Cl$_2$ | CF$_3$ | H | CH$_2$CH$_2$NHC(O)OPr-n |
| 3,5-Cl$_2$ | CF$_3$ | H | CH$_2$CH$_2$NHC(O)OCH$_2$CH$_2$Cl |
| 3,5-Cl$_2$ | CF$_3$ | H | CH$_2$CH$_2$NHC(O)N(CH$_3$)$_2$ |
| 3,5-Cl$_2$ | CF$_3$ | H | CH$_2$CH$_2$NHC(S)NHEt |
| 3,5-Cl$_2$ | CF$_3$ | H | CH$_2$CH$_2$N(CH$_3$)OCH$_3$ |
| 3,5-Cl$_2$ | CF$_3$ | H | CH$_2$CH$_2$NHSO$_2$CH$_3$ |
| 3,5-Cl$_2$ | CF$_3$ | H | CH$_2$CH$_2$N(CH$_3$)SO$_2$CH$_3$ |
| 3,5-Cl$_2$ | CF$_3$ | H | CH$_2$CH$_2$NHSO$_2$Et |
| 3,5-Cl$_2$ | CF$_3$ | H | CH$_2$CH$_2$NHSO$_2$CF$_3$ |
| 3,5-Cl$_2$ | CF$_3$ | H | CH$_2$CH$_2$N(CH$_3$)SO$_2$CF$_3$ |
| 3,5-Cl$_2$ | CF$_3$ | H | CH$_2$CH$_2$NHSO$_2$Ph |
| 3,5-Cl$_2$ | CF$_3$ | H | CH$_2$CH$_2$NHSO$_2$N(CH$_3$)$_2$ |
| 3,5-Cl$_2$ | CF$_3$ | H | CH$_2$CH$_2$NHP(S)(OCH$_3$)$_2$ |
| 3,5-Cl$_2$ | CF$_3$ | H | CH$_2$CH$_2$NHP(S)(OEt)$_2$ |
| 3,5-Cl$_2$ | CF$_3$ | H | CH$_2$CH(CH$_3$)NHC(O)CH$_3$ |
| 3,5-Cl$_2$ | CF$_3$ | H | CH$_2$CH(CH$_3$)NHC(O)OCH$_3$ |
| 3,5-Cl$_2$ | CF$_3$ | H | CH$_2$C(CH$_3$)$_2$NHC(O)CH$_3$ |
| 3,5-Cl$_2$ | CF$_3$ | H | CH$_2$C(CH$_3$)$_2$NHC(O)OCH$_3$ |
| 3,5-Cl$_2$ | CF$_3$ | H | CH(CH$_3$)CH$_2$N(CH$_3$)$_2$ |
| 3,5-Cl$_2$ | CF$_3$ | H | CH(CH$_3$)CH$_2$NHC(O)CH$_3$ |
| 3,5-Cl$_2$ | CF$_3$ | H | CH(CH$_3$)CH$_2$NHC(O)CF$_3$ |
| 3,5-Cl$_2$ | CF$_3$ | H | CH(CH$_3$)CH$_2$NHC(O)OCH$_3$ |
| 3,5-Cl$_2$ | CF$_3$ | H | CH(CH$_3$)CH$_2$NHC(O)OBu-t |
| 3,5-Cl$_2$ | CF$_3$ | H | CH(CH$_3$)CH$_2$NHC(O)N(CH$_3$)$_2$ |
| 3,5-Cl$_2$ | CF$_3$ | H | CH(CH$_3$)CH$_2$NHC(O)Ph |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH(CH$_3$)CH$_2$N(CH$_3$)OCH$_3$ |
| 3,5-Cl$_2$ | CF$_3$ | H | C(CH$_3$)$_2$CH$_2$NHC(O)OCH$_3$ |
| 3,5-Cl$_2$ | CF$_3$ | H | CH$_2$CH$_2$CH$_2$N(CH$_3$)$_2$ |
| 3,5-Cl$_2$ | CF$_3$ | H | CH$_2$CH$_2$CH$_2$NHC(O)OCH$_3$ |
| 3,5-Cl$_2$ | CF$_3$ | H | CH$_2$CH$_2$CH$_2$NHC(O)OBu-t |
| 3,5-Cl$_2$ | CF$_3$ | H | CH$_2$CH$_2$CH$_2$NHC(O)OCH$_2$CF$_3$ |
| 3,5-Cl$_2$ | CF$_3$ | H | CH$_2$CH$_2$CH$_2$N(CH$_3$)OCH$_3$ |
| 3,5-Cl$_2$ | CF$_3$ | H | CH$_2$CH$_2$CH(Et)NHC(O)CH$_3$ |
| 3,5-Cl$_2$ | CF$_3$ | H | CH$_2$CH$_2$CH(Et)NHC(O)OCH$_3$ |
| 3,5-Cl$_2$ | CF$_3$ | H | CH$_2$C(CH$_3$)$_2$CH$_2$N(CH$_3$)$_2$ |
| 3,5-Cl$_2$ | CF$_3$ | H | CH$_2$C(CH$_3$)$_2$CH$_2$NHC(O)CH$_3$ |
| 3,5-Cl$_2$ | CF$_3$ | H | CH$_2$C(CH$_3$)$_2$CH$_2$NHC(O)OCH$_3$ |
| 3,5-Cl$_2$ | CF$_3$ | H | CH$_2$CH(OH)CH$_2$NHC(O)CH$_3$ |
| 3,5-Cl$_2$ | CF$_3$ | H | CH$_2$CH(OH)CH$_2$NHC(O)OCH$_3$ |
| 3,5-Cl$_2$ | CF$_3$ | H | CH$_2$(E-8a)CH$_3$ |
| 3,5-Cl$_2$ | CF$_3$ | H | CH$_2$(E-8a)CH$_2$CF$_3$ |
| 3,5-Cl$_2$ | CF$_3$ | H | CH$_2$(E-8a)C(O)CH$_3$ |
| 3,5-Cl$_2$ | CF$_3$ | H | CH$_2$(E-9a)CH$_3$ |
| 3,5-Cl$_2$ | CF$_3$ | H | CH$_2$(E-9a)Et |
| 3,5-Cl$_2$ | CF$_3$ | H | CH$_2$(E-9a)C(O)CH$_3$ |
| 3,5-Cl$_2$ | CF$_3$ | H | CH$_2$(E-9a)C(O)OCH$_3$ |
| 3,5-Cl$_2$ | CF$_3$ | H | CH$_2$(E-29a)CH$_3$ |
| 3,5-Cl$_2$ | CF$_3$ | H | CH$_2$(E-29a)C(O)CH$_3$ |
| 3,5-Cl$_2$ | CF$_3$ | H | CH$_2$(E-30a)CH$_3$ |
| 3,5-Cl$_2$ | CF$_3$ | H | CH$_2$(E-30a)C(O)CH$_3$ |
| 3,5-Cl$_2$ | CF$_3$ | H | CH$_2$(E-31a)CH$_3$ |
| 3,5-Cl$_2$ | CF$_3$ | H | CH$_2$(E-31a)C(O)CH$_3$ |
| 3,5-Cl$_2$ | CF$_3$ | H | CH$_2$(E-31a)C(O)OCH$_3$ |
| 3,5-Cl$_2$ | CF$_3$ | H | CH$_2$(E-8b)H |
| 3,5-Cl$_2$ | CF$_3$ | H | CH$_2$(E-8b)CH$_2$Ph |
| 3,5-Cl$_2$ | CF$_3$ | H | CH$_2$(E-29b)H |
| 3,5-Cl$_2$ | CF$_3$ | H | CH$_2$(E-30c)H |
| 3,5-Cl$_2$ | CF$_3$ | H | CH$_2$(E-16a)H |
| 3,5-Cl$_2$ | CF$_3$ | H | CH$_2$(E-16a)Pr-n |
| 3,5-Cl$_2$ | CF$_3$ | H | CH$_2$(E-16a)C(O)OEt |
| 3,5-Cl$_2$ | CF$_3$ | H | CH$_2$(E-21a)CH$_2$Ph |
| 3,5-Cl$_2$ | CF$_3$ | H | CH$_2$(E-21b)H |
| 3,5-Cl$_2$ | CF$_3$ | H | CH$_2$(E-40a)H |
| 3,5-Cl$_2$ | CF$_3$ | H | CH$_2$CH$_2$(E-9a)CH$_3$ |
| 3,5-Cl$_2$ | CF$_3$ | H | (E-8a)C(O)OCH$_3$ |
| 3,5-Cl$_2$ | CF$_3$ | H | (E-8a)C(O)OEt |
| 3,5-Cl$_2$ | CF$_3$ | H | (E-8a)C(O)OBu-t |
| 3,5-Cl$_2$ | CF$_3$ | H | (E-8a)CN |
| 3,5-Cl$_2$ | CF$_3$ | H | (E-9a)CHO |
| 3,5-Cl$_2$ | CF$_3$ | H | (E-9a)C(O)CH$_3$ |
| 3,5-Cl$_2$ | CF$_3$ | H | (E-9a)C(O)CF$_3$ |
| 3,5-Cl$_2$ | CF$_3$ | H | (E-9a)C(O)Bu-t |
| 3,5-Cl$_2$ | CF$_3$ | H | (E-9a)C(O)OCH$_3$ |
| 3,5-Cl$_2$ | CF$_3$ | H | (E-9a)C(O)OEt |
| 3,5-Cl$_2$ | CF$_3$ | H | (E-30a)C(O)CH$_3$ |
| 3,5-Cl$_2$ | CF$_3$ | H | (E-30a)C(O)OCH$_3$ |
| 3,5-Cl$_2$ | CF$_3$ | H | (E-30c)OCH$_2$Ph |
| 3,5-Cl$_2$ | CF$_3$ | H | (E-31a)CH$_3$ |
| 3,5-Cl$_2$ | CF$_3$ | H | (E-31a)C(O)CH$_3$ |
| 3,5-Cl$_2$ | CF$_3$ | H | (E-31a)C(O)OCH$_3$ |
| 3,5-Cl$_2$ | CF$_3$ | | —CH$_2$CH$_2$N(CH$_3$)CH$_2$CH$_2$— |
| 3,5-Cl$_2$ | CF$_3$ | | —CH$_2$CH$_2$N[C(O)CH$_3$]CH$_2$CH$_2$— |
| 3,5-Cl$_2$ | CF$_3$ | | —CH$_2$CH$_2$N[C(O)OCH$_3$]CH$_2$CH$_2$— |
| 3,5-Cl$_2$ | CF$_3$ | | —CH$_2$CH$_2$N[C(O)Ph]CH$_2$CH$_2$— |
| 3,5-Cl$_2$ | CF$_3$ | H | CH$_2$Si(CH$_3$)$_3$ |
| 3,5-Cl$_2$ | CF$_3$ | H | CH$_2$CHO |
| 3,5-Cl$_2$ | CF$_3$ | H | C(CH$_3$)$_2$CHO |
| 3,5-Cl$_2$ | CF$_3$ | H | CH$_2$C(O)CH$_3$ |
| 3,5-Cl$_2$ | CF$_3$ | | —CH$_2$CH$_2$C(O)CH$_2$— |
| 3,5-Cl$_2$ | CF$_3$ | H | CH$_2$(T-19) |
| 3,5-Cl$_2$ | CF$_3$ | H | CH$_2$(M-2a)CH$_3$ |
| 3,5-Cl$_2$ | CF$_3$ | H | CH$_2$(M-3a)CH$_3$ |
| 3,5-Cl$_2$ | CF$_3$ | H | CH$_2$CH=NOH |
| 3,5-Cl$_2$ | CF$_3$ | H | CH$_2$CH=NOCH$_3$ |
| 3,5-Cl$_2$ | CF$_3$ | CH$_3$ | CH$_2$CH=NOCH$_3$ |
| 3,5-Cl$_2$ | CF$_3$ | CH$_2$OCH$_3$ | CH$_2$CH=NOCH$_3$ |
| 3,5-Cl$_2$ | CF$_3$ | CH$_2$OC(O)CH$_3$ | CH$_2$CH=NOCH$_3$ |
| 3,5-Cl$_2$ | CF$_3$ | CH$_2$CN | CH$_2$CH=NOCH$_3$ |
| 3,5-Cl$_2$ | CF$_3$ | C(O)CH$_3$ | CH$_2$CH=NOCH$_3$ |
| 3,5-Cl$_2$ | CF$_3$ | C(O)Et | CH$_2$CH=NOCH$_3$ |
| 3,5-Cl$_2$ | CF$_3$ | C(O)OCH$_3$ | CH$_2$CH=NOCH$_3$ |
| 3,5-Cl$_2$ | CF$_3$ | H | CH$_2$CH=NOEt |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$CH=NOPr-n |
| 3,5-Cl$_2$ | CF$_3$ | H | CH$_2$CH=NOCH$_2$Pr-c |
| 3,5-Cl$_2$ | CF$_3$ | H | CH$_2$CH=NOCH$_2$CH$_2$Cl |
| 3,5-Cl$_2$ | CF$_3$ | H | CH$_2$CH=NOCH$_2$CF$_3$ |
| 3,5-Cl$_2$ | CF$_3$ | H | CH$_2$CH=NOCH$_2$CH$_2$OEt |
| 3,5-Cl$_2$ | CF$_3$ | H | CH$_2$CH=NOCH$_2$CH$_2$SEt |
| 3,5-Cl$_2$ | CF$_3$ | H | CH$_2$CH=NOCH$_2$CN |
| 3,5-Cl$_2$ | CF$_3$ | H | CH$_2$CH=NOCH$_2$CH=CH$_2$ |
| 3,5-Cl$_2$ | CF$_3$ | H | CH$_2$CH=NOCH$_2$C≡CH |
| 3,5-Cl$_2$ | CF$_3$ | H | CH$_2$CH=NOCH$_2$Ph |
| 3,5-Cl$_2$ | CF$_3$ | H | CH$_2$CH=NOCH$_2$(Ph-4-Cl) |
| 3,5-Cl$_2$ | CF$_3$ | H | CH$_2$CH=NOCH$_2$CH$_2$Si(CH$_3$)$_3$ |
| 3,5-Cl$_2$ | CF$_3$ | H | CH$_2$C(CH$_3$)=NOH |
| 3,5-Cl$_2$ | CF$_3$ | H | CH$_2$C(CH$_3$)=NOCH$_3$ |
| 3,5-Cl$_2$ | CF$_3$ | CH$_3$ | CH$_2$C(CH$_3$)=NOCH$_3$ |
| 3,5-Cl$_2$ | CF$_3$ | CH$_2$OCH$_3$ | CH$_2$C(CH$_3$)=NOCH$_3$ |
| 3,5-Cl$_2$ | CF$_3$ | CH$_2$OC(O)CH$_3$ | CH$_2$C(CH$_3$)=NOCH$_3$ |
| 3,5-Cl$_2$ | CF$_3$ | CH$_2$CN | CH$_2$C(CH$_3$)=NOCH$_3$ |
| 3,5-Cl$_2$ | CF$_3$ | C(O)CH$_3$ | CH$_2$C(CH$_3$)=NOCH$_3$ |
| 3,5-Cl$_2$ | CF$_3$ | C(O)Et | CH$_2$C(CH$_3$)=NOCH$_3$ |
| 3,5-Cl$_2$ | CF$_3$ | C(O)OCH$_3$ | CH$_2$C(CH$_3$)=NOCH$_3$ |
| 3,5-Cl$_2$ | CF$_3$ | H | CH$_2$C(CH$_3$)=NOEt |
| 3,5-Cl$_2$ | CF$_3$ | H | CH$_2$C(CH$_3$)=NOPr-n |
| 3,5-Cl$_2$ | CF$_3$ | H | CH$_2$C(CH$_3$)=NOCH$_2$Pr-c |
| 3,5-Cl$_2$ | CF$_3$ | H | CH$_2$C(CH$_3$)=NOCH$_2$CH$_2$Cl |
| 3,5-Cl$_2$ | CF$_3$ | H | CH$_2$C(CH$_3$)=NOCH$_2$CF$_3$ |
| 3,5-Cl$_2$ | CF$_3$ | H | CH$_2$C(CH$_3$)=NOCH$_2$CH$_2$OEt |
| 3,5-Cl$_2$ | CF$_3$ | H | CH$_2$C(CH$_3$)=NOCH$_2$CH$_2$SEt |
| 3,5-Cl$_2$ | CF$_3$ | H | CH$_2$C(CH$_3$)=NOCH$_2$CN |
| 3,5-Cl$_2$ | CF$_3$ | H | CH$_2$C(CH$_3$)=NOCH$_2$CH=CH$_2$ |
| 3,5-Cl$_2$ | CF$_3$ | H | CH$_2$C(CH$_3$)=NOCH$_2$C≡CH |
| 3,5-Cl$_2$ | CF$_3$ | H | CH$_2$C(CH$_3$)=NOCH$_2$Ph |
| 3,5-Cl$_2$ | CF$_3$ | H | CH$_2$C(Ph)=NOCH$_3$ |
| 3,5-Cl$_2$ | CF$_3$ | H | CH(CH$_3$)CH=NOCH$_3$ |
| 3,5-Cl$_2$ | CF$_3$ | H | CH(CH$_3$)CH=NOCH$_2$CF$_3$ |
| 3,5-Cl$_2$ | CF$_3$ | H | CH(CH$_3$)C(CH$_3$)=NOCH$_3$ |
| 3,5-Cl$_2$ | CF$_3$ | H | C(CH$_3$)$_2$CH=NOH |
| 3,5-Cl$_2$ | CF$_3$ | H | C(CH$_3$)$_2$CH=NOCH$_3$ |
| 3,5-Cl$_2$ | CF$_3$ | H | CH$_2$CH$_2$CH=NOCH$_3$ |
| 3,5-Cl$_2$ | CF$_3$ | H | CH$_2$CH(CH$_3$)C(CH$_3$)=NOH |
| 3,5-Cl$_2$ | CF$_3$ | H | CH$_2$CH(CH$_3$)C(CH$_3$)=NOCH$_3$ |
| 3,5-Cl$_2$ | CF$_3$ | H | CH$_2$CH(CH$_3$)C(CH$_3$)=NOEt |
| 3,5-Cl$_2$ | CF$_3$ | H | CH(CH$_3$)CH$_2$CH=NOCH$_3$ |
| 3,5-Cl$_2$ | CF$_3$ | H | CH$_2$CH$_2$CH$_2$CH=NOEt |
| 3,5-Cl$_2$ | CF$_3$ | H | CH$_2$(T-20) |
| 3,5-Cl$_2$ | CF$_3$ | H | CH$_2$(T-21) |
| 3,5-Cl$_2$ | CF$_3$ | H | CH$_2$(M-5a)Cl |
| 3,5-Cl$_2$ | CF$_3$ | H | CH$_2$(M-5a)Br |
| 3,5-Cl$_2$ | CF$_3$ | H | CH$_2$(M-5a)CH$_3$ |
| 3,5-Cl$_2$ | CF$_3$ | H | CH$_2$(M-5a)CF$_3$ |
| 3,5-Cl$_2$ | CF$_3$ | H | CH$_2$(M-5a)CH$_2$CF$_3$ |
| 3,5-Cl$_2$ | CF$_3$ | H | CH$_2$(M-5a)CH$_2$OCH$_3$ |
| 3,5-Cl$_2$ | CF$_3$ | H | CH$_2$(M-14a)CH$_3$ |
| 3,5-Cl$_2$ | CF$_3$ | H | CH$_2$CN |
| 3,5-Cl$_2$ | CF$_3$ | CH$_3$ | CH$_2$CN |
| 3,5-Cl$_2$ | CF$_3$ | Et | CH$_2$CN |
| 3,5-Cl$_2$ | CF$_3$ | CH$_2$OCH$_3$ | CH$_2$CN |
| 3,5-Cl$_2$ | CF$_3$ | CH$_2$OEt | CH$_2$CN |
| 3,5-Cl$_2$ | CF$_3$ | CH$_2$OCH$_2$CF$_3$ | CH$_2$CN |
| 3,5-Cl$_2$ | CF$_3$ | CH$_2$OC(O)CH$_3$ | CH$_2$CN |
| 3,5-Cl$_2$ | CF$_3$ | CH$_2$CN | CH$_2$CN |
| 3,5-Cl$_2$ | CF$_3$ | C(O)CH$_3$ | CH$_2$CN |
| 3,5-Cl$_2$ | CF$_3$ | C(O)Et | CH$_2$CN |
| 3,5-Cl$_2$ | CF$_3$ | C(O)Pr-n | CH$_2$CN |
| 3,5-Cl$_2$ | CF$_3$ | C(O)Pr-i | CH$_2$CN |
| 3,5-Cl$_2$ | CF$_3$ | C(O)Pr-c | CH$_2$CN |
| 3,5-Cl$_2$ | CF$_3$ | C(O)Bu-t | CH$_2$CN |
| 3,5-Cl$_2$ | CF$_3$ | H | CH(CH$_3$)CN |
| 3,5-Cl$_2$ | CF$_3$ | H | CH(CF$_3$)CN |
| 3,5-Cl$_2$ | CF$_3$ | H | CH(OCH$_3$)CN |
| 3,5-Cl$_2$ | CF$_3$ | H | CH(OEt)CN |
| 3,5-Cl$_2$ | CF$_3$ | H | CH(OPr-n)CN |
| 3,5-Cl$_2$ | CF$_3$ | H | CH(OPr-i)CN |
| 3,5-Cl$_2$ | CF$_3$ | H | CH(OPr-c)CN |
| 3,5-Cl$_2$ | CF$_3$ | H | CH(OCH$_2$CF$_3$)CN |
| 3,5-Cl$_2$ | CF$_3$ | H | CH(OCH$_2$CH=CH$_2$)CN |
| 3,5-Cl$_2$ | CF$_3$ | H | CH(OCH$_2$C≡CH)CN |

TABLE 2-continued

In the table, the number showing the substitution position of substituent $(X)_m$ corresponds to the position number indicated in the following structural formulae. The indication "—" means no-substitution.

| | | | | |
|---|---|---|---|---|
| 3,5-Cl$_2$ | CF$_3$ | | H | CH(SEt)CN |
| 3,5-Cl$_2$ | CF$_3$ | | H | C(CH$_3$)$_2$CN |
| 3,5-Cl$_2$ | CF$_3$ | | H | CH$_2$C(O)OH |
| 3,5-Cl$_2$ | CF$_3$ | | H | CH$_2$C(O)OCH$_3$ |
| 3,5-Cl$_2$ | CF$_3$ | | H | CH$_2$C(O)OEt |
| 3,5-Cl$_2$ | CF$_3$ | | H | CH$_2$C(O)OPr-i |
| 3,5-Cl$_2$ | CF$_3$ | | H | CH$_2$C(O)OBu-t |
| 3,5-Cl$_2$ | CF$_3$ | | H | CH$_2$C(O)OCH$_2$CF$_3$ |
| 3,5-Cl$_2$ | CF$_3$ | | H | CH(CH$_3$)C(O)OCH$_3$ |
| 3,5-Cl$_2$ | CF$_3$ | | H | CH(CH$_3$)C(O)OCH$_3$(D) |
| 3,5-Cl$_2$ | CF$_3$ | | H | CH(CH$_3$)C(O)OCH$_3$(L) |
| 3,5-Cl$_2$ | CF$_3$ | | H | CH(CH$_3$)C(O)OEt |
| 3,5-Cl$_2$ | CF$_3$ | | H | CH(CH$_3$)C(O)OEt(D) |
| 3,5-Cl$_2$ | CF$_3$ | | H | CH(CH$_3$)C(O)OEt(L) |
| 3,5-Cl$_2$ | CF$_3$ | | H | CH(CH$_3$)C(O)OPr-i(D) |
| 3,5-Cl$_2$ | CF$_3$ | | H | CH(CH$_3$)C(O)OBu-t(D) |
| 3,5-Cl$_2$ | CF$_3$ | | H | CH(CH$_3$)C(O)OCH$_2$CF$_3$(D) |
| 3,5-Cl$_2$ | CF$_3$ | | H | CH(CH$_2$OH)C(O)OCH$_3$ |
| 3,5-Cl$_2$ | CF$_3$ | | H | CH(OH)C(O)OCH$_3$ |
| 3,5-Cl$_2$ | CF$_3$ | | H | CH(OCH$_3$)C(O)OCH$_3$ |
| 3,5-Cl$_2$ | CF$_3$ | | H | CH[C(O)OCH$_3$]$_2$ |
| 3,5-Cl$_2$ | CF$_3$ | | H | CH(Ph)C(O)OCH$_3$ |
| 3,5-Cl$_2$ | CF$_3$ | | H | CH(Ph)C(O)OCH$_3$(R) |
| 3,5-Cl$_2$ | CF$_3$ | | H | CH(Ph)C(O)OCH$_3$(S) |
| 3,5-Cl$_2$ | CF$_3$ | | H | CH(D-14a)C(O)OCH$_3$ |
| 3,5-Cl$_2$ | CF$_3$ | | H | CH$_2$CH$_2$C(O)OCH$_3$ |
| 3,5-Cl$_2$ | CF$_3$ | | H | CH$_2$CH$_2$C(O)OEt |
| 3,5-Cl$_2$ | CF$_3$ | | H | CH$_2$CH(CH$_3$)C(O)OCH$_3$ |
| 3,5-Cl$_2$ | CF$_3$ | | H | CH$_2$CH(CH$_3$)C(O)OEt |
| 3,5-Cl$_2$ | CF$_3$ | | H | CH(CH$_3$)CH$_2$C(O)OEt |
| 3,5-Cl$_2$ | CF$_3$ | | H | CH$_2$CH$_2$CH$_2$C(O)OEt |
| 3,5-Cl$_2$ | CF$_3$ | | H | CH$_2$(E-4b) |
| 3,5-Cl$_2$ | CF$_3$ | | H | CH$_2$(E-5c) |
| 3,5-Cl$_2$ | CF$_3$ | | H | E-4b |
| 3,5-Cl$_2$ | CF$_3$ | | H | E-5b |
| 3,5-Cl$_2$ | CF$_3$ | | H | E-5c |
| 3,5-Cl$_2$ | CF$_3$ | | H | E-25b |
| 3,5-Cl$_2$ | CF$_3$ | | | —CH$_2$OC(O)CH$_2$— |
| 3,5-Cl$_2$ | CF$_3$ | | | —CH$_2$OC(O)CH(CH$_3$)— |
| 3,5-Cl$_2$ | CF$_3$ | | | —CH$_2$OC(O)C(CH$_3$)$_2$— |
| 3,5-Cl$_2$ | CF$_3$ | | H | CH$_2$C(O)SCH$_3$ |
| 3,5-Cl$_2$ | CF$_3$ | | H | CH$_2$C(O)SEt |
| 3,5-Cl$_2$ | CF$_3$ | | H | CH$_2$C(O)SPr-i |
| 3,5-Cl$_2$ | CF$_3$ | | H | CH$_2$(E-7d) |
| 3,5-Cl$_2$ | CF$_3$ | | H | E-7e |
| 3,5-Cl$_2$ | CF$_3$ | | H | CH$_2$C(O)NH$_2$ |
| 3,5-Cl$_2$ | CF$_3$ | | H | CH$_2$C(O)NHCH$_3$ |
| 3,5-Cl$_2$ | CF$_3$ | | CH$_3$ | CH$_2$C(O)NHCH$_3$ |
| 3,5-Cl$_2$ | CF$_3$ | | CH$_2$OCH$_3$ | CH$_2$C(O)NHCH$_3$ |
| 3,5-Cl$_2$ | CF$_3$ | | CH$_2$OC(O)CH$_3$ | CH$_2$C(O)NHCH$_3$ |
| 3,5-Cl$_2$ | CF$_3$ | | CH$_2$CN | CH$_2$C(O)NHCH$_3$ |
| 3,5-Cl$_2$ | CF$_3$ | | C(O)CH$_3$ | CH$_2$C(O)NHCH$_3$ |
| 3,5-Cl$_2$ | CF$_3$ | | C(O)Et | CH$_2$C(O)NHCH$_3$ |
| 3,5-Cl$_2$ | CF$_3$ | | C(O)OCH$_3$ | CH$_2$C(O)NHCH$_3$ |
| 3,5-Cl$_2$ | CF$_3$ | | H | CH$_2$C(O)N(CH$_3$)$_2$ |
| 3,5-Cl$_2$ | CF$_3$ | | CH$_3$ | CH$_2$C(O)N(CH$_3$)$_2$ |
| 3,5-Cl$_2$ | CF$_3$ | | CH$_2$OCH$_3$ | CH$_2$C(O)N(CH$_3$)$_2$ |
| 3,5-Cl$_2$ | CF$_3$ | | CH$_2$OC(O)CH$_3$ | CH$_2$C(O)N(CH$_3$)$_2$ |
| 3,5-Cl$_2$ | CF$_3$ | | CH$_2$CN | CH$_2$C(O)N(CH$_3$)$_2$ |
| 3,5-Cl$_2$ | CF$_3$ | | C(O)CH$_3$ | CH$_2$C(O)N(CH$_3$)$_2$ |
| 3,5-Cl$_2$ | CF$_3$ | | C(O)Et | CH$_2$C(O)N(CH$_3$)$_2$ |
| 3,5-Cl$_2$ | CF$_3$ | | C(O)OCH$_3$ | CH$_2$C(O)N(CH$_3$)$_2$ |
| 3,5-Cl$_2$ | CF$_3$ | | H | CH$_2$C(O)NHEt |
| 3,5-Cl$_2$ | CF$_3$ | | H | CH$_2$C(O)N(CH$_3$)Et |
| 3,5-Cl$_2$ | CF$_3$ | | H | CH$_2$C(O)N(Et)$_2$ |
| 3,5-Cl$_2$ | CF$_3$ | | H | CH$_2$C(O)NHPr-n |
| 3,5-Cl$_2$ | CF$_3$ | | H | CH$_2$C(O)N(CH$_3$)Pr-n |
| 3,5-Cl$_2$ | CF$_3$ | | H | CH$_2$C(O)N(Pr-n)$_2$ |
| 3,5-Cl$_2$ | CF$_3$ | | H | CH$_2$C(O)NHPr-i |
| 3,5-Cl$_2$ | CF$_3$ | | H | CH$_2$C(O)N(CH$_3$)Pr-i |
| 3,5-Cl$_2$ | CF$_3$ | | H | CH$_2$C(O)NHPr-c |
| 3,5-Cl$_2$ | CF$_3$ | | H | CH$_2$C(O)NHBu-n |
| 3,5-Cl$_2$ | CF$_3$ | | H | CH$_2$C(O)NHBu-i |
| 3,5-Cl$_2$ | CF$_3$ | | H | CH$_2$C(O)NHCH$_2$Pr-c |
| 3,5-Cl$_2$ | CF$_3$ | | H | CH$_2$C(O)NHBu-s |
| 3,5-Cl$_2$ | CF$_3$ | | H | CH$_2$C(O)NHBu-c |
| 3,5-Cl$_2$ | CF$_3$ | | H | CH$_2$C(O)NHBu-t |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$C(O)NHCH$_2$Bu-t |
| 3,5-Cl$_2$ | CF$_3$ | H | CH$_2$C(O)NHCH$_2$CH$_2$F |
| 3,5-Cl$_2$ | CF$_3$ | H | CH$_2$C(O)N(CH$_3$)CH$_2$CH$_2$F |
| 3,5-Cl$_2$ | CF$_3$ | H | CH$_2$C(O)NHCH$_2$CH$_2$Cl |
| 3,5-Cl$_2$ | CF$_3$ | CH$_3$ | CH$_2$C(O)NHCH$_2$CH$_2$Cl |
| 3,5-Cl$_2$ | CF$_3$ | CH$_2$OCH$_3$ | CH$_2$C(O)NHCH$_2$CH$_2$Cl |
| 3,5-Cl$_2$ | CF$_3$ | CH$_2$OC(O)CH$_3$ | CH$_2$C(O)NHCH$_2$CH$_2$Cl |
| 3,5-Cl$_2$ | CF$_3$ | CH$_2$CN | CH$_2$C(O)NHCH$_2$CH$_2$Cl |
| 3,5-Cl$_2$ | CF$_3$ | C(O)CH$_3$ | CH$_2$C(O)NHCH$_2$CH$_2$Cl |
| 3,5-Cl$_2$ | CF$_3$ | C(O)Et | CH$_2$C(O)NHCH$_2$CH$_2$Cl |
| 3,5-Cl$_2$ | CF$_3$ | C(O)OCH$_3$ | CH$_2$C(O)NHCH$_2$CH$_2$Cl |
| 3,5-Cl$_2$ | CF$_3$ | H | CH$_2$C(O)N(CH$_3$)CH$_2$CH$_2$Cl |
| 3,5-Cl$_2$ | CF$_3$ | H | CH$_2$C(O)NHCH$_2$CH$_2$Br |
| 3,5-Cl$_2$ | CF$_3$ | H | CH$_2$C(O)NHCH$_2$CHF$_2$ |
| 3,5-Cl$_2$ | CF$_3$ | H | CH$_2$C(O)NHCH$_2$CF$_3$ |
| 3,5-Cl$_2$ | CF$_3$ | CH$_3$ | CH$_2$C(O)NHCH$_2$CF$_3$ |
| 3,5-Cl$_2$ | CF$_3$ | CH$_2$OCH$_3$ | CH$_2$C(O)NHCH$_2$CF$_3$ |
| 3,5-Cl$_2$ | CF$_3$ | CH$_2$OEt | CH$_2$C(O)NHCH$_2$CF$_3$ |
| 3,5-Cl$_2$ | CF$_3$ | CH$_2$OCH$_2$CF$_3$ | CH$_2$C(O)NHCH$_2$CF$_3$ |
| 3,5-Cl$_2$ | CF$_3$ | CH$_2$OC(O)CH$_3$ | CH$_2$C(O)NHCH$_2$CF$_3$ |
| 3,5-Cl$_2$ | CF$_3$ | CH$_2$CN | CH$_2$C(O)NHCH$_2$CF$_3$ |
| 3,5-Cl$_2$ | CF$_3$ | CH$_2$C≡CH | CH$_2$C(O)NHCH$_2$CF$_3$ |
| 3,5-Cl$_2$ | CF$_3$ | C(O)CH$_3$ | CH$_2$C(O)NHCH$_2$CF$_3$ |
| 3,5-Cl$_2$ | CF$_3$ | C(O)Et | CH$_2$C(O)NHCH$_2$CF$_3$ |
| 3,5-Cl$_2$ | CF$_3$ | C(O)OCH$_3$ | CH$_2$C(O)NHCH$_2$CF$_3$ |
| 3,5-Cl$_2$ | CF$_3$ | C(O)NH$_2$ | CH$_2$C(O)NHCH$_2$CF$_3$ |
| 3,5-Cl$_2$ | CF$_3$ | C(S)NH$_2$ | CH$_2$C(O)NHCH$_2$CF$_3$ |
| 3,5-Cl$_2$ | CF$_3$ | H | CH$_2$C(O)N(CH$_3$)CH$_2$CF$_3$ |
| 3,5-Cl$_2$ | CF$_3$ | H | CH$_2$C(O)NHCH$_2$CCl$_3$ |
| 3,5-Cl$_2$ | CF$_3$ | H | CH$_2$C(O)NHCF$_2$CF$_3$ |
| 3,5-Cl$_2$ | CF$_3$ | H | CH$_2$C(O)NHCH$_2$CH$_2$CH$_2$Cl |
| 3,5-Cl$_2$ | CF$_3$ | H | CH$_2$C(O)NHCH(CH$_3$)CF$_3$ |
| 3,5-Cl$_2$ | CF$_3$ | H | CH$_2$C(O)NHCH(CF$_3$)$_2$ |
| 3,5-Cl$_2$ | CF$_3$ | H | CH$_2$C(O)NHCH$_2$(T-3) |
| 3,5-Cl$_2$ | CF$_3$ | H | CH$_2$C(O)NHCH$_2$(T-4) |
| 3,5-Cl$_2$ | CF$_3$ | H | CH$_2$C(O)NHCH$_2$(T-5) |
| 3,5-Cl$_2$ | CF$_3$ | H | CH$_2$C(O)NHCH$_2$CH$_2$OH |
| 3,5-Cl$_2$ | CF$_3$ | H | CH$_2$C(O)N(CH$_3$)CH$_2$CH$_2$OH |
| 3,5-Cl$_2$ | CF$_3$ | H | CH$_2$C(O)NHCH$_2$CH$_2$OCH$_3$ |
| 3,5-Cl$_2$ | CF$_3$ | H | CH$_2$C(O)NHCH$_2$CH$_2$OEt |
| 3,5-Cl$_2$ | CF$_3$ | H | CH$_2$C(O)NHCH$_2$CH$_2$OCH$_2$CF$_3$ |
| 3,5-Cl$_2$ | CF$_3$ | H | CH$_2$C(O)NHCH(CH$_3$)CH$_2$OCH$_3$ |
| 3,5-Cl$_2$ | CF$_3$ | H | CH$_2$C(O)NHCH$_2$CH(OCH$_3$)$_2$ |
| 3,5-Cl$_2$ | CF$_3$ | H | CH$_2$C(O)NHCH$_2$CH(OEt)$_2$ |
| 3,5-Cl$_2$ | CF$_3$ | H | CH$_2$C(O)NHCH$_2$(E-10a) |
| 3,5-Cl$_2$ | CF$_3$ | H | CH$_2$C(O)NH(E-4a) |
| 3,5-Cl$_2$ | CF$_3$ | H | CH$_2$C(O)NHCH$_2$CH$_2$SCH$_3$ |
| 3,5-Cl$_2$ | CF$_3$ | H | CH$_2$C(O)NHCH$_2$CH$_2$SO$_2$CH$_3$ |
| 3,5-Cl$_2$ | CF$_3$ | H | CH$_2$C(O)NHCH(CH$_3$)CH$_2$SCH$_3$ |
| 3,5-Cl$_2$ | CF$_3$ | H | CH$_2$C(O)NHCH(CH$_3$)CH$_2$SO$_2$CH$_3$ |
| 3,5-Cl$_2$ | CF$_3$ | H | CH$_2$C(O)NHCH$_2$CN |
| 3,5-Cl$_2$ | CF$_3$ | H | CH$_2$C(O)NHCH$_2$C(O)NH$_2$ |
| 3,5-Cl$_2$ | CF$_3$ | H | CH$_2$C(O)NHCH$_2$C(O)NHCH$_3$ |
| 3,5-Cl$_2$ | CF$_3$ | H | CH$_2$C(O)NHCH$_2$C(O)NHEt |
| 3,5-Cl$_2$ | CF$_3$ | H | CH$_2$C(O)NHCH$_2$C(O)NHCH$_2$CF$_3$ |
| 3,5-Cl$_2$ | CF$_3$ | H | CH$_2$C(O)NHCH$_2$C(S)NH$_2$ |
| 3,5-Cl$_2$ | CF$_3$ | H | CH$_2$C(O)NHCH$_2$CH=CH$_2$ |
| 3,5-Cl$_2$ | CF$_3$ | H | CH$_2$C(O)N(CH$_3$)CH$_2$CH=CH$_2$ |
| 3,5-Cl$_2$ | CF$_3$ | H | CH$_2$C(O)N(CH$_2$CH=CH$_2$)$_2$ |
| 3,5-Cl$_2$ | CF$_3$ | H | CH$_2$C(O)NHCH$_2$CCl=CH$_2$ |
| 3,5-Cl$_2$ | CF$_3$ | H | CH$_2$C(O)NHCH$_2$CBr=CH$_2$ |
| 3,5-Cl$_2$ | CF$_3$ | H | CH$_2$C(O)NHCH$_2$CH=CCl$_2$ |
| 3,5-Cl$_2$ | CF$_3$ | H | CH$_2$C(O)NHCH$_2$CF=CF$_2$ |
| 3,5-Cl$_2$ | CF$_3$ | H | CH$_2$C(O)NHCH$_2$C≡CH |
| 3,5-Cl$_2$ | CF$_3$ | H | CH$_2$C(O)N(CH$_3$)CH$_2$C≡CH |
| 3,5-Cl$_2$ | CF$_3$ | H | CH$_2$C(O)NHCH$_2$Ph |
| 3,5-Cl$_2$ | CF$_3$ | H | CH$_2$C(O)NHCH$_2$(Ph-4-F) |
| 3,5-Cl$_2$ | CF$_3$ | H | CH$_2$C(O)NHCH$_2$(Ph-4-CN) |
| 3,5-Cl$_2$ | CF$_3$ | H | CH$_2$C(O)NHCH$_2$(Ph-4-NO$_2$) |
| 3,5-Cl$_2$ | CF$_3$ | H | CH$_2$C(O)NHCH$_2$(D-22a) |
| 3,5-Cl$_2$ | CF$_3$ | H | CH$_2$C(O)NHCH$_2$(D-47a) |
| 3,5-Cl$_2$ | CF$_3$ | H | CH$_2$C(O)(T-33) |
| 3,5-Cl$_2$ | CF$_3$ | H | CH$_2$C(O)(T-35) |
| 3,5-Cl$_2$ | CF$_3$ | H | CH$_2$C(O)(T-37) |
| 3,5-Cl$_2$ | CF$_3$ | H | CH$_2$C(O)(T-39) |
| 3,5-Cl$_2$ | CF$_3$ | H | CH$_2$C(O)(T-40) |
| 3,5-Cl$_2$ | CF$_3$ | H | CH$_2$C(O)(T-41) |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | H | CH$_2$C(O)NHOEt |
| 3,5-Cl$_2$ | CF$_3$ | H | CH$_2$C(O)NHOPr-n |
| 3,5-Cl$_2$ | CF$_3$ | H | CH$_2$C(O)NHOCH$_2$CH=CH$_2$ |
| 3,5-Cl$_2$ | CF$_3$ | H | CH$_2$C(O)NHNHCH$_2$CF$_3$ |
| 3,5-Cl$_2$ | CF$_3$ | H | CH$_2$C(O)NHN(CH$_3$)Ph |
| 3,5-Cl$_2$ | CF$_3$ | H | CH$_2$C(O)NHPh |
| 3,5-Cl$_2$ | CF$_3$ | H | CH$_2$C(O)NH(Ph-4-F) |
| 3,5-Cl$_2$ | CF$_3$ | H | CH$_2$C(O)NH(Ph-4-CN) |
| 3,5-Cl$_2$ | CF$_3$ | H | CH$_2$C(O)NH(Ph-4-NO$_2$) |
| 3,5-Cl$_2$ | CF$_3$ | H | CH(CH$_3$)C(O)NH$_2$ |
| 3,5-Cl$_2$ | CF$_3$ | H | CH(CH$_3$)C(O)NHCH$_3$ |
| 3,5-Cl$_2$ | CF$_3$ | H | CH(CH$_3$)C(O)NHCH$_3$(D) |
| 3,5-Cl$_2$ | CF$_3$ | H | CH(CH$_3$)C(O)NHCH$_3$(L) |
| 3,5-Cl$_2$ | CF$_3$ | H | CH(CH$_3$)C(O)N(CH$_3$)2(D) |
| 3,5-Cl$_2$ | CF$_3$ | H | CH(CH$_3$)C(O)NHEt |
| 3,5-Cl$_2$ | CF$_3$ | CH$_2$OCH$_3$ | CH(CH$_3$)C(O)NHEt |
| 3,5-Cl$_2$ | CF$_3$ | CH$_2$OC(O)CH$_3$ | CH(CH$_3$)C(O)NHEt |
| 3,5-Cl$_2$ | CF$_3$ | CH$_2$CN | CH(CH$_3$)C(O)NHEt |
| 3,5-Cl$_2$ | CF$_3$ | C(O)CH$_3$ | CH(CH$_3$)C(O)NHEt |
| 3,5-Cl$_2$ | CF$_3$ | C(O)Et | CH(CH$_3$)C(O)NHEt |
| 3,5-Cl$_2$ | CF$_3$ | C(O)OCH$_3$ | CH(CH$_3$)C(O)NHEt |
| 3,5-Cl$_2$ | CF$_3$ | H | CH(CH$_3$)C(O)NHPr-n |
| 3,5-Cl$_2$ | CF$_3$ | H | CH(CH$_3$)C(O)NHPr-i |
| 3,5-Cl$_2$ | CF$_3$ | H | CH(CH$_3$)C(O)NHPr-c |
| 3,5-Cl$_2$ | CF$_3$ | H | CH(CH$_3$)C(O)NHCH$_2$CH$_2$F |
| 3,5-Cl$_2$ | CF$_3$ | H | CH(CH$_3$)C(O)NHCH$_2$CH$_2$F(D) |
| 3,5-Cl$_2$ | CF$_3$ | H | CH(CH$_3$)C(O)NHCH$_2$CH$_2$Cl |
| 3,5-Cl$_2$ | CF$_3$ | H | CH(CH$_3$)C(O)NHCH$_2$CH$_2$Cl(D) |
| 3,5-Cl$_2$ | CF$_3$ | H | CH(CH$_3$)C(O)NHCH$_2$CF$_3$ |
| 3,5-Cl$_2$ | CF$_3$ | CH$_3$ | CH(CH$_3$)C(O)NHCH$_2$CF$_3$ |
| 3,5-Cl$_2$ | CF$_3$ | CH$_2$OCH$_3$ | CH(CH$_3$)C(O)NHCH$_2$CF$_3$ |
| 3,5-Cl$_2$ | CF$_3$ | CH$_2$OEt | CH(CH$_3$)C(O)NHCH$_2$CF$_3$ |
| 3,5-Cl$_2$ | CF$_3$ | CH$_2$OCH$_2$CF$_3$ | CH(CH$_3$)C(O)NHCH$_2$CF$_3$ |
| 3,5-Cl$_2$ | CF$_3$ | CH$_2$OC(O)CH$_3$ | CH(CH$_3$)C(O)NHCH$_2$CF$_3$ |
| 3,5-Cl$_2$ | CF$_3$ | CH$_2$CN | CH(CH$_3$)C(O)NHCH$_2$CF$_3$ |
| 3,5-Cl$_2$ | CF$_3$ | CH$_2$C≡CH | CH(CH$_3$)C(O)NHCH$_2$CF$_3$ |
| 3,5-Cl$_2$ | CF$_3$ | C(O)CH$_3$ | CH(CH$_3$)C(O)NHCH$_2$CF$_3$ |
| 3,5-Cl$_2$ | CF$_3$ | C(O)Et | CH(CH$_3$)C(O)NHCH$_2$CF$_3$ |
| 3,5-Cl$_2$ | CF$_3$ | C(O)OCH$_3$ | CH(CH$_3$)C(O)NHCH$_2$CF$_3$ |
| 3,5-Cl$_2$ | CF$_3$ | C(O)NH$_2$ | CH(CH$_3$)C(O)NHCH$_2$CF$_3$ |
| 3,5-Cl$_2$ | CF$_3$ | C(S)NH$_2$ | CH(CH$_3$)C(O)NHCH$_2$CF$_3$ |
| 3,5-Cl$_2$ | CF$_3$ | H | CH(CH$_3$)C(O)NHCH$_2$CF$_3$(D) |
| 3,5-Cl$_2$ | CF$_3$ | H | CH(CH$_3$)C(O)NHCH$_2$CH=CH$_2$ |
| 3,5-Cl$_2$ | CF$_3$ | H | CH(CH$_3$)C(O)NHCH$_2$CH=CH$_2$(D) |
| 3,5-Cl$_2$ | CF$_3$ | H | CH(CH$_3$)C(O)NHCH$_2$C≡CH |
| 3,5-Cl$_2$ | CF$_3$ | H | CH(CH$_3$)C(O)NHCH$_2$C≡CH(D) |
| 3,5-Cl$_2$ | CF$_3$ | H | CH(Et)C(O)NHEt |
| 3,5-Cl$_2$ | CF$_3$ | H | CH(Et)C(O)NHCH$_2$CH$_2$Cl |
| 3,5-Cl$_2$ | CF$_3$ | H | CH(Et)C(O)NHCH$_2$CF$_3$ |
| 3,5-Cl$_2$ | CF$_3$ | H | CH(Pr-n)C(O)NHEt |
| 3,5-Cl$_2$ | CF$_3$ | H | CH(Pr-i)C(O)NHEt |
| 3,5-Cl$_2$ | CF$_3$ | H | CH(Pr-i)C(O)NHCH$_2$CH$_2$Cl |
| 3,5-Cl$_2$ | CF$_3$ | H | CH(Pr-i)C(O)NHCH$_2$CF$_3$ |
| 3,5-Cl$_2$ | CF$_3$ | H | CH(Bu-s)C(O)NHCH$_2$CF$_3$ |
| 3,5-Cl$_2$ | CF$_3$ | H | CH(CHFCH$_3$)C(O)NHEt |
| 3,5-Cl$_2$ | CF$_3$ | H | CH(CHFCH$_3$)C(O)NHCH$_2$CF$_3$ |
| 3,5-Cl$_2$ | CF$_3$ | H | CH(CH$_2$OCH$_3$)C(O)NHEt |
| 3,5-Cl$_2$ | CF$_3$ | H | CH(CH$_2$OCH$_3$)C(O)NHCH$_2$CF$_3$ |
| 3,5-Cl$_2$ | CF$_3$ | H | CH(CH$_2$SCH$_3$)C(O)NHEt |
| 3,5-Cl$_2$ | CF$_3$ | H | CH(CH$_2$SCH$_3$)C(O)NHCH$_2$CF$_3$ |
| 3,5-Cl$_2$ | CF$_3$ | H | CH[C(O)NHCH$_3$]$_2$ |
| 3,5-Cl$_2$ | CF$_3$ | H | CH(Ph)C(O)NHCH$_3$ |
| 3,5-Cl$_2$ | CF$_3$ | H | CH(Ph)C(O)NHCH$_3$(D) |
| 3,5-Cl$_2$ | CF$_3$ | H | CH(Ph)C(O)NHCH$_3$(L) |
| 3,5-Cl$_2$ | CF$_3$ | H | CH$_2$CH$_2$C(O)NHCH$_2$CH$_2$Cl |
| 3,5-Cl$_2$ | CF$_3$ | H | CH$_2$CH(CH$_3$)C(O)NHCH$_3$ |
| 3,5-Cl$_2$ | CF$_3$ | H | CH$_2$CH(CH$_3$)C(O)N(CH$_3$)$_2$ |
| 3,5-Cl$_2$ | CF$_3$ | H | CH$_2$CH(CH$_3$)C(O)NHEt |
| 3,5-Cl$_2$ | CF$_3$ | H | CH$_2$CH(CH$_3$)C(O)N(Et)$_2$ |
| 3,5-Cl$_2$ | CF$_3$ | H | CH$_2$CH(CH$_3$)C(O)NHCH$_2$CF$_3$ |
| 3,5-Cl$_2$ | CF$_3$ | H | CH$_2$CH(CH$_3$)C(O)N(CH$_3$)Ph |
| 3,5-Cl$_2$ | CF$_3$ | H | CH(CH$_3$)CH$_2$C(O)NHCH$_3$ |
| 3,5-Cl$_2$ | CF$_3$ | H | CH(CH$_3$)CH$_2$C(O)NHCH$_2$CF$_3$ |
| 3,5-Cl$_2$ | CF$_3$ | H | CH$_2$CH$_2$CH$_2$C(O)NHCH$_2$CF$_3$ |
| 3,5-Cl$_2$ | CF$_3$ | H | CH$_2$(E-9b)H |
| 3,5-Cl$_2$ | CF$_3$ | H | CH$_2$(E-30b)H |
| 3,5-Cl$_2$ | CF$_3$ | H | (E-9b)H |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-$Cl_2$ | $CF_3$ | H | (E-9b)$CH_2CF_3$ |
| 3,5-$Cl_2$ | $CF_3$ | H | (E-9b)$CH_2C(O)OCH_3$ |
| 3,5-$Cl_2$ | $CF_3$ | H | (E-30b)H |
| 3,5-$Cl_2$ | $CF_3$ | H | (E-30b)$CH_2C(O)NH_2$ |
| 3,5-$Cl_2$ | $CF_3$ | H | (E-30b)$OCH_2Ph$ |
| 3,5-$Cl_2$ | $CF_3$ | H | (E-31b)H |
| 3,5-$Cl_2$ | $CF_3$ | H | (E-31b)$CH_2C(O)OEt$ |
| 3,5-$Cl_2$ | $CF_3$ | | —$CH_2NHC(O)CH_2$— |
| 3,5-$Cl_2$ | $CF_3$ | | —$CH_2N(CH_3)C(O)CH_2$— |
| 3,5-$Cl_2$ | $CF_3$ | | —$CH(CH_3)N(CH_3)C(O)CH_2$— |
| 3,5-$Cl_2$ | $CF_3$ | | —$C(CH_3)_2N(CH_3)C(O)CH_2$— |
| 3,5-$Cl_2$ | $CF_3$ | H | $CH_2C(OCH_3)$=NH |
| 3,5-$Cl_2$ | $CF_3$ | H | $CH_2C(OEt)$=NH |
| 3,5-$Cl_2$ | $CF_3$ | H | $CH_2C(OEt)$=$NCH_3$ |
| 3,5-$Cl_2$ | $CF_3$ | H | $CH_2C(OCH_2CF_3)$=NH |
| 3,5-$Cl_2$ | $CF_3$ | H | $CH_2$(T-22) |
| 3,5-$Cl_2$ | $CF_3$ | H | $CH_2$(T-23) |
| 3,5-$Cl_2$ | $CF_3$ | H | $CH_2$(T-24) |
| 3,5-$Cl_2$ | $CF_3$ | H | $CH_2$(T-29) |
| 3,5-$Cl_2$ | $CF_3$ | H | $CH_2$(M-8a)H |
| 3,5-$Cl_2$ | $CF_3$ | H | $CH_2$(M-8a)$CH_3$ |
| 3,5-$Cl_2$ | $CF_3$ | H | $CH_2$(M-8a)$CF_3$ |
| 3,5-$Cl_2$ | $CF_3$ | H | $CH_2$(M-9a)H |
| 3,5-$Cl_2$ | $CF_3$ | H | $CH_2$(M-9a)$CH_3$ |
| 3,5-$Cl_2$ | $CF_3$ | H | $CH_2$(M-9a)$CF_3$ |
| 3,5-$Cl_2$ | $CF_3$ | H | $CH_2$(M-15a)H |
| 3,5-$Cl_2$ | $CF_3$ | H | $CH_2$(M-15a)$CH_3$ |
| 3,5-$Cl_2$ | $CF_3$ | H | $CH_2$(M-15a)$CF_3$ |
| 3,5-$Cl_2$ | $CF_3$ | H | $CH_2$(M-16a)H |
| 3,5-$Cl_2$ | $CF_3$ | H | $CH_2$(M-16a)$CH_3$ |
| 3,5-$Cl_2$ | $CF_3$ | H | $CH_2$(M-16a)$CF_3$ |
| 3,5-$Cl_2$ | $CF_3$ | H | $CH_2C(S)OCH_3$ |
| 3,5-$Cl_2$ | $CF_3$ | H | $CH_2C(S)OEt$ |
| 3,5-$Cl_2$ | $CF_3$ | H | $CH(CH_3)C(S)OCH_3$ |
| 3,5-$Cl_2$ | $CF_3$ | H | $CH_2C(S)SCH_3$ |
| 3,5-$Cl_2$ | $CF_3$ | H | $CH_2C(S)SEt$ |
| 3,5-$Cl_2$ | $CF_3$ | H | $CH(CH_3)C(S)SCH_3$ |
| 3,5-$Cl_2$ | $CF_3$ | H | $CH_2C(S)NH_2$ |
| 3,5-$Cl_2$ | $CF_3$ | H | $CH_2C(S)NHCH_3$ |
| 3,5-$Cl_2$ | $CF_3$ | H | $CH_2C(S)NHEt$ |
| 3,5-$Cl_2$ | $CF_3$ | H | $CH_2C(S)NHPr$-i |
| 3,5-$Cl_2$ | $CF_3$ | H | $CH_2C(S)NHCH_2CF_3$ |
| 3,5-$Cl_2$ | $CF_3$ | H | $CH(CH_3)C(S)NH_2$ |
| 3,5-$Cl_2$ | $CF_3$ | H | $CH(CH_3)C(S)NHCH_3$ |
| 3,5-$Cl_2$ | $CF_3$ | H | $CH(CH_3)C(S)NHEt$ |
| 3,5-$Cl_2$ | $CF_3$ | H | $CH(CH_3)C(S)NHPr$-i |
| 3,5-$Cl_2$ | $CF_3$ | H | $CH(CH_3)C(S)NHCH_2CF_3$ |
| 3,5-$Cl_2$ | $CF_3$ | H | $CH_2C(SCH_3)$=NH |
| 3,5-$Cl_2$ | $CF_3$ | H | $CH_2C(SCH_3)$=$NCH_3$ |
| 3,5-$Cl_2$ | $CF_3$ | H | $CH_2C(SCH_3)$=$NCH_2CF_3$ |
| 3,5-$Cl_2$ | $CF_3$ | H | $CH(Ph)C(S)NH_2$ |
| 3,5-$Cl_2$ | $CF_3$ | H | $CH_2$(T-25) |
| 3,5-$Cl_2$ | $CF_3$ | H | $CH_2$(T-26) |
| 3,5-$Cl_2$ | $CF_3$ | H | $CH_2$(T-27) |
| 3,5-$Cl_2$ | $CF_3$ | H | $CH_2$(T-30) |
| 3,5-$Cl_2$ | $CF_3$ | H | $CH_2$(M-10a)H |
| 3,5-$Cl_2$ | $CF_3$ | H | $CH_2$(M-10a)$CH_3$ |
| 3,5-$Cl_2$ | $CF_3$ | H | $CH_2$(M-10a)$CF_3$ |
| 3,5-$Cl_2$ | $CF_3$ | H | $CH_2C(NH_2)$=NH |
| 3,5-$Cl_2$ | $CF_3$ | H | $CH_2$(T-28) |
| 3,5-$Cl_2$ | $CF_3$ | H | $CH_2$(T-31) |
| 3,5-$Cl_2$ | $CF_3$ | H | $CH_2C(NH_2)$=NOH |
| 3,5-$Cl_2$ | $CF_3$ | H | $CH_2C(NH_2)$=$NOCH_3$ |
| 3,5-$Cl_2$ | $CF_3$ | H | $CH_2SO_2OH$ |
| 3,5-$Cl_2$ | $CF_3$ | H | $CH_2SO_2NH_2$ |
| 3,5-$Cl_2$ | $CF_3$ | H | $CH_2SO_2NHCH_3$ |
| 3,5-$Cl_2$ | $CF_3$ | H | $CH_2SO_2N(CH_3)_2$ |
| 3,5-$Cl_2$ | $CF_3$ | H | $CH_2SO_2NHEt$ |
| 3,5-$Cl_2$ | $CF_3$ | H | $CH_2SO_2NHPr$-n |
| 3,5-$Cl_2$ | $CF_3$ | H | $CH_2SO_2NHPr$-i |
| 3,5-$Cl_2$ | $CF_3$ | H | $CH_2SO_2NHPr$-c |
| 3,5-$Cl_2$ | $CF_3$ | H | $CH_2SO_2NHBu$-t |
| 3,5-$Cl_2$ | $CF_3$ | H | $CH_2SO_2NHCH_2CH_2F$ |
| 3,5-$Cl_2$ | $CF_3$ | H | $CH_2SO_2NHCH_2CH_2Cl$ |
| 3,5-$Cl_2$ | $CF_3$ | H | $CH_2SO_2NHCH_2CF_3$ |
| 3,5-$Cl_2$ | $CF_3$ | H | $CH_2SO_2NHCH_2CH_2OCH_3$ |
| 3,5-$Cl_2$ | $CF_3$ | H | $CH_2SO_2NHCH_2CH(OCH_3)_2$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$SO$_2$NHCH$_2$CH(E-10a) |
| 3,5-Cl$_2$ | CF$_3$ | H | CH$_2$SO$_2$NHCH(CH$_3$)CH$_2$OCH$_3$ |
| 3,5-Cl$_2$ | CF$_3$ | H | CH$_2$SO$_2$NHCH$_2$CH$_2$SCH$_3$ |
| 3,5-Cl$_2$ | CF$_3$ | H | CH$_2$SO$_2$NHCH(CH$_3$)CH$_2$SCH$_3$ |
| 3,5-Cl$_2$ | CF$_3$ | H | CH$_2$SO$_2$NHCH$_2$CH$_2$SO$_2$CH$_3$ |
| 3,5-Cl$_2$ | CF$_3$ | H | CH$_2$SO$_2$NHCH(CH$_3$)CH$_2$SO$_2$CH$_3$ |
| 3,5-Cl$_2$ | CF$_3$ | H | CH$_2$SO$_2$NHCH$_2$CH$_2$CH$_2$SCH$_3$ |
| 3,5-Cl$_2$ | CF$_3$ | H | CH$_2$SO$_2$NHCH$_2$CH=CH$_2$ |
| 3,5-Cl$_2$ | CF$_3$ | H | CH$_2$SO$_2$NHCH$_2$Ph |
| 3,5-Cl$_2$ | CF$_3$ | H | CH$_2$SO$_2$NHCH$_2$(D-47a) |
| 3,5-Cl$_2$ | CF$_3$ | H | CH$_2$SO$_2$NHPh |
| 3,5-Cl$_2$ | CF$_3$ | H | CH$_2$CH$_2$SO$_2$NHCH$_3$ |
| 3,5-Cl$_2$ | CF$_3$ | H | CH$_2$CH$_2$SO$_2$N(CH$_3$)$_2$ |
| 3,5-Cl$_2$ | CF$_3$ | H | CH$_2$CH$_2$SO$_2$NHEt |
| 3,5-Cl$_2$ | CF$_3$ | H | CH$_2$CH$_2$SO$_2$N(Et)$_2$ |
| 3,5-Cl$_2$ | CF$_3$ | H | CH$_2$CH$_2$SO$_2$NHPr-n |
| 3,5-Cl$_2$ | CF$_3$ | H | CH$_2$CH$_2$SO$_2$NHPr-i |
| 3,5-Cl$_2$ | CF$_3$ | H | CH$_2$CH$_2$SO$_2$N(Pr-i)$_2$ |
| 3,5-Cl$_2$ | CF$_3$ | H | CH$_2$CH$_2$SO$_2$NHPr-c |
| 3,5-Cl$_2$ | CF$_3$ | H | CH$_2$CH$_2$SO$_2$NHBu-t |
| 3,5-Cl$_2$ | CF$_3$ | H | CH$_2$CH$_2$SO$_2$NHCH$_2$CF$_3$ |
| 3,5-Cl$_2$ | CF$_3$ | H | CH$_2$CH$_2$SO$_2$NHCH$_2$CH$_2$OCH$_3$ |
| 3,5-Cl$_2$ | CF$_3$ | H | CH$_2$CH$_2$SO$_2$NHCH$_2$CH$_2$SCH$_3$ |
| 3,5-Cl$_2$ | CF$_3$ | H | CH$_2$CH$_2$SO$_2$NHCH$_2$CH$_2$CH$_2$SCH$_3$ |
| 3,5-Cl$_2$ | CF$_3$ | H | CH$_2$CH$_2$SO$_2$NHCH$_2$CH=CH$_2$ |
| 3,5-Cl$_2$ | CF$_3$ | H | CH$_2$CH$_2$SO$_2$NHCH$_2$Ph |
| 3,5-Cl$_2$ | CF$_3$ | H | CH$_2$CH$_2$SO$_2$NHCH$_2$(D-47a) |
| 3,5-Cl$_2$ | CF$_3$ | H | CH$_2$CH$_2$SO$_2$NHCH$_2$(D-48a) |
| 3,5-Cl$_2$ | CF$_3$ | H | CH$_2$CH$_2$SO$_2$NHCH$_2$(D-49a) |
| 3,5-Cl$_2$ | CF$_3$ | H | CH$_2$CH$_2$SO$_2$NHPh |
| 3,5-Cl$_2$ | CF$_3$ | H | CH$_2$CH$_2$SO$_2$N(CH$_3$)Ph |
| 3,5-Cl$_2$ | CF$_3$ | H | CH$_2$CH$_2$SO$_2$(T-33) |
| 3,5-Cl$_2$ | CF$_3$ | H | CH$_2$CH$_2$SO$_2$(T-39) |
| 3,5-Cl$_2$ | CF$_3$ | H | CH$_2$CH$_2$SO$_2$(T-40) |
| 3,5-Cl$_2$ | CF$_3$ | H | CH$_2$CH$_2$SO$_2$(T-41) |
| 3,5-Cl$_2$ | CF$_3$ | H | CH=CH$_2$ |
| 3,5-Cl$_2$ | CF$_3$ | H | CH$_2$CH=CH$_2$ |
| 3,5-Cl$_2$ | CF$_3$ | Et | CH$_2$CH=CH$_2$ |
| 3,5-Cl$_2$ | CF$_3$ | CH$_2$OCH$_3$ | CH$_2$CH=CH$_2$ |
| 3,5-Cl$_2$ | CF$_3$ | CH$_2$OEt | CH$_2$CH=CH$_2$ |
| 3,5-Cl$_2$ | CF$_3$ | CH$_2$OCH$_2$CF$_3$ | CH$_2$CH=CH$_2$ |
| 3,5-Cl$_2$ | CF$_3$ | CH$_2$OC(O)CH$_3$ | CH$_2$CH=CH$_2$ |
| 3,5-Cl$_2$ | CF$_3$ | CH$_2$CN | CH$_2$CH=CH$_2$ |
| 3,5-Cl$_2$ | CF$_3$ | CH$_2$C≡CH | CH$_2$CH=CH$_2$ |
| 3,5-Cl$_2$ | CF$_3$ | C(O)CH$_3$ | CH$_2$CH=CH$_2$ |
| 3,5-Cl$_2$ | CF$_3$ | C(O)Et | CH$_2$CH=CH$_2$ |
| 3,5-Cl$_2$ | CF$_3$ | C(O)Pr-i | CH$_2$CH=CH$_2$ |
| 3,5-Cl$_2$ | CF$_3$ | C(O)OCH$_3$ | CH$_2$CH=CH$_2$ |
| 3,5-Cl$_2$ | CF$_3$ | C(O)OEt | CH$_2$CH=CH$_2$ |
| 3,5-Cl$_2$ | CF$_3$ | C(O)OPr-i | CH$_2$CH=CH$_2$ |
| 3,5-Cl$_2$ | CF$_3$ | H | CH$_2$CH=CHCH$_3$ |
| 3,5-Cl$_2$ | CF$_3$ | H | CH$_2$C(CH$_3$)=CH$_2$ |
| 3,5-Cl$_2$ | CF$_3$ | CH$_3$ | CH$_2$C(CH$_3$)=CH$_2$ |
| 3,5-Cl$_2$ | CF$_3$ | Et | CH$_2$C(CH$_3$)=CH$_2$ |
| 3,5-Cl$_2$ | CF$_3$ | H | CH$_2$C(Et)=CH$_2$ |
| 3,5-Cl$_2$ | CF$_3$ | H | C(CH$_3$)$_2$CH=CH$_2$ |
| 3,5-Cl$_2$ | CF$_3$ | H | CH$_2$C(CH$_3$)=CHCH$_3$ |
| 3,5-Cl$_2$ | CF$_3$ | H | CH$_2$CH=C(CH$_3$)$_2$ |
| 3,5-Cl$_2$ | CF$_3$ | H | CH$_2$C(Et)=CHCH$_3$ |
| 3,5-Cl$_2$ | CF$_3$ | H | CH$_2$CH=CHEt |
| 3,5-Cl$_2$ | CF$_3$ | H | CH$_2$C(CH$_3$)=CHEt |
| 3,5-Cl$_2$ | CF$_3$ | H | CH$_2$CH=CHPr-n |
| 3,5-Cl$_2$ | CF$_3$ | H | CH$_2$CH=CHBu-n |
| 3,5-Cl$_2$ | CF$_3$ | H | CH$_2$(T-17) |
| 3,5-Cl$_2$ | CF$_3$ | H | CH$_2$(T-18) |
| 3,5-Cl$_2$ | CF$_3$ | H | CH$_2$C(CH$_3$)=CHCH(CH$_3$)CH$_2$CH=CH$_2$ |
| 3,5-Cl$_2$ | CF$_3$ | H | CH$_2$CH=C(CH$_3$)CH$_2$CH$_2$CH=C(CH$_3$)$_2$ |
| 3,5-Cl$_2$ | CF$_3$ | H | CH$_2$(T-8) |
| 3,5-Cl$_2$ | CF$_3$ | H | CH$_2$CF=CH$_2$ |
| 3,5-Cl$_2$ | CF$_3$ | H | CH$_2$CH=CHCl |
| 3,5-Cl$_2$ | CF$_3$ | H | CH$_2$CCl=CH$_2$ |
| 3,5-Cl$_2$ | CF$_3$ | CH$_2$OCH$_3$ | CH$_2$CCl=CH$_2$ |
| 3,5-Cl$_2$ | CF$_3$ | CH$_2$OC(O)CH$_3$ | CH$_2$CCl=CH$_2$ |
| 3,5-Cl$_2$ | CF$_3$ | CH$_2$CN | CH$_2$CCl=CH$_2$ |
| 3,5-Cl$_2$ | CF$_3$ | C(O)CH$_3$ | CH$_2$CCl=CH$_2$ |
| 3,5-Cl$_2$ | CF$_3$ | C(O)Et | CH$_2$CCl=CH$_2$ |
| 3,5-Cl$_2$ | CF$_3$ | C(O)OCH$_3$ | CH$_2$CCl=CH$_2$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-$Cl_2$ | $CF_3$ | H | $CH_2CH=CHBr$ |
| 3,5-$Cl_2$ | $CF_3$ | H | $CH_2CBr=CH_2$ |
| 3,5-$Cl_2$ | $CF_3$ | H | $CH_2CH=CCl_2$ |
| 3,5-$Cl_2$ | $CF_3$ | H | $CH_2CCl=CHCl$ |
| 3,5-$Cl_2$ | $CF_3$ | $CH_3$ | $CH_2CCl=CHCl$ |
| 3,5-$Cl_2$ | $CF_3$ | $CH_2OCH_3$ | $CH_2CCl=CHCl$ |
| 3,5-$Cl_2$ | $CF_3$ | $CH_2OC(O)CH_3$ | $CH_2CCl=CHCl$ |
| 3,5-$Cl_2$ | $CF_3$ | $CH_2CN$ | $CH_2CCl=CHCl$ |
| 3,5-$Cl_2$ | $CF_3$ | $C(O)CH_3$ | $CH_2CCl=CHCl$ |
| 3,5-$Cl_2$ | $CF_3$ | $C(O)Et$ | $CH_2CCl=CHCl$ |
| 3,5-$Cl_2$ | $CF_3$ | $C(O)OCH_3$ | $CH_2CCl=CHCl$ |
| 3,5-$Cl_2$ | $CF_3$ | H | $CH_2CBr=CHBr$ |
| 3,5-$Cl_2$ | $CF_3$ | H | $CH_2CF=CF_2$ |
| 3,5-$Cl_2$ | $CF_3$ | H | $CH_2CCl=CCl_2$ |
| 3,5-$Cl_2$ | $CF_3$ | H | $CH_2C(CH_3)=CHBr$ |
| 3,5-$Cl_2$ | $CF_3$ | H | $CH_2CH=CClCH_3$ |
| 3,5-$Cl_2$ | $CF_3$ | H | $CH_2CH=CBrCH_3$ |
| 3,5-$Cl_2$ | $CF_3$ | H | $CH_2CH=CClCF_3$ |
| 3,5-$Cl_2$ | $CF_3$ | H | $CH_2C(OCH_3)=CH_2$ |
| 3,5-$Cl_2$ | $CF_3$ | H | $CH_2C(OCH_2OCH_3)=CH_2$ |
| 3,5-$Cl_2$ | $CF_3$ | H | $CH_2C[CH_2Si(CH_3)_3]=CH_2$ |
| 3,5-$Cl_2$ | $CF_3$ | H | $CH_2CBr=CHOCH_3$ |
| 3,5-$Cl_2$ | $CF_3$ | H | $CH_2C(CH_3)=CHOEt$ |
| 3,5-$Cl_2$ | $CF_3$ | H | $CH_2C(CH_3)=CHPh$ |
| 3,5-$Cl_2$ | $CF_3$ | H | $C\equiv CH_3$ |
| 3,5-$Cl_2$ | $CF_3$ | H | $CH_2C\equiv CH$ |
| 3,5-$Cl_2$ | $CF_3$ | Et | $CH_2C\equiv CH$ |
| 3,5-$Cl_2$ | $CF_3$ | $CH_2OCH_3$ | $CH_2C\equiv CH$ |
| 3,5-$Cl_2$ | $CF_3$ | $CH_2OEt$ | $CH_2C\equiv CH$ |
| 3,5-$Cl_2$ | $CF_3$ | $CH_2OCH_2CF_3$ | $CH_2C\equiv CH$ |
| 3,5-$Cl_2$ | $CF_3$ | $CH_2OC(O)CH_3$ | $CH_2C\equiv CH$ |
| 3,5-$Cl_2$ | $CF_3$ | $CH_2CN$ | $CH_2C\equiv CH$ |
| 3,5-$Cl_2$ | $CF_3$ | $CH_2C\equiv CH$ | $CH_2C\equiv CH$ |
| 3,5-$Cl_2$ | $CF_3$ | $C(O)CH_3$ | $CH_2C\equiv CH$ |
| 3,5-$Cl_2$ | $CF_3$ | $C(O)Et$ | $CH_2C\equiv CH$ |
| 3,5-$Cl_2$ | $CF_3$ | $C(O)Pr$-n | $CH_2C\equiv CH$ |
| 3,5-$Cl_2$ | $CF_3$ | $C(O)Pr$-i | $CH_2C\equiv CH$ |
| 3,5-$Cl_2$ | $CF_3$ | $C(O)Pr$-c | $CH_2C\equiv CH$ |
| 3,5-$Cl_2$ | $CF_3$ | $C(O)Bu$-t | $CH_2C\equiv CH$ |
| 3,5-$Cl_2$ | $CF_3$ | H | $CH_2C\equiv CCH_3$ |
| 3,5-$Cl_2$ | $CF_3$ | H | $CH(CH_3)C\equiv CH$ |
| 3,5-$Cl_2$ | $CF_3$ | H | $C(CH_3)_2C\equiv CH$ |
| 3,5-$Cl_2$ | $CF_3$ | H | $CH_2C\equiv CCl$ |
| 3,5-$Cl_2$ | $CF_3$ | H | $CH_2C\equiv CBr$ |
| 3,5-$Cl_2$ | $CF_3$ | H | $CH_2C\equiv CI$ |
| 3,5-$Cl_2$ | $CF_3$ | H | $CH_2C\equiv CCF_3$ |
| 3,5-$Cl_2$ | $CF_3$ | H | $CH_2C\equiv CCF_2Br$ |
| 3,5-$Cl_2$ | $CF_3$ | H | $CH_2C\equiv CSi(CH_3)_3$ |
| 3,5-$Cl_2$ | $CF_3$ | H | $CH_2C\equiv CPh$ |
| 3,5-$Cl_2$ | $CF_3$ | H | $CH_2C\equiv C(1$-Naph$)$ |
| 3,5-$Cl_2$ | $CF_3$ | H | $CH_2C\equiv C(D$-3a$)$ |
| 3,5-$Cl_2$ | $CF_3$ | H | $CH_2C\equiv C(D$-4a$)$ |
| 3,5-$Cl_2$ | $CF_3$ | H | $CH_2C\equiv C(D$-47a$)$ |
| 3,5-$Cl_2$ | $CF_3$ | H | $CH_2C\equiv C(D$-48a$)$ |
| 3,5-$Cl_2$ | $CF_3$ | H | $CH_2Ph$ |
| 3,5-$Cl_2$ | $CF_3$ | $CH_3$ | $CH_2Ph$ |
| 3,5-$Cl_2$ | $CF_3$ | Et | $CH_2Ph$ |
| 3,5-$Cl_2$ | $CF_3$ | $CH_2OCH_3$ | $CH_2Ph$ |
| 3,5-$Cl_2$ | $CF_3$ | $CH_2OEt$ | $CH_2Ph$ |
| 3,5-$Cl_2$ | $CF_3$ | $CH_2OCH_2CF_3$ | $CH_2Ph$ |
| 3,5-$Cl_2$ | $CF_3$ | $CH_2OC(O)CH_3$ | $CH_2Ph$ |
| 3,5-$Cl_2$ | $CF_3$ | $CH_2CN$ | $CH_2Ph$ |
| 3,5-$Cl_2$ | $CF_3$ | $CH_2C\equiv CH$ | $CH_2Ph$ |
| 3,5-$Cl_2$ | $CF_3$ | $C(O)CH_3$ | $CH_2Ph$ |
| 3,5-$Cl_2$ | $CF_3$ | $C(O)Et$ | $CH_2Ph$ |
| 3,5-$Cl_2$ | $CF_3$ | $C(O)Pr$-n | $CH_2Ph$ |
| 3,5-$Cl_2$ | $CF_3$ | $C(O)Pr$-i | $CH_2Ph$ |
| 3,5-$Cl_2$ | $CF_3$ | $C(O)Pr$-c | $CH_2Ph$ |
| 3,5-$Cl_2$ | $CF_3$ | $C(O)Bu$-t | $CH_2Ph$ |
| 3,5-$Cl_2$ | $CF_3$ | OH | $CH_2Ph$ |
| 3,5-$Cl_2$ | $CF_3$ | $OCH_3$ | $CH_2Ph$ |
| 3,5-$Cl_2$ | $CF_3$ | $OC(O)CH_3$ | $CH_2Ph$ |
| 3,5-$Cl_2$ | $CF_3$ | $OC(O)OCH_3$ | $CH_2Ph$ |
| 3,5-$Cl_2$ | $CF_3$ | $OSO_2CH_3$ | $CH_2Ph$ |
| 3,5-$Cl_2$ | $CF_3$ | H | $CH_2($Ph-2-F$)$ |
| 3,5-$Cl_2$ | $CF_3$ | H | $CH_2($Ph-3-F$)$ |
| 3,5-$Cl_2$ | $CF_3$ | H | $CH_2($Ph-4-F$)$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$(Ph-2-Cl) |
| 3,5-Cl$_2$ | CF$_3$ | H | CH$_2$(Ph-3-Cl) |
| 3,5-Cl$_2$ | CF$_3$ | H | CH$_2$(Ph-4-Cl) |
| 3,5-Cl$_2$ | CF$_3$ | H | CH$_2$(Ph-2-Br) |
| 3,5-Cl$_2$ | CF$_3$ | H | CH$_2$(Ph-3-Br) |
| 3,5-Cl$_2$ | CF$_3$ | H | CH$_2$(Ph-4-Br) |
| 3,5-Cl$_2$ | CF$_3$ | H | CH$_2$(Ph-3-I) |
| 3,5-Cl$_2$ | CF$_3$ | H | CH$_2$(Ph-4-I) |
| 3,5-Cl$_2$ | CF$_3$ | H | CH$_2$(Ph-3-CH$_2$SCH$_3$) |
| 3,5-Cl$_2$ | CF$_3$ | H | CH$_2$[Ph-3-CH$_2$S(O)CH$_3$] |
| 3,5-Cl$_2$ | CF$_3$ | H | CH$_2$(Ph-3-CH$_2$SO$_2$CH$_3$) |
| 3,5-Cl$_2$ | CF$_3$ | H | CH$_2$(Ph-4-CH$_2$SCH$_3$) |
| 3,5-Cl$_2$ | CF$_3$ | H | CH$_2$[Ph-4-CH$_2$S(O)CH$_3$] |
| 3,5-Cl$_2$ | CF$_3$ | H | CH$_2$(Ph-4-CH$_2$SO$_2$CH$_3$) |
| 3,5-Cl$_2$ | CF$_3$ | CH$_3$ | CH$_2$(Ph-2-OH) |
| 3,5-Cl$_2$ | CF$_3$ | H | CH$_2$(Ph-3-OCH$_3$) |
| 3,5-Cl$_2$ | CF$_3$ | H | CH$_2$(Ph-4-OCH$_3$) |
| 3,5-Cl$_2$ | CF$_3$ | C(O)OCH$_3$ | CH$_2$(Ph-4-OCH$_3$) |
| 3,5-Cl$_2$ | CF$_3$ | H | CH$_2$(Ph-2-OEt) |
| 3,5-Cl$_2$ | CF$_3$ | H | CH$_2$(Ph-2-OCHF$_2$) |
| 3,5-Cl$_2$ | CF$_3$ | H | CH$_2$(Ph-3-OCHF$_2$) |
| 3,5-Cl$_2$ | CF$_3$ | H | CH$_2$(Ph-4-OCHF$_2$) |
| 3,5-Cl$_2$ | CF$_3$ | H | CH$_2$(Ph-2-OCF$_3$) |
| 3,5-Cl$_2$ | CF$_3$ | H | CH$_2$(Ph-4-OCF$_3$) |
| 3,5-Cl$_2$ | CF$_3$ | H | CH$_2$[Ph-3-OC(O)NHCH$_3$] |
| 3,5-Cl$_2$ | CF$_3$ | H | CH$_2$[Ph-4-OC(O)NHCH$_3$] |
| 3,5-Cl$_2$ | CF$_3$ | H | CH$_2$(Ph-4-OSO$_2$CH$_3$) |
| 3,5-Cl$_2$ | CF$_3$ | H | CH$_2$(Ph-4-OSO$_2$CF$_3$) |
| 3,5-Cl$_2$ | CF$_3$ | H | CH$_2$(Ph-2-SCH$_3$) |
| 3,5-Cl$_2$ | CF$_3$ | H | CH$_2$[Ph-2-S(O)CH$_3$] |
| 3,5-Cl$_2$ | CF$_3$ | H | CH$_2$(Ph-2-SO$_2$CH$_3$) |
| 3,5-Cl$_2$ | CF$_3$ | H | CH$_2$(Ph-4-SCH$_3$) |
| 3,5-Cl$_2$ | CF$_3$ | H | CH$_2$[Ph-4-S(O)CH$_3$] |
| 3,5-Cl$_2$ | CF$_3$ | H | CH$_2$(Ph-4-SO$_2$CH$_3$) |
| 3,5-Cl$_2$ | CF$_3$ | H | CH$_2$(Ph-4-SEt) |
| 3,5-Cl$_2$ | CF$_3$ | H | CH$_2$[Ph-4-S(O)Et] |
| 3,5-Cl$_2$ | CF$_3$ | H | CH$_2$(Ph-4-SO$_2$Et) |
| 3,5-Cl$_2$ | CF$_3$ | H | CH$_2$(Ph-2-SCHF$_2$) |
| 3,5-Cl$_2$ | CF$_3$ | H | CH$_2$[Ph-2-S(O)CHF$_2$] |
| 3,5-Cl$_2$ | CF$_3$ | H | CH$_2$(Ph-2-SO$_2$CHF$_2$) |
| 3,5-Cl$_2$ | CF$_3$ | H | CH$_2$(Ph-3-SCHF$_2$) |
| 3,5-Cl$_2$ | CF$_3$ | H | CH$_2$[Ph-3-S(O)CHF$_2$] |
| 3,5-Cl$_2$ | CF$_3$ | H | CH$_2$(Ph-3-SO$_2$CHF$_2$) |
| 3,5-Cl$_2$ | CF$_3$ | H | CH$_2$(Ph-2-SCF$_3$) |
| 3,5-Cl$_2$ | CF$_3$ | H | CH$_2$[Ph-2-S(O)CF$_3$] |
| 3,5-Cl$_2$ | CF$_3$ | H | CH$_2$(Ph-2-SO$_2$CF$_3$) |
| 3,5-Cl$_2$ | CF$_3$ | H | CH$_2$(Ph-3-SCF$_3$) |
| 3,5-Cl$_2$ | CF$_3$ | H | CH$_2$[Ph-3-S(O)CF$_3$] |
| 3,5-Cl$_2$ | CF$_3$ | H | CH$_2$(Ph-3-SO$_2$CF$_3$) |
| 3,5-Cl$_2$ | CF$_3$ | H | CH$_2$(Ph-4-SCF$_3$) |
| 3,5-Cl$_2$ | CF$_3$ | H | CH$_2$[Ph-4-S(O)CF$_3$] |
| 3,5-Cl$_2$ | CF$_3$ | H | CH$_2$(Ph-4-SO$_2$CF$_3$) |
| 3,5-Cl$_2$ | CF$_3$ | H | CH$_2$(Ph-2-NO$_2$) |
| 3,5-Cl$_2$ | CF$_3$ | H | CH$_2$(Ph-3-NO$_2$) |
| 3,5-Cl$_2$ | CF$_3$ | H | CH$_2$(Ph-4-NO$_2$) |
| 3,5-Cl$_2$ | CF$_3$ | CH$_2$OCH$_3$ | CH$_2$(Ph-4-NO$_2$) |
| 3,5-Cl$_2$ | CF$_3$ | CH$_2$OC(O)CH$_3$ | CH$_2$(Ph-4-NO$_2$) |
| 3,5-Cl$_2$ | CF$_3$ | CH$_2$CN | CH$_2$(Ph-4-NO$_2$) |
| 3,5-Cl$_2$ | CF$_3$ | C(O)CH$_3$ | CH$_2$(Ph-4-NO$_2$) |
| 3,5-Cl$_2$ | CF$_3$ | C(O)Et | CH$_2$(Ph-4-NO$_2$) |
| 3,5-Cl$_2$ | CF$_3$ | C(O)OCH$_3$ | CH$_2$(Ph-4-NO$_2$) |
| 3,5-Cl$_2$ | CF$_3$ | H | CH$_2$[Ph-2-NHC(O)CH$_3$] |
| 3,5-Cl$_2$ | CF$_3$ | H | CH$_2$[Ph-3-NHC(O)CH$_3$] |
| 3,5-Cl$_2$ | CF$_3$ | H | CH$_2$[Ph-4-NHC(O)CH$_3$] |
| 3,5-Cl$_2$ | CF$_3$ | H | CH$_2$[Ph-2-NHC(O)CF$_3$] |
| 3,5-Cl$_2$ | CF$_3$ | H | CH$_2$[Ph-3-NHC(O)CF$_3$] |
| 3,5-Cl$_2$ | CF$_3$ | H | CH$_2$[Ph-4-NHC(O)CF$_3$] |
| 3,5-Cl$_2$ | CF$_3$ | H | CH$_2$[Ph-2-NHC(O)NHCH$_3$] |
| 3,5-Cl$_2$ | CF$_3$ | H | CH$_2$[Ph-3-NHC(O)NHCH$_3$] |
| 3,5-Cl$_2$ | CF$_3$ | H | CH$_2$[Ph-4-NHC(O)NHCH$_3$] |
| 3,5-Cl$_2$ | CF$_3$ | H | CH$_2$(Ph-2-NHSO$_2$CH$_3$) |
| 3,5-Cl$_2$ | CF$_3$ | H | CH$_2$(Ph-3-NHSO$_2$CH$_3$) |
| 3,5-Cl$_2$ | CF$_3$ | H | CH$_2$(Ph-4-NHSO$_2$CH$_3$) |
| 3,5-Cl$_2$ | CF$_3$ | H | CH$_2$(Ph-2-NHSO$_2$CF$_3$) |
| 3,5-Cl$_2$ | CF$_3$ | H | CH$_2$(Ph-3-NHSO$_2$CF$_3$) |
| 3,5-Cl$_2$ | CF$_3$ | H | CH$_2$(Ph-4-NHSO$_2$CF$_3$) |
| 3,5-Cl$_2$ | CF$_3$ | H | CH$_2$[Ph-2-N(CH$_3$)$_2$] |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$(Ph-2-CN) |
| 3,5-Cl$_2$ | CF$_3$ | H | CH$_2$(Ph-3-CN) |
| 3,5-Cl$_2$ | CF$_3$ | H | CH$_2$(Ph-4-CN) |
| 3,5-Cl$_2$ | CF$_3$ | C(O)OCH$_3$ | CH$_2$(Ph-4-CN) |
| 3,5-Cl$_2$ | CF$_3$ | H | CH$_2$[Ph-2-C(O)OCH$_3$] |
| 3,5-Cl$_2$ | CF$_3$ | H | CH$_2$[Ph-3-C(O)OCH$_3$] |
| 3,5-Cl$_2$ | CF$_3$ | H | CH$_2$[Ph-2-C(O)NH$_2$] |
| 3,5-Cl$_2$ | CF$_3$ | H | CH$_2$[Ph-3-C(O)NH$_2$] |
| 3,5-Cl$_2$ | CF$_3$ | H | CH$_2$[Ph-4-C(O)NH$_2$] |
| 3,5-Cl$_2$ | CF$_3$ | H | CH$_2$[Ph-2-C(S)NH$_2$] |
| 3,5-Cl$_2$ | CF$_3$ | H | CH$_2$[Ph-3-C(S)NH$_2$] |
| 3,5-Cl$_2$ | CF$_3$ | H | CH$_2$[Ph-4-C(S)NH$_2$] |
| 3,5-Cl$_2$ | CF$_3$ | H | CH$_2$(Ph-4-SO$_2$OCH$_3$) |
| 3,5-Cl$_2$ | CF$_3$ | H | CH$_2$(Ph-4-SO$_2$NH$_2$) |
| 3,5-Cl$_2$ | CF$_3$ | H | CH$_2$(Ph-4-SO$_2$NHCH$_3$) |
| 3,5-Cl$_2$ | CF$_3$ | H | CH$_2$[Ph-4-SO$_2$N(CH$_3$)$_2$] |
| 3,5-Cl$_2$ | CF$_3$ | H | CH$_2$(Ph-3-CH=NOCH$_3$) |
| 3,5-Cl$_2$ | CF$_3$ | H | CH$_2$(Ph-4-CH=NOCH$_3$) |
| 3,5-Cl$_2$ | CF$_3$ | H | CH$_2$[Ph-4-C(CH$_3$)=NOCH$_3$] |
| 3,5-Cl$_2$ | CF$_3$ | H | CH$_2$(Ph-2,4-F$_2$) |
| 3,5-Cl$_2$ | CF$_3$ | H | CH$_2$(Ph-2,5-F$_2$) |
| 3,5-Cl$_2$ | CF$_3$ | H | CH$_2$(Ph-2,6-F$_2$) |
| 3,5-Cl$_2$ | CF$_3$ | H | CH$_2$(Ph-3,4-F$_2$) |
| 3,5-Cl$_2$ | CF$_3$ | H | CH$_2$(Ph-3,5-F$_2$) |
| 3,5-Cl$_2$ | CF$_3$ | H | CH$_2$(Ph-2-F-4-Cl) |
| 3,5-Cl$_2$ | CF$_3$ | H | CH$_2$(Ph-2-Cl-4-F) |
| 3,5-Cl$_2$ | CF$_3$ | H | CH$_2$(Ph-2-F-6-Cl) |
| 3,5-Cl$_2$ | CF$_3$ | H | CH$_2$(Ph-3-F-4-Cl) |
| 3,5-Cl$_2$ | CF$_3$ | H | CH$_2$(Ph-2,3-Cl$_2$) |
| 3,5-Cl$_2$ | CF$_3$ | H | CH$_2$(Ph-2,4-Cl$_2$) |
| 3,5-Cl$_2$ | CF$_3$ | H | CH$_2$(Ph-2,6-Cl$_2$) |
| 3,5-Cl$_2$ | CF$_3$ | H | CH$_2$(Ph-2-F-4-Br) |
| 3,5-Cl$_2$ | CF$_3$ | H | CH$_2$(Ph-2-F-5-Br) |
| 3,5-Cl$_2$ | CF$_3$ | H | CH$_2$(Ph-3-Br-4-F) |
| 3,5-Cl$_2$ | CF$_3$ | H | CH$_2$(Ph-2-F-3-CF$_3$) |
| 3,5-Cl$_2$ | CF$_3$ | H | CH$_2$(Ph-2-F-4-CF$_3$) |
| 3,5-Cl$_2$ | CF$_3$ | H | CH$_2$(Ph-2-CF$_3$-4-F) |
| 3,5-Cl$_2$ | CF$_3$ | H | CH$_2$(Ph-2-F-5-CF$_3$) |
| 3,5-Cl$_2$ | CF$_3$ | H | CH$_2$(Ph-2-CF$_3$-5-F) |
| 3,5-Cl$_2$ | CF$_3$ | H | CH$_2$(Ph-2-F-6-CF$_3$) |
| 3,5-Cl$_2$ | CF$_3$ | H | CH$_2$(Ph-3-F-5-CF$_3$) |
| 3,5-Cl$_2$ | CF$_3$ | H | CH$_2$[Ph-3,4-(OH)$_2$] |
| 3,5-Cl$_2$ | CF$_3$ | H | CH$_2$(Ph-3-OCH$_3$-4-OH) |
| 3,5-Cl$_2$ | CF$_3$ | H | CH$_2$[Ph-2,3-(OCH$_3$)$_2$] |
| 3,5-Cl$_2$ | CF$_3$ | H | CH$_2$[Ph-2,4-(OCH$_3$)$_2$] |
| 3,5-Cl$_2$ | CF$_3$ | H | CH$_2$[Ph-2,6-(OCH$_3$)$_2$] |
| 3,5-Cl$_2$ | CF$_3$ | H | CH$_2$[Ph-3,5-(OCH$_3$)$_2$] |
| 3,5-Cl$_2$ | CF$_3$ | H | CH$_2$(Ph-2,3,4-F$_3$) |
| 3,5-Cl$_2$ | CF$_3$ | H | CH$_2$(Ph-2,3,5-F$_3$) |
| 3,5-Cl$_2$ | CF$_3$ | H | CH$_2$(Ph-2,3,6-F$_3$) |
| 3,5-Cl$_2$ | CF$_3$ | H | CH$_2$(Ph-2,4,5-F$_3$) |
| 3,5-Cl$_2$ | CF$_3$ | H | CH$_2$(Ph-3,4,5-F$_3$) |
| 3,5-Cl$_2$ | CF$_3$ | H | CH$_2$[Ph-2,4,6-(OCH$_3$)$_3$] |
| 3,5-Cl$_2$ | CF$_3$ | H | CH$_2$[Ph-3,4,5-(OCH$_3$)$_3$] |
| 3,5-Cl$_2$ | CF$_3$ | H | CH(CH$_3$)Ph |
| 3,5-Cl$_2$ | CF$_3$ | H | CH(CH$_3$)Ph(R) |
| 3,5-Cl$_2$ | CF$_3$ | H | CH(CH$_3$)Ph(S) |
| 3,5-Cl$_2$ | CF$_3$ | H | CH(CH$_3$)(Ph-4-F) |
| 3,5-Cl$_2$ | CF$_3$ | H | CH(CH$_3$)(Ph-4-F)(R) |
| 3,5-Cl$_2$ | CF$_3$ | H | CH(CH$_3$)(Ph-4-OCH$_3$) |
| 3,5-Cl$_2$ | CF$_3$ | H | CH(CH$_3$)(Ph-4-OCH$_3$)(R) |
| 3,5-Cl$_2$ | CF$_3$ | H | CH(CH$_3$)(Ph-4-NO$_2$) |
| 3,5-Cl$_2$ | CF$_3$ | CH$_2$OCH$_3$ | CH(CH$_3$)(Ph-4-NO$_2$)(R) |
| 3,5-Cl$_2$ | CF$_3$ | CH$_2$OC(O)CH$_3$ | CH(CH$_3$)(Ph-4-NO$_2$)(R) |
| 3,5-Cl$_2$ | CF$_3$ | CH$_2$CN | CH(CH$_3$)(Ph-4-NO$_2$)(R) |
| 3,5-Cl$_2$ | CF$_3$ | C(O)CH$_3$ | CH(CH$_3$)(Ph-4-NO$_2$)(R) |
| 3,5-Cl$_2$ | CF$_3$ | C(O)Et | CH(CH$_3$)(Ph-4-NO$_2$)(R) |
| 3,5-Cl$_2$ | CF$_3$ | C(O)OCH$_3$ | CH(CH$_3$)(Ph-4-NO$_2$)(R) |
| 3,5-Cl$_2$ | CF$_3$ | H | CH(CH$_3$)(Ph-4-CN) |
| 3,5-Cl$_2$ | CF$_3$ | H | CH(CH$_3$)(Ph-4-CN)(R) |
| 3,5-Cl$_2$ | CF$_3$ | H | CH(Et)Ph |
| 3,5-Cl$_2$ | CF$_3$ | H | CH(Et)Ph(R) |
| 3,5-Cl$_2$ | CF$_3$ | H | CH(CF$_3$)Ph |
| 3,5-Cl$_2$ | CF$_3$ | H | CH(CF$_3$)Ph(R) |
| 3,5-Cl$_2$ | CF$_3$ | H | CH(CF$_3$)Ph(S) |
| 3,5-Cl$_2$ | CF$_3$ | H | CH(CH$_2$OH)Ph |
| 3,5-Cl$_2$ | CF$_3$ | H | CH(CH$_2$OH)Ph(R) |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | H | CH(CH$_2$OH)Ph(S) |
| 3,5-Cl$_2$ | CF$_3$ | H | CH(CH$_2$OCH$_3$)Ph |
| 3,5-Cl$_2$ | CF$_3$ | H | CH(CH$_2$OCH$_3$)Ph(R) |
| 3,5-Cl$_2$ | CF$_3$ | H | CH(CH$_2$OCH$_3$)Ph(S) |
| 3,5-Cl$_2$ | CF$_3$ | H | CH(OCH$_3$)Ph |
| 3,5-Cl$_2$ | CF$_3$ | H | CH(OEt)Ph |
| 3,5-Cl$_2$ | CF$_3$ | H | CH(CN)Ph |
| 3,5-Cl$_2$ | CF$_3$ | H | CH(CN)Ph(R) |
| 3,5-Cl$_2$ | CF$_3$ | H | CH(CN)Ph(S) |
| 3,5-Cl$_2$ | CF$_3$ | H | C(CH$_3$)$_2$Ph |
| 3,5-Cl$_2$ | CF$_3$ | H | C(CH$_3$)$_2$CH$_2$Ph |
| 3,5-Cl$_2$ | CF$_3$ | H | CH(CH$_3$)CH$_2$CH$_2$Ph |
| 3,5-Cl$_2$ | CF$_3$ | CH$_3$ | CH$_2$(1-Naph) |
| 3,5-Cl$_2$ | CF$_3$ | H | CH$_2$(D-1a) |
| 3,5-Cl$_2$ | CF$_3$ | CH$_3$ | CH$_2$(D-1a) |
| 3,5-Cl$_2$ | CF$_3$ | H | CH$_2$(D-1b)Br |
| 3,5-Cl$_2$ | CF$_3$ | H | CH$_2$(D-1c)Cl |
| 3,5-Cl$_2$ | CF$_3$ | H | CH$_2$(D-1c)Br |
| 3,5-Cl$_2$ | CF$_3$ | H | CH$_2$(D-1c)CF$_3$ |
| 3,5-Cl$_2$ | CF$_3$ | H | CH$_2$(D-1c)SCH$_3$ |
| 3,5-Cl$_2$ | CF$_3$ | H | CH$_2$(D-1c)SO$_2$CH$_3$ |
| 3,5-Cl$_2$ | CF$_3$ | H | CH$_2$(D-1c)NO$_2$ |
| 3,5-Cl$_2$ | CF$_3$ | H | CH(CH$_3$)(D-1a) |
| 3,5-Cl$_2$ | CF$_3$ | H | CH(CH$_3$)(D-1a)(R) |
| 3,5-Cl$_2$ | CF$_3$ | H | CH(CF$_3$)(D-1a) |
| 3,5-Cl$_2$ | CF$_3$ | H | CH(CN)(D-1a) |
| 3,5-Cl$_2$ | CF$_3$ | H | CH$_2$(D-2a) |
| 3,5-Cl$_2$ | CF$_3$ | H | CH$_2$(D-2b)Br |
| 3,5-Cl$_2$ | CF$_3$ | H | CH$_2$(D-3a) |
| 3,5-Cl$_2$ | CF$_3$ | H | CH$_2$(D-3c)Cl |
| 3,5-Cl$_2$ | CF$_3$ | H | CH$_2$(D-3c)Br |
| 3,5-Cl$_2$ | CF$_3$ | H | CH$_2$(D-3c)SCH$_3$ |
| 3,5-Cl$_2$ | CF$_3$ | H | CH$_2$(D-3c)SO$_2$CH$_3$ |
| 3,5-Cl$_2$ | CF$_3$ | H | CH$_2$(D-3c)NO$_2$ |
| 3,5-Cl$_2$ | CF$_3$ | H | CH$_2$(D-3d)F |
| 3,5-Cl$_2$ | CF$_3$ | H | CH$_2$(D-3d)Cl |
| 3,5-Cl$_2$ | CF$_3$ | H | CH$_2$(D-3d)Br |
| 3,5-Cl$_2$ | CF$_3$ | H | CH$_2$(D-3d)I |
| 3,5-Cl$_2$ | CF$_3$ | H | CH$_2$(D-3d)CH$_3$ |
| 3,5-Cl$_2$ | CF$_3$ | H | CH$_2$(D-3d)CF$_3$ |
| 3,5-Cl$_2$ | CF$_3$ | H | CH$_2$(D-3d)NO$_2$ |
| 3,5-Cl$_2$ | CF$_3$ | H | CH$_2$(D-3d)SCH$_3$ |
| 3,5-Cl$_2$ | CF$_3$ | H | CH$_2$(D-3d)SO$_2$CH$_3$ |
| 3,5-Cl$_2$ | CF$_3$ | H | CH$_2$(D-3d)CN |
| 3,5-Cl$_2$ | CF$_3$ | H | CH(CH$_3$)(D-3a) |
| 3,5-Cl$_2$ | CF$_3$ | H | CH(CF$_3$)(D-3a) |
| 3,5-Cl$_2$ | CF$_3$ | H | CH(CN)(D-3a) |
| 3,5-Cl$_2$ | CF$_3$ | H | CH$_2$(D-4a) |
| 3,5-Cl$_2$ | CF$_3$ | H | CH$_2$(D-4b)Cl |
| 3,5-Cl$_2$ | CF$_3$ | H | CH$_2$(D-4b)Br |
| 3,5-Cl$_2$ | CF$_3$ | H | CH$_2$(D-4b)NO$_2$ |
| 3,5-Cl$_2$ | CF$_3$ | H | CH$_2$(D-4b)CN |
| 3,5-Cl$_2$ | CF$_3$ | H | CH$_2$(D-6b)Cl |
| 3,5-Cl$_2$ | CF$_3$ | H | CH$_2$(D-6b)Br |
| 3,5-Cl$_2$ | CF$_3$ | H | CH$_2$(D-6c)Cl |
| 3,5-Cl$_2$ | CF$_3$ | H | CH$_2$(D-6c)Br |
| 3,5-Cl$_2$ | CF$_3$ | H | CH$_2$(D-8a) |
| 3,5-Cl$_2$ | CF$_3$ | H | CH$_2$(D-8b)Cl |
| 3,5-Cl$_2$ | CF$_3$ | H | CH$_2$(D-8b)Br |
| 3,5-Cl$_2$ | CF$_3$ | H | CH$_2$(D-8b)CH$_3$ |
| 3,5-Cl$_2$ | CF$_3$ | H | CH$_2$(D-8b)CH$_2$F |
| 3,5-Cl$_2$ | CF$_3$ | H | CH$_2$(D-8b)CHF$_2$ |
| 3,5-Cl$_2$ | CF$_3$ | H | CH$_2$(D-8b)CF$_3$ |
| 3,5-Cl$_2$ | CF$_3$ | H | CH(CH$_3$)(D-8a) |
| 3,5-Cl$_2$ | CF$_3$ | H | CH$_2$(D-10a) |
| 3,5-Cl$_2$ | CF$_3$ | H | CH$_2$(D-10b)Cl |
| 3,5-Cl$_2$ | CF$_3$ | H | CH$_2$(D-10b)Br |
| 3,5-Cl$_2$ | CF$_3$ | H | CH$_2$(D-10b)CH$_3$ |
| 3,5-Cl$_2$ | CF$_3$ | H | CH$_2$(D-10b)CF$_3$ |
| 3,5-Cl$_2$ | CF$_3$ | H | CH$_2$(D-10b)OCH$_3$ |
| 3,5-Cl$_2$ | CF$_3$ | H | CH$_2$(D-10b)SCH$_3$ |
| 3,5-Cl$_2$ | CF$_3$ | H | CH$_2$(D-11a) |
| 3,5-Cl$_2$ | CF$_3$ | H | CH$_2$(D-11b)Cl |
| 3,5-Cl$_2$ | CF$_3$ | H | CH$_2$(D-11b)Br |
| 3,5-Cl$_2$ | CF$_3$ | H | CH$_2$(D-11b)CH$_3$ |
| 3,5-Cl$_2$ | CF$_3$ | H | CH$_2$(D-13a) |
| 3,5-Cl$_2$ | CF$_3$ | H | CH$_2$(D-13b)CH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$(D-14a) |
| 3,5-Cl$_2$ | CF$_3$ | H | CH$_2$(D-14b)Cl |
| 3,5-Cl$_2$ | CF$_3$ | H | CH$_2$(D-14b)CF$_3$ |
| 3,5-Cl$_2$ | CF$_3$ | C(O)OCH$_3$ | CH$_2$(D-14b)CF$_3$ |
| 3,5-Cl$_2$ | CF$_3$ | H | CH$_2$(D-14c)Cl |
| 3,5-Cl$_2$ | CF$_3$ | H | CH$_2$(D-14c)CF$_3$ |
| 3,5-Cl$_2$ | CF$_3$ | H | CH(CF$_3$)(D-14a) |
| 3,5-Cl$_2$ | CF$_3$ | H | CH(CN)(D-14a) |
| 3,5-Cl$_2$ | CF$_3$ | H | CH$_2$(D-15a)CH$_3$ |
| 3,5-Cl$_2$ | CF$_3$ | CH$_3$ | CH$_2$(D-15a)CH$_3$ |
| 3,5-Cl$_2$ | CF$_3$ | CH$_2$OCH$_3$ | CH$_2$(D-15a)CH$_3$ |
| 3,5-Cl$_2$ | CF$_3$ | CH$_2$OC(O)CH$_3$ | CH$_2$(D-15a)CH$_3$ |
| 3,5-Cl$_2$ | CF$_3$ | CH$_2$CN | CH$_2$(D-15a)CH$_3$ |
| 3,5-Cl$_2$ | CF$_3$ | C(O)CH$_3$ | CH$_2$(D-15a)CH$_3$ |
| 3,5-Cl$_2$ | CF$_3$ | C(O)Et | CH$_2$(D-15a)CH$_3$ |
| 3,5-Cl$_2$ | CF$_3$ | C(O)OCH$_3$ | CH$_2$(D-15a)CH$_3$ |
| 3,5-Cl$_2$ | CF$_3$ | H | CH(CH$_3$)(D-15a)CH$_3$ |
| 3,5-Cl$_2$ | CF$_3$ | H | CH(CF$_3$)(D-15a)CH$_3$ |
| 3,5-Cl$_2$ | CF$_3$ | H | CH(CN)(D-15a)CH$_3$ |
| 3,5-Cl$_2$ | CF$_3$ | H | CH$_2$(D-15b)Cl |
| 3,5-Cl$_2$ | CF$_3$ | H | CH$_2$(D-15c)Cl |
| 3,5-Cl$_2$ | CF$_3$ | H | CH$_2$(D-16a)CH$_3$ |
| 3,5-Cl$_2$ | CF$_3$ | H | CH$_2$(D-16a)CHF$_2$ |
| 3,5-Cl$_2$ | CF$_3$ | H | CH$_2$(D-16a)CF$_2$Br |
| 3,5-Cl$_2$ | CF$_3$ | H | CH$_2$(D-16b)Cl |
| 3,5-Cl$_2$ | CF$_3$ | CH$_3$ | CH$_2$(D-16b)Cl |
| 3,5-Cl$_2$ | CF$_3$ | CH$_2$OCH$_3$ | CH$_2$(D-16b)Cl |
| 3,5-Cl$_2$ | CF$_3$ | CH$_2$OC(O)CH$_3$ | CH$_2$(D-16b)Cl |
| 3,5-Cl$_2$ | CF$_3$ | CH$_2$CN | CH$_2$(D-16b)Cl |
| 3,5-Cl$_2$ | CF$_3$ | C(O)CH$_3$ | CH$_2$(D-16b)Cl |
| 3,5-Cl$_2$ | CF$_3$ | C(O)Et | CH$_2$(D-16b)Cl |
| 3,5-Cl$_2$ | CF$_3$ | C(O)OCH$_3$ | CH$_2$(D-16b)Cl |
| 3,5-Cl$_2$ | CF$_3$ | H | CH$_2$(D-16b)CH$_3$ |
| 3,5-Cl$_2$ | CF$_3$ | H | CH$_2$(D-16c)Cl |
| 3,5-Cl$_2$ | CF$_3$ | CH$_3$ | CH$_2$(D-16c)Cl |
| 3,5-Cl$_2$ | CF$_3$ | CH$_2$OCH$_3$ | CH$_2$(D-16c)Cl |
| 3,5-Cl$_2$ | CF$_3$ | CH$_2$OC(O)CH$_3$ | CH$_2$(D-16c)Cl |
| 3,5-Cl$_2$ | CF$_3$ | CH$_2$CN | CH$_2$(D-16c)Cl |
| 3,5-Cl$_2$ | CF$_3$ | C(O)CH$_3$ | CH$_2$(D-16c)Cl |
| 3,5-Cl$_2$ | CF$_3$ | C(O)Et | CH$_2$(D-16c)Cl |
| 3,5-Cl$_2$ | CF$_3$ | C(O)OCH$_3$ | CH$_2$(D-16c)Cl |
| 3,5-Cl$_2$ | CF$_3$ | H | CH$_2$(D-17a)CH$_3$ |
| 3,5-Cl$_2$ | CF$_3$ | CH$_3$ | CH$_2$(D-17a)CH$_3$ |
| 3,5-Cl$_2$ | CF$_3$ | CH$_2$OCH$_3$ | CH$_2$(D-17a)CH$_3$ |
| 3,5-Cl$_2$ | CF$_3$ | CH$_2$OC(O)CH$_3$ | CH$_2$(D-17a)CH$_3$ |
| 3,5-Cl$_2$ | CF$_3$ | CH$_2$CN | CH$_2$(D-17a)CH$_3$ |
| 3,5-Cl$_2$ | CF$_3$ | C(O)CH$_3$ | CH$_2$(D-17a)CH$_3$ |
| 3,5-Cl$_2$ | CF$_3$ | C(O)Et | CH$_2$(D-17a)CH$_3$ |
| 3,5-Cl$_2$ | CF$_3$ | C(O)OCH$_3$ | CH$_2$(D-17a)CH$_3$ |
| 3,5-Cl$_2$ | CF$_3$ | H | CH$_2$(D-17b)Cl |
| 3,5-Cl$_2$ | CF$_3$ | CH$_3$ | CH$_2$(D-17b)Cl |
| 3,5-Cl$_2$ | CF$_3$ | CH$_2$OCH$_3$ | CH$_2$(D-17b)Cl |
| 3,5-Cl$_2$ | CF$_3$ | CH$_2$OC(O)CH$_3$ | CH$_2$(D-17b)Cl |
| 3,5-Cl$_2$ | CF$_3$ | CH$_2$CN | CH$_2$(D-17b)Cl |
| 3,5-Cl$_2$ | CF$_3$ | C(O)CH$_3$ | CH$_2$(D-17b)Cl |
| 3,5-Cl$_2$ | CF$_3$ | C(O)Et | CH$_2$(D-17b)Cl |
| 3,5-Cl$_2$ | CF$_3$ | C(O)OCH$_3$ | CH$_2$(D-17b)Cl |
| 3,5-Cl$_2$ | CF$_3$ | H | CH$_2$(D-17b)Br |
| 3,5-Cl$_2$ | CF$_3$ | H | CH$_2$(D-17b)CH$_3$ |
| 3,5-Cl$_2$ | CF$_3$ | H | CH$_2$(D-17b)CF$_3$ |
| 3,5-Cl$_2$ | CF$_3$ | H | CH(CH$_3$)(D-17a)CH$_3$ |
| 3,5-Cl$_2$ | CF$_3$ | H | CH(CH$_3$)(D-17a)CH$_3$(R) |
| 3,5-Cl$_2$ | CF$_3$ | H | CH(CH$_3$)(D-17b)Cl |
| 3,5-Cl$_2$ | CF$_3$ | H | CH(CH$_3$)(D-17b)Cl(R) |
| 3,5-Cl$_2$ | CF$_3$ | H | CH(CF$_3$)(D-17a)CH$_3$ |
| 3,5-Cl$_2$ | CF$_3$ | H | CH(CF$_3$)(D-17b)Cl |
| 3,5-Cl$_2$ | CF$_3$ | H | CH(CN)(D-17a)CH$_3$ |
| 3,5-Cl$_2$ | CF$_3$ | H | CH(CN)(D-17b)Cl |
| 3,5-Cl$_2$ | CF$_3$ | H | CH$_2$(D-18a) |
| 3,5-Cl$_2$ | CF$_3$ | H | CH$_2$(D-18b)CH$_3$ |
| 3,5-Cl$_2$ | CF$_3$ | H | CH$_2$(D-18c)CH$_3$ |
| 3,5-Cl$_2$ | CF$_3$ | H | CH(CH$_3$)(D-18a) |
| 3,5-Cl$_2$ | CF$_3$ | H | CH$_2$(D-19a) |
| 3,5-Cl$_2$ | CF$_3$ | H | CH$_2$(D-19b)Cl |
| 3,5-Cl$_2$ | CF$_3$ | H | CH$_2$(D-19b)Br |
| 3,5-Cl$_2$ | CF$_3$ | H | CH$_2$(D-19b)CH$_3$ |
| 3,5-Cl$_2$ | CF$_3$ | H | CH$_2$(D-19b)CF$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH(CH$_3$)(D-19a) |
| 3,5-Cl$_2$ | CF$_3$ | H | CH$_2$(D-20a) |
| 3,5-Cl$_2$ | CF$_3$ | H | CH$_2$(D-20b)Cl |
| 3,5-Cl$_2$ | CF$_3$ | H | CH$_2$(D-20b)Br |
| 3,5-Cl$_2$ | CF$_3$ | H | CH$_2$(D-20b)CH$_3$ |
| 3,5-Cl$_2$ | CF$_3$ | H | CH$_2$(D-20b)CF$_3$ |
| 3,5-Cl$_2$ | CF$_3$ | H | CH(CH$_3$)(D-20a) |
| 3,5-Cl$_2$ | CF$_3$ | H | CH$_2$(D-21a) |
| 3,5-Cl$_2$ | CF$_3$ | CH$_3$ | CH$_2$(D-21a) |
| 3,5-Cl$_2$ | CF$_3$ | CH$_2$OCH$_3$ | CH$_2$(D-21a) |
| 3,5-Cl$_2$ | CF$_3$ | CH$_2$OC(O)CH$_3$ | CH$_2$(D-21a) |
| 3,5-Cl$_2$ | CF$_3$ | CH$_2$CN | CH$_2$(D-21a) |
| 3,5-Cl$_2$ | CF$_3$ | C(O)CH$_3$ | CH$_2$(D-21a) |
| 3,5-Cl$_2$ | CF$_3$ | C(O)Et | CH$_2$(D-21a) |
| 3,5-Cl$_2$ | CF$_3$ | C(O)OCH$_3$ | CH$_2$(D-21a) |
| 3,5-Cl$_2$ | CF$_3$ | H | CH$_2$(D-21b)Br |
| 3,5-Cl$_2$ | CF$_3$ | H | CH$_2$(D-21b)CH$_3$ |
| 3,5-Cl$_2$ | CF$_3$ | H | CH$_2$(D-21c)Cl |
| 3,5-Cl$_2$ | CF$_3$ | H | CH$_2$(D-21c)Br |
| 3,5-Cl$_2$ | CF$_3$ | H | CH$_2$(D-21c)CH$_3$ |
| 3,5-Cl$_2$ | CF$_3$ | H | CH$_2$(D-21c)CF$_3$ |
| 3,5-Cl$_2$ | CF$_3$ | H | CH$_2$(D-21c)NO$_2$ |
| 3,5-Cl$_2$ | CF$_3$ | H | CH(CH$_3$)(D-21a) |
| 3,5-Cl$_2$ | CF$_3$ | H | CH$_2$(D-22a) |
| 3,5-Cl$_2$ | CF$_3$ | CH$_3$ | CH$_2$(D-22a) |
| 3,5-Cl$_2$ | CF$_3$ | Et | CH$_2$(D-22a) |
| 3,5-Cl$_2$ | CF$_3$ | c-Pr | CH$_2$(D-22a) |
| 3,5-Cl$_2$ | CF$_3$ | CH$_2$CF$_3$ | CH$_2$(D-22a) |
| 3,5-Cl$_2$ | CF$_3$ | CH$_2$OCH$_3$ | CH$_2$(D-22a) |
| 3,5-Cl$_2$ | CF$_3$ | CH$_2$OEt | CH$_2$(D-22a) |
| 3,5-Cl$_2$ | CF$_3$ | CH$_2$OCH$_2$CH$_2$Cl | CH$_2$(D-22a) |
| 3,5-Cl$_2$ | CF$_3$ | CH$_2$OCH$_2$CF$_3$ | CH$_2$(D-22a) |
| 3,5-Cl$_2$ | CF$_3$ | CH$_2$OCH$_2$CH$_2$OCH$_3$ | CH$_2$(D-22a) |
| 3,5-Cl$_2$ | CF$_3$ | CH$_2$OC(O)CH$_3$ | CH$_2$(D-22a) |
| 3,5-Cl$_2$ | CF$_3$ | CH$_2$OC(O)Et | CH$_2$(D-22a) |
| 3,5-Cl$_2$ | CF$_3$ | CH$_2$OC(O)Pr-n | CH$_2$(D-22a) |
| 3,5-Cl$_2$ | CF$_3$ | CH$_2$OC(O)Pr-i | CH$_2$(D-22a) |
| 3,5-Cl$_2$ | CF$_3$ | CH$_2$OC(O)Pr-c | CH$_2$(D-22a) |
| 3,5-Cl$_2$ | CF$_3$ | CH$_2$OC(O)Bu-t | CH$_2$(D-22a) |
| 3,5-Cl$_2$ | CF$_3$ | CH$_2$OC(O)Ph | CH$_2$(D-22a) |
| 3,5-Cl$_2$ | CF$_3$ | CH$_2$OC(O)OCH$_3$ | CH$_2$(D-22a) |
| 3,5-Cl$_2$ | CF$_3$ | CH$_2$CH$_2$OCH$_3$ | CH$_2$(D-22a) |
| 3,5-Cl$_2$ | CF$_3$ | CH$_2$SCH$_3$ | CH$_2$(D-22a) |
| 3,5-Cl$_2$ | CF$_3$ | CH$_2$SC(O)CH$_3$ | CH$_2$(D-22a) |
| 3,5-Cl$_2$ | CF$_3$ | CH$_2$SC(S)OCH$_3$ | CH$_2$(D-22a) |
| 3,5-Cl$_2$ | CF$_3$ | CH$_2$SC(S)N(CH$_3$)$_2$ | CH$_2$(D-22a) |
| 3,5-Cl$_2$ | CF$_3$ | CH$_2$NHC(O)OCH$_3$ | CH$_2$(D-22a) |
| 3,5-Cl$_2$ | CF$_3$ | CH$_2$CN | CH$_2$(D-22a) |
| 3,5-Cl$_2$ | CF$_3$ | CH$_2$CH=CH$_2$ | CH$_2$(D-22a) |
| 3,5-Cl$_2$ | CF$_3$ | CH$_2$C≡CH | CH$_2$(D-22a) |
| 3,5-Cl$_2$ | CF$_3$ | C(O)CH$_3$ | CH$_2$(D-22a) |
| 3,5-Cl$_2$ | CF$_3$ | C(O)Et | CH$_2$(D-22a) |
| 3,5-Cl$_2$ | CF$_3$ | C(O)Pr-n | CH$_2$(D-22a) |
| 3,5-Cl$_2$ | CF$_3$ | C(O)Pr-i | CH$_2$(D-22a) |
| 3,5-Cl$_2$ | CF$_3$ | C(O)Pr-c | CH$_2$(D-22a) |
| 3,5-Cl$_2$ | CF$_3$ | C(O)Bu-t | CH$_2$(D-22a) |
| 3,5-Cl$_2$ | CF$_3$ | C(O)CH$_2$OCH$_3$ | CH$_2$(D-22a) |
| 3,5-Cl$_2$ | CF$_3$ | C(O)CH$_2$SCH$_3$ | CH$_2$(D-22a) |
| 3,5-Cl$_2$ | CF$_3$ | C(O)OCH$_3$ | CH$_2$(D-22a) |
| 3,5-Cl$_2$ | CF$_3$ | C(O)OEt | CH$_2$(D-22a) |
| 3,5-Cl$_2$ | CF$_3$ | C(O)OPr-n | CH$_2$(D-22a) |
| 3,5-Cl$_2$ | CF$_3$ | C(O)OPr-i | CH$_2$(D-22a) |
| 3,5-Cl$_2$ | CF$_3$ | C(O)OPr-c | CH$_2$(D-22a) |
| 3,5-Cl$_2$ | CF$_3$ | C(O)OCH$_2$Cl | CH$_2$(D-22a) |
| 3,5-Cl$_2$ | CF$_3$ | C(O)OCH$_2$CH$_2$Cl | CH$_2$(D-22a) |
| 3,5-Cl$_2$ | CF$_3$ | C(O)OCH$_2$CH$_2$OCH$_3$ | CH$_2$(D-22a) |
| 3,5-Cl$_2$ | CF$_3$ | C(O)OCH$_2$CH=CH$_2$ | CH$_2$(D-22a) |
| 3,5-Cl$_2$ | CF$_3$ | C(O)OCH$_2$C≡CH | CH$_2$(D-22a) |
| 3,5-Cl$_2$ | CF$_3$ | C(O)SCH$_3$ | CH$_2$(D-22a) |
| 3,5-Cl$_2$ | CF$_3$ | C(O)NH$_2$ | CH$_2$(D-22a) |
| 3,5-Cl$_2$ | CF$_3$ | C(S)OCH$_3$ | CH$_2$(D-22a) |
| 3,5-Cl$_2$ | CF$_3$ | C(S)SCH$_3$ | CH$_2$(D-22a) |
| 3,5-Cl$_2$ | CF$_3$ | C(S)NH$_2$ | CH$_2$(D-22a) |
| 3,5-Cl$_2$ | CF$_3$ | OH | CH$_2$(D-22a) |
| 3,5-Cl$_2$ | CF$_3$ | OC(O)CH$_3$ | CH$_2$(D-22a) |
| 3,5-Cl$_2$ | CF$_3$ | OC(O)OCH$_3$ | CH$_2$(D-22a) |
| 3,5-Cl$_2$ | CF$_3$ | OSO$_2$CH$_3$ | CH$_2$(D-22a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | SCCl$_3$ | CH$_2$(D-22a) |
| 3,5-Cl$_2$ | CF$_3$ | SN(Bu-n)$_2$ | CH$_2$(D-22a) |
| 3,5-Cl$_2$ | CF$_3$ | S(T-40) | CH$_2$(D-22a) |
| 3,5-Cl$_2$ | CF$_3$ | SN(Pr-i)CH$_2$CH$_2$C(O)OEt | CH$_2$(D-22a) |
| 3,5-Cl$_2$ | CF$_3$ | SN(CH$_2$Ph)CH$_2$CH$_2$C(O)OEt | CH$_2$(D-22a) |
| 3,5-Cl$_2$ | CF$_3$ | SN(CH$_3$)C(O)OBu-n | CH$_2$(D-22a) |
| 3,5-Cl$_2$ | CF$_3$ | H | CH$_2$(D-22b)Cl |
| 3,5-Cl$_2$ | CF$_3$ | H | CH$_2$(D-22b)Br |
| 3,5-Cl$_2$ | CF$_3$ | H | CH$_2$(D-22b)CH$_3$ |
| 3,5-Cl$_2$ | CF$_3$ | H | CH$_2$(D-22b)Et |
| 3,5-Cl$_2$ | CF$_3$ | H | CH$_2$(D-22b)Pr-i |
| 3,5-Cl$_2$ | CF$_3$ | H | CH$_2$(D-22b)CF$_3$ |
| 3,5-Cl$_2$ | CF$_3$ | H | CH$_2$(D-22b)CF$_2$Cl |
| 3,5-Cl$_2$ | CF$_3$ | H | CH$_2$(D-22b)CF$_2$Br |
| 3,5-Cl$_2$ | CF$_3$ | H | CH$_2$(D-22b)CH$_2$SO$_2$CH$_3$ |
| 3,5-Cl$_2$ | CF$_3$ | H | CH$_2$(D-22b)CH$_2$CN |
| 3,5-Cl$_2$ | CF$_3$ | H | CH$_2$(D-22b)OCH$_3$ |
| 3,5-Cl$_2$ | CF$_3$ | H | CH$_2$(D-22b)SCH$_3$ |
| 3,5-Cl$_2$ | CF$_3$ | H | CH$_2$(D-22b)NH$_2$ |
| 3,5-Cl$_2$ | CF$_3$ | H | CH$_2$(D-22b)NHCH$_3$ |
| 3,5-Cl$_2$ | CF$_3$ | H | CH$_2$(D-22b)N(CH$_3$)$_2$ |
| 3,5-Cl$_2$ | CF$_3$ | H | CH(CH$_3$)(D-22a) |
| 3,5-Cl$_2$ | CF$_3$ | H | CH(CH$_3$)(D-22a)(R) |
| 3,5-Cl$_2$ | CF$_3$ | H | CH(CF$_3$)(D-22a) |
| 3,5-Cl$_2$ | CF$_3$ | H | CH(CF$_3$)(D-22a)(R) |
| 3,5-Cl$_2$ | CF$_3$ | H | CH(CF$_3$)(D-22a)(S) |
| 3,5-Cl$_2$ | CF$_3$ | H | CH(CN)(D-22a) |
| 3,5-Cl$_2$ | CF$_3$ | H | CH$_2$(D-23a) |
| 3,5-Cl$_2$ | CF$_3$ | H | CH$_2$(D-23b)Cl |
| 3,5-Cl$_2$ | CF$_3$ | H | CH$_2$(D-23b)Br |
| 3,5-Cl$_2$ | CF$_3$ | H | CH$_2$(D-23b)CH$_3$ |
| 3,5-Cl$_2$ | CF$_3$ | H | CH$_2$(D-23c)Cl |
| 3,5-Cl$_2$ | CF$_3$ | H | CH$_2$(D-23c)Br |
| 3,5-Cl$_2$ | CF$_3$ | H | CH$_2$(D-23c)CH$_3$ |
| 3,5-Cl$_2$ | CF$_3$ | H | CH$_2$(D-24a) |
| 3,5-Cl$_2$ | CF$_3$ | H | CH(CF$_3$)(D-24a) |
| 3,5-Cl$_2$ | CF$_3$ | H | CH(CN)(D-24a) |
| 3,5-Cl$_2$ | CF$_3$ | H | CH$_2$(D-25a)CH$_3$ |
| 3,5-Cl$_2$ | CF$_3$ | H | CH$_2$(D-25b)Cl |
| 3,5-Cl$_2$ | CF$_3$ | H | CH$_2$(D-25b)Br |
| 3,5-Cl$_2$ | CF$_3$ | H | CH$_2$(D-25b)CF$_3$ |
| 3,5-Cl$_2$ | CF$_3$ | H | CH$_2$(D-25c)Cl |
| 3,5-Cl$_2$ | CF$_3$ | H | CH$_2$(D-25c)Br |
| 3,5-Cl$_2$ | CF$_3$ | H | CH$_2$(D-25c)NO$_2$ |
| 3,5-Cl$_2$ | CF$_3$ | H | CH$_2$(D-26a)CH$_3$ |
| 3,5-Cl$_2$ | CF$_3$ | H | CH$_2$(D-27a)CH$_3$ |
| 3,5-Cl$_2$ | CF$_3$ | H | CH$_2$(D-27b)Cl |
| 3,5-Cl$_2$ | CF$_3$ | H | CH$_2$(D-27b)Br |
| 3,5-Cl$_2$ | CF$_3$ | H | CH$_2$(D-27b)SCH$_3$ |
| 3,5-Cl$_2$ | CF$_3$ | H | CH$_2$(D-27b)NO$_2$ |
| 3,5-Cl$_2$ | CF$_3$ | H | CH$_2$(D-28a) |
| 3,5-Cl$_2$ | CF$_3$ | CH$_3$ | CH$_2$(D-28a) |
| 3,5-Cl$_2$ | CF$_3$ | CH$_2$OCH$_3$ | CH$_2$(D-28a) |
| 3,5-Cl$_2$ | CF$_3$ | CH$_2$OC(O)CH$_3$ | CH$_2$(D-28a) |
| 3,5-Cl$_2$ | CF$_3$ | CH$_2$CN | CH$_2$(D-28a) |
| 3,5-Cl$_2$ | CF$_3$ | C(O)CH$_3$ | CH$_2$(D-28a) |
| 3,5-Cl$_2$ | CF$_3$ | C(O)Et | CH$_2$(D-28a) |
| 3,5-Cl$_2$ | CF$_3$ | C(O)OCH$_3$ | CH$_2$(D-28a) |
| 3,5-Cl$_2$ | CF$_3$ | H | CH(CH$_3$)(D-28a) |
| 3,5-Cl$_2$ | CF$_3$ | H | CH$_2$(D-29a) |
| 3,5-Cl$_2$ | CF$_3$ | H | CH$_2$(D-29b)CH$_3$ |
| 3,5-Cl$_2$ | CF$_3$ | CH$_3$ | CH$_2$(D-29b)CH$_3$ |
| 3,5-Cl$_2$ | CF$_3$ | CH$_2$OCH$_3$ | CH$_2$(D-29b)CH$_3$ |
| 3,5-Cl$_2$ | CF$_3$ | CH$_2$OC(O)CH$_3$ | CH$_2$(D-29b)CH$_3$ |
| 3,5-Cl$_2$ | CF$_3$ | CH$_2$CN | CH$_2$(D-29b)CH$_3$ |
| 3,5-Cl$_2$ | CF$_3$ | C(O)CH$_3$ | CH$_2$(D-29b)CH$_3$ |
| 3,5-Cl$_2$ | CF$_3$ | C(O)Et | CH$_2$(D-29b)CH$_3$ |
| 3,5-Cl$_2$ | CF$_3$ | C(O)OCH$_3$ | CH$_2$(D-29b)CH$_3$ |
| 3,5-Cl$_2$ | CF$_3$ | H | CH$_2$(D-30a) |
| 3,5-Cl$_2$ | CF$_3$ | H | CH$_2$(D-30b)CF$_3$ |
| 3,5-Cl$_2$ | CF$_3$ | H | CH$_2$(D-30b)SCH$_3$ |
| 3,5-Cl$_2$ | CF$_3$ | H | CH$_2$(D-31a) |
| 3,5-Cl$_2$ | CF$_3$ | H | CH$_2$(D-31b)Cl |
| 3,5-Cl$_2$ | CF$_3$ | H | CH$_2$(D-31b)Br |
| 3,5-Cl$_2$ | CF$_3$ | H | CH$_2$(D-31b)CH$_3$ |
| 3,5-Cl$_2$ | CF$_3$ | H | CH$_2$(D-31b)CF$_3$ |
| 3,5-Cl$_2$ | CF$_3$ | H | CH$_2$(D-31b)SCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$(D-32a)Cl |
| 3,5-Cl$_2$ | CF$_3$ | H | CH$_2$(D-32a)CF$_3$ |
| 3,5-Cl$_2$ | CF$_3$ | H | CH$_2$(D-33a) |
| 3,5-Cl$_2$ | CF$_3$ | H | CH$_2$(D-33b)CH$_3$ |
| 3,5-Cl$_2$ | CF$_3$ | H | CH$_2$(D-33b)CF$_3$ |
| 3,5-Cl$_2$ | CF$_3$ | H | CH$_2$(D-34a) |
| 3,5-Cl$_2$ | CF$_3$ | CH$_3$ | CH$_2$(D-34a) |
| 3,5-Cl$_2$ | CF$_3$ | CH$_2$OCH$_3$ | CH$_2$(D-34a) |
| 3,5-Cl$_2$ | CF$_3$ | CH$_2$OC(O)CH$_3$ | CH$_2$(D-34a) |
| 3,5-Cl$_2$ | CF$_3$ | CH$_2$CN | CH$_2$(D-34a) |
| 3,5-Cl$_2$ | CF$_3$ | C(O)CH$_3$ | CH$_2$(D-34a) |
| 3,5-Cl$_2$ | CF$_3$ | C(O)Et | CH$_2$(D-34a) |
| 3,5-Cl$_2$ | CF$_3$ | C(O)OCH$_3$ | CH$_2$(D-34a) |
| 3,5-Cl$_2$ | CF$_3$ | H | CH$_2$(D-34b)Cl |
| 3,5-Cl$_2$ | CF$_3$ | H | CH$_2$(D-34b)Br |
| 3,5-Cl$_2$ | CF$_3$ | H | CH$_2$(D-34b)CH$_3$ |
| 3,5-Cl$_2$ | CF$_3$ | H | CH$_2$(D-34b)CF$_3$ |
| 3,5-Cl$_2$ | CF$_3$ | H | CH(CH$_3$)(D-34a) |
| 3,5-Cl$_2$ | CF$_3$ | H | CH$_2$(D-35a) |
| 3,5-Cl$_2$ | CF$_3$ | H | CH$_2$(D-35b)Cl |
| 3,5-Cl$_2$ | CF$_3$ | H | CH$_2$(D-35b)Br |
| 3,5-Cl$_2$ | CF$_3$ | H | CH$_2$(D-35b)CH$_3$ |
| 3,5-Cl$_2$ | CF$_3$ | H | CH$_2$(D-35b)CF$_3$ |
| 3,5-Cl$_2$ | CF$_3$ | H | CH$_2$(D-35b)SCH$_3$ |
| 3,5-Cl$_2$ | CF$_3$ | H | CH(CH$_3$)(D-35a) |
| 3,5-Cl$_2$ | CF$_3$ | H | CH$_2$(D-36a) |
| 3,5-Cl$_2$ | CF$_3$ | H | CH$_2$(D-36b)CH$_3$ |
| 3,5-Cl$_2$ | CF$_3$ | H | CH$_2$(D-37a) |
| 3,5-Cl$_2$ | CF$_3$ | H | CH$_2$(D-37b)CH$_3$ |
| 3,5-Cl$_2$ | CF$_3$ | H | CH$_2$(D-38a) |
| 3,5-Cl$_2$ | CF$_3$ | CH$_3$ | CH$_2$(D-38a) |
| 3,5-Cl$_2$ | CF$_3$ | CH$_2$OCH$_3$ | CH$_2$(D-38a) |
| 3,5-Cl$_2$ | CF$_3$ | CH$_2$OC(O)CH$_3$ | CH$_2$(D-38a) |
| 3,5-Cl$_2$ | CF$_3$ | CH$_2$CN | CH$_2$(D-38a) |
| 3,5-Cl$_2$ | CF$_3$ | C(O)CH$_3$ | CH$_2$(D-38a) |
| 3,5-Cl$_2$ | CF$_3$ | C(O)Et | CH$_2$(D-38a) |
| 3,5-Cl$_2$ | CF$_3$ | C(O)OCH$_3$ | CH$_2$(D-38a) |
| 3,5-Cl$_2$ | CF$_3$ | H | CH$_2$(D-38b)CF$_3$ |
| 3,5-Cl$_2$ | CF$_3$ | H | CH(CF$_3$)(D-38a) |
| 3,5-Cl$_2$ | CF$_3$ | H | CH(CN)(D-38a) |
| 3,5-Cl$_2$ | CF$_3$ | H | CH$_2$(D-39b)Cl |
| 3,5-Cl$_2$ | CF$_3$ | H | CH$_2$(D-39b)Br |
| 3,5-Cl$_2$ | CF$_3$ | H | CH$_2$(D-40a)CH$_3$ |
| 3,5-Cl$_2$ | CF$_3$ | H | CH$_2$(D-40b)Cl |
| 3,5-Cl$_2$ | CF$_3$ | H | CH$_2$(D-40b)Br |
| 3,5-Cl$_2$ | CF$_3$ | H | CH$_2$(D-42b)Cl |
| 3,5-Cl$_2$ | CF$_3$ | H | CH$_2$(D-42b)Br |
| 3,5-Cl$_2$ | CF$_3$ | H | CH$_2$(D-47a) |
| 3,5-Cl$_2$ | CF$_3$ | CH$_3$ | CH$_2$(D-47a) |
| 3,5-Cl$_2$ | CF$_3$ | Et | CH$_2$(D-47a) |
| 3,5-Cl$_2$ | CF$_3$ | n-Pr | CH$_2$(D-47a) |
| 3,5-Cl$_2$ | CF$_3$ | i-Pr | CH$_2$(D-47a) |
| 3,5-Cl$_2$ | CF$_3$ | c-Pr | CH$_2$(D-47a) |
| 3,5-Cl$_2$ | CF$_3$ | t-Bu | CH$_2$(D-47a) |
| 3,5-Cl$_2$ | CF$_3$ | CH$_2$Cl | CH$_2$(D-47a) |
| 3,5-Cl$_2$ | CF$_3$ | CH$_2$CF$_3$ | CH$_2$(D-47a) |
| 3,5-Cl$_2$ | CF$_3$ | CH$_2$OCH$_3$ | CH$_2$(D-47a) |
| 3,5-Cl$_2$ | CF$_3$ | CH$_2$OEt | CH$_2$(D-47a) |
| 3,5-Cl$_2$ | CF$_3$ | CH$_2$OCH$_2$CH$_2$Cl | CH$_2$(D-47a) |
| 3,5-Cl$_2$ | CF$_3$ | CH$_2$OCH$_2$CF$_3$ | CH$_2$(D-47a) |
| 3,5-Cl$_2$ | CF$_3$ | CH$_2$OCH$_2$CH$_2$OCH$_3$ | CH$_2$(D-47a) |
| 3,5-Cl$_2$ | CF$_3$ | CH$_2$OCH$_2$Ph | CH$_2$(D-47a) |
| 3,5-Cl$_2$ | CF$_3$ | CH$_2$OC(O)CH$_3$ | CH$_2$(D-47a) |
| 3,5-Cl$_2$ | CF$_3$ | CH$_2$OC(O)Et | CH$_2$(D-47a) |
| 3,5-Cl$_2$ | CF$_3$ | CH$_2$OC(O)Pr-n | CH$_2$(D-47a) |
| 3,5-Cl$_2$ | CF$_3$ | CH$_2$OC(O)Pr-i | CH$_2$(D-47a) |
| 3,5-Cl$_2$ | CF$_3$ | CH$_2$OC(O)Pr-c | CH$_2$(D-47a) |
| 3,5-Cl$_2$ | CF$_3$ | CH$_2$OC(O)Bu-n | CH$_2$(D-47a) |
| 3,5-Cl$_2$ | CF$_3$ | CH$_2$OC(O)Bu-i | CH$_2$(D-47a) |
| 3,5-Cl$_2$ | CF$_3$ | CH$_2$OC(O)Bu-s | CH$_2$(D-47a) |
| 3,5-Cl$_2$ | CF$_3$ | CH$_2$OC(O)Bu-t | CH$_2$(D-47a) |
| 3,5-Cl$_2$ | CF$_3$ | CH$_2$OC(O)CH$_2$Ph | CH$_2$(D-47a) |
| 3,5-Cl$_2$ | CF$_3$ | CH$_2$OC(O)Ph | CH$_2$(D-47a) |
| 3,5-Cl$_2$ | CF$_3$ | CH$_2$OC(O)OCH$_3$ | CH$_2$(D-47a) |
| 3,5-Cl$_2$ | CF$_3$ | CH$_2$OC(O)OEt | CH$_2$(D-47a) |
| 3,5-Cl$_2$ | CF$_3$ | CH$_2$OC(O)OBu-n | CH$_2$(D-47a) |
| 3,5-Cl$_2$ | CF$_3$ | CH$_2$OC(O)OBu-i | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | CH$_2$OC(O)OCH$_2$Ph | CH$_2$(D-47a) |
| 3,5-Cl$_2$ | CF$_3$ | CH$_2$OC(O)OPh | CH$_2$(D-47a) |
| 3,5-Cl$_2$ | CF$_3$ | CH$_2$OC(O)NHPh | CH$_2$(D-47a) |
| 3,5-Cl$_2$ | CF$_3$ | CH$_2$OPh | CH$_2$(D-47a) |
| 3,5-Cl$_2$ | CF$_3$ | CH(CH$_3$)OC(O)CH$_3$ | CH$_2$(D-47a) |
| 3,5-Cl$_2$ | CF$_3$ | CH(CH$_3$)OC(O)Bu-t | CH$_2$(D-47a) |
| 3,5-Cl$_2$ | CF$_3$ | CH(CH$_3$)OC(O)OCH$_3$ | CH$_2$(D-47a) |
| 3,5-Cl$_2$ | CF$_3$ | CH(CH$_3$)OC(O)SCH$_3$ | CH$_2$(D-47a) |
| 3,5-Cl$_2$ | CF$_3$ | CH$_2$CH$_2$OCH$_3$ | CH$_2$(D-47a) |
| 3,5-Cl$_2$ | CF$_3$ | CH$_2$SCH$_3$ | CH$_2$(D-47a) |
| 3,5-Cl$_2$ | CF$_3$ | CH$_2$SO$_2$CH$_3$ | CH$_2$(D-47a) |
| 3,5-Cl$_2$ | CF$_3$ | CH$_2$SC(O)CH$_3$ | CH$_2$(D-47a) |
| 3,5-Cl$_2$ | CF$_3$ | CH$_2$SC(O)Et | CH$_2$(D-47a) |
| 3,5-Cl$_2$ | CF$_3$ | CH$_2$SC(O)Ph | CH$_2$(D-47a) |
| 3,5-Cl$_2$ | CF$_3$ | CH$_2$SC(S)OCH$_3$ | CH$_2$(D-47a) |
| 3,5-Cl$_2$ | CF$_3$ | CH$_2$SC(S)OEt | CH$_2$(D-47a) |
| 3,5-Cl$_2$ | CF$_3$ | CH$_2$SC(S)OPr-n | CH$_2$(D-47a) |
| 3,5-Cl$_2$ | CF$_3$ | CH$_2$SC(S)OPr-i | CH$_2$(D-47a) |
| 3,5-Cl$_2$ | CF$_3$ | CH$_2$SC(S)N(CH$_3$)$_2$ | CH$_2$(D-47a) |
| 3,5-Cl$_2$ | CF$_3$ | CH$_2$SC(S)(T-33) | CH$_2$(D-47a) |
| 3,5-Cl$_2$ | CF$_3$ | CH$_2$N(CH$_3$)$_2$ | CH$_2$(D-47a) |
| 3,5-Cl$_2$ | CF$_3$ | CH$_2$N(CH$_3$)C(O)CH$_3$ | CH$_2$(D-47a) |
| 3,5-Cl$_2$ | CF$_3$ | CH$_2$NHC(O)OCH$_3$ | CH$_2$(D-47a) |
| 3,5-Cl$_2$ | CF$_3$ | CH$_2$N(CH$_3$)C(O)OCH$_3$ | CH$_2$(D-47a) |
| 3,5-Cl$_2$ | CF$_3$ | CH$_2$N(CH$_3$)SO$_2$CH$_3$ | CH$_2$(D-47a) |
| 3,5-Cl$_2$ | CF$_3$ | CH$_2$CN | CH$_2$(D-47a) |
| 3,5-Cl$_2$ | CF$_3$ | CH$_2$C(O)OCH$_3$ | CH$_2$(D-47a) |
| 3,5-Cl$_2$ | CF$_3$ | CH$_2$CH=CH$_2$ | CH$_2$(D-47a) |
| 3,5-Cl$_2$ | CF$_3$ | CH$_2$C≡CH | CH$_2$(D-47a) |
| 3,5-Cl$_2$ | CF$_3$ | CH$_2$Ph | CH$_2$(D-52a) |
| 3,5-Cl$_2$ | CF$_3$ | C(O)CH$_3$ | CH$_2$(D-47a) |
| 3,5-Cl$_2$ | CF$_3$ | C(O)Et | CH$_2$(D-47a) |
| 3,5-Cl$_2$ | CF$_3$ | C(O)Pr-n | CH$_2$(D-47a) |
| 3,5-Cl$_2$ | CF$_3$ | C(O)Pr-i | CH$_2$(D-47a) |
| 3,5-Cl$_2$ | CF$_3$ | C(O)Pr-c | CH$_2$(D-47a) |
| 3,5-Cl$_2$ | CF$_3$ | C(O)Bu-n | CH$_2$(D-47a) |
| 3,5-Cl$_2$ | CF$_3$ | C(O)Bu-i | CH$_2$(D-47a) |
| 3,5-Cl$_2$ | CF$_3$ | C(O)Bu-s | CH$_2$(D-47a) |
| 3,5-Cl$_2$ | CF$_3$ | C(O)Bu-t | CH$_2$(D-47a) |
| 3,5-Cl$_2$ | CF$_3$ | C(O)CH$_2$OCH$_3$ | CH$_2$(D-47a) |
| 3,5-Cl$_2$ | CF$_3$ | C(O)CH$_2$SCH$_3$ | CH$_2$(D-47a) |
| 3,5-Cl$_2$ | CF$_3$ | C(O)CH$_2$SO$_2$CH$_3$ | CH$_2$(D-47a) |
| 3,5-Cl$_2$ | CF$_3$ | C(O)CH=CH$_2$ | CH$_2$(D-47a) |
| 3,5-Cl$_2$ | CF$_3$ | C(O)Ph | CH$_2$(D-47a) |
| 3,5-Cl$_2$ | CF$_3$ | C(O)OCH$_3$ | CH$_2$(D-47a) |
| 3,5-Cl$_2$ | CF$_3$ | C(O)OEt | CH$_2$(D-47a) |
| 3,5-Cl$_2$ | CF$_3$ | C(O)OPr-n | CH$_2$(D-47a) |
| 3,5-Cl$_2$ | CF$_3$ | C(O)OPr-i | CH$_2$(D-47a) |
| 3,5-Cl$_2$ | CF$_3$ | C(O)OPr-c | CH$_2$(D-47a) |
| 3,5-Cl$_2$ | CF$_3$ | C(O)OBu-i | CH$_2$(D-47a) |
| 3,5-Cl$_2$ | CF$_3$ | C(O)OBu-t | CH$_2$(D-47a) |
| 3,5-Cl$_2$ | CF$_3$ | C(O)OCH$_2$Cl | CH$_2$(D-47a) |
| 3,5-Cl$_2$ | CF$_3$ | C(O)OCH$_2$CH$_2$Cl | CH$_2$(D-47a) |
| 3,5-Cl$_2$ | CF$_3$ | C(O)OCH$_2$CH$_2$OCH$_3$ | CH$_2$(D-47a) |
| 3,5-Cl$_2$ | CF$_3$ | C(O)OCH$_2$CH$_2$SO$_2$CH$_3$ | CH$_2$(D-47a) |
| 3,5-Cl$_2$ | CF$_3$ | C(O)OCH$_2$CH=CH$_2$ | CH$_2$(D-47a) |
| 3,5-Cl$_2$ | CF$_3$ | C(O)OCH$_2$C≡CH | CH$_2$(D-47a) |
| 3,5-Cl$_2$ | CF$_3$ | C(O)SCH$_3$ | CH$_2$(D-47a) |
| 3,5-Cl$_2$ | CF$_3$ | C(O)NH$_2$ | CH$_2$(D-47a) |
| 3,5-Cl$_2$ | CF$_3$ | C(S)OCH$_3$ | CH$_2$(D-47a) |
| 3,5-Cl$_2$ | CF$_3$ | C(S)SCH$_3$ | CH$_2$(D-47a) |
| 3,5-Cl$_2$ | CF$_3$ | C(S)NH$_2$ | CH$_2$(D-47a) |
| 3,5-Cl$_2$ | CF$_3$ | OH | CH$_2$(D-47a) |
| 3,5-Cl$_2$ | CF$_3$ | OCH$_3$ | CH$_2$(D-47a) |
| 3,5-Cl$_2$ | CF$_3$ | OCH$_2$Ph | CH$_2$(D-47a) |
| 3,5-Cl$_2$ | CF$_3$ | OC(O)CH$_3$ | CH$_2$(D-47a) |
| 3,5-Cl$_2$ | CF$_3$ | OC(O)CF$_3$ | CH$_2$(D-47a) |
| 3,5-Cl$_2$ | CF$_3$ | OC(O)OCH$_3$ | CH$_2$(D-47a) |
| 3,5-Cl$_2$ | CF$_3$ | OC(O)NHCH$_3$ | CH$_2$(D-47a) |
| 3,5-Cl$_2$ | CF$_3$ | OSO$_2$CH$_3$ | CH$_2$(D-47a) |
| 3,5-Cl$_2$ | CF$_3$ | OSO$_2$CF$_3$ | CH$_2$(D-47a) |
| 3,5-Cl$_2$ | CF$_3$ | SCCl$_3$ | CH$_2$(D-47a) |
| 3,5-Cl$_2$ | CF$_3$ | SN(Bu-n)$_2$ | CH$_2$(D-47a) |
| 3,5-Cl$_2$ | CF$_3$ | S(T-40) | CH$_2$(D-47a) |
| 3,5-Cl$_2$ | CF$_3$ | SN(Pr-i)CH$_2$OH$_2$C(O)OEt | CH$_2$(D-47a) |
| 3,5-Cl$_2$ | CF$_3$ | SN(CH$_2$Ph)CH$_2$OH$_2$C(O)OEt | CH$_2$(D-47a) |
| 3,5-Cl$_2$ | CF$_3$ | SN(CH$_3$)C(O)OBu-n | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | SO$_2$CH$_3$ | CH$_2$(D-47a) |
| 3,5-Cl$_2$ | CF$_3$ | SO$_2$Et | CH$_2$(D-47a) |
| 3,5-Cl$_2$ | CF$_3$ | NH$_2$ | CH$_2$(D-47a) |
| 3,5-Cl$_2$ | CF$_3$ | NHCH$_3$ | CH$_2$(D-47a) |
| 3,5-Cl$_2$ | CF$_3$ | N(CH$_3$)$_2$ | CH$_2$(D-47a) |
| 3,5-Cl$_2$ | CF$_3$ | NHEt | CH$_2$(D-47a) |
| 3,5-Cl$_2$ | CF$_3$ | NHPr-i | CH$_2$(D-47a) |
| 3,5-Cl$_2$ | CF$_3$ | NHCH$_2$C≡CH | CH$_2$(D-47a) |
| 3,5-Cl$_2$ | CF$_3$ | NHCHO | CH$_2$(D-47a) |
| 3,5-Cl$_2$ | CF$_3$ | NHC(O)CH$_3$ | CH$_2$(D-47a) |
| 3,5-Cl$_2$ | CF$_3$ | N(CH$_3$)C(O)CH$_3$ | CH$_2$(D-47a) |
| 3,5-Cl$_2$ | CF$_3$ | N[C(O)CH$_3$]$_2$ | CH$_2$(D-47a) |
| 3,5-Cl$_2$ | CF$_3$ | NHC(O)Et | CH$_2$(D-47a) |
| 3,5-Cl$_2$ | CF$_3$ | NHC(O)CF$_3$ | CH$_2$(D-47a) |
| 3,5-Cl$_2$ | CF$_3$ | NHC(O)Ph | CH$_2$(D-47a) |
| 3,5-Cl$_2$ | CF$_3$ | NHC(O)OCH$_3$ | CH$_2$(D-47a) |
| 3,5-Cl$_2$ | CF$_3$ | NHC(O)OEt | CH$_2$(D-47a) |
| 3,5-Cl$_2$ | CF$_3$ | NHC(O)OBu-t | CH$_2$(D-47a) |
| 3,5-Cl$_2$ | CF$_3$ | NHC(O)NHCH$_3$ | CH$_2$(D-47a) |
| 3,5-Cl$_2$ | CF$_3$ | NHC(O)NHPh | CH$_2$(D-47a) |
| 3,5-Cl$_2$ | CF$_3$ | NHPh | CH$_2$(D-47a) |
| 3,5-Cl$_2$ | CF$_3$ | NHSO$_2$CH$_3$ | CH$_2$(D-47a) |
| 3,5-Cl$_2$ | CF$_3$ | NHSO$_2$NH2 | CH$_2$(D-47a) |
| 3,5-Cl$_2$ | CF$_3$ | NHSO$_2$NHCH$_3$ | CH$_2$(D-47a) |
| 3,5-Cl$_2$ | CF$_3$ | NHSO$_2$NHPh | CH$_2$(D-47a) |
| 3,5-Cl$_2$ | CF$_3$ | NHSO$_2$Ph | CH$_2$(D-47a) |
| 3,5-Cl$_2$ | CF$_3$ | N=CHCH$_3$ | CH$_2$(D-47a) |
| 3,5-Cl$_2$ | CF$_3$ | N=C(CH$_3$)$_2$ | CH$_2$(D-47a) |
| 3,5-Cl$_2$ | CF$_3$ | N=CHPh | CH$_2$(D-47a) |
| 3,5-Cl$_2$ | CF$_3$ | Ph | CH$_2$(D-47a) |
| 3,5-Cl$_2$ | CF$_3$ | Ph-4-F | CH$_2$(D-47a) |
| 3,5-Cl$_2$ | CF$_3$ | H | CH$_2$(D-47b)Cl |
| 3,5-Cl$_2$ | CF$_3$ | H | CH$_2$(D-47b)Br |
| 3,5-Cl$_2$ | CF$_3$ | H | CH$_2$(D-47b)CH$_3$ |
| 3,5-Cl$_2$ | CF$_3$ | H | CH$_2$(D-47b)OCH$_3$ |
| 3,5-Cl$_2$ | CF$_3$ | H | CH$_2$(D-47b)SCH$_3$ |
| 3,5-Cl$_2$ | CF$_3$ | H | CH$_2$(D-47c)Cl |
| 3,5-Cl$_2$ | CF$_3$ | H | CH$_2$(D-47c)Br |
| 3,5-Cl$_2$ | CF$_3$ | H | CH$_2$(D-47c)CH$_3$ |
| 3,5-Cl$_2$ | CF$_3$ | H | CH$_2$(D-47c)CF$_3$ |
| 3,5-Cl$_2$ | CF$_3$ | H | CH$_2$(D-47c)OCH$_3$ |
| 3,5-Cl$_2$ | CF$_3$ | H | CH$_2$(D-47c)CN |
| 3,5-Cl$_2$ | CF$_3$ | H | CH$_2$(D-47d)F |
| 3,5-Cl$_2$ | CF$_3$ | H | CH$_2$(D-47d)Cl |
| 3,5-Cl$_2$ | CF$_3$ | H | CH$_2$(D-47d)Br |
| 3,5-Cl$_2$ | CF$_3$ | H | CH$_2$(D-47d)CH$_3$ |
| 3,5-Cl$_2$ | CF$_3$ | H | CH$_2$(D-47d)CF$_3$ |
| 3,5-Cl$_2$ | CF$_3$ | H | CH$_2$(D-47d)OCH$_3$ |
| 3,5-Cl$_2$ | CF$_3$ | H | CH$_2$(D-47d)NO$_2$ |
| 3,5-Cl$_2$ | CF$_3$ | H | CH$_2$(D-47d)CN |
| 3,5-Cl$_2$ | CF$_3$ | H | CH$_2$(D-47e)F |
| 3,5-Cl$_2$ | CF$_3$ | H | CH$_2$(D-47e)Cl |
| 3,5-Cl$_2$ | CF$_3$ | H | CH$_2$(D-47e)Br |
| 3,5-Cl$_2$ | CF$_3$ | H | CH$_2$(D-47e)CH$_3$ |
| 3,5-Cl$_2$ | CF$_3$ | H | CH$_2$(D-47e)CF$_3$ |
| 3,5-Cl$_2$ | CF$_3$ | H | CH$_2$(D-47e)OCH$_3$ |
| 3,5-Cl$_2$ | CF$_3$ | H | CH$_2$(D-47e)CN |
| 3,5-Cl$_2$ | CF$_3$ | H | CH$_2$[(D-47f)-3,5-Cl$_2$] |
| 3,5-Cl$_2$ | CF$_3$ | H | CH$_2$[(D-47g)-5,6-Cl$_2$] |
| 3,5-Cl$_2$ | CF$_3$ | H | CH(CH$_3$)(D-47a) |
| 3,5-Cl$_2$ | CF$_3$ | CH$_2$OCH$_3$ | CH(CH$_3$)(D-47a) |
| 3,5-Cl$_2$ | CF$_3$ | CH$_2$CN | CH(CH$_3$)(D-47a) |
| 3,5-Cl$_2$ | CF$_3$ | CH$_2$C≡CH | CH(CH$_3$)(D-47a) |
| 3,5-Cl$_2$ | CF$_3$ | C(O)CH$_3$ | CH(CH$_3$)(D-47a) |
| 3,5-Cl$_2$ | CF$_3$ | C(O)Et | CH(CH$_3$)(D-47a) |
| 3,5-Cl$_2$ | CF$_3$ | C(O)OCH$_3$ | CH(CH$_3$)(D-47a) |
| 3,5-Cl$_2$ | CF$_3$ | H | CH(CH$_3$)(D-47a)(R) |
| 3,5-Cl$_2$ | CF$_3$ | H | CH(CH$_3$)(D-47a)(S) |
| 3,5-Cl$_2$ | CF$_3$ | H | CH(CF$_3$)(D-47a) |
| 3,5-Cl$_2$ | CF$_3$ | H | CH(CF$_3$)(D-47a)(R) |
| 3,5-Cl$_2$ | CF$_3$ | H | CH(CF$_3$)(D-47a)(S) |
| 3,5-Cl$_2$ | CF$_3$ | H | CH(CN)(D-47a) |
| 3,5-Cl$_2$ | CF$_3$ | H | CH(CN)(D-47a)(R) |
| 3,5-Cl$_2$ | CF$_3$ | H | CH(CN)(D-47a)(S) |
| 3,5-Cl$_2$ | CF$_3$ | H | CH$_2$(D-48a) |
| 3,5-Cl$_2$ | CF$_3$ | H | CH$_2$(D-48b)F |
| 3,5-Cl$_2$ | CF$_3$ | H | CH$_2$(D-48b)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$(D-48b)Br |
| 3,5-Cl$_2$ | CF$_3$ | H | CH$_2$(D-48b)CH$_3$ |
| 3,5-Cl$_2$ | CF$_3$ | H | CH$_2$(D-48b)OCH$_3$ |
| 3,5-Cl$_2$ | CF$_3$ | H | CH$_2$(D-48b)SCH$_3$ |
| 3,5-Cl$_2$ | CF$_3$ | H | CH$_2$(D-48b)CN |
| 3,5-Cl$_2$ | CF$_3$ | H | CH$_2$(D-48c)Cl |
| 3,5-Cl$_2$ | CF$_3$ | H | CH$_2$(D-48c)CH$_3$ |
| 3,5-Cl$_2$ | CF$_3$ | H | CH$_2$(D-48c)CF$_3$ |
| 3,5-Cl$_2$ | CF$_3$ | H | CH$_2$(D-48c)CH$_2$OCH$_3$ |
| 3,5-Cl$_2$ | CF$_3$ | H | CH$_2$(D-48d)Br |
| 3,5-Cl$_2$ | CF$_3$ | H | CH$_2$(D-48d)CH$_3$ |
| 3,5-Cl$_2$ | CF$_3$ | H | CH$_2$(D-48d)OCH$_3$ |
| 3,5-Cl$_2$ | CF$_3$ | H | CH$_2$(D-48d)CN |
| 3,5-Cl$_2$ | CF$_3$ | H | CH$_2$(D-48e)F |
| 3,5-Cl$_2$ | CF$_3$ | H | CH$_2$(D-48e)Cl |
| 3,5-Cl$_2$ | CF$_3$ | Et | CH$_2$(D-48e)Cl |
| 3,5-Cl$_2$ | CF$_3$ | H | CH$_2$(D-48e)Br |
| 3,5-Cl$_2$ | CF$_3$ | H | CH$_2$(D-48e)CH$_3$ |
| 3,5-Cl$_2$ | CF$_3$ | H | CH$_2$(D-48e)CF$_3$ |
| 3,5-Cl$_2$ | CF$_3$ | H | CH$_2$(D-48e)OCH$_3$ |
| 3,5-Cl$_2$ | CF$_3$ | H | CH$_2$(D-48e)SCH$_3$ |
| 3,5-Cl$_2$ | CF$_3$ | H | CH$_2$(D-48e)CN |
| 3,5-Cl$_2$ | CF$_3$ | H | CH$_2$[(D-48f)-2,6-F$_2$] |
| 3,5-Cl$_2$ | CF$_3$ | H | CH$_2$[(D-48g)-4-CF$_3$-6-Cl] |
| 3,5-Cl$_2$ | CF$_3$ | H | CH$_2$[(D-48h)-5,6-Cl$_2$] |
| 3,5-Cl$_2$ | CF$_3$ | H | CH$_2$(D-49a) |
| 3,5-Cl$_2$ | CF$_3$ | c-Pr | CH$_2$(D-49a) |
| 3,5-Cl$_2$ | CF$_3$ | H | CH$_2$(D-49b)F |
| 3,5-Cl$_2$ | CF$_3$ | Et | CH$_2$(D-49b)F |
| 3,5-Cl$_2$ | CF$_3$ | H | CH$_2$(D-49b)Cl |
| 3,5-Cl$_2$ | CF$_3$ | H | CH$_2$(D-49b)Br |
| 3,5-Cl$_2$ | CF$_3$ | H | CH$_2$(D-49b)CH$_3$ |
| 3,5-Cl$_2$ | CF$_3$ | H | CH$_2$(D-49b)CN |
| 3,5-Cl$_2$ | CF$_3$ | H | CH$_2$(D-49c)Cl |
| 3,5-Cl$_2$ | CF$_3$ | H | CH$_2$(D-49c)OCH$_3$ |
| 3,5-Cl$_2$ | CF$_3$ | H | CH$_2$(D-49c)NO$_2$ |
| 3,5-Cl$_2$ | CF$_3$ | H | CH$_2$(D-49c)CN |
| 3,5-Cl$_2$ | CF$_3$ | H | CH$_2$(D-49e) |
| 3,5-Cl$_2$ | CF$_3$ | H | CH$_2$(D-50a) |
| 3,5-Cl$_2$ | CF$_3$ | CH$_2$OCH$_3$ | CH$_2$(D-50a) |
| 3,5-Cl$_2$ | CF$_3$ | CH$_2$CN | CH$_2$(D-50a) |
| 3,5-Cl$_2$ | CF$_3$ | C(O)CH$_3$ | CH$_2$(D-50a) |
| 3,5-Cl$_2$ | CF$_3$ | C(O)Et | CH$_2$(D-50a) |
| 3,5-Cl$_2$ | CF$_3$ | C(O)OCH$_3$ | CH$_2$(D-50a) |
| 3,5-Cl$_2$ | CF$_3$ | H | CH$_2$(D-50b)Cl |
| 3,5-Cl$_2$ | CF$_3$ | H | CH$_2$(D-50b)CH$_3$ |
| 3,5-Cl$_2$ | CF$_3$ | H | CH$_2$(D-50b)CF$_3$ |
| 3,5-Cl$_2$ | CF$_3$ | H | CH$_2$(D-50b)OCH$_3$ |
| 3,5-Cl$_2$ | CF$_3$ | H | CH$_2$(D-50c)F |
| 3,5-Cl$_2$ | CF$_3$ | H | CH$_2$(D-50c)Cl |
| 3,5-Cl$_2$ | CF$_3$ | H | CH$_2$(D-50c)Br |
| 3,5-Cl$_2$ | CF$_3$ | H | CH$_2$(D-50c)OCH$_3$ |
| 3,5-Cl$_2$ | CF$_3$ | H | CH$_2$(D-50c)NO$_2$ |
| 3,5-Cl$_2$ | CF$_3$ | H | CH$_2$(D-50c)CN |
| 3,5-Cl$_2$ | CF$_3$ | H | CH$_2$(D-50c)C(O)NH$_2$ |
| 3,5-Cl$_2$ | CF$_3$ | H | CH(CH$_3$)(D-50a) |
| 3,5-Cl$_2$ | CF$_3$ | H | CH$_2$(D-51a) |
| 3,5-Cl$_2$ | CF$_3$ | H | CH$_2$(D-51b)Cl |
| 3,5-Cl$_2$ | CF$_3$ | H | CH$_2$(D-51b)CH$_3$ |
| 3,5-Cl$_2$ | CF$_3$ | H | CH$_2$(D-51b)OCH$_3$ |
| 3,5-Cl$_2$ | CF$_3$ | H | CH$_2$(D-51b)SCH$_3$ |
| 3,5-Cl$_2$ | CF$_3$ | H | CH$_2$(D-51b)CN |
| 3,5-Cl$_2$ | CF$_3$ | H | CH$_2$(D-51c)Cl |
| 3,5-Cl$_2$ | CF$_3$ | H | CH$_2$(D-51c)CH$_3$ |
| 3,5-Cl$_2$ | CF$_3$ | H | CH$_2$(D-51c)OCH$_3$ |
| 3,5-Cl$_2$ | CF$_3$ | H | CH$_2$(D-51c)SCH$_3$ |
| 3,5-Cl$_2$ | CF$_3$ | H | CH$_2$(D-51c)CN |
| 3,5-Cl$_2$ | CF$_3$ | H | CH$_2$(D-51d)F |
| 3,5-Cl$_2$ | CF$_3$ | H | CH$_2$(D-51d)OCH$_3$ |
| 3,5-Cl$_2$ | CF$_3$ | H | CH$_2$(D-51d)CN |
| 3,5-Cl$_2$ | CF$_3$ | H | CH(CH$_3$)(D-51a) |
| 3,5-Cl$_2$ | CF$_3$ | H | CH$_2$(D-52a) |
| 3,5-Cl$_2$ | CF$_3$ | H | CH$_2$(D-52b)Cl |
| 3,5-Cl$_2$ | CF$_3$ | H | CH$_2$(D-52b)Br |
| 3,5-Cl$_2$ | CF$_3$ | H | CH$_2$(D-52b)OCH$_3$ |
| 3,5-Cl$_2$ | CF$_3$ | H | CH$_2$(D-52b)SCH$_3$ |
| 3,5-Cl$_2$ | CF$_3$ | H | CH$_2$(D-52c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH$_2$(D-52c)OCH$_3$ |
| 3,5-Cl$_2$ | CF$_3$ | H | CH$_2$(D-53a) |
| 3,5-Cl$_2$ | CF$_3$ | H | CH$_2$(D-53b)Cl |
| 3,5-Cl$_2$ | CF$_3$ | H | CH$_2$(D-53b)Br |
| 3,5-Cl$_2$ | CF$_3$ | H | CH$_2$(D-53b)CH$_3$ |
| 3,5-Cl$_2$ | CF$_3$ | H | CH$_2$(D-53b)OCH$_3$ |
| 3,5-Cl$_2$ | CF$_3$ | H | CH$_2$(D-53b)CN |
| 3,5-Cl$_2$ | CF$_3$ | H | CH$_2$(D-53b)C(O)NH$_2$ |
| 3,5-Cl$_2$ | CF$_3$ | H | CH$_2$(D-53c)F |
| 3,5-Cl$_2$ | CF$_3$ | H | CH$_2$(D-53c)Cl |
| 3,5-Cl$_2$ | CF$_3$ | H | CH$_2$(D-53c)CH$_3$ |
| 3,5-Cl$_2$ | CF$_3$ | H | CH$_2$(D-53c)OCH$_3$ |
| 3,5-Cl$_2$ | CF$_3$ | H | CH$_2$(D-53c)CN |
| 3,5-Cl$_2$ | CF$_3$ | H | CH$_2$(D-53d)Cl |
| 3,5-Cl$_2$ | CF$_3$ | H | CH$_2$(D-53d)OCH$_3$ |
| 3,5-Cl$_2$ | CF$_3$ | H | CH$_2$(D-53d)SCH$_3$ |
| 3,5-Cl$_2$ | CF$_3$ | H | CH$_2$(D-53d)CN |
| 3,5-Cl$_2$ | CF$_3$ | H | CH(CH$_3$)(D-53a) |
| 3,5-Cl$_2$ | CF$_3$ | H | CH$_2$(D-54a) |
| 3,5-Cl$_2$ | CF$_3$ | H | CH$_2$(D-54b)Cl |
| 3,5-Cl$_2$ | CF$_3$ | H | CH$_2$(D-54b)OCH$_3$ |
| 3,5-Cl$_2$ | CF$_3$ | H | CH(CH$_3$)(D-54a) |
| 3,5-Cl$_2$ | CF$_3$ | H | CH$_2$(D-55a) |
| 3,5-Cl$_2$ | CF$_3$ | H | CH$_2$(D-56a) |
| 3,5-Cl$_2$ | CF$_3$ | H | CH$_2$(D-57a) |
| 3,5-Cl$_2$ | CF$_3$ | H | CH$_2$(D-58a) |
| 3,5-Cl$_2$ | CF$_3$ | H | CH$_2$(D-59a) |
| 3,5-Cl$_2$ | CF$_3$ | H | CH$_2$(D-61a) |
| 3,5-Cl$_2$ | CF$_3$ | H | CH$_2$(D-62a)CH$_3$ |
| 3,5-Cl$_2$ | CF$_3$ | H | CH$_2$(D-63a)CH$_3$ |
| 3,5-Cl$_2$ | CF$_3$ | H | CH$_2$(D-64a) |
| 3,5-Cl$_2$ | CF$_3$ | H | CH$_2$(D-65a)CH$_3$ |
| 3,5-Cl$_2$ | CF$_3$ | H | CH$_2$CH$_2$(D-47a) |
| 3,5-Cl$_2$ | CF$_3$ | H | OCH$_3$ |
| 3,5-Cl$_2$ | CF$_3$ | C(O)OCH$_3$ | OCH$_3$ |
| 3,5-Cl$_2$ | CF$_3$ | H | OCH$_2$CH=CHCl |
| 3,5-Cl$_2$ | CF$_3$ | H | OCH$_2$Ph |
| 3,5-Cl$_2$ | CF$_3$ | H | SO$_2$N(CH$_3$)$_2$ |
| 3,5-Cl$_2$ | CF$_3$ | H | N(CH$_3$)$_2$ |
| 3,5-Cl$_2$ | CF$_3$ | C(O)OCH$_3$ | N(CH$_3$)$_2$ |
| 3,5-Cl$_2$ | CF$_3$ | H | N(Et)$_2$ |
| 3,5-Cl$_2$ | CF$_3$ | H | N(Pr-n)$_2$ |
| 3,5-Cl$_2$ | CF$_3$ | H | N(CH$_3$)Bu-n |
| 3,5-Cl$_2$ | CF$_3$ | H | N(Bu-n)$_2$ |
| 3,5-Cl$_2$ | CF$_3$ | H | N(Bu-i)$_2$ |
| 3,5-Cl$_2$ | CF$_3$ | H | T-32 |
| 3,5-Cl$_2$ | CF$_3$ | H | T-33 |
| 3,5-Cl$_2$ | CF$_3$ | H | T-34 |
| 3,5-Cl$_2$ | CF$_3$ | H | T-39 |
| 3,5-Cl$_2$ | CF$_3$ | H | T-43 |
| 3,5-Cl$_2$ | CF$_3$ | H | NHCH$_2$CF$_3$ |
| 3,5-Cl$_2$ | CF$_3$ | H | N(CH$_3$)CH$_2$CF$_3$ |
| 3,5-Cl$_2$ | CF$_3$ | H | T-40 |
| 3,5-Cl$_2$ | CF$_3$ | H | T-42 |
| 3,5-Cl$_2$ | CF$_3$ | H | N(CH$_2$CH=CH$_2$)$_2$ |
| 3,5-Cl$_2$ | CF$_3$ | H | NHCHO |
| 3,5-Cl$_2$ | CF$_3$ | H | N(CH$_3$)CHO |
| 3,5-Cl$_2$ | CF$_3$ | H | N(Et)CHO |
| 3,5-Cl$_2$ | CF$_3$ | H | N(Bu-n)CHO |
| 3,5-Cl$_2$ | CF$_3$ | H | N(Ph)CHO |
| 3,5-Cl$_2$ | CF$_3$ | H | NHC(O)CH$_3$ |
| 3,5-Cl$_2$ | CF$_3$ | H | N(CH$_3$)C(O)CH$_3$ |
| 3,5-Cl$_2$ | CF$_3$ | H | N(Ph)C(O)CH$_3$ |
| 3,5-Cl$_2$ | CF$_3$ | H | N(Ph)C(O)Et |
| 3,5-Cl$_2$ | CF$_3$ | H | N(CH$_2$Ph)C(O)CH$_2$OPh |
| 3,5-Cl$_2$ | CF$_3$ | H | NHC(O)Ph |
| 3,5-Cl$_2$ | CF$_3$ | H | NHC(O)OCH$_3$ |
| 3,5-Cl$_2$ | CF$_3$ | H | N(CH$_3$)C(O)OCH$_3$ |
| 3,5-Cl$_2$ | CF$_3$ | H | N(Ph)C(O)OCH$_3$ |
| 3,5-Cl$_2$ | CF$_3$ | H | NHC(O)OCH$_2$CF$_3$ |
| 3,5-Cl$_2$ | CF$_3$ | H | N(CH$_3$)C(O)OCH$_2$CF$_3$ |
| 3,5-Cl$_2$ | CF$_3$ | H | NHC(O)OCH$_2$Ph |
| 3,5-Cl$_2$ | CF$_3$ | H | NHC(O)OPh |
| 3,5-Cl$_2$ | CF$_3$ | H | T-36 |
| 3,5-Cl$_2$ | CF$_3$ | H | N(Ph)C(O)SCH$_3$ |
| 3,5-Cl$_2$ | CF$_3$ | H | N(CH$_3$)C(O)NHEt |
| 3,5-Cl$_2$ | CF$_3$ | H | N(CH$_3$)C(O)NHPr-i |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-$Cl_2$ | $CF_3$ | H | $N(CH_3)C(O)NHCH_2CH_2F$ |
| 3,5-$Cl_2$ | $CF_3$ | H | $N(CH_3)C(O)NHCH_2CH_2Cl$ |
| 3,5-$Cl_2$ | $CF_3$ | H | $N(CH_3)C(O)NHCH_2CF_3$ |
| 3,5-$Cl_2$ | $CF_3$ | H | $N(CH_3)C(O)NHCH_2CH=CH_2$ |
| 3,5-$Cl_2$ | $CF_3$ | H | $N(CH_3)C(O)NHCH_2C\equiv CH$ |
| 3,5-$Cl_2$ | $CF_3$ | H | $N(Ph)C(S)OCH_3$ |
| 3,5-$Cl_2$ | $CF_3$ | H | $N(CH_3)C(S)SCH_3$ |
| 3,5-$Cl_2$ | $CF_3$ | H | $N(Ph)C(S)SCH_3$ |
| 3,5-$Cl_2$ | $CF_3$ | H | $N(CH_3)C(S)NH_2$ |
| 3,5-$Cl_2$ | $CF_3$ | H | $N(CH_3)C(S)NHCH_3$ |
| 3,5-$Cl_2$ | $CF_3$ | H | $NHC(S)N(CH_3)_2$ |
| 3,5-$Cl_2$ | $CF_3$ | H | $N(CH_3)C(S)NHPh$ |
| 3,5-$Cl_2$ | $CF_3$ | H | $N(Ph)C(S)NHPh$ |
| 3,5-$Cl_2$ | $CF_3$ | H | T-38 |
| 3,5-$Cl_2$ | $CF_3$ | H | NHPh |
| 3,5-$Cl_2$ | $CF_3$ | H | $N(CH_3)Ph$ |
| 3,5-$Cl_2$ | $CF_3$ | $CH_3$ | $N(CH_3)Ph$ |
| 3,5-$Cl_2$ | $CF_3$ | Et | $N(CH_3)Ph$ |
| 3,5-$Cl_2$ | $CF_3$ | $CH_2OCH_3$ | $N(CH_3)Ph$ |
| 3,5-$Cl_2$ | $CF_3$ | $CH_2OC(O)CH_3$ | $N(CH_3)Ph$ |
| 3,5-$Cl_2$ | $CF_3$ | $CH_2CN$ | $N(CH_3)Ph$ |
| 3,5-$Cl_2$ | $CF_3$ | $CH_2CH=CH_2$ | $N(CH_3)Ph$ |
| 3,5-$Cl_2$ | $CF_3$ | $CH_2CCH$ | $N(CH_3)Ph$ |
| 3,5-$Cl_2$ | $CF_3$ | $C(O)CH_3$ | $N(CH_3)Ph$ |
| 3,5-$Cl_2$ | $CF_3$ | $C(O)Et$ | $N(CH_3)Ph$ |
| 3,5-$Cl_2$ | $CF_3$ | $C(O)OCH_3$ | $N(CH_3)Ph$ |
| 3,5-$Cl_2$ | $CF_3$ | H | $N(CH_2OCH_3)Ph$ |
| 3,5-$Cl_2$ | $CF_3$ | H | $N(CH_2OEt)Ph$ |
| 3,5-$Cl_2$ | $CF_3$ | H | $N(CH_2SCH_3)Ph$ |
| 3,5-$Cl_2$ | $CF_3$ | H | $N(CH_2CN)Ph$ |
| 3,5-$Cl_2$ | $CF_3$ | H | $N(CH_2CH=CH_2)Ph$ |
| 3,5-$Cl_2$ | $CF_3$ | H | $N(CH_2C\equiv CH)Ph$ |
| 3,5-$Cl_2$ | $CF_3$ | $CH_3$ | $N(CH_2C\equiv CH)Ph$ |
| 3,5-$Cl_2$ | $CF_3$ | $CH_2OCH_3$ | $N(CH_2C\equiv CH)Ph$ |
| 3,5-$Cl_2$ | $CF_3$ | $CH_2OC(O)CH_3$ | $N(CH_2C\equiv CH)Ph$ |
| 3,5-$Cl_2$ | $CF_3$ | $CH_2CN$ | $N(CH_2C\equiv CH)Ph$ |
| 3,5-$Cl_2$ | $CF_3$ | $C(O)CH_3$ | $N(CH_2C\equiv CH)Ph$ |
| 3,5-$Cl_2$ | $CF_3$ | $C(O)Et$ | $N(CH_2C\equiv CH)Ph$ |
| 3,5-$Cl_2$ | $CF_3$ | $C(O)OCH_3$ | $N(CH_2C\equiv CH)Ph$ |
| 3,5-$Cl_2$ | $CF_3$ | H | $N(CH_2Ph)Ph$ |
| 3,5-$Cl_2$ | $CF_3$ | H | $N(CH_3)(Ph-2-F)$ |
| 3,5-$Cl_2$ | $CF_3$ | H | $N(CH_3)(Ph-3-F)$ |
| 3,5-$Cl_2$ | $CF_3$ | H | $N(CH_3)(Ph-4-F)$ |
| 3,5-$Cl_2$ | $CF_3$ | H | $N(CH_3)(Ph-2-Cl)$ |
| 3,5-$Cl_2$ | $CF_3$ | H | $N(CH_3)(Ph-3-Cl)$ |
| 3,5-$Cl_2$ | $CF_3$ | H | $NH(Ph-4-Cl)$ |
| 3,5-$Cl_2$ | $CF_3$ | H | $N(CH_3)(Ph-4-Cl)$ |
| 3,5-$Cl_2$ | $CF_3$ | H | $N(CH_3)(Ph-4-Br)$ |
| 3,5-$Cl_2$ | $CF_3$ | H | $N(CH_3)(Ph-2-CH_3)$ |
| 3,5-$Cl_2$ | $CF_3$ | H | $N(CH_3)(Ph-3-CH_3)$ |
| 3,5-$Cl_2$ | $CF_3$ | H | $N(CH_3)(Ph-4-CH_3)$ |
| 3,5-$Cl_2$ | $CF_3$ | H | $N(CH_3)(Ph-4-CF_3)$ |
| 3,5-$Cl_2$ | $CF_3$ | H | $N(CH_3)(Ph-4-OCH_3)$ |
| 3,5-$Cl_2$ | $CF_3$ | H | $N(CH_3)(Ph-4-OCHF_2)$ |
| 3,5-$Cl_2$ | $CF_3$ | H | $N(CH_3)(Ph-4-OCF_3)$ |
| 3,5-$Cl_2$ | $CF_3$ | H | $N(CH_3)(Ph-4-SCH_3)$ |
| 3,5-$Cl_2$ | $CF_3$ | H | $N(CH_3)(Ph-4-SO_2CH_3)$ |
| 3,5-$Cl_2$ | $CF_3$ | H | $N(CH_3)(Ph-4-SCF_3)$ |
| 3,5-$Cl_2$ | $CF_3$ | H | $N(CH_3)(Ph-4-SO_2NH_2)$ |
| 3,5-$Cl_2$ | $CF_3$ | H | $N(CH_3)[Ph-4-N(CH_3)_2]$ |
| 3,5-$Cl_2$ | $CF_3$ | H | $N(CH_3)(Ph-2-NO_2)$ |
| 3,5-$Cl_2$ | $CF_3$ | H | $NH(Ph-3-NO_2)$ |
| 3,5-$Cl_2$ | $CF_3$ | H | $N(CH_3)(Ph-3-NO_2)$ |
| 3,5-$Cl_2$ | $CF_3$ | H | $NH(Ph-4-NO_2)$ |
| 3,5-$Cl_2$ | $CF_3$ | H | $N(CH_3)(Ph-4-NO_2)$ |
| 3,5-$Cl_2$ | $CF_3$ | H | $NH(Ph-4-CN)$ |
| 3,5-$Cl_2$ | $CF_3$ | H | $N(CH_3)(Ph-4-CN)$ |
| 3,5-$Cl_2$ | $CF_3$ | H | $N(CH_3)(Ph-2,4-F_2)$ |
| 3,5-$Cl_2$ | $CF_3$ | H | $N(CH_3)(Ph-2,5-F_2)$ |
| 3,5-$Cl_2$ | $CF_3$ | H | $N(CH_3)(Ph-2,6-F_2)$ |
| 3,5-$Cl_2$ | $CF_3$ | H | $N(CH_3)(Ph-3,4-F_2)$ |
| 3,5-$Cl_2$ | $CF_3$ | H | $N(CH_3)(Ph-3,5-F_2)$ |
| 3,5-$Cl_2$ | $CF_3$ | H | $NH(D-3a)$ |
| 3,5-$Cl_2$ | $CF_3$ | H | $N(CH_3)(D-3a)$ |
| 3,5-$Cl_2$ | $CF_3$ | H | $NH(D-4a)$ |
| 3,5-$Cl_2$ | $CF_3$ | H | $N(CH_3)(D-4a)$ |
| 3,5-$Cl_2$ | $CF_3$ | H | $NH(D-21a)$ |

TABLE 2-continued

In the table, the number showing the substitution position of substituent $(X)_m$ corresponds to the position number indicated in the following structural formulae. The indication "—" means no-substitution.

| | | | | |
|---|---|---|---|---|
| 3,5-Cl$_2$ | CF$_3$ | | H | N(CH$_3$)(D-21a) |
| 3,5-Cl$_2$ | CF$_3$ | | H | N(Et)(D-21a) |
| 3,5-Cl$_2$ | CF$_3$ | | H | NH(D-47a) |
| 3,5-Cl$_2$ | CF$_3$ | | H | N(CH$_3$)(D-47a) |
| 3,5-Cl$_2$ | CF$_3$ | | CH$_3$ | N(CH$_3$)(D-47a) |
| 3,5-Cl$_2$ | CF$_3$ | | CH$_2$OCH$_3$ | N(CH$_3$)(D-47a) |
| 3,5-Cl$_2$ | CF$_3$ | | CH$_2$OC(O)CH$_3$ | N(CH$_3$)(D-47a) |
| 3,5-Cl$_2$ | CF$_3$ | | CH$_2$CN | N(CH$_3$)(D-47a) |
| 3,5-Cl$_2$ | CF$_3$ | | C(O)CH$_3$ | N(CH$_3$)(D-47a) |
| 3,5-Cl$_2$ | CF$_3$ | | C(O)Et | N(CH$_3$)(D-47a) |
| 3,5-Cl$_2$ | CF$_3$ | | C(O)OCH$_3$ | N(CH$_3$)(D-47a) |
| 3,5-Cl$_2$ | CF$_3$ | | H | N(Et)(D-47a) |
| 3,5-Cl$_2$ | CF$_3$ | | H | NH(D-47b)Cl |
| 3,5-Cl$_2$ | CF$_3$ | | H | NH(D-47d)F |
| 3,5-Cl$_2$ | CF$_3$ | | H | NH(D-47d)Cl |
| 3,5-Cl$_2$ | CF$_3$ | | H | N(CH$_3$)(D-47d)Cl |
| 3,5-Cl$_2$ | CF$_3$ | | H | NH(D-47d)CF$_3$ |
| 3,5-Cl$_2$ | CF$_3$ | | H | NH(D-47d)NO$_2$ |
| 3,5-Cl$_2$ | CF$_3$ | | H | NH(D-47e)Cl |
| 3,5-Cl$_2$ | CF$_3$ | | H | NH(D-47e)OCH$_3$ |
| 3,5-Cl$_2$ | CF$_3$ | | H | NH[(D-47f)-3-Cl-5-CF$_3$] |
| 3,5-Cl$_2$ | CF$_3$ | | H | N(CH$_3$)[(D-47f)-3-Cl-5-CF$_3$] |
| 3,5-Cl$_2$ | CF$_3$ | | H | NH(D-50a) |
| 3,5-Cl$_2$ | CF$_3$ | | CH$_3$ | NH(D-50a) |
| 3,5-Cl$_2$ | CF$_3$ | | Et | NH(D-50a) |
| 3,5-Cl$_2$ | CF$_3$ | | H | N(CH$_3$)(D-50a) |
| 3,5-Cl$_2$ | CF$_3$ | | CH$_3$ | N(CH$_3$)(D-50a) |
| 3,5-Cl$_2$ | CF$_3$ | | CH$_2$OCH$_3$ | N(CH$_3$)(D-50a) |
| 3,5-Cl$_2$ | CF$_3$ | | CH$_2$OC(O)CH$_3$ | N(CH$_3$)(D-50a) |
| 3,5-Cl$_2$ | CF$_3$ | | CH$_2$CN | N(CH$_3$)(D-50a) |
| 3,5-Cl$_2$ | CF$_3$ | | C(O)CH$_3$ | N(CH$_3$)(D-50a) |
| 3,5-Cl$_2$ | CF$_3$ | | C(O)Et | N(CH$_3$)(D-50a) |
| 3,5-Cl$_2$ | CF$_3$ | | C(O)OCH$_3$ | N(CH$_3$)(D-50a) |
| 3,5-Cl$_2$ | CF$_3$ | | H | N(Et)(D-50a) |
| 3,5-Cl$_2$ | CF$_3$ | | CH$_3$ | N(Et)(D-50a) |
| 3,5-Cl$_2$ | CF$_3$ | | CH$_2$OCH$_3$ | N(Et)(D-50a) |
| 3,5-Cl$_2$ | CF$_3$ | | CH$_2$OC(O)CH$_3$ | N(Et)(D-50a) |
| 3,5-Cl$_2$ | CF$_3$ | | CH$_2$CN | N(Et)(D-50a) |
| 3,5-Cl$_2$ | CF$_3$ | | C(O)CH$_3$ | N(Et)(D-50a) |
| 3,5-Cl$_2$ | CF$_3$ | | C(O)Et | N(Et)(D-50a) |
| 3,5-Cl$_2$ | CF$_3$ | | C(O)OCH$_3$ | N(Et)(D-50a) |
| 3,5-Cl$_2$ | CF$_3$ | | H | NH(D-50b)CF$_3$ |
| 3,5-Cl$_2$ | CF$_3$ | | H | NH(D-51a) |
| 3,5-Cl$_2$ | CF$_3$ | | H | N(CH$_3$)(D-51a) |
| 3,5-Cl$_2$ | CF$_3$ | | H | NH(D-53a) |
| 3,5-Cl$_2$ | CF$_3$ | | H | N(CH$_3$)(D-53a) |
| 3,5-Cl$_2$ | CF$_3$ | | H | NH(D-53b)CH$_3$ |
| 3,5-Cl$_2$ | CF$_3$ | | H | NH(D-53b)OCH$_3$ |
| 3,5-Cl$_2$ | CF$_3$ | | H | NH(D-53c)CH$_3$ |
| 3,5-Cl$_2$ | CF$_3$ | | H | NH(D-54a) |
| 3,5-Cl$_2$ | CF$_3$ | | H | N(CH$_3$)(D-54a) |
| 3,5-Cl$_2$ | CF$_3$ | | H | NH(D-54b)Cl |
| 3,5-Cl$_2$ | CF$_3$ | | H | NH(D-54b)CH$_3$ |
| 3,5-Cl$_2$ | CF$_3$ | | H | NH(D-54b)OCH$_3$ |
| 3,5-Cl$_2$ | CF$_3$ | | —CH$_2$CH$_2$C(O)NH— | |
| 3,5-Cl$_2$ | CF$_3$ | | —CH$_2$CH$_2$C(O)N(CH$_3$)— | |
| 3,5-Cl$_2$ | CF$_3$ | | H | N=C(OH$_3$)$_2$ |
| 3,5-Cl$_2$ | CF$_3$ | | H | N=C(CH$_3$)OCH$_3$ |
| 3,5-Cl$_2$ | CF$_3$ | | H | N=C(Et)OCH$_3$ |
| 3,5-Cl$_2$ | CF$_3$ | | H | N=C(n-Pr)OCH$_3$ |
| 3,5-Cl$_2$ | CF$_3$ | | H | N=C(CH$_3$)OEt |
| 3,5-Cl$_2$ | CF$_3$ | | H | N=C(Et)OEt |
| 3,5-Cl$_2$ | CF$_3$ | | H | N=C(n-Pr)OEt |
| 3,5-Cl$_2$ | CF$_3$ | | H | N=CHN(CH$_3$)$_2$ |
| 3,5-Cl$_2$ | CF$_3$ | | H | N=C(CH$_3$)N(CH$_3$)$_2$ |
| 3,5-Cl$_2$ | CF$_3$ | | H | N=C(Et)N(CH$_3$)$_2$ |
| 3,5-Cl$_2$ | CF$_3$ | | H | N=CHPh |
| 3,5-Cl$_2$ | CF$_3$ | | H | N=C(CH$_3$)Ph |
| 3,5-Cl$_2$ | CF$_3$ | | H | N=CH(D-47a) |
| 3,5-Cl$_2$ | CF$_3$ | | H | N=C(CH$_3$)(D-47a) |
| 3,5-Cl$_2$ | CF$_3$ | | H | CHO |
| 3,5-Cl$_2$ | CF$_3$ | | H | C(O)CH$_3$ |
| 3,5-Cl$_2$ | CF$_3$ | | C(O)CH$_3$ | C(O)CH$_3$ |
| 3,5-Cl$_2$ | CF$_3$ | | H | C(O)Et |
| 3,5-Cl$_2$ | CF$_3$ | | H | C(O)CH$_2$CF$_3$ |
| 3,5-Cl$_2$ | CF$_3$ | | H | C(O)(D-47a) |
| 3,5-Cl$_2$ | CF$_3$ | | H | C(O)OCH$_2$Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | C(O)CH$_3$ | C(O)OCH$_2$Cl |
| 3,5-Cl$_2$ | CF$_3$ | H | C(O)OCH$_2$CH$_2$F |
| 3,5-Cl$_2$ | CF$_3$ | C(O)CH$_3$ | C(O)OCH$_2$CH$_2$F |
| 3,5-Cl$_2$ | CF$_3$ | H | C(O)OCH$_2$CH$_2$Cl |
| 3,5-Cl$_2$ | CF$_3$ | H | C(O)OCH$_2$CHF$_2$ |
| 3,5-Cl$_2$ | CF$_3$ | H | C(O)OCH$_2$CHCl$_2$ |
| 3,5-Cl$_2$ | CF$_3$ | H | C(O)OCH$_2$CF$_3$ |
| 3,5-Cl$_2$ | CF$_3$ | H | C(O)OCH$_2$CCl$_3$ |
| 3,5-Cl$_2$ | CF$_3$ | H | C(O)OCH$_2$CH$_2$CF$_3$ |
| 3,5-Cl$_2$ | CF$_3$ | C(O)CH$_3$ | C(O)OCH$_2$CH$_2$CF$_3$ |
| 3,5-Cl$_2$ | CF$_3$ | H | C(O)OCH(CH$_2$F)$_2$ |
| 3,5-Cl$_2$ | CF$_3$ | H | C(O)OCH(CH$_2$F)CH$_2$Cl |
| 3,5-Cl$_2$ | CF$_3$ | H | C(O)OCH(CH$_2$Cl)$_2$ |
| 3,5-Cl$_2$ | CF$_3$ | H | C(O)OCH(CF$_3$)$_2$ |
| 3,5-Cl$_2$ | CF$_3$ | H | C(O)OCH$_2$CH$_2$CH$_2$CH$_2$Cl |
| 3,5-Cl$_2$ | CF$_3$ | H | C(O)OCH(CH$_3$)CHClCH$_3$ |
| 3,5-Cl$_2$ | CF$_3$ | H | C(O)OCH$_2$C(CF$_3$)$_2$CH$_3$ |
| 3,5-Cl$_2$ | CF$_3$ | C(O)CH$_3$ | C(O)OCH$_2$C(CF$_3$)$_2$CH$_3$ |
| 3,5-Cl$_2$ | CF$_3$ | H | C(O)NHCH$_3$ |
| 3,5-Cl$_2$ | CF$_3$ | H | C(O)N(CH$_3$)$_2$ |
| 3,5-Cl$_2$ | CF$_3$ | CH$_3$ | C(O)N(CH$_3$)$_2$ |
| 3,5-Cl$_2$ | CF$_3$ | CH$_2$OCH$_3$ | C(O)N(CH$_3$)$_2$ |
| 3,5-Cl$_2$ | CF$_3$ | CH$_2$OC(O)CH$_3$ | C(O)N(CH$_3$)$_2$ |
| 3,5-Cl$_2$ | CF$_3$ | CH$_2$CN | C(O)N(CH$_3$)$_2$ |
| 3,5-Cl$_2$ | CF$_3$ | C(O)CH$_3$ | C(O)N(CH$_3$)$_2$ |
| 3,5-Cl$_2$ | CF$_3$ | C(O)Et | C(O)N(CH$_3$)$_2$ |
| 3,5-Cl$_2$ | CF$_3$ | C(O)OCH$_3$ | C(O)N(CH$_3$)$_2$ |
| 3,5-Cl$_2$ | CF$_3$ | H | C(O)NHEt |
| 3,5-Cl$_2$ | CF$_3$ | CH$_3$ | C(O)NHEt |
| 3,5-Cl$_2$ | CF$_3$ | Et | C(O)NHEt |
| 3,5-Cl$_2$ | CF$_3$ | CH$_2$OCH$_3$ | C(O)NHEt |
| 3,5-Cl$_2$ | CF$_3$ | CH$_2$OC(O)CH$_3$ | C(O)NHEt |
| 3,5-Cl$_2$ | CF$_3$ | CH$_2$CN | C(O)NHEt |
| 3,5-Cl$_2$ | CF$_3$ | CH$_2$C≡CH | C(O)NHEt |
| 3,5-Cl$_2$ | CF$_3$ | H | C(O)N(CH$_3$)Et |
| 3,5-Cl$_2$ | CF$_3$ | H | C(O)N(Et)$_2$ |
| 3,5-Cl$_2$ | CF$_3$ | H | C(O)NHPr-n |
| 3,5-Cl$_2$ | CF$_3$ | H | C(O)N(CH$_3$)Pr-n |
| 3,5-Cl$_2$ | CF$_3$ | H | C(O)N(Pr-n)$_2$ |
| 3,5-Cl$_2$ | CF$_3$ | H | C(O)NHPr-i |
| 3,5-Cl$_2$ | CF$_3$ | H | C(O)N(CH$_3$)Pr-i |
| 3,5-Cl$_2$ | CF$_3$ | H | C(O)NHPr-c |
| 3,5-Cl$_2$ | CF$_3$ | H | C(O)NHBu-n |
| 3,5-Cl$_2$ | CF$_3$ | H | C(O)NHBu-i |
| 3,5-Cl$_2$ | CF$_3$ | H | C(O)NHCH$_2$Pr-c |
| 3,5-Cl$_2$ | CF$_3$ | H | C(O)NHBu-s |
| 3,5-Cl$_2$ | CF$_3$ | H | C(O)NHBu-c |
| 3,5-Cl$_2$ | CF$_3$ | H | C(O)NHBu-t |
| 3,5-Cl$_2$ | CF$_3$ | H | C(O)NHCH$_2$CH$_2$F |
| 3,5-Cl$_2$ | CF$_3$ | H | C(O)N(CH$_3$)CH$_2$CH$_2$F |
| 3,5-Cl$_2$ | CF$_3$ | H | C(O)NHCH$_2$CH$_2$Cl |
| 3,5-Cl$_2$ | CF$_3$ | CH$_3$ | C(O)NHCH$_2$CH$_2$Cl |
| 3,5-Cl$_2$ | CF$_3$ | Et | C(O)NHCH$_2$CH$_2$Cl |
| 3,5-Cl$_2$ | CF$_3$ | CH$_2$OCH$_3$ | C(O)NHCH$_2$CH$_2$Cl |
| 3,5-Cl$_2$ | CF$_3$ | CH$_2$OC(O)CH$_3$ | C(O)NHCH$_2$CH$_2$Cl |
| 3,5-Cl$_2$ | CF$_3$ | CH$_2$CN | C(O)NHCH$_2$CH$_2$Cl |
| 3,5-Cl$_2$ | CF$_3$ | CH$_2$C≡CH | C(O)NHCH$_2$CH$_2$Cl |
| 3,5-Cl$_2$ | CF$_3$ | H | C(O)N(CH$_3$)CH$_2$CH$_2$Cl |
| 3,5-Cl$_2$ | CF$_3$ | H | C(O)NHCH$_2$CH$_2$Br |
| 3,5-Cl$_2$ | CF$_3$ | H | C(O)NHCH$_2$CF$_3$ |
| 3,5-Cl$_2$ | CF$_3$ | CH$_3$ | C(O)NHCH$_2$CF$_3$ |
| 3,5-Cl$_2$ | CF$_3$ | Et | C(O)NHCH$_2$CF$_3$ |
| 3,5-Cl$_2$ | CF$_3$ | CH$_2$OCH$_3$ | C(O)NHCH$_2$CF$_3$ |
| 3,5-Cl$_2$ | CF$_3$ | CH$_2$OC(O)CH$_3$ | C(O)NHCH$_2$CF$_3$ |
| 3,5-Cl$_2$ | CF$_3$ | CH$_2$CN | C(O)NHCH$_2$CF$_3$ |
| 3,5-Cl$_2$ | CF$_3$ | CH$_2$C≡CH | C(O)NHCH$_2$CF$_3$ |
| 3,5-Cl$_2$ | CF$_3$ | H | C(O)N(CH$_3$)CH$_2$CF$_3$ |
| 3,5-Cl$_2$ | CF$_3$ | H | C(O)NHCH$_2$CH$_2$Cl |
| 3,5-Cl$_2$ | CF$_3$ | H | C(O)NHCH$_2$CH$_2$OCH$_3$ |
| 3,5-Cl$_2$ | CF$_3$ | H | C(O)NHCH$_2$CH$_2$SCH$_3$ |
| 3,5-Cl$_2$ | CF$_3$ | H | C(O)NHCH$_2$CH$_2$SO$_2$CH$_3$ |
| 3,5-Cl$_2$ | CF$_3$ | H | C(O)NHCH$_2$CN |
| 3,5-Cl$_2$ | CF$_3$ | H | C(O)NHCH$_2$C(O)NHCH$_2$CF$_3$ |
| 3,5-Cl$_2$ | CF$_3$ | H | C(O)NHCH$_2$CH=CH$_2$ |
| 3,5-Cl$_2$ | CF$_3$ | H | C(O)N(CH$_3$)CH$_2$CH=CH$_2$ |
| 3,5-Cl$_2$ | CF$_3$ | H | C(O)N(CH$_2$CH=CH$_2$)$_2$ |
| 3,5-Cl$_2$ | CF$_3$ | H | C(O)NHCH$_2$CCl=CH$_2$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | C(O)NHCH$_2$C≡CH |
| 3,5-Cl$_2$ | CF$_3$ | H | C(O)N(CH$_3$)CH$_2$C≡CH |
| 3,5-Cl$_2$ | CF$_3$ | H | C(O)NHCH$_2$Ph |
| 3,5-Cl$_2$ | CF$_3$ | H | C(O)NHCH$_2$(Ph-2-F) |
| 3,5-Cl$_2$ | CF$_3$ | H | C(O)NHCH$_2$(Ph-3-F) |
| 3,5-Cl$_2$ | CF$_3$ | H | C(O)NHCH$_2$(Ph-4-F) |
| 3,5-Cl$_2$ | CF$_3$ | CH$_3$ | C(O)NHCH$_2$(Ph-4-F) |
| 3,5-Cl$_2$ | CF$_3$ | Et | C(O)NHCH$_2$(Ph-4-F) |
| 3,5-Cl$_2$ | CF$_3$ | CH$_2$OCH$_3$ | C(O)NHCH$_2$(Ph-4-F) |
| 3,5-Cl$_2$ | CF$_3$ | CH$_2$OC(O)CH$_3$ | C(O)NHCH$_2$(Ph-4-F) |
| 3,5-Cl$_2$ | CF$_3$ | CH$_2$CN | C(O)NHCH$_2$(Ph-4-F) |
| 3,5-Cl$_2$ | CF$_3$ | CH$_2$C≡CH | C(O)NHCH$_2$(Ph-4-F) |
| 3,5-Cl$_2$ | CF$_3$ | H | C(O)NHCH$_2$(Ph-4-NO$_2$) |
| 3,5-Cl$_2$ | CF$_3$ | H | C(O)NHCH$_2$(Ph-4-CN) |
| 3,5-Cl$_2$ | CF$_3$ | H | C(O)NHCH(CH$_3$)Ph |
| 3,5-Cl$_2$ | CF$_3$ | H | C(O)NHCH$_2$(D-22a) |
| 3,5-Cl$_2$ | CF$_3$ | H | C(O)NHCH$_2$(D-47a) |
| 3,5-Cl$_2$ | CF$_3$ | H | C(O)NHPh |
| 3,5-Cl$_2$ | CF$_3$ | H | C(O)NH(Ph-4-F) |
| 3,5-Cl$_2$ | CF$_3$ | H | C(O)(T-33) |
| 3,5-Cl$_2$ | CF$_3$ | H | C(O)(T-35) |
| 3,5-Cl$_2$ | CF$_3$ | H | C(O)(T-37) |
| 3,5-Cl$_2$ | CF$_3$ | H | C(O)(T-39) |
| 3,5-Cl$_2$ | CF$_3$ | H | C(O)(T-40) |
| 3,5-Cl$_2$ | CF$_3$ | H | C(O)(T-41) |
| 3,5-Cl$_2$ | CF$_3$ | H | T-22 |
| 3,5-Cl$_2$ | CF$_3$ | H | T-23 |
| 3,5-Cl$_2$ | CF$_3$ | H | T-24 |
| 3,5-Cl$_2$ | CF$_3$ | H | C(S)NHCH$_3$ |
| 3,5-Cl$_2$ | CF$_3$ | H | C(S)N(CH$_3$)$_2$ |
| 3,5-Cl$_2$ | CF$_3$ | H | C(S)NHEt |
| 3,5-Cl$_2$ | CF$_3$ | H | C(S)NHPr-n |
| 3,5-Cl$_2$ | CF$_3$ | H | C(S)NHPr-i |
| 3,5-Cl$_2$ | CF$_3$ | H | C(S)NHPr-c |
| 3,5-Cl$_2$ | CF$_3$ | H | C(S)NHBu-n |
| 3,5-Cl$_2$ | CF$_3$ | H | C(S)NHBu-i |
| 3,5-Cl$_2$ | CF$_3$ | H | C(S)NHCH$_2$Pr-c |
| 3,5-Cl$_2$ | CF$_3$ | H | C(S)NHBu-s |
| 3,5-Cl$_2$ | CF$_3$ | H | C(S)NHBu-c |
| 3,5-Cl$_2$ | CF$_3$ | H | C(S)NHBu-t |
| 3,5-Cl$_2$ | CF$_3$ | H | C(S)NHCH$_2$CH$_2$F |
| 3,5-Cl$_2$ | CF$_3$ | H | C(S)NHCH$_2$CH$_2$Cl |
| 3,5-Cl$_2$ | CF$_3$ | H | C(S)NHCH$_2$CH$_2$Br |
| 3,5-Cl$_2$ | CF$_3$ | H | C(S)NHCH$_2$CF$_3$ |
| 3,5-Cl$_2$ | CF$_3$ | H | C(S)NHCH$_2$CH$_2$CH$_2$Cl |
| 3,5-Cl$_2$ | CF$_3$ | H | C(S)NHCH$_2$CH$_2$OCH$_3$ |
| 3,5-Cl$_2$ | CF$_3$ | H | C(S)NHCH$_2$CH$_2$SCH$_3$ |
| 3,5-Cl$_2$ | CF$_3$ | H | C(S)NHCH$_2$CH$_2$SO$_2$CH$_3$ |
| 3,5-Cl$_2$ | CF$_3$ | H | C(S)NHCH$_2$CN |
| 3,5-Cl$_2$ | CF$_3$ | H | C(S)NHCH$_2$CH=CH$_2$ |
| 3,5-Cl$_2$ | CF$_3$ | H | C(S)NHCH$_2$CCl=CH$_2$ |
| 3,5-Cl$_2$ | CF$_3$ | H | C(S)NHCH$_2$C≡CH |
| 3,5-Cl$_2$ | CF$_3$ | H | C(S)NHCH$_2$Ph |
| 3,5-Cl$_2$ | CF$_3$ | H | C(S)NHCH$_2$(Ph-4-F) |
| 3,5-Cl$_2$ | CF$_3$ | H | C(S)NHCH$_2$(D-22a) |
| 3,5-Cl$_2$ | CF$_3$ | H | C(S)NHCH$_2$(D-47a) |
| 3,5-Cl$_2$ | CF$_3$ | H | C(S)NHPh |
| 3,5-Cl$_2$ | CF$_3$ | H | T-25 |
| 3,5-Cl$_2$ | CF$_3$ | H | T-26 |
| 3,5-Cl$_2$ | CF$_3$ | H | T-27 |
| 3,5-Cl$_2$ | CF$_3$ | H | Ph |
| 3,5-Cl$_2$ | CF$_3$ | H | Ph-2-F |
| 3,5-Cl$_2$ | CF$_3$ | H | Ph-3-F |
| 3,5-Cl$_2$ | CF$_3$ | H | Ph-4-F |
| 3,5-Cl$_2$ | CF$_3$ | H | Ph-4-Cl |
| 3,5-Cl$_2$ | CF$_3$ | H | Ph-4-CH$_2$SCH$_3$ |
| 3,5-Cl$_2$ | CF$_3$ | H | Ph-4-CH$_2$S(O)CH$_3$ |
| 3,5-Cl$_2$ | CF$_3$ | H | Ph-4-CH$_2$SO$_2$CH$_3$ |
| 3,5-Cl$_2$ | CF$_3$ | H | Ph-4-OCH$_3$ |
| 3,5-Cl$_2$ | CF$_3$ | H | Ph-4-OCHF$_2$ |
| 3,5-Cl$_2$ | CF$_3$ | H | Ph-4-OSO$_2$CH$_3$ |
| 3,5-Cl$_2$ | CF$_3$ | H | Ph-4-SCH$_3$ |
| 3,5-Cl$_2$ | CF$_3$ | H | Ph-4-S(O)CH$_3$ |
| 3,5-Cl$_2$ | CF$_3$ | H | Ph-4-SO$_2$CH$_3$ |
| 3,5-Cl$_2$ | CF$_3$ | H | Ph-4-SO$_2$NH$_2$ |
| 3,5-Cl$_2$ | CF$_3$ | H | Ph-4-NHC(O)CH$_3$ |
| 3,5-Cl$_2$ | CF$_3$ | H | Ph-4-NHSO$_2$CH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | Ph-3-NO$_2$ |
| 3,5-Cl$_2$ | CF$_3$ | H | Ph-4-NO$_2$ |
| 3,5-Cl$_2$ | CF$_3$ | H | Ph-2-CN |
| 3,5-Cl$_2$ | CF$_3$ | H | Ph-3-CN |
| 3,5-Cl$_2$ | CF$_3$ | H | Ph-4-CN |
| 3,5-Cl$_2$ | CF$_3$ | H | Ph-4-C(O)NH$_2$ |
| 3,5-Cl$_2$ | CF$_3$ | H | Ph-4-C(S)NH$_2$ |
| 3,5-Cl$_2$ | CF$_3$ | H | Ph-2,4-F$_2$ |
| 3,5-Cl$_2$ | CF$_3$ | H | Ph-2,5-F$_2$ |
| 3,5-Cl$_2$ | CF$_3$ | H | Ph-3,4-F$_2$ |
| 3,5-Cl$_2$ | CF$_3$ | H | Ph-2-F-4-Cl |
| 3,5-Cl$_2$ | CF$_3$ | H | Ph-2-F-4-CN |
| 3,5-Cl$_2$ | CF$_3$ | H | D-1a |
| 3,5-Cl$_2$ | CF$_3$ | H | (D-1c)CN |
| 3,5-Cl$_2$ | CF$_3$ | H | D-2a |
| 3,5-Cl$_2$ | CF$_3$ | H | D-3a |
| 3,5-Cl$_2$ | CF$_3$ | H | (D-3d)Cl |
| 3,5-Cl$_2$ | CF$_3$ | H | (D-3d)NO$_2$ |
| 3,5-Cl$_2$ | CF$_3$ | H | (D-3d)CN |
| 3,5-Cl$_2$ | CF$_3$ | H | D-4a |
| 3,5-Cl$_2$ | CF$_3$ | H | (D-4b)Cl |
| 3,5-Cl$_2$ | CF$_3$ | H | (D-4b)NO$_2$ |
| 3,5-Cl$_2$ | CF$_3$ | H | (D-4b)CN |
| 3,5-Cl$_2$ | CF$_3$ | H | D-5a |
| 3,5-Cl$_2$ | CF$_3$ | H | (D-6a)CH$_3$ |
| 3,5-Cl$_2$ | CF$_3$ | H | D-8a |
| 3,5-Cl$_2$ | CF$_3$ | H | (D-8b)CH$_3$ |
| 3,5-Cl$_2$ | CF$_3$ | H | (D-8b)CF$_3$ |
| 3,5-Cl$_2$ | CF$_3$ | H | (D-8b)CF$_2$CF$_3$ |
| 3,5-Cl$_2$ | CF$_3$ | H | (D-8b)CH$_2$OCH$_3$ |
| 3,5-Cl$_2$ | CF$_3$ | H | (D-8b)OCH$_3$ |
| 3,5-Cl$_2$ | CF$_3$ | H | D-9a |
| 3,5-Cl$_2$ | CF$_3$ | H | D-10a |
| 3,5-Cl$_2$ | CF$_3$ | H | (D-10b)CH$_3$ |
| 3,5-Cl$_2$ | CF$_3$ | H | (D-10b)Et |
| 3,5-Cl$_2$ | CF$_3$ | H | (D-10b)CF$_3$ |
| 3,5-Cl$_2$ | CF$_3$ | H | (D-10b)CF$_2$CF$_3$ |
| 3,5-Cl$_2$ | CF$_3$ | H | (D-11b)CH$_3$ |
| 3,5-Cl$_2$ | CF$_3$ | H | D-12a |
| 3,5-Cl$_2$ | CF$_3$ | H | (D-12b)Cl |
| 3,5-Cl$_2$ | CF$_3$ | H | D-13a |
| 3,5-Cl$_2$ | CF$_3$ | H | (D-13b)CH$_3$ |
| 3,5-Cl$_2$ | CF$_3$ | H | (D-13b)Et |
| 3,5-Cl$_2$ | CF$_3$ | H | D-14a |
| 3,5-Cl$_2$ | CF$_3$ | H | (D-14b)Cl |
| 3,5-Cl$_2$ | CF$_3$ | H | (D-14b)Br |
| 3,5-Cl$_2$ | CF$_3$ | H | (D-14b)CH$_3$ |
| 3,5-Cl$_2$ | CF$_3$ | H | (D-14b)CF$_3$ |
| 3,5-Cl$_2$ | CF$_3$ | H | (D-14b)NO$_2$ |
| 3,5-Cl$_2$ | CF$_3$ | H | (D-14b)CN |
| 3,5-Cl$_2$ | CF$_3$ | H | (D-14b)Ph |
| 3,5-Cl$_2$ | CF$_3$ | H | (D-14c)F |
| 3,5-Cl$_2$ | CF$_3$ | H | (D-14c)Cl |
| 3,5-Cl$_2$ | CF$_3$ | H | (D-14c)Br |
| 3,5-Cl$_2$ | CF$_3$ | H | (D-14c)I |
| 3,5-Cl$_2$ | CF$_3$ | H | (D-14c)CH$_3$ |
| 3,5-Cl$_2$ | CF$_3$ | H | (D-14c)OCH$_3$ |
| 3,5-Cl$_2$ | CF$_3$ | H | (D-14c)OCH$_2$CF$_3$ |
| 3,5-Cl$_2$ | CF$_3$ | H | (D-14c)NO$_2$ |
| 3,5-Cl$_2$ | CF$_3$ | H | (D-14c)CN |
| 3,5-Cl$_2$ | CF$_3$ | H | (D-14c)C(O)OCH$_3$ |
| 3,5-Cl$_2$ | CF$_3$ | H | (D-15a)CH$_3$ |
| 3,5-Cl$_2$ | CF$_3$ | H | (D-15a)Et |
| 3,5-Cl$_2$ | CF$_3$ | H | (D-15a)CH$_2$OCH$_2$Ph |
| 3,5-Cl$_2$ | CF$_3$ | H | (D-15a)CH$_2$C(O)NHPh |
| 3,5-Cl$_2$ | CF$_3$ | H | (D-15a)CH$_2$Ph |
| 3,5-Cl$_2$ | CF$_3$ | H | (D-15c)Br |
| 3,5-Cl$_2$ | CF$_3$ | H | (D-15c)CH$_3$ |
| 3,5-Cl$_2$ | CF$_3$ | H | (D-15c)CN |
| 3,5-Cl$_2$ | CF$_3$ | H | (D-16a)CH$_3$ |
| 3,5-Cl$_2$ | CF$_3$ | H | (D-17a)CH$_3$ |
| 3,5-Cl$_2$ | CF$_3$ | H | (D-17b)Cl |
| 3,5-Cl$_2$ | CF$_3$ | H | (D-17b)CH$_3$ |
| 3,5-Cl$_2$ | CF$_3$ | H | D-18a |
| 3,5-Cl$_2$ | CF$_3$ | H | (D-18b)CH$_3$ |
| 3,5-Cl$_2$ | CF$_3$ | H | (D-18c)C(O)CH$_3$ |
| 3,5-Cl$_2$ | CF$_3$ | H | D-21a |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | (D-21b)CH$_3$ |
| 3,5-Cl$_2$ | CF$_3$ | H | (D-21b)CF$_3$ |
| 3,5-Cl$_2$ | CF$_3$ | H | (D-21b)O(E-5a) |
| 3,5-Cl$_2$ | CF$_3$ | H | (D-21c)Cl |
| 3,5-Cl$_2$ | CF$_3$ | H | (D-21c)Br |
| 3,5-Cl$_2$ | CF$_3$ | H | (D-21c)CH$_3$ |
| 3,5-Cl$_2$ | CF$_3$ | H | (D-21c)CF$_3$ |
| 3,5-Cl$_2$ | CF$_3$ | H | (D-21c)SCH$_3$ |
| 3,5-Cl$_2$ | CF$_3$ | H | (D-21c)SCN |
| 3,5-Cl$_2$ | CF$_3$ | H | (D-21c)NO$_2$ |
| 3,5-Cl$_2$ | CF$_3$ | H | (D-21c)N(CH$_3$)$_2$ |
| 3,5-Cl$_2$ | CF$_3$ | H | (D-21c)CN |
| 3,5-Cl$_2$ | CF$_3$ | H | D-22a |
| 3,5-Cl$_2$ | CF$_3$ | H | (D-22b)Br |
| 3,5-Cl$_2$ | CF$_3$ | H | (D-22b)CH$_3$ |
| 3,5-Cl$_2$ | CF$_3$ | H | (D-22b)CH$_2$Cl |
| 3,5-Cl$_2$ | CF$_3$ | H | D-23a |
| 3,5-Cl$_2$ | CF$_3$ | H | (D-23b)Cl |
| 3,5-Cl$_2$ | CF$_3$ | H | (D-23b)Br |
| 3,5-Cl$_2$ | CF$_3$ | H | (D-23b)CH$_3$ |
| 3,5-Cl$_2$ | CF$_3$ | H | (D-23b)SCH$_3$ |
| 3,5-Cl$_2$ | CF$_3$ | H | D-24a |
| 3,5-Cl$_2$ | CF$_3$ | H | (D-25a)CH$_3$ |
| 3,5-Cl$_2$ | CF$_3$ | H | (D-25b)Cl |
| 3,5-Cl$_2$ | CF$_3$ | H | (D-25b)Br |
| 3,5-Cl$_2$ | CF$_3$ | H | (D-25c)NO$_2$ |
| 3,5-Cl$_2$ | CF$_3$ | H | (D-26a)CH$_3$ |
| 3,5-Cl$_2$ | CF$_3$ | H | (D-27a)CH$_3$ |
| 3,5-Cl$_2$ | CF$_3$ | H | (D-27b)CH$_3$ |
| 3,5-Cl$_2$ | CF$_3$ | H | (D-27b)SO$_2$CH$_3$ |
| 3,5-Cl$_2$ | CF$_3$ | H | D-28a |
| 3,5-Cl$_2$ | CF$_3$ | H | D-29a |
| 3,5-Cl$_2$ | CF$_3$ | H | (D-30b)CH$_3$ |
| 3,5-Cl$_2$ | CF$_3$ | H | (D-30b)CF$_2$CF$_2$CF$_3$ |
| 3,5-Cl$_2$ | CF$_3$ | H | (D-30b)OEt |
| 3,5-Cl$_2$ | CF$_3$ | H | (D-31b)Cl |
| 3,5-Cl$_2$ | CF$_3$ | H | (D-31b)CH$_3$ |
| 3,5-Cl$_2$ | CF$_3$ | H | (D-31b)CH$_2$Cl |
| 3,5-Cl$_2$ | CF$_3$ | H | (D-31b)CH$_2$SCH$_3$ |
| 3,5-Cl$_2$ | CF$_3$ | H | (D-31b)OEt |
| 3,5-Cl$_2$ | CF$_3$ | H | (D-31b)SCH$_3$ |
| 3,5-Cl$_2$ | CF$_3$ | H | (D-31b)S(O)CH$_3$ |
| 3,5-Cl$_2$ | CF$_3$ | H | (D-31b)SO$_2$CH$_3$ |
| 3,5-Cl$_2$ | CF$_3$ | H | (D-32a)Cl |
| 3,5-Cl$_2$ | CF$_3$ | H | (D-32a)CH$_3$ |
| 3,5-Cl$_2$ | CF$_3$ | H | (D-32a)SPr-i |
| 3,5-Cl$_2$ | CF$_3$ | H | (D-32a)NHC(O)OEt |
| 3,5-Cl$_2$ | CF$_3$ | H | D-33a |
| 3,5-Cl$_2$ | CF$_3$ | H | (D-33b)CH$_3$ |
| 3,5-Cl$_2$ | CF$_3$ | H | (D-33b)OCH$_3$ |
| 3,5-Cl$_2$ | CF$_3$ | H | (D-33b)SCH$_3$ |
| 3,5-Cl$_2$ | CF$_3$ | H | (D-33b)SO$_2$CH$_3$ |
| 3,5-Cl$_2$ | CF$_3$ | H | D-34a |
| 3,5-Cl$_2$ | CF$_3$ | H | (D-34b)CH$_3$ |
| 3,5-Cl$_2$ | CF$_3$ | H | (D-34b)CF$_2$CF$_2$CF$_3$ |
| 3,5-Cl$_2$ | CF$_3$ | H | (D-34b)CN |
| 3,5-Cl$_2$ | CF$_3$ | H | D-35a |
| 3,5-Cl$_2$ | CF$_3$ | H | (D-35b)Br |
| 3,5-Cl$_2$ | CF$_3$ | H | (D-35b)CH$_3$ |
| 3,5-Cl$_2$ | CF$_3$ | H | (D-35b)CF$_3$ |
| 3,5-Cl$_2$ | CF$_3$ | H | (D-35b)CF$_2$SO$_2$NH$_2$ |
| 3,5-Cl$_2$ | CF$_3$ | H | (D-35b)OCH$_3$ |
| 3,5-Cl$_2$ | CF$_3$ | H | (D-35b)SCH$_3$ |
| 3,5-Cl$_2$ | CF$_3$ | H | (D-35b)N(CH$_3$)$_2$ |
| 3,5-Cl$_2$ | CF$_3$ | H | D-36a |
| 3,5-Cl$_2$ | CF$_3$ | H | (D-36b)F |
| 3,5-Cl$_2$ | CF$_3$ | H | (D-36b)Cl |
| 3,5-Cl$_2$ | CF$_3$ | H | (D-36b)Br |
| 3,5-Cl$_2$ | CF$_3$ | H | (D-36b)I |
| 3,5-Cl$_2$ | CF$_3$ | H | (D-36b)CH$_3$ |
| 3,5-Cl$_2$ | CF$_3$ | H | D-37a |
| 3,5-Cl$_2$ | CF$_3$ | H | D-38a |
| 3,5-Cl$_2$ | CF$_3$ | H | (D-39a)CH$_3$ |
| 3,5-Cl$_2$ | CF$_3$ | H | (D-39a)C(O)CH$_3$ |
| 3,5-Cl$_2$ | CF$_3$ | H | (D-39a)C(O)OEt |
| 3,5-Cl$_2$ | CF$_3$ | H | (D-39b)CH$_3$ |
| 3,5-Cl$_2$ | CF$_3$ | H | (D-39b)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | (D-39b)SCH$_3$ |
| 3,5-Cl$_2$ | CF$_3$ | H | (D-39b)N(CH$_3$)$_2$ |
| 3,5-Cl$_2$ | CF$_3$ | H | (D-40a)CH$_3$ |
| 3,5-Cl$_2$ | CF$_3$ | H | (D-40b)Cl |
| 3,5-Cl$_2$ | CF$_3$ | H | (D-40b)CH$_3$ |
| 3,5-Cl$_2$ | CF$_3$ | H | (D-40b)OCH$_3$ |
| 3,5-Cl$_2$ | CF$_3$ | H | (D-40b)SCH$_3$ |
| 3,5-Cl$_2$ | CF$_3$ | H | (D-40b)NO$_2$ |
| 3,5-Cl$_2$ | CF$_3$ | H | (D-40b)N(CH$_3$)$_2$ |
| 3,5-Cl$_2$ | CF$_3$ | H | D-41a |
| 3,5-Cl$_2$ | CF$_3$ | H | (D-42a)CH$_3$ |
| 3,5-Cl$_2$ | CF$_3$ | H | (D-42b)CH$_3$ |
| 3,5-Cl$_2$ | CF$_3$ | H | (D-42b)SCH$_3$ |
| 3,5-Cl$_2$ | CF$_3$ | H | D-43a |
| 3,5-Cl$_2$ | CF$_3$ | H | (D-43b)CH$_3$ |
| 3,5-Cl$_2$ | CF$_3$ | H | (D-43b)SCH$_3$ |
| 3,5-Cl$_2$ | CF$_3$ | H | D-44a |
| 3,5-Cl$_2$ | CF$_3$ | H | (D-44b)CH$_3$ |
| 3,5-Cl$_2$ | CF$_3$ | H | (D-45a)CH$_3$ |
| 3,5-Cl$_2$ | CF$_3$ | H | (D-46a)CH$_3$ |
| 3,5-Cl$_2$ | CF$_3$ | H | (D-46a)Et |
| 3,5-Cl$_2$ | CF$_3$ | H | (D-46a)CH$_2$Ph |
| 3,5-Cl$_2$ | CF$_3$ | H | D-47a |
| 3,5-Cl$_2$ | CF$_3$ | H | (D-47c)Cl |
| 3,5-Cl$_2$ | CF$_3$ | H | (D-47c)Br |
| 3,5-Cl$_2$ | CF$_3$ | H | (D-47c)CH$_3$ |
| 3,5-Cl$_2$ | CF$_3$ | H | (D-47c)CF$_3$ |
| 3,5-Cl$_2$ | CF$_3$ | H | (D-47c)NO$_2$ |
| 3,5-Cl$_2$ | CF$_3$ | H | (D-47c)CN |
| 3,5-Cl$_2$ | CF$_3$ | H | (D-47d)F |
| 3,5-Cl$_2$ | CF$_3$ | H | (D-47d)Cl |
| 3,5-Cl$_2$ | CF$_3$ | H | (D-47d)Br |
| 3,5-Cl$_2$ | CF$_3$ | H | (D-47d)I |
| 3,5-Cl$_2$ | CF$_3$ | H | (D-47d)CH$_3$ |
| 3,5-Cl$_2$ | CF$_3$ | H | (D-47d)CF$_3$ |
| 3,5-Cl$_2$ | CF$_3$ | H | (D-47d)OCHF$_2$ |
| 3,5-Cl$_2$ | CF$_3$ | H | (D-47d)OCF$_2$CHF$_2$ |
| 3,5-Cl$_2$ | CF$_3$ | H | (D-47d)SCF$_2$CHFCl |
| 3,5-Cl$_2$ | CF$_3$ | H | (D-47d)NO$_2$ |
| 3,5-Cl$_2$ | CF$_3$ | H | (D-47d)CN |
| 3,5-Cl$_2$ | CF$_3$ | H | (D-47d)C(O)OCH$_3$ |
| 3,5-Cl$_2$ | CF$_3$ | H | (D-47d)C(O)NH$_2$ |
| 3,5-Cl$_2$ | CF$_3$ | H | (D-47e)F |
| 3,5-Cl$_2$ | CF$_3$ | H | (D-47e)Cl |
| 3,5-Cl$_2$ | CF$_3$ | H | (D-47e)Br |
| 3,5-Cl$_2$ | CF$_3$ | H | (D-47e)CH$_3$ |
| 3,5-Cl$_2$ | CF$_3$ | H | (D-47e)CF$_3$ |
| 3,5-Cl$_2$ | CF$_3$ | H | (D-47e)OCH$_3$ |
| 3,5-Cl$_2$ | CF$_3$ | H | (D-47e)NO$_2$ |
| 3,5-Cl$_2$ | CF$_3$ | H | (D-47f)-3-F-5-Cl |
| 3,5-Cl$_2$ | CF$_3$ | H | (D-47f)-3,5-Cl$_2$ |
| 3,5-Cl$_2$ | CF$_3$ | H | D-48a |
| 3,5-Cl$_2$ | CF$_3$ | H | (D-48d)F |
| 3,5-Cl$_2$ | CF$_3$ | H | (D-48d)Cl |
| 3,5-Cl$_2$ | CF$_3$ | H | (D-48d)Br |
| 3,5-Cl$_2$ | CF$_3$ | H | (D-48d)NO$_2$ |
| 3,5-Cl$_2$ | CF$_3$ | H | (D-48d)CN |
| 3,5-Cl$_2$ | CF$_3$ | H | (D-48e)F |
| 3,5-Cl$_2$ | CF$_3$ | H | (D-48e)Cl |
| 3,5-Cl$_2$ | CF$_3$ | H | (D-48e)Br |
| 3,5-Cl$_2$ | CF$_3$ | H | (D-48e)I |
| 3,5-Cl$_2$ | CF$_3$ | H | (D-48e)CH$_3$ |
| 3,5-Cl$_2$ | CF$_3$ | H | (D-48e)CF$_3$ |
| 3,5-Cl$_2$ | CF$_3$ | H | (D-48e)OCH$_3$ |
| 3,5-Cl$_2$ | CF$_3$ | H | (D-48e)NO$_2$ |
| 3,5-Cl$_2$ | CF$_3$ | H | (D-48e)CN |
| 3,5-Cl$_2$ | CF$_3$ | H | (D-48f)-2,6-F$_2$ |
| 3,5-Cl$_2$ | CF$_3$ | H | (D-48g)-4-F-6-Cl |
| 3,5-Cl$_2$ | CF$_3$ | H | D-49a |
| 3,5-Cl$_2$ | CF$_3$ | H | (D-49b)Cl |
| 3,5-Cl$_2$ | CF$_3$ | H | (D-49b)Br |
| 3,5-Cl$_2$ | CF$_3$ | H | D-50a |
| 3,5-Cl$_2$ | CF$_3$ | H | (D-50b)Cl |
| 3,5-Cl$_2$ | CF$_3$ | H | (D-50b)CH$_3$ |
| 3,5-Cl$_2$ | CF$_3$ | H | (D-50b)CF$_3$ |
| 3,5-Cl$_2$ | CF$_3$ | H | (D-50c)F |
| 3,5-Cl$_2$ | CF$_3$ | H | (D-50c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | (D-50c)Br |
| 3,5-Cl$_2$ | CF$_3$ | H | (D-50c)I |
| 3,5-Cl$_2$ | CF$_3$ | H | (D-50c)CH$_3$ |
| 3,5-Cl$_2$ | CF$_3$ | H | (D-50c)NO$_2$ |
| 3,5-Cl$_2$ | CF$_3$ | H | (D-50c)CH=NOCH$_3$ |
| 3,5-Cl$_2$ | CF$_3$ | H | (D-50c)CN |
| 3,5-Cl$_2$ | CF$_3$ | H | (D-50c)C(O)OEt |
| 3,5-Cl$_2$ | CF$_3$ | H | D-51a |
| 3,5-Cl$_2$ | CF$_3$ | H | (D-51b)Cl |
| 3,5-Cl$_2$ | CF$_3$ | H | (D-51b)CH$_3$ |
| 3,5-Cl$_2$ | CF$_3$ | H | (D-51b)Et |
| 3,5-Cl$_2$ | CF$_3$ | H | (D-51b)Pr-i |
| 3,5-Cl$_2$ | CF$_3$ | H | (D-51c)Cl |
| 3,5-Cl$_2$ | CF$_3$ | H | (D-51c)I |
| 3,5-Cl$_2$ | CF$_3$ | H | (D-51c)CH$_3$ |
| 3,5-Cl$_2$ | CF$_3$ | H | (D-51c)OCH$_3$ |
| 3,5-Cl$_2$ | CF$_3$ | H | (D-51c)OCHF$_2$ |
| 3,5-Cl$_2$ | CF$_3$ | H | D-52a |
| 3,5-Cl$_2$ | CF$_3$ | H | (D-52b)F |
| 3,5-Cl$_2$ | CF$_3$ | H | (D-52b)Cl |
| 3,5-Cl$_2$ | CF$_3$ | H | (D-52b)Br |
| 3,5-Cl$_2$ | CF$_3$ | H | (D-52b)CH$_3$ |
| 3,5-Cl$_2$ | CF$_3$ | H | (D-52b)CN |
| 3,5-Cl$_2$ | CF$_3$ | H | (D-52b)OCH$_3$ |
| 3,5-Cl$_2$ | CF$_3$ | H | (D-52b)SCH$_3$ |
| 3,5-Cl$_2$ | CF$_3$ | H | (D-52b)SO$_2$CH$_3$ |
| 3,5-Cl$_2$ | CF$_3$ | H | (D-52b)N(CH$_3$)$_2$ |
| 3,5-Cl$_2$ | CF$_3$ | H | D-53a |
| 3,5-Cl$_2$ | CF$_3$ | H | (D-53b)Cl |
| 3,5-Cl$_2$ | CF$_3$ | H | (D-53b)Br |
| 3,5-Cl$_2$ | CF$_3$ | H | (D-53b)CH$_3$ |
| 3,5-Cl$_2$ | CF$_3$ | H | (D-53b)NO$_2$ |
| 3,5-Cl$_2$ | CF$_3$ | H | (D-53b)CN |
| 3,5-Cl$_2$ | CF$_3$ | H | (D-53c)Cl |
| 3,5-Cl$_2$ | CF$_3$ | H | D-54a |
| 3,5-Cl$_2$ | CF$_3$ | H | (D-54b)F |
| 3,5-Cl$_2$ | CF$_3$ | H | (D-54b)Cl |
| 3,5-Cl$_2$ | CF$_3$ | H | (D-54b)Br |
| 3,5-Cl$_2$ | CF$_3$ | H | (D-54b)I |
| 3,5-Cl$_2$ | CF$_3$ | H | (D-54b)CH$_3$ |
| 3,5-Cl$_2$ | CF$_3$ | H | (D-54b)OCH$_3$ |
| 3,5-Cl$_2$ | CF$_3$ | H | D-55a |
| 3,5-Cl$_2$ | CF$_3$ | H | D-56a |
| 3,5-Cl$_2$ | CF$_3$ | H | (D-56b)Cl |
| 3,5-Cl$_2$ | CF$_3$ | H | D-57a |
| 3,5-Cl$_2$ | CF$_3$ | H | (D-57b)I |
| 3,5-Cl$_2$ | CF$_3$ | H | (D-57b)CH$_3$ |
| 3,5-Cl$_2$ | CF$_3$ | H | (D-57b)CF$_3$ |
| 3,5-Cl$_2$ | CF$_3$ | H | D-58a |
| 3,5-Cl$_2$ | CF$_3$ | H | (D-58b)CH$_3$ |
| 3,5-Cl$_2$ | CF$_3$ | H | (D-60b)Cl |
| 3,5-Cl$_2$ | CF$_3$ | H | D-61a |
| 3,5-Cl$_2$ | CF$_3$ | H | (D-62a)CH$_3$ |
| 3,5-Cl$_2$ | CF$_3$ | H | (D-62a)Et |
| 3,5-Cl$_2$ | CF$_3$ | H | (D-63a)CH$_3$ |
| 3,5-Cl$_2$ | CF$_3$ | H | (D-65a)CH$_3$ |
| 3,5-Cl$_2$ | CF$_3$ | H | (D-65a)Et |
| 3,5-Cl$_2$ | CF$_3$ | | T-44 |
| 3,5-Cl$_2$ | CF$_3$ | | T-45 |
| 3,5-Cl$_2$ | CF$_3$ | | T-46 |
| 3,5-Cl$_2$ | CF$_3$ | | T-47 |
| 3,5-Cl$_2$ | CF$_3$ | | T-48 |
| 3,5-Cl$_2$ | CF$_3$ | | T-49 |
| 3,5-Cl$_2$ | CF$_2$Cl | H | Et |
| 3,5-Cl$_2$ | CF$_2$Cl | Et | Et |
| 3,5-Cl$_2$ | CF$_2$Cl | H | c-Pr |
| 3,5-Cl$_2$ | CF$_2$Cl | H | CH$_2$Pr-c |
| 3,5-Cl$_2$ | CF$_2$Cl | H | c-Bu |
| 3,5-Cl$_2$ | CF$_2$Cl | H | CH$_2$CH$_2$Cl |
| 3,5-Cl$_2$ | CF$_2$Cl | H | CH$_2$CHF$_2$ |
| 3,5-Cl$_2$ | CF$_2$Cl | H | CH$_2$CF$_3$ |
| 3,5-Cl$_2$ | CF$_2$Cl | C(O)CH$_3$ | CH$_2$CF$_3$ |
| 3,5-Cl$_2$ | CF$_2$Cl | H | CH$_2$CH$_2$CF$_3$ |
| 3,5-Cl$_2$ | CF$_2$Cl | H | CH$_2$OCH$_3$ |
| 3,5-Cl$_2$ | CF$_2$Cl | H | CH$_2$OEt |
| 3,5-Cl$_2$ | CF$_2$Cl | C(O)CH$_3$ | CH$_2$OEt |
| 3,5-Cl$_2$ | CF$_2$Cl | H | CH$_2$OCH$_2$CH$_2$Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_2$Cl | H | CH$_2$OCH$_2$CHF$_2$ |
| 3,5-Cl$_2$ | CF$_2$Cl | H | CH$_2$OCH$_2$CF$_3$ |
| 3,5-Cl$_2$ | CF$_2$Cl | C(O)CH$_3$ | CH$_2$OCH$_2$CF$_3$ |
| 3,5-Cl$_2$ | CF$_2$Cl | H | CH(CH$_3$)OCH$_2$CF$_3$ |
| 3,5-Cl$_2$ | CF$_2$Cl | H | CH(CF$_3$)OCH$_3$ |
| 3,5-Cl$_2$ | CF$_2$Cl | H | CH$_2$CH$_2$OCH$_3$ |
| 3,5-Cl$_2$ | CF$_2$Cl | H | CH$_2$CH$_2$OEt |
| 3,5-Cl$_2$ | CF$_2$Cl | H | CH$_2$CH(OCH$_3$)$_2$ |
| 3,5-Cl$_2$ | CF$_2$Cl | H | CH$_2$(E-4a) |
| 3,5-Cl$_2$ | CF$_2$Cl | H | CH$_2$(E-5a) |
| 3,5-Cl$_2$ | CF$_2$Cl | H | CH$_2$(E-10a) |
| 3,5-Cl$_2$ | CF$_2$Cl | H | CH$_2$(E-10b)CH$_3$ |
| 3,5-Cl$_2$ | CF$_2$Cl | H | E-4a |
| 3,5-Cl$_2$ | CF$_2$Cl | H | E-5a(R) |
| 3,5-Cl$_2$ | CF$_2$Cl | H | CH$_2$SCH$_3$ |
| 3,5-Cl$_2$ | CF$_2$Cl | H | CH$_2$S(O)CH$_3$ |
| 3,5-Cl$_2$ | CF$_2$Cl | H | CH$_2$SO$_2$CH$_3$ |
| 3,5-Cl$_2$ | CF$_2$Cl | H | CH$_2$CH$_2$SO$_2$CH$_3$ |
| 3,5-Cl$_2$ | CF$_2$Cl | H | CH$_2$CH$_2$SO$_2$Et |
| 3,5-Cl$_2$ | CF$_2$Cl | H | CH$_2$CH(CH$_3$)S(O)CH$_3$ |
| 3,5-Cl$_2$ | CF$_2$Cl | H | CH$_2$CH(CH$_3$)SO$_2$CH$_3$ |
| 3,5-Cl$_2$ | CF$_2$Cl | H | CH(CH$_3$)CH$_2$SO$_2$CH$_3$ |
| 3,5-Cl$_2$ | CF$_2$Cl | H | CH$_2$NHCH$_2$CF$_3$ |
| 3,5-Cl$_2$ | CF$_2$Cl | H | CH$_2$NHC(O)OCH$_3$ |
| 3,5-Cl$_2$ | CF$_2$Cl | H | CH(CH$_3$)NHC(O)OCH$_3$ |
| 3,5-Cl$_2$ | CF$_2$Cl | H | CH$_2$NHC(O)OCH$_2$CF$_3$ |
| 3,5-Cl$_2$ | CF$_2$Cl | H | CH$_2$CH=NOCH$_3$ |
| 3,5-Cl$_2$ | CF$_2$Cl | H | CH$_2$C(CH$_3$)=NOCH$_3$ |
| 3,5-Cl$_2$ | CF$_2$Cl | H | CH$_2$CN |
| 3,5-Cl$_2$ | CF$_2$Cl | H | CH$_2$C(O)NHCH$_3$ |
| 3,5-Cl$_2$ | CF$_2$Cl | H | CH$_2$C(O)N(CH$_3$)$_2$ |
| 3,5-Cl$_2$ | CF$_2$Cl | H | CH$_2$C(O)NHEt |
| 3,5-Cl$_2$ | CF$_2$Cl | H | CH$_2$C(O)NHPr-n |
| 3,5-Cl$_2$ | CF$_2$Cl | H | CH$_2$C(O)NHPr-i |
| 3,5-Cl$_2$ | CF$_2$Cl | H | CH$_2$C(O)NHCH$_2$CH$_2$F |
| 3,5-Cl$_2$ | CF$_2$Cl | H | CH$_2$C(O)NHCH$_2$CH$_2$Cl |
| 3,5-Cl$_2$ | CF$_2$Cl | H | CH$_2$C(O)NHCH$_2$CF$_3$ |
| 3,5-Cl$_2$ | CF$_2$Cl | H | CH$_2$C(O)NHCH$_2$CH=CH$_2$ |
| 3,5-Cl$_2$ | CF$_2$Cl | H | CH$_2$C(O)NHCH$_2$C≡CH |
| 3,5-Cl$_2$ | CF$_2$Cl | H | CH(CH$_3$)C(O)NHEt |
| 3,5-Cl$_2$ | CF$_2$Cl | H | CH(CH$_3$)C(O)NHCH$_2$CF$_3$ |
| 3,5-Cl$_2$ | CF$_2$Cl | H | CH(CH$_3$)C(O)NHCH$_2$CH$_2$Cl(D) |
| 3,5-Cl$_2$ | CF$_2$Cl | H | CH(CH$_3$)C(O)NHCH$_2$CF$_3$(D) |
| 3,5-Cl$_2$ | CF$_2$Cl | H | CH$_2$C(S)NH$_2$ |
| 3,5-Cl$_2$ | CF$_2$Cl | H | CH$_2$CH=CH$_2$ |
| 3,5-Cl$_2$ | CF$_2$Cl | H | CH$_2$CCl=CH$_2$ |
| 3,5-Cl$_2$ | CF$_2$Cl | H | CH$_2$CCl=CHCl |
| 3,5-Cl$_2$ | CF$_2$Cl | H | CH$_2$C≡CH |
| 3,5-Cl$_2$ | CF$_2$Cl | H | CH(CH$_3$)Ph(R) |
| 3,5-Cl$_2$ | CF$_2$Cl | H | CH(CF$_3$)Ph |
| 3,5-Cl$_2$ | CF$_2$Cl | H | CH(CN)Ph |
| 3,5-Cl$_2$ | CF$_2$Cl | H | CH$_2$(Ph-4-OCH$_3$) |
| 3,5-Cl$_2$ | CF$_2$Cl | H | CH$_2$(Ph-4-NO$_2$) |
| 3,5-Cl$_2$ | CF$_2$Cl | H | CH$_2$(Ph-4-CN) |
| 3,5-Cl$_2$ | CF$_2$Cl | H | CH$_2$(D-1a) |
| 3,5-Cl$_2$ | CF$_2$Cl | H | CH$_2$(D-16b)Cl |
| 3,5-Cl$_2$ | CF$_2$Cl | H | CH$_2$(D-17a)CH$_3$ |
| 3,5-Cl$_2$ | CF$_2$Cl | H | CH$_2$(D-17b)Cl |
| 3,5-Cl$_2$ | CF$_2$Cl | H | CH$_2$(D-21a) |
| 3,5-Cl$_2$ | CF$_2$Cl | H | CH$_2$(D-22a) |
| 3,5-Cl$_2$ | CF$_2$Cl | C(O)CH$_3$ | CH$_2$(D-22a) |
| 3,5-Cl$_2$ | CF$_2$Cl | C(O)Et | CH$_2$(D-22a) |
| 3,5-Cl$_2$ | CF$_2$Cl | H | CH$_2$(D-28a) |
| 3,5-Cl$_2$ | CF$_2$Cl | H | CH$_2$(D-29b)CH$_3$ |
| 3,5-Cl$_2$ | CF$_2$Cl | H | CH$_2$(D-34a) |
| 3,5-Cl$_2$ | CF$_2$Cl | H | CH$_2$(D-35a) |
| 3,5-Cl$_2$ | CF$_2$Cl | H | CH$_2$(D-38a) |
| 3,5-Cl$_2$ | CF$_2$Cl | H | CH$_2$(D-47a) |
| 3,5-Cl$_2$ | CF$_2$Cl | Et | CH$_2$(D-47a) |
| 3,5-Cl$_2$ | CF$_2$Cl | CH$_2$OCH$_3$ | CH$_2$(D-47a) |
| 3,5-Cl$_2$ | CF$_2$Cl | CH$_2$CN | CH$_2$(D-47a) |
| 3,5-Cl$_2$ | CF$_2$Cl | CH$_2$C≡CH | CH$_2$(D-47a) |
| 3,5-Cl$_2$ | CF$_2$Cl | C(O)CH$_3$ | CH$_2$(D-47a) |
| 3,5-Cl$_2$ | CF$_2$Cl | C(O)Et | CH$_2$(D-47a) |
| 3,5-Cl$_2$ | CF$_2$Cl | C(O)Pr-n | CH$_2$(D-47a) |
| 3,5-Cl$_2$ | CF$_2$Cl | C(O)Pr-i | CH$_2$(D-47a) |
| 3,5-Cl$_2$ | CF$_2$Cl | C(O)Pr-c | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_2$Cl | C(O)Bu-t | CH$_2$(D-47a) |
| 3,5-Cl$_2$ | CF$_2$Cl | C(O)CH$_2$OCH$_3$ | CH$_2$(D-47a) |
| 3,5-Cl$_2$ | CF$_2$Cl | C(O)CH=CH$_2$ | CH$_2$(D-47a) |
| 3,5-Cl$_2$ | CF$_2$Cl | C(O)OCH$_3$ | CH$_2$(D-47a) |
| 3,5-Cl$_2$ | CF$_2$Cl | C(O)OEt | CH$_2$(D-47a) |
| 3,5-Cl$_2$ | CF$_2$Cl | C(O)OCH$_2$CH$_2$OCH$_3$ | CH$_2$(D-47a) |
| 3,5-Cl$_2$ | CF$_2$Cl | C(O)OCH$_2$CH=CH$_2$ | CH$_2$(D-47a) |
| 3,5-Cl$_2$ | CF$_2$Cl | H | CH(CH$_3$)(D-47a) |
| 3,5-Cl$_2$ | CF$_2$Cl | H | CH$_2$(D-50a) |
| 3,5-Cl$_2$ | CF$_2$Cl | H | NHCH$_2$CF$_3$ |
| 3,5-Cl$_2$ | CF$_2$Cl | H | NHC(O)OCH$_3$ |
| 3,5-Cl$_2$ | CF$_2$Cl | H | N(CH$_3$)Ph |
| 3,5-Cl$_2$ | CF$_2$Cl | H | N(CH$_2$CH=CH$_2$)Ph |
| 3,5-Cl$_2$ | CF$_2$Cl | H | N(CH$_2$C≡CH)Ph |
| 3,5-Cl$_2$ | CF$_2$Cl | H | N(CH$_3$)(D-47a) |
| 3,5-Cl$_2$ | CF$_2$Cl | H | NH(D-50a) |
| 3,5-Cl$_2$ | CF$_2$Cl | CH$_3$ | NH(D-50a) |
| 3,5-Cl$_2$ | CF$_2$Cl | H | N(CH$_3$)(D-50a) |
| 3,5-Cl$_2$ | CF$_2$Cl | H | N(Et)(D-50a) |
| 3,5-Cl$_2$ | CF$_2$Cl | C(O)OCH$_3$ | C(O)N(CH$_3$)$_2$ |
| 3,5-Cl$_2$ | CF$_2$Cl | H | C(O)NHEt |
| 3,5-Cl$_2$ | CF$_2$Cl | CH$_3$ | C(O)NHEt |
| 3,5-Cl$_2$ | CF$_2$Cl | H | C(O)NHCH$_2$CH$_2$Cl |
| 3,5-Cl$_2$ | CF$_2$Cl | H | C(O)NHCH$_2$CF$_3$ |
| 3,5-Cl$_2$ | CF$_2$Cl | H | C(O)NHCH$_2$(Ph-4-F) |
| 3,5-Cl$_2$ | CF$_2$Cl | H | C(S)NHCH$_3$ |
| 3,5-Cl$_2$ | CF$_2$Cl | H | Ph-4-F |
| 3,5-Cl$_2$ | CF$_2$Cl | H | Ph-4-CN |
| 3,5-Cl$_2$ | CF$_2$Cl | H | Ph-2,4-F$_2$ |
| 3,5-Cl$_2$ | CF$_2$Cl | H | Ph-2,6-F$_2$ |
| 3,5-Cl$_2$ | CF$_2$Cl | H | Ph-2,4,6-F$_3$ |
| 3,5-Cl$_2$ | CF$_2$Cl | H | (D-13b)CH$_3$ |
| 3,5-Cl$_2$ | CF$_2$Cl | H | (D-15a)CH$_3$ |
| 3,5-Cl$_2$ | CF$_2$Cl | H | D-21a |
| 3,5-Cl$_2$ | CF$_2$Cl | H | (D-47d)Cl |
| 3,5-Cl$_2$ | CF$_2$Cl | H | (D-47d)Br |
| 3,5-Cl$_2$ | CF$_2$Cl | H | (D-47d)CN |
| 3,5-Cl$_2$ | CF$_2$Cl | H | (D-47e)Br |
| 3,5-Cl$_2$ | CF$_2$Cl | H | (D-48e)Cl |
| 3,5-Cl$_2$ | CF$_2$Cl | H | D-50a |
| 3,5-Cl$_2$ | CF$_2$Cl | H | (D-50c)Cl |
| 3,5-Cl$_2$ | CF$_2$Cl | H | (D-50c)Br |
| 3,5-Cl$_2$ | CF$_2$Cl | H | D-51a |
| 3,5-Cl$_2$ | CF$_2$Cl | H | D-52a |
| 3,5-Cl$_2$ | CF$_2$Cl | H | D-53a |
| 3,5-Cl$_2$ | CF$_2$Cl | H | (D-54b)Cl |
| 3,5-Cl$_2$ | CFCl$_2$ | C(O)OCH$_3$ | CH$_2$(D-47a) |
| 3,5-Cl$_2$ | CCl$_3$ | H | N(CH$_3$)Ph |
| 3,5-Cl$_2$ | CF$_2$Br | H | CH$_2$CF$_3$ |
| 3,5-Cl$_2$ | CF$_2$Br | C(O)CH$_3$ | CH$_2$CF$_3$ |
| 3,5-Cl$_2$ | CF$_2$Br | H | CH$_2$OCH$_2$CF$_3$ |
| 3,5-Cl$_2$ | CF$_2$Br | H | E-4a |
| 3,5-Cl$_2$ | CF$_2$Br | H | CH$_2$C(O)NHCH$_2$CF$_3$ |
| 3,5-Cl$_2$ | CF$_2$Br | H | CH(CH$_3$)C(O)NHCH$_2$CF$_3$(D) |
| 3,5-Cl$_2$ | CF$_2$Br | H | CH(CH$_3$)Ph(R) |
| 3,5-Cl$_2$ | CF$_2$Br | H | CH$_2$(D-22a) |
| 3,5-Cl$_2$ | CF$_2$Br | H | CH$_2$(D-47a) |
| 3,5-Cl$_2$ | CF$_2$Br | CH$_2$CN | CH$_2$(D-47a) |
| 3,5-Cl$_2$ | CF$_2$Br | C(O)Et | CH$_2$(D-47a) |
| 3,5-Cl$_2$ | CF$_2$Br | C(O)OCH$_3$ | CH$_2$(D-47a) |
| 3,5-Cl$_2$ | CF$_2$Br | H | N(CH$_3$)Ph |
| 3,5-Cl$_2$ | CF$_2$Br | H | (D-50c)Cl |
| 3,5-Cl$_2$ | CF$_2$Br | H | D-52a |
| 3,5-Cl$_2$ | CFClBr | H | (D-50c)Cl |
| 3,5-Cl$_2$ | CFBr$_2$ | H | CH$_2$CF$_3$ |
| 3,5-Cl$_2$ | CF$_2$I | H | CH$_2$OCH$_2$CF$_3$ |
| 3,5-Cl$_2$ | CF$_2$CHF$_2$ | H | CH$_2$CF$_3$ |
| 3,5-Cl$_2$ | CF$_2$CHF$_2$ | C(O)CH$_3$ | CH$_2$CF$_3$ |
| 3,5-Cl$_2$ | CF$_2$CHF$_2$ | H | CH$_2$OCH$_2$CF$_3$ |
| 3,5-Cl$_2$ | CF$_2$CHF$_2$ | H | E-4a |
| 3,5-Cl$_2$ | CF$_2$CHF$_2$ | H | CH$_2$C(O)NHCH$_2$CF$_3$ |
| 3,5-Cl$_2$ | CF$_2$CHF$_2$ | H | CH(CH$_3$)C(O)NHCH$_2$CF$_3$(D) |
| 3,5-Cl$_2$ | CF$_2$CHF$_2$ | H | CH(CH$_3$)Ph(R) |
| 3,5-Cl$_2$ | CF$_2$CHF$_2$ | H | CH$_2$(D-22a) |
| 3,5-Cl$_2$ | CF$_2$CHF$_2$ | H | CH$_2$(D-47a) |
| 3,5-Cl$_2$ | CF$_2$CHF$_2$ | CH$_2$CN | CH$_2$(D-47a) |
| 3,5-Cl$_2$ | CF$_2$CHF$_2$ | C(O)Et | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_2$CHF$_2$ | C(O)OCH$_3$ | CH$_2$(D-47a) |
| 3,5-Cl$_2$ | CF$_2$CHF$_2$ | H | N(CH$_3$)Ph |
| 3,5-Cl$_2$ | CF$_2$CHF$_2$ | H | (D-50c)Cl |
| 3,5-Cl$_2$ | CF$_2$CHF$_2$ | H | D-52a |
| 3,5-Cl$_2$ | CF$_2$CF$_3$ | H | CH$_2$CF$_3$ |
| 3,5-Cl$_2$ | CF$_2$CF$_3$ | H | CH$_2$OCH$_2$CF$_3$ |
| 3,5-Cl$_2$ | CF$_2$CF$_3$ | H | E-4a |
| 3,5-Cl$_2$ | CF$_2$CF$_3$ | H | CH$_2$C(O)NHCH$_2$CF$_3$ |
| 3,5-Cl$_2$ | CF$_2$CF$_3$ | H | CH(CH$_3$)C(O)NHCH$_2$CF$_3$(D) |
| 3,5-Cl$_2$ | CF$_2$CF$_3$ | H | CH$_2$(D-22a) |
| 3,5-Cl$_2$ | CF$_2$CF$_3$ | H | CH$_2$(D-47a) |
| 3,5-Cl$_2$ | CF$_2$CF$_3$ | C(O)OCH$_3$ | CH$_2$(D-47a) |
| 3,5-Cl$_2$ | CF$_2$CF$_3$ | H | N(CH$_3$)Ph |
| 3,5-Cl$_2$ | CF$_2$CF$_3$ | H | C(O)(D-47a) |
| 3,5-Cl$_2$ | CF$_2$CF$_3$ | H | (D-50c)Cl |
| 3,5-Cl$_2$ | CF$_2$CF$_2$Cl | H | E-4a |
| 3,5-Cl$_2$ | CFClCF$_3$ | H | CH$_2$C(O)NHCH$_2$CF$_3$ |
| 3,5-Cl$_2$ | CFClCF$_2$Cl | H | CH$_2$(D-22a) |
| 3,5-Cl$_2$ | CF$_2$CF$_2$Br | H | CH$_2$(D-47a) |
| 3,5-Cl$_2$ | CFBrCF$_3$ | C(O)OCH$_3$ | CH$_2$(D-47a) |
| 3,5-Cl$_2$ | CF$_2$CHFCF$_3$ | H | N(CH$_3$)Ph |
| 3,5-Cl$_2$ | CF$_2$CF$_2$CF$_3$ | H | CH$_2$CF$_3$ |
| 3,5-Cl$_2$ | CF$_2$CF$_2$CF$_3$ | H | E-4a |
| 3,5-Cl$_2$ | CF$_2$CF$_2$CF$_3$ | H | CH$_2$C(O)NHCH$_2$CF$_3$ |
| 3,5-Cl$_2$ | CF$_2$CF$_2$CF$_3$ | H | CH$_2$(D-22a) |
| 3,5-Cl$_2$ | CF$_2$CF$_2$CF$_3$ | H | CH$_2$(D-47a) |
| 3,5-Cl$_2$ | CF$_2$CF$_2$CF$_3$ | H | (D-50c)Cl |
| 3,5-Cl$_2$ | CF(CF$_3$)$_2$ | H | (D-50c)Cl |
| 3,5-Cl$_2$ | CF$_2$CFClCF$_2$Cl | H | CH$_2$CF$_3$ |
| 3,5-Cl$_2$ | CF$_2$CFBrCF$_2$Cl | H | CH$_2$OCH$_2$CF$_2$ |
| 3,5-Cl$_2$ | CF$_2$CF$_2$CF$_2$CHF$_2$ | H | E-4a |
| 3,5-Cl$_2$ | CF$_2$CF$_2$CF$_2$CF$_3$ | H | CH$_2$C(O)NHCH$_2$CF$_3$ |
| 3,5-Cl$_2$ | CF(CF$_3$)CF$_2$CF$_3$ | H | CH$_2$(D-22a) |
| 3,5-Cl$_2$ | CF$_2$CF$_2$CF$_2$CF$_2$Cl | H | CH$_2$(D-47a) |
| 3,5-Cl$_2$ | CF$_2$CF$_2$CF$_2$CF$_2$CF$_3$ | C(O)OCH$_3$ | CH$_2$(D-47a) |
| 3,5-Cl$_2$ | CH$_2$OCH$_3$ | H | N(CH$_3$)Ph |
| 3,5-Cl$_2$ | CH$_2$OEt | H | (D-50c)Cl |
| 3,5-Cl$_2$ | CH$_2$OCH$_2$CF$_3$ | H | CH$_2$CF$_3$ |
| 3,5-Cl$_2$ | CH$_2$OCH$_2$CF$_3$ | H | CH$_2$(D-47a) |
| 3,5-Cl$_2$ | CH$_2$OCH(CF$_3$)$_2$ | H | CH$_2$OCH$_2$CF$_3$ |
| 3,5-Cl$_2$ | CF$_2$OCH$_3$ | H | CH$_2$CF$_3$ |
| 3,5-Cl$_2$ | CF$_2$OCH$_3$ | H | CH$_2$OCH$_2$CF$_3$ |
| 3,5-Cl$_2$ | CF$_2$OCH$_3$ | H | E-4a |
| 3,5-Cl$_2$ | CF$_2$OCH$_3$ | H | CH$_2$C(O)NHCH$_2$CF$_3$ |
| 3,5-Cl$_2$ | CF$_2$OCH$_3$ | H | CH(CH$_3$)C(O)NHCH$_2$CF$_3$(D) |
| 3,5-Cl$_2$ | CF$_2$OCH$_3$ | H | CH$_2$(D-22a) |
| 3,5-Cl$_2$ | CF$_2$OCH$_3$ | H | CH$_2$(D-47a) |
| 3,5-Cl$_2$ | CF$_2$OCH$_3$ | C(O)OCH$_3$ | CH$_2$(D-47a) |
| 3,5-Cl$_2$ | CF$_2$OCH$_3$ | H | N(CH$_3$)Ph |
| 3,5-Cl$_2$ | CF$_2$OCH$_3$ | H | (D-50c)Cl |
| 3,5-Cl$_2$ | CF$_2$OCF$_2$CF$_2$CF$_3$ | H | E-4a |
| 3,5-Cl$_2$ | CF$_2$OCF$_2$CF$_2$OCF$_3$ | H | CH$_2$C(O)NHCH$_2$CF$_3$ |
| 3,5-Cl$_2$ | CF(CF$_3$)OCH$_3$ | H | CH$_2$(D-22a) |
| 3,5-Cl$_2$ | CF(CF$_3$)OCF$_2$CF$_2$CF$_3$ | H | CH$_2$(D-47a) |
| 3,5-Cl$_2$ | CH(OEt)$_2$ | H | CH$_2$(D-47a) |
| 3,5-Cl$_2$ | CH$_2$SCH$_3$ | C(O)OCH$_3$ | CH$_2$(D-47a) |
| 3,5-Cl$_2$ | CH$_2$SO$_2$CH$_3$ | H | N(CH$_3$)Ph |
| 3,5-Cl$_2$ | CH$_2$SEt | H | (D-50c)Cl |
| 3,5-Cl$_2$ | CH$_2$SCF$_3$ | H | CH$_2$CF$_3$ |
| 3,5-Cl$_2$ | CH$_2$SPh | H | CH$_2$OCH$_2$CF$_3$ |
| 3,5-Cl$_2$ | CH$_2$CH$_2$SCH$_3$ | H | E-4a |
| 3,5-Cl$_2$ | CH$_2$CH$_2$SCF$_3$ | H | CH$_2$C(O)NHCH$_2$CF$_3$ |
| 3,5-Cl$_2$ | CF$_2$SCH$_3$ | H | CH$_2$CF$_3$ |
| 3,5-Cl$_2$ | CF$_2$SCH$_3$ | H | E-4a |
| 3,5-Cl$_2$ | CF$_2$SCH$_2$ | H | CH$_2$C(O)NHCH$_2$CF$_2$ |
| 3,5-Cl$_2$ | CF$_2$SCH$_2$ | H | CH$_2$(D-22a) |
| 3,5-Cl$_2$ | CF$_2$SCH$_3$ | H | CH$_2$(D-47a) |
| 3,5-Cl$_2$ | CF$_2$SCH$_3$ | H | (D-50c)Cl |
| 3,5-Cl$_2$ | CF$_2$SEt | H | CH$_2$(D-22a) |
| 3,5-Cl$_2$ | CF$_2$SPr-n | H | CH$_2$(D-47a) |
| 3,5-Cl$_2$ | CF$_2$SPr-i | C(O)OCH$_3$ | CH$_2$(D-47a) |
| 3,5-Cl$_2$ | CF$_2$SCH$_2$Ph | H | N(CH$_3$)Ph |
| 3,5-Cl$_2$ | CF$_2$SPh | H | (D-50c)Cl |
| 3,5-Cl$_2$ | CF$_2$CN | H | CH$_2$CF$_2$ |
| 3,5-Cl$_2$ | CF$_2$C(O)OCH$_3$ | H | CH$_2$OCH$_2$CF$_3$ |
| 3,5-Cl$_2$ | CF$_2$C(O)OEt | H | E-4a |
| 3,5-Cl$_2$ | CF$_2$C(O)NH$_2$ | H | CH$_2$C(O)NHCH$_2$CF$_2$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_2$SO$_2$N(CH$_3$)$_2$ | H | CH$_2$(D-22a) |
| 3,5-Cl$_2$ | CH$_2$Si(CH$_3$)$_3$ | H | CH$_2$CF$_2$ |
| 3,5-Cl$_2$ | CH$_2$Si(CH$_3$)$_3$ | H | CH$_2$(D-47a) |
| 3,5-Cl$_2$ | T-3 | H | CH$_2$CF$_3$ |
| 3,5-Cl$_2$ | T-3 | H | CH$_2$OCH$_2$CF$_3$ |
| 3,5-Cl$_2$ | T-3 | H | E-4a |
| 3,5-Cl$_2$ | T-3 | H | CH$_2$C(O)NHCH$_2$CF$_2$ |
| 3,5-Cl$_2$ | T-3 | H | CH(CH$_3$)C(O)NHCH$_2$CF$_3$(D) |
| 3,5-Cl$_2$ | T-3 | H | CH$_2$(D-22a) |
| 3,5-Cl$_2$ | T-3 | H | CH$_2$(D-47a) |
| 3,5-Cl$_2$ | T-3 | C(O)OCH$_3$ | CH$_2$(D-47a) |
| 3,5-Cl$_2$ | T-3 | H | N(CH$_3$)Ph |
| 3,5-Cl$_2$ | T-3 | H | (D-50c)Cl |
| 3,5-Cl$_2$ | T-4 | H | CH$_2$CF$_2$ |
| 3,5-Cl$_2$ | T-4 | H | E-4a |
| 3,5-Cl$_2$ | T-4 | H | CH$_2$C(O)NHCH$_2$CF$_2$ |
| 3,5-Cl$_2$ | T-4 | H | CH$_2$(D-22a) |
| 3,5-Cl$_2$ | T-4 | H | CH$_2$(D-47a) |
| 3,5-Cl$_2$ | T-4 | H | (D-50c)Cl |
| 3,5-Cl$_2$ | T-5 | H | CH$_2$(D-47a) |
| 3,5-Cl$_2$ | CN | C(O)OCH$_3$ | CH$_2$(D-47a) |
| 3,5-Cl$_2$ | C(O)OCH$_3$ | H | N(CH$_3$)Ph |
| 3,5-Cl$_2$ | C(O)NH$_2$ | H | (D-50c)Cl |
| 3,5-Cl$_2$ | C(S)NH$_2$ | H | CH$_2$CF$_3$ |
| 3,5-Cl$_2$ | C(CH$_3$)=NOCH$_3$ | H | CH$_2$OCH$_2$CF$_3$ |
| 3,5-Cl$_2$ | Ph | H | E-4a |
| 3,5-Cl$_2$ | Ph-2-F | H | CH$_2$C(O)NHCH$_2$CF$_3$ |
| 3,5-Cl$_2$ | Ph-3-F | H | CH$_2$(D-22a) |
| 3,5-Cl$_2$ | Ph-4-F | H | CH$_2$(D-47a) |
| 3,5-Cl$_2$ | Ph-2-Cl | C(O)OCH$_3$ | CH$_2$(D-47a) |
| 3,5-Cl$_2$ | Ph-3-Cl | H | N(CH$_3$)Ph |
| 3,5-Cl$_2$ | Ph-4-Cl | H | (D-50c)Cl |
| 3,5-Cl$_2$ | D-47a | H | CH$_2$CF$_3$ |
| 3,5-Cl$_2$ | D-47a | H | CH$_2$(D-47a) |
| 3,5-Cl$_2$ | OCH$_3$ | H | CH$_2$CF$_3$ |
| 3,5-Cl$_2$ | OEt | H | CH$_2$OCH$_2$CF$_3$ |
| 3,5-Cl$_2$ | OCH$_2$CF$_3$ | H | E-4a |
| 3,5-Cl$_2$ | Si(CH$_3$)$_3$ | H | CH$_2$CF$_3$ |
| 3,5-Cl$_2$ | Si(CH$_3$)$_3$ | H | CH$_2$(D-47a) |
| 3-Br-4-F | CHF$_2$ | H | CH$_2$C(O)NHCH$_2$CF$_3$ |
| 3-Br-4-F | CF$_3$ | H | c-Pr |
| 3-Br-4-F | CF$_3$ | H | CH$_2$Pr-c |
| 3-Br-4-F | CF$_3$ | H | c-Bu |
| 3-Br-4-F | CF$_3$ | H | CH$_2$CF$_3$ |
| 3-Br-4-F | CF$_3$ | C(O)CH$_3$ | CH$_2$CF$_3$ |
| 3-Br-4-F | CF$_3$ | H | CH$_2$CH$_2$CF$_3$ |
| 3-Br-4-F | CF$_3$ | H | CH$_2$OCH$_3$ |
| 3-Br-4-F | CF$_3$ | H | CH$_2$OEt |
| 3-Br-4-F | CF$_3$ | C(O)CH$_3$ | CH$_2$OEt |
| 3-Br-4-F | CF$_3$ | H | CH$_2$OCH$_2$CF$_3$ |
| 3-Br-4-F | CF$_3$ | C(O)CH$_3$ | CH$_2$OCH$_2$CF$_3$ |
| 3-Br-4-F | CF$_3$ | H | CH$_2$CH$_2$OCH$_3$ |
| 3-Br-4-F | CF$_3$ | H | CH$_2$(E-10a) |
| 3-Br-4-F | CF$_3$ | H | E-4a |
| 3-Br-4-F | CF$_3$ | H | E-5a(R) |
| 3-Br-4-F | CF$_3$ | H | CH$_2$CH=NOCH$_3$ |
| 3-Br-4-F | CF$_3$ | H | CH$_2$C(O)NHCH$_2$Cl |
| 3-Br-4-F | CF$_3$ | H | CH$_2$C(O)NHCH$_2$CF$_3$ |
| 3-Br-4-F | CF$_3$ | H | CH(CH$_3$)C(O)NHEt |
| 3-Br-4-F | CF$_3$ | H | CH(CH$_3$)C(O)NHCH$_2$CF$_3$ |
| 3-Br-4-F | CF$_3$ | H | CH(CH$_3$)C(O)NHCH$_2$CF$_3$(D) |
| 3-Br-4-F | CF$_3$ | H | CH$_2$CH=CH$_2$ |
| 3-Br-4-F | CF$_3$ | H | CH$_2$CCl=CH$_2$ |
| 3-Br-4-F | CF$_3$ | H | CH(CH$_3$)Ph(R) |
| 3-Br-4-F | CF$_3$ | H | CH$_2$(Ph-4-NO$_2$) |
| 3-Br-4-F | CF$_3$ | H | CH$_2$(Ph-4-CN) |
| 3-Br-4-F | CF$_3$ | H | CH$_2$(D-17b)Cl |
| 3-Br-4-F | CF$_3$ | H | CH$_2$(D-21a) |
| 3-Br-4-F | CF$_3$ | H | CH$_2$(D-22a) |
| 3-Br-4-F | CF$_3$ | C(O)CH$_3$ | CH$_2$(D-22a) |
| 3-Br-4-F | CF$_3$ | C(O)Et | CH$_2$(D-22a) |
| 3-Br-4-F | CF$_3$ | H | CH$_2$(D-47a) |
| 3-Br-4-F | CF$_3$ | CH$_2$OCH$_3$ | CH$_2$(D-47a) |
| 3-Br-4-F | CF$_3$ | CH$_2$CN | CH$_2$(D-47a) |
| 3-Br-4-F | CF$_3$ | C(O)CH$_3$ | CH$_2$(D-47a) |
| 3-Br-4-F | CF$_3$ | C(O)Et | CH$_2$(D-47a) |
| 3-Br-4-F | CF$_3$ | C(O)Pr-c | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Br-4-F | $CF_3$ | $C(O)OCH_3$ | $CH_2$(D-47a) |
| 3-Br-4-F | $CF_3$ | H | $CH(CH_3)$(D-47a) |
| 3-Br-4-F | $CF_3$ | H | $CH_2$(D-50a) |
| 3-Br-4-F | $CF_3$ | H | $N(CH_3)Ph$ |
| 3-Br-4-F | $CF_3$ | H | $N(CH_3)$(D-50a) |
| 3-Br-4-F | $CF_3$ | $C(O)OCH_3$ | $C(O)N(CH_3)_2$ |
| 3-Br-4-F | $CF_3$ | H | $C(O)NHEt$ |
| 3-Br-4-F | $CF_3$ | $CH_3$ | $C(O)NHEt$ |
| 3-Br-4-F | $CF_3$ | H | $C(O)NHCH_2CH_2Cl$ |
| 3-Br-4-F | $CF_3$ | H | $C(O)NHCH_2$(Ph-4-F) |
| 3-Br-4-F | $CF_3$ | H | Ph-4-CN |
| 3-Br-4-F | $CF_3$ | H | Ph-2,4-$F_2$ |
| 3-Br-4-F | $CF_3$ | H | (D-15a)$CH_3$ |
| 3-Br-4-F | $CF_3$ | H | (D-47d)CN |
| 3-Br-4-F | $CF_3$ | H | (D-47e)Br |
| 3-Br-4-F | $CF_3$ | H | D-50a |
| 3-Br-4-F | $CF_3$ | H | (D-50c)Cl |
| 3-Br-4-F | $CF_3$ | H | (D-50c)Br |
| 3-Br-4-F | $CF_3$ | H | D-52a |
| 3-Br-4-F | $CF_3$ | H | D-53a |
| 3-Br-4-F | $CF_2Cl$ | H | $CH_2CF_3$ |
| 3-Br-4-F | $CF_2Cl$ | $C(O)CH_3$ | $CH_2CF_3$ |
| 3-Br-4-F | $CF_2Cl$ | H | $CH_2OCH_2CF_3$ |
| 3-Br-4-F | $CF_2Cl$ | H | E-4a |
| 3-Br-4-F | $CF_2Cl$ | H | $CH_2C(O)NHCH_2CF_3$ |
| 3-Br-4-F | $CF_2Cl$ | H | $CH(CH_3)C(O)NHCH_2CF_3$(D) |
| 3-Br-4-F | $CF_2Cl$ | H | $CH(CH_3)Ph(R)$ |
| 3-Br-4-F | $CF_2Cl$ | H | $CH_2$(D-22a) |
| 3-Br-4-F | $CF_2Cl$ | H | $CH_2$(D-47a) |
| 3-Br-4-F | $CF_2Cl$ | $CH_2CN$ | $CH_2$(D-47a) |
| 3-Br-4-F | $CF_2Cl$ | $C(O)Et$ | $CH_2$(D-47a) |
| 3-Br-4-F | $CF_2Cl$ | $C(O)OCH_3$ | $CH_2$(D-47a) |
| 3-Br-4-F | $CF_2Cl$ | H | $N(CH_3)Ph$ |
| 3-Br-4-F | $CF_2Cl$ | H | (D-50c)Cl |
| 3-Br-4-F | $CF_2Cl$ | H | D-52a |
| 3-Br-4-F | $CF_2Br$ | H | $CH_2$(D-22a) |
| 3-Br-4-F | $CF_2CHF_2$ | H | $CH_2$(D-47a) |
| 2-F-4-Br | $CF_3$ | $C(O)OCH_3$ | $CH_2$(D-47a) |
| 3-F-4-Br | $CF_3$ | H | $N(CH_3)Ph$ |
| 2-F-5-Br | $CF_3$ | H | (D-50c)Cl |
| 3-F-5-Br | $CHF_2$ | H | $CH_2CF_3$ |
| 3-F-5-Br | $CF_3$ | H | c-Pr |
| 3-F-5-Br | $CF_3$ | H | $CH_2$Pr-c |
| 3-F-5-Br | $CF_3$ | H | c-Bu |
| 3-F-5-Br | $CF_3$ | H | $CH_2CF_3$ |
| 3-F-5-Br | $CF_3$ | $C(O)CH_3$ | $CH_2CF_3$ |
| 3-F-5-Br | $CF_3$ | H | $CH_2CH_2CF_3$ |
| 3-F-5-Br | $CF_3$ | H | $CH_2OCH_3$ |
| 3-F-5-Br | $CF_3$ | H | $CH_2OEt$ |
| 3-F-5-Br | $CF_3$ | $C(O)CH_3$ | $CH_2OEt$ |
| 3-F-5-Br | $CF_3$ | H | $CH_2OCH_2CF_3$ |
| 3-F-5-Br | $CF_3$ | $C(O)CH_3$ | $CH_2OCH_2CF_3$ |
| 3-F-5-Br | $CF_3$ | H | $CH_2CH_2OCH_3$ |
| 3-F-5-Br | $CF_3$ | H | $CH_2$(E-10a) |
| 3-F-5-Br | $CF_3$ | H | E-4a |
| 3-F-5-Br | $CF_3$ | H | E-5a(R) |
| 3-F-5-Br | $CF_3$ | H | $CH_2CH\!=\!NOCH_3$ |
| 3-F-5-Br | $CF_3$ | H | $CH_2C(O)NHCH_2CH_2Cl$ |
| 3-F-5-Br | $CF_3$ | H | $CH_2C(O)NHCH_2CF_3$ |
| 3-F-5-Br | $CF_3$ | H | $CH(CH_3)C(O)NHEt$ |
| 3-F-5-Br | $CF_3$ | H | $CH(CH_3)C(O)NHCH_2CF_3$ |
| 3-F-5-Br | $CF_3$ | H | $CH(CH_3)C(O)NHCH_2CF_3$(D) |
| 3-F-5-Br | $CF_3$ | H | $CH_2CH\!=\!CH_2$ |
| 3-F-5-Br | $CF_3$ | H | $CH_2CCl\!=\!CH_2$ |
| 3-F-5-Br | $CF_3$ | H | $CH(CH_3)Ph(R)$ |
| 3-F-5-Br | $CF_3$ | H | $CH_2$(Ph-4-$NO_2$) |
| 3-F-5-Br | $CF_3$ | H | $CH_2$(Ph-4-CN) |
| 3-F-5-Br | $CF_3$ | H | $CH_2$(D-17b)Cl |
| 3-F-5-Br | $CF_3$ | H | $CH_2$(D-21a) |
| 3-F-5-Br | $CF_3$ | H | $CH_2$(D-22a) |
| 3-F-5-Br | $CF_3$ | $C(O)CH_3$ | $CH_2$(D-22a) |
| 3-F-5-Br | $CF_3$ | $C(O)Et$ | $CH_2$(D-22a) |
| 3-F-5-Br | $CF_3$ | H | $CH_2$(D-47a) |
| 3-F-5-Br | $CF_3$ | $CH_2OCH_3$ | $CH_2$(D-47a) |
| 3-F-5-Br | $CF_3$ | $CH_2CN$ | $CH_2$(D-47a) |
| 3-F-5-Br | $CF_3$ | $C(O)CH_3$ | $CH_2$(D-47a) |
| 3-F-5-Br | $CF_3$ | $C(O)Et$ | $CH_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-F-5-Br | $CF_3$ | C(O)Pr-c | $CH_2$(D-47a) |
| 3-F-5-Br | $CF_3$ | C(O)$OCH_3$ | $CH_2$(D-47a) |
| 3-F-5-Br | $CF_3$ | H | $CH(CH_3)$(D-47a) |
| 3-F-5-Br | $CF_3$ | H | $CH_2$(D-50a) |
| 3-F-5-Br | $CF_3$ | H | $N(CH_3)$Ph |
| 3-F-5-Br | $CF_3$ | H | $N(CH_3)$(D-50a) |
| 3-F-5-Br | $CF_3$ | C(O)$OCH_3$ | C(O)$N(CH_3)_2$ |
| 3-F-5-Br | $CF_3$ | H | C(O)NHEt |
| 3-F-5-Br | $CF_3$ | $CH_3$ | C(O)NHEt |
| 3-F-5-Br | $CF_3$ | H | C(O)$NHCH_2CH_2Cl$ |
| 3-F-5-Br | $CF_3$ | H | C(O)$NHCH_2$(Ph-4-F) |
| 3-F-5-Br | $CF_3$ | H | Ph-4-CN |
| 3-F-5-Br | $CF_3$ | H | Ph-2,4-$F_2$ |
| 3-F-5-Br | $CF_3$ | H | (D-15a)$CH_3$ |
| 3-F-5-Br | $CF_3$ | H | (D-47d)CN |
| 3-F-5-Br | $CF_3$ | H | (D-47e)Br |
| 3-F-5-Br | $CF_3$ | H | D-50a |
| 3-F-5-Br | $CF_3$ | H | (D-50c)Cl |
| 3-F-5-Br | $CF_3$ | H | (D-50c)Br |
| 3-F-5-Br | $CF_3$ | H | D-52a |
| 3-F-5-Br | $CF_3$ | H | D-53a |
| 3-F-5-Br | $CF_2Cl$ | H | $CH_2CF_3$ |
| 3-F-5-Br | $CF_2Cl$ | C(O)$CH_3$ | $CH_2CF_3$ |
| 3-F-5-Br | $CF_2Cl$ | H | $CH_2OCH_2CF_3$ |
| 3-F-5-Br | $CF_2Cl$ | H | E-4a |
| 3-F-5-Br | $CF_2Cl$ | H | $CH_2C(O)NHCH_2CF_3$ |
| 3-F-5-Br | $CF_2Cl$ | H | $CH(CH_3)C(O)NHCH_2CF_3$(D) |
| 3-F-5-Br | $CF_2Cl$ | H | $CH(CH_3)$Ph(R) |
| 3-F-5-Br | $CF_2Cl$ | H | $CH_2$(D-22a) |
| 3-F-5-Br | $CF_2Cl$ | H | $CH_2$(D-47a) |
| 3-F-5-Br | $CF_2Cl$ | $CH_2CN$ | $CH_2$(D-47a) |
| 3-F-5-Br | $CF_2Cl$ | C(O)Et | $CH_2$(D-47a) |
| 3-F-5-Br | $CF_2Cl$ | C(O)$OCH_3$ | $CH_2$(D-47a) |
| 3-F-5-Br | $CF_2Cl$ | H | $N(CH_3)$Ph |
| 3-F-5-Br | $CF_2Cl$ | H | (D-50c)Cl |
| 3-F-5-Br | $CF_2Cl$ | H | D-52a |
| 3-F-5-Br | $CF_2Br$ | H | $CH_2OCH_2CF_3$ |
| 3-F-5-Br | $CF_2CHF_2$ | H | E-4a |
| 3-Cl-5-Br | $CHF_2$ | H | $CH_2CF_3$ |
| 3-Cl-5-Br | $CHF_2$ | H | $CH_2OCH_2CF_3$ |
| 3-Cl-5-Br | $CHF_2$ | H | E-4a |
| 3-Cl-5-Br | $CHF_2$ | H | $CH_2C(O)NHCH_2CF_3$ |
| 3-Cl-5-Br | $CHF_2$ | H | $CH(CH_3)C(O)NHCH_2CF_3$(D) |
| 3-Cl-5-Br | $CHF_2$ | H | $CH_2$(D-22a) |
| 3-Cl-5-Br | $CHF_2$ | H | $CH_2$(D-47a) |
| 3-Cl-5-Br | $CHF_2$ | C(O)$OCH_3$ | $CH_2$(D-47a) |
| 3-Cl-5-Br | $CHF_2$ | H | $N(CH_3)$Ph |
| 3-Cl-5-Br | $CHF_2$ | H | (D-50c)Cl |
| 3-Cl-5-Br | CHFCl | H | $CH_2C(O)NHCH_2CF_3$ |
| 3-Cl-5-Br | $CHCl_2$ | H | $CH_2$(D-22a) |
| 3-Cl-5-Br | CHFBr | H | $CH_2$(D-47a) |
| 3-Cl-5-Br | $CF_3$ | H | H |
| 3-Cl-5-Br | $CF_3$ | H | Et |
| 3-Cl-5-Br | $CF_3$ | Et | Et |
| 3-Cl-5-Br | $CF_3$ | H | c-Pr |
| 3-Cl-5-Br | $CF_3$ | H | $CH_2$Pr-c |
| 3-Cl-5-Br | $CF_3$ | H | c-Bu |
| 3-Cl-5-Br | $CF_3$ | H | $CH_2CH_2Cl$ |
| 3-Cl-5-Br | $CF_3$ | H | $CH_2CHF_2$ |
| 3-Cl-5-Br | $CF_3$ | H | $CH_2CF_3$ |
| 3-Cl-5-Br | $CF_3$ | C(O)$CH_3$ | $CH_2CF_3$ |
| 3-Cl-5-Br | $CF_3$ | H | $CH_2CH_2CF_3$ |
| 3-Cl-5-Br | $CF_3$ | H | $CH_2OCH_3$ |
| 3-Cl-5-Br | $CF_3$ | H | $CH_2OEt$ |
| 3-Cl-5-Br | $CF_3$ | C(O)$CH_3$ | $CH_2OEt$ |
| 3-Cl-5-Br | $CF_3$ | H | $CH_2OCH_2CH_2Cl$ |
| 3-Cl-5-Br | $CF_3$ | H | $CH_2OCH_2CHF_2$ |
| 3-Cl-5-Br | $CF_3$ | H | $CH_2OCH_2CF_3$ |
| 3-Cl-5-Br | $CF_3$ | C(O)$CH_3$ | $CH_2OCH_2CF_3$ |
| 3-Cl-5-Br | $CF_3$ | H | $CH(CH_3)OCH_2CF_3$ |
| 3-Cl-5-Br | $CF_3$ | H | $CH(CF_3)OCH_3$ |
| 3-Cl-5-Br | $CF_3$ | H | $CH_2CH_2OCH_3$ |
| 3-Cl-5-Br | $CF_3$ | H | $CH_2CH_2OEt$ |
| 3-Cl-5-Br | $CF_3$ | H | $CH_2CH(OCH_3)_2$ |
| 3-Cl-5-Br | $CF_3$ | H | $CH_2$(E-4a) |
| 3-Cl-5-Br | $CF_3$ | H | $CH_2$(E-5a) |
| 3-Cl-5-Br | $CF_3$ | H | $CH_2$(E-10a) |

TABLE 2-continued

In the table, the number showing the substitution position of substituent $(X)_m$ corresponds to the position number indicated in the following structural formulae. The indication "—" means no-substitution.

| | | | | |
|---|---|---|---|---|
| 3-Cl-5-Br | $CF_3$ | H | | $CH_2$(E-10b)$CH_3$ |
| 3-Cl-5-Br | $CF_3$ | H | | E-4a |
| 3-Cl-5-Br | $CF_3$ | H | | E-5a(R) |
| 3-Cl-5-Br | $CF_3$ | H | | $CH_2SCH_3$ |
| 3-Cl-5-Br | $CF_3$ | H | | $CH_2S(O)CH_3$ |
| 3-Cl-5-Br | $CF_3$ | H | | $CH_2SO_2CH_3$ |
| 3-Cl-5-Br | $CF_3$ | H | | $CH_2CH_2SO_2CH_3$ |
| 3-Cl-5-Br | $CF_3$ | H | | $CH_2CH_2SO_2Et$ |
| 3-Cl-5-Br | $CF_3$ | H | | $CH_2CH(CH_3)S(O)CH_3$ |
| 3-Cl-5-Br | $CF_3$ | H | | $CH_2CH(CH_3)SO_2CH_3$ |
| 3-Cl-5-Br | $CF_3$ | H | | $CH(CH_3)CH_2SO_2CH_3$ |
| 3-Cl-5-Br | $CF_3$ | H | | $CH_2NHCH_2CF_3$ |
| 3-Cl-5-Br | $CF_3$ | H | | $CH_2NHC(O)OCH_3$ |
| 3-Cl-5-Br | $CF_3$ | H | | $CH(CH_3)NHC(O)OCH_3$ |
| 3-Cl-5-Br | $CF_3$ | H | | $CH_2NHC(O)OCH_2CF_3$ |
| 3-Cl-5-Br | $CF_3$ | H | | $CH_2CH\!=\!NOCH_3$ |
| 3-Cl-5-Br | $CF_3$ | H | | $CH_2C(CH_3)\!=\!NOCH_3$ |
| 3-Cl-5-Br | $CF_3$ | H | | $CH_2CN$ |
| 3-Cl-5-Br | $CF_3$ | H | | $CH_2C(O)NHCH_3$ |
| 3-Cl-5-Br | $CF_3$ | H | | $CH_2C(O)N(CH_3)_2$ |
| 3-Cl-5-Br | $CF_3$ | H | | $CH_2C(O)NHEt$ |
| 3-Cl-5-Br | $CF_3$ | H | | $CH_2C(O)NHPr-n$ |
| 3-Cl-5-Br | $CF_3$ | H | | $CH_2C(O)NHPr-i$ |
| 3-Cl-5-Br | $CF_3$ | H | | $CH_2C(O)NHCH_2CH_2F$ |
| 3-Cl-5-Br | $CF_3$ | H | | $CH_2C(O)NHCH_2CH_2Cl$ |
| 3-Cl-5-Br | $CF_3$ | H | | $CH_2C(O)NHCH_2CF_3$ |
| 3-Cl-5-Br | $CF_3$ | H | | $CH_2C(O)NHCH_2CH\!=\!CH_2$ |
| 3-Cl-5-Br | $CF_3$ | H | | $CH_2C(O)NHCH_2C\!\equiv\!CH$ |
| 3-Cl-5-Br | $CF_3$ | H | | $CH(CH_3)C(O)NHEt$ |
| 3-Cl-5-Br | $CF_3$ | H | | $CH(CH_3)C(O)NHCH_2CF_3$ |
| 3-Cl-5-Br | $CF_3$ | H | | $CH(CH_3)C(O)NHCH_2CH_2Cl$(D) |
| 3-Cl-5-Br | $CF_3$ | H | | $CH(CH_3)C(O)NHCH_2CF_3$(D) |
| 3-Cl-5-Br | $CF_3$ | H | | $CH_2C(S)NH_2$ |
| 3-Cl-5-Br | $CF_3$ | H | | $CH_2CH\!=\!CH_2$ |
| 3-Cl-5-Br | $CF_3$ | H | | $CH_2CCl\!=\!CH_2$ |
| 3-Cl-5-Br | $CF_3$ | H | | $CH_2CCl\!=\!CHCl$ |
| 3-Cl-5-Br | $CF_3$ | H | | $CH_2C\!\equiv\!CH$ |
| 3-Cl-5-Br | $CF_3$ | H | | $CH(CH_3)Ph(R)$ |
| 3-Cl-5-Br | $CF_3$ | H | | $CH(CF_3)Ph$ |
| 3-Cl-5-Br | $CF_3$ | H | | $CH(CN)Ph$ |
| 3-Cl-5-Br | $CF_3$ | H | | $CH_2(Ph-4-OCH_3)$ |
| 3-Cl-5-Br | $CF_3$ | H | | $CH_2(Ph-4-NO_2)$ |
| 3-Cl-5-Br | $CF_3$ | H | | $CH_2(Ph-4-CN)$ |
| 3-Cl-5-Br | $CF_3$ | H | | $CH_2$(D-1a) |
| 3-Cl-5-Br | $CF_3$ | H | | $CH_2$(D-16b)Cl |
| 3-Cl-5-Br | $CF_3$ | H | | $CH_2$(D-17a)$CH_3$ |
| 3-Cl-5-Br | $CF_3$ | H | | $CH_2$(D-17b)Cl |
| 3-Cl-5-Br | $CF_3$ | H | | $CH_2$(D-21a) |
| 3-Cl-5-Br | $CF_3$ | H | | $CH_2$(D-22a) |
| 3-Cl-5-Br | $CF_3$ | $C(O)CH_3$ | | $CH_2$(D-22a) |
| 3-Cl-5-Br | $CF_3$ | C(O)Et | | $CH_2$(D-22a) |
| 3-Cl-5-Br | $CF_3$ | H | | $CH_2$(D-28a) |
| 3-Cl-5-Br | $CF_3$ | H | | $CH_2$(D-29b)$CH_3$ |
| 3-Cl-5-Br | $CF_3$ | H | | $CH_2$(D-34a) |
| 3-Cl-5-Br | $CF_3$ | H | | $CH_2$(D-35a) |
| 3-Cl-5-Br | $CF_3$ | H | | $CH_2$(D-38a) |
| 3-Cl-5-Br | $CF_3$ | H | | $CH_2$(D-47a) |
| 3-Cl-5-Br | $CF_3$ | Et | | $CH_2$(D-47a) |
| 3-Cl-5-Br | $CF_3$ | $CH_2OCH_3$ | | $CH_2$(D-47a) |
| 3-Cl-5-Br | $CF_3$ | $CH_2CN$ | | $CH_2$(D-47a) |
| 3-Cl-5-Br | $CF_3$ | $CH_2C\!\equiv\!CH$ | | $CH_2$(D-47a) |
| 3-Cl-5-Br | $CF_3$ | $C(O)CH_3$ | | $CH_2$(D-47a) |
| 3-Cl-5-Br | $CF_3$ | C(O)Et | | $CH_2$(D-47a) |
| 3-Cl-5-Br | $CF_3$ | C(O)Pr-n | | $CH_2$(D-47a) |
| 3-Cl-5-Br | $CF_3$ | C(O)Pr-i | | $CH_2$(D-47a) |
| 3-Cl-5-Br | $CF_3$ | C(O)Pr-c | | $CH_2$(D-47a) |
| 3-Cl-5-Br | $CF_3$ | C(O)Bu-t | | $CH_2$(D-47a) |
| 3-Cl-5-Br | $CF_3$ | $C(O)CH_2OCH_3$ | | $CH_2$(D-47a) |
| 3-Cl-5-Br | $CF_3$ | $C(O)CH\!=\!CH_2$ | | $CH_2$(D-47a) |
| 3-Cl-5-Br | $CF_3$ | $C(O)OCH_3$ | | $CH_2$(D-47a) |
| 3-Cl-5-Br | $CF_3$ | C(O)OEt | | $CH_2$(D-47a) |
| 3-Cl-5-Br | $CF_3$ | $C(O)OCH_2CH_2OCH_3$ | | $CH_2$(D-47a) |
| 3-Cl-5-Br | $CF_3$ | $C(O)OCH_2CH\!=\!CH_2$ | | $CH_2$(D-47a) |
| 3-Cl-5-Br | $CF_3$ | H | | $CH(CH_3)$(D-47a) |
| 3-Cl-5-Br | $CF_3$ | H | | $CH_2$(D-50a) |
| 3-Cl-5-Br | $CF_3$ | H | | $NHCH_2CF_3$ |
| 3-Cl-5-Br | $CF_3$ | H | | $NHC(O)OCH_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-5-Br | CF$_3$ | H | N(CH$_3$)Ph |
| 3-Cl-5-Br | CF$_3$ | H | N(CH$_2$CH=CH$_2$)Ph |
| 3-Cl-5-Br | CF$_3$ | H | N(CH$_2$C≡CH)Ph |
| 3-Cl-5-Br | CF$_3$ | H | N(CH$_3$)(D-47a) |
| 3-Cl-5-Br | CF$_3$ | H | NH(D-50a) |
| 3-Cl-5-Br | CF$_3$ | CH$_3$ | NH(D-50a) |
| 3-Cl-5-Br | CF$_3$ | H | N(CH$_3$)(D-50a) |
| 3-Cl-5-Br | CF$_3$ | H | N(Et)(D-50a) |
| 3-Cl-5-Br | CF$_3$ | C(O)OCH$_3$ | C(O)N(CH$_3$)$_2$ |
| 3-Cl-5-Br | CF$_3$ | H | C(O)NHEt |
| 3-Cl-5-Br | CF$_3$ | CH$_3$ | C(O)NHEt |
| 3-Cl-5-Br | CF$_3$ | H | C(O)NHCH$_2$CH$_2$Cl |
| 3-Cl-5-Br | CF$_3$ | H | C(O)NHCH$_2$CF$_3$ |
| 3-Cl-5-Br | CF$_3$ | H | C(O)NHCH$_2$(Ph-4-F) |
| 3-Cl-5-Br | CF$_3$ | H | C(S)NHCH$_3$ |
| 3-Cl-5-Br | CF$_3$ | H | Ph-4-F |
| 3-Cl-5-Br | CF$_3$ | H | Ph-4-CN |
| 3-Cl-5-Br | CF$_3$ | H | Ph-2,4-F$_2$ |
| 3-Cl-5-Br | CF$_3$ | H | Ph-2,6-F$_2$ |
| 3-Cl-5-Br | CF$_3$ | H | Ph-2,4,6-F$_3$ |
| 3-Cl-5-Br | CF$_3$ | H | (D-13b)CH$_3$ |
| 3-Cl-5-Br | CF$_3$ | H | (D-15a)CH$_3$ |
| 3-Cl-5-Br | CF$_3$ | H | D-21a |
| 3-Cl-5-Br | CF$_3$ | H | (D-47d)Cl |
| 3-Cl-5-Br | CF$_3$ | H | (D-47d)Br |
| 3-Cl-5-Br | CF$_3$ | H | (D-47d)CN |
| 3-Cl-5-Br | CF$_3$ | H | (D-47e)Br |
| 3-Cl-5-Br | CF$_3$ | H | (D-48e)Cl |
| 3-Cl-5-Br | CF$_3$ | H | D-50a |
| 3-Cl-5-Br | CF$_3$ | H | (D-50c)Cl |
| 3-Cl-5-Br | CF$_3$ | H | (D-50c)Br |
| 3-Cl-5-Br | CF$_3$ | H | D-51a |
| 3-Cl-5-Br | CF$_3$ | H | D-52a |
| 3-Cl-5-Br | CF$_3$ | H | D-53a |
| 3-Cl-5-Br | CF$_3$ | H | (D-54b)Cl |
| 3-Cl-5-Br | CF$_2$Cl | H | c-Pr |
| 3-Cl-5-Br | CF$_2$Cl | H | CH$_2$Pr-c |
| 3-Cl-5-Br | CF$_2$Cl | H | c-Bu |
| 3-Cl-5-Br | CF$_2$Cl | H | CH$_2$CF$_3$ |
| 3-Cl-5-Br | CF$_2$Cl | C(O)CH$_3$ | CH$_2$CF$_3$ |
| 3-Cl-5-Br | CF$_2$Cl | H | CH$_2$CH$_2$CF$_3$ |
| 3-Cl-5-Br | CF$_2$Cl | H | CH$_2$OCH$_3$ |
| 3-Cl-5-Br | CF$_2$Cl | H | CH$_2$OEt |
| 3-Cl-5-Br | CF$_2$Cl | C(O)CH$_3$ | CH$_2$OEt |
| 3-Cl-5-Br | CF$_2$Cl | H | CH$_2$OCH$_2$CF$_3$ |
| 3-Cl-5-Br | CF$_2$Cl | C(O)CH$_3$ | CH$_2$OCH$_2$CF$_3$ |
| 3-Cl-5-Br | CF$_2$Cl | H | CH$_2$CH$_2$OCH$_3$ |
| 3-Cl-5-Br | CF$_2$Cl | H | CH$_2$(E-10a) |
| 3-Cl-5-Br | CF$_2$Cl | H | E-4a |
| 3-Cl-5-Br | CF$_2$Cl | H | E-5a(R) |
| 3-Cl-5-Br | CF$_2$Cl | H | CH$_2$CH=NOCH$_3$ |
| 3-Cl-5-Br | CF$_2$Cl | H | CH$_2$C(O)NHCH$_2$CH$_2$Cl |
| 3-Cl-5-Br | CF$_2$Cl | H | CH$_2$C(O)NHCH$_2$CF$_3$ |
| 3-Cl-5-Br | CF$_2$Cl | H | CH(CH$_3$)C(O)NHEt |
| 3-Cl-5-Br | CF$_2$Cl | H | CH(CH$_3$)C(O)NHCH$_2$CF$_3$ |
| 3-Cl-5-Br | CF$_2$Cl | H | CH(CH$_3$)C(O)NHCH$_2$CF$_3$(D) |
| 3-Cl-5-Br | CF$_2$Cl | H | CH$_2$CH=CH$_2$ |
| 3-Cl-5-Br | CF$_2$Cl | H | CH$_2$CCl=CH$_2$ |
| 3-Cl-5-Br | CF$_2$Cl | H | CH(CH$_3$)Ph(R) |
| 3-Cl-5-Br | CF$_2$Cl | H | CH$_2$(Ph-4-NO$_2$) |
| 3-Cl-5-Br | CF$_2$Cl | H | CH$_2$(Ph-4-CN) |
| 3-Cl-5-Br | CF$_2$Cl | H | CH$_2$(D-17b)Cl |
| 3-Cl-5-Br | CF$_2$Cl | H | CH$_2$(D-21a) |
| 3-Cl-5-Br | CF$_2$Cl | H | CH$_2$(D-22a) |
| 3-Cl-5-Br | CF$_2$Cl | C(O)CH$_3$ | CH$_2$(D-22a) |
| 3-Cl-5-Br | CF$_2$Cl | C(O)Et | CH$_2$(D-22a) |
| 3-Cl-5-Br | CF$_2$Cl | H | CH$_2$(D-47a) |
| 3-Cl-5-Br | CF$_2$Cl | CH$_2$OCH$_3$ | CH$_2$(D-47a) |
| 3-Cl-5-Br | CF$_2$Cl | CH$_2$CN | CH$_2$(D-47a) |
| 3-Cl-5-Br | CF$_2$Cl | C(O)CH$_3$ | CH$_2$(D-47a) |
| 3-Cl-5-Br | CF$_2$Cl | C(O)Et | CH$_2$(D-47a) |
| 3-Cl-5-Br | CF$_2$Cl | C(O)Pr-c | CH$_2$(D-47a) |
| 3-Cl-5-Br | CF$_2$Cl | C(O)OCH$_3$ | CH$_2$(D-47a) |
| 3-Cl-5-Br | CF$_2$Cl | H | CH(CH$_3$)(D-47a) |
| 3-Cl-5-Br | CF$_2$Cl | H | CH$_2$(D-50a) |
| 3-Cl-5-Br | CF$_2$Cl | H | N(CH$_3$)Ph |
| 3-Cl-5-Br | CF$_2$Cl | H | N(CH$_3$)(D-50a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-Br | $CF_2Cl$ | $C(O)OCH_3$ | $C(O)N(CH_3)_2$ |
| 3-Cl-5-Br | $CF_2Cl$ | H | C(O)NHEt |
| 3-Cl-5-Br | $CF_2Cl$ | $CH_3$ | C(O)NHEt |
| 3-Cl-5-Br | $CF_2Cl$ | H | $C(O)NHCH_2CH_2Cl$ |
| 3-Cl-5-Br | $CF_2Cl$ | H | $C(O)NHCH_2(Ph-4-F)$ |
| 3-Cl-5-Br | $CF_2Cl$ | H | Ph-4-CN |
| 3-Cl-5-Br | $CF_2Cl$ | H | $Ph-2,4-F_2$ |
| 3-Cl-5-Br | $CF_2Cl$ | H | $(D-15a)CH_3$ |
| 3-Cl-5-Br | $CF_2Cl$ | H | (D-47d)CN |
| 3-Cl-5-Br | $CF_2Cl$ | H | (D-47e)Br |
| 3-Cl-5-Br | $CF_2Cl$ | H | D-50a |
| 3-Cl-5-Br | $CF_2Cl$ | H | (D-50c)Cl |
| 3-Cl-5-Br | $CF_2Cl$ | H | (D-50c)Br |
| 3-Cl-5-Br | $CF_2Cl$ | H | D-52a |
| 3-Cl-5-Br | $CF_2Cl$ | H | D-53a |
| 3-Cl-5-Br | $CF_2Br$ | H | $CH_2CF_3$ |
| 3-Cl-5-Br | $CF_2Br$ | H | $CH_2OCH_2CF_3$ |
| 3-Cl-5-Br | $CF_2Br$ | H | E-4a |
| 3-Cl-5-Br | $CF_2Br$ | H | $CH_2C(O)NHCH_2CF_3$ |
| 3-Cl-5-Br | $CF_2Br$ | H | $CH(CH_3)C(O)NHCH_2CF_3(D)$ |
| 3-Cl-5-Br | $CF_2Br$ | H | $CH_2(D-22a)$ |
| 3-Cl-5-Br | $CF_2Br$ | H | $CH_2(D-47a)$ |
| 3-Cl-5-Br | $CF_2Br$ | $C(O)OCH_3$ | $CH_2(D-47a)$ |
| 3-Cl-5-Br | $CF_2Br$ | H | $N(CH_3)Ph$ |
| 3-Cl-5-Br | $CF_2Br$ | H | (D-50c)Cl |
| 3-Cl-5-Br | $CF_2CHF_2$ | H | $CH_2CF_3$ |
| 3-Cl-5-Br | $CF_2CHF_2$ | H | $CH_2OCH_2CF_3$ |
| 3-Cl-5-Br | $CF_2CHF_2$ | H | E-4a |
| 3-Cl-5-Br | $CF_2CHF_2$ | H | $CH_2C(O)NHCH_2CF_3$ |
| 3-Cl-5-Br | $CF_2CHF_2$ | H | $CH(CH_3)C(O)NHCH_2CF_3(D)$ |
| 3-Cl-5-Br | $CF_2CHF_2$ | H | $CH_2(D-22a)$ |
| 3-Cl-5-Br | $CF_2CHF_2$ | H | $CH_2(D-47a)$ |
| 3-Cl-5-Br | $CF_2CHF_2$ | $C(O)OCH_3$ | $CH_2(D-47a)$ |
| 3-Cl-5-Br | $CF_2CHF_2$ | H | $N(CH_3)Ph$ |
| 3-Cl-5-Br | $CF_2CHF_2$ | H | (D-50c)Cl |
| 3-Cl-5-Br | $CF_2CF_3$ | $C(O)OCH_3$ | $CH_2(D-47a)$ |
| 3-Cl-5-Br | $CF_2OCH_3$ | H | $N(CH_3)Ph$ |
| 3-Cl-5-Br | $CF_2SCH_3$ | H | (D-50c)Cl |
| 3-Cl-5-Br | T-3 | H | $CH_2CF_3$ |
| $3,4-Br_2$ | $CF_3$ | H | c-Bu |
| $3,4-Br_2$ | $CF_3$ | H | $CH_2CF_3$ |
| $3,4-Br_2$ | $CF_3$ | H | $CH_2OEt$ |
| $3,4-Br_2$ | $CF_3$ | H | $CH_2OCH_2CF_3$ |
| $3,4-Br_2$ | $CF_3$ | $C(O)CH_3$ | $CH_2OCH_2CF_3$ |
| $3,4-Br_2$ | $CF_3$ | H | $CH_2CH_2OCH_3$ |
| $3,4-Br_2$ | $CF_3$ | H | $CH_2(E-10a)$ |
| $3,4-Br_2$ | $CF_3$ | H | E-4a |
| $3,4-Br_2$ | $CF_3$ | H | $CH_2C(O)NHCH_2CH_2Cl$ |
| $3,4-Br_2$ | $CF_3$ | H | $CH_2C(O)NHCH_2CF_3$ |
| $3,4-Br_2$ | $CF_3$ | H | $CH(CH_3)C(O)NHCH_2CF_3$ |
| $3,4-Br_2$ | $CF_3$ | H | $CH(CH_3)C(O)NHCH_2CF_3(D)$ |
| $3,4-Br_2$ | $CF_3$ | H | $CH(CH_3)Ph(R)$ |
| $3,4-Br_2$ | $CF_3$ | H | $CH_2(D-22a)$ |
| $3,4-Br_2$ | $CF_3$ | $C(O)CH_3$ | $CH_2(D-22a)$ |
| $3,4-Br_2$ | $CF_3$ | C(O)Et | $CH_2(D-22a)$ |
| $3,4-Br_2$ | $CF_3$ | H | $CH_2(D-47a)$ |
| $3,4-Br_2$ | $CF_3$ | $CH_2OCH_3$ | $CH_2(D-47a)$ |
| $3,4-Br_2$ | $CF_3$ | $CH_2CN$ | $CH_2(D-47a)$ |
| $3,4-Br_2$ | $CF_3$ | $C(O)CH_3$ | $CH_2(D-47a)$ |
| $3,4-Br_2$ | $CF_3$ | C(O)Et | $CH_2(D-47a)$ |
| $3,4-Br_2$ | $CF_3$ | $C(O)OCH_3$ | $CH_2(D-47a)$ |
| $3,4-Br_2$ | $CF_3$ | H | $N(CH_3)Ph$ |
| $3,4-Br_2$ | $CF_3$ | H | $N(CH_3)(D-50a)$ |
| $3,4-Br_2$ | $CF_3$ | H | $C(O)NHCH_2CF_3$ |
| $3,4-Br_2$ | $CF_3$ | H | $Ph-2,4-F_2$ |
| $3,4-Br_2$ | $CF_3$ | H | (D-50c)Cl |
| $3,4-Br_2$ | $CF_3$ | H | D-52a |
| $3,4-Br_2$ | $CF_2Cl$ | H | $CH_2CF_3$ |
| $3,4-Br_2$ | $CF_2Cl$ | H | $CH_2OCH_2CF_3$ |
| $3,4-Br_2$ | $CF_2Cl$ | H | E-4a |
| $3,4-Br_2$ | $CF_2Cl$ | H | $CH_2C(O)NHCH_2CF_3$ |
| $3,4-Br_2$ | $CF_2Cl$ | H | $CH(CH_3)C(O)NHCH_2CF_3(D)$ |
| $3,4-Br_2$ | $CF_2Cl$ | H | $CH_2(D-22a)$ |
| $3,4-Br_2$ | $CF_2Cl$ | H | $CH_2(D-47a)$ |
| $3,4-Br_2$ | $CF_2Cl$ | $C(O)OCH_3$ | $CH_2(D-47a)$ |
| $3,4-Br_2$ | $CF_2Cl$ | H | $N(CH_3)Ph$ |
| $3,4-Br_2$ | $CF_2Cl$ | H | (D-50c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Br$_2$ | CHF$_2$ | H | CH$_2$CF$_3$ |
| 3,5-Br$_2$ | CHF$_2$ | H | CH$_2$OCH$_2$CF$_3$ |
| 3,5-Br$_2$ | CHF$_2$ | H | E-4a |
| 3,5-Br$_2$ | CHF$_2$ | H | CH$_2$C(O)NHCH$_2$CF$_3$ |
| 3,5-Br$_2$ | CHF$_2$ | H | CH(CH$_3$)C(O)NHCH$_2$CF$_3$(D) |
| 3,5-Br$_2$ | CHF$_2$ | H | CH$_2$(D-22a) |
| 3,5-Br$_2$ | CHF$_2$ | H | CH$_2$(D-47a) |
| 3,5-Br$_2$ | CHF$_2$ | C(O)OCH$_3$ | CH$_2$(D-47a) |
| 3,5-Br$_2$ | CHF$_2$ | H | N(CH$_3$)Ph |
| 3,5-Br$_2$ | CHF$_2$ | | (D-50c)Cl |
| 3,5-Br$_2$ | CHFCl | H | CH$_2$OCH$_2$CF$_3$ |
| 3,5-Br$_2$ | CHCl$_2$ | H | E-4a |
| 3,5-Br$_2$ | CHFBr | H | CH$_2$C(O)NHCH$_2$CF$_3$ |
| 3,5-Br$_2$ | CF$_3$ | H | H |
| 3,5-Br$_2$ | CF$_3$ | H | Et |
| 3,5-Br$_2$ | CF$_3$ | Et | Et |
| 3,5-Br$_2$ | CF$_3$ | H | c-Pr |
| 3,5-Br$_2$ | CF$_3$ | H | CH$_2$Pr-c |
| 3,5-Br$_2$ | CF$_3$ | H | c-Bu |
| 3,5-Br$_2$ | CF$_3$ | H | CH$_2$CH$_2$Cl |
| 3,5-Br$_2$ | CF$_3$ | H | CH$_2$CHF$_2$ |
| 3,5-Br$_2$ | CF$_3$ | H | CH$_2$CF$_3$ |
| 3,5-Br$_2$ | CF$_3$ | C(O)CH$_3$ | CH$_2$CF$_3$ |
| 3,5-Br$_2$ | CF$_3$ | H | CH$_2$CH$_2$CF$_3$ |
| 3,5-Br$_2$ | CF$_3$ | H | CH$_2$OCH$_3$ |
| 3,5-Br$_2$ | CF$_3$ | H | CH$_2$OEt |
| 3,5-Br$_2$ | CF$_3$ | C(O)CH$_3$ | CH$_2$OEt |
| 3,5-Br$_2$ | CF$_3$ | H | CH$_2$OCH$_2$CH$_2$Cl |
| 3,5-Br$_2$ | CF$_3$ | H | CH$_2$OCH$_2$CHF$_2$ |
| 3,5-Br$_2$ | CF$_3$ | H | CH$_2$OCH$_2$CF$_3$ |
| 3,5-Br$_2$ | CF$_3$ | C(O)CH$_3$ | CH$_2$OCH$_2$CF$_3$ |
| 3,5-Br$_2$ | CF$_3$ | H | CH(CH$_3$)OCH$_2$CF$_3$ |
| 3,5-Br$_2$ | CF$_3$ | H | CH(CF$_3$)OCH$_3$ |
| 3,5-Br$_2$ | CF$_3$ | H | CH$_2$CH$_2$OCH$_3$ |
| 3,5-Br$_2$ | CF$_3$ | H | CH$_2$CH$_2$OEt |
| 3,5-Br$_2$ | CF$_3$ | H | CH$_2$CH(OCH$_3$)$_2$ |
| 3,5-Br$_2$ | CF$_3$ | H | CH$_2$(E-4a) |
| 3,5-Br$_2$ | CF$_3$ | H | CH$_2$(E-5a) |
| 3,5-Br$_2$ | CF$_3$ | H | CH$_2$(E-10a) |
| 3,5-Br$_2$ | CF$_3$ | H | CH$_2$(E-10b)CH$_3$ |
| 3,5-Br$_2$ | CF$_3$ | H | E-4a |
| 3,5-Br$_2$ | CF$_3$ | H | E-5a(R) |
| 3,5-Br$_2$ | CF$_3$ | H | CH$_2$SCH$_3$ |
| 3,5-Br$_2$ | CF$_3$ | H | CH$_2$S(O)CH$_3$ |
| 3,5-Br$_2$ | CF$_3$ | H | CH$_2$SO$_2$CH$_3$ |
| 3,5-Br$_2$ | CF$_3$ | H | CH$_2$CH$_2$SO$_2$CH$_3$ |
| 3,5-Br$_2$ | CF$_3$ | H | CH$_2$CH$_2$SO$_2$Et |
| 3,5-Br$_2$ | CF$_3$ | H | CH$_2$CH(CH$_3$)S(O)CH$_3$ |
| 3,5-Br$_2$ | CF$_3$ | H | CH$_2$CH(CH$_3$)SO$_2$CH$_3$ |
| 3,5-Br$_2$ | CF$_3$ | H | CH(CH$_3$)CH$_2$SO$_2$CH$_3$ |
| 3,5-Br$_2$ | CF$_3$ | H | CH$_2$NHCH$_2$CF$_3$ |
| 3,5-Br$_2$ | CF$_3$ | H | CH$_2$NHC(O)OCH$_3$ |
| 3,5-Br$_2$ | CF$_3$ | H | CH(CH$_3$)NHC(O)OCH$_3$ |
| 3,5-Br$_2$ | CF$_3$ | H | CH$_2$NHC(O)OCH$_2$CF$_3$ |
| 3,5-Br$_2$ | CF$_3$ | H | CH$_2$CH=NOCH$_3$ |
| 3,5-Br$_2$ | CF$_3$ | H | CH$_2$C(CH$_3$)=NOCH$_3$ |
| 3,5-Br$_2$ | CF$_3$ | H | CH$_2$CN |
| 3,5-Br$_2$ | CF$_3$ | H | CH$_2$C(O)OCH$_3$ |
| 3,5-Br$_2$ | CF$_3$ | H | CH$_2$C(O)NHCH$_3$ |
| 3,5-Br$_2$ | CF$_3$ | H | CH$_2$C(O)N(CH$_3$)$_2$ |
| 3,5-Br$_2$ | CF$_3$ | H | CH$_2$C(O)NHEt |
| 3,5-Br$_2$ | CF$_3$ | H | CH$_2$C(O)NHPr-n |
| 3,5-Br$_2$ | CF$_3$ | H | CH$_2$C(O)NHPr-i |
| 3,5-Br$_2$ | CF$_3$ | H | CH$_2$C(O)NHCH$_2$F |
| 3,5-Br$_2$ | CF$_3$ | H | CH$_2$C(O)NHCH$_2$Cl |
| 3,5-Br$_2$ | CF$_3$ | H | CH$_2$C(O)NHCH$_2$CF$_3$ |
| 3,5-Br$_2$ | CF$_3$ | H | CH$_2$C(O)NHCH$_2$CH=CH$_2$ |
| 3,5-Br$_2$ | CF$_3$ | H | CH$_2$C(O)NHCH$_2$C≡CH |
| 3,5-Br$_2$ | CF$_3$ | H | CH(CH$_3$)C(O)NHEt |
| 3,5-Br$_2$ | CF$_3$ | H | CH(CH$_3$)C(O)NHCH$_2$CF$_3$ |
| 3,5-Br$_2$ | CF$_3$ | H | CH(CH$_3$)C(O)NHCH$_2$CH$_2$Cl(D) |
| 3,5-Br$_2$ | CF$_3$ | H | CH(CH$_3$)C(O)NHCH$_2$CF$_3$(D) |
| 3,5-Br$_2$ | CF$_3$ | H | CH$_2$C(S)NH$_2$ |
| 3,5-Br$_2$ | CF$_3$ | H | CH$_2$CH=CH$_2$ |
| 3,5-Br$_2$ | CF$_3$ | H | CH$_2$CCl=CH$_2$ |
| 3,5-Br$_2$ | CF$_3$ | H | CH$_2$CCl=CHCl |
| 3,5-Br$_2$ | CF$_3$ | H | CH$_2$C≡CH |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Br$_2$ | CF$_3$ | H | CH(CH$_3$)Ph(R) |
| 3,5-Br$_2$ | CF$_3$ | H | CH(CF$_3$)Ph |
| 3,5-Br$_2$ | CF$_3$ | H | CH(CN)Ph |
| 3,5-Br$_2$ | CF$_3$ | H | CH$_2$(Ph-4-OCH$_3$) |
| 3,5-Br$_2$ | CF$_3$ | H | CH$_2$(Ph-4-NO$_2$) |
| 3,5-Br$_2$ | CF$_3$ | H | CH$_2$(Ph-4-CN) |
| 3,5-Br$_2$ | CF$_3$ | H | CH$_2$(D-1a) |
| 3,5-Br$_2$ | CF$_3$ | H | CH$_2$(D-16b)Cl |
| 3,5-Br$_2$ | CF$_3$ | H | CH$_2$(D-17a)CH$_3$ |
| 3,5-Br$_2$ | CF$_3$ | H | CH$_2$(D-17b)Cl |
| 3,5-Br$_2$ | CF$_3$ | H | CH$_2$(D-21a) |
| 3,5-Br$_2$ | CF$_3$ | H | CH$_2$(D-22a) |
| 3,5-Br$_2$ | CF$_3$ | C(O)CH$_3$ | CH$_2$(D-22a) |
| 3,5-Br$_2$ | CF$_3$ | C(O)Et | CH$_2$(D-22a) |
| 3,5-Br$_2$ | CF$_3$ | H | CH$_2$(D-28a) |
| 3,5-Br$_2$ | CF$_3$ | H | CH$_2$(D-29b)CH$_3$ |
| 3,5-Br$_2$ | CF$_3$ | H | CH$_2$(D-34a) |
| 3,5-Br$_2$ | CF$_3$ | H | CH$_2$(D-35a) |
| 3,5-Br$_2$ | CF$_3$ | H | CH$_2$(D-38a) |
| 3,5-Br$_2$ | CF$_3$ | H | CH$_2$(D-47a) |
| 3,5-Br$_2$ | CF$_3$ | Et | CH$_2$(D-47a) |
| 3,5-Br$_2$ | CF$_3$ | CH$_2$OCH$_3$ | CH$_2$(D-47a) |
| 3,5-Br$_2$ | CF$_3$ | CH$_2$CN | CH$_2$(D-47a) |
| 3,5-Br$_2$ | CF$_3$ | CH$_2$C≡CH | CH$_2$(D-47a) |
| 3,5-Br$_2$ | CF$_3$ | C(O)CH$_3$ | CH$_2$(D-47a) |
| 3,5-Br$_2$ | CF$_3$ | C(O)Et | CH$_2$(D-47a) |
| 3,5-Br$_2$ | CF$_3$ | C(O)Pr-n | CH$_2$(D-47a) |
| 3,5-Br$_2$ | CF$_3$ | C(O)Pr-i | CH$_2$(D-47a) |
| 3,5-Br$_2$ | CF$_3$ | C(O)Pr-c | CH$_2$(D-47a) |
| 3,5-Br$_2$ | CF$_3$ | C(O)Bu-t | CH$_2$(D-47a) |
| 3,5-Br$_2$ | CF$_3$ | C(O)CH$_2$OCH$_3$ | CH$_2$(D-47a) |
| 3,5-Br$_2$ | CF$_3$ | C(O)CH=CH$_2$ | CH$_2$(D-47a) |
| 3,5-Br$_2$ | CF$_3$ | C(O)OCH$_3$ | CH$_2$(D-47a) |
| 3,5-Br$_2$ | CF$_3$ | C(O)OEt | CH$_2$(D-47a) |
| 3,5-Br$_2$ | CF$_3$ | C(O)OCH$_2$CH$_2$OCH$_3$ | CH$_2$(D-47a) |
| 3,5-Br$_2$ | CF$_3$ | C(O)OCH$_2$CH=CH$_2$ | CH$_2$(D-47a) |
| 3,5-Br$_2$ | CF$_3$ | H | CH(CH$_3$)(D-47a) |
| 3,5-Br$_2$ | CF$_3$ | H | CH$_2$(D-50a) |
| 3,5-Br$_2$ | CF$_3$ | H | NHCH$_2$CF$_3$ |
| 3,5-Br$_2$ | CF$_3$ | H | NHC(O)OCH$_3$ |
| 3,5-Br$_2$ | CF$_3$ | H | N(CH$_3$)Ph |
| 3,5-Br$_2$ | CF$_3$ | H | N(CH$_2$CH=CH$_2$)Ph |
| 3,5-Br$_2$ | CF$_3$ | H | N(CH$_2$C≡CH)Ph |
| 3,5-Br$_2$ | CF$_3$ | H | N(CH$_3$)(D-47a) |
| 3,5-Br$_2$ | CF$_3$ | H | NH(D-50a) |
| 3,5-Br$_2$ | CF$_3$ | CH$_3$ | NH(D-50a) |
| 3,5-Br$_2$ | CF$_3$ | H | N(CH$_3$)(D-50a) |
| 3,5-Br$_2$ | CF$_3$ | H | N(Et)(D-50a) |
| 3,5-Br$_2$ | CF$_3$ | C(O)OCH$_3$ | C(O)N(CH$_3$)$_2$ |
| 3,5-Br$_2$ | CF$_3$ | H | C(O)NHEt |
| 3,5-Br$_2$ | CF$_3$ | CH$_3$ | C(O)NHEt |
| 3,5-Br$_2$ | CF$_3$ | H | C(O)NHCH$_2$Cl |
| 3,5-Br$_2$ | CF$_3$ | H | C(O)NHCH$_2$CF$_3$ |
| 3,5-Br$_2$ | CF$_3$ | H | C(O)NHCH$_2$(Ph-4-F) |
| 3,5-Br$_2$ | CF$_3$ | H | C(S)NHCH$_3$ |
| 3,5-Br$_2$ | CF$_3$ | H | Ph-4-F |
| 3,5-Br$_2$ | CF$_3$ | H | Ph-4-CN |
| 3,5-Br$_2$ | CF$_3$ | H | Ph-2,4-F$_2$ |
| 3,5-Br$_2$ | CF$_3$ | H | Ph-2,6-F$_2$ |
| 3,5-Br$_2$ | CF$_3$ | H | Ph-2,4,6-F$_3$ |
| 3,5-Br$_2$ | CF$_3$ | H | (D-13b)CH$_3$ |
| 3,5-Br$_2$ | CF$_3$ | H | (D-15a)CH$_3$ |
| 3,5-Br$_2$ | CF$_3$ | H | D-21a |
| 3,5-Br$_2$ | CF$_3$ | H | (D-47d)Cl |
| 3,5-Br$_2$ | CF$_3$ | H | (D-47d)Br |
| 3,5-Br$_2$ | CF$_3$ | H | (D-47d)CN |
| 3,5-Br$_2$ | CF$_3$ | H | (D-47e)Br |
| 3,5-Br$_2$ | CF$_3$ | H | (D-48e)Cl |
| 3,5-Br$_2$ | CF$_3$ | H | D-50a |
| 3,5-Br$_2$ | CF$_3$ | H | (D-50c)Cl |
| 3,5-Br$_2$ | CF$_3$ | H | (D-50c)Br |
| 3,5-Br$_2$ | CF$_3$ | H | D-51a |
| 3,5-Br$_2$ | CF$_3$ | H | D-52a |
| 3,5-Br$_2$ | CF$_3$ | H | D-53a |
| 3,5-Br$_2$ | CF$_3$ | H | (D-54b)Cl |
| 3,5-Br$_2$ | CF$_2$Cl | H | c-Pr |
| 3,5-Br$_2$ | CF$_2$Cl | H | CH$_2$Pr-c |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Br$_2$ | CF$_2$Cl | H | c-Bu |
| 3,5-Br$_2$ | CF$_2$Cl | H | CH$_2$CF$_3$ |
| 3,5-Br$_2$ | CF$_2$Cl | C(O)CH$_3$ | CH$_2$CF$_3$ |
| 3,5-Br$_2$ | CF$_2$Cl | H | CH$_2$CH$_2$CF$_3$ |
| 3,5-Br$_2$ | CF$_2$Cl | H | CH$_2$OCH$_3$ |
| 3,5-Br$_2$ | CF$_2$Cl | H | CH$_2$OEt |
| 3,5-Br$_2$ | CF$_2$Cl | C(O)CH$_3$ | CH$_2$OEt |
| 3,5-Br$_2$ | CF$_2$Cl | H | CH$_2$OCH$_2$CF$_3$ |
| 3,5-Br$_2$ | CF$_2$Cl | C(O)CH$_3$ | CH$_2$OCH$_2$CF$_3$ |
| 3,5-Br$_2$ | CF$_2$Cl | H | CH$_2$CH$_2$OCH$_3$ |
| 3,5-Br$_2$ | CF$_2$Cl | H | CH$_2$(E-10a) |
| 3,5-Br$_2$ | CF$_2$Cl | H | E-4a |
| 3,5-Br$_2$ | CF$_2$Cl | H | E-5a(R) |
| 3,5-Br$_2$ | CF$_2$Cl | H | CH$_2$CH=NOCH$_3$ |
| 3,5-Br$_2$ | CF$_2$Cl | H | CH$_2$C(O)NHCH$_2$CH$_2$Cl |
| 3,5-Br$_2$ | CF$_2$Cl | H | CH$_2$C(O)NHCH$_2$CF$_3$ |
| 3,5-Br$_2$ | CF$_2$Cl | H | CH(CH$_3$)C(O)NHEt |
| 3,5-Br$_2$ | CF$_2$Cl | H | CH(CH$_3$)C(O)NHCH$_2$CF$_3$ |
| 3,5-Br$_2$ | CF$_2$Cl | H | CH(CH$_3$)C(O)NHCH$_2$CF$_3$(D) |
| 3,5-Br$_2$ | CF$_2$Cl | H | CH$_2$CH=CH$_2$ |
| 3,5-Br$_2$ | CF$_2$Cl | H | CH$_2$CCl=CH$_2$ |
| 3,5-Br$_2$ | CF$_2$Cl | H | CH(CH$_3$)Ph(R) |
| 3,5-Br$_2$ | CF$_2$Cl | H | CH$_2$(Ph-4-NO$_2$) |
| 3,5-Br$_2$ | CF$_2$Cl | H | CH$_2$(Ph-4-CN) |
| 3,5-Br$_2$ | CF$_2$Cl | H | CH$_2$(D-17b)Cl |
| 3,5-Br$_2$ | CF$_2$Cl | H | CH$_2$(D-21a) |
| 3,5-Br$_2$ | CF$_2$Cl | H | CH$_2$(D-22a) |
| 3,5-Br$_2$ | CF$_2$Cl | C(O)CH$_3$ | CH$_2$(D-22a) |
| 3,5-Br$_2$ | CF$_2$Cl | C(O)Et | CH$_2$(D-22a) |
| 3,5-Br$_2$ | CF$_2$Cl | H | CH$_2$(D-47a) |
| 3,5-Br$_2$ | CF$_2$Cl | CH$_2$OCH$_3$ | CH$_2$(D-47a) |
| 3,5-Br$_2$ | CF$_2$Cl | CH$_2$CN | CH$_2$(D-47a) |
| 3,5-Br$_2$ | CF$_2$Cl | C(O)CH$_3$ | CH$_2$(D-47a) |
| 3,5-Br$_2$ | CF$_2$Cl | C(O)Et | CH$_2$(D-47a) |
| 3,5-Br$_2$ | CF$_2$Cl | C(O)Pr-c | CH$_2$(D-47a) |
| 3,5-Br$_2$ | CF$_2$Cl | C(O)OCH$_3$ | CH$_2$(D-47a) |
| 3,5-Br$_2$ | CF$_2$Cl | H | CH(CH$_3$)(D-47a) |
| 3,5-Br$_2$ | CF$_2$Cl | H | CH$_2$(D-50a) |
| 3,5-Br$_2$ | CF$_2$Cl | H | N(CH$_3$)Ph |
| 3,5-Br$_2$ | CF$_2$Cl | H | N(CH$_3$)(D-50a) |
| 3,5-Br$_2$ | CF$_2$Cl | C(O)OCH$_3$ | C(O)N(CH$_3$)$_2$ |
| 3,5-Br$_2$ | CF$_2$Cl | H | C(O)NHEt |
| 3,5-Br$_2$ | CF$_2$Cl | CH$_3$ | C(O)NHEt |
| 3,5-Br$_2$ | CF$_2$Cl | H | C(O)NHCH$_2$CH$_2$Cl |
| 3,5-Br$_2$ | CF$_2$Cl | H | C(O)NHCH$_2$(Ph-4-F) |
| 3,5-Br$_2$ | CF$_2$Cl | H | Ph-4-CN |
| 3,5-Br$_2$ | CF$_2$Cl | H | Ph-2,4-F$_2$ |
| 3,5-Br$_2$ | CF$_2$Cl | H | (D-15a)CH$_3$ |
| 3,5-Br$_2$ | CF$_2$Cl | H | (D-47d)CN |
| 3,5-Br$_2$ | CF$_2$Cl | H | (D-47e)Br |
| 3,5-Br$_2$ | CF$_2$Cl | H | D-50a |
| 3,5-Br$_2$ | CF$_2$Cl | H | (D-50c)Cl |
| 3,5-Br$_2$ | CF$_2$Cl | H | (D-50c)Br |
| 3,5-Br$_2$ | CF$_2$Cl | H | D-52a |
| 3,5-Br$_2$ | CF$_2$Cl | H | D-53a |
| 3,5-Br$_2$ | CF$_2$Br | H | CH$_2$CF$_3$ |
| 3,5-Br$_2$ | CF$_2$Br | H | CH$_2$OCH$_2$CF$_3$ |
| 3,5-Br$_2$ | CF$_2$Br | H | E-4a |
| 3,5-Br$_2$ | CF$_2$Br | H | CH$_2$C(O)NHCH$_2$CF$_3$ |
| 3,5-Br$_2$ | CF$_2$Br | H | CH(CH$_3$)C(O)NHCH$_2$CF$_3$(D) |
| 3,5-Br$_2$ | CF$_2$Br | H | CH$_2$(D-22a) |
| 3,5-Br$_2$ | CF$_2$Br | H | CH$_2$(D-47a) |
| 3,5-Br$_2$ | CF$_2$Br | C(O)OCH$_3$ | CH$_2$(D-47a) |
| 3,5-Br$_2$ | CF$_2$Br | H | N(CH$_3$)Ph |
| 3,5-Br$_2$ | CF$_2$Br | H | (D-50c)Cl |
| 3,5-Br$_2$ | CF$_2$CHF$_2$ | H | CH$_2$CF$_3$ |
| 3,5-Br$_2$ | CF$_2$CHF$_2$ | H | CH$_2$OCH$_2$CF$_3$ |
| 3,5-Br$_2$ | CF$_2$CHF$_2$ | H | E-4a |
| 3,5-Br$_2$ | CF$_2$CHF$_2$ | H | CH$_2$C(O)NHCH$_2$CF$_3$ |
| 3,5-Br$_2$ | CF$_2$CHF$_2$ | H | CH(CH$_3$)C(O)NHCH$_2$CF$_3$(D) |
| 3,5-Br$_2$ | CF$_2$CHF$_2$ | H | CH$_2$(D-22a) |
| 3,5-Br$_2$ | CF$_2$CHF$_2$ | H | CH$_2$(D-47a) |
| 3,5-Br$_2$ | CF$_2$CHF$_2$ | C(O)OCH$_3$ | CH$_2$(D-47a) |
| 3,5-Br$_2$ | CF$_2$CHF$_2$ | H | N(CH$_3$)Ph |
| 3,5-Br$_2$ | CF$_2$CHF$_2$ | H | (D-50c)Cl |
| 3,5-Br$_2$ | CF$_2$CF$_3$ | H | CH$_2$(D-22a) |
| 3,5-Br$_2$ | CF$_2$OCH$_3$ | H | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Br$_2$ | CF$_2$SCH$_3$ | C(O)OCH$_3$ | CH$_2$(D-47a) |
| 3,5-Br$_2$ | T-3 | H | N(CH$_3$)Ph |
| 3-F-5-I | CF$_3$ | H | c-Bu |
| 3-F-5-I | CF$_3$ | H | CH$_2$CF$_3$ |
| 3-F-5-I | CF$_3$ | H | CH$_2$OEt |
| 3-F-5-I | CF$_3$ | H | CH$_2$OCH$_2$CF$_3$ |
| 3-F-5-I | CF$_3$ | C(O)CH$_3$ | CH$_2$OCH$_2$CF$_3$ |
| 3-F-5-I | CF$_3$ | H | CH$_2$CH$_2$OCH$_3$ |
| 3-F-5-I | CF$_3$ | H | CH$_2$(E-10a) |
| 3-F-5-I | CF$_3$ | H | E-4a |
| 3-F-5-I | CF$_3$ | H | CH$_2$C(O)NHCH$_2$CH$_2$Cl |
| 3-F-5-I | CF$_3$ | H | CH$_2$C(O)NHCH$_2$CF$_3$ |
| 3-F-5-I | CF$_3$ | H | CH(CH$_3$)C(O)NHCH$_2$CF$_3$ |
| 3-F-5-I | CF$_3$ | H | CH(CH$_3$)C(O)NHCH$_2$CF$_3$(D) |
| 3-F-5-I | CF$_3$ | H | CH(CH$_3$)Ph(R) |
| 3-F-5-I | CF$_3$ | H | CH$_2$(D-22a) |
| 3-F-5-I | CF$_3$ | C(O)CH$_3$ | CH$_2$(D-22a) |
| 3-F-5-I | CF$_3$ | C(O)Et | CH$_2$(D-22a) |
| 3-F-5-I | CF$_3$ | H | CH$_2$(D-47a) |
| 3-F-5-I | CF$_3$ | CH$_2$OCH$_3$ | CH$_2$(D-47a) |
| 3-F-5-I | CF$_3$ | CH$_2$CN | CH$_2$(D-47a) |
| 3-F-5-I | CF$_3$ | C(O)CH$_3$ | CH$_2$(D-47a) |
| 3-F-5-I | CF$_3$ | C(O)Et | CH$_2$(D-47a) |
| 3-F-5-I | CF$_3$ | C(O)OCH$_3$ | CH$_2$(D-47a) |
| 3-F-5-I | CF$_3$ | H | N(CH$_3$)Ph |
| 3-F-5-I | CF$_3$ | H | N(CH$_3$)(D-50a) |
| 3-F-5-I | CF$_3$ | H | C(O)NHCH$_2$CF$_3$ |
| 3-F-5-I | CF$_3$ | H | Ph-2,4-F$_2$ |
| 3-F-5-I | CF$_3$ | H | (D-50c)Cl |
| 3-F-5-I | CF$_3$ | H | D-52a |
| 3-F-5-I | CF$_2$Cl | H | CH$_2$CF$_3$ |
| 3-F-5-I | CF$_2$Cl | H | CH$_2$OCH$_2$CF$_3$ |
| 3-F-5-I | CF$_2$Cl | H | E-4a |
| 3-F-5-I | CF$_2$Cl | H | CH$_2$C(O)NHCH$_2$CF$_3$ |
| 3-F-5-I | CF$_2$Cl | H | CH(CH$_3$)C(O)NHCH$_2$CF$_3$(D) |
| 3-F-5-I | CF$_2$Cl | H | CH$_2$(D-22a) |
| 3-F-5-I | CF$_2$Cl | H | CH$_2$(D-47a) |
| 3-F-5-I | CF$_2$Cl | C(O)OCH$_3$ | CH$_2$(D-47a) |
| 3-F-5-I | CF$_2$Cl | H | N(CH$_3$)Ph |
| 3-F-5-I | CF$_2$Cl | H | (D-50c)Cl |
| 3-Cl-5-I | CHF$_2$ | H | (D-50c)Cl |
| 3-Cl-5-I | CF$_3$ | H | c-Pr |
| 3-Cl-5-I | CF$_3$ | H | CH$_2$Pr-c |
| 3-Cl-5-I | CF$_3$ | H | c-Bu |
| 3-Cl-5-I | CF$_3$ | H | CH$_2$CF$_3$ |
| 3-Cl-5-I | CF$_3$ | C(O)CH$_3$ | CH$_2$CF$_3$ |
| 3-Cl-5-I | CF$_3$ | H | CH$_2$CH$_2$CF$_3$ |
| 3-Cl-5-I | CF$_3$ | H | CH$_2$OCH$_3$ |
| 3-Cl-5-I | CF$_3$ | H | CH$_2$OEt |
| 3-Cl-5-I | CF$_3$ | C(O)CH$_3$ | CH$_2$OEt |
| 3-Cl-5-I | CF$_3$ | H | CH$_2$OCH$_2$CF$_3$ |
| 3-Cl-5-I | CF$_3$ | C(O)CH$_3$ | CH$_2$OCH$_2$CF$_3$ |
| 3-Cl-5-I | CF$_3$ | H | CH$_2$CH$_2$OCH$_3$ |
| 3-Cl-5-I | CF$_3$ | H | CH$_2$(E-10a) |
| 3-Cl-5-I | CF$_3$ | H | E-4a |
| 3-Cl-5-I | CF$_3$ | H | E-5a(R) |
| 3-Cl-5-I | CF$_3$ | H | CH$_2$CH=NOCH$_3$ |
| 3-Cl-5-I | CF$_3$ | H | CH$_2$C(O)NHCH$_2$CH$_2$Cl |
| 3-Cl-5-I | CF$_3$ | H | CH$_2$C(O)NHCH$_2$CF$_3$ |
| 3-Cl-5-I | CF$_3$ | H | CH(CH$_3$)C(O)NHEt |
| 3-Cl-5-I | CF$_3$ | H | CH(CH$_3$)C(O)NHCH$_2$CF$_3$ |
| 3-Cl-5-I | CF$_3$ | H | CH(CH$_3$)C(O)NHCH$_2$CF$_3$(D) |
| 3-Cl-5-I | CF$_3$ | H | CH$_2$CH=CH$_2$ |
| 3-Cl-5-I | CF$_3$ | H | CH$_2$CCl=CH$_2$ |
| 3-Cl-5-I | CF$_3$ | H | CH(CH$_3$)Ph(R) |
| 3-Cl-5-I | CF$_3$ | H | CH$_2$(Ph-4-NO$_2$) |
| 3-Cl-5-I | CF$_3$ | H | CH$_2$(Ph-4-CN) |
| 3-Cl-5-I | CF$_3$ | H | CH$_2$(D-17b)Cl |
| 3-Cl-5-I | CF$_3$ | H | CH$_2$(D-21a) |
| 3-Cl-5-I | CF$_3$ | H | CH$_2$(D-22a) |
| 3-Cl-5-I | CF$_3$ | C(O)CH$_3$ | CH$_2$(D-22a) |
| 3-Cl-5-I | CF$_3$ | C(O)Et | CH$_2$(D-22a) |
| 3-Cl-5-I | CF$_3$ | H | CH$_2$(D-47a) |
| 3-Cl-5-I | CF$_3$ | CH$_2$OCH$_3$ | CH$_2$(D-47a) |
| 3-Cl-5-I | CF$_3$ | CH$_2$CN | CH$_2$(D-47a) |
| 3-Cl-5-I | CF$_3$ | C(O)CH$_3$ | CH$_2$(D-47a) |
| 3-Cl-5-I | CF$_3$ | C(O)Et | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-I | $CF_3$ | C(O)Pr-c | $CH_2$(D-47a) |
| 3-Cl-5-I | $CF_3$ | C(O)OCH$_3$ | $CH_2$(D-47a) |
| 3-Cl-5-I | $CF_3$ | H | CH(CH$_3$)(D-47a) |
| 3-Cl-5-I | $CF_3$ | H | $CH_2$(D-50a) |
| 3-Cl-5-I | $CF_3$ | H | N(CH$_3$)Ph |
| 3-Cl-5-I | $CF_3$ | H | N(CH$_3$)(D-50a) |
| 3-Cl-5-I | $CF_3$ | C(O)OCH$_3$ | C(O)N(CH$_3$)$_2$ |
| 3-Cl-5-I | $CF_3$ | H | C(O)NHEt |
| 3-Cl-5-I | $CF_3$ | CH$_3$ | C(O)NHEt |
| 3-Cl-5-I | $CF_3$ | H | C(O)NHCH$_2$CH$_2$Cl |
| 3-Cl-5-I | $CF_3$ | H | C(O)NHCH$_2$(Ph-4-F) |
| 3-Cl-5-I | $CF_3$ | H | Ph-4-CN |
| 3-Cl-5-I | $CF_3$ | H | Ph-2,4-F$_2$ |
| 3-Cl-5-I | $CF_3$ | H | (D-15a)CH$_3$ |
| 3-Cl-5-I | $CF_3$ | H | (D-47d)CN |
| 3-Cl-5-I | $CF_3$ | H | (D-47e)Br |
| 3-Cl-5-I | $CF_3$ | H | D-50a |
| 3-Cl-5-I | $CF_3$ | H | (D-50c)Cl |
| 3-Cl-5-I | $CF_3$ | H | (D-50c)Br |
| 3-Cl-5-I | $CF_3$ | H | D-52a |
| 3-Cl-5-I | $CF_3$ | H | D-53a |
| 3-Cl-5-I | $CF_2Cl$ | H | $CH_2CF_3$ |
| 3-Cl-5-I | $CF_2Cl$ | C(O)CH$_3$ | $CH_2CF_3$ |
| 3-Cl-5-I | $CF_2Cl$ | H | $CH_2OCH_2CF_3$ |
| 3-Cl-5-I | $CF_2Cl$ | H | E-4a |
| 3-Cl-5-I | $CF_2Cl$ | H | $CH_2C(O)NHCH_2CF_3$ |
| 3-Cl-5-I | $CF_2Cl$ | H | CH(CH$_3$)C(O)NHCH$_2$CF$_3$(D) |
| 3-Cl-5-I | $CF_2Cl$ | H | CH(CH$_3$)Ph(R) |
| 3-Cl-5-I | $CF_2Cl$ | H | $CH_2$(D-22a) |
| 3-Cl-5-I | $CF_2Cl$ | H | $CH_2$(D-47a) |
| 3-Cl-5-I | $CF_2Cl$ | CH$_2$CN | $CH_2$(D-47a) |
| 3-Cl-5-I | $CF_2Cl$ | C(O)Et | $CH_2$(D-47a) |
| 3-Cl-5-I | $CF_2Cl$ | C(O)OCH$_3$ | $CH_2$(D-47a) |
| 3-Cl-5-I | $CF_2Cl$ | H | N(CH$_3$)Ph |
| 3-Cl-5-I | $CF_2Cl$ | H | (D-50c)Cl |
| 3-Cl-5-I | $CF_2Cl$ | H | D-52a |
| 3-Cl-5-I | $CF_2Br$ | H | $CH_2CF_3$ |
| 3-Cl-5-I | $CF_2CHF_2$ | H | $CH_2OCH_2CF_3$ |
| 3,5-I$_2$ | $CF_3$ | H | $CH_2CF_3$ |
| 3,5-I$_2$ | $CF_3$ | H | $CH_2OCH_2CF_3$ |
| 3,5-I$_2$ | $CF_3$ | H | E-4a |
| 3,5-I$_2$ | $CF_3$ | H | $CH_2C(O)NHCH_2CF_3$ |
| 3,5-I$_2$ | $CF_3$ | H | CH(CH$_3$)C(O)NHCH$_2$CF$_3$(D) |
| 3,5-I$_2$ | $CF_3$ | H | $CH_2$(D-22a) |
| 3,5-I$_2$ | $CF_3$ | H | $CH_2$(D-47a) |
| 3,5-I$_2$ | $CF_3$ | C(O)OCH$_3$ | $CH_2$(D-47a) |
| 3,5-I$_2$ | $CF_3$ | H | N(CH$_3$)Ph |
| 3,5-I$_2$ | $CF_3$ | H | (D-50c)Cl |
| 3-CH$_3$-4-F | $CF_3$ | H | $CH_2CF_3$ |
| 3-CH$_3$-4-F | $CF_3$ | H | E-4a |
| 3-CH$_3$-4-F | $CF_3$ | H | $CH_2$Ph |
| 3-F-4-CH$_3$ | $CF_3$ | H | $CH_2C(O)NHCH_2CF_3$ |
| 2-F-5-CH$_3$ | $CF_3$ | H | $CH_2$(D-22a) |
| 3-F-5-CH$_3$ | $CF_3$ | H | $CH_2$(D-47a) |
| 3-CH$_3$-4-Cl | $CF_3$ | C(O)OCH$_3$ | $CH_2$(D-47a) |
| 3-Cl-4-CH$_3$ | $CF_3$ | H | N(CH$_3$)Ph |
| 3-Cl-5-CH$_3$ | $CF_3$ | H | $CH_2CF_3$ |
| 3-Cl-5-CH$_3$ | $CF_3$ | C(O)CH$_3$ | $CH_2CF_3$ |
| 3-Cl-5-CH$_3$ | $CF_3$ | H | $CH_2OCH_2CF_3$ |
| 3-Cl-5-CH$_3$ | $CF_3$ | H | E-4a |
| 3-Cl-5-CH$_3$ | $CF_3$ | H | $CH_2C(O)NHCH_2CF_3$ |
| 3-Cl-5-CH$_3$ | $CF_3$ | H | CH(CH$_3$)C(O)NHCH$_2$CF$_3$(D) |
| 3-Cl-5-CH$_3$ | $CF_3$ | H | CH(CH$_3$)Ph(R) |
| 3-Cl-5-CH$_3$ | $CF_3$ | H | $CH_2$(D-22a) |
| 3-Cl-5-CH$_3$ | $CF_3$ | H | $CH_2$(D-47a) |
| 3-Cl-5-CH$_3$ | $CF_3$ | CH$_2$CN | $CH_2$(D-47a) |
| 3-Cl-5-CH$_3$ | $CF_3$ | C(O)Et | $CH_2$(D-47a) |
| 3-Cl-5-CH$_3$ | $CF_3$ | C(O)OCH$_3$ | $CH_2$(D-47a) |
| 3-Cl-5-CH$_3$ | $CF_3$ | H | N(CH$_3$)Ph |
| 3-Cl-5-CH$_3$ | $CF_3$ | H | (D-50c)Cl |
| 3-Cl-5-CH$_3$ | $CF_3$ | H | D-52a |
| 3-Cl-5-CH$_3$ | $CF_2Cl$ | H | $CH_2CF_3$ |
| 3-Cl-5-CH$_3$ | $CF_2Cl$ | H | E-4a |
| 3-Cl-5-CH$_3$ | $CF_2Cl$ | H | $CH_2C(O)NHCH_2CF_3$ |
| 3-Cl-5-CH$_3$ | $CF_2Cl$ | H | $CH_2$(D-22a) |
| 3-Cl-5-CH$_3$ | $CF_2Cl$ | H | $CH_2$(D-47a) |
| 3-Cl-5-CH$_3$ | $CF_2Cl$ | H | (D-50c)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-CH$_3$-4-Br | CF$_3$ | H | (D-50c)Cl |
| 3-Br-5-CH$_3$ | CF$_3$ | H | CH$_2$CF$_3$ |
| 3-Br-5-CH$_3$ | CF$_3$ | C(O)CH$_3$ | CH$_2$CF$_3$ |
| 3-Br-5-CH$_3$ | CF$_3$ | H | CH$_2$OCH$_2$CF$_3$ |
| 3-Br-5-CH$_3$ | CF$_3$ | H | E-4a |
| 3-Br-5-CH$_3$ | CF$_3$ | H | CH$_2$C(O)NHCH$_2$CF$_3$ |
| 3-Br-5-CH$_3$ | CF$_3$ | H | CH(CH$_3$)C(O)NHCH$_2$CF$_3$(D) |
| 3-Br-5-CH$_3$ | CF$_3$ | H | CH(CH$_3$)Ph(R) |
| 3-Br-5-CH$_3$ | CF$_3$ | H | CH$_2$(D-22a) |
| 3-Br-5-CH$_3$ | CF$_3$ | H | CH$_2$(D-47a) |
| 3-Br-5-CH$_3$ | CF$_3$ | CH$_2$CN | CH$_2$(D-47a) |
| 3-Br-5-CH$_3$ | CF$_3$ | C(O)Et | CH$_2$(D-47a) |
| 3-Br-5-CH$_3$ | CF$_3$ | C(O)OCH$_3$ | CH$_2$(D-47a) |
| 3-Br-5-CH$_3$ | CF$_3$ | H | N(CH$_3$)Ph |
| 3-Br-5-CH$_3$ | CF$_3$ | H | (D-50c)Cl |
| 3-Br-5-CH$_3$ | CF$_3$ | H | D-52a |
| 3-Br-5-CH$_3$ | CF$_2$Cl | H | CH$_2$CF$_3$ |
| 2,4-(CH$_3$)$_2$ | CF$_3$ | H | CH$_2$OCH$_2$CF$_3$ |
| 2,6-(CH$_3$)$_2$ | CF$_3$ | H | E-4a |
| 3,4-(CH$_3$)$_2$ | CF$_3$ | H | CH$_2$C(O)NHCH$_2$CF$_3$ |
| 3,5-(CH$_3$)$_2$ | CF$_3$ | H | CH$_2$CF$_3$ |
| 3,5-(CH$_3$)$_2$ | CF$_3$ | H | CH$_2$OCH$_2$CF$_3$ |
| 3,5-(CH$_3$)$_2$ | CF$_3$ | H | E-4a |
| 3,5-(CH$_3$)$_2$ | CF$_3$ | H | CH$_2$C(O)NHCH$_2$CF$_3$ |
| 3,5-(CH$_3$)$_2$ | CF$_3$ | H | CH(CH$_3$)C(O)NHCH$_2$CF$_3$(D) |
| 3,5-(CH$_3$)$_2$ | CF$_3$ | H | CH$_2$(D-22a) |
| 3,5-(CH$_3$)$_2$ | CF$_3$ | H | CH$_2$(D-47a) |
| 3,5-(CH$_3$)$_2$ | CF$_3$ | C(O)OCH$_3$ | CH$_2$(D-47a) |
| 3,5-(CH$_3$)$_2$ | CF$_3$ | H | N(CH$_3$)Ph |
| 3,5-(CH$_3$)$_2$ | CF$_3$ | H | (D-50c)Cl |
| 3-Br-5-Et | CF$_3$ | H | CH$_2$(D-22a) |
| 3-CH$_3$-5-Et | CF$_3$ | H | CH$_2$(D-47a) |
| 3,5-(Et)$_2$ | CF$_3$ | C(O)OCH$_3$ | CH$_2$(D-47a) |
| 3-Cl-5-Pr-i | CF$_3$ | H | N(CH$_3$)Ph |
| 3-Br-5-Pr-i | CF$_3$ | H | (D-50c)Cl |
| 3-CH$_3$-5-Pr-i | CF$_3$ | H | CH$_2$CF$_3$ |
| 3,5-(Pr-i)$_2$ | CF$_3$ | H | CH$_2$OCH$_2$CF$_3$ |
| 3-CH$_3$-5-Bu-n | CF$_3$ | H | E-4a |
| 3,5-(Bu-s)$_2$ | CF$_3$ | H | CH$_2$C(O)NHCH$_2$CF$_3$ |
| 3-Cl-5-Bu-t | CF$_3$ | H | CH$_2$(D-22a) |
| 3-Br-5-Bu-t | CF$_3$ | H | CH$_2$(D-47a) |
| 3-CH$_3$-5-Bu-t | CF$_3$ | C(O)OCH$_3$ | CH$_2$(D-47a) |
| 3,5-(Bu-t)$_2$ | CF$_3$ | H | N(CH$_3$)Ph |
| 2-CF$_3$-4-F | CF$_3$ | H | (D-50c)Cl |
| 2-CF$_3$-5-F | CF$_3$ | H | CH$_2$CF$_3$ |
| 2-F-3-CF$_3$ | CF$_3$ | H | CH$_2$OCH$_2$CF$_3$ |
| 3-CF$_3$-4-F | CHF$_2$ | H | E-4a |
| 3-CF$_3$-4-F | CF$_3$ | H | c-Pr |
| 3-CF$_3$-4-F | CF$_3$ | H | CH$_2$Pr-c |
| 3-CF$_3$-4-F | CF$_3$ | H | c-Bu |
| 3-CF$_3$-4-F | CF$_3$ | H | CH$_2$CF$_3$ |
| 3-CF$_3$-4-F | CF$_3$ | C(O)CH$_3$ | CH$_2$CF$_3$ |
| 3-CF$_3$-4-F | CF$_3$ | H | CH$_2$CH$_2$CF$_3$ |
| 3-CF$_3$-4-F | CF$_3$ | H | CH$_2$OCH$_3$ |
| 3-CF$_3$-4-F | CF$_3$ | H | CH$_2$OEt |
| 3-CF$_3$-4-F | CF$_3$ | C(O)CH$_3$ | CH$_2$OEt |
| 3-CF$_3$-4-F | CF$_3$ | H | CH$_2$OCH$_2$CF$_3$ |
| 3-CF$_3$-4-F | CF$_3$ | C(O)CH$_3$ | CH$_2$OCH$_2$CF$_3$ |
| 3-CF$_3$-4-F | CF$_3$ | H | CH$_2$CH$_2$OCH$_3$ |
| 3-CF$_3$-4-F | CF$_3$ | H | CH$_2$(E-10a) |
| 3-CF$_3$-4-F | CF$_3$ | H | E-4a |
| 3-CF$_3$-4-F | CF$_3$ | H | E-5a(R) |
| 3-CF$_3$-4-F | CF$_3$ | H | CH$_2$CH=NOCH$_3$ |
| 3-CF$_3$-4-F | CF$_3$ | H | CH$_2$C(O)NHCH$_2$Cl |
| 3-CF$_3$-4-F | CF$_3$ | H | CH$_2$C(O)NHCH$_2$CF$_3$ |
| 3-CF$_3$-4-F | CF$_3$ | H | CH(CH$_3$)C(O)NHEt |
| 3-CF$_3$-4-F | CF$_3$ | H | CH(CH$_3$)C(O)NHCH$_2$CF$_3$ |
| 3-CF$_3$-4-F | CF$_3$ | H | CH(CH$_3$)C(O)NHCH$_2$CF$_3$(D) |
| 3-CF$_3$-4-F | CF$_3$ | H | CH$_2$CH=CH$_2$ |
| 3-CF$_3$-4-F | CF$_3$ | H | CH$_2$CCl=CH$_2$ |
| 3-CF$_3$-4-F | CF$_3$ | H | CH(CH$_3$)Ph(R) |
| 3-CF$_3$-4-F | CF$_3$ | H | CH$_2$(Ph-4-NO$_2$) |
| 3-CF$_3$-4-F | CF$_3$ | H | CH$_2$(Ph-4-CN) |
| 3-CF$_3$-4-F | CF$_3$ | H | CH$_2$(D-17b)Cl |
| 3-CF$_3$-4-F | CF$_3$ | H | CH$_2$(D-21a) |
| 3-CF$_3$-4-F | CF$_3$ | H | CH$_2$(D-22a) |
| 3-CF$_3$-4-F | CF$_3$ | C(O)CH$_3$ | CH$_2$(D-22a) |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-CF$_3$-4-F | CF$_3$ | C(O)Et | CH$_2$(D-22a) |
| 3-CF$_3$-4-F | CF$_3$ | H | CH$_2$(D-47a) |
| 3-CF$_3$-4-F | CF$_3$ | CH$_2$OCH$_3$ | CH$_2$(D-47a) |
| 3-CF$_3$-4-F | CF$_3$ | CH$_2$CN | CH$_2$(D-47a) |
| 3-CF$_3$-4-F | CF$_3$ | C(O)CH$_3$ | CH$_2$(D-47a) |
| 3-CF$_3$-4-F | CF$_3$ | C(O)Et | CH$_2$(D-47a) |
| 3-CF$_3$-4-F | CF$_3$ | C(O)Pr-c | CH$_2$(D-47a) |
| 3-CF$_3$-4-F | CF$_3$ | C(O)OCH$_3$ | CH$_2$(D-47a) |
| 3-CF$_3$-4-F | CF$_3$ | H | CH(CH$_3$)(D-47a) |
| 3-CF$_3$-4-F | CF$_3$ | H | CH$_2$(D-50a) |
| 3-CF$_3$-4-F | CF$_3$ | H | N(CH$_3$)Ph |
| 3-CF$_3$-4-F | CF$_3$ | H | N(CH$_3$)(D-50a) |
| 3-CF$_3$-4-F | CF$_3$ | C(O)OCH$_3$ | C(O)N(CH$_3$)$_2$ |
| 3-CF$_3$-4-F | CF$_3$ | H | C(O)NHEt |
| 3-CF$_3$-4-F | CF$_3$ | CH$_3$ | C(O)NHEt |
| 3-CF$_3$-4-F | CF$_3$ | H | C(O)NHCH$_2$CH$_2$Cl |
| 3-CF$_3$-4-F | CF$_3$ | H | C(O)NHCH$_2$(Ph-4-F) |
| 3-CF$_3$-4-F | CF$_3$ | H | Ph-4-CN |
| 3-CF$_3$-4-F | CF$_3$ | H | Ph-2,4-F$_2$ |
| 3-CF$_3$-4-F | CF$_3$ | H | (D-15a)CH$_3$ |
| 3-CF$_3$-4-F | CF$_3$ | H | (D-47d)CN |
| 3-CF$_3$-4-F | CF$_3$ | H | (D-47e)Br |
| 3-CF$_3$-4-F | CF$_3$ | H | D-50a |
| 3-CF$_3$-4-F | CF$_3$ | H | (D-50c)Cl |
| 3-CF$_3$-4-F | CF$_3$ | H | (D-50c)Br |
| 3-CF$_3$-4-F | CF$_3$ | H | D-52a |
| 3-CF$_3$-4-F | CF$_3$ | H | D-53a |
| 3-CF$_3$-4-F | CF$_2$Cl | H | CH$_2$CF$_3$ |
| 3-CF$_3$-4-F | CF$_2$Cl | C(O)CH$_3$ | CH$_2$CF$_3$ |
| 3-CF$_3$-4-F | CF$_2$Cl | H | CH$_2$OCH$_2$CF$_3$ |
| 3-CF$_3$-4-F | CF$_2$Cl | H | E-4a |
| 3-CF$_3$-4-F | CF$_2$Cl | H | CH$_2$C(O)NHCH$_2$CF$_3$ |
| 3-CF$_3$-4-F | CF$_2$Cl | H | CH(CH$_3$)C(O)NHCH$_2$CF$_3$(D) |
| 3-CF$_3$-4-F | CF$_2$Cl | H | CH(CH$_3$)Ph(R) |
| 3-CF$_3$-4-F | CF$_2$Cl | H | CH$_2$(D-22a) |
| 3-CF$_3$-4-F | CF$_2$Cl | H | CH$_2$(D-47a) |
| 3-CF$_3$-4-F | CF$_2$Cl | CH$_2$CN | CH$_2$(D-47a) |
| 3-CF$_3$-4-F | CF$_2$Cl | C(O)Et | CH$_2$(D-47a) |
| 3-CF$_3$-4-F | CF$_2$Cl | C(O)OCH$_3$ | CH$_2$(D-47a) |
| 3-CF$_3$-4-F | CF$_2$Cl | H | N(CH$_3$)Ph |
| 3-CF$_3$-4-F | CF$_2$Cl | H | (D-50c)Cl |
| 3-CF$_3$-4-F | CF$_2$Cl | H | D-52a |
| 3-CF$_3$-4-F | CF$_2$Br | H | CH$_2$C(O)NHCH$_2$CF$_3$ |
| 3-CF$_3$-4-F | CF$_2$CHF$_2$ | H | CH$_2$(D-22a) |
| 2-F-4-CF$_3$ | CF$_3$ | H | CH$_2$(D-47a) |
| 3-F-4-CF$_3$ | CF$_3$ | C(O)OCH$_3$ | CH$_2$(D-47a) |
| 2-F-5-CF$_3$ | CF$_3$ | H | N(CH$_3$)Ph |
| 3-F-5-CF$_3$ | CHF$_2$ | H | (D-50c)Cl |
| 3-F-5-CF$_3$ | CF$_3$ | H | c-Pr |
| 3-F-5-CF$_3$ | CF$_3$ | H | CH$_2$Pr-c |
| 3-F-5-CF$_3$ | CF$_3$ | H | c-Bu |
| 3-F-5-CF$_3$ | CF$_3$ | H | CH$_2$CF$_3$ |
| 3-F-5-CF$_3$ | CF$_3$ | C(O)CH$_3$ | CH$_2$CF$_3$ |
| 3-F-5-CF$_3$ | CF$_3$ | H | CH$_2$CH$_2$CF$_3$ |
| 3-F-5-CF$_3$ | CF$_3$ | H | CH$_2$OCH$_3$ |
| 3-F-5-CF$_3$ | CF$_3$ | H | CH$_2$OEt |
| 3-F-5-CF$_3$ | CF$_3$ | C(O)CH$_3$ | CH$_2$OEt |
| 3-F-5-CF$_3$ | CF$_3$ | H | CH$_2$OCH$_2$CF$_3$ |
| 3-F-5-CF$_3$ | CF$_3$ | C(O)CH$_3$ | CH$_2$OCH$_2$CF$_3$ |
| 3-F-5-CF$_3$ | CF$_3$ | H | CH$_2$CH$_2$OCH$_3$ |
| 3-F-5-CF$_3$ | CF$_3$ | H | CH$_2$(E-10a) |
| 3-F-5-CF$_3$ | CF$_3$ | H | E-4a |
| 3-F-5-CF$_3$ | CF$_3$ | H | E-5a(R) |
| 3-F-5-CF$_3$ | CF$_3$ | H | CH$_2$CH=NOCH$_3$ |
| 3-F-5-CF$_3$ | CF$_3$ | H | CH$_2$C(O)NHCH$_2$CH$_2$Cl |
| 3-F-5-CF$_3$ | CF$_3$ | H | CH$_2$C(O)NHCH$_2$CF$_3$ |
| 3-F-5-CF$_3$ | CF$_3$ | H | CH(CH$_3$)C(O)NHEt |
| 3-F-5-CF$_3$ | CF$_3$ | H | CH(CH$_3$)C(O)NHCH$_2$CF$_3$ |
| 3-F-5-CF$_3$ | CF$_3$ | H | CH(CH$_3$)C(O)NHCH$_2$CF$_3$(D) |
| 3-F-5-CF$_3$ | CF$_3$ | H | CH$_2$CH=CH$_2$ |
| 3-F-5-CF$_3$ | CF$_3$ | H | CH$_2$CCl=CH$_2$ |
| 3-F-5-CF$_3$ | CF$_3$ | H | CH(CH$_3$)Ph(R) |
| 3-F-5-CF$_3$ | CF$_3$ | H | CH$_2$(Ph-4-NO$_2$) |
| 3-F-5-CF$_3$ | CF$_3$ | H | CH$_2$(Ph-4-CN) |
| 3-F-5-CF$_3$ | CF$_3$ | H | CH$_2$(D-17b)Cl |
| 3-F-5-CF$_3$ | CF$_3$ | H | CH$_2$(D-21a) |
| 3-F-5-CF$_3$ | CF$_3$ | H | CH$_2$(D-22a) |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-F-5-CF$_3$ | CF$_3$ | C(O)CH$_3$ | CH$_2$(D-22a) |
| 3-F-5-CF$_3$ | CF$_3$ | C(O)Et | CH$_2$(D-22a) |
| 3-F-5-CF$_3$ | CF$_3$ | H | CH$_2$(D-47a) |
| 3-F-5-CF$_3$ | CF$_3$ | CH$_2$OCH$_3$ | CH$_2$(D-47a) |
| 3-F-5-CF$_3$ | CF$_3$ | CH$_2$CN | CH$_2$(D-47a) |
| 3-F-5-CF$_3$ | CF$_3$ | C(O)CH$_3$ | CH$_2$(D-47a) |
| 3-F-5-CF$_3$ | CF$_3$ | C(O)Et | CH$_2$(D-47a) |
| 3-F-5-CF$_3$ | CF$_3$ | C(O)Pr-c | CH$_2$(D-47a) |
| 3-F-5-CF$_3$ | CF$_3$ | C(O)OCH$_3$ | CH$_2$(D-47a) |
| 3-F-5-CF$_3$ | CF$_3$ | H | CH(CH$_3$)(D-47a) |
| 3-F-5-CF$_3$ | CF$_3$ | H | CH$_2$(D-50a) |
| 3-F-5-CF$_3$ | CF$_3$ | H | N(CH$_3$)Ph |
| 3-F-5-CF$_3$ | CF$_3$ | H | N(CH$_3$)(D-50a) |
| 3-F-5-CF$_3$ | CF$_3$ | C(O)OCH$_3$ | C(O)N(CH$_3$)$_2$ |
| 3-F-5-CF$_3$ | CF$_3$ | H | C(O)NHEt |
| 3-F-5-CF$_3$ | CF$_3$ | CH$_3$ | C(O)NHEt |
| 3-F-5-CF$_3$ | CF$_3$ | H | C(O)NHCH$_2$CH$_2$Cl |
| 3-F-5-CF$_3$ | CF$_3$ | H | C(O)NHCH$_2$(Ph-4-F) |
| 3-F-5-CF$_3$ | CF$_3$ | H | Ph-4-CN |
| 3-F-5-CF$_3$ | CF$_3$ | H | Ph-2,4-F$_2$ |
| 3-F-5-CF$_3$ | CF$_3$ | H | (D-15a)CH$_3$ |
| 3-F-5-CF$_3$ | CF$_3$ | H | (D-47d)CN |
| 3-F-5-CF$_3$ | CF$_3$ | H | (D-47e)Br |
| 3-F-5-CF$_3$ | CF$_3$ | H | D-50a |
| 3-F-5-CF$_3$ | CF$_3$ | H | (D-50c)Cl |
| 3-F-5-CF$_3$ | CF$_3$ | H | (D-50c)Br |
| 3-F-5-CF$_3$ | CF$_3$ | H | D-52a |
| 3-F-5-CF$_3$ | CF$_3$ | H | D-53a |
| 3-F-5-CF$_3$ | CF$_2$Cl | H | CH$_2$CF$_3$ |
| 3-F-5-CF$_3$ | CF$_2$Cl | C(O)CH$_3$ | CH$_2$CF$_3$ |
| 3-F-5-CF$_3$ | CF$_2$Cl | H | CH$_2$OCH$_2$CF$_3$ |
| 3-F-5-CF$_3$ | CF$_2$Cl | H | E-4a |
| 3-F-5-CF$_3$ | CF$_2$Cl | H | CH$_2$C(O)NHCH$_2$CF$_3$ |
| 3-F-5-CF$_3$ | CF$_2$Cl | H | CH(CH$_3$)C(O)NHCH$_2$CF$_3$(D) |
| 3-F-5-CF$_3$ | CF$_2$Cl | H | CH(CH$_3$)Ph(R) |
| 3-F-5-CF$_3$ | CF$_2$Cl | H | CH$_2$(D-22a) |
| 3-F-5-CF$_3$ | CF$_2$Cl | H | CH$_2$(D-47a) |
| 3-F-5-CF$_3$ | CF$_2$Cl | CH$_2$CN | CH$_2$(D-47a) |
| 3-F-5-CF$_3$ | CF$_2$Cl | C(O)Et | CH$_2$(D-47a) |
| 3-F-5-CF$_3$ | CF$_2$Cl | C(O)OCH$_3$ | CH$_2$(D-47a) |
| 3-F-5-CF$_3$ | CF$_2$Cl | H | N(CH$_3$)Ph |
| 3-F-5-CF$_3$ | CF$_2$Cl | H | (D-50c)Cl |
| 3-F-5-CF$_3$ | CF$_2$Cl | H | D-52a |
| 3-F-5-CF$_3$ | CF$_2$Br | H | CH$_2$CF$_3$ |
| 3-F-5-CF$_3$ | CF$_2$CHF$_2$ | H | CH$_2$OCH$_2$CF$_3$ |
| 2-F-6-CF$_3$ | CF$_3$ | H | E-4a |
| 3-CF$_3$-4-Cl | CHF$_2$ | H | CH$_2$C(O)NHCH$_2$CF$_3$ |
| 3-CF$_3$-4-Cl | CF$_3$ | H | c-Pr |
| 3-CF$_3$-4-Cl | CF$_3$ | H | CH$_2$Pr-c |
| 3-CF$_3$-4-Cl | CF$_3$ | H | c-Bu |
| 3-CF$_3$-4-Cl | CF$_3$ | H | CH$_2$CF$_3$ |
| 3-CF$_3$-4-Cl | CF$_3$ | C(O)CH$_3$ | CH$_2$CF$_3$ |
| 3-CF$_3$-4-Cl | CF$_3$ | H | CH$_2$CH$_2$CF$_3$ |
| 3-CF$_3$-4-Cl | CF$_3$ | H | CH$_2$OCH$_3$ |
| 3-CF$_3$-4-Cl | CF$_3$ | H | CH$_2$OEt |
| 3-CF$_3$-4-Cl | CF$_3$ | C(O)CH$_3$ | CH$_2$OEt |
| 3-CF$_3$-4-Cl | CF$_3$ | H | CH$_2$OCH$_2$CF$_3$ |
| 3-CF$_3$-4-Cl | CF$_3$ | C(O)CH$_3$ | CH$_2$OCH$_2$CF$_3$ |
| 3-CF$_3$-4-Cl | CF$_3$ | H | CH$_2$CH$_2$OCH$_3$ |
| 3-CF$_3$-4-Cl | CF$_3$ | H | CH$_2$(E-10a) |
| 3-CF$_3$-4-Cl | CF$_3$ | H | E-4a |
| 3-CF$_3$-4-Cl | CF$_3$ | H | E-5a(R) |
| 3-CF$_3$-4-Cl | CF$_3$ | H | CH$_2$CH=NOCH$_3$ |
| 3-CF$_3$-4-Cl | CF$_3$ | H | CH$_2$C(O)NHCH$_2$Cl |
| 3-CF$_3$-4-Cl | CF$_3$ | H | CH$_2$C(O)NHCH$_2$CF$_3$ |
| 3-CF$_3$-4-Cl | CF$_3$ | H | CH(CH$_3$)C(O)NHEt |
| 3-CF$_3$-4-Cl | CF$_3$ | H | CH(CH$_3$)C(O)NHCH$_2$CF$_3$ |
| 3-CF$_3$-4-Cl | CF$_3$ | H | CH(CH$_3$)C(O)NHCH$_2$CF$_3$(D) |
| 3-CF$_3$-4-Cl | CF$_3$ | H | CH$_2$CH=CH$_2$ |
| 3-CF$_3$-4-Cl | CF$_3$ | H | CH$_2$CCl=CH$_2$ |
| 3-CF$_3$-4-Cl | CF$_3$ | H | CH(CH$_3$)Ph(R) |
| 3-CF$_3$-4-Cl | CF$_3$ | H | CH$_2$(Ph-4-NO$_2$) |
| 3-CF$_3$-4-Cl | CF$_3$ | H | CH$_2$(Ph-4-CN) |
| 3-CF$_3$-4-Cl | CF$_3$ | H | CH$_2$(D-17b)Cl |
| 3-CF$_3$-4-Cl | CF$_3$ | H | CH$_2$(D-21a) |
| 3-CF$_3$-4-Cl | CF$_3$ | H | CH$_2$(D-22a) |
| 3-CF$_3$-4-Cl | CF$_3$ | C(O)CH$_3$ | CH$_2$(D-22a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CF$_3$-4-Cl | CF$_3$ | C(O)Et | CH$_2$(D-22a) |
| 3-CF$_3$-4-Cl | CF$_3$ | H | CH$_2$(D-47a) |
| 3-CF$_3$-4-Cl | CF$_3$ | CH$_2$OCH$_3$ | CH$_2$(D-47a) |
| 3-CF$_3$-4-Cl | CF$_3$ | CH$_2$CN | CH$_2$(D-47a) |
| 3-CF$_3$-4-Cl | CF$_3$ | C(O)CH$_3$ | CH$_2$(D-47a) |
| 3-CF$_3$-4-Cl | CF$_3$ | C(O)Et | CH$_2$(D-47a) |
| 3-CF$_3$-4-Cl | CF$_3$ | C(O)Pr-c | CH$_2$(D-47a) |
| 3-CF$_3$-4-Cl | CF$_3$ | C(O)OCH$_3$ | CH$_2$(D-47a) |
| 3-CF$_3$-4-Cl | CF$_3$ | H | CH(CH$_3$)(D-47a) |
| 3-CF$_3$-4-Cl | CF$_3$ | H | CH$_2$(D-50a) |
| 3-CF$_3$-4-Cl | CF$_3$ | H | N(CH$_3$)Ph |
| 3-CF$_3$-4-Cl | CF$_3$ | H | N(CH$_3$)(D-50a) |
| 3-CF$_3$-4-Cl | CF$_3$ | C(O)OCH$_3$ | C(O)N(CH$_3$)$_2$ |
| 3-CF$_3$-4-Cl | CF$_3$ | H | C(O)NHEt |
| 3-CF$_3$-4-Cl | CF$_3$ | CH$_3$ | C(O)NHEt |
| 3-CF$_3$-4-Cl | CF$_3$ | H | C(O)NHCH$_2$CH$_2$Cl |
| 3-CF$_3$-4-Cl | CF$_3$ | H | C(O)NHCH$_2$(Ph-4-F) |
| 3-CF$_3$-4-Cl | CF$_3$ | H | Ph-4-CN |
| 3-CF$_3$-4-Cl | CF$_3$ | H | Ph-2,4-F$_2$ |
| 3-CF$_3$-4-Cl | CF$_3$ | H | (D-15a)CH$_3$ |
| 3-CF$_3$-4-Cl | CF$_3$ | H | (D-47d)CN |
| 3-CF$_3$-4-Cl | CF$_3$ | H | (D-47e)Br |
| 3-CF$_3$-4-Cl | CF$_3$ | H | D-50a |
| 3-CF$_3$-4-Cl | CF$_3$ | H | (D-50c)Cl |
| 3-CF$_3$-4-Cl | CF$_3$ | H | (D-50c)Br |
| 3-CF$_3$-4-Cl | CF$_3$ | H | D-52a |
| 3-CF$_3$-4-Cl | CF$_3$ | H | D-53a |
| 3-CF$_3$-4-Cl | CF$_2$Cl | H | CH$_2$CF$_3$ |
| 3-CF$_3$-4-Cl | CF$_2$Cl | C(O)CH$_3$ | CH$_2$CF$_3$ |
| 3-CF$_3$-4-Cl | CF$_2$Cl | H | CH$_2$OCH$_2$CF$_3$ |
| 3-CF$_3$-4-Cl | CF$_2$Cl | H | E-4a |
| 3-CF$_3$-4-Cl | CF$_2$Cl | H | CH$_2$C(O)NHCH$_2$CF$_3$ |
| 3-CF$_3$-4-Cl | CF$_2$Cl | H | CH(CH$_3$)C(O)NHCH$_2$CF$_3$(D) |
| 3-CF$_3$-4-Cl | CF$_2$Cl | H | CH(CH$_3$)Ph(R) |
| 3-CF$_3$-4-Cl | CF$_2$Cl | H | CH$_2$(D-22a) |
| 3-CF$_3$-4-Cl | CF$_2$Cl | H | CH$_2$(D-47a) |
| 3-CF$_3$-4-Cl | CF$_2$Cl | CH$_2$CN | CH$_2$(D-47a) |
| 3-CF$_3$-4-Cl | CF$_2$Cl | C(O)Et | CH$_2$(D-47a) |
| 3-CF$_3$-4-Cl | CF$_2$Cl | C(O)OCH$_3$ | CH$_2$(D-47a) |
| 3-CF$_3$-4-Cl | CF$_2$Cl | H | N(CH$_3$)Ph |
| 3-CF$_3$-4-Cl | CF$_2$Cl | H | (D-50c)Cl |
| 3-CF$_3$-4-Cl | CF$_2$Cl | H | D-52a |
| 3-CF$_3$-4-Cl | CF$_2$Br | H | CH$_2$(D-22a) |
| 3-CF$_3$-4-Cl | CF$_2$CHF$_2$ | H | CH$_2$(D-47a) |
| 2-Cl-4-CF$_3$ | CF$_3$ | C(O)OCH$_3$ | CH$_2$(D-47a) |
| 2-Cl-5-CF$_3$ | CF$_3$ | H | N(CH$_3$)Ph |
| 3-Cl-5-CF$_3$ | CHF$_2$ | H | CH$_2$CF$_3$ |
| 3-Cl-5-CF$_3$ | CHF$_2$ | H | E-4a |
| 3-Cl-5-CF$_3$ | CHF$_2$ | H | CH$_2$C(O)NHCH$_2$CF$_3$ |
| 3-Cl-5-CF$_3$ | CHF$_2$ | H | CH$_2$(D-22a) |
| 3-Cl-5-CF$_3$ | CHF$_2$ | H | CH$_2$(D-47a) |
| 3-Cl-5-CF$_3$ | CHF$_2$ | H | (D-50c)Cl |
| 3-Cl-5-CF$_3$ | CF$_3$ | H | c-Pr |
| 3-Cl-5-CF$_3$ | CF$_3$ | H | CH$_2$Pr-c |
| 3-Cl-5-CF$_3$ | CF$_3$ | H | c-Bu |
| 3-Cl-5-CF$_3$ | CF$_3$ | H | CH$_2$CF$_3$ |
| 3-Cl-5-CF$_3$ | CF$_3$ | H | CH$_2$CH$_2$CF$_3$ |
| 3-Cl-5-CF$_3$ | CF$_3$ | H | CH$_2$OCH$_3$ |
| 3-Cl-5-CF$_3$ | CF$_3$ | H | CH$_2$OEt |
| 3-Cl-5-CF$_3$ | CF$_3$ | C(O)CH$_3$ | CH$_2$OEt |
| 3-Cl-5-CF$_3$ | CF$_3$ | H | CH$_2$OCH$_2$CF$_3$ |
| 3-Cl-5-CF$_3$ | CF$_3$ | C(O)CH$_3$ | CH$_2$OCH$_2$CF$_3$ |
| 3-Cl-5-CF$_3$ | CF$_3$ | H | CH(CH$_3$)OCH$_2$CF$_3$ |
| 3-Cl-5-CF$_3$ | CF$_3$ | H | CH$_2$CH$_2$OCH$_3$ |
| 3-Cl-5-CF$_3$ | CF$_3$ | H | CH$_2$(E-5a) |
| 3-Cl-5-CF$_3$ | CF$_3$ | H | CH$_2$(E-10a) |
| 3-Cl-5-CF$_3$ | CF$_3$ | H | CH$_2$(E-10b)CH$_3$ |
| 3-Cl-5-CF$_3$ | CF$_3$ | H | E-4a |
| 3-Cl-5-CF$_3$ | CF$_3$ | H | E-5a(R) |
| 3-Cl-5-CF$_3$ | CF$_3$ | H | CH$_2$CH=NOCH$_3$ |
| 3-Cl-5-CF$_3$ | CF$_3$ | H | CH$_2$C(CH$_3$)=NOCH$_3$ |
| 3-Cl-5-CF$_3$ | CF$_3$ | H | CH$_2$C(O)NHCH$_3$ |
| 3-Cl-5-CF$_3$ | CF$_3$ | H | CH$_2$C(O)N(CH$_3$)$_2$ |
| 3-Cl-5-CF$_3$ | CF$_3$ | H | CH$_2$C(O)NHPr-n |
| 3-Cl-5-CF$_3$ | CF$_3$ | H | CH$_2$C(O)NHPr-i |
| 3-Cl-5-CF$_3$ | CF$_3$ | H | CH$_2$C(O)NHCH$_2$CH$_2$F |
| 3-Cl-5-CF$_3$ | CF$_3$ | H | CH$_2$C(O)NHCH$_2$CH$_2$Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-CF$_3$ | CF$_3$ | H | CH$_2$C(O)NHCH$_2$CF$_3$ |
| 3-Cl-5-CF$_3$ | CF$_3$ | H | CH$_2$C(O)NHCH$_2$CH=CH$_2$ |
| 3-Cl-5-CF$_3$ | CF$_3$ | H | CH$_2$C(O)NHCH$_2$C≡CH |
| 3-Cl-5-CF$_3$ | CF$_3$ | H | CH(CH$_3$)C(O)NHEt |
| 3-Cl-5-CF$_3$ | CF$_3$ | H | CH(CH$_3$)C(O)NHCH$_2$CF$_3$ |
| 3-Cl-5-CF$_3$ | CF$_3$ | H | CH(CH$_3$)C(O)NHCH$_2$CF$_3$(D) |
| 3-Cl-5-CF$_3$ | CF$_3$ | H | CH$_2$CH=CH$_2$ |
| 3-Cl-5-CF$_3$ | CF$_3$ | H | CH$_2$CCl=CH$_2$ |
| 3-Cl-5-CF$_3$ | CF$_3$ | H | CH(CH$_3$)Ph(R) |
| 3-Cl-5-CF$_3$ | CF$_3$ | H | CH$_2$(Ph-4-NO$_2$) |
| 3-Cl-5-CF$_3$ | CF$_3$ | H | CH$_2$(Ph-4-CN) |
| 3-Cl-5-CF$_3$ | CF$_3$ | H | CH$_2$(D-16b)Cl |
| 3-Cl-5-CF$_3$ | CF$_3$ | H | CH$_2$(D-17a)CH$_3$ |
| 3-Cl-5-CF$_3$ | CF$_3$ | H | CH$_2$(D-17b)Cl |
| 3-Cl-5-CF$_3$ | CF$_3$ | H | CH$_2$(D-21a) |
| 3-Cl-5-CF$_3$ | CF$_3$ | H | CH$_2$(D-22a) |
| 3-Cl-5-CF$_3$ | CF$_3$ | C(O)CH$_3$ | CH$_2$(D-22a) |
| 3-Cl-5-CF$_3$ | CF$_3$ | C(O)Et | CH$_2$(D-22a) |
| 3-Cl-5-CF$_3$ | CF$_3$ | H | CH$_2$(D-29b)CH$_3$ |
| 3-Cl-5-CF$_3$ | CF$_3$ | H | CH$_2$(D-34a) |
| 3-Cl-5-CF$_3$ | CF$_3$ | H | CH$_2$(D-38a) |
| 3-Cl-5-CF$_3$ | CF$_3$ | H | CH$_2$(D-47a) |
| 3-Cl-5-CF$_3$ | CF$_3$ | Et | CH$_2$(D-47a) |
| 3-Cl-5-CF$_3$ | CF$_3$ | CH$_2$OCH$_3$ | CH$_2$(D-47a) |
| 3-Cl-5-CF$_3$ | CF$_3$ | CH$_2$CN | CH$_2$(D-47a) |
| 3-Cl-5-CF$_3$ | CF$_3$ | CH$_2$C≡CH | CH$_2$(D-47a) |
| 3-Cl-5-CF$_3$ | CF$_3$ | C(O)CH$_3$ | CH$_2$(D-47a) |
| 3-Cl-5-CF$_3$ | CF$_3$ | C(O)Et | CH$_2$(D-47a) |
| 3-Cl-5-CF$_3$ | CF$_3$ | C(O)Pr-n | CH$_2$(D-47a) |
| 3-Cl-5-CF$_3$ | CF$_3$ | C(O)Pr-i | CH$_2$(D-47a) |
| 3-Cl-5-CF$_3$ | CF$_3$ | C(O)Pr-c | CH$_2$(D-47a) |
| 3-Cl-5-CF$_3$ | CF$_3$ | C(O)Bu-t | CH$_2$(D-47a) |
| 3-Cl-5-CF$_3$ | CF$_3$ | C(O)CH$_2$OCH$_3$ | CH$_2$(D-47a) |
| 3-Cl-5-CF$_3$ | CF$_3$ | C(O)CH=CH$_2$ | CH$_2$(D-47a) |
| 3-Cl-5-CF$_3$ | CF$_3$ | C(O)OCH$_3$ | CH$_2$(D-47a) |
| 3-Cl-5-CF$_3$ | CF$_3$ | C(O)OCH$_2$CH$_2$OCH$_3$ | CH$_2$(D-47a) |
| 3-Cl-5-CF$_3$ | CF$_3$ | C(O)OCH$_2$CH=CH$_2$ | CH$_2$(D-47a) |
| 3-Cl-5-CF$_3$ | CF$_3$ | H | CH(CH$_3$)(D-47a) |
| 3-Cl-5-CF$_3$ | CF$_3$ | H | CH$_2$(D-50a) |
| 3-Cl-5-CF$_3$ | CF$_3$ | H | NHC(O)OCH$_3$ |
| 3-Cl-5-CF$_3$ | CF$_3$ | H | N(CH$_3$)Ph |
| 3-Cl-5-CF$_3$ | CF$_3$ | H | N(CH$_2$CH=CH$_2$)Ph |
| 3-Cl-5-CF$_3$ | CF$_3$ | H | N(CH$_2$C≡CH)Ph |
| 3-Cl-5-CF$_3$ | CF$_3$ | H | NH(D-50a) |
| 3-Cl-5-CF$_3$ | CF$_3$ | CH$_3$ | NH(D-50a) |
| 3-Cl-5-CF$_3$ | CF$_3$ | H | N(CH$_3$)(D-50a) |
| 3-Cl-5-CF$_3$ | CF$_3$ | H | N(Et)(D-50a) |
| 3-Cl-5-CF$_3$ | CF$_3$ | C(O)OCH$_3$ | C(O)N(CH$_3$)$_2$ |
| 3-Cl-5-CF$_3$ | CF$_3$ | H | C(O)NHEt |
| 3-Cl-5-CF$_3$ | CF$_3$ | CH$_3$ | C(O)NHEt |
| 3-Cl-5-CF$_3$ | CF$_3$ | H | C(O)NHCH$_2$CH$_2$Cl |
| 3-Cl-5-CF$_3$ | CF$_3$ | H | C(O)NHCH$_2$CF$_3$ |
| 3-Cl-5-CF$_3$ | CF$_3$ | H | C(O)NHCH$_2$(Ph-4-F) |
| 3-Cl-5-CF$_3$ | CF$_3$ | H | Ph-4-F |
| 3-Cl-5-CF$_3$ | CF$_3$ | H | Ph-4-CN |
| 3-Cl-5-CF$_3$ | CF$_3$ | H | Ph-2,4-F$_2$ |
| 3-Cl-5-CF$_3$ | CF$_3$ | H | (D-13b)CH$_3$ |
| 3-Cl-5-CF$_3$ | CF$_3$ | H | (D-15a)CH$_3$ |
| 3-Cl-5-CF$_3$ | CF$_3$ | H | D-21a |
| 3-Cl-5-CF$_3$ | CF$_3$ | H | (D-47d)CN |
| 3-Cl-5-CF$_3$ | CF$_3$ | H | (D-47e)Br |
| 3-Cl-5-CF$_3$ | CF$_3$ | H | D-50a |
| 3-Cl-5-CF$_3$ | CF$_3$ | H | (D-50c)Cl |
| 3-Cl-5-CF$_3$ | CF$_3$ | H | (D-50c)Br |
| 3-Cl-5-CF$_3$ | CF$_3$ | H | D-51a |
| 3-Cl-5-CF$_3$ | CF$_3$ | H | D-52a |
| 3-Cl-5-CF$_3$ | CF$_3$ | H | D-53a |
| 3-Cl-5-CF$_3$ | CF$_2$Cl | H | c-Bu |
| 3-Cl-5-CF$_3$ | CF$_2$Cl | H | CH$_2$CF$_3$ |
| 3-Cl-5-CF$_3$ | CF$_2$Cl | H | CH$_2$OEt |
| 3-Cl-5-CF$_3$ | CF$_2$Cl | H | CH$_2$OCH$_2$CF$_3$ |
| 3-Cl-5-CF$_3$ | CF$_2$Cl | C(O)CH$_3$ | CH$_2$OCH$_2$CF$_3$ |
| 3-Cl-5-CF$_3$ | CF$_2$Cl | H | CH$_2$CH$_2$OCH$_3$ |
| 3-Cl-5-CF$_3$ | CF$_2$Cl | H | CH$_2$(E-10a) |
| 3-Cl-5-CF$_3$ | CF$_2$Cl | H | E-4a |
| 3-Cl-5-CF$_3$ | CF$_2$Cl | H | CH$_2$C(O)NHCH$_2$CH$_2$Cl |
| 3-Cl-5-CF$_3$ | CF$_2$Cl | H | CH$_2$C(O)NHCH$_2$CF$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-CF$_3$ | CF$_2$Cl | H | CH(CH$_3$)C(O)NHCH$_2$CF$_3$ |
| 3-Cl-5-CF$_3$ | CF$_2$Cl | H | CH(CH$_3$)C(O)NHCH$_2$CF$_3$(D) |
| 3-Cl-5-CF$_3$ | CF$_2$Cl | H | CH(CH$_3$)Ph(R) |
| 3-Cl-5-CF$_3$ | CF$_2$Cl | H | CH$_2$(D-22a) |
| 3-Cl-5-CF$_3$ | CF$_2$Cl | C(O)CH$_3$ | CH$_2$(D-22a) |
| 3-Cl-5-CF$_3$ | CF$_2$Cl | C(O)Et | CH$_2$(D-22a) |
| 3-Cl-5-CF$_3$ | CF$_2$Cl | H | CH$_2$(D-47a) |
| 3-Cl-5-CF$_3$ | CF$_2$Cl | CH$_2$OCH$_3$ | CH$_2$(D-47a) |
| 3-Cl-5-CF$_3$ | CF$_2$Cl | CH$_2$CN | CH$_2$(D-47a) |
| 3-Cl-5-CF$_3$ | CF$_2$Cl | C(O)CH$_3$ | CH$_2$(D-47a) |
| 3-Cl-5-CF$_3$ | CF$_2$Cl | C(O)Et | CH$_2$(D-47a) |
| 3-Cl-5-CF$_3$ | CF$_2$Cl | C(O)OCH$_3$ | CH$_2$(D-47a) |
| 3-Cl-5-CF$_3$ | CF$_2$Cl | H | N(CH$_3$)Ph |
| 3-Cl-5-CF$_3$ | CF$_2$Cl | H | N(CH$_3$)(D-50a) |
| 3-Cl-5-CF$_3$ | CF$_2$Cl | H | C(O)NHCH$_2$CF$_3$ |
| 3-Cl-5-CF$_3$ | CF$_2$Cl | H | Ph-2,4-F$_2$ |
| 3-Cl-5-CF$_3$ | CF$_2$Cl | H | (D-50c)Cl |
| 3-Cl-5-CF$_3$ | CF$_2$Cl | H | D-52a |
| 3-Cl-5-CF$_3$ | CF$_2$Br | H | CH$_2$CF$_3$ |
| 3-Cl-5-CF$_3$ | CF$_2$Br | H | E-4a |
| 3-Cl-5-CF$_3$ | CF$_2$Br | H | CH$_2$C(O)NHCH$_2$CF$_3$ |
| 3-Cl-5-CF$_3$ | CF$_2$Br | H | CH$_2$(D-22a) |
| 3-Cl-5-CF$_3$ | CF$_2$Br | H | CH$_2$(D-47a) |
| 3-Cl-5-CF$_3$ | CF$_2$Br | H | (D-50c)Cl |
| 3-Cl-5-CF$_3$ | CF$_2$CHF$_2$ | H | CH$_2$CF$_3$ |
| 3-Cl-5-CF$_3$ | CF$_2$CHF$_2$ | H | E-4a |
| 3-Cl-5-CF$_3$ | CF$_2$CHF$_2$ | H | CH$_2$C(O)NHCH$_2$CF$_3$ |
| 3-Cl-5-CF$_3$ | CF$_2$CHF$_2$ | H | CH$_2$(D-22a) |
| 3-Cl-5-CF$_3$ | CF$_2$CHF$_2$ | H | CH$_2$(D-47a) |
| 3-Cl-5-CF$_3$ | CF$_2$CHF$_2$ | H | (D-50c)Cl |
| 3-Br-5-CF$_3$ | CHF$_2$ | H | CH$_2$CF$_3$ |
| 3-Br-5-CF$_3$ | CHF$_2$ | H | E-4a |
| 3-Br-5-CF$_3$ | CHF$_2$ | H | CH$_2$C(O)NHCH$_2$CF$_3$ |
| 3-Br-5-CF$_3$ | CHF$_2$ | H | CH$_2$(D-22a) |
| 3-Br-5-CF$_3$ | CHF$_2$ | H | CH$_2$(D-47a) |
| 3-Br-5-CF$_3$ | CHF$_2$ | H | (D-50c)Cl |
| 3-Br-5-CF$_3$ | CF$_3$ | H | c-Pr |
| 3-Br-5-CF$_3$ | CF$_3$ | H | CH$_2$Pr-c |
| 3-Br-5-CF$_3$ | CF$_3$ | H | c-Bu |
| 3-Br-5-CF$_3$ | CF$_3$ | H | CH$_2$CF$_3$ |
| 3-Br-5-CF$_3$ | CF$_3$ | H | CH$_2$CH$_2$CF$_3$ |
| 3-Br-5-CF$_3$ | CF$_3$ | H | CH$_2$OCH$_3$ |
| 3-Br-5-CF$_3$ | CF$_3$ | H | CH$_2$OEt |
| 3-Br-5-CF$_3$ | CF$_3$ | C(O)CH$_3$ | CH$_2$OEt |
| 3-Br-5-CF$_3$ | CF$_3$ | H | CH$_2$OCH$_2$CF$_3$ |
| 3-Br-5-CF$_3$ | CF$_3$ | C(O)CH$_3$ | CH$_2$OCH$_2$CF$_3$ |
| 3-Br-5-CF$_3$ | CF$_3$ | H | CH(CH$_3$)OCH$_2$CF$_3$ |
| 3-Br-5-CF$_3$ | CF$_3$ | H | CH$_2$CH$_2$OCH$_3$ |
| 3-Br-5-CF$_3$ | CF$_3$ | H | CH$_2$(E-5a) |
| 3-Br-5-CF$_3$ | CF$_3$ | H | CH$_2$(E-10a) |
| 3-Br-5-CF$_3$ | CF$_3$ | H | CH$_2$(E-10b)CH$_3$ |
| 3-Br-5-CF$_3$ | CF$_3$ | H | E-4a |
| 3-Br-5-CF$_3$ | CF$_3$ | H | E-5a(R) |
| 3-Br-5-CF$_3$ | CF$_3$ | H | CH$_2$CH=NOCH$_3$ |
| 3-Br-5-CF$_3$ | CF$_3$ | H | CH$_2$C(CH$_3$)=NOCH$_3$ |
| 3-Br-5-CF$_3$ | CF$_3$ | H | CH$_2$C(O)NHCH$_3$ |
| 3-Br-5-CF$_3$ | CF$_3$ | H | CH$_2$C(O)N(CH$_3$)$_2$ |
| 3-Br-5-CF$_3$ | CF$_3$ | H | CH$_2$C(O)NHPr-n |
| 3-Br-5-CF$_3$ | CF$_3$ | H | CH$_2$C(O)NHPr-i |
| 3-Br-5-CF$_3$ | CF$_3$ | H | CH$_2$C(O)NHCH$_2$F |
| 3-Br-5-CF$_3$ | CF$_3$ | H | CH$_2$C(O)NHCH$_2$Cl |
| 3-Br-5-CF$_3$ | CF$_3$ | H | CH$_2$C(O)NHCH$_2$CF$_3$ |
| 3-Br-5-CF$_3$ | CF$_3$ | H | CH$_2$C(O)NHCH$_2$CH=CH$_2$ |
| 3-Br-5-CF$_3$ | CF$_3$ | H | CH$_2$C(O)NHCH$_2$C≡CH |
| 3-Br-5-CF$_3$ | CF$_3$ | H | CH(CH$_3$)C(O)NHEt |
| 3-Br-5-CF$_3$ | CF$_3$ | H | CH(CH$_3$)C(O)NHCH$_2$CF$_3$ |
| 3-Br-5-CF$_3$ | CF$_3$ | H | CH(CH$_3$)C(O)NHCH$_2$CF$_3$(D) |
| 3-Br-5-CF$_3$ | CF$_3$ | H | CH$_2$CH=CH$_2$ |
| 3-Br-5-CF$_3$ | CF$_3$ | H | CH$_2$CCl=CH$_2$ |
| 3-Br-5-CF$_3$ | CF$_3$ | H | CH(CH$_3$)Ph(R) |
| 3-Br-5-CF$_3$ | CF$_3$ | H | CH$_2$(Ph-4-NO$_2$) |
| 3-Br-5-CF$_3$ | CF$_3$ | H | CH$_2$(Ph-4-CN) |
| 3-Br-5-CF$_3$ | CF$_3$ | H | CH$_2$(D-16b)Cl |
| 3-Br-5-CF$_3$ | CF$_3$ | H | CH$_2$(D-17a)CH$_3$ |
| 3-Br-5-CF$_3$ | CF$_3$ | H | CH$_2$(D-17b)Cl |
| 3-Br-5-CF$_3$ | CF$_3$ | H | CH$_2$(D-21a) |
| 3-Br-5-CF$_3$ | CF$_3$ | H | CH$_2$(D-22a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Br-5-CF$_3$ | CF$_3$ | C(O)CH$_3$ | CH$_2$(D-22a) |
| 3-Br-5-CF$_3$ | CF$_3$ | C(O)Et | CH$_2$(D-22a) |
| 3-Br-5-CF$_3$ | CF$_3$ | H | CH$_2$(D-29b)CH$_3$ |
| 3-Br-5-CF$_3$ | CF$_3$ | H | CH$_2$(D-34a) |
| 3-Br-5-CF$_3$ | CF$_3$ | H | CH$_2$(D-38a) |
| 3-Br-5-CF$_3$ | CF$_3$ | H | CH$_2$(D-47a) |
| 3-Br-5-CF$_3$ | CF$_3$ | Et | CH$_2$(D-47a) |
| 3-Br-5-CF$_3$ | CF$_3$ | CH$_2$OCH$_3$ | CH$_2$(D-47a) |
| 3-Br-5-CF$_3$ | CF$_3$ | CH$_2$CN | CH$_2$(D-47a) |
| 3-Br-5-CF$_3$ | CF$_3$ | CH$_2$C≡CH | CH$_2$(D-47a) |
| 3-Br-5-CF$_3$ | CF$_3$ | C(O)CH$_3$ | CH$_2$(D-47a) |
| 3-Br-5-CF$_3$ | CF$_3$ | C(O)Et | CH$_2$(D-47a) |
| 3-Br-5-CF$_3$ | CF$_3$ | C(O)Pr-n | CH$_2$(D-47a) |
| 3-Br-5-CF$_3$ | CF$_3$ | C(O)Pr-i | CH$_2$(D-47a) |
| 3-Br-5-CF$_3$ | CF$_3$ | C(O)Pr-c | CH$_2$(D-47a) |
| 3-Br-5-CF$_3$ | CF$_3$ | C(O)Bu-t | CH$_2$(D-47a) |
| 3-Br-5-CF$_3$ | CF$_3$ | C(O)CH$_2$OCH$_3$ | CH$_2$(D-47a) |
| 3-Br-5-CF$_3$ | CF$_3$ | C(O)CH=CH$_2$ | CH$_2$(D-47a) |
| 3-Br-5-CF$_3$ | CF$_3$ | C(O)OCH$_3$ | CH$_2$(D-47a) |
| 3-Br-5-CF$_3$ | CF$_3$ | C(O)OCH$_2$CH$_2$OCH$_3$ | CH$_2$(D-47a) |
| 3-Br-5-CF$_3$ | CF$_3$ | C(O)OCH$_2$CH=CH$_2$ | CH$_2$(D-47a) |
| 3-Br-5-CF$_3$ | CF$_3$ | H | CH(CH$_3$)(D-47a) |
| 3-Br-5-CF$_3$ | CF$_3$ | H | CH$_2$(D-50a) |
| 3-Br-5-CF$_3$ | CF$_3$ | H | NHC(O)OCH$_3$ |
| 3-Br-5-CF$_3$ | CF$_3$ | H | N(CH$_3$)Ph |
| 3-Br-5-CF$_3$ | CF$_3$ | H | N(CH$_2$CH=CH$_2$)Ph |
| 3-Br-5-CF$_3$ | CF$_3$ | H | N(CH$_2$C≡CH)Ph |
| 3-Br-5-CF$_3$ | CF$_3$ | H | NH(D-50a) |
| 3-Br-5-CF$_3$ | CF$_3$ | CH$_3$ | NH(D-50a) |
| 3-Br-5-CF$_3$ | CF$_3$ | H | N(CH$_3$)(D-50a) |
| 3-Br-5-CF$_3$ | CF$_3$ | H | N(Et)(D-50a) |
| 3-Br-5-CF$_3$ | CF$_3$ | C(O)OCH$_3$ | C(O)N(CH$_3$)$_2$ |
| 3-Br-5-CF$_3$ | CF$_3$ | H | C(O)NHEt |
| 3-Br-5-CF$_3$ | CF$_3$ | CH$_3$ | C(O)NHEt |
| 3-Br-5-CF$_3$ | CF$_3$ | H | C(O)NHCH$_2$CH$_2$Cl |
| 3-Br-5-CF$_3$ | CF$_3$ | H | C(O)NHCH$_2$CF$_3$ |
| 3-Br-5-CF$_3$ | CF$_3$ | H | C(O)NHCH$_2$(Ph-4-F) |
| 3-Br-5-CF$_3$ | CF$_3$ | H | Ph-4-F |
| 3-Br-5-CF$_3$ | CF$_3$ | H | Ph-4-CN |
| 3-Br-5-CF$_3$ | CF$_3$ | H | Ph-2,4-F$_2$ |
| 3-Br-5-CF$_3$ | CF$_3$ | H | (D-13b)CH$_3$ |
| 3-Br-5-CF$_3$ | CF$_3$ | H | (D-15a)CH$_3$ |
| 3-Br-5-CF$_3$ | CF$_3$ | H | D-21a |
| 3-Br-5-CF$_3$ | CF$_3$ | H | (D-47d)CN |
| 3-Br-5-CF$_3$ | CF$_3$ | H | (D-47e)Br |
| 3-Br-5-CF$_3$ | CF$_3$ | H | D-50a |
| 3-Br-5-CF$_3$ | CF$_3$ | H | (D-50c)Cl |
| 3-Br-5-CF$_3$ | CF$_3$ | H | (D-50c)Br |
| 3-Br-5-CF$_3$ | CF$_3$ | H | D-51a |
| 3-Br-5-CF$_3$ | CF$_3$ | H | D-52a |
| 3-Br-5-CF$_3$ | CF$_3$ | H | D-53a |
| 3-Br-5-CF$_3$ | CF$_2$Cl | H | c-Bu |
| 3-Br-5-CF$_3$ | CF$_2$Cl | H | CH$_2$CF$_3$ |
| 3-Br-5-CF$_3$ | CF$_2$Cl | H | CH$_2$OEt |
| 3-Br-5-CF$_3$ | CF$_2$Cl | H | CH$_2$OCH$_2$CF$_3$ |
| 3-Br-5-CF$_3$ | CF$_2$Cl | C(O)CH$_3$ | CH$_2$OCH$_2$CF$_3$ |
| 3-Br-5-CF$_3$ | CF$_2$Cl | H | CH$_2$CH$_2$OCH$_3$ |
| 3-Br-5-CF$_3$ | CF$_2$Cl | H | CH$_2$(E-10a) |
| 3-Br-5-CF$_3$ | CF$_2$Cl | H | E-4a |
| 3-Br-5-CF$_3$ | CF$_2$Cl | H | CH$_2$C(O)NHCH$_2$CH$_2$Cl |
| 3-Br-5-CF$_3$ | CF$_2$Cl | H | CH$_2$C(O)NHCH$_2$CF$_3$ |
| 3-Br-5-CF$_3$ | CF$_2$Cl | H | CH(CH$_3$)C(O)NHCH$_2$CF$_3$ |
| 3-Br-5-CF$_3$ | CF$_2$Cl | H | CH(CH$_3$)C(O)NHCH$_2$CF$_3$(D) |
| 3-Br-5-CF$_3$ | CF$_2$Cl | H | CH(CH$_3$)Ph(R) |
| 3-Br-5-CF$_3$ | CF$_2$Cl | H | CH$_2$(D-22a) |
| 3-Br-5-CF$_3$ | CF$_2$Cl | C(O)CH$_3$ | CH$_2$(D-22a) |
| 3-Br-5-CF$_3$ | CF$_2$Cl | C(O)Et | CH$_2$(D-22a) |
| 3-Br-5-CF$_3$ | CF$_2$Cl | H | CH$_2$(D-47a) |
| 3-Br-5-CF$_3$ | CF$_2$Cl | CH$_2$OCH$_3$ | CH$_2$(D-47a) |
| 3-Br-5-CF$_3$ | CF$_2$Cl | CH$_2$CN | CH$_2$(D-47a) |
| 3-Br-5-CF$_3$ | CF$_2$Cl | C(O)CH$_3$ | CH$_2$(D-47a) |
| 3-Br-5-CF$_3$ | CF$_2$Cl | C(O)Et | CH$_2$(D-47a) |
| 3-Br-5-CF$_3$ | CF$_2$Cl | C(O)OCH$_3$ | CH$_2$(D-47a) |
| 3-Br-5-CF$_3$ | CF$_2$Cl | H | N(CH$_3$)Ph |
| 3-Br-5-CF$_3$ | CF$_2$Cl | H | N(CH$_3$)(D-50a) |
| 3-Br-5-CF$_3$ | CF$_2$Cl | H | C(O)NHCH$_2$CF$_2$ |
| 3-Br-5-CF$_3$ | CF$_2$Cl | H | Ph-2,4-F$_2$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Br-5-CF$_3$ | CF$_2$Cl | H | (D-50c)Cl |
| 3-Br-5-CF$_3$ | CF$_2$Cl | H | D-52a |
| 3-Br-5-CF$_3$ | CF$_2$Br | H | CH$_2$CF$_3$ |
| 3-Br-5-CF$_3$ | CF$_2$Br | H | E-4a |
| 3-Br-5-CF$_3$ | CF$_2$Br | H | CH$_2$C(O)NHCH$_2$CF$_2$ |
| 3-Br-5-CF$_3$ | CF$_2$Br | H | CH$_2$(D-22a) |
| 3-Br-5-CF$_3$ | CF$_2$Br | H | CH$_2$(D-47a) |
| 3-Br-5-CF$_3$ | CF$_2$Br | H | (D-50c)Cl |
| 3-Br-5-CF$_3$ | CF$_2$CHF$_2$ | H | CH$_2$CF$_3$ |
| 3-Br-5-CF$_3$ | CF$_2$CHF$_2$ | H | E-4a |
| 3-Br-5-CF$_3$ | CF$_2$CHF$_2$ | H | CH$_2$C(O)NHCH$_2$CF$_3$ |
| 3-Br-5-CF$_3$ | CF$_2$CHF$_2$ | H | CH$_2$(D-22a) |
| 3-Br-5-CF$_3$ | CF$_2$CHF$_2$ | H | CH$_2$(D-47a) |
| 3-Br-5-CF$_3$ | CF$_2$CHF$_2$ | H | (D-50c)Cl |
| 3-CH$_3$-5-CF$_3$ | CF$_3$ | H | CH$_2$CF$_3$ |
| 3-CH$_3$-5-CF$_3$ | CF$_3$ | C(O)CH$_3$ | CH$_2$CF$_3$ |
| 3-CH$_3$-5-CF$_3$ | CF$_3$ | H | CH$_2$OCH$_2$CF$_3$ |
| 3-CH$_3$-5-CF$_3$ | CF$_3$ | H | E-4a |
| 3-CH$_3$-5-CF$_3$ | CF$_3$ | H | CH$_2$C(O)NHCH$_2$CF$_3$ |
| 3-CH$_3$-5-CF$_3$ | CF$_3$ | H | CH(CH$_3$)C(O)NHCH$_2$CF$_3$(D) |
| 3-CH$_3$-5-CF$_3$ | CF$_3$ | H | CH(CH$_3$)Ph(R) |
| 3-CH$_3$-5-CF$_3$ | CF$_3$ | H | CH$_2$(D-22a) |
| 3-CH$_3$-5-CF$_3$ | CF$_3$ | H | CH$_2$(D-47a) |
| 3-CH$_3$-5-CF$_3$ | CF$_3$ | CH$_2$CN | CH$_2$(D-47a) |
| 3-CH$_3$-5-CF$_3$ | CF$_3$ | C(O)Et | CH$_2$(D-47a) |
| 3-CH$_3$-5-CF$_3$ | CF$_3$ | C(O)OCH$_3$ | CH$_2$(D-47a) |
| 3-CH$_3$-5-CF$_3$ | CF$_3$ | H | N(CH$_3$)Ph |
| 3-CH$_3$-5-CF$_3$ | CF$_3$ | H | (D-50c)Cl |
| 3-CH$_3$-5-CF$_3$ | CF$_3$ | H | D-52a |
| 3-CH$_3$-5-CF$_3$ | CF$_2$Cl | H | CH$_2$CF$_3$ |
| 3-CH$_3$-5-CF$_3$ | CF$_2$Cl | H | E-4a |
| 3-CH$_3$-5-CF$_3$ | CF$_2$Cl | H | CH$_2$C(O)NHCH$_2$CF$_3$ |
| 3-CH$_3$-5-CF$_3$ | CF$_2$Cl | H | CH$_2$(D-22a) |
| 3-CH$_3$-5-CF$_3$ | CF$_2$Cl | H | CH$_2$(D-47a) |
| 3-CH$_3$-5-CF$_3$ | CF$_2$Cl | H | (D-50c)Cl |
| 3-Et-5-CF$_3$ | CF$_3$ | H | (D-50c)Cl |
| 3-i-Pr-5-CF$_3$ | CF$_3$ | H | CH$_2$CF$_3$ |
| 3-t-Bu-5-CF$_3$ | CF$_3$ | H | CHOCH$_2$CF$_3$ |
| 3,5-(CF$_3$)$_2$ | CHF$_2$ | H | CH$_2$CF$_3$ |
| 3,5-(CF$_3$)$_2$ | CHF$_2$ | H | CH$_2$OCH$_2$CF$_3$ |
| 3,5-(CF$_3$)$_2$ | CHF$_2$ | H | E-4a |
| 3,5-(CF$_3$)$_2$ | CHF$_2$ | H | CH$_2$C(O)NHCH$_2$CF$_3$ |
| 3,5-(CF$_3$)$_2$ | CHF$_2$ | H | CH(CH$_3$)C(O)NHCH$_2$CF$_3$(D) |
| 3,5-(CF$_3$)$_2$ | CHF$_2$ | H | CH$_2$(D-22a) |
| 3,5-(CF$_3$)$_2$ | CHF$_2$ | H | CH$_2$(D-47a) |
| 3,5-(CF$_3$)$_2$ | CHF$_2$ | C(O)OCH$_3$ | CH$_2$(D-47a) |
| 3,5-(CF$_3$)$_2$ | CHF$_2$ | H | N(CH$_3$)Ph |
| 3,5-(CF$_3$)$_2$ | CHF$_2$ | H | (D-50c)Cl |
| 3,5-(CF$_3$)$_2$ | CHFCl | H | E-4a |
| 3,5-(CF$_3$)$_2$ | CHCl$_2$ | H | CH$_2$C(O)NHCH$_2$CF$_3$ |
| 3,5-(CF$_3$)$_2$ | CHFBr | H | CH$_2$(D-22a) |
| 3,5-(CF$_3$)$_2$ | CF$_3$ | H | H |
| 3,5-(CF$_3$)$_2$ | CF$_3$ | H | Et |
| 3,5-(CF$_3$)$_2$ | CF$_3$ | Et | Et |
| 3,5-(CF$_3$)$_2$ | CF$_3$ | H | c-Pr |
| 3,5-(CF$_3$)$_2$ | CF$_3$ | H | CH$_2$Pr-c |
| 3,5-(CF$_3$)$_2$ | CF$_3$ | H | c-Bu |
| 3,5-(CF$_3$)$_2$ | CF$_3$ | H | CH$_2$CH$_2$Cl |
| 3,5-(CF$_3$)$_2$ | CF$_3$ | H | CH$_2$CHF$_2$ |
| 3,5-(CF$_3$)$_2$ | CF$_3$ | H | CH$_2$CF$_3$ |
| 3,5-(CF$_3$)$_2$ | CF$_3$ | C(O)CH$_3$ | CH$_2$CF$_3$ |
| 3,5-(CF$_3$)$_2$ | CF$_3$ | H | CH$_2$CH$_2$CF$_3$ |
| 3,5-(CF$_3$)$_2$ | CF$_3$ | H | CH$_2$OCH$_3$ |
| 3,5-(CF$_3$)$_2$ | CF$_3$ | H | CH$_2$OEt |
| 3,5-(CF$_3$)$_2$ | CF$_3$ | C(O)CH$_3$ | CH$_2$OEt |
| 3,5-(CF$_3$)$_2$ | CF$_3$ | H | CH$_2$OCH$_2$CH$_2$Cl |
| 3,5-(CF$_3$)$_2$ | CF$_3$ | H | CH$_2$OCH$_2$CHF$_2$ |
| 3,5-(CF$_3$)$_2$ | CF$_3$ | H | CH$_2$OCH$_2$CF$_3$ |
| 3,5-(CF$_3$)$_2$ | CF$_3$ | C(O)CH$_3$ | CH$_2$OCH$_2$CF$_3$ |
| 3,5-(CF$_3$)$_2$ | CF$_3$ | H | CH(CH$_3$)OCH$_2$CF$_3$ |
| 3,5-(CF$_3$)$_2$ | CF$_3$ | H | CH(CF$_3$)OCH$_3$ |
| 3,5-(CF$_3$)$_2$ | CF$_3$ | H | CH$_2$CH$_2$OCH$_3$ |
| 3,5-(CF$_3$)$_2$ | CF$_3$ | H | CH$_2$CH$_2$OEt |
| 3,5-(CF$_3$)$_2$ | CF$_3$ | H | CH$_2$CH(OCH$_3$)$_2$ |
| 3,5-(CF$_3$)$_2$ | CF$_3$ | H | CH$_2$(E-4a) |
| 3,5-(CF$_3$)$_2$ | CF$_3$ | H | CH$_2$(E-5a) |
| 3,5-(CF$_3$)$_2$ | CF$_3$ | H | CH$_2$(E-10a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-$(CF_3)_2$ | $CF_3$ | H | $CH_2$(E-10b)$CH_3$ |
| 3,5-$(CF_3)_2$ | $CF_3$ | H | E-4a |
| 3,5-$(CF_3)_2$ | $CF_3$ | H | E-5a(R) |
| 3,5-$(CF_3)_2$ | $CF_3$ | H | $CH_2SCH_3$ |
| 3,5-$(CF_3)_2$ | $CF_3$ | H | $CH_2S(O)CH_3$ |
| 3,5-$(CF_3)_2$ | $CF_3$ | H | $CH_2SO_2CH_3$ |
| 3,5-$(CF_3)_2$ | $CF_3$ | H | $CH_2CH_2SO_2CH_3$ |
| 3,5-$(CF_3)_2$ | $CF_3$ | H | $CH_2CH_2SO_2Et$ |
| 3,5-$(CF_3)_2$ | $CF_3$ | H | $CH_2CH(CH_3)S(O)CH_3$ |
| 3,5-$(CF_3)_2$ | $CF_3$ | H | $CH_2CH(CH_3)SO_2CH_3$ |
| 3,5-$(CF_3)_2$ | $CF_3$ | H | $CH(CH_3)CH_2SO_2CH_3$ |
| 3,5-$(CF_3)_2$ | $CF_3$ | H | $CH_2NHCH_2CF_3$ |
| 3,5-$(CF_3)_2$ | $CF_3$ | H | $CH_2NHC(O)OCH_3$ |
| 3,5-$(CF_3)_2$ | $CF_3$ | H | $CH(CH_3)NHC(O)OCH_3$ |
| 3,5-$(CF_3)_2$ | $CF_3$ | H | $CH_2NHC(O)OCH_2CF_3$ |
| 3,5-$(CF_3)_2$ | $CF_3$ | H | $CH_2CH\!=\!NOCH_3$ |
| 3,5-$(CF_3)_2$ | $CF_3$ | H | $CH_2C(CH_3)\!=\!NOCH_3$ |
| 3,5-$(CF_3)_2$ | $CF_3$ | H | $CH_2CN$ |
| 3,5-$(CF_3)_2$ | $CF_3$ | H | $CH_2C(O)NHCH_3$ |
| 3,5-$(CF_3)_2$ | $CF_3$ | H | $CH_2C(O)N(CH_3)_2$ |
| 3,5-$(CF_3)_2$ | $CF_3$ | H | $CH_2C(O)NHEt$ |
| 3,5-$(CF_3)_2$ | $CF_3$ | H | $CH_2C(O)NHPr\text{-}n$ |
| 3,5-$(CF_3)_2$ | $CF_3$ | H | $CH_2C(O)NHPr\text{-}i$ |
| 3,5-$(CF_3)_2$ | $CF_3$ | H | $CH_2C(O)NHCH_2CH_2F$ |
| 3,5-$(CF_3)_2$ | $CF_3$ | H | $CH_2C(O)NHCH_2CH_2Cl$ |
| 3,5-$(CF_3)_2$ | $CF_3$ | H | $CH_2C(O)NHCH_2CF_3$ |
| 3,5-$(CF_3)_2$ | $CF_3$ | H | $CH_2C(O)NHCH_2CH\!=\!CH_2$ |
| 3,5-$(CF_3)_2$ | $CF_3$ | H | $CH_2C(O)NHCH_2C\!\equiv\!CH$ |
| 3,5-$(CF_3)_2$ | $CF_3$ | H | $CH(CH_3)C(O)NHEt$ |
| 3,5-$(CF_3)_2$ | $CF_3$ | H | $CH(CH_3)C(O)NHCH_2CF_3$ |
| 3,5-$(CF_3)_2$ | $CF_3$ | H | $CH(CH_3)C(O)NHCH_2CH_2Cl(D)$ |
| 3,5-$(CF_3)_2$ | $CF_3$ | H | $CH(CH_3)C(O)NHCH_2CF_3(D)$ |
| 3,5-$(CF_3)_2$ | $CF_3$ | H | $CH_2C(S)NH_2$ |
| 3,5-$(CF_3)_2$ | $CF_3$ | H | $CH_2CH\!=\!CH_2$ |
| 3,5-$(CF_3)_2$ | $CF_3$ | H | $CH_2CCl\!=\!CH_2$ |
| 3,5-$(CF_3)_2$ | $CF_3$ | H | $CH_2CCl\!=\!CHCl$ |
| 3,5-$(CF_3)_2$ | $CF_3$ | H | $CH_2C\!\equiv\!CH$ |
| 3,5-$(CF_3)_2$ | $CF_3$ | H | $CH(CH_3)Ph(R)$ |
| 3,5-$(CF_3)_2$ | $CF_3$ | H | $CH(CF_3)Ph$ |
| 3,5-$(CF_3)_2$ | $CF_3$ | H | $CH(CN)Ph$ |
| 3,5-$(CF_3)_2$ | $CF_3$ | H | $CH_2(Ph\text{-}4\text{-}OCH_3)$ |
| 3,5-$(CF_3)_2$ | $CF_3$ | H | $CH_2(Ph\text{-}4\text{-}NO_2)$ |
| 3,5-$(CF_3)_2$ | $CF_3$ | H | $CH_2(Ph\text{-}4\text{-}CN)$ |
| 3,5-$(CF_3)_2$ | $CF_3$ | H | $CH_2$(D-1a) |
| 3,5-$(CF_3)_2$ | $CF_3$ | H | $CH_2$(D-16b)Cl |
| 3,5-$(CF_3)_2$ | $CF_3$ | H | $CH_2$(D-17a)$CH_3$ |
| 3,5-$(CF_3)_2$ | $CF_3$ | H | $CH_2$(D-17b)Cl |
| 3,5-$(CF_3)_2$ | $CF_3$ | H | $CH_2$(D-21a) |
| 3,5-$(CF_3)_2$ | $CF_3$ | H | $CH_2$(D-22a) |
| 3,5-$(CF_3)_2$ | $CF_3$ | $C(O)CH_3$ | $CH_2$(D-22a) |
| 3,5-$(CF_3)_2$ | $CF_3$ | $C(O)Et$ | $CH_2$(D-22a) |
| 3,5-$(CF_3)_2$ | $CF_3$ | H | $CH_2$(D-28a) |
| 3,5-$(CF_3)_2$ | $CF_3$ | H | $CH_2$(D-29b)$CH_3$ |
| 3,5-$(CF_3)_2$ | $CF_3$ | H | $CH_2$(D-34a) |
| 3,5-$(CF_3)_2$ | $CF_3$ | H | $CH_2$(D-35a) |
| 3,5-$(CF_3)_2$ | $CF_3$ | H | $CH_2$(D-38a) |
| 3,5-$(CF_3)_2$ | $CF_3$ | H | $CH_2$(D-47a) |
| 3,5-$(CF_3)_2$ | $CF_3$ | Et | $CH_2$(D-47a) |
| 3,5-$(CF_3)_2$ | $CF_3$ | $CH_2OCH_3$ | $CH_2$(D-47a) |
| 3,5-$(CF_3)_2$ | $CF_3$ | $CH_2CN$ | $CH_2$(D-47a) |
| 3,5-$(CF_3)_2$ | $CF_3$ | $CH_2C\!\equiv\!CH$ | $CH_2$(D-47a) |
| 3,5-$(CF_3)_2$ | $CF_3$ | $C(O)CH_3$ | $CH_2$(D-47a) |
| 3,5-$(CF_3)_2$ | $CF_3$ | $C(O)Et$ | $CH_2$(D-47a) |
| 3,5-$(CF_3)_2$ | $CF_3$ | $C(O)Pr\text{-}n$ | $CH_2$(D-47a) |
| 3,5-$(CF_3)_2$ | $CF_3$ | $C(O)Pr\text{-}i$ | $CH_2$(D-47a) |
| 3,5-$(CF_3)_2$ | $CF_3$ | $C(O)Pr\text{-}c$ | $CH_2$(D-47a) |
| 3,5-$(CF_3)_2$ | $CF_3$ | $C(O)Bu\text{-}t$ | $CH_2$(D-47a) |
| 3,5-$(CF_3)_2$ | $CF_3$ | $C(O)CH_2OCH_3$ | $CH_2$(D-47a) |
| 3,5-$(CF_3)_2$ | $CF_3$ | $C(O)CH\!=\!CH_2$ | $CH_2$(D-47a) |
| 3,5-$(CF_3)_2$ | $CF_3$ | $C(O)OCH_3$ | $CH_2$(D-47a) |
| 3,5-$(CF_3)_2$ | $CF_3$ | $C(O)OEt$ | $CH_2$(D-47a) |
| 3,5-$(CF_3)_2$ | $CF_3$ | $C(O)OCH_2CH_2OCH_3$ | $CH_2$(D-47a) |
| 3,5-$(CF_3)_2$ | $CF_3$ | $C(O)OCH_2CH\!=\!CH_2$ | $CH_2$(D-47a) |
| 3,5-$(CF_3)_2$ | $CF_3$ | H | $CH(CH_3)$(D-47a) |
| 3,5-$(CF_3)_2$ | $CF_3$ | H | $CH_2$(D-50a) |
| 3,5-$(CF_3)_2$ | $CF_3$ | H | $NHCH_2CF_3$ |
| 3,5-$(CF_3)_2$ | $CF_3$ | H | $NHC(O)OCH_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-$(CF_3)_2$ | $CF_3$ | H | $N(CH_3)Ph$ |
| 3,5-$(CF_3)_2$ | $CF_3$ | H | $N(CH_2CH=CH_2)Ph$ |
| 3,5-$(CF_3)_2$ | $CF_3$ | H | $N(CH_2C\equiv CH)Ph$ |
| 3,5-$(CF_3)_2$ | $CF_3$ | H | $N(CH_3)(D-47a)$ |
| 3,5-$(CF_3)_2$ | $CF_3$ | H | $NH(D-50a)$ |
| 3,5-$(CF_3)_2$ | $CF_3$ | $CH_3$ | $NH(D-50a)$ |
| 3,5-$(CF_3)_2$ | $CF_3$ | H | $N(CH_3)(D-50a)$ |
| 3,5-$(CF_3)_2$ | $CF_3$ | H | $N(Et)(D-50a)$ |
| 3,5-$(CF_3)_2$ | $CF_3$ | $C(O)OCH_3$ | $C(O)N(CH_3)_2$ |
| 3,5-$(CF_3)_2$ | $CF_3$ | H | $C(O)NHEt$ |
| 3,5-$(CF_3)_2$ | $CF_3$ | $CH_3$ | $C(O)NHEt$ |
| 3,5-$(CF_3)_2$ | $CF_3$ | H | $C(O)NHCH_2CH_2Cl$ |
| 3,5-$(CF_3)_2$ | $CF_3$ | H | $C(O)NHCH_2CF_3$ |
| 3,5-$(CF_3)_2$ | $CF_3$ | H | $C(O)NHCH_2(Ph-4-F)$ |
| 3,5-$(CF_3)_2$ | $CF_3$ | H | $C(S)NHCH_3$ |
| 3,5-$(CF_3)_2$ | $CF_3$ | H | Ph-4-F |
| 3,5-$(CF_3)_2$ | $CF_3$ | H | Ph-4-CN |
| 3,5-$(CF_3)_2$ | $CF_3$ | H | Ph-2,4-$F_2$ |
| 3,5-$(CF_3)_2$ | $CF_3$ | H | Ph-2,6-$F_2$ |
| 3,5-$(CF_3)_2$ | $CF_3$ | H | Ph-2,4,6-$F_3$ |
| 3,5-$(CF_3)_2$ | $CF_3$ | H | $(D-13b)CH_3$ |
| 3,5-$(CF_3)_2$ | $CF_3$ | H | $(D-15a)CH_3$ |
| 3,5-$(CF_3)_2$ | $CF_3$ | H | D-21a |
| 3,5-$(CF_3)_2$ | $CF_3$ | H | (D-47d)Cl |
| 3,5-$(CF_3)_2$ | $CF_3$ | H | (D-47d)Br |
| 3,5-$(CF_3)_2$ | $CF_3$ | H | (D-47d)CN |
| 3,5-$(CF_3)_2$ | $CF_3$ | H | (D-47e)Br |
| 3,5-$(CF_3)_2$ | $CF_3$ | H | (D-48e)Cl |
| 3,5-$(CF_3)_2$ | $CF_3$ | H | D-50a |
| 3,5-$(CF_3)_2$ | $CF_3$ | H | (D-50c)Cl |
| 3,5-$(CF_3)_2$ | $CF_3$ | H | (D-50c)Br |
| 3,5-$(CF_3)_2$ | $CF_3$ | H | D-51a |
| 3,5-$(CF_3)_2$ | $CF_3$ | H | D-52a |
| 3,5-$(CF_3)_2$ | $CF_3$ | H | D-53a |
| 3,5-$(CF_3)_2$ | $CF_3$ | H | (D-54b)Cl |
| 3,5-$(CF_3)_2$ | $CF_2Cl$ | H | c-Pr |
| 3,5-$(CF_3)_2$ | $CF_2Cl$ | H | $CH_2Pr$-c |
| 3,5-$(CF_3)_2$ | $CF_2Cl$ | H | c-Bu |
| 3,5-$(CF_3)_2$ | $CF_2Cl$ | H | $CH_2CF_3$ |
| 3,5-$(CF_3)_2$ | $CF_2Cl$ | $C(O)CH_3$ | $CH_2CF_3$ |
| 3,5-$(CF_3)_2$ | $CF_2Cl$ | H | $CH_2CH_2CF_3$ |
| 3,5-$(CF_3)_2$ | $CF_2Cl$ | H | $CH_2OCH_3$ |
| 3,5-$(CF_3)_2$ | $CF_2Cl$ | H | $CH_2OEt$ |
| 3,5-$(CF_3)_2$ | $CF_2Cl$ | $C(O)CH_3$ | $CH_2OEt$ |
| 3,5-$(CF_3)_2$ | $CF_2Cl$ | H | $CH_2OCH_2CF_3$ |
| 3,5-$(CF_3)_2$ | $CF_2Cl$ | $C(O)CH_3$ | $CH_2OCH_2CF_3$ |
| 3,5-$(CF_3)_2$ | $CF_2Cl$ | H | $CH_2CH_2OCH_3$ |
| 3,5-$(CF_3)_2$ | $CF_2Cl$ | H | $CH_2(E-10a)$ |
| 3,5-$(CF_3)_2$ | $CF_2Cl$ | H | E-4a |
| 3,5-$(CF_3)_2$ | $CF_2Cl$ | H | E-5a(R) |
| 3,5-$(CF_3)_2$ | $CF_2Cl$ | H | $CH_2CH=NOCH_3$ |
| 3,5-$(CF_3)_2$ | $CF_2Cl$ | H | $CH_2C(O)NHCH_2CH_2Cl$ |
| 3,5-$(CF_3)_2$ | $CF_2Cl$ | H | $CH_2C(O)NHCH_2CF_3$ |
| 3,5-$(CF_3)_2$ | $CF_2Cl$ | H | $CH(CH_3)C(O)NHEt$ |
| 3,5-$(CF_3)_2$ | $CF_2Cl$ | H | $CH(CH_3)C(O)NHCH_2CF_3$ |
| 3,5-$(CF_3)_2$ | $CF_2Cl$ | H | $CH(CH_3)C(O)NHCH_2CF_3(D)$ |
| 3,5-$(CF_3)_2$ | $CF_2Cl$ | H | $CH_2CH=CH_2$ |
| 3,5-$(CF_3)_2$ | $CF_2Cl$ | H | $CH_2CCl=CH_2$ |
| 3,5-$(CF_3)_2$ | $CF_2Cl$ | H | $CH(CH_3)Ph(R)$ |
| 3,5-$(CF_3)_2$ | $CF_2Cl$ | H | $CH_2(Ph-4-NO_2)$ |
| 3,5-$(CF_3)_2$ | $CF_2Cl$ | H | $CH_2(Ph-4-CN)$ |
| 3,5-$(CF_3)_2$ | $CF_2Cl$ | H | $CH_2(D-17b)Cl$ |
| 3,5-$(CF_3)_2$ | $CF_2Cl$ | H | $CH_2(D-21a)$ |
| 3,5-$(CF_3)_2$ | $CF_2Cl$ | H | $CH_2(D-22a)$ |
| 3,5-$(CF_3)_2$ | $CF_2Cl$ | $C(O)CH_3$ | $CH_2(D-22a)$ |
| 3,5-$(CF_3)_2$ | $CF_2Cl$ | $C(O)Et$ | $CH_2(D-22a)$ |
| 3,5-$(CF_3)_2$ | $CF_2Cl$ | H | $CH_2(D-47a)$ |
| 3,5-$(CF_3)_2$ | $CF_2Cl$ | $CH_2OCH_3$ | $CH_2(D-47a)$ |
| 3,5-$(CF_3)_2$ | $CF_2Cl$ | $CH_2CN$ | $CH_2(D-47a)$ |
| 3,5-$(CF_3)_2$ | $CF_2Cl$ | $C(O)CH_3$ | $CH_2(D-47a)$ |
| 3,5-$(CF_3)_2$ | $CF_2Cl$ | $C(O)Et$ | $CH_2(D-47a)$ |
| 3,5-$(CF_3)_2$ | $CF_2Cl$ | $C(O)Pr$-c | $CH_2(D-47a)$ |
| 3,5-$(CF_3)_2$ | $CF_2Cl$ | $C(O)OCH_3$ | $CH_2(D-47a)$ |
| 3,5-$(CF_3)_2$ | $CF_2Cl$ | H | $CH(CH_3)(D-47a)$ |
| 3,5-$(CF_3)_2$ | $CF_2Cl$ | H | $CH_2(D-50a)$ |
| 3,5-$(CF_3)_2$ | $CF_2Cl$ | H | $N(CH_3)Ph$ |
| 3,5-$(CF_3)_2$ | $CF_2Cl$ | H | $N(CH_3)(D-50a)$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-(CF$_3$)$_2$ | CF$_2$Cl | C(O)OCH$_3$ | C(O)N(CH$_3$)$_2$ |
| 3,5-(CF$_3$)$_2$ | CF$_2$Cl | H | C(O)NHEt |
| 3,5-(CF$_3$)$_2$ | CF$_2$Cl | CH$_3$ | C(O)NHEt |
| 3,5-(CF$_3$)$_2$ | CF$_2$Cl | H | C(O)NHCH$_2$CH$_2$Cl |
| 3,5-(CF$_3$)$_2$ | CF$_2$Cl | H | C(O)NHCH$_2$(Ph-4-F) |
| 3,5-(CF$_3$)$_2$ | CF$_2$Cl | H | Ph-4-CN |
| 3,5-(CF$_3$)$_2$ | CF$_2$Cl | H | Ph-2,4-F$_2$ |
| 3,5-(CF$_3$)$_2$ | CF$_2$Cl | H | (D-15a)CH$_3$ |
| 3,5-(CF$_3$)$_2$ | CF$_2$Cl | H | (D-47d)CN |
| 3,5-(CF$_3$)$_2$ | CF$_2$Cl | H | (D-47e)Br |
| 3,5-(CF$_3$)$_2$ | CF$_2$Cl | H | D-50a |
| 3,5-(CF$_3$)$_2$ | CF$_2$Cl | H | (D-50c)Cl |
| 3,5-(CF$_3$)$_2$ | CF$_2$Cl | H | (D-50c)Br |
| 3,5-(CF$_3$)$_2$ | CF$_2$Cl | H | D-52a |
| 3,5-(CF$_3$)$_2$ | CF$_2$Cl | H | D-53a |
| 3,5-(CF$_3$)$_2$ | CF$_2$Br | H | CH$_2$CF$_3$ |
| 3,5-(CF$_3$)$_2$ | CF$_2$Br | H | CH$_2$OCH$_2$CF$_3$ |
| 3,5-(CF$_3$)$_2$ | CF$_2$Br | H | E-4a |
| 3,5-(CF$_3$)$_2$ | CF$_2$Br | H | OH$_2$C(O)NHCH$_2$CF$_3$ |
| 3,5-(CF$_3$)$_2$ | CF$_2$Br | H | CH(CH$_3$)C(O)NHCH$_2$CF$_3$(D) |
| 3,5-(CF$_3$)$_2$ | CF$_2$Br | H | CH$_2$(D-22a) |
| 3,5-(CF$_3$)$_2$ | CF$_2$Br | H | CH$_2$(D-47a) |
| 3,5-(CF$_3$)$_2$ | CF$_2$Br | C(O)OCH$_3$ | CH$_2$(D-47a) |
| 3,5-(CF$_3$)$_2$ | CF$_2$Br | H | N(CH$_3$)Ph |
| 3,5-(CF$_3$)$_2$ | CF$_2$Br | H | (D-50c)Cl |
| 3,5-(CF$_3$)$_2$ | CF$_2$CHF$_2$ | H | CH$_2$CF$_3$ |
| 3,5-(CF$_3$)$_2$ | CF$_2$CHF$_2$ | H | CH$_2$OCH$_2$CF$_3$ |
| 3,5-(CF$_3$)$_2$ | CF$_2$CHF$_2$ | H | E-4a |
| 3,5-(CF$_3$)$_2$ | CF$_2$CHF$_2$ | H | OH$_2$C(O)NHCH$_2$CF$_3$ |
| 3,5-(CF$_3$)$_2$ | CF$_2$CHF$_2$ | H | CH(CH$_3$)C(O)NHCH$_2$CF$_3$(D) |
| 3,5-(CF$_3$)$_2$ | CF$_2$CHF$_2$ | H | CH$_2$(D-22a) |
| 3,5-(CF$_3$)$_2$ | CF$_2$CHF$_2$ | H | CH$_2$(D-47a) |
| 3,5-(CF$_3$)$_2$ | CF$_2$CHF$_2$ | C(O)OCH$_3$ | CH$_2$(D-47a) |
| 3,5-(CF$_3$)$_2$ | CF$_2$CHF$_2$ | H | N(CH$_3$)Ph |
| 3,5-(CF$_3$)$_2$ | CF$_2$CHF$_2$ | H | (D-50c)Cl |
| 3,5-(CF$_3$)$_2$ | CF$_2$CF$_3$ | H | CH$_2$(D-47a) |
| 3,5-(CF$_3$)$_2$ | CF$_2$OCH$_3$ | C(O)OCH$_3$ | CH$_2$(D-47a) |
| 3,5-(CF$_3$)$_2$ | CF$_2$SCH$_3$ | H | N(CH$_3$)Ph |
| 3,5-(CF$_3$)$_2$ | T-3 | H | (D-50c)Cl |
| 3-Cl-5-CF$_2$CF$_3$ | CF$_3$ | H | CH$_2$CF$_3$ |
| 3-Cl-5-CF$_2$CF$_3$ | CF$_3$ | H | CH$_2$OCH$_2$CF$_3$ |
| 3-Cl-5-CF$_2$CF$_3$ | CF$_3$ | H | E-4a |
| 3-Cl-5-CF$_2$CF$_3$ | CF$_3$ | H | CH$_2$C(O)NHCH$_2$CF$_3$ |
| 3-Cl-5-CF$_2$CF$_3$ | CF$_3$ | H | CH(CH$_3$)C(O)NHCH$_2$CF$_3$(D) |
| 3-Cl-5-CF$_2$CF$_3$ | CF$_3$ | H | CH$_2$(D-22a) |
| 3-Cl-5-CF$_2$CF$_3$ | CF$_3$ | H | CH$_2$(D-47a) |
| 3-Cl-5-CF$_2$CF$_3$ | CF$_3$ | C(O)OCH$_3$ | CH$_2$(D-47a) |
| 3-Cl-5-CF$_2$CF$_3$ | CF$_3$ | H | N(CH$_3$)Ph |
| 3-Cl-5-CF$_2$CF$_3$ | CF$_3$ | H | (D-50c)Cl |
| 3-Br-5-CF$_2$CF$_3$ | CF$_3$ | H | CH$_2$CF$_3$ |
| 3-Br-5-CF$_2$CF$_3$ | CF$_3$ | H | CH$_2$OCH$_2$CF$_3$ |
| 3-Br-5-CF$_2$CF$_3$ | CF$_3$ | H | E-4a |
| 3-Br-5-CF$_2$CF$_3$ | CF$_3$ | H | CH$_2$C(O)NHCH$_2$CF$_3$ |
| 3-Br-5-CF$_2$CF$_3$ | CF$_3$ | H | CH(CH$_3$)C(O)NHCH$_2$CF$_3$(D) |
| 3-Br-5-CF$_2$CF$_3$ | CF$_3$ | H | CH$_2$(D-22a) |
| 3-Br-5-CF$_2$CF$_3$ | CF$_3$ | H | CH$_2$(D-47a) |
| 3-Br-5-CF$_2$CF$_3$ | CF$_3$ | C(O)OCH$_3$ | CH$_2$(D-47a) |
| 3-Br-5-CF$_2$CF$_3$ | CF$_3$ | H | N(CH$_3$)Ph |
| 3-Br-5-CF$_2$CF$_3$ | CF$_3$ | H | (D-50c)Cl |
| 3-CH$_3$-5-CF$_2$CF$_3$ | CF$_3$ | H | CH$_2$CF$_3$ |
| 3-CH$_3$-5-CF$_2$CF$_3$ | CF$_3$ | H | E-4a |
| 3-CH$_3$-5-CF$_2$CF$_3$ | CF$_3$ | H | CH$_2$C(O)NHCH$_2$CF$_3$ |
| 3-CH$_3$-5-CF$_2$CF$_3$ | CF$_3$ | H | CH$_2$(D-22a) |
| 3-CH$_3$-5-CF$_2$CF$_3$ | CF$_3$ | H | CH$_2$(D-47a) |
| 3-CH$_3$-5-CF$_2$CF$_3$ | CF$_3$ | H | (D-50c)Cl |
| 3-Cl-5-CF$_2$CF$_2$CF$_3$ | CF$_3$ | H | CH$_2$CF$_3$ |
| 3-Cl-5-CF$_2$CF$_2$CF$_3$ | CF$_3$ | H | E-4a |
| 3-Cl-5-CF$_2$CF$_2$CF$_3$ | CF$_3$ | H | CH$_2$C(O)NHCH$_2$CF$_3$ |
| 3-Cl-5-CF$_2$CF$_2$CF$_3$ | CF$_3$ | H | CH$_2$(D-22a) |
| 3-Cl-5-CF$_2$CF$_2$CF$_3$ | CF$_3$ | H | CH$_2$(D-47a) |
| 3-Cl-5-CF$_2$CF$_2$CF$_3$ | CF$_3$ | H | (D-50c)Cl |
| 3-Br-5-CF$_2$CF$_2$CF$_3$ | CF$_3$ | H | CH$_2$CF$_3$ |
| 3-Br-5-CF$_2$CF$_2$CF$_3$ | CF$_3$ | H | E-4a |
| 3-Br-5-CF$_2$CF$_2$CF$_3$ | CF$_3$ | H | CH$_2$C(O)NHCH$_2$CF$_3$ |
| 3-Br-5-CF$_2$CF$_2$CF$_3$ | CF$_3$ | H | CH$_2$(D-22a) |
| 3-Br-5-CF$_2$CF$_2$CF$_3$ | CF$_3$ | H | CH$_2$(D-47a) |
| 3-Br-5-CF$_2$CF$_2$CF$_3$ | CF$_3$ | H | (D-50c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CH$_3$-5-CF$_2$CF$_2$CF$_3$ | CF$_3$ | H | CH$_2$CF$_3$ |
| 3-CH$_3$-5-CF$_2$CF$_2$CF$_3$ | CF$_3$ | H | E-4a |
| 3-CH$_3$-5-CF$_2$CF$_2$CF$_3$ | CF$_3$ | H | CH$_2$C(O)NHCH$_2$CF$_3$ |
| 3-CH$_3$-5-CF$_2$CF$_2$CF$_3$ | CF$_3$ | H | CH$_2$(D-22a) |
| 3-CH$_3$-5-CF$_2$CF$_2$CF$_3$ | CF$_3$ | H | CH$_2$(D-47a) |
| 3-CH$_3$-5-CF$_2$CF$_2$CF$_3$ | CF$_3$ | H | (D-50c)Cl |
| 3-Cl-5-CF(CF$_3$)$_2$ | CF$_3$ | H | CH$_2$CF$_3$ |
| 3-Cl-5-CF(CF$_3$)$_2$ | CF$_3$ | H | E-4a |
| 3-Cl-5-CF(CF$_3$)$_2$ | CF$_3$ | H | CH$_2$C(O)NHCH$_2$CF$_3$ |
| 3-Cl-5-CF(CF$_3$)$_2$ | CF$_3$ | H | CH$_2$(D-22a) |
| 3-Cl-5-CF(CF$_3$)$_2$ | CF$_3$ | H | CH$_2$(D-47a) |
| 3-Cl-5-CF(CF$_3$)$_2$ | CF$_3$ | H | (D-50c)Cl |
| 3-Br-5-CF(CF$_3$)$_2$ | CF$_3$ | H | CH$_2$CF$_3$ |
| 3-Br-5-CF(CF$_3$)$_2$ | CF$_3$ | H | E-4a |
| 3-Br-5-CF(CF$_3$)$_2$ | CF$_3$ | H | CH$_2$C(O)NHCH$_2$CF$_3$ |
| 3-Br-5-CF(CF$_3$)$_2$ | CF$_3$ | H | CH$_2$(D-22a) |
| 3-Br-5-CF(CF$_3$)$_2$ | CF$_3$ | H | CH$_2$(D-47a) |
| 3-Br-5-CF(CF$_3$)$_2$ | CF$_3$ | H | (D-50c)Cl |
| 3-CH$_3$-5-CF(CF$_3$)$_2$ | CF$_3$ | H | CH$_2$CF$_3$ |
| 3-CH$_3$-5-CF(CF$_3$)$_2$ | CF$_3$ | H | E-4a |
| 3-CH$_3$-5-CF(CF$_3$)$_2$ | CF$_3$ | H | CH$_2$C(O)NHCH$_2$CF$_3$ |
| 3-CH$_3$-5-CF(CF$_3$)$_2$ | CF$_3$ | H | CH$_2$(D-22a) |
| 3-CH$_3$-5-CF(CF$_3$)$_2$ | CF$_3$ | H | CH$_2$(D-47a) |
| 3-CH$_3$-5-CF(CF$_3$)$_2$ | CF$_3$ | H | (D-50c)Cl |
| 3-Cl-5-CH$_2$OCH$_3$ | CF$_3$ | H | CH$_2$CF$_3$ |
| 3,5-(CH$_2$OCH$_3$)$_2$ | CF$_3$ | H | CH$_2$OCH$_2$CF$_3$ |
| 3-Cl-5-CH$_2$OCH$_2$CF$_3$ | CF$_3$ | H | E-4a |
| 3-Cl-5-C(CF$_3$)$_2$OH | CF$_3$ | H | CH$_2$CF$_3$ |
| 3-Cl-5-C(CF$_3$)$_2$OH | CF$_3$ | H | E-4a |
| 3-Cl-5-C(CF$_3$)$_2$OH | CF$_3$ | H | CH$_2$C(O)NHCH$_2$CF$_3$ |
| 3-Cl-5-C(CF$_3$)$_2$OH | CF$_3$ | H | CH$_2$(D-22a) |
| 3-Cl-5-C(CF$_3$)$_2$OH | CF$_3$ | H | CH$_2$(D-47a) |
| 3-Cl-5-C(CF$_3$)$_2$OH | CF$_3$ | H | (D-50c)Cl |
| 3-Br-5-C(CF$_3$)$_2$OH | CF$_3$ | H | CH$_2$CF$_3$ |
| 3-Br-5-C(CF$_3$)$_2$OH | CF$_3$ | H | E-4a |
| 3-Br-5-C(CF$_3$)$_2$OH | CF$_3$ | H | CH$_2$C(O)NHCH$_2$CF$_3$ |
| 3-Br-5-C(CF$_3$)$_2$OH | CF$_3$ | H | CH$_2$(D-22a) |
| 3-Br-5-C(CF$_3$)$_2$OH | CF$_3$ | H | CH$_2$(D-47a) |
| 3-Br-5-C(CF$_3$)$_2$OH | CF$_3$ | H | (D-50c)Cl |
| 3-CH$_3$-5-C(CF$_3$)$_2$OH | CF$_3$ | H | CH$_2$CF$_3$ |
| 3-CH$_3$-5-C(CF$_3$)$_2$OH | CF$_3$ | H | E-4a |
| 3-CH$_3$-5-C(CF$_3$)$_2$OH | CF$_3$ | H | CH$_2$C(O)NHCH$_2$CF$_3$ |
| 3-CH$_3$-5-C(CF$_3$)$_2$OH | CF$_3$ | H | CH$_2$(D-22a) |
| 3-CH$_3$-5-C(CF$_3$)$_2$OH | CF$_3$ | H | CH$_2$(D-47a) |
| 3-CH$_3$-5-C(CF$_3$)$_2$OH | CF$_3$ | H | (D-50c)Cl |
| 3,5-[C(CF$_3$)$_2$OH]$_2$ | CF$_3$ | H | CH$_2$C(O)NHCH$_2$CF$_3$ |
| 3-Cl-5-C(CF$_3$)$_2$OCH$_3$ | CF$_3$ | H | CH$_2$CF$_3$ |
| 3-Cl-5-C(CF$_3$)$_2$OCH$_3$ | CF$_3$ | H | E-4a |
| 3-Cl-5-C(CF$_3$)$_2$OCH$_3$ | CF$_3$ | H | CH$_2$C(O)NHCH$_2$CF$_3$ |
| 3-Cl-5-C(CF$_3$)$_2$OCH$_3$ | CF$_3$ | H | CH$_2$(D-22a) |
| 3-Cl-5-C(CF$_3$)$_2$OCH$_3$ | CF$_3$ | H | CH$_2$(D-47a) |
| 3-Cl-5-C(CF$_3$)$_2$OCH$_3$ | CF$_3$ | H | (D-50c)Cl |
| 3-Br-5-C(CF$_3$)$_2$OCH$_3$ | CF$_3$ | H | CH$_2$CF$_3$ |
| 3-Br-5-C(CF$_3$)$_2$OCH$_3$ | CF$_3$ | H | E-4a |
| 3-Br-5-C(CF$_3$)$_2$OCH$_3$ | CF$_3$ | H | CH$_2$C(O)NHCH$_2$CF$_3$ |
| 3-Br-5-C(CF$_3$)$_2$OCH$_3$ | CF$_3$ | H | CH$_2$(D-22a) |
| 3-Br-5-C(CF$_3$)$_2$OCH$_3$ | CF$_3$ | H | CH$_2$(D-47a) |
| 3-Br-5-C(CF$_3$)$_2$OCH$_3$ | CF$_3$ | H | (D-50c)Cl |
| 3-CH$_3$-5-C(CF$_3$)$_2$OCH$_3$ | CF$_3$ | H | CH$_2$CF$_3$ |
| 3-CH$_3$-5-C(CF$_3$)$_2$OCH$_3$ | CF$_3$ | H | E-4a |
| 3-CH$_3$-5-C(CF$_3$)$_2$OCH$_3$ | CF$_3$ | H | CH$_2$C(O)NHCH$_2$CF$_3$ |
| 3-CH$_3$-5-C(CF$_3$)$_2$OCH$_3$ | CF$_3$ | H | CH$_2$(D-22a) |
| 3-CH$_3$-5-C(CF$_3$)$_2$OCH$_3$ | CF$_3$ | H | CH$_2$(D-47a) |
| 3-CH$_3$-5-C(CF$_3$)$_2$OCH$_3$ | CF$_3$ | H | (D-50c)Cl |
| 3,5-[C(CF$_3$)$_2$OCH$_3$]$_2$ | CF$_3$ | H | CH$_2$(D-22a) |
| 3-CF$_3$-5-CH$_2$SCH$_3$ | CF$_3$ | H | CH$_2$(D-47a) |
| 3-CF$_3$-5-CH$_2$S(O)CH$_3$ | CF$_3$ | C(O)OCH$_3$ | CH$_2$(D-47a) |
| 3-CF$_3$-5-CH$_2$SO$_2$CH$_3$ | CF$_3$ | H | N(CH$_3$)Ph |
| 3-OCH$_3$-4-F | CF$_3$ | H | (D-50c)Cl |
| 2-F-4-OCH$_3$ | CF$_3$ | H | CH$_2$CF$_3$ |
| 2-F-5-OCH$_3$ | CF$_3$ | H | CH$_2$OCH$_2$CF$_3$ |
| 3-Cl-4-OCH$_3$ | CF$_3$ | H | E-4a |
| 3-Cl-5-OCH$_3$ | CF$_3$ | H | CH$_2$C(O)NHCH$_2$CF$_3$ |
| 3-Br-5-OCH$_3$ | CF$_3$ | H | CH$_2$CF$_3$ |
| 3-Br-5-OCH$_3$ | CF$_3$ | H | E-4a |
| 3-Br-5-OCH$_2$ | CF$_3$ | H | CH$_2$C(O)NHCH$_2$CF$_3$ |
| 3-Br-5-OCH$_3$ | CF$_3$ | H | CH$_2$(D-22a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Br-5-OCH$_3$ | CF$_3$ | H | CH$_2$(D-47a) |
| 3-Br-5-OCH$_3$ | CF$_3$ | H | (D-50c)Cl |
| 3-CH$_3$-5-OCH$_3$ | CF$_3$ | H | CH$_2$(D-22a) |
| 3-CF$_3$-5-OCH$_3$ | CF$_3$ | H | CH$_2$CF$_3$ |
| 3-CF$_3$-5-OCH$_3$ | CF$_3$ | C(O)CH$_3$ | CH$_2$CF$_3$ |
| 3-CF$_3$-5-OCH$_3$ | CF$_3$ | H | CH$_2$OCH$_2$CF$_3$ |
| 3-CF$_3$-5-OCH$_3$ | CF$_3$ | H | E-4a |
| 3-CF$_3$-5-OCH$_3$ | CF$_3$ | H | CH$_2$C(O)NHCH$_2$CF$_3$ |
| 3-CF$_3$-5-OCH$_3$ | CF$_3$ | H | CH(CH$_3$)C(O)NHCH$_2$CF$_3$(D) |
| 3-CF$_3$-5-OCH$_3$ | CF$_3$ | H | CH(CH$_3$)Ph(R) |
| 3-CF$_3$-5-OCH$_3$ | CF$_3$ | H | CH$_2$(D-22a) |
| 3-CF$_3$-5-OCH$_3$ | CF$_3$ | H | CH$_2$(D-47a) |
| 3-CF$_3$-5-OCH$_3$ | CF$_3$ | CH$_2$CN | CH$_2$(D-47a) |
| 3-CF$_3$-5-OCH$_3$ | CF$_3$ | C(O)Et | CH$_2$(D-47a) |
| 3-CF$_3$-5-OCH$_3$ | CF$_3$ | C(O)OCH$_3$ | CH$_2$(D-47a) |
| 3-CF$_3$-5-OCH$_3$ | CF$_3$ | H | N(CH$_3$)Ph |
| 3-CF$_3$-5-OCH$_3$ | CF$_3$ | H | (D-50c)Cl |
| 3-CF$_3$-5-OCH$_3$ | CF$_3$ | H | D-52a |
| 3-CF$_3$-5-OCH$_3$ | CF$_2$Cl | H | CH$_2$CF$_3$ |
| 3-CF$_3$-5-OCH$_3$ | CF$_2$Cl | H | E-4a |
| 3-CF$_3$-5-OCH$_3$ | CF$_2$Cl | H | CH$_2$C(O)NHCH$_2$CF$_3$ |
| 3-CF$_3$-5-OCH$_3$ | CF$_2$Cl | H | CH$_2$(D-22a) |
| 3-CF$_3$-5-OCH$_3$ | CF$_2$Cl | H | CH$_2$(D-47a) |
| 3-CF$_3$-5-OCH$_3$ | CF$_2$Cl | H | (D-50c)Cl |
| 3-CH$_2$OCH$_3$-5-OCH$_3$ | CF$_3$ | H | CH$_2$(D-47a) |
| 3-CH$_2$SCH$_3$-5-OCH$_3$ | CF$_3$ | C(O)OCH$_3$ | CH$_2$(D-47a) |
| 3-OCH$_3$-4-OH | CF$_3$ | H | N(CH$_3$)Ph |
| 2,3-(OCH$_3$)$_2$ | CF$_3$ | H | (D-50c)Cl |
| 2,4-(OCH$_3$)$_2$ | CF$_3$ | H | CH$_2$CF$_3$ |
| 2,6-(OCH$_3$)$_2$ | CF$_3$ | H | CH$_2$OCH$_2$CF$_3$ |
| 3,4-(OCH$_3$)$_2$ | CF$_3$ | H | E-4a |
| 3,5-(OCH$_3$)$_2$ | CF$_3$ | H | CH$_2$C(O)NHCH$_2$CF$_3$ |
| 3-OEt-4-Cl | CF$_3$ | H | CH$_2$(D-22a) |
| 3,5-(OEt)$_2$ | CF$_3$ | H | CH$_2$(D-47a) |
| 3,5-(OPr-n)$_2$ | CF$_3$ | C(O)OCH$_3$ | CH$_2$(D-47a) |
| 3-OCH$_2$O-4 | CF$_3$ | H | CH$_2$CF$_3$ |
| 3-OCH$_2$O-4 | CF$_3$ | CH$_3$ | CH$_2$Ph |
| 3-OCH$_2$O-4 | CF$_3$ | H | N(CH$_3$)Ph |
| 3-OCH$_2$CH$_2$O-4 | CF$_3$ | H | (D-50c)Cl |
| 3-F-4-OCHF$_2$ | CF$_3$ | H | CH$_2$CF$_3$ |
| 3-Cl-4-OCHF$_2$ | CF$_3$ | H | CH$_2$OCH$_2$CF$_3$ |
| 3-Cl-5-OCHF$_2$ | CHF$_2$ | H | E-4a |
| 3-Cl-5-OCHF$_2$ | CF$_3$ | H | c-Pr |
| 3-Cl-5-OCHF$_2$ | CF$_3$ | H | CH$_2$Pr-c |
| 3-Cl-5-OCHF$_2$ | CF$_3$ | H | c-Bu |
| 3-Cl-5-OCHF$_2$ | CF$_3$ | H | CH$_2$CF$_3$ |
| 3-Cl-5-OCHF$_2$ | CF$_3$ | C(O)CH$_3$ | CH$_2$CF$_3$ |
| 3-Cl-5-OCHF$_2$ | CF$_3$ | H | CH$_2$CH$_2$CF$_3$ |
| 3-Cl-5-OCHF$_2$ | CF$_3$ | H | CH$_2$OCH$_3$ |
| 3-Cl-5-OCHF$_2$ | CF$_3$ | H | CH$_2$OEt |
| 3-Cl-5-OCHF$_2$ | CF$_3$ | C(O)CH$_3$ | CH$_2$OEt |
| 3-Cl-5-OCHF$_2$ | CF$_3$ | H | CH$_2$OCH$_2$CF$_3$ |
| 3-Cl-5-OCHF$_2$ | CF$_3$ | C(O)CH$_3$ | CH$_2$OCH$_2$CF$_3$ |
| 3-Cl-5-OCHF$_2$ | CF$_3$ | H | CH$_2$CH$_2$OCH$_3$ |
| 3-Cl-5-OCHF$_2$ | CF$_3$ | H | CH$_2$(E-10a) |
| 3-Cl-5-OCHF$_2$ | CF$_3$ | H | E-4a |
| 3-Cl-5-OCHF$_2$ | CF$_3$ | H | E-5a(R) |
| 3-Cl-5-OCHF$_2$ | CF$_3$ | H | CH$_2$CH=NOCH$_3$ |
| 3-Cl-5-OCHF$_2$ | CF$_3$ | H | CH$_2$C(O)NHCH$_2$CH$_2$Cl |
| 3-Cl-5-OCHF$_2$ | CF$_3$ | H | CH$_2$C(O)NHCH$_2$CF$_3$ |
| 3-Cl-5-OCHF$_2$ | CF$_3$ | H | CH(CH$_3$)C(O)NHEt |
| 3-Cl-5-OCHF$_2$ | CF$_3$ | H | CH(CH$_3$)C(O)NHCH$_2$CF$_3$ |
| 3-Cl-5-OCHF$_2$ | CF$_3$ | H | CH(CH$_3$)C(O)NHCH$_2$CF$_3$(D) |
| 3-Cl-5-OCHF$_2$ | CF$_3$ | H | CH$_2$CH=CH$_2$ |
| 3-Cl-5-OCHF$_2$ | CF$_3$ | H | CH$_2$CCl=CH$_2$ |
| 3-Cl-5-OCHF$_2$ | CF$_3$ | H | CH(CH$_3$)Ph(R) |
| 3-Cl-5-OCHF$_2$ | CF$_3$ | H | CH$_2$(Ph-4-NO$_2$) |
| 3-Cl-5-OCHF$_2$ | CF$_3$ | H | CH$_2$(Ph-4-CN) |
| 3-Cl-5-OCHF$_2$ | CF$_3$ | H | CH$_2$(D-17b)Cl |
| 3-Cl-5-OCHF$_2$ | CF$_3$ | H | CH$_2$(D-21a) |
| 3-Cl-5-OCHF$_2$ | CF$_3$ | H | CH$_2$(D-22a) |
| 3-Cl-5-OCHF$_2$ | CF$_3$ | C(O)CH$_3$ | CH$_2$(D-22a) |
| 3-Cl-5-OCHF$_2$ | CF$_3$ | C(O)Et | CH$_2$(D-22a) |
| 3-Cl-5-OCHF$_2$ | CF$_3$ | H | CH$_2$(D-47a) |
| 3-Cl-5-OCHF$_2$ | CF$_3$ | CH$_2$OCH$_3$ | CH$_2$(D-47a) |
| 3-Cl-5-OCHF$_2$ | CF$_3$ | CH$_2$CN | CH$_2$(D-47a) |
| 3-Cl-5-OCHF$_2$ | CF$_3$ | C(O)CH$_3$ | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-OCHF$_2$ | CF$_3$ | C(O)Et | CH$_2$(D-47a) |
| 3-Cl-5-OCHF$_2$ | CF$_3$ | C(O)Pr-c | CH$_2$(D-47a) |
| 3-Cl-5-OCHF$_2$ | CF$_3$ | C(O)OCH$_3$ | CH$_2$(D-47a) |
| 3-Cl-5-OCHF$_2$ | CF$_3$ | H | CH(CH$_3$)(D-47a) |
| 3-Cl-5-OCHF$_2$ | CF$_3$ | H | CH$_2$(D-50a) |
| 3-Cl-5-OCHF$_2$ | CF$_3$ | H | N(CH$_3$)Ph |
| 3-Cl-5-OCHF$_2$ | CF$_3$ | H | N(CH$_3$)(D-50a) |
| 3-Cl-5-OCHF$_2$ | CF$_3$ | C(O)OCH$_3$ | C(O)N(CH$_3$)$_2$ |
| 3-Cl-5-OCHF$_2$ | CF$_3$ | H | C(O)NHEt |
| 3-Cl-5-OCHF$_2$ | CF$_3$ | CH$_3$ | C(O)NHEt |
| 3-Cl-5-OCHF$_2$ | CF$_3$ | H | C(O)NHCH$_2$CH$_2$Cl |
| 3-Cl-5-OCHF$_2$ | CF$_3$ | H | C(O)NHCH$_2$(Ph-4-F) |
| 3-Cl-5-OCHF$_2$ | CF$_3$ | H | Ph-4-CN |
| 3-Cl-5-OCHF$_2$ | CF$_3$ | H | Ph-2,4-F$_2$ |
| 3-Cl-5-OCHF$_2$ | CF$_3$ | H | (D-15a)CH$_3$ |
| 3-Cl-5-OCHF$_2$ | CF$_3$ | H | (D-47d)CN |
| 3-Cl-5-OCHF$_2$ | CF$_3$ | H | (D-47e)Br |
| 3-Cl-5-OCHF$_2$ | CF$_3$ | H | D-50a |
| 3-Cl-5-OCHF$_2$ | CF$_3$ | H | (D-50c)Cl |
| 3-Cl-5-OCHF$_2$ | CF$_3$ | H | (D-50c)Br |
| 3-Cl-5-OCHF$_2$ | CF$_3$ | H | D-52a |
| 3-Cl-5-OCHF$_2$ | CF$_3$ | H | D-53a |
| 3-Cl-5-OCHF$_2$ | CF$_2$Cl | H | CH$_2$CF$_3$ |
| 3-Cl-5-OCHF$_2$ | CF$_2$Cl | C(O)CH$_3$ | CH$_2$CF$_3$ |
| 3-Cl-5-OCHF$_2$ | CF$_2$Cl | H | CH$_2$OCH$_2$CF$_3$ |
| 3-Cl-5-OCHF$_2$ | CF$_2$Cl | H | E-4a |
| 3-Cl-5-OCHF$_2$ | CF$_2$Cl | H | CH$_2$C(O)NHCH$_2$CF$_2$ |
| 3-Cl-5-OCHF$_2$ | CF$_2$Cl | H | CH(CH$_3$)C(O)NHCH$_2$CF$_3$(D) |
| 3-Cl-5-OCHF$_2$ | CF$_2$Cl | H | CH(CH$_3$)Ph(R) |
| 3-Cl-5-OCHF$_2$ | CF$_2$Cl | H | CH$_2$(D-22a) |
| 3-Cl-5-OCHF$_2$ | CF$_2$Cl | H | CH$_2$(D-47a) |
| 3-Cl-5-OCHF$_2$ | CF$_2$Cl | CH$_2$CN | CH$_2$(D-47a) |
| 3-Cl-5-OCHF$_2$ | CF$_2$Cl | C(O)Et | CH$_2$(D-47a) |
| 3-Cl-5-OCHF$_2$ | CF$_2$Cl | C(O)OCH$_3$ | CH$_2$(D-47a) |
| 3-Cl-5-OCHF$_2$ | CF$_2$Cl | H | N(CH$_3$)Ph |
| 3-Cl-5-OCHF$_2$ | CF$_2$Cl | H | (D-50c)Cl |
| 3-Cl-5-OCHF$_2$ | CF$_2$Cl | H | D-52a |
| 3-Cl-5-OCHF$_2$ | CF$_2$Br | H | CH$_2$C(O)NHCH$_2$CF$_3$ |
| 3-Cl-5-OCHF$_2$ | CF$_2$CHF$_2$ | H | CH$_2$(D-22a) |
| 3-Br-4-OCHF$_2$ | CF$_3$ | H | CH$_2$(D-47a) |
| 3-Br-5-OCHF$_2$ | CF$_3$ | H | c-Bu |
| 3-Br-5-OCHF$_2$ | CF$_3$ | H | CH$_2$CF$_3$ |
| 3-Br-5-OCHF$_2$ | CF$_3$ | H | CH$_2$OEt |
| 3-Br-5-OCHF$_2$ | CF$_3$ | H | CH$_2$OCH$_2$CF$_3$ |
| 3-Br-5-OCHF$_2$ | CF$_3$ | C(O)CH$_3$ | CH$_2$OCH$_2$CF$_3$ |
| 3-Br-5-OCHF$_2$ | CF$_3$ | H | CH$_2$CH$_2$OCH$_3$ |
| 3-Br-5-OCHF$_2$ | CF$_3$ | H | CH$_2$(E-10a) |
| 3-Br-5-OCHF$_2$ | CF$_3$ | H | E-4a |
| 3-Br-5-OCHF$_2$ | CF$_3$ | H | CH$_2$C(O)NHCH$_2$CH$_2$Cl |
| 3-Br-5-OCHF$_2$ | CF$_3$ | H | CH$_2$C(O)NHCH$_2$CF$_3$ |
| 3-Br-5-OCHF$_2$ | CF$_3$ | H | CH(CH$_3$)C(O)NHCH$_2$CF$_3$ |
| 3-Br-5-OCHF$_2$ | CF$_3$ | H | CH(CH$_3$)C(O)NHCH$_2$CF$_3$(D) |
| 3-Br-5-OCHF$_2$ | CF$_3$ | H | CH(CH$_3$)Ph(R) |
| 3-Br-5-OCHF$_2$ | CF$_3$ | H | CH$_2$(D-22a) |
| 3-Br-5-OCHF$_2$ | CF$_3$ | C(O)CH$_3$ | CH$_2$(D-22a) |
| 3-Br-5-OCHF$_2$ | CF$_3$ | C(O)Et | CH$_2$(D-22a) |
| 3-Br-5-OCHF$_2$ | CF$_3$ | H | CH$_2$(D-47a) |
| 3-Br-5-OCHF$_2$ | CF$_3$ | CH$_2$OCH$_3$ | CH$_2$(D-47a) |
| 3-Br-5-OCHF$_2$ | CF$_3$ | CH$_2$CN | CH$_2$(D-47a) |
| 3-Br-5-OCHF$_2$ | CF$_3$ | C(O)CH$_3$ | CH$_2$(D-47a) |
| 3-Br-5-OCHF$_2$ | CF$_3$ | C(O)Et | CH$_2$(D-47a) |
| 3-Br-5-OCHF$_2$ | CF$_3$ | C(O)OCH$_3$ | CH$_2$(D-47a) |
| 3-Br-5-OCHF$_2$ | CF$_3$ | H | N(CH$_3$)Ph |
| 3-Br-5-OCHF$_2$ | CF$_3$ | H | N(CH$_3$)(D-50a) |
| 3-Br-5-OCHF$_2$ | CF$_3$ | H | C(O)NHCH$_2$CF$_3$ |
| 3-Br-5-OCHF$_2$ | CF$_3$ | H | Ph-2,4-F$_2$ |
| 3-Br-5-OCHF$_2$ | CF$_3$ | H | (D-50c)Cl |
| 3-Br-5-OCHF$_2$ | CF$_3$ | H | D-52a |
| 3-Br-5-OCHF$_2$ | CF$_2$Cl | H | CH$_2$CF$_3$ |
| 3-Br-5-OCHF$_2$ | CF$_2$Cl | H | CH$_2$OCH$_2$CF$_3$ |
| 3-Br-5-OCHF$_2$ | CF$_2$Cl | H | E-4a |
| 3-Br-5-OCHF$_2$ | CF$_2$Cl | H | CH$_2$C(O)NHCH$_2$CF$_3$ |
| 3-Br-5-OCHF$_2$ | CF$_2$Cl | H | CH(CH$_3$)C(O)NHCH$_2$CF$_3$(D) |
| 3-Br-5-OCHF$_2$ | CF$_2$Cl | H | CH$_2$(D-22a) |
| 3-Br-5-OCHF$_2$ | CF$_2$Cl | H | CH$_2$(D-47a) |
| 3-Br-5-OCHF$_2$ | CF$_2$Cl | C(O)OCH$_3$ | CH$_2$(D-47a) |
| 3-Br-5-OCHF$_2$ | CF$_2$Cl | H | N(CH$_3$)Ph |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Br-5-OCHF$_2$ | CF$_2$Cl | H | (D-50c)Cl |
| 3-CH$_3$-5-OCHF$_2$ | CF$_3$ | C(O)OCH$_3$ | CH$_2$(D-47a) |
| 3-CF$_3$-5-OCHF$_2$ | CF$_3$ | H | c-Bu |
| 3-CF$_3$-5-OCHF$_2$ | CF$_3$ | H | CH$_2$CF$_3$ |
| 3-CF$_3$-5-OCHF$_2$ | CF$_3$ | H | CH$_2$OEt |
| 3-CF$_3$-5-OCHF$_2$ | CF$_3$ | H | CH$_2$OCH$_2$CF$_3$ |
| 3-CF$_3$-5-OCHF$_2$ | CF$_3$ | C(O)CH$_3$ | CH$_2$OCH$_2$CF$_3$ |
| 3-CF$_3$-5-OCHF$_2$ | CF$_3$ | H | CH$_2$CH$_2$OCH$_3$ |
| 3-CF$_3$-5-OCHF$_2$ | CF$_3$ | H | CH$_2$(E-10a) |
| 3-CF$_3$-5-OCHF$_2$ | CF$_3$ | H | E-4a |
| 3-CF$_3$-5-OCHF$_2$ | CF$_3$ | H | CH$_2$C(O)NHCH$_2$CH$_2$Cl |
| 3-CF$_3$-5-OCHF$_2$ | CF$_3$ | H | CH$_2$C(O)NHCH$_2$CF$_3$ |
| 3-CF$_3$-5-OCHF$_2$ | CF$_3$ | H | CH(CH$_3$)C(O)NHCH$_2$CF$_3$ |
| 3-CF$_3$-5-OCHF$_2$ | CF$_3$ | H | CH(CH$_3$)C(O)NHCH$_2$CF$_3$(D) |
| 3-CF$_3$-5-OCHF$_2$ | CF$_3$ | H | CH(CH$_3$)Ph(R) |
| 3-CF$_3$-5-OCHF$_2$ | CF$_3$ | H | CH$_2$(D-22a) |
| 3-CF$_3$-5-OCHF$_2$ | CF$_3$ | C(O)CH$_3$ | CH$_2$(D-22a) |
| 3-CF$_3$-5-OCHF$_2$ | CF$_3$ | C(O)Et | CH$_2$(D-22a) |
| 3-CF$_3$-5-OCHF$_2$ | CF$_3$ | H | CH$_2$(D-47a) |
| 3-CF$_3$-5-OCHF$_2$ | CF$_3$ | CH$_2$OCH$_3$ | CH$_2$(D-47a) |
| 3-CF$_3$-5-OCHF$_2$ | CF$_3$ | CH$_2$CN | CH$_2$(D-47a) |
| 3-CF$_3$-5-OCHF$_2$ | CF$_3$ | C(O)CH$_3$ | CH$_2$(D-47a) |
| 3-CF$_3$-5-OCHF$_2$ | CF$_3$ | C(O)Et | CH$_2$(D-47a) |
| 3-CF$_3$-5-OCHF$_2$ | CF$_3$ | C(O)OCH$_3$ | CH$_2$(D-47a) |
| 3-CF$_3$-5-OCHF$_2$ | CF$_3$ | H | N(CH$_3$)Ph |
| 3-CF$_3$-5-OCHF$_2$ | CF$_3$ | H | N(CH$_3$)(D-50a) |
| 3-CF$_3$-5-OCHF$_2$ | CF$_3$ | H | C(O)NHCH$_2$CF$_3$ |
| 3-CF$_3$-5-OCHF$_2$ | CF$_3$ | H | Ph-2,4-F$_2$ |
| 3-CF$_3$-5-OCHF$_2$ | CF$_3$ | H | (D-50c)Cl |
| 3-CF$_3$-5-OCHF$_2$ | CF$_3$ | H | D-52a |
| 3-CF$_3$-5-OCHF$_2$ | CF$_2$Cl | H | CH$_2$CF$_3$ |
| 3-CF$_3$-5-OCHF$_2$ | CF$_2$Cl | H | CH$_2$OCH$_2$CF$_3$ |
| 3-CF$_3$-5-OCHF$_2$ | CF$_2$Cl | H | E-4a |
| 3-CF$_3$-5-OCHF$_2$ | CF$_2$Cl | H | CH$_2$C(O)NHCH$_2$CF$_3$ |
| 3-CF$_3$-5-OCHF$_2$ | CF$_2$Cl | H | CH(CH$_3$)C(O)NHCH$_2$CF$_3$(D) |
| 3-CF$_3$-5-OCHF$_2$ | CF$_2$Cl | H | CH$_2$(D-22a) |
| 3-CF$_3$-5-OCHF$_2$ | CF$_2$Cl | H | CH$_2$(D-47a) |
| 3-CF$_3$-5-OCHF$_2$ | CF$_2$Cl | C(O)OCH$_3$ | CH$_2$(D-47a) |
| 3-CF$_3$-5-OCHF$_2$ | CF$_2$Cl | H | N(CH$_3$)Ph |
| 3-CF$_3$-5-OCHF$_2$ | CF$_2$Cl | H | (D-50c)Cl |
| 3,5-(OCHF$_2$)$_2$ | CF$_3$ | H | N(CH$_3$)Ph |
| 3-F-4-OCF$_3$ | CF$_3$ | H | (D-50c)Cl |
| 3-Cl-4-OCF$_3$ | CF$_3$ | H | CH$_2$CF$_3$ |
| 3-Cl-5-OCF$_3$ | CHF$_2$ | H | CH$_2$OCH$_2$CF$_3$ |
| 3-Cl-5-OCF$_3$ | CF$_3$ | H | c-Pr |
| 3-Cl-5-OCF$_3$ | CF$_3$ | H | CH$_2$Pr-c |
| 3-Cl-5-OCF$_3$ | CF$_3$ | H | c-Bu |
| 3-Cl-5-OCF$_3$ | CF$_3$ | H | CH$_2$CF$_3$ |
| 3-Cl-5-OCF$_3$ | CF$_3$ | C(O)CH$_3$ | CH$_2$CF$_3$ |
| 3-Cl-5-OCF$_3$ | CF$_3$ | H | CH$_2$CH$_2$CF$_3$ |
| 3-Cl-5-OCF$_3$ | CF$_3$ | H | CH$_2$OCH$_3$ |
| 3-Cl-5-OCF$_3$ | CF$_3$ | H | CH$_2$OEt |
| 3-Cl-5-OCF$_3$ | CF$_3$ | C(O)CH$_3$ | CH$_2$OEt |
| 3-Cl-5-OCF$_3$ | CF$_3$ | H | CH$_2$OCH$_2$CF$_3$ |
| 3-Cl-5-OCF$_3$ | CF$_3$ | C(O)CH$_3$ | CH$_2$OCH$_2$CF$_3$ |
| 3-Cl-5-OCF$_3$ | CF$_3$ | H | CH$_2$CH$_2$OCH$_3$ |
| 3-Cl-5-OCF$_3$ | CF$_3$ | H | CH$_2$(E-10a) |
| 3-Cl-5-OCF$_3$ | CF$_3$ | H | E-4a |
| 3-Cl-5-OCF$_3$ | CF$_3$ | H | E-5a(R) |
| 3-Cl-5-OCF$_3$ | CF$_3$ | H | CH$_2$CH=NOCH$_3$ |
| 3-Cl-5-OCF$_3$ | CF$_3$ | H | CH$_2$C(O)NHCH$_2$CH$_2$Cl |
| 3-Cl-5-OCF$_3$ | CF$_3$ | H | CH$_2$C(O)NHCH$_2$CF$_3$ |
| 3-Cl-5-OCF$_3$ | CF$_3$ | H | CH(CH$_3$)C(O)NHEt |
| 3-Cl-5-OCF$_3$ | CF$_3$ | H | CH(CH$_3$)C(O)NHCH$_2$CF$_3$ |
| 3-Cl-5-OCF$_3$ | CF$_3$ | H | CH(CH$_3$)C(O)NHCH$_2$CF$_3$(D) |
| 3-Cl-5-OCF$_3$ | CF$_3$ | H | CH$_2$CH=CH$_2$ |
| 3-Cl-5-OCF$_3$ | CF$_3$ | H | CH$_2$CCl=CH$_2$ |
| 3-Cl-5-OCF$_3$ | CF$_3$ | H | CH(CH$_3$)Ph(R) |
| 3-Cl-5-OCF$_3$ | CF$_3$ | H | CH$_2$(Ph-4-NO$_2$) |
| 3-Cl-5-OCF$_3$ | CF$_3$ | H | CH$_2$(Ph-4-CN) |
| 3-Cl-5-OCF$_3$ | CF$_3$ | H | CH$_2$(D-17b)Cl |
| 3-Cl-5-OCF$_3$ | CF$_3$ | H | CH$_2$(D-21a) |
| 3-Cl-5-OCF$_3$ | CF$_3$ | H | CH$_2$(D-22a) |
| 3-Cl-5-OCF$_3$ | CF$_3$ | C(O)CH$_3$ | CH$_2$(D-22a) |
| 3-Cl-5-OCF$_3$ | CF$_3$ | C(O)Et | CH$_2$(D-22a) |
| 3-Cl-5-OCF$_3$ | CF$_3$ | H | CH$_2$(D-47a) |
| 3-Cl-5-OCF$_3$ | CF$_3$ | CH$_2$OCH$_3$ | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-OCF$_3$ | CF$_3$ | CH$_2$CN | CH$_2$(D-47a) |
| 3-Cl-5-OCF$_3$ | CF$_3$ | C(O)CH$_3$ | CH$_2$(D-47a) |
| 3-Cl-5-OCF$_3$ | CF$_3$ | C(O)Et | CH$_2$(D-47a) |
| 3-Cl-5-OCF$_3$ | CF$_3$ | C(O)Pr-c | CH$_2$(D-47a) |
| 3-Cl-5-OCF$_3$ | CF$_3$ | C(O)OCH$_3$ | CH$_2$(D-47a) |
| 3-Cl-5-OCF$_3$ | CF$_3$ | H | CH(CH$_3$)(D-47a) |
| 3-Cl-5-OCF$_3$ | CF$_3$ | H | CH$_2$(D-50a) |
| 3-Cl-5-OCF$_3$ | CF$_3$ | H | N(CH$_3$)Ph |
| 3-Cl-5-OCF$_3$ | CF$_3$ | H | N(CH$_3$)(D-50a) |
| 3-Cl-5-OCF$_3$ | CF$_3$ | C(O)OCH$_3$ | C(O)N(CH$_3$)$_2$ |
| 3-Cl-5-OCF$_3$ | CF$_3$ | H | C(O)NHEt |
| 3-Cl-5-OCF$_3$ | CF$_3$ | CH$_3$ | C(O)NHEt |
| 3-Cl-5-OCF$_3$ | CF$_3$ | H | C(O)NHCH$_2$CH$_2$Cl |
| 3-Cl-5-OCF$_3$ | CF$_3$ | H | C(O)NHCH$_2$(Ph-4-F) |
| 3-Cl-5-OCF$_3$ | CF$_3$ | H | Ph-4-CN |
| 3-Cl-5-OCF$_3$ | CF$_3$ | H | Ph-2,4-F$_2$ |
| 3-Cl-5-OCF$_3$ | CF$_3$ | H | (D-15a)CH$_3$ |
| 3-Cl-5-OCF$_3$ | CF$_3$ | H | (D-47d)CN |
| 3-Cl-5-OCF$_3$ | CF$_3$ | H | (D-47e)Br |
| 3-Cl-5-OCF$_3$ | CF$_3$ | H | D-50a |
| 3-Cl-5-OCF$_3$ | CF$_3$ | H | (D-50c)Cl |
| 3-Cl-5-OCF$_3$ | CF$_3$ | H | (D-50c)Br |
| 3-Cl-5-OCF$_3$ | CF$_3$ | H | D-52a |
| 3-Cl-5-OCF$_3$ | CF$_3$ | H | D-53a |
| 3-Cl-5-OCF$_3$ | CF$_2$Cl | H | CH$_2$CF$_3$ |
| 3-Cl-5-OCF$_3$ | CF$_2$Cl | C(O)CH$_3$ | CH$_2$CF$_3$ |
| 3-Cl-5-OCF$_3$ | CF$_2$Cl | H | CH$_2$OCH$_2$CF$_3$ |
| 3-Cl-5-OCF$_3$ | CF$_2$Cl | H | E-4a |
| 3-Cl-5-OCF$_3$ | CF$_2$Cl | H | CH$_2$C(O)NHCH$_2$CF$_3$ |
| 3-Cl-5-OCF$_3$ | CF$_2$Cl | H | CH(CH$_3$)C(O)NHCH$_2$CF$_3$(D) |
| 3-Cl-5-OCF$_3$ | CF$_2$Cl | H | CH(CH$_3$)Ph(R) |
| 3-Cl-5-OCF$_3$ | CF$_2$Cl | H | CH$_2$(D-22a) |
| 3-Cl-5-OCF$_3$ | CF$_2$Cl | H | CH$_2$(D-47a) |
| 3-Cl-5-OCF$_3$ | CF$_2$Cl | CH$_2$CN | CH$_2$(D-47a) |
| 3-Cl-5-OCF$_3$ | CF$_2$Cl | C(O)Et | CH$_2$(D-47a) |
| 3-Cl-5-OCF$_3$ | CF$_2$Cl | C(O)OCH$_3$ | CH$_2$(D-47a) |
| 3-Cl-5-OCF$_3$ | CF$_2$Cl | H | N(CH$_3$)Ph |
| 3-Cl-5-OCF$_3$ | CF$_2$Cl | H | (D-50c)Cl |
| 3-Cl-5-OCF$_3$ | CF$_2$Cl | H | D-52a |
| 3-Cl-5-OCF$_3$ | CF$_2$Br | H | E-4a |
| 3-Cl-5-OCF$_3$ | CF$_2$CHF$_2$ | H | CH$_2$C(O)NHCH$_2$CF$_3$ |
| 3-Br-4-OCF$_3$ | CF$_3$ | H | CH$_2$(D-22a) |
| 3-Br-5-OCF$_3$ | CF$_3$ | H | c-Bu |
| 3-Br-5-OCF$_3$ | CF$_3$ | H | CH$_2$CF$_3$ |
| 3-Br-5-OCF$_3$ | CF$_3$ | H | CH$_2$OEt |
| 3-Br-5-OCF$_3$ | CF$_3$ | H | CH$_2$OCH$_2$CF$_3$ |
| 3-Br-5-OCF$_3$ | CF$_3$ | C(O)CH$_3$ | CH$_2$OCH$_2$CF$_3$ |
| 3-Br-5-OCF$_3$ | CF$_3$ | H | CH$_2$CH$_2$OCH$_3$ |
| 3-Br-5-OCF$_3$ | CF$_3$ | H | CH$_2$(E-10a) |
| 3-Br-5-OCF$_3$ | CF$_3$ | H | E-4a |
| 3-Br-5-OCF$_3$ | CF$_3$ | H | CH$_2$C(O)NHCH$_2$Cl |
| 3-Br-5-OCF$_3$ | CF$_3$ | H | CH$_2$C(O)NHCH$_2$CF$_3$ |
| 3-Br-5-OCF$_3$ | CF$_3$ | H | CH(CH$_3$)C(O)NHCH$_2$CF$_3$ |
| 3-Br-5-OCF$_3$ | CF$_3$ | H | CH(CH$_3$)C(O)NHCH$_2$CF$_3$(D) |
| 3-Br-5-OCF$_3$ | CF$_3$ | H | CH(CH$_3$)Ph(R) |
| 3-Br-5-OCF$_3$ | CF$_3$ | H | CH$_2$(D-22a) |
| 3-Br-5-OCF$_3$ | CF$_3$ | C(O)CH$_3$ | CH$_2$(D-22a) |
| 3-Br-5-OCF$_3$ | CF$_3$ | C(O)Et | CH$_2$(D-22a) |
| 3-Br-5-OCF$_3$ | CF$_3$ | H | CH$_2$(D-47a) |
| 3-Br-5-OCF$_3$ | CF$_3$ | CH$_2$OCH$_3$ | CH$_2$(D-47a) |
| 3-Br-5-OCF$_3$ | CF$_3$ | CH$_2$CN | CH$_2$(D-47a) |
| 3-Br-5-OCF$_3$ | CF$_3$ | C(O)CH$_3$ | CH$_2$(D-47a) |
| 3-Br-5-OCF$_3$ | CF$_3$ | C(O)Et | CH$_2$(D-47a) |
| 3-Br-5-OCF$_3$ | CF$_3$ | C(O)OCH$_3$ | CH$_2$(D-47a) |
| 3-Br-5-OCF$_3$ | CF$_3$ | H | N(CH$_3$)Ph |
| 3-Br-5-OCF$_3$ | CF$_3$ | H | N(CH$_3$)(D-50a) |
| 3-Br-5-OCF$_3$ | CF$_3$ | H | C(O)NHCH$_2$CF$_3$ |
| 3-Br-5-OCF$_3$ | CF$_3$ | H | Ph-2,4-F$_2$ |
| 3-Br-5-OCF$_3$ | CF$_3$ | H | (D-50c)Cl |
| 3-Br-5-OCF$_3$ | CF$_3$ | H | D-52a |
| 3-Br-5-OCF$_3$ | CF$_2$Cl | H | CH$_2$CF$_3$ |
| 3-Br-5-OCF$_3$ | CF$_2$Cl | H | CH$_2$OCH$_2$CF$_3$ |
| 3-Br-5-OCF$_3$ | CF$_2$Cl | H | E-4a |
| 3-Br-5-OCF$_3$ | CF$_2$Cl | H | CH$_2$C(O)NHCH$_2$CF$_3$ |
| 3-Br-5-OCF$_3$ | CF$_2$Cl | H | CH(CH$_3$)C(O)NHCH$_2$CF$_3$(D) |
| 3-Br-5-OCF$_3$ | CF$_2$Cl | H | CH$_2$(D-22a) |
| 3-Br-5-OCF$_3$ | CF$_2$Cl | H | CH$_2$(D-47a) |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Br-5-OCF$_3$ | CF$_2$Cl | C(O)OCH$_3$ | CH$_2$(D-47a) |
| 3-Br-5-OCF$_3$ | CF$_2$Cl | H | N(CH$_3$)Ph |
| 3-Br-5-OCF$_3$ | CF$_2$Cl | H | (D-50c)Cl |
| 3-CH$_3$-5-OCF$_3$ | CF$_3$ | H | CH$_2$(D-47a) |
| 3-CF$_3$-5-OCF$_3$ | CF$_3$ | H | c-Bu |
| 3-CF$_3$-5-OCF$_3$ | CF$_3$ | H | CH$_2$CF$_3$ |
| 3-CF$_3$-5-OCF$_3$ | CF$_3$ | H | CH$_2$OEt |
| 3-CF$_3$-5-OCF$_3$ | CF$_3$ | H | CH$_2$OCH$_2$CF$_3$ |
| 3-CF$_3$-5-OCF$_3$ | CF$_3$ | C(O)CH$_3$ | CH$_2$OCH$_2$CF$_3$ |
| 3-CF$_3$-5-OCF$_3$ | CF$_3$ | H | CH$_2$CH$_2$OCH$_3$ |
| 3-CF$_3$-5-OCF$_3$ | CF$_3$ | H | CH$_2$(E-10a) |
| 3-CF$_3$-5-OCF$_3$ | CF$_3$ | H | E-4a |
| 3-CF$_3$-5-OCF$_3$ | CF$_3$ | H | CH$_2$C(O)NHCH$_2$CH$_2$Cl |
| 3-CF$_3$-5-OCF$_3$ | CF$_3$ | H | CH$_2$C(O)NHCH$_2$CF$_3$ |
| 3-CF$_3$-5-OCF$_3$ | CF$_3$ | H | CH(CH$_3$)C(O)NHCH$_2$CF$_3$ |
| 3-CF$_3$-5-OCF$_3$ | CF$_3$ | H | CH(CH$_3$)C(O)NHCH$_2$CF$_3$(D) |
| 3-CF$_3$-5-OCF$_3$ | CF$_3$ | H | CH(CH$_3$)Ph(R) |
| 3-CF$_3$-5-OCF$_3$ | CF$_3$ | H | CH$_2$(D-22a) |
| 3-CF$_3$-5-OCF$_3$ | CF$_3$ | C(O)CH$_3$ | CH$_2$(D-22a) |
| 3-CF$_3$-5-OCF$_3$ | CF$_3$ | C(O)Et | CH$_2$(D-22a) |
| 3-CF$_3$-5-OCF$_3$ | CF$_3$ | H | CH$_2$(D-47a) |
| 3-CF$_3$-5-OCF$_3$ | CF$_3$ | CH$_2$OCH$_3$ | CH$_2$(D-47a) |
| 3-CF$_3$-5-OCF$_3$ | CF$_3$ | CH$_2$CN | CH$_2$(D-47a) |
| 3-CF$_3$-5-OCF$_3$ | CF$_3$ | C(O)CH$_3$ | CH$_2$(D-47a) |
| 3-CF$_3$-5-OCF$_3$ | CF$_3$ | C(O)Et | CH$_2$(D-47a) |
| 3-CF$_3$-5-OCF$_3$ | CF$_3$ | C(O)OCH$_3$ | CH$_2$(D-47a) |
| 3-CF$_3$-5-OCF$_3$ | CF$_3$ | H | N(CH$_3$)Ph |
| 3-CF$_3$-5-OCF$_3$ | CF$_3$ | H | N(CH$_3$)(D-50a) |
| 3-CF$_3$-5-OCF$_3$ | CF$_3$ | H | C(O)NHCH$_2$CF$_3$ |
| 3-CF$_3$-5-OCF$_3$ | CF$_3$ | H | Ph-2,4-F$_2$ |
| 3-CF$_3$-5-OCF$_3$ | CF$_3$ | H | (D-50c)Cl |
| 3-CF$_3$-5-OCF$_3$ | CF$_3$ | H | D-52a |
| 3-CF$_3$-5-OCF$_3$ | CF$_2$Cl | H | CH$_2$CF$_3$ |
| 3-CF$_3$-5-OCF$_3$ | CF$_2$Cl | H | CH$_2$OCH$_2$CF$_3$ |
| 3-CF$_3$-5-OCF$_3$ | CF$_2$Cl | H | E-4a |
| 3-CF$_3$-5-OCF$_3$ | CF$_2$Cl | H | CH$_2$C(O)NHCH$_2$CF$_3$ |
| 3-CF$_3$-5-OCF$_3$ | CF$_2$Cl | H | CH(CH$_3$)C(O)NHCH$_2$CF$_3$(D) |
| 3-CF$_3$-5-OCF$_3$ | CF$_2$Cl | H | CH$_2$(D-22a) |
| 3-CF$_3$-5-OCF$_3$ | CF$_2$Cl | H | CH$_2$(D-47a) |
| 3-CF$_3$-5-OCF$_3$ | CF$_2$Cl | C(O)OCH$_3$ | CH$_2$(D-47a) |
| 3-CF$_3$-5-OCF$_3$ | CF$_2$Cl | H | N(CH$_3$)Ph |
| 3-CF$_3$-5-OCF$_3$ | CF$_2$Cl | H | (D-50c)Cl |
| 3-F-5-OCF$_2$Br | CF$_3$ | C(O)OCH$_3$ | CH$_2$(D-47a) |
| 3-Cl-5-OCF$_2$Br | CF$_3$ | H | N(CH$_3$)Ph |
| 3-CH$_3$-5-OCF$_2$Br | CF$_3$ | H | (D-50c)Cl |
| 3-F-5-OCF$_2$CHF$_2$ | CF$_3$ | H | CH$_2$CF$_3$ |
| 3-Cl-5-OCF$_2$CHF$_2$ | CF$_3$ | H | CH$_2$OCH$_2$CF$_3$ |
| 3-CH$_3$-5-OCF$_2$CHF$_2$ | CF$_3$ | H | E-4a |
| 3-F-5-OCF$_2$CHFCl | CF$_3$ | H | CH$_2$C(O)NHCH$_2$CF$_3$ |
| 3-Cl-5-OCF$_2$CHFCl | CF$_3$ | H | CH$_2$(D-22a) |
| 3-Br-5-OCF$_2$CHFCl | CF$_3$ | H | CH$_2$(D-47a) |
| 3-F-5-OCF$_2$CHFCF$_3$ | CF$_3$ | C(O)OCH$_3$ | CH$_2$(D-47a) |
| 3-Cl-5-OCF$_2$CHFCF$_3$ | CF$_3$ | H | N(CH$_3$)Ph |
| 3-CH$_3$-5-OCF$_2$CHFCF$_3$ | CF$_3$ | H | (D-50c)Cl |
| 3-F-5-OCF$_2$CHFOCF$_3$ | CF$_3$ | H | CH$_2$CF$_3$ |
| 3-Cl-5-OCF$_2$CHFOCF$_3$ | CF$_3$ | H | CH$_2$OCH$_2$CF$_3$ |
| 3-CH$_3$-5-OCF$_2$CHFOCF$_3$ | CF$_3$ | H | E-4a |
| 3-CF$_2$OCF$_2$O-4 | CF$_3$ | H | CH$_2$C(O)NHCH$_2$CF$_3$ |
| 3-OCF$_2$O-4 | CF$_3$ | H | CH$_2$(D-22a) |
| 3-OCF$_2$CF$_2$O-4 | CF$_3$ | H | CH$_2$(D-47a) |
| 3-OPh-4-F | CF$_3$ | C(O)OCH$_3$ | CH$_2$(D-47a) |
| 3-F-5-SCH$_3$ | CF$_3$ | H | CH$_2$(D-47a) |
| 3-F-5-SCH$_3$ | CF$_3$ | H | N(CH$_3$)Ph |
| 3-Cl-5-SCH$_3$ | CF$_3$ | H | CH$_2$(D-47a) |
| 3-Cl-5-SCH$_3$ | CF$_3$ | H | (D-50c)Cl |
| 3-Cl-5-S(O)CH$_3$ | CF$_3$ | H | CH$_2$CF$_3$ |
| 3-Cl-5-SO$_2$CH$_3$ | CF$_3$ | H | CH$_2$OCH$_2$CF$_3$ |
| 3-Br-5-SCH$_3$ | CF$_3$ | H | E-4a |
| 3-Br-5-S(O)CH$_3$ | CF$_3$ | H | CH$_2$C(O)NHCH$_2$CF$_3$ |
| 3-Br-5-SO$_2$CH$_3$ | CF$_3$ | H | CH$_2$(D-22a) |
| 3,5-(SCH$_3$)$_2$ | CF$_3$ | H | CH$_2$(D-47a) |
| 3-Cl-5-SCF$_3$ | CHF$_2$ | C(O)OCH$_3$ | CH$_2$(D-47a) |
| 3-Cl-5-SCF$_3$ | CF$_3$ | H | c-Pr |
| 3-Cl-5-SCF$_3$ | CF$_3$ | H | CH$_2$Pr-c |
| 3-Cl-5-SCF$_3$ | CF$_3$ | H | c-Bu |
| 3-Cl-5-SCF$_3$ | CF$_3$ | H | CH$_2$CF$_3$ |
| 3-Cl-5-SCF$_3$ | CF$_3$ | C(O)CH$_3$ | CH$_2$CF$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-5-SCF$_3$ | CF$_3$ | H | CH$_2$CH$_2$CF$_3$ |
| 3-Cl-5-SCF$_3$ | CF$_3$ | H | CH$_2$OCH$_3$ |
| 3-Cl-5-SCF$_3$ | CF$_3$ | H | CH$_2$OEt |
| 3-Cl-5-SCF$_3$ | CF$_3$ | C(O)CH$_3$ | CH$_2$OEt |
| 3-Cl-5-SCF$_3$ | CF$_3$ | H | CH$_2$OCH$_2$CF$_3$ |
| 3-Cl-5-SCF$_3$ | CF$_3$ | C(O)CH$_3$ | CH$_2$OCH$_2$CF$_3$ |
| 3-Cl-5-SCF$_3$ | CF$_3$ | H | CH$_2$CH$_2$OCH$_3$ |
| 3-Cl-5-SCF$_3$ | CF$_3$ | H | CH$_2$(E-10a) |
| 3-Cl-5-SCF$_3$ | CF$_3$ | H | E-4a |
| 3-Cl-5-SCF$_3$ | CF$_3$ | H | E-5a(R) |
| 3-Cl-5-SCF$_3$ | CF$_3$ | H | CH$_2$CH=NOCH$_3$ |
| 3-Cl-5-SCF$_3$ | CF$_3$ | H | CH$_2$C(O)NHCH$_2$CH$_2$Cl |
| 3-Cl-5-SCF$_3$ | CF$_3$ | H | CH$_2$C(O)NHCH$_2$CF$_3$ |
| 3-Cl-5-SCF$_3$ | CF$_3$ | H | CH(CH$_3$)C(O)NHEt |
| 3-Cl-5-SCF$_3$ | CF$_3$ | H | CH(CH$_3$)C(O)NHCH$_2$CF$_3$ |
| 3-Cl-5-SCF$_3$ | CF$_3$ | H | CH(CH$_3$)C(O)NHCH$_2$CF$_3$(D) |
| 3-Cl-5-SCF$_3$ | CF$_3$ | H | CH$_2$CH=CH$_2$ |
| 3-Cl-5-SCF$_3$ | CF$_3$ | H | CH$_2$CCl=CH$_2$ |
| 3-Cl-5-SCF$_3$ | CF$_3$ | H | CH(CH$_3$)Ph(R) |
| 3-Cl-5-SCF$_3$ | CF$_3$ | H | CH$_2$(Ph-4-NO$_2$) |
| 3-Cl-5-SCF$_3$ | CF$_3$ | H | CH$_2$(Ph-4-CN) |
| 3-Cl-5-SCF$_3$ | CF$_3$ | H | CH$_2$(D-17b)Cl |
| 3-Cl-5-SCF$_3$ | CF$_3$ | H | CH$_2$(D-21a) |
| 3-Cl-5-SCF$_3$ | CF$_3$ | H | CH$_2$(D-22a) |
| 3-Cl-5-SCF$_3$ | CF$_3$ | C(O)CH$_3$ | CH$_2$(D-22a) |
| 3-Cl-5-SCF$_3$ | CF$_3$ | C(O)Et | CH$_2$(D-22a) |
| 3-Cl-5-SCF$_3$ | CF$_3$ | H | CH$_2$(D-47a) |
| 3-Cl-5-SCF$_3$ | CF$_3$ | CH$_2$OCH$_3$ | CH$_2$(D-47a) |
| 3-Cl-5-SCF$_3$ | CF$_3$ | CH$_2$CN | CH$_2$(D-47a) |
| 3-Cl-5-SCF$_3$ | CF$_3$ | C(O)CH$_3$ | CH$_2$(D-47a) |
| 3-Cl-5-SCF$_3$ | CF$_3$ | C(O)Et | CH$_2$(D-47a) |
| 3-Cl-5-SCF$_3$ | CF$_3$ | C(O)Pr-c | CH$_2$(D-47a) |
| 3-Cl-5-SCF$_3$ | CF$_3$ | C(O)OCH$_3$ | CH$_2$(D-47a) |
| 3-Cl-5-SCF$_3$ | CF$_3$ | H | CH(CH$_3$)(D-47a) |
| 3-Cl-5-SCF$_3$ | CF$_3$ | H | CH$_2$(D-50a) |
| 3-Cl-5-SCF$_3$ | CF$_3$ | H | N(CH$_3$)Ph |
| 3-Cl-5-SCF$_3$ | CF$_3$ | H | N(CH$_3$)(D-50a) |
| 3-Cl-5-SCF$_3$ | CF$_3$ | C(O)OCH$_3$ | C(O)N(CH$_3$)$_2$ |
| 3-Cl-5-SCF$_3$ | CF$_3$ | H | C(O)NHEt |
| 3-Cl-5-SCF$_3$ | CF$_3$ | CH$_3$ | C(O)NHEt |
| 3-Cl-5-SCF$_3$ | CF$_3$ | H | C(O)NHCH$_2$CH$_2$Cl |
| 3-Cl-5-SCF$_3$ | CF$_3$ | H | C(O)NHCH$_2$(Ph-4-F) |
| 3-Cl-5-SCF$_3$ | CF$_3$ | H | Ph-4-CN |
| 3-Cl-5-SCF$_3$ | CF$_3$ | H | Ph-2,4-F$_2$ |
| 3-Cl-5-SCF$_3$ | CF$_3$ | H | (D-15a)CH$_3$ |
| 3-Cl-5-SCF$_3$ | CF$_3$ | H | (D-47d)CN |
| 3-Cl-5-SCF$_3$ | CF$_3$ | H | (D-47e)Br |
| 3-Cl-5-SCF$_3$ | CF$_3$ | H | D-50a |
| 3-Cl-5-SCF$_3$ | CF$_3$ | H | (D-50c)Cl |
| 3-Cl-5-SCF$_3$ | CF$_3$ | H | (D-50c)Br |
| 3-Cl-5-SCF$_3$ | CF$_3$ | H | D-52a |
| 3-Cl-5-SCF$_3$ | CF$_3$ | H | D-53a |
| 3-Cl-5-SCF$_3$ | CF$_2$Cl | H | CH$_2$CF$_3$ |
| 3-Cl-5-SCF$_3$ | CF$_2$Cl | C(O)CH$_3$ | CH$_2$CF$_3$ |
| 3-Cl-5-SCF$_3$ | CF$_2$Cl | H | CH$_2$OCH$_2$CF$_3$ |
| 3-Cl-5-SCF$_3$ | CF$_2$Cl | H | E-4a |
| 3-Cl-5-SCF$_3$ | CF$_2$Cl | H | CH$_2$C(O)NHCH$_2$CF$_3$ |
| 3-Cl-5-SCF$_3$ | CF$_2$Cl | H | CH(CH$_3$)C(O)NHCH$_2$CF$_3$(D) |
| 3-Cl-5-SCF$_3$ | CF$_2$Cl | H | CH(CH$_3$)Ph(R) |
| 3-Cl-5-SCF$_3$ | CF$_2$Cl | H | CH$_2$(D-22a) |
| 3-Cl-5-SCF$_3$ | CF$_2$Cl | H | CH$_2$(D-47a) |
| 3-Cl-5-SCF$_3$ | CF$_2$Cl | CH$_2$CN | CH$_2$(D-47a) |
| 3-Cl-5-SCF$_3$ | CF$_2$Cl | C(O)Et | CH$_2$(D-47a) |
| 3-Cl-5-SCF$_3$ | CF$_2$Cl | C(O)OCH$_3$ | CH$_2$(D-47a) |
| 3-Cl-5-SCF$_3$ | CF$_2$Cl | H | N(CH$_3$)Ph |
| 3-Cl-5-SCF$_3$ | CF$_2$Cl | H | (D-50c)Cl |
| 3-Cl-5-SCF$_3$ | CF$_2$Cl | H | D-52a |
| 3-Cl-5-SCF$_3$ | CF$_2$Br | H | N(CH$_3$)Ph |
| 3-Cl-5-SCF$_3$ | CF$_2$CHF$_2$ | H | (D-50c)Cl |
| 3-Cl-5-S(O)CF$_3$ | CF$_3$ | H | CH$_2$CF$_3$ |
| 3-Cl-5-S(O)CF$_3$ | CF$_3$ | H | CHOCH$_2$CF$_3$ |
| 3-Cl-5-S(O)CF$_3$ | CF$_3$ | H | E-4a |
| 3-Cl-5-S(O)CF$_3$ | CF$_3$ | H | CH$_2$C(O)NHCH$_2$CF$_3$ |
| 3-Cl-5-S(O)CF$_3$ | CF$_3$ | H | CH(CH$_3$)C(O)NHCH$_2$CF$_3$(D) |
| 3-Cl-5-S(O)CF$_3$ | CF$_3$ | H | CH$_2$(D-22a) |
| 3-Cl-5-S(O)CF$_3$ | CF$_3$ | H | CH$_2$(D-47a) |
| 3-Cl-5-S(O)CF$_3$ | CF$_3$ | C(O)OCH$_3$ | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-S(O)CF$_3$ | CF$_3$ | H | N(CH$_3$)Ph |
| 3-Cl-5-S(O)CF$_3$ | CF$_3$ | H | (D-50c)Cl |
| 3-Cl-5-SO$_2$CF$_3$ | CF$_3$ | H | CH$_2$CF$_3$ |
| 3-Cl-5-SO$_2$CF$_3$ | CF$_3$ | H | CHOCH$_2$CF$_3$ |
| 3-Cl-5-SO$_2$CF$_3$ | CF$_3$ | H | E-4a |
| 3-Cl-5-SO$_2$CF$_3$ | CF$_3$ | H | CH$_2$C(O)NHCH$_2$CF$_3$ |
| 3-Cl-5-SO$_2$CF$_3$ | CF$_3$ | H | CH(CH$_3$)C(O)NHCH$_2$CF$_3$(D) |
| 3-Cl-5-SO$_2$CF$_3$ | CF$_3$ | H | CH$_2$(D-22a) |
| 3-Cl-5-SO$_2$CF$_3$ | CF$_3$ | H | CH$_2$(D-47a) |
| 3-Cl-5-SO$_2$CF$_3$ | CF$_3$ | C(O)OCH$_3$ | CH$_2$(D-47a) |
| 3-Cl-5-SO$_2$CF$_3$ | CF$_3$ | H | N(CH$_3$)Ph |
| 3-Cl-5-SO$_2$CF$_3$ | CF$_3$ | H | (D-50c)Cl |
| 3-Br-5-SCF$_3$ | CF$_3$ | H | c-Bu |
| 3-Br-5-SCF$_3$ | CF$_3$ | H | CH$_2$CF$_3$ |
| 3-Br-5-SCF$_3$ | CF$_3$ | H | CH$_2$OEt |
| 3-Br-5-SCF$_3$ | CF$_3$ | H | CH$_2$OCH$_2$CF$_3$ |
| 3-Br-5-SCF$_3$ | CF$_3$ | C(O)CH$_3$ | CH$_2$OCH$_2$CF$_3$ |
| 3-Br-5-SCF$_3$ | CF$_3$ | H | CH$_2$CH$_2$OCH$_3$ |
| 3-Br-5-SCF$_3$ | CF$_3$ | H | CH$_2$(E-10a) |
| 3-Br-5-SCF$_3$ | CF$_3$ | H | E-4a |
| 3-Br-5-SCF$_3$ | CF$_3$ | H | CH$_2$C(O)NHCH$_2$CH$_2$Cl |
| 3-Br-5-SCF$_3$ | CF$_3$ | H | CH$_2$C(O)NHCH$_2$CF$_3$ |
| 3-Br-5-SCF$_3$ | CF$_3$ | H | CH(CH$_3$)C(O)NHCH$_2$CF$_3$ |
| 3-Br-5-SCF$_3$ | CF$_3$ | H | CH(CH$_3$)C(O)NHCH$_2$CF$_3$(D) |
| 3-Br-5-SCF$_3$ | CF$_3$ | H | CH(CH$_3$)Ph(R) |
| 3-Br-5-SCF$_3$ | CF$_3$ | H | CH$_2$(D-22a) |
| 3-Br-5-SCF$_3$ | CF$_3$ | C(O)CH$_3$ | CH$_2$(D-22a) |
| 3-Br-5-SCF$_3$ | CF$_3$ | C(O)Et | CH$_2$(D-22a) |
| 3-Br-5-SCF$_3$ | CF$_3$ | H | CH$_2$(D-47a) |
| 3-Br-5-SCF$_3$ | CF$_3$ | CH$_2$OCH$_3$ | CH$_2$(D-47a) |
| 3-Br-5-SCF$_3$ | CF$_3$ | CH$_2$CN | CH$_2$(D-47a) |
| 3-Br-5-SCF$_3$ | CF$_3$ | C(O)CH$_3$ | CH$_2$(D-47a) |
| 3-Br-5-SCF$_3$ | CF$_3$ | C(O)Et | CH$_2$(D-47a) |
| 3-Br-5-SCF$_3$ | CF$_3$ | C(O)OCH$_3$ | CH$_2$(D-47a) |
| 3-Br-5-SCF$_3$ | CF$_3$ | H | N(CH$_3$)Ph |
| 3-Br-5-SCF$_3$ | CF$_3$ | H | N(CH$_3$)(D-50a) |
| 3-Br-5-SCF$_3$ | CF$_3$ | H | C(O)NHCH$_2$CF$_3$ |
| 3-Br-5-SCF$_3$ | CF$_3$ | H | Ph-2,4-F$_2$ |
| 3-Br-5-SCF$_3$ | CF$_3$ | H | (D-50c)Cl |
| 3-Br-5-SCF$_3$ | CF$_3$ | H | D-52a |
| 3-Br-5-SCF$_3$ | CF$_2$Cl | H | CH$_2$CF$_3$ |
| 3-Br-5-SCF$_3$ | CF$_2$Cl | H | CH$_2$OCH$_2$CF$_3$ |
| 3-Br-5-SCF$_3$ | CF$_2$Cl | H | E-4a |
| 3-Br-5-SCF$_3$ | CF$_2$Cl | H | CH$_2$C(O)NHCH$_2$CF$_3$ |
| 3-Br-5-SCF$_3$ | CF$_2$Cl | H | CH(CH$_3$)C(O)NHCH$_2$CF$_3$(D) |
| 3-Br-5-SCF$_3$ | CF$_2$Cl | H | CH$_2$(D-22a) |
| 3-Br-5-SCF$_3$ | CF$_2$Cl | H | CH$_2$(D-47a) |
| 3-Br-5-SCF$_3$ | CF$_2$Cl | C(O)OCH$_3$ | CH$_2$(D-47a) |
| 3-Br-5-SCF$_3$ | CF$_2$Cl | H | N(CH$_3$)Ph |
| 3-Br-5-SCF$_3$ | CF$_2$Cl | H | (D-50c)Cl |
| 3-Br-5-S(O)CF$_3$ | CF$_3$ | H | CH$_2$CF$_3$ |
| 3-Br-5-S(O)CF$_3$ | CF$_3$ | H | CH$_2$OCH$_2$CF$_3$ |
| 3-Br-5-S(O)CF$_3$ | CF$_3$ | H | E-4a |
| 3-Br-5-S(O)CF$_3$ | CF$_3$ | H | CH$_2$C(O)NHCH$_2$CF$_3$ |
| 3-Br-5-S(O)CF$_3$ | CF$_3$ | H | CH(CH$_3$)C(O)NHCH$_2$CF$_3$(D) |
| 3-Br-5-S(O)CF$_3$ | CF$_3$ | H | CH$_2$(D-22a) |
| 3-Br-5-S(O)CF$_3$ | CF$_3$ | H | CH$_2$(D-47a) |
| 3-Br-5-S(O)CF$_3$ | CF$_3$ | C(O)OCH$_3$ | CH$_2$(D-47a) |
| 3-Br-5-S(O)CF$_3$ | CF$_3$ | H | N(CH$_3$)Ph |
| 3-Br-5-S(O)CF$_3$ | CF$_3$ | H | (D-50c)Cl |
| 3-Br-5-SO$_2$CF$_3$ | CF$_3$ | H | CH$_2$CF$_3$ |
| 3-Br-5-SO$_2$CF$_3$ | CF$_3$ | H | CH$_2$OCH$_2$CF$_3$ |
| 3-Br-5-SO$_2$CF$_3$ | CF$_3$ | H | E-4a |
| 3-Br-5-SO$_2$CF$_3$ | CF$_3$ | H | CH$_2$C(O)NHCH$_2$CF$_3$ |
| 3-Br-5-SO$_2$CF$_3$ | CF$_3$ | H | CH(CH$_3$)C(O)NHCH$_2$CF$_3$(D) |
| 3-Br-5-SO$_2$CF$_3$ | CF$_3$ | H | CH$_2$(D-22a) |
| 3-Br-5-SO$_2$CF$_3$ | CF$_3$ | H | CH$_2$(D-47a) |
| 3-Br-5-SO$_2$CF$_3$ | CF$_3$ | C(O)OCH$_3$ | CH$_2$(D-47a) |
| 3-Br-5-SO$_2$CF$_3$ | CF$_3$ | H | N(CH$_3$)Ph |
| 3-Br-5-SO$_2$CF$_3$ | CF$_3$ | H | (D-50c)Cl |
| 3-Cl-5-SCF$_2$CHFCl | CF$_3$ | H | CH$_2$CF$_3$ |
| 3-Cl-5-SCF$_2$CHFCl | CF$_3$ | H | CH$_2$OCH$_2$CF$_3$ |
| 3-Cl-5-SCF$_2$CHFCl | CF$_3$ | H | E-4a |
| 3-Cl-5-SCF$_2$CHFCl | CF$_3$ | H | CH$_2$C(O)NHCH$_2$CF$_3$ |
| 3-Cl-5-SCF$_2$CHFCl | CF$_3$ | H | CH(CH$_3$)C(O)NHCH$_2$CF$_3$(D) |
| 3-Cl-5-SCF$_2$CHFCl | CF$_3$ | H | CH$_2$(D-22a) |
| 3-Cl-5-SCF$_2$CHFCl | CF$_3$ | H | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-SCF$_2$CHFCl | CF$_3$ | C(O)OCH$_3$ | CH$_2$(D-47a) |
| 3-Cl-5-SCF$_2$CHFCl | CF$_3$ | H | N(CH$_3$)Ph |
| 3-Cl-5-SCF$_2$CHFCl | CF$_3$ | H | (D-50c)Cl |
| 3-Cl-5-S(O)CF$_2$CHFCl | CF$_3$ | H | CH$_2$CF$_3$ |
| 3-Cl-5-SO$_2$CF$_2$CHFCl | CF$_3$ | H | CH$_2$OCH$_2$CF$_3$ |
| 3-Br-5-SCF$_2$CHFCl | CF$_3$ | H | CH$_2$CF$_3$ |
| 3-Br-5-SCF$_2$CHFCl | CF$_3$ | H | CH$_2$OCH$_2$CF$_3$ |
| 3-Br-5-SCF$_2$CHFCl | CF$_3$ | H | E-4a |
| 3-Br-5-SCF$_2$CHFCl | CF$_3$ | H | CH$_2$C(O)NHCH$_2$CF$_3$ |
| 3-Br-5-SCF$_2$CHFCl | CF$_3$ | H | CH(CH$_3$)C(O)NHCH$_2$CF$_3$(D) |
| 3-Br-5-SCF$_2$CHFCl | CF$_3$ | H | CH$_2$(D-22a) |
| 3-Br-5-SCF$_2$CHFCl | CF$_3$ | H | CH$_2$(D-47a) |
| 3-Br-5-SCF$_2$CHFCl | CF$_3$ | C(O)OCH$_3$ | CH$_2$(D-47a) |
| 3-Br-5-SCF$_2$CHFCl | CF$_3$ | H | N(CH$_3$)Ph |
| 3-Br-5-SCF$_2$CHFCl | CF$_3$ | H | (D-50c)Cl |
| 3-Br-5-S(O)CF$_2$CHFCl | CF$_3$ | H | E-4a |
| 3-Br-5-SO$_2$CF$_2$CHFCl | CF$_3$ | H | CH$_2$C(O)NHCH$_2$CF$_3$ |
| 3-Cl-5-SPh | CF$_3$ | H | CH$_2$(D-22a) |
| 3-Cl-5-S(O)Ph | CF$_3$ | H | CH$_2$(D-47a) |
| 3-Cl-5-SO$_2$Ph | CF$_3$ | C(O)OCH$_3$ | CH$_2$(D-47a) |
| 3-NO$_2$-4-F | CF$_3$ | H | N(CH$_3$)Ph |
| 2-F-5-NO$_2$ | CF$_3$ | H | (D-50c)Cl |
| 3-F-5-NO$_2$ | CF$_3$ | H | CH$_2$CF$_3$ |
| 3-NO$_2$-4-Cl | CF$_3$ | H | CH$_2$OCH$_2$CF$_3$ |
| 3-Cl-5-NO$_2$ | CF$_3$ | H | CH$_2$CF$_3$ |
| 3-Cl-5-NO$_2$ | CF$_3$ | H | CH$_2$OCH$_2$CF$_3$ |
| 3-Cl-5-NO$_2$ | CF$_3$ | H | E-4a |
| 3-Cl-5-NO$_2$ | CF$_3$ | H | CH$_2$C(O)NHCH$_2$CF$_3$ |
| 3-Cl-5-NO$_2$ | CF$_3$ | H | CH(CH$_3$)C(O)NHCH$_2$CF$_3$(D) |
| 3-Cl-5-NO$_2$ | CF$_3$ | H | CH$_2$(D-22a) |
| 3-Cl-5-NO$_2$ | CF$_3$ | H | CH$_2$(D-47a) |
| 3-Cl-5-NO$_2$ | CF$_3$ | C(O)OCH$_3$ | CH$_2$(D-47a) |
| 3-Cl-5-NO$_2$ | CF$_3$ | H | N(CH$_3$)Ph |
| 3-Cl-5-NO$_2$ | CF$_3$ | H | (D-50c)Cl |
| 3-Br-5-NO$_2$ | CF$_3$ | H | CH$_2$CF$_3$ |
| 3-Br-5-NO$_2$ | CF$_3$ | H | CH$_2$OCH$_2$CF$_3$ |
| 3-Br-5-NO$_2$ | CF$_3$ | H | E-4a |
| 3-Br-5-NO$_2$ | CF$_3$ | H | CH$_2$C(O)NHCH$_2$CF$_3$ |
| 3-Br-5-NO$_2$ | CF$_3$ | H | CH(CH$_3$)C(O)NHCH$_2$CF$_3$(D) |
| 3-Br-5-NO$_2$ | CF$_3$ | H | CH$_2$(D-22a) |
| 3-Br-5-NO$_2$ | CF$_3$ | H | CH$_2$(D-47a) |
| 3-Br-5-NO$_2$ | CF$_3$ | C(O)OCH$_3$ | CH$_2$(D-47a) |
| 3-Br-5-NO$_2$ | CF$_3$ | H | N(CH$_3$)Ph |
| 3-Br-5-NO$_2$ | CF$_3$ | H | (D-50c)Cl |
| 3-CH$_3$-5-NO$_2$ | CF$_3$ | H | E-4a |
| 3-CF$_3$-4-NO$_2$ | CF$_3$ | H | CH$_2$C(O)NHCH$_2$CF$_3$ |
| 3-CF$_3$-5-NO$_2$ | CF$_3$ | H | CH$_2$CF$_3$ |
| 3-CF$_3$-5-NO$_2$ | CF$_3$ | C(O)CH$_3$ | CH$_2$CF$_3$ |
| 3-CF$_3$-5-NO$_2$ | CF$_3$ | H | CH$_2$OCH$_2$CF$_3$ |
| 3-CF$_3$-5-NO$_2$ | CF$_3$ | H | E-4a |
| 3-CF$_3$-5-NO$_2$ | CF$_3$ | H | CH$_2$C(O)NHCH$_2$CF$_3$ |
| 3-CF$_3$-5-NO$_2$ | CF$_3$ | H | CH(CH$_3$)C(O)NHCH$_2$CF$_3$(D) |
| 3-CF$_3$-5-NO$_2$ | CF$_3$ | H | CH(CH$_3$)Ph(R) |
| 3-CF$_3$-5-NO$_2$ | CF$_3$ | H | CH$_2$(D-22a) |
| 3-CF$_3$-5-NO$_2$ | CF$_3$ | H | CH$_2$(D-47a) |
| 3-CF$_3$-5-NO$_2$ | CF$_3$ | CH$_2$CN | CH$_2$(D-47a) |
| 3-CF$_3$-5-NO$_2$ | CF$_3$ | C(O)Et | CH$_2$(D-47a) |
| 3-CF$_3$-5-NO$_2$ | CF$_3$ | C(O)OCH$_3$ | CH$_2$(D-47a) |
| 3-CF$_3$-5-NO$_2$ | CF$_3$ | H | N(CH$_3$)Ph |
| 3-CF$_3$-5-NO$_2$ | CF$_3$ | H | (D-50c)Cl |
| 3-CF$_3$-5-NO$_2$ | CF$_3$ | H | D-52a |
| 3-CF$_3$-5-NO$_2$ | CF$_2$Cl | H | CH$_2$CF$_3$ |
| 3-CF$_3$-5-NO$_2$ | CF$_2$Cl | H | E-4a |
| 3-CF$_3$-5-NO$_2$ | CF$_2$Cl | H | CH$_2$C(O)NHCH$_2$CF$_3$ |
| 3-CF$_3$-5-NO$_2$ | CF$_2$Cl | H | CH$_2$(D-22a) |
| 3-CF$_3$-5-NO$_2$ | CF$_2$Cl | H | CH$_2$(D-47a) |
| 3-CF$_3$-5-NO$_2$ | CF$_2$Cl | H | (D-50c)Cl |
| 3,5-(NO$_2$)$_2$ | CF$_3$ | H | CH$_2$(D-22a) |
| 3-Cl-5-NHC(O)CF$_3$ | CF$_3$ | H | CH$_2$(D-47a) |
| 3-Cl-5-N(CH$_3$)C(O)CF$_3$ | CF$_3$ | C(O)OCH$_3$ | CH$_2$(D-47a) |
| 3-Cl-5-N(Et)C(O)CF$_3$ | CF$_3$ | H | N(CH$_3$)Ph |
| 3-Cl-5-N(CH$_3$)C(O)CF$_2$Cl | CF$_3$ | H | (D-50c)Cl |
| 3-Cl-5-N(Et)C(O)CF$_2$Cl | CF$_3$ | H | CH$_2$CF$_3$ |
| 3-Cl-5-N(CH$_3$)C(O)CF$_2$Br | CF$_3$ | H | CH$_2$OCH$_2$CF$_3$ |
| 3-Cl-5-N(Et)C(O)CF$_2$Br | CF$_3$ | H | E-4a |
| 3-Cl-5-N(CH$_3$)SO$_2$CF$_3$ | CF$_3$ | H | CH$_2$C(O)NHCH$_2$CF$_3$ |
| 3-Cl-5-N(Et)SO$_2$CF$_3$ | CF$_3$ | H | CH$_2$(D-22a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CF$_3$-5-NHC(O)CH$_3$ | CF$_3$ | H | CH$_2$(D-47a) |
| 3-CF$_3$-5-NHC(O)CF$_3$ | CF$_3$ | C(O)OCH$_3$ | CH$_2$(D-47a) |
| 3-CF$_3$-5-N(CH$_3$)C(O)CH$_3$ | CF$_3$ | H | N(CH$_3$)Ph |
| 3-CF$_3$-5-N(Et)C(O)CH$_3$ | CF$_3$ | H | (D-50c)Cl |
| 3-CF$_3$-5-N(CH$_3$)C(O)CF$_3$ | CF$_3$ | H | CH$_2$CF$_3$ |
| 3-CF$_3$-5-N(Et)C(O)CF$_3$ | CF$_3$ | H | CH$_2$OCH$_2$CF$_3$ |
| 3-CF$_3$-5-N(CH$_3$)C(O)CF$_2$Cl | CF$_3$ | H | E-4a |
| 3-CF$_3$-5-N(Et)C(O)CF$_2$Cl | CF$_3$ | H | CH$_2$C(O)NHCH$_2$CF$_3$ |
| 3-CF$_3$-5-N(CH$_3$)C(O)CF$_2$Br | CF$_3$ | H | CH$_2$(D-22a) |
| 3-CF$_3$-5-N(Et)C(O)CF$_2$Br | CF$_3$ | H | CH$_2$(D-47a) |
| 3-CF$_3$-5-N(CH$_3$)SO$_2$CF$_3$ | CF$_3$ | C(O)OCH$_3$ | CH$_2$(D-47a) |
| 3-CF$_3$-5-N(Et)SO$_2$CF$_3$ | CF$_3$ | H | N(CH$_3$)Ph |
| 3-NO$_2$-5-NHC(O)CH$_3$ | CF$_3$ | H | (D-50c)Cl |
| 3,5-(CHO)$_2$ | CF$_3$ | H | CH$_2$CF$_3$ |
| 3-CN-4-F | CF$_3$ | H | CH$_2$OCH$_2$CF$_3$ |
| 3-F-4-CN | CF$_3$ | H | E-4a |
| 3-F-5-CN | CF$_3$ | H | CH$_2$C(O)NHCH$_2$CF$_3$ |
| 3-Cl-4-CN | CF$_3$ | H | CH$_2$(D-22a) |
| 3-Cl-5-CN | CF$_3$ | H | CH$_2$CF$_3$ |
| 3-Cl-5-CN | CF$_3$ | C(O)CH$_3$ | CH$_2$CF$_3$ |
| 3-Cl-5-CN | CF$_3$ | H | CHOCH$_2$CF$_3$ |
| 3-Cl-5-CN | CF$_3$ | H | E-4a |
| 3-Cl-5-CN | CF$_3$ | H | CH$_2$C(O)NHCH$_2$CF$_3$ |
| 3-Cl-5-CN | CF$_3$ | H | CH(CH$_3$)C(O)NHCH$_2$CF$_3$(D) |
| 3-Cl-5-CN | CF$_3$ | H | CH(CH$_3$)Ph(R) |
| 3-Cl-5-CN | CF$_3$ | H | CH$_2$(D-22a) |
| 3-Cl-5-CN | CF$_3$ | H | CH$_2$(D-47a) |
| 3-Cl-5-CN | CF$_3$ | CH$_2$CN | CH$_2$(D-47a) |
| 3-Cl-5-CN | CF$_3$ | C(O)Et | CH$_2$(D-47a) |
| 3-Cl-5-CN | CF$_3$ | C(O)OCH$_3$ | CH$_2$(D-47a) |
| 3-Cl-5-CN | CF$_3$ | H | N(CH$_3$)Ph |
| 3-Cl-5-CN | CF$_3$ | H | (D-50c)Cl |
| 3-Cl-5-CN | CF$_3$ | H | D-52a |
| 3-Cl-5-CN | CF$_2$Cl | H | CH$_2$(D-47a) |
| 3-Br-4-CN | CF$_3$ | C(O)OCH$_3$ | CH$_2$(D-47a) |
| 3-Br-5-CN | CF$_3$ | H | CH$_2$CF$_3$ |
| 3-Br-5-CN | CF$_3$ | C(O)CH$_3$ | CH$_2$CF$_3$ |
| 3-Br-5-CN | CF$_3$ | H | CH$_2$OCH$_2$CF$_3$ |
| 3-Br-5-CN | CF$_3$ | H | E-4a |
| 3-Br-5-CN | CF$_3$ | H | CH$_2$C(O)NHCH$_2$CF$_3$ |
| 3-Br-5-CN | CF$_3$ | H | CH(CH$_3$)C(O)NHCH$_2$CF$_3$(D) |
| 3-Br-5-CN | CF$_3$ | H | CH(CH$_3$)Ph(R) |
| 3-Br-5-CN | CF$_3$ | H | CH$_2$(D-22a) |
| 3-Br-5-CN | CF$_3$ | H | CH$_2$(D-47a) |
| 3-Br-5-CN | CF$_3$ | CH$_2$CN | CH$_2$(D-47a) |
| 3-Br-5-CN | CF$_3$ | C(O)Et | CH$_2$(D-47a) |
| 3-Br-5-CN | CF$_3$ | C(O)OCH$_3$ | CH$_2$(D-47a) |
| 3-Br-5-CN | CF$_3$ | H | N(CH$_3$)Ph |
| 3-Br-5-CN | CF$_3$ | H | (D-50c)Cl |
| 3-Br-5-CN | CF$_3$ | H | D-52a |
| 3-Br-5-CN | CF$_2$Cl | H | N(CH$_3$)Ph |
| 3-CH$_3$-4-CN | CF$_3$ | H | (D-50c)Cl |
| 3-CH$_3$-5-CN | CF$_3$ | H | CH$_2$CF$_3$ |
| 3-CF$_3$-5-CN | CF$_3$ | H | c-Bu |
| 3-CF$_3$-5-CN | CF$_3$ | H | CH$_2$CF$_3$ |
| 3-CF$_3$-5-CN | CF$_3$ | H | CH$_2$OEt |
| 3-CF$_3$-5-CN | CF$_3$ | H | CH$_2$OCH$_2$CF$_3$ |
| 3-CF$_3$-5-CN | CF$_3$ | C(O)CH$_3$ | CH$_2$OCH$_2$CF$_3$ |
| 3-CF$_3$-5-CN | CF$_3$ | H | CH$_2$CH$_2$OCH$_3$ |
| 3-CF$_3$-5-CN | CF$_3$ | H | CH$_2$(E-10a) |
| 3-CF$_3$-5-CN | CF$_3$ | H | E-4a |
| 3-CF$_3$-5-CN | CF$_3$ | H | CH$_2$C(O)NHCH$_2$CH$_2$Cl |
| 3-CF$_3$-5-CN | CF$_3$ | H | CH$_2$C(O)NHCH$_2$CF$_3$ |
| 3-CF$_3$-5-CN | CF$_3$ | H | CH(CH$_3$)C(O)NHCH$_2$CF$_3$ |
| 3-CF$_3$-5-CN | CF$_3$ | H | CH(CH$_3$)C(O)NHCH$_2$CF$_3$(D) |
| 3-CF$_3$-5-CN | CF$_3$ | H | CH(CH$_3$)Ph(R) |
| 3-CF$_3$-5-CN | CF$_3$ | H | CH$_2$(D-22a) |
| 3-CF$_3$-5-CN | CF$_3$ | C(O)CH$_3$ | CH$_2$(D-22a) |
| 3-CF$_3$-5-CN | CF$_3$ | C(O)Et | CH$_2$(D-22a) |
| 3-CF$_3$-5-CN | CF$_3$ | H | CH$_2$(D-47a) |
| 3-CF$_3$-5-CN | CF$_3$ | CH$_2$OCH$_3$ | CH$_2$(D-47a) |
| 3-CF$_3$-5-CN | CF$_3$ | CH$_2$CN | CH$_2$(D-47a) |
| 3-CF$_3$-5-CN | CF$_3$ | C(O)CH$_3$ | CH$_2$(D-47a) |
| 3-CF$_3$-5-CN | CF$_3$ | C(O)Et | CH$_2$(D-47a) |
| 3-CF$_3$-5-CN | CF$_3$ | C(O)OCH$_3$ | CH$_2$(D-47a) |
| 3-CF$_3$-5-CN | CF$_3$ | H | N(CH$_3$)Ph |
| 3-CF$_3$-5-CN | CF$_3$ | H | N(CH$_3$)(D-50a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CF$_3$-5-CN | CF$_3$ | H | C(O)NHCH$_2$CF$_3$ |
| 3-CF$_3$-5-CN | CF$_3$ | H | Ph-2,4-F$_2$ |
| 3-CF$_3$-5-CN | CF$_3$ | H | (D-50c)Cl |
| 3-CF$_3$-5-CN | CF$_3$ | H | D-52a |
| 3-CF$_3$-5-CN | CF$_2$Cl | H | CH$_2$CF$_3$ |
| 3-CF$_3$-5-CN | CF$_2$Cl | H | CH$_2$OCH$_2$CF$_3$ |
| 3-CF$_3$-5-CN | CF$_2$Cl | H | E-4a |
| 3-CF$_3$-5-CN | CF$_2$Cl | H | CH$_2$C(O)NHCH$_2$CF$_3$ |
| 3-CF$_3$-5-CN | CF$_2$Cl | H | CH(CH$_3$)C(O)NHCH$_2$CF$_3$(D) |
| 3-CF$_3$-5-CN | CF$_2$Cl | H | CH$_2$(D-22a) |
| 3-CF$_3$-5-CN | CF$_2$Cl | H | CH$_2$(D-47a) |
| 3-CF$_3$-5-CN | CF$_2$Cl | C(O)OCH$_3$ | CH$_2$(D-47a) |
| 3-CF$_3$-5-CN | CF$_2$Cl | H | N(CH$_3$)Ph |
| 3-CF$_3$-5-CN | CF$_2$Cl | H | (D-50c)Cl |
| 3-NO$_2$-5-CN | CF$_3$ | H | CH$_2$OCH$_2$CF$_3$ |
| 3,5-(CN)$_2$ | CF$_3$ | H | E-4a |
| 3-F-5-C(O)OCH$_3$ | CF$_3$ | H | CH$_2$C(O)NHCH$_2$CF$_3$ |
| 3-F-5-C(O)NH$_2$ | CF$_3$ | H | CH$_2$(D-22a) |
| 3-F-5-C(O)NHCH$_3$ | CF$_3$ | H | CH$_2$(D-47a) |
| 3-F-5-C(O)N(CH$_3$)$_2$ | CF$_3$ | C(O)OCH$_3$ | CH$_2$(D-47a) |
| 3-Cl-5-C(O)OCH$_3$ | CF$_3$ | H | N(CH$_3$)Ph |
| 3-Cl-5-C(O)NH$_2$ | CF$_3$ | H | (D-50c)Cl |
| 3-Cl-5-C(O)NHCH$_3$ | CF$_3$ | H | CH$_2$CF$_3$ |
| 3-Cl-5-C(O)N(CH$_3$)$_2$ | CF$_3$ | H | CH$_2$OCH$_2$CF$_3$ |
| 3-Br-5-C(O)OCH$_3$ | CF$_3$ | H | E-4a |
| 3-Br-5-C(O)NH$_2$ | CF$_3$ | H | CH$_2$C(O)NHCH$_2$CF$_3$ |
| 3-Br-5-C(O)NHCH$_3$ | CF$_3$ | H | CH$_2$(D-22a) |
| 3-Br-5-C(O)N(CH$_3$)$_2$ | CF$_3$ | H | CH$_2$(D-47a) |
| 3-CH$_3$-5-C(O)OCH$_3$ | CF$_3$ | C(O)OCH$_3$ | CH$_2$(D-47a) |
| 3-CH$_3$-5-C(O)NH$_2$ | CF$_3$ | H | N(CH$_3$)Ph |
| 3-CH$_3$-5-C(O)NHCH$_3$ | CF$_3$ | H | (D-50c)Cl |
| 3-CH$_3$-5-C(O)N(CH$_3$)$_2$ | CF$_3$ | H | CH$_2$CF$_3$ |
| 3-CF$_3$-5-C(O)OCH$_3$ | CF$_3$ | H | CH$_2$OCH$_2$CF$_3$ |
| 3-CF$_3$-5-C(O)NH$_2$ | CF$_3$ | H | E-4a |
| 3-CF$_3$-5-C(O)NHCH$_3$ | CF$_3$ | H | CH$_2$C(O)NHCH$_2$CF$_3$ |
| 3-CF$_3$-5-C(O)N(CH$_3$)$_2$ | CF$_3$ | H | CH$_2$(D-22a) |
| 3-OCH$_3$-5-C(O)OCH$_3$ | CF$_3$ | H | CH$_2$(D-47a) |
| 3-OCH$_3$-5-C(O)NH$_2$ | CF$_3$ | C(O)OCH$_3$ | CH$_2$(D-47a) |
| 3-OCH$_3$-5-C(O)NHCH$_3$ | CF$_3$ | H | N(CH$_3$)Ph |
| 3-OCH$_3$-5-C(O)N(CH$_3$)$_2$ | CF$_3$ | H | (D-50c)Cl |
| 3-NO$_2$-5-C(O)OCH$_3$ | CF$_3$ | H | CH$_2$CF$_3$ |
| 3-NO$_2$-5-C(O)NH$_2$ | CF$_3$ | H | CH$_2$OCH$_2$CF$_3$ |
| 3-NO$_2$-5-C(O)NHCH$_3$ | CF$_3$ | H | E-4a |
| 3-NO$_2$-5-C(O)N(CH$_3$)$_2$ | CF$_3$ | H | CH$_2$C(O)NHCH$_2$CF$_3$ |
| 3,5-[C(O)OCH$_3$]$_2$ | CF$_3$ | H | CH$_2$(D-22a) |
| 3,5-[C(O)NH$_2$]$_2$ | CF$_3$ | H | CH$_2$(D-47a) |
| 3,5-[C(O)NHCH$_3$]$_2$ | CF$_3$ | C(O)OCH$_3$ | CH$_2$(D-47a) |
| 3,5-[C(O)N(CH$_3$)$_2$]$_2$ | CF$_3$ | H | N(CH$_3$)Ph |
| 3-Cl-5-SO$_2$OCH$_3$ | CF$_3$ | H | (D-50c)Cl |
| 3-CH$_3$-5-SO$_2$OCH$_3$ | CF$_3$ | H | CH$_2$CF$_3$ |
| 3-Cl-5-SO$_2$NH$_2$ | CF$_3$ | H | CH$_2$OCH$_2$CF$_3$ |
| 3-CH$_3$-5-SO$_2$NH$_2$ | CF$_3$ | H | E-4a |
| 3-Cl-5-SO$_2$NHCH$_3$ | CF$_3$ | H | CH$_2$C(O)NHCH$_2$CF$_3$ |
| 3-Cl-5-SO$_2$N(CH$_3$)$_2$ | CF$_3$ | H | CH$_2$(D-22a) |
| 3-CH$_3$-5-Ph | CF$_3$ | H | CH$_2$(D-47a) |
| 2-CH=CHCH=CH-3 | CF$_3$ | C(O)OCH$_3$ | CH$_2$(D-47a) |
| 3-CH=CHCH=CH-4 | CF$_3$ | H | N(CH$_3$)Ph |
| 2,3,4-F3 | CF$_3$ | H | (D-50c)Cl |
| 2,3,5-F$_3$ | CF$_3$ | H | CH$_2$CF$_3$ |
| 2,3,6-F$_3$ | CF$_3$ | H | CH$_2$OCH$_2$CF$_3$ |
| 2,4,5-F$_3$ | CF$_3$ | H | E-4a |
| 2,4,6-F$_3$ | CF$_3$ | H | CH$_2$C(O)NHCH$_2$CF$_3$ |
| 3,4,5-F$_3$ | CF$_3$ | H | c-Bu |
| 3,4,5-F$_3$ | CF$_3$ | H | CH$_2$CF$_3$ |
| 3,4,5-F$_3$ | CF$_3$ | H | CH$_2$OEt |
| 3,4,5-F$_3$ | CF$_3$ | H | CH$_2$OCH$_2$CF$_3$ |
| 3,4,5-F$_3$ | CF$_3$ | C(O)CH$_3$ | CH$_2$OCH$_2$CF$_3$ |
| 3,4,5-F$_3$ | CF$_3$ | H | CH$_2$CH$_2$OCH$_3$ |
| 3,4,5-F$_3$ | CF$_3$ | H | CH$_2$(E-10a) |
| 3,4,5-F$_3$ | CF$_3$ | H | E-4a |
| 3,4,5-F$_3$ | CF$_3$ | H | CH$_2$C(O)NHCH$_2$Cl |
| 3,4,5-F$_3$ | CF$_3$ | H | CH$_2$C(O)NHCH$_2$CF$_3$ |
| 3,4,5-F$_3$ | CF$_3$ | H | CH(CH$_3$)C(O)NHCH$_2$CF$_3$ |
| 3,4,5-F$_3$ | CF$_3$ | H | CH(CH$_3$)C(O)NHCH$_2$CF$_3$(D) |
| 3,4,5-F$_3$ | CF$_3$ | H | CH$_2$Ph |
| 3,4,5-F$_3$ | CF$_3$ | H | CH(CH$_3$)Ph(R) |
| 3,4,5-F$_3$ | CF$_3$ | H | CH$_2$(D-22a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4,5-F$_3$ | CF$_3$ | C(O)CH$_3$ | CH$_2$(D-22a) |
| 3,4,5-F$_3$ | CF$_3$ | C(O)Et | CH$_2$(D-22a) |
| 3,4,5-F$_3$ | CF$_3$ | H | CH$_2$(D-47a) |
| 3,4,5-F$_3$ | CF$_3$ | CH$_2$OCH$_3$ | CH$_2$(D-47a) |
| 3,4,5-F$_3$ | CF$_3$ | CH$_2$CN | CH$_2$(D-47a) |
| 3,4,5-F$_3$ | CF$_3$ | C(O)CH$_3$ | CH$_2$(D-47a) |
| 3,4,5-F$_3$ | CF$_3$ | C(O)Et | CH$_2$(D-47a) |
| 3,4,5-F$_3$ | CF$_3$ | C(O)OCH$_3$ | CH$_2$(D-47a) |
| 3,4,5-F$_3$ | CF$_3$ | H | N(CH$_3$)Ph |
| 3,4,5-F$_3$ | CF$_3$ | H | N(CH$_3$)(D-50a) |
| 3,4,5-F$_3$ | CF$_3$ | H | C(O)NHCH$_2$CF$_3$ |
| 3,4,5-F$_3$ | CF$_3$ | H | Ph-2,4-F$_2$ |
| 3,4,5-F$_3$ | CF$_3$ | H | (D-50c)Cl |
| 3,4,5-F$_3$ | CF$_3$ | H | D-52a |
| 3,4,5-F$_3$ | CF$_2$Cl | H | CH$_2$CF$_3$ |
| 3,4,5-F$_3$ | CF$_2$Cl | H | CH$_2$OCH$_2$CF$_3$ |
| 3,4,5-F$_3$ | CF$_2$Cl | H | E-4a |
| 3,4,5-F$_3$ | CF$_2$Cl | H | CH$_2$C(O)NHCH$_2$CF$_3$ |
| 3,4,5-F$_3$ | CF$_2$Cl | H | CH(CH$_3$)C(O)NHCH$_2$CF$_3$(D) |
| 3,4,5-F$_3$ | CF$_2$Cl | H | CH$_2$(D-22a) |
| 3,4,5-F$_3$ | CF$_2$Cl | H | CH$_2$(D-47a) |
| 3,4,5-F$_3$ | CF$_2$Cl | C(O)OCH$_3$ | CH$_2$(D-47a) |
| 3,4,5-F$_3$ | CF$_2$Cl | H | N(CH$_3$)Ph |
| 3,4,5-F$_3$ | CF$_2$Cl | H | (D-50c)Cl |
| 2,6-F$_2$-3-Cl | CF$_3$ | H | CH$_2$(D-22a) |
| 3,5-Cl$_2$-4-F | CHF$_2$ | H | CH$_2$CF$_3$ |
| 3,5-Cl$_2$-4-F | CHF$_2$ | H | E-4a |
| 3,5-Cl$_2$-4-F | CHF$_2$ | H | CH$_2$C(O)NHCH$_2$CF$_3$ |
| 3,5-Cl$_2$-4-F | CHF$_2$ | H | CH$_2$(D-22a) |
| 3,5-Cl$_2$-4-F | CHF$_2$ | H | CH$_2$(D-47a) |
| 3,5-Cl$_2$-4-F | CHF$_2$ | H | (D-50c)Cl |
| 3,5-Cl$_2$-4-F | CF$_3$ | H | c-Pr |
| 3,5-Cl$_2$-4-F | CF$_3$ | H | CH$_2$Pr-c |
| 3,5-Cl$_2$-4-F | CF$_3$ | H | c-Bu |
| 3,5-Cl$_2$-4-F | CF$_3$ | H | CH$_2$CF$_3$ |
| 3,5-Cl$_2$-4-F | CF$_3$ | H | CH$_2$CH$_2$CF$_3$ |
| 3,5-Cl$_2$-4-F | CF$_3$ | H | CH$_2$OCH$_3$ |
| 3,5-Cl$_2$-4-F | CF$_3$ | H | CH$_2$OEt |
| 3,5-Cl$_2$-4-F | CF$_3$ | C(O)CH$_3$ | CH$_2$OEt |
| 3,5-Cl$_2$-4-F | CF$_3$ | H | CH$_2$OCH$_2$CF$_3$ |
| 3,5-Cl$_2$-4-F | CF$_3$ | C(O)CH$_3$ | CH$_2$OCH$_2$CF$_3$ |
| 3,5-Cl$_2$-4-F | CF$_3$ | H | CH(CH$_3$)OCH$_2$CF$_3$ |
| 3,5-Cl$_2$-4-F | CF$_3$ | H | CH$_2$CH$_2$OCH$_3$ |
| 3,5-Cl$_2$-4-F | CF$_3$ | H | CH$_2$(E-5a) |
| 3,5-Cl$_2$-4-F | CF$_3$ | H | CH$_2$(E-10a) |
| 3,5-Cl$_2$-4-F | CF$_3$ | H | CH$_2$(E-10b)CH$_3$ |
| 3,5-Cl$_2$-4-F | CF$_3$ | H | E-4a |
| 3,5-Cl$_2$-4-F | CF$_3$ | H | E-5a(R) |
| 3,5-Cl$_2$-4-F | CF$_3$ | H | CH$_2$CH=NOCH$_3$ |
| 3,5-Cl$_2$-4-F | CF$_3$ | H | CH$_2$C(CH$_3$)=NOCH$_3$ |
| 3,5-Cl$_2$-4-F | CF$_3$ | H | CH$_2$C(O)NHCH$_3$ |
| 3,5-Cl$_2$-4-F | CF$_3$ | H | CH$_2$C(O)N(CH$_3$)$_2$ |
| 3,5-Cl$_2$-4-F | CF$_3$ | H | CH$_2$C(O)NHPr-n |
| 3,5-Cl$_2$-4-F | CF$_3$ | H | CH$_2$C(O)NHPr-i |
| 3,5-Cl$_2$-4-F | CF$_3$ | H | CH$_2$C(O)NHCH$_2$F |
| 3,5-Cl$_2$-4-F | CF$_3$ | H | CH$_2$C(O)NHCH$_2$CH$_2$Cl |
| 3,5-Cl$_2$-4-F | CF$_3$ | H | CH$_2$C(O)NHCH$_2$CF$_3$ |
| 3,5-Cl$_2$-4-F | CF$_3$ | H | CH$_2$C(O)NHCH$_2$CH=CH$_2$ |
| 3,5-Cl$_2$-4-F | CF$_3$ | H | CH$_2$C(O)NHCH$_2$C≡CH |
| 3,5-Cl$_2$-4-F | CF$_3$ | H | CH(CH$_3$)C(O)NHEt |
| 3,5-Cl$_2$-4-F | CF$_3$ | H | CH(CH$_3$)C(O)NHCH$_2$CF$_3$ |
| 3,5-Cl$_2$-4-F | CF$_3$ | H | CH(CH$_3$)C(O)NHCH$_2$CF$_3$(D) |
| 3,5-Cl$_2$-4-F | CF$_3$ | H | CH$_2$CH=CH$_2$ |
| 3,5-Cl$_2$-4-F | CF$_3$ | H | CH$_2$CCl=CH$_2$ |
| 3,5-Cl$_2$-4-F | CF$_3$ | H | CH(CH$_3$)Ph(R) |
| 3,5-Cl$_2$-4-F | CF$_3$ | H | CH$_2$(Ph-4-NO$_2$) |
| 3,5-Cl$_2$-4-F | CF$_3$ | H | CH$_2$(Ph-4-CN) |
| 3,5-Cl$_2$-4-F | CF$_3$ | H | CH$_2$(D-16b)Cl |
| 3,5-Cl$_2$-4-F | CF$_3$ | H | CH$_2$(D-17a)CH$_3$ |
| 3,5-Cl$_2$-4-F | CF$_3$ | H | CH$_2$(D-17b)Cl |
| 3,5-Cl$_2$-4-F | CF$_3$ | H | CH$_2$(D-21a) |
| 3,5-Cl$_2$-4-F | CF$_3$ | H | CH$_2$(D-22a) |
| 3,5-Cl$_2$-4-F | CF$_3$ | C(O)CH$_3$ | CH$_2$(D-22a) |
| 3,5-Cl$_2$-4-F | CF$_3$ | C(O)Et | CH$_2$(D-22a) |
| 3,5-Cl$_2$-4-F | CF$_3$ | H | CH$_2$(D-29b)CH$_3$ |
| 3,5-Cl$_2$-4-F | CF$_3$ | H | CH$_2$(D-34a) |
| 3,5-Cl$_2$-4-F | CF$_3$ | H | CH$_2$(D-38a) |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$-4-F | CF$_3$ | H | CH$_2$(D-47a) |
| 3,5-Cl$_2$-4-F | CF$_3$ | Et | CH$_2$(D-47a) |
| 3,5-Cl$_2$-4-F | CF$_3$ | CH$_2$OCH$_3$ | CH$_2$(D-47a) |
| 3,5-Cl$_2$-4-F | CF$_3$ | CH$_2$CN | CH$_2$(D-47a) |
| 3,5-Cl$_2$-4-F | CF$_3$ | CH$_2$C≡CH | CH$_2$(D-47a) |
| 3,5-Cl$_2$-4-F | CF$_3$ | C(O)CH$_3$ | CH$_2$(D-47a) |
| 3,5-Cl$_2$-4-F | CF$_3$ | C(O)Et | CH$_2$(D-47a) |
| 3,5-Cl$_2$-4-F | CF$_3$ | C(O)Pr-n | CH$_2$(D-47a) |
| 3,5-Cl$_2$-4-F | CF$_3$ | C(O)Pr-i | CH$_2$(D-47a) |
| 3,5-Cl$_2$-4-F | CF$_3$ | C(O)Pr-c | CH$_2$(D-47a) |
| 3,5-Cl$_2$-4-F | CF$_3$ | C(O)Bu-t | CH$_2$(D-47a) |
| 3,5-Cl$_2$-4-F | CF$_3$ | C(O)CH$_2$OCH$_3$ | CH$_2$(D-47a) |
| 3,5-Cl$_2$-4-F | CF$_3$ | C(O)CH=CH$_2$ | CH$_2$(D-47a) |
| 3,5-Cl$_2$-4-F | CF$_3$ | C(O)OCH$_3$ | CH$_2$(D-47a) |
| 3,5-Cl$_2$-4-F | CF$_3$ | C(O)OCH$_2$CH$_2$OCH$_3$ | CH$_2$(D-47a) |
| 3,5-Cl$_2$-4-F | CF$_3$ | C(O)OCH$_2$CH=CH$_2$ | CH$_2$(D-47a) |
| 3,5-Cl$_2$-4-F | CF$_3$ | H | CH(CH$_3$)(D-47a) |
| 3,5-Cl$_2$-4-F | CF$_3$ | H | CH$_2$(D-50a) |
| 3,5-Cl$_2$-4-F | CF$_3$ | H | NHC(O)OCH$_3$ |
| 3,5-Cl$_2$-4-F | CF$_3$ | H | N(CH$_3$)Ph |
| 3,5-Cl$_2$-4-F | CF$_3$ | H | N(CH$_2$CH=CH$_2$)Ph |
| 3,5-Cl$_2$-4-F | CF$_3$ | H | N(CH$_2$C≡CH)Ph |
| 3,5-Cl$_2$-4-F | CF$_3$ | H | NH(D-50a) |
| 3,5-Cl$_2$-4-F | CF$_3$ | CH$_3$ | NH(D-50a) |
| 3,5-Cl$_2$-4-F | CF$_3$ | H | N(CH$_3$)(D-50a) |
| 3,5-Cl$_2$-4-F | CF$_3$ | H | N(Et)(D-50a) |
| 3,5-Cl$_2$-4-F | CF$_3$ | C(O)OCH$_3$ | C(O)N(CH$_3$)$_2$ |
| 3,5-Cl$_2$-4-F | CF$_3$ | H | C(O)NHEt |
| 3,5-Cl$_2$-4-F | CF$_3$ | CH$_3$ | C(O)NHEt |
| 3,5-Cl$_2$-4-F | CF$_3$ | H | C(O)NHCH$_2$CH$_2$Cl |
| 3,5-Cl$_2$-4-F | CF$_3$ | H | C(O)NHCH$_2$CF$_3$ |
| 3,5-Cl$_2$-4-F | CF$_3$ | H | C(O)NHCH$_2$(Ph-4-F) |
| 3,5-Cl$_2$-4-F | CF$_3$ | H | Ph-4-F |
| 3,5-Cl$_2$-4-F | CF$_3$ | H | Ph-4-CN |
| 3,5-Cl$_2$-4-F | CF$_3$ | H | Ph-2,4-F$_2$ |
| 3,5-Cl$_2$-4-F | CF$_3$ | H | (D-13b)CH$_3$ |
| 3,5-Cl$_2$-4-F | CF$_3$ | H | (D-15a)CH$_3$ |
| 3,5-Cl$_2$-4-F | CF$_3$ | H | D-21a |
| 3,5-Cl$_2$-4-F | CF$_3$ | H | (D-47d)CN |
| 3,5-Cl$_2$-4-F | CF$_3$ | H | (D-47e)Br |
| 3,5-Cl$_2$-4-F | CF$_3$ | H | D-50a |
| 3,5-Cl$_2$-4-F | CF$_3$ | H | (D-50c)Cl |
| 3,5-Cl$_2$-4-F | CF$_3$ | H | (D-50c)Br |
| 3,5-Cl$_2$-4-F | CF$_3$ | H | D-51a |
| 3,5-Cl$_2$-4-F | CF$_3$ | H | D-52a |
| 3,5-Cl$_2$-4-F | CF$_3$ | H | D-53a |
| 3,5-Cl$_2$-4-F | CF$_2$Cl | H | c-Bu |
| 3,5-Cl$_2$-4-F | CF$_2$Cl | H | CH$_2$CF$_3$ |
| 3,5-Cl$_2$-4-F | CF$_2$Cl | H | CH$_2$OEt |
| 3,5-Cl$_2$-4-F | CF$_2$Cl | H | CH$_2$OCH$_2$CF$_3$ |
| 3,5-Cl$_2$-4-F | CF$_2$Cl | C(O)CH$_3$ | CH$_2$OCH$_2$CF$_3$ |
| 3,5-Cl$_2$-4-F | CF$_2$Cl | H | CH$_2$CH$_2$OCH$_3$ |
| 3,5-Cl$_2$-4-F | CF$_2$Cl | H | CH$_2$(E-10a) |
| 3,5-Cl$_2$-4-F | CF$_2$Cl | H | E-4a |
| 3,5-Cl$_2$-4-F | CF$_2$Cl | H | CH$_2$C(O)NHCH$_2$CH$_2$Cl |
| 3,5-Cl$_2$-4-F | CF$_2$Cl | H | CH$_2$C(O)NHCH$_2$CF$_3$ |
| 3,5-Cl$_2$-4-F | CF$_2$Cl | H | CH(CH$_3$)C(O)NHCH$_2$CF$_3$ |
| 3,5-Cl$_2$-4-F | CF$_2$Cl | H | CH(CH$_3$)C(O)NHCH$_2$CF$_3$(D) |
| 3,5-Cl$_2$-4-F | CF$_2$Cl | H | CH(CH$_3$)Ph(R) |
| 3,5-Cl$_2$-4-F | CF$_2$Cl | H | CH$_2$(D-22a) |
| 3,5-Cl$_2$-4-F | CF$_2$Cl | C(O)CH$_3$ | CH$_2$(D-22a) |
| 3,5-Cl$_2$-4-F | CF$_2$Cl | C(O)Et | CH$_2$(D-22a) |
| 3,5-Cl$_2$-4-F | CF$_2$Cl | H | CH$_2$(D-47a) |
| 3,5-Cl$_2$-4-F | CF$_2$Cl | CH$_2$OCH$_3$ | CH$_2$(D-47a) |
| 3,5-Cl$_2$-4-F | CF$_2$Cl | CH$_2$CN | CH$_2$(D-47a) |
| 3,5-Cl$_2$-4-F | CF$_2$Cl | C(O)CH$_3$ | CH$_2$(D-47a) |
| 3,5-Cl$_2$-4-F | CF$_2$Cl | C(O)Et | CH$_2$(D-47a) |
| 3,5-Cl$_2$-4-F | CF$_2$Cl | C(O)OCH$_3$ | CH$_2$(D-47a) |
| 3,5-Cl$_2$-4-F | CF$_2$Cl | H | N(CH$_3$)Ph |
| 3,5-Cl$_2$-4-F | CF$_2$Cl | H | N(CH$_3$)(D-50a) |
| 3,5-Cl$_2$-4-F | CF$_2$Cl | H | C(O)NHCH$_2$CF$_3$ |
| 3,5-Cl$_2$-4-F | CF$_2$Cl | H | Ph-2,4-F$_2$ |
| 3,5-Cl$_2$-4-F | CF$_2$Cl | H | (D-50c)Cl |
| 3,5-Cl$_2$-4-F | CF$_2$Cl | H | D-52a |
| 3,5-Cl$_2$-4-F | CF$_2$Br | H | CH$_2$CF$_3$ |
| 3,5-Cl$_2$-4-F | CF$_2$Br | H | E-4a |
| 3,5-Cl$_2$-4-F | CF$_2$Br | H | CH$_2$C(O)NHCH$_2$CF$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-$Cl_2$-4-F | $CF_2Br$ | H | $CH_2$(D-22a) |
| 3,5-$Cl_2$-4-F | $CF_2Br$ | H | $CH_2$(D-47a) |
| 3,5-$Cl_2$-4-F | $CF_2Br$ | H | (D-50c)Cl |
| 3,5-$Cl_2$-4-F | $CF_2CHF_2$ | H | $CH_2CF_3$ |
| 3,5-$Cl_2$-4-F | $CF_2CHF_2$ | H | E-4a |
| 3,5-$Cl_2$-4-F | $CF_2CHF_2$ | H | $CH_2C(O)NHCH_2CF_3$ |
| 3,5-$Cl_2$-4-F | $CF_2CHF_2$ | H | $CH_2$(D-22a) |
| 3,5-$Cl_2$-4-F | $CF_2CHF_2$ | H | $CH_2$(D-47a) |
| 3,5-$Cl_2$-4-F | $CF_2CHF_2$ | H | (D-50c)Cl |
| 3,4,5-$Cl_3$ | $CHF_2$ | H | $CH_2CF_3$ |
| 3,4,5-$Cl_3$ | $CHF_2$ | H | $CH_2OCH_2CF_3$ |
| 3,4,5-$Cl_3$ | $CHF_2$ | H | E-4a |
| 3,4,5-$Cl_3$ | $CHF_2$ | H | $CH_2C(O)NHCH_2CF_3$ |
| 3,4,5-$Cl_3$ | $CHF_2$ | H | $CH(CH_3)C(O)NHCH_2CF_3$(D) |
| 3,4,5-$Cl_3$ | $CHF_2$ | H | $CH_2$(D-22a) |
| 3,4,5-$Cl_3$ | $CHF_2$ | H | $CH_2$(D-47a) |
| 3,4,5-$Cl_3$ | $CHF_2$ | $C(O)OCH_3$ | $CH_2$(D-47a) |
| 3,4,5-$Cl_3$ | $CHF_2$ | H | $N(CH_3)Ph$ |
| 3,4,5-$Cl_3$ | $CHF_2$ | H | (D-50c)Cl |
| 3,4,5-$Cl_3$ | CHFCl | H | $CH_2$(D-47a) |
| 3,4,5-$Cl_3$ | $CHCl_2$ | $C(O)OCH_3$ | $CH_2$(D-47a) |
| 3,4,5-$Cl_3$ | CHFBr | H | $N(CH_3)Ph$ |
| 3,4,5-$Cl_3$ | $CF_3$ | H | H |
| 3,4,5-$Cl_3$ | $CF_3$ | H | Et |
| 3,4,5-$Cl_3$ | $CF_3$ | Et | Et |
| 3,4,5-$Cl_3$ | $CF_3$ | H | c-Pr |
| 3,4,5-$Cl_3$ | $CF_3$ | H | $CH_2$Pr-c |
| 3,4,5-$Cl_3$ | $CF_3$ | H | c-Bu |
| 3,4,5-$Cl_3$ | $CF_3$ | H | $CH_2CH_2Cl$ |
| 3,4,5-$Cl_3$ | $CF_3$ | H | $CH_2CHF_2$ |
| 3,4,5-$Cl_3$ | $CF_3$ | H | $CH_2CF_3$ |
| 3,4,5-$Cl_3$ | $CF_3$ | $C(O)CH_3$ | $CH_2CF_3$ |
| 3,4,5-$Cl_3$ | $CF_3$ | H | $CH_2CH_2CF_3$ |
| 3,4,5-$Cl_3$ | $CF_3$ | H | $CH_2OCH_3$ |
| 3,4,5-$Cl_3$ | $CF_3$ | H | $CH_2OEt$ |
| 3,4,5-$Cl_3$ | $CF_3$ | $C(O)CH_3$ | $CH_2OEt$ |
| 3,4,5-$Cl_3$ | $CF_3$ | H | $CH_2OCH_2CH_2Cl$ |
| 3,4,5-$Cl_3$ | $CF_3$ | H | $CH_2OCH_2CHF_2$ |
| 3,4,5-$Cl_3$ | $CF_3$ | H | $CH_2OCH_2CF_3$ |
| 3,4,5-$Cl_3$ | $CF_3$ | $C(O)CH_3$ | $CH_2OCH_2CF_3$ |
| 3,4,5-$Cl_3$ | $CF_3$ | H | $CH(CH_3)OCH_2CF_3$ |
| 3,4,5-$Cl_3$ | $CF_3$ | H | $CH(CF_3)OCH_3$ |
| 3,4,5-$Cl_3$ | $CF_3$ | H | $CH_2CH_2OCH_3$ |
| 3,4,5-$Cl_3$ | $CF_3$ | H | $CH_2CH_2OEt$ |
| 3,4,5-$Cl_3$ | $CF_3$ | H | $CH_2CH(OCH_3)_2$ |
| 3,4,5-$Cl_3$ | $CF_3$ | H | $CH_2$(E-4a) |
| 3,4,5-$Cl_3$ | $CF_3$ | H | $CH_2$(E-5a) |
| 3,4,5-$Cl_3$ | $CF_3$ | H | $CH_2$(E-10a) |
| 3,4,5-$Cl_3$ | $CF_3$ | H | $CH_2$(E-10b)$CH_3$ |
| 3,4,5-$Cl_3$ | $CF_3$ | H | E-4a |
| 3,4,5-$Cl_3$ | $CF_3$ | H | E-5a(R) |
| 3,4,5-$Cl_3$ | $CF_3$ | H | $CH_2SCH_3$ |
| 3,4,5-$Cl_3$ | $CF_3$ | H | $CH_2S(O)CH_3$ |
| 3,4,5-$Cl_3$ | $CF_3$ | H | $CH_2SO_2CH_3$ |
| 3,4,5-$Cl_3$ | $CF_3$ | H | $CH_2CH_2SO_2CH_3$ |
| 3,4,5-$Cl_3$ | $CF_3$ | H | $CH_2CH_2SO_2Et$ |
| 3,4,5-$Cl_3$ | $CF_3$ | H | $CH_2CH(CH_3)S(O)CH_3$ |
| 3,4,5-$Cl_3$ | $CF_3$ | H | $CH_2CH(CH_3)SO_2CH_3$ |
| 3,4,5-$Cl_3$ | $CF_3$ | H | $CH(CH_3)CH_2SO_2CH_3$ |
| 3,4,5-$Cl_3$ | $CF_3$ | H | $CH_2NHCH_2CF_3$ |
| 3,4,5-$Cl_3$ | $CF_3$ | H | $CH_2NHC(O)OCH_3$ |
| 3,4,5-$Cl_3$ | $CF_3$ | H | $CH(CH_3)NHC(O)OCH_3$ |
| 3,4,5-$Cl_3$ | $CF_3$ | H | $CH_2NHC(O)OCH_2CF_3$ |
| 3,4,5-$Cl_3$ | $CF_3$ | H | $CH_2CH=NOCH_3$ |
| 3,4,5-$Cl_3$ | $CF_3$ | H | $CH_2C(CH_3)=NOCH_3$ |
| 3,4,5-$Cl_3$ | $CF_3$ | H | $CH_2CN$ |
| 3,4,5-$Cl_3$ | $CF_3$ | H | $CH_2C(O)NHCH_3$ |
| 3,4,5-$Cl_3$ | $CF_3$ | H | $CH_2C(O)N(CH_3)_2$ |
| 3,4,5-$Cl_3$ | $CF_3$ | H | $CH_2C(O)NHEt$ |
| 3,4,5-$Cl_3$ | $CF_3$ | H | $CH_2C(O)NHPr$-n |
| 3,4,5-$Cl_3$ | $CF_3$ | H | $CH_2C(O)NHPr$-i |
| 3,4,5-$Cl_3$ | $CF_3$ | H | $CH_2C(O)NHCH_2CH_2F$ |
| 3,4,5-$Cl_3$ | $CF_3$ | H | $CH_2C(O)NHCH_2CH_2Cl$ |
| 3,4,5-$Cl_3$ | $CF_3$ | H | $CH_2C(O)NHCH_2CF_3$ |
| 3,4,5-$Cl_3$ | $CF_3$ | H | $CH_2C(O)NHCH_2CH=CH_2$ |
| 3,4,5-$Cl_3$ | $CF_3$ | H | $CH_2C(O)NHCH_2C\equiv CH$ |
| 3,4,5-$Cl_3$ | $CF_3$ | H | $CH(CH_3)C(O)NHEt$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4,5-Cl$_3$ | CF$_3$ | H | CH(CH$_3$)C(O)NHCH$_2$CF$_3$ |
| 3,4,5-Cl$_3$ | CF$_3$ | H | CH(CH$_3$)C(O)NHCH$_2$CH$_2$Cl(D) |
| 3,4,5-Cl$_3$ | CF$_3$ | H | CH(CH$_3$)C(O)NHCH$_2$CF$_3$(D) |
| 3,4,5-Cl$_3$ | CF$_3$ | H | CH$_2$C(S)NH$_2$ |
| 3,4,5-Cl$_3$ | CF$_3$ | H | CH$_2$CH=CH$_2$ |
| 3,4,5-Cl$_3$ | CF$_3$ | H | CH$_2$CCl=CH$_2$ |
| 3,4,5-Cl$_3$ | CF$_3$ | H | CH$_2$CCl=CHCl |
| 3,4,5-Cl$_3$ | CF$_3$ | H | CH$_2$C≡CH |
| 3,4,5-Cl$_3$ | CF$_3$ | H | CH(CH$_3$)Ph(R) |
| 3,4,5-Cl$_3$ | CF$_3$ | H | CH(CF$_3$)Ph |
| 3,4,5-Cl$_3$ | CF$_3$ | H | CH(CN)Ph |
| 3,4,5-Cl$_3$ | CF$_3$ | H | CH$_2$(Ph-4-OCH$_3$) |
| 3,4,5-Cl$_3$ | CF$_3$ | H | CH$_2$(Ph-4-NO$_2$) |
| 3,4,5-Cl$_3$ | CF$_3$ | H | CH$_2$(Ph-4-CN) |
| 3,4,5-Cl$_3$ | CF$_3$ | H | CH$_2$(D-1a) |
| 3,4,5-Cl$_3$ | CF$_3$ | H | CH$_2$(D-16b)Cl |
| 3,4,5-Cl$_3$ | CF$_3$ | H | CH$_2$(D-17a)CH$_3$ |
| 3,4,5-Cl$_3$ | CF$_3$ | H | CH$_2$(D-17b)Cl |
| 3,4,5-Cl$_3$ | CF$_3$ | H | CH$_2$(D-21a) |
| 3,4,5-Cl$_3$ | CF$_3$ | H | CH$_2$(D-22a) |
| 3,4,5-Cl$_3$ | CF$_3$ | C(O)CH$_3$ | CH$_2$(D-22a) |
| 3,4,5-Cl$_3$ | CF$_3$ | C(O)Et | CH$_2$(D-22a) |
| 3,4,5-Cl$_3$ | CF$_3$ | H | CH$_2$(D-28a) |
| 3,4,5-Cl$_3$ | CF$_3$ | H | CH$_2$(D-29b)CH$_3$ |
| 3,4,5-Cl$_3$ | CF$_3$ | H | CH$_2$(D-34a) |
| 3,4,5-Cl$_3$ | CF$_3$ | H | CH$_2$(D-35a) |
| 3,4,5-Cl$_3$ | CF$_3$ | H | CH$_2$(D-38a) |
| 3,4,5-Cl$_3$ | CF$_3$ | H | CH$_2$(D-47a) |
| 3,4,5-Cl$_3$ | CF$_3$ | Et | CH$_2$(D-47a) |
| 3,4,5-Cl$_3$ | CF$_3$ | CH$_2$OCH$_3$ | CH$_2$(D-47a) |
| 3,4,5-Cl$_3$ | CF$_3$ | CH$_2$CN | CH$_2$(D-47a) |
| 3,4,5-Cl$_3$ | CF$_3$ | CH$_2$C≡CH | CH$_2$(D-47a) |
| 3,4,5-Cl$_3$ | CF$_3$ | C(O)CH$_3$ | CH$_2$(D-47a) |
| 3,4,5-Cl$_3$ | CF$_3$ | C(O)Et | CH$_2$(D-47a) |
| 3,4,5-Cl$_3$ | CF$_3$ | C(O)Pr-n | CH$_2$(D-47a) |
| 3,4,5-Cl$_3$ | CF$_3$ | C(O)Pr-i | CH$_2$(D-47a) |
| 3,4,5-Cl$_3$ | CF$_3$ | C(O)Pr-c | CH$_2$(D-47a) |
| 3,4,5-Cl$_3$ | CF$_3$ | C(O)Bu-t | CH$_2$(D-47a) |
| 3,4,5-Cl$_3$ | CF$_3$ | C(O)CH$_2$OCH$_3$ | CH$_2$(D-47a) |
| 3,4,5-Cl$_3$ | CF$_3$ | C(O)CH=CH$_2$ | CH$_2$(D-47a) |
| 3,4,5-Cl$_3$ | CF$_3$ | C(O)OCH$_3$ | CH$_2$(D-47a) |
| 3,4,5-Cl$_3$ | CF$_3$ | C(O)OEt | CH$_2$(D-47a) |
| 3,4,5-Cl$_3$ | CF$_3$ | C(O)OCH$_2$CH$_2$OCH$_3$ | CH$_2$(D-47a) |
| 3,4,5-Cl$_3$ | CF$_3$ | C(O)OCH$_2$CH=CH$_2$ | CH$_2$(D-47a) |
| 3,4,5-Cl$_3$ | CF$_3$ | H | CH(CH$_3$)(D-47a) |
| 3,4,5-Cl$_3$ | CF$_3$ | H | CH$_2$(D-50a) |
| 3,4,5-Cl$_3$ | CF$_3$ | H | NHCH$_2$CF$_3$ |
| 3,4,5-Cl$_3$ | CF$_3$ | H | NHC(O)OCH$_3$ |
| 3,4,5-Cl$_3$ | CF$_3$ | H | N(CH$_3$)Ph |
| 3,4,5-Cl$_3$ | CF$_3$ | H | N(CH$_2$CH=CH$_2$)Ph |
| 3,4,5-Cl$_3$ | CF$_3$ | H | N(CH$_2$C≡CH)Ph |
| 3,4,5-Cl$_3$ | CF$_3$ | H | N(CH$_3$)(D-47a) |
| 3,4,5-Cl$_3$ | CF$_3$ | H | NH(D-50a) |
| 3,4,5-Cl$_3$ | CF$_3$ | CH$_3$ | NH(D-50a) |
| 3,4,5-Cl$_3$ | CF$_3$ | H | N(CH$_3$)(D-50a) |
| 3,4,5-Cl$_3$ | CF$_3$ | H | N(Et)(D-50a) |
| 3,4,5-Cl$_3$ | CF$_3$ | C(O)OCH$_3$ | C(O)N(CH$_3$)$_2$ |
| 3,4,5-Cl$_3$ | CF$_3$ | H | C(O)NHEt |
| 3,4,5-Cl$_3$ | CF$_3$ | CH$_3$ | C(O)NHEt |
| 3,4,5-Cl$_3$ | CF$_3$ | H | C(O)NHCH$_2$CH$_2$Cl |
| 3,4,5-Cl$_3$ | CF$_3$ | H | C(O)NHCH$_2$CF$_3$ |
| 3,4,5-Cl$_3$ | CF$_3$ | H | C(O)NHCH$_2$(Ph-4-F) |
| 3,4,5-Cl$_3$ | CF$_3$ | H | C(S)NHCH$_3$ |
| 3,4,5-Cl$_3$ | CF$_3$ | H | Ph-4-F |
| 3,4,5-Cl$_3$ | CF$_3$ | H | Ph-4-CN |
| 3,4,5-Cl$_3$ | CF$_3$ | H | Ph-2,4-F$_2$ |
| 3,4,5-Cl$_3$ | CF$_3$ | H | Ph-2,6-F$_2$ |
| 3,4,5-Cl$_3$ | CF$_3$ | H | Ph-2,4,6-F$_3$ |
| 3,4,5-Cl$_3$ | CF$_3$ | H | (D-13b)CH$_3$ |
| 3,4,5-Cl$_3$ | CF$_3$ | H | (D-15a)CH$_3$ |
| 3,4,5-Cl$_3$ | CF$_3$ | H | D-21a |
| 3,4,5-Cl$_3$ | CF$_3$ | H | (D-47d)Cl |
| 3,4,5-Cl$_3$ | CF$_3$ | H | (D-47d)Br |
| 3,4,5-Cl$_3$ | CF$_3$ | H | (D-47d)CN |
| 3,4,5-Cl$_3$ | CF$_3$ | H | (D-47e)Br |
| 3,4,5-Cl$_3$ | CF$_3$ | H | (D-48e)Cl |
| 3,4,5-Cl$_3$ | CF$_3$ | H | D-50a |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4,5-Cl$_3$ | CF$_3$ | H | (D-50c)Cl |
| 3,4,5-Cl$_3$ | CF$_3$ | H | (D-50c)Br |
| 3,4,5-Cl$_3$ | CF$_3$ | H | D-51a |
| 3,4,5-Cl$_3$ | CF$_3$ | H | D-52a |
| 3,4,5-Cl$_3$ | CF$_3$ | H | D-53a |
| 3,4,5-Cl$_3$ | CF$_3$ | H | (D-54b)Cl |
| 3,4,5-Cl$_3$ | CF$_2$Cl | H | c-Pr |
| 3,4,5-Cl$_3$ | CF$_2$Cl | H | CH$_2$Pr-c |
| 3,4,5-Cl$_3$ | CF$_2$Cl | H | c-Bu |
| 3,4,5-Cl$_3$ | CF$_2$Cl | H | CH$_2$CF$_3$ |
| 3,4,5-Cl$_3$ | CF$_2$Cl | C(O)CH$_3$ | CH$_2$CF$_3$ |
| 3,4,5-Cl$_3$ | CF$_2$Cl | H | CH$_2$CH$_2$CF$_3$ |
| 3,4,5-Cl$_3$ | CF$_2$Cl | H | CH$_2$OCH$_3$ |
| 3,4,5-Cl$_3$ | CF$_2$Cl | H | CH$_2$OEt |
| 3,4,5-Cl$_3$ | CF$_2$Cl | C(O)CH$_3$ | CH$_2$OEt |
| 3,4,5-Cl$_3$ | CF$_2$Cl | H | CH$_2$OCH$_2$CF$_3$ |
| 3,4,5-Cl$_3$ | CF$_2$Cl | C(O)CH$_3$ | CH$_2$OCH$_2$CF$_3$ |
| 3,4,5-Cl$_3$ | CF$_2$Cl | H | CH$_2$CH$_2$OCH$_3$ |
| 3,4,5-Cl$_3$ | CF$_2$Cl | H | CH$_2$(E-10a) |
| 3,4,5-Cl$_3$ | CF$_2$Cl | H | E-4a |
| 3,4,5-Cl$_3$ | CF$_2$Cl | H | E-5a(R) |
| 3,4,5-Cl$_3$ | CF$_2$Cl | H | CH$_2$CH=NOCH$_3$ |
| 3,4,5-Cl$_3$ | CF$_2$Cl | H | CH$_2$C(O)NHCH$_2$CH$_2$Cl |
| 3,4,5-Cl$_3$ | CF$_2$Cl | H | CH$_2$C(O)NHCH$_2$CF$_3$ |
| 3,4,5-Cl$_3$ | CF$_2$Cl | H | CH(CH$_3$)C(O)NHEt |
| 3,4,5-Cl$_3$ | CF$_2$Cl | H | CH(CH$_3$)C(O)NHCH$_2$CF$_3$ |
| 3,4,5-Cl$_3$ | CF$_2$Cl | H | CH(CH$_3$)C(O)NHCH$_2$CF$_3$(D) |
| 3,4,5-Cl$_3$ | CF$_2$Cl | H | CH$_2$CH=CH$_2$ |
| 3,4,5-Cl$_3$ | CF$_2$Cl | H | CH$_2$CCl=CH$_2$ |
| 3,4,5-Cl$_3$ | CF$_2$Cl | H | CH(CH$_3$)Ph(R) |
| 3,4,5-Cl$_3$ | CF$_2$Cl | H | CH$_2$(Ph-4-NO$_2$) |
| 3,4,5-Cl$_3$ | CF$_2$Cl | H | CH$_2$(Ph-4-CN) |
| 3,4,5-Cl$_3$ | CF$_2$Cl | H | CH$_2$(D-17b)Cl |
| 3,4,5-Cl$_3$ | CF$_2$Cl | H | CH$_2$(D-21a) |
| 3,4,5-Cl$_3$ | CF$_2$Cl | H | CH$_2$(D-22a) |
| 3,4,5-Cl$_3$ | CF$_2$Cl | C(O)CH$_3$ | CH$_2$(D-22a) |
| 3,4,5-Cl$_3$ | CF$_2$Cl | C(O)Et | CH$_2$(D-22a) |
| 3,4,5-Cl$_3$ | CF$_2$Cl | H | CH$_2$(D-47a) |
| 3,4,5-Cl$_3$ | CF$_2$Cl | CH$_2$OCH$_3$ | CH$_2$(D-47a) |
| 3,4,5-Cl$_3$ | CF$_2$Cl | CH$_2$CN | CH$_2$(D-47a) |
| 3,4,5-Cl$_3$ | CF$_2$Cl | C(O)CH$_3$ | CH$_2$(D-47a) |
| 3,4,5-Cl$_3$ | CF$_2$Cl | C(O)Et | CH$_2$(D-47a) |
| 3,4,5-Cl$_3$ | CF$_2$Cl | C(O)Pr-c | CH$_2$(D-47a) |
| 3,4,5-Cl$_3$ | CF$_2$Cl | C(O)OCH$_3$ | CH$_2$(D-47a) |
| 3,4,5-Cl$_3$ | CF$_2$Cl | H | CH(CH$_3$)(D-47a) |
| 3,4,5-Cl$_3$ | CF$_2$Cl | H | CH$_2$(D-50a) |
| 3,4,5-Cl$_3$ | CF$_2$Cl | H | N(CH$_3$)Ph |
| 3,4,5-Cl$_3$ | CF$_2$Cl | H | N(CH$_3$)(D-50a) |
| 3,4,5-Cl$_3$ | CF$_2$Cl | C(O)OCH$_3$ | C(O)N(CH$_3$)$_2$ |
| 3,4,5-Cl$_3$ | CF$_2$Cl | H | C(O)NHEt |
| 3,4,5-Cl$_3$ | CF$_2$Cl | CH$_3$ | C(O)NHEt |
| 3,4,5-Cl$_3$ | CF$_2$Cl | H | C(O)NHCH$_2$CH$_2$Cl |
| 3,4,5-Cl$_3$ | CF$_2$Cl | H | C(O)NHCH$_2$(Ph-4-F) |
| 3,4,5-Cl$_3$ | CF$_2$Cl | H | Ph-4-CN |
| 3,4,5-Cl$_3$ | CF$_2$Cl | H | Ph-2,4-F$_2$ |
| 3,4,5-Cl$_3$ | CF$_2$Cl | H | (D-15a)CH$_3$ |
| 3,4,5-Cl$_3$ | CF$_2$Cl | H | (D-47d)CN |
| 3,4,5-Cl$_3$ | CF$_2$Cl | H | (D-47e)Br |
| 3,4,5-Cl$_3$ | CF$_2$Cl | H | D-50a |
| 3,4,5-Cl$_3$ | CF$_2$Cl | H | (D-50c)Cl |
| 3,4,5-Cl$_3$ | CF$_2$Cl | H | (D-50c)Br |
| 3,4,5-Cl$_3$ | CF$_2$Cl | H | D-52a |
| 3,4,5-Cl$_3$ | CF$_2$Cl | H | D-53a |
| 3,4,5-Cl$_3$ | CF$_2$Br | H | CH$_2$CF$_3$ |
| 3,4,5-Cl$_3$ | CF$_2$Br | H | CH$_2$OCH$_2$CF$_3$ |
| 3,4,5-Cl$_3$ | CF$_2$Br | H | E-4a |
| 3,4,5-Cl$_3$ | CF$_2$Br | H | CH$_2$C(O)NHCH$_2$CF$_3$ |
| 3,4,5-Cl$_3$ | CF$_2$Br | H | CH(CH$_3$)C(O)NHCH$_2$CF$_3$(D) |
| 3,4,5-Cl$_3$ | CF$_2$Br | H | CH$_2$(D-22a) |
| 3,4,5-Cl$_3$ | CF$_2$Br | H | CH$_2$(D-47a) |
| 3,4,5-Cl$_3$ | CF$_2$Br | C(O)OCH$_3$ | CH$_2$(D-47a) |
| 3,4,5-Cl$_3$ | CF$_2$Br | H | N(CH$_3$)Ph |
| 3,4,5-Cl$_3$ | CF$_2$Br | H | (D-50c)Cl |
| 3,4,5-Cl$_3$ | CF$_2$CHF$_2$ | H | CH$_2$CF$_3$ |
| 3,4,5-Cl$_3$ | CF$_2$CHF$_2$ | H | CH$_2$OCH$_2$CF$_3$ |
| 3,4,5-Cl$_3$ | CF$_2$CHF$_2$ | H | E-4a |
| 3,4,5-Cl$_3$ | CF$_2$CHF$_2$ | H | CH$_2$C(O)NHCH$_2$CF$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4,5-Cl$_3$ | CF$_2$CHF$_2$ | H | CH(CH$_3$)C(O)NHCH$_2$CF$_3$(D) |
| 3,4,5-Cl$_3$ | CF$_2$CHF$_2$ | H | CH$_2$(D-22a) |
| 3,4,5-Cl$_3$ | CF$_2$CHF$_2$ | H | CH$_2$(D-47a) |
| 3,4,5-Cl$_3$ | CF$_2$CHF$_2$ | C(O)OCH$_3$ | CH$_2$(D-47a) |
| 3,4,5-Cl$_3$ | CF$_2$CHF$_2$ | H | N(CH$_3$)Ph |
| 3,4,5-Cl$_3$ | CF$_2$CHF$_2$ | H | (D-50c)Cl |
| 3,4,5-Cl$_3$ | CF$_2$CF$_3$ | H | (D-50c)Cl |
| 3,4,5-Cl$_3$ | CF$_2$OCH$_3$ | H | CH$_2$CF$_3$ |
| 3,4,5-Cl$_3$ | CF$_2$SCH$_3$ | H | CH$_2$OCH$_2$CF$_3$ |
| 3,4,5-Cl$_3$ | T-3 | H | E-4a |
| 3,5-Br$_2$-4-F | CHF$_2$ | H | CH$_2$CF$_3$ |
| 3,5-Br$_2$-4-F | CHF$_2$ | H | E-4a |
| 3,5-Br$_2$-4-F | CHF$_2$ | H | CH$_2$C(O)NHCH$_2$CF$_3$ |
| 3,5-Br$_2$-4-F | CHF$_2$ | H | CH$_2$(D-22a) |
| 3,5-Br$_2$-4-F | CHF$_2$ | H | CH$_2$(D-47a) |
| 3,5-Br$_2$-4-F | CHF$_2$ | H | (D-50c)Cl |
| 3,5-Br$_2$-4-F | CF$_3$ | H | c-Pr |
| 3,5-Br$_2$-4-F | CF$_3$ | H | CH$_2$Pr-c |
| 3,5-Br$_2$-4-F | CF$_3$ | H | c-Bu |
| 3,5-Br$_2$-4-F | CF$_3$ | H | CH$_2$CF$_3$ |
| 3,5-Br$_2$-4-F | CF$_3$ | H | CH$_2$CH$_2$CF$_3$ |
| 3,5-Br$_2$-4-F | CF$_3$ | H | CH$_2$OCH$_3$ |
| 3,5-Br$_2$-4-F | CF$_3$ | H | CH$_2$OEt |
| 3,5-Br$_2$-4-F | CF$_3$ | C(O)CH$_3$ | CH$_2$OEt |
| 3,5-Br$_2$-4-F | CF$_3$ | H | CH$_2$OCH$_2$CF$_3$ |
| 3,5-Br$_2$-4-F | CF$_3$ | C(O)CH$_3$ | CH$_2$OCH$_2$CF$_3$ |
| 3,5-Br$_2$-4-F | CF$_3$ | H | CH(CH$_3$)OCH$_2$CF$_3$ |
| 3,5-Br$_2$-4-F | CF$_3$ | H | CH$_2$CH$_2$OCH$_3$ |
| 3,5-Br$_2$-4-F | CF$_3$ | H | CH$_2$(E-5a) |
| 3,5-Br$_2$-4-F | CF$_3$ | H | CH$_2$(E-10a) |
| 3,5-Br$_2$-4-F | CF$_3$ | H | CH$_2$(E-10b)CH$_3$ |
| 3,5-Br$_2$-4-F | CF$_3$ | H | E-4a |
| 3,5-Br$_2$-4-F | CF$_3$ | H | E-5a(R) |
| 3,5-Br$_2$-4-F | CF$_3$ | H | CH$_2$CH=NOCH$_3$ |
| 3,5-Br$_2$-4-F | CF$_3$ | H | CH$_2$C(CH$_3$)=NOCH$_3$ |
| 3,5-Br$_2$-4-F | CF$_3$ | H | CH$_2$C(O)NHCH$_3$ |
| 3,5-Br$_2$-4-F | CF$_3$ | H | CH$_2$C(O)N(CH$_3$)$_2$ |
| 3,5-Br$_2$-4-F | CF$_3$ | H | CH$_2$C(O)NHPr-n |
| 3,5-Br$_2$-4-F | CF$_3$ | H | CH$_2$C(O)NHPr-i |
| 3,5-Br$_2$-4-F | CF$_3$ | H | CH$_2$C(O)NHCH$_2$CH$_2$F |
| 3,5-Br$_2$-4-F | CF$_3$ | H | CH$_2$C(O)NHCH$_2$CH$_2$Cl |
| 3,5-Br$_2$-4-F | CF$_3$ | H | CH$_2$C(O)NHCH$_2$CF$_3$ |
| 3,5-Br$_2$-4-F | CF$_3$ | H | CH$_2$C(O)NHCH$_2$CH=CH$_2$ |
| 3,5-Br$_2$-4-F | CF$_3$ | H | CH$_2$C(O)NHCH$_2$C≡CH |
| 3,5-Br$_2$-4-F | CF$_3$ | H | CH(CH$_3$)C(O)NHEt |
| 3,5-Br$_2$-4-F | CF$_3$ | H | CH(CH$_3$)C(O)NHCH$_2$CF$_3$ |
| 3,5-Br$_2$-4-F | CF$_3$ | H | CH(CH$_3$)C(O)NHCH$_2$CF$_3$(D) |
| 3,5-Br$_2$-4-F | CF$_3$ | H | CH$_2$CH=CH$_2$ |
| 3,5-Br$_2$-4-F | CF$_3$ | H | CH$_2$CCl=CH$_2$ |
| 3,5-Br$_2$-4-F | CF$_3$ | H | CH(CH$_3$)Ph(R) |
| 3,5-Br$_2$-4-F | CF$_3$ | H | CH$_2$(Ph-4-NO$_2$) |
| 3,5-Br$_2$-4-F | CF$_3$ | H | CH$_2$(Ph-4-CN) |
| 3,5-Br$_2$-4-F | CF$_3$ | H | CH$_2$(D-16b)Cl |
| 3,5-Br$_2$-4-F | CF$_3$ | H | CH$_2$(D-17a)CH$_3$ |
| 3,5-Br$_2$-4-F | CF$_3$ | H | CH$_2$(D-17b)Cl |
| 3,5-Br$_2$-4-F | CF$_3$ | H | CH$_2$(D-21a) |
| 3,5-Br$_2$-4-F | CF$_3$ | H | CH$_2$(D-22a) |
| 3,5-Br$_2$-4-F | CF$_3$ | C(O)CH$_3$ | CH$_2$(D-22a) |
| 3,5-Br$_2$-4-F | CF$_3$ | C(O)Et | CH$_2$(D-22a) |
| 3,5-Br$_2$-4-F | CF$_3$ | H | CH$_2$(D-29b)CH$_3$ |
| 3,5-Br$_2$-4-F | CF$_3$ | H | CH$_2$(D-34a) |
| 3,5-Br$_2$-4-F | CF$_3$ | H | CH$_2$(D-38a) |
| 3,5-Br$_2$-4-F | CF$_3$ | H | CH$_2$(D-47a) |
| 3,5-Br$_2$-4-F | CF$_3$ | Et | CH$_2$(D-47a) |
| 3,5-Br$_2$-4-F | CF$_3$ | CH$_2$OCH$_3$ | CH$_2$(D-47a) |
| 3,5-Br$_2$-4-F | CF$_3$ | CH$_2$CN | CH$_2$(D-47a) |
| 3,5-Br$_2$-4-F | CF$_3$ | CH$_2$C≡CH | CH$_2$(D-47a) |
| 3,5-Br$_2$-4-F | CF$_3$ | C(O)CH$_3$ | CH$_2$(D-47a) |
| 3,5-Br$_2$-4-F | CF$_3$ | C(O)Et | CH$_2$(D-47a) |
| 3,5-Br$_2$-4-F | CF$_3$ | C(O)Pr-n | CH$_2$(D-47a) |
| 3,5-Br$_2$-4-F | CF$_3$ | C(O)Pr-i | CH$_2$(D-47a) |
| 3,5-Br$_2$-4-F | CF$_3$ | C(O)Pr-c | CH$_2$(D-47a) |
| 3,5-Br$_2$-4-F | CF$_3$ | C(O)Bu-t | CH$_2$(D-47a) |
| 3,5-Br$_2$-4-F | CF$_3$ | C(O)CH$_2$OCH$_3$ | CH$_2$(D-47a) |
| 3,5-Br$_2$-4-F | CF$_3$ | C(O)CH=CH$_2$ | CH$_2$(D-47a) |
| 3,5-Br$_2$-4-F | CF$_3$ | C(O)OCH$_3$ | CH$_2$(D-47a) |
| 3,5-Br$_2$-4-F | CF$_3$ | C(O)OCH$_2$CH$_2$OCH$_3$ | CH$_2$(D-47a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Br$_2$-4-F | CF$_3$ | C(O)OCH$_2$CH=CH$_2$ | CH$_2$(D-47a) |
| 3,5-Br$_2$-4-F | CF$_3$ | H | CH(CH$_3$)(D-47a) |
| 3,5-Br$_2$-4-F | CF$_3$ | H | CH$_2$(D-50a) |
| 3,5-Br$_2$-4-F | CF$_3$ | H | NHC(O)OCH$_3$ |
| 3,5-Br$_2$-4-F | CF$_3$ | H | N(CH$_3$)Ph |
| 3,5-Br$_2$-4-F | CF$_3$ | H | N(CH$_2$CH=CH$_2$)Ph |
| 3,5-Br$_2$-4-F | CF$_3$ | H | N(CH$_2$C≡CH)Ph |
| 3,5-Br$_2$-4-F | CF$_3$ | H | NH(D-50a) |
| 3,5-Br$_2$-4-F | CF$_3$ | CH$_3$ | NH(D-50a) |
| 3,5-Br$_2$-4-F | CF$_3$ | H | N(CH$_3$)(D-50a) |
| 3,5-Br$_2$-4-F | CF$_3$ | H | N(Et)(D-50a) |
| 3,5-Br$_2$-4-F | CF$_3$ | C(O)OCH$_3$ | C(O)N(CH$_3$)$_2$ |
| 3,5-Br$_2$-4-F | CF$_3$ | H | C(O)NHEt |
| 3,5-Br$_2$-4-F | CF$_3$ | CH$_3$ | C(O)NHEt |
| 3,5-Br$_2$-4-F | CF$_3$ | H | C(O)NHCH$_2$CH$_2$Cl |
| 3,5-Br$_2$-4-F | CF$_3$ | H | C(O)NHCH$_2$CF$_3$ |
| 3,5-Br$_2$-4-F | CF$_3$ | H | C(O)NHCH$_2$(Ph-4-F) |
| 3,5-Br$_2$-4-F | CF$_3$ | H | Ph-4-F |
| 3,5-Br$_2$-4-F | CF$_3$ | H | Ph-4-CN |
| 3,5-Br$_2$-4-F | CF$_3$ | H | Ph-2,4-F$_2$ |
| 3,5-Br$_2$-4-F | CF$_3$ | H | (D-13b)CH$_3$ |
| 3,5-Br$_2$-4-F | CF$_3$ | H | (D-15a)CH$_3$ |
| 3,5-Br$_2$-4-F | CF$_3$ | H | D-21a |
| 3,5-Br$_2$-4-F | CF$_3$ | H | (D-47d)CN |
| 3,5-Br$_2$-4-F | CF$_3$ | H | (D-47e)Br |
| 3,5-Br$_2$-4-F | CF$_3$ | H | D-50a |
| 3,5-Br$_2$-4-F | CF$_3$ | H | (D-50c)Cl |
| 3,5-Br$_2$-4-F | CF$_3$ | H | (D-50c)Br |
| 3,5-Br$_2$-4-F | CF$_3$ | H | D-51a |
| 3,5-Br$_2$-4-F | CF$_3$ | H | D-52a |
| 3,5-Br$_2$-4-F | CF$_3$ | H | D-53a |
| 3,5-Br$_2$-4-F | CF$_2$Cl | H | c-Bu |
| 3,5-Br$_2$-4-F | CF$_2$Cl | H | CH$_2$CF$_3$ |
| 3,5-Br$_2$-4-F | CF$_2$Cl | H | CH$_2$OEt |
| 3,5-Br$_2$-4-F | CF$_2$Cl | H | CH$_2$OCH$_2$CF$_3$ |
| 3,5-Br$_2$-4-F | CF$_2$Cl | C(O)CH$_3$ | CH$_2$OCH$_2$CF$_3$ |
| 3,5-Br$_2$-4-F | CF$_2$Cl | H | CH$_2$CH$_2$OCH$_3$ |
| 3,5-Br$_2$-4-F | CF$_2$Cl | H | CH$_2$(E-10a) |
| 3,5-Br$_2$-4-F | CF$_2$Cl | H | E-4a |
| 3,5-Br$_2$-4-F | CF$_2$Cl | H | CH$_2$C(O)NHCH$_2$CH$_2$Cl |
| 3,5-Br$_2$-4-F | CF$_2$Cl | H | CH$_2$C(O)NHCH$_2$CF$_3$ |
| 3,5-Br$_2$-4-F | CF$_2$Cl | H | CH(CH$_3$)C(O)NHCH$_2$CF$_3$ |
| 3,5-Br$_2$-4-F | CF$_2$Cl | H | CH(CH$_3$)C(O)NHCH$_2$CF$_3$(D) |
| 3,5-Br$_2$-4-F | CF$_2$Cl | H | CH(CH$_3$)Ph(R) |
| 3,5-Br$_2$-4-F | CF$_2$Cl | H | CH$_2$(D-22a) |
| 3,5-Br$_2$-4-F | CF$_2$Cl | C(O)CH$_3$ | CH$_2$(D-22a) |
| 3,5-Br$_2$-4-F | CF$_2$Cl | C(O)Et | CH$_2$(D-22a) |
| 3,5-Br$_2$-4-F | CF$_2$Cl | H | CH$_2$(D-47a) |
| 3,5-Br$_2$-4-F | CF$_2$Cl | CH$_2$OCH$_3$ | CH$_2$(D-47a) |
| 3,5-Br$_2$-4-F | CF$_2$Cl | CH$_2$CN | CH$_2$(D-47a) |
| 3,5-Br$_2$-4-F | CF$_2$Cl | C(O)CH$_3$ | CH$_2$(D-47a) |
| 3,5-Br$_2$-4-F | CF$_2$Cl | C(O)Et | CH$_2$(D-47a) |
| 3,5-Br$_2$-4-F | CF$_2$Cl | C(O)OCH$_3$ | CH$_2$(D-47a) |
| 3,5-Br$_2$-4-F | CF$_2$Cl | H | N(CH$_3$)Ph |
| 3,5-Br$_2$-4-F | CF$_2$Cl | H | N(CH$_3$)(D-50a) |
| 3,5-Br$_2$-4-F | CF$_2$Cl | H | C(O)NHCH$_2$CF$_3$ |
| 3,5-Br$_2$-4-F | CF$_2$Cl | H | Ph-2,4-F$_2$ |
| 3,5-Br$_2$-4-F | CF$_2$Cl | H | (D-50c)Cl |
| 3,5-Br$_2$-4-F | CF$_2$Cl | H | D-52a |
| 3,5-Br$_2$-4-F | CF$_2$Br | H | CH$_2$CF$_3$ |
| 3,5-Br$_2$-4-F | CF$_2$Br | H | E-4a |
| 3,5-Br$_2$-4-F | CF$_2$Br | H | CH$_2$C(O)NHCH$_2$CF$_3$ |
| 3,5-Br$_2$-4-F | CF$_2$Br | H | CH$_2$(D-22a) |
| 3,5-Br$_2$-4-F | CF$_2$Br | H | CH$_2$(D-47a) |
| 3,5-Br$_2$-4-F | CF$_2$Br | H | (D-50c)Cl |
| 3,5-Br$_2$-4-F | CF$_2$CHF$_2$ | H | CH$_2$CF$_3$ |
| 3,5-Br$_2$-4-F | CF$_2$CHF$_2$ | H | E-4a |
| 3,5-Br$_2$-4-F | CF$_2$CHF$_2$ | H | CH$_2$C(O)NHCH$_2$CF$_3$ |
| 3,5-Br$_2$-4-F | CF$_2$CHF$_2$ | H | CH$_2$(D-22a) |
| 3,5-Br$_2$-4-F | CF$_2$CHF$_2$ | H | CH$_2$(D-47a) |
| 3,5-Br$_2$-4-F | CF$_2$CHF$_2$ | H | (D-50c)Cl |
| 3,4,5-Br$_3$ | CF$_3$ | H | c-Bu |
| 3,4,5-Br$_3$ | CF$_3$ | H | CH$_2$CF$_3$ |
| 3,4,5-Br$_3$ | CF$_3$ | H | CH$_2$OEt |
| 3,4,5-Br$_3$ | CF$_3$ | H | CH$_2$OCH$_2$CF$_3$ |
| 3,4,5-Br$_3$ | CF$_3$ | C(O)CH$_3$ | CH$_2$OCH$_2$CF$_3$ |
| 3,4,5-Br$_3$ | CF$_3$ | H | CH$_2$CH$_2$OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4,5-Br$_3$ | CF$_3$ | H | CH$_2$(E-10a) |
| 3,4,5-Br$_3$ | CF$_3$ | H | E-4a |
| 3,4,5-Br$_3$ | CF$_3$ | H | CH$_2$C(O)NHCH$_2$CH$_2$Cl |
| 3,4,5-Br$_3$ | CF$_3$ | H | CH$_2$C(O)NHCH$_2$CF$_3$ |
| 3,4,5-Br$_3$ | CF$_3$ | H | CH(CH$_3$)C(O)NHCH$_2$CF$_3$ |
| 3,4,5-Br$_3$ | CF$_3$ | H | CH(CH$_3$)C(O)NHCH$_2$CF$_3$(D) |
| 3,4,5-Br$_3$ | CF$_3$ | H | CH(CH$_3$)Ph(R) |
| 3,4,5-Br$_3$ | CF$_3$ | H | CH$_2$(D-22a) |
| 3,4,5-Br$_3$ | CF$_3$ | C(O)CH$_3$ | CH$_2$(D-22a) |
| 3,4,5-Br$_3$ | CF$_3$ | C(O)Et | CH$_2$(D-22a) |
| 3,4,5-Br$_3$ | CF$_3$ | H | CH$_2$(D-47a) |
| 3,4,5-Br$_3$ | CF$_3$ | CH$_2$OCH$_3$ | CH$_2$(D-47a) |
| 3,4,5-Br$_3$ | CF$_3$ | CH$_2$CN | CH$_2$(D-47a) |
| 3,4,5-Br$_3$ | CF$_3$ | C(O)CH$_3$ | CH$_2$(D-47a) |
| 3,4,5-Br$_3$ | CF$_3$ | C(O)Et | CH$_2$(D-47a) |
| 3,4,5-Br$_3$ | CF$_3$ | C(O)OCH$_3$ | CH$_2$(D-47a) |
| 3,4,5-Br$_3$ | CF$_3$ | H | N(CH$_3$)Ph |
| 3,4,5-Br$_3$ | CF$_3$ | H | N(CH$_3$)(D-50a) |
| 3,4,5-Br$_3$ | CF$_3$ | H | C(O)NHCH$_2$CF$_3$ |
| 3,4,5-Br$_3$ | CF$_3$ | H | Ph-2,4-F$_2$ |
| 3,4,5-Br$_3$ | CF$_3$ | H | (D-50c)Cl |
| 3,4,5-Br$_3$ | CF$_3$ | H | D-57a |
| 3,4,5-Br$_3$ | CF$_2$Cl | H | CH$_2$CF$_3$ |
| 3,4,5-Br$_3$ | CF$_2$Cl | H | CH$_2$OCH$_2$CF$_3$ |
| 3,4,5-Br$_3$ | CF$_2$Cl | H | E-4a |
| 3,4,5-Br$_3$ | CF$_2$Cl | H | CH$_2$C(O)NHCH$_2$CF$_3$ |
| 3,4,5-Br$_3$ | CF$_2$Cl | H | CH(CH$_3$)C(O)NHCH$_2$CF$_3$(D) |
| 3,4,5-Br$_3$ | CF$_2$Cl | H | CH$_2$(D-22a) |
| 3,4,5-Br$_3$ | CF$_2$Cl | H | CH$_2$(D-47a) |
| 3,4,5-Br$_3$ | CF$_2$Cl | C(O)OCH$_3$ | CH$_2$(D-47a) |
| 3,4,5-Br$_3$ | CF$_2$Cl | H | N(CH$_3$)Ph |
| 3,4,5-Br$_3$ | CF$_2$Cl | H | (D-50c)Cl |
| 2,6-F$_2$-3-CH$_3$ | CF$_3$ | H | CH$_2$C(O)NHCH$_2$CF$_3$ |
| 2,3-F$_2$-4-CH$_3$ | CF$_3$ | H | CH$_2$(D-22a) |
| 3,5-F$_2$-4-CH$_3$ | CF$_3$ | H | CH$_2$(D-47a) |
| 2-F-3-CH$_3$-5-Cl | CF$_3$ | C(O)OCH$_3$ | CH$_2$(D-47a) |
| 2,4-Cl$_2$-6-CH$_3$ | CF$_3$ | H | N(CH$_3$)Ph |
| 3,5-Cl$_2$-4-CH$_3$ | CF$_3$ | H | CH$_2$CF$_3$ |
| 3,5-Cl$_2$-4-CH$_3$ | CF$_3$ | H | E-4a |
| 3,5-Cl$_2$-4-CH$_3$ | CF$_3$ | H | CH$_2$C(O)NHCH$_2$CF$_3$ |
| 3,5-Cl$_2$-4-CH$_3$ | CF$_3$ | H | CH$_2$(D-22a) |
| 3,5-Cl$_2$-4-CH$_3$ | CF$_3$ | H | CH$_2$(D-47a) |
| 3,5-Cl$_2$-4-CH$_3$ | CF$_3$ | H | (D-50c)Cl |
| 3,5-Br$_2$-4-CH$_3$ | CF$_3$ | H | CH$_2$CF$_3$ |
| 3,5-Br$_2$-4-CH$_3$ | CF$_3$ | H | E-4a |
| 3,5-Br$_2$-4-CH$_3$ | CF$_3$ | H | CH$_2$C(O)NHCH$_2$CF$_3$ |
| 3,5-Br$_2$-4-CH$_3$ | CF$_3$ | H | CH$_2$(D-22a) |
| 3,5-Br$_2$-4-CH$_3$ | CF$_3$ | H | CH$_2$(D-47a) |
| 3,5-Br$_2$-4-CH$_3$ | CF$_3$ | H | (D-50c)Cl |
| 2,3-F$_2$-4-CF$_3$ | CF$_3$ | H | (D-50c)Cl |
| 3,4-F$_2$-5-CF$_3$ | CHF$_2$ | H | CH$_2$CF$_3$ |
| 3,4-F$_2$-5-CF$_3$ | CHF$_2$ | H | E-4a |
| 3,4-F$_2$-5-CF$_3$ | CHF$_2$ | H | CH$_2$C(O)NHCH$_2$CF$_3$ |
| 3,4-F$_2$-5-CF$_3$ | CHF$_2$ | H | CH$_2$(D-22a) |
| 3,4-F$_2$-5-CF$_3$ | CHF$_2$ | H | CH$_2$(D-47a) |
| 3,4-F$_2$-5-CF$_3$ | CHF$_2$ | H | (D-50c)Cl |
| 3,4-F$_2$-5-CF$_3$ | CF$_3$ | H | c-Pr |
| 3,4-F$_2$-5-CF$_3$ | CF$_3$ | H | CH$_2$Pr-c |
| 3,4-F$_2$-5-CF$_3$ | CF$_3$ | H | c-Bu |
| 3,4-F$_2$-5-CF$_3$ | CF$_3$ | H | CH$_2$CF$_3$ |
| 3,4-F$_2$-5-CF$_3$ | CF$_3$ | H | CH$_2$CH$_2$CF$_3$ |
| 3,4-F$_2$-5-CF$_3$ | CF$_3$ | H | CH$_2$OCH$_3$ |
| 3,4-F$_2$-5-CF$_3$ | CF$_3$ | H | CH$_2$OEt |
| 3,4-F$_2$-5-CF$_3$ | CF$_3$ | C(O)CH$_3$ | CH$_2$OEt |
| 3,4-F$_2$-5-CF$_3$ | CF$_3$ | H | CH$_2$OCH$_2$CF$_3$ |
| 3,4-F$_2$-5-CF$_3$ | CF$_3$ | C(O)CH$_3$ | CH$_2$OCH$_2$CF$_3$ |
| 3,4-F$_2$-5-CF$_3$ | CF$_3$ | H | CH(CH$_3$)OCH$_2$CF$_3$ |
| 3,4-F$_2$-5-CF$_3$ | CF$_3$ | H | CH$_2$CH$_2$OCH$_3$ |
| 3,4-F$_2$-5-CF$_3$ | CF$_3$ | H | CH$_2$(E-5a) |
| 3,4-F$_2$-5-CF$_3$ | CF$_3$ | H | CH$_2$(E-10a) |
| 3,4-F$_2$-5-CF$_3$ | CF$_3$ | H | CH$_2$(E-10b)CH$_3$ |
| 3,4-F$_2$-5-CF$_3$ | CF$_3$ | H | E-4a |
| 3,4-F$_2$-5-CF$_3$ | CF$_3$ | H | E-5a(R) |
| 3,4-F$_2$-5-CF$_3$ | CF$_3$ | H | CH$_2$CH=NOCH$_3$ |
| 3,4-F$_2$-5-CF$_3$ | CF$_3$ | H | CH$_2$C(CH$_3$)=NOCH$_3$ |
| 3,4-F$_2$-5-CF$_3$ | CF$_3$ | H | CH$_2$C(O)NHCH$_3$ |
| 3,4-F$_2$-5-CF$_3$ | CF$_3$ | H | CH$_2$C(O)N(CH$_3$)$_2$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4-$F_2$-5-$CF_3$ | $CF_3$ | H | $CH_2C(O)NHPr$-n |
| 3,4-$F_2$-5-$CF_3$ | $CF_3$ | H | $CH_2C(O)NHPr$-i |
| 3,4-$F_2$-5-$CF_3$ | $CF_3$ | H | $CH_2C(O)NHCH_2CH_2F$ |
| 3,4-$F_2$-5-$CF_3$ | $CF_3$ | H | $CH_2C(O)NHCH_2CH_2Cl$ |
| 3,4-$F_2$-5-$CF_3$ | $CF_3$ | H | $CH_2C(O)NHCH_2CF_3$ |
| 3,4-$F_2$-5-$CF_3$ | $CF_3$ | H | $CH_2C(O)NHCH_2CH{=}CH_2$ |
| 3,4-$F_2$-5-$CF_3$ | $CF_3$ | H | $CH_2C(O)NHCH_2C{\equiv}CH$ |
| 3,4-$F_2$-5-$CF_3$ | $CF_3$ | H | $CH(CH_3)C(O)NHEt$ |
| 3,4-$F_2$-5-$CF_3$ | $CF_3$ | H | $CH(CH_3)C(O)NHCH_2CF_3$ |
| 3,4-$F_2$-5-$CF_3$ | $CF_3$ | H | $CH(CH_3)C(O)NHCH_2CF_3(D)$ |
| 3,4-$F_2$-5-$CF_3$ | $CF_3$ | H | $CH_2CH{=}CH_2$ |
| 3,4-$F_2$-5-$CF_3$ | $CF_3$ | H | $CH_2CCl{=}CH_2$ |
| 3,4-$F_2$-5-$CF_3$ | $CF_3$ | H | $CH(CH_3)Ph(R)$ |
| 3,4-$F_2$-5-$CF_3$ | $CF_3$ | H | $CH_2(Ph$-4-$NO_2)$ |
| 3,4-$F_2$-5-$CF_3$ | $CF_3$ | H | $CH_2(Ph$-4-$CN)$ |
| 3,4-$F_2$-5-$CF_3$ | $CF_3$ | H | $CH_2(D$-16b$)Cl$ |
| 3,4-$F_2$-5-$CF_3$ | $CF_3$ | H | $CH_2(D$-17a$)CH_3$ |
| 3,4-$F_2$-5-$CF_3$ | $CF_3$ | H | $CH_2(D$-17b$)Cl$ |
| 3,4-$F_2$-5-$CF_3$ | $CF_3$ | H | $CH_2(D$-21a$)$ |
| 3,4-$F_2$-5-$CF_3$ | $CF_3$ | H | $CH_2(D$-22a$)$ |
| 3,4-$F_2$-5-$CF_3$ | $CF_3$ | $C(O)CH_3$ | $CH_2(D$-22a$)$ |
| 3,4-$F_2$-5-$CF_3$ | $CF_3$ | $C(O)Et$ | $CH_2(D$-22a$)$ |
| 3,4-$F_2$-5-$CF_3$ | $CF_3$ | H | $CH_2(D$-29b$)CH_3$ |
| 3,4-$F_2$-5-$CF_3$ | $CF_3$ | H | $CH_2(D$-34a$)$ |
| 3,4-$F_2$-5-$CF_3$ | $CF_3$ | H | $CH_2(D$-38a$)$ |
| 3,4-$F_2$-5-$CF_3$ | $CF_3$ | H | $CH_2(D$-47a$)$ |
| 3,4-$F_2$-5-$CF_3$ | $CF_3$ | Et | $CH_2(D$-47a$)$ |
| 3,4-$F_2$-5-$CF_3$ | $CF_3$ | $CH_2OCH_3$ | $CH_2(D$-47a$)$ |
| 3,4-$F_2$-5-$CF_3$ | $CF_3$ | $CH_2CN$ | $CH_2(D$-47a$)$ |
| 3,4-$F_2$-5-$CF_3$ | $CF_3$ | $CH_2C{\equiv}CH$ | $CH_2(D$-47a$)$ |
| 3,4-$F_2$-5-$CF_3$ | $CF_3$ | $C(O)CH_3$ | $CH_2(D$-47a$)$ |
| 3,4-$F_2$-5-$CF_3$ | $CF_3$ | $C(O)Et$ | $CH_2(D$-47a$)$ |
| 3,4-$F_2$-5-$CF_3$ | $CF_3$ | $C(O)Pr$-n | $CH_2(D$-47a$)$ |
| 3,4-$F_2$-5-$CF_3$ | $CF_3$ | $C(O)Pr$-i | $CH_2(D$-47a$)$ |
| 3,4-$F_2$-5-$CF_3$ | $CF_3$ | $C(O)Pr$-c | $CH_2(D$-47a$)$ |
| 3,4-$F_2$-5-$CF_3$ | $CF_3$ | $C(O)Bu$-t | $CH_2(D$-47a$)$ |
| 3,4-$F_2$-5-$CF_3$ | $CF_3$ | $C(O)CH_2OCH_3$ | $CH_2(D$-47a$)$ |
| 3,4-$F_2$-5-$CF_3$ | $CF_3$ | $C(O)CH{=}CH_2$ | $CH_2(D$-47a$)$ |
| 3,4-$F_2$-5-$CF_3$ | $CF_3$ | $C(O)OCH_3$ | $CH_2(D$-47a$)$ |
| 3,4-$F_2$-5-$CF_3$ | $CF_3$ | $C(O)OCH_2CH_2OCH_3$ | $CH_2(D$-47a$)$ |
| 3,4-$F_2$-5-$CF_3$ | $CF_3$ | $C(O)OCH_2CH{=}CH_2$ | $CH_2(D$-47a$)$ |
| 3,4-$F_2$-5-$CF_3$ | $CF_3$ | H | $CH(CH_3)(D$-47a$)$ |
| 3,4-$F_2$-5-$CF_3$ | $CF_3$ | H | $CH_2(D$-50a$)$ |
| 3,4-$F_2$-5-$CF_3$ | $CF_3$ | H | $NHC(O)OCH_3$ |
| 3,4-$F_2$-5-$CF_3$ | $CF_3$ | H | $N(CH_3)Ph$ |
| 3,4-$F_2$-5-$CF_3$ | $CF_3$ | H | $N(CH_2CH{=}CH_2)Ph$ |
| 3,4-$F_2$-5-$CF_3$ | $CF_3$ | H | $N(CH_2C{\equiv}CH)Ph$ |
| 3,4-$F_2$-5-$CF_3$ | $CF_3$ | H | $NH(D$-50a$)$ |
| 3,4-$F_2$-5-$CF_3$ | $CF_3$ | $CH_3$ | $NH(D$-50a$)$ |
| 3,4-$F_2$-5-$CF_3$ | $CF_3$ | H | $N(CH_3)(D$-50a$)$ |
| 3,4-$F_2$-5-$CF_3$ | $CF_3$ | H | $N(Et)(D$-50a$)$ |
| 3,4-$F_2$-5-$CF_3$ | $CF_3$ | $C(O)OCH_3$ | $C(O)N(CH_3)_2$ |
| 3,4-$F_2$-5-$CF_3$ | $CF_3$ | H | $C(O)NHEt$ |
| 3,4-$F_2$-5-$CF_3$ | $CF_3$ | $CH_3$ | $C(O)NHEt$ |
| 3,4-$F_2$-5-$CF_3$ | $CF_3$ | H | $C(O)NHCH_2CH_2Cl$ |
| 3,4-$F_2$-5-$CF_3$ | $CF_3$ | H | $C(O)NHCH_2CF_3$ |
| 3,4-$F_2$-5-$CF_3$ | $CF_3$ | H | $C(O)NHCH_2(Ph$-4-$F)$ |
| 3,4-$F_2$-5-$CF_3$ | $CF_3$ | H | $Ph$-4-$F$ |
| 3,4-$F_2$-5-$CF_3$ | $CF_3$ | H | $Ph$-4-$CN$ |
| 3,4-$F_2$-5-$CF_3$ | $CF_3$ | H | $Ph$-2,4-$F_2$ |
| 3,4-$F_2$-5-$CF_3$ | $CF_3$ | H | $(D$-13b$)CH_3$ |
| 3,4-$F_2$-5-$CF_3$ | $CF_3$ | H | $(D$-15a$)CH_3$ |
| 3,4-$F_2$-5-$CF_3$ | $CF_3$ | H | $D$-21a |
| 3,4-$F_2$-5-$CF_3$ | $CF_3$ | H | $(D$-47d$)CN$ |
| 3,4-$F_2$-5-$CF_3$ | $CF_3$ | H | $(D$-47e$)Br$ |
| 3,4-$F_2$-5-$CF_3$ | $CF_3$ | H | $D$-50a |
| 3,4-$F_2$-5-$CF_3$ | $CF_3$ | H | $(D$-50c$)Cl$ |
| 3,4-$F_2$-5-$CF_3$ | $CF_3$ | H | $(D$-50c$)Br$ |
| 3,4-$F_2$-5-$CF_3$ | $CF_3$ | H | $D$-51a |
| 3,4-$F_2$-5-$CF_3$ | $CF_3$ | H | $D$-52a |
| 3,4-$F_2$-5-$CF_3$ | $CF_3$ | H | $D$-53a |
| 3,4-$F_2$-5-$CF_3$ | $CF_2Cl$ | H | c-Bu |
| 3,4-$F_2$-5-$CF_3$ | $CF_2Cl$ | H | $CH_2CF_3$ |
| 3,4-$F_2$-5-$CF_3$ | $CF_2Cl$ | H | $CH_2OEt$ |
| 3,4-$F_2$-5-$CF_3$ | $CF_2Cl$ | H | $CH_2OCH_2CF_3$ |
| 3,4-$F_2$-5-$CF_3$ | $CF_2Cl$ | $C(O)CH_3$ | $CH_2OCH_2CF_3$ |
| 3,4-$F_2$-5-$CF_3$ | $CF_2Cl$ | H | $CH_2CH_2OCH_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4-F$_2$-5-CF$_3$ | CF$_2$Cl | H | CH$_2$(E-10a) |
| 3,4-F$_2$-5-CF$_3$ | CF$_2$Cl | H | E-4a |
| 3,4-F$_2$-5-CF$_3$ | CF$_2$Cl | H | CH$_2$C(O)NHCH$_2$CH$_2$Cl |
| 3,4-F$_2$-5-CF$_3$ | CF$_2$Cl | H | CH$_2$C(O)NHCH$_2$CF$_3$ |
| 3,4-F$_2$-5-CF$_3$ | CF$_2$Cl | H | CH(CH$_3$)C(O)NHCH$_2$CF$_3$ |
| 3,4-F$_2$-5-CF$_3$ | CF$_2$Cl | H | CH(CH$_3$)C(O)NHCH$_2$CF$_3$(D) |
| 3,4-F$_2$-5-CF$_3$ | CF$_2$Cl | H | CH(CH$_3$)Ph(R) |
| 3,4-F$_2$-5-CF$_3$ | CF$_2$Cl | H | CH$_2$(D-22a) |
| 3,4-F$_2$-5-CF$_3$ | CF$_2$Cl | C(O)CH$_3$ | CH$_2$(D-22a) |
| 3,4-F$_2$-5-CF$_3$ | CF$_2$Cl | C(O)Et | CH$_2$(D-22a) |
| 3,4-F$_2$-5-CF$_3$ | CF$_2$Cl | H | CH$_2$(D-47a) |
| 3,4-F$_2$-5-CF$_3$ | CF$_2$Cl | CH$_2$OCH$_3$ | CH$_2$(D-47a) |
| 3,4-F$_2$-5-CF$_3$ | CF$_2$Cl | CH$_2$CN | CH$_2$(D-47a) |
| 3,4-F$_2$-5-CF$_3$ | CF$_2$Cl | C(O)CH$_3$ | CH$_2$(D-47a) |
| 3,4-F$_2$-5-CF$_3$ | CF$_2$Cl | C(O)Et | CH$_2$(D-47a) |
| 3,4-F$_2$-5-CF$_3$ | CF$_2$Cl | C(O)OCH$_3$ | CH$_2$(D-47a) |
| 3,4-F$_2$-5-CF$_3$ | CF$_2$Cl | H | N(CH$_3$)Ph |
| 3,4-F$_2$-5-CF$_3$ | CF$_2$Cl | H | N(CH$_3$)(D-50a) |
| 3,4-F$_2$-5-CF$_3$ | CF$_2$Cl | H | C(O)NHCH$_2$CF$_3$ |
| 3,4-F$_2$-5-CF$_3$ | CF$_2$Cl | H | Ph-2,4-F$_2$ |
| 3,4-F$_2$-5-CF$_3$ | CF$_2$Cl | H | (D-50c)Cl |
| 3,4-F$_2$-5-CF$_3$ | CF$_2$Cl | H | D-52a |
| 3,4-F$_2$-5-CF$_3$ | CF$_2$Br | H | CH$_2$CF$_3$ |
| 3,4-F$_2$-5-CF$_3$ | CF$_2$Br | H | E-4a |
| 3,4-F$_2$-5-CF$_3$ | CF$_2$Br | H | CH$_2$C(O)NHCH$_2$CF$_3$ |
| 3,4-F$_2$-5-CF$_3$ | CF$_2$Br | H | CH$_2$(D-22a) |
| 3,4-F$_2$-5-CF$_3$ | CF$_2$Br | H | CH$_2$(D-47a) |
| 3,4-F$_2$-5-CF$_3$ | CF$_2$Br | H | (D-50c)Cl |
| 3,4-F$_2$-5-CF$_3$ | CF$_2$CHF$_2$ | H | CH$_2$CF$_3$ |
| 3,4-F$_2$-5-CF$_3$ | CF$_2$CHF$_2$ | H | E-4a |
| 3,4-F$_2$-5-CF$_3$ | CF$_2$CHF$_2$ | H | CH$_2$C(O)NHCH$_2$CF$_3$ |
| 3,4-F$_2$-5-CF$_3$ | CF$_2$CHF$_2$ | H | CH$_2$(D-22a) |
| 3,4-F$_2$-5-CF$_3$ | CF$_2$CHF$_2$ | H | CH$_2$(D-47a) |
| 3,4-F$_2$-5-CF$_3$ | CF$_2$CHF$_2$ | H | (D-50c)Cl |
| 2-F-3-Cl-5-CF$_3$ | CF$_3$ | H | CH$_2$CF$_3$ |
| 3-Cl-4-F-5-CF$_3$ | CHF$_2$ | H | CH$_2$CF$_3$ |
| 3-Cl-4-F-5-CF$_3$ | CHF$_2$ | H | E-4a |
| 3-Cl-4-F-5-CF$_3$ | CHF$_2$ | H | CH$_2$C(O)NHCH$_2$CF$_3$ |
| 3-Cl-4-F-5-CF$_3$ | CHF$_2$ | H | CH$_2$(D-22a) |
| 3-Cl-4-F-5-CF$_3$ | CHF$_2$ | H | CH$_2$(D-47a) |
| 3-Cl-4-F-5-CF$_2$ | CHF$_2$ | H | (D-50c)Cl |
| 3-Cl-4-F-5-CF$_2$ | CF$_3$ | H | c-Pr |
| 3-Cl-4-F-5-CF$_3$ | CF$_3$ | H | CH$_2$Pr-c |
| 3-Cl-4-F-5-CF$_3$ | CF$_3$ | H | c-Bu |
| 3-Cl-4-F-5-CF$_3$ | CF$_3$ | H | CH$_2$CF$_3$ |
| 3-Cl-4-F-5-CF$_3$ | CF$_3$ | H | CH$_2$CH$_2$CF$_3$ |
| 3-Cl-4-F-5-CF$_3$ | CF$_3$ | H | CH$_2$OCH$_3$ |
| 3-Cl-4-F-5-CF$_3$ | CF$_3$ | H | CH$_2$OEt |
| 3-Cl-4-F-5-CF$_3$ | CF$_3$ | C(O)CH$_3$ | CH$_2$OEt |
| 3-Cl-4-F-5-CF$_3$ | CF$_3$ | H | CH$_2$OCH$_2$CF$_3$ |
| 3-Cl-4-F-5-CF$_3$ | CF$_3$ | C(O)CH$_3$ | CH$_2$OCH$_2$CF$_3$ |
| 3-Cl-4-F-5-CF$_3$ | CF$_3$ | H | CH(CH$_3$)OCH$_2$CF$_3$ |
| 3-Cl-4-F-5-CF$_3$ | CF$_3$ | H | CH$_2$CH$_2$OCH$_3$ |
| 3-Cl-4-F-5-CF$_3$ | CF$_3$ | H | CH$_2$(E-5a) |
| 3-Cl-4-F-5-CF$_3$ | CF$_3$ | H | CH$_2$(E-10a) |
| 3-Cl-4-F-5-CF$_3$ | CF$_3$ | H | CH$_2$(E-10b)CH$_3$ |
| 3-Cl-4-F-5-CF$_3$ | CF$_3$ | H | E-4a |
| 3-Cl-4-F-5-CF$_3$ | CF$_3$ | H | E-5a(R) |
| 3-Cl-4-F-5-CF$_3$ | CF$_3$ | H | CH$_2$CH=NOCH$_3$ |
| 3-Cl-4-F-5-CF$_3$ | CF$_3$ | H | CH$_2$C(CH$_3$)=NOCH$_3$ |
| 3-Cl-4-F-5-CF$_3$ | CF$_3$ | H | CH$_2$C(O)NHCH$_3$ |
| 3-Cl-4-F-5-CF$_3$ | CF$_3$ | H | CH$_2$C(O)N(CH$_3$)$_2$ |
| 3-Cl-4-F-5-CF$_3$ | CF$_3$ | H | CH$_2$C(O)NHPr-n |
| 3-Cl-4-F-5-CF$_3$ | CF$_3$ | H | CH$_2$C(O)NHPr-i |
| 3-Cl-4-F-5-CF$_3$ | CF$_3$ | H | CH$_2$C(O)NHCH$_2$CH$_2$F |
| 3-Cl-4-F-5-CF$_3$ | CF$_3$ | H | CH$_2$C(O)NHCH$_2$CH$_2$Cl |
| 3-Cl-4-F-5-CF$_3$ | CF$_3$ | H | CH$_2$C(O)NHCH$_2$CF$_3$ |
| 3-Cl-4-F-5-CF$_3$ | CF$_3$ | H | CH$_2$C(O)NHCH$_2$CH=CH$_2$ |
| 3-Cl-4-F-5-CF$_3$ | CF$_3$ | H | CH$_2$C(O)NHCH$_2$C≡CH |
| 3-Cl-4-F-5-CF$_3$ | CF$_3$ | H | CH(CH$_3$)C(O)NHEt |
| 3-Cl-4-F-5-CF$_3$ | CF$_3$ | H | CH(CH$_3$)C(O)NHCH$_2$CF$_3$ |
| 3-Cl-4-F-5-CF$_3$ | CF$_3$ | H | CH(CH$_3$)C(O)NHCH$_2$CF$_3$(D) |
| 3-Cl-4-F-5-CF$_3$ | CF$_3$ | H | CH$_2$CH=CH$_2$ |
| 3-Cl-4-F-5-CF$_3$ | CF$_3$ | H | CH$_2$CCl=CH$_2$ |
| 3-Cl-4-F-5-CF$_3$ | CF$_3$ | H | CH(CH$_3$)Ph(R) |
| 3-Cl-4-F-5-CF$_3$ | CF$_3$ | H | CH$_2$(Ph-4-NO$_2$) |
| 3-Cl-4-F-5-CF$_3$ | CF$_3$ | H | CH$_2$(Ph-4-CN) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-4-F-5-CF$_3$ | CF$_3$ | H | CH$_2$(D-16b)Cl |
| 3-Cl-4-F-5-CF$_3$ | CF$_3$ | H | CH$_2$(D-17a)CH$_3$ |
| 3-Cl-4-F-5-CF$_3$ | CF$_3$ | H | CH$_2$(D-17b)Cl |
| 3-Cl-4-F-5-CF$_3$ | CF$_3$ | H | CH$_2$(D-21a) |
| 3-Cl-4-F-5-CF$_3$ | CF$_3$ | H | CH$_2$(D-22a) |
| 3-Cl-4-F-5-CF$_3$ | CF$_3$ | C(O)CH$_3$ | CH$_2$(D-22a) |
| 3-Cl-4-F-5-CF$_3$ | CF$_3$ | C(O)Et | CH$_2$(D-22a) |
| 3-Cl-4-F-5-CF$_3$ | CF$_3$ | H | CH$_2$(D-29b)CH$_3$ |
| 3-Cl-4-F-5-CF$_3$ | CF$_3$ | H | CH$_2$(D-34a) |
| 3-Cl-4-F-5-CF$_3$ | CF$_3$ | H | CH$_2$(D-38a) |
| 3-Cl-4-F-5-CF$_3$ | CF$_3$ | H | CH$_2$(D-47a) |
| 3-Cl-4-F-5-CF$_3$ | CF$_3$ | Et | CH$_2$(D-47a) |
| 3-Cl-4-F-5-CF$_3$ | CF$_3$ | CH$_2$OCH$_3$ | CH$_2$(D-47a) |
| 3-Cl-4-F-5-CF$_3$ | CF$_3$ | CH$_2$CN | CH$_2$(D-47a) |
| 3-Cl-4-F-5-CF$_3$ | CF$_3$ | CH$_2$C≡CH | CH$_2$(D-47a) |
| 3-Cl-4-F-5-CF$_3$ | CF$_3$ | C(O)CH$_3$ | CH$_2$(D-47a) |
| 3-Cl-4-F-5-CF$_3$ | CF$_3$ | C(O)Et | CH$_2$(D-47a) |
| 3-Cl-4-F-5-CF$_3$ | CF$_3$ | C(O)Pr-n | CH$_2$(D-47a) |
| 3-Cl-4-F-5-CF$_3$ | CF$_3$ | C(O)Pr-i | CH$_2$(D-47a) |
| 3-Cl-4-F-5-CF$_3$ | CF$_3$ | C(O)Pr-c | CH$_2$(D-47a) |
| 3-Cl-4-F-5-CF$_3$ | CF$_3$ | C(O)Bu-t | CH$_2$(D-47a) |
| 3-Cl-4-F-5-CF$_3$ | CF$_3$ | C(O)CH$_2$OCH$_3$ | CH$_2$(D-47a) |
| 3-Cl-4-F-5-CF$_3$ | CF$_3$ | C(O)CH=CH$_2$ | CH$_2$(D-47a) |
| 3-Cl-4-F-5-CF$_3$ | CF$_3$ | C(O)OCH$_3$ | CH$_2$(D-47a) |
| 3-Cl-4-F-5-CF$_3$ | CF$_3$ | C(O)OCH$_2$CH$_2$OCH$_3$ | CH$_2$(D-47a) |
| 3-Cl-4-F-5-CF$_3$ | CF$_3$ | C(O)OCH$_2$CH=CH$_2$ | CH$_2$(D-47a) |
| 3-Cl-4-F-5-CF$_3$ | CF$_3$ | H | CH(CH$_3$)(D-47a) |
| 3-Cl-4-F-5-CF$_3$ | CF$_3$ | H | CH$_2$(D-50a) |
| 3-Cl-4-F-5-CF$_3$ | CF$_3$ | H | NHC(O)OCH$_3$ |
| 3-Cl-4-F-5-CF$_3$ | CF$_3$ | H | N(CH$_3$)Ph |
| 3-Cl-4-F-5-CF$_3$ | CF$_3$ | H | N(CH$_2$CH=CH$_2$)Ph |
| 3-Cl-4-F-5-CF$_3$ | CF$_3$ | H | N(CH$_2$C≡CH)Ph |
| 3-Cl-4-F-5-CF$_3$ | CF$_3$ | H | NH(D-50a) |
| 3-Cl-4-F-5-CF$_3$ | CF$_3$ | CH$_3$ | NH(D-50a) |
| 3-Cl-4-F-5-CF$_3$ | CF$_3$ | H | N(CH$_3$)(D-50a) |
| 3-Cl-4-F-5-CF$_3$ | CF$_3$ | H | N(Et)(D-50a) |
| 3-Cl-4-F-5-CF$_3$ | CF$_3$ | C(O)OCH$_3$ | C(O)N(CH$_3$)$_2$ |
| 3-Cl-4-F-5-CF$_3$ | CF$_3$ | H | C(O)NHEt |
| 3-Cl-4-F-5-CF$_3$ | CF$_3$ | CH$_3$ | C(O)NHEt |
| 3-Cl-4-F-5-CF$_3$ | CF$_3$ | H | C(O)NHCH$_2$CH$_2$Cl |
| 3-Cl-4-F-5-CF$_3$ | CF$_3$ | H | C(O)NHCH$_2$CF$_3$ |
| 3-Cl-4-F-5-CF$_3$ | CF$_3$ | H | C(O)NHCH$_2$(Ph-4-F) |
| 3-Cl-4-F-5-CF$_3$ | CF$_3$ | H | Ph-4-F |
| 3-Cl-4-F-5-CF$_3$ | CF$_3$ | H | Ph-4-CN |
| 3-Cl-4-F-5-CF$_3$ | CF$_3$ | H | Ph-2,4-F$_2$ |
| 3-Cl-4-F-5-CF$_3$ | CF$_3$ | H | (D-13b)CH$_3$ |
| 3-Cl-4-F-5-CF$_3$ | CF$_3$ | H | (D-15a)CH$_3$ |
| 3-Cl-4-F-5-CF$_3$ | CF$_3$ | H | D-21a |
| 3-Cl-4-F-5-CF$_3$ | CF$_3$ | H | (D-47d)CN |
| 3-Cl-4-F-5-CF$_3$ | CF$_3$ | H | (D-47e)Br |
| 3-Cl-4-F-5-CF$_3$ | CF$_3$ | H | D-50a |
| 3-Cl-4-F-5-CF$_3$ | CF$_3$ | H | (D-50c)Cl |
| 3-Cl-4-F-5-CF$_3$ | CF$_3$ | H | (D-50c)Br |
| 3-Cl-4-F-5-CF$_3$ | CF$_3$ | H | D-51a |
| 3-Cl-4-F-5-CF$_3$ | CF$_3$ | H | D-52a |
| 3-Cl-4-F-5-CF$_3$ | CF$_3$ | H | D-53a |
| 3-Cl-4-F-5-CF$_3$ | CF$_2$Cl | H | c-Bu |
| 3-Cl-4-F-5-CF$_3$ | CF$_2$Cl | H | CH$_2$CF$_3$ |
| 3-Cl-4-F-5-CF$_3$ | CF$_2$Cl | H | CH$_2$OEt |
| 3-Cl-4-F-5-CF$_3$ | CF$_2$Cl | H | CH$_2$OCH$_2$CF$_3$ |
| 3-Cl-4-F-5-CF$_3$ | CF$_2$Cl | C(O)CH$_3$ | CH$_2$OCH$_2$CF$_3$ |
| 3-Cl-4-F-5-CF$_3$ | CF$_2$Cl | H | CH$_2$CH$_2$OCH$_3$ |
| 3-Cl-4-F-5-CF$_3$ | CF$_2$Cl | H | CH$_2$(E-10a) |
| 3-Cl-4-F-5-CF$_3$ | CF$_2$Cl | H | E-4a |
| 3-Cl-4-F-5-CF$_3$ | CF$_2$Cl | H | CH$_2$C(O)NHCH$_2$CH$_2$Cl |
| 3-Cl-4-F-5-CF$_3$ | CF$_2$Cl | H | CH$_2$C(O)NHCH$_2$CF$_3$ |
| 3-Cl-4-F-5-CF$_3$ | CF$_2$Cl | H | CH(CH$_3$)C(O)NHCH$_2$CF$_3$ |
| 3-Cl-4-F-5-CF$_3$ | CF$_2$Cl | H | CH(CH$_3$)C(O)NHCH$_2$CF$_3$(D) |
| 3-Cl-4-F-5-CF$_3$ | CF$_2$Cl | H | CH(CH$_3$)Ph(R) |
| 3-Cl-4-F-5-CF$_3$ | CF$_2$Cl | H | CH$_2$(D-22a) |
| 3-Cl-4-F-5-CF$_3$ | CF$_2$Cl | C(O)CH$_3$ | CH$_2$(D-22a) |
| 3-Cl-4-F-5-CF$_3$ | CF$_2$Cl | C(O)Et | CH$_2$(D-22a) |
| 3-Cl-4-F-5-CF$_3$ | CF$_2$Cl | H | CH$_2$(D-47a) |
| 3-Cl-4-F-5-CF$_3$ | CF$_2$Cl | CH$_2$OCH$_3$ | CH$_2$(D-47a) |
| 3-Cl-4-F-5-CF$_3$ | CF$_2$Cl | CH$_2$CN | CH$_2$(D-47a) |
| 3-Cl-4-F-5-CF$_3$ | CF$_2$Cl | C(O)CH$_3$ | CH$_2$(D-47a) |
| 3-Cl-4-F-5-CF$_3$ | CF$_2$Cl | C(O)Et | CH$_2$(D-47a) |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-4-F-5-CF$_3$ | CF$_2$Cl | C(O)OCH$_3$ | CH$_2$(D-47a) |
| 3-Cl-4-F-5-CF$_3$ | CF$_2$Cl | H | N(CH$_3$)Ph |
| 3-Cl-4-F-5-CF$_3$ | CF$_2$Cl | H | N(CH$_3$)(D-50a) |
| 3-Cl-4-F-5-CF$_3$ | CF$_2$Cl | H | C(O)NHCH$_2$CF$_3$ |
| 3-Cl-4-F-5-CF$_3$ | CF$_2$Cl | H | Ph-2,4-F$_2$ |
| 3-Cl-4-F-5-CF$_3$ | CF$_2$Cl | H | (D-50c)Cl |
| 3-Cl-4-F-5-CF$_3$ | CF$_2$Cl | H | D-52a |
| 3-Cl-4-F-5-CF$_3$ | CF$_2$Br | H | CH$_2$CF$_3$ |
| 3-Cl-4-F-5-CF$_3$ | CF$_2$Br | H | E-4a |
| 3-Cl-4-F-5-CF$_3$ | CF$_2$Br | H | CH$_2$C(O)NHCH$_2$CF$_3$ |
| 3-Cl-4-F-5-CF$_3$ | CF$_2$Br | H | CH$_2$(D-22a) |
| 3-Cl-4-F-5-CF$_3$ | CF$_2$Br | H | CH$_2$(D-47a) |
| 3-Cl-4-F-5-CF$_3$ | CF$_2$Br | H | (D-50c)Cl |
| 3-Cl-4-F-5-CF$_3$ | CF$_2$CHF$_2$ | H | CH$_2$CF$_3$ |
| 3-Cl-4-F-5-CF$_3$ | CF$_2$CHF$_2$ | H | E-4a |
| 3-Cl-4-F-5-CF$_3$ | CF$_2$CHF$_2$ | H | CH$_2$C(O)NHCH$_2$CF$_3$ |
| 3-Cl-4-F-5-CF$_3$ | CF$_2$CHF$_2$ | H | CH$_2$(D-22a) |
| 3-Cl-4-F-5-CF$_3$ | CF$_2$CHF$_2$ | H | CH$_2$(D-47a) |
| 3-Cl-4-F-5-CF$_3$ | CF$_2$CHF$_2$ | H | (D-50c)Cl |
| 3,4-Cl$_2$-5-CF$_3$ | CHF$_2$ | H | CH$_2$CF$_3$ |
| 3,4-Cl$_2$-5-CF$_3$ | CHF$_2$ | H | E-4a |
| 3,4-Cl$_2$-5-CF$_3$ | CHF$_2$ | H | CH$_2$C(O)NHCH$_2$CF$_3$ |
| 3,4-Cl$_2$-5-CF$_3$ | CHF$_2$ | H | CH$_2$(D-22a) |
| 3,4-Cl$_2$-5-CF$_3$ | CHF$_2$ | H | CH$_2$(D-52a) |
| 3,4-Cl$_2$-5-CF$_3$ | CHF$_2$ | H | (D-55c)Cl |
| 3,4-Cl$_2$-5-CF$_3$ | CF$_3$ | H | c-Pr |
| 3,4-Cl$_2$-5-CF$_2$ | CF$_3$ | H | CH$_2$Pr-c |
| 3,4-Cl$_2$-5-CF$_3$ | CF$_3$ | H | c-Bu |
| 3,4-Cl$_2$-5-CF$_3$ | CF$_3$ | H | CH$_2$CF$_3$ |
| 3,4-Cl$_2$-5-CF$_3$ | CF$_3$ | H | CH$_2$CH$_2$CF$_3$ |
| 3,4-Cl$_2$-5-CF$_3$ | CF$_3$ | H | CH$_2$OCH$_3$ |
| 3,4-Cl$_2$-5-CF$_3$ | CF$_3$ | H | CH$_2$OEt |
| 3,4-Cl$_2$-5-CF$_3$ | CF$_3$ | C(O)CH$_3$ | CH$_2$OEt |
| 3,4-Cl$_2$-5-CF$_3$ | CF$_3$ | H | CH$_2$OCH$_2$CF$_3$ |
| 3,4-Cl$_2$-5-CF$_3$ | CF$_3$ | C(O)CH$_3$ | CH$_2$OCH$_2$CF$_3$ |
| 3,4-Cl$_2$-5-CF$_3$ | CF$_3$ | H | CH(CH$_3$)OCH$_2$CF$_3$ |
| 3,4-Cl$_2$-5-CF$_3$ | CF$_3$ | H | CH$_2$CH$_2$OCH$_3$ |
| 3,4-Cl$_2$-5-CF$_3$ | CF$_3$ | H | CH$_2$(E-5a) |
| 3,4-Cl$_2$-5-CF$_3$ | CF$_3$ | H | CH$_2$(E-10a) |
| 3,4-Cl$_2$-5-CF$_3$ | CF$_3$ | H | CH$_2$(E-10b)CH$_3$ |
| 3,4-Cl$_2$-5-CF$_3$ | CF$_3$ | H | E-4a |
| 3,4-Cl$_2$-5-CF$_3$ | CF$_3$ | H | E-5a(R) |
| 3,4-Cl$_2$-5-CF$_3$ | CF$_3$ | H | CH$_2$CH=NOCH$_3$ |
| 3,4-Cl$_2$-5-CF$_3$ | CF$_3$ | H | CH$_2$C(CH$_3$)=NOCH$_3$ |
| 3,4-Cl$_2$-5-CF$_3$ | CF$_3$ | H | CH$_2$C(O)NHCH$_3$ |
| 3,4-Cl$_2$-5-CF$_3$ | CF$_3$ | H | CH$_2$C(O)N(CH$_3$)$_2$ |
| 3,4-Cl$_2$-5-CF$_3$ | CF$_3$ | H | CH$_2$C(O)NHPr-n |
| 3,4-Cl$_2$-5-CF$_3$ | CF$_3$ | H | CH$_2$C(O)NHPr-i |
| 3,4-Cl$_2$-5-CF$_3$ | CF$_3$ | H | CH$_2$C(O)NHCH$_2$CH$_2$F |
| 3,4-Cl$_2$-5-CF$_3$ | CF$_3$ | H | CH$_2$C(O)NHCH$_2$CH$_2$Cl |
| 3,4-Cl$_2$-5-CF$_3$ | CF$_3$ | H | CH$_2$C(O)NHCH$_2$CF$_3$ |
| 3,4-Cl$_2$-5-CF$_3$ | CF$_3$ | H | CH$_2$C(O)NHCH$_2$CH=CH$_2$ |
| 3,4-Cl$_2$-5-CF$_3$ | CF$_3$ | H | CH$_2$C(O)NHCH$_2$C≡CH |
| 3,4-Cl$_2$-5-CF$_3$ | CF$_3$ | H | CH(CH$_3$)C(O)NHEt |
| 3,4-Cl$_2$-5-CF$_3$ | CF$_3$ | H | CH(CH$_3$)C(O)NHCH$_2$CF$_3$ |
| 3,4-Cl$_2$-5-CF$_3$ | CF$_3$ | H | CH(CH$_3$)C(O)NHCH$_2$CF$_3$(D) |
| 3,4-Cl$_2$-5-CF$_3$ | CF$_3$ | H | CH$_2$CH=CH$_2$ |
| 3,4-Cl$_2$-5-CF$_3$ | CF$_3$ | H | CH$_2$CCl=CH$_2$ |
| 3,4-Cl$_2$-5-CF$_3$ | CF$_3$ | H | CH(CH$_3$)Ph(R) |
| 3,4-Cl$_2$-5-CF$_3$ | CF$_3$ | H | CH$_2$(Ph-4-NO$_2$) |
| 3,4-Cl$_2$-5-CF$_3$ | CF$_3$ | H | CH$_2$(Ph-4-CN) |
| 3,4-Cl$_2$-5-CF$_3$ | CF$_3$ | H | CH$_2$(D-16b)Cl |
| 3,4-Cl$_2$-5-CF$_3$ | CF$_3$ | H | CH$_2$(D-17a)CH$_3$ |
| 3,4-Cl$_2$-5-CF$_3$ | CF$_3$ | H | CH$_2$(D-17b)Cl |
| 3,4-Cl$_2$-5-CF$_3$ | CF$_3$ | H | CH$_2$(D-21a) |
| 3,4-Cl$_2$-5-CF$_3$ | CF$_3$ | H | CH$_2$(D-22a) |
| 3,4-Cl$_2$-5-CF$_3$ | CF$_3$ | C(O)CH$_3$ | CH$_2$(D-22a) |
| 3,4-Cl$_2$-5-CF$_3$ | CF$_3$ | C(O)Et | CH$_2$(D-22a) |
| 3,4-Cl$_2$-5-CF$_3$ | CF$_3$ | H | CH$_2$(D-29b)CH$_3$ |
| 3,4-Cl$_2$-5-CF$_3$ | CF$_3$ | H | CH$_2$(D-34a) |
| 3,4-Cl$_2$-5-CF$_3$ | CF$_3$ | H | CH$_2$(D-41a) |
| 3,4-Cl$_2$-5-CF$_3$ | CF$_3$ | H | CH$_2$(D-52a) |
| 3,4-Cl$_2$-5-CF$_3$ | CF$_3$ | Et | CH$_2$(D-52a) |
| 3,4-Cl$_2$-5-CF$_3$ | CF$_3$ | CH$_2$OCH$_3$ | CH$_2$(D-52a) |
| 3,4-Cl$_2$-5-CF$_3$ | CF$_3$ | CH$_2$CN | CH$_2$(D-52a) |
| 3,4-Cl$_2$-5-CF$_3$ | CF$_3$ | CH$_2$C≡CH | CH$_2$(D-52a) |
| 3,4-Cl$_2$-5-CF$_3$ | CF$_3$ | C(O)CH$_3$ | CH$_2$(D-52a) |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4-Cl$_2$-5-CF$_3$ | CF$_3$ | C(O)Et | CH$_2$(D-52a) |
| 3,4-Cl$_2$-5-CF$_3$ | CF$_3$ | C(O)Pr-n | CH$_2$(D-52a) |
| 3,4-Cl$_2$-5-CF$_3$ | CF$_3$ | C(O)Pr-i | CH$_2$(D-52a) |
| 3,4-Cl$_2$-5-CF$_3$ | CF$_3$ | C(O)Pr-c | CH$_2$(D-52a) |
| 3,4-Cl$_2$-5-CF$_3$ | CF$_3$ | C(O)Bu-t | CH$_2$(D-52a) |
| 3,4-Cl$_2$-5-CF$_3$ | CF$_3$ | C(O)CH$_2$OCH$_3$ | CH$_2$(D-52a) |
| 3,4-Cl$_2$-5-CF$_3$ | CF$_3$ | C(O)CH=CH$_2$ | CH$_2$(D-52a) |
| 3,4-Cl$_2$-5-CF$_3$ | CF$_3$ | C(O)OCH$_3$ | CH$_2$(D-52a) |
| 3,4-Cl$_2$-5-CF$_3$ | CF$_3$ | C(O)OCH$_2$CH$_2$OCH$_3$ | CH$_2$(D-52a) |
| 3,4-Cl$_2$-5-CF$_3$ | CF$_3$ | C(O)OCH$_2$CH=CH$_2$ | CH$_2$(D-52a) |
| 3,4-Cl$_2$-5-CF$_3$ | CF$_3$ | H | CH(CH$_3$)(D-52a) |
| 3,4-Cl$_2$-5-CF$_3$ | CF$_3$ | H | CH$_2$(D-55a) |
| 3,4-Cl$_2$-5-CF$_3$ | CF$_3$ | H | NHC(O)OCH$_3$ |
| 3,4-Cl$_2$-5-CF$_3$ | CF$_3$ | H | N(CH$_3$)Ph |
| 3,4-Cl$_2$-5-CF$_3$ | CF$_3$ | H | N(CH$_2$CH=CH$_2$)Ph |
| 3,4-Cl$_2$-5-CF$_3$ | CF$_3$ | H | N(CH$_2$C≡CH)Ph |
| 3,4-Cl$_2$-5-CF$_3$ | CF$_3$ | H | NH(D-55a) |
| 3,4-Cl$_2$-5-CF$_3$ | CF$_3$ | CH$_3$ | NH(D-55a) |
| 3,4-Cl$_2$-5-CF$_3$ | CF$_3$ | H | N(CH$_3$)(D-55a) |
| 3,4-Cl$_2$-5-CF$_3$ | CF$_3$ | H | N(Et)(D-55a) |
| 3,4-Cl$_2$-5-CF$_3$ | CF$_3$ | C(O)OCH$_3$ | C(O)N(CH$_3$)$_2$ |
| 3,4-Cl$_2$-5-CF$_3$ | CF$_3$ | H | C(O)NHEt |
| 3,4-Cl$_2$-5-CF$_3$ | CF$_3$ | CH$_3$ | C(O)NHEt |
| 3,4-Cl$_2$-5-CF$_3$ | CF$_3$ | H | C(O)NHCH$_2$CH$_2$Cl |
| 3,4-Cl$_2$-5-CF$_3$ | CF$_3$ | H | C(O)NHCH$_2$CF$_3$ |
| 3,4-Cl$_2$-5-CF$_3$ | CF$_3$ | H | C(O)NHCH$_2$(Ph-4-F) |
| 3,4-Cl$_2$-5-CF$_3$ | CF$_3$ | H | Ph-4-F |
| 3,4-Cl$_2$-5-CF$_3$ | CF$_3$ | H | Ph-4-CN |
| 3,4-Cl$_2$-5-CF$_3$ | CF$_3$ | H | Ph-2,4-F$_2$ |
| 3,4-Cl$_2$-5-CF$_3$ | CF$_3$ | H | (D-13b)CH$_3$ |
| 3,4-Cl$_2$-5-CF$_3$ | CF$_3$ | H | (D-15a)CH$_3$ |
| 3,4-Cl$_2$-5-CF$_3$ | CF$_3$ | H | D-21a |
| 3,4-Cl$_2$-5-CF$_3$ | CF$_3$ | H | (D-52d)CN |
| 3,4-Cl$_2$-5-CF$_3$ | CF$_3$ | H | (D-52e)Br |
| 3,4-Cl$_2$-5-CF$_3$ | CF$_3$ | H | D-55a |
| 3,4-Cl$_2$-5-CF$_3$ | CF$_3$ | H | (D-55c)Cl |
| 3,4-Cl$_2$-5-CF$_3$ | CF$_3$ | H | (D-55c)Br |
| 3,4-Cl$_2$-5-CF$_3$ | CF$_3$ | H | D-56a |
| 3,4-Cl$_2$-5-CF$_3$ | CF$_3$ | H | D-57a |
| 3,4-Cl$_2$-5-CF$_3$ | CF$_3$ | H | D-58a |
| 3,4-Cl$_2$-5-CF$_3$ | CF$_2$Cl | H | c-Bu |
| 3,4-Cl$_2$-5-CF$_3$ | CF$_2$Cl | H | CH$_2$CF$_3$ |
| 3,4-Cl$_2$-5-CF$_3$ | CF$_2$Cl | H | CH$_2$OEt |
| 3,4-Cl$_2$-5-CF$_3$ | CF$_2$Cl | H | CH$_2$OCH$_2$CF$_3$ |
| 3,4-Cl$_2$-5-CF$_3$ | CF$_2$Cl | C(O)CH$_3$ | CH$_2$OCH$_2$CF$_3$ |
| 3,4-Cl$_2$-5-CF$_3$ | CF$_2$Cl | H | CH$_2$CH$_2$OCH$_3$ |
| 3,4-Cl$_2$-5-CF$_3$ | CF$_2$Cl | H | CH$_2$(E-10a) |
| 3,4-Cl$_2$-5-CF$_3$ | CF$_2$Cl | H | E-4a |
| 3,4-Cl$_2$-5-CF$_3$ | CF$_2$Cl | H | CH$_2$C(O)NHCH$_2$CH$_2$Cl |
| 3,4-Cl$_2$-5-CF$_3$ | CF$_2$Cl | H | CH$_2$C(O)NHCH$_2$CF$_3$ |
| 3,4-Cl$_2$-5-CF$_3$ | CF$_2$Cl | H | CH(CH$_3$)C(O)NHCH$_2$CF$_3$ |
| 3,4-Cl$_2$-5-CF$_3$ | CF$_2$Cl | H | CH(CH$_3$)C(O)NHCH$_2$CF$_3$(D) |
| 3,4-Cl$_2$-5-CF$_3$ | CF$_2$Cl | H | CH(CH$_3$)Ph(R) |
| 3,4-Cl$_2$-5-CF$_3$ | CF$_2$Cl | H | CH$_2$(D-22a) |
| 3,4-Cl$_2$-5-CF$_3$ | CF$_2$Cl | C(O)CH$_3$ | CH$_2$(D-22a) |
| 3,4-Cl$_2$-5-CF$_3$ | CF$_2$Cl | C(O)Et | CH$_2$(D-22a) |
| 3,4-Cl$_2$-5-CF$_3$ | CF$_2$Cl | H | CH$_2$(D-52a) |
| 3,4-Cl$_2$-5-CF$_3$ | CF$_2$Cl | CH$_2$OCH$_3$ | CH$_2$(D-52a) |
| 3,4-Cl$_2$-5-CF$_3$ | CF$_2$Cl | CH$_2$CN | CH$_2$(D-52a) |
| 3,4-Cl$_2$-5-CF$_3$ | CF$_2$Cl | C(O)CH$_3$ | CH$_2$(D-52a) |
| 3,4-Cl$_2$-5-CF$_3$ | CF$_2$Cl | C(O)Et | CH$_2$(D-52a) |
| 3,4-Cl$_2$-5-CF$_3$ | CF$_2$Cl | C(O)OCH$_3$ | CH$_2$(D-52a) |
| 3,4-Cl$_2$-5-CF$_3$ | CF$_2$Cl | H | N(CH$_3$)Ph |
| 3,4-Cl$_2$-5-CF$_3$ | CF$_2$Cl | H | N(CH$_3$)(D-55a) |
| 3,4-Cl$_2$-5-CF$_3$ | CF$_2$Cl | H | C(O)NHCH$_2$CF$_3$ |
| 3,4-Cl$_2$-5-CF$_3$ | CF$_2$Cl | H | Ph-2,4-F$_2$ |
| 3,4-Cl$_2$-5-CF$_3$ | CF$_2$Cl | H | (D-55c)Cl |
| 3,4-Cl$_2$-5-CF$_3$ | CF$_2$Cl | H | D-57a |
| 3,4-Cl$_2$-5-CF$_3$ | CF$_2$Br | H | CH$_2$CF$_3$ |
| 3,4-Cl$_2$-5-CF$_3$ | CF$_2$Br | H | E-4a |
| 3,4-Cl$_2$-5-CF$_3$ | CF$_2$Br | H | CH$_2$C(O)NHCH$_2$CF$_3$ |
| 3,4-Cl$_2$-5-CF$_3$ | CF$_2$Br | H | CH$_2$(D-22a) |
| 3,4-Cl$_2$-5-CF$_3$ | CF$_2$Br | H | CH$_2$(D-52a) |
| 3,4-Cl$_2$-5-CF$_3$ | CF$_2$Br | H | (D-55c)Cl |
| 3,4-Cl$_2$-5-CF$_3$ | CF$_2$CHF$_2$ | H | CH$_2$CF$_3$ |
| 3,4-Cl$_2$-5-CF$_3$ | CF$_2$CHF$_2$ | H | E-4a |
| 3,4-Cl$_2$-5-CF$_3$ | CF$_2$CHF$_2$ | H | CH$_2$C(O)NHCH$_2$CF$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4-Cl$_2$-5-CF$_3$ | CF$_2$CHF$_2$ | H | CH$_2$(D-22a) |
| 3,4-Cl$_2$-5-CF$_3$ | CF$_2$CHF$_2$ | H | CH$_2$(D-52a) |
| 3,4-Cl$_2$-5-CF$_3$ | CF$_2$CHF$_2$ | H | (D-55c)Cl |
| 3,5-(CF$_3$)$_2$-4-Cl | CHF$_2$ | H | CH$_2$CF$_3$ |
| 3,5-(CF$_3$)$_2$-4-Cl | CHF$_2$ | H | E-4a |
| 3,5-(CF$_3$)$_2$-4-Cl | CHF$_2$ | H | CH$_2$C(O)NHCH$_2$CF$_3$ |
| 3,5-(CF$_3$)$_2$-4-Cl | CHF$_2$ | H | CH$_2$(D-22a) |
| 3,5-(CF$_3$)$_2$-4-Cl | CHF$_2$ | H | CH$_2$(D-47a) |
| 3,5-(CF$_3$)$_2$-4-Cl | CHF$_2$ | H | (D-50c)Cl |
| 3,5-(CF$_3$)$_2$-4-Cl | CF$_3$ | H | c-Pr |
| 3,5-(CF$_3$)$_2$-4-Cl | CF$_3$ | H | CH$_2$Pr-c |
| 3,5-(CF$_3$)$_2$-4-Cl | CF$_3$ | H | c-Bu |
| 3,5-(CF$_3$)$_2$-4-Cl | CF$_3$ | H | CH$_2$CF$_3$ |
| 3,5-(CF$_3$)$_2$-4-Cl | CF$_3$ | H | CH$_2$CH$_2$CF$_3$ |
| 3,5-(CF$_3$)$_2$-4-Cl | CF$_3$ | H | CH$_2$OCH$_3$ |
| 3,5-(CF$_3$)$_2$-4-Cl | CF$_3$ | H | CH$_2$OEt |
| 3,5-(CF$_3$)$_2$-4-Cl | CF$_3$ | C(O)CH$_3$ | CH$_2$OEt |
| 3,5-(CF$_3$)$_2$-4-Cl | CF$_3$ | H | CH$_2$OCH$_2$CF$_3$ |
| 3,5-(CF$_3$)$_2$-4-Cl | CF$_3$ | C(O)CH$_3$ | CH$_2$OCH$_2$CF$_3$ |
| 3,5-(CF$_3$)$_2$-4-Cl | CF$_3$ | H | CH(CH$_3$)OCH$_2$CF$_3$ |
| 3,5-(CF$_3$)$_2$-4-Cl | CF$_3$ | H | CH$_2$CH$_2$OCH$_3$ |
| 3,5-(CF$_3$)$_2$-4-Cl | CF$_3$ | H | CH$_2$(E-5a) |
| 3,5-(CF$_3$)$_2$-4-Cl | CF$_3$ | H | CH$_2$(E-10a) |
| 3,5-(CF$_3$)$_2$-4-Cl | CF$_3$ | H | CH$_2$(E-10b)CH$_3$ |
| 3,5-(CF$_3$)$_2$-4-Cl | CF$_3$ | H | E-4a |
| 3,5-(CF$_3$)$_2$-4-Cl | CF$_3$ | H | E-5a(R) |
| 3,5-(CF$_3$)$_2$-4-Cl | CF$_3$ | H | CH$_2$CH=NOCH$_3$ |
| 3,5-(CF$_3$)$_2$-4-Cl | CF$_3$ | H | CH$_2$C(CH$_3$)=NOCH$_3$ |
| 3,5-(CF$_3$)$_2$-4-Cl | CF$_3$ | H | CH$_2$C(O)NHCH$_3$ |
| 3,5-(CF$_3$)$_2$-4-Cl | CF$_3$ | H | CH$_2$C(O)N(CH$_3$)$_2$ |
| 3,5-(CF$_3$)$_2$-4-Cl | CF$_3$ | H | CH$_2$C(O)NHPr-n |
| 3,5-(CF$_3$)$_2$-4-Cl | CF$_3$ | H | CH$_2$C(O)NHPr-i |
| 3,5-(CF$_3$)$_2$-4-Cl | CF$_3$ | H | CH$_2$C(O)NHCH$_2$CH$_2$F |
| 3,5-(CF$_3$)$_2$-4-Cl | CF$_3$ | H | CH$_2$C(O)NHCH$_2$CH$_2$Cl |
| 3,5-(CF$_3$)$_2$-4-Cl | CF$_3$ | H | CH$_2$C(O)NHCH$_2$CF$_3$ |
| 3,5-(CF$_3$)$_2$-4-Cl | CF$_3$ | H | CH$_2$C(O)NHCH$_2$CH=CH$_2$ |
| 3,5-(CF$_3$)$_2$-4-Cl | CF$_3$ | H | CH$_2$C(O)NHCH$_2$C≡CH |
| 3,5-(CF$_3$)$_2$-4-Cl | CF$_3$ | H | CH(CH$_3$)C(O)NHEt |
| 3,5-(CF$_3$)$_2$-4-Cl | CF$_3$ | H | CH(CH$_3$)C(O)NHCH$_2$CF$_3$ |
| 3,5-(CF$_3$)$_2$-4-Cl | CF$_3$ | H | CH(CH$_3$)C(O)NHCH$_2$CF$_3$(D) |
| 3,5-(CF$_3$)$_2$-4-Cl | CF$_3$ | H | CH$_2$CH=CH$_2$ |
| 3,5-(CF$_3$)$_2$-4-Cl | CF$_3$ | H | CH$_2$CCl=CH$_2$ |
| 3,5-(CF$_3$)$_2$-4-Cl | CF$_3$ | H | CH(CH$_3$)Ph(R) |
| 3,5-(CF$_3$)$_2$-4-Cl | CF$_3$ | H | CH$_2$(Ph-4-NO$_2$) |
| 3,5-(CF$_3$)$_2$-4-Cl | CF$_3$ | H | CH$_2$(Ph-4-CN) |
| 3,5-(CF$_3$)$_2$-4-Cl | CF$_3$ | H | CH$_2$(D-16b)Cl |
| 3,5-(CF$_3$)$_2$-4-Cl | CF$_3$ | H | CH$_2$(D-17a)CH$_3$ |
| 3,5-(CF$_3$)$_2$-4-Cl | CF$_3$ | H | CH$_2$(D-17b)Cl |
| 3,5-(CF$_3$)$_2$-4-Cl | CF$_3$ | H | CH$_2$(D-21a) |
| 3,5-(CF$_3$)$_2$-4-Cl | CF$_3$ | H | CH$_2$(D-22a) |
| 3,5-(CF$_3$)$_2$-4-Cl | CF$_3$ | C(O)CH$_3$ | CH$_2$(D-22a) |
| 3,5-(CF$_3$)$_2$-4-Cl | CF$_3$ | C(O)Et | CH$_2$(D-22a) |
| 3,5-(CF$_3$)$_2$-4-Cl | CF$_3$ | H | CH$_2$(D-29b)CH$_3$ |
| 3,5-(CF$_3$)$_2$-4-Cl | CF$_3$ | H | CH$_2$(D-34a) |
| 3,5-(CF$_3$)$_2$-4-Cl | CF$_3$ | H | CH$_2$(D-38a) |
| 3,5-(CF$_3$)$_2$-4-Cl | CF$_3$ | H | CH$_2$(D-47a) |
| 3,5-(CF$_3$)$_2$-4-Cl | CF$_3$ | Et | CH$_2$(D-47a) |
| 3,5-(CF$_3$)$_2$-4-Cl | CF$_3$ | CH$_2$OCH$_3$ | CH$_2$(D-47a) |
| 3,5-(CF$_3$)$_2$-4-Cl | CF$_3$ | CH$_2$CN | CH$_2$(D-47a) |
| 3,5-(CF$_3$)$_2$-4-Cl | CF$_3$ | CH$_2$C≡CH | CH$_2$(D-47a) |
| 3,5-(CF$_3$)$_2$-4-Cl | CF$_3$ | C(O)CH$_3$ | CH$_2$(D-47a) |
| 3,5-(CF$_3$)$_2$-4-Cl | CF$_3$ | C(O)Et | CH$_2$(D-47a) |
| 3,5-(CF$_3$)$_2$-4-Cl | CF$_3$ | C(O)Pr-n | CH$_2$(D-47a) |
| 3,5-(CF$_3$)$_2$-4-Cl | CF$_3$ | C(O)Pr-i | CH$_2$(D-47a) |
| 3,5-(CF$_3$)$_2$-4-Cl | CF$_3$ | C(O)Pr-c | CH$_2$(D-47a) |
| 3,5-(CF$_3$)$_2$-4-Cl | CF$_3$ | C(O)Bu-t | CH$_2$(D-47a) |
| 3,5-(CF$_3$)$_2$-4-Cl | CF$_3$ | C(O)CH$_2$OCH$_3$ | CH$_2$(D-47a) |
| 3,5-(CF$_3$)$_2$-4-Cl | CF$_3$ | C(O)CH=CH$_2$ | CH$_2$(D-47a) |
| 3,5-(CF$_3$)$_2$-4-Cl | CF$_3$ | C(O)OCH$_3$ | CH$_2$(D-47a) |
| 3,5-(CF$_3$)$_2$-4-Cl | CF$_3$ | C(O)OCH$_2$CH$_2$OCH$_3$ | CH$_2$(D-47a) |
| 3,5-(CF$_3$)$_2$-4-Cl | CF$_3$ | C(O)OCH$_2$CH=CH$_2$ | CH$_2$(D-47a) |
| 3,5-(CF$_3$)$_2$-4-Cl | CF$_3$ | H | CH(CH$_3$)(D-47a) |
| 3,5-(CF$_3$)$_2$-4-Cl | CF$_3$ | H | CH$_2$(D-50a) |
| 3,5-(CF$_3$)$_2$-4-Cl | CF$_3$ | H | NHC(O)OCH$_3$ |
| 3,5-(CF$_3$)$_2$-4-Cl | CF$_3$ | H | N(CH$_3$)Ph |
| 3,5-(CF$_3$)$_2$-4-Cl | CF$_3$ | H | N(CH$_2$CH=CH$_2$)Ph |
| 3,5-(CF$_3$)$_2$-4-Cl | CF$_3$ | H | N(CH$_2$C≡CH)Ph |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-(CF$_3$)$_2$-4-Cl | CF$_3$ | H | NH(D-50a) |
| 3,5-(CF$_3$)$_2$-4-Cl | CF$_3$ | CH$_3$ | NH(D-50a) |
| 3,5-(CF$_3$)$_2$-4-Cl | CF$_3$ | H | N(CH$_3$)(D-50a) |
| 3,5-(CF$_3$)$_2$-4-Cl | CF$_3$ | H | N(Et)(D-50a) |
| 3,5-(CF$_3$)$_2$-4-Cl | CF$_3$ | C(O)OCH$_3$ | C(O)N(CH$_3$)$_2$ |
| 3,5-(CF$_3$)$_2$-4-Cl | CF$_3$ | H | C(O)NHEt |
| 3,5-(CF$_3$)$_2$-4-Cl | CF$_3$ | CH$_3$ | C(O)NHEt |
| 3,5-(CF$_3$)$_2$-4-Cl | CF$_3$ | H | C(O)NHCH$_2$CH$_2$Cl |
| 3,5-(CF$_3$)$_2$-4-Cl | CF$_3$ | H | C(O)NHCH$_2$CF$_3$ |
| 3,5-(CF$_3$)$_2$-4-Cl | CF$_3$ | H | C(O)NHCH$_2$(Ph-4-F) |
| 3,5-(CF$_3$)$_2$-4-Cl | CF$_3$ | H | Ph-4-F |
| 3,5-(CF$_3$)$_2$-4-Cl | CF$_3$ | H | Ph-4-CN |
| 3,5-(CF$_3$)$_2$-4-Cl | CF$_3$ | H | Ph-2,4-F$_2$ |
| 3,5-(CF$_3$)$_2$-4-Cl | CF$_3$ | H | (D-13b)CH$_3$ |
| 3,5-(CF$_3$)$_2$-4-Cl | CF$_3$ | H | (D-15a)CH$_3$ |
| 3,5-(CF$_3$)$_2$-4-Cl | CF$_3$ | H | D-21a |
| 3,5-(CF$_3$)$_2$-4-Cl | CF$_3$ | H | (D-47d)CN |
| 3,5-(CF$_3$)$_2$-4-Cl | CF$_3$ | H | (D-47e)Br |
| 3,5-(CF$_3$)$_2$-4-Cl | CF$_3$ | H | D-50a |
| 3,5-(CF$_3$)$_2$-4-Cl | CF$_3$ | H | (D-50c)Cl |
| 3,5-(CF$_3$)$_2$-4-Cl | CF$_3$ | H | (D-50c)Br |
| 3,5-(CF$_3$)$_2$-4-Cl | CF$_3$ | H | D-51a |
| 3,5-(CF$_3$)$_2$-4-Cl | CF$_3$ | H | D-52a |
| 3,5-(CF$_3$)$_2$-4-Cl | CF$_3$ | H | D-53a |
| 3,5-(CF$_3$)$_2$-4-Cl | CF$_2$Cl | H | c-Bu |
| 3,5-(CF$_3$)$_2$-4-Cl | CF$_2$Cl | H | CH$_2$CF$_3$ |
| 3,5-(CF$_3$)$_2$-4-Cl | CF$_2$Cl | H | CH$_2$OEt |
| 3,5-(CF$_3$)$_2$-4-Cl | CF$_2$Cl | H | CH$_2$OCH$_2$CF$_3$ |
| 3,5-(CF$_3$)$_2$-4-Cl | CF$_2$Cl | C(O)CH$_3$ | CH$_2$OCH$_2$CF$_3$ |
| 3,5-(CF$_3$)$_2$-4-Cl | CF$_2$Cl | H | CH$_2$CH$_2$OCH$_3$ |
| 3,5-(CF$_3$)$_2$-4-Cl | CF$_2$Cl | H | CH$_2$(E-10a) |
| 3,5-(CF$_3$)$_2$-4-Cl | CF$_2$Cl | H | E-4a |
| 3,5-(CF$_3$)$_2$-4-Cl | CF$_2$Cl | H | CH$_2$C(O)NHCH$_2$CH$_2$Cl |
| 3,5-(CF$_3$)$_2$-4-Cl | CF$_2$Cl | H | CH$_2$C(O)NHCH$_2$CF$_3$ |
| 3,5-(CF$_3$)$_2$-4-Cl | CF$_2$Cl | H | CH(CH$_3$)C(O)NHCH$_2$CF$_3$ |
| 3,5-(CF$_3$)$_2$-4-Cl | CF$_2$Cl | H | CH(CH$_3$)C(O)NHCH$_2$CF$_3$(D) |
| 3,5-(CF$_3$)$_2$-4-Cl | CF$_2$Cl | H | CH(CH$_3$)Ph(R) |
| 3,5-(CF$_3$)$_2$-4-Cl | CF$_2$Cl | H | CH$_2$(D-22a) |
| 3,5-(CF$_3$)$_2$-4-Cl | CF$_2$Cl | C(O)CH$_3$ | CH$_2$(D-22a) |
| 3,5-(CF$_3$)$_2$-4-Cl | CF$_2$Cl | C(O)Et | CH$_2$(D-22a) |
| 3,5-(CF$_3$)$_2$-4-Cl | CF$_2$Cl | H | CH$_2$(D-47a) |
| 3,5-(CF$_3$)$_2$-4-Cl | CF$_2$Cl | CH$_2$OCH$_2$ | CH$_2$(D-47a) |
| 3,5-(CF$_3$)$_2$-4-Cl | CF$_2$Cl | CH$_2$CN | CH$_2$(D-47a) |
| 3,5-(CF$_3$)$_2$-4-Cl | CF$_2$Cl | C(O)CH$_3$ | CH$_2$(D-47a) |
| 3,5-(CF$_3$)$_2$-4-Cl | CF$_2$Cl | C(O)Et | CH$_2$(D-47a) |
| 3,5-(CF$_3$)$_2$-4-Cl | CF$_2$Cl | C(O)OCH$_3$ | CH$_2$(D-47a) |
| 3,5-(CF$_3$)$_2$-4-Cl | CF$_2$Cl | H | N(CH$_3$)Ph |
| 3,5-(CF$_3$)$_2$-4-Cl | CF$_2$Cl | H | N(CH$_3$)(D-50a) |
| 3,5-(CF$_3$)$_2$-4-Cl | CF$_2$Cl | H | C(O)NHCH$_2$CF$_3$ |
| 3,5-(CF$_3$)$_2$-4-Cl | CF$_2$Cl | H | Ph-2,4-F$_2$ |
| 3,5-(CF$_3$)$_2$-4-Cl | CF$_2$Cl | H | (D-50c)Cl |
| 3,5-(CF$_3$)$_2$-4-Cl | CF$_2$Cl | H | D-52a |
| 3,5-(CF$_3$)$_2$-4-Cl | CF$_2$Br | H | CH$_2$CF$_3$ |
| 3,5-(CF$_3$)$_2$-4-Cl | CF$_2$Br | H | E-4a |
| 3,5-(CF$_3$)$_2$-4-Cl | CF$_2$Br | H | CH$_2$C(O)NHCH$_2$CF$_3$ |
| 3,5-(CF$_3$)$_2$-4-Cl | CF$_2$Br | H | CH$_2$(D-22a) |
| 3,5-(CF$_3$)$_2$-4-Cl | CF$_2$Br | H | CH$_2$(D-47a) |
| 3,5-(CF$_3$)$_2$-4-Cl | CF$_2$Br | H | (D-50c)Cl |
| 3,5-(CF$_3$)$_2$-4-Cl | CF$_2$CHF$_2$ | H | CH$_2$CF$_3$ |
| 3,5-(CF$_3$)$_2$-4-Cl | CF$_2$CHF$_2$ | H | E-4a |
| 3,5-(CF$_3$)$_2$-4-Cl | CF$_2$CHF$_2$ | H | CH$_2$C(O)NHCH$_2$CF$_3$ |
| 3,5-(CF$_3$)$_2$-4-Cl | CF$_2$CHF$_2$ | H | CH$_2$(D-22a) |
| 3,5-(CF$_3$)$_2$-4-Cl | CF$_2$CHF$_2$ | H | CH$_2$(D-47a) |
| 3,5-(CF$_3$)$_2$-4-Cl | CF$_2$CHF$_2$ | H | (D-50c)Cl |
| 3,5-(CH$_3$)$_2$-4-CF$_3$ | CF$_3$ | H | E-4a |
| 3,5-Cl$_2$-4-OH | CF$_3$ | H | CH$_2$C(O)NHCH$_2$CF$_3$ |
| 3,5-Br$_2$-4-OH | CF$_3$ | H | CH$_2$(D-22a) |
| 3,5-I$_2$-4-OH | CF$_3$ | H | CH$_2$(D-47a) |
| 3,5-F$_2$-4-OCH$_3$ | CF$_3$ | C(O)OCH$_3$ | CH$_2$(D-47a) |
| 3,5-Cl$_2$-4-OCH$_3$ | CF$_3$ | H | CH$_2$CF$_3$ |
| 3,5-Cl$_2$-4-OCH$_3$ | CF$_3$ | H | CH$_2$(D-47a) |
| 3,5-Cl$_2$-4-OCH$_3$ | CF$_3$ | H | N(CH$_3$)Ph |
| 3-F-5-Br-4-OCH$_3$ | CF$_3$ | H | (D-50c)Cl |
| 3-Cl-5-Br-4-OCH$_3$ | CF$_3$ | H | CH$_2$CF$_3$ |
| 3,5-Br$_2$-4-OCH$_3$ | CF$_3$ | H | CH$_2$OCH$_2$CF$_3$ |
| 3,5-Cl$_2$-4-OEt | CF$_3$ | H | E-4a |
| 3,5-Br$_2$-4-OEt | CF$_3$ | H | CH$_2$C(O)NHCH$_2$CF$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$-4-OPr-n | CF$_3$ | H | CH$_2$(D-22a) |
| 3,5-Cl$_2$-4-OCHF$_2$ | CF$_3$ | H | CH$_2$CF$_3$ |
| 3,5-Cl$_2$-4-OCHF$_2$ | CF$_3$ | H | E-4a |
| 3,5-Cl$_2$-4-OCHF$_2$ | CF$_3$ | H | CH$_2$C(O)NHCH$_2$CF$_3$ |
| 3,5-Cl$_2$-4-OCHF$_2$ | CF$_3$ | H | CH$_2$(D-22a) |
| 3,5-Cl$_2$-4-OCHF$_2$ | CF$_3$ | H | CH$_2$(D-47a) |
| 3,5-Cl$_2$-4-OCHF$_2$ | CF$_3$ | H | (D-50c)Cl |
| 3,5-Br$_2$-4-OCHF$_2$ | CF$_3$ | H | CH$_2$CF$_3$ |
| 3,5-Br$_2$-4-OCHF$_2$ | CF$_3$ | H | E-4a |
| 3,5-Br$_2$-4-OCHF$_2$ | CF$_3$ | H | CH$_2$C(O)NHCH$_2$CF$_3$ |
| 3,5-Br$_2$-4-OCHF$_2$ | CF$_3$ | H | CH$_2$(D-22a) |
| 3,5-Br$_2$-4-OCHF$_2$ | CF$_3$ | H | CH$_2$(D-47a) |
| 3,5-Br$_2$-4-OCHF$_2$ | CF$_3$ | H | (D-50c)Cl |
| 3,5-F$_2$-4-OCF$_3$ | CF$_3$ | H | CH$_2$(D-47a) |
| 3,5-Cl$_2$-4-OCH$_2$CH=CH$_2$ | CF$_3$ | C(O)OCH$_3$ | CH$_2$(D-47a) |
| 3,5-Cl$_2$-4-OCH$_2$C≡CH | CF$_3$ | H | N(CH$_3$)Ph |
| 3,5-Cl$_2$-4-OC(O)OBu-t | CF$_3$ | H | (D-50c)Cl |
| 3,5-Cl$_2$-4-OSi(CH$_3$)$_3$ | CF$_3$ | H | CH$_2$CF$_3$ |
| 3,5-Cl$_2$-4-OSi(CH$_3$)$_2$Bu-t | CF$_3$ | H | CH$_2$OCH$_2$CF$_3$ |
| 2,4,6-(OCH$_3$)$_3$ | CF$_3$ | H | E-4a |
| 3,4,5-(OCH$_3$)$_3$ | CF$_3$ | H | CH$_2$C(O)NHCH$_2$CF$_3$ |
| 3,5-F$_2$-4-NO$_2$ | CF$_3$ | H | CH$_2$(D-22a) |
| 3,5-Cl$_2$-4-NO$_2$ | CF$_3$ | H | CH$_2$(D-47a) |
| 3,5-Cl$_2$-4-NH$_2$ | CF$_3$ | H | CH$_2$CF$_3$ |
| 3,5-Cl$_2$-4-NH$_2$ | CF$_3$ | H | CH$_2$OCH$_2$CF$_3$ |
| 3,5-Cl$_2$-4-NH$_2$ | CF$_3$ | H | E-4a |
| 3,5-Cl$_2$-4-NH$_2$ | CF$_3$ | H | CH$_2$C(O)NHCH$_2$CF$_3$ |
| 3,5-Cl$_2$-4-NH$_2$ | CF$_3$ | H | CH(CH$_3$)C(O)NHCH$_2$CF$_3$(D) |
| 3,5-Cl$_2$-4-NH$_2$ | CF$_3$ | H | CH$_2$(D-22a) |
| 3,5-Cl$_2$-4-NH$_2$ | CF$_3$ | H | CH$_2$(D-47a) |
| 3,5-Cl$_2$-4-NH$_2$ | CF$_3$ | C(O)OCH$_3$ | CH$_2$(D-47a) |
| 3,5-Cl$_2$-4-NH$_2$ | CF$_3$ | H | N(CH$_3$)Ph |
| 3,5-Cl$_2$-4-NH$_2$ | CF$_3$ | H | (D-50c)Cl |
| 3,5-Br$_2$-4-NH$_2$ | CF$_3$ | H | CH$_2$CF$_3$ |
| 3,5-Br$_2$-4-NH$_2$ | CF$_3$ | H | CH$_2$OCH$_2$CF$_3$ |
| 3,5-Br$_2$-4-NH$_2$ | CF$_3$ | H | E-4a |
| 3,5-Br$_2$-4-NH$_2$ | CF$_3$ | H | CH$_2$C(O)NHCH$_2$CF$_3$ |
| 3,5-Br$_2$-4-NH$_2$ | CF$_3$ | H | CH(CH$_3$)C(O)NHCH$_2$CF$_3$(D) |
| 3,5-Br$_2$-4-NH$_2$ | CF$_3$ | H | CH$_2$(D-22a) |
| 3,5-Br$_2$-4-NH$_2$ | CF$_3$ | H | CH$_2$(D-47a) |
| 3,5-Br$_2$-4-NH$_2$ | CF$_3$ | C(O)OCH$_3$ | CH$_2$(D-47a) |
| 3,5-Br$_2$-4-NH$_2$ | CF$_3$ | H | N(CH$_3$)Ph |
| 3,5-Br$_2$-4-NH$_2$ | CF$_3$ | H | (D-50c)Cl |
| 3,5-I$_2$-4-NH$_2$ | CF$_3$ | C(O)OCH$_3$ | CH$_2$(D-47a) |
| 3,5-Cl$_2$-4-N(CH$_3$)$_2$ | CF$_3$ | H | CH$_2$CF$_3$ |
| 3,5-Cl$_2$-4-N(CH$_3$)$_2$ | CF$_3$ | H | CH$_2$(D-47a) |
| 3,5-Cl$_2$-4-N(CH$_3$)$_2$ | CF$_3$ | H | N(CH$_3$)Ph |
| 3,5-Cl$_2$-4-NHC(O)OBu-t | CF$_3$ | H | CH$_2$CF$_3$ |
| 3,5-Cl$_2$-4-NHC(O)OBu-t | CF$_3$ | H | CH$_2$(D-47a) |
| 3,5-Cl$_2$-4-NHC(O)OBu-t | CF$_3$ | H | (D-50c)Cl |
| 3,5-F$_2$-4-CN | CF$_3$ | H | CH$_2$CF$_3$ |
| 3,5-Cl$_2$-4-CN | CF$_3$ | H | CH$_2$CF$_3$ |
| 3,5-Cl$_2$-4-CN | CF$_3$ | H | E-4a |
| 3,5-Cl$_2$-4-CN | CF$_3$ | H | CH$_2$C(O)NHCH$_2$CF$_3$ |
| 3,5-Cl$_2$-4-CN | CF$_3$ | H | CH$_2$(D-22a) |
| 3,5-Cl$_2$-4-CN | CF$_3$ | H | CH$_2$(D-47a) |
| 3,5-Cl$_2$-4-CN | CF$_3$ | H | (D-50c)Cl |
| 3,5-Br$_2$-4-CN | CF$_3$ | H | CH$_2$CF$_3$ |
| 3,5-Br$_2$-4-CN | CF$_3$ | H | E-4a |
| 3,5-Br$_2$-4-CN | CF$_3$ | H | CH$_2$C(O)NHCH$_2$CF$_3$ |
| 3,5-Br$_2$-4-CN | CF$_3$ | H | CH$_2$(D-22a) |
| 3,5-Br$_2$-4-CN | CF$_3$ | H | CH$_2$(D-47a) |
| 3,5-Br$_2$-4-CN | CF$_3$ | H | (D-50c)Cl |
| 2,3,5,6-F$_4$ | CF$_3$ | H | CH$_2$OCH$_2$CF$_3$ |
| 2,3,4,5,6-F$_5$ | CF$_3$ | H | E-4a |

TABLE 3

In the table, the number showing the substitution position of substituents $(X)_m$ and $(Y)_n$ corresponds to the position number indicated in the following structural formulae. The indication "-" means no-substitution.

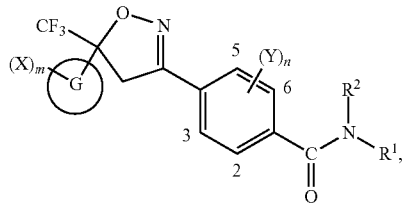

[2] - 1

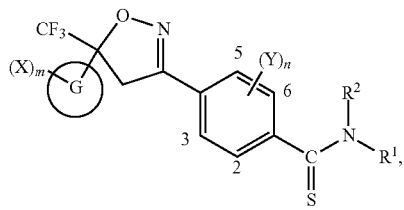

[2] - 2

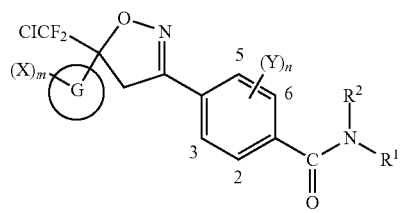

[2] - 3

または

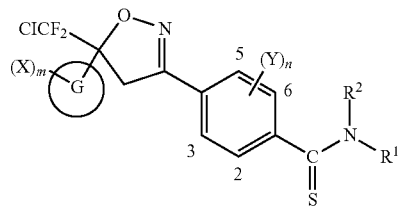

[2] - 4

In addition, substituent G in the formulae [2]-1 to [2]-4 is the structure shown by the following G-1 to G-22, respectively.

| G | $(X)_m$ | $(Y)_n$ | $R^2$ | $R^1$ |
|---|---|---|---|---|
| G-1 | 3-CF$_3$ | 2-Pr-i | H | CH$_2$CF$_3$ |
| G-1 | 3-CF$_3$ | 2-OEt | H | CH$_2$OCH$_2$CF$_3$ |
| G-1 | 3-CF$_3$ | 2-OPr-i | H | E-4a |
| G-1 | 3-CF$_3$ | 2-OSO$_2$CH$_3$ | H | CH$_2$C(O)NHCH$_2$CF$_3$ |
| G-1 | 3-CF$_3$ | 2-SEt | H | CH$_2$(D-22a) |
| G-1 | 3-CF$_3$ | 2-SPr-i | H | CH$_2$(D-47a) |
| G-1 | 3-CF$_3$ | 2-NHEt | C(O)OCH$_3$ | CH$_2$(D-47a) |
| G-1 | 3-CF$_3$ | 2-NHPr-i | H | N(CH$_3$)Ph |
| G-1 | 3-CF$_3$ | 2-N(CH$_3$)$_2$ | H | (D-50c)Cl |
| G-1 | 3-CF$_3$ | 2-NHC(O)CH$_3$ | H | CH$_2$CF$_3$ |
| G-1 | 3-CF$_2$CF$_3$ | 2-Pr-i | H | CH$_2$OCH$_2$CF$_3$ |
| G-1 | 3-CF$_2$CF$_3$ | 2-OEt | H | E-4a |
| G-1 | 3-CF$_2$CF$_3$ | 2-OPr-i | H | CH$_2$C(O)NHCH$_2$CF$_3$ |
| G-1 | 3-CF$_2$CF$_3$ | 2-OSO$_2$CH$_3$ | H | CH$_2$(D-22a) |
| G-1 | 3-CF$_2$CF$_3$ | 2-SEt | H | CH$_2$(D-47a) |
| G-1 | 3-CF$_2$CF$_3$ | 2-SPr-i | C(O)OCH$_3$ | CH$_2$(D-47a) |
| G-1 | 3-CF$_2$CF$_3$ | 2-NHEt | H | N(CH$_3$)Ph |
| G-1 | 3-CF$_2$CF$_3$ | 2-NHPr-i | H | (D-50c)Cl |
| G-1 | 3-CF$_2$CF$_3$ | 2-N(CH$_3$)$_2$ | H | CH$_2$CF$_3$ |

TABLE 3-continued

| | | | | |
|---|---|---|---|---|
| G-1 | 3-CF$_2$CF$_3$ | 2-NHC(O)CH$_3$ | H | CH$_2$OCH$_2$CF$_3$ |
| G-1 | 3-SF$_5$ | 2-Pr-i | H | E-4a |
| G-1 | 3-SF$_5$ | 2-OEt | H | CH$_2$C(O)NHCH$_2$CF$_3$ |
| G-1 | 3-SF$_5$ | 2-OPr-i | H | CH$_2$(D-22a) |
| G-1 | 3-SF$_5$ | 2-OSO$_2$CH$_3$ | H | CH$_2$(D-47a) |
| G-1 | 3-SF$_5$ | 2-SEt | C(O)OCH$_3$ | CH$_2$(D-47a) |
| G-1 | 3-SF$_5$ | 2-SPr-i | H | N(CH$_3$)Ph |
| G-1 | 3-SF$_5$ | 2-NHEt | H | (D-50c)Cl |
| G-1 | 3-SF$_5$ | 2-NHPr-i | H | CH$_2$CF$_3$ |
| G-1 | 3-SF$_5$ | 2-N(CH$_3$)$_2$ | H | CH$_2$OCH$_2$CF$_3$ |
| G-1 | 3-SF$_5$ | 2-NHC(O)CH$_3$ | H | E-4a |
| G-1 | 3,5-Cl$_2$ | 3-F | H | CH$_2$C(O)NHCH$_2$CF$_3$ |
| G-1 | 3,5-Cl$_2$ | 3-Cl | H | CH$_2$(D-22a) |
| G-1 | 3,5-Cl$_2$ | 3-Br | H | CH$_2$(D-47a) |
| G-1 | 3,5-Cl$_2$ | 3-CH$_3$ | C(O)OCH$_3$ | CH$_2$(D-47a) |
| G-1 | 3,5-Cl$_2$ | 3-Et | H | N(CH$_3$)Ph |
| G-1 | 3,5-Cl$_2$ | 2-Pr-n | H | (D-50c)Cl |
| G-1 | 3,5-Cl$_2$ | 2-Pr-i | H | CH$_2$CF$_3$ |
| G-1 | 3,5-Cl$_2$ | 2-Pr-i | C(O)CH$_3$ | CH$_2$CF$_3$ |
| G-1 | 3,5-Cl$_2$ | 2-Pr-i | H | CH$_2$OCH$_2$CF$_3$ |
| G-1 | 3,5-Cl$_2$ | 2-Pr-i | H | E-4a |
| G-1 | 3,5-Cl$_2$ | 2-Pr-i | H | CH$_2$C(O)NHCH$_2$CF$_3$ |
| G-1 | 3,5-Cl$_2$ | 2-Pr-i | H | CH(CH$_3$)C(O)NHCH$_2$CF$_3$(D) |
| G-1 | 3,5-Cl$_2$ | 2-Pr-i | H | CH(CH$_3$)Ph(R) |
| G-1 | 3,5-Cl$_2$ | 2-Pr-i | H | CH$_2$(D-22a) |
| G-1 | 3,5-Cl$_2$ | 2-Pr-i | H | CH$_2$(D-47a) |
| G-1 | 3,5-Cl$_2$ | 2-Pr-i | CH$_2$CN | CH$_2$(D-47a) |
| G-1 | 3,5-Cl$_2$ | 2-Pr-i | C(O)Et | CH$_2$(D-47a) |
| G-1 | 3,5-Cl$_2$ | 2-Pr-i | C(O)OCH$_3$ | CH$_2$(D-47a) |
| G-1 | 3,5-Cl$_2$ | 2-Pr-i | H | N(CH$_3$)Ph |
| G-1 | 3,5-Cl$_2$ | 2-Pr-i | H | (D-50c)Cl |
| G-1 | 3,5-Cl$_2$ | 2-Pr-i | H | D-52a |
| G-1 | 3,5-Cl$_2$ | 2-Bu-n | H | CH$_2$CF$_3$ |
| G-1 | 3,5-Cl$_2$ | 2-Bu-s | H | CH$_2$OCH$_2$CF$_3$ |
| G-1 | 3,5-Cl$_2$ | 2-Bu-t | H | E-4a |
| G-1 | 3,5-Cl$_2$ | 2-CF$_2$CF$_3$ | H | CH$_2$C(O)NHCH$_2$CF$_3$ |
| G-1 | 3,5-Cl$_2$ | 2-CH$_2$OH | H | CH$_2$(D-22a) |
| G-1 | 3,5-Cl$_2$ | 2-CH$_2$OCH$_3$ | H | CH$_2$CF$_3$ |
| G-1 | 3,5-Cl$_2$ | 2-CH$_2$OCH$_3$ | H | CH$_2$OCH$_2$CF$_3$ |
| G-1 | 3,5-Cl$_2$ | 2-CH$_2$OCH$_3$ | H | E-4a |
| G-1 | 3,5-Cl$_2$ | 2-CH$_2$OCH$_3$ | H | CH$_2$C(O)NHCH$_2$CF$_3$ |
| G-1 | 3,5-Cl$_2$ | 2-CH$_2$OCH$_3$ | H | CH(CH$_3$)C(O)NHCH$_2$CF$_3$(D) |
| G-1 | 3,5-Cl$_2$ | 2-CH$_2$OCH$_3$ | H | CH$_2$(D-22a) |
| G-1 | 3,5-Cl$_2$ | 2-CH$_2$OCH$_3$ | H | CH$_2$(D-47a) |
| G-1 | 3,5-Cl$_2$ | 2-CH$_2$OCH$_3$ | C(O)OCH$_3$ | CH$_2$(D-47a) |
| G-1 | 3,5-Cl$_2$ | 2-CH$_2$OCH$_3$ | H | N(CH$_3$)Ph |
| G-1 | 3,5-Cl$_2$ | 2-CH$_2$OCH$_3$ | H | (D-50c)Cl |
| G-1 | 3,5-Cl$_2$ | 2-CH$_2$OEt | H | CH$_2$(D-47a) |
| G-1 | 3,5-Cl$_2$ | 2-CH$_2$OPr-n | C(O)OCH$_3$ | CH$_2$(D-47a) |
| G-1 | 3,5-Cl$_2$ | 2-CH$_2$OPr-i | H | N(CH$_3$)Ph |
| G-1 | 3,5-Cl$_2$ | 2-CH$_2$OPr-c | H | (D-50c)Cl |
| G-1 | 3,5-Cl$_2$ | 2-CH$_2$OCH$_2$CF$_3$ | H | CH$_2$CF$_3$ |
| G-1 | 3,5-Cl$_2$ | 2-CH$_2$CH$_2$OCH$_3$ | H | CH$_2$OCH$_2$CF$_3$ |
| G-1 | 3,5-Cl$_2$ | 2-CH$_2$SCH$_3$ | H | CH$_2$CF$_3$ |
| G-1 | 3,5-Cl$_2$ | 2-CH$_2$SCH$_3$ | H | CH$_2$OCH$_2$CF$_3$ |
| G-1 | 3,5-Cl$_2$ | 2-CH$_2$SCH$_3$ | H | E-4a |
| G-1 | 3,5-Cl$_2$ | 2-CH$_2$SCH$_3$ | H | CH$_2$C(O)NHCH$_2$CF$_3$ |
| G-1 | 3,5-Cl$_2$ | 2-CH$_2$SCH$_3$ | H | CH(CH$_3$)C(O)NHCH$_2$CF$_3$(D) |
| G-1 | 3,5-Cl$_2$ | 2-CH$_2$SCH$_3$ | H | CH$_2$(D-22a) |
| G-1 | 3,5-Cl$_2$ | 2-CH$_2$SCH$_3$ | H | CH$_2$(D-47a) |
| G-1 | 3,5-Cl$_2$ | 2-CH$_2$SCH$_3$ | C(O)OCH$_3$ | CH$_2$(D-47a) |
| G-1 | 3,5-Cl$_2$ | 2-CH$_2$SCH$_3$ | H | N(CH$_3$)Ph |
| G-1 | 3,5-Cl$_2$ | 2-CH$_2$SCH$_3$ | H | (D-50c)Cl |
| G-1 | 3,5-Cl$_2$ | 2-CH$_2$S(O)CH$_3$ | H | E-4a |
| G-1 | 3,5-Cl$_2$ | 2-CH$_2$SO$_2$CH$_3$ | H | CH$_2$C(O)NHCH$_2$CF$_3$ |
| G-1 | 3,5-Cl$_2$ | 2-CH$_2$SCF$_3$ | H | CH$_2$CF$_3$ |
| G-1 | 3,5-Cl$_2$ | 2-CH$_2$SCF$_3$ | H | CH$_2$OCH$_2$CF$_3$ |
| G-1 | 3,5-Cl$_2$ | 2-CH$_2$SCF$_3$ | H | E-4a |
| G-1 | 3,5-Cl$_2$ | 2-CH$_2$SCF$_3$ | H | CH$_2$C(O)NHCH$_2$CF$_3$ |
| G-1 | 3,5-Cl$_2$ | 2-CH$_2$SCF$_3$ | H | CH(CH$_3$)C(O)NHCH$_2$CF$_3$(D) |
| G-1 | 3,5-Cl$_2$ | 2-CH$_2$SCF$_3$ | H | CH$_2$(D-22a) |
| G-1 | 3,5-Cl$_2$ | 2-CH$_2$SCF$_3$ | H | CH$_2$(D-47a) |
| G-1 | 3,5-Cl$_2$ | 2-CH$_2$SCF$_3$ | C(O)OCH$_3$ | CH$_2$(D-47a) |
| G-1 | 3,5-Cl$_2$ | 2-CH$_2$SCF$_3$ | H | N(CH$_3$)Ph |
| G-1 | 3,5-Cl$_2$ | 2-CH$_2$SCF$_3$ | H | (D-50c)Cl |
| G-1 | 3,5-Cl$_2$ | 2-CH$_2$S(O)CF$_3$ | H | CH$_2$(D-22a) |
| G-1 | 3,5-Cl$_2$ | 2-CH$_2$SO$_2$CF$_3$ | H | CH$_2$(D-47a) |
| G-1 | 3,5-Cl$_2$ | 2-CH$_2$Ph | C(O)OCH$_3$ | CH$_2$(D-47a) |
| G-1 | 3,5-Cl$_2$ | 2-CH$_2$(D-14a) | H | N(CH$_3$)Ph |
| G-1 | 3,5-Cl$_2$ | 2-CH$_2$(D-24a) | H | (D-50c)Cl |

TABLE 3-continued

| | | | | |
|---|---|---|---|---|
| G-1 | 3,5-Cl$_2$ | 2-CH$_2$(D-38a) | H | CH$_2$CF$_3$ |
| G-1 | 3,5-Cl$_2$ | 3-OCH$_3$ | H | CH$_2$OCH$_2$CF$_3$ |
| G-1 | 3,5-Cl$_2$ | 2-OEt | H | CH$_2$CF$_3$ |
| G-1 | 3,5-Cl$_2$ | 2-OEt | C(O)CH$_3$ | CH$_2$CF$_3$ |
| G-1 | 3,5-Cl$_2$ | 2-OEt | H | CH$_2$OCH$_2$CF$_3$ |
| G-1 | 3,5-Cl$_2$ | 2-OEt | H | E-4a |
| G-1 | 3,5-Cl$_2$ | 2-OEt | H | CH$_2$C(O)NHCH$_2$CF$_3$ |
| G-1 | 3,5-Cl$_2$ | 2-OEt | H | CH(CH$_3$)C(O)NHCH$_2$CF$_3$(D) |
| G-1 | 3,5-Cl$_2$ | 2-OEt | H | CH(CH$_3$)Ph(R) |
| G-1 | 3,5-Cl$_2$ | 2-OEt | H | CH$_2$(D-22a) |
| G-1 | 3,5-Cl$_2$ | 2-OEt | H | CH$_2$(D-47a) |
| G-1 | 3,5-Cl$_2$ | 2-OEt | CH$_2$CN | CH$_2$(D-47a) |
| G-1 | 3,5-Cl$_2$ | 2-OEt | C(O)Et | CH$_2$(D-47a) |
| G-1 | 3,5-Cl$_2$ | 2-OEt | C(O)OCH$_3$ | CH$_2$(D-47a) |
| G-1 | 3,5-Cl$_2$ | 2-OEt | H | N(CH$_3$)Ph |
| G-1 | 3,5-Cl$_2$ | 2-OEt | H | (D-50c)Cl |
| G-1 | 3,5-Cl$_2$ | 2-OEt | H | D-52a |
| G-1 | 3,5-Cl$_2$ | 2-OPr-n | H | E-4a |
| G-1 | 3,5-Cl$_2$ | 2-OPr-i | H | CH$_2$CF$_3$ |
| G-1 | 3,5-Cl$_2$ | 2-OPr-i | C(O)CH$_3$ | CH$_2$CF$_3$ |
| G-1 | 3,5-Cl$_2$ | 2-OPr-i | H | CH$_2$OCH$_2$CF$_3$ |
| G-1 | 3,5-Cl$_2$ | 2-OPr-i | H | E-4a |
| G-1 | 3,5-Cl$_2$ | 2-OPr-i | H | CH$_2$C(O)NHCH$_2$CF$_3$ |
| G-1 | 3,5-Cl$_2$ | 2-OPr-i | H | CH(CH$_3$)C(O)NHCH$_2$CF$_3$(D) |
| G-1 | 3,5-Cl$_2$ | 2-OPr-i | H | CH(CH$_3$)Ph(R) |
| G-1 | 3,5-Cl$_2$ | 2-OPr-i | H | CH$_2$(D-22a) |
| G-1 | 3,5-Cl$_2$ | 2-OPr-i | H | CH$_2$(D-47a) |
| G-1 | 3,5-Cl$_2$ | 2-OPr-i | CH$_2$CN | CH$_2$(D-47a) |
| G-1 | 3,5-Cl$_2$ | 2-OPr-i | C(O)Et | CH$_2$(D-47a) |
| G-1 | 3,5-Cl$_2$ | 2-OPr-i | C(O)OCH$_3$ | CH$_2$(D-47a) |
| G-1 | 3,5-Cl$_2$ | 2-OPr-i | H | N(CH$_3$)Ph |
| G-1 | 3,5-Cl$_2$ | 2-OPr-i | H | (D-50c)Cl |
| G-1 | 3,5-Cl$_2$ | 2-OPr-i | H | D-52a |
| G-1 | 3,5-Cl$_2$ | 2-OBu-n | H | CH$_2$C(O)NHCH$_2$CF$_3$ |
| G-1 | 3,5-Cl$_2$ | 2-OPen-n | H | CH$_2$(D-22a) |
| G-1 | 3,5-Cl$_2$ | 2-OHex-n | H | CH$_2$(D-47a) |
| G-1 | 3,5-Cl$_2$ | 2-OCF$_2$Br | C(O)OCH$_3$ | CH$_2$(D-47a) |
| G-1 | 3,5-Cl$_2$ | 2-OCF$_2$CHF$_2$ | H | N(CH$_3$)Ph |
| G-1 | 3,5-Cl$_2$ | 2-OCF$_2$CHFCl | H | (D-50c)Cl |
| G-1 | 3,5-Cl$_2$ | 2-OCF$_2$CHFCF$_3$ | H | CH$_2$CF$_3$ |
| G-1 | 3,5-Cl$_2$ | 2-OCF$_2$CHFOCF$_3$ | H | CH$_2$OCH$_2$CF$_3$ |
| G-1 | 3,5-Cl$_2$ | 2-OSO$_2$CH$_3$ | H | CH$_2$CF$_3$ |
| G-1 | 3,5-Cl$_2$ | 2-OSO$_2$CH$_3$ | C(O)CH$_3$ | CH$_2$CF$_3$ |
| G-1 | 3,5-Cl$_2$ | 2-OSO$_2$CH$_3$ | H | CH$_2$OCH$_2$CF$_3$ |
| G-1 | 3,5-Cl$_2$ | 2-OSO$_2$CH$_3$ | H | E-4a |
| G-1 | 3,5-Cl$_2$ | 2-OSO$_2$CH$_3$ | H | CH$_2$C(O)NHCH$_2$CF$_3$ |
| G-1 | 3,5-Cl$_2$ | 2-OSO$_2$CH$_3$ | H | CH(CH$_3$)C(O)NHCH$_2$CF$_3$(D) |
| G-1 | 3,5-Cl$_2$ | 2-OSO$_2$CH$_3$ | H | CH(CH$_3$)Ph(R) |
| G-1 | 3,5-Cl$_2$ | 2-OSO$_2$CH$_3$ | H | CH$_2$(D-22a) |
| G-1 | 3,5-Cl$_2$ | 2-OSO$_2$CH$_3$ | H | CH$_2$(D-47a) |
| G-1 | 3,5-Cl$_2$ | 2-OSO$_2$CH$_3$ | CH$_2$CN | CH$_2$(D-47a) |
| G-1 | 3,5-Cl$_2$ | 2-OSO$_2$CH$_3$ | C(O)Et | CH$_2$(D-47a) |
| G-1 | 3,5-Cl$_2$ | 2-OSO$_2$CH$_3$ | C(O)OCH$_3$ | CH$_2$(D-47a) |
| G-1 | 3,5-Cl$_2$ | 2-OSO$_2$CH$_3$ | H | N(CH$_3$)Ph |
| G-1 | 3,5-Cl$_2$ | 2-OSO$_2$CH$_3$ | H | (D-50c)Cl |
| G-1 | 3,5-Cl$_2$ | 2-OSO$_2$CH$_3$ | H | D-52a |
| G-1 | 3,5-Cl$_2$ | 2-OSO$_2$Et | H | E-4a |
| G-1 | 3,5-Cl$_2$ | 2-OSO$_2$Pr-i | H | CH$_2$C(O)NHCH$_2$CF$_3$ |
| G-1 | 3,5-Cl$_2$ | 2-OSO$_2$CF$_3$ | H | CH$_2$(D-22a) |
| G-1 | 3,5-Cl$_2$ | 2-OPh | H | CH$_2$(D-47a) |
| G-1 | 3,5-Cl$_2$ | 2-S(O)CH$_3$ | C(O)OCH$_3$ | CH$_2$(D-47a) |
| G-1 | 3,5-Cl$_2$ | 2-SO$_2$CH$_3$ | H | N(CH$_3$)Ph |
| G-1 | 3,5-Cl$_2$ | 2-SEt | H | CH$_2$CF$_3$ |
| G-1 | 3,5-Cl$_2$ | 2-SEt | C(O)CH$_3$ | CH$_2$CF$_3$ |
| G-1 | 3,5-Cl$_2$ | 2-SEt | H | CH$_2$OCH$_2$CF$_3$ |
| G-1 | 3,5-Cl$_2$ | 2-SEt | H | E-4a |
| G-1 | 3,5-Cl$_2$ | 2-SEt | H | CH$_2$C(O)NHCH$_2$CF$_3$ |
| G-1 | 3,5-Cl$_2$ | 2-SEt | H | CH(CH$_3$)C(O)NHCH$_2$CF$_3$(D) |
| G-1 | 3,5-Cl$_2$ | 2-SEt | H | CH(CH$_3$)Ph(R) |
| G-1 | 3,5-Cl$_2$ | 2-SEt | H | CH$_2$(D-22a) |
| G-1 | 3,5-Cl$_2$ | 2-SEt | H | CH$_2$(D-47a) |
| G-1 | 3,5-Cl$_2$ | 2-SEt | CH$_2$CN | CH$_2$(D-47a) |
| G-1 | 3,5-Cl$_2$ | 2-SEt | C(O)Et | CH$_2$(D-47a) |
| G-1 | 3,5-Cl$_2$ | 2-SEt | C(O)OCH$_3$ | CH$_2$(D-47a) |
| G-1 | 3,5-Cl$_2$ | 2-SEt | H | N(CH$_3$)Ph |
| G-1 | 3,5-Cl$_2$ | 2-SEt | H | (D-50c)Cl |
| G-1 | 3,5-Cl$_2$ | 2-SEt | H | D-52a |
| G-1 | 3,5-Cl$_2$ | 2-S(O)Et | H | (D-50c)Cl |
| G-1 | 3,5-Cl$_2$ | 2-SO$_2$Et | H | CH$_2$CF$_3$ |
| G-1 | 3,5-Cl$_2$ | 2-SPr-n | H | CH$_2$OCH$_2$CF$_3$ |

TABLE 3-continued

| | | | | |
|---|---|---|---|---|
| G-1 | 3,5-Cl$_2$ | 2-S(O)Pr-n | H | E-4a |
| G-1 | 3,5-Cl$_2$ | 2-SO$_2$Pr-n | H | CH$_2$C(O)NHCH$_2$CF$_3$ |
| G-1 | 3,5-Cl$_2$ | 2-SPr-i | H | CH$_2$CF$_3$ |
| G-1 | 3,5-Cl$_2$ | 2-SPr-i | C(O)CH$_3$ | CH$_2$CF$_3$ |
| G-1 | 3,5-Cl$_2$ | 2-SPr-i | H | CH$_2$OCH$_2$CF$_3$ |
| G-1 | 3,5-Cl$_2$ | 2-SPr-i | H | E-4a |
| G-1 | 3,5-Cl$_2$ | 2-SPr-i | H | CH$_2$C(O)NHCH$_2$CF$_3$ |
| G-1 | 3,5-Cl$_2$ | 2-SPr-i | H | CH(CH$_3$)C(O)NHCH$_2$CF$_3$(D) |
| G-1 | 3,5-Cl$_2$ | 2-SPr-i | H | CH(CH$_3$)Ph(R) |
| G-1 | 3,5-Cl$_2$ | 2-SPr-i | H | CH$_2$(D-22a) |
| G-1 | 3,5-Cl$_2$ | 2-SPr-i | H | CH$_2$(D-47a) |
| G-1 | 3,5-Cl$_2$ | 2-SPr-i | CH$_2$CN | CH$_2$(D-47a) |
| G-1 | 3,5-Cl$_2$ | 2-SPr-i | C(O)Et | CH$_2$(D-47a) |
| G-1 | 3,5-Cl$_2$ | 2-SPr-i | C(O)OCH$_3$ | CH$_2$(D-47a) |
| G-1 | 3,5-Cl$_2$ | 2-SPr-i | H | N(CH$_3$)Ph |
| G-1 | 3,5-Cl$_2$ | 2-SPr-i | H | (D-50c)Cl |
| G-1 | 3,5-Cl$_2$ | 2-SPr-i | H | D-52a |
| G-1 | 3,5-Cl$_2$ | 2-S(O)Pr-i | H | CH$_2$(D-22a) |
| G-1 | 3,5-Cl$_2$ | 2-SO$_2$Pr-i | H | CH$_2$(D-47a) |
| G-1 | 3,5-Cl$_2$ | 2-S(O)CHF$_2$ | C(O)OCH$_3$ | CH$_2$(D-47a) |
| G-1 | 3,5-Cl$_2$ | 2-SO$_2$CHF$_2$ | H | N(CH$_3$)Ph |
| G-1 | 3,5-Cl$_2$ | 2-S(O)CF$_3$ | H | (D-50c)Cl |
| G-1 | 3,5-Cl$_2$ | 2-SO$_2$CF$_3$ | H | CH$_2$CF$_3$ |
| G-1 | 3,5-Cl$_2$ | 2-SCF$_2$Br | H | CH$_2$OCH$_2$CF$_3$ |
| G-1 | 3,5-Cl$_2$ | 2-S(O)CF$_2$Br | H | E-4a |
| G-1 | 3,5-Cl$_2$ | 2-SO$_2$CF$_2$Br | H | CH$_2$C(O)NHCH$_2$CF$_3$ |
| G-1 | 3,5-Cl$_2$ | 2-SCF$_2$CHFCl | H | CH$_2$(D-22a) |
| G-1 | 3,5-Cl$_2$ | 2-S(O)CF$_2$CHFCl | H | CH$_2$(D-47a) |
| G-1 | 3,5-Cl$_2$ | 2-SO$_2$CF$_2$CHFCl | C(O)OCH$_3$ | CH$_2$(D-47a) |
| G-1 | 3,5-Cl$_2$ | 2-SPh | H | N(CH$_3$)Ph |
| G-1 | 3,5-Cl$_2$ | 2-S(O)Ph | H | (D-50c)Cl |
| G-1 | 3,5-Cl$_2$ | 2-SO$_2$Ph | H | CH$_2$CF$_3$ |
| G-1 | 3,5-Cl$_2$ | 2-NHEt | H | CH$_2$CF$_3$ |
| G-1 | 3,5-Cl$_2$ | 2-NHEt | C(O)CH$_3$ | CH$_2$CF$_3$ |
| G-1 | 3,5-Cl$_2$ | 2-NHEt | H | CH$_2$OCH$_2$CF$_3$ |
| G-1 | 3,5-Cl$_2$ | 2-NHEt | H | E-4a |
| G-1 | 3,5-Cl$_2$ | 2-NHEt | H | CH$_2$C(O)NHCH$_2$CF$_3$ |
| G-1 | 3,5-Cl$_2$ | 2-NHEt | H | CH(CH$_3$)C(O)NHCH$_2$CF$_3$(D) |
| G-1 | 3,5-Cl$_2$ | 2-NHEt | H | CH(CH$_3$)Ph(R) |
| G-1 | 3,5-Cl$_2$ | 2-NHEt | H | CH$_2$(D-22a) |
| G-1 | 3,5-Cl$_2$ | 2-NHEt | H | CH$_2$(D-47a) |
| G-1 | 3,5-Cl$_2$ | 2-NHEt | CH$_2$CN | CH$_2$(D-47a) |
| G-1 | 3,5-Cl$_2$ | 2-NHEt | C(O)Et | CH$_2$(D-47a) |
| G-1 | 3,5-Cl$_2$ | 2-NHEt | C(O)OCH$_3$ | CH$_2$(D-47a) |
| G-1 | 3,5-Cl$_2$ | 2-NHEt | H | N(CH$_3$)Ph |
| G-1 | 3,5-Cl$_2$ | 2-NHEt | H | (D-50c)Cl |
| G-1 | 3,5-Cl$_2$ | 2-NHEt | H | D-52a |
| G-1 | 3,5-Cl$_2$ | 2-NHPr-n | H | CH$_2$CF$_3$ |
| G-1 | 3,5-Cl$_2$ | 2-NHPr-n | H | CH$_2$OCH$_2$CF$_3$ |
| G-1 | 3,5-Cl$_2$ | 2-NHPr-n | H | E-4a |
| G-1 | 3,5-Cl$_2$ | 2-NHPr-n | H | CH$_2$C(O)NHCH$_2$CF$_3$ |
| G-1 | 3,5-Cl$_2$ | 2-NHPr-n | H | CH(CH$_3$)C(O)NHCH$_2$CF$_3$(D) |
| G-1 | 3,5-Cl$_2$ | 2-NHPr-n | H | CH$_2$(D-22a) |
| G-1 | 3,5-Cl$_2$ | 2-NHPr-n | H | CH$_2$(D-47a) |
| G-1 | 3,5-Cl$_2$ | 2-NHPr-n | C(O)OCH$_3$ | CH$_2$(D-47a) |
| G-1 | 3,5-Cl$_2$ | 2-NHPr-n | H | N(CH$_3$)Ph |
| G-1 | 3,5-Cl$_2$ | 2-NHPr-n | H | (D-50c)Cl |
| G-1 | 3,5-Cl$_2$ | 2-NHPr-i | H | CH$_2$CF$_3$ |
| G-1 | 3,5-Cl$_2$ | 2-NHPr-i | C(O)CH$_3$ | CH$_2$CF$_3$ |
| G-1 | 3,5-Cl$_2$ | 2-NHPr-i | H | CH$_2$OCH$_2$CF$_3$ |
| G-1 | 3,5-Cl$_2$ | 2-NHPr-i | H | E-4a |
| G-1 | 3,5-Cl$_2$ | 2-NHPr-i | H | CH$_2$C(O)NHCH$_2$CF$_3$ |
| G-1 | 3,5-Cl$_2$ | 2-NHPr-i | H | CH(CH$_3$)C(O)NHCH$_2$CF$_3$(D) |
| G-1 | 3,5-Cl$_2$ | 2-NHPr-i | H | CH(CH$_3$)Ph(R) |
| G-1 | 3,5-Cl$_2$ | 2-NHPr-i | H | CH$_2$(D-22a) |
| G-1 | 3,5-Cl$_2$ | 2-NHPr-i | H | CH$_2$(D-47a) |
| G-1 | 3,5-Cl$_2$ | 2-NHPr-i | CH$_2$CN | CH$_2$(D-47a) |
| G-1 | 3,5-Cl$_2$ | 2-NHPr-i | C(O)Et | CH$_2$(D-47a) |
| G-1 | 3,5-Cl$_2$ | 2-NHPr-i | C(O)OCH$_3$ | CH$_2$(D-47a) |
| G-1 | 3,5-Cl$_2$ | 2-NHPr-i | H | N(CH$_3$)Ph |
| G-1 | 3,5-Cl$_2$ | 2-NHPr-i | H | (D-50c)Cl |
| G-1 | 3,5-Cl$_2$ | 2-NHPr-i | H | D-52a |
| G-1 | 3,5-Cl$_2$ | 2-N(CH$_3$)$_2$ | H | CH$_2$CF$_3$ |
| G-1 | 3,5-Cl$_2$ | 2-N(CH$_3$)$_2$ | H | CH$_2$OCH$_2$CF$_3$ |
| G-1 | 3,5-Cl$_2$ | 2-N(CH$_3$)$_2$ | H | E-4a |
| G-1 | 3,5-Cl$_2$ | 2-N(CH$_3$)$_2$ | H | CH$_2$C(O)NHCH$_2$CF$_3$ |
| G-1 | 3,5-Cl$_2$ | 2-N(CH$_3$)$_2$ | H | CH(CH$_3$)C(O)NHCH$_2$CF$_3$(D) |
| G-1 | 3,5-Cl$_2$ | 2-N(CH$_3$)$_2$ | H | CH$_2$(D-22a) |
| G-1 | 3,5-Cl$_2$ | 2-N(CH$_3$)$_2$ | H | CH$_2$(D-47a) |
| G-1 | 3,5-Cl$_2$ | 2-N(CH$_3$)$_2$ | C(O)OCH$_3$ | CH$_2$(D-47a) |

TABLE 3-continued

| | | | | |
|---|---|---|---|---|
| G-1 | 3,5-Cl$_2$ | 2-N(CH$_3$)$_2$ | H | N(CH$_3$)Ph |
| G-1 | 3,5-Cl$_2$ | 2-N(CH$_3$)$_2$ | H | (D-50c)Cl |
| G-1 | 3,5-Cl$_2$ | 2-N(CH$_3$)Et | H | CH$_2$OCH$_2$CF$_3$ |
| G-1 | 3,5-Cl$_2$ | 2-N(Et)$_2$ | H | E-4a |
| G-1 | 3,5-Cl$_2$ | 2-NHCHO | H | CH$_2$CF$_3$ |
| G-1 | 3,5-Cl$_2$ | 2-NHCHO | H | CH$_2$OCH$_2$CF$_3$ |
| G-1 | 3,5-Cl$_2$ | 2-NHCHO | H | E-4a |
| G-1 | 3,5-Cl$_2$ | 2-NHCHO | H | CH$_2$C(O)NHCH$_2$CF$_3$ |
| G-1 | 3,5-Cl$_2$ | 2-NHCHO | H | CH(CH$_3$)C(O)NHCH$_2$CF$_3$(D) |
| G-1 | 3,5-Cl$_2$ | 2-NHCHO | H | CH$_2$(D-22a) |
| G-1 | 3,5-Cl$_2$ | 2-NHCHO | H | CH$_2$(D-47a) |
| G-1 | 3,5-Cl$_2$ | 2-NHCHO | C(O)OCH$_3$ | CH$_2$(D-47a) |
| G-1 | 3,5-Cl$_2$ | 2-NHCHO | H | N(CH$_3$)Ph |
| G-1 | 3,5-Cl$_2$ | 2-NHCHO | H | (D-50c)Cl |
| G-1 | 3,5-Cl$_2$ | 2-NHC(O)CH$_3$ | H | CH$_2$CF$_3$ |
| G-1 | 3,5-Cl$_2$ | 2-NHC(O)CH$_3$ | C(O)CH$_3$ | CH$_2$CF$_3$ |
| G-1 | 3,5-Cl$_2$ | 2-NHC(O)CH$_3$ | H | CH$_2$OCH$_2$CF$_3$ |
| G-1 | 3,5-Cl$_2$ | 2-NHC(O)CH$_3$ | H | E-4a |
| G-1 | 3,5-Cl$_2$ | 2-NHC(O)CH$_3$ | H | CH$_2$C(O)NHCH$_2$CF$_3$ |
| G-1 | 3,5-Cl$_2$ | 2-NHC(O)CH$_3$ | H | CH(CH$_3$)C(O)NHCH$_2$CF$_3$(D) |
| G-1 | 3,5-Cl$_2$ | 2-NHC(O)CH$_3$ | H | CH(CH$_3$)Ph(R) |
| G-1 | 3,5-Cl$_2$ | 2-NHC(O)CH$_3$ | H | CH$_2$(D-22a) |
| G-1 | 3,5-Cl$_2$ | 2-NHC(O)CH$_3$ | H | CH$_2$(D-47a) |
| G-1 | 3,5-Cl$_2$ | 2-NHC(O)CH$_3$ | CH$_2$CN | CH$_2$(D-47a) |
| G-1 | 3,5-Cl$_2$ | 2-NHC(O)CH$_3$ | C(O)Et | CH$_2$(D-47a) |
| G-1 | 3,5-Cl$_2$ | 2-NHC(O)CH$_3$ | C(O)OCH$_3$ | CH$_2$(D-47a) |
| G-1 | 3,5-Cl$_2$ | 2-NHC(O)CH$_3$ | H | N(CH$_3$)Ph |
| G-1 | 3,5-Cl$_2$ | 2-NHC(O)CH$_3$ | H | (D-50c)Cl |
| G-1 | 3,5-Cl$_2$ | 2-NHC(O)CH$_3$ | H | D-52a |
| G-1 | 3,5-Cl$_2$ | 2-NHC(O)Et | H | CH$_2$C(O)NHCH$_2$CF$_3$ |
| G-1 | 3,5-Cl$_2$ | 2-NHC(O)Pr-n | H | CH$_2$(D-22a) |
| G-1 | 3,5-Cl$_2$ | 2-NHC(O)Pr-i | H | CH$_2$(D-47a) |
| G-1 | 3,5-Cl$_2$ | 2-NHC(O)Pr-c | C(O)OCH$_3$ | CH$_2$(D-47a) |
| G-1 | 3,5-Cl$_2$ | 2-NHC(O)Bu-t | H | N(CH$_3$)Ph |
| G-1 | 3,5-Cl$_2$ | 2-NHC(O)CF$_3$ | H | CH$_2$CF$_3$ |
| G-1 | 3,5-Cl$_2$ | 2-NHC(O)CF$_3$ | H | CH$_2$OCH$_2$CF$_3$ |
| G-1 | 3,5-Cl$_2$ | 2-NHC(O)CF$_3$ | H | E-4a |
| G-1 | 3,5-Cl$_2$ | 2-NHC(O)CF$_3$ | H | CH$_2$C(O)NHCH$_2$CF$_3$ |
| G-1 | 3,5-Cl$_2$ | 2-NHC(O)CF$_3$ | H | CH(CH$_3$)C(O)NHCH$_2$CF$_3$(D) |
| G-1 | 3,5-Cl$_2$ | 2-NHC(O)CF$_3$ | H | CH$_2$(D-22a) |
| G-1 | 3,5-Cl$_2$ | 2-NHC(O)CF$_3$ | H | CH$_2$(D-47a) |
| G-1 | 3,5-Cl$_2$ | 2-NHC(O)CF$_3$ | C(O)OCH$_3$ | CH$_2$(D-47a) |
| G-1 | 3,5-Cl$_2$ | 2-NHC(O)CF$_3$ | H | N(CH$_3$)Ph |
| G-1 | 3,5-Cl$_2$ | 2-NHC(O)CF$_3$ | H | (D-50c)Cl |
| G-1 | 3,5-Cl$_2$ | 2-NHC(O)OCH$_3$ | H | CH$_2$CF$_3$ |
| G-1 | 3,5-Cl$_2$ | 2-NHC(O)OCH$_3$ | H | CH$_2$OCH$_2$CF$_3$ |
| G-1 | 3,5-Cl$_2$ | 2-NHC(O)OCH$_3$ | H | E-4a |
| G-1 | 3,5-Cl$_2$ | 2-NHC(O)OCH$_3$ | H | CH$_2$C(O)NHCH$_2$CF$_3$ |
| G-1 | 3,5-Cl$_2$ | 2-NHC(O)OCH$_3$ | H | CH(CH$_3$)C(O)NHCH$_2$CF$_3$(D) |
| G-1 | 3,5-Cl$_2$ | 2-NHC(O)OCH$_3$ | H | CH$_2$(D-22a) |
| G-1 | 3,5-Cl$_2$ | 2-NHC(O)OCH$_3$ | H | CH$_2$(D-47a) |
| G-1 | 3,5-Cl$_2$ | 2-NHC(O)OCH$_3$ | C(O)OCH$_3$ | CH$_2$(D-47a) |
| G-1 | 3,5-Cl$_2$ | 2-NHC(O)OCH$_3$ | H | N(CH$_3$)Ph |
| G-1 | 3,5-Cl$_2$ | 2-NHC(O)OCH$_3$ | H | (D-50c)Cl |
| G-1 | 3,5-Cl$_2$ | 2-NHC(O)OEt | H | (D-50c)Cl |
| G-1 | 3,5-Cl$_2$ | 2-NHC(O)SCH$_3$ | H | CH$_2$CF$_3$ |
| G-1 | 3,5-Cl$_2$ | 2-NHC(O)SCH$_3$ | H | CH$_2$OCH$_2$CF$_3$ |
| G-1 | 3,5-Cl$_2$ | 2-NHC(O)SCH$_3$ | H | E-4a |
| G-1 | 3,5-Cl$_2$ | 2-NHC(O)SCH$_3$ | H | CH$_2$C(O)NHCH$_2$CF$_3$ |
| G-1 | 3,5-Cl$_2$ | 2-NHC(O)SCH$_3$ | H | CH(CH$_3$)C(O)NHCH$_2$CF$_3$(D) |
| G-1 | 3,5-Cl$_2$ | 2-NHC(O)SCH$_3$ | H | CH$_2$(D-22a) |
| G-1 | 3,5-Cl$_2$ | 2-NHC(O)SCH$_3$ | H | CH$_2$(D-47a) |
| G-1 | 3,5-Cl$_2$ | 2-NHC(O)SCH$_3$ | C(O)OCH$_3$ | CH$_2$(D-47a) |
| G-1 | 3,5-Cl$_2$ | 2-NHC(O)SCH$_3$ | H | N(CH$_3$)Ph |
| G-1 | 3,5-Cl$_2$ | 2-NHC(O)SCH$_3$ | H | (D-50c)Cl |
| G-1 | 3,5-Cl$_2$ | 2-NHC(O)SEt | H | CH$_2$CF$_3$ |
| G-1 | 3,5-Cl$_2$ | 2-NHC(S)OCH$_3$ | H | CH$_2$CF$_3$ |
| G-1 | 3,5-Cl$_2$ | 2-NHC(S)OCH$_3$ | H | CH$_2$OCH$_2$CF$_3$ |
| G-1 | 3,5-Cl$_2$ | 2-NHC(S)OCH$_3$ | H | E-4a |
| G-1 | 3,5-Cl$_2$ | 2-NHC(S)OCH$_3$ | H | CH$_2$C(O)NHCH$_2$CF$_3$ |
| G-1 | 3,5-Cl$_2$ | 2-NHC(S)OCH$_3$ | H | CH(CH$_3$)C(O)NHCH$_2$CF$_3$(D) |
| G-1 | 3,5-Cl$_2$ | 2-NHC(S)OCH$_3$ | H | CH$_2$(D-22a) |
| G-1 | 3,5-Cl$_2$ | 2-NHC(S)OCH$_3$ | H | CH$_2$(D-47a) |
| G-1 | 3,5-Cl$_2$ | 2-NHC(S)OCH$_3$ | C(O)OCH$_3$ | CH$_2$(D-47a) |
| G-1 | 3,5-Cl$_2$ | 2-NHC(S)OCH$_3$ | H | N(CH$_3$)Ph |
| G-1 | 3,5-Cl$_2$ | 2-NHC(S)OCH$_3$ | H | (D-50c)Cl |
| G-1 | 3,5-Cl$_2$ | 2-NHC(S)OEt | H | CH$_2$OCH$_2$CF$_3$ |
| G-1 | 3,5-Cl$_2$ | 2-NHC(S)SCH$_3$ | H | CH$_2$CF$_3$ |
| G-1 | 3,5-Cl$_2$ | 2-NHC(S)SCH$_3$ | H | CH$_2$OCH$_2$CF$_3$ |
| G-1 | 3,5-Cl$_2$ | 2-NHC(S)SCH$_3$ | H | E-4a |

TABLE 3-continued

| | | | | |
|---|---|---|---|---|
| G-1 | 3,5-Cl$_2$ | 2-NHC(S)SCH$_3$ | H | CH$_2$C(O)NHCH$_2$CF$_3$ |
| G-1 | 3,5-Cl$_2$ | 2-NHC(S)SCH$_3$ | H | CH(CH$_3$)C(O)NHCH$_2$CF$_3$(D) |
| G-1 | 3,5-Cl$_2$ | 2-NHC(S)SCH$_3$ | H | CH$_2$(D-22a) |
| G-1 | 3,5-Cl$_2$ | 2-NHC(S)SCH$_3$ | H | CH$_2$(D-47a) |
| G-1 | 3,5-Cl$_2$ | 2-NHC(S)SCH$_3$ | C(O)OCH$_3$ | CH$_2$(D-47a) |
| G-1 | 3,5-Cl$_2$ | 2-NHC(S)SCH$_3$ | H | N(CH$_3$)Ph |
| G-1 | 3,5-Cl$_2$ | 2-NHC(S)SCH$_3$ | H | (D-50c)Cl |
| G-1 | 3,5-Cl$_2$ | 2-NHC(S)SEt | H | E-4a |
| G-1 | 3,5-Cl$_2$ | 2-NHSO$_2$CH$_3$ | H | CH$_2$CF$_3$ |
| G-1 | 3,5-Cl$_2$ | 2-NHSO$_2$CH$_3$ | H | CH$_2$OCH$_2$CF$_3$ |
| G-1 | 3,5-Cl$_2$ | 2-NHSO$_2$CH$_3$ | H | E-4a |
| G-1 | 3,5-Cl$_2$ | 2-NHSO$_2$CH$_3$ | H | CH$_2$C(O)NHCH$_2$CF$_3$ |
| G-1 | 3,5-Cl$_2$ | 2-NHSO$_2$CH$_3$ | H | CH(CH$_3$)C(O)NHCH$_2$CF$_3$(D) |
| G-1 | 3,5-Cl$_2$ | 2-NHSO$_2$CH$_3$ | H | CH$_2$(D-22a) |
| G-1 | 3,5-Cl$_2$ | 2-NHSO$_2$CH$_3$ | H | CH$_2$(D-47a) |
| G-1 | 3,5-Cl$_2$ | 2-NHSO$_2$CH$_3$ | C(O)OCH$_3$ | CH$_2$(D-47a) |
| G-1 | 3,5-Cl$_2$ | 2-NHSO$_2$CH$_3$ | H | N(CH$_3$)Ph |
| G-1 | 3,5-Cl$_2$ | 2-NHSO$_2$CH$_3$ | H | (D-50c)Cl |
| G-1 | 3,5-Cl$_2$ | 2-NHSO$_2$CF$_3$ | H | CH$_2$CF$_3$ |
| G-1 | 3,5-Cl$_2$ | 2-NHSO$_2$CF$_3$ | H | CH$_2$OCH$_2$CF$_3$ |
| G-1 | 3,5-Cl$_2$ | 2-NHSO$_2$CF$_3$ | H | E-4a |
| G-1 | 3,5-Cl$_2$ | 2-NHSO$_2$CF$_3$ | H | CH$_2$C(O)NHCH$_2$CF$_3$ |
| G-1 | 3,5-Cl$_2$ | 2-NHSO$_2$CF$_3$ | H | CH(CH$_3$)C(O)NHCH$_2$CF$_3$(D) |
| G-1 | 3,5-Cl$_2$ | 2-NHSO$_2$CF$_3$ | H | CH$_2$(D-22a) |
| G-1 | 3,5-Cl$_2$ | 2-NHSO$_2$CF$_3$ | H | CH$_2$(D-47a) |
| G-1 | 3,5-Cl$_2$ | 2-NHSO$_2$CF$_3$ | C(O)OCH$_3$ | CH$_2$(D-47a) |
| G-1 | 3,5-Cl$_2$ | 2-NHSO$_2$CF$_3$ | H | N(CH$_3$)Ph |
| G-1 | 3,5-Cl$_2$ | 2-NHSO$_2$CF$_3$ | H | (D-50c)Cl |
| G-1 | 3,5-Cl$_2$ | 2-N(CH$_3$)CHO | H | CH$_2$CF$_3$ |
| G-1 | 3,5-Cl$_2$ | 2-N(CH$_3$)CHO | H | CH$_2$OCH$_2$CF$_3$ |
| G-1 | 3,5-Cl$_2$ | 2-N(CH$_3$)CHO | H | E-4a |
| G-1 | 3,5-Cl$_2$ | 2-N(CH$_3$)CHO | H | CH$_2$C(O)NHCH$_2$CF$_3$ |
| G-1 | 3,5-Cl$_2$ | 2-N(CH$_3$)CHO | H | CH(CH$_3$)C(O)NHCH$_2$CF$_3$(D) |
| G-1 | 3,5-Cl$_2$ | 2-N(CH$_3$)CHO | H | CH$_2$(D-22a) |
| G-1 | 3,5-Cl$_2$ | 2-N(CH$_3$)CHO | H | CH$_2$(D-47a) |
| G-1 | 3,5-Cl$_2$ | 2-N(CH$_3$)CHO | C(O)OCH$_3$ | CH$_2$(D-47a) |
| G-1 | 3,5-Cl$_2$ | 2-N(CH$_3$)CHO | H | N(CH$_3$)Ph |
| G-1 | 3,5-Cl$_2$ | 2-N(CH$_3$)CHO | H | (D-50c)Cl |
| G-1 | 3,5-Cl$_2$ | 2-N(CH$_3$)C(O)CH$_3$ | H | CH$_2$C(O)NHCH$_2$CF$_3$ |
| G-1 | 3,5-Cl$_2$ | 2-N(CH$_3$)C(O)Et | H | CH$_2$(D-22a) |
| G-1 | 3,5-Cl$_2$ | 2-N(CH$_3$)C(O)Pr-n | H | CH$_2$(D-47a) |
| G-1 | 3,5-Cl$_2$ | 2-N(CH$_3$)C(O)Pr-i | C(O)OCH$_3$ | CH$_2$(D-47a) |
| G-1 | 3,5-Cl$_2$ | 2-N(CH$_3$)C(O)Pr-c | H | N(CH$_3$)Ph |
| G-1 | 3,5-Cl$_2$ | 2-N(CH$_3$)C(O)Bu-t | H | (D-50c)Cl |
| G-1 | 3,5-Cl$_2$ | 2-N(CH$_3$)C(O)CF$_3$ | H | CH$_2$CF$_3$ |
| G-1 | 3,5-Cl$_2$ | 2-N(CH$_3$)C(O)OCH$_3$ | H | CH$_2$OCH$_2$CF$_3$ |
| G-1 | 3,5-Cl$_2$ | 2-N(CH$_3$)C(O)OEt | H | E-4a |
| G-1 | 3,5-Cl$_2$ | 2-N(CH$_3$)C(O)SCH$_3$ | H | CH$_2$C(O)NHCH$_2$CF$_3$ |
| G-1 | 3,5-Cl$_2$ | 2-N(CH$_3$)C(O)SEt | H | CH$_2$(D-22a) |
| G-1 | 3,5-Cl$_2$ | 2-N(CH$_3$)C(S)OCH$_3$ | H | CH$_2$(D-47a) |
| G-1 | 3,5-Cl$_2$ | 2-N(CH$_3$)C(S)OEt | C(O)OCH$_3$ | CH$_2$(D-47a) |
| G-1 | 3,5-Cl$_2$ | 2-N(CH$_3$)C(S)SCH$_3$ | H | N(CH$_3$)Ph |
| G-1 | 3,5-Cl$_2$ | 2-N(CH$_3$)C(S)SEt | H | (D-50c)Cl |
| G-1 | 3,5-Cl$_2$ | 2-N(CH$_3$)SO$_2$CH$_3$ | H | CH$_2$CF$_3$ |
| G-1 | 3,5-Cl$_2$ | 2-N(CH$_3$)SO$_2$CF$_3$ | H | CH$_2$OCH$_2$CF$_3$ |
| G-1 | 3,5-Cl$_2$ | 2-N(Et)CHO | H | E-4a |
| G-1 | 3,5-Cl$_2$ | 2-N(Et)C(O)CH$_3$ | H | CH$_2$C(O)NHCH$_2$CF$_3$ |
| G-1 | 3,5-Cl$_2$ | 2-N(Et)C(O)Et | H | CH$_2$(D-22a) |
| G-1 | 3,5-Cl$_2$ | 2-N(Et)C(O)Pr-n | H | CH$_2$(D-47a) |
| G-1 | 3,5-Cl$_2$ | 2-N(Et)C(O)Pr-i | C(O)OCH$_3$ | CH$_2$(D-47a) |
| G-1 | 3,5-Cl$_2$ | 2-N(Et)C(O)Pr-c | H | N(CH$_3$)Ph |
| G-1 | 3,5-Cl$_2$ | 2-N(Et)C(O)Bu-t | H | (D-50c)Cl |
| G-1 | 3,5-Cl$_2$ | 2-N(Et)C(O)CF$_3$ | H | CH$_2$CF$_3$ |
| G-1 | 3,5-Cl$_2$ | 2-N(Et)C(O)OCH$_3$ | H | CH$_2$OCH$_2$CF$_3$ |
| G-1 | 3,5-Cl$_2$ | 2-N(Et)C(O)OEt | H | E-4a |
| G-1 | 3,5-Cl$_2$ | 2-N(Et)C(O)SCH$_3$ | H | CH$_2$C(O)NHCH$_2$CF$_3$ |
| G-1 | 3,5-Cl$_2$ | 2-N(Et)C(O)SEt | H | CH$_2$(D-22a) |
| G-1 | 3,5-Cl$_2$ | 2-N(Et)C(S)OCH$_3$ | H | CH$_2$(D-47a) |
| G-1 | 3,5-Cl$_2$ | 2-N(Et)C(S)OEt | C(O)OCH$_3$ | CH$_2$(D-47a) |
| G-1 | 3,5-Cl$_2$ | 2-N(Et)C(S)SCH$_3$ | H | N(CH$_3$)Ph |
| G-1 | 3,5-Cl$_2$ | 2-N(Et)C(S)SEt | H | (D-50c)Cl |
| G-1 | 3,5-Cl$_2$ | 2-N(CH$_3$)SO$_2$CH$_3$ | H | CH$_2$CF$_3$ |
| G-1 | 3,5-Cl$_2$ | 2-N(CH$_3$)SO$_2$CF$_3$ | H | CH$_2$OCH$_2$CF$_3$ |
| G-1 | 3,5-Cl$_2$ | 2-N=CHOCH$_3$ | H | E-4a |
| G-1 | 3,5-Cl$_2$ | 2-N=C(CH$_3$)OCH$_3$ | H | CH$_2$CF$_3$ |
| G-1 | 3,5-Cl$_2$ | 2-N=C(CH$_3$)OCH$_3$ | H | CH$_2$OCH$_2$CF$_3$ |
| G-1 | 3,5-Cl$_2$ | 2-N=C(CH$_3$)OCH$_3$ | H | E-4a |
| G-1 | 3,5-Cl$_2$ | 2-N=C(CH$_3$)OCH$_3$ | H | CH$_2$C(O)NHCH$_2$CF$_3$ |
| G-1 | 3,5-Cl$_2$ | 2-N=C(CH$_3$)OCH$_3$ | H | CH(CH$_3$)C(O)NHCH$_2$CF$_3$(D) |
| G-1 | 3,5-Cl$_2$ | 2-N=C(CH$_3$)OCH$_3$ | H | CH$_2$(D-22a) |

TABLE 3-continued

| | | | | |
|---|---|---|---|---|
| G-1 | 3,5-Cl$_2$ | 2-N=C(CH$_3$)OCH$_3$ | H | CH$_2$(D-47a) |
| G-1 | 3,5-Cl$_2$ | 2-N=C(CH$_3$)OCH$_3$ | C(O)OCH$_3$ | CH$_2$(D-47a) |
| G-1 | 3,5-Cl$_2$ | 2-N=C(CH$_3$)OCH$_3$ | H | N(CH$_3$)Ph |
| G-1 | 3,5-Cl$_2$ | 2-N=C(CH$_3$)OCH$_3$ | H | (D-50c)Cl |
| G-1 | 3,5-Cl$_2$ | 2-(D-5a) | H | CH$_2$C(O)NHCH$_2$CF$_3$ |
| G-1 | 3,5-Cl$_2$ | 2-NHCH$_2^-$ | | CH$_2$(D-22a) |
| G-1 | 3,5-Cl$_2$ | 2-N(CH$_3$)CH$_2^-$ | | CH$_2$(D-47a) |
| G-1 | 3,5-Cl$_2$ | 2-N(Et)CH$_2^-$ | | (D-50c)Cl |
| G-1 | 3,5-Cl$_2$ | 2-C(O)OCH$_3$ | H | CH$_2$CF$_3$ |
| G-1 | 3,5-Cl$_2$ | 2-C(O)NH$_2$ | H | CH$_2$OCH$_2$CF$_3$ |
| G-1 | 3,5-Cl$_2$ | 2-(T-22) | H | E-4a |
| G-1 | 3,5-Cl$_2$ | 2-C(S)NH$_2$ | H | CH$_2$CF$_3$ |
| G-1 | 3,5-Cl$_2$ | 2-C(S)NH$_2$ | H | CH$_2$OCH$_2$CF$_3$ |
| G-1 | 3,5-Cl$_2$ | 2-C(S)NH$_2$ | H | E-4a |
| G-1 | 3,5-Cl$_2$ | 2-C(S)NH$_2$ | H | CH$_2$C(O)NHCH$_2$CF$_3$ |
| G-1 | 3,5-Cl$_2$ | 2-C(S)NH$_2$ | H | CH(CH$_3$)C(O)NHCH$_2$CF$_3$(D) |
| G-1 | 3,5-Cl$_2$ | 2-C(S)NH$_2$ | H | CH$_2$(D-22a) |
| G-1 | 3,5-Cl$_2$ | 2-C(S)NH$_2$ | H | CH$_2$(D-47a) |
| G-1 | 3,5-Cl$_2$ | 2-C(S)NH$_2$ | C(O)OCH$_2$ | CH$_2$(D-47a) |
| G-1 | 3,5-Cl$_2$ | 2-C(S)NH$_2$ | H | N(CH$_3$)Ph |
| G-1 | 3,5-Cl$_2$ | 2-C(S)NH$_2$ | H | (D-50c)Cl |
| G-1 | 3,5-Cl$_2$ | 2-(T-25) | H | CH$_2$C(O)NHCH$_2$CF$_3$ |
| G-1 | 3,5-Cl$_2$ | 2-Ph | H | CH$_2$(D-22a) |
| G-1 | 3,5-Cl$_2$ | 2-(D-14a) | H | CH$_2$(D-47a) |
| G-1 | 3,5-Cl$_2$ | 2-(D-24a) | C(O)OCH$_3$ | CH$_2$(D-47a) |
| G-1 | 3,5-Cl$_2$ | 2-(D-38a) | H | N(CH$_3$)Ph |
| G-1 | 3,5-Cl$_2$ | 2-(D-43a) | H | (D-50c)Cl |
| G-1 | 3,5-Cl$_2$ | 2-(D-43b)CH$_3$ | H | CH$_2$CF$_3$ |
| G-1 | 3,5-Cl$_2$ | 2-(D-44a) | H | CH$_2$OCH$_2$CF$_3$ |
| G-1 | 3,5-Cl$_2$ | 2-(D-45a)H | H | E-4a |
| G-1 | 3,5-Cl$_2$ | 2-(D-45a)CH$_3$ | H | CH$_2$C(O)NHCH$_2$CF$_3$ |
| G-1 | 3,5-Cl$_2$ | 2-(D-46a)H | H | CH$_2$(D-22a) |
| G-1 | 3,5-Cl$_2$ | 2-(D-46a)CH$_3$ | H | CH$_2$(D-47a) |
| G-1 | 3,5-Cl$_2$ | 2,3-F$_2$ | C(O)OCH$_3$ | CH$_2$(D-47a) |
| G-1 | 3,5-Cl$_2$ | 2-F-3-Cl | H | N(CH$_3$)Ph |
| G-1 | 3,5-Cl$_2$ | 2-F-3-Br | H | (D-50c)Cl |
| G-1 | 3,5-Cl$_2$ | 2-F-3-CN | H | CH$_2$CF$_3$ |
| G-1 | 3,5-Cl$_2$ | 2-F-3-OCH$_3$ | H | CH$_2$OCH$_2$CF$_3$ |
| G-1 | 3,5-Cl$_2$ | 2,5-F$_2$ | H | E-4a |
| G-1 | 3,5-Cl$_2$ | 2-F-5-Cl | H | CH$_2$C(O)NHCH$_2$CF$_3$ |
| G-1 | 3,5-Cl$_2$ | 2-F-5-Br | H | CH$_2$(D-22a) |
| G-1 | 3,5-Cl$_2$ | 2-F-5-CH$_3$ | H | CH$_2$(D-47a) |
| G-1 | 3,5-Cl$_2$ | 2-F-5-CF$_3$ | C(O)OCH$_3$ | CH$_2$(D-47a) |
| G-1 | 3,5-Cl$_2$ | 2-F-5-OCH$_3$ | H | N(CH$_3$)Ph |
| G-1 | 3,5-Cl$_2$ | 2,6-F$_2$ | H | (D-50c)Cl |
| G-1 | 3,5-Cl$_2$ | 2-F-6-Cl | H | CH$_2$CF$_3$ |
| G-1 | 3,5-Cl$_2$ | 2-F-6-Br | H | CH$_2$OCH$_2$CF$_3$ |
| G-1 | 3,5-Cl$_2$ | 2-F-6-CF$_3$ | H | E-4a |
| G-1 | 3,5-Cl$_2$ | 2-F-6-NO$_2$ | H | CH$_2$C(O)NHCH$_2$CF$_3$ |
| G-1 | 3,5-Cl$_2$ | 2-Cl-3-F | H | CH$_2$(D-22a) |
| G-1 | 3,5-Cl$_2$ | 2,3-Cl$_2$ | H | CH$_2$(D-47a) |
| G-1 | 3,5-Cl$_2$ | 2-Cl-3-CH$_3$ | C(O)OCH | 3CH$_2$(D-47a) |
| G-1 | 3,5-Cl$_2$ | 2-Cl-3-OCH$_3$ | H | N(CH$_3$)Ph |
| G-1 | 3,5-Cl$_2$ | 2-Cl-3-CN | H | (D-50c)Cl |
| G-1 | 3,5-Cl$_2$ | 2-Cl-5-F | H | CH$_2$CF$_3$ |
| G-1 | 3,5-Cl$_2$ | 2,5-Cl$_2$ | H | CH$_2$OCH$_2$CF$_3$ |
| G-1 | 3,5-Cl$_2$ | 2-Cl-5-Br | H | E-4a |
| G-1 | 3,5-Cl$_2$ | 2-Cl-5-CH$_3$ | H | CH$_2$C(O)NHCH$_2$CF$_3$ |
| G-1 | 3,5-Cl$_2$ | 2-Cl-5-CF$_3$ | H | CH$_2$(D-22a) |
| G-1 | 3,5-Cl$_2$ | 2-Cl-5-OCH$_3$ | H | CH$_2$(D-47a) |
| G-1 | 3,5-Cl$_2$ | 2,6-Cl$_2$ | C(O)OCH$_3$ | CH$_2$(D-47a) |
| G-1 | 3,5-Cl$_2$ | 2-Cl-6-Br | H | N(CH$_3$)Ph |
| G-1 | 3,5-Cl$_2$ | 2-Cl-6-CH$_3$ | H | (D-50c)Cl |
| G-1 | 3,5-Cl$_2$ | 2-Cl-6-CF$_3$ | H | CH$_2$CF$_3$ |
| G-1 | 3,5-Cl$_2$ | 2-Cl-6-OCH$_3$ | H | CH$_2$OCH$_2$CF$_3$ |
| G-1 | 3,5-Cl$_2$ | 2-Br-3-F | H | E-4a |
| G-1 | 3,5-Cl$_2$ | 2-Br-3-OCH$_3$ | H | CH$_2$C(O)NHCH$_2$CF$_3$ |
| G-1 | 3,5-Cl$_2$ | 2-Br-5-F | H | CH$_2$(D-22a) |
| G-1 | 3,5-Cl$_2$ | 2-Br-5-Cl | H | CH$_2$(D-47a) |
| G-1 | 3,5-Cl$_2$ | 2,5-Br$_2$ | C(O)OCH$_3$ | CH$_2$(D-47a) |
| G-1 | 3,5-Cl$_2$ | 2-Br-5-CH$_3$ | H | N(CH$_3$)Ph |
| G-1 | 3,5-Cl$_2$ | 2-Br-5-CF$_3$ | H | (D-50c)Cl |
| G-1 | 3,5-Cl$_2$ | 2-Br-5-OCH$_3$ | H | CH$_2$CF$_3$ |
| G-1 | 3,5-Cl$_2$ | 2,6-Br$_2$ | H | CH$_2$OCH$_2$CF$_3$ |
| G-1 | 3,5-Cl$_2$ | 2-CH$_3$-3-F | H | CH$_2$CF$_3$ |
| G-1 | 3,5-Cl$_2$ | 2-CH$_3$-3-F | H | CH$_2$OCH$_2$CF$_3$ |
| G-1 | 3,5-Cl$_2$ | 2-CH$_3$-3-F | H | E-4a |
| G-1 | 3,5-Cl$_2$ | 2-CH$_3$-3-F | H | CH$_2$C(O)NHCH$_2$CF$_3$ |
| G-1 | 3,5-Cl$_2$ | 2-CH$_3$-3-F | H | CH(CH$_3$)C(O)NHCH$_2$CF$_3$(D) |
| G-1 | 3,5-Cl$_2$ | 2-CH$_3$-3-F | H | CH$_2$(D-22a) |

TABLE 3-continued

| | | | | |
|---|---|---|---|---|
| G-1 | 3,5-Cl$_2$ | 2-CH$_3$-3-F | H | CH$_2$(D-47a) |
| G-1 | 3,5-Cl$_2$ | 2-CH$_3$-3-F | C(O)OCH$_3$ | CH$_2$(D-47a) |
| G-1 | 3,5-Cl$_2$ | 2-CH$_3$-3-F | H | N(CH$_3$)Ph |
| G-1 | 3,5-Cl$_2$ | 2-CH$_3$-3-F | H | (D-50c)Cl |
| G-1 | 3,5-Cl$_2$ | 2-CH$_3$-3-Cl | H | E-4a |
| G-1 | 3,5-Cl$_2$ | 2-CH$_3$-3-Br | H | CH$_2$C(O)NHCH$_2$CF$_3$ |
| G-1 | 3,5-Cl$_2$ | 2,3-(CH$_3$)$_2$ | H | CH$_2$(D-22a) |
| G-1 | 3,5-Cl$_2$ | 2-CH$_3$-3-CF$_3$ | H | CH$_2$(D-47a) |
| G-1 | 3,5-Cl$_2$ | 2-CH$_3$-3-OCH$_3$ | C(O)OCH$_3$ | CH$_2$(D-47a) |
| G-1 | 3,5-Cl$_2$ | 2-CH$_3$-3-CN | H | N(CH$_3$)Ph |
| G-1 | 3,5-Cl$_2$ | 2-CH$_3$-5-F | H | (D-50c)Cl |
| G-1 | 3,5-Cl$_2$ | 2-CH$_3$-5-Cl | H | CH$_2$CF$_3$ |
| G-1 | 3,5-Cl$_2$ | 2-CH$_3$-5-Br | H | CH$_2$OCH$_2$CF$_3$ |
| G-1 | 3,5-Cl$_2$ | 2,5-(CH$_3$)$_2$ | H | E-4a |
| G-1 | 3,5-Cl$_2$ | 2-CH$_3$-5-CF$_3$ | H | CH$_2$C(O)NHCH$_2$CF$_3$ |
| G-1 | 3,5-Cl$_2$ | 2-CH$_3$-5-OCH$_3$ | H | CH$_2$(D-22a) |
| G-1 | 3,5-Cl$_2$ | 2-CH$_3$-6-F | H | CH$_2$CF$_3$ |
| G-1 | 3,5-Cl$_2$ | 2-CH$_3$-6-F | H | CH$_2$OCH$_2$CF$_3$ |
| G-1 | 3,5-Cl$_2$ | 2-CH$_3$-6-F | H | E-4a |
| G-1 | 3,5-Cl$_2$ | 2-CH$_3$-6-F | H | CH$_2$C(O)NHCH$_2$CF$_3$ |
| G-1 | 3,5-Cl$_2$ | 2-CH$_3$-6-F | H | CH(CH$_3$)C(O)NHCH$_2$CF$_3$(D) |
| G-1 | 3,5-Cl$_2$ | 2-CH$_3$-6-F | H | CH$_2$(D-22a) |
| G-1 | 3,5-Cl$_2$ | 2-CH$_3$-6-F | H | CH$_2$(D-47a) |
| G-1 | 3,5-Cl$_2$ | 2-CH$_3$-6-F | C(O)OCH$_3$ | CH$_2$(D-47a) |
| G-1 | 3,5-Cl$_2$ | 2-CH$_3$-6-F | H | N(CH$_3$)Ph |
| G-1 | 3,5-Cl$_2$ | 2-CH$_3$-6-F | H | (D-50c)Cl |
| G-1 | 3,5-Cl$_2$ | 2-CH$_3$-6-Cl | H | CH$_2$(D-47a) |
| G-1 | 3,5-Cl$_2$ | 2,6-(CH$_3$)$_2$ | C(O)OCH$_3$ | CH$_2$(D-47a) |
| G-1 | 3,5-Cl$_2$ | 2-CH$_3$-6-CF$_3$ | H | N(CH$_3$)Ph |
| G-1 | 3,5-Cl$_2$ | 2-CH$_3$-6-OCH$_3$ | H | (D-50c)Cl |
| G-1 | 3,5-Cl$_2$ | 2-CF$_3$-5-F | H | CH$_2$CF$_3$ |
| G-1 | 3,5-Cl$_2$ | 2-CF$_3$-5-Cl | H | CH$_2$OCH$_2$CF$_3$ |
| G-1 | 3,5-Cl$_2$ | 2-CF$_3$-5-Br | H | E-4a |
| G-1 | 3,5-Cl$_2$ | 2-CF$_3$-5-CH$_3$ | H | CH$_2$C(O)NHCH$_2$CF$_3$ |
| G-1 | 3,5-Cl$_2$ | 2-CF$_3$-6-OCH$_3$ | H | CH$_2$(D-22a) |
| G-1 | 3,5-Cl$_2$ | 2-OCH$_3$-3-F | H | CH$_2$(D-47a) |
| G-1 | 3,5-Cl$_2$ | 2-OCH$_3$-3-Br | C(O)OCH$_3$ | CH$_2$(D-47a) |
| G-1 | 3,5-Cl$_2$ | 2-OCH$_3$-5-F | H | N(CH$_3$)Ph |
| G-1 | 3,5-Cl$_2$ | 2-OCH$_3$-5-Cl | H | (D-50c)Cl |
| G-1 | 3,5-Cl$_2$ | 2-OCH$_3$-5-Br | H | CH$_2$CF$_3$ |
| G-1 | 3,5-Cl$_2$ | 2-OCH$_3$-5-CH$_3$ | H | CH$_2$OCH$_2$CF$_3$ |
| G-1 | 3,5-Cl$_2$ | 2-CN-3-F | H | E-4a |
| G-1 | 3-Cl-5-Br | 2-Pr-i | H | CH$_2$C(O)NHCH$_2$CF$_3$ |
| G-1 | 3-Cl-5-Br | 2-OEt | H | CH$_2$(D-22a) |
| G-1 | 3-Cl-5-Br | 2-OPr-i | H | CH$_2$(D-47a) |
| G-1 | 3-Cl-5-Br | 2-OSO$_2$CH$_3$ | C(O)OCH$_3$ | CH$_2$(D-47a) |
| G-1 | 3-Cl-5-Br | 2-SEt | H | N(CH$_3$)Ph |
| G-1 | 3-Cl-5-Br | 2-SPr-i | H | (D-50c)Cl |
| G-1 | 3-Cl-5-Br | 2-NHEt | H | CH$_2$CF$_3$ |
| G-1 | 3-Cl-5-Br | 2-NHPr-i | H | CH$_2$OCH$_2$CF$_3$ |
| G-1 | 3-Cl-5-Br | 2-N(CH$_3$)$_2$ | H | E-4a |
| G-1 | 3-Cl-5-Br | 2-NHC(O)CH$_3$ | H | CH$_2$C(O)NHCH$_2$CF$_3$ |
| G-1 | 3,5-Br$_2$ | 2-Pr-i | H | CH$_2$(D-22a) |
| G-1 | 3,5-Br$_2$ | 2-OEt | H | CH$_2$(D-47a) |
| G-1 | 3,5-Br$_2$ | 2-OPr-i | C(O)OCH$_3$ | CH$_2$(D-47a) |
| G-1 | 3,5-Br$_2$ | 2-OSO$_2$CH$_3$ | H | N(CH$_3$)Ph |
| G-1 | 3,5-Br$_2$ | 2-SEt | H | (D-50c)Cl |
| G-1 | 3,5-Br$_2$ | 2-SPr-i | H | CH$_2$CF$_3$ |
| G-1 | 3,5-Br$_2$ | 2-NHEt | H | CH$_2$OCH$_2$CF$_3$ |
| G-1 | 3,5-Br$_2$ | 2-NHPr-i | H | E-4a |
| G-1 | 3,5-Br$_2$ | 2-N(CH$_3$)$_2$ | H | CH$_2$C(O)NHCH$_2$CF$_3$ |
| G-1 | 3,5-Br$_2$ | 2-NHC(O)CH$_3$ | H | CH$_2$(D-22a) |
| G-1 | 3-Cl-5-I | 2-Pr-i | H | CH$_2$(D-47a) |
| G-1 | 3-Cl-5-I | 2-OEt | C(O)OCH$_3$ | CH$_2$(D-47a) |
| G-1 | 3-Cl-5-I | 2-OPr-i | H | N(CH$_3$)Ph |
| G-1 | 3-Cl-5-I | 2-OSO$_2$CH$_3$ | H | (D-50c)Cl |
| G-1 | 3-Cl-5-I | 2-SEt | H | CH$_2$CF$_3$ |
| G-1 | 3-Cl-5-I | 2-SPr-i | H | CH$_2$OCH$_2$CF$_3$ |
| G-1 | 3-Cl-5-I | 2-NHEt | H | E-4a |
| G-1 | 3-Cl-5-I | 2-NHPr-i | H | CH$_2$C(O)NHCH$_2$CF$_3$ |
| G-1 | 3-Cl-5-I | 2-N(CH$_3$)$_2$ | H | CH$_2$(D-22a) |
| G-1 | 3-Cl-5-I | 2-NHC(O)CH$_3$ | H | CH$_2$(D-47a) |
| G-1 | 3-CF$_3$-4-F | 2-Pr-i | C(O)OCH$_3$ | CH$_2$(D-47a) |
| G-1 | 3-CF$_3$-4-F | 2-OEt | H | N(CH$_3$)Ph |
| G-1 | 3-CF$_3$-4-F | 2-OPr-i | H | (D-50c)Cl |
| G-1 | 3-CF$_3$-4-F | 2-OSO$_2$CH$_3$ | H | CH$_2$CF$_3$ |
| G-1 | 3-CF$_3$-4-F | 2-SEt | H | CH$_2$OCH$_2$CF$_3$ |
| G-1 | 3-CF$_3$-4-F | 2-SPr-i | H | E-4a |
| G-1 | 3-CF$_3$-4-F | 2-NHEt | H | CH$_2$C(O)NHCH$_2$CF$_3$ |
| G-1 | 3-CF$_3$-4-F | 2-NHPr-i | H | CH$_2$(D-22a) |

TABLE 3-continued

| | | | | |
|---|---|---|---|---|
| G-1 | 3-CF₃-4-F | 2-N(CH₃)₂ | H | CH₂(D-47a) |
| G-1 | 3-CF₃-4-F | 2-NHC(O)CH₃ | C(O)OCH₃ | CH₂(D-47a) |
| G-1 | 3-F-5-CF₃ | 2-Pr-i | H | N(CH₃)Ph |
| G-1 | 3-F-5-CF₃ | 2-OEt | H | (D-50c)Cl |
| G-1 | 3-F-5-CF₃ | 2-OPr-i | H | CH₂CF₃ |
| G-1 | 3-F-5-CF₃ | 2-OSO₂CH₃ | H | CH₂OCH₂CF₃ |
| G-1 | 3-F-5-CF₃ | 2-SEt | H | E-4a |
| G-1 | 3-F-5-CF₃ | 2-SPr-i | H | CH₂C(O)NHCH₂CF₃ |
| G-1 | 3-F-5-CF₃ | 2-NHEt | H | CH₂(D-22a) |
| G-1 | 3-F-5-CF₃ | 2-NHPr-i | H | CH₂(D-47a) |
| G-1 | 3-F-5-CF₃ | 2-N(CH₃)₂ | C(O)OCH₃ | CH₂(D-47a) |
| G-1 | 3-F-5-CF₃ | 2-NHC(O)CH₃ | H | N(CH₃)Ph |
| G-1 | 3-CF₃-4-Cl | 2-Pr-i | H | (D-50c)Cl |
| G-1 | 3-CF₃-4-Cl | 2-OEt | H | CH₂CF₃ |
| G-1 | 3-CF₃-4-Cl | 2-OPr-i | H | CH₂OCH₂CF₃ |
| G-1 | 3-CF₃-4-Cl | 2-OSO₂CH₃ | H | E-4a |
| G-1 | 3-CF₃-4-Cl | 2-SEt | H | CH₂C(O)NHCH₂CF₃ |
| G-1 | 3-CF₃-4-Cl | 2-SPr-i | H | CH₂(D-22a) |
| G-1 | 3-CF₃-4-Cl | 2-NHEt | H | CH₂(D-47a) |
| G-1 | 3-CF₃-4-Cl | 2-NHPr-i | C(O)OCH₃ | CH₂(D-47a) |
| G-1 | 3-CF₃-4-Cl | 2-N(CH₃)₂ | H | N(CH₃)Ph |
| G-1 | 3-CF₃-4-Cl | 2-NHC(O)CH₃ | H | (D-50c)Cl |
| G-1 | 3-Cl-5-CF₃ | 2-Pr-i | H | CH₂CF₃ |
| G-1 | 3-Cl-5-CF₃ | 2-OEt | H | CH₂OCH₂CF₃ |
| G-1 | 3-Cl-5-CF₃ | 2-OPr-i | H | E-4a |
| G-1 | 3-Cl-5-CF₃ | 2-OSO₂CH₃ | H | CH₂C(O)NHCH₂CF₃ |
| G-1 | 3-Cl-5-CF₃ | 2-SEt | H | CH₂(D-22a) |
| G-1 | 3-Cl-5-CF₃ | 2-SPr-i | H | CH₂(D-47a) |
| G-1 | 3-Cl-5-CF₃ | 2-NHEt | C(O)OCH₃ | CH₂(D-47a) |
| G-1 | 3-Cl-5-CF₃ | 2-NHPr-i | H | N(CH₃)Ph |
| G-1 | 3-Cl-5-CF₃ | 2-N(CH₃)₂ | H | (D-50c)Cl |
| G-1 | 3-Cl-5-CF₃ | 2-NHC(O)CH₃ | H | CH₂CF₃ |
| G-1 | 3-Br-5-CF₃ | 2-Pr-i | H | CH₂OCH₂CF₃ |
| G-1 | 3-Br-5-CF₃ | 2-OEt | H | E-4a |
| G-1 | 3-Br-5-CF₃ | 2-OPr-i | H | CH₂C(O)NHCH₂CF₃ |
| G-1 | 3-Br-5-CF₃ | 2-OSO₂CH₃ | H | CH₂(D-22a) |
| G-1 | 3-Br-5-CF₃ | 2-SEt | H | CH₂(D-47a) |
| G-1 | 3-Br-5-CF₃ | 2-SPr-i | C(O)OCH₃ | CH₂(D-47a) |
| G-1 | 3-Br-5-CF₃ | 2-NHEt | H | N(CH₃)Ph |
| G-1 | 3-Br-5-CF₃ | 2-NHPr-i | H | (D-50c)Cl |
| G-1 | 3-Br-5-CF₃ | 2-N(CH₃)₂ | H | CH₂CF₃ |
| G-1 | 3-Br-5-CF₃ | 2-NHC(O)CH₃ | H | CH₂OCH₂CF₃ |
| G-1 | 3,5-(CF₃)₂ | 2-Pr-i | H | E-4a |
| G-1 | 3,5-(CF₃)₂ | 2-OEt | H | CH₂C(O)NHCH₂CF₃ |
| G-1 | 3,5-(CF₃)₂ | 2-OPr-i | H | CH₂(D-22a) |
| G-1 | 3,5-(CF₃)₂ | 2-OSO₂CH₃ | H | CH₂(D-47a) |
| G-1 | 3,5-(CF₃)₂ | 2-SEt | C(O)OCH₃ | CH₂(D-47a) |
| G-1 | 3,5-(CF₃)₂ | 2-SPr-i | H | N(CH₃)Ph |
| G-1 | 3,5-(CF₃)₂ | 2-NHEt | H | (D-50c)Cl |
| G-1 | 3,5-(CF₃)₂ | 2-NHPr-i | H | CH₂CF₃ |
| G-1 | 3,5-(CF₃)₂ | 2-N(CH₃)₂ | H | CH₂OCH₂CF₃ |
| G-1 | 3,5-(CF₃)₂ | 2-NHC(O)CH₃ | H | E-4a |
| G-1 | 3,5-Cl₂4-F | 2-Pr-i | H | CH₂C(O)NHCH₂CF₃ |
| G-1 | 3,5-Cl₂4-F | 2-OEt | H | CH₂(D-22a) |
| G-1 | 3,5-Cl₂4-F | 2-OPr-i | H | CH₂(D-47a) |
| G-1 | 3,5-Cl₂4-F | 2-OSO₂CH₃ | C(O)OCH₃ | CH₂(D-47a) |
| G-1 | 3,5-Cl₂4-F | 2-SEt | H | N(CH₃)Ph |
| G-1 | 3,5-Cl₂4-F | 2-SPr-i | H | (D-50c)Cl |
| G-1 | 3,5-Cl₂4-F | 2-NHEt | H | CH₂CF₃ |
| G-1 | 3,5-Cl₂4-F | 2-NHPr-i | H | CH₂OCH₂CF₃ |
| G-1 | 3,5-Cl₂4-F | 2-N(CH₃)₂ | H | E-4a |
| G-1 | 3,5-Cl₂4-F | 2-NHC(O)CH₃ | H | CH₂C(O)NHCH₂CF₃ |
| G-1 | 3,4,5-Cl₃ | 2-Pr-i | H | CH₂(D-22a) |
| G-1 | 3,4,5-Cl₃ | 2-OEt | H | CH₂(D-47a) |
| G-1 | 3,4,5-Cl₃ | 2-OPr-i | C(O)OCH₃ | CH₂(D-47a) |
| G-1 | 3,4,5-Cl₃ | 2-OSO₂CH₃ | H | N(CH₃)Ph |
| G-1 | 3,4,5-Cl₃ | 2-SEt | H | (D-50c)Cl |
| G-1 | 3,4,5-Cl₃ | 2-SPr-i | H | CH₂CF₃ |
| G-1 | 3,4,5-Cl₃ | 2-NHEt | H | CH₂OCH₂CF₃ |
| G-1 | 3,4,5-Cl₃ | 2-NHPr-i | H | E-4a |
| G-1 | 3,4,5-Cl₃ | 2-N(CH₃)₂ | H | CH₂C(O)NHCH₂CF₃ |
| G-1 | 3,4,5-Cl₃ | 2-NHC(O)CH₃ | H | CH₂(D-22a) |
| G-1 | 3,5-Br₂-4-F | 2-Pr-i | H | CH₂(D-47a) |
| G-1 | 3,5-Br₂-4-F | 2-OEt | C(O)OCH₃ | CH₂(D-47a) |
| G-1 | 3,5-Br₂-4-F | 2-OPr-i | H | N(CH₃)Ph |
| G-1 | 3,5-Br₂-4-F | 2-OSO₂CH₃ | H | (D-50c)Cl |
| G-1 | 3,5-Br₂-4-F | 2-SEt | H | CH₂CF₃ |
| G-1 | 3,5-Br₂-4-F | 2-SPr-i | H | CH₂OCH₂CF₃ |
| G-1 | 3,5-Br₂-4-F | 2-NHEt | H | E-4a |
| G-1 | 3,5-Br₂-4-F | 2-NHPr-i | H | CH₂C(O)NHCH₂CF₃ |

TABLE 3-continued

| | | | | |
|---|---|---|---|---|
| G-1 | 3,5-Br$_2$-4-F | 2-N(CH$_3$)$_2$ | H | CH$_2$(D-22a) |
| G-1 | 3,5-Br$_2$-4-F | 2-NHC(O)CH$_3$ | H | CH$_2$(D-47a) |
| G-1 | 3,4-F$_2$-5-CF$_3$ | 2-Pr-i | C(O)OCH$_3$ | CH$_2$(D-47a) |
| G-1 | 3,4-F$_2$-5-CF$_3$ | 2-OEt | H | N(CH$_3$)Ph |
| G-1 | 3,4-F$_2$-5-CF$_3$ | 2-OPr-i | H | (D-50c)Cl |
| G-1 | 3,4-F$_2$-5-CF$_3$ | 2-OSO$_2$CH$_3$ | H | CH$_2$CF$_3$ |
| G-1 | 3,4-F$_2$-5-CF$_3$ | 2-SEt | H | CH$_2$OCH$_2$CF$_3$ |
| G-1 | 3,4-F$_2$-5-CF$_3$ | 2-SPr-i | H | E-4a |
| G-1 | 3,4-F$_2$-5-CF$_3$ | 2-NHEt | H | CH$_2$C(O)NHCH$_2$CF$_3$ |
| G-1 | 3,4-F$_2$-5-CF$_3$ | 2-NHPr-i | H | CH$_2$(D-22a) |
| G-1 | 3,4-F$_2$-5-CF$_3$ | 2-N(CH$_3$)$_2$ | H | CH$_2$(D-47a) |
| G-1 | 3,4-F$_2$-5-CF$_3$ | 2-NHC(O)CH$_3$ | C(O)OCH$_3$ | CH$_2$(D-47a) |
| G-1 | 3-Cl-4-F-5-CF$_3$ | 2-Pr-i | H | N(CH$_3$)Ph |
| G-1 | 3-Cl-4-F-5-CF$_3$ | 2-OEt | H | (D-50c)Cl |
| G-1 | 3-Cl-4-F-5-CF$_3$ | 2-OPr-i | H | CH$_2$CF$_3$ |
| G-1 | 3-Cl-4-F-5-CF$_3$ | 2-OSO$_2$CH$_3$ | H | CH$_2$OCH$_2$CF$_3$ |
| G-1 | 3-Cl-4-F-5-CF$_3$ | 2-SEt | H | E-4a |
| G-1 | 3-Cl-4-F-5-CF$_3$ | 2-SPr-i | H | CH$_2$C(O)NHCH$_2$CF$_3$ |
| G-1 | 3-Cl-4-F-5-CF$_3$ | 2-NHEt | H | CH$_2$(D-22a) |
| G-1 | 3-Cl-4-F-5-CF$_3$ | 2-NHPr-i | H | CH$_2$(D-47a) |
| G-1 | 3-Cl-4-F-5-CF$_3$ | 2-N(CH$_3$)$_2$ | C(O)OCH$_3$ | CH$_2$(D-47a) |
| G-1 | 3-Cl-4-F-5-CF$_3$ | 2-NHC(O)CH$_3$ | H | N(CH$_3$)Ph |
| G-1 | 3,4-Cl$_2$-5-CF$_3$ | 2-Pr-i | H | (D-55c)Cl |
| G-1 | 3,4-Cl$_2$-5-CF$_3$ | 2-OEt | H | CH$_2$CF$_3$ |
| G-1 | 3,4-Cl$_2$-5-CF$_3$ | 2-OPr-i | H | CH$_2$OCH$_2$CF$_3$ |
| G-1 | 3,4-Cl$_2$-5-CF$_3$ | 2-OSO$_2$CH$_3$ | H | E-4a |
| G-1 | 3,4-Cl$_2$-5-CF$_3$ | 2-SEt | H | CH$_2$C(O)NHCH$_2$CF$_3$ |
| G-1 | 3,4-Cl$_2$-5-CF$_3$ | 2-SPr-i | H | CH$_2$(D-22a) |
| G-1 | 3,4-Cl$_2$-5-CF$_3$ | 2-NHEt | H | CH$_2$(D-52a) |
| G-1 | 3,4-Cl$_2$-5-CF$_3$ | 2-NHPr-i | C(O)OCH$_3$ | CH$_2$(D-52a) |
| G-1 | 3,4-Cl$_2$-5-CF$_3$ | 2-N(CH$_3$)$_2$ | H | N(CH$_3$)Ph |
| G-1 | 3,4-Cl$_2$-5-CF$_3$ | 2-NHC(O)CH$_3$ | H | (D-55c)Cl |
| G-1 | 3,5-(CF$_3$)$_2$-4-Cl | 2-Pr-i | H | (D-50c)Cl |
| G-1 | 3,5-(CF$_3$)$_2$-4-Cl | 2-OEt | H | CH$_2$CF$_3$ |
| G-1 | 3,5-(CF$_3$)$_2$-4-Cl | 2-OPr-i | H | CH$_2$OCH$_2$CF$_3$ |
| G-1 | 3,5-(CF$_3$)$_2$-4-Cl | 2-OSO$_2$CH$_3$ | H | E-4a |
| G-1 | 3,5-(CF$_3$)$_2$-4-Cl | 2-SEt | H | CH$_2$C(O)NHCH$_2$CF$_3$ |
| G-1 | 3,5-(CF$_3$)$_2$-4-Cl | 2-SPr-i | H | CH$_2$(D-22a) |
| G-1 | 3,5-(CF$_3$)$_2$-4-Cl | 2-NHEt | H | CH$_2$(D-47a) |
| G-1 | 3,5-(CF$_3$)$_2$-4-Cl | 2-NHPr-i | C(O)OCH$_3$ | CH$_2$(D-47a) |
| G-1 | 3,5-(CF$_3$)$_2$-4-Cl | 2-N(CH$_3$)$_2$ | H | N(CH$_3$)Ph |
| G-1 | 3,5-(CF$_3$)$_2$-4-Cl | 2-NHC(O)CH$_3$ | H | (D-50c)Cl |
| G-2 | 4-Cl | 2-CH$_3$ | H | CH$_2$CF$_3$ |
| G-2 | 4-Br | 2-CH$_3$ | H | CH$_2$OCH$_2$CF$_3$ |
| G-2 | 4-CF$_3$ | 2-CH$_3$ | H | CH$_2$CF$_3$ |
| G-2 | 4-CF$_3$ | 2-CH$_3$ | H | E-4a |
| G-2 | 4-CF$_3$ | 2-CH$_3$ | H | CH$_2$C(O)NHCH$_2$CF$_3$ |
| G-2 | 4-CF$_3$ | 2-CH$_3$ | H | CH$_2$(D-22a) |
| G-2 | 4-CF$_3$ | 2-CH$_3$ | H | CH$_2$(D-47a) |
| G-2 | 4-CF$_3$ | 2-CH$_3$ | H | (D-50c)Cl |
| G-2 | 6-CF$_3$ | 2-CH$_3$ | H | CH$_2$CF$_3$ |
| G-2 | 6-CF$_3$ | 2-CH$_3$ | H | E-4a |
| G-2 | 6-CF$_3$ | 2-CH$_3$ | H | CH$_2$C(O)NHCH$_2$CF$_3$ |
| G-2 | 6-CF$_3$ | 2-CH$_3$ | H | CH$_2$(D-22a) |
| G-2 | 6-CF$_3$ | 2-CH$_3$ | H | CH$_2$(D-47a) |
| G-2 | 6-CF$_3$ | 2-CH$_3$ | H | (D-50c)Cl |
| G-2 | 4-CF$_3$-6-CH$_3$ | 2-CH$_3$ | H | E-4a |
| G-3 | 5-Cl | 2-CH$_3$ | H | CH$_2$C(O)NHCH$_2$CF$_3$ |
| G-3 | 5-CF$_3$ | 2-CH$_3$ | H | CH$_2$CF$_3$ |
| G-3 | 5-CF$_3$ | 2-CH$_3$ | H | CH$_2$OCH$_2$CF$_3$ |
| G-3 | 5-CF$_3$ | 2-CH$_3$ | H | E-4a |
| G-3 | 5-CF$_3$ | 2-CH$_3$ | H | CH$_2$C(O)NHCH$_2$CF$_3$ |
| G-3 | 5-CF$_3$ | 2-CH$_3$ | H | CH(CH$_3$)C(O)NHCH$_2$CF$_3$(D) |
| G-3 | 5-CF$_3$ | 2-CH$_3$ | H | CH$_2$(D-22a) |
| G-3 | 5-CF$_3$ | 2-CH$_3$ | H | CH$_2$(D-47a) |
| G-3 | 5-CF$_3$ | 2-CH$_3$ | C(O)OCH$_3$ | CH$_2$(D-47a) |
| G-3 | 5-CF$_3$ | 2-CH$_3$ | H | N(CH$_3$)Ph |
| G-3 | 5-CF$_3$ | 2-CH$_3$ | H | (D-50c)Cl |
| G-3 | 5-CF$_3$-6-Cl | 2-CH$_3$ | H | CH$_2$(D-22a) |
| G-3 | 5-NO$_2$-6-Cl | 2-CH$_3$ | H | CH$_2$(D-47a) |
| G-4 | 2-Cl | 2-CH$_3$ | C(O)OCH$_3$ | CH$_2$(D-47a) |
| G-4 | 2-Br | 2-CH$_3$ | H | N(CH$_3$)Ph |
| G-4 | 2-CF$_3$ | 2-CH$_3$ | H | CH$_2$CF$_3$ |
| G-4 | 2-CF$_3$ | 2-CH$_3$ | H | CH$_2$OCH$_2$CF$_3$ |
| G-4 | 2-CF$_3$ | 2-CH$_3$ | H | E-4a |
| G-4 | 2-CF$_3$ | 2-CH$_3$ | H | CH$_2$C(O)NHCH$_2$CF$_3$ |
| G-4 | 2-CF$_3$ | 2-CH$_3$ | H | CH(CH$_3$)C(O)NHCH$_2$CF$_3$(D) |
| G-4 | 2-CF$_3$ | 2-CH$_3$ | H | CH$_2$(D-22a) |
| G-4 | 2-CF$_3$ | 2-CH$_3$ | H | CH$_2$(D-47a) |
| G-4 | 2-CF$_3$ | 2-CH$_3$ | C(O)OCH$_3$ | CH$_2$(D-47a) |

TABLE 3-continued

| | | | | |
|---|---|---|---|---|
| G-4 | 2-CF$_3$ | 2-CH$_3$ | H | N(CH$_3$)Ph |
| G-4 | 2-CF$_3$ | 2-CH$_3$ | H | (D-50c)Cl |
| G-4 | 2,6-F$_2$ | 2-CH$_3$ | H | (D-50c)Cl |
| G-4 | 2,6-Cl$_2$ | — | H | CH$_2$CF$_3$ |
| G-4 | 2,6-Cl$_2$ | 2-F | H | CH$_2$OCH$_2$CF$_3$ |
| G-4 | 2,6-Cl$_2$ | 2-Cl | H | CH$_2$CF$_3$ |
| G-4 | 2,6-Cl$_2$ | 2-Cl | H | CH$_2$OCH$_2$CF$_3$ |
| G-4 | 2,6-Cl$_2$ | 2-Cl | H | E-4a |
| G-4 | 2,6-Cl$_2$ | 2-Cl | H | CH$_2$C(O)NHCH$_2$CF$_3$ |
| G-4 | 2,6-Cl$_2$ | 2-Cl | H | CH(CH$_3$)C(O)NHCH$_2$CF$_3$(D) |
| G-4 | 2,6-Cl$_2$ | 2-Cl | H | CH$_2$(D-22a) |
| G-4 | 2,6-Cl$_2$ | 2-Cl | H | CH$_2$(D-47a) |
| G-4 | 2,6-Cl$_2$ | 2-Cl | C(O)OCH$_3$ | CH$_2$(D-47a) |
| G-4 | 2,6-Cl$_2$ | 2-Cl | H | N(CH$_3$)Ph |
| G-4 | 2,6-Cl$_2$ | 2-Cl | H | (D-50c)Cl |
| G-4 | 2,6-Cl$_2$ | 2-Br | H | CH$_2$CF$_3$ |
| G-4 | 2,6-Cl$_2$ | 2-Br | H | CH$_2$OCH$_2$CF$_3$ |
| G-4 | 2,6-Cl$_2$ | 2-Br | H | E-4a |
| G-4 | 2,6-Cl$_2$ | 2-Br | H | CH$_2$C(O)NHCH$_2$CF$_3$ |
| G-4 | 2,6-Cl$_2$ | 2-Br | H | CH(CH$_3$)C(O)NHCH$_2$CF$_3$(D) |
| G-4 | 2,6-Cl$_2$ | 2-Br | H | CH$_2$(D-22a) |
| G-4 | 2,6-Cl$_2$ | 2-Br | H | CH$_2$(D-47a) |
| G-4 | 2,6-Cl$_2$ | 2-Br | C(O)OCH$_3$ | CH$_2$(D-47a) |
| G-4 | 2,6-Cl$_2$ | 2-Br | H | N(CH$_3$)Ph |
| G-4 | 2,6-Cl$_2$ | 2-Br | H | (D-50c)Cl |
| G-4 | 2,6-Cl$_2$ | 2-I | H | CH$_2$CF$_3$ |
| G-4 | 2,6-Cl$_2$ | 2-I | H | CH$_2$OCH$_2$CF$_3$ |
| G-4 | 2,6-Cl$_2$ | 2-I | H | E-4a |
| G-4 | 2,6-Cl$_2$ | 2-I | H | CH$_2$C(O)NHCH$_2$CF$_3$ |
| G-4 | 2,6-Cl$_2$ | 2-I | H | CH(CH$_3$)C(O)NHCH$_2$CF$_3$(D) |
| G-4 | 2,6-Cl$_2$ | 2-I | H | CH$_2$(D-22a) |
| G-4 | 2,6-Cl$_2$ | 2-I | H | CH$_2$(D-47a) |
| G-4 | 2,6-Cl$_2$ | 2-I | C(O)OCH$_3$ | CH$_2$(D-47a) |
| G-4 | 2,6-Cl$_2$ | 2-I | H | N(CH$_3$)Ph |
| G-4 | 2,6-Cl$_2$ | 2-I | H | (D-50c)Cl |
| G-4 | 2,6-Cl$_2$ | 2-CH$_3$ | H | CH$_2$CF$_3$ |
| G-4 | 2,6-Cl$_2$ | 2-CH$_3$ | C(O)CH$_3$ | CH$_2$CF$_3$ |
| G-4 | 2,6-Cl$_2$ | 2-CH$_3$ | H | CH$_2$OCH$_2$CF$_3$ |
| G-4 | 2,6-Cl$_2$ | 2-CH$_3$ | H | E-4a |
| G-4 | 2,6-Cl$_2$ | 2-CH$_3$ | H | CH$_2$C(O)NHCH$_2$CF$_3$ |
| G-4 | 2,6-Cl$_2$ | 2-CH$_3$ | H | CH(CH$_3$)C(O)NHCH$_2$CF$_3$(D) |
| G-4 | 2,6-Cl$_2$ | 2-CH$_3$ | H | CH(CH$_3$)Ph(R) |
| G-4 | 2,6-Cl$_2$ | 2-CH$_3$ | H | CH$_2$(D-22a) |
| G-4 | 2,6-Cl$_2$ | 2-CH$_3$ | H | CH$_2$(D-47a) |
| G-4 | 2,6-Cl$_2$ | 2-CH$_3$ | CH$_2$CN | CH$_2$(D-47a) |
| G-4 | 2,6-Cl$_2$ | 2-CH$_3$ | C(O)Et | CH$_2$(D-47a) |
| G-4 | 2,6-Cl$_2$ | 2-CH$_3$ | C(O)OCH$_3$ | CH$_2$(D-47a) |
| G-4 | 2,6-Cl$_2$ | 2-CH$_3$ | H | N(CH$_3$)Ph |
| G-4 | 2,6-Cl$_2$ | 2-CH$_3$ | H | (D-50c)Cl |
| G-4 | 2,6-Cl$_2$ | 2-CH$_3$ | H | D-52a |
| G-4 | 2,6-Cl$_2$ | 2-Et | H | CH$_2$CF$_3$ |
| G-4 | 2,6-Cl$_2$ | 2-Et | H | CH$_2$OCH$_2$CF$_3$ |
| G-4 | 2,6-Cl$_2$ | 2-Et | H | E-4a |
| G-4 | 2,6-Cl$_2$ | 2-Et | H | CH$_2$C(O)NHCH$_2$CF$_3$ |
| G-4 | 2,6-Cl$_2$ | 2-Et | H | CH(CH$_3$)C(O)NHCH$_2$CF$_3$(D) |
| G-4 | 2,6-Cl$_2$ | 2-Et | H | CH$_2$(D-22a) |
| G-4 | 2,6-Cl$_2$ | 2-Et | H | CH$_2$(D-47a) |
| G-4 | 2,6-Cl$_2$ | 2-Et | C(O)OCH$_3$ | CH$_2$(D-47a) |
| G-4 | 2,6-Cl$_2$ | 2-Et | H | N(CH$_3$)Ph |
| G-4 | 2,6-Cl$_2$ | 2-Et | H | (D-50c)Cl |
| G-4 | 2,6-Cl$_2$ | 2-CF$_3$ | H | CH$_2$CF$_3$ |
| G-4 | 2,6-Cl$_2$ | 2-CF$_3$ | H | CH$_2$OCH$_2$CF$_3$ |
| G-4 | 2,6-Cl$_2$ | 2-CF$_3$ | H | E-4a |
| G-4 | 2,6-Cl$_2$ | 2-CF$_3$ | H | CH$_2$C(O)NHCH$_2$CF$_3$ |
| G-4 | 2,6-Cl$_2$ | 2-CF$_3$ | H | CH(CH$_3$)C(O)NHCH$_2$CF$_3$(D) |
| G-4 | 2,6-Cl$_2$ | 2-CF$_3$ | H | CH$_2$(D-22a) |
| G-4 | 2,6-Cl$_2$ | 2-CF$_3$ | H | CH$_2$(D-47a) |
| G-4 | 2,6-Cl$_2$ | 2-CF$_3$ | C(O)OCH$_3$ | CH$_2$(D-47a) |
| G-4 | 2,6-Cl$_2$ | 2-CF$_3$ | H | N(CH$_3$)Ph |
| G-4 | 2,6-Cl$_2$ | 2-CF$_3$ | H | (D-50c)Cl |
| G-4 | 2,6-Cl$_2$ | 2-OCH$_3$ | H | E-4a |
| G-4 | 2,6-Cl$_2$ | 2-OCHF$_2$ | H | CH$_2$C(O)NHCH$_2$CF$_3$ |
| G-4 | 2,6-Cl$_2$ | 2-OCF$_3$ | H | CH$_2$(D-22a) |
| G-4 | 2,6-Cl$_2$ | 2-SCH$_3$ | H | CH$_2$(D-47a) |
| G-4 | 2,6-Cl$_2$ | 2-SCF$_3$ | C(O)OCH$_3$ | CH$_2$(D-47a) |
| G-4 | 2,6-Cl$_2$ | 2-NO$_2$ | H | N(CH$_3$)Ph |
| G-4 | 2,6-Cl$_2$ | 2-NHCH$_3$ | H | (D-50c)Cl |
| G-4 | 2,6-Cl$_2$ | 2-NHEt | H | CH$_2$CF$_3$ |
| G-4 | 2,6-Br$_2$ | 2-CH$_3$ | H | CH$_2$CF$_3$ |
| G-4 | 2,6-Br$_2$ | 2-CH$_3$ | H | CH$_2$OCH$_2$CF$_3$ |

TABLE 3-continued

| | | | | |
|---|---|---|---|---|
| G-4 | 2,6-Br$_2$ | 2-CH$_3$ | H | E-4a |
| G-4 | 2,6-Br$_2$ | 2-CH$_3$ | H | CH$_2$C(O)NHCH$_2$CF$_3$ |
| G-4 | 2,6-Br$_2$ | 2-CH$_3$ | H | CH(CH$_3$)C(O)NHCH$_2$CF$_3$(D) |
| G-4 | 2,6-Br$_2$ | 2-CH$_3$ | H | CH$_2$(D-22a) |
| G-4 | 2,6-Br$_2$ | 2-CH$_3$ | H | CH$_2$(D-47a) |
| G-4 | 2,6-Br$_2$ | 2-CH$_3$ | C(O)OCH$_3$ | CH$_2$(D-47a) |
| G-4 | 2,6-Br$_2$ | 2-CH$_3$ | H | N(CH$_3$)Ph |
| G-4 | 2,6-Br$_2$ | 2-CH$_3$ | H | (D-50c)Cl |
| G-4 | 2-Br-6-CF$_3$ | 2-CH$_3$ | H | CH$_2$CF$_3$ |
| G-4 | 2-Br-6-CF$_3$ | 2-CH$_3$ | H | CH$_2$OCH$_2$CF$_3$ |
| G-4 | 2-Br-6-CF$_3$ | 2-CH$_3$ | H | E-4a |
| G-4 | 2-Br-6-CF$_3$ | 2-CH$_3$ | H | CH$_2$C(O)NHCH$_2$CF$_3$ |
| G-4 | 2-Br-6-CF$_3$ | 2-CH$_3$ | H | CH(CH$_3$)C(O)NHCH$_2$CF$_3$(D) |
| G-4 | 2-Br-6-CF$_3$ | 2-CH$_3$ | H | CH$_2$(D-22a) |
| G-4 | 2-Br-6-CF$_3$ | 2-CH$_3$ | H | CH$_2$(D-47a) |
| G-4 | 2-Br-6-CF$_3$ | 2-CH$_3$ | C(O)OCH$_3$ | CH$_2$(D-47a) |
| G-4 | 2-Br-6-CF$_3$ | 2-CH$_3$ | H | N(CH$_3$)Ph |
| G-4 | 2-Br-6-CF$_3$ | 2-CH$_3$ | H | (D-50c)Cl |
| G-4 | 2,6-(CF$_3$)$_2$ | 2-CH$_3$ | H | CH$_2$CF$_3$ |
| G-4 | 2,6-(CF$_3$)$_2$ | 2-CH$_3$ | H | CH$_2$OCH$_2$CF$_3$ |
| G-4 | 2,6-(CF$_3$)$_2$ | 2-CH$_3$ | H | E-4a |
| G-4 | 2,6-(CF$_3$)$_2$ | 2-CH$_3$ | H | CH$_2$C(O)NHCH$_2$CF$_3$ |
| G-4 | 2,6-(CF$_3$)$_2$ | 2-CH$_3$ | H | CH(CH$_3$)C(O)NHCH$_2$CF$_3$(D) |
| G-4 | 2,6-(CF$_3$)$_2$ | 2-CH$_3$ | H | CH$_2$(D-22a) |
| G-4 | 2,6-(CF$_3$)$_2$ | 2-CH$_3$ | H | CH$_2$(D-47a) |
| G-4 | 2,6-(CF$_3$)$_2$ | 2-CH$_3$ | C(O)OCH$_3$ | CH$_2$(D-47a) |
| G-4 | 2,6-(CF$_3$)$_2$ | 2-CH$_3$ | H | N(CH$_3$)Ph |
| G-4 | 2,6-(CF$_3$)$_2$ | 2-CH$_3$ | H | (D-50c)Cl |
| G-5 | 2-CF$_3$ | 2-CH$_3$ | H | CH$_2$CF$_3$ |
| G-5 | 2-CF$_3$ | 2-CH$_3$ | H | E-4a |
| G-5 | 2-CF$_3$ | 2-CH$_3$ | H | CH$_2$C(O)NHCH$_2$CF$_3$ |
| G-5 | 2-CF$_3$ | 2-CH$_3$ | H | CH$_2$(D-22a) |
| G-5 | 2-CF$_3$ | 2-CH$_3$ | H | CH$_2$(D-47a) |
| G-5 | 2-CF$_3$ | 2-CH$_3$ | H | (D-50c)Cl |
| G-5 | 6-CF$_3$ | 2-CH$_3$ | H | CH$_2$CF$_3$ |
| G-5 | 6-CF$_3$ | 2-CH$_3$ | H | E-4a |
| G-5 | 6-CF$_3$ | 2-CH$_3$ | H | CH$_2$C(O)NHCH$_2$CF$_3$ |
| G-5 | 6-CF$_3$ | 2-CH$_3$ | H | CH$_2$(D-22a) |
| G-5 | 6-CF$_3$ | 2-CH$_3$ | H | CH$_2$(D-47a) |
| G-5 | 6-CF$_3$ | 2-CH$_3$ | H | (D-50c)Cl |
| G-5 | 2,6-Cl$_2$ | 2-CH$_3$ | H | CH$_2$CF$_3$ |
| G-5 | 2,6-Cl$_2$ | 2-CH$_3$ | H | E-4a |
| G-5 | 2,6-Cl$_2$ | 2-CH$_3$ | H | CH$_2$C(O)NHCH$_2$CF$_3$ |
| G-5 | 2,6-Cl$_2$ | 2-CH$_3$ | H | CH$_2$(D-22a) |
| G-5 | 2,6-Cl$_2$ | 2-CH$_3$ | H | CH$_2$(D-47a) |
| G-5 | 2,6-Cl$_2$ | 2-CH$_3$ | H | (D-50c)Cl |
| G-5 | 2-CH$_3$-6-Cl | 2-CH$_3$ | H | CH$_2$OCH$_2$CF$_3$ |
| G-5 | 2-Cl-6-CF$_3$ | 2-CH$_3$ | H | CH$_2$CF$_3$ |
| G-5 | 2-Cl-6-CF$_3$ | 2-CH$_3$ | H | E-4a |
| G-5 | 2-Cl-6-CF$_3$ | 2-CH$_3$ | H | CH$_2$C(O)NHCH$_2$CF$_3$ |
| G-5 | 2-Cl-6-CF$_3$ | 2-CH$_3$ | H | CH$_2$(D-22a) |
| G-5 | 2-Cl-6-CF$_3$ | 2-CH$_3$ | H | CH$_2$(D-47a) |
| G-5 | 2-Cl-6-CF$_3$ | 2-CH$_3$ | H | (D-50c)Cl |
| G-5 | 2-Br-6-CF$_3$ | 2-CH$_3$ | H | CH$_2$CF$_3$ |
| G-5 | 2-Br-6-CF$_3$ | 2-CH$_3$ | H | E-4a |
| G-5 | 2-Br-6-CF$_3$ | 2-CH$_3$ | H | CH$_2$C(O)NHCH$_2$CF$_3$ |
| G-5 | 2-Br-6-CF$_3$ | 2-CH$_3$ | H | CH$_2$(D-22a) |
| G-5 | 2-Br-6-CF$_3$ | 2-CH$_3$ | H | CH$_2$(D-47a) |
| G-5 | 2-Br-6-CF$_3$ | 2-CH$_3$ | H | (D-50c)Cl |
| G-5 | 2-CH$_3$-6-CF$_3$ | 2-CH$_3$ | H | CH$_2$CF$_3$ |
| G-5 | 2-CH$_3$-6-CF$_3$ | 2-CH$_3$ | H | E-4a |
| G-5 | 2-CH$_3$-6-CF$_3$ | 2-CH$_3$ | H | CH$_2$C(O)NHCH$_2$CF$_3$ |
| G-5 | 2-CH$_3$-6-CF$_3$ | 2-CH$_3$ | H | CH$_2$(D-22a) |
| G-5 | 2-CH$_3$-6-CF$_3$ | 2-CH$_3$ | H | CH$_2$(D-47a) |
| G-5 | 2-CH$_3$-6-CF$_3$ | 2-CH$_3$ | H | (D-50c)Cl |
| G-5 | 2,6-(CF$_3$)$_2$ | 2-CH$_3$ | H | CH$_2$CF$_3$ |
| G-5 | 2,6-(CF$_3$)$_2$ | 2-CH$_3$ | H | E-4a |
| G-5 | 2,6-(CF$_3$)$_2$ | 2-CH$_3$ | H | CH$_2$C(O)NHCH$_2$CF$_3$ |
| G-5 | 2,6-(CF$_3$)$_2$ | 2-CH$_3$ | H | CH$_2$(D-22a) |
| G-5 | 2,6-(CF$_3$)$_2$ | 2-CH$_3$ | H | CH$_2$(D-47a) |
| G-5 | 2,6-(CF$_3$)$_2$ | 2-CH$_3$ | H | (D-50c)Cl |
| G-5 | 2-SCH$_3$-6-Cl | 2-CH$_3$ | H | E-4a |
| G-5 | 2-SCH$_3$-6-CF$_3$ | 2-CH$_3$ | H | CH$_2$C(O)NHCH$_2$CF$_3$ |
| G-11 | 4-CF$_3$ | 2-CH$_3$ | H | CH$_2$CF$_3$ |
| G-11 | 4-CF$_3$ | 2-CH$_3$ | H | E-4a |
| G-11 | 4-CF$_3$ | 2-CH$_3$ | H | CH$_2$C(O)NHCH$_2$CF$_3$ |
| G-11 | 4-CF$_3$ | 2-CH$_3$ | H | CH$_2$(D-22a) |
| G-11 | 4-CF$_3$ | 2-CH$_3$ | H | CH$_2$(D-47a) |
| G-11 | 4-CF$_3$ | 2-CH$_3$ | H | (D-50c)Cl |
| G-11 | 5-CF$_3$ | 2-CH$_3$ | H | CH$_2$CF$_3$ |

TABLE 3-continued

| | | | | |
|---|---|---|---|---|
| G-11 | 5-CF$_3$ | 2-CH$_3$ | H | E-4a |
| G-11 | 5-CF$_3$ | 2-CH$_3$ | H | CH$_2$C(O)NHCH$_2$CF$_3$ |
| G-11 | 5-CF$_3$ | 2-CH$_3$ | H | CH$_2$(D-22a) |
| G-11 | 5-CF$_3$ | 2-CH$_3$ | H | CH$_2$(D-47a) |
| G-11 | 5-CF$_3$ | 2-CH$_3$ | H | (D-50c)Cl |
| G-12 | 5-CF$_3$ | 2-CH$_3$ | H | CH$_2$CF$_3$ |
| G-12 | 5-CF$_3$ | 2-CH$_3$ | H | E-4a |
| G-12 | 5-CF$_3$ | 2-CH$_3$ | H | CH$_2$C(O)NHCH$_2$CF$_3$ |
| G-12 | 5-CF$_3$ | 2-CH$_3$ | H | CH$_2$(D-22a) |
| G-12 | 5-CF$_3$ | 2-CH$_3$ | H | CH$_2$(D-47a) |
| G-12 | 5-CF$_3$ | 2-CH$_3$ | H | (D-50c)Cl |
| G-13 | 4-CF$_3$ | 2-CH$_3$ | H | CH$_2$CF$_3$ |
| G-13 | 4-CF$_3$ | 2-CH$_3$ | H | CH$_2$OCH$_2$CF$_3$ |
| G-13 | 4-CF$_3$ | 2-CH$_3$ | H | E-4a |
| G-13 | 4-CF$_3$ | 2-CH$_3$ | H | CH$_2$C(O)NHCH$_2$CF$_3$ |
| G-13 | 4-CF$_3$ | 2-CH$_3$ | H | CH(CH$_3$)C(O)NHCH$_2$CF$_3$(D) |
| G-13 | 4-CF$_3$ | 2-CH$_3$ | H | CH$_2$(D-22a) |
| G-13 | 4-CF$_3$ | 2-CH$_3$ | H | CH$_2$(D-47a) |
| G-13 | 4-CF$_3$ | 2-CH$_3$ | C(O)OCH$_3$ | CH$_2$(D-47a) |
| G-13 | 4-CF$_3$ | 2-CH$_3$ | H | N(CH$_3$)Ph |
| G-13 | 4-CF$_3$ | 2-CH$_3$ | H | (D-50c)Cl |
| G-13 | 5-CF$_3$ | 2-CH$_3$ | H | CH$_2$CF$_3$ |
| G-13 | 5-CF$_3$ | 2-CH$_3$ | H | CH$_2$OCH$_2$CF$_3$ |
| G-13 | 5-CF$_3$ | 2-CH$_3$ | H | E-4a |
| G-13 | 5-CF$_3$ | 2-CH$_3$ | H | CH$_2$C(O)NHCH$_2$CF$_3$ |
| G-13 | 5-CF$_3$ | 2-CH$_3$ | H | CH(CH$_3$)C(O)NHCH$_2$CF$_3$(D) |
| G-13 | 5-CF$_3$ | 2-CH$_3$ | H | CH$_2$(D-22a) |
| G-13 | 5-CF$_3$ | 2-CH$_3$ | H | CH$_2$(D-47a) |
| G-13 | 5-CF$_3$ | 2-CH$_3$ | C(O)OCH$_3$ | CH$_2$(D-47a) |
| G-13 | 5-CF$_3$ | 2-CH$_3$ | H | N(CH$_3$)Ph |
| G-13 | 5-CF$_3$ | 2-CH$_3$ | H | (D-50c)Cl |
| G-13 | 4,5-Cl$_2$ | 2-CH$_3$ | H | CH$_2$CF$_3$ |
| G-13 | 4,5-Cl$_2$ | 2-CH$_3$ | H | CH$_2$OCH$_2$CF$_3$ |
| G-13 | 4,5-Cl$_2$ | 2-CH$_3$ | H | E-4a |
| G-13 | 4,5-Cl$_2$ | 2-CH$_3$ | H | CH$_2$C(O)NHCH$_2$CF$_3$ |
| G-13 | 4,5-Cl$_2$ | 2-CH$_3$ | H | CH(CH$_3$)C(O)NHCH$_2$CF$_3$(D) |
| G-13 | 4,5-Cl$_2$ | 2-CH$_3$ | H | CH$_2$(D-22a) |
| G-13 | 4,5-Cl$_2$ | 2-CH$_3$ | H | CH$_2$(D-47a) |
| G-13 | 4,5-Cl$_2$ | 2-CH$_3$ | C(O)OCH$_3$ | CH$_2$(D-47a) |
| G-13 | 4,5-Cl$_2$ | 2-CH$_3$ | H | N(CH$_3$)Ph |
| G-13 | 4,5-Cl$_2$ | 2-CH$_3$ | H | (D-50c)Cl |
| G-13 | 4-Cl-5-Br | 2-CH$_3$ | H | CH$_2$CF$_3$ |
| G-13 | 4-Cl-5-Br | 2-CH$_3$ | H | E-4a |
| G-13 | 4-Cl-5-Br | 2-CH$_3$ | H | CH$_2$C(O)NHCH$_2$CF$_3$ |
| G-13 | 4-Cl-5-Br | 2-CH$_3$ | H | CH$_2$(D-22a) |
| G-13 | 4-Cl-5-Br | 2-CH$_3$ | H | CH$_2$(D-47a) |
| G-13 | 4-Cl-5-Br | 2-CH$_3$ | H | (D-50c)Cl |
| G-13 | 4-Br-5-Cl | 2-CH$_3$ | H | CH$_2$CF$_3$ |
| G-13 | 4-Br-5-Cl | 2-CH$_3$ | H | E-4a |
| G-13 | 4-Br-5-Cl | 2-CH$_3$ | H | CH$_2$C(O)NHCH$_2$CF$_3$ |
| G-13 | 4-Br-5-Cl | 2-CH$_3$ | H | CH$_2$(D-22a) |
| G-13 | 4-Br-5-Cl | 2-CH$_3$ | H | CH$_2$(D-47a) |
| G-13 | 4-Br-5-Cl | 2-CH$_3$ | H | (D-50c)Cl |
| G-13 | 4,5-Br$_2$ | 2-CH$_3$ | H | CH$_2$CF$_3$ |
| G-13 | 4,5-Br$_2$ | 2-CH$_3$ | H | E-4a |
| G-13 | 4,5-Br$_2$ | 2-CH$_3$ | H | CH$_2$C(O)NHCH$_2$CF$_3$ |
| G-13 | 4,5-Br$_2$ | 2-CH$_3$ | H | CH$_2$(D-22a) |
| G-13 | 4,5-Br$_2$ | 2-CH$_3$ | H | CH$_2$(D-47a) |
| G-13 | 4,5-Br$_2$ | 2-CH$_3$ | H | (D-50c)Cl |
| G-14 | 5-CF$_3$ | 2-CH$_3$ | H | CH$_2$CF$_3$ |
| G-14 | 5-CF$_3$ | 2-CH$_3$ | H | CH$_2$OCH$_2$CF$_3$ |
| G-14 | 5-CF$_3$ | 2-CH$_3$ | H | E-4a |
| G-14 | 5-CF$_3$ | 2-CH$_3$ | H | CH$_2$C(O)NHCH$_2$CF$_3$ |
| G-14 | 5-CF$_3$ | 2-CH$_3$ | H | CH(CH$_3$)C(O)NHCH$_2$CF$_3$(D) |
| G-14 | 5-CF$_3$ | 2-CH$_3$ | H | CH$_2$(D-22a) |
| G-14 | 5-CF$_3$ | 2-CH$_3$ | H | CH$_2$(D-47a) |
| G-14 | 5-CF$_3$ | 2-CH$_3$ | C(O)OCH$_3$ | CH$_2$(D-47a) |
| G-14 | 5-CF$_3$ | 2-CH$_3$ | H | N(CH$_3$)Ph |
| G-14 | 5-CF$_3$ | 2-CH$_3$ | H | (D-50c)Cl |
| G-16 | 3-CF$_3$ | 2-CH$_3$ | H | CH$_2$CF$_3$ |
| G-16 | 3-CF$_3$ | 2-CH$_3$ | H | E-4a |
| G-16 | 3-CF$_3$ | 2-CH$_3$ | H | CH$_2$C(O)NHCH$_2$CF$_3$ |
| G-16 | 3-CF$_3$ | 2-CH$_3$ | H | CH$_2$(D-22a) |
| G-16 | 3-CF$_3$ | 2-CH$_3$ | H | CH$_2$(D-47a) |
| G-16 | 3-CF$_3$ | 2-CH$_3$ | H | (D-50c)Cl |
| G-17a | 5-CF$_3$ | 2-CH$_3$ | H | CH$_2$CF$_3$ |
| G-17a | 5-CF$_3$ | 2-CH$_3$ | H | CH$_2$OCH$_2$CF$_3$ |
| G-17a | 5-CF$_3$ | 2-CH$_3$ | H | E-4a |
| G-17a | 5-CF$_3$ | 2-CH$_3$ | H | CH$_2$C(O)NHCH$_2$CF$_3$ |
| G-17a | 5-CF$_3$ | 2-CH$_3$ | H | CH(CH$_3$)C(O)NHCH$_2$CF$_3$(D) |

TABLE 3-continued

| | | | | |
|---|---|---|---|---|
| G-17a | 5-$CF_3$ | 2-$CH_3$ | H | $CH_2$(D-22a) |
| G-17a | 5-$CF_3$ | 2-$CH_3$ | H | $CH_2$(D-47a) |
| G-17a | 5-$CF_3$ | 2-$CH_3$ | C(O)O$CH_3$ | $CH_2$(D-47a) |
| G-17a | 5-$CF_3$ | 2-$CH_3$ | H | N($CH_3$)Ph |
| G-17a | 5-$CF_3$ | 2-$CH_3$ | H | (D-50c)Cl |
| G-19a | 3-$CF_3$ | 2-$CH_3$ | H | $CH_2CF_3$ |
| G-19a | 3-$CF_3$ | 2-$CH_3$ | H | E-4a |
| G-19a | 3-$CF_3$ | 2-$CH_3$ | H | $CH_2$C(O)NH$CH_2CF_3$ |
| G-19a | 3-$CF_3$ | 2-$CH_3$ | H | $CH_2$(D-22a) |
| G-19a | 3-$CF_3$ | 2-$CH_3$ | H | $CH_2$(D-47a) |
| G-19a | 3-$CF_3$ | 2-$CH_3$ | H | (D-50c)Cl |
| G-20 | 4-$CF_3$ | 2-$CH_3$ | H | $CH_2CF_3$ |
| G-20 | 4-$CF_3$ | 2-$CH_3$ | H | $CH_2$O$CH_2CF_3$ |
| G-20 | 4-$CF_3$ | 2-$CH_3$ | H | E-4a |
| G-20 | 4-$CF_3$ | 2-$CH_3$ | H | $CH_2$C(O)NH$CH_2CF_3$ |
| G-20 | 4-$CF_3$ | 2-$CH_3$ | H | CH($CH_3$)C(O)NH$CH_2CF_3$(D) |
| G-20 | 4-$CF_3$ | 2-$CH_3$ | H | $CH_2$(D-22a) |
| G-20 | 4-$CF_3$ | 2-$CH_3$ | H | $CH_2$(D-47a) |
| G-20 | 4-$CF_3$ | 2-$CH_3$ | C(O)O$CH_3$ | $CH_2$(D-47a) |
| G-20 | 4-$CF_3$ | 2-$CH_3$ | H | N($CH_3$)Ph |
| G-20 | 4-$CF_3$ | 2-$CH_3$ | H | (D-50c)Cl |
| G-20 | 5-$CF_3$ | 2-$CH_3$ | H | $CH_2CF_3$ |
| G-20 | 5-$CF_3$ | 2-$CH_3$ | H | $CH_2$O$CH_2CF_3$ |
| G-20 | 5-$CF_3$ | 2-$CH_3$ | H | E-4a |
| G-20 | 5-$CF_3$ | 2-$CH_3$ | H | $CH_2$C(O)NH$CH_2CF_3$ |
| G-20 | 5-$CF_3$ | 2-$CH_3$ | H | CH($CH_3$)C(O)NH$CH_2CF_3$(D) |
| G-20 | 5-$CF_3$ | 2-$CH_3$ | H | $CH_2$(D-22a) |
| G-20 | 5-$CF_3$ | 2-$CH_3$ | H | $CH_2$(D-47a) |
| G-20 | 5-$CF_3$ | 2-$CH_3$ | C(O)O$CH_3$ | $CH_2$(D-47a) |
| G-20 | 5-$CF_3$ | 2-$CH_3$ | H | N($CH_3$)Ph |
| G-20 | 5-$CF_3$ | 2-$CH_3$ | H | (D-50c)Cl |
| G-21 | 2-$CF_3$ | 2-$CH_3$ | H | $CH_2CF_3$ |
| G-21 | 2-$CF_3$ | 2-$CH_3$ | H | $CH_2$O$CH_2CF_3$ |
| G-21 | 2-$CF_3$ | 2-$CH_3$ | H | E-4a |
| G-21 | 2-$CF_3$ | 2-$CH_3$ | H | $CH_2$C(O)NH$CH_2CF_3$ |
| G-21 | 2-$CF_3$ | 2-$CH_3$ | H | CH($CH_3$)C(O)NH$CH_2CF_3$(D) |
| G-21 | 2-$CF_3$ | 2-$CH_3$ | H | $CH_2$(D-22a) |
| G-21 | 2-$CF_3$ | 2-$CH_3$ | H | $CH_2$(D-47a) |
| G-21 | 2-$CF_3$ | 2-$CH_3$ | C(O)O$CH_3$ | $CH_2$(D-47a) |
| G-21 | 2-$CF_3$ | 2-$CH_3$ | H | N($CH_3$)Ph |
| G-21 | 2-$CF_3$ | 2-$CH_3$ | H | (D-50c)Cl |
| G-22 | 2-Cl | 2-$CH_3$ | H | $CH_2CF_3$ |
| G-22 | 2-Cl | 2-$CH_3$ | H | E-4a |
| G-22 | 2-Cl | 2-$CH_3$ | H | $CH_2$C(O)NH$CH_2CF_3$ |
| G-22 | 2-Cl | 2-$CH_3$ | H | $CH_2$(D-22a) |
| G-22 | 2-Cl | 2-$CH_3$ | H | $CH_2$(D-47a) |
| G-22 | 2-Cl | 2-$CH_3$ | H | (D-50c)Cl |

TABLE 4

In the table, the number showing the substitution position of substituents $(X)_m$ and $(Y)_n$ corresponds to the position number indicated in the following structural formulae. The indication "-" means no-substitution.

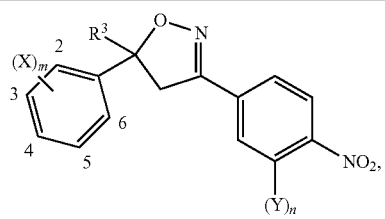

[3]-1

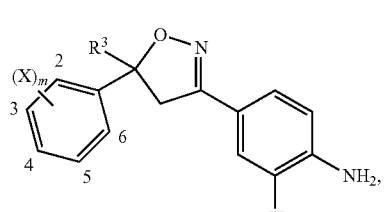

[3]-2

TABLE 4-continued
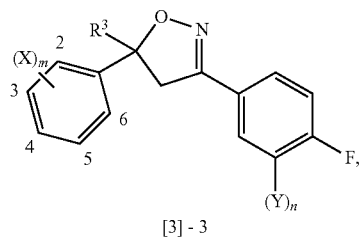
[3] - 3
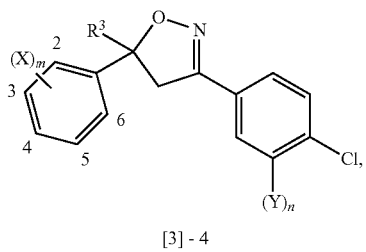
[3] - 4
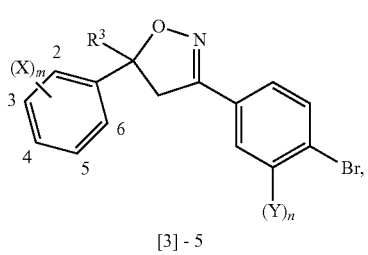
[3] - 5
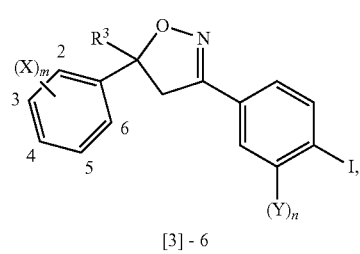
[3] - 6
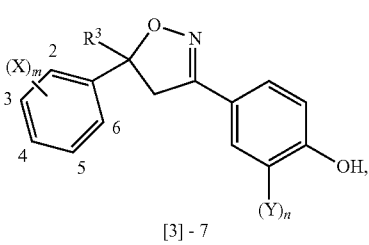
[3] - 7
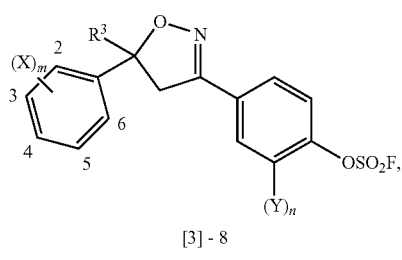
[3] - 8

TABLE 4-continued
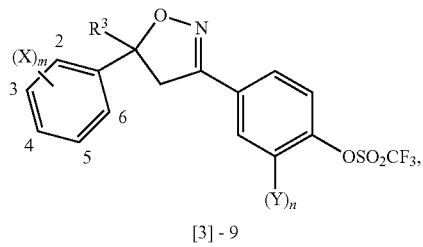
[3] - 9
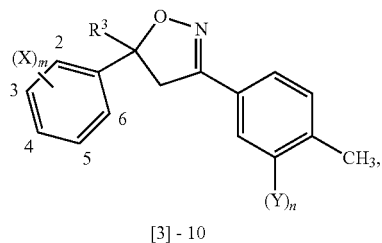
[3] - 10
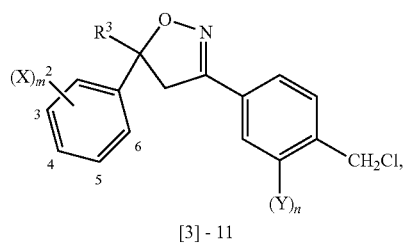
[3] - 11
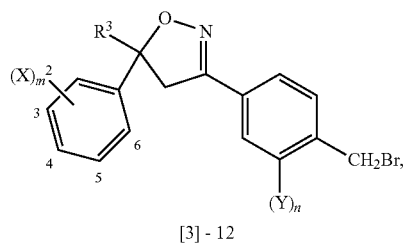
[3] - 12
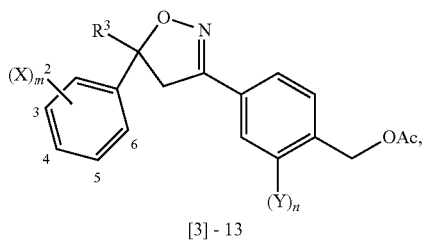
[3] - 13
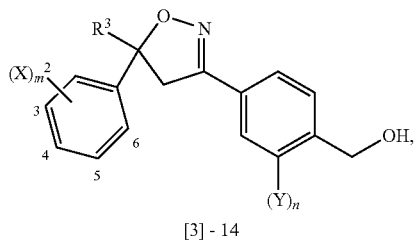
[3] - 14

TABLE 4-continued
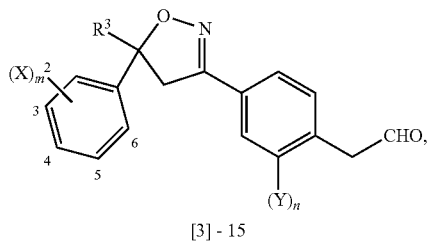
[3] - 15
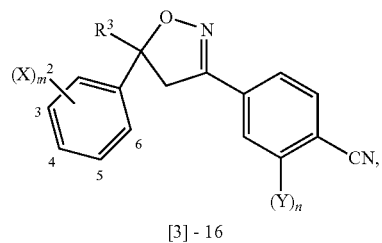
[3] - 16
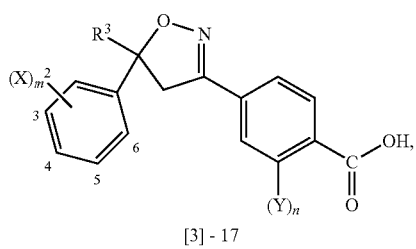
[3] - 17
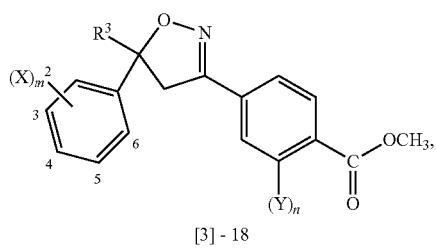
[3] - 18
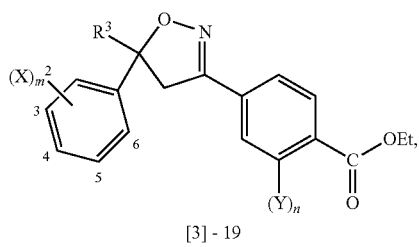
[3] - 19
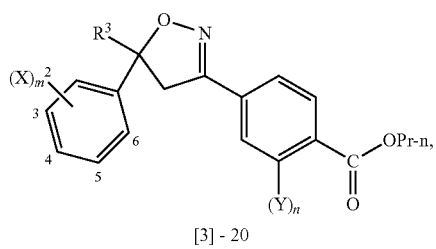
[3] - 20

TABLE 4-continued
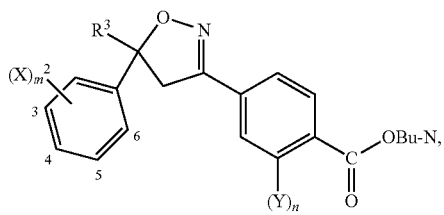
[3] - 21
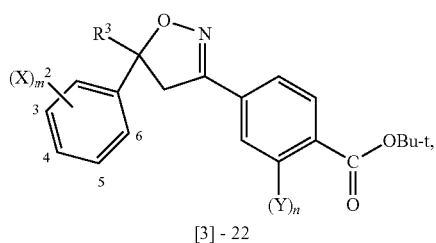
[3] - 22
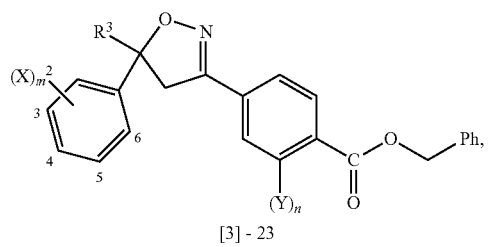
[3] - 23
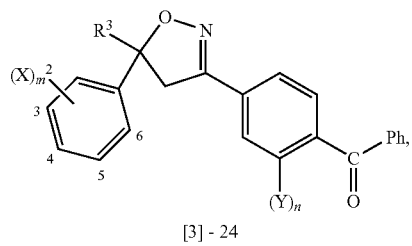
[3] - 24
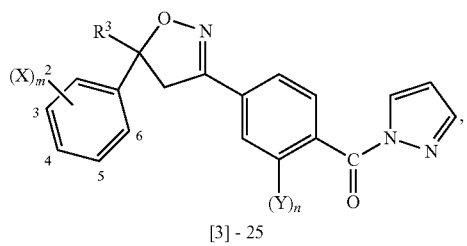
[3] - 25
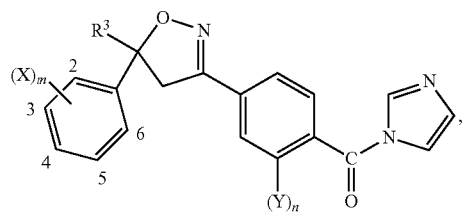
[3]-26

TABLE 4-continued
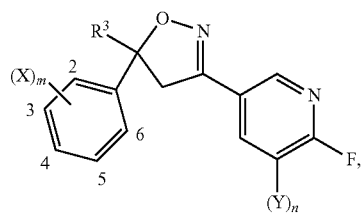
[3] - 27
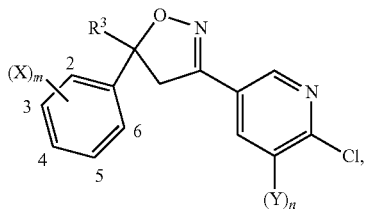
[3] - 28
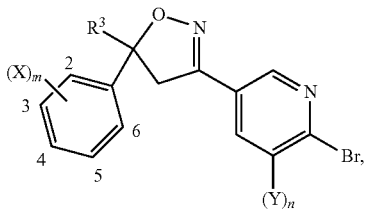
[3] - 29
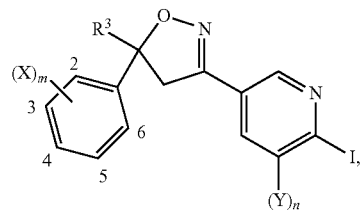
[3] - 30
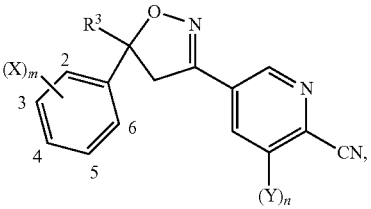
[3] - 31
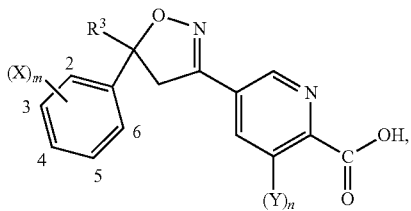
[3] - 32

TABLE 4-continued

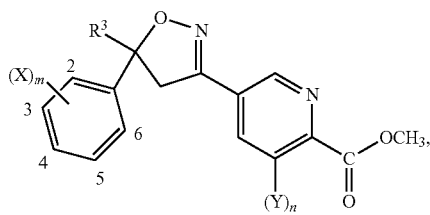

[3] - 33

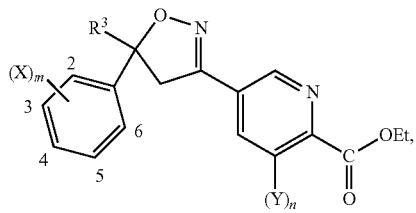

[3] - 34

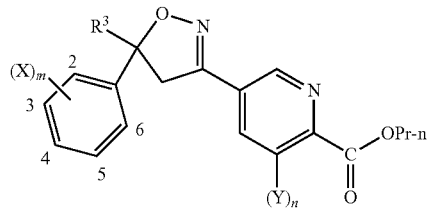

[3] - 35

または

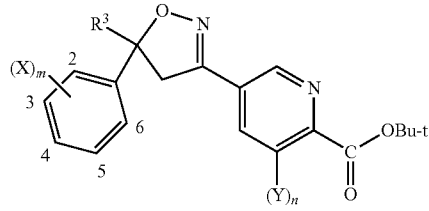

[3] - 36

| (X)$_m$ | R$^3$ | (Y)$_n$ | (X)$_m$ | R$^3$ | (Y)$_n$ |
|---|---|---|---|---|---|
| 3-F | CF$_3$ | CH$_3$ | 3,5-Br$_2$ | CF$_2$Br | CH$_3$ |
| 3-Cl | CF$_3$ | CH$_3$ | 3,5-Br$_2$ | CF$_2$Br | CF$_3$ |
| 3-Br | CF$_3$ | F | 3,5-Br$_2$ | CF$_2$CHF$_2$ | Cl |
| 3-Br | CF$_3$ | Cl | 3,5-Br$_2$ | CF$_2$CHF$_2$ | Br |
| 3-Br | CF$_3$ | Br | 3,5-Br$_2$ | CF$_2$CHF$_2$ | I |
| 3-Br | CF$_3$ | I | 3,5-Br$_2$ | CF$_2$CHF$_2$ | CH$_3$ |
| 3-Br | CF$_3$ | CH$_3$ | 3,5-Br$_2$ | CF$_2$CHF$_2$ | CF$_3$ |
| 3-Br | CF$_3$ | Et | 3,5-Br$_2$ | CF$_2$CF$_3$ | CH$_3$ |
| 3-Br | CF$_3$ | CF$_3$ | 3,5-Br$_2$ | CF$_2$OCH$_3$ | CH$_3$ |
| 3-Br | CF$_3$ | SCH$_3$ | 3,5-Br$_2$ | T-3 | CH$_3$ |
| 3-Br | CF$_3$ | NO$_2$ | 3-F-5-I | CF$_3$ | Cl |
| 3-Br | CF$_2$Cl | CH$_3$ | 3-F-5-I | CF$_3$ | Br |
| 3-I | CF$_3$ | F | 3-F-5-I | CF$_3$ | I |
| 3-I | CF$_3$ | Cl | 3-F-5-I | CF$_3$ | CH$_3$ |
| 3-I | CF$_3$ | Br | 3-F-5-I | CF$_3$ | CF$_3$ |
| 3-I | CF$_3$ | I | 3-Cl-5-I | CF$_3$ | F |
| 3-I | CF$_3$ | CH$_3$ | 3-Cl-5-I | CF$_3$ | Cl |
| 3-I | CF$_3$ | Et | 3-Cl-5-I | CF$_3$ | Br |
| 3-I | CF$_3$ | CF$_3$ | 3-Cl-5-I | CF$_3$ | I |
| 3-I | CF$_3$ | SCH$_3$ | 3-Cl-5-I | CF$_3$ | CH$_3$ |
| 3-I | CF$_3$ | NO$_2$ | 3-Cl-5-I | CF$_3$ | Et |
| 3-I | CF$_2$Cl | CH$_3$ | 3-Cl-5-I | CF$_3$ | CF$_3$ |
| 3-CF$_3$ | CF$_3$ | — | 3-Cl-5-I | CF$_3$ | SCH$_3$ |
| 3-CF$_3$ | CF$_3$ | F | 3-Cl-5-I | CF$_3$ | NO$_2$ |
| 3-CF$_3$ | CF$_3$ | Cl | 3-Cl-5-I | CF$_2$Cl | CH$_3$ |

TABLE 4-continued

| | | | | | |
|---|---|---|---|---|---|
| 3-CF₃ | CF₃ | Br | 3,5-I₂ | CF₃ | CH₃ |
| 3-CF₃ | CF₃ | I | 3-Cl-5-CH₃ | CF₃ | CH₃ |
| 3-CF₃ | CF₃ | CH₃ | 3-Br-5-CH₃ | CF₃ | CH₃ |
| 3-CF₃ | CF₃ | Et | 3-CF₃-4-F | CF₃ | F |
| 3-CF₃ | CF₃ | CF₃ | 3-CF₃-4-F | CF₃ | Cl |
| 3-CF₃ | CF₃ | OCH₃ | 3-CF₃-4-F | CF₃ | Br |
| 3-CF₃ | CF₃ | OCHF₂ | 3-CF₃-4-F | CF₃ | I |
| 3-CF₃ | CF₃ | OCF₃ | 3-CF₃-4-F | CF₃ | CH₃ |
| 3-CF₃ | CF₃ | SCH₃ | 3-CF₃-4-F | CF₃ | Et |
| 3-CF₃ | CF₃ | SCHF₂ | 3-CF₃-4-F | CF₃ | CF₃ |
| 3-CF₃ | CF₃ | SCF₃ | 3-CF₃-4-F | CF₃ | SCH₃ |
| 3-CF₃ | CF₃ | NO₂ | 3-CF₃-4-F | CF₃ | NO₂ |
| 3-CF₃ | CF₂Cl | Cl | 3-CF₃-4-F | CF₂Cl | CH₃ |
| 3-CF₃ | CF₂Cl | Br | 3-F-5-CF₃ | CF₃ | — |
| 3-CF₃ | CF₂Cl | I | 3-F-5-CF₃ | CF₃ | F |
| 3-CF₃ | CF₂Cl | CH₃ | 3-F-5-CF₃ | CF₃ | Cl |
| 3-CF₃ | CF₂Cl | CF₃ | 3-F-5-CF₃ | CF₃ | Br |
| 3-CF₂CF₃ | CF₃ | — | 3-F-5-CF₃ | CF₃ | I |
| 3-CF₂CF₃ | CF₃ | F | 3-F-5-CF₃ | CF₃ | CH₃ |
| 3-CF₂CF₃ | CF₃ | Cl | 3-F-5-CF₃ | CF₃ | Et |
| 3-CF₂CF₃ | CF₃ | Br | 3-F-5-CF₃ | CF₃ | CF₃ |
| 3-CF₂CF₃ | CF₃ | I | 3-F-5-CF₃ | CF₃ | OCH₃ |
| 3-CF₂CF₃ | CF₃ | CH₃ | 3-F-5-CF₃ | CF₃ | OCHF₂ |
| 3-CF₂CF₃ | CF₃ | Et | 3-F-5-CF₃ | CF₃ | OCF₃ |
| 3-CF₂CF₃ | CF₃ | CF₃ | 3-F-5-CF₃ | CF₃ | SCH₃ |
| 3-CF₂CF₃ | CF₃ | OCH₃ | 3-F-5-CF₃ | CF₃ | SCHF₂ |
| 3-CF₂CF₃ | CF₃ | OCHF₃ | 3-F-5-CF₃ | CF₃ | SCF₃ |
| 3-CF₂CF₃ | CF₃ | OCF₃ | 3-F-5-CF₃ | CF₃ | NO₂ |
| 3-CF₂CF₃ | CF₃ | SCH₃ | 3-F-5-CF₃ | CF₂Cl | Cl |
| 3-CF₂CF₃ | CF₃ | SCHF₂ | 3-F-5-CF₃ | CF₂Cl | Br |
| 3-CF₂CF₃ | CF₃ | SCF₃ | 3-F-5-CF₃ | CF₂Cl | I |
| 3-CF₂CF₃ | CF₃ | NO₂ | 3-F-5-CF₃ | CF₂Cl | CH₃ |
| 3-CF₂CF₃ | CF₂Cl | Cl | 3-F-5-CF₃ | CF₂Cl | CF₃ |
| 3-CF₂CF₃ | CF₂Cl | Br | 3-CF₃-4-Cl | CF₃ | F |
| 3-CF₂CF₃ | CF₂Cl | I | 3-CF₃-4-Cl | CF₃ | Cl |
| 3-CF₂CF₃ | CF₂Cl | CH₃ | 3-CF₃-4-Cl | CF₃ | Br |
| 3-CF₂CF₃ | CF₂Cl | CF₃ | 3-CF₃-4-Cl | CF₃ | I |
| 3-CF₂CF₂CF₃ | CF₃ | F | 3-CF₃-4-Cl | CF₃ | CH₃ |
| 3-CF₂CF₂CF₃ | CF₃ | Cl | 3-CF₃-4-Cl | CF₃ | Et |
| 3-CF₂CF₂CF₃ | CF₃ | Br | 3-CF₃-4-Cl | CF₃ | CF₃ |
| 3-CF₂CF₂CF₃ | CF₃ | I | 3-CF₃-4-Cl | CF₃ | SCH₃ |
| 3-CF₂CF₂CF₃ | CF₃ | CH₃ | 3-CF₃-4-Cl | CF₃ | NO₂ |
| 3-CF₂CF₂CF₃ | CF₃ | Et | 3-CF₃-4-Cl | CF₂Cl | CH₃ |
| 3-CF₂CF₂CF₃ | CF₃ | CF₃ | 3-Cl-5-CF₃ | CHF₂ | CH₃ |
| 3-CF₂CF₂CF₃ | CF₃ | SCH₃ | 3-Cl-5-CF₃ | CF₃ | — |
| 3-CF₂CF₂CF₃ | CF₃ | NO₂ | 3-Cl-5-CF₃ | CF₃ | F |
| 3-CF₂CF₂CF₃ | CF₂Cl | CH₃ | 3-Cl-5-CF₃ | CF₃ | Cl |
| 3-CF(CF₃)₂ | CF₃ | F | 3-Cl-5-CF₃ | CF₃ | Br |
| 3-CF(CF₃)₂ | CF₃ | Cl | 3-Cl-5-CF₃ | CF₃ | I |
| 3-CF(CF₃)₂ | CF₃ | Br | 3-Cl-5-CF₃ | CF₃ | CH₃ |
| 3-CF(CF₃)₂ | CF₃ | I | 3-Cl-5-CF₃ | CF₃ | Et |
| 3-CF(CF₃)₂ | CF₃ | CH₃ | 3-Cl-5-CF₃ | CF₃ | CF₃ |
| 3-CF(CF₃)₂ | CF₃ | Et | 3-Cl-5-CF₃ | CF₃ | OCH₃ |
| 3-CF(CF₃)₂ | CF₃ | CF₃ | 3-Cl-5-CF₃ | CF₃ | OCHF₂ |
| 3-CF(CF₃)₂ | CF₃ | SCH₃ | 3-Cl-5-CF₃ | CF₃ | OCF₃ |
| 3-CF(CF₃)₂ | CF₃ | NO₂ | 3-Cl-5-CF₃ | CF₃ | OSO₂CH₃ |
| 3-CF(CF₃)₂ | CF₂Cl | CH₃ | 3-Cl-5-CF₃ | CF₃ | SCH₃ |
| 3-CF₂CF₂CF₂CF₃ | CF₃ | Cl | 3-Cl-5-CF₃ | CF₃ | SCHF₂ |
| 3-CF₂CF₂CF₂CF₃ | CF₃ | Br | 3-Cl-5-CF₃ | CF₃ | SCF₃ |
| 3-CF₂CF₂CF₂CF₃ | CF₃ | I | 3-Cl-5-CF₃ | CF₃ | NO₂ |
| 3-CF₂CF₂CF₂CF₃ | CF₃ | CH₃ | 3-Cl-5-CF₃ | CF₃ | N(CH₃)₂ |
| 3-CF₂CF₂CF₂CF₃ | CF₃ | CF₃ | 3-Cl-5-CF₃ | CF₃ | CN |
| 3-C(CF₃)₂OH | CF₃ | Cl | 3-Cl-5-CF₃ | CF₂Cl | Cl |
| 3-C(CF₃)₂OH | CF₃ | Br | 3-Cl-5-CF₃ | CF₂Cl | Br |
| 3-C(CF₃)₂OH | CF₃ | I | 3-Cl-5-CF₃ | CF₂Cl | I |
| 3-C(CF₃)₂OH | CF₃ | CH₃ | 3-Cl-5-CF₃ | CF₂Cl | CH₃ |
| 3-C(CF₃)₂OH | CF₃ | CF₃ | 3-Cl-5-CF₃ | CF₂Cl | CF₃ |
| 3-C(CF₃)₂OCH₃ | CF₃ | Cl | 3-Cl-5-CF₃ | CF₂Br | CH₃ |
| 3-C(CF₃)₂OCH₃ | CF₃ | Br | 3-Cl-5-CF₃ | CF₂CHF₂ | CH₃ |
| 3-C(CF₃)₂OCH₃ | CF₃ | I | 3-Br-5-CF₃ | CHF₂ | CH₃ |
| 3-C(CF₃)₂OCH₃ | CF₃ | CH₃ | 3-Br-5-CF₃ | CF₃ | — |
| 3-C(CF₃)₂OCH₃ | CF₃ | CF₃ | 3-Br-5-CF₃ | CF₃ | F |
| 3-OCF₃ | CF₃ | CH₃ | 3-Br-5-CF₃ | CF₃ | Cl |
| 3-OCF₂Br | CF₃ | CH₃ | 3-Br-5-CF₃ | CF₃ | Br |
| 3-OCF₂CHF₂ | CF₃ | CH₃ | 3-Br-5-CF₃ | CF₃ | I |
| 3-OCF₂CHFCl | CF₃ | CH₃ | 3-Br-5-CF₃ | CF₃ | CH₃ |
| 3-OCF₂CHFOF₃ | CF₃ | CH₃ | 3-Br-5-CF₃ | CF₃ | Et |
| 3-OCF₂CHFOCF₃ | CF₃ | CH₃ | 3-Br-5-CF₃ | CF₃ | CF₃ |
| 3-SCF₃ | CF₃ | Cl | 3-Br-5-CF₃ | CF₃ | OCH₃ |
| 3-SCF₃ | CF₃ | Br | 3-Br-5-CF₃ | CF₃ | OCHF₂ |

TABLE 4-continued

| | | | | | |
|---|---|---|---|---|---|
| 3-SCF$_3$ | CF$_3$ | I | 3-Br-5-CF$_3$ | CF$_3$ | OCF$_3$ |
| 3-SCF$_3$ | CF$_3$ | CH$_3$ | 3-Br-5-CF$_3$ | CF$_3$ | OSO$_2$CH$_3$ |
| 3-SCF$_3$ | CF$_3$ | CF$_3$ | 3-Br-5-CF$_3$ | CF$_3$ | SCH$_3$ |
| 3-S(O)CF$_3$ | CF$_3$ | CH$_3$ | 3-Br-5-CF$_3$ | CF$_3$ | SCHF$_2$ |
| 3-SO$_2$CF$_3$ | CF$_3$ | CH$_3$ | 3-Br-5-CF$_3$ | CF$_3$ | SCF$_3$ |
| 3-SCF$_2$Cl | CF$_3$ | Cl | 3-Br-5-CF$_3$ | CF$_3$ | NO$_2$ |
| 3-SCF$_2$Cl | CF$_3$ | Br | 3-Br-5-CF$_3$ | CF$_3$ | N(CH$_3$)$_2$ |
| 3-SCF$_2$Cl | CF$_3$ | I | 3-Br-5-CF$_3$ | CF$_3$ | CN |
| 3-SCF$_2$Cl | CF$_3$ | CH$_3$ | 3-Br-5-CF$_3$ | CF$_2$Cl | Cl |
| 3-SCF$_2$Cl | CF$_3$ | CF$_3$ | 3-Br-5-CF$_3$ | CF$_2$Cl | Br |
| 3-S(O)CF$_2$Cl | CF$_3$ | CH$_3$ | 3-Br-5-CF$_3$ | CF$_2$Cl | I |
| 3-SO$_2$CF$_2$Cl | CF$_3$ | CH$_3$ | 3-Br-5-CF$_3$ | CF$_2$Cl | CH$_3$ |
| 3-SCF$_2$Br | CF$_3$ | Cl | 3-Br-5-CF$_3$ | CF$_2$Cl | CF$_3$ |
| 3-SCF$_2$Br | CF$_3$ | Br | 3-Br-5-CF$_3$ | CF$_2$Br | CH$_3$ |
| 3-SCF$_2$Br | CF$_3$ | I | 3-Br-5-CF$_3$ | CF$_2$CHF$_2$ | CH$_3$ |
| 3-SCF$_2$Br | CF$_3$ | CH$_3$ | 3-CH$_3$-5-CF$_3$ | CF$_3$ | Cl |
| 3-SCF$_2$Br | CF$_3$ | CF$_3$ | 3-CH$_3$-5-CF$_3$ | CF$_3$ | Br |
| 3-S(O)CF$_2$Br | CF$_3$ | CH$_3$ | 3-CH$_3$-5-CF$_3$ | CF$_3$ | I |
| 3-SO$_2$CF$_2$Br | CF$_3$ | CH$_3$ | 3-CH$_3$-5-CF$_3$ | CF$_3$ | CH$_3$ |
| 3-SF$_5$ | CF$_3$ | — | 3-CH$_3$-5-CF$_3$ | CF$_3$ | CF$_3$ |
| 3-SF$_5$ | CF$_3$ | F | 3,5-(CF$_3$)$_2$ | CHF$_2$ | Cl |
| 3-SF$_5$ | CF$_3$ | Cl | 3,5-(CF$_3$)$_2$ | CHF$_2$ | Br |
| 3-SF$_5$ | CF$_3$ | Br | 3,5-(CF$_3$)$_2$ | CHF$_2$ | I |
| 3-SF$_5$ | CF$_3$ | I | 3,5-(CF$_3$)$_2$ | CHF$_2$ | CH$_3$ |
| 3-SF$_5$ | CF$_3$ | CH$_3$ | 3,5-(CF$_3$)$_2$ | CHF$_2$ | CF$_3$ |
| 3-SF$_5$ | CF$_3$ | Et | 3,5-(CF$_3$)$_2$ | CHFCl | CH$_3$ |
| 3-SF$_5$ | CF$_3$ | CF$_3$ | 3,5-(CF$_3$)$_2$ | CHC$_2$ | CH$_3$ |
| 3-SF$_5$ | CF$_3$ | OCH$_3$ | 3,5-(CF$_3$)$_2$ | CHFBr | CH$_3$ |
| 3-SF$_5$ | CF$_3$ | OCHF$_2$ | 3,5-(CF$_3$)$_2$ | CF$_3$ | — |
| 3-SF$_5$ | CF$_3$ | OCF$_3$ | 3,5-(CF$_3$)$_2$ | CF$_3$ | F |
| 3-SF$_5$ | CF$_3$ | SCH$_3$ | 3,5-(CF$_3$)$_2$ | CF$_3$ | Cl |
| 3-SF$_5$ | CF$_3$ | SCHF$_2$ | 3,5-(CF$_3$)$_2$ | CF$_3$ | Br |
| 3-SF$_5$ | CF$_3$ | SCF$_3$ | 3,5-(CF$_3$)$_2$ | CF$_3$ | I |
| 3-SF$_5$ | CF$_3$ | NO$_2$ | 3,5-(CF$_3$)$_2$ | CF$_3$ | CH$_3$ |
| 3-SF$_5$ | CF$_2$Cl | Cl | 3,5-(CF$_3$)$_2$ | CF$_3$ | Et |
| 3-SF$_5$ | CF$_2$Cl | Br | 3,5-(CF$_3$)$_2$ | CF$_3$ | i-Pr |
| 3-SF$_5$ | CF$_2$Cl | I | 3,5-(CF$_3$)$_2$ | CF$_3$ | CF$_3$ |
| 3-SF$_5$ | CF$_2$Cl | CH$_3$ | 3,5-(CF$_3$)$_2$ | CF$_3$ | OCH$_3$ |
| 3-SF$_5$ | CF$_2$Cl | CF$_3$ | 3,5-(CF$_3$)$_2$ | CF$_3$ | OEt |
| 3,5-F$_2$ | CF$_3$ | CH$_3$ | 3,5-(CF$_3$)$_2$ | CF$_3$ | OPr-i |
| 3-Cl-4-F | CF$_3$ | F | 3,5-(CF$_3$)$_2$ | CF$_3$ | OCHF$_2$ |
| 3-Cl-4-F | CF$_3$ | Cl | 3,5-(CF$_3$)$_2$ | CF$_3$ | OCF$_3$ |
| 3-Cl-4-F | CF$_3$ | Br | 3,5-(CF$_3$)$_2$ | CF$_3$ | OSO$_2$CH$_3$ |
| 3-Cl-4-F | CF$_3$ | I | 3,5-(CF$_3$)$_2$ | CF$_3$ | SCH$_3$ |
| 3-Cl-4-F | CF$_3$ | CH$_3$ | 3,5-(CF$_3$)$_2$ | CF$_3$ | SEt |
| 3-Cl-4-F | CF$_3$ | Et | 3,5-(CF$_3$)$_2$ | CF$_3$ | SPr-i |
| 3-Cl-4-F | CF$_3$ | CF$_3$ | 3,5-(CF$_3$)$_2$ | CF$_3$ | SCHF$_2$ |
| 3-Cl-4-F | CF$_3$ | SCH$_3$ | 3,5-(CF$_3$)$_2$ | CF$_3$ | SCF$_3$ |
| 3-Cl-4-F | CF$_3$ | NO$_2$ | 3,5-(CF$_3$)$_2$ | CF$_3$ | NO$_2$ |
| 3-Cl-4-F | CF$_2$Cl | CH$_3$ | 3,5-(CF$_3$)$_2$ | CF$_3$ | N(CH$_3$)$_2$ |
| 3-F-5-Cl | CF$_3$ | F | 3,5-(CF$_3$)$_2$ | CF$_3$ | CN |
| 3-F-5-Cl | CF$_3$ | Cl | 3,5-(CF$_3$)$_2$ | CF$_2$Cl | F |
| 3-F-5-Cl | CF$_3$ | Br | 3,5-(CF$_3$)$_2$ | CF$_2$Cl | Cl |
| 3-F-5-Cl | CF$_3$ | I | 3,5-(CF$_3$)$_2$ | CF$_2$Cl | Br |
| 3-F-5-Cl | CF$_3$ | CH$_3$ | 3,5-(CF$_3$)$_2$ | CF$_2$Cl | I |
| 3-F-5-Cl | CF$_3$ | Et | 3,5-(CF$_3$)$_2$ | CF$_2$Cl | CH$_3$ |
| 3-F-5-Cl | CF$_3$ | CF$_3$ | 3,5-(CF$_3$)$_2$ | CF$_2$Cl | Et |
| 3-F-5-Cl | CF$_3$ | SCH$_3$ | 3,5-(CF$_3$)$_2$ | CF$_2$Cl | CF$_3$ |
| 3-F-5-Cl | CF$_3$ | NO$_2$ | 3,5-(CF$_3$)$_2$ | CF$_2$Cl | SCH$_3$ |
| 3-F-5-Cl | CF$_2$Cl | CH$_3$ | 3,5-(CF$_3$)$_2$ | CF$_2$Cl | NO$_2$ |
| 3,4-Cl$_2$ | CF$_3$ | F | 3,5-(CF$_3$)$_2$ | CF$_2$Br | Cl |
| 3,4-Cl$_2$ | CF$_3$ | Cl | 3,5-(CF$_3$)$_2$ | CF$_2$Br | Br |
| 3,4-Cl$_2$ | CF$_3$ | Br | 3,5-(CF$_3$)$_2$ | CF$_2$Br | I |
| 3,4-Cl$_2$ | CF$_3$ | I | 3,5-(CF$_3$)$_2$ | CF$_2$Br | CH$_3$ |
| 3,4-Cl$_2$ | CF$_3$ | CH$_3$ | 3,5-(CF$_3$)$_2$ | CF$_2$Br | CF$_3$ |
| 3,4-Cl$_2$ | CF$_3$ | Et | 3,5-(CF$_3$)$_2$ | CF$_2$CHF$_2$ | Cl |
| 3,4-Cl$_2$ | CF$_3$ | CF$_3$ | 3,5-(CF$_3$)$_2$ | CF$_2$CHF$_2$ | Br |
| 3,4-Cl$_2$ | CF$_3$ | SCH$_3$ | 3,5-(CF$_3$)$_2$ | CF$_2$CHF$_2$ | I |
| 3,4-Cl$_2$ | CF$_3$ | NO$_2$ | 3,5-(CF$_3$)$_2$ | CF$_2$CHF$_2$ | CH$_3$ |
| 3,4-Cl$_2$ | CF$_2$Cl | CH$_3$ | 3,5-(CF$_3$)$_2$ | CF$_2$CHF$_2$ | CF$_3$ |
| 3,5-Cl$_2$ | CHF$_2$ | Cl | 3,5-(CF$_3$)$_2$ | CF$_2$CF$_3$ | CH$_3$ |
| 3,5-Cl$_2$ | CHF$_2$ | Br | 3,5-(CF$_3$)$_2$ | CF$_2$OCH$_3$ | CH$_3$ |
| 3,5-Cl$_2$ | CHF$_2$ | I | 3,5-(CF$_3$)$_2$ | T-3 | CH$_3$ |
| 3,5-Cl$_2$ | CHF$_2$ | CH$_3$ | 3-Cl-5-CF$_2$CF$_3$ | CF$_3$ | CH$_3$ |
| 3,5-Cl$_2$ | CHF$_2$ | CF$_3$ | 3-Br-5-CF$_2$CF$_3$ | CF$_3$ | CH$_3$ |
| 3,5-Cl$_2$ | CHFCl | Cl | 3-CH$_3$-5-CF$_2$CF$_3$ | CF$_3$ | CH$_3$ |
| 3,5-Cl$_2$ | CHFCl | Br | 3-Cl-5-CF$_2$CF$_2$CF$_3$ | CF$_3$ | CH$_3$ |
| 3,5-Cl$_2$ | CHFCl | I | 3-Br-5-CF$_2$CF$_2$CF$_3$ | CF$_3$ | CH$_3$ |
| 3,5-Cl$_2$ | CHFCl | CH$_3$ | 3-Cl-5-CF(CF$_3$)$_2$ | CF$_3$ | CH$_3$ |
| 3,5-Cl$_2$ | CHFCl | CF$_3$ | 3-Br-5-CF(CF$_3$)$_2$ | CF$_3$ | CH$_3$ |

TABLE 4-continued

| | | | | | |
|---|---|---|---|---|---|
| 3,5-Cl$_2$ | CHCl$_2$ | Cl | 3-CF$_3$-5-OCH$_3$ | CF$_3$ | CH$_3$ |
| 3,5-Cl$_2$ | CHCl$_2$ | Br | 3-Cl-5-OCHF$_2$ | CF$_3$ | F |
| 3,5-Cl$_2$ | CHCl$_2$ | I | 3-Cl-5-OCHF$_2$ | CF$_3$ | Cl |
| 3,5-Cl$_2$ | CHCl$_2$ | CH$_3$ | 3-Cl-5-OCHF$_2$ | CF$_3$ | Br |
| 3,5-Cl$_2$ | CHCl$_2$ | CF$_3$ | 3-Cl-5-OCHF$_2$ | CF$_3$ | I |
| 3,5-Cl$_2$ | CHFBr | Cl | 3-Cl-5-OCHF$_2$ | CF$_3$ | CH$_3$ |
| 3,5-Cl$_2$ | CHFBr | Br | 3-Cl-5-OCHF$_2$ | CF$_3$ | Et |
| 3,5-Cl$_2$ | CHFBr | I | 3-Cl-5-OCHF$_2$ | CF$_3$ | CF$_3$ |
| 3,5-Cl$_2$ | CHFBr | CH$_3$ | 3-Cl-5-OCHF$_2$ | CF$_3$ | SCH$_3$ |
| 3,5-Cl$_2$ | CHFBr | CF$_3$ | 3-Cl-5-OCHF$_2$ | CF$_3$ | NO$_2$ |
| 3,5-Cl$_2$ | CF$_3$ | — | 3-Cl-5-OCHF$_2$ | CF$_2$Cl | CH$_3$ |
| 3,5-Cl$_2$ | CF$_3$ | F | 3-Br-5-OCHF$_2$ | CF$_3$ | Cl |
| 3,5-Cl$_2$ | CF$_3$ | Cl | 3-Br-5-OCHF$_2$ | CF$_3$ | Br |
| 3,5-Cl$_2$ | CF$_3$ | Br | 3-Br-5-OCHF$_2$ | CF$_3$ | I |
| 3,5-Cl$_2$ | CF$_3$ | I | 3-Br-5-OCHF$_2$ | CF$_3$ | CH$_3$ |
| 3,5-Cl$_2$ | CF$_3$ | CH$_3$ | 3-Br-5-OCHF$_2$ | CF$_3$ | CF$_3$ |
| 3,5-Cl$_2$ | CF$_3$ | Et | 3-CF$_3$-5-OCHF$_2$ | CF$_3$ | Cl |
| 3,5-Cl$_2$ | CF$_3$ | i-Pr | 3-CF$_3$-5-OCHF$_2$ | CF$_3$ | Br |
| 3,5-Cl$_2$ | CF$_3$ | CF$_3$ | 3-CF$_3$-5-OCHF$_2$ | CF$_3$ | I |
| 3,5-Cl$_2$ | CF$_3$ | CF$_2$CF$_3$ | 3-CF$_3$-5-OCHF$_2$ | CF$_3$ | CH$_3$ |
| 3,5-Cl$_2$ | CF$_3$ | CH$_2$OCH$_3$ | 3-CF$_3$-5-OCHF$_2$ | CF$_3$ | CF$_3$ |
| 3,5-Cl$_2$ | CF$_3$ | CH$_2$OCH$_2$CF$_3$ | 3-Cl-5-OCF$_3$ | CF$_3$ | F |
| 3,5-Cl$_2$ | CF$_3$ | CH$_2$SCH$_3$ | 3-Cl-5-OCF$_3$ | CF$_3$ | Cl |
| 3,5-Cl$_2$ | CF$_3$ | CH$_2$S(O)CH$_3$ | 3-Cl-5-OCF$_3$ | CF$_3$ | Br |
| 3,5-Cl$_2$ | CF$_3$ | CH$_2$SO$_2$CH$_3$ | 3-Cl-5-OCF$_3$ | CF$_3$ | I |
| 3,5-Cl$_2$ | CF$_3$ | CH$_2$SCF$_3$ | 3-Cl-5-OCF$_3$ | CF$_3$ | CH$_3$ |
| 3,5-Cl$_2$ | CF$_3$ | CH$_2$S(O)CF$_3$ | 3-Cl-5-OCF$_3$ | CF$_3$ | Et |
| 3,5-Cl$_2$ | CF$_3$ | CH$_2$SO$_2$CF$_3$ | 3-Cl-5-OCF$_3$ | CF$_3$ | CF$_3$ |
| 3,5-Cl$_2$ | CF$_3$ | OCH$_3$ | 3-Cl-5-OCF$_3$ | CF$_3$ | SCH$_3$ |
| 3,5-Cl$_2$ | CF$_3$ | OEt | 3-Cl-5-OCF$_3$ | CF$_3$ | NO$_2$ |
| 3,5-Cl$_2$ | CF$_3$ | OPr-i | 3-Cl-5-OCF$_3$ | CF$_2$Cl | CH$_3$ |
| 3,5-Cl$_2$ | CF$_3$ | OCHF$_2$ | 3-Br-5-OCF$_3$ | CF$_3$ | Cl |
| 3,5-Cl$_2$ | CF$_3$ | OCF$_3$ | 3-Br-5-OCF$_3$ | CF$_3$ | Br |
| 3,5-Cl$_2$ | CF$_3$ | OCF$_2$Br | 3-Br-5-OCF$_3$ | CF$_3$ | I |
| 3,5-Cl$_2$ | CF$_3$ | OCF$_2$CHF$_2$ | 3-Br-5-OCF$_3$ | CF$_3$ | CH$_3$ |
| 3,5-Cl$_2$ | CF$_3$ | OCF$_2$CHFCF$_3$ | 3-Br-5-OCF$_3$ | CF$_3$ | CF$_3$ |
| 3,5-Cl$_2$ | CF$_3$ | OSO$_2$CH$_3$ | 3-CF$_3$-5-OCF$_3$ | CF$_3$ | Cl |
| 3,5-Cl$_2$ | CF$_3$ | OSO$_2$Et | 3-CF$_3$-5-OCF$_3$ | CF$_3$ | Br |
| 3,5-Cl$_2$ | CF$_3$ | OSO$_2$CF$_3$ | 3-CF$_3$-5-OCF$_3$ | CF$_3$ | I |
| 3,5-Cl$_2$ | CF$_3$ | SCH$_3$ | 3-CF$_3$-5-OCF$_3$ | CF$_3$ | CH$_3$ |
| 3,5-Cl$_2$ | CF$_3$ | S(O)CH$_3$ | 3-CF$_3$-5-OCF$_3$ | CF$_3$ | CF$_3$ |
| 3,5-Cl$_2$ | CF$_3$ | SO$_2$CH$_3$ | 3-Cl-5-SCF$_3$ | CF$_3$ | F |
| 3,5-Cl$_2$ | CF$_3$ | SEt | 3-Cl-5-SCF$_3$ | CF$_3$ | Cl |
| 3,5-Cl$_2$ | CF$_3$ | SPr-i | 3-Cl-5-SCF$_3$ | CF$_3$ | Br |
| 3,5-Cl$_2$ | CF$_3$ | SCHF$_2$ | 3-Cl-5-SCF$_3$ | CF$_3$ | I |
| 3,5-Cl$_2$ | CF$_3$ | SCF$_3$ | 3-Cl-5-SCF$_3$ | CF$_3$ | CH$_3$ |
| 3,5-Cl$_2$ | CF$_3$ | S(O)CF$_3$ | 3-Cl-5-SCF$_3$ | CF$_3$ | Et |
| 3,5-Cl$_2$ | CF$_3$ | SO$_2$CF$_3$ | 3-Cl-5-SCF$_3$ | CF$_3$ | CF$_3$ |
| 3,5-Cl$_2$ | CF$_3$ | SCF$_2$Br | 3-Cl-5-SCF$_3$ | CF$_3$ | SCH$_3$ |
| 3,5-Cl$_2$ | CF$_3$ | NO$_2$ | 3-Cl-5-SCF$_3$ | CF$_3$ | NO$_2$ |
| 3,5-Cl$_2$ | CF$_3$ | N(CH$_3$)$_2$ | 3-Cl-5-SCF$_3$ | CF$_2$Cl | CH$_3$ |
| 3,5-Cl$_2$ | CF$_3$ | CN | 3-Cl-5-S(O)CF$_3$ | CF$_3$ | CH$_3$ |
| 3,5-Cl$_2$ | CF$_3$ | C(O)OCH$_3$ | 3-Cl-5-SO$_2$CF$_3$ | CF$_3$ | CH$_3$ |
| 3,5-Cl$_2$ | CF$_3$ | C(O)NH$_2$ | 3-Br-5-SCF$_3$ | CF$_3$ | Cl |
| 3,5-Cl$_2$ | CF$_3$ | T-22 | 3-Br-5-SCF$_3$ | CF$_3$ | Br |
| 3,5-Cl$_2$ | CF$_3$ | C(S)NH$_2$ | 3-Br-5-SCF$_3$ | CF$_3$ | I |
| 3,5-Cl$_2$ | CF$_3$ | T-25 | 3-Br-5-SCF$_3$ | CF$_3$ | CH$_3$ |
| 3,5-Cl$_2$ | CF$_2$Cl | — | 3-Br-5-SCF$_3$ | CF$_3$ | CF$_3$ |
| 3,5-Cl$_2$ | CF$_2$Cl | F | 3-Br-5-S(O)CF$_3$ | CF$_3$ | CH$_3$ |
| 3,5-Cl$_2$ | CF$_2$Cl | Cl | 3-Br-5-SO$_2$CF$_3$ | CF$_3$ | CH$_3$ |
| 3,5-Cl$_2$ | CF$_2$Cl | Br | 3-Cl-5-SCF$_2$CHFCl | CF$_3$ | CH$_3$ |
| 3,5-Cl$_2$ | CF$_2$Cl | I | 3-Br-5-SCF$_2$CHFCl | CF$_3$ | CH$_3$ |
| 3,5-Cl$_2$ | CF$_2$Cl | CH$_3$ | 3-Cl-5-NO$_2$ | CF$_3$ | CH$_3$ |
| 3,5-Cl$_2$ | CF$_2$Cl | Et | 3-Br-5-NO$_2$ | CF$_3$ | CH$_3$ |
| 3,5-Cl$_2$ | CF$_2$Cl | i-Pr | 3-CF$_3$-5-NO$_2$ | CF$_3$ | CH$_3$ |
| 3,5-Cl$_2$ | CF$_2$Cl | CF$_3$ | 3-Cl-5-CN | CF$_3$ | CH$_3$ |
| 3,5-Cl$_2$ | CF$_2$Cl | OCH$_3$ | 3-Br-5-CN | CF$_3$ | CH$_3$ |
| 3,5-Cl$_2$ | CF$_2$Cl | OEt | 3-CF$_3$-5-CN | CF$_3$ | Cl |
| 3,5-Cl$_2$ | CF$_2$Cl | OPr-i | 3-CF$_3$-5-CN | CF$_3$ | Br |
| 3,5-Cl$_2$ | CF$_2$Cl | OCHF$_2$ | 3-CF$_3$-5-CN | CF$_3$ | I |
| 3,5-Cl$_2$ | CF$_2$Cl | OCF$_3$ | 3-CF$_3$-5-CN | CF$_3$ | CH$_3$ |
| 3,5-Cl$_2$ | CF$_2$Cl | OSO$_2$CH$_3$ | 3-CF$_3$-5-CN | CF$_3$ | CF$_3$ |
| 3,5-Cl$_2$ | CF$_2$Cl | SCH$_3$ | 3,4,5-F$_3$ | CF$_3$ | CH$_3$ |
| 3,5-Cl$_2$ | CF$_2$Cl | SEt | 3,5-Cl$_2$-4-F | CF$_3$ | — |
| 3,5-Cl$_2$ | CF$_2$Cl | SPr-i | 3,5-Cl$_2$-4-F | CF$_3$ | F |
| 3,5-Cl$_2$ | CF$_2$Cl | SCHF$_2$ | 3,5-Cl$_2$-4-F | CF$_3$ | Cl |
| 3,5-Cl$_2$ | CF$_2$Cl | SCF$_3$ | 3,5-Cl$_2$-4-F | CF$_3$ | Br |
| 3,5-Cl$_2$ | CF$_2$Cl | NO$_2$ | 3,5-Cl$_2$-4-F | CF$_3$ | I |
| 3,5-Cl$_2$ | CF$_2$Cl | N(CH$_3$)$_2$ | 3,5-Cl$_2$-4-F | CF$_3$ | CH$_3$ |
| 3,5-Cl$_2$ | CF$_2$Cl | CN | 3,5-Cl$_2$-4-F | CF$_3$ | Et |

TABLE 4-continued

| | | | | | |
|---|---|---|---|---|---|
| 3,5-Cl$_2$ | CF$_2$Br | Cl | 3,5-Cl$_2$-4-F | CF$_3$ | CF$_3$ |
| 3,5-Cl$_2$ | CF$_2$Br | Br | 3,5-Cl$_2$-4-F | CF$_3$ | OCH$_3$ |
| 3,5-Cl$_2$ | CF$_2$Br | I | 3,5-Cl$_2$-4-F | CF$_3$ | OCHF$_2$ |
| 3,5-Cl$_2$ | CF$_2$Br | CH$_3$ | 3,5-Cl$_2$-4-F | CF$_3$ | OCF$_3$ |
| 3,5-Cl$_2$ | CF$_2$Br | CF$_3$ | 3,5-Cl$_2$-4-F | CF$_3$ | SCH$_3$ |
| 3,5-Cl$_2$ | CF$_2$I | CH$_3$ | 3,5-Cl$_2$-4-F | CF$_3$ | SCHF$_2$ |
| 3,5-Cl$_2$ | CFCl$_2$ | CH$_3$ | 3,5-Cl$_2$-4-F | CF$_3$ | SCF$_3$ |
| 3,5-Cl$_2$ | CFClBr | CH$_3$ | 3,5-Cl$_2$-4-F | CF$_3$ | NO$_2$ |
| 3,5-Cl$_2$ | CFBr$_2$ | CH$_3$ | 3,5-Cl$_2$-4-F | CF$_2$Cl | Cl |
| 3,5-Cl$_2$ | CCl$_3$ | CH$_3$ | 3,5-Cl$_2$-4-F | CF$_2$Cl | Br |
| 3,5-Cl$_2$ | CF$_2$CHF$_2$ | Cl | 3,5-Cl$_2$-4-F | CF$_2$Cl | I |
| 3,5-Cl$_2$ | CF$_2$CHF$_2$ | Br | 3,5-Cl$_2$-4-F | CF$_2$Cl | CH$_3$ |
| 3,5-Cl$_2$ | CF$_2$CHF$_2$ | I | 3,5-Cl$_2$-4-F | CF$_2$Cl | CF$_3$ |
| 3,5-Cl$_2$ | CF$_2$CHF$_2$ | CH$_3$ | 3,4,5-Cl$_3$ | CHF$_2$ | Cl |
| 3,5-Cl$_2$ | CF$_2$CHF$_2$ | CF$_3$ | 3,4,5-Cl$_3$ | CHF$_2$ | Br |
| 3,5-Cl$_2$ | CF$_2$CF$_3$ | Cl | 3,4,5-Cl$_3$ | CHF$_2$ | I |
| 3,5-Cl$_2$ | CF$_2$CF$_3$ | Br | 3,4,5-Cl$_3$ | CHF$_2$ | CH$_3$ |
| 3,5-Cl$_2$ | CF$_2$CF$_3$ | I | 3,4,5-Cl$_3$ | CHF$_2$ | CF$_3$ |
| 3,5-Cl$_2$ | CF$_2$CF$_3$ | CH$_3$ | 3,4,5-Cl$_3$ | CHFCl | CH$_3$ |
| 3,5-Cl$_2$ | CF$_2$CF$_3$ | CF$_3$ | 3,4,5-Cl$_3$ | CHCl$_2$ | CH$_3$ |
| 3,5-Cl$_2$ | CF$_2$CF$_2$Cl | CH$_3$ | 3,4,5-Cl$_3$ | CHFBr | CH$_3$ |
| 3,5-Cl$_2$ | CF$_2$CF$_2$Cl | CH$_3$ | 3,4,5-Cl$_3$ | CF$_3$ | — |
| 3,5-Cl$_2$ | CF$_2$CHCF$_3$ | CH$_3$ | 3,4,5-Cl$_3$ | CF$_3$ | F |
| 3,5-Cl$_2$ | CF$_2$CF$_2$CF$_3$ | CH$_3$ | 3,4,5-Cl$_3$ | CF$_3$ | Cl |
| 3,5-Cl$_2$ | CF$_2$OCH$_3$ | Cl | 3,4,5-Cl$_3$ | CF$_3$ | Br |
| 3,5-Cl$_2$ | CF$_2$OCH$_3$ | Br | 3,4,5-Cl$_3$ | CF$_3$ | I |
| 3,5-Cl$_2$ | CF$_2$OCH$_3$ | I | 3,4,5-Cl$_3$ | CF$_3$ | CH$_3$ |
| 3,5-Cl$_2$ | CF$_2$OCH$_3$ | CH$_3$ | 3,4,5-Cl$_3$ | CF$_3$ | Et |
| 3,5-Cl$_2$ | CF$_2$OCH$_3$ | CF$_3$ | 3,4,5-Cl$_3$ | CF$_3$ | i-Pr |
| 3,5-Cl$_2$ | CF$_2$SCH$_3$ | CH$_3$ | 3,4,5-Cl$_3$ | CF$_3$ | CF$_3$ |
| 3,5-Cl$_2$ | T-3 | Cl | 3,4,5-Cl$_3$ | CF$_3$ | OCH$_3$ |
| 3,5-Cl$_2$ | T-3 | Br | 3,4,5-Cl$_3$ | CF$_3$ | OEt |
| 3,5-Cl$_2$ | T-3 | I | 3,4,5-Cl$_3$ | CF$_3$ | OPr-i |
| 3,5-Cl$_2$ | T-3 | CH$_3$ | 3,4,5-Cl$_3$ | CF$_3$ | OCHF$_2$ |
| 3,5-Cl$_2$ | T-3 | CF$_3$ | 3,4,5-Cl$_3$ | CF$_3$ | OCF$_3$ |
| 3,5-Cl$_2$ | T-4 | CH$_3$ | 3,4,5-Cl$_3$ | CF$_3$ | OSO$_2$CH$_3$ |
| 3,5-Cl$_2$ | T-5 | CH$_3$ | 3,4,5-Cl$_3$ | CF$_3$ | SCH$_3$ |
| 3-Br-4-F | CF$_3$ | F | 3,4,5-Cl$_3$ | CF$_3$ | SEt |
| 3-Br-4-F | CF$_3$ | Cl | 3,4,5-Cl$_3$ | CF$_3$ | SPr-i |
| 3-Br-4-F | CF$_3$ | Br | 3,4,5-Cl$_3$ | CF$_3$ | SCHF$_2$ |
| 3-Br-4-F | CF$_3$ | I | 3,4,5-Cl$_3$ | CF$_3$ | SCF$_3$ |
| 3-Br-4-F | CF$_3$ | CH$_3$ | 3,4,5-Cl$_3$ | CF$_3$ | NO$_2$ |
| 3-Br-4-F | CF$_3$ | Et | 3,4,5-Cl$_3$ | CF$_3$ | N(CH$_3$)$_2$ |
| 3-Br-4-F | CF$_3$ | CF$_3$ | 3,4,5-Cl$_3$ | CF$_3$ | CN |
| 3-Br-4-F | CF$_3$ | SCH$_3$ | 3,4,5-Cl$_3$ | CF$_2$Cl | F |
| 3-Br-4-F | CF$_3$ | NO$_2$ | 3,4,5-Cl$_3$ | CF$_2$Cl | Cl |
| 3-Br-4-F | CF$_2$Cl | CH$_3$ | 3,4,5-Cl$_3$ | CF$_2$Cl | Br |
| 3-F-5-Br | CF$_3$ | F | 3,4,5-Cl$_3$ | CF$_2$Cl | I |
| 3-F-5-Br | CF$_3$ | Cl | 3,4,5-Cl$_3$ | CF$_2$Cl | CH$_3$ |
| 3-F-5-Br | CF$_3$ | Br | 3,4,5-Cl$_3$ | CF$_2$Cl | Et |
| 3-F-5-Br | CF$_3$ | I | 3,4,5-Cl$_3$ | CF$_2$Cl | CF$_3$ |
| 3-F-5-Br | CF$_3$ | CH$_3$ | 3,4,5-Cl$_3$ | CF$_2$Cl | SCH$_3$ |
| 3-F-5-Br | CF$_3$ | Et | 3,4,5-Cl$_3$ | CF$_2$Cl | NO$_2$ |
| 3-F-5-Br | CF$_3$ | CF$_3$ | 3,4,5-Cl$_3$ | CF$_2$Br | Cl |
| 3-F-5-Br | CF$_3$ | SCH$_3$ | 3,4,5-Cl$_3$ | CF$_2$Br | Br |
| 3-F-5-Br | CF$_3$ | NO$_2$ | 3,4,5-Cl$_3$ | CF$_2$Br | I |
| 3-F-5-Br | CF$_2$Cl | CH$_3$ | 3,4,5-Cl$_3$ | CF$_2$Br | CH$_3$ |
| 3-Cl-5-Br | CHF$_2$ | Cl | 3,4,5-Cl$_3$ | CF$_2$Br | CF$_3$ |
| 3-Cl-5-Br | CHF$_2$ | Br | 3,4,5-Cl$_3$ | CF$_2$CHF$_2$ | Cl |
| 3-Cl-5-Br | CHF$_2$ | I | 3,4,5-Cl$_3$ | CF$_2$CHF$_2$ | Br |
| 3-Cl-5-Br | CHF$_2$ | CH$_3$ | 3,4,5-Cl$_3$ | CF$_2$CHF$_2$ | I |
| 3-Cl-5-Br | CHF$_2$ | CF$_3$ | 3,4,5-Cl$_3$ | CF$_2$CHF$_2$ | CH$_3$ |
| 3-Cl-5-Br | CHFCl | CH$_3$ | 3,4,5-Cl$_3$ | CF$_2$CHF$_2$ | CF$_3$ |
| 3-Cl-5-Br | CHCl$_2$ | CH$_3$ | 3,4,5-Cl$_3$ | CF$_2$CF$_3$ | CH$_3$ |
| 3-Cl-5-Br | CHFBr | CH$_3$ | 3,4,5-Cl$_3$ | CF$_2$OCH$_3$ | CH$_3$ |
| 3-Cl-5-Br | CF$_3$ | — | 3,4,5-Cl$_3$ | T-3 | CH$_3$ |
| 3-Cl-5-Br | CF$_3$ | F | 3,5-Br$_2$-4-F | CF$_3$ | — |
| 3-Cl-5-Br | CF$_3$ | Cl | 3,5-Br$_2$-4-F | CF$_3$ | F |
| 3-Cl-5-Br | CF$_3$ | Br | 3,5-Br$_2$-4-F | CF$_3$ | Cl |
| 3-Cl-5-Br | CF$_3$ | I | 3,5-Br$_2$-4-F | CF$_3$ | Br |
| 3-Cl-5-Br | CF$_3$ | CH$_3$ | 3,5-Br$_2$-4-F | CF$_3$ | I |
| 3-Cl-5-Br | CF$_3$ | Et | 3,5-Br$_2$-4-F | CF$_3$ | CH$_3$ |
| 3-Cl-5-Br | CF$_3$ | i-Pr | 3,5-Br$_2$-4-F | CF$_3$ | Et |
| 3-Cl-5-Br | CF$_3$ | CF$_3$ | 3,5-Br$_2$-4-F | CF$_3$ | CF$_3$ |
| 3-Cl-5-Br | CF$_3$ | OCH$_3$ | 3,5-Br$_2$-4-F | CF$_3$ | OCH$_3$ |
| 3-Cl-5-Br | CF$_3$ | OEt | 3,5-Br$_2$-4-F | CF$_3$ | OCHF$_2$ |
| 3-Cl-5-Br | CF$_3$ | OPr-i | 3,5-Br$_2$-4-F | CF$_3$ | OCF$_3$ |
| 3-Cl-5-Br | CF$_3$ | OCHF$_2$ | 3,5-Br$_2$-4-F | CF$_3$ | SCH$_3$ |
| 3-Cl-5-Br | CF$_3$ | OCF$_3$ | 3,5-Br$_2$-4-F | CF$_3$ | SCHF$_2$ |
| 3-Cl-5-Br | CF$_3$ | OSO$_2$CH$_3$ | 3,5-Br$_2$-4-F | CF$_3$ | SCF$_3$ |

TABLE 4-continued

| | | | | | |
|---|---|---|---|---|---|
| 3-Cl-5-Br | $CF_3$ | $SCH_3$ | 3,5-$Br_2$-4-F | $CF_3$ | $NO_2$ |
| 3-Cl-5-Br | $CF_3$ | SEt | 3,5-$Br_2$-4-F | $CF_2Cl$ | Cl |
| 3-Cl-5-Br | $CF_3$ | SPr-i | 3,5-$Br_2$-4-F | $CF_2Cl$ | Br |
| 3-Cl-5-Br | $CF_3$ | $SCHF_2$ | 3,5-$Br_2$-4-F | $CF_2Cl$ | I |
| 3-Cl-5-Br | $CF_3$ | $SCF_3$ | 3,5-$Br_2$-4-F | $CF_2Cl$ | $CH_3$ |
| 3-Cl-5-Br | $CF_3$ | $NO_2$ | 3,5-$Br_2$-4-F | $CF_2Cl$ | $CF_3$ |
| 3-Cl-5-Br | $CF_3$ | $N(CH_3)_2$ | 3,4,5-$Br_3$ | $CF_3$ | $CH_3$ |
| 3-Cl-5-Br | $CF_3$ | CN | 3,5-$F_2$-4-$CH_3$ | $CF_3$ | $CH_3$ |
| 3-Cl-5-Br | $CF_2Cl$ | F | 3,5-$Cl_2$-4-$CH_3$ | $CF_3$ | $CH_3$ |
| 3-Cl-5-Br | $CF_2Cl$ | Cl | 3,5-$Br_2$-4-$CH_3$ | $CF_3$ | $CH_3$ |
| 3-Cl-5-Br | $CF_2Cl$ | Br | 3,4-$F_2$-5-$CF_3$ | $CF_3$ | — |
| 3-Cl-5-Br | $CF_2Cl$ | I | 3,4-$F_2$-5-$CF_3$ | $CF_3$ | F |
| 3-Cl-5-Br | $CF_2Cl$ | $CH_3$ | 3,4-$F_2$-5-$CF_3$ | $CF_3$ | Cl |
| 3-Cl-5-Br | $CF_2Cl$ | Et | 3,4-$F_2$-5-$CF_3$ | $CF_3$ | Br |
| 3-Cl-5-Br | $CF_2Cl$ | $CF_3$ | 3,4-$F_2$-5-$CF_3$ | $CF_3$ | I |
| 3-Cl-5-Br | $CF_2Cl$ | $SCH_3$ | 3,4-$F_2$-5-$CF_3$ | $CF_3$ | $CH_3$ |
| 3-Cl-5-Br | $CF_2Cl$ | $NO_2$ | 3,4-$F_2$-5-$CF_3$ | $CF_3$ | Et |
| 3-Cl-5-Br | $CF_2Br$ | Cl | 3,4-$F_2$-5-$CF_3$ | $CF_3$ | $CF_3$ |
| 3-Cl-5-Br | $CF_2Br$ | Br | 3,4-$F_2$-5-$CF_3$ | $CF_3$ | $OCH_3$ |
| 3-Cl-5-Br | $CF_2Br$ | I | 3,4-$F_2$-5-$CF_3$ | $CF_3$ | $OCHF_2$ |
| 3-Cl-5-Br | $CF_2Br$ | $CH_3$ | 3,4-$F_2$-5-$CF_3$ | $CF_3$ | $OCF_3$ |
| 3-Cl-5-Br | $CF_2Br$ | $CF_3$ | 3,4-$F_2$-5-$CF_3$ | $CF_3$ | $SCH_3$ |
| 3-Cl-5-Br | $CF_2CHF_2$ | Cl | 3,4-$F_2$-5-$CF_3$ | $CF_3$ | $SCHF_2$ |
| 3-Cl-5-Br | $CF_2CHF_2$ | Br | 3,4-$F_2$-5-$CF_3$ | $CF_3$ | $SCF_3$ |
| 3-Cl-5-Br | $CF_2CHF_2$ | I | 3,4-$F_2$-5-$CF_3$ | $CF_3$ | $NO_2$ |
| 3-Cl-5-Br | $CF_2CHF_2$ | $CH_3$ | 3,4-$F_2$-5-$CF_3$ | $CF_2Cl$ | Cl |
| 3-Cl-5-Br | $CF_2CHF_2$ | $CF_3$ | 3,4-$F_2$-5-$CF_3$ | $CF_2Cl$ | Br |
| 3-Cl-5-Br | $CF_2CF_3$ | $CH_3$ | 3,4-$F_2$-5-$CF_3$ | $CF_2Cl$ | I |
| 3-Cl-5-Br | $CF_2OCH_3$ | $CH_3$ | 3,4-$F_2$-5-$CF_3$ | $CF_2Cl$ | $CH_3$ |
| 3-Cl-5-Br | T-3 | $CH_3$ | 3,4-$F_2$-5-$CF_3$ | $CF_2Cl$ | $CF_3$ |
| 3,4-$Br_2$ | $CF_3$ | Cl | 3-Cl-4-F-5-$CF_3$ | $CF_3$ | — |
| 3,4-$Br_2$ | $CF_3$ | Br | 3-Cl-4-F-5-$CF_3$ | $CF_3$ | F |
| 3,4-$Br_2$ | $CF_3$ | I | 3-Cl-4-F-5-$CF_3$ | $CF_3$ | Cl |
| 3,4-$Br_2$ | $CF_3$ | $CH_3$ | 3-Cl-4-F-5-$CF_3$ | $CF_3$ | Br |
| 3,4-$Br_2$ | $CF_3$ | $CF_3$ | 3-Cl-4-F-5-$CF_3$ | $CF_3$ | I |
| 3,5-$Br_2$ | $CHF_2$ | Cl | 3-Cl-4-F-5-$CF_3$ | $CF_3$ | $CH_3$ |
| 3,5-$Br_2$ | $CHF_2$ | Br | 3-Cl-4-F-5-$CF_3$ | $CF_3$ | Et |
| 3,5-$Br_2$ | $CHF_2$ | I | 3-Cl-4-F-5-$CF_3$ | $CF_3$ | $CF_3$ |
| 3,5-$Br_2$ | $CHF_2$ | $CH_3$ | 3-Cl-4-F-5-$CF_3$ | $CF_3$ | $OCH_3$ |
| 3,5-$Br_2$ | $CHF_2$ | $CF_3$ | 3-Cl-4-F-5-$CF_3$ | $CF_3$ | $OCHF_2$ |
| 3,5-$Br_2$ | $CHFCl$ | $CH_3$ | 3-Cl-4-F-5-$CF_3$ | $CF_3$ | $OCF_3$ |
| 3,5-$Br_2$ | $CHCl_2$ | $CH_3$ | 3-Cl-4-F-5-$CF_3$ | $CF_3$ | $SCH_3$ |
| 3,5-$Br_2$ | $CHFBr$ | $CH_3$ | 3-Cl-4-F-5-$CF_3$ | $CF_3$ | $SCHF_2$ |
| 3,5-$Br_2$ | $CF_3$ | — | 3-Cl-4-F-5-$CF_3$ | $CF_3$ | $SCF_3$ |
| 3,5-$Br_2$ | $CF_3$ | F | 3-Cl-4-F-5-$CF_3$ | $CF_3$ | $NO_2$ |
| 3,5-$Br_2$ | $CF_3$ | Cl | 3-Cl-4-F-5-$CF_3$ | $CF_2Cl$ | Cl |
| 3,5-$Br_2$ | $CF_3$ | Br | 3-Cl-4-F-5-$CF_3$ | $CF_2Cl$ | Br |
| 3,5-$Br_2$ | $CF_3$ | I | 3-Cl-4-F-5-$CF_3$ | $CF_2Cl$ | I |
| 3,5-$Br_2$ | $CF_3$ | $CH_3$ | 3-Cl-4-F-5-$CF_3$ | $CF_2Cl$ | $CH_3$ |
| 3,5-$Br_2$ | $CF_3$ | Et | 3-Cl-4-F-5-$CF_3$ | $CF_2Cl$ | $CF_3$ |
| 3,5-$Br_2$ | $CF_3$ | i-Pr | 3,5-$(CF_3)_2$-4-Cl | $CF_3$ | — |
| 3,5-$Br_2$ | $CF_3$ | $CF_3$ | 3,5-$(CF_3)_2$-4-Cl | $CF_3$ | F |
| 3,5-$Br_2$ | $CF_3$ | $OCH_3$ | 3,5-$(CF_3)_2$-4-Cl | $CF_3$ | Cl |
| 3,5-$Br_2$ | $CF_3$ | OEt | 3,5-$(CF_3)_2$-4-Cl | $CF_3$ | Br |
| 3,5-$Br_2$ | $CF_3$ | OPr-i | 3,5-$(CF_3)_2$-4-Cl | $CF_3$ | I |
| 3,5-$Br_2$ | $CF_3$ | $OCHF_2$ | 3,5-$(CF_3)_2$-4-Cl | $CF_3$ | $CH_3$ |
| 3,5-$Br_2$ | $CF_3$ | $OCF_3$ | 3,5-$(CF_3)_2$-4-Cl | $CF_3$ | Et |
| 3,5-$Br_2$ | $CF_3$ | $OSO_2CH_3$ | 3,5-$(CF_3)_2$-4-Cl | $CF_3$ | $CF_3$ |
| 3,5-$Br_2$ | $CF_3$ | $SCH_3$ | 3,5-$(CF_3)_2$-4-Cl | $CF_3$ | $OCH_3$ |
| 3,5-$Br_2$ | $CF_3$ | SEt | 3,5-$(CF_3)_2$-4-Cl | $CF_3$ | $OCHF_2$ |
| 3,5-$Br_2$ | $CF_3$ | SPr-i | 3,5-$(CF_3)_2$-4-Cl | $CF_3$ | $OCF_3$ |
| 3,5-$Br_2$ | $CF_3$ | $SCHF_2$ | 3,5-$(CF_3)_2$-4-Cl | $CF_3$ | $SCH_3$ |
| 3,5-$Br_2$ | $CF_3$ | $SCF_3$ | 3,5-$(CF_3)_2$-4-Cl | $CF_3$ | $SCHF_2$ |
| 3,5-$Br_2$ | $CF_3$ | $NO_2$ | 3,5-$(CF_3)_2$-4-Cl | $CF_3$ | $SCF_3$ |
| 3,5-$Br_2$ | $CF_3$ | $N(CH_3)_2$ | 3,5-$(CF_3)_2$-4-Cl | $CF_3$ | $NO_2$ |
| 3,5-$Br_2$ | $CF_3$ | CN | 3,5-$(CF_3)_2$-4-Cl | $CF_2Cl$ | Cl |
| 3,5-$Br_2$ | $CF_2Cl$ | F | 3,5-$(CF_3)_2$-4-Cl | $CF_2Cl$ | Br |
| 3,5-$Br_2$ | $CF_2Cl$ | Cl | 3,5-$(CF_3)_2$-4-Cl | $CF_2Cl$ | I |
| 3,5-$Br_2$ | $CF_2Cl$ | Br | 3,5-$(CF_3)_2$-4-Cl | $CF_2Cl$ | $CH_3$ |
| 3,5-$Br_2$ | $CF_2Cl$ | I | 3,5-$(CF_3)_2$-4-Cl | $CF_2Cl$ | $CF_3$ |
| 3,5-$Br_2$ | $CF_2Cl$ | $CH_3$ | 3,5-$Cl_2$-4-OH | $CF_3$ | $CH_3$ |
| 3,5-$Br_2$ | $CF_2Cl$ | Et | 3,5-$Br_2$-4-OH | $CF_3$ | $CH_3$ |
| 3,5-$Br_2$ | $CF_2Cl$ | $CF_3$ | 3,5-$Cl_2$-4-$OCHF_2$ | $CF_3$ | $CH_3$ |
| 3,5-$Br_2$ | $CF_2Cl$ | $SCH_3$ | 3,5-$Br_2$-4-$OCHF_2$ | $CF_3$ | $CH_3$ |
| 3,5-$Br_2$ | $CF_2Cl$ | $NO_2$ | 3,5-$Cl_2$-4-$NH_2$ | $CF_3$ | $CH_3$ |
| 3,5-$Br_2$ | $CF_2Br$ | Cl | 3,5-$Br_2$-4-$NH_2$ | $CF_3$ | $CH_3$ |
| 3,5-$Br_2$ | $CF_2Br$ | Br | 3,5-$Cl_2$-4-CN | $CF_3$ | $CH_3$ |
| 3,5-$Br_2$ | $CF_2Br$ | I | 3,5-$Br_2$-4-CN | $CF_3$ | $CH_3$ |
| 3,4-$Cl_2$-5-$CF_3$ | $CF_3$ | — | 3,4-$Cl_2$-5-$CF_3$ | $CF_3$ | $SCHF_2$ |
| 3,4-$Cl_2$-5-$CF_3$ | $CF_3$ | F | 3,4-$Cl_2$-5-$CF_3$ | $CF_3$ | $SCF_3$ |

TABLE 4-continued

| 3,4-Cl$_2$-5-CF$_3$ | CF$_3$ | Cl | 3,4-Cl$_2$-5-CF$_3$ | CF$_3$ | NO$_2$ |
|---|---|---|---|---|---|
| 3,4-Cl$_2$-5-CF$_3$ | CF$_3$ | Br | 3,4-Cl$_2$-5-CF$_3$ | CF$_3$ | NH$_2$ |
| 3,4-Cl$_2$5-CF$_3$ | CF$_3$ | I | 3,4-Cl$_2$-5-CF$_3$ | CF$_3$ | N(CH$_3$)$_2$ |
| 3,4-Cl$_2$5-CF$_3$ | CF$_3$ | CH$_3$ | 3,4-Cl$_2$-5-CF$_3$ | CF$_3$ | CN |
| 3,4-Cl$_2$-5-CF$_3$ | CF$_3$ | Et | 3,4-Cl$_2$-5-CF$_3$ | CF$_2$Cl | Cl |
| 3,4-Cl$_2$-5-CF$_3$ | CF$_3$ | CF$_3$ | 3,4-Cl$_2$-5-CF$_3$ | CF$_2$Cl | Br |
| 3,4-Cl$_2$-5-CF$_3$ | CF$_3$ | OCH$_3$ | 3,4-Cl$_2$-5-CF$_3$ | CF$_2$Cl | I |
| 3,4-Cl$_2$-5-CF$_3$ | CF$_3$ | OCHF$_2$ | 3,4-Cl$_2$-5-CF$_3$ | CF$_2$Cl | CH$_3$ |
| 3,4-Cl$_2$-5-CF$_3$ | CF$_3$ | OCF$_3$ | 3,4-Cl$_2$-5-CF$_3$ | CF$_2$Cl | Et |
| 3,4-Cl$_2$-5-CF$_3$ | CF$_3$ | SCH$_3$ | 3,4-Cl$_2$-5-CF$_3$ | CF$_2$Cl | CF$_3$ |

TABLE 5

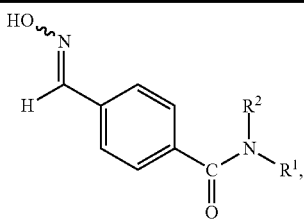

[4]-1

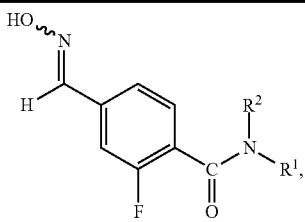

[4]-2

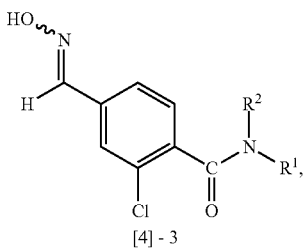

[4] - 3

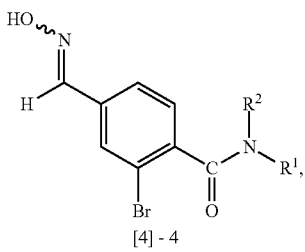

[4] - 4

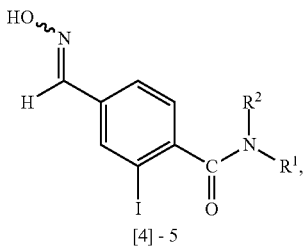

[4] - 5

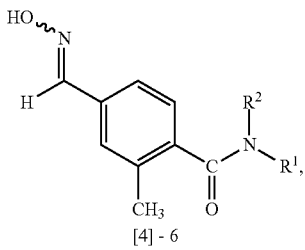

[4] - 6

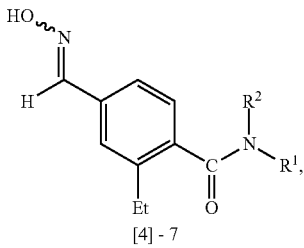

[4] - 7

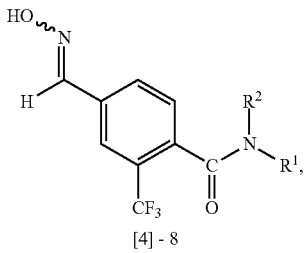

[4] - 8

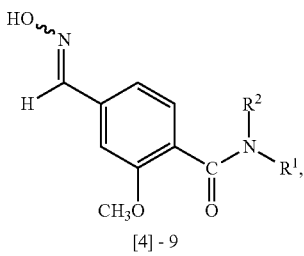

[4] - 9

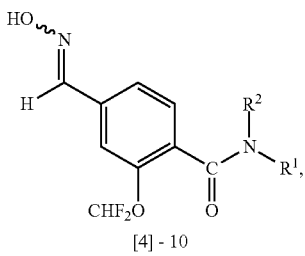

[4] - 10

TABLE 5-continued
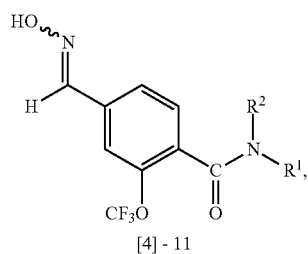
[4] - 11
[4] - 12
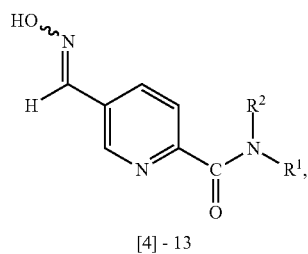
[4] - 13
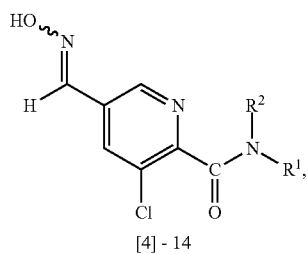
[4] - 14
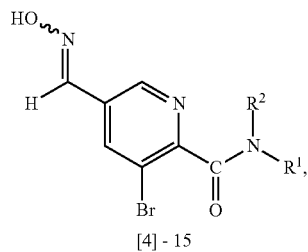
[4] - 15
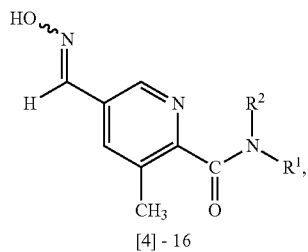
[4] - 16
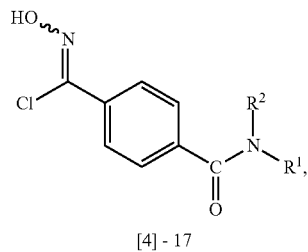
[4] - 17
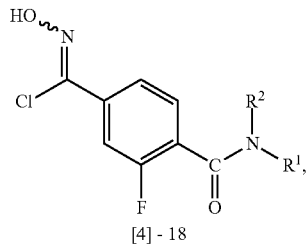
[4] - 18
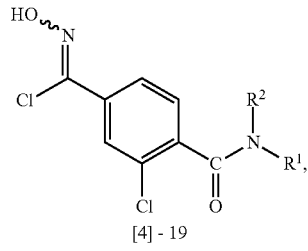
[4] - 19
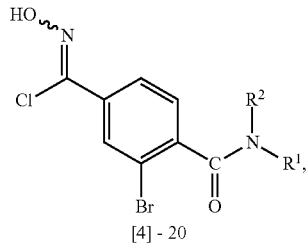
[4] - 20
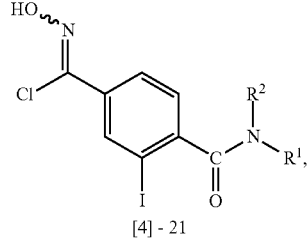
[4] - 21
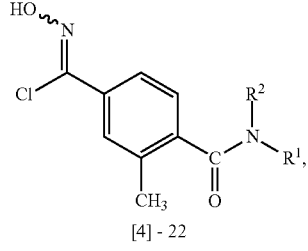
[4] - 22

TABLE 5-continued
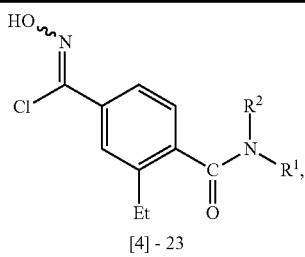
[4] - 23
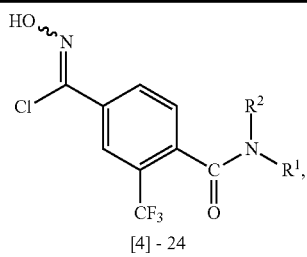
[4] - 24
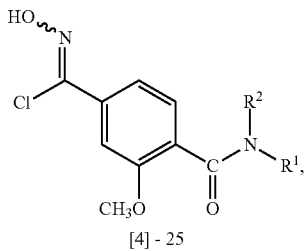
[4] - 25
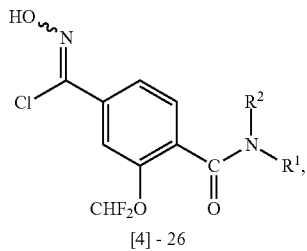
[4] - 26
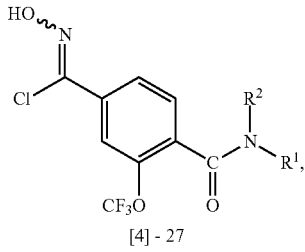
[4] - 27
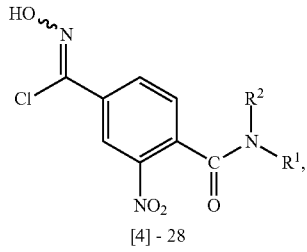
[4] - 28
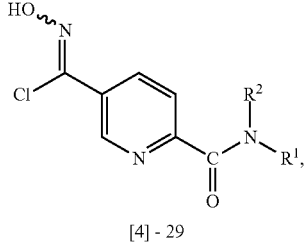
[4] - 29
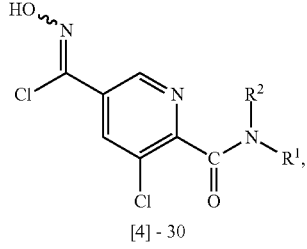
[4] - 30
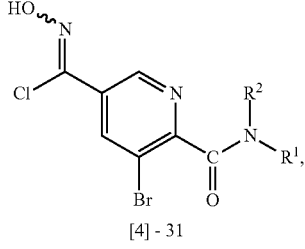
[4] - 31
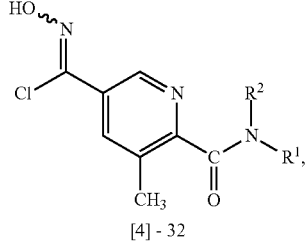
[4] - 32
または
| R² | R¹ | R² | R¹ |
|---|---|---|---|
| H | Et | H | CH₂(D-17b)Cl |
| Et | Et | H | CH₂(D-17b)CF₃ |
| H | c-Pr | H | CH₂(D-21a) |
| CH₂OCH₃ | c-Pr | H | CH(CH₃)(D-21a) |
| CH₂CN | c-Pr | H | CH₂(D-21b)CF₃ |
| C(O)CH₃ | c-Pr | H | CH₂(D-22a) |
| C(O)Et | c-Pr | CH₂OCH₃ | CH₂(D-22a) |
| C(O)OCH₃ | c-Pr | CH₂CN | CH₂(D-22a) |
| H | CH₂Pr-c | CH₂C≡CH | CH₂(D-22a) |
| CH₂OCH₃ | CH₂Pr-c | C(O)CH₃ | CH₂(D-22a) |
| CH₂CN | CH₂Pr-c | C(O)Et | CH₂(D-22a) |
| C(O)CH₃ | CH₂Pr-c | C(O)OCH₃ | CH₂(D-22a) |
| C(O)Et | CH₂Pr-c | H | CH(CH₃)(D-22a) |
| C(O)OCH₃ | CH₂Pr-c | H | CH₂(D-23b)Cl |

TABLE 5-continued

| | | | |
|---|---|---|---|
| H | c-Bu | H | CH₂(D-28a) |
| CH₂OCH₃ | c-Bu | H | CH₂(D-29b)CH₃ |
| CH₂CN | c-Bu | H | CH₂(D-30a) |
| C(O)CH₃ | c-Bu | H | CH₂(D-34a) |
| C(O)Et | c-Bu | H | CH₂(D-34b)CH₃ |
| C(O)OCH₃ | c-Bu | H | CH₂(D-35a) |
| H | c-Pen | H | CH₂(D-38a) |
| H | CH₂CH₂F | H | CH(CH₃)(D-38a) |
| H | CH₂CH₂Cl | H | CH(CF₃)(D-38a) |
| H | CH₂CHF₂ | H | CH₂(D-47a) |
| H | CH₂CF₃ | CH₃ | CH₂(D-47a) |
| CH₂OCH₃ | CH₂CF₃ | Et | CH₂(D-47a) |
| CH₂CN | CH₂CF₃ | i-Pr | CH₂(D-47a) |
| CH₂C≡CH | CH₂CF₃ | c-Pr | CH₂(D-47a) |
| C(O)CH₃ | CH₂CF₃ | CH₂CF₃ | CH₂(D-47a) |
| C(O)Et | CH₂CF₃ | CH₂OCH₃ | CH₂(D-47a) |
| C(O)OCH₃ | CH₂CF₃ | CH₂OEt | CH₂(D-47a) |
| H | CH₂CH₂CF₃ | CH₂CH₂OCH₃ | CH₂(D-47a) |
| CH₂OCH₃ | CH₂CH₂CF₃ | CH₂CN | CH₂(D-47a) |
| CH₂CN | CH₂CH₂CF₃ | CH₂CH=CH₂ | CH₂(D-47a) |
| C(O)CH₃ | CH₂CH₂CF₃ | CH₂C≡CH | CH₂(D-47a) |
| C(O)Et | CH₂CH₂CF₃ | C(O)CH₃ | CH₂(D-47a) |
| C(O)OCH₃ | CH₂CH₂CF₃ | C(O)Et | CH₂(D-47a) |
| H | CH₂CF₂CF₃ | C(O)Pr-n | CH₂(D-47a) |
| H | CH₂CF₂CF₂CF₃ | C(O)Pr-i | CH₂(D-47a) |
| H | CH₂OCH₃ | C(O)Pr-c | CH₂(D-47a) |
| H | CH₂OEt | C(O)Bu-t | CH₂(D-47a) |
| CH₂OEt | CH₂OEt | C(O)CH₂OCH₃ | CH₂(D-47a) |
| C(O)CH₃ | CH₂OEt | C(O)CH=CH₂ | CH₂(D-47a) |
| H | CH₂OPr-n | C(O)OCH₃ | CH₂(D-47a) |
| H | CH₂OPr-i | C(O)OEt | CH₂(D-47a) |
| H | CH₂OCH₂CH₂Cl | C(O)OPr-i | CH₂(D-47a) |
| H | CH₂OCH₂CHF₂ | C(O)OCH₂CH₂OCH₃ | CH₂(D-47a) |
| H | CH₂OCH₂OF₃ | C(O)OCH₂CH=CH₂ | CH₂(D-47a) |
| CH₃ | CH₂OCH₂CF₃ | H | CH₂(D-47c)Cl |
| C(O)CH₃ | CH₂OCH₂F₃ | H | CH(CH₃)(D-47a) |
| H | CH(CH₃)OCH₂CF₃ | CH₂OCH₃ | CH(CH₃)(D-47a) |
| H | CH(CF₃)OCH₃ | CH₂CN | CH(CH₃)(D-47a) |
| H | CH₂CH₂OCH₃ | CH₂C≡CH | CH(CH₃)(D-47a) |
| CH₃ | CH₂CH₂OCH₃ | C(O)CH₃ | CH(CH₃)(D-47a) |
| C(O)CH₃ | CH₂CH₂OCH₃ | C(O)Et | CH(CH₃)(D-47a) |
| H | CH₂CH₂OEt | C(O)OCH₃ | CH(CH₃)(D-47a) |
| H | CH₂CH(OCH₃)₂ | H | CH₂(D-48e)Cl |
| H | CH₂(E-4a) | H | CH₂(D-49a) |
| H | CH₂(E-5a) | c-Pr | CH₂(D-49a) |
| H | CH₂(E-10a) | H | CH₂(D-50a) |
| H | CH₂(E-10b)CH₃ | CH₂OCH₃ | CH₂(D-50a) |
| H | E-4a | CH₂CN | CH₂(D-50a) |
| CH₂OCH₃ | E-4a | C(O)CH₃ | CH₂(D-50a) |
| CH₂CN | E-4a | C(O)Et | CH₂(D-50a) |
| C(O)CH₃ | E-4a | C(O)OCH₃ | CH₂(D-50a) |
| C(O)Et | E-4a | H | CH₂(D-51a) |
| C(O)Pr-i | E-4a | H | CH₂(D-53a) |
| H | E-5a | H | CH₂(D-53b)CH₃ |
| H | E-5a(R) | H | NHC(O)Pr-n |
| CH₂OCH₃ | E-5a(R) | H | NHC(O)OCH₃ |
| CH₂CN | E-5a(R) | H | NHC(O)OEt |
| C(O)CH₃ | E-5a(R) | H | C(O)CH₂CH₂F |
| C(O)Et | E-5a(R) | H | C(O)CH₂CF₃ |
| C(O)Pr-i | E-5a(R) | H | C(O)CH₂CH₂CF₃ |
| C(O)OCH₃ | E-5a(R) | CH₃ | C(O)CH₂CH₂CF₃ |
| H | E-23a | H | C(O)OCH₂C(CF₃)₂CH₃ |
| H | CH₂SO₂CH₃ | H | C(O)NHCH₃ |
| H | CH₂CH₂SO₂CH₃ | H | C(O)N(CH₃)₂ |
| H | CH₂CH₂SO₂Et | C(0)OCH₃ | C(O)N(CH₃)₂ |
| H | CH₂CH(CH₃)SO₂CH₃ | H | C(O)NHEt |
| H | CH(CH₃)CH₂SO₂CH₃ | CH₃ | C(O)NHEt |
| H | C(CH₃)₂CH₂SO₂CH₃ | H | C(O)NHPr-i |
| H | CH₂NHC(O)OCH₃ | H | C(O)NHPr-c |
| H | CH₂N(CH₂CF₃)C(O)OCH₃ | H | C(O)NHCH₂CH₂Cl |
| H | CH₂NHC(O)OEt | H | C(O)NHCH₂CF₃ |
| H | CH₂NHC(O)OCH₂CF₃ | CH₃ | C(O)NHCH₂CF₃ |
| H | CH(CH₃)NHC(O)OCH₃ | H | (O)NHCH₂CH=CH₂ |
| H | CH₂C(O)CH₃ | H | C(O)NHCH₂(Ph-4-F) |
| H | CH₂C(CH₃)=NOCH₃ | H | C(O)NHCH₂(D-47a) |
| H | CH₂CN | H | C(S)NHCH₃ |
| CH₂OCH₃ | CH₂CN | H | C(S)NHEt |
| CH₂CN | CH₂CN | H | C(S)NHPr-n |
| C(O)CH₃ | CH₂CN | H | C(S)NHPr-i |
| C(O)Et | CH₂CN | H | C(S)NHCH₂CH₂Cl |

TABLE 5-continued

| | | | |
|---|---|---|---|
| C(O)Pr-i | CH$_2$CN | H | C(S)NHCH$_2$CF$_3$ |
| H | CH$_2$C(O)NHCH$_3$ | H | Ph |
| H | CH$_2$C(O)N(CH$_3$)$_2$ | H | Ph-3-F |
| H | CH$_2$C(O)NHEt | H | Ph-4-F |
| H | CH$_2$C(O)NHPr-n | H | Ph-4-OSO$_2$CH$_3$ |
| H | CH$_2$C(O)NHPr-i | H | Ph-4-NO$_2$ |
| H | CH$_2$C(O)NHPr-c | H | Ph-3-CN |
| H | CH$_2$C(O)NHCH$_2$CH$_2$F | H | Ph-4-CN |
| H | CH$_2$C(O)NHCH$_2$CH$_2$Cl | H | Ph-2,4-F$_2$ |
| H | CH$_2$C(O)NHCH$_2$CF$_3$ | H | Ph-2,6-F$_2$ |
| C(O)OCH$_3$ | CH$_2$C(O)NHCH$_2$CF$_3$ | H | Ph-3-NO$_2$-4-F |
| H | CH$_2$C(O)NHCH$_2$CH$_2$OCH$_3$ | H | Ph-2,4,6-F$_3$ |
| H | CH$_2$C(O)NHCH$_2$CH=CH$_2$ | H | D-8a |
| H | CH$_2$C(O)N(CH$_3$)CH$_2$CH=CH$_2$ | H | (D-8b)CH$_3$ |
| H | CH$_2$C(O)NHCH$_2$C≡CH | H | D-11a |
| H | CH(CH$_3$)C(O)NHEt | H | (D-13b)CH$_3$ |
| H | CH(CH$_3$)C(O)NHPr-i | H | D-14a |
| H | CH(CH$_3$)C(O)NHCH$_2$CH$_2$Cl | H | (D-15a)CH$_3$ |
| H | CH(CH$_3$)C(O)NHCH$_2$CH$_2$Cl(D) | H | (D-17a)CH$_3$ |
| H | CH(CH$_3$)C(O)NHCH$_2$CF$_3$ | H | D-21a |
| H | CH(CH$_3$)C(O)NHCH$_2$CF$_3$(D) | H | (D-21b)CF$_3$ |
| H | CH(CH$_3$)C(O)NHCH$_2$CH=CH$_2$ | H | D-35a |
| H | CH$_2$C(S)NH$_2$ | H | D-47a |
| H | CH=CH$_2$ | H | (D-47d)F |
| H | CH$_2$CH=CH$_2$ | H | (D-47d)Cl |
| CH$_2$OCH$_3$ | CH$_2$CH=CH$_2$ | H | (D-47d)Br |
| CH$_2$CN | CH$_2$CH=CH$_2$ | H | (D-47d)CF$_3$ |
| C(O)CH$_3$ | CH$_2$CH=CH$_2$ | H | (D-47d)OCHF$_2$ |
| C(O)Et | CH$_2$CH=CH$_2$ | H | (D-47d)NO$_2$ |
| C(O)Pr-i | CH$_2$CH=CH$_2$ | H | (D-47d)CN |
| C(O)OCH$_3$ | CH$_2$CH=CH$_2$ | H | (D-47e)Cl |
| H | CH$_2$C(F)=CH$_2$ | H | (D-47e)Br |
| H | CH$_2$CCl=CH$_2$ | H | D-48a |
| H | CH$_2$CCl=CHCl | H | (D-48e)F |
| H | CH$_2$C≡CH | H | (D-48e)Cl |
| CH$_2$OCH$_3$ | CH$_2$C≡CH | H | (D-48e)Br |
| CH$_2$CN | CH$_2$C≡CH | H | (D-48e)CN |
| C(O)CH$_3$ | CH$_2$C≡CH | H | D-50a |
| C(O)Et | CH$_2$C≡CH | H | (D-50b)CH$_3$ |
| C(O)Pr-i | CH$_2$C≡CH | H | (D-50c)F |
| H | CH$_2$Ph | H | (D-50c)Cl |
| H | CH$_2$(Ph-4-F) | H | (D-50c)Br |
| H | CH$_2$(Ph-4-OCH$_3$) | H | (D-50c)I |
| H | CH$_2$(Ph-4-NO$_2$) | H | (D-50c)NO$_2$ |
| H | CH$_2$(Ph-4-CN) | H | (D-50c)CN |
| H | CH(CH$_3$)Ph | H | D-51a |
| H | CH(CH$_3$)Ph(R) | H | D-52a |
| H | CH(CF$_3$)Ph | H | (D-52b)F |
| H | CH(CN)Ph | H | (D-52b)Cl |
| H | CH(Ph)C(S)NH$_2$ | H | (D-52b)Br |
| H | CH$_2$(D-1a) | H | (D-52b)CN |
| H | CH(CN)(D-1a) | H | D-53a |
| H | CH$_2$(D-8b)CH$_2$ | H | (D-53b)Cl |
| H | CH$_2$(D-11a) | H | (D-53b)Br |
| H | CH(CF$_3$)(D-14a) | H | (D-53b)NO$_2$ |
| H | CH$_2$(D-15a)CH$_3$ | H | (D-53b)CN |
| H | CH$_2$(D-16b)Cl | H | D-54a |
| H | CH$_2$(D-16c)Cl | H | (D-54b)F |
| H | CH$_2$(D-17a)CH$_3$ | H | (D-54b)Cl |

TABLE 6

In the table, the number showing the substitution position of substituents $(X^2)_{m1}$ corresponds to the position number indicated in the following structural formulae.
The indication "—" means no-substitution.

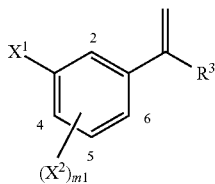

[5]-1

| $X^1$ | $(X^2)_{m1}$ | $R^3$ | $X^1$ | $(X^2)_{m1}$ | $R^3$ |
|---|---|---|---|---|---|
| F | 4-F | $CF_3$ | $CF_3$ | 5-Br | $CF_2Cl$ |
| F | 4,5-$F_2$ | $CF_3$ | $CF_3$ | 5-Br | $CF_2Br$ |
| F | 4,5-$F_2$ | $CF_2Cl$ | $CF_3$ | 5-Br | $CF_2CHF_2$ |
| Cl | — | $CF_2Cl$ | $CF_3$ | 5-$CH_3$ | $CF_3$ |
| Cl | 4-F | $CF_3$ | $CF_3$ | 5-$CH_3$ | $CF_2Cl$ |
| Cl | 4-F | $CF_2Cl$ | $CF_3$ | 5-$CF_3$ | $CHF_2$ |
| Cl | 5-F | $CF_3$ | $CF_3$ | 5-$CF_3$ | $CF_2Cl$ |
| Cl | 5-F | $CF_2Cl$ | $CF_3$ | 5-$CF_3$ | $CF_2Br$ |
| Cl | 4-Cl | $CF_3$ | $CF_3$ | 5-$CF_3$ | $CF_2CHF_2$ |
| Cl | 4-Cl | $CF_2Cl$ | $CF_3$ | 5-$OCH_3$ | $CF_3$ |
| Cl | 5-Cl | $CHF_2$ | $CF_3$ | 5-$OCH_3$ | $CF_2Cl$ |
| Cl | 5-Cl | $CHFCl$ | $CF_3$ | 5-$NO_2$ | $CF_3$ |
| Cl | 5-Cl | $CHCl_2$ | $CF_3$ | 5-$NO_2$ | $CF_2Cl$ |
| Cl | 5-Cl | $CHFBr$ | $CF_3$ | 5-CN | $CF_3$ |
| Cl | 5-Cl | $CF_3$ | $CF_3$ | 5-CN | $CF_2Cl$ |
| Cl | 5-Cl | $CF_2Cl$ | $CF_3$ | 4,5-$F_2$ | $CHF_2$ |
| Cl | 5-Cl | $CF_2Br$ | $CF_3$ | 4,5-$F_2$ | $CF_3$ |
| Cl | 5-Cl | $CF_2CHF_2$ | $CF_3$ | 4,5-$F_2$ | $CF_2Cl$ |
| Cl | 5-Cl | $CF_2CF_3$ | $CF_3$ | 4,5-$F_2$ | $CF_2Br$ |
| Cl | 5-Cl | $CF_2CF_2CF_3$ | $CF_3$ | 4,5-$F_2$ | $CF_2CHF_2$ |
| Cl | 5-Cl | $CF_2OCH_3$ | $CF_3$ | 4-F-5-Cl | $CHF_2$ |
| Cl | 5-Cl | $CF_2SCH_3$ | $CF_3$ | 4-F-5-Cl | $CF_3$ |
| Cl | 5-Cl | T-3 | $CF_3$ | 4-F-5-Cl | $CF_2Cl$ |
| Cl | 5-Cl | T-4 | $CF_3$ | 4-F-5-Cl | $CF_2Br$ |
| Cl | 5-$CH_3$ | $CF_3$ | $CF_3$ | 4-F-5-Cl | $CF_2CHF_2$ |
| Cl | 5-$CH_3$ | $CF_2Cl$ | $CF_3$ | 4-Cl-5-$CF_3$ | $CHF_2$ |
| Cl | 5-$NO_2$ | $CF_3$ | $CF_3$ | 4-Cl-5-$CF_3$ | $CF_3$ |
| Cl | 5-CN | $CF_3$ | $CF_3$ | 4-Cl-5-$CF_3$ | $CF_2Cl$ |
| Cl | 4-F-5-Cl | $CHF_2$ | $CF_3$ | 4-Cl-5-$CF_3$ | $CF_2Br$ |
| Cl | 4-F-5-Cl | $CF_3$ | $CF_3$ | 4-Cl-5-$CF_3$ | $CF_2CHF_2$ |
| Cl | 4-F-5-Cl | $CF_2Cl$ | $CF_2CF_3$ | — | $CF_3$ |
| Cl | 4-F-5-Cl | $CF_2Br$ | $CF_2CF_3$ | — | $CF_2Cl$ |
| Cl | 4-F-5-Cl | $CF_2CHF_2$ | $CF_2CF_3$ | 5-Cl | $CF_3$ |
| Cl | 4,5-$Cl_2$ | $CHF_2$ | $CF_2CF_3$ | 5-Br | $CF_3$ |
| Cl | 4,5-$Cl_2$ | $CF_3$ | $CF_2CF_3$ | 5-$CH_3$ | $CF_3$ |
| Cl | 4,5-$Cl_2$ | $CF_2Cl$ | $CF_2CF_2CF_3$ | — | $CF_3$ |
| Cl | 4,5-$Cl_2$ | $CF_2Br$ | $CF_2CF_2CF_3$ | — | $CF_2Cl$ |
| Cl | 4,5-$Cl_2$ | $CF_2CHF_2$ | $CF_2CF_2CF_3$ | 5-Cl | $CF_3$ |
| Cl | 4-$CH_3$-5-Cl | $CF_3$ | $CF_2CF_2CF_3$ | 5-Br | $CF_3$ |
| Cl | 4-$OCHF_2$-5-Cl | $CF_3$ | $CF_2CF_2CF_3$ | 5-$CH_3$ | $CF_3$ |
| Cl | 4-CN-5-Cl | $CF_3$ | $CF(CF_3)_2$ | — | $CF_3$ |
| Br | — | $CF_3$ | $CF(CF_3)_2$ | — | $CF_2Cl$ |
| Br | — | $CF_2Cl$ | $CF(CF_3)_2$ | 5-Cl | $CF_3$ |
| Br | 4-F | $CF_3$ | $CF(CF_3)_2$ | 5-Br | $CF_3$ |
| Br | 4-F | $CF_2Cl$ | $CF(CF_3)_2$ | 5-$CH_3$ | $CF_3$ |
| Br | 5-F | $CF_3$ | $CF_2CF_2CF_2CF_3$ | — | $CF_3$ |
| Br | 5-F | $CF_2Cl$ | $C(CF_3)_2OH$ | — | $CF_3$ |
| Br | 5-Cl | $CHF_2$ | $C(CF_3)_2OH$ | 5-Cl | $CF_3$ |
| Br | 5-Cl | $CF_3$ | $C(CF_3)_2OH$ | 5-Br | $CF_3$ |
| Br | 5-Cl | $CF_2Cl$ | $C(CF_3)_2OH$ | 5-$CH_3$ | $CF_3$ |
| Br | 5-Cl | $CF_2Br$ | $C(CF_3)_2OCH_3$ | — | $CF_3$ |
| Br | 5-Cl | $CF_2CHF_2$ | $C(CF_3)_2OCH_3$ | 5-Cl | $CF_3$ |
| Br | 4-Br | $CF_3$ | $C(CF_3)_2OCH_3$ | 5-Br | $CF_3$ |
| Br | 4-Br | $CF_2Cl$ | $C(CF_3)_2OCH_3$ | 5-$CH_3$ | $CF_3$ |
| Br | 5-Br | $CHF_2$ | $OCHF_2$ | 5-Cl | $CF_3$ |
| Br | 5-Br | $CF_3$ | $OCHF_2$ | 5-Cl | $CF_2Cl$ |
| Br | 5-Br | $CF_2Cl$ | $OCHF_2$ | 5-Br | $CF_3$ |
| Br | 5-Br | $CF_2Br$ | $OCHF_2$ | 5-Br | $CF_2Cl$ |
| Br | 5-Br | $CF_2CHF_2$ | $OCHF_2$ | 5-$CF_3$ | $CF_3$ |
| Br | 5-$CH_3$ | $CF_3$ | $OCHF_2$ | 5-$CF_3$ | $CF_2Cl$ |
| Br | 5-$OCH_3$ | $CF_3$ | $OCF_3$ | — | $CF_3$ |

TABLE 6-continued

In the table, the number showing the substitution position of substituents $(X^2)_{m1}$ corresponds to the position number indicated in the following structural formulae.
The indication "—" means no-substitution.

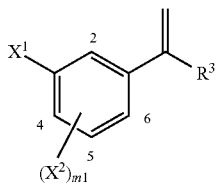

[5]-1

| $X^1$ | $(X^2)_{m1}$ | $R^3$ | $X^1$ | $(X^2)_{m1}$ | $R^3$ |
|---|---|---|---|---|---|
| Br | 5-NO$_2$ | CF$_3$ | OCF$_3$ | — | CF$_2$Cl |
| Br | 5-CN | CF$_3$ | OCF$_3$ | 5-Cl | CF$_3$ |
| Br | 4-F-5-Br | CHF$_2$ | OCF$_3$ | 5-Cl | CF$_2$Cl |
| Br | 4-F-5-Br | CF$_3$ | OCF$_3$ | 5-Br | CF$_3$ |
| Br | 4-F-5-Br | CF$_2$Cl | OCF$_3$ | 5-Br | CF$_2$Cl |
| Br | 4-F-5-Br | CF$_2$Br | OCF$_3$ | 5-CF$_3$ | CF$_3$ |
| Br | 4-F-5-Br | CF$_2$CHF$_2$ | OCF$_3$ | 5-CF$_3$ | CF$_2$Cl |
| Br | 4,5-Br$_2$ | CF$_3$ | OCF$_2$Br | — | CF$_3$ |
| Br | 4,5-Br$_2$ | CF$_2$Cl | OCF$_2$Br | — | CF$_2$Cl |
| Br | 4-CH$_3$-5-Br | CF$_3$ | OCF$_2$CHF$_2$ | — | CF$_3$ |
| Br | 4-OCHF$_2$-5-Br | CF$_3$ | OCF$_2$CHFCl | — | CF$_3$ |
| Br | 4-CN-5-Br | CF$_3$ | OCF$_2$CHFCF$_3$ | — | CF$_3$ |
| I | — | CF$_3$ | OCF$_2$CHFOCF$_3$ | — | CF$_3$ |
| I | — | CF$_2$Cl | OCF$_2$CHFOCF$_2$CF$_2$CF$_3$ | — | CF$_3$ |
| I | 5-F | CF$_3$ | SCF$_3$ | — | CF$_3$ |
| I | 5-F | CF$_2$Cl | SCF$_3$ | — | CF$_2$Cl |
| I | 5-Cl | CF$_3$ | SCF$_3$ | 5-Cl | CF$_3$ |
| I | 5-Cl | CF$_2$Cl | SCF$_3$ | 5-Cl | CF$_2$Cl |
| I | 5-I | CF$_3$ | SCF$_3$ | 5-Br | CF$_3$ |
| CH$_3$ | 5-CH$_3$ | CF$_3$ | SCF$_3$ | 5-Br | CF$_2$Cl |
| CF$_3$ | — | CF$_2$Cl | S(O)CF$_3$ | — | CF$_3$ |
| CF$_3$ | 4-F | CF$_3$ | S(O)CF$_3$ | 5-Cl | CF$_3$ |
| CF$_3$ | 4-F | CF$_2$Cl | S(O)CF$_3$ | 5-Br | CF$_3$ |
| CF$_3$ | 5-F | CF$_3$ | SO$_2$CF$_3$ | — | CF$_3$ |
| CF$_3$ | 5-F | CF$_2$Cl | SO$_2$CF$_3$ | 5-Cl | CF$_3$ |
| CF$_3$ | 4-Cl | CF$_3$ | SO$_2$CF$_3$ | 5-Br | CF$_3$ |
| CF$_3$ | 4-Cl | CF$_2$Cl | SCF$_2$Cl | — | CF$_3$ |
| CF$_3$ | 5-Cl | CHF$_2$ | SCF$_2$Cl | — | CF$_2$Cl |
| CF$_3$ | 5-Cl | CF$_3$ | SCF$_2$Br | — | CF$_3$ |
| CF$_3$ | 5-Cl | CF$_2$Cl | SCF$_2$Br | — | CF$_2$Cl |
| CF$_3$ | 5-Cl | CF$_2$Br | SCF$_2$CHFCl | 5-Cl | CF$_3$ |
| CF$_3$ | 5-Cl | CF$_2$CHF$_2$ | SCF$_2$CHFCl | 5-Br | CF$_3$ |
| CF$_3$ | 5-Br | CHF$_2$ | SF$_5$ | — | CF$_3$ |
| CF$_3$ | 5-Br | CF$_3$ | SF$_5$ | — | CF$_2$Cl |
| F | 5-F | CF$_2$Cl | CF$_3$ | 4,5-Cl$_2$ | CF$_2$Cl |
| CF$_3$ | 4,5-Cl$_2$ | CHF$_2$ | CF$_3$ | 4,5-Cl$_2$ | CF$_2$Br |
| CF$_3$ | 4,5-Cl$_2$ | CF$_3$ | CF$_3$ | 4,5-Cl$_2$ | CF$_2$CHF$_2$ |

The compounds of the present invention can effectively control in a low concentration so-called agricultural insects injuring agricultural and horticultural crops and trees, so-called domestic animal pests parasitizing domestic animals and domestic fowls, so-called hygienic pests having an adverse affect on human being's environment such as houses, insects as so-called stored grain insects injuring grains and the like stored in storehouses, and any pests of acarids, crustaceans, mollusks and nematodes generating in the similar scenes.

The insects, acarids, crustaceans, mollusks and nematodes that the compounds of the present invention can control concretely include for example the followings:

Lepidoptera insects, such as Adoxophyes honmai, Adoxophyes orana faciata, Archips breviplicanus, Archips fuscocupreanus, Grapholita molesta, Homona magnanima, Leguminivora glycinivorella, Matsumuraeses phaseoli, Pandemis heparana, Bucculatrix pyrivorella, Lyonetia clerkella, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Cydla pomonella, Chilo suppressalis, Cnaphalocrocis medinalis, Conogethes punctiferalis, Diaphania indica, Etiella zinckenella, Glyphodes pyloalis, Hellula undalis, Ostrinia furnacalis, Ostrinia scapulalis, Ostrinia nubilalis, Parapediasia teterrella, Parnara guttata, Pieris brassicae, Pieris rapae crucivora, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Helicoverpa armigera, Helicoverpa assulta, Helicoverpa zea, Heliothis virescens, Mamestra brassicae, Mythimna separata, Naranga aenescens, Spodoptera eridania, Spodoptera exigua, Spodoptera

*frugiperda, Spodoptera littoralis, Spodoptera litura, Spodoptera depravata, Trichoplusia ni, Endopiza viteana, Manduca quinquemaculata, Manduca sexta*, or the like;

Thysanoptera insects, such as *Frankliniella intonsa, Frankliniella occidentalis, Heliothrips haemorrhoidalis, Scirtothrips dorsalis, Thrips palmi, Thrips tabaci, Ponticulothrips diospyrosi*, or the like;

Hemiptera insects, such as *Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipterus, Dysdercus cingulatus, Stephanitis pyrioides, Halticus insularis, Lygus lineolaris, Stenodema sibiricum, Stenotus rubrovittatus, Trigonotylus caelestialium, Arboridia apicalis, Balclutha saltuella, Epiacanthus stramineus, Empoasca fabae, Empoasca nipponica, Empoasca onukii, Empoasca sakaii, Macrosteles striifrons, Nephotettix cinctinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bemisia tabaci, Dialeurodes citri, Trialeurodes vaporariorum, Viteus vitifolii, Aphis gossypii, Aphis spiraecola, Myzus persicae, Toxoptera aurantii, Drosicha corpulenta, Icerya purchasi, Phenacoccus solani, Planococcus citri, Planococcus kuraunhiae, Pseudococcus comstocki, Ceroplastes ceriferus, Ceroplastes rubens, Aonidiella aurantii, Comstockaspis perniciosa, Fiorinia theae, Pseudaonidia paeoniae, Pseudaulacaspis pentagona, Pseudaulacaspis prunicola, Unaspis euonymi, Unaspis yanonensis, Cimex lectularius*, or the like;

Coleoptera insects, such as *Anomala cuprea, Anomala rufocuprea, Gametis jucunda, Heptophylla picea, Popillia japonica, Lepinotarsa decemlineata, Melanotus fortnumi, Melanotus tamsuyensis, Lasioderma serricorne, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Chaetocnema concinna, Diabrotica undecimpunctata, Diabrotica virgifera, Diabrotica barberi, Oulema oryzae, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sulcatus, Sitophilus granarius, Sitophilus zeamais, Sphenophorus venatus vestitus, Paederus fuscipes*, or the like;

Diptera insects, such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Pegomya cunicularia, Rhagoletis pomonella, Mayetiola destructor, Musca domestica, Stomoxys calcitrans, Melophagus ovinus, Hypoderma bovis, Hypoderma lineatum, Oestrus ovis, Glossina palpalis, Glossina morsitans, Prosimulium yezoensis, Tabanus trigonus, Telmatoscopus albipunctatus, Leptoconops nipponensis, Culex pipiens pallens, Aedes aegypti, Aedes albopicutus, Anopheles hyracanus sinesis*, or the like;

Hymenoptera insects, such as *Apethymus kuri, Athalia rosae, Arge pagana, Neodiprion sertifer, Dryocosmus kuriphilus, Eciton burchelli, Eciton schmitti, Camponotus japonicus, Vespa mandarina, Myrmecia* spp., *Solenopsis* spp., *Monomorium pharaonis*, or the like;

Orthoptera insects, such as *Teleogryllus emma, Gryllotalpa orientalis, Locusta migratoria, Oxya yezoensis, Schistocerca gregaria*, or the like;

Collembola insects, such as *Onychiurus folsomi, Onychiurus sibiricus, Bourletiella hortensis*, or the like;

Dictyoptera insect, such as *Periplaneta fuliginosa, Periplaneta japonica, Blattella germanica*, or the like;

Isoptera insects, such as *Coptotermes formosanus, Reticulitermes speratus, Odontotermes formosanus*, or the like;

Siphonaptera insects, such as *Ctenocephalidae felis, Ctenocephalides canis, Echidnophaga gallinacea, Pulex irritans, Xenopsylla cheopis*, or the like;

Mallophaga insects, such as *Menacanthus stramineus, Bovicola bovis*, or the like;

Anoplura insects, such as *Haematopinus eurysternus, Haematopinus suis, Linognathus vituli, Solenopotes capillatus*, or the like;

Tarsonemid mites, such as *Phytonemus pallidus, Polyphagotarsonemus latus, Tarsonemus bilobatus*, or the like;

Eupodid mites, such as *Penthaleus erythrocephalus, Penthaleus major*, or the like;

Spider mites, such as *Oligonychus shinkajii, Panonychus citri, Panonychus mori, Panonychus ulmi, Tetranychus kanzawai, Tetranychus urticae*, or the like;

Eriophyid mites, such as *Acaphylla theavagrans, Aceria tulipae, Aculops lycopersici, Aculops pelekassi, Aculus schlechtendali, Eriophyes chibaensis, Phyllocoptruta oleivora*, or the like;

Acarid mites, such as *Rhizoglyphus robini, Tyrophagus putrescentiae, Tyrophagus similis*, or the like;

Bee brood mites, such as *Varroa jacobsoni*, or the like;

Ixodides, such as *Boophilus microplus, Rhipicephalus sanguineus, Haemaphysalis longicornis, Haemophysalis flava, Haemophysalis campanulata, Ixodes ovatus, Ixodes persulcatus, Amblyomma* spp., *Dermacentor* spp., or the like;

Cheyletidae, such as *Cheyletiella yasguri, Cheyletiella blakei*, or the like;

Demodicidae, such as *Demodex canis, Demodex cati*, or the like;

Psoroptidae, such as *Psoroptes ovis*, or the like;

Scarcoptidae, such as *Sarcoptes scabiei, Notoedres cati, Knemidocoptes* spp., or the like;

Crustacea, such as *Armadillidium vulgare*, or the like;

Gastropoda, such as *Pomacea canaliculata, Achatina fulica, Meghimatium bilineatum, Limax Valentiana, Acusta despecta sieboldiana, Euhadra peliomphala*, or the like;

Nematodes, such as *Prathylenchus coffeae, Prathylenchus penetrans, Prathylenchus vulnus, Globodera rostochiensis, Heterodera glycines, Meloidogyne hapla, Meloidogyne incognita, Aphelenchoides besseyi, Bursaphelenchus xylophilus*, or the like. But the present invention is not limited thereto.

The endo-parasites of domestic animals, domestic fowls, pets and the like that the compounds of the present invention can control concretely include for example the followings:

Nematodes, such as *Haemonchus, Trichostrongylus, Ostertagia, Nematodirus, Cooperia, Ascaris, Bunostomum, Oesophagostomum, Chabertia, Trichuris, Storongylus, Trichonema, Dictyocaulus, Capillaria, Heterakis, Toxocara, Ascaridia, Oxyuris, Ancylostoma, Uncinaria, Toxascaris, Parascaris*, or the like;

Filariidae in nematodes, such as *Wuchereria, Brugia, Onchoceca, Dirofilaria, Loa*, or the like;

Dracunculidae in nematodes, such as *Deacunculus*, or the like;

Cestoda, such as *Dipylidium caninum, Taenia taeniaeformis, Taenia solium, Taenia saginata, Hymenolepis diminuta,*

*Moniezia benedeni, Diphyllobothrium latum, Diphyllobothrium erinacei, Echinococcus granulosus, Echinococcus multilocularis*, or the like;

Trematoda, such as *Fasciola hepatica, F. gigantica, Paragonimus westermanii, Fasciolopsic bruski, Eurytrema pancreaticum, E. coelomaticum, Clonorchis sinensis, Schistosoma japonicum, Schistosoma haematobium, Schistosoma mansoni*, or the like;

*Eimeria* spp., such as *Eimeria tenella, Eimeria acervulina, Eimeria brunetti, Eimeria maxima, Eimeria necatrix, Eimeria bovis, Eimeria ovinoidalis*, or the like;

*Trypanosomsa cruzi, Leishmania* spp., *Plasmodium* spp., *Babesis* spp.,

*Trichomonadidae* spp., *Histomanas* spp., *Giardia* spp., *Toxoplasma* spp., *Entamoeba histolytica, Theileria* spp., or the like. But the present invention is not limited thereto.

Further, the compounds of the present invention are effective for pests acquiring high resistance against existing insecticides such as organic phosphorus compounds, carbamate compounds or pyrethroid compounds, etc.

That is, the compounds of the present invention can effectively control pests that belong to insects such as Collembola, Dictyoptera, Orthoptera, *Isoptera*, Thysanoptera, Hemiptera, Lepidoptera, Coleoptera, *Hymenoptera*, Diptera, *Isoptera* and Anoplura, Acarina, Gastropoda and Nematoda, in a low concentration. On the other hand, the compounds of the present invention have an extremely useful characteristic that they have little adverse affect on mammals, fishes, crustaceans and useful insects (beneficial insect such as honeybee, bumblebee or the like, or, natural enemies such as *Aphytis lingnanensis, Aphidius colemani, Orius strigicollis, Amblyseius californicus*, or the like).

When the compounds of the present invention are used, they can be generally mixed with a suitable solid carrier or liquid carrier, optionally along with surfactant, penetrating agent, spreading agent, thickner, anti-freezing agent, binder, anti-caking agent, disintegrating agent, anti-foaming agent, preservative, stabilizer, and the like, and can be formulated into any desired forms for practical use, such as soluble concentrates, emulsifiable concentrates, wettable powders, water soluble powders, water dispersible granules, water soluble granules, suspension concentrates, concentrated emulsions, suspoemulsions, microemulsions, dustable powders, granules, tablets and emulsifiable gels. From the viewpoint of an elimination or reduction of labor and an improvement of safety, the formulations in any desired forms described above may be included into a water-soluble bag made of water-soluble capsule or water-soluble film.

The solid carrier includes, for example, natural minerals such as quartz, calcite, sepiolite, dolomaite, chalk, kaolinite, pyrofilite, celicite, halocite, methahalocite, kibushi clay, gairome clay, pottery stone, zeaklite, allophane, white sand, mica, talc, bentonite, activeted earth, acid china clay, pumice, attapulgite, zeolite and diatomaceous earth, etc., calcined products of natural minerals such as calcined clay, perlite, white sand balloon (loam balloon), vermiculite, attapulgus clay and calcined diatomaceous earth, etc., inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate and potassium chloride, etc., saccharides such as glucose, fructose, sucrose and lactose, etc., polysaccharides such as starch, powder cellulose and dextrin, etc., organic materials such as urea, urea derivatives, benzoic acid and a salt of benzoic acid, etc., plants such as wood powder, cork powder, corn head stem, walnut shell and tobacco stem, etc., fly ash, white carbon (e.g., hydrated synthetic silica, anhydrous synthetic silica and hydrated synthetic silicate, etc.) and fertilizers, etc.

As the liquid carrier, there may be mentioned, for example, aromatic hydrocarbons such as xylene, alkyl($C_9$ or $C_{10}$, etc.) benzene, phenylxylylethane and alkyl($C_1$ or $C_3$, etc.)naphthalene, etc., aliphatic hydrocarbons such as machine oil, normal paraffin, isoparaffin and naphthene, etc., a mixture of aromatic hydrocarbons and aliphatic hydrocarbons such as kerosene, etc., alcohols such as ethanol, isopropanol, cyclohexanol, phenoxyethanol and benzylalcohol, etc., polyvalent alcohols such as ethylene glycol, propyleneglycol, diethylene glycol, hexylene glycol, polyethylene glycol and polypropyleneglycol, etc., ethers such as propyl cellosolve, butyl cellosolve, phenyl cellosolve, propyleneglycol monomethyl ether, propyleneglycol monoethyl ether, propyleneglycol monopropyl ether, propyleneglycol monobutyl ether and propyleneglycol monophenyl ether, etc., ketones such as acetophenone, cyclohexanone and -butyrolactone, etc., esters such as aliphatic acid methyl ester, dialkyl succinate, dialkyl glutamate, dialkyl adipate and dialkyl phthalate, etc., acid amides such as N-alkyl($C_1$, $C_8$ or $C_{12}$, etc.) pyrrolidone, etc., oil and fats such as soybean oil, linseed oil, rapeseed oil, coconut oil, cottonseed oil and caster oil, etc., dimethylsulfoxide and water.

These solid and liquid carriers may be used alone or in combination of two or more kinds in combination.

As the surfactant, there may be mentioned, for example, nonionic surfactants such as polyoxyethylene alkyl ether, polyoxyethylene alkyl (mono- or di-)phenyl ether, polyoxyethylene (mono-, di- or tri-)styrylphenyl ether, polyoxyethylene polyoxypropylene block copolymer, polyoxyethylene fatty acid (mono- or di-)ester, sorbitan fatty acid ester, polyoxyethylene sorbitan fatty acid ester, caster oil-ethylene oxide adducts, acetylene glycol, acetylene alcohol, ethylene oxide adducts of acetylene glycol, ethylene oxide adducts of acetylene alcohol and alkyl glycoside, etc., anionic surfactants such as alkyl sulfate, alkylbenzenesulfonate, lignine sulfonate, alkylsulfosuccinate, naphthalene sulfonate, alkylnaphthalene sulfonate, formalin condensate salt of naphthalene sulfonic acid, formalin condensate salt of alkylnaphthalene sulfonic acid, polyoxyethylene alkyl ether sulfate or phosphate, polyoxyethylene (mono- or di-)alkylphenyl ether sulfate or phosphate, polyoxyethylene (mono-, di- or tri-) styrylphenyl ether sulfate or phosphate, polycarboxylate (e.g., polyacrylates, polymaleates and copolymer materials of maleic acid and olefin, etc.) and polystyrenesulfonate, etc., cationic surfactants such as alkylamine salt and alkyl quaternary ammonium salt, etc., amphoteric surfactants such as amino acid type and betaine type, etc., silicone type surfactants and fluorine type surfactants.

A content of these surfactants is not specifically limited, and it is desirably in the range of 0.05 to 20 parts by weight in general based on 100 parts by weight of the preparation according to the present invention. Also, these surfactants may be used alone or in combination of two or more kinds in combination.

A dose of the compound of the present invention to be applied may vary depending on the place to be applied, time to be applied, method to be applied, crops to cultivate, etc., and in general, it is suitable in an amount of about 0.005 to 50 kg or so per a hectare (ha) as an amount of the effective ingredient.

On the other hand, when the compound of the present invention is used for controlling ecto- or endo-parasites of mammals and birds as domestic animals and pets, the effective amount of the compound of the present invention together with additives for formulations can be administered through oral administration, parenteral administration such as injection (intramuscular, subcutaneous, intravenous, intraperitoneal) or the like; transdermal administration such as dipping, spray, bathing, washing, pouring-on and spotting-on, and dusting, or the like; transnasal administration. The compound of the present invention can be also administrated through a formed product by use of a strip, a plate, a band, a collar, an ear mark, a limb band, a labe apparatus, or the like. In administration, the compound of the present invention can be formed in an arbitrary dosage form that is suited for the administration route.

The arbitrary dosage form includes solid preparations such as a dustable powder, a granule, wettable powder, a pellete, a tablet, a bolus, a capsule, a formed product containing an active compound; liquid formulations such as an injectable liquid formulation, an oral liquid formulation, a liquid formulation used on skin or in body cavity; solution preparations such as a pour-on agent, a spot-on agent, a flowable agent, an emulsifiable concentrate; semi-solid preparations such as an ointment, gel or the like.

The solid preparations can be mainly used through oral administration or transdermal administration by diluting with water or the like, or by environmental treatment. The solid preparations can be prepared by mixing the active compound with suitable excipients and optionally auxiliary substances and converting to a desired form. The suitable excipients include for example inorganic substances such as carbonates, hydrogen carbonates, phosphates, aluminum oxide, silica, clay or the like, organic substances such as sugar, cellulose, milled cereal, starch or the like.

The injectable liquid formulation can be administered intravenously, intramuscularly and subcutaneously. The injectable liquid formulation can be prepared by dissolving an active compound in a suitable solvent and optionally by adding an additive such as a solubilizing agent, an acid, a base, a buffering salt, an antioxidant, and a protective agent or the like. Suitable solvent is for example water, ethanol, butanol, benzyl alcohol, glycerin, propylene glycol, poethylene glycol, N-methylpyrrolidone, and a mixture thereof, a physiologically permissible vegetable oil, a synthetic oil suitable for injection, or the like. The solubilizing agent includes polyvinyl pyrrolidone, polyoxyethylated castor oil and polyoxyethylated sorbitan ester, or the like. The protective agent includes benzyl alcohol, trichlorobutanol, p-hydroxybenzoic acid ester and n-butanol or the like.

The oral liquid formulation can be administered directly or after dilution. It can be prepared similarly to the injectable liquid formulation.

The flowable agent and the emulsifiable concentrate can be administered directly or after dilution through transdermal administration or environmental treatment.

The liquid formulation used on skin can be administered by pouring on, spreading, rubbing, atomizing, spraying, or dipping (dipping, bathing or washing). These liquid can be prepared similarly to the injectable liquid formulation.

The pour-on agent and the spot-on agent are poured or atomized on the limited spot on the skin, thereby the active compound can be penetrated into the skin and act in the whole body. The pour-on agent and the spot-on agent can be prepared by dissolving, suspending or emulsifying an active ingredient in a suitable skin-fitted solvent or solvent mixture. If required, an auxiliary substance such as a surfactant, a colorant, an absorption promoting agent, an antioxidant, a light stabilizer and an adhesive, etc. may be added.

Suitable solvent includes water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbon, vegetable or synthetic oil, DMF, liquid paraffin, light-duty liquid paraffin, silicone, dimethylacetamide, N-methylpyrrolidone or 2,2-dimethyl-4-oxy-methylene-1,3-dioxolane. The absorption promoting agent includes DMSO, isopropyl myristate, dipropylene glycol pelargonate, silicone oil, aliphatic ester, triglyceride and fatty alcohol. The antioxidant includes sulfite, metabisulfite, ascorbic acid, butylhydroxytoluene, butylhydroxyanisole and tocopherol.

The emulsifiable concentrate can be administrated orally, subcutaneously or injectably. The emulsifiable concentrate can be prepared by dissolving an active ingredient in a hydrophobic phase or a hydrophilic phase, and then homogenating the resulting solution with a suitable emulsifying agent optionally with further an auxiliary substance such as a colorant, an absorption promoting agent, a protective agent, an antioxidant, a light screen and a thickening agent.

The hydrophobic phase (oil) includes paraffin oil, silicone oil, sesame-seed oil, oil of almonds, castor oil, synthetic triglyceride, ethyl stearate, di-n-butyryl adipate, hexyl laurate, dipropylene glycol pelargonate, ester of branched short chain length aliphatic acid with saturated aliphatic acid of chain length C16 to C18, isopropyl myristate, isopropyl palmitate, capryl/caprylic acid ester of saturated fatty alcohol of chain length C12 to C18, isopropyl stearate, oleyl oleate, decyl oleate, ethyl oleate, ethyl lactate, wax-like fatty acid ester, dibutyl phthalate, diisopropyl adipate, isotridecyl alcohol, 2-octyldodecanol, cetylstearyl alcohol, oleyl alcohol.

The hydrophilic phase includes water, propylene glycol, glycerin, sorbitol.

The emulsifying agent includes non-ionic surfactants such as polyoxyethylated castor oil, polyoxyethylated sorbitan mono-olefinate, sorbitan monostearate, glycerin monostearate, polyoxyethyl stearate, alkylphenol polyglycol ether; amphoteric surfactants such as di-sodium N-lauryl-iminodipropionate, lecithin or the like; anionic surfactants such as sodium lauryl sulfate, fatty alcohol sulfuric acid ether, monoethanol amine salt of mono/dialkylpolyglycol orthophosphate or the like; cationic surfactants such as cetyl chloride trimethylammonium or the like.

The other auxiliary substance includes carboxymethylcellulose, methylcellulose, polyacrylate, arginate, gelatin, gum arabic, polyvinyl pyrrolidone, polyvinyl alcohol, methylvinyl ether, copolymer of maleic anhydride, polyethylene glycol, wax, colloidal silica.

The semi-solid preparation can be administered by coating or spreading on the skin, or by introducing in body cavity. The gel can be prepared by adding a thickener in an amount enough to provide a clear substance having a viscosity of ointment in a solution prepared for the injectable liquid formulation as mentioned above.

Next, formulation examples of the preparation in case where the compound of the present invention is used are shown below. Provided that formulation examples of the present invention are not limited only thereto. In the interim, in the following Formulation Examples, "part(s)" mean part(s) by weight.

(Wettable Powder)

| | |
|---|---|
| Compound of the present invention | 0.1 to 80 parts |
| Solid carrier | 5 to 98.9 parts |
| Surfactant | 1 to 10 parts |
| Others | 0 to 5 parts |

As other components, there may be mentioned, for example, a non-caking agent, a decomposition preventing agent, and the like.
(Emulsifiable Concentrate)

| Compound of the present invention | 0.1 to 30 parts |
|---|---|
| Liquid carrier | 45 to 95 parts |
| Surfactant | 4.9 to 15 parts |
| Others | 0 to 10 parts |

As other components, there may be mentioned, for example, a spreading agent, a decomposition preventing agent, and the like.
(Suspension Concentrate)

| Compound of the present invention | 0.1 to 70 parts |
|---|---|
| Liquid carrier | 15 to 98.89 parts |
| Surfactant | 1 to 12 parts |
| Others | 0.01 to 30 parts |

As other components, there may be mentioned, for example, an antifreezing agent, a thickening agent, and the like.
(Water Dispersible Granule)

| Compound of the present invention | 0.1 to 90 parts |
|---|---|
| Solid carrier | 0 to 98.9 parts |
| Surfactant | 1 to 20 parts |
| Others | 0 to 10 parts |

As other components, there may be mentioned, for example, a binder, a decomposition preventing agent, and the like.
(Soluble Concentrate)

| Compound of the present invention | 0.01 to 70 parts |
|---|---|
| Liquid carrier | 20 to 99.99 parts |
| Others | 0 to 10 parts |

As other components, there may be mentioned, for example, an antifreezing agent, a spreading agent, and the like.
(Granule)

| Compound of the present invention | 0.01 to 80 parts |
|---|---|
| Solid carrier | 10 to 99.99 parts |
| Others | 0 to 10 parts |

As other components, there may be mentioned, for example, a binder, a decomposition preventing agent, and the like.
(Dustable Powder)

| Compound of the present invention | 0.01 to 30 parts |
|---|---|
| Solid carrier | 65 to 99.99 parts |
| Others | 0 to 5 parts |

As other components, there may be mentioned, for example, a drift preventing agent, a decomposition preventing agent, and the like.
Next, formulation examples using the compound of the present invention as an effective ingredient are described in more detail, but the present invention is not limited thereto. In the interim, in the following Formulation Examples, "part(s)" mean part(s) by weight.

Formulation Example 1

Wettable Powder

| Compound of the present invention No. 5-075 | 20 parts |
|---|---|
| Pyrophylite | 74 parts |
| Solpol 5039 | 4 parts |
| (A mixture of a nonionic surfactant and an anionic surfactant: available from TOHO Chemical Industry Co., LTD, Tradename) | |
| CARPREX #80D | 2 parts |
| (Synthetic hydrated silicic acid: available from Shionogi & Co., Ltd., Tradename) | |

The above materials are uniformly mixed and pulverized to make wettable powder.

Formulation Example 2

Emulsion

| Compound of the present invention No. 5-075 | 5 parts |
|---|---|
| Xylene | 75 parts |
| N-methylpyrrolidone | 15 parts |
| Solpol 2680 | 5 parts |
| (A mixture of a nonionic surfactant and an anionic surfactant: available from TOHO Chemical Industry Co., LTD, Tradename) | |

The above materials are uniformly mixed to make emulsifiable concentrate.

Formulation Example 3

Suspension Concentrate

| Compound of the present invention No. 5-075 | 25 parts |
|---|---|
| Agrisol S-710 | 10 parts |
| (a nonionic surfactant: available from KAO CORPORATION, Tradename) | |
| Lunox 1000C | 0.5 part |
| (an anionic surfactant: available from TOHO Chemical Industry Co., LTD, Tradename) | |
| Xanthan gum | 0.2 part |
| Water | 64.3 parts |

The above materials are uniformly mixed, and then, wet pulverized to make suspension concentrate.

Formulation Example 4

Water Dispersible Granule

| Compound of the present invention No. 5-075 | 75 parts |
|---|---|
| HITENOL NE-15 | 5 parts |
| (an anionic surfactant: available from | |

| | |
|---|---|
| DAI-ICHI KOGYO SEIYAKU CO., LTD., Tradename) | |
| VANILLEX N | 10 parts |
| (an anionic surfactant: available from Nippon Paper Chemicals Co., Ltd., Tradename) | |
| CARPREX #80D | 10 parts |
| (Synthetic hydrated silicic acid: available from Shionogi & Co., Ltd., Tradename) | |

The above materials are uniformly mixed and pulverized, and then, a small amount of water is added to the mixture and the resulting mixture is mixed under stirring, granulated by an extrusion granulator, and dried to make water dispersible granule.

Formulation Example 5

Granule

| | |
|---|---|
| Compound of the present invention No. 5-075 | 5 parts |
| Bentonite | 50 parts |
| Talc | 45 parts |

The above materials are uniformly mixed and pulverized, and then, a small amount of water is added to the mixture and the resulting mixture is mixed under stirring, granulated by an extrusion granulator, and dried to make granule.

Formulation Example 6

Dustable Powder

| | |
|---|---|
| Compound of the present invention No. 5-075 | 3 parts |
| CARPREX #80D | 0.5 parts |
| (Synthetic hydrated silicic acid: available from Shionogi & Co., Ltd., Tradename) | |
| Kaolinite | 95 parts |
| Diisopropyl phosphate | 1.5 parts |

The above materials are uniformly mixed and pulverized to make dustable powder. When the formulation is used, it is sprayed by diluting with water in 1- to 1000-fold concentration, or directly without dilution.

Formulation Example 7

Wettable Powder Preparation

| | |
|---|---|
| Compound of the present invention No. 5-086 | 25 parts |
| Sodium diisobutylnaphthalenesulfonate | 1 part |
| Calcium n-dodecylbenzenesulfonate | 10 parts |
| Alkylaryl polyglycol ether | 12 parts |
| Sodium salt of naphthalenesulfonic acid formalin condensate | 3 parts |
| Emulsion type silicone | 1 part |
| Silicon dioxide | 3 parts |
| Kaoline | 45 parts |

Formulation Example 8

Water-Soluble Concentrate Preparation

| | |
|---|---|
| Compound of the present invention No. 5-086 | 20 parts |
| Polyoxyethylene lauryl ether | 3 parts |
| Sodium dioctylsulfosuccinate | 3.5 parts |
| Dimethylsulfoxide | 37 parts |
| 2-Propanol | 36.5 parts |

Formulation Example 9

Liquid Formulation for Atomization

| | |
|---|---|
| Compound of the present invention No. 5-086 | 2 parts |
| Dimethylsulfoxide | 10 parts |
| 2-Propanol | 35 parts |
| Acetone | 53 parts |

Formulation Example 10

Liquid Formulation for Transdermal Administration

| | |
|---|---|
| Compound of the present invention No. 5-086 | 5 parts |
| Hexylene glycol | 50 parts |
| Isopropanol | 45 parts |

Formulation Example 11

Liquid Formulation for Transdermal Administration

| | |
|---|---|
| Compound of the present invention No. 5-086 | 5 parts |
| Propylene glycol monomethyl ether | 50 parts |
| Dipropylene glycol | 45 parts |

Formulation Example 12

Liquid Formulation for Transdermal Administration (Pouring-on)

| | |
|---|---|
| Compound of the present invention No. 5-086 | 2 parts |
| Light-duty liquid paraffin | 98 parts |

Formulation Example 13

Liquid Formulation for Transdermal Administration (Pouring-On)

| | |
|---|---|
| Compound of the present invention No. 5-086 | 2 parts |
| Light-duty liquid paraffin | 58 parts |
| Olive oil | 30 parts |
| ODO-H | 9 parts |
| Shinetsu silicone | 1 part |

Also, when the compound of the present invention is used as an agricultural chemicals, it may be mixed with other kinds of herbicides, various kinds of insecticides, acaricides, nematocides, fungicides, vegetable growth regulators, synergists, fertilizers, soil improvers, etc., and applied, at the time of preparing the formulation or at the time of spreading, if necessary.

In particular, by mixing with the other agricultural chemicals or plant hormones and applying the mixture, it can be expected that a cost is reduced due to reduction in a dose to be applied, enlargement in insecticidal spectrum or higher prevention and extinction effect of noxious organisms due to synergistic effect by mixing agricultural chemicals. At this time, it is possible to use the compound with a plural number of the conventionally known agricultural chemicals in combination simultaneously. As the kinds of the agricultural chemicals to be used in admixture with the compound of the present invention, there may be mentioned, for example, the compounds described in Farm Chemicals Handbook, 1999 ed. and the like. Specific examples of the general names can be enumerated below, but the invention is not necessarily limited only thereto.

Fungicides: acibenzolar-S-methyl, acylaminobenzamide, amobam, ampropyfos, anilazine, azaconazole, azoxystrobin, benalaxyl, benodanil, benomyl, benthiazole, benzamacril, binapacryl, biphenyl, bitertanol, bethoxazine, bordeaux mixture, blasticidin-S, bromoconazole, bupirimate, buthiobate, calcium polysulfide, captafol, captan, copper oxychloride, carpropamid, carbendazim, carboxin, CGA-279202 (test name), chinomethionat, chlobenthiazone, chlorfenazol, chloroneb, chlorothalonil, chlozolinate, cufraneb, cymoxanil, cyproconazol, cyprodinil, cyprofuram, dazomet, debacarb, dichlorophen, diclobutrazol, dichlorfluanid, diclomedine, dicloran, diethofencarb, diclocymet, difenoconazole, diflumetorim, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadone, fenarimol, febuconazole, fenamidone, fendazosulam, fenfuram, fenhexamid, fenpiclonil, fenpropidin, fenpropimorph, fentin, ferbam, ferimzone, fluazinam, fludioxonil, fluoroimide, fluquinconazole, flusilazole, flusulfamide, flutolanil, flutriafol, folpet, fosetyl-aluminium, fuberidazole, furalaxyl, furametpyr, guazatine, hexachlorobenzene, hexaconazole, hymexazol, imazalil, imibenconazole, iminoctadine, ipconazole, iprobenfos, iprodione, isoprothiolane, iprovalicarb, kasugamycin, kresoxim-methyl, mancopper, mancozeb, maneb, mepanipyrim, mepronil, metalaxyl, metconazole, methasulfocarb, metiram, metominostrobin, myclobutanil, MTF-753 (test name), nabam, nickel bis(dimethyldithiocarbamate), nitrothal-isopropyl, nuarimol, NNF-9425 (test name), octhilinone, ofurace, oxadixyl, oxycarboxin, oxpoconazole fumarate, pefurzoate, penconazole, pencycuron, phthalide, piperalin, polyoxins, potassium hydrogen carbonate, probenazole, prochloraz, procymidone, propamocarb hydrochloride, propiconazole, propineb, pyrazophos, pyrifenox, pyrimethanil, pyroquilon, quinomethionate, quinoxyfen, quintozene, RH 7281 (test name), sodium hydrogen carbonate, sodium hypochlorite, sulfur, spiroxamine, tebuconazole, tecnazene, tetraconazole, thiabendazole, thiadiazin/milneb, thifluzamide, thiophanate-methyl, thiram, tolclofos-methyl, tolylfluanid, triadimefon, toriadimenol, triazoxide, tricyclazole, tridemorph, triflumizole, triforine, triticonazole, validamycin, vinclozolin, zinc sulfate, zineb, ziram, and shiitake mushroom hyphae extract, etc.;

Bactericides: streptomycin, tecloftalam, oxyterracycline, and oxolinic acid, etc.;

Nematocides: aldoxycarb, cadusafos, fosthiazate, fosthietan, oxamyl, and fenamiphos, etc.;

Acaricides: acequinocyl, amitraz, bifenazate, bromopropylate, chinomethionat, chlorobezilate, clofentezine, cyhexatine, dicofol, dienochlor, etoxazole, fenazaquin, fenbutatin oxide, fenpropathrin, fenproximate, halfenprox, hexythiazox, milbemectin, propargite, pyridaben, pyrimidifen, and tebufenpyrad, etc.;

Insecticides: abamectin, acephate, acetamipirid, aldicarb, allethrin, azinphos-methyl, bendiocarb, benfuracarb, bensultap, bifenthrin, buprofezin, butocarboxim, carbaryl, carbofuran, carbosulfan, cartap, chlorfenapyr, chlorpyrifos, chlorfenvinphos, chlorfluazuron, clothianidin, chromafenozide, chlorpyrifos-methyl, cycloprothrin, cyfluthrin, beta-cyfluthrin, cypermethrin, cyromazine, cyhalothrin, lambda-cyhalothrin, deltamethrin, diafenthiuron, diazinon, diacloden, diflubenzuron, dimethylvinphos, diofenolan, disulfoton, dimethoate, emamectin-benzoate, EPN, esfenvalerate, ethiofencarb, ethiprole, etofenprox, etrimfos, fenitrothion, fenobucarb, fenoxycarb, fenpropathrin, fenvalerate, fipronil, fluacrypyrim, flucythrinate, flufenoxuron, flufenprox, tau-fluvalinate, fonophos, formetanate, formothion, furathiocarb, halofenozide, hexaflumuron, hydramethylnon, imidacloprid, isofenphos, indoxacarb, isoprocarb, isoxathion, lufenuron, malathion, metaldehyde, methamidophos, methidathion, methacrifos, metalcarb, methomyl, methoprene, methoxychlor, methoxyfenozide, monocrotophos, muscalure, nidinotefuran, nitenpyram, omethoate, oxydemeton-methyl, oxamyl, parathion, parathion-methyl, permethrin, phenthoate, phoxim, phorate, phosalone, phosmet, phosphamidon, pirimicarb, pirimiphos-methyl, profenofos, protrifenbute, pymetrozine, pyraclofos, pyriproxyfen, rotenone, sulprofos, silafluofen, spinosad, sulfotep, tebfenozide, teflubenzuron, tefluthorin, terbufos, tetrachlorvinphos, thiacloprid, thiocyclam, thiodicarb, thiamethoxam, thiofanox, thiometon, tolfenpyrad, tralomethrin, trichlorfon, triazuron, triflumuron, and vamidothion, etc.

Examples

Hereinafter, the present invention will be explained in more detail by specifically referring to Synthetic Examples and Test Examples of the compound of the present invention as working examples to which the present invention is not limited.

Synthetic Examples

Synthetic Example 1

Production of the Compound of the Present Invention by Use of L-COS (Parallel Liquid-Phase Synthesis System of MORITEX Corporation)

In 15 bials of L-COS in which stirrers were placed, 1.5 mmol of each n-propylamine, i-propylamine, s-butylamine, t-butylamine, n-pentylamine, 2,2-dimethylpropylamine, n-hexylamine, cyclohexylamine, benzylamine, 4-trifluoromethylbenzylamine, 1-phenylethylamine, 2-phenylethylamine, 2-(4-phenoxyphenyl)ethylamine, 3-phenylpropylamine and trans-2-phenylcyclopropylamine was weighed, each bial was covered and placed in a reaction vessel of L-COS. With stirring at room temperature, in each bial, 5 ml of a solution of 4-[5-(3,4-dichlorophenyl)-5-trifluoromethyl-4,5-dihydroisoxazole-3-yl]benzoic acid in N,N-dimethylformamide-chloroform (1:3) (0.2 mmol/ml), 1 ml of a solution of 4-(dimethylamino)pyridine in chloroform (0.25 mmol/ml), and then 1.5 ml of a solution of 1-ethyl-3-(3-dimethylaminopropyl) carbodiimide hydrochloride in chloroform (1.0 mmol/ml) were added in that order, and continued to stir at the same temperature for 16 hours. After the completion of the reaction, 3 ml of cold water was added in each bials, and the organic phases were collected, and subjected to purification with medium-pressure preparative liquid chromatography (Yamazen Corporation, medium pressure preparative system; YFLC-Wprep) that was eluted with ethyl acetate-hexane (1:3 to 1:1 gradient), and the aimed product was obtained as white to yellow solid. In addition, the product was confirmed with LC-MS (Waters LC-MS system, detector: ZMD, analysis condition: 254 nm, 80% $CH_3CN$-20% $H_2O$-0.1% HCOOH, ionization: positive electrospray).

4-[5-(3,4-dichlorophenyl)-5-trifluoromethyl-4,5-dihydroisoxazole-3-yl]-N-n-propylbenzoic acid amide; 0.26 g, $[M^++H]$=444.94.

4-[5-(3,4-dichlorophenyl)-5-trifluoromethyl-4,5-dihydroisoxazole-3-yl]-N-1-propylbenzoic acid amide; 0.23 g, $[M^++H]$=444.94.

N-s-butyl-4-[5-(3,4-dichlorophenyl)-5-trifluoromethyl-4,5-dihydroisoxazole-3-yl]benzoic acid amide; 0.20 g, $[M^++H]$=458.93.

N-t-butyl-4-[5-(3,4-dichlorophenyl)-5-trifluoromethyl-4,5-dihydroisoxazole-3-yl]benzoic acid amide; 0.21 g, $[M^++H]$=458.92.

4-[5-(3,4-dichlorophenyl)-5-trifluoromethyl-4,5-dihydroisoxazole-3-yl]-N-n-pentylbenzoic acid amide; 0.31 g, $[M^++H]$=473.02.

4-[5-(3,4-dichlorophenyl)-5-trifluoromethyl-4,5-dihydroisoxazole-3-yl]-N-(2,2-dimethyl propyl)benzoic acid amide; 0.27 g, $[M^++H]$=472.94.

4-[5-(3,4-dichlorophenyl)-5-trifluoromethyl-4,5-dihydroisoxazole-3-yl]-N-n-hexylbenzoic acid amide; 0.26 g, $[M^++H]$=486.96.

N-cyclohexyl-4-[5-(3,4-dichlorophenyl)-5-trifluoromethyl-4,5-dihydroisoxazole-3-yl]benzoic acid amide; 0.26 g, $[M^++H]$=484.93.

N-benzyl-4-[5-(3,4-dichlorophenyl)-5-trifluoromethyl-4,5-dihydroisoxazole-3-yl]benzoic acid amide; 0.34 g, $[M^++H]$=492.86.

4-[5-(3,4-dichlorophenyl)-5-trifluoromethyl-4,5-dihydroisoxazole-3-yl]-N-(4-trifluoromethylbenzyl)benzoic acid amide; 0.34 g, $[M^++H]$=560.97.

4-[5-(3,4-dichlorophenyl)-5-trifluoromethyl-4,5-dihydroisoxazole-3-yl]-N-(1-phenylethyl)benzoic acid amide; 0.26 g, $[M^++H]$=506.88.

4-[5-(3,4-dichlorophenyl)-5-trifluoromethyl-4,5-dihydroisoxazole-3-yl]-N-(2-phenylethyl benzoic acid amide; 0.37 g, $[M^++H]$=507.01.

4-[5-(3,4-dichlorophenyl)-5-trifluoromethyl-4,5-dihydroisoxazole-3-yl]-N-[2-(4-phenoxy phenyl)ethyl]benzoic acid amide; 0.36 g, $[M^++H]$=598.95.

4-[5-(3,4-dichlorophenyl)-5-trifluoromethyl-4,5-dihydroisoxazole-3-yl]-N-(3-phenylpropyl)benzoic acid amide; 0.31 g, $[M^++H]$=520.97.

4-[5-(3,4-dichlorophenyl)-5-trifluoromethyl-4,5-dihydroisoxazole-3-yl]-N-(trans-2-phenylcyclopropyl)benzoic acid amide; 0.21 g, $[M^++H]$=518.88.

Synthetic Example 2

Production of the Compound of the Present Invention by Use of L-COS (Parallel Liquid-Phase Synthesis System of MORITEX Corporation)

Ten (10) bials of L-COS in which stirrers were placed were assigned a number of 1 to 10, respectively. 1.0 mmol of 3-chloro-4-fluorophenyl boric acid was weighed in the bials of Nos. 1 and 6, 1.0 mmol of 3,5-bis(trifluoromethyl)phenyl boric acid was weighed in the bials of Nos. 2 and 7, 1.0 mmol of 3-trifluoromethylphenyl boric acid was weighed in the bials of Nos. 3 and 8, 1.0 mmol of 3-trifluoromethoxyphenyl boric acid was weighed in the bials of Nos. 4 and 9, and 1.0 mmol of 2-naphthyl boric acid was weighed in the bials of Nos. 5 and 10, Then, 0.05 mmol of dichlorobis(triphenylphosphine) palladium (II) was added in each bial, the bial was filled with nitrogen and covered, and placed in a reaction vessel of L-COS. With stirring at room temperature, in each bial, 3 ml of a solution of 2-bromo-3,3,3-trifluoropropene in 1,2-dimethoxyethane (0.5 mmol/ml), 1.5 ml of water, and then 1 ml of a solution of triethylamine in 1,2-dimethoxyethane (6.0 mmol/ml) were added in that order, and stirred at 75° C. for 3.5 hours. Then, the bials were cooled to 0° C., 1.5 ml of a solution of N-benzyl-4-(chlorohydroxyiminomethyl) benzoic acid amide in 1,2-dimethoxyethane (0.7 mmol/ml) was added in the bials of Nos. 1 to 5, and 1.5 ml of a solution of 4-chlorohydroxyiminomethyl-N-(2,2,2-trifluoroethyl) benzoic acid amide in 1,2-dimethoxyethan (0.7 mmol/ml) was added in the bials of Nos. 6 to 10, and the bials were continued to stir at room temperature for 16 hours. After the completion of the reaction, the organic phase was collected, aqueous phase was extracted with 5 ml of chloroform, the chloroform was added to the organic phase, and the solvent was distilled off under reduced pressure. The residue was subjected to purification with medium-pressure preparative liquid chromatography (Yamazen Corporation, medium pressure preparative system; YFLC-Wprep) that was eluted with ethyl acetate-hexane (1:3 to 1:1 gradient), and the aimed product was obtained as white to yellow solid. In addition, the product was confirmed with LC-MS (Waters LC-MS system, detector: ZMD, analysis condition: 254 nm, 80% $CH_3CN$-20% $H_2O$-0.1% HCOOH, ionization: positive electrospray).

N-benzyl-4-[5-(3-chloro-4-fluorophenyl)-5-trifluoromethyl-4,5-dihydroisoxazole-3-yl]benzoic acid amide; 0.28 g, $[M^++H]$=476.80.

N-benzyl-4-[5-[3,5-bis(trifluoromethyl)phenyl]-5-trifluoromethyl-4,5-dihydroisoxazole-3-yl]benzoic acid amide; 0.25 g, $[M^++H]$=560.76.

N-benzyl-4-[5-(3-trifluoromethylphenyl)-5-trifluoromethyl-4,5-dihydroisoxazole-3-yl]benzoic acid amide; 0.26 g, $[M^++H]$=492.82.

N-benzyl-4-[5-(3-trifluoromethoxyphenyl)-5-trifluoromethyl-4,5-dihydroisoxazole-3-yl]benzoic acid amide; 0.25 g, $[M^++H]$=508.80.

N-benzyl-4-[5-(2-naphthyl)-5-trifluoromethyl-4,5-dihydroisoxazole-3-yl]benzoic acid amide; 0.09 g, $[M^++H]$=474.86.

4-[5-(3-chloro-4-fluorophenyl)-5-trifluoromethyl-4,5-dihydroisoxazole-3-yl]-N-(2,2,2-trifluoroethyl)benzoic acid amide; 0.29 g, $[M^++H]$=468.76.

4-[5-[3,5-bis(trifluoromethyl)phenyl]-5-trifluoromethyl-4,5-dihydroisoxazole-3-yl]-N-(2,2,2-trifluoroethyl)benzoic acid amide; 0.29 g, [M$^+$+H]=552.72.

4-[5-(3-trifluoromethylphenyl)-5-trifluoromethyl-4,5-dihydroisoxazole-3-yl]-N-(2,2,2-trifluoroethyl)benzoic acid amide; 0.18 g, [M$^+$+H]=484.78.

4-[5-(3-trifluoromethoxyphenyl)-5-trifluoromethyl-4,5-dihydroisoxazole-3-yl]-N-(2,2,2-trifluoroethyl)benzoic acid amide; 0.27 g, [M$^+$+H]=500.76.

4-[5-(2-naphthyl)-5-trifluoromethyl-4,5-dihydroisoxazole-3-yl]-N-(2,2,2-trifluoroethyl)benzoic acid amide; 0.14 g, [M$^+$+H]=466.83.

Synthetic Example 3

4-[5-(3,5-Dichlorophenyl)-5-trifluoromethyl-4,5-dihydroisoxazole-3-yl]-N-(2,2,2-trifluoroethyl)benzoic acid amide (Compound of the present invention No. 3-060)

Step 1: Production of 3,5-dichloro-1-(1-trifluoromethylethenyl)benzene

In a solution of 25.0 g of 3,5-dichlorophenyl boric acid in 200 ml of tetrahydrofuran and 100 ml of water, 27.5 g of 2-bromo-3,3,3-trifluoropropene, 38.0 g of potassium carbonate and 1.84 g of dichlorobis(triphenylphosphine) palladium (II) were added, and stirred under reflux with heat for 3 hours. After the completion of the reaction and cooling to room temperature, 500 ml of ice water was added, and extracted with ethyl acetate (500 ml×1). The organic phase was washed with water, dried over anhydrous sodium sulfate, the solvent was distilled off under reduced pressure. The residue was purified with silica gel column chromatography that was eluated with hexane, and 25.7 g of the aimed product was obtained as colorless oily substance.

$^1$H NMR (CDCl$_3$, Me$_4$Si, 300 MHz) δ 7.41 (t, J=2.0 Hz, 1H), 7.3-7.35 (m, 2H), 6.05 (q, J=3.2 Hz, 1H), 5.82 (q, J=3.2 Hz, 1H).

Step 2: Production of 4-[5-(3,5-dichlorophenyl)-5-trifluoromethyl-4,5-dihydroisoxazole-3-yl]benzoic acid methyl ester In a solution of 2.70 g of 4-(hydroxyiminomethyl)benzoic acid methyl ester in 15 ml of N,N-dimethylformamide, 2.04 g of N-chlorosuccinic acid imide was added, and stirred at 40° C. for 40 minutes. Then, the reaction mixture was cooled to 0° C., 3.40 g of 3,5-dichloro-1-(1-trifluoromethylethenyl)benzene and 1.72 g of triethylamine were added, continued to stir at room temperature for 18 hours. After the completion of the reaction, the reaction mixture was poured into 100 ml of ice water, extracted with ethyl acetate (50 ml×2), the organic phase was washed with water, dehydrated with saturated sodium chloride aqueous solution and dried over anhydrous sodium sulfate, and then the solvent was distilled off under reduced pressure. The residual solid was subjected to purification with medium-pressure preparative liquid chromatography (Yamazen Corporation, medium pressure preparative system; YFLC-Wprep) that was eluted with ethyl acetate-hexane (1:1 to 1:3 gradient), and 4.05 g of the aimed product was obtained as white crystal.

Melting point 94.0 to 96.0° C.
$^1$H NMR (CDCl$_3$, Me$_4$Si, 300 MHz) δ 8.10 (d, J=8.4 Hz, 2H), 7.74 (d, J=8.4 Hz, 2H), 7.43 (s, 2H), 7.26 (s, 1H), 4.12 (d, J=17.3 Hz, 1H), 3.94 (s, 3H), 3.74 (d, J=17.3 Hz, 1H).

Step 3: Production of 4-[5-(3,5-dichlorophenyl)-5-trifluoromethyl-4,5-dihydroisoxazole-3-yl]benzoic acid In a solution of 3.99 g of 4-[5-(3,5-dichlorophenyl)-5-trifluoromethyl-4,5-dihydroisoxazole-3-yl]benzoic acid methyl ester in 50 ml of methanol, a solution of 2.00 g of potassium hydroxide in 25 ml of water was added, stirred at room temperature for 3 days and then at 40° C. for 5 hours. After the completion of the reaction, the reaction mixture was cooled with ice, and poured in 200 ml of water, and adjusted to pH 1-2 with concentrated hydrochloric acid, and then extracted with ethyl acetate (50 ml×2), the organic phase was washed with water, dehydrated with saturated sodium chloride aqueous solution and dried over anhydrous sodium sulfate, and then the solvent was distilled off under reduced pressure to obtain 3.87 g of the aimed product as pale yellow crystal.

Melting point 237.0 to 240.0° C.
$^1$H NMR (CDCl$_3$-DMSO-d$_6$, Me$_4$Si, 300 MHz) δ 8.09 (d, J=8.4 Hz, 2H), 7.76 (d, J=8.4 Hz, 2H), 7.54 (s, 2H), 7.44 (s, 1H), 4.18 (d, J=17.7 Hz, 1H), 3.86 (d, J=17.7 Hz, 1H).

Step 4: Production of 4-[5-(3,5-dichlorophenyl)-5-trifluoromethyl-4,5-dihydroisoxazole-3-yl]-N-(2,2,2-trifluoro ethyl)benzoic acid amide In a suspension of 1.00 g of 4-[5-(3,5-dichlorophenyl)-5-trifluoromethyl-4,5-dihydroisoxazole-3-yl]benzoic acid in 10 ml of benzene, 0.44 g of thionyl chloride and a catalytic amount (2 to 3 drops) of N,N-dimethylformamide were added, and stirred under reflux with heat for 2.5 hours. After the completion of the reaction, the solvent was distilled off under reduced pressure to obtain 1.81 g of crude 4-[5-(3,5-dichlorophenyl)-5-trifluoromethyl-4,5-dihydroisoxazole-3-yl]benzoic acid chloride as pale yellow oily substance.

In a solution of 0.29 g of 2,2,2-trifluoroethylamine and 0.37 g of triethylamine in 20 ml of chloroform, 1.81 g of the crude 4-[5-(3,5-dichlorophenyl)-5-trifluoromethyl-4,5-dihydroisoxazole-3-yl]benzoic acid chloride dissolved in 10 ml of chloroform was added dropwise with cooling with ice and with stirring. After the completion of addition dropwise, the mixture was continued to stir at room temperature further for 30 minutes. After the completion of the reaction, the reaction mixture was poured in 100 ml of water, and extracted with chloroform (20 ml×3), the organic phase was washed with water, dehydrated with saturated sodium chloride aqueous solution and dried over anhydrous sodium sulfate, and passed through a glass filter packed with silica gel, and then the solvent was distilled off under reduced pressure. The residual solid was washed with hexane to obtain 1.05 g of the aimed product as white crystal.

Melting point 94.0 to 96.0° C.
$^1$H NMR (CDCl$_3$, Me$_4$Si, 300 MHz) δ 7.86 (d, J=8.4 Hz, 2H), 7.76 (d, J=8.4 Hz, 2H), 7.51 (s, 2H), 7.44 (s, 1H), 6.47 (t, J=6.3 Hz, 1H), 4.14 (qd, J=18.5, 6.3 Hz, 2H), 4.11 (d, J=17.4 Hz, 1H), 3.73 (d, J=17.4 Hz, 1H).

Synthetic Example 4

N-Benzyl-4-[5-(3,5-dichlorophenyl)-5-trifluoromethyl-4,5-dihydroisoxazole-3-yl]-2-fluoro benzoic acid amide (Compound of the present invention No. 5-039)

Step 1: Production of 3-(4-bromomethyl-3-fluorophenyl)-5-(3,5-dichlorophenyl)-5-trifluoromethyl-4,5-dihydroisoxazole In a solution of 1.50 g of 5-(3,5-dichlorophenyl)-3-(3-fluoro-4-methylphenyl)-5-trifluoromethyl-4,5-dihydroisoxazole synthesized from 3-fluoro-4-methylphenylaldoxime and 3,5-dichloro-1-(1-trifluoromethylethenyl)benzene similarly to Step 2 of Synthetic Example 3 in 50 ml of 1,2-dichloroethane, 0.68 g of N-bromosuccinic acid imide and a catalytic amount of azobisisobutyronitrile were added, and stirred under nitrogen atmosphere and under reflux with heat for 1 hour. After the completion of the reaction, the reaction mixture was left and cooled to room temperature, poured in 50 ml of water, extracted with chloroform (50 ml×1). The organic phase was dehydrated with saturated sodium chloride aqueous solution and dried over anhydrous sodium sulfate, and then the solvent was distilled off under reduced pressure to obtain crude aimed product as pale yellow oily substance. The resulting product was used as such without purification for the next step.

$^1$H NMR (CDCl$_3$, Me$_4$Si, 400 MHz) δ 7.45-7.6 (m, 6H), 4.51 (s, 2H), 4.05 (d, J=17.2 Hz, 1H), 3.67 (d, J=17.2 Hz, 1H).

Step 2: Production of 3-(4-acetoxymethyl-3-fluorophenyl)-5-(3,5-dichlorophenyl)-5-trifluoromethyl-4,5-dihydroisoxazole In a solution of crude 3-(4-bromomethyl-3-fluorophenyl)-5-(3,5-dichlorophenyl)-5-trifluoromethyl-4,5-dihydroisoxazole in 30 ml of acetic acid, 1.50 g of potassium acetate was added, and stirred under reflux with heat for 1.5 hour. After the completion of the reaction, the reaction mixture was left and cooled to room temperature, and neutralized by pouring in 100 ml of saturated sodium hydrogen carbonate aqueous solution. The organic phase was collected, dehydrated with saturated sodium chloride aqueous solution and dried over anhydrous sodium sulfate, and then the solvent was distilled off under reduced pressure to obtain 1.50 g of crude aimed product as pale yellow oily substance. The resulting product was used as such without purification for the next step.

$^1$H NMR (CDCl$_3$, Me$_4$Si, 400 MHz) δ 7.2-7.55 (m, 6H), 5.20 (s, 2H), 4.05 (d, J=17.2 Hz, 1H), 3.67 (d, J=17.2 Hz, 1H), 2.14 (s, 3H).

Step 3: Production of 5-(3,5-dichlorophenyl)-3-(3-fluoro-4-hydroxymethylphenyl)-5-trifluoromethyl-4,5-dihydroisoxazole In a solution of 1.50 g of crude 3-(4-acetoxymethyl-3-fluorophenyl)-5-(3,5-dichlorophenyl)-5-trifluoromethyl-4,5-dihydroisoxazole in 10 ml of ethanol, 2.00 g of sodium hydroxide dissolved in 20 ml of water was added, and stirred under reflux with heat for 4.5 hours. After the completion of the reaction, the reaction mixture was cooled with ice, and adjusted to pH 2-3 by carefully adding concentrated hydrochloric acid, and extracted with ethyl acetate (50 ml×1). The organic phase was dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (1:2) to obtain 0.95 g of the aimed product as pale yellow resinous substance.

$^1$H NMR (CDCl$_3$, Me$_4$Si, 400 MHz) δ 7.5-7.6 (m, 3H), 7.4-7.45 (m, 3H), 4.81 (s, 2H), 4.06 (d, J=17.2 Hz, 1H), 3.68 (d, J=17.2 Hz, 1H), 1.87 (bs, 1H).

Step 4: Production of 4-[5-(3,5-dichlorophenyl)-5-trifluoromethyl-4,5-dihydroisoxazole-3-yl]-2-fluoro benzoic acid In a solution of 0.95 g of 5-(3,5-dichlorophenyl)-3-(3-fluoro-4-hydroxymethylphenyl)-5-trifluoromethyl-4,5-dihydroisoxazole in 25 ml of acetone, Johnes' Reagent prepared from 1.50 g of chromic acid, 1.2 ml of concentrated sulfuric acid and 7 ml of water was added dropwise under cooling with ice and with stirring, after the completion of the addition dropwise, continued to stir at room temperature for further 1.5 hour. After the completion of the reaction, the reaction mixture was poured in 50 ml of water and extracted with diethyl ether (50 ml×1). The organic phase was dehydrated with saturated sodium chloride aqueous solution and dried over anhydrous sodium sulfate, and then the solvent was distilled off under reduced pressure. The residual solid was washed with hexane to obtain 0.67 g of the aimed product as beige crystal.

Melting point 172.0 to 174.0° C.

$^1$H NMR (CDCl$_3$, Me$_4$Si, 300 MHz) δ 8.05-8.15 (m, 1H), 7.45-7.55 (m, 5H), 4.08 (d, J=17.3 Hz, 1H), 3.71 (d, J=17.3 Hz, 1H).

Step 5: Production of N-benzyl-4-[5-(3,5-dichlorophenyl)-5-trifluoromethyl-4,5-dihydroisoxazole-3-yl]-2-fluoro benzoic acid amide In a solution of 0.15 g of 4-[5-(3,5-dichlorophenyl)-5-trifluoromethyl-4,5-dihydroisoxazole-3-yl]-2-fluoro benzoic acid in 10 ml of dichloromethane, 0.3 ml of oxalyl chloride and 2 drops of N,N-dimethylformamide were added at room temperature, and stirred at the same temperature for 10 minutes. After the completion of the reaction, the solvent was distilled off under reduced pressure, the remaining white solid was dissolved in 10 ml of chloroform, and 0.3 ml of benzylamine and then 0.3 ml of triethylamine were added under cooling with ice, after the completion of the addition, continued to stir at room temperature for further 20 minutes. After the completion of the reaction, 40 ml of water was poured in the reaction mixture, and extracted with ethyl acetate (50 ml×1). The organic phase was dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (1:2) to obtain 0.14 g of the aimed product as white crystal.

Melting point 172.0 to 176.0° C.

$^1$H NMR (CDCl$_3$, Me$_4$Si, 400 MHz) δ 8.20 (t, J=8.0 Hz, 1H), 7.25-7.55 (m, 10H), 7.05 (t, J=5.6 Hz, 1H), 4.68 (d, J=5.6 Hz, 2H), 4.07 (d, J=17.6 Hz, 1H), 3.70 (d, J=17.6 Hz, 1H).

Synthetic Example 5

4-[5-(3,5-Dichlorophenyl)-5-trifluoromethyl-4,5-dihydroisoxazole-3-yl]-2-nitro-N-(2-pyridylmethyl) benzoic acid amide (Compound of the present invention No. 5-339)

Step 1: Production of 4-bromo-3-nitrobenzaldoxime

In a solution of 5.0 g of 4-bromo-3-nitrobenzaldehyde in 50 ml of methanol, 3.6 ml of 50% hydroxyamine aqueous solution was added with stirring at room temperature, and continued to stir at the same temperature for 18 hours. After the completion of the reaction, 60 ml of water was added in the reaction mixture, and precipitated solid was filtered off, washed with water and then dried to obtain 5.0 g of the aimed product as yellow crystal.

$^1$H NMR (CDCl$_3$-DMSO-d$_6$, Me$_4$Si, 400 MHz) δ 11.18 (s, 1H), 8.09 (s, 1H), 8.07 (d, J=2.0 Hz, 1H), 7.73 (d, J=8.4 Hz, 1H), 7.62 (dd, J=8.4, 2.0 Hz, 1H).

Step 2: Production of 3-(4-bromo-3-nitrophenyl)-5-(3,5-dichlorophenyl)-5-trifluoromethyl-4,5-dihydroisoxazole In a solution of 1.27 g of 4-bromo-3-nitrobenzaldoxime in 16 ml of N,N-dimethylformamide, 0.74 g of N-chlorosuccinic acid imide was added, and stirred at 35° C. for 90 minutes. Then, the reaction mixture was cooled with ice, 1.20 g of 3,5-dichloro-1-(1-trifluoromethylethenyl)benzene synthesized in Step 1 of Synthetic Example 3 and 0.60 g of triethylamine were added, continued to stir at room temperature for 18 hours. After the completion of the reaction, the reaction mixture was poured in 50 ml of ice water, extracted with ethyl acetate (50 ml×2), the organic phase was dehydrated with saturated sodium chloride aqueous solution and dried over anhydrous sodium sulfate, and then the solvent was distilled off under reduced pressure. The residual solid was subjected to purification with medium-pressure preparative liquid chromatography (Yamazen Corporation, medium pressure preparative system; YFLC-Wprep) that was eluted with ethyl acetate-hexane (1:2 to 1:4 gradient), and 1.10 g of the aimed product was obtained as yellow crystal.

Melting point 179.0 to 181.0° C.

$^1$H NMR (CDCl$_3$, Me$_4$Si, 400 MHz) δ 8.06 (d, J=2.0 Hz, 1H), 7.84 (d, J=8.4 Hz, 1H), 7.78 (dd, J=8.4, 2.0 Hz, 1H), 7.45-7.55 (m, 2H), 7.45 (t, J=1.8 Hz, 1H), 4.09 (d, J=17.2 Hz, 1H), 3.72 (d, J=17.4 Hz, 1H).

Step 3: Production of 4-[5-(3,5-dichlorophenyl)-5-trifluoromethyl-4,5-dihydroisoxazole-3-yl]-2-nitrobenzoic acid ethyl ester In a solution of 2.0 g of 3-(4-bromo-3-nitrophenyl)-5-(3,5-dichlorophenyl)-5-trifluoromethyl-4,5-dihydroisoxazole in 30 ml of ethanol in an autoclave, 0.40 g of sodium acetate, 88.0 mg of 1,1'-bis(diphenylphosphino) ferrocene and 18.0 mg of palladium (II) acetate were added, and stirred under 0.9 MPa carbon monoxide atmosphere at 100° C. for 3 hours. After the completion of the reaction, the reaction mixture was left and cooled to room temperature, and the solvent was distilled off under reduced pressure, and the residue was dissolved in 100 ml of ethyl acetate, washed with water, dried over anhydrous sodium sulfate and the solvent was distilled off under reduced pressure. The residual solid was subjected to purification with medium-pressure preparative liquid chromatography (Yamazen Corporation, medium pressure preparative system; YFLC-Wprep) that was eluted with ethyl acetate-hexane (1:2 to 1:4 gradient), and 0.66 g of the aimed product was obtained as pale yellow crystal.

Melting point 160.0 to 162.0° C.

$^1$H NMR (CDCl$_3$, Me$_4$Si, 400 MHz) δ 8.13 (d, J=1.6 Hz, 1H), 7.99 (dd, J=8.1, 1.6 Hz, 1H), 7.83 (d, J=8.1 Hz, 1H), 7.45-7.55 (m, 2H), 7.45 (t, J=1.8 Hz, 1H), 4.41 (q, J=7.1 Hz, 2H), 4.11 (d, J=17.2 Hz, 1H), 3.74 (d, J=17.8 Hz, 1H), 1.37 (t, J=7.1 Hz, 3H).

Step 4: Production of 4-[5-(3,5-dichlorophenyl)-5-trifluoromethyl-4,5-dihydroisoxazole-3-yl]-2-nitro-N-(2-pyridylmethyl)benzoic acid amide In a solution of 0.36 g of 4-[5-(3,5-dichlorophenyl)-5-trifluoromethyl-4,5-dihydroisoxazole-3-yl]-2-nitrobenzoic acid ethyl ester in 8 ml of ethanol, a solution of 0.40 g of potassium hydroxide in 2 ml of water was added, and stirred at room temperature for 3 hours. After the completion of the reaction, the reaction mixture was poured in 15 ml of water, adjusted to pH 4 with concentrated hydrochloric acid, then extracted with ethyl acetate (20 ml×2), the organic phase was washed with water, and then dehydrated with saturated sodium chloride aqueous solution and dried over anhydrous sodium sulfate and the solvent was distilled off under reduced pressure to obtain 0.40 g of crude 4-[5-(3,5-dichlorophenyl)-5-trifluoromethyl-4,5-dihydroisoxazole-3-yl]-2-nitro benzoic acid as pale yellow oily substance. The substance was dissolved in 10 ml of chloroform, and 0.24 g of 2-picolylamine, 0.01 g of 4-(N,N-dimethylamino)pyridine and 0.35 g of 1-[3-(diethylamino)propyl]-3-ethylcarbodiimide hydrochloride were added, and stirred at room temperature for 18 hours. After the completion of the reaction, the solvent was distilled off under reduced pressure. The residue was subjected to purification with medium-pressure preparative liquid chromatography (Yamazen Corporation, medium pressure preparative system; YFLC-Wprep) that was eluted with ethyl acetate-hexane (1:1 to 1:0 gradient), and 0.14 g of the aimed product was obtained as colorless resinous substance.

$^1$H NMR (CDCl$_3$-DMSO-d$_6$, Me$_4$Si, 300 MHz) δ 8.50 (d, J=4.8 Hz, 1H), 8.25 (d, J=1.7 Hz, 1H), 8.03 (dd, J=8.1, 1.6 Hz, 1H), 7.72 (td, J=7.7, 1.6 Hz, 1H), 7.68 (d, J=8.1 Hz, 1H), 7.51 (d, J=1.5 Hz, 2H), 7.45 (t, J=1.8 Hz, 1H), 7.43 (bs, 1H), 7.36 (d, J=7.9 Hz, 1H), 7.23 (dd, J=6.8, 5.3 Hz, 1H), 4.76 (d, J=4.8 Hz, 2H), 4.13 (d, J=17.4 Hz, 1H), 3.76 (d, J=17.4 Hz, 1H).

Synthetic Example 6

4-[5-(3,5-Dichlorophenyl)-5-trifluoromethyl-4,5-dihydroisoxazole-3-yl]-2-methoxy-N-(2,2,2-trifluoroethyl)benzoic acid amide (Compound of the present invention No. 5-317)

Step 1: Production of 4-hydroxyiminomethyl-2-methoxyphenyl trifluoromethane sulfonate In a solution of 3.0 g of 4-hydroxy-3-methoxybenzaldehyde and 2.4 g of triethylamine in 50 ml of dichloromethane, 5.8 g of trifluoromethane sulfonic acid anhydride was added dropwise under cooling with ice and with stirring, after the completion of the addition dropwise, continued to stir at the same temperature for 30 minutes. After the completion of the reaction, the reaction mixture was washed with 50 ml of water and then with 30 ml of saturated sodium hydrogen carbonate aqueous solution, and dehydrated with saturated sodium chloride aqueous solution and dried over anhydrous magnesium sulfate, and then the solvent was distilled off under reduced pressure. The residue was dissolved in a mixture of 30 ml of ethanol and 15 ml of water, 1.4 g of hydroxyamine hydrochloride and 1.7 g of sodium acetate were added with stirring at room temperature, and continued to stir at the same temperature for further 1 hour. After the completion of the reaction, the solvent was distilled off under reduced pressure, extracted with ethyl acetate (40 ml×2), the organic phase was washed with water (30 ml×1), and then dehydrated with saturated sodium chloride aqueous solution and dried over anhydrous magnesium sulfate, and then the solvent was distilled off under reduced pressure to obtain 5.25 g of the aimed product as brown oily substance.

Refractive index $n_D^{20.2°\,C.}$=1.5082

$^1$H NMR (CDCl$_3$-DMSO-d$_6$, Me$_4$Si, 300 MHz) δ 8.47 (bs, 1H), 8.11 (s, 1H), 7.32 (s, 1H), 7.24 (d, J=8.1 Hz, 1H), 7.10 (d, J=8.1 Hz, 1H), 3.94 (s, 3H).

Step 2: Production of 4-[5-(3,5-dichlorophenyl)-5-trifluoromethyl-4,5-dihydroisoxazole-3-yl]-2-methoxyphenyl trifluoromethane sulfonate In a solution of 2.0 g of 4-hydroxyiminomethyl-2-methoxyphenyl trifluoromethane sulfonate in 30 ml of N,N-dimethylformamide, 0.9 g of N-chlorosuccinic acid imide was added, and stirred at 40 to 50° C. for 30 minutes. Then, the reaction mixture was left and cooled to room temperature, 1.5 g of 3,5-dichloro-1-(1-trifluoromethylethenyl)benzene synthesized in Step 1 of Synthetic Example 3 and 0.7 g of triethylamine were added, and stirred at room temperature for 90 minutes. After the completion of the reaction, the reaction mixture was poured in 100 ml of ice water, extracted with ethyl acetate (50 ml×2), the organic phase was dehydrated with saturated sodium chloride aqueous solution and dried over anhydrous magnesium sulfate, and then the solvent was distilled off under reduced pressure. The residue was purified with silica gel column chromatography that was eluated with ethyl acetate-hexane (1:7), and 1.4 g of the aimed product was obtained as colorless resinous substance.

$^1$H NMR (CDCl$_3$, Me$_4$Si, 300 MHz) δ 7.50 (s, 2H), 7.44 (s, 1H), 7.25-7.3 (m, 2H), 7.11 (d, J=8.4 Hz, 1H), 4.08 (d, J=17.1 Hz, 1H), 3.97 (s, 3H), 3.69 (d, J=17.1 Hz, 1H).

Step 3: Production of 4-[5-(3,5-dichlorophenyl)-5-trifluoromethyl-4,5-dihydroisoxazole-3-yl]-2-methoxy benzoic acid ethyl ester In a solution of 1.50 g of 4-[5-(3,5-dichlorophenyl)-5-trifluoromethyl-4,5-dihydroisoxazole-3-yl]-2-methoxyphenyl trifluoromethane sulfonate in 25 ml of ethanol in an autoclave, 0.27 g of sodium acetate, 31.0 mg of 1,1'-bis(diphenylphosphino) ferrocene and 7.0 mg of palladium (II) acetate were added, and stirred under 0.96 MPa carbon monoxide atmosphere at 100° C. for 2 hours. After the completion of the reaction, the reaction mixture was left and cooled to room temperature, and the reaction mixture was poured in 100 ml of ice water, extracted with ethyl acetate (40 ml×2). The organic phases together were dehydrated with saturated sodium chloride aqueous solution and dried over anhydrous magnesium sulfate, and then the solvent was distilled off under reduced pressure. The residue was purified with silica gel column chromatography that was eluated with ethyl acetate-hexane (1:5), and 1.20 g of the aimed product was obtained as white crystal.

Melting point 142.0-144.0° C.

$^1$H NMR (CDCl$_3$, Me$_4$Si, 300 MHz) δ 7.82 (d, J=7.8 Hz, 1H), 7.51 (s, 2H), 7.4-7.45 (m, 2H), 7.10 (d, J=7.8 Hz, 1H), 4.37 (q, J=7.2 Hz, 2H), 4.10 (d, J=17.4 Hz, 1H), 3.95 (s, 3H), 3.71 (d, J=17.4 Hz, 1H), 1.39 (t, J=7.2 Hz, 3H).

Step 4: Production of 4-[5-(3,5-dichlorophenyl)-5-trifluoromethyl-4,5-dihydroisoxazole-3-yl]-2-methoxy benzoic acid In a solution of 1.07 g of 4-[5-(3,5-dichlorophenyl)-5-trifluoromethyl-4,5-dihydroisoxazole-3-yl]-2-methoxy benzoic acid ethyl ester in 30 ml of ethanol, a solution of 1.0 g of sodium hydroxide in 30 ml of water was added, stirred at 85° C. for 1 hour. After the completion of the reaction, the solvent was distilled off under reduced pressure. The residue was adjusted to pH 2 to 3 with concentrated hydrochloric acid, and extracted with ethyl acetate (30 ml×2). The organic phase was dehydrated with saturated sodium chloride aqueous solution and dried over anhydrous magnesium sulfate, and then the solvent was distilled off under reduced pressure to obtain 1.0 g of the aimed product as pale yellow resinous substance.

$^1$H NMR (CDCl$_3$, Me$_4$Si, 300 MHz) δ 10.67 (bs, 1H), 8.24 (d, J=7.8 Hz, 1H), 7.57 (s, 1H), 7.51 (s, 2H), 7.45 (s, 1H), 7.22 (d, J=7.8 Hz, 1H), 4.05-4.15 (m, 4H), 3.74 (d, J=17.4 Hz, 1H).

Step 5: Production of 4-[5-(3,5-dichlorophenyl)-5-trifluoromethyl-4,5-dihydroisoxazole-3-yl]-2-methoxy-N-(2,2,2-trifluoroethyl)benzoic acid amide In a suspension of 0.25 g of 4-[5-(3,5-dichlorophenyl)-5-trifluoromethyl-4,5-dihydroisoxazole-3-yl]-2-methoxy benzoic acid in 15 ml of dichloromethane, 0.09 g of oxalyl chloride and 1 drop of N,N-dimethylformamide were added, and stirred at room temperature for 1 hour. After the completion of the reaction, the solvent was distilled off under reduced pressure, the residue was dissolved in 15 ml of dichloromethane, and 0.09 g of triethylamine was added under cooling with ice, then 0.07 g of 2,2,2-trifluoroethylamine was added dropwise. After the completion of addition dropwise, the mixture was continued to stir at the same temperature for further 2 hours. Thereafter, the reaction mixture was diluted with 60 ml of chloroform, washed with 50 ml of water, then dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (1:2) to obtain 0.25 g of the aimed product as colorless resinous substance.

$^1$H NMR (CDCl$_3$, Me$_4$Si, 300 MHz) δ 8.2-8.3 (m, 2H), 7.51 (s, 3H), 7.43 (s, 1H), 7.17 (d, J=7.8 Hz, 1H), 4.05-4.2 (m, 3H), 4.05 (s, 3H), 3.74 (d, J=17.4 Hz, 1H).

Synthetic Example 7

4-[5-(4-Fluoro-3-methylphenyl)-5-trifluoromethyl-4,5-dihydroisoxazole-3-yl]-N-(2,2,2-trifluoroethyl) benzoic acid amide (Compound of the present invention No. 3-141)

Step 1: Production of 4-formyl-N-(2,2,2-trifluoroethyl)benzoic acid amide

In a suspension of 1.00 g of 4-formyl benzoic acid in 15 ml of benzene, 0.87 g of thionyl chloride and 2 drops of N,N-dimethylformamide were added, and stirred under reflux with heat for 2 hours. After the completion of the reaction, the reaction mixture was left and cooled to room temperature, and the solvent was distilled off under reduced pressure to obtain 1.14 g of crude 4-formyl benzoic acid chloride as white crystal. In a solution of 0.66 g of 2,2,2-trifluoroethylamine and 0.81 g of triethylamine in 6 ml of chlororform, the solution of 1.14 g of the crude 4-formyl benzoic acid chloride in 6 ml of chloroform was added dropwise under cooling with ice and with stirring, after the completion of the addition dropwise, continued to stir at room temperature for further 18 hours. After the completion of the reaction, the reaction mixture was added in 30 ml of water, extracted with chloroform (20 ml×3). The organic phase was washed with water, dried over anhydrous sodium sulfate, the solvent was distilled off under reduced pressure, the residual solid was washed with hexane to obtain 1.32 g of the aimed product as white crystal.

Melting point 83.0 to 84.0° C.

$^1$H NMR (CDCl$_3$, Me$_4$Si, 400 MHz) δ 10.09 (s, 1H), 7.96 (bs, 4H), 6.80 (bs, 1H), 4.05-4.25 (m, 2H).

Step 2: Production of 4-hydroxyiminomethyl-N-(2,2,2-trifluoroethyl)benzoic acid amide In a solution of 4.11 g of 4-formyl-N-(2,2,2-trifluoroethyl) benzoic acid amide in 30 ml of ethanol and 10 ml of water, 1.99 g of hydroxyamine hydrochloride and 2.51 g of anhydrous sodium acetate were added, stirred at room temperature for 3.5 hours. After the completion of the reaction, the reaction mixture was poured in 100 ml of water, and then extracted with ethyl acetate (30 ml×3), the organic phase was washed with 50 ml of saturated sodium hydrogen carbonate aqueous solution, then dehydrated with saturated sodium chloride aqueous solution and dried over anhydrous sodium sulfate, and then the solvent was distilled off under reduced pressure. The residual solid was washed with hexane to obtain 3.92 g of the aimed product as white crystal.

Melting point 153.0 to 154.0° C.

$^1$H NMR (CDCl$_3$, Me$_4$Si, 400 MHz) δ 10.89 (s, 1H), 8.08 (s, 1H), 8.03 (bs, 1H), 7.84 (d, J=8.2 Hz, 2H), 7.60 (d, J=8.2 Hz, 2H), 3.95-4.1 (m, 2H).

Step 3: Production of 4-chlorohydroxyiminomethyl-(2,2,2-trifluoroethyl)benzoic acid amide In a solution of 3.80 g of 4-hydroxyiminomethyl-N-(2,2,2-trifluoroethyl)benzoic acid amide in 50 ml of tetrahydrofyran, 20 ml of 3N hydrochloric acid was added, 14 ml of 8% sodium hypochlorite aqueous solution was added dropwise with stirring under ice cooling over 10 minutes, after the completion of addition dropwise, continued to stir at the same temperature for further 15 minutes. After the completion of the reaction, the reaction mixture was poured in 200 ml of water, extracted with ethyl acetate (30 ml×3), the organic phase was dehydrated with saturated sodium chloride aqueous solution and dried over anhydrous sodium sulfate, and the solvent was distilled off under reduced pressure. The residual solid was washed with hexane to obtain 4.15 g of the product as white crystal.

Melting point 158.0 to 160.0° C.

$^1$H NMR (CDCl$_3$, Me$_4$Si, 400 MHz) δ 12.03 (s, 1H), 8.05 (t, J=6.0 Hz, 1H), 7.93 (bs, 4H), 3.95-4.15 (m, 2H).

Step 4: Production of 4-[5-(4-fluoro-3-methylphenyl)-5-trifluoromethyl-4,5-dihydrooxazole-3-yl]-N-(2,2,2-trifluoroethyl)benzoic acid amide In a solution of 0.21 g of 4-fluoro-3-methylphenyl boric acid and 0.23 g of 2-bromo-3,3,3-trifluoropropene in 6 ml of 1,2-dimethoxyethane and 2 ml of water, 0.24 g of sodium carbonate and 0.05 g of dichlorobis(triphenylphosphine) palladium (II) were added, stirred at 75° C. for 3 hours. Then, the reaction mixture was left and cooled to room temperature, then a solution of 0.25 g of 4-chlorohydroxyiminomethyl-N-(2,2,2-trifluoroethyl)benzoic acid amide in 4 ml of 1,2-dimethoxyethane was added, continued to stir at the same temperature for further 18 hours. After the completion of the reaction, the reaction mixture was poured in 50 ml of water, extracted with ethyl acetate (10 ml×3), the organic phase was dehydrated with saturated sodium chloride aqueous solution and dried over anhydrous sodium sulfate, and the solvent was distilled off under reduced pressure. The residual solid was purified with silica gel column chromatography that was eluated with chloroform to obtain 0.24 g of the product as white crystal.

Melting point 151.0 to 152.0° C.

$^1$H NMR (CDCl$_3$, Me$_4$Si, 400 MHz) δ 7.86 (d, J=8.4 Hz, 2H), 7.76 (d, J=8.4 Hz, 2H), 7.35-7.5 (m, 2H), 7.0-7.15 (m, 1H), 6.39 (t, J=6.3 Hz, 1H), 4.05-4.25 (m, 2H), 4.09 (d, J=17.3 Hz, 1H), 3.74 (d, J=17.3 Hz, 1H), 2.32 (d, J=1.7 Hz, 3H).

Synthetic Example 8

4-[5-(3,5-Dichlorophenyl)-5-trifluoromethyl-4,5-dihydroisoxazole-3-yl]-2-methyl-N-(2,2,2-trifluoroethyl)benzoic acid amide (Compound of the present invention No. 5-075)

Step 1: Production of 4-bromo-2-methyl-N-(2,2,2-trifluoroethyl)benzoic acid amide In a solution of 5.00 g of 4-bromo-2-methyl benzoic acid and 3.45 g of 2,2,2-trifluoroethylamine in 30 ml of N,N-dimethylformamide, 5.79 g of 1-[3-(diethylamino)propyl]-3-ethylcarbodiimide hydrochloride was added with stirring at room temperature, and stirred at the same temperature for 1.5 hour. After the completion of the reaction, 80 ml of water was added, and precipitated crystal was filtered off, washed with water and dried to obtain 4.00 g of the aimed product as white crystal.

Melting point 124.0 to 125.5° C.

$^1$H NMR (CDCl$_3$, Me$_4$Si, 400 MHz) δ 7.40 (s, 1H), 7.36 (d, J=8.4 Hz, 1H), 7.22 (d, J=8.4 Hz, 1H), 6.15 (bs, 1H), 4.0-4.15 (m, 2H), 2.39 (s, 3H).

Step 2: Production of 4-formyl-2-methyl-N-(2,2,2-trifluoroethyl)benzoic acid amide In a solution of 1.00 g of 4-bromo-2-methyl-N-(2,2,2-trifluoroethyl)benzoic acid amide in 15 ml of tetrahydrofuran under nitrogen atmosphere, 4.7 ml of n-butyl lithium (1.58M hexane solution) was added dropwise at −70° C. with stirring, and then 0.4 ml of N,N-dimethylformamide were added dropwise. After stirring at the same temperature for 30 minutes, 10 ml of 1N hydrochloric acid and then 30 ml of water were added, and extracted with ethyl acetate (30 ml×2). The organic phase was dehydrated with saturated sodium chloride aqueous solution and dried over anhydrous magnesium sulfate, the solvent was distilled off under reduced pressure to obtain 0.80 g of the aimed product as pale yellow crystal.

Melting point 99.0 to 104.0° C.

$^1$H NMR (CDCl$_3$, Me$_4$Si, 400 MHz) δ 10.00 (s, 1H), 7.7-7.75 (m, 2H), 7.50 (d, J=7.5 Hz, 1H), 6.27 (bs, 1H), 4.05-4.2 (m, 2H), 2.49 (s, 3H).

Step 3: Production of 4-hydroxyiminomethyl-2-methyl-N-(2,2,2-trifluoroethyl)benzoic acid amide In a solution of 0.8 g of 4-formyl-2-methyl-N-(2,2,2-trifluoroethyl)benzoic acid amide in 10 ml of ethanol and 5 ml of water, 0.3 g of hydroxyamine hydrochloride and 0.4 g of anhydrous sodium acetate were added with stirring at room temperature, and stirred at the same temperature for 30 minutes. After the completion of the reaction, the solvent was distilled off under reduced pressure, and precipitated crystal was filtered off, washed with water and dried to obtain 0.5 g of the aimed product as white crystal.

Melting point 190.5 to 194.0° C.

$^1$H NMR (CDCl$_3$-DMSO-d$_6$, Me$_4$Si, 400 MHz) δ 10.98 (s, 1H), 8.43 (bs, 1H), 8.07 (s, 1H), 7.35-7.55 (m, 3H), 3.95-4.1 (m, 2H), 2.43 (s, 3H).

Step 4: Production of 4-[5-(3,5-dichlorophenyl)-5-trifluoromethyl-4,5-dihydroisoxazole-3-yl]-2-methyl-N-(2,2,2-trifluoroethyl)benzoic acid amide In a solution of 0.40 g of 4-hydroxyiminomethyl-2-methyl-N-(2,2,2-trifluoroethyl)benzoic acid amide in 15 ml of N,N-dimethylformamide, 0.21 g of N-chlorosuccinc acid imide was added, and stirred at 50° C. for 30 minutes. Then, the reaction mixture was left and cooled to room temperature, 0.34 g of 3,5-dichloro-1-(1-trifluoromethylethenyl)benzene synthesized in Step 1 of Synthetic Example 3 and 0.16 g of triethylamine were added, and stirred at room temperature for 18 hours. After the completion of the reaction, the reaction mixture was poured in 50 ml of ice water, extracted with ethyl acetate (50 ml×1), the organic phase was dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (1:2), and 0.45 g of the aimed product was obtained as white crystal.

Melting point 155.5 to 157.0° C.

$^1$H NMR (CDCl$_3$, Me$_4$Si, 400 MHz) δ 7.4-7.55 (m, 6H), 6.13 (bs, 1H), 4.05-4.2 (m, 3H), 3.71 (d, J=17.4 Hz, 1H), 2.45 (s, 3H).

Synthetic Example 9

4-[5-(3,5-Dichlorophenyl)-5-trifluoromethyl-4,5-dihydroisoxazole-3-yl]-2-methyl-N-(2-pyridylmethyl)benzoic acid amide (Compound of the present invention No. 5-234)

Step 1: Production of 4-bromo-2-methyl-N-(2-pyridylmethyl)benzoic acid amide

In a solution of 3.0 g of 4-bromo-2-methyl benzoic acid in 30 ml of dichloromethane, 2.7 g of oxalyl chloride and 3 drops of N,N-dimethylformamide were added under cooling with ice with stirring, and stirred at room temperature for 1 hour. After the completion of the reaction, the solvent was distilled off under reduced pressure, the residue was dissolved in 30 ml of dichloromethane, 2.1 g of triethylamine and 2.0 g of 2-picolylamine were added under cooling with ice with stirring, and continued to stir at room temperature for 3 hours. After the completion of the reaction, 50 ml of water was added in the reaction mixture, extracted with chloroform (50 ml×2), the organic phase was washed with water, dehydrated with saturated sodium chloride aqueous solution and dried over anhydrous sodium sulfate, and then the solvent was distilled off under reduced pressure. The residual solid was washed with diisopropylether to obtain 3.7 g of the aimed product as yellow crystal.

Melting point 86.0 to 87.5° C.

$^1$H NMR (CDCl$_3$, Me$_4$Si, 300 MHz) δ 8.52 (d, J=4.8 Hz, 1H), 7.69 (td, J=7.8, 1.8 Hz, 1H), 7.15-7.4 (m, 6H), 4.73 (d, J=4.8 Hz, 2H), 2.45 (s, 3H).

Step 2: Production of 4-formyl-2-methyl-N-(2-pyridylmethyl)benzoic acid amide

In a solution of 2.0 g of 4-bromo-2-methyl-N-(2-pyridylmethyl)benzoic acid amide in 20 ml of N,N-dimethylformamide in an autoclave, 0.67 g of sodium formate and 0.10 g of dichlorobis(triphenylphosphine) palladium (II) were added, and stirred under 1.05 MPa carbon monoxide atmosphere at 110° C. for 3 hours. After the completion of the reaction, the reaction mixture was left and cooled to room temperature, and poured in 100 ml of water, and extracted with ethyl acetate (50 ml×2). The organic phases together were dehydrated with saturated sodium chloride aqueous solution and dried over anhydrous magnesium sulfate, and then the solvent was distilled off under reduced pressure. The residue was purified with silica gel column chromatography that was eluated with ethyl acetate-hexane (9:1), and 0.50 g of the aimed product was obtained as pale yellow crystal.

Melting point 79.5 to 83.0° C.

$^1$H NMR (CDCl$_3$, Me$_4$Si, 300 MHz) δ 10.02 (s, 1H), 8.54 (d, J=5.1 Hz, 1H), 7.6-7.8 (m, 4H), 7.15-7.4 (m, 3H), 4.77 (d, J=4.8 Hz, 2H), 2.55 (s, 3H).

Step 3: Production of 4-hydroxyiminomethyl-2-methyl-N-(2-pyridylmethyl)benzoic acid amide In a solution of 0.50 g of 4-formyl-2-methyl-N-(2-pyridylmethyl)benzoic acid amide in 10 ml of ethanol and 5 ml of water, 0.18 g of hydroxyamine hydrochloride was added with stirring at room temperature, and stirred at the same temperature for 12 hours. After the completion of the reaction, solid was filtered off, ethanol was distilled off under reduced pressure, and 30 ml of saturated sodium hydrogen carbonate aqueous solution was added in the remaining aqueous solution. The precipitated crystal was filtered off, washed with water and dried to obtain 0.45 g of the aimed product as pale yellow crystal.

Melting point 159.5 to 161.0° C.

$^1$H NMR (CDCl$_3$-DMSO-d$_6$, Me$_4$Si, 300 MHz) δ 11.89 (bs, 1H), 8.56 (d, J=4.2 Hz, 1H), 8.03 (s, 1H), 7.90 (bs, 1H), 7.77 (t, J=7.8 Hz, 1H), 7.47 (d, J=7.5 Hz, 1H), 7.0-7.35 (m, 4H), 4.76 (d, J=6.0 Hz, 2H), 2.36 (s, 3H).

Step 4: Production of 4-[5-(3,5-dichlorophenyl)-5-trifluoromethyl-4,5-dihydroisoxazole-3-yl]-2-methyl-N-(2-pyridylmethyl)benzoic acid amide In a solution of 0.45 g of 4-hydroxyiminomethyl-2-methyl-N-(2-pyridylmethyl)benzoic acid amide in 10 ml of N,N-dimethylformamide, 0.25 g of N-chlorosuccinc acid imide was added, and stirred at 70° C. for 1 hour. Then, the reaction mixture was left and cooled to room temperature, 0.41 g of 3,5-dichloro-1-(1-trifluoromethylethenyl)benzene synthesized in Step 1 of Synthetic Example 3 and 0.25 g of potassium hydrogen carbonate were added, and stirred at room temperature for 3 hours. After the completion of the reaction, the reaction mixture was poured in 50 ml of ice water, extracted with ethyl acetate (60 ml×1), the organic phase was dehydrated with saturated sodium chloride aqueous solution and dried over anhydrous magnesium sulfate, and then the solvent was distilled off under reduced pressure. The residue was purified with silica gel column chromatography that was eluated with ethyl acetate-hexane (3:1), and 0.30 g of the aimed product was obtained as white crystal.

Melting point 131.0 to 135.5° C.

$^1$H NMR (CDCl$_3$, Me$_4$Si, 300 MHz) δ 8.53 (d, J=5.0 Hz, 1H), 7.65-7.75 (m, 1H), 7.2-7.55 (m, 9H), 4.75 (d, J=4.9 Hz, 2H), 4.09 (d, J=17.3 Hz, 1H), 3.71 (d, J=17.3 Hz, 1H), 2.50 (s, 3H).

Synthetic Example 10

4-[5-(3,5-Dichlorophenyl)-5-trifluoromethyl-4,5-dihydroisoxazole-3-yl]-N-(2-pyridylmethyl)-2-trifluoromethyl benzoic acid amide (Compound of the present invention No. 5-315)

Step 1: Production of 4-[5-(3,5-dichlorophenyl)-5-trifluoromethyl-4,5-dihydroisoxazole-3-yl]-2-iodo benzoic acid methyl ester In a solution of 0.60 g of 4-[5-(3,5-dichlorophenyl)-5-trifluoromethyl-4,5-dihydroisoxazole-3-yl]-2-iodo benzoic acid synthesized similarly to Steps 1 to 4 of Synthetic Example 4 in 10 ml of methanol, 2 drops of concentrated sulfuric acid was added, and stirred under reflux with heat for 20 hours. After the completion of the reaction, the solvent was distilled off under reduced pressure, the residue was neutralized with 10 ml of saturated sodium hydrogen carbonate aqueous solution, then extracted with ethyl acetate (10 ml×2). The organic phase was washed with water, dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (1:4), and 0.56 g of the aimed product was obtained as colorless oily substance.

$^1$H NMR (CDCl$_3$, Me$_4$Si, 400 MHz) δ 8.22 (d, J=1.5 Hz, 1H), 7.85 (d, J=8.2 Hz, 1H), 7.75-7.8 (m, 1H), 7.5-7.55 (m, 2H), 7.4-7.45 (m, 1H), 4.07 (d, J=17.7 Hz, 1H), 3.95 (s, 3H), 3.69 (d, J=17.2 Hz, 1H).

Step 2: Production of 4-[5-(3,5-dichlorophenyl)-5-trifluoromethyl-4,5-dihydroisoxazole-3-yl]-2-trifluoromethyl benzoic acid methyl ester In a solution of 0.51 g of 4-[5-(3,5-dichlorophenyl)-5-trifluoromethyl-4,5-dihydroisoxazole-3-yl]-2-iodo benzoic acid methyl ester in 5 ml of N,N-dimethylformamide, 0.18 g of copper (I) iodide, 0.06 g of potassium fluoride and 0.27 g of chlorodifluoro acetic acid methyl ester were added, and stirred at 120° C. for 5 hours. After the completion of the reaction, the reaction mixture was left and cooled to room temperature, 50 ml of water was added and extracted with ethyl acetate (50 ml×2). The organic phase was washed with water, dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (1:4), and 0.45 g of the aimed product was obtained as pale yellow oily substance.

$^1$H NMR (CDCl$_3$, Me$_4$Si, 400 MHz) δ 8.00 (d, J=1.1 Hz, 1H), 7.85-7.95 (m, 2H), 7.5-7.55 (m, 2H), 7.4-7.45 (m, 1H), 4.12 (d, J=7.1 Hz, 1H), 3.96 (s, 3H), 3.94 (d, J=7.8 Hz, 1H).

Step 3: Production of 4-[5-(3,5-dichlorophenyl)-5-trifluoromethyl-4,5-dihydroisoxazole-3-yl]-2-trifluoromethyl benzoic acid In a solution of 0.40 g of 4-[5-(3,5-dichlorophenyl)-5-trifluoromethyl-4,5-dihydroisoxazole-3-yl]-2-trifluoromethyl benzoic acid methyl ester in 5 ml of methanol, a solution of 0.10 g of sodium hydroxide in 2 ml of water was added, and stirred at room temperature for 18 hours. After the completion of the reaction, 10 ml of water was added in the reaction mixture, washed with 5 ml of toluene, aqueous phase was collected, adjusted to pH 1 to 2 with concentrated hydrochloric acid and then extracted with ethyl acetate (20 ml×2). The organic phase was washed with water, dehydrated with saturated sodium chloride aqueous solution and dried over anhydrous sodium sulfate, and then the solvent was distilled off under reduced pressure to obtain 0.34 g of the aimed product as pale yellow resinous substance. The resulting product was used as such without purification for the next step.

Step 4: Production of 4-[5-(3,5-dichlorophenyl)-5-trifluoromethyl-4,5-dihydroisoxazole-3-yl]-N-(2-pyridylmethyl)-2-trifluoromethyl benzoic acid amide In a solution of 0.15 g of 4-[5-(3,5-dichlorophenyl)-5-trifluoromethyl-4,5-dihydroisoxazole-3-yl]-2-trifluoromethyl benzoic acid in 3 ml of dichloromethane, 0.06 g of oxalyl chloride and 1 drop of N,N-dimethylformamide were added under cooling with ice with stirring, and stirred at room temperature for 2 hours. After the completion of the reaction, the solvent was distilled off under reduced pressure, the residue was dissolved in 3 ml of dichloromethane, and a solution of 0.05 g of 2-picolylamine and 0.06 g of triethylamine in 1 ml of dichloromethane was added dropwise, after the completion of the addition dropwise, continued to stir at room temperature for 3 hours. After the completion of the reaction, 5 ml of water was added in the reaction mixture, extracted with chloroform (5 ml×2). The organic phase was washed with water, dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (1:3), and 0.05 g of the aimed product was obtained as white crystal.

Melting point 69.0 to 70.0° C.

$^1$H NMR (CDCl$_3$, Me$_4$Si, 400 MHz) δ 8.5-8.55 (m, 1H), 7.95 (bs, 1H), 7.91 (d, J=1.9 Hz, 1H), 7.65-7.8 (m, 2H), 7.5-7.55 (m, 2H), 7.35-7.45 (m, 3H), 7.26 (t, J=4.9 Hz, 1H), 4.77 (d, J=4.9 Hz, 2H), 4.11 (d, J=17.4 Hz, 1H), 3.73 (d, J=17.2 Hz, 1H).

Synthetic Example 11

4-[5-(3,5-Dichlorophenyl)-5-trifluoromethyl-4,5-dihydroisoxazole-3-yl]-2-phenyl-N-(2-pyridylmethyl)benzoic acid amide (Compound of the present invention No. 5-344)

Step 1: Production of 4-[5-(3,5-dichlorophenyl)-5-trifluoromethyl-4,5-dihydroisoxazole-3-yl]-2-phenyl benzoic acid methyl ester In a solution of 0.70 g of 2-bromo-4-[5-(3,5-dichlorophenyl)-5-trifluoromethyl-4,5-dihydroisoxazole-3-yl]benzoic acid methyl ester synthesized similarly to Step 1 of Synthetic Example 10 in 20 ml of tetrahydrofuran and 10 ml of water, 0.18 g of phenyl boric acid, 0.39 g of potassium carbonate and 0.05 g of dichlorobis(triphenylphosphine) palladium (II) were added, and stirred under reflux with heat for 1.5 hour. After the completion of the reaction, the solvent was distilled off under reduced pressure, the residue was poured in 30 ml of water, then extracted with ethyl acetate (50 ml×1). The organic phase was washed with water, dehydrated with saturated sodium chloride aqueous solution and dried over anhydrous sodium sulfate, and then the solvent was distilled off under reduced pressure. The residue was purified with silica gel column chromatography that was eluated with ethyl acetate, and 0.78 g of the aimed product was obtained as brown resinous substance.

$^1$H NMR (CDCl$_3$, Me$_4$Si, 400 MHz) δ 7.89 (d, J=8.4 Hz, 1H), 7.74 (dd, J=8.0, 1.8 Hz, 1H), 7.62 (d, J=1.4 Hz, 1H), 7.51 (d, J=1.8 Hz, 2H), 7.35-7.45 (m, 4H), 7.25-7.35 (m, 2H), 4.11 (d, J=16.8 Hz, 1H), 3.73 (d, J=16.8 Hz, 1H), 3.65 (s, 3H).

Step 2: Production of 4-[5-(3,5-dichlorophenyl)-5-trifluoromethyl-4,5-dihydroisoxazole-3-yl]-2-phenyl benzoic acid In a solution of 0.78 g of 4-[5-(3,5-dichlorophenyl)-5-trifluoromethyl-4,5-dihydroisoxazole-3-yl]-2-phenyl benzoic acid methyl ester in 15 ml of ethanol, a solution of 0.30 g of sodium hydroxide in 15 ml of water was added, and stirred at 60° C. for 3 hours. After the completion of the reaction, ethanol was distilled off under reduced pressure, adjusted to pH 1 to 2 with 12N hydrochloric acid, and then extracted with ethyl acetate (50 ml×1). The organic phase was washed with water, dehydrated with saturated sodium chloride aqueous solution and dried over anhydrous sodium sulfate, and then the solvent was distilled off under reduced pressure to obtain 0.70 g of the aimed product as brown glass substance. The resulting product was used as such without purification for the next step.

Step 3: Production of 4-[5-(3,5-dichlorophenyl)-5-trifluoromethyl-4,5-dihydroisoxazole-3-yl]-2-phenyl-N-(2-pyridylmethyl)benzoic acid amide In a solution of 0.3 g of 4-[5-(3,5-dichlorophenyl)-5-trifluoromethyl-4,5-dihydroisoxazole-3-yl]-2-phenyl benzoic acid in 10 ml of chloroform, 0.3 ml of oxalyl chloride and a catalytic amount (2 to 3 drops) of N,N-dimethylformamide were added with stirring at room temperature, and stirred at the same temperature for 10 minutes. After the completion of the reaction, the solvent was distilled off under reduced pressure, the residue was dissolved in 10 ml of chloroform, and under cooling with ice with stirring 0.3 ml of 2-picolylamine and then 0.3 ml of triethylamine were added, and continued to stir at room temperature for 20 minutes. After the completion of the reaction, the reaction mixture was poured in 40 ml of water, extracted with ethyl acetate (50 ml×1). The organic phase was washed with water, dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (2:1), and 0.2 g of the aimed product was obtained as white crystal.

Melting point 194.0 to 198.0° C.
$^1$H NMR (CDCl$_3$, Me$_4$Si, 400 MHz) δ 8.3-8.35 (m, 1H), 7.25-7.8 (m, 12H), 7.1-7.15 (m, 1H), 7.40 (d, J=7.8 Hz, 1H), 6.65-6.7 (m, 1H), 4.47 (d, J=5.0 Hz, 2H), 4.12 (d, J=17.0 Hz, 1H), 3.74 (d, J=17.0 Hz, 1H).

Synthetic Example 12

2-Amino-4-[5-(3,5-dichlorophenyl)-5-trifluoromethyl-4,5-dihydroisoxazole-3-yl]-N-(2,2,2-trifluoroethyl)benzoic acid amide (Compound of the present invention No. 5-329)

Step 1: Production of 2-amino-4-[5-(3,5-dichlorophenyl)-5-trifluoromethyl-4,5-dihydroisoxazole-3-yl]benzoic acid ethyl ester In a solution of 0.60 g of 4-[5-(3,5-dichlorophenyl)-5-trifluoromethyl-4,5-dihydroisoxazole-3-yl]-2-nitro benzoic acid ethyl ester synthesized in Steps 1 to 3 of Synthetic Example 5 in 6 ml of ethyl acetate, 2.0 ml of water, 0.6 ml of acetic acid and 0.46 g of reduced iron were added, and stirred at 75° C. for 2 hours. After the completion of the reaction, the organic phase was collected, and the aqueous phase was extracted with ethyl acetate (10 ml×2). The organic phases together were washed with water, dehydrated with saturated sodium chloride aqueous solution and dried over anhydrous sodium sulfate, and then the solvent was distilled off under reduced pressure to obtain 0.60 g of crude aimed product as brown oily substance. The resulting product was used as such without purification for the next step.

Step 2: Production of 2-amino-4-[5-(3,5-dichlorophenyl)-5-trifluoromethyl-4,5-dihydroisoxazole-3-yl]benzoic acid In a solution of 0.6 g of crude 2-amino-4-[5-(3,5-dichlorophenyl)-5-trifluoromethyl-4,5-dihydroisoxazole-3-yl]benzoic acid ethyl ester in 7 ml of ethanol, a solution of 0.5 g of potassium hydroxide in 2.0 ml of water was added, and stirred at room temperature for 18 hours. After the completion of the reaction, 20 ml of ice water was added in the reaction mixture, adjusted to pH 2 to 3 with concentrated hydrochloric acid, and then extracted with ethyl acetate (20 ml×2). The organic phase was washed with water, dehydrated with saturated sodium chloride aqueous solution and dried over anhydrous sodium sulfate, and then the solvent was distilled off under reduced pressure to obtain 0.6 g of crude aimed product as yellow oily substance. The resulting product was used as such without purification for the next step.

Step 3: Production of 2-amino-4-[5-(3,5-dichlorophenyl)-5-trifluoromethyl-4,5-dihydroisoxazole-3-yl]-N-(2,2,2-trifluoroethyl)benzoic acid amide In a solution of 0.60 g of crude 2-amino-4-[5-(3,5-dichlorophenyl)-5-trifluoromethyl-4,5-dihydroisoxazole-3-yl]benzoic acid in 6 ml of chloroform, 0.20 g of 2,2,2-trifluoroethylamine, 0.02 g of 4-(N,N-dimethylamino) pyridine and 0.33 g of 1-[3-(diethylamino)propyl]-3-ethylcarbodiimide hydrochloride were added, and stirred at room temperature for 20 hours. After the completion of the reaction, the reaction mixture was subjected to purification with medium-pressure preparative liquid chromatography (Yamazen Corporation, medium pressure preparative system; YFLC-Wprep) that was eluted with ethyl acetate-hexane (1:4), and 0.14 g of the aimed product was obtained as pale yellow crystal.

Melting point 78.0 to 79.0° C.
$^1$H NMR (CDCl$_3$, Me$_4$Si, 400 MHz) δ 7.50 (d, J=1.8 Hz, 2H), 7.43 (t, J=1.8 Hz, 1H), 7.39 (d, J=8.6 Hz, 1H), 6.95-7.0 (m, 2H), 6.29 (t, J=7.0 Hz, 1H), 5.68 (bs, 2H), 4.05-4.15 (m, 2H), 4.04 (d, J=17.2 Hz, 1H), 3.67 (d, J=17.2 Hz, 1H).

Synthetic Example 13

4-[5-(3,5-dichlorophenyl)-5-trifluoromethyl-4,5-dihydroisoxazole-3-yl]-2-methylthio-N-(2-pyridylmethyl)benzoic acid amide (Compound of the present invention No. 5-323)

In a solution of 0.92 g of 4-[5-(3,5-dichlorophenyl)-5-trifluoromethyl-4,5-dihydroisoxazole-3-yl]-2-fluoro-N-(2-pyridylmethyl)benzoic acid amide (Compound of the present invention No. 5-041) synthesized similarly to Synthetic Example 4 in 12 ml of dimethylsulfoxide, 0.12 g of sodium methane thiolate was added with stirring at room temperature, and stirred at 100° C. for 90 minutes. After the completion of the reaction, the reaction mixture was poured in 30 ml of water, and extracted with ethyl acetate (20 ml×3). The organic phase was washed with 30 ml of water, dehydrated with saturated sodium chloride aqueous solution and dried over anhydrous sodium sulfate, and then the solvent was distilled off under reduced pressure. The residue was purified with silica gel column chromatography that was eluated with chloroform, and 0.89 g of the aimed product was obtained as colorless oily substance.
$^1$H NMR (CDCl$_3$, Me$_4$Si, 300 MHz) δ 8.51 (d, J=4.8 Hz, 1H), 7.6-7.75 (m, 4H), 7.52 (bs, 2H), 7.42 (bs, 1H), 7.37 (bs, 1H), 7.34 (bs, 1H), 7.20 (dd, J=6.9, 1.8 Hz, 1H), 4.74 (d, J=4.8 Hz, 2H), 4.10 (d, J=17.1 Hz, 1H), 3.75 (d, J=17.1 Hz, 1H), 2.47 (s, 3H).

Synthetic Example 14

4-[5-(3,5-dichlorophenyl)-5-trifluoromethyl-4,5-dihydroisoxazole-3-yl]-2-methylsulfinyl-N-(2,2,2-trifluoroethyl)benzoic acid amide (Compound of the present invention No. 5-324)

In a solution of 0.38 g of 4-[5-(3,5-dichlorophenyl)-5-trifluoromethyl-4,5-dihydroisoxazole-3-yl]-2-methylthio-N-(2,2,2-trifluoroethyl)benzoic acid amide (Compound of the present invention No. 5-322) synthesized similarly to Synthetic Example 13 in 6 ml of 1,2-dichloroethane, 0.10 g of N-chlorosuccinic acid imide was added with stirring at room temperature, and stirred at the same temperature for 11 hours. After the completion of the reaction, the reaction mixture was poured in 30 ml of water, and extracted with ethyl acetate (20 ml×3). The organic phase was washed with 30 ml of saturated sodium hydrogen carbonate, dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (1:2), and 0.17 g of the aimed product was obtained as colorless oily substance.

$^1$H NMR (CDCl$_3$, Me$_4$Si, 300 MHz) δ 8.16 (t, J=8.1 Hz, 1H), 7.6-7.8 (m, 3H), 7.55 (d, J=8.1 Hz, 1H), 7.51 (d, J=8.1 Hz, 1H), 7.15 and 7.11 (t, J=6.3 Hz, 1H), 4.18 (qd, J=18.5, 6.3 Hz, 2H), 4.15 (d, J=17.7 Hz, 1H), 3.80 (d, J=17.7 Hz, 1H), 2.79 and 2.78 (s, 3H).

Synthetic Example 15

4-[5-(3,5-dichlorophenyl)-5-trifluoromethyl-4,5-dihydroisoxazole-3-yl]-2-methylsulfonyl-N-(2,2,2-trifluoroethyl)benzoic acid amide (Compound of the present invention No. 5-326)

In a solution of 0.25 g of 4-[5-(3,5-dichlorophenyl)-5-trifluoromethyl-4,5-dihydroisoxazole-3-yl]-2-methylthio-N-(2,2,2-trifluoroethyl)benzoic acid amide (Compound of the present invention No. 5-322) synthesized similarly to Synthetic Example 13 in 6 ml of dichloromethane, 0.17 g of 3-chloroperbenzoic acid was added with stirring at room temperature, and stirred at the same temperature for 3 days. After the completion of the reaction, the reaction mixture was poured in 30 ml of sodium thiosulfate aqueous solution, and extracted with chloroform (10 ml×3). The organic phase was dehydrated with saturated sodium chloride aqueous solution and dried over anhydrous sodium sulfate, and then the solvent was distilled off under reduced pressure. The residue was purified with silica gel column chromatography that was eluated with chloroform, and 0.20 g of the aimed product was obtained as colorless oily substance.

$^1$H NMR (CDCl$_3$, Me$_4$Si, 300 MHz) δ 8.16 (t, J=8.4 Hz, 1H), 8.05 (bs, 1H), 8.00 (s, 1H), 7.92 (s, 1H), 7.55 (d, J=8.4 Hz, 1H), 7.52 (d, J=8.4 Hz, 1H), 7.06 and 7.02 (t, J=6.4 Hz, 1H), 4.17 (d, J=17.4 Hz, 1H), 4.16 (qd, J=18.5, 6.3 Hz, 2H), 3.79 (d, J=17.4 Hz, 1H), 2.12 (s, 3H).

Synthetic Example 16

2-Cyano-4-[5-(3,5-dichlorophenyl)-5-trifluoromethyl-4,5-dihydroisoxazole-3-yl]-N-(2-pyridylmethyl)benzoic acid amide (Compound of the present invention No. 5-341)

In a solution of 0.19 g of 4-[5-(3,5-dichlorophenyl)-5-trifluoromethyl-4,5-dihydroisoxazole-3-yl]-2-iodo-N-(2-pyridylmethyl)benzoic acid amide (Compound of the present invention No. 5-065) synthesized similarly to Synthetic Example 4 in 10 ml of dimethylacetamide, 36.0 mg of zinc cyanide, 4.8 mg of zinc, 11.0 mg of tris(dibenzylideneacetone) dipalladium and 13.5 mg of 1,1'-bis(diphenylphosphino)ferrocene were added, and stirred under nitrogen atmosphere at 80 to 120° C. for 5 hours. After the completion of the reaction, 30 ml of ammonia water and 20 ml of water were added in the reaction mixture, and extracted with ethyl acetate (50 ml×1). The organic phase was washed with 30 ml of water, dehydrated with saturated sodium chloride aqueous solution and dried over anhydrous sodium sulfate, and then the solvent was distilled off under reduced pressure. The residue was purified with silica gel column chromatography that was eluated with ethylacetate-hexane (2:1), and 0.05 g of the aimed product was obtained as brown resinous substance.

$^1$H NMR (CDCl$_3$, Me$_4$Si, 400 MHz) δ 8.5-8.6 (m, 1H), 8.12 (bs, 1H), 7.9-8.0 (m, 2H), 7.15-7.7 (m, 7H), 5.13 (bs, 2H), 4.14 (d, J=17.4 Hz, 1H), 3.78 (d, J=17.4 Hz, 1H).

Synthetic Example 17

2-Acetylamino-4-[5-(3,5-dichlorophenyl)-5-trifluoromethyl-4,5-dihydroisoxazole-3-yl]-N-(2,2,2-trifluoroethyl)benzoic acid amide (Compound of the present invention No. 5-333)

In a solution of 0.05 g of 2-amino-4-[5-(3,5-dichlorophenyl)-5-trifluoromethyl-4,5-dihydroisoxazole-3-yl]-N-(2,2,2-trifluoroethyl)benzoic acid amide (Compound of the present invention No. 5-329) synthesized in Synthetic Example 12 and 0.15 ml of triethylamine in 2 ml of chloroform, 0.10 ml of acetic anhydride was added under cooling with ice with stirring, and stirred at room temperature for 20 hours. After the completion of the reaction, the reaction mixture was subjected to purification with medium-pressure preparative liquid chromatography (Yamazen Corporation, medium pressure preparative system; YFLC-Wprep) that was eluted with ethyl acetate-hexane (1:8 to 1:1 gradient), and 0.045 g of the aimed product was obtained as pale yellow resinous substance.

$^1$H NMR (CDCl$_3$, Me$_4$Si, 400 MHz) 10.90 (bs, 1H), 8.77 (d, J=1.3 Hz, 1H), 7.57 (dd, J=8.4, 1.5 Hz, 1H), 7.53 (d, J=8.4 Hz, 1H), 7.50 (d, J=1.7 Hz, 2H), 7.45 (t, J=1.8 Hz, 1H), 6.82 (bs, 1H), 4.1-4.2 (m, 2H), 4.11 (d, J=17.0 Hz, 1H), 3.73 (d, J=17.0 Hz, 1H), 2.22 (s, 3H).

Synthetic Example 18

4-[5-(3,5-Dichlorophenyl)-5-trifluoromethyl-4,5-dihydroisoxazole-3-yl]-2-methylamino-N-(2,2,2-trifluoroethyl)benzoic acid amide (Compound of the present invention No. 5-331) and 4-[5-(3,5-dichlorophenyl)-5-trifluoromethyl-4,5-dihydroisoxazole-3-yl]-2-dimethylamino-N-(2,2,2-trifluoroethyl)benzoic acid amide (Compound of the present invention No. 5-334)

In a solution of 0.25 g of 2-amino-4-[5-(3,5-dichlorophenyl)-5-trifluoromethyl-4,5-dihydroisoxazole-3-yl]-N-(2,2,2-trifluoroethyl)benzoic acid amide (Compound of the present invention No. 5-329) synthesized in Synthetic Example 12 and 0.06 g of 36% formaldehyde aqueous solution in 7 ml of 1,2-dichloroethane, 1.00 g of sodium triacetoxy borohydride was added with stirring at room temperature in three portions at 1 hour-interval, and continued to stir at the same temperature for further 2 hours. After the completion of the reaction, the reaction mixture was poured to 5 ml of ice water, the organic phase was collected, and the solvent was distilled under reduced pressure. The residue was subjected to purification with medium-pressure preparative liquid chromatography (Yamazen Corporation, medium pressure preparative system; YFLC-Wprep) that was eluted with ethyl acetate-hexane (0:1 to 1:3 gradient), and 0.13 g of 4-[5-(3,5-dichlorophenyl)-5-trifluoromethyl-4,5-dihydroisoxazole-3-yl]-2-methylamino-N-(2,2,2-trifluoroethyl)benzoic acid amide was obtained as pale yellow crystal, and 0.13 g of 4-[5-(3,5-dichlorophenyl)-5-trifluoromethyl-4,5-dihydroisoxazole-3-yl]-2-dimethylamino-N-(2,2,2-trifluoroethyl)benzoic acid amide was obtained as pale yellow resinous substance. 4-[5-(3,5-dichlorophenyl)-5-trifluoromethyl-4,5-dihydroisoxazole-3-yl]-2-methylamino-N-(2,2,2-trifluoroethyl)benzoic acid amide;

Melting point 156.0 to 158.0° C.
$^1$H NMR (CDCl$_3$, Me$_4$Si, 400 MHz) δ 7.57 (bs, 1H), 7.52 (d, J=1.6 Hz, 2H), 7.43 (t, J=1.8 Hz, 1H), 7.38 (d, J=8.2 Hz, 1H), 6.92 (d, J=1.6 Hz, 1H), 6.84 (dd, J=8.2, 1.6 Hz, 1H), 6.31 (t, J=6.4 Hz, 1H), 4.0-4.15 (m, 2H), 4.08 (d, J=17.2 Hz, 1H), 3.70 (d, J=17.2 Hz, 1H), 2.91 (s, 3H).

4-[5-(3,5-dichlorophenyl)-5-trifluoromethyl-4,5-dihydroisoxazole-3-yl]2-dimethylamino-N-(2,2,2-trifluoroethyl)benzoic acid amide;

$^1$H NMR (CDCl$_3$, Me$_4$Si, 400 MHz) δ 10.29 (t, J=6.2 Hz, 1H), 8.22 (d, J=8.1 Hz, 1H), 7.73 (d, J=1.7 Hz, 1H), 7.52 (d, J=1.7 Hz, 2H), 7.44 (t, J=1.8 Hz, 1H), 7.33 (dd, J=8.1, 1.6 Hz, 1H), 4.13 (qd, J=9.2, 6.2 Hz, 2H), 4.10 (d, J=17.2 Hz, 1H), 3.72 (d, J=17.2 Hz, 1H), 2.78 (s, 6H).

Synthetic Example 19

4-[5-(3,5-Dichlorophenyl)-5-trifluoromethyl-4,5-dihydroisoxazole-3-yl]-N-(2-methoxyiminoethyl)-2-methyl benzoic acid amide (Compound of the present invention No. 5-113)

In a solution of 152 mg of 4-[5-(3,5-dichlorophenyl)-5-trifluoromethyl-4,5-dihydroisoxazole-3-yl]-N-(2,2-dimethoxyethyl)-2-methyl benzoic acid amide (Compound of the present invention No. 5-083) synthesized similarly to Synthetic Example 5 in 14 ml of methanol-water (6:1) mixed solvent, 38 mg of methoxyamine hydrochloride was added, and stirred under reflux with heat for 8 hours. After the completion of the reaction, the reaction mixture was left and cooled to room temperature, diluted by adding 80 ml of ethyl acetate, washed with water (30 ml×2), and dehydrated with saturated sodium chloride aqueous solution and dried over anhydrous sodium sulfate, and then the solvent was distilled off under reduced pressure. The residue was purified with silica gel column chromatography that was eluated with ethylacetate-hexane (1:1), and 102 mg of the aimed product was obtained as colorless resinous substance.

$^1$H NMR (CDCl$_3$, Me$_4$Si, 300 MHz) δ 7.45-7.55 (m, 6H), 7.45-7.55 and 6.83 (t, J=4.5 Hz, 1H), 7.4-7.45 (m, 1H), 6.28 and 6.16 (t, J=4.7 Hz, 1H), 4.27 and 4.22 (t, J=4.7 Hz, 2H), 4.08 (d, J=17.1 Hz, 1H), 3.92 and 3.85 (s, 3H), 3.70 (d, J=17.4 Hz, 1H), 2.50 and 2.48 (s, 3H).

Synthetic Example 20

N-[4-[5-(3,5-Dichlorophenyl)-5-trifluoromethyl-4,5-dihydroisoxazole-3-yl]-2-methylbenzoyl]glycine (Compound of the present invention No. 5-127)

In a solution of 2.6 g of methyl N-[4-[5-(3,5-dichlorophenyl)-5-trifluoromethyl-4,5-dihydroisoxazole-3-yl]-2-methylbenzoyl]glycine (Compound of the present invention No. 5-128) synthesized similarly to Synthetic Example 5 in 10 ml of methanol, a solution of 1.0 g of potassium hydroxide in 10 ml of water was added with stirring at room temperature, and stirred at the same temperature for further 1 hour. After the completion of the reaction, 10 ml of 12N hydrochloric acid was added and extracted with ethyl acetate (50 ml×1), the organic phase was dehydrated with saturated sodium chloride aqueous solution and dried over anhydrous sodium sulfate, and then the solvent was distilled off under reduced pressure to obtain 2.4 g of the aimed product as pale yellow resinous resinous substance.

$^1$H NMR (CDCl$_3$, Me$_4$Si, 300 MHz) δ 7.4-7.55 (m, 6H), 6.35-6.85 (m, 2H), 4.23 (d, J=5.7 Hz, 2H), 4.08 (d, J=17.1 Hz, 1H), 3.71 (d, J=17.1 Hz, 1H), 2.44 (s, 3H).

Synthetic Example 21

4-[5-(3,5-Dichlorophenyl)-5-trifluoromethyl-4,5-dihydroisoxazole-3-yl]-2-methyl-N—[N-(2,2,2-trifluoroethyl) carbamoylmethyl]benzoic acid amide (Compound of the present invention No. 5-151)

In a solution of 1.00 g of N-[4-[5-(3,5-dichlorophenyl)-5-trifluoromethyl-4,5-dihydroisoxazole-3-yl]-2-methylbenzoyl]glycine (Compound of the present invention No. 5-127) synthesized in Synthetic Example 20 in 30 ml of dichloromethane, 0.65 g of 1-[3-(diethylamino)propyl]-3-ethylcarbodiimide hydrochloride was added, and stirred at room temperature for 15 minutes, then 0.40 g of 2,2,2-trifluoroethylamine and 0.40 g of 4-(N,N-dimethylamino)pyridine were added and stirred at the same temperature for further 2 hours. After the completion of the reaction, the solvent was distilled off under reduced pressure, the residue was purified with silica gel column chromatography that was eluated with ethyl acetate-hexane (1:3), and then crystallized from hexane to obtain 0.48 g of the aimed product as white crystal.

Melting point 173.5 to 175.5° C.
$^1$H NMR (CDCl$_3$, Me$_4$Si, 300 MHz) δ 7.35-7.55 (m, 7H), 7.03 (t, J=5.1 Hz, 1H), 4.21 (d, J=5.1 Hz, 2H), 4.09 (d, J=17.4 Hz, 1H), 3.85-4.0 (m, 2H), 3.71 (d, J=17.4 Hz, 1H), 2.43 (s, 3H).

Synthetic Example 22

4-[5-(3,5-Dichlorophenyl)-5-trifluoromethyl-4,5-dihydroisoxazole-3-yl]-2-methyl-N-(N-phenylcarbamoylmethyl)benzoic acid amide (Compound of the present invention No. 5-169)

In a solution of 0.40 g of N-[4-[5-(3,5-dichlorophenyl)-5-trifluoromethyl-4,5-dihydroisoxazole-3-yl]-2-methylbenzoyl]glycine (Compound of the present invention No. 5-127) synthesized in Synthetic Example 20 and 0.08 g of pyridine in 10 ml of dichloromethane, 0.12 g of pivaloyl chloride was added, and stirred at room temperature for 2 hours, then 0.50 g of aniline and 3 ml of triethylamine were added and stirred at the same temperature for further 1 hour. After the completion of the reaction, 20 ml of water was added in the reaction mixture and extracted with ethyl acetate (50 ml×1), the organic phase was dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (2:1) to obtain 0.12 g of the aimed product as white crystal.

Melting point 181.0 to 183.0° C.

$^1$H NMR (CDCl$_3$, Me$_4$Si, 300 MHz) δ 8.54 (bs, 1H), 7.5-7.55 (m, 7H), 7.44 (t, J=2.0 Hz, 1H), 7.31 (t, J=8.0 Hz, 2H), 7.1-7.2 (m, 1H), 6.95 (bs, 1H), 4.34 (d, J=5.0 Hz, 2H), 4.19 (d, J=17.2 Hz, 1H), 3.70 (d, J=17.2 Hz, 1H), 2.49 (s, 3H).

Synthetic Example 23

4-[5-(3,5-Dichlorophenyl)-5-trifluoromethyl-4,5-dihydroisoxazole-3-yl]-2-methyl-N-methyl-N-(2-pyridylmethyl)benzoic acid amide (Compound of the present invention No. 6-020)

In a solution of 0.35 g of 4-[5-(3,5-dichlorophenyl)-5-trifluoromethyl-4,5-dihydroisoxazole-3-yl]-2-methyl-N-(2-pyridylmethyl)benzoic acid amide (Compound of the present invention No. 5-234) synthesized similarly to Synthetic Example 5 in 20 ml of N,N-dimethylformamide, 0.04 g of 55% oily sodium hydride was added under cooling with ice with stirring, and stirred at the same temperature for 30 minutes. Then, 0.12 g of methyl iodide was added and thereafter the temperature was raised to room temperature, and continued to stir at the same temperature for further 2 hours. After the completion of the reaction, the reaction mixture was diluted with 80 ml of ethyl acetate, washed with water (50 ml×2), dehydrated with saturated sodium chloride aqueous solution and dried over anhydrous magnesium sulfate, and then the solvent was distilled off under reduced pressure. The residue was purified with high performance liquid chromatography that was eluated with acetonitrile-water (85:15) to obtain 0.25 g of the aimed product as colorless resinous substance.

$^1$H NMR (CDCl$_3$, Me$_4$Si, 300 MHz) δ 8.5-8.6 (m, 1H), 7.6-7.75 (m, 1H), 7.05-7.55 (m, 8H), 4.43 and 4.89 (bs, 2H), 4.06 and 4.09 (d, J=17.4 and 17.1 Hz, 1H), 3.68 and 3.71 (d, J=17.4 and 17.1 Hz, 1H), 2.85 and 3.13 (s, 3H), 2.35 and 2.38 (s, 3H).

Synthetic Example 24

7-[5-(3,5-Dichlorophenyl)-5-trifluoromethyl-4,5-dihydroisoxazole-3-yl]-1-methyl-3-(2-pyridylmethyl)-1,2,3,4-tetrahydroquinazoline-4-one (Compound of the present invention No. 6-071)

In a solution of 0.06 g of 4-[5-(3,5-dichlorophenyl)-5-trifluoromethyl-4,5-dihydroisoxazole-3-yl]-2-methylamino-N-(2-pyridylmethyl)benzoic acid amide (Compound of the present invention No. 5-332) synthesized similarly to Synthetic Example 18 in 5 ml of dichloromethane, 0.03 g of chloromethylether was added, and stirred at the same temperature for 15 hours After the completion of the reaction, the solvent was distilled off under reduced pressure, and the residue was purified with silica gel column chromatography that was eluated with ethyl acetate-hexane (3:1) to obtain 0.04 g of the aimed product as colorless oily substance.

$^1$H NMR (CDCl$_3$, Me$_4$Si, 300 MHz) δ 8.5-8.6 (m, 1H), 8.04 (d, J=7.8 Hz, 1H), 7.6-7.75 (m, 1H), 7.4-7.55 (m, 4H), 7.15-7.3 (m, 1H), 7.10 (bs, 1H), 6.95-7.05 (m, 1H), 4.86 (s, 2H), 4.06 (s, 2H), 4.09 (d, J=17.4 Hz, 1H), 3.70 (d, J=17.4 Hz, 1H), 2.90 (s, 3H).

Synthetic Example 25

4-[5-(3,5-Dichlorophenyl)-5-trifluoromethyl-4,5-dihydroisoxazole-3-yl]-2-methyl-N-(2,2,2-trifluoroethyl)benzoic acid thioamide (Compound of the present invention No. 7-007)

A solution of 0.50 g of 4-[5-(3,5-dichlorophenyl)-5-trifluoromethyl-4,5-dihydroisoxazole-3-yl]-2-methyl-N-(2,2,2-trifluoroethyl)benzoic acid amide (Compound of the present invention No. 5-075) synthesized in Synthetic Example 8 and 0.41 g of Lawesson's Reagent (2,4-bis(4-methoxyphenyl)-1,3,2,4-dithiadiphosphetan-2,4-disulfide) in 15 ml of toluene was stirred under reflux with heat for 20 hours. After the completion of the reaction, the reaction mixture was left and cooled to room temperature, and the reaction mixture was diluted with 60 ml of ethyl acetate, washed with water (50 ml×1), then dehydrated with saturated sodium chloride aqueous solution and dried over anhydrous magnesium sulfate, and then the solvent was distilled off under reduced pressure. The residue was purified with silica gel column chromatography that was eluated with ethyl acetate-hexane (3:1) to obtain 0.40 g of the aimed product as yellow resinous substance.

$^1$H NMR (CDCl$_3$, Me$_4$Si, 300 MHz) δ 7.2-7.5 (m, 7H), 4.55-4.7 (m, 2H), 4.06 (d, J=17.1 Hz, 1H), 3.68 (d, J=17.1 Hz, 1H), 2.38 (s, 3H).

Synthetic Example 26

4-[5-(3-Bromodifluoromethoxyphenyl)-5-trifluoromethyl-4,5-dihydroisoxazole-3-yl]-2-methyl-N-(2,2,2-trifluoroethyl)benzoic acid amide (Compound of the present invention No. 5-014)

Step 1: Production of 3-bromodifluoromethoxy-1-iodobenzene

In a suspension of 0.87 g of 55% oily sodium hydride in 20 ml of N,N-dimethylformamide, a solution of 4.00 g of 3-iodophenol in 10 ml of N,N-dimethylformamide was added dropwise with stirring under ice cooling, after the completion of the addition dropwise, stirred at room temperature for 30 minutes. The reaction mixture was added dropwise in a solution of 11.40 g of dibromodifluoromethane in 20 ml of N,N-dimethylformamide under cooling with ice with stirring, after the completion of the addition dropwise, continued to stir at room temperature for 2 hours. After the completion of the reaction, 50 ml of water was added in the reaction mixture, extracted with ethyl acetate (100 ml×1), the organic phase was washed with water, then dehydrated with saturated sodium chloride aqueous solution and dried over anhydrous magnesium sulfate, and then the solvent was distilled off under reduced pressure. The residue was purified with silica gel column chromatography that was eluated with hexane to obtain 2.10 g of the aimed product as colorless oily substance.

$^1$H NMR (CDCl$_3$, Me$_4$Si, 300 MHz) δ 7.65-7.7 (m, 1H), 7.55-7.65 (m, 1H), 7.2-7.3 (m, 1H), 7.15 (t, J=9.0 Hz, 1H).

Step 2: Production of 3-bromodifluoromethoxy-1-(1-trifluoromethylethenyl)benzene In 10 ml of a solution of 1-trifluoromethylethenyl zinc bromide prepared according to the method described in documents in 1M tetrahydrofuran, 1.0 g of 3-bromodifluoromethoxy-1-iodobenzene and 0.05 g of dichlorobis(triphenylphosphine) palladium (II) were added, and stirred under reflux with heat for 2 hours. After the completion of the reaction, the reaction mixture was poured in 20 ml of diluted hydrochloric acid, extracted with ethyl acetate (50 ml×1). The organic phase was dehydrated with saturated sodium chloride aqueous solution and dried over anhydrous sodium sulfate, and then the solvent was distilled off under reduced pressure. The residue was dissolved in hexane, and high polar impurities were excluded by treating with silica gel to obtain 0.77 g of crude aimed product as colorless oily substance. The resulting product was used as such without purification for the next step.

Step 3: Production of 4-[5-(3-bromodifluoromethoxyphenyl)-5-trifluoromethyl-4,5-dihydroisoxazole-3-yl]-2-methyl-N-(2,2,2-trifluoroethyl)benzoic acid amide In a solution of 0.3 g of 4-chlorohydroxyiminomethyl-2-methyl-N-(2,2,2-trifluoroethyl)benzoic acid amide synthesized similarly to Steps 1 to 3 of Synthetic Example 7 and 0.2 g of crude 3-bromodifluoromethoxy-1-(1-trifluoromethylethenyl)benzene in 10 ml of 1,2-dimethoxyethane, 0.4 g of potassium hydrogen carbonate was added, and stirred at room temperature for 18 hours. After the completion of the reaction, the reaction mixture was poured in 20 ml of water, extracted with ethyl acetate (50 ml×1). The organic phase was dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (1:1) to obtain 0.29 g of the aimed product as colorless glass substance.

$^1$H NMR (CDCl$_3$, Me$_4$Si, 400 MHz) δ 7.5-7.6 (m, 5H), 7.41 (d, J=7.8 Hz, 1H), 7.3-7.5 (m, 1H), 6.16 (t, J=6.6 Hz, 1H), 4.05-4.15 (m, 3H), 3.74 (d, J=17.2 Hz, 1H), 2.45 (s, 3H).

Synthetic Example 27

4-[5-Chlorodifluoromethyl-5-(3,5-dichlorophenyl)-4,5-dihydroisoxazole-3-yl]-2-methyl-N-(2,2,2-trifluoroethyl)benzoic acid amide (Compound of the present invention No. 5-355)

Step 1: Production of 2,3',5'-trichloro-2,2-difluoroacetophenone

In a solution of 5.0 g of 3,5-dichloro-1-iodobenzene in 50 ml of t-butylmethylether, 12.2 ml of n-butyl lithium (1.58M hexane solution) was added dropwise at −78° C. with stirring, after the completion of the addition dropwise, stirred at the same temperature for 30 minutes. 6.6 g of chlorodifluoroacetic acid methyl ester was added dropwise at −78° C. with stirring in the reaction mixture, after the completion of the addition dropwise, continued to stir at 0° C. for further 30 minutes. After the completion of the reaction, the reaction mixture was poured in 100 ml of saturated ammonium chloride aqueous solution, extracted with ethyl acetate (100 ml×1). The organic phase was dehydrated with saturated sodium chloride aqueous solution and dried over anhydrous magnesium sulfate, and then the solvent was distilled off under reduced pressure to obtain 4.6 g of crude aimed product as pale yellow oily substance. The resulting product was used as such without purification for the next step.

$^1$H NMR (CDCl$_3$, Me$_4$Si, 300 MHz) δ 7.97 (s, 2H), 7.68 (s, 1H).

Step 2: Production of 3,5-dichloro-1-[1-(chlorodifluorofluoromethyl)ethenyl]benzene In a solution of 2.89 g of methyltriphenylphosphonium bromide in 15 ml of tetrahydrofuran, 0.91 g of potassium t-butoxide was added, and stirred at room temperature for 1 hour. Then, a solution of 2.00 g of 2,3',5'-trichloro-2,2-difluoroacetophenone in 5 ml of tetrahydrofuran was added dropwise in the reaction mixture under cooling with ice with stirring, after the completion of the addition dropwise, continued to stir at room temperature for 1 hour. After the completion of the reaction, the reaction mixture was poured in 50 ml of ice water, extracted with ethyl acetate (50 ml×1), the organic phase was dehydrated with saturated sodium chloride aqueous solution and dried over anhydrous sodium sulfate, and then the solvent was distilled off under reduced pressure. The residue was purified with silica gel column chromatography that was eluated with hexane to obtain 1.50 g of the aimed product as yellow oily substance.

$^1$H NMR (CDCl$_3$, Me$_4$Si, 300 MHz) δ 7.40 (s, 1H), 7.35 (s, 2H), 5.99 (s, 1H), 5.65 (s, 1H).

Step 3: Production of 4-[5-chlorodifluoromethyl-5-(3,5-dichlorophenyl)-4,5-dihydroisoxazole-3-yl]-2-methyl-N-(2,2,2-trifluoroethyl)benzoic acid amide In a solution of 0.25 g of 4-chlorohydroxyiminomethyl-2-methyl-N-(2,2,2-trifluoroethyl)benzoic acid amide synthesized similarly to Steps 1 to 3 of Synthetic Example 7 and 0.26 g of 3,5-dichloro-1-[1-(chlorodifluorofluoromethyl)ethenyl]benzene in 3 ml of 1,2-dimethoxyethane, 0.43 g of potassium hydrogen carbonate and a small amount of water were added, and stirred at room temperature for 15 hours. After the completion of the reaction, the reaction mixture was filtered and thereby solid substance was excluded, and the filtrate was concentrated under reduced pressure. The residue was purified with silica gel column chromatography that was eluated with ethyl acetate-hexane (2:3) to obtain 0.28 g of the aimed product as yellow oily substance.

$^1$H NMR (CDCl$_3$, Me$_4$Si, 300 MHz) δ 7.35-7.65 (m, 6H), 6.06 (t, J=6.1 Hz, 1H), 4.0-4.25 (m, 3H), 3.72 (d, J=17.1 Hz, 1H), 2.47 (s, 3H).

Synthetic Example 28

4-[5-(3,5-Dichlorophenyl)-5-trifluoromethyl-4,5-dihydroisoxazole-3-yl]-2-methyl-N-methoxycarbonyl-N-(2-pyridylmethyl)benzoic acid amide (Compound of the present invention No. 6-043)

Step 1: Production of 5-(3,5-dichlorophenyl)-3-(3-methyl-4-nitrophenyl)-5-trifluoromethyl-4,5-dihydroisoxazole In a solution of 1.31 g of 3,5-dichloro-1-(1-trifluoromethylethenyl)benzene synthesized in Step 1 of Synthetic Example 3 and 1.17 g of α-chloro-3-methyl-4-nitrobenzaldoxime in 10 ml of tetrahydrofuran, 1.15 g of potassium hydrogen carbonate and 1.50 g of water were added, and stirred at room temperature for 18 hours. After the completion of the reaction, tetrahydrofuran was removed from the reaction mixture, 3 ml of water was added, and stirred under colloing with ice for further 30 minutes. Precipitated crystal was filtered off, washed with 5 ml of water and then 5 ml of diisopropyl ether to obtain 1.29 g of the aimed product as white crystal.

Melting point 135.0 to 136.0° C.

$^1$H NMR (CDCl$_3$, Me$_4$Si, 300 MHz) δ 8.03 (d, J=7.5 Hz, 1H), 7.6-7.75 (m, 2H), 7.51 (bs, 2H), 7.44 (t, J=1.8 Hz, 1H), 4.11 (d, J=17.4 Hz, 1H), 3.73 (d, J=17.4 Hz, 1H), 2.64 (s, 3H).

Step 2: Production of 3-(4-amino-3-methylphenyl)-5-(3,5-dichlorophenyl)-5-trifluoromethyl-4,5-dihydroisoxazole In a solution of 1.23 g of 5-(3,5-dichlorophenyl)-3-(3-methyl-4-nitrophenyl)-5-trifluoromethyl-4,5-dihydroisoxazole in 10 ml of ethyl acetate, 5.0 ml of water, 5.0 ml of acetic acid and 0.66 g of reduced iron were added and stirred at 100° C. for 2 hours. After the completion of the reaction, the reaction mixture was filtered through Celite, 20 ml of water was added in the filtrate, extracted with ethyl acetate (20 ml×2). The organic phases together were washed with 10 ml of saturated sodium hydrogen carbonate aqueous solution, and then with 10 ml of water, thereafter dehydrated with saturated sodium chloride aqueous solution and dried over anhydrous sodium sulfate, and then the solvent was distilled off under reduced pressure to obtain 1.05 g of crude aimed product as red-brown oily substance. The resulting product was used as such without purification for the next step.

$^1$H NMR (CDCl$_3$, Me$_4$Si, 300 MHz) δ 7.52 (s, 2H), 7.35-7.5 (m, 2H), 7.31 (dd, J=8.0, 2.0 Hz, 1H), 6.65 (d, J=8.4 Hz, 1H), 4.05 (d, J=17.1 Hz, 1H), 3.93 (bs, 2H), 3.64 (d, J=17.1 Hz, 1H), 2.17 (s, 3H).

Step 3: Production of 3-(4-bromo-3-methylphenyl)-5-(3,5-dichlorophenyl)-5-trifluoromethyl-4,5-dihydroisoxazole In a solution of 0.50 g of 3-(4-amino-3-methylphenyl)-5-(3,5-dichlorophenyl)-5-trifluoromethyl-4,5-dihydroisoxazole in 1.0 ml of 1,4-dioxane and 2.0 ml of water, 1.0 ml of 47% hydrobromic acid was added, and stirred under reflux with heat for 1 hour. Then, the reaction mixture was cooled with ice, and a solution of 0.10 g of sodium nitrite in 1.0 ml of water was slowly added dropwise with stirring at a temperature of 5° C. or less, after the completion of the addition dropwise, continued to stir at the same temperature for further 1 hour. The diazo mixture was slowly added dropwise in a mixture of 1.0 ml of 47% hydrobromic acid and 0.28 g of copper (I) bromide at 60° C. with stirring, after the completion of the addition dropwise, continued to stir at 60° C. for further 2 hours. After the completion of the reaction, 10 ml of water was added in the reaction mixture, extracted with ethyl acetate (20 ml×2), the organic phases together were washed with water, then dehydrated with saturated sodium chloride aqueous solution and dried over anhydrous sodium sulfate, and then the solvent was distilled off under reduced pressure. The residue was purified with silica gel column chromatography that was eluated with ethyl acetate-hexane (1:10) to obtain 0.43 g of the aimed product as pale yellow crystal.

Melting point 105.0 to 108.0° C.

$^1$H NMR (CDCl$_3$, Me$_4$Si, 300 MHz) δ 7.59 (d, J=8.4 Hz, 1H), 7.45-7.55 (m, 3H), 7.42 (t, J=1.8 Hz, 1H), 7.33 (dd, J=8.4, 2.1 Hz, 1H), 4.07 (d, J=17.1 Hz, 1H), 3.68 (d, J=17.1 Hz, 1H), 2.43 (s, 3H).

Step 4: Production of 4-[5-(3,5-dichlorophenyl)-5-trifluoromethyl-4,5-dihydroisoxazole-3-yl]-2-methylbenzoic acid ethyl ester In a solution of 15.0 g of 3-(4-bromo-3-methylphenyl)-5-(3,5-dichlorophenyl)-5-trifluoromethyl-4,5-dihydroisoxazole in 60 ml of ethanol in an autoclave, 3.26 g of sodium acetate, 0.37 g of 1,1'-bis(diphenylphosphino) ferrocene and 0.08 g of palladium (II) acetate were added, and stirred under 2.0 MPa carbon monoxide atmosphere at 110° C. for 3 hours. After the completion of the reaction, the reaction mixture was left and cooled to room temperature, 200 ml of water was added and extracted with ethyl acetate (200 ml×2), the organic phase was washed with water, dehydrated with saturated sodium chloride aqueous solution and dried over anhydrous sodium sulfate and the solvent was distilled off under reduced pressure. The residue was purified with silica gel column chromatography that was eluted with ethyl acetate-hexane (1:8) to obtain 10.8 g of the aimed product as colorless clear liquid. Refractive index $n_D^{21.4°\ C.}$=1.5474

$^1$H NMR (CDCl$_3$, Me$_4$Si, 300 MHz) δ 7.95 (d, J=8.4 Hz, 1H), 7.45-7.65 (m, 4H), 7.43 (t, J=1.8 Hz, 1H), 4.37 (q, J=7.2 Hz, 2H), 4.10 (d, J=17.4 Hz, 1H), 3.71 (d, J=17.1 Hz, 1H), 2.62 (s, 3H), 1.40 (t, J=7.2 Hz, 3H).

Step 5: Production of 4-[5-(3,5-dichlorophenyl)-5-trifluoromethyl-4,5-dihydroisoxazole-3-yl]-2-methyl benzoic acid In a solution of 10.79 g of 4-[5-(3,5-dichlorophenyl)-5-trifluoromethyl-4,5-dihydroisoxazole-3-yl]-2-methylbenzoic acid ethyl ester in 50 ml of ethanol and 10 ml of water, a solution of 2.0 g of sodium hydroxide in 10 ml of water was slowly added with stirring at room temperature. Then, the reaction mixture was stirred at 80° C. for 2 hours, after the completion of the reaction, ethanol was distilled off under reduced pressure. The residue was adjusted to pH 1-2 with concentrated hydrochloric acid with stirring at 50° C., then continued to stir at the same temperature for 1 hour and then at 5° C. for 1 hour. Precipitated crystal was filtered off, washed with water and dried to obtain 9.36 g of the aimed product as white crystal.

Melting point 146.0 to 148.5° C.

$^1$H NMR (CDCl$_3$, Me$_4$Si, 300 MHz) δ 8.12 (d, J=8.7 Hz, 1H), 7.5-7.7 (m, 2H), 7.52 (d, J=1.5 Hz, 2H), 7.43 (d, J=1.5 Hz, 1H), 4.11 (d, J=16.8 Hz, 1H), 3.73 (d, J=17.4 Hz, 1H), 2.69 (s, 3H).

Step 6: Production of 4-[5-(3,5-dichlorophenyl)-5-trifluoromethyl-4,5-dihydroisoxazole-3-yl]-2-methyl-N-methoxycarbonyl-N-(2-pyridylmethyl)benzoic acid amide In a solution of 1.00 g of 4-[5-(3,5-dichlorophenyl)-5-trifluoromethyl-4,5-dihydroisoxazole-3-yl]-2-methyl benzoic acid in 30 ml of toluene, 0.43 g of thionyl chloride and 3 drops of N,N-dimethylformamide were added, and stirred at 90° C. for 1 hour. After the completion of the reaction, the solvent was distilled off under reduced pressure, and the residue was dissolved in 5 ml of tetrahydrofuran. In a solution of 0.40 g of N-(2-pyridylmethyl) carbamic acid methyl ester in 5 ml of tetrahydrofuran, 0.27 g of t-butoxy potassium was added at room temperature with stirring, and stirred at the same temperature for 3 minutes. Then, the above-mentioned solution of acid chloride in tetrahydrofuran was added dropwise in the reaction mixture, after the completion of the addition dropwise, continued to stir at the same temperature for further 1 hour. After the completion of the reaction, the reaction mixture was diluted with 60 ml of ethyl acetate, washed with 50 ml of water, then dehydrated with saturated sodium chloride aqueous solution and dried over anhydrous sodium sulfate and the solvent was distilled off under reduced pressure. The residue was purified with silica gel column chromatography that was eluted with ethyl acetate-hexane (1:2 to 1:1) to obtain 0.75 g of the aimed product as yellow resinous substance.

$^1$H NMR (CDCl$_3$, Me$_4$Si, 300 MHz) δ 8.56 (d, J=4.8 Hz, 1H), 7.65-7.7 (m, 1H), 7.5-7.55 (m, 4H), 7.35-7.45 (m, 2H), 7.15-7.3 (m, 2H), 5.21 (s, 2H), 4.09 (d, J=17.4 Hz, 1H), 3.70 (d, J=17.4 Hz, 1H), 3.58 (s, 3H), 2.40 (s, 3H).

Synthetic Example 29

4-[5-(3,5-Dichlorophenyl)-5-trifluoromethyl-4,5-dihydroisoxazole-3-yl]-2-methylbenzoic acid amide (Compound of the present invention No. 5-066)

Step 1: Production of 4-bromo-α-chloro-3-methylbenzaldoxime

In a solution of 82.0 g of 4-bromo-3-methylbenzaldoxime in 450 ml of tetrahydrofuran, 120.0 g of concentrated hydrochloric acid was added a dropwise with stirring under ice cooling over 45 minutes. Then, 220 ml of 8% sodium hypochlorite aqueous solution was carefully added dropwise over 75 minutes so that the temperature of the reaction mixture would not exceed 5° C., after the completion of the addition, continued to stir at 10° C. or less further for 90 minutes. After the completion of the reaction, nitrogen gas was blown through the reaction mixture for 45 minutes and precipitated insoluble material was filtered off, and tetrahydrofuran was distilled off under reduced pressure. The remaining aqueous solution was extracted with 240.0 g of ethyl acetate. The organic phase was washed with water (240 ml×2) and then insoluble material was filtered off, the solvent was distilled off under reduced pressure to obtain 93.5 g of the aimed product as pale yellow crystal.

Melting point 77.0 to 78.0° C.

$^1$H NMR (CDCl$_3$, Me$_4$Si, 400 MHz) δ 8.00 (bs, 1H), 7.71 (d, J=2.2 Hz, 1H), 7.57 (d, J=8.4 Hz, 1H), 7.51 (dd, J=8.4, 2.2 Hz, 1H), 2.44 (s, 3H).

Step 2: Production of 3-(4-bromo-3-methylphenyl)-5-(3,5-dichlorophenyl)-5-trifluoromethyl-4,5-dihydroisoxazole In a solution of 22.7 g of 3,5-dichloro-1-(1-trifluoromethylethenyl)benzene produced in Step 1 of Synthetic Example 3 and 26.0 g of 4-bromo-α-chloro-3-methylbenzaldoxime in 120 ml of tetrahydrofuran, 15.7 g of potassium hydrogen carbonate was added, and stirred under reflux with heat for 5 hours. After the completion of the reaction, the reaction mixture was left and cooled to room temperature, insoluble material was filtered off, then the solvent was distilled off under reduced pressure. 150 ml of water was added in the residue, stirred at room temperature for 18 hours, and precipitated crystal was filtered off and dried to obtain 38.6 g of the aimed product as white crystal.

Melting point 105.0 to 108.0° C.

$^1$H NMR (CDCl$_3$, Me$_4$Si, 300 MHz) δ 7.59 (d, J=8.4 Hz, 1H), 7.45-7.55 (m, 3H), 7.42 (t, J=1.8 Hz, 1H), 7.33 (dd, J=8.4, 2.1 Hz, 1H), 4.07 (d, J=17.1 Hz, 1H), 3.68 (d, J=17.1 Hz, 1H), 2.43 (s, 3H).

Step 3: Production of 4-[5-(3,5-dichlorophenyl)-5-trifluoromethyl-4,5-dihydroisoxazole-3-yl]-2-methylbenzoyl chloride In a solution of 18.1 g of 3-(4-bromo-3-methylphenyl)-5-(3,5-dichlorophenyl)-5-trifluoromethyl-4,5-dihydroisoxazole and 3.94 g of sodium acetate in 42 ml of 1,2-dimethoxyethane and 42 ml of water in an autoclave, 0.42 g of triphenylphosphine and 0.09 g of palladium (II) acetate were added, and stirred under 1.5 MPa carbon monoxide atmosphere at 110° C. for 7 hours. After the completion of the reaction, the reaction mixture was left and cooled to room temperature, the solid was filtered off, then added in 100 ml of ethyl acetate. The organic phase was washed with 1% sodium hydrogen carbonate aqueous solution (70 ml×2), then with 1N hydrochloric acid (55 ml×2), dried with saturated sodium chloride aqueous solution and then the solvent was displaced by toluene. 2 drops of N,N-dimethylformamide was added in the resulting toluene solution, and 6.0 g of thionyl chloride was added dropwise with stirring at 80° C., and continued to stir at the same temperature further for 1.5 hour. After the completion of the reaction, insoluble material was filtered off, the solvent was distilled off under reduced pressure until the volume of the solvent was reduced to about one-third. Then, 50 ml of hexane was gradually added dropwise with stirring at 60° C., after the completion of the addition, left and cooled to room temperature with stirring, and continued to stir at room temperature further for 1 hour. Precipitated crystal was filtered off and dried to obtain 13.4 g of the aimed product as white crystal.

Melting point 140.5 to 143.0° C.

$^1$H NMR (CDCl$_3$, Me$_4$Si, 300 MHz) δ 8.25 (d, J=8.7 Hz, 1H), 7.64 (d, J=8.7 Hz, 1H), 7.59 (s, 1H), 7.51 (s, 2H), 7.43 (s, 1H), 4.11 (d, J=17.4 Hz, 1H), 3.73 (d, J=17.4 Hz, 1H), 2.60 (s, 3H).

Step 4: Production of 4-[5-(3,5-dichlorophenyl)-5-trifluoromethyl-4,5-dihydroisoxazole-3-yl]-2-methylbenzoic acid amide In a mixture of 3.0 g of concentrated ammonia water and 15 ml of tetrahydrofuran, a solution of 3.0 g of 4-[5-(3,5-dichlorophenyl)-5-trifluoromethyl-4,5-dihydroisoxazole-3-yl]-2-methylbenzoyl chloride in 20 ml of tetrahydrofuran was added dropwise, after the completion of the addition, continued to stir further for 18 hours. After the completion of the reaction, the solvent was distilled off under reduced pressure, the residue was dissolved in 50 ml of ethyl acetate, washed with 50 ml of water, dehydrated and dried with saturated sodium chloride aqueous solution and anhydrous sodium sulfate in that order, and the solvent was distilled off under reduced pressure to obtain 2.9 g of the aimed product as orange crystal.

Melting point 162.5 to 164.0° C.

$^1$H NMR (CDCl$_3$, Me$_4$Si, 400 MHz) δ 7.45-7.55 (m, 6H), 6.40 (bs, 1H), 6.00 (bs, 1H), 4.09 (d, J=17.0 Hz, 1H), 3.71 (d, J=17.0 Hz, 1H), 2.49 (s, 3H).

Synthetic Example 30

4-[5-(3,5-Dichlorophenyl)-5-trifluoromethyl-4,5-dihydroisoxazole-3-yl]-2-methyl-N-(2,2,2-trifluoroethoxymethyl)benzoic acid amide (Compound of the present invention No. 5-480)

Step 1: Production of 4-[5-(3,5-dichlorophenyl)-5-trifluoromethyl-4,5-dihydroisoxazole-3-yl]-2-methyl-N-hydroxymethyl)benzoic acid amide In a solution of 7.00 g of 4-[5-(3,5-dichlorophenyl)-5-trifluoromethyl-4,5-dihydroisoxazole-3-yl]-2-methylbenzoic acid amide synthesized in Synthetic Example 29 in 70 ml of 1,4-dioxane, 1.82 g of 37% formalin aqueous solution, 7.00 g of potassium carbonate and 15 ml of water were added, stirred at the same temperature for 3 hours. After the completion of the reaction, the reaction mixture was diluted by adding 200 ml of ethyl acetate, washed with water (50 ml×1) and then dehydrated and dried with saturated sodium chloride aqueous solution and anhydrous magnesium sulfate in that order, and filtered through silica gel, the solvent was distilled off under reduced pressure to obtain 7.00 g of crude aimed product as white crystal.

Melting point 69.0 to 73.0° C.

Step 2: Production of 4-[5-(3,5-dichlorophenyl)-5-trifluoromethyl-4,5-dihydroisoxazole-3-yl]-2-methyl-N-(2,2,2-trifluoroethoxymethyl)benzoic acid amide In a solution of 1.70 g of 4-[5-(3,5-dichlorophenyl)-5-trifluoromethyl-4,5-dihydroisoxazole-3-yl]-2-methyl-N-(hydroxymethyl)benzoic acid amide in 20 ml of dichloromethane, 0.68 g of thionyl chloride was added with stirring at room temperature, stirred at the same temperature for 2 hours, then the solvent was distilled off under reduced pressure, and the residue was dissolved in 10 ml of tetrahydrofuran. In 0.33 g of 60% oily sodium hydride suspended in 30 ml of tetrahydrofuran, 1.50 g of 2,2,2-trifluoroethanol was added dropwise with stirring under ice cooling, and stirred at the same temperature for 10 minutes. Then, the solution of benzoic acid chloride in tetrahydrofuran prepared above was added dropwise in the reaction mixture with stirring under ice cooling, after the completion of the addition, continued to stir at room temperature for 1 hour. After the completion of the reaction, 50 ml of water was added in the reaction mixture, extracted with ethyl acetate (70 ml×1), and the organic phase was dehydrated and dried with saturated sodium chloride aqueous solution and anhydrous magnesium sulfate in that order, and then the solvent was distilled off under reduced pressure. The residue was purified with silica gel column chromatography that was eluated with ethyl acetate-hexane (2:3) to obtain 1.20 g of the aimed product as colorless resinous substance.

$^1$H NMR (CDCl$_3$, Me$_4$Si, 400 MHz) δ 7.5-7.55 (m, 4H), 7.4-7.5 (m, 2H), 6.64 (t, J=6.4 Hz, 1H), 5.02 (d, J=7.2 Hz, 2H), 4.05-4.15 (m, 3H), 3.70 (d, J=17.4 Hz, 1H), 2.49 (s, 3H).

Synthetic Example 31

N-Carbamoylmethyl-4-[5-(3,5-dichlorophenyl)-5-trifluoromethyl-4,5-dihydroisoxazole-3-yl]-2-methyl benzoic acid amide (Compound of the present invention No. 5-137)

In a solution of 0.37 g of glycine amide hydrochloride and 0.71 g of pyridine in 20 ml of dichloromethane, a solution of 1.31 g of 4-[5-(3,5-dichlorophenyl)-5-trifluoromethyl-4,5-dihydroisoxazole-3-yl]-2-methylbenzoyl chloride synthesized in Step 3 of Synthetic Example 29 in 10 ml of dichloromethane was added dropwise with stirring under ice cooling, after the completion of the addition, stirred at room temperature for 3 hours, then 3.00 g of triethyl amine was added in the reaction mixture, and continued to stir at the same temperature further for 30 minutes. After the completion of the reaction, the solvent was distilled off under reduced pressure, 50 ml of ethyl acetate and 50 ml of water were added in the residue, and the organic phase was collected, and the aqueous phase was further extracted with ethyl acetate (50 ml×2). The organic phases together were dehydrated and dried with saturated sodium chloride aqueous solution and anhydrous sodium sulfate in that order, and the solvent was distilled off under reduced pressure, the residual solid was washed with hexane to obtain 1.24 g of the aimed product as white crystal.

Melting point 87.0 to 91.0° C.

$^1$H NMR (CDCl$_3$, Me$_4$Si, 300 MHz) δ 7.4-7.55 (m, 6H), 7.15-7.25 (m, 1H), 6.86 (s, 1H), 5.88 (s, 1H), 4.12 (d, J=5.1 Hz, 2H), 4.11 (d, J=17.4 Hz, 1H), 3.74 (d, J=17.4 Hz, 1H), 2.49 (s, 3H).

Synthetic Example 32

N-Aminomethyl-4-[5-(3,5-dichlorophenyl)-5-trifluoromethyl-4,5-dihydroisoxazole-3-yl]-2-methyl benzoic acid amide hydrochloride (Compound of the present invention No. 5-507)

In a solution of 0.47 g of [bis(trifluoroacetoxy)iodo]benzene in 12 ml of acetonitrile-water (1:1), a solution of 0.47 g of N-carbamoylmethyl-4-[5-(3,5-dichlorophenyl)-5-trifluoromethyl-4,5-dihydroisoxazole-3-yl]-2-methyl benzoic acid amide synthesized in Synthetic Example 31 was added with stirring at room temperature, and stirred at room temperature for 5 hours. After the completion of the reaction, 75 ml of water was added in the reaction mixture, 8 ml of concentrated hydrochloric acid was added, then washed with 100 ml of diethyl ether, and the organic phase was subjected to back extraction with 2N hydrochloric acid aqueous solution (20 ml×2). The aqueous phase was combined with the organic phase, water was distilled off, and the residual solid was washed with ethyl acetate to obtain 0.21 g of the aimed product as white crystal.

Melting point 155.0 to 157.0° C.

$^1$H NMR (CDCl$_3$, Me$_4$Si, 300 MHz) δ 9.0-9.1 (m, 1H), 7.4-7.7 (m, 8H), 4.64 (d, J=5.7 Hz, 2H), 4.16 (d, J=17.4 Hz, 1H), 3.80 (d, J=17.4 Hz, 1H), 2.50 (s, 3H).

Synthetic Example 33

N-[4-[5-(3,5-Dichlorophenyl)-5-trifluoromethyl-4,5-dihydroisoxazole-3-yl]-2-methyl benzoylaminomethyl]carbamic acid methyl ester (Compound of the present invention No. 5-515)

In a suspended solution of 0.13 g of N-aminomethyl-4-[5-(3,5-dichlorophenyl)-5-trifluoromethyl-4,5-dihydroisoxazole-3-yl]-2-methyl benzoic acid amide hydrochloride synthesized in Synthetic Example 32 in 4 ml of dichloromethane, 0.03 g of methyl chloroformate and 0.08 g of triethyl amine were added with stirring at room temperature, and stirred at room temperature for 3 hours. After the completion of the reaction, the solvent was distilled under reduced pressure, the residue was purified with silica gel column chromatography that was eluated with ethyl acetate-hexane (1:1) to obtain 0.06 g of the aimed product as colorless resinous substance.

$^1$H NMR (CDCl$_3$, Me$_4$Si, 300 MHz) δ 7.35-7.55 (m, 6H), 7.17 (bs, 1H), 6.12 (bs, 1H), 4.73 (t, J=6.6 Hz, 2H), 4.09 (d, J=17.4 Hz, 1H), 3.71 (d, J=17.4 Hz, 1H), 3.68 (s, 3H), 2.42 (s, 3H).

Synthetic Example 34

N-[4-[5-(3,5-Dichlorophenyl)-5-trifluoromethyl-4,5-dihydroisoxazole-3-yl]-2-methyl-N-(2-tetrahydrofuranyl)benzoic acid amide (Compound of the present invention No. 5-494)

In a solution of 1.25 g of N-[4-[5-(3,5-dichlorophenyl)-5-trifluoromethyl-4,5-dihydroisoxazole-3-yl]-2-methyl benzoic acid amide synthesized in Synthetic Example 29 and 0.32 g of 2,3-dihydrofuran in 30 ml of dichloromethane, 0.01 g of p-toluene sulfonic acid monohydrate was added with stirring at room temperature, and stirred at room temperature for 3 days. After the completion of the reaction, 30 ml of saturated sodium hydrogen carbonate aqueous solution was added in the reaction mixture, and extracted with ethyl acetate (30 ml×2), the organic phase was dehydrated and dried with saturated sodium chloride aqueous solution and anhydrous sodium sulfate in that order, and the solvent was distilled under reduced pressure. The residue was purified with silica gel column chromatography that was eluated with ethyl acetate-hexane (1:1) to obtain 1.18 g of the aimed product as colorless resinous substance.

Melting point 144.0 to 147.0° C.

$^1$H NMR (CDCl$_3$, Me$_4$Si, 300 MHz) δ 7.3-7.55 (m, 6H), 6.49 (d, J=8.1 Hz, 1H), 5.8-5.9 (m, 1H), 4.09 (d, J=17.1 Hz, 1H), 3.8-4.0 (m, 2H), 3.72 (d, J=17.1 Hz, 1H), 2.42 (s, 3H), 2.2-2.4 (m, 1H), 1.8-2.1 (m, 3H).

Synthetic Example 35

4-[5-(3,5-Dichlorophenyl)-5-trifluoromethyl-4,5-dihydroisoxazole-3-yl]-2-methyl-N-methyl-N-(2-tetrahydrothienyl)benzoic acid amide (Compound of the present invention No. 6-133)

In a solution of 0.43 g of 4-[5-(3,5-dichlorophenyl)-5-trifluoromethyl-4,5-dihydroisoxazole-3-yl]-2-methyl-N-methyl benzoic acid amide synthesized similarly to Synthetic Example 29 and 0.20 g of triethylamine in 5 ml of toluene, 0.45 g of trimethyl silyl trifurate was added and stirred vigorously. 10 minutes after the stirring, the reaction mixture was cooled to 0° C., 0.10 g of tetrahydrothiophene-1-oxide and 0.06 g of zinc iodide were added with stirring, and continued to stir at room temperature further for 4 days. After the completion of the reaction, 10 ml of ice water was added in the reaction mixture, and extracted with ethyl acetate (20 ml×2), the organic phase was dehydrated and dried with saturated sodium chloride aqueous solution and anhydrous sodium sulfate in that order, and the solvent was distilled under reduced pressure. The residue was purified with silica gel column chromatography that was eluated with ethyl acetate-hexane (1:2) to obtain 0.09 g of the aimed product as white crystal.

Melting point 146.0 to 151.0° C.

$^1$H NMR (CDCl$_3$, Me$_4$Si, 300 MHz) δ 7.4-7.7 (m, 5H), 7.15-7.25 (m, 1H), 6.65-6.75 and 5.3-5.4 (m, 1H), 4.09 (d, J=17.1 Hz, 1H), 3.71 (d, J=17.1 Hz, 1H), 3.12 and 2.77 (s, 3H), 2.85-3.15 (m, 2H), 2.33 and 2.30 (s, 3H), 1.7-2.3 (m, 4H).

Synthetic Example 36

4-[5-(3,5-Dichlorophenyl)-5-trifluoromethyl-4,5-dihydroisoxazole-3-yl]-N-ethenyl-2-methylbenzoic acid amide (Compound of the present invention No. 5-660)

In a solution of 0.50 g of 4-[5-(3,5-dichlorophenyl)-5-trifluoromethyl-4,5-dihydroisoxazole-3-yl]-2-methyl-2-methyl benzoic acid amide synthesized in Synthetic Example 29, 0.865 g of ethyl vinyl ether and 0.022 g of 1,10-phenanthroline in 10 ml of 1,2-dimethoxyethane, 0.04 g of bis(trifluoroacetoxy)palladium (II) was added and stirred at room temperature for 19 hours. After the completion of the reaction, 30 ml of water was added in the reaction mixture, and extracted with ethyl acetate (40 ml×1), the organic phase was dehydrated and dried with saturated sodium chloride aqueous solution and anhydrous sodium sulfate in that order, then filtered through silica gel, and the solvent was distilled under reduced pressure to obtain 0.45 g of the aimed product as pale yellow resinous substance.

$^1$H NMR (CDCl$_3$, Me$_4$Si, 300 MHz) δ 7.3-7.6 (m, 7H), 7.05-7.25 (m, 1H), 4.75 (d, J=15.6 Hz, 1H), 4.57 (d, J=8.8 Hz, 1H), 4.09 (d, J=17.4 Hz, 1H), 3.70 (d, J=17.1 Hz, 1H), 2.50 (s, 3H).

Synthetic Example 37

4-[5-(3,5-Dichlorophenyl)-5-trifluoromethyl-4,5-dihydroisoxazole-3-yl]-2-methylbenzhydroxamic acid N-(2,2,2-trifluoroethyl) carbamic acid anhydride (Compound of the present invention No. 5-663)

In a solution of 0.30 g of hydroxylamine hydrochloride in 10 ml of methanol, a solution of 0.65 g of potassium hydroxide in 5 ml of methanol was added, then a solution of 1.00 g of 4-[5-(3,5-dichlorophenyl)-5-trifluoromethyl-4,5-dihydroisoxazole-3-yl]-2-methylbenzoic acid methyl ester synthesized similarly to Steps 1 to 4 of Synthetic Example 28 in 10 ml of methanol was added, and stirred at 40° C. for 1 hour. After the completion of the reaction, the solvent was distilled off under reduced pressure, 10 ml of acetic acid aqueous solution (1:1) was added in the residue, and extracted with ethyl acetate (20 ml×2), the organic phase was dehydrated and dried with saturated sodium chloride aqueous solution and anhydrous sodium sulfate in that order, and the solvent was distilled under reduced pressure. Toluene was added in the residue and the remaining acetic acid was distilled off azeotropically to obtain 1.01 g of crude 4-[5-(3,5-dichlorophenyl)-5-trifluoromethyl-4,5-dihydroisoxazole-3-yl]-2-methylbenzhydroxamic acid as white crystal.

In a solution of 0.16 g of carbonyl diimidazole in 2 ml of tetrahydrofuran, 0.10 g of 2,2,2-trifluoroethylamine was added, and stirred at room temperature for 1 hour. Then, a solution of 0.10 g of 4-[5-(3,5-dichlorophenyl)-5-trifluoromethyl-4,5-dihydroisoxazole-3-yl]-2-methylbenzhydroxamic acid in 2 ml of tetrahydrofuran was added in the reaction mixture, and continued to stir at room temperature further for 1 hour. After the completion of the reaction, the solvent was distilled off under reduced pressure, 10 ml of water was added in the residue, and extracted with ethyl acetate (10 ml×1). The organic phase was washed with 5 ml of 2N hydrochloric acid aqueous solution, dehydrated and dried with saturated sodium chloride aqueous solution and anhydrous sodium sulfate in that order, and the solvent was distilled under reduced pressure. The residue was purified with silica gel thin-layer chromatography (Kanto Chemical Co., Ltd.: PLC plates silica gel 60 F254 20×20 cm layer thickness 2 mm) that was developed with ethyl acetate-hexane (1:1) to obtain 0.12 g of the aimed product as white crystal.

Melting point 111.0 to 114.0° C.

$^1$H NMR (CDCl$_3$, Me$_4$Si, 300 MHz) δ 9.08 (bs, 1H), 7.4-7.6 (m, 6H), 6.07 (bs, 1H), 4.08 (d, J=17.4 Hz, 1H), 3.8-3.95 (m, 2H), 3.70 (d, J=17.4 Hz, 1H), 2.56 (s, 3H).

The compounds of the present invention can be produced according to the above-mentioned production methods and working examples. The examples of the compounds produced similarly to Synthetic Examples 1 to 37 are shown in Tables 7 to 20 to which the present invention is not limited. In the meantime, in Tables, the indication "Et" means ethyl, hereinafter similarly thereto, "n-Pr" and "Pr-n" mean normal propyl, "i-Pr" and "Pr-i" mean isopropyl, "c-Pr" and "Pr-c"

mean cyclopropyl, "n-Bu" and "Bu-n" mean normal butyl, "s-Bu" and "Bu-s" mean secondary butyl, "i-Bu" and "Bu-i" mean isobutyl, "t-Bu" and "Bu-t" mean tertiary butyl, "c-Bu" and "Bu-c" mean cyclobutyl, "n-Pen" and "Pen-n" means normal pentyl, c-Pen" and "Pen-c" mean cyclopentyl, "n-Hex" and "Hex-n" mean normal hexyl, "c-Hex" and "Hex-c" mean cyclohexyl, "Ph" means phenyl, "TMS" means trimethylsilyl, "·Q1" means hydrochloride, "·Q2" means p-toluenesulfonate, "·Q3" means fumarate, "·Q4" means maleate, "·Q5" means triethylamine salt, and in Tables, aromatic heterocyclic rings of D-1a to D-54b are the following structures, respectively.

D-1a: 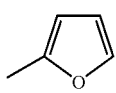

D-1c: 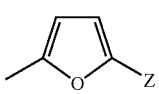

D-2a: 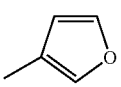

D-3a: 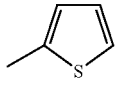

D-3b: 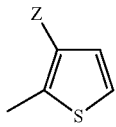

D-3d: 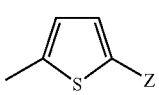

D-5a: 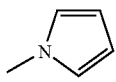

D-6a: 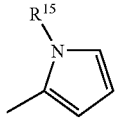

D-8a: 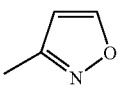

D-8b: 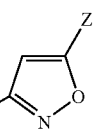

-continued

D-10b: 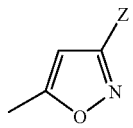

D-11a: 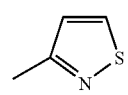

D-11b: 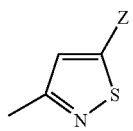

D-11c: 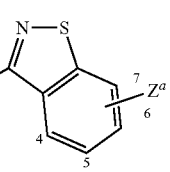

D-13b: 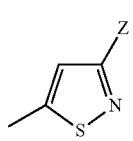

D-14a: 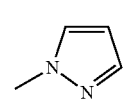

D-14b: 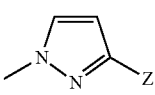

D-14c: 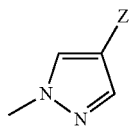

D-15a: 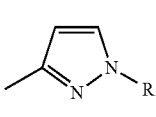

D-16b: 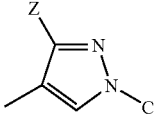

D-16c: 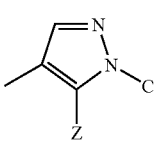

-continued
D-16d: 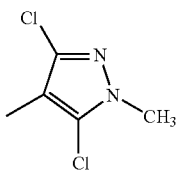
D-17a: 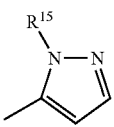
D-17b: 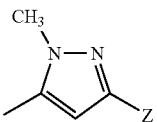
D-21a: 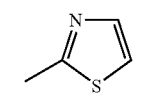
D-21b: 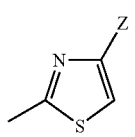
D-21c: 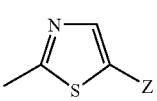
D-21d: 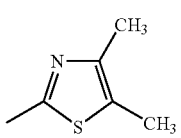
D-21e: 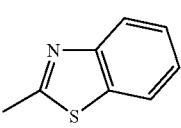
D-21f: 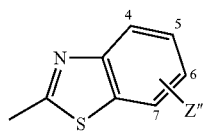
D-22a: 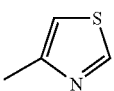
D-22b: 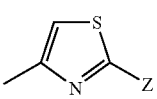
-continued
D-23a: 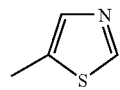
D-23b: 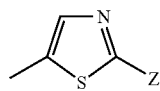
D-24a: 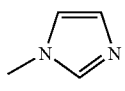
D-24b: 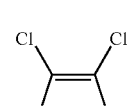
D-24c: 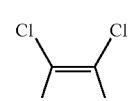
D-25a: 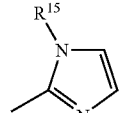
D-25c: 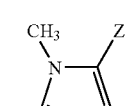
D-25d: 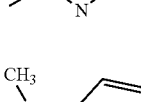
D-26a: 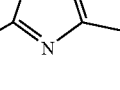
D-27a: 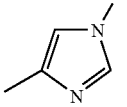
D-28a: 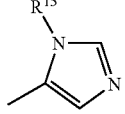

-continued

D-29b:

D-30a:

D-31a:

D-34a:

D-34b:

D-35a:

D-35b:

D-37a:

D-38a:

D-39c:

D-41a:

D-42a:

-continued

D-61b:

D-47a:

D-47b:

D-47c:

D-47d:

D-47e:

D-47f:

D-47h:

D-47i:

D-48a:

D-48e:

D-49a: 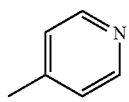
D-49b: 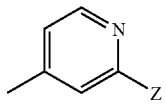
D-49c: 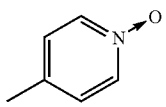
D-50a: 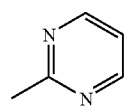
D-50b: 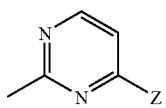
D-50c: 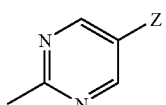
D-50d: 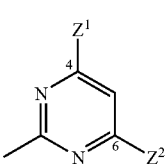
D-51a: 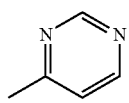
D-51b: 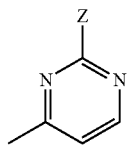
D-51c: 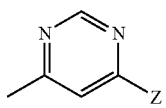
D-52a: 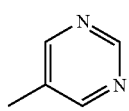
D-52b: 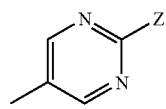
D-53a: 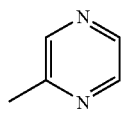
D-53b: 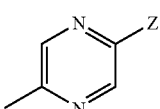
D-54b: 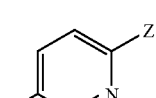
in Tables, saturated heterocyclic rings of E-4a to E-43a are the following structures, respectively.
E-4a: 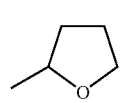
E-5a: 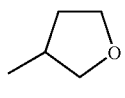
E-5b: 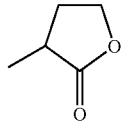
E-5d: 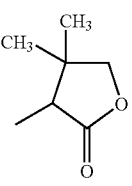
E-7e: 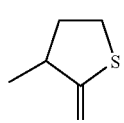
E-9b: 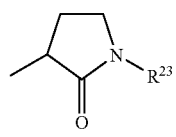

E-10a: 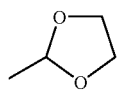
E-10b: 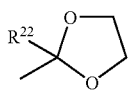
E-11c: 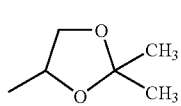
E-17a: 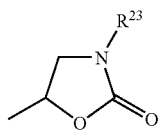
E-18a: 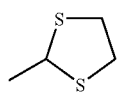
E-18c: 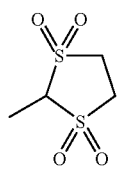
E-23a: 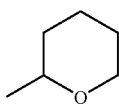
E-23b: 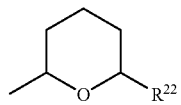
E-32a: 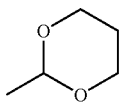
E-43a: 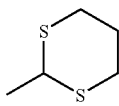
In Tables, partially saturated heterocyclic ring of M-5a is the following structure
M-5a: 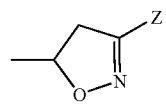
In Tables, T-4 to T-51 are the following structures, respectively
T-4: 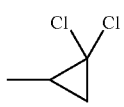
T-9: 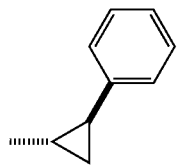
T-13: 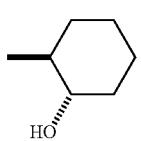
T-17: 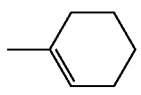
T-22: 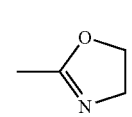
T-25: 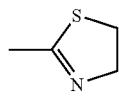
T-33: 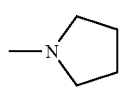
T-34a: 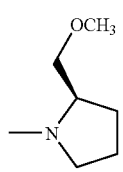

T-34b: 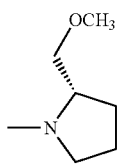

T-37: 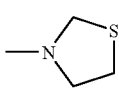

T-39: 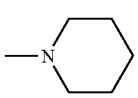

T-40: 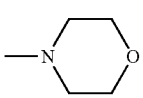

T-42: 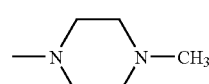

T-44: 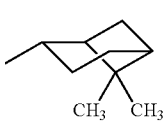

T-45: 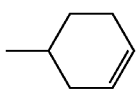

T-46: 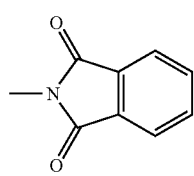

T-47: 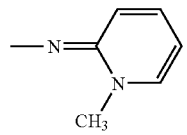

T-48: 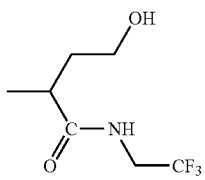

T-49: 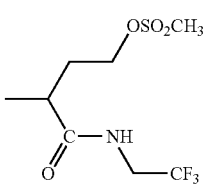

T-50: 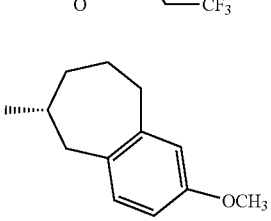

T-51: 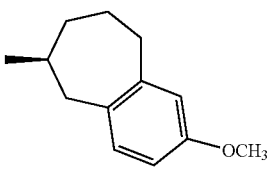

In addition, in Tables, the number showing the substitution position of substituents $(X)_m$ and $(Y)_n$ correspond to the position number indicated in the following structural formulae. The indication "–" means no-substitution.

Further, in Tables, the indication of "Mw" shows the calculated value of molecular weight, the indication of "M⁺+H" shows the measured value of molecular ion peak, and "*1", "*2" or "*3" means "resinous", "oily" or "decomposition", respectively.

TABLE 7

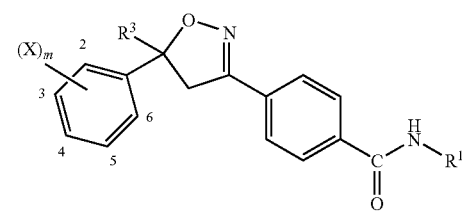

| No. | $(X)_m$ | $R^3$ | $R^1$ | Mw | M⁺ + H |
|---|---|---|---|---|---|
| 1-001 | — | C(O)OCH$_3$ | CH$_2$CF$_3$ | 406.36 | 407.00 |
| 1-002 | — | C(O)OCH$_3$ | CH$_2$Ph | 414.46 | 415.07 |
| 1-003 | 2-F | C(O)OCH$_3$ | CH$_2$CF$_3$ | 424.35 | 424.99 |
| 1-004 | 2-Cl | C(O)OCH$_3$ | CH$_2$CF$_3$ | 440.81 | 440.94 |
| 1-005 | 3-Br | CF$_3$ | CH$_2$Ph | 503.31 | 502.75 |

TABLE 7-continued

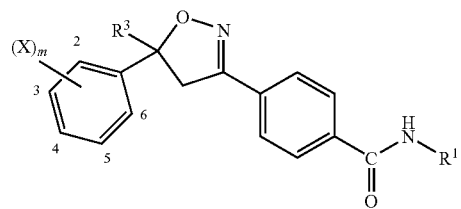

| No. | (X)ₘ | R³ | R¹ | Mw | M⁺ + H |
|---|---|---|---|---|---|
| 1-006 | 4-Br | CF₃ | CH₂CF₃ | 495.21 | 494.68 |
| 1-007 | 4-Br | CF₃ | CH₂Ph | 503.31 | 502.74 |
| 1-008 | 3-CH₃ | CF₃ | CH₂CF₃ | 430.34 | 430.91 |
| 1-009 | 3-CH₃ | CF₃ | CH₂Ph | 438.44 | 438.95 |
| 1-010 | 4-CH₃ | CF₃ | CH₂CF₃ | 430.34 | 430.92 |
| 1-011 | 4-CH₃ | CF₃ | CH₂Ph | 438.44 | 438.91 |
| 1-012 | 4-Bu-t | CF₃ | CH₂CF₃ | 472.42 | 472.94 |
| 1-013 | 4-Bu-t | CF₃ | CH₂Ph | 480.52 | 480.99 |
| 1-014 | 2-CF₃ | C(O)OCH₃ | CH₂CF₃ | 474.36 | 474.87 |
| 1-015 | 3-CF₃ | CF₃ | CH₂CF₃ | 484.32 | 484.78 |
| 1-016 | 3-CF₃ | CF₃ | CH₂Ph | 492.41 | 492.82 |
| 1-017 | 4-CF₃ | CF₃ | CH₂CF₃ | 484.32 | 484.80 |
| 1-018 | 4-CF₃ | CF₃ | CH₂Ph | 492.41 | 492.85 |
| 1-019 | 2-OCH₃ | C(O)OCH₃ | CH₂CF₃ | 436.39 | 436.99 |
| 1-020 | 3-OCH₃ | CF₃ | CH₂CF₃ | 446.34 | 446.89 |
| 1-021 | 3-OCH₃ | CF₃ | CH₂Ph | 454.44 | 454.94 |
| 1-022 | 4-OCH₃ | CF₃ | CH₂CF₃ | 446.34 | 446.89 |
| 1-023 | 4-OCH₃ | CF₃ | CH₂Ph | 454.44 | 454.91 |
| 1-024 | 4-OCH₃ | C(O)OCH₃ | CH₂CF₃ | 436.39 | 437.00 |
| 1-025 | 3-OCF₃ | CF₃ | CH₂CF₃ | 500.31 | 500.76 |
| 1-026 | 3-OCF₃ | CF₃ | CH₂Ph | 508.41 | 508.80 |
| 1-027 | 4-OCF₃ | CF₃ | CH₂CF₃ | 500.31 | 500.76 |
| 1-028 | 4-OCF₃ | CF₃ | CH₂Ph | 508.41 | 508.82 |
| 1-029 | 4-OPh | CF₃ | CH₂CF₃ | 508.41 | 508.85 |
| 1-030 | 4-OPh | CF₃ | CH₂Ph | 516.51 | 516.88 |
| 1-031 | 4-SCH₃ | CF₃ | CH₂CF₃ | 462.41 | 462.84 |
| 1-032 | 4-SCH₃ | CF₃ | CH₂Ph | 470.51 | 470.88 |
| 1-033 | 4-SO₂CH₃ | CF₃ | CH₂CF₃ | 494.41 | 494.86 |
| 1-034 | 3-NHC(O)OH₃ | CF₃ | CH₂CF₃ | 473.37 | 473.90 |
| 1-035 | 3-NHC(O)OH₃ | CF₃ | CH₂Ph | 481.47 | 481.93 |
| 1-036 | 4-NHC(O)OH₃ | CF₃ | CH₂CF₃ | 473.37 | 473.81 |
| 1-037 | 4-NHC(O)OH₃ | CF₃ | CH₂Ph | 481.47 | 481.94 |
| 1-038 | 4-N(CH₃)₂ | CF₃ | CH₂CF₃ | 459.38 | 459.90 |
| 1-039 | 4-N(CH₃)₂ | CF₃ | CH₂Ph | 467.48 | 467.94 |
| 1-040 | 3-NO₂ | CF₃ | CH₂CF₃ | 461.31 | 461.82 |
| 1-041 | 3-NO₂ | CF₃ | CH₂Ph | 469.41 | 469.86 |
| 1-042 | 3-TMS | CF₃ | CH₂CF₃ | 488.50 | 488.87 |
| 1-043 | 3-CN | CF₃ | CH₂Ph | 449.42 | 449.89 |
| 1-044 | 4-CN | CF₃ | CH₂Ph | 449.42 | 449.89 |
| 1-045 | 3-CHO | CF₃ | CH₂CF₃ | 444.33 | 444.89 |
| 1-046 | 3-C(O)CH₃ | CF₃ | CH₂CF₃ | 458.35 | 458.82 |
| 1-047 | 3-C(O)CH₃ | CF₃ | CH₂Ph | 466.45 | 466.81 |
| 1-048 | 4-C(O)OH₃ | CF₃ | CH₂CF₃ | 458.35 | 458.80 |
| 1-049 | 4-C(O)CH₃ | CF₃ | CH₂Ph | 466.45 | 466.86 |
| 1-050 | 3-C(O)OEt | CF₃ | CH₂CF₃ | 488.38 | 488.89 |
| 1-051 | 3-C(O)OEt | CF₃ | CH₂Ph | 496.48 | 496.92 |
| 1-052 | 4-Ph | CF₃ | CH₂CF₃ | 492.41 | 492.81 |
| 1-053 | 3,4-F2 | CF₃ | CH₂Pr-c | 424.36 | 424.91 |
| 1-054 | 3,4-F2 | CF₃ | CH₂Ph | 460.40 | 460.87 |
| 1-055 | 3,5-F2 | CF₃ | CH₂CF₃ | 452.30 | 452.84 |
| 1-056 | 3,5-F2 | CF₃ | CH₂Ph | 460.40 | 460.89 |
| 1-057 | 3-Cl-4-F | CF₃ | CH₂CF₃ | 468.75 | 468.76 |
| 1-058 | 3-Cl-4-F | CF₃ | CH₂Ph | 476.85 | 476.80 |
| 1-059 | 2,5-Cl₂ | CF₃ | CH₂CF₃ | 485.21 | 484.79 |
| 1-060 | 2,5-Cl₂ | CF₃ | CH₂Ph | 493.30 | 492.82 |
| 1-061 | 2,5-Cl₂ | CF₃ | CH₂(D-47a) | 494.29 | 493.84 |
| 1-062 | 3,4-Cl₂ | CF₃ | Et | 431.24 | 430.93 |
| 1-063 | 3,4-Cl₂ | CF₃ | n-Pr | 445.27 | 444.94 |
| 1-064 | 3,4-Cl₂ | CF₃ | i-Pr | 445.27 | 444.94 |
| 1-065 | 3,4-Cl₂ | CF₃ | n-Bu | 459.29 | 458.97 |
| 1-066 | 3,4-Cl₂ | CF₃ | CH₂Pr-c | 457.28 | 456.94 |
| 1-067 | 3,4-Cl₂ | CF₃ | s-Bu | 459.29 | 458.93 |
| 1-068 | 3,4-Cl₂ | CF₃ | t-Bu | 459.29 | 458.92 |
| 1-069 | 3,4-Cl₂ | CF₃ | c-Bu | 457.27 | 456.79 |
| 1-070 | 3,4-Cl₂ | CF₃ | n-Pen | 473.32 | 473.02 |
| 1-071 | 3,4-Cl₂ | CF₃ | CH₂Bu-s | 473.32 | 472.82 |
| 1-072 | 3,4-Cl₂ | CF₃ | CH₂Bu-t | 473.32 | 472.94 |

TABLE 7-continued

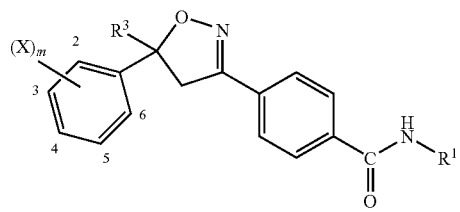

| No. | (X)$_m$ | R$^3$ | R$^1$ | Mw | M$^+$ + H |
|---|---|---|---|---|---|
| 1-073 | 3,4-Cl$_2$ | CF$_3$ | CH(CH$_3$)Pr-n | 473.32 | 472.94 |
| 1-074 | 3,4-Cl$_2$ | CF$_3$ | c-Pen | 471.31 | 470.99 |
| 1-075 | 3,4-Cl$_2$ | CF$_3$ | n-Hex | 487.35 | 486.96 |
| 1-076 | 3,4-Cl$_2$ | CF$_3$ | c-Hex | 485.33 | 484.93 |
| 1-077 | 3,4-Cl$_2$ | CF$_3$ | CH$_2$Hex-c | 499.35 | 498.88 |
| 1-078 | 3,4-Cl$_2$ | CF$_3$ | CH$_2$(T-39) | 539.42 | 538.88 |
| 1-079 | 3,4-Cl$_2$ | CF$_3$ | CH$_2$CH$_2$Cl | 465.69 | 464.73 |
| 1-080 | 3,4-Cl$_2$ | CF$_3$ | CH$_2$CF$_3$ | 485.21 | 484.85 |
| 1-081 | 3,4-Cl$_2$ | CF$_3$ | CH$_2$CF$_2$CF$_2$CF$_3$ | 585.23 | 584.65 |
| 1-082 | 3,4-Cl$_2$ | CF$_3$ | CH$_2$CH(CH$_3$)OH(R) | 461.26 | 460.78 |
| 1-083 | 3,4-Cl$_2$ | CF$_3$ | CH$_2$CH(CH$_3$)OH(S) | 461.26 | 460.82 |
| 1-084 | 3,4-Cl$_2$ | CF$_3$ | CH$_2$CH(CH$_3$)OC(O)NHEt(S) | 532.34 | 531.78 |
| 1-085 | 3,4-Cl$_2$ | CF$_3$ | CH(CH$_3$)CH$_2$OCH$_3$ | 475.29 | 474.94 |
| 1-086 | 3,4-Cl$_2$ | CF$_3$ | CH$_2$CH(Et)OH | 475.29 | 474.82 |
| 1-087 | 3,4-Cl$_2$ | CF$_3$ | CH(Et)CH$_2$OCH$_3$ | 489.32 | 488.95 |
| 1-088 | 3,4-Cl$_2$ | CF$_3$ | CH$_2$OH(OCH$_3$)$_2$ | 491.29 | 490.80 |
| 1-089 | 3,4-Cl$_2$ | CF$_3$ | CH$_2$CH$_2$OH | 461.27 | 460.97 |
| 1-090 | 3,4-Cl$_2$ | CF$_3$ | CH$_2$CH$_2$CH$_2$OCH$_3$ | 475.29 | 474.98 |
| 1-091 | 3,4-Cl$_2$ | CF$_3$ | CH$_2$(T-13) | 515.35 | 514.80 |
| 1-092 | 3,4-Cl$_2$ | CF$_3$ | CH$_2$(E-11c) | 517.33 | 516.79 |
| 1-093 | 3,4-Cl$_2$ | CF$_3$ | CH$_2$CH$_2$SCH$_3$ | 477.33 | 476.75 |
| 1-094 | 3,4-Cl$_2$ | CF$_3$ | CH$_2$CH$_2$SBu-t | 519.41 | 518.96 |
| 1-095 | 3,4-Cl$_2$ | CF$_3$ | CH$_2$CH$_2$CH$_2$SCH$_3$ | 491.35 | 490.92 |
| 1-096 | 3,4-Cl$_2$ | CF$_3$ | CH$_2$CH$_2$NHC(O)OBu-t | 546.37 | 545.75 |
| 1-097 | 3,4-Cl$_2$ | CF$_3$ | CH$_2$CH$_2$CH$_2$Si(OCH$_3$)3 | 565.44 | 564.77 |
| 1-098 | 3,4-Cl$_2$ | CF$_3$ | CH$_2$CH$_2$CH$_2$Si(CH$_3$)(OEt)$_2$ | 577.49 | 576.79 |
| 1-099 | 3,4-Cl$_2$ | CF$_3$ | CH$_2$C(O)OCH$_3$ | 475.25 | 474.89 |
| 1-100 | 3,4-Cl$_2$ | CF$_3$ | CH$_2$CH$_2$C(O)OCH$_3$ | 489.28 | 488.80 |
| 1-101 | 3,4-Cl$_2$ | CF$_3$ | CH$_2$C(O)NH$_2$ | 460.24 | 459.74 |
| 1-102 | 3,4-Cl$_2$ | CF$_3$ | CH$_2$OH=CH$_2$ | 443.25 | 442.81 |
| 1-103 | 3,4-Cl$_2$ | CF$_3$ | CH$_2$CH$_2$(T-17) | 511.36 | 510.76 |
| 1-104 | 3,4-Cl$_2$ | CF$_3$ | CH$_2$C≡CH | 441.24 | 440.91 |
| 1-105 | 3,4-Cl$_2$ | CF$_3$ | CH$_2$Ph | 493.31 | 492.86 |
| 1-106 | 3,4-Cl$_2$ | CF$_3$ | CH$_2$(Ph-2-F) | 511.30 | 510.80 |
| 1-107 | 3,4-Cl$_2$ | CF$_3$ | CH$_2$(Ph-3-F) | 511.30 | 510.81 |
| 1-108 | 3,4-Cl$_2$ | CF$_3$ | CH$_2$(Ph-2-Cl) | 527.75 | 526.74 |
| 1-109 | 3,4-Cl$_2$ | CF$_3$ | CH$_2$(Ph-3-Cl) | 527.75 | 526.75 |
| 1-110 | 3,4-Cl$_2$ | CF$_3$ | CH$_2$(Ph-2-CH$_3$) | 507.33 | 506.78 |
| 1-111 | 3,4-Cl$_2$ | CF$_3$ | CH$_2$(Ph-4-CH$_3$) | 507.33 | 506.73 |
| 1-112 | 3,4-Cl$_2$ | CF$_3$ | CH$_2$(Ph-4-Bu-t) | 549.41 | 548.77 |
| 1-113 | 3,4-Cl$_2$ | CF$_3$ | CH$_2$(Ph-2-CF$_3$) | 561.30 | 560.72 |
| 1-114 | 3,4-Cl$_2$ | CF$_3$ | CH$_2$(Ph-3-CF$_3$) | 561.30 | 560.69 |
| 1-115 | 3,4-Cl$_2$ | CF$_3$ | CH$_2$(Ph-4-CF$_3$) | 561.30 | 560.97 |
| 1-116 | 3,4-Cl$_2$ | CF$_3$ | CH$_2$(Ph-2-OCH$_3$) | 523.33 | 522.77 |
| 1-117 | 3,4-Cl$_2$ | CF$_3$ | CH$_2$(Ph-3-OCH$_3$) | 523.33 | 522.74 |
| 1-118 | 3,4-Cl$_2$ | CF$_3$ | CH$_2$(Ph-4-OCH$_3$) | 523.33 | 522.68 |
| 1-119 | 3,4-Cl$_2$ | CF$_3$ | CH$_2$(Ph-3-0CF$_3$) | 577.30 | 576.69 |
| 1-120 | 3,4-Cl$_2$ | CF$_3$ | CH$_2$(Ph-4-SO$_2$CH$_3$) | 571.40 | 570.71 |
| 1-121 | 3,4-Cl$_2$ | CF$_3$ | CH$_2$[Ph-4-N(CH$_3$)$_2$] | 536.37 | 535.81 |
| 1-122 | 3,4-Cl$_2$ | CF$_3$ | CH$_2$(Ph-3-NO$_2$) | 538.30 | 537.64 |
| 1-123 | 3,4-Cl$_2$ | CF$_3$ | CH$_2$(Ph-4-NO$_2$) | 538.30 | 537.66 |
| 1-124 | 3,4-Cl$_2$ | CF$_3$ | CH$_2$[Ph-4-C(O)OCH$_3$] | 551.34 | 550.74 |
| 1-125 | 3,4-Cl$_2$ | CF$_3$ | CH$_2$(Ph-2,5-F$_2$) | 529.29 | 528.72 |
| 1-126 | 3,4-Cl$_2$ | CF$_3$ | CH$_2$(Ph-2,6-F$_2$) | 529.29 | 528.81 |
| 1-127 | 3,4-Cl$_2$ | CF$_3$ | CH$_2$(Ph-3,5-F$_2$) | 529.29 | 528.73 |
| 1-128 | 3,4-Cl$_2$ | CF$_3$ | CH$_2$(Ph-3-Cl-4-F) | 545.74 | 544.67 |
| 1-129 | 3,4-Cl$_2$ | CF$_3$ | CH$_2$(Ph-2,3-Cl$_2$) | 562.20 | 560.72 |
| 1-130 | 3,4-Cl$_2$ | CF$_3$ | CH$_2$(Ph-2,4-Cl$_2$) | 562.20 | 560.72 |
| 1-131 | 3,4-Cl$_2$ | CF$_3$ | CH$_2$(Ph-2,5-Cl$_2$) | 562.20 | 560.72 |
| 1-132 | 3,4-Cl$_2$ | CF$_3$ | CH$_2$(Ph-2,6-Cl$_2$) | 562.20 | 560.73 |
| 1-133 | 3,4-Cl$_2$ | CF$_3$ | CH$_2$(Ph-3,5-Cl$_2$) | 562.20 | 560.64 |
| 1-134 | 3,4-Cl$_2$ | CF$_3$ | CH$_2$(Ph-3-CF$_3$-4-F) | 579.29 | 578.70 |
| 1-135 | 3,4-Cl$_2$ | CF$_3$ | CH$_2$[Ph-3,4-(OCH$_3$)$_2$] | 553.36 | 552.76 |
| 1-136 | 3,4-Cl$_2$ | CF$_3$ | CH$_2$(Ph-3-OCH$_2$O-4) | 537.31 | 536.73 |
| 1-137 | 3,4-Cl$_2$ | CF$_3$ | CH$_2$(1-Naph) | 543.36 | 542.80 |
| 1-138 | 3,4-Cl$_2$ | CF$_3$ | CH(CH$_3$)Ph | 507.34 | 506.88 |
| 1-139 | 3,4-Cl$_2$ | CF$_3$ | CH(CH$_3$)(Ph-3-Cl) | 541.78 | 540.70 |

TABLE 7-continued

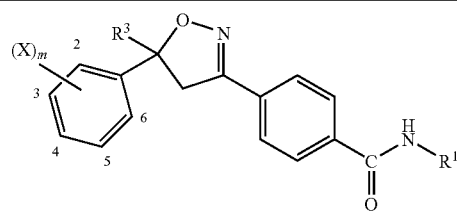

| No. | (X)$_m$ | R$^3$ | R$^1$ | Mw | M$^+$ + H |
|---|---|---|---|---|---|
| 1-140 | 3,4-Cl$_2$ | CF$_3$ | C(CH$_3$)$_2$Ph | 521.37 | 520.99 |
| 1-141 | 3,4-Cl$_2$ | CF$_3$ | CH$_2$CH$_2$Ph | 507.34 | 507.01 |
| 1-142 | 3,4-Cl$_2$ | CF$_3$ | CH$_2$CH$_2$(Ph-4-OPh) | 599.44 | 598.95 |
| 1-143 | 3,4-Cl$_2$ | CF$_3$ | CH$_2$OH(CH$_3$)Ph | 521.37 | 520.93 |
| 1-144 | 3,4-Cl$_2$ | CF$_3$ | CH$_2$CHPh$_2$ | 583.43 | 582.79 |
| 1-145 | 3,4-Cl$_2$ | CF$_3$ | CH(CH$_3$)CH$_2$(Ph-4-Cl) | 555.81 | 554.78 |
| 1-146 | 3,4-Cl$_2$ | CF$_3$ | T-9 | 519.35 | 518.88 |
| 1-147 | 3,4-Cl$_2$ | CF$_3$ | CH$_2$CH$_2$CH$_2$Ph | 521.37 | 520.97 |
| 1-148 | 3,4-Cl$_2$ | CF$_3$ | CH$_2$CH$_2$SCH$_2$Ph | 553.43 | 552.75 |
| 1-149 | 3,4-Cl$_2$ | CF$_3$ | CH$_2$C(O)(Ph-4-OCH$_3$) | 551.34 | 550.66 |
| 1-150 | 3,4-Cl$_2$ | CF$_3$ | CH$_2$(D-1c)CH$_3$ | 497.29 | 496.80 |
| 1-151 | 3,4-Cl$_2$ | CF$_3$ | CH$_2$(D-3a) | 499.33 | 498.70 |
| 1-152 | 3,4-Cl$_2$ | CF$_3$ | CH$_2$(D-3b)CH$_3$ | 513.36 | 512.74 |
| 1-153 | 3,4-Cl$_2$ | CF$_3$ | CH$_2$(D-47a) | 494.29 | 493.84 |
| 1-154 | 3,4-Cl$_2$ | CF$_3$ | CH$_2$(D-47f) | 596.74 | 595.79 |
| 1-155 | 3,4-Cl$_2$ | CF$_3$ | CH$_2$(D-48a) | 494.29 | 493.84 |
| 1-156 | 3,4-Cl$_2$ | CF$_3$ | CH$_2$(D-49a) | 494.29 | 493.86 |
| 1-157 | 3,4-Cl$_2$ | CF$_3$ | CH$_2$(D-53b)CH$_3$ | 509.31 | 508.78 |
| 1-158 | 3,4-Cl$_2$ | CF$_3$ | CH$_2$CH$_2$(D-3a) | 513.36 | 512.71 |
| 1-159 | 3,4-Cl$_2$ | CF$_3$ | CH$_2$CH$_2$(D-47a) | 508.32 | 507.76 |
| 1-160 | 3,4-Cl$_2$ | CF$_3$ | CH$_2$CH$_2$(D-48a) | 508.32 | 507.77 |
| 1-161 | 3,4-Cl$_2$ | CF$_3$ | CH$_2$CH$_2$CH$_2$(D-24a) | 511.32 | 510.84 |
| 1-162 | 3,4-Cl$_2$ | CF$_3$ | T-21 | 472.24 | 471.77 |
| 1-163 | 3,4-Cl$_2$ | CF$_3$ | T-22 | 488.31 | 487.72 |
| 1-164 | 3,4-Cl$_2$ | CF$_3$ | (D-8b)CH$_3$ | 484.25 | 483.75 |
| 1-165 | 3,4-Cl$_2$ | CF$_3$ | D-11c | 581.35 | 580.66 |
| 1-166 | 3,4-Cl$_2$ | CF$_3$ | D-21a | 486.29 | 485.70 |
| 1-167 | 3,4-Cl$_2$ | CF$_3$ | (D-21b)CH$_3$ | 500.32 | 499.70 |
| 1-168 | 3,4-Cl$_2$ | CF$_3$ | (D-21c)CH$_3$ | 500.32 | 499.70 |
| 1-169 | 3,4-Cl$_2$ | CF$_3$ | (D-21c)NO$_2$ | 531.29 | 530.60 |
| 1-170 | 3,4-Cl$_2$ | CF$_3$ | D-25d | 533.33 | 532.73 |
| 1-171 | 3,4-Cl$_2$ | CF$_3$ | D-48a | 480.27 | 479.76 |
| 1-172 | 3,4-Cl$_2$ | CF$_3$ | D-49a | 480.27 | 479.76 |
| 1-173 | 3,4-Cl$_2$ | CF$_3$ | OPr-n | 461.27 | 460.94 |
| 1-174 | 3,4-Cl$_2$ | CF$_3$ | N(CH$_3$)$_2$ | 446.26 | 445.92 |
| 1-175 | 3,5-Cl$_2$ | CF$_3$ | CH$_2$Pr-c | 457.27 | 456.83 |
| 1-176 | 3,5-Cl$_2$ | CF$_3$ | CH$_2$CH$_2$CF$_3$ | 499.23 | 498.79 |
| 1-177 | 3,5-Cl$_2$ | CF$_3$ | CH$_2$CH$_2$OEt | 475.29 | 474.86 |
| 1-178 | 3,5-Cl$_2$ | CF$_3$ | CH$_2$CH$_2$OCH$_2$CH$_2$OH | 491.29 | 490.78 |
| 1-179 | 3,5-Cl$_2$ | CF$_3$ | CH$_2$CH(CH$_3$)OH | 461.27 | 460.88 |
| 1-180 | 3,5-Cl$_2$ | CF$_3$ | CH$_2$CH$_2$CH$_2$OEt | 489.31 | 488.90 |
| 1-181 | 3,5-Cl$_2$ | CF$_3$ | CH$_2$CH$_2$CH$_2$OPr-i | 503.34 | 502.86 |
| 1-182 | 3,5-Cl$_2$ | CF$_3$ | CH$_2$CH$_2$SEt | 491.35 | 490.99 |
| 1-183 | 3,5-Cl$_2$ | CF$_3$ | CH$_2$(Ph-3-Br) | 572.20 | 570.68 |
| 1-184 | 3,5-Cl$_2$ | CF$_3$ | CH$_2$(Ph-3-OCH$_3$) | 523.33 | 522.80 |
| 1-185 | 3,5-Cl$_2$ | CF$_3$ | CH$_2$(Ph-4-OCH$_3$) | 523.33 | 522.74 |
| 1-186 | 3,5-Cl$_2$ | CF$_3$ | CH$_2$(Ph-4-OCF$_3$) | 577.30 | 576.75 |
| 1-187 | 3,5-Cl$_2$ | CF$_3$ | CH$_2$(Ph-4-SO$_2$NH$_2$) | 572.38 | 571.78 |
| 1-188 | 3,5-Cl$_2$ | CF$_3$ | CH$_2$(Ph-3-NO$_2$) | 538.30 | 537.76 |
| 1-189 | 3,5-Cl$_2$ | CF$_3$ | CH$_2$(Ph-4-NO$_2$) | 538.30 | 537.76 |
| 1-190 | 3,5-Cl$_2$ | CF$_3$ | CH$_2$CH$_2$(Ph-3-Cl) | 541.78 | 540.71 |
| 1-191 | 3,5-Cl$_2$ | CF$_3$ | CH$_2$CH$_2$(Ph-4-OCH$_3$) | 537.36 | 536.79 |
| 1-192 | 3,5-Cl$_2$ | CF$_3$ | CH$_2$CH$_2$(Ph-3,4-Cl$_2$) | 576.22 | 574.60 |
| 1-193 | 3,5-Cl$_2$ | CF$_3$ | CH$_2$CH$_2$[Ph-3,4-(OCH$_3$)$_2$] | 567.38 | 566.77 |
| 1-194 | 3,5-Cl$_2$ | CF$_3$ | CH$_2$CH$_2$OPh | 523.33 | 522.85 |
| 1-195 | 3,5-Cl$_2$ | CF$_3$ | Ph-4-OCH$_3$ | 509.30 | 508.75 |
| 1-196 | 3,5-Cl$_2$ | CF$_3$ | (D-21b)CH$_2$C(O)OEt | 572.38 | 571.70 |
| 1-197 | 3,5-Cl$_2$ | CF$_3$ | (D-21c)Br | 565.19 | 563.59 |
| 1-198 | 3,5-Cl$_2$ | CF$_3$ | (D-21c)SO$_2$(Ph-4-NO$_2$) | 671.45 | 670.55 |
| 1-199 | 3,5-Cl$_2$ | CF$_3$ | D-21d | 514.35 | 513.72 |
| 1-200 | 3,5-Cl$_2$ | CF$_3$ | D-21e | 536.35 | 535.70 |
| 1-201 | 3,5-Cl$_2$ | CF$_3$ | D-21f | 570.80 | 569.68 |
| 1-202 | 3,5-Cl$_2$ | CF$_3$ | D-21g | 570.80 | 569.68 |
| 1-203 | 3,5-Cl$_2$ | CF$_3$ | D-21h | 566.38 | 565.71 |
| 1-204 | 3,5-Cl$_2$ | CF$_3$ | D-21i | 566.38 | 565.76 |
| 1-205 | 3,5-Cl$_2$ | CF$_3$ | D-21j | 581.35 | 580.69 |
| 1-206 | 3,5-Cl$_2$ | CF$_3$ | NHPh | 494.29 | 493.81 |

TABLE 7-continued

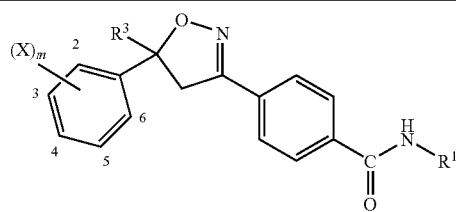

| No. | (X)$_m$ | R$^3$ | R$^1$ | Mw | M$^+$ + H |
|---|---|---|---|---|---|
| 1-207 | 3,5-Br$_2$ | CF$_3$ | CH$_2$CF$_3$ | 574.11 | 572.49 |
| 1-208 | 3,5-Br$_2$ | CF$_3$ | CH$_2$Ph | 582.21 | 580.61 |
| 1-209 | 3-CH$_3$-4-F | CF$_3$ | CH$_2$Ph | 456.43 | 456.87 |
| 1-210 | 3,4-(CH$_3$)$_2$ | CF$_3$ | CH$_2$CF$_3$ | 444.37 | 444.89 |
| 1-211 | 3,4-(CH$_3$)$_2$ | CF$_3$ | CH$_2$Ph | 452.47 | 452.94 |
| 1-212 | 3,5-(CH$_3$)$_2$ | CF$_3$ | CH$_2$CF$_3$ | 444.37 | 444.86 |
| 1-213 | 3,5-(CH$_3$)$_2$ | CF$_3$ | CH$_2$Ph | 452.47 | 452.95 |
| 1-214 | 3,5-(CF$_3$)$_2$ | CF$_3$ | CH$_2$CF$_3$ | 552.31 | 552.72 |
| 1-215 | 3,5-(CF$_3$)$_2$ | CF$_3$ | CH$_2$Ph | 560.41 | 560.76 |
| 1-216 | 3-OEt-4-Cl | CF$_3$ | CH$_2$CF$_3$ | 494.81 | 494.76 |
| 1-217 | 3-OEt-4-Cl | CF$_3$ | CH$_2$Ph | 502.91 | 502.81 |
| 1-218 | 3,4-(OCH$_3$)$_2$ | CF$_3$ | CH$_2$CF$_3$ | 476.37 | 476.83 |
| 1-219 | 3,4-(OCH$_3$)$_2$ | CF$_3$ | CH$_2$Ph | 484.47 | 484.90 |
| 1-220 | 3-OCH$_2$O-4 | CF$_3$ | CH$_2$Pr-c | 432.39 | 432.89 |
| 1-221 | 3-OCH$_2$O-4 | CF$_3$ | CH$_2$Ph | 468.42 | 468.86 |
| 1-222 | 3,5-(CHO)$_2$ | CF$_3$ | CH$_2$CF$_3$ | 472.34 | 472.92 |
| 1-223 | 3-CH=CHCH=CH-4 | CF$_3$ | CH$_2$CF$_3$ | 466.38 | 466.83 |
| 1-224 | 3-CH=CHCH=CH-4 | CF$_3$ | CH$_2$Ph | 474.47 | 474.86 |
| 1-225 | 3,4,5-F$_3$ | CF$_3$ | CH$_2$CF$_3$ | 470.29 | 470.77 |
| 1-226 | 3,4,5-F$_3$ | CF$_3$ | CH$_2$Ph | 478.39 | 478.82 |

TABLE 8

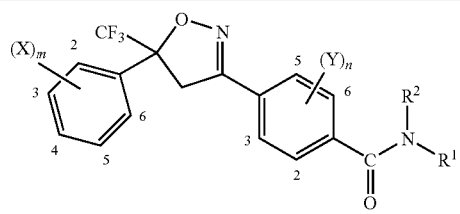

| No. | (X)$_m$ | (Y)$_n$ | R$^2$ | R$^1$ | Mw | M$^+$ + H |
|---|---|---|---|---|---|---|
| 2-001 | 3,4-F$_2$ | — | CH$_3$ | CH$_2$Ph | 474.42 | 474.88 |
| 2-002 | 3,4-Cl$_2$ | — | CH$_3$ | CH3 | 431.24 | 430.91 |
| 2-003 | 3,4-Cl$_2$ | — | Et | Et | 459.29 | 458.94 |
| 2-004 | 3,4-Cl$_2$ | — | CH$_3$ | n-Bu | 473.32 | 472.97 |
| 2-005 | 3,4-Cl$_2$ | — | CH$_3$ | i-Bu | 473.32 | 472.89 |
| 2-006 | 3,4-Cl$_2$ | — | —CH$_2$CH$_2$CH$_2$CH$_2$— | | 457.28 | 456.85 |
| 2-007 | 3,4-Cl$_2$ | — | —CH$_2$CH$_2$CH$_2$CH$_2$CH$_2$— | | 471.31 | 470.84 |
| 2-008 | 3,4-Cl$_2$ | — | —CH$_2$CH$_2$CH$_2$CH$_2$CH(CH$_3$)— | | 485.33 | 484.83 |
| 2-009 | 3,4-Cl$_2$ | — | —CH$_2$CH$_2$CH$_2$CH(CH$_3$)CH$_2$— | | 485.33 | 484.82 |
| 2-010 | 3,4-Cl$_2$ | — | —CH$_2$CH(CH$_3$)CH$_2$CH(CH$_3$)CH$_2$— | | 499.35 | 498.82 |
| 2-011 | 3,4-Cl$_2$ | — | —CH$_2$CH$_2$OCH$_2$CH$_2$— | | 473.28 | 472.75 |
| 2-012 | 3,4-Cl$_2$ | — | —CH$_2$CH(CH$_3$)OCH(CH$_3$)CH$_2$— | | 501.33 | 500.77 |
| 2-013 | 3,4-Cl$_2$ | — | —CH$_2$CH$_2$SCH$_2$CH$_2$— | | 489.34 | 488.74 |
| 2-014 | 3,4-Cl$_2$ | — | —CH$_2$CH$_2$N(CHO)CH$_2$CH$_2$— | | 500.30 | 499.76 |
| 2-015 | 3,4-Cl$_2$ | — | CH$_3$ | CH$_2$CH=CH$_2$ | 457.27 | 456.87 |
| 2-016 | 3,4-Cl$_2$ | — | CH$_2$CH=CH$_2$ | CH$_2$CH=CH$_2$ | 483.31 | 482.85 |
| 2-017 | 3,4-Cl$_2$ | — | CH$_3$ | CH$_2$C≡CH | 455.26 | 454.86 |
| 2-018 | 3,4-Cl$_2$ | — | CH$_3$ | CH$_2$Ph | 507.34 | 506.93 |
| 2-019 | 3,4-Cl$_2$ | — | Et | CH$_2$(D-48e)Cl | 556.79 | 555.73 |
| 2-020 | 3,5-Cl$_2$ | — | Et | Et | 459.29 | 458.85 |
| 2-021 | 3,5-Cl$_2$ | — | CH$_3$ | CH$_2$Ph | 507.33 | 506.79 |
| 2-022 | 3,5-Cl$_2$ | — | Et | CH$_2$Ph | 521.36 | 520.79 |
| 2-023 | 3,5-Cl$_2$ | — | CH$_2$Ph | CH$_2$Ph | 583.43 | 582.79 |
| 2-024 | 3,5-Cl$_2$ | 2-CH$_3$ | H | CH$_2$CH$_2$OH | 461.26 | 460.99 |
| 2-025 | 3,5-Cl$_2$ | 2-CH$_3$ | H | CH$_2$CH$_2$OPr-n | 503.34 | 502.99 |
| 2-026 | 3,5-Cl$_2$ | 2-CH$_3$ | H | CH$_2$CH$_2$OPr-i | 503.34 | 502.98 |
| 2-027 | 3,5-Cl$_2$ | 2-CH$_3$ | H | CH$_2$CH$_2$OCH$_2$CH$_2$OH | 505.31 | 504.95 |
| 2-028 | 3,5-Cl$_2$ | 2-CH$_3$ | H | CH$_2$CH$_2$OPh | 537.36 | 536.94 |
| 2-029 | 3,5-Cl$_2$ | 2-CH$_3$ | H | CH(CH$_3$)CH$_2$OCH$_3$ | 489.31 | 488.98 |

TABLE 8-continued

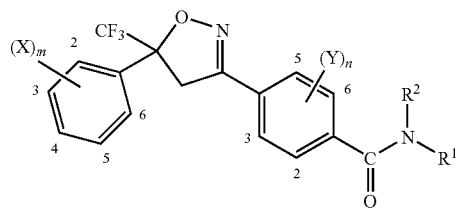

| No. | $(X)_m$ | $(Y)_n$ | $R^2$ | $R^1$ | Mw | $M^+ + H$ |
|---|---|---|---|---|---|---|
| 2-030 | 3,5-Cl$_2$ | 2-CH$_3$ | H | CH$_2$CH$_2$N(CH$_3$)$_2$ | 488.33 | 487.98 |
| 2-031 | 3,5-Cl$_2$ | 2-CH$_3$ | H | CH(Ph)C(O)OCH$_3$(R) | 565.37 | 564.84 |
| 2-032 | 3,5-Cl$_2$ | 2-CH$_3$ | H | CH(Ph)C(O)OCH$_3$(S) | 565.37 | 564.92 |
| 2-033 | 3,5-Cl$_2$ | 2-CH$_3$ | H | CH$_2$CH$_2$C(O)OCH$_3$ | 503.30 | 502.91 |
| 2-034 | 3,5-Cl$_2$ | 2-CH$_3$ | H | CH$_2$(Ph-4-OCH$_3$) | 537.36 | 536.98 |
| 2-035 | 3,5-Cl$_2$ | 2-CH$_3$ | H | CH$_2$(Ph-4-CN) | 532.34 | 531.94 |
| 2-036 | 3,5-Cl$_2$ | 2-CH$_3$ | H | CH$_2$CH$_2$(D-47a) | 522.35 | 521.94 |
| 2-037 | 3,5-Cl$_2$ | 2-CH$_3$ | H | T-29b | 562.32 | 559.80* |
| 2-038 | 3,5-Cl$_2$ | 2-CH$_3$ | H | NHCH$_2$C(O)OEt | 518.31 | 517.93 |
| 2-039 | 3,5-Cl$_2$ | 2-CH$_3$ | H | NHCHO | 460.23 | 457.86* |
| 2-040 | 3,5-Cl$_2$ | 2-CH$_3$ | H | NHC(O)CH$_2$(D-3a) | 556.38 | 553.71* |
| 2-041 | 3,5-Cl$_2$ | 2-CH$_3$ | H | N(CH$_3$)C(S)NH$_2$ | 505.34 | 504.82 |
| 2-042 | 3,5-Cl$_2$ | 2-CH$_3$ | H | N(CH$_3$)C(S)NHCH$_3$ | 519.37 | 518.88 |
| 2-043 | 3,5-Cl$_2$ | 2-CH$_3$ | H | T-40 | 530.37 | 529.98 |
| 2-044 | 3,5-Cl$_2$ | 2-CH$_3$ | H | NH(Ph-2-F) | 526.31 | 525.92 |
| 2-045 | 3,5-Cl$_2$ | 2-CH$_3$ | H | NH(Ph-3-F) | 526.31 | 525.92 |
| 2-046 | 3,5-Cl$_2$ | 2-CH$_3$ | H | NH(Ph-4-F) | 526.31 | 523.89* |
| 2-047 | 3,5-Cl$_2$ | 2-CH$_3$ | H | NH(Ph-4-Br) | 587.22 | 585.91 |
| 2-048 | 3,5-Cl$_2$ | 2-CH$_3$ | H | NH(Ph-4-CH$_3$) | 522.35 | 521.93 |
| 2-049 | 3,5-Cl$_2$ | 2-CH$_3$ | H | NH(Ph-4-Pr-i) | 550.40 | 549.94 |
| 2-050 | 3,5-Cl$_2$ | 2-CH$_3$ | H | NH(Ph-4-OCF$_3$) | 592.32 | 591.97 |
| 2-051 | 3,5-Cl$_2$ | 2-CH$_3$ | H | NH(Ph-4-CN) | 533.33 | 533.01 |
| 2-052 | 3,5-Cl$_2$ | 2-CH$_3$ | H | N(CH$_3$)(D-47d)CF$_3$ | 591.33 | 590.99 |
| 2-053 | 3,5-Cl$_2$ | 2-CH$_3$ | H | N=CHC(CH$_3$)=CHPh | 560.39 | 559.95 |
| 2-054 | 3,5-Cl$_2$ | 2-CH$_3$ | H | D-47a | 494.29 | 493.94 |
| 2-055 | 3,5-Cl$_2$ | 2-CH$_3$ | H | D-49a | 494.29 | 493.97 |
| 2-056 | 3-OCH$_2$O-4 | — | CH$_3$ | CH$_2$Ph | 482.45 | 482.86 |
| 2-057 | 3,5-Cl$_2$ | 2-CH$_3$ | C(O)OCH$_3$CH$_2$CH=CH$_2$ | | 515.31 | 514.97 |
| 2-058 | 3,5-Cl$_2$ | 2-CH$_3$ | C(O)OPr-i | CH$_2$CH=CH$_2$ | 543.36 | 541.04* |
| 2-059 | 3,5-Cl$_2$ | 2-CH$_3$ | H | C(O)OCH$_2$CH$_2$Cl | 523.72 | 522.84 |
| 2-060 | 3,5-Cl$_2$ | 2-CH$_3$ | H | C(O)OCH$_2$CHCl$_2$ | 558.16 | 554.92* |
| 2-061 | 3,5-Cl$_2$ | 2-CH$_3$ | H | C(O)OCH$_2$CCl$_3$ | 592.61 | 588.88* |
| 2-062 | 3,5-Cl$_2$ | 2-CH$_3$ | H | C(O)OCH$_2$CH$_2$CF$_3$ | 557.27 | 557.03 |
| 2-063 | 3,5-Cl$_2$ | 2-CH$_3$ | H | C(O)OCH(CH$_2$Cl)$_2$ | 572.19 | 570.94* |
| 2-064 | 3,5-Cl$_2$ | 2-CH$_3$ | H | C(O)OCH(CF$_3$)$_2$ | 611.24 | 608.86* |
| 2-065 | 3,5-Cl$_2$ | 2-CH$_3$ | H | C(O)OCH(CH$_3$)CHClCH$_3$ | 551.77 | 548.95* |
| 2-066 | 3,5-Cl$_2$ | 2-CH$_3$ | H | C(O)OCH$_2$CH$_2$CH$_2$Cl | 551.77 | 550.99 |
| 2-067 | 3,5-Cl$_2$ | 2-CH$_3$ | H | C(O)OCH$_2$C(CF$_3$)$_2$CH$_3$ | 639.29 | 636.95* |
| 2-068 | 3,5-Cl$_2$ | 2-CH$_3$ | H | T-25 | 501.33 | 502.05 |
| 2-069 | 3,5-Cl$_2$ | 2-CH$_3$ | H | (D-21c)C(O)OEt | 571.38 | 572.04 |

In Table above, the indication of "*" shows the measured value of molecular ion peak of M + H measured with negative mode.

TABLE 9

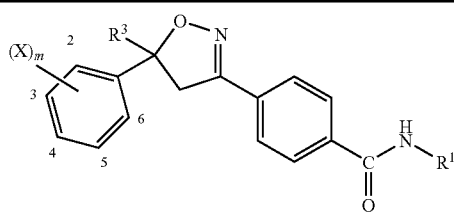

| No. | $(X)_m$ | $R^3$ | $R^1$ | m.p. (° C.) |
|---|---|---|---|---|
| 3-001 | — | CF$_3$ | CH$_2$CF$_3$ | 172.0-173.0 |
| 3-002 | 3-Cl | CF$_3$ | CH$_2$CF$_3$ | 157.0-158.0 |
| 3-003 | 3-Cl | CF$_3$ | CH$_2$Ph | 168.0-169.0 |
| 3-004 | 4-Cl | CF$_3$ | CH$_2$CF$_3$ | 190.0-191.0 |
| 3-005 | 4-Cl | CF$_3$ | CH$_2$Ph | 212.0-214.0 |
| 3-006 | 3-Br | CF$_3$ | CH$_2$CF$_3$ | 132.0-135.0 |
| 3-007 | 3-OCF$_3$ | CF$_3$ | CH$_2$(D-47a) | 145.0-147.0 |

TABLE 9-continued

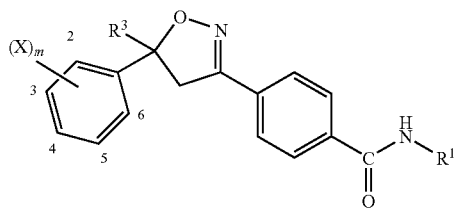

| No. | (X)$_m$ | R$^3$ | R$^1$ | m.p. (° C.) |
|---|---|---|---|---|
| 3-008 | 3-OCH$_2$Ph | CF$_3$ | CH$_2$CF$_3$ | 146.0-149.0 |
| 3-009 | 3-OCH$_2$(Ph-2-Cl) | CF$_3$ | CH$_2$CF$_3$ | 158.0-159.0 |
| 3-010 | 3-OCH$_2$(Ph-2-Cl) | CF$_3$ | CH$_2$(D-47a) | *1 |
| 3-011 | 3-SEt | CF$_3$ | CH$_2$CF$_3$ | 105.0-106.0 |
| 3-012 | 3-CN | CF$_3$ | CH$_2$CF$_3$ | 93.0-96.0 |
| 3-013 | 4-CN | CF$_3$ | CH$_2$CF$_3$ | 149.0-151.0 |
| 3-014 | 3-CH=NOH | CF$_3$ | CH$_2$CF$_3$ | 168.0-169.0 |
| 3-015 | 3-CH=NOCH$_3$ | CF$_3$ | CH$_2$CF$_3$ | *1 |
| 3-016 | 4-C(CH$_3$)=NOCH$_3$(E) | CF$_3$ | CH$_2$CF$_3$ | 160.0-162.0 |
| 3-017 | 4-C(CH$_3$)=NOCH$_3$(Z) | CF$_3$ | CH$_2$CF$_3$ | *1 |
| 3-018 | 3,4-F$_2$ | CF$_3$ | CH$_2$CF$_3$ | 150.0-152.0 |
| 3-019 | 2,4-Cl$_2$ | CF$_3$ | CH$_2$CF$_3$ | 149.0-151.0 |
| 3-020 | 3,4-Cl$_2$ | H | CH$_2$CF$_3$ | 161.0-162.0 |
| 3-021 | 3,4-Cl$_2$ | H | CH$_2$Ph | 147.0-148.0 |
| 3-022 | 3,4-Cl$_2$ | CH$_3$ | CH$_2$Pr-c | 157.0-158.0 |
| 3-023 | 3,4-Cl$_2$ | CH$_3$ | CH$_2$CF$_3$ | 120.0-122.0 |
| 3-024 | 3,4-Cl$_2$ | CH$_3$ | CH$_2$Ph | 153.0-155.0 |
| 3-025 | 3,4-Cl$_2$ | CF$_3$ | CH$_3$ | 139.0-140.0 |
| 3-026 | 3,4-Cl$_2$ | CF$_3$ | c-Pr | 193.0-194.0 |
| 3-027 | 3,4-Cl$_2$ | CF$_3$ | i-Bu | 158.0-159.0 |
| 3-028 | 3,4-Cl$_2$ | CF$_3$ | CH$_2$Bu-c | 177.0-179.0 |
| 3-029 | 3,4-Cl$_2$ | CF$_3$ | CH$_2$CH(Et)Bu-n | 125.0-127.0 |
| 3-030 | 3,4-Cl$_2$ | CF$_3$ | CH$_2$CF$_2$CF$_3$ | 171.0-173.0 |
| 3-031 | 3,4-Cl$_2$ | CF$_3$ | CH$_2$(E-4a) | 136.0-138.0 |
| 3-032 | 3,4-Cl$_2$ | CF$_3$ | CH(CH$_3$)CH$_2$SCH$_3$ | 145.0-147. |
| 3-033 | 3,4-Cl$_2$ | CF$_3$ | C(CH$_3$)$_2$CH$_2$SCH$_3$ | 150.0-152.0 |
| 3-034 | 3,4-Cl$_2$ | CF$_3$ | C(CH$_3$)$_2$CH$_2$S(O)CH$_3$ | *1 |
| 3-035 | 3,4-Cl$_2$ | CF$_3$ | C(CH$_3$)$_2$CH$_2$SO$_2$CH$_3$ | 161.0-163.0 |
| 3-036 | 3,4-Cl$_2$ | CF$_3$ | CH$_2$CH$_2$CH$_2$C(O)OEt | 105.0-107.0 |
| 3-037 | 3,4-Cl$_2$ | CF$_3$ | CH$_2$(Ph-4-F) | 155.0-156.0 |
| 3-038 | 3,4-Cl$_2$ | CF$_3$ | CH$_2$(Ph-4-Cl) | 191.0-193.0 |
| 3-039 | 3,4-Cl$_2$ | CF$_3$ | CH$_2$(Ph-3-CH$_3$) | 198.0-200.0 |
| 3-040 | 3,4-Cl$_2$ | CF$_3$ | CH$_2$(Ph-3,4-Cl$_2$) | 161.0-162.0 |
| 3-041 | 3,4-Cl$_2$ | CF$_3$ | CH$_2$CH(Ph)OH | 211.0-213.0 |
| 3-042 | 3,4-Cl$_2$ | CF$_3$ | CH$_2$C(O)(Ph-4-Br) | 193.0-195.0 |
| 3-043 | 3,4-Cl$_2$ | CF$_3$ | CH$_2$(D-1a) | 179.0-180.0 |
| 3-044 | 3,4-Cl$_2$ | CF$_3$ | CH$_2$(D-48e)Cl | 154.0-157.0 |
| 3-045 | 3,4-Cl$_2$ | CF$_3$ | CH$_2$(D-50d) | 183.0-186.0 |
| 3-046 | 3,4-Cl$_2$ | CF$_3$ | CH$_2$CH$_2$(D-49a) | 113.0-116.0 |
| 3-047 | 3,4-Cl$_2$ | CF$_3$ | NHPh | 160.0-162.0 |
| 3-048 | 3,4-Cl$_2$ | CF$_3$ | Ph | 208.0-210.0 |
| 3-049 | 3,4-Cl$_2$ | CF$_3$ | Ph-2-CH$_3$-4-Cl | 237.0-238.0 |
| 3-050 | 3,4-Cl$_2$ | CF$_3$ | D-35a | 238.0-241.0 |
| 3-051 | 3,4-Cl$_2$ | CF$_3$ | D-47a | 167.0-169.0 |
| 3-052 | 3,4-Cl$_2$ | CN | CH$_2$CF$_3$ | 162.0-164.0 |
| 3-053 | 3,4-Cl$_2$ | Ph | CH$_2$Pr-c | 153.0-154.0 |
| 3-054 | 3,4-Cl$_2$ | Ph | CH$_2$CF$_3$ | 157.0-158.0 |
| 3-055 | 3,4-Cl$_2$ | Ph | CH$_2$Ph | 173.0-175.0 |
| 3-056 | 3,5-Cl$_2$ | c-Pr | CH$_2$CF$_3$ | 144.0-145.0 |
| 3-057 | 3,5-Cl$_2$ | CF$_3$ | H | 256.0-258.0 |
| 3-058 | 3,5-Cl$_2$ | CF$_3$ | i-Bu | 167.0-170.0 |
| 3-059 | 3,5-Cl$_2$ | CF$_3$ | CH$_2$Cl | *1 |
| 3-060 | 3,5-Cl$_2$ | CF$_3$ | CH$_2$CF$_3$ | 94.0-96.0 |
| 3-061 | 3,5-Cl$_2$ | CF$_3$ | CH$_2$(T-4) | 84.0-87.0 |
| 3-062 | 3,5-Cl$_2$ | CF$_3$ | CH$_2$OH | 254.0-260.0 |
| 3-063 | 3,5-Cl$_2$ | CF$_3$ | CH$_2$CH(OCH$_3$)$_2$ | 198.0-200.0 |
| 3-064 | 3,5-Cl$_2$ | CF$_3$ | CH$_2$CH(OEt)$_2$ | *1 |
| 3-065 | 3,5-Cl$_2$ | CF$_3$ | CH$_2$CH(CH$_3$)OC(O)NHEt | 127.0-129.0 |
| 3-066 | 3,5-Cl$_2$ | CF$_3$ | CH$_2$CH(CH$_3$)OC(O)NH(Ph-4-F) | 162.0-165.0 |
| 3-067 | 3,5-Cl$_2$ | CF$_3$ | CH$_2$CH(OH)CH$_2$OH | *1 |
| 3-068 | 3,5-Cl$_2$ | CF$_3$ | CH$_2$(E-4a) | 123.5-126.0 |
| 3-069 | 3,5-Cl$_2$ | CF$_3$ | CH$_2$(E-5a) | *1 |
| 3-070 | 3,5-Cl$_2$ | CF$_3$ | CH$_2$(E-10a) | 152.0-153.0 |
| 3-071 | 3,5-Cl$_2$ | CF$_3$ | CH$_2$(E-10b)CH$_3$ | 151.0-153.0 |
| 3-072 | 3,5-Cl$_2$ | CF$_3$ | CH$_2$(E-32a) | *1 |
| 3-073 | 3,5-Cl$_2$ | CF$_3$ | C(CH$_3$)$_2$CH$_2$SCH$_3$ | 91.0-92.0 |
| 3-074 | 3,5-Cl$_2$ | CF$_3$ | C(CH$_3$)$_2$CH$_2$SO$_2$CH$_3$ | *1 |

TABLE 9-continued

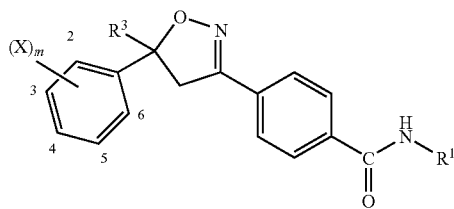

| No. | (X)$_m$ | R$^3$ | R$^1$ | m.p. (° C.) |
|---|---|---|---|---|
| 3-075 | 3,5-Cl$_2$ | CF$_3$ | CH$_2$(E-18a) | 124.0-126.0 |
| 3-076 | 3,5-Cl$_2$ | CF$_3$ | CH$_2$(E-18c) | 253.0-255.0 |
| 3-077 | 3,5-Cl$_2$ | CF$_3$ | CH$_2$CHO | *1 |
| 3-078 | 3,5-Cl$_2$ | CF$_3$ | CH$_2$CH=NOH | *1 |
| 3-079 | 3,5-Cl$_2$ | CF$_3$ | CH$_2$CH=NOCH$_3$ | *1 |
| 3-080 | 3,5-Cl$_2$ | CF$_3$ | CH$_2$C(CH$_3$)=NOCH$_3$ | 71.0-75.0 |
| 3-081 | 3,5-Cl$_2$ | CF$_3$ | CH$_2$CN | 145.0-151.0 |
| 3-082 | 3,5-Cl$_2$ | CF$_3$ | CH$_2$C(O)OH | *1 |
| 3-083 | 3,5-Cl$_2$ | CF$_3$ | CH$_2$C(O)OCH$_3$ | *1 |
| 3-084 | 3,5-Cl$_2$ | CF$_3$ | CH$_2$C(O)NH$_2$ | 100.0-107.0 |
| 3-085 | 3,5-Cl$_2$ | CF$_3$ | CH$_2$C(O)NHCH$_2$CH$_2$Cl | 161.5-165.0 |
| 3-086 | 3,5-Cl$_2$ | CF$_3$ | CH$_2$C(O)NHCH$_2$CF$_3$ | 108.0-114.0 |
| 3-087 | 3,5-Cl$_2$ | CF$_3$ | CH$_2$C(S)NH$_2$ | *1 |
| 3-088 | 3,5-Cl$_2$ | CF$_3$ | CH$_2$C(=NOH)NH$_2$•HCl | 140.0-144.5 |
| 3-089 | 3,5-Cl$_2$ | CF$_3$ | CH$_2$CH=CH$_2$ | *1 |
| 3-090 | 3,5-Cl$_2$ | CF$_3$ | CH$_2$C(CH$_3$)=CH$_2$ | 133.0-136.0 |
| 3-091 | 3,5-Cl$_2$ | CF$_3$ | CH$_2$CCl=CH$_2$ | 121.0-123.0 |
| 3-092 | 3,5-Cl$_2$ | CF$_3$ | CH$_2$CH=CCl$_2$ | 118.0-120.0 |
| 3-093 | 3,5-Cl$_2$ | CF$_3$ | CH$_2$CCl=CHCl | 153.0-154.0 |
| 3-094 | 3,5-Cl$_2$ | CF$_3$ | CH$_2$C≡CH | 144.0-146.0 |
| 3-095 | 3,5-Cl$_2$ | CF$_3$ | CH$_2$Ph | 174.0-177.0 |
| 3-096 | 3,5-Cl$_2$ | CF$_3$ | CH$_2$(Ph-4-Br) | 203.0-205.0 |
| 3-097 | 3,5-Cl$_2$ | CF$_3$ | CH$_2$(Ph-4-SCH$_3$) | 182.0-184.0 |
| 3-098 | 3,5-Cl$_2$ | CF$_3$ | CH$_2$[Ph-4-S(O)CH$_3$] | 170.0-174.0 |
| 3-099 | 3,5-Cl$_2$ | CF$_3$ | CH$_2$(Ph-4-SO$_2$CH$_3$) | 214.0-216.0 |
| 3-100 | 3,5-Cl$_2$ | CF$_3$ | CH$_2$(Ph-2-NO$_2$) | 165.0-167.0 |
| 3-101 | 3,5-Cl$_2$ | CF$_3$ | CH$_2$(D-1a) | 178.5-181.0 |
| 3-102 | 3,5-Cl$_2$ | CF$_3$ | CH$_2$(D-3a) | 201.0-202.0 |
| 3-103 | 3,5-Cl$_2$ | CF$_3$ | CH$_2$(D-3d)Cl | 144.0-146.0 |
| 3-104 | 3,5-Cl$_2$ | CF$_3$ | CH$_2$(D-10b)Cl | 87.0-95.0 |
| 3-105 | 3,5-Cl$_2$ | CF$_3$ | CH$_2$(D-15a)CH$_3$ | 154.0-155.0 |
| 3-106 | 3,5-Cl$_2$ | CF$_3$ | CH$_2$(D-16b)Cl | 224.0-225.0 |
| 3-107 | 3,5-Cl$_2$ | CF$_3$ | CH$_2$(D-16c)Cl | *1 |
| 3-108 | 3,5-Cl$_2$ | CF$_3$ | CH$_2$(D-16d) | *1 |
| 3-109 | 3,5-Cl$_2$ | CF$_3$ | CH$_2$(D-17a)CH$_3$ | 59.0-61.0 |
| 3-110 | 3,5-Cl$_2$ | CF$_3$ | CH$_2$(D-17b)Cl | *1 |
| 3-111 | 3,5-Cl$_2$ | CF$_3$ | CH$_2$(D-21a) | 178.0-179.0 |
| 3-112 | 3,5-Cl$_2$ | CF$_3$ | CH$_2$(D-22a) | 156.0-158.0 |
| 3-113 | 3,5-Cl$_2$ | CF$_3$ | CH$_2$(D-22b)Cl | 94.0-96.0 |
| 3-114 | 3,5-Cl$_2$ | CF$_3$ | CH$_2$(D-22b)CH$_3$ | *1 |
| 3-115 | 3,5-Cl$_2$ | CF$_3$ | CH$_2$(D-23a) | 191.0-193.0 |
| 3-116 | 3,5-Cl$_2$ | CF$_3$ | CH$_2$(D-23b)Cl | 165.0-167.0 |
| 3-117 | 3,5-Cl$_2$ | CF$_3$ | CH$_2$(D-24b) | 218.0-220.0 |
| 3-118 | 3,5-Cl$_2$ | CF$_3$ | CH$_2$(D-24c) | *1 |
| 3-119 | 3,5-Cl$_2$ | CF$_3$ | CH$_2$(D-25a)CH$_3$ | *1 |
| 3-120 | 3,5-Cl$_2$ | CF$_3$ | CH$_2$(D-27a)CH$_3$ | *1 |
| 3-121 | 3,5-Cl$_2$ | CF$_3$ | CH$_2$(D-29b)CH$_3$ | *1 |
| 3-122 | 3,5-Cl$_2$ | CF$_3$ | CH$_2$(D-34a) | *1 |
| 3-123 | 3,5-Cl$_2$ | CF$_3$ | CH$_2$(D-35a) | 157.5-161.0 |
| 3-124 | 3,5-Cl$_2$ | CF$_3$ | CH$_2$(D-38a) | 224.5-226.0 |
| 3-125 | 3,5-Cl$_2$ | CF$_3$ | CH$_2$(D-47a) | 150.0-151.0 |
| 3-126 | 3,5-Cl$_2$ | CF$_3$ | CH$_2$(D-47c)Cl | 124.0-126.0 |
| 3-127 | 3,5-Cl$_2$ | CF$_3$ | CH$_2$(D-47e)CH$_3$ | *2 |
| 3-128 | 3,5-Cl$_2$ | CF$_3$ | CH$_2$(D-47i) | 121.0-124.0 |
| 3-129 | 3,5-Cl$_2$ | CF$_3$ | CH$_2$(D-48e)Cl | 159.5-163.0 |
| 3-130 | 3,5-Cl$_2$ | CF$_3$ | CH$_2$(D-50d) | 250.0-255.0 |
| 3-131 | 3,5-Cl$_2$ | CF$_3$ | CH$_2$(D-53b)CH$_3$ | *1 |
| 3-132 | 3,5-Cl$_2$ | CF$_3$ | CH(CH$_3$)Ph | 137.5-141.0 |
| 3-133 | 3,5-Cl$_2$ | CF$_3$ | C(O)(D-47a) | *1 |
| 3-134 | 3,5-Cl$_2$ | CF$_3$ | OCH$_3$ | *1 |
| 3-135 | 3,5-Cl$_2$ | CF$_3$ | NH(D-47a) | *1 |
| 3-136 | 3,5-Cl$_2$ | CF$_3$ | NH(D-50a) | 202.0-204.0 |
| 3-137 | 3,5-Cl$_2$ | CF$_3$ | NH(D-50b)CF$_3$ | 146.0-149.0 |
| 3-138 | 3,5-Cl$_2$ | CF$_3$ | NH(D-54b)Cl | 124.0-130.0 |
| 3-139 | 3,5-Cl$_2$ | CF$_3$ | N(CH$_3$)Ph | 174.0-178.0 |
| 3-140 | 3,5-Cl$_2$ | CF$_3$ | D-21a | 268.0-273.0 |
| 3-141 | 3-CH$_3$-4-F | CF$_3$ | CH$_2$CF$_3$ | 151.0-152.0 |

TABLE 9-continued

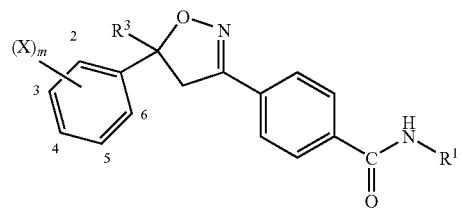

| No. | (X)$_m$ | R$^3$ | R$^1$ | m.p. (° C.) |
|---|---|---|---|---|
| 3-142 | 3-Cl-5-CH$_3$ | CF$_3$ | CH$_2$CF$_3$ | 74.0-76.0 |
| 3-143 | 3-Cl-5-CH$_3$ | CF$_3$ | CH$_2$(D-47a) | *1 |
| 3-144 | 3-Cl-4-OCH$_3$ | CF$_3$ | CH$_2$CF$_3$ | 135.0-138.0 |
| 3-145 | 3-CF$_3$-5-OCH$_3$ | CF$_3$ | CH$_2$CF$_3$ | 161.0-162.0 |
| 3-146 | 3-OCH$_2$O-4 | CF$_3$ | CH$_2$CF$_3$ | 149.0-151.0 |
| 3-147 | 2-F-3-CH$_3$-5-Cl | CF$_3$ | CH$_2$CF$_3$ | *1 |
| 3-148 | 3,5-Cl$_2$ | CF$_3$ | CH$_2$(D-34b)CH$_3$ | 143.0-144.5 |
| 3-149 | 3,5-Cl$_2$ | CF$_3$ | NH$_2$ | 170.0-172.0 |
| 3-150 | 3,5-Cl$_2$ | CF$_3$ | Ph-4-F | 166.0-168.0 |
| 3-151 | 3,5-Cl$_2$ | CF$_3$ | E-4a | 210.0-213.0 |

TABLE 10

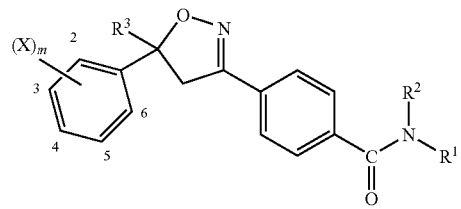

| No. | (X)$_m$ | R$^3$ | R$^2$ | R$^1$ | m.p. (° C.) |
|---|---|---|---|---|---|
| 4-001 | 3,4-Cl$_2$ | CF$_3$ | —CH$_2$CH$_2$CH(CH$_3$)CH$_2$CH$_2$— | | 132.0-134.0 |
| 4-002 | 3,4-Cl$_2$ | CF$_3$ | —CH$_2$CH$_2$CH$_2$CH$_2$CH$_2$CH$_2$— | | 160.0-163.0 |
| 4-003 | 3,5-Cl$_2$ | CF$_3$ | CH$_2$OCH$_3$ | CH$_2$(D-47a) | *1 |
| 4-004 | 3,5-Cl$_2$ | CF$_3$ | CH$_2$OEt | CH$_2$(D-47a) | *1 |
| 4-005 | 3,5-Cl$_2$ | CF$_3$ | CH$_2$SO$_2$CH$_3$ | CH$_2$(D-47a) | *1 |
| 4-006 | 3,5-Cl$_2$ | CF$_3$ | CH$_2$CH=CH$_2$ | CH$_2$(D-47a) | *1 |
| 4-007 | 3,5-Cl$_2$ | CF$_3$ | CH(CH=CH$_2$)CH$_2$CH=CH$_2$ | CH$_2$(D-47a) | *1 |
| 4-008 | 3,5-Cl$_2$ | CF$_3$ | CH$_2$Ph | CH$_2$(D-47a) | *1 |
| 4-009 | 3,5-Cl$_2$ | CF$_3$ | C(O)OCH$_3$ | CH$_2$(D-47a) | *1 |
| 4-010 | 3,5-Cl$_2$ | CF$_3$ | Et | CH$_2$(D-48e)Cl | *1 |
| 4-011 | 3,5-Cl$_2$ | CF$_3$ | CH$_3$ | OCH$_3$ | *1 |

TABLE 11

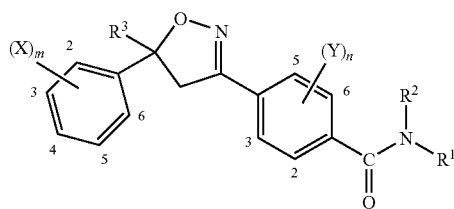

| No. | (X)$_m$ | R$^3$ | (Y)$_n$ | R$^1$ | m.p. (C. °) |
|---|---|---|---|---|---|
| 5-001 | 3-Cl | CF$_3$ | 2-CH$_3$ | CH$_2$(D-47a) | *1 |
| 5-002 | 3-Br | CF$_3$ | 2-CH$_3$ | CH$_2$CF$_3$ | 158.5-161.0 |
| 5-003 | 3-Br | CF$_3$ | 2-CH$_3$ | CH$_2$(D-47a) | *1 |
| 5-004 | 3-I | CF$_3$ | 2-CH$_3$ | CH$_2$CF$_3$ | 168.0-172.5 |
| 5-005 | 3-I | CF$_3$ | 2-CH$_3$ | CH$_2$(D-47a) | 135.5-138.0 |
| 5-006 | 4-I | CF$_3$ | 2-CH$_3$ | CH$_2$CF$_3$ | 134.0-135.0 |
| 5-007 | 4-I | CF$_3$ | 2-CH$_3$ | CH$_2$(D-47a) | *1 |
| 5-008 | 3-CF$_3$ | CF$_3$ | 2-CH$_3$ | CH$_2$CF$_3$ | 135.5-137.5 |
| 5-009 | 3-CF$_3$ | CF$_3$ | 2-CH$_3$ | CH$_2$(D-47a) | *1 |
| 5-010 | 3-(T-4) | CF$_3$ | 2-CH$_3$ | CH$_2$CF$_3$ | *2 |

TABLE 11-continued

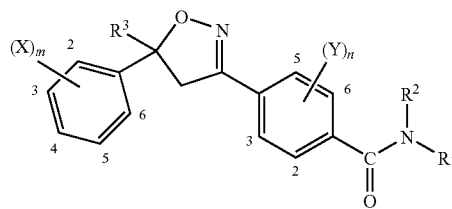

| No. | (X)$_m$ | R$^3$ | (Y)$_n$ | R$^1$ | m.p. (C. °) |
|---|---|---|---|---|---|
| 5-011 | 3-(T-4) | CF$_3$ | 2-CH$_3$ | CH$_2$(D-47a) | *2 |
| 5-012 | 3-OCF$_3$ | CF$_3$ | 2-CH$_3$ | CH$_2$CF$_3$ | *2 |
| 5-013 | 3-OCF$_3$ | CF$_3$ | 2-CH$_3$ | CH$_2$(D-47a) | *1 |
| 5-014 | 3-OCF$_2$Br | CF$_3$ | 2-CH$_3$ | CH$_2$CF$_3$ | *1 |
| 5-015 | 3-OCF$_2$Br | CF$_3$ | 2-CH$_3$ | CH$_2$(D-47a) | *2 |
| 5-016 | 3-OCF$_2$CHFOCF$_2$CF$_2$CF$_3$ | CF$_3$ | 2-CH$_3$ | CH$_2$CF$_3$ | *1 |
| 5-017 | 3-OCF$_2$CHFOCF$_2$CF$_2$CF$_3$ | CF$_3$ | 2-CH$_3$ | CH$_2$(D-47a) | *1 |
| 5-018 | 3-OCH$_2$(Ph-2-Cl) | CF$_3$ | 2-CH$_3$ | CH$_2$(D-47a) | *1 |
| 5-019 | 3-O[(D-47f)-3-Cl-5-CF$_3$] | CF$_3$ | 2-CH$_3$ | CH$_2$CF$_3$ | *1 |
| 5-020 | 3-O[(D-47f)-3-Cl-5-CF$_3$] | CF$_3$ | 2-CH$_3$ | CH$_2$(D-47a) | *1 |
| 5-021 | 3-SEt | CF$_3$ | 2-CH$_3$ | CH$_2$(D-47a) | *1 |
| 5-022 | 3-SCF$_3$ | CF$_3$ | 2-CH$_3$ | CH$_2$CF$_3$ | *1 |
| 5-023 | 3-SCF$_3$ | CF$_3$ | 2-CH$_3$ | CH$_2$(D-47a) | *1 |
| 5-024 | 3-N(CH$_3$)C(O)CF$_3$ | CF$_3$ | 2-CH$_3$ | CH$_2$CF$_3$ | *1 |
| 5-025 | 3-N(CH$_3$)C(O)CF$_3$ | CF$_3$ | 2-CH$_3$ | CH$_2$(D-47a) | *1 |
| 5-026 | 3-N(CH$_3$)SO$_2$CF$_3$ | CF$_3$ | 2-CH$_3$ | CH$_2$CF$_3$ | *1 |
| 5-027 | 3-N(CH$_3$)SO$_2$CF$_3$ | CF$_3$ | 2-CH$_3$ | CH$_2$(D-47a) | *1 |
| 5-028 | 3-Ph | CF$_3$ | 2-CH$_3$ | CH$_2$(D-47a) | *1 |
| 5-029 | 3,5-F$_2$ | CF$_3$ | 2-CH$_3$ | CH$_2$(D-47a) | *1 |
| 5-030 | 3,5-Cl$_2$ | CH$_3$ | 2-CH$_3$ | CH$_2$CF$_3$ | *1 |
| 5-031 | 3,5-Cl$_2$ | i-Pr | 2-CH$_3$ | CH$_2$CF$_3$ | *1 |
| 5-032 | 3,5-Cl$_2$ | c-Pr | 2-CH$_3$ | CH$_2$CF$_3$ | 157.0-158.0 |
| 5-033 | 3,5-Cl$_2$ | c-Pr | 2-CH$_3$ | CH$_2$(D-47a) | *1 |
| 5-034 | 3,5-Cl$_2$ | CH$_2$Cl | 2-CH$_3$ | CH$_2$CF$_3$ | 117.0-119.0 |
| 5-035 | 3,5-Cl$_2$ | CH$_2$Cl | 2-CH$_3$ | CH$_2$(D-47a) | *1 |
| 5-036 | 3,5-Cl$_2$ | CHF$_2$ | 2-CH$_3$ | CH$_2$CF$_3$ | 94.0-97.5 |
| 5-037 | 3,5-Cl$_2$ | CHF$_2$ | 2-CH$_3$ | CH$_2$(D-47a) | *1 |
| 5-038 | 3,5-Cl$_2$ | CF$_3$ | 2-F | CH$_2$CF$_3$ | *1 |
| 5-039 | 3,5-Cl$_2$ | CF$_3$ | 2-F | CH$_2$Ph | 172.0-176.0 |
| 5-040 | 3,5-Cl$_2$ | CF$_3$ | 2-F | CH$_2$(D-22a) | *1 |
| 5-041 | 3,5-Cl$_2$ | CF$_3$ | 2-F | CH$_2$(D-47a) | 126.0-129.0 |
| 5-042 | 3,5-Cl$_2$ | CF$_3$ | 3-F | CH$_2$CF$_3$ | *1 |
| 5-043 | 3,5-Cl$_2$ | CF$_3$ | 3-F | CH$_2$Ph | 178.0-181.0 |
| 5-044 | 3,5-Cl$_2$ | CF$_3$ | 3-F | CH$_2$(D-47a) | 125.0-127.0 |
| 5-045 | 3,5-Cl$_2$ | CF$_3$ | 2-Cl | CH$_2$Pr-c | 132.0-134.0 |
| 5-046 | 3,5-Cl$_2$ | CF$_3$ | 2-Cl | CH$_2$CF$_3$ | 124.0-125.0 |
| 5-047 | 3,5-Cl$_2$ | CF$_3$ | 2-Cl | CH$_2$Ph | 57.0-58.0 |
| 5-048 | 3,5-Cl$_2$ | CF$_3$ | 2-Cl | CH$_2$(Ph-4-NO$_2$) | *1 |
| 5-049 | 3,5-Cl$_2$ | CF$_3$ | 2-Cl | CH$_2$(D-21a) | *1 |
| 5-050 | 3,5-Cl$_2$ | CF$_3$ | 2-Cl | CH$_2$(D-22a) | *1 |
| 5-051 | 3,5-Cl$_2$ | CF$_3$ | 2-Cl | CH$_2$(D-22b)Ol | *2 |
| 5-052 | 3,5-Cl$_2$ | CF$_3$ | 2-Cl | CH$_2$(D-28a) | *1 |
| 5-053 | 3,5-Cl$_2$ | CF$_3$ | 2-Cl | CH$_2$(D-47a) | *1 |
| 5-054 | 3,5-Cl$_2$ | CF$_3$ | 3-Cl | CH$_2$CF$_3$ | 149.0-150.0 |
| 5-055 | 3,5-Cl$_2$ | CF$_3$ | 3-Cl | CH$_2$Ph | 119.0-121.0 |
| 5-056 | 3,5-Cl$_2$ | CF$_3$ | 3-Cl | CH$_2$(D-47a) | *1 |
| 5-057 | 3,5-Cl$_2$ | CF$_3$ | 2-Br | CH$_2$CF$_3$ | 145.0-147.0 |
| 5-058 | 3,5-Cl$_2$ | CF$_3$ | 2-Br | CH$_2$(D-47a) | *1 |
| 5-059 | 3,5-Cl$_2$ | CF$_3$ | 2-I | CH$_2$CF$_3$ | 128.0-130.0 |
| 5-060 | 3,5-Cl$_2$ | CF$_3$ | 2-I | CH$_2$CH$_2$OEt | *1 |
| 5-061 | 3,5-Cl$_2$ | CF$_3$ | 2-I | CH$_2$CH(OCH$_3$)$_2$ | *1 |
| 5-062 | 3,5-Cl$_2$ | CF$_3$ | 2-I | CH$_2$C(O)NHCH$_3$ | *1 |
| 5-063 | 3,5-Cl$_2$ | CF$_3$ | 2-I | CH$_2$C(O)NHCH$_2$CH$_2$Cl | 68.0-70.0 |
| 5-064 | 3,5-Cl$_2$ | CF$_3$ | 2-I | CH$_2$CH=CH$_2$ | 97.0-100.0 |
| 5-065 | 3,5-Cl$_2$ | CF$_3$ | 2-I | CH$_2$(D-47a) | *1 |
| 5-066 | 3,5-Cl$_2$ | CF$_3$ | 2-CH$_3$ | H | 162.0-164.0 |
| 5-067 | 3,5-Cl$_2$ | CF$_3$ | 2-CH$_3$ | Et | 129.5-133.0 |
| 5-068 | 3,5-Cl$_2$ | CF$_3$ | 2-CH$_3$ | c-Pr | 84.0-86.0 |
| 5-069 | 3,5-Cl$_2$ | CF$_3$ | 2-CH$_3$ | i-Bu | 138.0-140.0 |
| 5-070 | 3,5-Cl$_2$ | CF$_3$ | 2-CH$_3$ | CH$_2$Pr-c | *1 |
| 5-071 | 3,5-Cl$_2$ | CF$_3$ | 2-CH$_3$ | c-Bu | 139.0-141.0 |
| 5-072 | 3,5-Cl$_2$ | CF$_3$ | 2-CH$_3$ | CH$_2$Bu-c | *1 |
| 5-073 | 3,5-Cl$_2$ | CF$_3$ | 2-CH$_3$ | c-Pen | 155.0-158.0 |
| 5-074 | 3,5-Cl$_2$ | CF$_3$ | 2-CH$_3$ | CH$_2$CH$_2$Cl | 161.5-164.5 |
| 5-075 | 3,5-Cl$_2$ | CF$_3$ | 2-CH$_3$ | CH$_2$CF$_3$ | 155.5-157.0 |
| 5-075(+) | 99% e.e. | | [α]$_D^{23.0}$ + 74.38° | (EtOH, c = 0.621) | *1 |
| 5-075(−) | 99% e.e. | | [α]$_D^{22.8}$ − 70.98° | (EtOH, c = 0.648) | *1 |

TABLE 11-continued

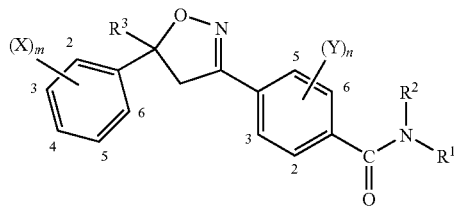

| No. | (X)$_m$ | R$^3$ | (Y)$_n$ | R$^1$ | m.p. (C. °) |
|---|---|---|---|---|---|
| 5-076 | 3,5-Cl$_2$ | CF$_3$ | 2-CH$_3$ | CH$_2$CH$_2$OCH$_3$ | 115.0-117.0 |
| 5-077 | 3,5-Cl$_2$ | CF$_3$ | 2-CH$_3$ | CH$_2$CH$_2$OEt | *1 |
| 5-078 | 3,5-Cl$_2$ | CF$_3$ | 2-CH$_3$ | CH$_2$CH$_2$OCH$_2$CH$_2$Cl | 140.0-142.0 |
| 5-079 | 3,5-Cl$_2$ | CF$_3$ | 2-CH$_3$ | CH$_2$CH$_2$OC(O)CH$_3$ | *2 |
| 5-080 | 3,5-Cl$_2$ | CF$_3$ | 2-CH$_3$ | CH$_2$CH$_2$OC(O)NHEt | *2 |
| 5-081 | 3,5-Cl$_2$ | CF$_3$ | 2-CH$_3$ | CH$_2$OH(CH$_3$)OH | 67.0-70.0 |
| 5-082 | 3,5-Cl$_2$ | CF$_3$ | 2-CH$_3$ | CH$_2$OH(CH$_3$)OCH$_3$ | 179.0-181.0 |
| 5-083 | 3,5-Cl$_2$ | CF$_3$ | 2-CH$_3$ | CH$_2$OH(OCH$_3$)$_2$ | *1 |
| 5-084 | 3,5-Cl$_2$ | CF$_3$ | 2-CH$_3$ | CH$_2$CH(OEt)$_2$ | *2 |
| 5-085 | 3,5-Cl$_2$ | CF$_3$ | 2-CH$_3$ | CH(CH$_3$)CH$_2$OC(O)NHEt | *1 |
| 5-086 | 3,5-Cl$_2$ | CF$_3$ | 2-CH$_3$ | CH$_2$(E-4a) | *1 |
| 5-087 | 3,5-Cl$_2$ | CF$_3$ | 2-CH$_3$ | CH$_2$(E-5a) | *2 |
| 5-088 | 3,5-Cl$_2$ | CF$_3$ | 2-CH$_3$ | CH$_2$(E-10a) | 158.5-160.5 |
| 5-089 | 3,5-Cl$_2$ | CF$_3$ | 2-CH$_3$ | CH$_2$(E-10b)CH$_3$ | 153.0-154.0 |
| 5-090 | 3,5-Cl$_2$ | CF$_3$ | 2-CH$_3$ | CH$_2$(E-32a) | *1 |
| 5-091 | 3,5-Cl$_2$ | CF$_3$ | 2-CH$_3$ | CH$_2$CH$_2$SCH$_3$ | 121.0-127.0 |
| 5-092 | 3,5-Cl$_2$ | CF$_3$ | 2-CH$_3$ | CH$_2$CH$_2$S(O)CH$_3$ | *1 |
| 5-093 | 3,5-Cl$_2$ | CF$_3$ | 2-CH$_3$ | CH$_2$CH$_2$SEt | 106.0-109.0 |
| 5-094 | 3,5-Cl$_2$ | CF$_3$ | 2-CH$_3$ | CH$_2$CH$_2$SO$_2$Et | *1 |
| 5-095 | 3,5-Cl$_2$ | CF$_3$ | 2-CH$_3$ | CH$_2$CH$_2$SCH$_2$Ph | *1 |
| 5-096 | 3,5-Cl$_2$ | CF$_3$ | 2-CH$_3$ | CH$_2$CH$_2$SO$_2$CH$_2$Ph | *1 |
| 5-097 | 3,5-Cl$_2$ | CF$_3$ | 2-CH$_3$ | CH$_2$CH$_2$SCH$_2$(D-1a) | *1 |
| 5-098 | 3,5-Cl$_2$ | CF$_3$ | 2-CH$_3$ | CH$_2$CH$_2$SO$_2$CH$_2$(D-1a) | *1 |
| 5-099 | 3,5-Cl$_2$ | CF$_3$ | 2-CH$_3$ | CH$_2$CH(CH$_3$)SCH$_3$ | *1 |
| 5-100 | 3,5-Cl$_2$ | CF$_3$ | 2-CH$_3$ | CH$_2$CH(CH$_3$)S(O)CH$_3$ | *1 |
| 5-101 | 3,5-Cl$_2$ | CF$_3$ | 2-CH$_3$ | CH$_2$CH(CH$_3$)SO$_2$CH$_3$ | *1 |
| 5-102 | 3,5-Cl$_2$ | CF$_3$ | 2-CH$_3$ | CH(CH$_3$)CH$_2$SCH$_3$ | *1 |
| 5-103 | 3,5-Cl$_2$ | CF$_3$ | 2-CH$_3$ | CH(CH$_3$)CH$_2$SO$_2$CH$_3$ | *1 |
| 5-104 | 3,5-Cl$_2$ | CF$_3$ | 2-CH$_3$ | C(CH$_3$)$_2$CH$_2$SCH$_3$ | *1 |
| 5-105 | 3,5-Cl$_2$ | CF$_3$ | 2-CH$_3$ | C(CH$_3$)$_2$CH$_2$SO$_2$CH$_3$ | 167.0-169.0 |
| 5-106 | 3,5-Cl$_2$ | CF$_3$ | 2-CH$_3$ | CH$_2$(E-18a) | 204.0-206.0 |
| 5-107 | 3,5-Cl$_2$ | CF$_3$ | 2-CH$_3$ | CH$_2$(E-18c) | 249.0-251.0 |
| 5-108 | 3,5-Cl$_2$ | CF$_3$ | 2-CH$_3$ | CH$_2$(E-43a) | 199.0-201.0 |
| 5-109 | 3,5-Cl$_2$ | CF$_3$ | 2-CH$_3$ | CH$_2$CH$_2$NHC(O)CF$_3$ | 81.0-84.0 |
| 5-110 | 3,5-Cl$_2$ | CF$_3$ | 2-CH$_3$ | CH$_2$CH$_2$NHC(O)CH$_2$CF$_3$ | 143.0-146.0 |
| 5-111 | 3,5-Cl$_2$ | CF$_3$ | 2-CH$_3$ | CH$_2$C(O)CH$_3$ | 155.0-160.0 |
| 5-112 | 3,5-Cl$_2$ | CF$_3$ | 2-CH$_3$ | CH$_2$CH=NOH | *1 |
| 5-113 | 3,5-Cl$_2$ | CF$_3$ | 2-CH$_3$ | CH$_2$CH=NOCH$_3$ | *2 |
| 5-114 | 3,5-Cl$_2$ | CF$_3$ | 2-CH$_3$ | CH$_2$CH=NOCH$_2$Pr-c | *1 |
| 5-115 | 3,5-Cl$_2$ | CF$_3$ | 2-CH$_3$ | CH$_2$CH=NOCH$_2$(Ph-4-Cl) | *2 |
| 5-116 | 3,5-Cl$_2$ | CF$_3$ | 2-CH$_3$ | CH$_2$CH=NOCH$_2$CH$_2$-TMS | *1 |
| 5-117 | 3,5-Cl$_2$ | CF$_3$ | 2-CH$_3$ | CH$_2$C(CH$_3$)=NOCH$_3$ | 101.0-105.0 |
| 5-118 | 3,5-Cl$_2$ | CF$_3$ | 2-CH$_3$ | CH$_2$(M-5a)CH$_3$ | *1 |
| 5-119 | 3,5-Cl$_2$ | CF$_3$ | 2-CH$_3$ | CH$_2$CN | 186.5-189.0 |
| 5-120 | 3,5-Cl$_2$ | CF$_3$ | 2-CH$_3$ | CH(OCH$_2$CF$_3$)CN | *1 |
| 5-121 | 3,5-Cl$_2$ | CF$_3$ | 2-CH$_3$ | CH(Ph)CN | 165.5-167.0 |
| 5-122 | 3,5-Cl$_2$ | CF$_3$ | 2-CH$_3$ | CH(D-1a)CN | *1 |
| 5-123 | 3,5-Cl$_2$ | CF$_3$ | 2-CH$_3$ | CH(D-3a)CN | *1 |
| 5-124 | 3,5-Cl$_2$ | CF$_3$ | 2-CH$_3$ | CH(D-14a)CN | 192.0-194.5 |
| 5-125 | 3,5-Cl$_2$ | CF$_3$ | 2-CH$_3$ | CH(D-38a)CN | 185.0-189.5 |
| 5-126 | 3,5-Cl$_2$ | CF$_3$ | 2-CH$_3$ | CH(D-47a)CN | *1 |
| 5-127 | 3,5-Cl$_2$ | CF$_3$ | 2-CH$_3$ | CH$_2$C(O)OH | 195.0-197.0 |
| 5-128 | 3,5-Cl$_2$ | CF$_3$ | 2-CH$_3$ | CH$_2$C(O)OCH$_3$ | *2 |
| 5-129 | 3,5-Cl$_2$ | CF$_3$ | 2-CH$_3$ | CH$_2$C(O)OCH$_2$CF$_3$ | 157.0-158.0 |
| 5-130 | 3,5-Cl$_2$ | CF$_3$ | 2-CH$_3$ | CH(CH$_3$)C(O)OCH$_3$(D) | *1 |
| 5-131 | 3,5-Cl$_2$ | CF$_3$ | 2-CH$_3$ | CH(CH$_3$)C(O)OEt(L) | *1 |
| 5-132 | 3,5-Cl$_2$ | CF$_3$ | 2-CH$_3$ | CH(CH$_3$)C(O)OCH$_2$CF$_3$ | *1 |
| 5-133 | 3,5-Cl$_2$ | CF$_3$ | 2-CH$_3$ | CH(OH)C(O)OCH$_3$ | *1 |
| 5-134 | 3,5-Cl$_2$ | CF$_3$ | 2-CH$_3$ | CH(OCH$_3$)C(O)OCH$_3$ | *1 |
| 5-135 | 3,5-Cl$_2$ | CF$_3$ | 2-CH$_3$ | CH(D-14a)C(O)OCH$_3$ | 93.5-97.0 |
| 5-136 | 3,5-Cl$_2$ | CF$_3$ | 2-CH$_3$ | CH$_2$CH$_2$C(O)OEt | *1 |
| 5-137 | 3,5-Cl$_2$ | CF$_3$ | 2-CH$_3$ | CH$_2$C(O)NH$_2$ | 87.0-91.0 |
| 5-138 | 3,5-Cl$_2$ | CF$_3$ | 2-CH$_3$ | CH$_2$C(O)NHCH$_3$ | *1 |
| 5-139 | 3,5-Cl$_2$ | CF$_3$ | 2-CH$_3$ | CH$_2$C(O)N(CH$_3$)$_2$ | *1 |
| 5-140 | 3,5-Cl$_2$ | CF$_3$ | 2-CH$_3$ | CH$_2$C(O)NHEt | 137.5-141.0 |
| 5-141 | 3,5-Cl$_2$ | CF$_3$ | 2-CH$_3$ | CH$_2$C(O)NHPr-n | *1 |
| 5-142 | 3,5-Cl$_2$ | CF$_3$ | 2-CH$_3$ | CH$_2$C(O)NHPr-i | 152.0-155.0 |

TABLE 11-continued

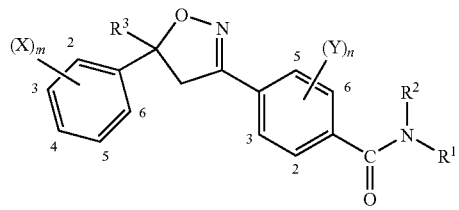

| No. | (X)$_m$ | R$^3$ | (Y)$_n$ | R$^1$ | m.p. (C. °) |
|---|---|---|---|---|---|
| 5-143 | 3,5-Cl$_2$ | CF$_3$ | 2-CH$_3$ | CH$_2$C(O)NHBu-i | *1 |
| 5-144 | 3,5-Cl$_2$ | CF$_3$ | 2-CH$_3$ | CH$_2$C(O)NHBu-c | 174.0-177.0 |
| 5-145 | 3,5-Cl$_2$ | CF$_3$ | 2-CH$_3$ | CH$_2$C(O)NHBu-t | *1 |
| 5-146 | 3,5-Cl$_2$ | CF$_3$ | 2-CH$_3$ | CH$_2$C(O)NHCH$_2$Bu-t | *1 |
| 5-147 | 3,5-Cl$_2$ | CF$_3$ | 2-CH$_3$ | CH$_2$C(O)NHCH$_2$CH$_2$F | *1 |
| 5-148 | 3,5-Cl$_2$ | CF$_3$ | 2-CH$_3$ | CH$_2$C(O)NHCH$_2$CH$_2$Cl | 109.0-112.0 |
| 5-149 | 3,5-Cl$_2$ | CF$_3$ | 2-CH$_3$ | CH$_2$C(O)N(CH$_3$)CH$_2$CH$_2$Cl | *2 |
| 5-150 | 3,5-Cl$_2$ | CF$_3$ | 2-CH$_3$ | CH$_2$C(O)NHCH$_2$CH$_2$Br | *1 |
| 5-151 | 3,5-Cl$_2$ | CF$_3$ | 2-CH$_3$ | CH$_2$C(O)NHCH$_2$CF$_3$ | 173.5-175.5 |
| 5-151(+) | | 99% e.e. | [α]$_D^{23.1}$ + 61.96° | (EtOH, c = 1.098) | *1 |
| 5-151(−) | | 99% e.e. | [α]$_D^{23.1}$ − 58.95° | (EtOH, c = 1.153) | *1 |
| 5-152 | 3,5-Cl$_2$ | CF$_3$ | 2-CH$_3$ | CH$_2$C(O)NHCH$_2$CH$_2$CH$_2$Cl | *1 |
| 5-153 | 3,5-Cl$_2$ | CF$_3$ | 2-CH$_3$ | CH$_2$C(O)NHCH$_2$(T-4) | *1 |
| 5-154 | 3,5-Cl$_2$ | CF$_3$ | 2-CH$_3$ | CH$_2$C(O)NHCH$_2$CH$_2$OH | *1 |
| 5-155 | 3,5-Cl$_2$ | CF$_3$ | 2-CH$_3$ | CH$_2$C(O)N(CH$_3$)CH$_2$CH$_2$OH | *1 |
| 5-156 | 3,5-Cl$_2$ | CF$_3$ | 2-CH$_3$ | CH$_2$C(O)NHCH$_2$CH$_2$OCH$_3$ | 146.0-149.0 |
| 5-157 | 3,5-Cl$_2$ | CF$_3$ | 2-CH$_3$ | CH$_2$C(O)NHCH$_2$CH$_2$OEt | *1 |
| 5-158 | 3,5-Cl$_2$ | CF$_3$ | 2-CH$_3$ | CH$_2$C(O)NHCH$_2$CH$_2$SCH$_3$ | 138.0-143.0 |
| 5-159 | 3,5-Cl$_2$ | CF$_3$ | 2-CH$_3$ | CH$_2$C(O)NHCH$_2$CH$_2$SO$_2$CH$_3$ | *1 |
| 5-160 | 3,5-Cl$_2$ | CF$_3$ | 2-CH$_3$ | CH$_2$C(O)NHCH$_2$CH=CH$_2$ | 76.0-79.0 |
| 5-161 | 3,5-Cl$_2$ | CF$_3$ | 2-CH$_3$ | CH$_2$C(O)N(CH$_3$)CH$_2$CH=CH$_2$ | *1 |
| 5-162 | 3,5-Cl$_2$ | CF$_3$ | 2-CH$_3$ | CH$_2$C(O)N(CH$_2$OH=CH$_2$)$_2$ | *1 |
| 5-163 | 3,5-Cl$_2$ | CF$_3$ | 2-CH$_3$ | CH$_2$C(O)NHCH$_2$CCl=CH$_2$ | *1 |
| 5-164 | 3,5-Cl$_2$ | CF$_3$ | 2-CH$_3$ | CH$_2$C(O)NHCH$_2$CH=CCl$_2$ | 188.0-192.0 |
| 5-165 | 3,5-Cl$_2$ | CF$_3$ | 2-CH$_3$ | CH$_2$C(O)NHCH$_2$C≡CH | *1 |
| 5-166 | 3,5-Cl$_2$ | CF$_3$ | 2-CH$_3$ | CH$_2$C(O)NHCH$_2$Ph | 187.0-191.0 |
| 5-167 | 3,5-Cl$_2$ | CF$_3$ | 2-CH$_3$ | CH$_2$C(O)NHCH$_2$(D-22a) | *1 |
| 5-168 | 3,5-Cl$_2$ | CF$_3$ | 2-CH$_3$ | CH$_2$C(O)NHCH$_2$(D-47a) | *1 |
| 5-169 | 3,5-Cl$_2$ | CF$_3$ | 2-CH$_3$ | CH$_2$C(O)NHPh | 181.0-183.0 |
| 5-170 | 3,5-Cl$_2$ | CF$_3$ | 2-CH$_3$ | CH$_2$C(O)(T-37) | 118.0-121.0 |
| 5-171 | 3,5-Cl$_2$ | CF$_3$ | 2-CH$_3$ | CH$_2$C(O)(T-40) | *1 |
| 5-172 | 3,5-Cl$_2$ | CF$_3$ | 2-CH$_3$ | CH$_2$C(O)NHNHCH$_2$CF$_3$ | 118.0-120.0 |
| 5-173 | 3,5-Cl$_2$ | CF$_3$ | 2-CH$_3$ | CH$_2$C(O)NHN(CH$_3$)Ph | *1 |
| 5-174 | 3,5-Cl$_2$ | CF$_3$ | 2-CH$_3$ | CH(CH$_3$)C(O)NHCH$_2$CH$_2$Cl | 146.0-149.0 |
| 5-175 | 3,5-Cl$_2$ | CF$_3$ | 2-CH$_3$ | CH(Ph)C(O)NHCH$_3$(R) | 118.0-121.0 |
| 5-176 | 3,5-Cl$_2$ | CF$_3$ | 2-CH$_3$ | CH(Ph)C(O)NHCH$_3$(S) | *1 |
| 5-177 | 3,5-Cl$_2$ | CF$_3$ | 2-CH$_3$ | CH$_2$CH$_2$C(O)NHCH$_2$CH$_2$Cl | 153.0-157.0 |
| 5-178 | 3,5-Cl$_2$ | CF$_3$ | 2-CH$_3$ | CH$_2$(T-22) | *1 |
| 5-179 | 3,5-Cl$_2$ | CF$_3$ | 2-CH$_3$ | CH$_2$C(S)NH$_2$ | *1 |
| 5-180 | 3,5-Cl$_2$ | CF$_3$ | 2-CH$_3$ | CH(Ph)O(S)NH$_2$ | *1 |
| 5-181 | 3,5-Cl$_2$ | CF$_3$ | 2-CH$_3$ | CH$_2$Si(CH$_3$)$_3$ | *1 |
| 5-182 | 3,5-Cl$_2$ | CF$_3$ | 2-CH$_3$ | CH$_2$CH=CH$_2$ | *1 |
| 5-183 | 3,5-Cl$_2$ | CF$_3$ | 2-CH$_3$ | CH$_2$CCl=CH$_2$ | *1 |
| 5-184 | 3,5-Cl$_2$ | CF$_3$ | 2-CH$_3$ | CH$_2$CH=CCl$_2$ | *1 |
| 5-185 | 3,5-Cl$_2$ | CF$_3$ | 2-CH$_3$ | CH$_2$CCl=CHCl | *1 |
| 5-186 | 3,5-Cl$_2$ | CF$_3$ | 2-CH$_3$ | CH$_2$C≡CH | *1 |
| 5-187 | 3,5-Cl$_2$ | CF$_3$ | 2-CH$_3$ | CH$_2$Ph | 142.0-144.5 |
| 5-188 | 3,5-Cl$_2$ | CF$_3$ | 2-CH$_3$ | CH(CH$_3$)Ph | 121.5-123.5 |
| 5-189 | 3,5-Cl$_2$ | CF$_3$ | 2-CH$_3$ | CH(CH$_3$)Ph(R) | *1 |
| 5-189(+) | | 99% d.e. | [α]$_D^{22.9}$ + 59.13° | (EtOH, c = 0.262) | *1 |
| 5-189(−) | | 99% d.e. | [α]$_D^{23.0}$ − 86.72° | (EtOH, c = 0.250) | *1 |
| 5-190 | 3,5-Cl$_2$ | CF$_3$ | 2-CH$_3$ | CH(CH$_3$)Ph(S) | *1 |
| 5-190(+) | | 99% d.e. | [α]$_D^{23.0}$ + 89.06° | (EtOH, c = 0.466) | *1 |
| 5-190(−) | | 99% d.e. | [α]$_D^{23.0}$ − 117.66° | (EtOH, c = 0.322) | *1 |
| 5-191 | 3,5-Cl$_2$ | CF$_3$ | 2-CH$_3$ | CH(Et)Ph | *1 |
| 5-192 | 3,5-Cl$_2$ | CF$_3$ | 2-CH$_3$ | C(CH$_3$)$_2$Ph | 91.0-93.5 |
| 5-193 | 3,5-Cl$_2$ | CF$_3$ | 2-CH$_3$ | CH(CF$_3$)Ph | 175.5-180.0 |
| 5-194 | 3,5-Cl$_2$ | CF$_3$ | 2-CH$_3$ | CH(OEt)Ph | *2 |
| 5-195 | 3,5-Cl$_2$ | CF$_3$ | 2-CH$_3$ | CH$_2$(Ph-2-F) | 151.0-153.0 |
| 5-196 | 3,5-Cl$_2$ | CF$_3$ | 2-CH$_3$ | CH$_2$(Ph-3-F) | 134.0-136.0 |
| 5-197 | 3,5-Cl$_2$ | CF$_3$ | 2-CH$_3$ | CH$_2$(Ph-4-F) | 153.0-155.0 |
| 5-198 | 3,5-Cl$_2$ | CF$_3$ | 2-CH$_3$ | CH$_2$(Ph-2-Cl) | 147.0-149.0 |
| 5-199 | 3,5-Cl$_2$ | CF$_3$ | 2-CH$_3$ | CH$_2$(Ph-3-Cl) | 160.0-162.0 |
| 5-200 | 3,5-Cl$_2$ | CF$_3$ | 2-CH$_3$ | CH$_2$(Ph-4-Cl) | 164.0-166.0 |
| 5-201 | 3,5-Cl$_2$ | CF$_3$ | 2-CH$_3$ | CH$_2$(Ph-3-NO$_2$) | 198.0-200.0 |
| 5-202 | 3,5-Cl$_2$ | CF$_3$ | 2-CH$_3$ | CH$_2$(Ph-4-NO$_2$) | 204.0-206.0 |
| 5-203 | 3,5-Cl$_2$ | CF$_3$ | 2-CH$_3$ | CH$_2$(Ph-2,5-F$_2$) | 153.0-155.0 |

TABLE 11-continued

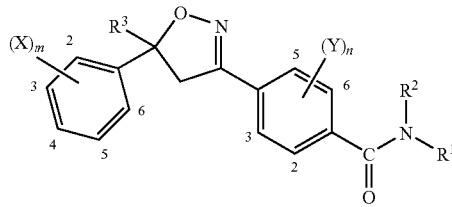

| No. | (X)$_m$ | R$^3$ | (Y)$_n$ | R$^1$ | m.p. (C. °) |
|---|---|---|---|---|---|
| 5-204 | 3,5-Cl$_2$ | CF$_3$ | 2-CH$_3$ | CH$_2$(Ph-3,5-F$_2$) | 146.0-149.0 |
| 5-205 | 3,5-Cl$_2$ | CF$_3$ | 2-CH$_3$ | CH$_2$(D-1a) | *1 |
| 5-206 | 3,5-Cl$_2$ | CF$_3$ | 2-CH$_3$ | CH$_2$(D-3a) | 147.0-148.5 |
| 5-207 | 3,5-Cl$_2$ | CF$_3$ | 2-CH$_3$ | CH$_2$(D-3d)Cl | *1 |
| 5-208 | 3,5-Cl$_2$ | CF$_3$ | 2-CH$_3$ | CH$_2$(D-8b)CH$_3$ | *1 |
| 5-209 | 3,5-Cl$_2$ | CF$_3$ | 2-CH$_3$ | CH$_2$(D-10b)Cl | *1 |
| 5-210 | 3,5-Cl$_2$ | CF$_3$ | 2-CH$_3$ | CH$_2$(D-15a)CH$_3$ | 147.0-148.0 |
| 5-211 | 3,5-Cl$_2$ | CF$_3$ | 2-CH$_3$ | CH$_2$(D-16b)Cl | 237.0-238.0 |
| 5-212 | 3,5-Cl$_2$ | CF$_3$ | 2-CH$_3$ | CH$_2$(D-16c)Cl | *1 |
| 5-213 | 3,5-Cl$_2$ | CF$_3$ | 2-CH$_3$ | CH$_2$(D-16d) | *1 |
| 5-214 | 3,5-Cl$_2$ | CF$_3$ | 2-CH$_3$ | CH$_2$(D-17a)CH$_3$ | 76.0-77.0 |
| 5-215 | 3,5-Cl$_2$ | CF$_3$ | 2-CH$_3$ | CH$_2$(D-17b)Cl | 157.0-158.0 |
| 5-216 | 3,5-Cl$_2$ | CF$_3$ | 2-CH$_3$ | CH$_2$(D-21a) | *1 |
| 5-217 | 3,5-Cl$_2$ | CF$_3$ | 2-CH$_3$ | CH(Ph)(D-21a) | *1 |
| 5-218 | 3,5-Cl$_2$ | CF$_3$ | 2-CH$_3$ | CH$_2$(D-21b)CF$_3$ | *1 |
| 5-219 | 3,5-Cl$_2$ | CF$_3$ | 2-CH$_3$ | CH$_2$(D-22a) | 135.0-136.5 |
| 5-219(+) | | 97% e.e. | | [α]$_D^{22.6}$ + 56.54° (EtOH, c = 0.384) | *1 |
| 5-219(−) | | 99% e.e. | | [α]$_D^{22.4}$ − 58.65° (EtOH, c = 0.393) | *1 |
| 5-220 | 3,5-Cl$_2$ | CF$_3$ | 2-CH$_3$ | CH$_2$(D-22b)Cl | *1 |
| 5-221 | 3,5-Cl$_2$ | CF$_3$ | 2-CH$_3$ | CH$_2$(D-22b)CH$_3$ | *1 |
| 5-222 | 3,5-Cl$_2$ | CF$_3$ | 2-CH$_3$ | CH$_2$(D-23a) | *1 |
| 5-223 | 3,5-Cl$_2$ | CF$_3$ | 2-CH$_3$ | CH$_2$(D-23b)Cl | *1 |
| 5-224 | 3,5-Cl$_2$ | CF$_3$ | 2-CH$_3$ | CH$_2$(D-25a)CH$_3$ | *1 |
| 5-225 | 3,5-Cl$_2$ | CF$_3$ | 2-CH$_3$ | CH$_2$(D-27a)CH$_3$ | *1 |
| 5-226 | 3,5-Cl$_2$ | CF$_3$ | 2-CH$_3$ | CH$_2$(D-28a) | *1 |
| 5-227 | 3,5-Cl$_2$ | CF$_3$ | 2-CH$_3$ | CH$_2$(D-29b)CH$_3$ | *1 |
| 5-228 | 3,5-Cl$_2$ | CF$_3$ | 2-CH$_3$ | CH$_2$(D-30a) | 120.0-123.5 |
| 5-229 | 3,5-Cl$_2$ | CF$_3$ | 2-CH$_3$ | CH$_2$(D-31a) | 122.0-125.0 |
| 5-230 | 3,5-Cl$_2$ | CF$_3$ | 2-CH$_3$ | CH$_2$(D-34a) | *1 |
| 5-231 | 3,5-Cl$_2$ | CF$_3$ | 2-CH$_3$ | CH$_2$(D-34b)CH$_3$ | *1 |
| 5-232 | 3,5-Cl$_2$ | CF$_3$ | 2-CH$_3$ | CH$_2$(D-35a) | *1 |
| 5-233 | 3,5-Cl$_2$ | CF$_3$ | 2-CH$_3$ | CH$_2$(D-38a) | *1 |
| 5-234 | 3,5-Cl$_2$ | CF$_3$ | 2-CH$_3$ | CH$_2$(D-47a) | 131.0-135.5 |
| 5-235 | 3,5-Cl$_2$ | CF$_3$ | 2-CH$_3$ | CH(CH$_3$)(D-47a) | *1 |
| 5-236 | 3,5-Cl$_2$ | CF$_3$ | 2-CH$_3$ | CH$_2$(D-47c)Cl | 164.0-166.0 |
| 5-237 | 3,5-Cl$_2$ | CF$_3$ | 2-CH$_3$ | CH$_2$(D-47c)NO$_2$ | 129.0-131.0 |
| 5-238 | 3,5-Cl$_2$ | CF$_3$ | 2-CH$_3$ | CH$_2$(D-47e)Cl | *1 |
| 5-239 | 3,5-Cl$_2$ | CF$_3$ | 2-CH$_3$ | CH$_2$(D-47i) | *1 |
| 5-240 | 3,5-Cl$_2$ | CF$_3$ | 2-CH$_3$ | CH$_2$(D-48a) | *1 |
| 5-241 | 3,5-Cl$_2$ | CF$_3$ | 2-CH$_3$ | CH$_2$(D-48e)Cl | 200.5-202.0 |
| 5-242 | 3,5-Cl$_2$ | CF$_3$ | 2-CH$_3$ | CH$_2$(D-49a) | *1 |
| 5-243 | 3,5-Cl$_2$ | CF$_3$ | 2-CH$_3$ | CH$_2$(D-50a) | *1 |
| 5-244 | 3,5-Cl$_2$ | CF$_3$ | 2-CH$_3$ | CH$_2$[(D-50d)-4,6-(OCH$_3$)$_2$] | 58.0-65.0 |
| 5-245 | 3,5-Cl$_2$ | CF$_3$ | 2-CH$_3$ | CH$_2$(D-51a) | *1 |
| 5-246 | 3,5-Cl$_2$ | CF$_3$ | 2-CH$_3$ | CH$_2$(D-53a) | *1 |
| 5-247 | 3,5-Cl$_2$ | CF$_3$ | 2-CH$_3$ | CH$_2$(D-53b)CH$_3$ | *1 |
| 5-248 | 3,5-Cl$_2$ | CF$_3$ | 2-CH$_3$ | NH$_2$ | 87.0-89.0 |
| 5-249 | 3,5-Cl$_2$ | CF$_3$ | 2-CH$_3$ | N(CH$_3$)$_2$ | 79.0-84.0 |
| 5-250 | 3,5-Cl$_2$ | CF$_3$ | 2-CH$_3$ | NHBu-t | 71.0-76.0 |
| 5-251 | 3,5-Cl$_2$ | CF$_3$ | 2-CH$_3$ | NHCH$_2$CF$_3$ | 158.0-159.0 |
| 5-252 | 3,5-Cl$_2$ | CF$_3$ | 2-CH$_3$ | NHCH$_2$CH$_2$OH | 61.0-70.0 |
| 5-253 | 3,5-Cl$_2$ | CF$_3$ | 2-CH$_3$ | T-34a | 59.0-63.0 |
| 5-254 | 3,5-Cl$_2$ | CF$_3$ | 2-CH$_3$ | T-40 | 95.0-105.0 |
| 5-255 | 3,5-Cl$_2$ | CF$_3$ | 2-CH$_3$ | T-42 | 155.0-157.0 |
| 5-256 | 3,5-Cl$_2$ | CF$_3$ | 2-CH$_3$ | NHC(O)CH$_3$ | 117.0-118.0 |
| 5-257 | 3,5-Cl$_2$ | CF$_3$ | 2-CH$_3$ | N(Ph)C(O)CH$_3$ | 89.0-99.0 |
| 5-258 | 3,5-Cl$_2$ | CF$_3$ | 2-CH$_3$ | NHC(O)Pr-n | 109.0-111.0 |
| 5-259 | 3,5-Cl$_2$ | CF$_3$ | 2-CH$_3$ | NHC(O)CH$_2$CH$_2$Cl | 109.0-110.0 |
| 5-260 | 3,5-Cl$_2$ | CF$_3$ | 2-CH$_3$ | NHC(O)CH$_2$CN | 121.0-125.0 |
| 5-261 | 3,5-Cl$_2$ | CF$_3$ | 2-CH$_3$ | NHC(O)OCH$_3$ | 86.0-93.0 |
| 5-262 | 3,5-Cl$_2$ | CF$_3$ | 2-CH$_3$ | N(CH$_3$)C(O)OCH$_3$ | 131.0-132.0 |
| 5-263 | 3,5-Cl$_2$ | CF$_3$ | 2-CH$_3$ | N(Ph)C(O)OCH$_3$ | 98.0-106.0 |
| 5-264 | 3,5-Cl$_2$ | CF$_3$ | 2-CH$_3$ | NHC(O)OEt | 75.0-84.0 |
| 5-265 | 3,5-Cl$_2$ | CF$_3$ | 2-CH$_3$ | NHC(O)OBu-t | *1 |
| 5-266 | 3,5-Cl$_2$ | CF$_3$ | 2-CH$_3$ | NHC(O)OCH$_2$Ph | 155.0-156.0 |
| 5-267 | 3,5-Cl$_2$ | CF$_3$ | 2-CH$_3$ | NHC(O)NHPh | 212.0-214.0 |
| 5-268 | 3,5-Cl$_2$ | CF$_3$ | 2-CH$_3$ | NHC(O)Ph | 213.0-214.0 |

TABLE 11-continued

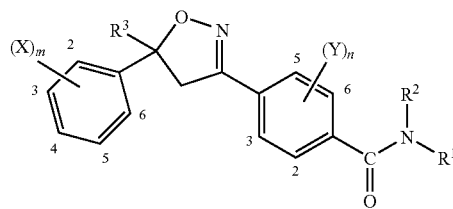

| No. | (X)$_m$ | R$^3$ | (Y)$_n$ | R$^1$ | m.p. (C. °) |
|---|---|---|---|---|---|
| 5-269 | 3,5-Cl$_2$ | CF$_3$ | 2-CH$_3$ | NHC(O)(D-1a) | 230.0-232.0 |
| 5-270 | 3,5-Cl$_2$ | CF$_3$ | 2-CH$_3$ | NHC(O)(D-47a) | 116.0-117.0 |
| 5-271 | 3,5-Cl$_2$ | CF$_3$ | 2-CH$_3$ | NHC(S)NHCH$_3$ | 143.0-145.0 |
| 5-272 | 3,5-Cl$_2$ | CF$_3$ | 2-CH$_3$ | NHC(S)N(CH$_3$)$_2$ | 179.0-182.0 |
| 5-273 | 3,5-Cl$_2$ | CF$_3$ | 2-CH$_3$ | NHPh | 88.0-96.0 |
| 5-274 | 3,5-Cl$_2$ | CF$_3$ | 2-CH$_3$ | N(CH$_3$)Ph | 158.0-160.0 |
| 5-275 | 3,5-Cl$_2$ | CF$_3$ | 2-CH$_3$ | N(CH$_2$CH=CH$_2$)Ph | 78.0-86.0 |
| 5-276 | 3,5-Cl$_2$ | CF$_3$ | 2-CH$_3$ | N(CH$_2$Ph)Ph | 58.0-60.0 |
| 5-277 | 3,5-Cl$_2$ | CF$_3$ | 2-CH$_3$ | NH(Ph-2-Cl) | *1 |
| 5-278 | 3,5-Cl$_2$ | CF$_3$ | 2-CH$_3$ | NH(Ph-3-Cl) | *1 |
| 5-279 | 3,5-Cl$_2$ | CF$_3$ | 2-CH$_3$ | NH(Ph-4-Cl) | *1 |
| 5-280 | 3,5-Cl$_2$ | CF$_3$ | 2-CH$_3$ | NH(Ph-4-CF$_3$) | *1 |
| 5-281 | 3,5-Cl$_2$ | CF$_3$ | 2-CH$_3$ | NH(Ph-2-NO$_2$) | 89.0-95.0 |
| 5-282 | 3,5-Cl$_2$ | CF$_3$ | 2-CH$_3$ | NH(Ph-3-NO$_2$) | 104.0-109.0 |
| 5-283 | 3,5-Cl$_2$ | CF$_3$ | 2-CH$_3$ | NH(Ph-4-NO$_2$) | 120.0-126.0 |
| 5-284 | 3,5-Cl$_2$ | CF$_3$ | 2-CH$_3$ | N(CH$_3$)(D-21a) | 181.0-185.0 |
| 5-285 | 3,5-Cl$_2$ | CF$_3$ | 2-CH$_3$ | NH(D-47a) | 213.0-217.0 |
| 5-286 | 3,5-Cl$_2$ | CF$_3$ | 2-CH$_3$ | N(CH$_3$)(D-47a) | 202.0-203.0 |
| 5-287 | 3,5-Cl$_2$ | CF$_3$ | 2-CH$_3$ | NH(D-47b)Cl | 102.0-103.0 |
| 5-288 | 3,5-Cl$_2$ | CF$_3$ | 2-CH$_3$ | NH(D-47d)Cl | 91.0-92.0 |
| 5-289 | 3,5-Cl$_2$ | CF$_3$ | 2-CH$_3$ | NH(D-47e)Cl | 89.0-90.0 |
| 5-290 | 3,5-Cl$_2$ | CF$_3$ | 2-CH$_3$ | NH[(D-47f)-3-Cl-5-CF$_3$] | 137.0-140.0 |
| 5-291 | 3,5-Cl$_2$ | CF$_3$ | 2-CH$_3$ | NH(D-50a) | 209.0-211.0 |
| 5-292 | 3,5-Cl$_2$ | CF$_3$ | 2-CH$_3$ | NH(D-50b)CF$_3$ | 95.0-100.0 |
| 5-293 | 3,5-Cl$_2$ | CF$_3$ | 2-CH$_3$ | NH[(D-50d)-4,6-(OCH$_3$)$_2$] | 91.0-98.0 |
| 5-294 | 3,5-Cl$_2$ | CF$_3$ | 2-CH$_3$ | N(CH$_3$)(D-50a) | 194.0-196.0 |
| 5-295 | 3,5-Cl$_2$ | CF$_3$ | 2-CH$_3$ | N(Et)(D-50a) | 60.0-67.0 |
| 5-296 | 3,5-Cl$_2$ | CF$_3$ | 2-CH$_3$ | NH(D-51b)SCH$_3$ | *1 |
| 5-297 | 3,5-Cl$_2$ | CF$_3$ | 2-CH$_3$ | NH(D-51b)S(O)CH$_3$ | 156.0-162.0 |
| 5-298 | 3,5-Cl$_2$ | CF$_3$ | 2-CH$_3$ | NH(D-51b)SO$_2$CH$_3$ | 147.0-151.0 |
| 5-299 | 3,5-Cl$_2$ | CF$_3$ | 2-CH$_3$ | NH(D-51c)Cl | *1 |
| 5-300 | 3,5-Cl$_2$ | CF$_3$ | 2-CH$_3$ | NH(D-53a) | 111.0-112.0 |
| 5-301 | 3,5-Cl$_2$ | CF$_3$ | 2-CH$_3$ | NH(D-54b)Cl | *1 |
| 5-302 | 3,5-Cl$_2$ | CF$_3$ | 2-CH$_3$ | N=C(CH$_3$)Ph | 134.0-135.0 |
| 5-303 | 3,5-Cl$_2$ | CF$_3$ | 2-CH$_3$ | N=CH(D-47a) | *1 |
| 5-304 | 3,5-Cl$_2$ | CF$_3$ | 2-CH$_3$ | T-47 | 146.0-148.0 |
| 5-305 | 3,5-Cl$_2$ | CF$_3$ | 2-CH$_3$ | D-8a | 127.5-129.0 |
| 5-306 | 3,5-Cl$_2$ | CF$_3$ | 2-CH$_3$ | (D-13b)CH$_3$ | 271.0-275.0 |
| 5-307 | 3,5-Cl$_2$ | CF$_3$ | 2-CH$_3$ | D-21a | 281.0-284.0 |
| 5-308 | 3,5-Cl$_2$ | CF$_3$ | 2-CH$_3$ | D-48a | 188.0-190.0 |
| 5-309 | 3,5-Cl$_2$ | CF$_3$ | 2-CH$_3$ | D-50a | 98.0-100.0 |
| 5-310 | 3,5-Cl$_2$ | CF$_3$ | 2-CH$_3$ | D-51a | 90.0-91.0 |
| 5-311 | 3,5-Cl$_2$ | CF$_3$ | 3-CH$_3$ | CH$_2$CF$_3$ | *1 |
| 5-312 | 3,5-Cl$_2$ | CF$_3$ | 2-Et | CH$_2$CF$_3$ | *1 |
| 5-313 | 3,5-Cl$_2$ | CF$_3$ | 2-Et | CH$_2$(D-47a) | *1 |
| 5-314 | 3,5-Cl$_2$ | CF$_3$ | 2-CF$_3$ | CH$_2$CF$_3$ | 70.0-72.0 |
| 5-315 | 3,5-Cl$_2$ | CF$_3$ | 2-CF$_3$ | CH$_2$(D-47a) | 69.0-70.0 |
| 5-316 | 3,5-Cl$_2$ | CF$_3$ | 2-CH$_2$OH | CH$_2$CF$_3$ | *1 |
| 5-317 | 3,5-Cl$_2$ | CF$_3$ | 2-OCH$_3$ | CH$_2$CF$_3$ | *1 |
| 5-318 | 3,5-Cl$_2$ | CF$_3$ | 2-OCH$_3$ | CH$_2$Ph | *1 |
| 5-319 | 3,5-Cl$_2$ | CF$_3$ | 2-OCH$_3$ | CH$_2$(D-47a) | 173.5-176.0 |
| 5-320 | 3,5-Cl$_2$ | CF$_3$ | 2-OCF$_3$ | CH$_2$CF$_3$ | *2 |
| 5-321 | 3,5-Cl$_2$ | CF$_3$ | 2-OCF$_3$ | CH$_2$(D-47a) | 145.0-148.5 |
| 5-322 | 3,5-Cl$_2$ | CF$_3$ | 2-SCH$_3$ | CH$_2$CF$_3$ | *2 |
| 5-323 | 3,5-Cl$_2$ | CF$_3$ | 2-SCH$_3$ | CH$_2$(D-47a) | *2 |
| 5-324 | 3,5-Cl$_2$ | CF$_3$ | 2-S(O)CH$_3$ | CH$_2$CF$_3$ | *2 |
| 5-325 | 3,5-Cl$_2$ | CF$_3$ | 2-S(O)CH$_3$ | CH$_2$(D-47a) | *1 |
| 5-326 | 3,5-Cl$_2$ | CF$_3$ | 2-SO$_2$CH$_3$ | CH$_2$CF$_3$ | *1 |
| 5-327 | 3,5-Cl$_2$ | CF$_3$ | 2-SO$_2$CH$_3$ | CH$_2$(D-47a) | 120.0-121.0 |
| 5-328 | 3,5-Cl$_2$ | CF$_3$ | 2-S(O)CH$_2$Cl | CH$_2$CF$_3$ | *2 |
| 5-329 | 3,5-Cl$_2$ | CF$_3$ | 2-NH$_2$ | CH$_2$CF$_3$ | 78.0-79.0 |
| 5-330 | 3,5-Cl$_2$ | CF$_3$ | 2-NH$_2$ | CH$_2$(D-47a) | *2 |
| 5-331 | 3,5-Cl$_2$ | CF$_3$ | 2-NHCH$_3$ | CH$_2$CF$_3$ | 156.0-158.0 |
| 5-332 | 3,5-Cl$_2$ | CF$_3$ | 2-NHCH$_3$ | CH$_2$(D-47a) | *1 |
| 5-333 | 3,5-Cl$_2$ | CF$_3$ | 2-NHC(O)CH$_3$ | CH$_2$CF$_3$ | *2 |
| 5-334 | 3,5-Cl$_2$ | CF$_3$ | 2-N(CH$_3$)2 | CH$_2$CF$_3$ | *2 |
| 5-335 | 3,5-Cl$_2$ | CF$_3$ | 2-N(CH$_3$)2 | CH$_2$(D-47a) | *1 |

TABLE 11-continued

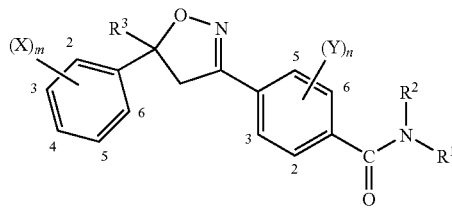

| No. | (X)$_m$ | R$^3$ | (Y)$_n$ | R$^1$ | m.p. (C. °) |
|---|---|---|---|---|---|
| 5-336 | 3,5-Cl$_2$ | CF$_3$ | 2-N(CH$_3$)CHO | CH$_2$(D-47a) | *1 |
| 5-337 | 3,5-Cl$_2$ | CF$_3$ | 2-N(CH$_3$)C(O)CH$_3$ | CH$_2$(D-47a) | *1 |
| 5-338 | 3,5-Cl$_2$ | CF$_3$ | 2-NO$_2$ | CH$_2$CF$_3$ | 180.0-181.0 |
| 5-339 | 3,5-Cl$_2$ | CF$_3$ | 2-NO$_2$ | CH$_2$(D-47a) | *2 |
| 5-340 | 3,5-Cl$_2$ | CF$_3$ | 2-CN | CH$_2$CF$_3$ | *1 |
| 5-341 | 3,5-Cl$_2$ | CF$_3$ | 2-CN | CH$_2$(D-47a) | *1 |
| 5-342 | 3,5-Cl$_2$ | CF$_3$ | 2-C≡C-TMS | CH$_2$CF$_3$ | *1 |
| 5-343 | 3,5-Cl$_2$ | CF$_3$ | 2-Ph | CH$_2$CF$_3$ | *1 |
| 5-344 | 3,5-Cl$_2$ | CF$_3$ | 2-Ph | CH$_2$(D-47a) | 194.0-198.0 |
| 5-345 | 3,5-Cl$_2$ | CF$_3$ | 2-(D-38a) | CH$_2$(D-47a) | *2 |
| 5-346 | 3,5-Cl$_2$ | CF$_3$ | 2,3-F$_2$ | CH$_2$CF$_3$ | *1 |
| 5-347 | 3,5-Cl$_2$ | CF$_3$ | 2,3-F$_2$ | CH$_2$Ph | *1 |
| 5-348 | 3,5-Cl$_2$ | CF$_3$ | 2,3-F$_2$ | CH$_2$(D-47a) | *1 |
| 5-349 | 3,5-Cl$_2$ | CF$_3$ | 2,6-F$_2$ | CH$_2$CF$_3$ | 140.0-141.0 |
| 5-350 | 3,5-Cl$_2$ | CF$_3$ | 2,6-Cl$_2$ | CH$_2$(D-47a) | 131.0-132.0 |
| 5-351 | 3,5-Cl$_2$ | CF$_3$ | 2,6-(CH$_3$)$_2$ | CH$_2$CF$_3$ | 125.0-129.0 |
| 5-352 | 3,5-Cl$_2$ | CF$_3$ | 2,6-(CH$_3$)$_2$ | CH$_2$(D-47a) | *1 |
| 5-353 | 3,5-Cl$_2$ | CF$_2$CF$_3$ | 2-Cl | CH$_2$(D-22a) | *1 |
| 5-354 | 3,5-Cl$_2$ | CF$_2$CF$_3$ | 2-Cl | CH$_2$(D-47a) | *1 |
| 5-355 | 3,5-Cl$_2$ | CF$_2$CF$_3$ | 2-CH$_3$ | CH$_2$CF$_3$ | *1 |
| 5-356 | 3,5-Cl$_2$ | CF$_2$CF$_3$ | 2-CH$_3$ | CH$_2$CH$_2$OEt | *1 |
| 5-357 | 3,5-Cl$_2$ | CF$_2$CF$_3$ | 2-CH$_3$ | CH$_2$CH(OCH$_3$)$_2$ | *1 |
| 5-358 | 3,5-Cl$_2$ | CF$_2$CF$_3$ | 2-CH$_3$ | CH$_2$CH=CH$_2$ | *1 |
| 5-359 | 3,5-Cl$_2$ | CF$_2$CF$_3$ | 2-CH$_3$ | CH$_2$(D-22a) | *1 |
| 5-360 | 3,5-Cl$_2$ | CF$_2$CF$_3$ | 2-CH$_3$ | CH$_2$(D-47a) | *1 |
| 5-361 | 3,5-Cl$_2$ | CF$_2$CF$_3$ | 2-CH$_3$ | CH$_2$CF$_3$ | *1 |
| 5-362 | 3,5-Cl$_2$ | CF$_2$CF$_3$ | 2-CH$_3$ | CH$_2$(D-47a) | *1 |
| 5-363 | 3,5-Cl$_2$ | CF$_2$CF$_3$ | 2-CH$_3$ | C(O)(D-47a) | *1 |
| 5-364 | 3,5-Cl$_2$ | CH$_2$OCH$_2$CF$_3$ | 2-CH$_3$ | CH$_2$CF$_3$ | *1 |
| 5-365 | 3,5-Cl$_2$ | CH$_2$OCH$_2$CF$_3$ | 2-CH$_3$ | CH$_2$(D-47a) | *1 |
| 5-366 | 3,5-Cl$_2$ | CF$_2$SCH$_3$ | 2-CH$_3$ | CH$_2$CF$_3$ | *2 |
| 5-367 | 3,5-Cl$_2$ | CF$_2$SCH$_3$ | 2-CH$_3$ | CH$_2$(D-47a) | 51.0-52.0 |
| 5-368 | 3,5-Cl$_2$ | CH$_2$-TMS | 2-CH$_3$ | CH$_2$CF$_3$ | *1 |
| 5-369 | 3,5-Cl$_2$ | CH$_2$-TMS | 2-CH$_3$ | CH$_2$(D-47a) | *1 |
| 5-370 | 3,5-Cl$_2$ | TMS | 2-CH$_3$ | CH$_2$CF$_3$ | *1 |
| 5-371 | 3,5-Cl$_2$ | TMS | 2-CH$_3$ | CH$_2$(D-47a) | *1 |
| 5-372 | 3,5-Cl$_2$ | D-47a | 2-CH$_3$ | CH$_2$CF$_3$ | *1 |
| 5-373 | 3,5-Cl$_2$ | D-47a | 2-CH$_3$ | CH$_2$(D-47a) | *1 |
| 5-374 | 3-Cl-5-Br | CF$_3$ | 2-CH$_3$ | CH$_2$CF$_3$ | *1 |
| 5-375 | 3-Cl-5-Br | CF$_3$ | 2-CH$_3$ | CH$_2$(D-47a) | *1 |
| 5-376 | 3,5-Br$_2$ | CF$_3$ | 2-Cl | CH$_2$(D-22a) | 63.0-64.0 |
| 5-377 | 3,5-Br$_2$ | CF$_3$ | 2-Cl | CH$_2$(D-47a) | *2 |
| 5-378 | 3,5-Br$_2$ | CF$_3$ | 2-CH$_3$ | CH$_2$CF$_3$ | *1 |
| 5-379 | 3,5-Br$_2$ | CF$_3$ | 2-CH$_3$ | CH$_2$CH$_2$OCH$_3$ | *2 |
| 5-380 | 3,5-Br$_2$ | CF$_3$ | 2-CH$_3$ | CH$_2$CH$_2$OEt | *2 |
| 5-381 | 3,5-Br$_2$ | CF$_3$ | 2-CH$_3$ | CH$_2$OH(OCH$_3$)$_2$ | *2 |
| 5-382 | 3,5-Br$_2$ | CF$_3$ | 2-CH$_3$ | CH$_2$C(O)OCH$_3$ | *2 |
| 5-383 | 3,5-Br$_2$ | CF$_3$ | 2-CH$_3$ | CH$_2$C(O)NHCH$_2$CH$_2$Cl | 69.0-70.0 |
| 5-384 | 3,5-Br$_2$ | CF$_3$ | 2-CH$_3$ | CH$_2$C(O)NHCH$_2$CF$_3$ | 173.0-175.0 |
| 5-385 | 3,5-Br$_2$ | CF$_3$ | 2-CH$_3$ | CH$_2$OH=CH$_2$ | *2 |
| 5-386 | 3,5-Br$_2$ | CF$_3$ | 2-CH$_3$ | CH$_2$(D-22a) | *1 |
| 5-387 | 3,5-Br$_2$ | CF$_3$ | 2-CH$_3$ | CH$_2$(D-47a) | *1 |
| 5-388 | 3-Cl-5-CH$_3$ | CF$_3$ | 2-CH$_3$ | CH$_2$(D-47a) | *2 |
| 5-389 | 3,5-(CF$_3$)$_2$ | CF$_3$ | 2-CH$_3$ | CH$_2$CF$_3$ | *1 |
| 5-390 | 3,5-(CF$_3$)$_2$ | CF$_3$ | 2-CH$_3$ | CH$_2$(D-47a) | *1 |
| 5-391 | 3-F-5-SCH$_3$ | CF$_3$ | 2-CH$_3$ | CH$_2$(D-47a) | *1 |
| 5-392 | 3-Cl-5-SCH$_3$ | CF$_3$ | 2-SOH3 | CH$_2$(D-47a) | *2 |
| 5-393 | 3-CF$_3$-5-OCH$_3$ | CF$_3$ | 2-CH$_3$ | CH$_2$(D-47a) | *1 |
| 5-394 | 3,5-(SCH$_3$)$_2$ | CF$_3$ | 2-CH$_3$ | CH$_2$(D-47a) | *1 |
| 5-395 | 3-CF$_3$-5-CN | CF$_3$ | 2-CH$_3$ | CH$_2$CF$_3$ | 72.0-73.0 |
| 5-396 | 3-CF$_3$-5-CN | CF$_3$ | 2-CH$_3$ | CH$_2$(D-47a) | 63.0-64.0 |
| 5-397 | 3,4,5-Cl$_3$ | CF$_3$ | 2-CH$_3$ | CH$_2$CF$_3$ | 194.0-197.0 |
| 5-398 | 3,4,5-Cl$_3$ | CF$_3$ | 2-CH$_3$ | CH$_2$(D-47a) | *1 |
| 5-399 | 3,5-Cl$_2$ | CF$_3$ | 2-CH$_3$ | CH$_2$CH$_2$CF$_3$ | *1 |
| 5-400 | 3,5-Cl$_2$ | CF$_3$ | 2-CH$_3$ | OH(CF$_3$)OH | *1 |
| 5-401 | 3,5-Cl$_2$ | CF$_3$ | 2-CH$_3$ | CH(CF$_3$)OCH$_3$ | *1 |
| 5-402 | 3,5-Cl$_2$ | CF$_3$ | 2-CH$_3$ | E-5b | 197.0-199.0 |

TABLE 11-continued

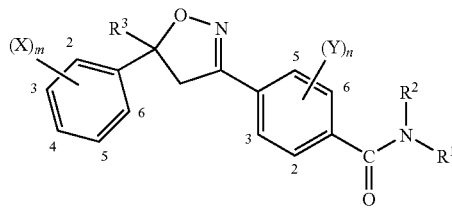

| No. | (X)$_m$ | R$^3$ | (Y)$_n$ | R$^1$ | m.p. (C. °) |
|---|---|---|---|---|---|
| 5-403 | 3,5-Cl$_2$ | CF$_3$ | 2-CH$_3$ | CH$_2$CH$_2$(T-33) | *1 |
| 5-404 | 3,5-Cl$_2$ | CF$_3$ | 2-CH$_3$ | CH$_2$CH$_2$(T-39) | *1 |
| 5-405 | 3,5-Cl$_2$ | CF$_3$ | 2-CH$_3$ | (E-9b)CH$_2$CF$_3$ | *2 |
| 5-406 | 3,5-Cl$_2$ | CF$_3$ | 2-CH$_3$ | CH$_2$(E-17a)H | *1 |
| 5-407 | 3,5-Cl$_2$ | CF$_3$ | 2-CH$_3$ | CH[C(O)OCH$_3$]$_2$ | *2 |
| 5-408 | 3,5-Cl$_2$ | CF$_3$ | 2-CH$_3$ | CH$_2$C(O)NHOEt | 141.0-145.0 |
| 5-409 | 3,5-Cl$_2$ | CF$_3$ | 2-CH$_3$ | CH$_2$C(O)NHOCH$_2$OH=CH$_2$ | *1 |
| 5-410 | 3,5-Cl$_2$ | CF$_3$ | 2-CH$_3$ | CH(CH$_3$)C(O)NHEt | *1 |
| 5-411 | 3,5-Cl$_2$ | CF$_3$ | 2-CH$_3$ | CH(CH$_3$)C(O)NHPr-i | 172.0-174.0 |
| 5-412 | 3,5-Cl$_2$ | CF$_3$ | 2-CH$_3$ | OH(CH$_3$)C(O)NHCH$_2$CF$_3$ | 161.0-163.0 |
| 5-413 | 3,5-Cl$_2$ | CF$_3$ | 2-CH$_3$ | CH(CH$_3$)C(O)NHCH$_2$CH=CH$_2$ | 175.0-178.0 |
| 5-414 | 3,5-Cl$_2$ | CF$_3$ | 2-CH$_3$ | T-48 | *2 |
| 5-415 | 3,5-Cl$_2$ | CF$_3$ | 2-CH$_3$ | T-49 | *2 |
| 5-416 | 3,5-Cl$_2$ | CF$_3$ | 2-CH$_3$ | CH[C(O)NHCH$_3$]$_2$ | 146.0-149.0 |
| 5-417 | 3,5-Cl$_2$ | CF$_3$ | 2-CH$_3$ | CH(OCH$_3$)Ph | *1 |
| 5-418 | 3,5-Cl$_2$ | CF$_3$ | 2-CH$_3$ | CH(CH$_3$)(D-1a) | 142.0-144.0 |
| 5-419 | 3,5-Cl$_2$ | CF$_3$ | 2-CH$_3$ | CH$_2$(D-6a)CH$_3$ | 155.0-157.0 |
| 5-420 | 3,5-Cl$_2$ | CF$_3$ | 2-CH$_3$ | CH(CF$_3$)(D-6a)H | *1 |
| 5-421 | 3,5-Cl$_2$ | CF$_3$ | 2-CH$_3$ | CH$_2$(D-11a) | *1 |
| 5-422 | 3,5-Cl$_2$ | CF$_3$ | 2-CH$_3$ | CH(CF$_3$)(D-14a) | 114.0-118.0 |
| 5-423 | 3,5-Cl$_2$ | CF$_3$ | 2-CH$_3$ | CH(CH$_3$)(D-21a) | *2 |
| 5-424 | 3,5-Cl$_2$ | CF$_3$ | 2-CH$_3$ | CH(CF$_3$)(D-24a) | *1 |
| 5-425 | 3,5-Cl$_2$ | CF$_3$ | 2-CH$_3$ | CH$_2$(D-26a)CH$_3$ | *1 |
| 5-426 | 3,5-Cl$_2$ | CF$_3$ | 2-CH$_3$ | CH(CH$_3$)(D-38a) | *1 |
| 5-427 | 3,5-Cl$_2$ | CF$_3$ | 2-CH$_3$ | CH(CF$_3$)(D-38a) | *1 |
| 5-428 | 3,5-Cl$_2$ | CF$_3$ | 2-CH$_3$ | C(O)OCH$_2$CF$_3$ | *1 |
| 5-429 | 3,5-Cl$_2$ | CF$_3$ | 2-CH$_3$ | C(O)NHCH$_2$CF$_3$ | 81.5-83.0 |
| 5-430 | 3,5-Cl$_2$ | CF$_3$ | 2-CH$_3$ | C(S)NHCH$_2$CF$_3$ | 137.5-140.0 |
| 5-431 | 3,5-Cl$_2$ | CF$_3$ | 2-CH$_3$ | C(D-49a)=C(CN)$_2$ | 122.0-124.0 |
| 5-432 | 3,5-Cl$_2$ | CF$_3$ | 2-CH$_3$ | NHC(O)NHCH$_2$CH$_2$Cl | 105.0-108.0 |
| 5-433 | 3,5-Cl$_2$ | CF$_3$ | 2-CH$_3$ | N(CH$_2$C≡CH)Ph | 76.0-84.0 |
| 5-434 | 3,5-Cl$_2$ | CF$_3$ | 2-CH$_3$ | Ph-4-CN | *1 |
| 5-435 | 3,5-Cl$_2$ | CF$_3$ | 2-CH$_3$ | Ph-4-C(O)OH | 248.0-251.0 |
| 5-436 | 3,5-Cl$_2$ | CF$_3$ | 2-CH$_3$ | Ph-4-C(O)OEt | 230.0-232.0 |
| 5-437 | 3,5-Cl$_2$ | CF$_3$ | 2-CH$_3$ | Ph-4-C(O)NHCH$_2$Cl | 188.0-195.0 |
| 5-438 | 3,5-Cl$_2$ | CF$_3$ | 2-CH$_3$ | Ph-4-C(O)NHCH$_2$CF$_3$ | 110.0-120.0 |
| 5-439 | 3,5-Cl$_2$ | CF$_3$ | 2-CH$_3$ | (D-8b)CH$_3$ | 163.0-165.0 |
| 5-440 | 3,5-Cl$_2$ | CF$_3$ | 2-CH$_3$ | (D-15a)CH$_3$ | 96.0-110.0 |
| 5-441 | 3,5-Cl$_2$ | CF$_3$ | 2-CH$_3$ | (D-17a)CH$_3$ | 95.0-101.0 |
| 5-442 | 3,5-Cl$_2$ | CF$_3$ | 2-CH$_3$ | (D-17b)Cl | 100.0-108.0 |
| 5-443 | 3,5-Cl$_2$ | CF$_3$ | 2-CH$_3$ | (D-21b)CH$_3$ | 110.0-114.0 |
| 5-444 | 3,5-Cl$_2$ | CF$_3$ | 2-CH$_3$ | (D-21c)Cl | 288.0-292.0 |
| 5-445 | 3,5-Cl$_2$ | CF$_3$ | 2-CH$_3$ | (D-21c)CH$_3$ | 271.0-273.0 |
| 5-446 | 3,5-Cl$_2$ | CF$_3$ | 2-CH$_3$ | D-35a | 117.0-126.0 |
| 5-447 | 3,5-Cl$_2$ | CF$_3$ | 2-CH$_3$ | (D-35b)CH$_3$ | 227.0-230.0 |
| 5-448 | 3,5-Cl$_2$ | CF$_3$ | 2-CH$_3$ | (D-39c)SCH$_3$ | 188.0-190.0 |
| 5-449 | 3,5-Cl$_2$ | CF$_3$ | 2-CH$_3$ | (D-42a)H | 109.0-112.0 |
| 5-450 | 3,5-Cl$_2$ | CH(OEt)2 | 2-CH$_3$ | CH$_2$(D-47a) | *1 |
| 5-451 | 3,5-Br$_2$ | CF$_3$ | 2-CH$_3$ | CH$_2$C(O)OH | 102.0-106.0 |
| 5-452 | 3-CF$_3$-5-NO$_2$ | CF$_3$ | 2-CH$_3$ | CH$_2$CF$_3$ | *1 |
| 5-453 | 3-CF$_3$-5-NO$_2$ | CF$_3$ | 2-CH$_3$ | CH$_2$(D-47a) | *1 |
| 5-454 | 3,5-Cl$_2$-4-NH$_2$ | CF$_3$ | 2-CH$_3$ | CH$_2$CF$_3$ | 153.0-154.0 |
| 5-455 | 3,5-Cl$_2$-4-NH$_2$ | CF$_3$ | 2-CH$_3$ | CH$_2$(D-47a) | *1 |
| 5-456 | 3,5-Cl$_2$-4-NHC(O)OBu-t | CF$_3$ | 2-CH$_3$ | CH$_2$CF$_3$ | *1 |
| 5-457 | 3,5-Cl$_2$-4-NHC(O)OBu-t | CF$_3$ | 2-CH$_3$ | CH$_2$(D-47a) | *1 |
| 5-458 | 3,4-Cl$_2$ | CF$_3$ | 2-CH$_3$ | CH$_2$CF$_3$ | 138.0-140.0 |
| 5-459 | 3,4-Cl$_2$ | CF$_3$ | 2-CH$_3$ | CH$_2$C(O)NHCH$_2$CF$_3$ | 165.0-167.0 |
| 5-460 | 3,4-Cl$_2$ | CF$_3$ | 2-CH$_3$ | CH$_2$(D-22a) | *2 |
| 5-461 | 3,4-Cl$_2$ | CF$_3$ | 2-CH$_3$ | CH$_2$(D-47a) | *2 |
| 5-462 | 3,5-Cl$_2$ | CF$_3$ | 2-Cl | H | *1 |
| 5-463 | 3,5-Cl$_2$ | CF$_3$ | 2-Cl | CH$_2$C(O)NHCH$_2$CF$_3$ | *1 |
| 5-464 | 3,5-Cl$_2$ | CF$_3$ | 2-Cl | (D-50c)Cl | 115.0-117.0 |
| 5-465 | 3,5-Cl$_2$ | CF$_3$ | 2-Br | CH$_2$C(O)NHCH$_2$CF$_3$ | 159.0-163.0 |
| 5-466 | 3,5-Cl$_2$ | CF$_3$ | 2-Br | (D-57d)Cl | 172.0-174.0 |
| 5-467 | 3,5-Cl$_2$ | CF$_3$ | 2-I | H | 126.0-128.0 |
| 5-468 | 3,5-Cl$_2$ | CF$_3$ | 2-I | CH$_2$C(O)NHCH$_2$CF$_3$ | *1 |
| 5-469 | 3,5-Cl$_2$ | CF$_3$ | 2-I | (D-47d)Cl | 125.0-128.0 |

TABLE 11-continued

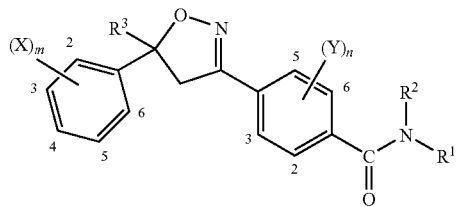

| No. | (X)$_m$ | R$^3$ | (Y)$_n$ | R$^1$ | m.p. (C. °) |
|---|---|---|---|---|---|
| 5-470 | 3,5-Cl$_2$ | CF$_3$ | 2-I | (D-50c)Cl | *1 |
| 5-471 | 3,5-Cl$_2$ | CF$_3$ | 2-CH$_3$ | CH$_3$ | *1 |
| 5-472 | 3,5-Cl$_2$ | CF$_3$ | 2-CH$_3$ | CH$_2$CHF$_2$ | *1 |
| 5-473 | 3,5-Cl$_2$ | CF$_3$ | 2-CH$_3$ | CH$_2$OCH$_3$ | *1 |
| 5-474 | 3,5-Cl$_2$ | CF$_3$ | 2-CH$_3$ | CH$_2$OEt | *1 |
| 5-475 | 3,5-Cl$_2$ | CF$_3$ | 2-CH$_3$ | CH$_2$OPr-n | *1 |
| 5-476 | 3,5-Cl$_2$ | CF$_3$ | 2-CH$_3$ | CH$_2$OPr-i | *1 |
| 5-477 | 3,5-Cl$_2$ | CF$_3$ | 2-CH$_3$ | CH$_2$OCH$_2$CH$_2$Cl | *1 |
| 5-478 | 3,5-Cl$_2$ | CF$_3$ | 2-CH$_3$ | CH$_2$OCH$_2$CHF$_2$ | *1 |
| 5-479 | 3,5-Cl$_2$ | CF$_3$ | 2-CH$_3$ | CH$_2$OCH$_2$CHCl$_2$ | *1 |
| 5-480 | 3,5-Cl$_2$ | CF$_3$ | 2-CH$_3$ | CH$_2$OCH$_2$CF$_3$ | 111.0-114.0 |
| 5-481 | 3,5-Cl$_2$ | CF$_3$ | 2-CH$_3$ | CH$_2$OCH$_2$CCl$_3$ | *1 |
| 5-482 | 3,5-Cl$_2$ | CF$_3$ | 2-CH$_3$ | CH$_2$OCH$_2$CH$_2$OCH$_3$ | *1 |
| 5-483 | 3,5-Cl$_2$ | CF$_3$ | 2-CH$_3$ | CH$_2$OCH$_2$OH=CH$_2$ | *1 |
| 5-484 | 3,5-Cl$_2$ | CF$_3$ | 2-CH$_3$ | CH$_2$OCH$_2$C≡CH | *1 |
| 5-485 | 3,5-Cl$_2$ | CF$_3$ | 2-CH$_3$ | CH$_2$OCH$_2$Ph | *1 |
| 5-486 | 3,5-Cl$_2$ | CF$_3$ | 2-CH$_3$ | CH$_2$OC(O)CH$_3$ | *1 |
| 5-487 | 3,5-Cl$_2$ | CF$_3$ | 2-CH$_3$ | CH(CH$_3$)OH | *1 |
| 5-488 | 3,5-Cl$_2$ | CF$_3$ | 2-CH$_3$ | CH(CH$_3$)OCH$_2$CF$_3$ | *1 |
| 5-489 | 3,5-Cl$_2$ | CF$_3$ | 2-CH$_3$ | CH$_2$CH$_2$OCH$_2$CF$_3$ | 156.0-159.0 |
| 5-490 | 3,5-Cl$_2$ | CF$_3$ | 2-CH$_3$ | CH$_2$CH$_2$OCH$_2$CH$_2$OCH$_2$CH$_2$OCH$_3$ | *2 |
| 5-491 | 3,5-Cl$_2$ | CF$_3$ | 2-CH$_3$ | CH(CH$_3$)CH$_2$OH | 160.0-164.0 |
| 5-492 | 3,5-Cl$_2$ | CF$_3$ | 2-CH$_3$ | CH(CH$_3$)CH$_2$OC(O)CH$_3$ | *1 |
| 5-493 | 3,5-Cl$_2$ | CF$_3$ | 2-CH$_3$ | CH(CH$_3$)CH$_2$OC(O)NHCH$_2$CH$_2$Cl | *1 |
| 5-494 | 3,5-Cl$_2$ | CF$_3$ | 2-CH$_3$ | E-4a | 144.0-147.0 |
| 5-495 | 3,5-Cl$_2$ | CF$_3$ | 2-CH$_3$ | E-5a(R) | *1 |
| 5-496 | 3,5-Cl$_2$ | CF$_3$ | 2-CH$_3$ | E-23a | *1 |
| 5-497 | 3,5-Cl$_2$ | CF$_3$ | 2-CH$_3$ | CH$_2$SCH$_3$ | *1 |
| 5-498 | 3,5-Cl$_2$ | CF$_3$ | 2-CH$_3$ | CH$_2$S(O)CH$_3$ | 159.0-161.0 |
| 5-499 | 3,5-Cl$_2$ | CF$_3$ | 2-CH$_3$ | CH$_2$SC$_2$CH$_3$ | 207.0-209.0 |
| 5-500 | 3,5-Cl$_2$ | CF$_3$ | 2-CH$_3$ | CH$_2$SC(O)CH$_3$ | *1 |
| 5-501 | 3,5-Cl$_2$ | CF$_3$ | 2-CH$_3$ | CH$_2$SC(S)OEt | *1 |
| 5-502 | 3,5-Cl$_2$ | CF$_3$ | 2-CH$_3$ | CH$_2$SO$_2$OH·Q5 | *1 |
| 5-503 | 3,5-Cl$_2$ | CF$_3$ | 2-CH$_3$ | CH$_2$CH$_2$SC(O)NHEt | 148.0-150.0 |
| 5-504 | 3,5-Cl$_2$ | CF$_3$ | 2-CH$_3$ | CH$_2$CH$_2$SC(O)NH(Ph-4-F) | *2 |
| 5-505 | 3,5-Cl$_2$ | CF$_3$ | 2-CH$_3$ | CH$_2$CH$_2$S(D-50a) | *2 |
| 5-506 | 3,5-Cl$_2$ | CF$_3$ | 2-CH$_3$ | CH$_2$CH$_2$SO$_2$(D-50a) | *2 |
| 5-507 | 3,5-Cl$_2$ | CF$_3$ | 2-CH$_3$ | CH$_2$NH$_2$·Q1 | 155.0-157.0 |
| 5-508 | 3,5-Cl$_2$ | CF$_3$ | 2-CH$_3$ | CH$_2$NHEt | *1 |
| 5-509 | 3,5-Cl$_2$ | CF$_3$ | 2-CH$_3$ | CH$_2$NHCH$_2$CF$_3$ | *1 |
| 5-510 | 3,5-Cl$_2$ | CF$_3$ | 2-CH$_3$ | CH$_2$N(CH$_2$CF$_3$)C(O)CH$_3$ | *1 |
| 5-511 | 3,5-Cl$_2$ | CF$_3$ | 2-CH$_3$ | CH$_2$N(CH$_2$CF$_3$)C(O)OCH$_3$ | *1 |
| 5-512 | 3,5-Cl$_2$ | CF$_3$ | 2-CH$_3$ | CH$_2$NHC(O)CH$_3$ | 112.0-114.0 |
| 5-513 | 3,5-Cl$_2$ | CF$_3$ | 2-CH$_3$ | CH$_2$NHC(O)CF$_3$ | 191.0-194.0 |
| 5-514 | 3,5-Cl$_2$ | CF$_3$ | 2-CH$_3$ | CH$_2$NHC(O)CH$_2$CF$_3$ | 212.0-217.0 |
| 5-515 | 3,5-Cl$_2$ | CF$_3$ | 2-CH$_3$ | CH$_2$NHC(O)OCH$_3$ | *1 |
| 5-516 | 3,5-Cl$_2$ | CF$_3$ | 2-CH$_3$ | CH$_2$NHC(O)OEt | 110.0-120.0 |
| 5-517 | 3,5-Cl$_2$ | CF$_3$ | 2-CH$_3$ | CH$_2$NHC(O)OCH$_2$CF$_3$ | 118.0-119.0 |
| 5-518 | 3,5-Cl$_2$ | CF$_3$ | 2-CH$_3$ | CH$_2$NHC(O)NHEt | 152.0-154.0 |
| 5-519 | 3,5-Cl$_2$ | CF$_3$ | 2-CH$_3$ | CH(CH$_3$)NHC(O)OCH$_3$ | 88.0-90.0 |
| 5-520 | 3,5-Cl$_2$ | CF$_3$ | 2-CH$_3$ | CH$_2$CH$_2$NHC(O)OCH$_2$CH$_2$Cl | 96.0-99.0 |
| 5-521 | 3,5-Cl$_2$ | CF$_3$ | 2-CH$_3$ | CH$_2$CH$_2$NHSO$_2$Et | *1 |
| 5-522 | 3,5-Cl$_2$ | CF$_3$ | 2-CH$_3$ | CH$_2$CH=NOCH$_2$CF$_3$ | *1 |
| 5-523 | 3,5-Cl$_2$ | CF$_3$ | 2-CH$_3$ | CH(CH$_3$)CH=NOCH$_3$ | *1 |
| 5-524 | 3,5-Cl$_2$ | CF$_3$ | 2-CH$_3$ | CH(CH$_2$OH)C(O)OCH$_3$ | *1 |
| 5-525 | 3,5-Cl$_2$ | CF$_3$ | 2-CH$_3$ | CH$_2$CH$_2$CH$_2$C(O)OEt | *1 |
| 5-526 | 3,5-Cl$_2$ | CF$_3$ | 2-CH$_3$ | E-7e | 192.0-194.5 |
| 5-527 | 3,5-Cl$_2$ | CF$_3$ | 2-CH$_3$ | CH$_2$C(O)N(CH$_3$)Et | *1 |
| 5-528 | 3,5-Cl$_2$ | CF$_3$ | 2-CH$_3$ | CH$_2$C(O)N(Et)$_2$ | *1 |
| 5-529 | 3,5-Cl$_2$ | CF$_3$ | 2-CH$_3$ | CH$_2$C(O)NHPr-c | 146.0-147.0 |
| 5-530 | 3,5-Cl$_2$ | CF$_3$ | 2-CH$_3$ | CH$_2$C(O)NHBu-s | 148.0-149.0 |
| 5-531 | 3,5-Cl$_2$ | CF$_3$ | 2-CH$_3$ | CH$_2$C(O)NHCH$_2$Pr-c | 195.0-197.0 |
| 5-532 | 3,5-Cl$_2$ | CF$_3$ | 2-CH$_3$ | CH$_2$C(O)NHCH$_2$OH(OEt)$_2$ | *1 |
| 5-533 | 3,5-Cl$_2$ | CF$_3$ | 2-CH$_3$ | CH$_2$C(O)NHCH$_2$CN | 198.0-201.0 |
| 5-534 | 3,5-Cl$_2$ | CF$_3$ | 2-CH$_3$ | CH$_2$C(O)NHCH$_2$C(O)NHCH$_3$ | 170.0-172.0 |
| 5-535 | 3,5-Cl$_2$ | CF$_3$ | 2-CH$_3$ | CH$_2$C(O)NHCH$_2$C(O)NHOH$_2$CF$_3$ | 180.0-183.0 |
| 5-536 | 3,5-Cl$_2$ | CF$_3$ | 2-CH$_3$ | CH$_2$C(O)NH(Ph-4-F) | 235.0-237.0 |

TABLE 11-continued

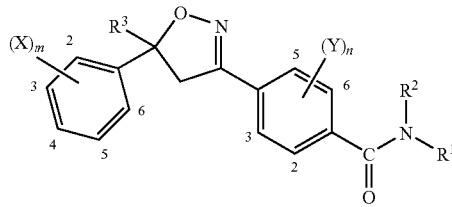

| No. | (X)$_m$ | R$^3$ | (Y)$_n$ | R$^1$ | m.p. (C. °) |
|---|---|---|---|---|---|
| 5-537 | 3,5-Cl$_2$ | CF$_3$ | 2-CH$_3$ | CH$_2$C(O)NH(Ph-4-CN) | 267.0-269.0 |
| 5-538 | 3,5-Cl$_2$ | CF$_3$ | 2-CH$_3$ | CH(CH$_3$)C(O)NH$_2$ | *1 |
| 5-539 | 3,5-Cl$_2$ | CF$_3$ | 2-CH$_3$ | CH(CH$_3$)C(O)NHCH$_2$CH$_2$Cl(D) | 162.0-164.0 |
| 5-540 | 3,5-Cl$_2$ | CF$_3$ | 2-CH$_3$ | CH(CH$_3$)C(O)NHCH$_2$CH$_2$Cl(L) | 149.0-151.0 |
| 5-540(+) | | 99% d.e. | [α]$_D^{22.9}$ + 54.77° | (EtOH, c = 0.652) | 103.0-105.0 |
| 5-541 | 3,5-Cl$_2$ | CF$_3$ | 2-CH$_3$ | CH(CH$_3$)C(O)NHCH$_2$CF$_3$(D) | 188.0-190.0 |
| | | | [α]$_D^{24.7}$ + 14.89° | (EtOH, c = 0.744) | |
| 5-541(R) | | 95% d.e. | [α]$_D^{24.9}$ − 54.42° | (EtOH, c = 0.890) | 164.0-166.0 |
| 5-541(S) | | 95% d.e. | [α]$_D^{24.9}$ + 50.27° | (EtOH, c = 0.650) | 216.0-217.0 |
| 5-542 | 3,5-Cl$_2$ | CF$_3$ | 2-CH$_3$ | CH(CH$_3$)C(O)NHCH$_2$CF$_3$(L) | 181.0-183.0 |
| 5-543 | 3,5-Cl$_2$ | CF$_3$ | 2-CH$_3$ | CH(Et)C(O)NHCH$_2$CF$_3$ | 197.0-205.0 |
| 5-544 | 3,5-Cl$_2$ | CF$_3$ | 2-CH$_3$ | CH(Pr-i)C(O)NHCH$_2$CF$_3$ | 220.0-224.0 |
| 5-545 | 3,5-Cl$_2$ | CF$_3$ | 2-CH$_3$ | CH$_2$CH$_2$CH$_2$C(O)NHCH$_2$CF$_3$ | 172.0-175.0 |
| 5-546 | 3,5-Cl$_2$ | CF$_3$ | 2-CH$_3$ | T-50 | *2 |
| 5-547 | 3,5-Cl$_2$ | CF$_3$ | 2-CH$_3$ | T-51 | *2 |
| 5-548 | 3,5-Cl$_2$ | CF$_3$ | 2-CH$_3$ | CH$_2$(D-14b)CF$_3$ | *1 |
| 5-549 | 3,5-Cl$_2$ | CF$_3$ | 2-CH$_3$ | CH$_2$(D-17b)CF$_3$ | 219.0-222.0 |
| 5-550 | 3,5-Cl$_2$ | CF$_3$ | 2-CH$_3$ | CH$_2$(D-21e) | 71.0-79.0 |
| 5-551 | 3,5-Cl$_2$ | CF$_3$ | 2-CH$_3$ | CH$_2$(D-22a)•Q1 | 177.0-177.5 |
| 5-552 | 3,5-Cl$_2$ | CF$_3$ | 2-CH$_3$ | CH$_2$(D-22a)•Q2 | 95.0-103.0 |
| 5-553 | 3,5-Cl$_2$ | CF$_3$ | 2-CH$_3$ | CH$_2$(D-22a)•Q3 | 135.0-137.0 |
| 5-554 | 3,5-Cl$_2$ | CF$_3$ | 2-CH$_3$ | CH$_2$(D-22a)•Q4 | 125.0-130.0 |
| 5-555 | 3,5-Cl$_2$ | CF$_3$ | 2-CH$_3$ | CH$_2$(D-22b)SCH$_3$ | *1 |
| 5-556 | 3,5-Cl$_2$ | CF$_3$ | 2-CH$_3$ | CH$_2$(D-22b)SO$_2$CH$_3$ | *1 |
| 5-557 | 3,5-Cl$_2$ | CF$_3$ | 2-CH$_3$ | CH$_2$(D-22b)CF$_3$ | *1 |
| 5-558 | 3,5-Cl$_2$ | CF$_3$ | 2-CH$_3$ | CH$_2$(D-37a) | *2 |
| 5-559 | 3,5-Cl$_2$ | CF$_3$ | 2-CH$_3$ | CH$_2$(D-61b) | *1 |
| 5-560 | 3,5-Cl$_2$ | CF$_3$ | 2-CH$_3$ | CH(CH$_3$)(D-14a) | *1 |
| 5-561 | 3,5-Cl$_2$ | CF$_3$ | 2-CH$_3$ | OCH$_3$ | *1 |
| 5-562 | 3,5-Cl$_2$ | CF$_3$ | 2-CH$_3$ | OCH$_2$CH=CH$_2$ | 158.0-160.0 |
| 5-563 | 3,5-Cl$_2$ | CF$_3$ | 2-CH$_3$ | SO$_2$CH$_3$ | *1 |
| 5-564 | 3,5-Cl$_2$ | CF$_3$ | 2-CH$_3$ | SO$_2$N(CH$_3$)$_2$ | *2 |
| 5-565 | 3,5-Cl$_2$ | CF$_3$ | 2-CH$_3$ | N(Ph)C(O)CH$_2$Cl | *1 |
| 5-566 | 3,5-Cl$_2$ | CF$_3$ | 2-CH$_3$ | N=CHN(CH$_3$)$_2$ | 100.0-106.0 |
| 5-567 | 3,5-Cl$_2$ | CF$_3$ | 2-CH$_3$ | N=C(CH$_3$)N(CH$_3$)$_2$ | 79.0-84.0 |
| 5-568 | 3,5-Cl$_2$ | CF$_3$ | 2-CH$_3$ | CHO | 179.0-181.0 |
| 5-569 | 3,5-Cl$_2$ | CF$_3$ | 2-CH$_3$ | C(O)CH$_2$CF$_3$ | 148.0-150.0 |
| 5-570 | 3,5-Cl$_2$ | CF$_3$ | 2-CH$_3$ | C(O)OCH$_2$CH$_2$F | 144.0-146.0 |
| 5-571 | 3,5-Cl$_2$ | CF$_3$ | 2-CH$_3$ | C(O)OCH$_2$CHF$_2$ | 165.0-168.0 |
| 5-572 | 3,5-Cl$_2$ | CF$_3$ | 2-CH$_3$ | C(O)OCH(CH$_2$F)$_2$ | *1 |
| 5-573 | 3,5-Cl$_2$ | CF$_3$ | 2-CH$_3$ | C(O)OCH(CH$_2$F)CH$_2$Cl | *1 |
| 5-574 | 3,5-Cl$_2$ | CF$_3$ | 2-CH$_3$ | C(O)NHCH$_3$ | 161.0-163.0 |
| 5-575 | 3,5-Cl$_2$ | CF$_3$ | 2-CH$_3$ | C(O)N(CH$_3$)$_2$ | *2 |
| 5-576 | 3,5-Cl$_2$ | CF$_3$ | 2-CH$_3$ | C(O)NHEt | 178.0-180.0 |
| 5-577 | 3,5-Cl$_2$ | CF$_3$ | 2-CH$_3$ | C(O)NHCH$_2$CH$_2$Cl | 210.0-213.0 |
| 5-578 | 3,5-Cl$_2$ | CF$_3$ | 2-CH$_3$ | C(O)NHCH$_2$C(O)NHCH$_2$CF$_3$ | 231.0-232.0 |
| 5-579 | 3,5-Cl$_2$ | CF$_3$ | 2-CH$_3$ | C(O)NHCH$_2$CH=CH$_2$ | 160.0-162.0 |
| 5-580 | 3,5-Cl$_2$ | CF$_3$ | 2-CH$_3$ | C(O)NHCH$_2$(Ph-4-F) | 101.0-104.0 |
| 5-581 | 3,5-Cl$_2$ | CF$_3$ | 2-CH$_3$ | C(O)NHCH$_2$(D-47a) | *1 |
| 5-582 | 3,5-Cl$_2$ | CF$_3$ | 2-CH$_3$ | C(O)NH(Ph-4-F) | 188.0-191.0 |
| 5-583 | 3,5-Cl$_2$ | CF$_3$ | 2-CH$_3$ | C(O)(T-33) | *2 |
| 5-584 | 3,5-Cl$_2$ | CF$_3$ | 2-CH$_3$ | O(S)NHCH$_3$ | 98.0-101.0 |
| 5-585 | 3,5-Cl$_2$ | CF$_3$ | 2-CH$_3$ | Ph | *1 |
| 5-586 | 3,5-Cl$_2$ | CF$_3$ | 2-CH$_3$ | Ph-2-F | 164.0-167.0 |
| 5-587 | 3,5-Cl$_2$ | CF$_3$ | 2-CH$_3$ | Ph-3-F | 163.0-171.0 |
| 5-588 | 3,5-Cl$_2$ | CF$_3$ | 2-CH$_3$ | Ph-4-F | *1 |
| 5-589 | 3,5-Cl$_2$ | CF$_3$ | 2-CH$_3$ | Ph-4-Cl | 165.0-169.0 |
| 5-590 | 3,5-Cl$_2$ | CF$_3$ | 2-CH$_3$ | Ph-4-CF$_3$ | 95.0-99.0 |
| 5-591 | 3,5-Cl$_2$ | CF$_3$ | 2-CH$_3$ | Ph-2-OH | *1 |
| 5-592 | 3,5-Cl$_2$ | CF$_3$ | 2-CH$_3$ | Ph-4-OCH$_3$ | 180.0-182.0 |
| 5-593 | 3,5-Cl$_2$ | CF$_3$ | 2-CH$_3$ | Ph-4-OCF$_3$ | 165.0-167.0 |
| 5-594 | 3,5-Cl$_2$ | CF$_3$ | 2-CH$_3$ | Ph-4-OSO$_2$CH$_3$ | 160.0-163.0 |
| 5-595 | 3,5-Cl$_2$ | CF$_3$ | 2-CH$_3$ | Ph-4-SCH$_3$ | 181.0-183.0 |
| 5-596 | 3,5-Cl$_2$ | CF$_3$ | 2-CH$_3$ | Ph-4-S(O)CH$_3$ | 119.0-126.0 |
| 5-597 | 3,5-Cl$_2$ | CF$_3$ | 2-CH$_3$ | Ph-4-SO$_2$CH$_3$ | 222.0-225.0 |
| 5-598 | 3,5-Cl$_2$ | CF$_3$ | 2-CH$_3$ | Ph-4-SO$_2$NH$_2$ | 126.0-130.0 |
| 5-599 | 3,5-Cl$_2$ | CF$_3$ | 2-CH$_3$ | Ph-4-NO$_2$ | 141.0-148.0 |

TABLE 11-continued

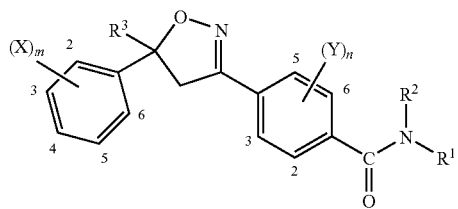

| No. | (X)$_m$ | R$^3$ | (Y)$_n$ | R$^1$ | m.p. (C. °) |
|---|---|---|---|---|---|
| 5-600 | 3,5-Cl$_2$ | CF$_3$ | 2-CH$_3$ | Ph-2-CN | 168.0-175.0 |
| 5-601 | 3,5-Cl$_2$ | CF$_3$ | 2-CH$_3$ | Ph-3-CN | *1 |
| 5-602 | 3,5-Cl$_2$ | CF$_3$ | 2-CH$_3$ | Ph-4-C(O)NH$_2$ | 209.0-213.0 |
| 5-603 | 3,5-Cl$_2$ | CF$_3$ | 2-CH$_3$ | Ph-2-C(O)NHPr-i | *1 |
| 5-604 | 3,5-Cl$_2$ | CF$_3$ | 2-CH$_3$ | Ph-2,4-F$_2$ | *1 |
| 5-605 | 3,5-Cl$_2$ | CF$_3$ | 2-CH$_3$ | Ph-2,5-F$_2$ | *1 |
| 5-606 | 3,5-Cl$_2$ | CF$_3$ | 2-CH$_3$ | Ph-2,6-F$_2$ | 177.5-181.0 |
| 5-607 | 3,5-Cl$_2$ | CF$_3$ | 2-CH$_3$ | Ph-3,4-F2 | 154.0-160.0 |
| 5-608 | 3,5-Cl$_2$ | CF$_3$ | 2-CH$_3$ | Ph-2-F-4-Cl | 140.0-142.0 |
| 5-609 | 3,5-Cl$_2$ | CF$_3$ | 2-CH$_3$ | Ph-3,4-Cl$_2$ | *1 |
| 5-610 | 3,5-Cl$_2$ | CF$_3$ | 2-CH$_3$ | Ph-3,5-Cl$_2$ | *1 |
| 5-611 | 3,5-Cl$_2$ | CF$_3$ | 2-CH$_3$ | Ph-3-NO$_2$-4-F | *1 |
| 5-612 | 3,5-Cl$_2$ | CF$_3$ | 2-CH$_3$ | Ph-2,4,6-F$_3$ | *1 |
| 5-613 | 3,5-Cl$_2$ | CF$_3$ | 2-CH$_3$ | Ph-2,6-F2-4-Br | 215.0-217.0 |
| 5-614 | 3,5-Cl$_2$ | CF$_3$ | 2-CH$_3$ | D-3a | 102.0-107.0 |
| 5-615 | 3,5-Cl$_2$ | CF$_3$ | 2-CH$_3$ | D-5a | *1 |
| 5-616 | 3,5-Cl$_2$ | CF$_3$ | 2-CH$_3$ | (D-10b)CH$_3$ | 190.0-193.0 |
| 5-617 | 3,5-Cl$_2$ | CF$_3$ | 2-CH$_3$ | D-14a | *1 |
| 5-618 | 3,5-Cl$_2$ | CF$_3$ | 2-CH$_3$ | (D-14c)Br | *1 |
| 5-619 | 3,5-Cl$_2$ | CF$_3$ | 2-CH$_3$ | (D-21b)CF$_3$ | *1 |
| 5-620 | 3,5-Cl$_2$ | CF$_3$ | 2-CH$_3$ | D-21e | 182.0-187.0 |
| 5-621 | 3,5-Cl$_2$ | CF$_3$ | 2-CH$_3$ | D-61b | *1 |
| 5-622 | 3,5-Cl$_2$ | CF$_3$ | 2-CH$_3$ | D-41a | 223.0-224.0 |
| 5-623 | 3,5-Cl$_2$ | CF$_3$ | 2-CH$_3$ | (D-47d)Cl | 129.0-132.5 |
| 5-624 | 3,5-Cl$_2$ | CF$_3$ | 2-CH$_3$ | (D-47d)Br | 181.0-183.0 |
| 5-625 | 3,5-Cl$_2$ | CF$_3$ | 2-CH$_3$ | (D-47d)I | 180.0-186.0 |
| 5-626 | 3,5-Cl$_2$ | CF$_3$ | 2-CH$_3$ | (D-47d)CH$_3$ | 110.0-113.0 |
| 5-627 | 3,5-Cl$_2$ | CF$_3$ | 2-CH$_3$ | (D-47d)CF$_3$ | 184.0-186.0 |
| 5-628 | 3,5-Cl$_2$ | CF$_3$ | 2-CH$_3$ | (D-47d)NO$_2$ | 113.0-116.0 |
| 5-629 | 3,5-Cl$_2$ | CF$_3$ | 2-CH$_3$ | (D-47d)CN | *1 |
| 5-630 | 3,5-Cl$_2$ | CF$_3$ | 2-CH$_3$ | (D-47e)Cl | *1 |
| 5-631 | 3,5-Cl$_2$ | CF$_3$ | 2-CH$_3$ | (D-47e)Br | *1 |
| 5-632 | 3,5-Cl$_2$ | CF$_3$ | 2-CH$_3$ | (D-47f)-3,5-Cl$_2$ | 120.0-124.0 |
| 5-633 | 3,5-Cl$_2$ | CF$_3$ | 2-CH$_3$ | (D-48e)Cl | *1 |
| 5-634 | 3,5-Cl$_2$ | CF$_3$ | 2-CH$_3$ | (D-48e)CN | *1 |
| 5-635 | 3,5-Cl$_2$ | CF$_3$ | 2-CH$_3$ | (D-49b)Cl | *1 |
| 5-636 | 3,5-Cl$_2$ | CF$_3$ | 2-CH$_3$ | D-49e | 173.0-177.0 |
| 5-637 | 3,5-Cl$_2$ | CF$_3$ | 2-CH$_3$ | (D-50b)CH$_3$ | *1 |
| 5-638 | 3,5-Cl$_2$ | CF$_3$ | 2-CH$_3$ | (D-50c)Cl | 137.0-141.0 |
| 5-639 | 3,5-Cl$_2$ | CF$_3$ | 2-CH$_3$ | (D-50c)Br | 178.0-181.0 |
| 5-640 | 3,5-Cl$_2$ | CF$_3$ | 2-CH$_3$ | (D-50c)I | *1 |
| 5-641 | 3,5-Cl$_2$ | CF$_3$ | 2-CH$_3$ | (D-51c)Cl | 85.0-87.0 |
| 5-642 | 3,5-Cl$_2$ | CF$_3$ | 2-CH$_3$ | D-52a | 207.0-211.0 |
| 5-643 | 3,5-Cl$_2$ | CF$_3$ | 2-CH$_3$ | D-53a | 139.0-144.0 |
| 5-644 | 3,5-Cl$_2$ | CF$_3$ | 2-CH$_3$ | (D-53b)Br | 251.0-253.0 |
| 5-645 | 3,5-Cl$_2$ | CF$_3$ | 2-CH$_3$ | (D-54b)Cl | 99.0-102.5 |
| 5-646 | 3,5-Cl$_2$ | CF$_2$CF$_3$ | 2-CH$_3$ | CH$_2$0(O)NHCH$_2$CF$_3$ | 171.0-173.0 |
| 5-647 | 3,5-Cl$_2$-4-CH$_3$ | CF$_3$ | 2-CH$_3$ | CH$_2$CF$_3$ | *2 |
| 5-648 | 3,5-Cl$_2$-4-CH$_3$ | CF$_3$ | 2-CH$_3$ | CH$_2$(D-47a) | *2 |
| 5-649 | 3,5-Cl$_2$-4-OH | CF$_3$ | 2-CH$_3$ | CH$_2$(D-47a) | *2 |
| 5-650 | 3,5-Cl$_2$-4-OCH$_3$ | CF$_3$ | 2-CH$_3$ | CH$_2$CF$_3$ | 198.0-199.0 |
| 5-651 | 3,5-Cl$_2$-4-OCH$_3$ | CF$_3$ | 2-CH$_3$ | CH$_2$(D-47a) | *2 |
| 5-652 | 3,5-Cl$_2$-4-OC(O)OBu-t | CF$_3$ | 2-CH$_3$CH$_2$(D-47a) | *2 | |
| 5-653 | 3,5-Cl$_2$-4-N(CH$_3$)2 | CF$_3$ | 2-CH$_3$ | CH$_2$CF$_3$ | *2 |
| 5-654 | 3,5-Cl$_2$-4-N(CH$_3$)2 | CF$_3$ | 2-CH$_3$ | CH$_2$(D-47a) | *2 |
| 5-655 | 3,5-Cl$_2$ | CF$_3$ | 2-I | CH$_2$OCH$_2$CF$_3$ | *1 |
| 5-656 | 3,5-Cl$_2$ | CF$_3$ | 2-I | E-4a | *1 |
| 5-657 | 3,5-Cl$_2$ | CF$_3$ | 3-I | CH$_2$C(O)NHCH$_2$CF$_3$ | *1 |
| 5-658 | 3,5-Cl$_2$ | CF$_3$ | 2-CH$_3$ | (E-23b)OCH$_3$ | *1 |
| 5-659 | 3,5-Cl$_2$ | CF$_3$ | 2-CH$_3$ | CH$_2$C(O)NH(E-4a) | 86.0-91.0 |
| 5-660 | 3,5-Cl$_2$ | CF$_3$ | 2-CH$_3$ | CH=CH$_2$ | *1 |
| 5-661 | 3,5-Cl$_2$ | CF$_3$ | 2-CH$_3$ | CH$_2$C≡CBr | 166.0-169.0 |
| 5-662 | 3,5-Cl$_2$ | CF$_3$ | 2-CH$_3$ | N(CH$_3$)C(O)NHCH$_2$CF$_3$ | *1 |
| 5-663 | 3,5-Cl$_2$ | CF$_3$ | 2-CH$_3$ | OC(O)NHCH$_2$CF$_3$ | 111.0-114.0 |
| 5-664 | 3,5-Cl$_2$ | CF$_3$ | 2-CH$_3$ | C(O)CH$_3$ | 151.0-154.5 |
| 5-665 | 3,5-Cl$_2$ | CF$_3$ | 2-CH$_3$ | C(O)Et | 169.0-172.0 |
| 5-666 | 3,5-Cl$_2$ | CF$_3$ | 2-CH$_3$ | D-22a | 228.0-230.0 |

TABLE 11-continued

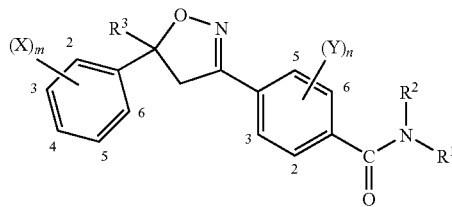

| No. | (X)$_m$ | R$^3$ | (Y)$_n$ | R$^1$ | m.p. (C. °) |
|---|---|---|---|---|---|
| 5-667 | 3,5-Cl$_2$ | CF$_3$ | 2-CH$_3$ | (D-22b)Br | *1 |
| 5-668 | 3,5-Cl$_2$ | CF$_3$ | 2-CH$_3$ | (D-47b)Cl | *1 |
| 5-669 | 3,5-Cl$_2$ | CF$_2$Cl | 2-Cl | H | *1 |
| 5-670 | 3-Cl-5-Br | CF$_3$ | 2-CH$_3$ | H | *1 |
| 5-671 | 3,5-Br$_2$ | CF$_3$ | 2-Cl | H | 105.0-108.0 |
| 5-672 | 3,5-(CF$_3$)$_2$ | CF$_3$ | 2-CH$_3$ | H | *1 |
| 5-673 | 3,5-Cl$_2$ | CF$_3$ | 2-CH$_3$ | D-2a | 105.0-110.0 |
| 5-674 | 3,5-Cl$_2$ | CF$_3$ | 2-CH$_3$ | (D-50c)CN | 118.0-121.0 |
| 5-675 | 3,5-Cl$_2$ | CF$_3$ | 2-CH$_3$ | (D-52b)Cl | 231.0-234.0 |
| 5-676 | 3,5-Cl$_2$ | CF$_3$ | 2-CH$_3$ | (D-53b)Cl | 242.0-243.0 |
| 5-677 | 3,5-Cl$_2$ | CF$_3$ | 2-Et | H | *1 |
| 5-678 | 3,5-Cl$_2$ | CF$_3$ | 2-CH$_2$OCH$_3$ | H | 186.0-188.0 |
| 5-679 | 3,5-Cl$_2$ | CF$_3$ | 2-OCHF$_2$ | H | *1 |
| 5-680 | 3,5-Cl$_2$ | CF$_3$ | 2-NO$_2$ | H | *1 |
| 5-681 | 3,5-Cl$_2$ | CF$_3$ | 2-NH$_2$ | H | 190.0-193.0 |
| 5-682 | 3,5-Cl$_2$ | CF$_3$ | 2-NHC(O)CH$_3$ | H | *1 |
| 5-683 | 3,4,5-Cl$_3$ | CF$_3$ | 2-CH$_3$ | H | 153.0-155.0 |
| 5-684 | 3-Cl-5-CF$_3$ | CF$_3$ | 2-CH$_3$ | CH$_2$CF$_3$ | *1 |
| 5-685 | 3,5-Cl$_2$-4-F | CF$_3$ | 2-CH$_3$ | CH$_2$CF$_3$ | *1 |
| 5-686 | 3-Cl-4-F-5-CF$_3$ | CF$_3$ | 2-CH$_3$ | CH$_2$CF$_3$ | *1 |

In Table above, the indications of "5-529 (R)*" and "5-529 (S)*" show optical isomers in which the absolute configuration of 5-position of 4,5-dihydroisooxazole ring is R- and S-configuration, respectively.

TABLE 12

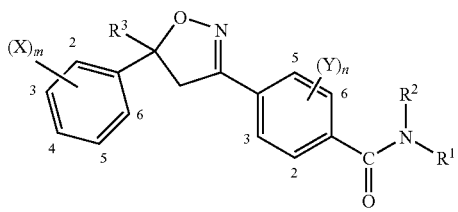

| No. | (X)$_m$ | R$^3$ | (Y)$_n$ | R$^2$ | R$^1$ | m.p. (° C.) |
|---|---|---|---|---|---|---|
| 6-001 | 3,5-Cl$_2$ | CF$_3$ | 2-Cl | Et | Et | *1 |
| 6-002 | 3,5-Cl$_2$ | CF$_3$ | 2-CH$_3$ | NH$_2$ | CH$_3$ | 138.0-139.0 |
| 6-003 | 3,5-Cl$_2$ | CF$_3$ | 2-CH$_3$ | Et | Et | *1 |
| 6-004 | 3,5-Cl$_2$ | CF$_3$ | 2-CH$_3$ | NH$_2$ | Et | 76.0-78.0 |
| 6-005 | 3,5-Cl$_2$ | CF$_3$ | 2-CH$_3$ | NHC(O)CH$_3$ | Et | *1 |
| 6-006 | 3,5-Cl$_2$ | CF$_3$ | 2-CH$_3$ | N=C(CH$_3$)$_2$ | Et | *1 |
| 6-007 | 3,5-Cl$_2$ | CF$_3$ | 2-CH$_3$ | CH$_2$CN | n-Bu | *1 |
| 6-008 | 3,5-Cl$_2$ | CF$_3$ | 2-CH$_3$ | CH$_2$CN | CH$_2$CN | *1 |
| 6-009 | 3,5-Cl$_2$ | CF$_3$ | 2-CH$_3$ | OH | CH$_2$Ph | 175.0-177.0 |
| 6-010 | 3,5-Cl$_2$ | CF$_3$ | 2-CH$_3$ | OCH$_3$ | CH$_2$Ph | *1 |
| 6-011 | 3,5-Cl$_2$ | CF$_3$ | 2-CH$_3$ | OC(O)CH$_3$ | CH$_2$Ph | *1 |
| 6-012 | 3,5-Cl$_2$ | CF$_3$ | 2-CH$_3$ | OC(O)OCH$_3$ | CH$_2$Ph | *1 |
| 6-013 | 3,5-Cl$_2$ | CF$_3$ | 2-CH$_3$ | OSO$_2$CH$_3$ | CH$_2$Ph | *1 |
| 6-014 | 3,5-Cl$_2$ | CF$_3$ | 2-CH$_3$ | NH$_2$ | CH$_2$Ph | 135.0-136.0 |
| 6-015 | 3,5-Cl$_2$ | CF$_3$ | 2-CH$_3$ | CH$_2$CN | CH$_2$(D-22a) | *1 |
| 6-016 | 3,5-Cl$_2$ | CF$_3$ | 2-CH$_3$ | CH$_2$=CH | CH$_2$(D-22a) | *1 |
| 6-017 | 3,5-Cl$_2$ | CF$_3$ | 2-CH$_3$ | C(O)CH$_3$ | CH$_2$(D-22a) | *1 |
| 6-018 | 3,5-Cl$_2$ | CF$_3$ | 2-CH$_3$ | C(O)Et | CH$_2$(D-22a) | *1 |
| 6-019 | 3,5-Cl$_2$ | CF$_3$ | 2-CH$_3$ | C(O)OCH$_3$ | CH$_2$(D-22a) | *1 |
| 6-020 | 3,5-Cl$_2$ | CF$_3$ | 2-CH$_3$ | CH$_3$ | CH$_2$(D-47a) | *1 |
| 6-021 | 3,5-Cl$_2$ | CF$_3$ | 2-CH$_3$ | Et | CH$_2$(D-47a) | *1 |
| 6-022 | 3,5-Cl$_2$ | CF$_3$ | 2-CH$_3$ | n-Pr | CH$_2$(D-47a) | *1 |
| 6-023 | 3,5-Cl$_2$ | CF$_3$ | 2-CH$_3$ | i-Pr | CH$_2$(D-47a) | *1 |
| 6-024 | 3,5-Cl$_2$ | CF$_3$ | 2-CH$_3$ | c-Pr | CH$_2$(D-47a) | *1 |
| 6-025 | 3,5-Cl$_2$ | CF$_3$ | 2-CH$_3$ | t-Bu | CH$_2$(D-47a) | *1 |
| 6-026 | 3,5-Cl$_2$ | CF$_3$ | 2-CH$_3$ | CH$_2$CF$_3$ | CH$_2$(D-47a) | *1 |

TABLE 12-continued

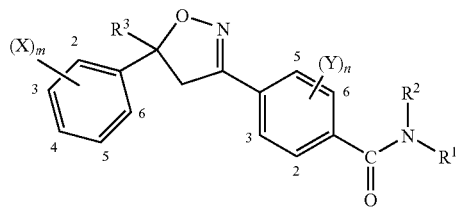

| No. | (X)$_m$ | R$^3$ | (Y)$_n$ | R$^2$ | R$^1$ | m.p. (° C.) |
|---|---|---|---|---|---|---|
| 6-027 | 3,5-Cl$_2$ | CF$_3$ | 2-CH$_3$ | CH$_2$OCH$_3$ | CH$_2$(D-47a) | *1 |
| 6-028 | 3,5-Cl$_2$ | CF$_3$ | 2-CH$_3$ | CH$_2$CH$_2$OCH$_3$ | CH$_2$(D-47a) | *1 |
| 6-029 | 3,5-Cl$_2$ | CF$_3$ | 2-CH$_3$ | CH$_2$SCH$_3$ | CH$_2$(D-47a) | *1 |
| 6-030 | 3,5-Cl$_2$ | CF$_3$ | 2-CH$_3$ | CH$_2$C(O)OCH$_3$ | CH$_2$(D-47a) | *1 |
| 6-031 | 3,5-Cl$_2$ | CF$_3$ | 2-CH$_3$ | CH$_2$CN | CH$_2$(D-47a) | *1 |
| 6-032 | 3,5-Cl$_2$ | CF$_3$ | 2-CH$_3$ | CH$_2$CH=CH$_2$ | CH$_2$(D-47a) | *1 |
| 6-033 | 3,5-Cl$_2$ | CF$_3$ | 2-CH$_3$ | CH$_2$C≡CH | CH$_2$(D-47a) | *1 |
| 6-034 | 3,5-Cl$_2$ | CF$_3$ | 2-CH$_3$ | C(O)CH$_3$ | CH$_2$(D-47a) | *1 |
| 6-035 | 3,5-Cl$_2$ | CF$_3$ | 2-CH$_3$ | C(O)Et | CH$_2$(D-47a) | *1 |
| 6-036 | 3,5-Cl$_2$ | CF$_3$ | 2-CH$_3$ | C(O)Pr-n | CH$_2$(D-47a) | *1 |
| 6-037 | 3,5-Cl$_2$ | CF$_3$ | 2-CH$_3$ | C(O)Pr-i | CH$_2$(D-47a) | *1 |
| 6-038 | 3,5-Cl$_2$ | CF$_3$ | 2-CH$_3$ | C(O)Pr-c | CH$_2$(D-47a) | *1 |
| 6-039 | 3,5-Cl$_2$ | CF$_3$ | 2-CH$_3$ | C(O)Bu-t | CH$_2$(D-47a) | *1 |
| 6-040 | 3,5-Cl$_2$ | CF$_3$ | 2-CH$_3$ | C(O)CH$_2$OCH$_3$ | CH$_2$(D-47a) | 53.0-55.0 |
| 6-041 | 3,5-Cl$_2$ | CF$_3$ | 2-CH$_3$ | C(O)CH=CH$_2$ | CH$_2$(D-47a) | *1 |
| 6-042 | 3,5-Cl$_2$ | CF$_3$ | 2-CH$_3$ | C(O)Ph | CH$_2$(D-47a) | *1 |
| 6-043 | 3,5-Cl$_2$ | CF$_3$ | 2-CH$_3$ | C(O)OCH$_3$ | CH$_2$(D-47a) | *1 |
| 6-044 | 3,5-Cl$_2$ | CF$_3$ | 2-CH$_3$ | C(O)OEt | CH$_2$(D-47a) | *1 |
| 6-045 | 3,5-Cl$_2$ | CF$_3$ | 2-CH$_3$ | C(O)OPr-i | CH$_2$(D-47a) | *1 |
| 6-046 | 3,5-Cl$_2$ | CF$_3$ | 2-CH$_3$ | C(O)OBu-i | CH$_2$(D-47a) | *1 |
| 6-047 | 3,5-Cl$_2$ | CF$_3$ | 2-CH$_3$ | C(O)OCH$_2$CH$_2$Cl | CH$_2$(D-47a) | *1 |
| 6-048 | 3,5-Cl$_2$ | CF$_3$ | 2-CH$_3$ | C(O)OCH$_2$CH$_2$OCH$_3$ | CH$_2$(D-47a) | *1 |
| 6-049 | 3,5-Cl$_2$ | CF$_3$ | 2-CH$_3$ | C(O)OCH$_2$CH=CH$_2$ | CH$_2$(D-47a) | *1 |
| 6-050 | 3,5-Cl$_2$ | CF$_3$ | 2-CH$_3$ | C(O)SCH$_3$ | CH$_2$(D-47a) | *1 |
| 6-051 | 3,5-Cl$_2$ | CF$_3$ | 2-CH$_3$ | SO$_2$CH$_3$ | CH$_2$(D-47a) | *1 |
| 6-052 | 3,5-Cl$_2$ | CF$_3$ | 2-CH$_3$ | NH$_2$ | CH$_2$(D-47a) | 126.0-130.0 |
| 6-053 | 3,5-Cl$_2$ | CF$_3$ | 2-CH$_3$ | N(CH$_3$)$_2$ | CH$_2$(D-47a) | *1 |
| 6-054 | 3,5-Cl$_2$ | CF$_3$ | 2-CH$_3$ | Et | CH$_2$(D-48e)Cl | *1 |
| 6-055 | 3,5-Cl$_2$ | CF$_3$ | 2-CH$_3$ | c-Pr | CH$_2$(D-49a) | *1 |
| 6-056 | 3,5-Cl$_2$ | CF$_3$ | 2-CH$_3$ | C(O)Et | CH$_2$(D-50a) | *1 |
| 6-057 | 3,5-Cl$_2$ | CF$_3$ | 2-CH$_3$ | —CH$_2$CH$_2$SCH$_2$CH$_2$— | | 209.5-211.5 |
| 6-058 | 3,5-Cl$_2$ | CF$_3$ | 2-CH$_3$ | CH$_3$ | N(CH$_3$)Ph | 153.0-154.0 |
| 6-059 | 3,5-Cl$_2$ | CF$_3$ | 2-CH$_3$ | Et | N(CH$_3$)Ph | 78.0-79.0 |
| 6-060 | 3,5-Cl$_2$ | CF$_3$ | 2-CH$_3$ | CH$_2$OCH$_3$ | N(CH$_3$)Ph | 72.0-73.0 |
| 6-061 | 3,5-Cl$_2$ | CF$_3$ | 2-CH$_3$ | CH$_2$CH=CH$_2$ | N(CH$_3$)Ph | 76.0-77.0 |
| 6-062 | 3,5-Cl$_2$ | CF$_3$ | 2-CH$_3$ | CH$_2$C≡CH | N(CH$_3$)Ph | 83.0-84.0 |
| 6-063 | 3,5-Cl$_2$ | CF$_3$ | 2-CH$_3$ | CH$_2$CN | N(CH$_3$)Ph | 69.0-70.0 |
| 6-064 | 3,5-Cl$_2$ | CF$_3$ | 2-CH$_3$ | C(O)CH$_3$ | N(CH$_3$)Ph | 82.0-83.0 |
| 6-065 | 3,5-Cl$_2$ | CF$_3$ | 2-CH$_3$ | C(O)OCH$_3$ | N(CH$_3$)Ph | 70.0-71.0 |
| 6-066 | 3,5-Cl$_2$ | CF$_3$ | 2-CH$_3$ | CH$_3$ | NH(D-50a) | 107.0-109.0 |
| 6-067 | 3,5-Cl$_2$ | CF$_3$ | 2-CH$_3$ | Et | NH(D-50a) | 185.0-187.0 |
| 6-068 | 3,5-Cl$_2$ | CF$_3$ | 2-CH$_2$— | | H | 234.0-236.0 |
| 6-069 | 3,5-Cl$_2$ | CF$_3$ | 2-CH$_2$— | | CH$_3$ | *1 |
| 6-070 | 3,5-Cl$_2$ | CF$_3$ | 2-CH$_2$— | | CH$_2$(D-47a) | *1 |
| 6-071 | 3,5-Cl$_2$ | CF$_3$ | 2-N(CH$_3$)CH$_2$— | | CH$_2$(D-47a) | *1 |
| 6-072 | 3,5-Cl$_2$ | CF$_3$ | 2-N=CH— | | H | 249.0-251.0 |
| 6-073 | 3,5-Cl$_2$ | CF$_3$ | 2-N=CH— | | CH$_2$(D-47a) | *1 |
| 6-074 | 3,5-Cl$_2$ | CF$_2$Cl | 2-CH$_3$ | C(O)CH$_3$ | CH$_2$CF$_3$ | *1 |
| 6-075 | 3,5-Br$_2$ | CF$_3$ | 2-CH$_3$ | C(O)CH$_3$ | CH$_2$CF$_3$ | *1 |
| 6-076 | 3,5-Br$_2$ | CF$_3$ | 2-CH$_3$ | C(O)CH$_3$ | CH$_2$(D-47a) | *1 |
| 6-077 | 3,5-Cl$_2$ | CF$_3$ | 2-CH$_3$ | C(O)OCH$_3$ | CH$_2$CF$_3$ | *2 |
| 6-078 | 3,5-Cl$_2$ | CF$_3$ | 2-CH$_3$ | CH$_2$OCH$_3$ | CH$_2$(D-22a) | *1 |
| 6-079 | 3,5-Cl$_2$ | CF$_3$ | 2-CH$_3$ | CH$_2$OEt | CH$_2$(D-47a) | *1 |
| 6-080 | 3,5-Cl$_2$ | CF$_3$ | 2-CH$_3$ | C(O)OCH$_3$ | CH(CH$_3$)(D-47a) | *2 |
| 6-080(+)* | 98% e.e | [α]$_D^{22.4}$ +35.40° | (CHCL$_3$, c = 0.397) | | | *2 |
| 6-080(−)* | 99% e.e | [α]$_D^{22.2}$ −37.20° | (CHCl$_3$, c = 0.473) | | | *2 |
| 6-081 | 3,5-Cl$_2$ | CF$_3$ | 2-CH$_3$ | C(O)CH$_3$ | N(CH$_3$)(D-47a) | *1 |
| 6-082 | 3,5-Cl$_2$ | CF$_3$ | 2-CH$_3$ | C(O)OCH$_3$ | N(CH$_3$)(D-47a) | *1 |
| 6-083 | 3,5-Cl$_2$ | CF$_3$ | 2-CH$_3$ | C(O)CH$_3$ | N(CH$_3$)(D-50a) | *2 |
| 6-084 | 3,5-Cl$_2$ | CF$_3$ | 2-CH$_3$ | C(O)OCH$_3$ | N(CH$_3$)(D-50a) | *1 |
| 6-085 | 3,5-Cl$_2$ | CF$_3$ | 2-CH$_3$ | —C(O)CH$_2$CH$_2$CH$_2$— | | *1 |
| 6-086 | 3,5-Cl$_2$ | CF$_3$ | 2-CH$_3$ | —C(O)CH$_2$CH$_2$C(O)— | | *1 |
| 6-087 | 3,5-Cl$_2$ | CF$_3$ | 2-CH$_3$ | —CH$_2$CH$_2$N(Ph)CH$_2$CH$_2$— | | 84.0-88.0 |
| 6-088 | 3,5-Cl$_2$ | CF$_3$ | 2-CH$_3$ | —CH$_2$CH$_2$N(D-47a)CH$_2$CH$_2$— | | 87.0-92.0 |
| 6-089 | 3,5-Cl$_2$ | CF$_3$ | 2-CH$_3$ | C(O)Et | CH$_3$ | *1 |
| 6-090 | 3,5-Cl$_2$ | CF$_3$ | 2-CH$_3$ | C(O)CF$_3$ | CH$_3$ | 181.0-183.0 |
| 6-091 | 3,5-Cl$_2$ | CF$_3$ | 2-CH$_3$ | C(O)OCH$_2$CH$_2$CF$_3$ | CH$_3$ | 148.0-150.0 |

TABLE 12-continued

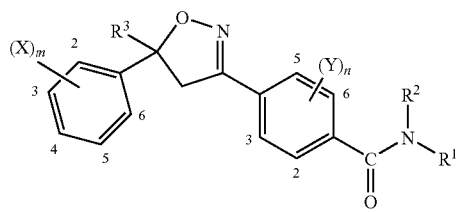

| No. | (X)$_m$ | R$^3$ | (Y)$_n$ | R$^2$ | R$^1$ | m.p. (° C.) |
|---|---|---|---|---|---|---|
| 6-092 | 3,5-Cl$_2$ | CF$_3$ | 2-CH$_3$ | CH$_2$OEt | CH$_2$OEt | *1 |
| 6-093 | 3,5-Cl$_2$ | CF$_3$ | 2-CH$_3$ | C(O)CH$_3$ | CH$_2$OEt | *1 |
| 6-094 | 3,5-Cl$_2$ | CF$_3$ | 2-CH$_3$ | CH$_3$ | CH$_2$OCH$_2$CF$_3$ | *1 |
| 6-095 | 3,5-Cl$_2$ | CF$_3$ | 2-CH$_3$ | C(O)CH$_3$ | CH$_2$OCH$_2$CF$_3$ | *1 |
| 6-096 | 3,5-Cl$_2$ | CF$_3$ | 2-CH$_3$ | C(O)OCH$_3$ | CH$_2$CH$_2$OCH$_3$ | *1 |
| 6-097 | 3,5-Cl$_2$ | CF$_3$ | 2-CH$_3$ | CH$_3$ | CH$_2$(E-10a) | *1 |
| 6-098 | 3,5-Cl$_2$ | CF$_3$ | 2-CH$_3$ | C(O)CH$_3$ | CH$_2$(E-10a) | *1 |
| 6-099 | 3,5-Cl$_2$ | CF$_3$ | 2-CH$_3$ | C(O)OCH$_3$ | CH$_2$(E-10a) | *1 |
| 6-100 | 3,5-Cl$_2$ | CF$_3$ | 2-CH$_3$ | C(O)CH$_3$ | E-4a | *1 |
| 6-101 | 3,5-Cl$_2$ | CF$_3$ | 2-CH$_3$ | CH$_3$ | CH$_2$CH=NOCH$_3$ | *1 |
| 6-102 | 3,5-Cl$_2$ | CF$_3$ | 2-CH$_3$ | C(O)CH$_3$ | CH$_2$CH=NOCH$_3$ | *1 |
| 6-103 | 3,5-Cl$_2$ | CF$_3$ | 2-CH$_3$ | C(O)OCH$_3$ | CH$_2$CH=NOCH$_3$ | *1 |
| 6-104 | 3,5-Cl$_2$ | CF$_3$ | 2-CH$_3$ | C(O)OCH$_3$ | CH$_2$C(O)NHCH$_2$CF$_3$ | 115.0-120.0 |
| 6-105 | 3,5-Cl$_2$ | CF$_3$ | 2-CH$_3$ | C(O)OCH$_3$ | CH$_2$(Ph-4-OCH$_3$) | *1 |
| 6-106 | 3,5-Cl$_2$ | CF$_3$ | 2-CH$_3$ | C(O)OCH$_3$ | CH$_2$(Ph-4-NO$_2$) | *1 |
| 6-107 | 3,5-Cl$_2$ | CF$_3$ | 2-CH$_3$ | C(O)OCH$_3$ | CH$_2$(Ph-4-Ph) | *1 |
| 6-108 | 3,5-Cl$_2$ | CF$_3$ | 2-CH$_3$ | C(O)OBu-t | CH$_2$(D-14b)CF$_3$ | *1 |
| 6-109 | 3,5-Cl$_2$ | CF$_3$ | 2-CH$_3$ | C(O)OCH$_3$ | CH$_2$(D-61b) | *1 |
| 6-110 | 3,5-Cl$_2$ | CF$_3$ | 2-CH$_3$ | C(O)OCH$_3$ | CH$_2$(D-47a)·Q1 | 70.0-100.0 |
| 6-111 | 3,5-Cl$_2$ | CF$_3$ | 2-CH$_3$ | Ph-4-F | CH$_2$(D-47a) | *1 |
| 6-112 | 3,5-Cl$_2$ | CF$_3$ | 2-CH$_3$ | C(O)OCH$_3$ | CH$_2$(D-50a) | *1 |
| 6-113 | 3,5-Cl$_2$ | CF$_3$ | 2-CH$_3$ | —CH$_2$CH$_2$CH$_2$CH[C(O)NHCH$_2$CF$_3$]— | | *1 |
| 6-114 | 3,5-Cl$_2$ | CF$_3$ | 2-CH$_3$ | —CH$_2$OCH$_2$CH$_2$— | | *1 |
| 6-115 | 3,5-Cl$_2$ | CF$_3$ | 2-CH$_3$ | —CH$_2$SCH$_2$CH$_2$— | | *1 |
| 6-116 | 3,5-Cl$_2$ | CF$_3$ | 2-CH$_3$ | —CH$_2$SO$_2$CH$_2$CH$_2$— | | 206.0-208.0 |
| 6-117 | 3,5-Cl$_2$ | CF$_3$ | 2-CH$_3$ | —CH$_2$CH$_2$OCH$_2$CH$_2$— | | 217.0-219.0 |
| 6-118 | 3,5-Cl$_2$ | CF$_3$ | 2-CH$_3$ | —CH$_2$CH$_2$SO$_2$CH$_2$CH$_2$— | | 223.0-226.0 |
| 6-119 | 3,5-Cl$_2$ | CF$_3$ | 2-CH$_3$ | —CH$_2$CH$_2$N(CH$_3$)CH$_2$CH$_2$— | | *1 |
| 6-120 | 3,5-Cl$_2$ | CF$_3$ | 2-CH$_3$ | C(O)OCH$_3$ | OCH$_3$ | *1 |
| 6-121 | 3,5-Cl$_2$ | CF$_3$ | 2-CH$_3$ | C(O)OCH$_3$ | N(CH$_3$)2 | *1 |
| 6-122 | 3,5-Cl$_2$ | CF$_3$ | 2-CH$_3$ | C(O)CH$_3$ | C(O)CH$_3$ | *1 |
| 6-123 | 3,5-Cl$_2$ | CF$_3$ | 2-CH$_3$ | —CH$_2$CH(CH$_2$F)OC(O)— | | *1 |
| 6-124 | 3,5-Cl$_2$ | CF$_3$ | 2-CH$_3$ | C(O)OCH$_3$ | C(O)N(CH$_3$)$_2$ | *1 |
| 6-125 | 3,5-Cl$_2$ | CF$_3$ | 2-CH$_3$ | CH$_3$ | C(O)NHEt | *1 |
| 6-126 | 3,5-Cl$_2$ | CF$_3$ | 2-CH$_3$ | CH$_3$ | C(O)NHCH$_2$CF$_3$ | *1 |
| 6-127 | 3,5-Cl$_2$ | CF$_3$ | 2-CH$_3$ | —CH$_2$CH$_2$N(CH$_2$CF$_3$)C(O)— | | 167.0-170.0 |
| 6-128 | 3,5-Cl$_2$ | CF$_3$ | 2-C(=CH$_2$)— | | CH$_2$CF$_3$ | 141.0-144.0 |
| 6-129 | 3,5-Cl$_2$ | CF$_3$ | 2-CH$_3$ | CH$_3$ | E-4a | 155.0-157.0 |
| 6-130 | 3,5-Cl$_2$ | CF$_3$ | 2-CH$_3$ | CH$_2$OCH$_3$ | E-4a | *1 |
| 6-131 | 3,5-Cl$_2$ | CF$_3$ | 2-CH$_3$ | O(O)Et | E-4a | *1 |
| 6-132 | 3,5-Cl$_2$ | CF$_3$ | 2-CH$_3$ | C(O)Pr-i | E-4a | *1 |
| 6-133 | 3,5-Cl$_2$ | CF$_3$ | 2-CH$_3$ | CH$_3$ | E-6a | 146.0-151.0 |
| 6-134 | 3,5-Cl$_2$ | CF$_3$ | 2-CH$_3$ | CH$_3$ | CH$_3$ | 166.5-168.5 |

In Table above, the indications of "6-080 (+)*" and "6-080 (−)*" show optically active forms of 1-(2-pyridyl) ethylamine moiety.

TABLE 13

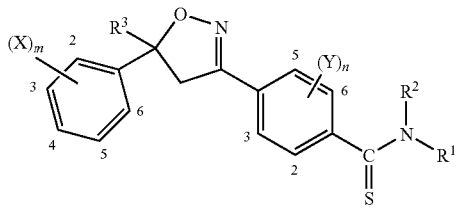

| No. | (X)$_m$ | R$^3$ | (Y)$_n$ | R$^2$ | R$^1$ | m.p. (° C.) |
|---|---|---|---|---|---|---|
| 7-001 | 3,5-Cl$_2$ | CF$_3$ | — | H | H | 227.0-232.0 |
| 7-002 | 3,5-Cl$_2$ | CF$_3$ | — | H | CH$_2$CF$_3$ | *1 |
| 7-003 | 3,5-Cl$_2$ | CF$_3$ | — | H | CH$_2$(D-22a) | *1 |
| 7-004 | 3,5-Cl$_2$ | CF$_3$ | — | H | CH$_2$(D-47a) | 165.0-167.0 |
| 7-005 | 3,5-Cl$_2$ | CF$_3$ | 2-F | H | CH$_2$(D-22a) | 171.0-173.0 |
| 7-006 | 3,5-Cl$_2$ | CF$_3$ | 2-Cl | H | CH$_2$(D-22a) | 90.0-92.0 |
| 7-007 | 3,5-Cl$_2$ | CF$_3$ | 2-CH$_3$ | H | CH$_2$CF$_3$ | *1 |
| 7-008 | 3,5-Cl$_2$ | CF$_3$ | 2-CH$_3$ | H | CH$_2$(D-22a) | *1 |
| 7-009 | 3,5-Cl$_2$ | CF$_3$ | 2-CH$_3$ | H | CH$_2$(D-47a) | *1 |
| 7-010 | 3,5-Cl$_2$ | CF$_3$ | 2-CH$_3$ | H | N(CH$_3$)Ph | 100.0-111.0 |

TABLE 14

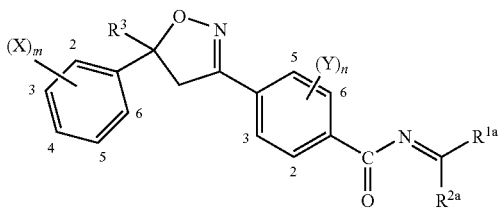

| No. | (X)$_m$ | R$^3$ | (Y)$_n$ | R$^{1a}$ | R$^{2a}$ | m.p. (° C.) |
|---|---|---|---|---|---|---|
| 8-001 | 3,5-Cl$_2$ | CF$_3$ | — | | —N(CH$_3$)CH=CHS— | *1 |
| 8-002 | 3,5-Cl$_2$ | CF$_3$ | 2-CH$_3$ | | —N(CH$_3$)CH=CHS— | *1 |
| 8-003 | 3,5-Cl$_2$ | CF$_3$ | 2-CH$_3$ | | —N(Pr-n)CH=CHS— | *1 |
| 8-004 | 3,5-Cl$_2$ | CF$_3$ | 2-CH$_3$ | | —N(CH$_3$)N=CHCH$_2$S— | *1 |
| 8-005 | 3,5-Cl$_2$ | CF$_3$ | 2-CH$_3$ | O | —N(CH$_3$)CH=CHCH=N— | *1 |
| 8-006 | 3,5-Cl$_2$ | CF$_3$ | 2-CH$_3$ | O | —N(CH$_3$)N=CHS— | *1 |
| 8-007 | 3,5-Cl$_2$ | CF$_3$ | 2-CH$_3$ | O | —N(CH$_3$)N=CClCH=CH— | *2 |

TABLE 15

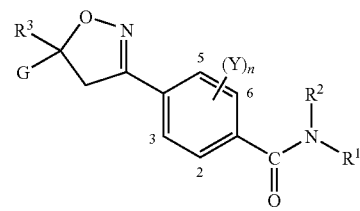

| No. | G | (X)$_m$ | R$^3$ | (Y)$_n$ | R$^2$ | R$^1$ | m.p. (° C.) |
|---|---|---|---|---|---|---|---|
| 9-001 | G-3 | 6-F | CF$_3$ | — | H | CH$_2$CF$_3$ | 175.0-177.0 |
| 9-002 | G-3 | 6-Cl | CF$_3$ | — | H | CH$_2$CF$_3$ | 192.0-195.0 |
| 9-003 | G-3 | 5-Br | CF$_3$ | 2-CH$_3$ | H | CH$_2$CF$_3$ | *1 |
| 9-004 | G-3 | 6-OCH$_3$ | CF$_3$ | — | H | CH$_2$CF$_3$ | 150.0-152.0 |
| 9-005 | G-6 | 4,6-Cl$_2$ | CF$_3$ | — | H | CH$_2$CF$_3$ | 140.0-142.0 |
| 9-006 | G-6 | 4,6-Cl$_2$ | CF$_3$ | 2-CH$_3$ | H | CH$_2$CF$_3$ | 131.0-134.0 |
| 9-007 | G-18 | — | CF$_3$ | — | H | CH$_2$CF$_3$ | 156.0-157.0 |
| 9-008 | G-20 | 4-CF$_3$ | CF$_3$ | 2-CH$_3$ | H | CH$_2$CF$_3$ | *1 |
| 9-009 | G-20 | 4-CF$_3$ | CF$_3$ | 2-CH$_3$ | H | CH$_2$(D-47a) | *1 |

TABLE 15-continued

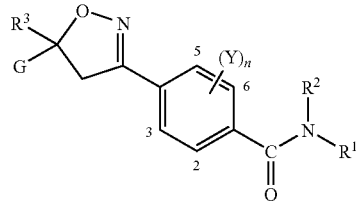

| No. | G | (X)$_m$ | R$^3$ | (Y)$_n$ | R$^2$ | R$^1$ | m.p. (° C.) |
|---|---|---|---|---|---|---|---|
| 9-010 | G-13 | 5-Cl | CF$_3$ | 2-CH$_3$ | H | CH$_2$CF$_3$ | *1 |
| 9-011 | G-13 | 5-Cl | CF$_3$ | 2-CH$_3$ | H | CH$_2$(D-47a) | *1 |

Substituent G in the above-mentioned formula is the structure of G-3, G-6, G-18 or G-20 mentioned below.

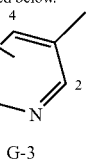

G-3

TABLE 15-continued

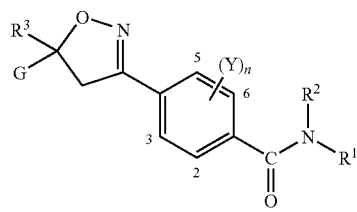

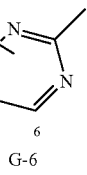

G-6

TABLE 15-continued

[Structure with R³, G, (X)ₘ, (Y)ₙ, R², R¹ substituents on isoxazoline-phenyl-carboxamide]

| No. | G | (X)ₘ | R³ | (Y)ₙ | R² | R¹ | m.p. (°C.) |
|-----|---|------|-----|------|-----|-----|-----------|

G-18: [pyrazole structure with (X)ₘ at 3, methyl at 4, N-CH₃]

G-20: [thiazole structure with (X)ₘ at 4, methyl at 2]

TABLE 16

[Structure with CF₃-isoxazoline, phenyl with (X)ₘ, and A¹/A²/A³ heterocycle-carboxamide with (Y)ₙ and R¹]

| No. | (X)ₘ | A¹ | A² | A³ | (Y)ₙ | R¹ | m.p. (°C.) |
|-----|------|-----|-----|-----|------|-----|-----------|
| 10-001 | 3,5-Cl₂ | N | C | C | — | CH₂CF₃ | *1 |
| 10-002 | 3,5-Cl₂ | N | C | C | — | CH₂(D-47a) | *1 |
| 10-003 | 3,5-Cl₂ | N(O) | C | C | — | CH₂CF₃ | *1 |
| 10-004 | 3,5-Cl₂ | C | N | C | — | CH₂CF₃ | *1 |
| 10-005 | 3,5-Cl₂ | C | N | C | — | CH₂(D-47a) | *1 |

TABLE 17

[Structure with (X)ₘ-phenyl-R³-isoxazoline-phenyl-(Y)ₙ-R]

| No. | (X)ₘ | R³ | (Y)ₙ | R | m.p. (°C.) |
|-----|------|-----|------|---|-----------|
| 11-001 | 3-Cl | CF₃ | — | C(O)OH | 220.0-225.0 |
| 11-002 | 3-Cl | CF₃ | — | C(O)OCH₃ | 100.0-101.0 |
| 11-003 | 4-Cl | CF₃ | — | C(O)OH | 255.0-257.0 |
| 11-004 | 4-Cl | CF₃ | — | C(O)OCH₃ | *1 |
| 11-005 | 3-I | CF₃ | 2-CH₃ | C(O)OH | 169.0-172.0 |
| 11-006 | 3-I | CF₃ | 2-CH₃ | C(O)OCH₃ | *1 |
| 11-007 | 3-NO₂ | CF₃ | 2-CH₃ | C(O)OCH₃ | *1 |
| 11-008 | 3,4-F₂ | CF₃ | — | C(O)OH | 246.0-248.0 |
| 11-009 | 3,4-F₂ | CF₃ | — | C(O)OCH₃ | 132.0-133.0 |
| 11-010 | 2,4-Cl₂ | CF₃ | — | C(O)OH | 104.0-106.0 |
| 11-011 | 2,4-Cl₂ | CF₃ | — | C(O)OCH₃ | 103.0-106.0 |
| 11-012 | 2,5-Cl₂ | CF₃ | — | C(O)OH | 97.0-100.0 |
| 11-013 | 2,5-Cl₂ | CF₃ | — | C(O)OCH₃ | 163.0-165.0 |
| 11-014 | 3,4-Cl₂ | H | — | C(O)OCH₃ | 115.0-117.0 |
| 11-015 | 3,4-Cl₂ | CH₃ | — | C(O)OCH₃ | 98.0-100.0 |
| 11-016 | 3,4-Cl₂ | CF₃ | — | C(O)OH | 215.0-217.0 |
| 11-017 | 3,4-Cl₂ | CF₃ | — | C(O)OCH₃ | 95.0-97.0 |
| 11-018 | 3,4-Cl₂ | CF₃ | — | C(O)OBu-t | 94.0-95.0 |
| 11-019 | 3,4-Cl₂ | CF₃ | — | C(O)OCH₂Ph | 94.0-95.0 |
| 11-020 | 3,4-Cl₂ | Ph | — | C(O)OCH₃ | 143.0-145.0 |
| 11-021 | 3,5-Cl₂ | CF₃ | — | CH₂OH | 108.0-110.0 |
| 11-022 | 3,5-Cl₂ | CF₃ | — | OH | 153.0-155.5 |
| 11-023 | 3,5-Cl₂ | CF₃ | — | OCH₃ | 93.0-96.5 |
| 11-024 | 3,5-Cl₂ | CF₃ | — | NO₂ | 161.0-162.0 |
| 11-025 | 3,5-Cl₂ | CF₃ | — | NH₂ | 98.0-99.0 |
| 11-026 | 3,5-Cl₂ | CF₃ | — | CN | 140.0-142.0 |
| 11-027 | 3,5-Cl₂ | CF₃ | — | O(O)OH | 237.0-240.0 |
| 11-028 | 3,5-Cl₂ | CF₃ | — | O(O)OCH₃ | 94.0-96.0 |
| 11-029 | 3,5-Cl₂ | CF₃ | 2-F | CH₂Br | *2 |
| 11-030 | 3,5-Cl₂ | CF₃ | 2-F | CH₂OC(O)CH₃ | *2 |
| 11-031 | 3,5-Cl₂ | CF₃ | 2-F | CH₂OH | *1 |
| 11-032 | 3,5-Cl₂ | CF₃ | 2-F | C(O)OH | 172.0-174.0 |
| 11-033 | 3,5-Cl₂ | CF₃ | 3-F | Br | 136.0-138.0 |

TABLE 17-continued

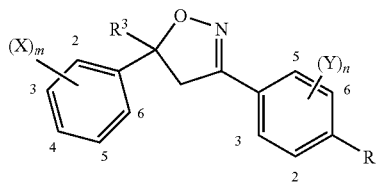

| No. | $(X)_m$ | $R^3$ | $(Y)_n$ | R | m.p. (° C.) |
|---|---|---|---|---|---|
| 11-034 | 3,5-Cl$_2$ | CF$_3$ | 3-F | C(O)OH | *1 |
| 11-035 | 3,5-Cl$_2$ | CF$_3$ | 3-F | C(O)OEt | 94.0-96.0 |
| 11-036 | 3,5-Cl$_2$ | CF$_3$ | 2-Cl | OSO$_2$CF$_3$ | 154.0-157.5 |
| 11-037 | 3,5-Cl$_2$ | CF$_3$ | 2-Cl | C(O)OH | 150.0-151.0 |
| 11-038 | 3,5-Cl$_2$ | CF$_3$ | 2-Cl | C(O)OCH$_3$ | *2 |
| 11-039 | 3,5-Cl$_2$ | CF$_3$ | 3-Cl | Br | *2 |
| 11-040 | 3,5-Cl$_2$ | CF$_3$ | 3-Cl | C(O)OH | 187.0-188.0 |
| 11-041 | 3,5-Cl$_2$ | CF$_3$ | 3-Cl | C(O)OEt | *1 |
| 11-042 | 3,5-Cl$_2$ | CF$_3$ | 2-Br | C(O)OCH$_3$ | 83.0-86.0 |
| 11-043 | 3,5-Cl$_2$ | CF$_3$ | 2-I | CH$_3$ | 130.0-132.0 |
| 11-044 | 3,5-Cl$_2$ | CF$_3$ | 2-I | CH$_2$Br | *1 |
| 11-045 | 3,5-Cl$_2$ | CF$_3$ | 2-I | CH$_2$OC(O)CH$_3$ | *1 |
| 11-046 | 3,5-Cl$_2$ | CF$_3$ | 2-I | CH$_2$OH | *1 |
| 11-047 | 3,5-Cl$_2$ | CF$_3$ | 2-I | C(O)OH | *1 |
| 11-048 | 3,5-Cl$_2$ | CF$_3$ | 2-I | C(O)OCH$_3$ | *2 |
| 11-049 | 3,5-Cl$_2$ | CF$_3$ | 2-CH$_3$ | NO$_2$ | 135.0-136.0 |
| 11-050 | 3,5-Cl$_2$ | CF$_3$ | 2-CH$_3$ | NH$_2$ | *1 |
| 11-051 | 3,5-Cl$_2$ | CF$_3$ | 2-CH$_3$ | F | 67.0-68.0 |
| 11-052 | 3,5-Cl$_2$ | CF$_3$ | 2-CH$_3$ | Br | 113.0-114.5 |
| 11-053 | 3,5-Cl$_2$ | CF$_3$ | 2-CH$_3$ | C(O)OH | 150.0-152.0 |
| 11-054 | 3,5-Cl$_2$ | CF$_3$ | 2-CH$_3$ | C(O)OCH$_3$ | 96.0-99.5 |
| 11-055 | 3,5-Cl$_2$ | CF$_3$ | 2-CH$_3$ | C(O)OEt | $n_D^{21.4\,°C}$1.5474 |
| 11-056 | 3,5-Cl$_2$ | CF$_3$ | 2-CH$_3$ | C(O)OCH$_2$(D-47a) | *2 |
| 11-057 | 3,5-Cl$_2$ | CF$_3$ | 2-CH$_3$ | C(O)(D-14a) | *1 |
| 11-058 | 3,5-Cl$_2$ | CF$_3$ | 2-CH$_3$ | C(O)(D-38a) | 58.0-59.0 |
| 11-059 | 3,5-Cl$_2$ | CF$_3$ | 2-Et | C(O)OCH$_3$ | *2 |
| 11-060 | 3,5-Cl$_2$ | CF$_3$ | 2-CH$_2$Br | C(O)OCH$_3$ | *2 |
| 11-061 | 3,5-Cl$_2$ | CF$_3$ | 2-CF$_3$ | F | *1 |
| 11-062 | 3,5-Cl$_2$ | CF$_3$ | 2-CF$_3$ | CN | *1 |
| 11-063 | 3,5-Cl$_2$ | CF$_3$ | 2-CF$_3$ | C(O)OCH$_3$ | *2 |
| 11-064 | 3,5-Cl$_2$ | CF$_3$ | 2-OH | NO$_2$ | 110.0-113.0 |
| 11-065 | 3,5-Cl$_2$ | CF$_3$ | 2-OH | NH$_2$ | 178.0-181.0 |
| 11-066 | 3,5-Cl$_2$ | CF$_3$ | 2-OCH$_3$ | OSO$_2$CF$_3$ | *1 |
| 11-067 | 3,5-Cl$_2$ | CF$_3$ | 2-OCH$_3$ | C(O)OH | *1 |
| 11-068 | 3,5-Cl$_2$ | CF$_3$ | 2-OCH$_3$ | C(O)OEt | 142.0-144.0 |
| 11-069 | 3,5-Cl$_2$ | CF$_3$ | 2-OCF$_3$ | NH$_2$ | 81.5-84.0 |
| 11-070 | 3,5-Cl$_2$ | CF$_3$ | 2-OCF$_3$ | I | *1 |
| 11-071 | 3,5-Cl$_2$ | CF$_3$ | 2-OCF$_3$ | C(O)OCH$_3$ | *1 |
| 11-072 | 3,5-Cl$_2$ | CF$_3$ | 2-SCH$_3$ | C(O)OH | 151.0-152.0 |
| 11-073 | 3,5-Cl$_2$ | CF$_3$ | 2-SCH$_3$ | C(O)OCH$_3$ | *2 |
| 11-074 | 3,5-Cl$_2$ | CF$_3$ | 2-NO$_2$ | Br | 179.0-181.0 |
| 11-075 | 3,5-Cl$_2$ | CF$_3$ | 2-NO$_2$ | C(O)OEt | 160.0-162.0 |
| 11-076 | 3,5-Cl$_2$ | CF$_3$ | 2-NH$_2$ | Br | *2 |
| 11-077 | 3,5-Cl$_2$ | CF$_3$ | 2-NH$_2$ | C(O)OH | *2 |
| 11-078 | 3,5-Cl$_2$ | CF$_3$ | 2-NH$_2$ | C(O)OEt | *2 |
| 11-079 | 3,5-Cl$_2$ | CF$_3$ | 2-Ph | C(O)OH | *1 |
| 11-080 | 3,5-Cl$_2$ | CF$_3$ | 2-Ph | C(O)OCH$_3$ | *1 |
| 11-081 | 3,5-Cl$_2$ | CF$_3$ | 2,3-F$_2$ | CH$_3$ | *1 |
| 11-082 | 3,5-Cl$_2$ | CF$_3$ | 2,3-F$_2$ | CH$_2$Br | *1 |
| 11-083 | 3,5-Cl$_2$ | CF$_3$ | 2,3-F$_2$ | CH$_2$OH | *1 |
| 11-084 | 3,5-Cl$_2$ | CF$_3$ | 2,6-Cl$_2$ | C(O)OEt | *2 |
| 11-085 | 3,5-Cl$_2$ | CF$_3$ | 2-Cl-6-CH$_3$ | NH$_2$ | *1 |
| 11-086 | 3,5-Cl$_2$ | CF$_3$ | 2,6-(CH$_3$)$_2$ | OH | 209.0-214.0 |
| 11-087 | 3,5-Cl$_2$ | CF$_3$ | 2,6-(CH$_3$)$_2$ | OSO$_2$CF$_3$ | $n_D^{21.6\,°C}$1.5194 |
| 11-088 | 3,5-Cl$_2$ | CF$_3$ | 2,6-(CH$_3$)$_2$ | C(O)OH | 128.5-130.5 |
| 11-089 | 3,5-Cl$_2$ | CF$_3$ | 2,6-(CH$_3$)$_2$ | C(O)OCH$_3$ | 135.0-138.0 |
| 11-090 | 3,5-Cl$_2$ | CF$_2$Cl | 2-Cl | C(O)OH | 100.0-104.5 |
| 11-091 | 3,5-Cl$_2$ | CF$_2$Cl | 2-CH$_3$ | C(O)OH | 76.0-80.0 |
| 11-092 | 3,5-Cl$_2$ | CF$_2$Cl | 2-CH$_3$ | C(O)OEt | *1 |
| 11-093 | 3,5-Br$_2$ | CF$_3$ | 2-Cl | C(O)OH | 144.5-147.0 |
| 11-094 | 3,5-Br$_2$ | CF$_3$ | 2-CH$_3$ | C(O)OH | 135.0-138.5 |
| 11-095 | 3,5-Br$_2$ | CF$_3$ | 2-CH$_3$ | C(O)OEt | *1 |
| 11-096 | 3-OCH$_2$O-4 | CF$_3$ | — | CO(O)OH | 208.0-210.0 |
| 11-097 | 3-OCH$_2$O-4 | CF$_3$ | — | C(O)OCH$_3$ | 172.0-173.0 |
| 11-098 | 3,5-Cl$_2$ | CF$_3$ | — | Br | 122.0-124.0 |
| 11-099 | 3,5-Cl$_2$ | CF$_3$ | — | I | 144.0-146.0 |
| 11-100 | 3,5-Cl$_2$ | CF$_3$ | — | CH$_2$Cl | 98.0-100.0 |
| 11-101 | 3,5-Cl$_2$ | CF$_3$ | 2-F | CH$_3$ | 87.0-89.0 |

TABLE 17-continued

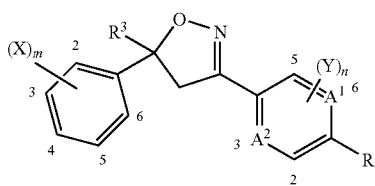

| No. | (X)$_m$ | R$^3$ | (Y)$_n$ | R | m.p. (° C.) |
|---|---|---|---|---|---|
| 11-102 | 3,5-Cl$_2$ | CF$_3$ | 2-F | CHBr$_2$ | *1 |
| 11-103 | 3,5-Cl$_2$ | CF$_3$ | 2-Cl | CH$_3$ | 97.0-99.0 |
| 11-104 | 3,5-Cl$_2$ | CF$_3$ | 2-Cl | CH$_2$Br | 94.0-97.0 |
| 11-105 | 3,5-Cl$_2$ | CF$_3$ | 2-Cl | CHBr$_2$ | *1 |
| 11-106 | 3,5-Cl$_2$ | CF$_3$ | 2-Cl | CH$_2$OH | 32.0-35.0 |
| 11-107 | 3,5-Cl$_2$ | CF$_3$ | 2-Cl | CH$_2$OC(O)CH$_3$ | *1 |
| 11-108 | 3,5-Cl$_2$ | CF$_3$ | 2-Cl | NO$_2$ | 97.0-103.0 |
| 11-109 | 3,5-Cl$_2$ | CF$_3$ | 2-Cl | NH$_2$ | 158.0-160.0 |
| 11-110 | 3,5-Cl$_2$ | CF$_3$ | 2-Cl | CHO | 129.0-130.0 |
| 11-111 | 3,5-Cl$_2$ | CF$_3$ | 2-Br | CH$_3$ | 119.0-121.0 |
| 11-112 | 3,5-Cl$_2$ | CF$_3$ | 2-Br | CHBr$_2$ | *1 |
| 11-113 | 3,5-Cl$_2$ | CF$_3$ | 2-Br | CH$_2$OH | *1 |
| 11-114 | 3,5-Cl$_2$ | CF$_3$ | 2-Br | CH$_2$OC(O)CH$_3$ | *1 |
| 11-115 | 3,5-Cl$_2$ | CF$_3$ | 2-I | CHBr$_2$ | 125.0-128.0 |
| 11-116 | 3,5-Cl$_2$ | CF$_3$ | 2-I | CHO | *1 |
| 11-117 | 3,5-Cl$_2$ | CF$_3$ | 2-CH$_3$ | Cl | 115.5-117.0 |
| 11-118 | 3,5-Cl$_2$ | CF$_3$ | 2-CH$_3$ | CH$_2$Cl | *1 |
| 11-119 | 3,5-Cl$_2$ | CF$_3$ | 2-CH$_3$ | CH$_2$OH | *1 |
| 11-120 | 3,5-Cl$_2$ | CF$_3$ | 2-CH$_3$ | CN | 141.0-142.0 |
| 11-121 | 3,5-Cl$_2$ | CF$_3$ | 2-CH$_3$ | C(O)Cl | 140.5-143.0 |
| 11-122 | 3,5-Cl$_2$ | CF$_3$ | 3-OH | C(O)OEt | *1 |
| 11-123 | 3,5-Cl$_2$ | CF$_3$ | 2-NO$_2$ | F | 86.0-89.0 |
| 11-124 | 3,5-(CF$_3$)$_2$ | CF$_3$ | — | NO$_2$ | 170.0-172.0 |
| 11-125 | 3,5-Cl$_2$ | CF$_3$ | 2-OCHF$_2$ | NO$_2$ | *1 |
| 11-126 | 3,5-Cl$_2$ | CF$_3$ | 2-OCHF$_2$ | NH$_2$ | *1 |
| 11-127 | 3,5-Cl$_2$ | CF$_3$ | 2-OCHF$_2$ | I | *1 |
| 11-128 | 3,5-Cl$_2$ | CF$_3$ | 2-NO$_2$ | CH$_3$ | 119.0-122.0 |
| 11-129 | 3-Cl-5-Br | CF$_3$ | 2-CH$_3$ | C(O)OEt | *1 |
| 11-130 | 3,5-(CF$_3$)$_2$ | CF$_3$ | 2-CH$_3$ | C(O)OEt | *2 |
| 11-131 | 3,5-Cl$_2$ | CF$_3$ | 2-OH | CH$_3$ | 145.0-147.0 |
| 11-132 | 3,5-Cl$_2$ | CF$_3$ | 2-OCH$_3$ | CH$_3$ | 86.0-89.0 |

TABLE 18

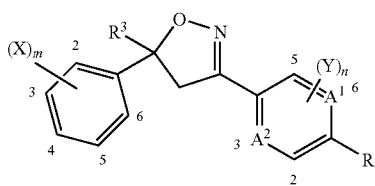

| No. | (X)$_m$ | R$^3$ | A$^1$ | A$^2$ | (Y)$_n$ | R | m.p. (° C.) |
|---|---|---|---|---|---|---|---|
| 12-001 | 3,5-Cl$_2$ | CF$_3$ | N | C | — | Cl | 139.0-140.0 |
| 12-002 | 3,5-Cl$_2$ | CF$_3$ | N | C | — | Br | 147.0-148.0 |
| 12-003 | 3,5-Cl$_2$ | CF$_3$ | N | C | — | C(O)OH | 118.0-120.0 |
| 12-004 | 3,5-Cl$_2$ | CF$_3$ | N | C | — | C(O)OEt | 154.0-155.0 |
| 12-005 | 3,5-Cl$_2$ | CF$_3$ | C | N | — | C(O)OH | 195.5-198.5 |
| 12-006 | 3,5-Cl$_2$ | CF$_3$ | C | N | — | C(O)OCH$_3$ | 147.0-151.5 |

TABLE 19

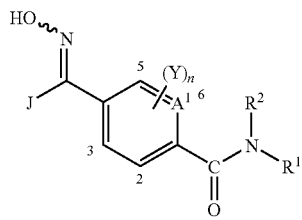

| No. | A$^1$ | (Y)$_n$ | R$^2$ | R$^1$ | J | m.p. (° C.) |
|---|---|---|---|---|---|---|
| 13-001 | C | — | H | CH$_2$CF$_3$ | H | 153.0-154.0 |
| 13-002 | C | — | H | CH$_2$CF$_3$ | Cl | 158.0-160.0 |
| 13-003 | C | — | H | CH$_2$Ph | H | 191.0-192.0 |
| 13-004 | C | — | H | CH$_2$Ph | Cl | 131.0-133.0 |
| 13-005 | C | — | H | CH$_2$(D-47a) | H | 166.0-168.0 |
| 13-006 | C | 2-CH$_3$ | H | CH$_2$CF$_3$ | H | 190.5-194.0 |
| 13-007 | C | 2-CH$_3$ | H | CH$_2$CF$_3$ | Cl | 134.0-137.0 |
| 13-008 | C | 2-CH$_3$ | H | CH$_2$(D-47a) | H | 163.0-164.0 |
| 13-009 | C | 2-CH$_3$ | H | CH$_2$(D-47a) | Cl | 174.0-176.0 |
| 13-010 | C | 3-CH$_3$ | H | CH$_2$CF$_3$ | H | 163.0-168.0 |

TABLE 20

[Structure: benzene ring with positions 2,4,5,6; X¹ at position adjacent to position 2 which bears a vinyl group =CH₂ with R³; (X²)ₘ₁ at position 5]

| No. | X¹ | (X²)ₘ₁ | R³ | m.p./b.p. (° C.) |
|---|---|---|---|---|
| 14-001 | Cl | 5-Cl | Pr-i | $n_D^{20.6°C}$ 1.5472 |
| 14-002 | Cl | 5-Cl | CHF₂ | $n_D^{20.6°C}$ 1.5370 |
| 14-003 | Cl | 5-Cl | CF₃ | 64.0-66.0/2 mmHg |
| 14-004 | Cl | 5-Cl | CF₂Cl | *2 |
| 14-005 | Cl | 5-Cl | CF₂CF₃ | *2 |
| 14-006 | Cl | 5-Cl | CH₂OCH₂CF₃ | *2 |
| 14-007 | Cl | 5-Cl | CH₂Si(CH₃)₃ | *2 |
| 14-008 | Cl | 5-Cl | D-47a | *2 |
| 14-009 | Cl | 5-Br | CF₃ | *2 |
| 14-010 | Cl | 5-CH₃ | CF₃ | *2 |
| 14-011 | Cl | 5-CH₃-6-F | CF₃ | $n_D^{20.6°C}$ 1.4895 |
| 14-012 | Cl | 4-F-5-Cl | CF₃ | *2 |
| 14-013 | Cl | 4,5-Cl₂ | CF₃ | *1 |
| 14-014 | Cl | 4-NHC(O)OBu-t-5-Cl | CF₃ | 67.0-68.0 |
| 14-015 | Br | — | CF₃ | $n_D^{20.7°C}$ 1.5258 |
| 14-016 | Br | 5-Br | CF₃ | *2 |
| 14-017 | CF₃ | — | CF₃ | $n_D^{20.6°C}$ 1.4228 |
| 14-018 | CF₃ | 5-Cl | CF₃ | *2 |
| 14-019 | CF₃ | 5-NO₂ | CF₃ | $n_D^{20.6°C}$ 1.4553 |
| 14-020 | CF₃ | 4-F-5-Cl | CF₃ | *2 |
| 14-021 | T-4 | — | CF₃ | *2 |
| 14-022 | OCF₂CHFOCF₂CF₂CF₃ | — | CF₃ | *2 |
| 14-023 | OCH₂Ph | — | CF₃ | *2 |
| 14-024 | OCH₂(Ph-2-Cl) | — | CF₃ | *2 |
| 14-025 | O[(D-47f)-3-Cl-5-CF₃] | — | CF₃ | *2 |
| 14-026 | SCF₃ | — | CF₃ | *2 |
| 14-027 | NO₂ | — | CF₃ | *2 |

Among the compounds of the present invention, ¹H NMR data of the compounds that the measured value of molecular ion peak, melting point or refractive index is not shown are shown in Table 21.
In the meantime, the indication of "(A)" in the table shows a condition in which tetramethylsilane is used as standard substance in chloroform-d solvent and measurement is carried out at 300 MHz (CDCl₃, Me₄Si, 300 MHz), hereinafter, the indication "(B)" shows the measurement condition of (CDCl₃, Me₄Si, 400 MHz), the indication of "(C)" shows the measurement condition of (CDCl₃-DMSO-d₆, Me₄Si, 300 MHz), and the indication of "(D)" shows the measurement condition of (CDCl₃-DMSO-d₆, Me₄Si, 400 MHz).

TABLE 21

| No. | ¹H NMR |
|---|---|
| 3-010 | (A) δ 8.55-8.6 (m, 1H), 7.15-8.05 (m, 15H), 6.95-7.1 (m, 1H), 5.20 (s, 2H), 4.76 (d, J = 4.4 Hz, 2H), 4.10 (d, J = 17.2 Hz, 1H), 3.78 (d, J = 17.2 Hz, 1H). |
| 3-034 | (A) δ 7.2-7.5 (m, 7H), 4.55-4.7 (m, 2H), 4.06 (d, J = 17.1 Hz, 1H), 3.67 (d, J = 17.1 Hz, 1H), 2.38 (s, 3H). |
| 3-059 | (B) δ 7.9-7.95 (m, 2H), 7.8-7.9 (m, 1H), 7.7-7.8 (m, 2H), 7.51 (s, 2H), 7.4-7.45 (m, 1H), 5.02 (d, J = 7.0 Hz, 2H), 4.12 (d, J = 17.0 Hz, 1H), 3.73 (d, J = 17.0 Hz, 1H). |
| 3-064 | (A) δ 7.84 (d, J = 8.4 Hz, 2H), 7.74 (d, J = 8.4 Hz, 2H), 7.51 (bs, 2H), 7.43 (bs, 1H), 6.42 (bs, 1H), 4.63 (t, J = 5.1 Hz, 1H), 4.11 (d, J = 17.4 Hz, 1H), 3.65-3.85 (m, 3H), 3.5-3.65 (m, 4H), 1.24 (t, J = 6.8 Hz, 6H). |
| 3-067 | (A) δ 7.6-7.8 (m, 3H), 7.54 (d, J = 7.8 Hz, 2H), 7.44 (bs, 2H), 7.38 (bs, 1H), 3.4-4.25 (m, 7H), 4.04 (d, J = 17.7 Hz, 1H), 3.69 (d, J = 17.4 Hz, 1H). |
| 3-069 | (A) δ 7.82 (d, J = 8.7 Hz, 2H), 7.71 (d, J = 8.7 Hz, 2H), 7.51 (bs, 2H), 7.42 (bs, 1H), 6.71 (bs, 1H), 4.11 (d, J = 17.4 Hz, 1H), 3.6-3.95 (m, 4H), 3.74 (d, J = 17.1 Hz, 1H), 3.48 (t, J = 6.3 Hz, 2H), 2.55-2.7 (m, 1H), 2.0-2.15 (m, 1H), 1.6-1.75 (m, 1H). |
| 3-072 | (A) δ 7.85 (d, J = 8.4 Hz, 2H), 7.73 (d, J = 8.4 Hz, 2H), 7.51 (bs, 2H), 7.4-7.5 (m, 1H), 6.44 (bs, 1H), 4.75 (t, J = 4.8 Hz, 1H), 4.1-4.2 (m, 2H), 4.10 (d, J = 17.4 Hz, 1H), 3.75-3.9 and 3.6-3.65 (m, 2H), 3.72 (d, J = 17.4 Hz, 1H), 3.6-3.65 (m, 2H), 2.0-2.15 (m, 1H), 1.35-1.45 (m, 1H). |

TABLE 21-continued

| No. | ¹H NMR |
|---|---|
| 3-074 | (A) δ 7.82 (d, J = 8.4 Hz, 2H), 7.72 (d, J = 8.4 Hz, 2H), 7.51 (bs, 2H), 7.4-7.45 (m, 1H), 6.53 (bs, 1H), 4.09 (d, J = 17.4 Hz, 1H), 3.72 (s, 2H), 3.71 (d, J = 17.4 Hz, 1H), 2.92 (s, 3H), 1.72 (s, 6H). |
| 3-077 | (A) δ 9.79 (s, 1H), 7.89 (d, J = 8.4 Hz, 2H), 7.76 (d, J = 8.4 Hz, 2H), 7.61 (bs, 2H), 7.51 (bs, 1H), 6.91 (bs, 1H), 4.46 (d, J = 4.5 Hz, 2H), 4.11 (d, J = 17.4 Hz, 1H), 3.72 (d, J = 17.1 Hz, 1H). |
| 3-078 | (A) δ 9.27 (bs, 1H), 7.85 (d, J = 8.5 Hz, 2H), 7.74 (d, J = 8.7 Hz, 2H), 7.60 and 6.93 (t, J = 4.4 Hz, 1H), 7.51 (bs, 2H), 7.44 (bs, 1H), 6.71 (bs, 1H), 4.37 and 4.26 (d, J = 4.7 Hz, 2H), 4.11 (d, J = 16.8 Hz, 1H), 3.72 (d, J = 17.4 Hz, 1H). |
| 3-079 | (A) δ 7.8-7.9 (m, 2H), 7.7-7.8 (m, 2H), 7.45-7.55 (m, 2H), 7.45-7.55 and 6.82 (t, J = 4.4 Hz, 1H), 7.43 (t, J = 2.0 Hz, 1H), 6.71 and 6.60 (bs, 1H), 4.31 and 4.24 (t, J = 4.5 Hz, 2H), 4.11 (d, J = 17.4 Hz, 1H), 3.94 and 3.88 (s, 3H), 3.72 (d, J = 17.4 Hz, 1H). |
| 3-082 | (A) δ 7.90 (d, J = 8.7 Hz, 2H), 7.73 (d, J = 8.7 Hz, 2H), 7.52 (bs, 2H), 7.43 (s, 1H), 7.10 (t, J = 4.8 Hz, 1H), 4.21 (d, J = 4.8 Hz, 2H), 4.12 (d, J = 17.4 Hz, 1H), 3.74 (d, J = 17.4 Hz, 1H). |
| 3-083 | (A) δ 7.87 (d, J = 8.1 Hz, 2H), 7.74 (d, J = 8.1 Hz, 2H), 7.52 (s, 2H), 7.43 (s, 1H), 6.73 (bs, 1H), 4.26 (d, J = 5.1 Hz, 2H), 4.11 (d, J = 17.4 Hz, 1H), 3.82 (s, 3H), 3.73 (d, J = 17.4 Hz, 1H). |
| 3-087 | (A) δ 8.52 (bs, 1H), 7.97 (bs, 1H), 7.88 (d, J = 8.4 Hz, 2H), 7.7-7.8 (m, 3H), 7.51 (s, 2H), 7.43 (s, 1H), 4.45 (d, J = 4.8 Hz, 2H), 4.11 (d, J = 17.4 Hz, 1H), 3.74 (d, J = 17.4 Hz, 1H). |
| 3-089 | (A) δ 7.84 (d, J = 8.5 Hz, 2H), 7.73 (d, J = 8.5 Hz, 2H), 7.51 (bs, 2H), 7.43 (bs, 1H), 6.18 (bs, 1H), 5.85-6.05 (m, 1H), 5.2-5.35 (m, 2H), 4.05-4.15 (m, 3H), 3.72 (d, J = 17.4 Hz, 1H). |
| 3-107 | (A) δ 7.82 (d, J = 8.1 Hz, 2H), 7.72 (d, J = 8.4 Hz, 2H), 7.55 (s, 1H), 7.51 (bs, 2H), 7.43 (s, 1H), 6.27 (bs, 1H), 4.48 (d, J = 5.1 Hz, 2H), 4.10 (d, J = 17.1 Hz, 1H), 3.79 (s, 3H), 3.71 (d, J = 17.4 Hz, 1H). |
| 3-108 | (A) δ 7.82 (d, J = 8.1 Hz, 2H), 7.72 (d, J = 8.4 Hz, 2H), 7.51 (bs, 2H), 7.4-7.45 (m, 1H), 6.34 (bs, 1H), 4.48 (d, J = 5.4 Hz, 2H), 4.10 (d, J = 17.1 Hz, 1H), 3.81 (s, 3H), 3.71 (d, J = 17.4 Hz, 1H). |
| 3-110 | (A) δ 7.82 (d, J = 8.1 Hz, 2H), 7.74 (d, J = 8.7 Hz, 2H), 7.51 (bs, 2H), 7.43 (bs, 1H), 6.36 (bs, 1H), 6.17 (s, 1H), 4.65 (d, J = 5.7 Hz, 2H), 4.08 (d, J = 17.1 Hz, 1H), 3.85 (s, 3H), 3.69 (d, J = 17.4 Hz, 1H). |
| 3-114 | (A) δ 7.86 (d, J = 8.1 Hz, 2H), 7.71 (d, J = 8.4 Hz, 2H), 7.51 (bs, 2H), 7.4-7.45 (m, 2H), 7.08 (s, 1H), 6.98 (bs, 1H), 4.68 (d, J = 5.4 Hz, 2H), 4.07 (d, J = 17.4 Hz, 1H), 3.68 (d, J = 17.4 Hz, 1H), 2.72 (s, 3H). |
| 3-118 | (D) δ 7.95-8.0 (m, 2H), 7.75-7.8 (m, 2H), 7.35-7.55 (m, 4H), 5.45-5.5 (m, 2H), 4.15-4.2 (m, 1H), 3.8-3.85 (m, 1H), 2.57 (s, 3H). |
| 3-119 | (B) δ 8.55-8.65 (m, 1H), 7.91 (d, J = 8.2 Hz, 2H), 7.65 (d, J = 8.2 Hz, 2H), 7.50 (s, 2H), 7.42 (s, 1H), 6.91 (s, 1H), 6.86 (s, 1H), 4.67 (d, J = 5.3 Hz, 2H), 4.08 (d, J = 17.0 Hz, 1H), 3.77 (s, 3H), 3.70 (d, J = 17.0 Hz, 1H). |
| 3-120 | (B) δ 7.35-8.0 (m, 8H), 6.95 (m, 2H), 6.6-6.75 (m, 2H), 4.08 (d, J = 17.0 Hz, 1H), 3.70 (d, J = 17.0 Hz, 1H), 3.63 (s, 3H). |
| 3-121 | (B) δ 8.1-8.2 (m, 1H), 7.65-7.9 (m, 3H), 7.4-7.6 (m, 3H), 7.1-7.2 (m, 1H), 4.86 (d, J = 5.8 Hz, 2H), 4.05-4.15 (m, 1H), 3.65-3.8 (m, 1H), 2.72 (s, 3H). |
| 3-122 | (A) δ 8.43 (s, 1H), 7.88 (d, J = 8.1 Hz, 2H), 7.72 (d, J = 8.1 Hz, 2H), 7.51 (s, 2H), 7.44 (s, 1H), 7.30 (t, J = 5.4 Hz, 1H), 4.93 (d, J = 5.4 Hz, 2H), 4.10 (d, J = 17.1 Hz, 1H), 3.72 (d, J = 17.1 Hz, 1H). |
| 3-127 | (B) δ 7.93 (d, J = 8.2 Hz, 2H), 7.82 (t, J = 4.8 Hz, 1H), 7.74 (d, J = 8.2 Hz, 2H), 7.58 (t, J = 7.7 Hz, 1H), 7.5-7.55 (m, 2H), 7.43 (t, J = 1.8 Hz, 1H), 7.16 (d, J = 7.7 Hz, 1H), 7.09 (d, J = 7.7 Hz, 1H), 4.71 (d, J = 4.8 Hz, 2H), 3.93 (d, J = 17.2 Hz, 1H), 3.74 (d, J = 17.4 Hz, 1H), 2.57 (s, 3H). |
| 3-131 | (A) δ 8.55 (s, 1H), 8.40 (s, 1H), 7.91 (d, J = 8.2 Hz, 2H), 7.72 (d, J = 8.2 Hz, 2H), 7.53 (s, 3H), 7.42 (s, 1H), 4.7-4.8 (m, 2H), 4.13 (d, J = 17.0 Hz, 1H), 3.74 (d, J = 17.0 Hz, 1H), 2.57 (s, 3H). |
| 3-134 | (A) δ 9.64 (bs, 1H), 7.81 (d, J = 8.1 Hz, 2H), 7.69 (d, J = 8.1 Hz, 2H), 7.50 (s, 2H), 7.43 (s, 1H), 4.10 (d, J = 17.4 Hz, 1H), 3.86 (s, 3H), 3.73 (d, J = 17.4 Hz, 1H). |
| 3-135 | (A) δ 8.19 (d, J = 4.2 Hz, 1H), 7.95 (d, J = 8.4 Hz, 2H), 7.76 (d, J = 8.4 Hz, 2H), 7.5-7.6 (m, 4H), 7.44 (s, 1H), 7.10 (bs, 1H), 6.84 (t, J = 8.4 Hz, 1H), 6.78 (d, J = 8.4 Hz, 1H), 4.11 (d, J = 17.4 Hz, 1H), 3.73 (d, J = 17.4 Hz, 1H). |
| 3-143 | (A) δ 8.57 (d, J = 5.1 Hz, 1H), 8.21 (bs, 1H), 7.85-8.05 (m, 2H), 7.6-7.8 (m, 3H), 7.15-7.45 (m, 5H), 4.72 (d, J = 5.1 Hz, 2H), 4.10 (d, J = 17.4 Hz, 1H), 3.76 (d, J = 17.4 Hz, 1H), 2.38 (s, 3H). |
| 3-147 | (A) δ 7.86 (d, J = 8.5 Hz, 2H), 7.77 (d, J = 8.5 Hz, 2H), 7.55-7.65 (m, 1H), 7.2-7.3 (m, 1H), 4.05-4.25 (m, 3H), 3.86 (d, J = 17.0 Hz, 1H), 2.30 (s, 3H). |
| 4-003 | (A) δ 8.5-8.7 (m, 1H), 7.35-7.9 (m, 9H), 7.1-7.3 (m, 1H), 4.5-5.1 (m, 4H), 4.0-4.2 (m, 1H), 3.6-3.8 (m, 1H), 3.15-3.55 (m, 3H). |
| 4-004 | (A) δ 8.55-8.65 (m, 1H), 7.35-7.8 (m, 9H), 7.1-7.3 (m, 1H), 4.6-5.15 (m, 4H), 3.3-4.2 (m, 4H), 1.1-1.35 (m, 3H). |
| 4-005 | (A) δ 8.2-8.3 (m, 1H), 7.15-7.8 (m, 10H), 4.75-5.35 (m, 4H), 4.08 (d, J = 17.0 Hz, 1H), 3.70 (d, J = 17.0 Hz, 1H), 3.04 and 2.84 (bs, 3H). |
| 4-006 | (B) δ 8.5-8.6 (m, 1H), 7.1-7.75 (m, 10H), 5.65-5.95 (m, 1H), 5.1-5.3 (m, 2H), 4.85 and 4.53 (s, 2H), 3.6-4.2 (m, 4H). |

TABLE 21-continued

| No. | $^1$H NMR |
|---|---|
| 4-007 | (B) δ 8.5-8.7 (m, 1H), 6.95-7.75 (m, 10H), 5.65-6.1 (m, 2H), 5.1-5.45 (m, 4H), 4.4-4.9 (m, 4H), 3.75-4.2 (m, 3H). |
| 4-008 | (A) δ 8.50 (bs, 1H), 7.0-7.75 (m, 15H), 4.35-4.9 (m, 4H), 4.05 (d, J = 17.0 Hz, 1H), 3.68 (d, J = 17.0 Hz, 1H). |
| 4-009 | (A) δ 8.5-8.55 (m, 1H), 7.65-7.75 (m, 5H), 7.51 (s, 2H), 7.42 (s, 1H), 7.25-7.3 (m, 1H), 7.15-7.25 (m, 1H), 5.17 (s, 2H), 4.10 (d, J = 17.0 Hz, 1H), 3.71 (d, J = 17.0 Hz, 1H), 3.60 (s, 3H). |
| 4-010 | (A) δ 8.37 (bs, 1H), 7.65-7.8 (m, 3H), 7.3-7.55 (m, 6H), 4.4-4.9 (m, 2H), 4.10 (d, J = 17.0 Hz, 1H), 3.70 (d, J = 17.0 Hz, 1H), 3.1-3.65 (m, 2H), 1.12 (bs, 3H). |
| 4-011 | (B) δ 7.7-7.8 (m, 4H), 7.52 (s, 2H), 7.43 (s, 1H), 4.10 (d, J = 17.0 Hz, 1H), 3.72 (d, J = 17.0 Hz, 1H), 3.53 (s, 3H), 3.37 (s, 3H). |
| 5-001 | (A) δ 8.51 (d, J = 4.8 Hz, 1H), 7.69 (t, J = 5.1 Hz, 1H), 7.62 (s, 1H), 7.45-7.55 (m, 2H), 7.25-7.4 (m, 4H), 7.22 (dd, J = 6.9, 2.5 Hz, 1H), 4.73 (d, J = 5.1 Hz, 2H), 4.09 (d, J = 16.8 Hz, 1H), 3.73 (d, J = 16.8 Hz, 1H), 2.48 (s, 3H). |
| 5-003 | (A) δ 8.51 (d, J = 4.8 Hz, 1H), 7.77 (s, 1H), 7.68 (t, J = 4.5 Hz, 1H), 7.45-7.6 (m, 5H), 7.25-7.35 (m, 3H), 7.22 (dd, J = 7.5, 1.8 Hz, 1H), 4.73 (d, J = 4.5 Hz, 2H), 4.09 (d, J = 17.4 Hz, 1H), 3.73 (d, J = 17.4 Hz, 1H), 2.49 (s, 3H). |
| 5-007 | (A) δ 8.52 (d, J = 4.2 Hz, 1H), 7.78 (d, J = 9.3 Hz, 2H), 7.67 (t, J = 5.1 Hz, 1H), 7.51 (bs, 3H), 7.3-7.4 (m, 4H), 7.15-7.25 (m, 1H), 4.73 (d, J = 5.1 Hz, 2H), 4.07 (d, J = 17.4 Hz, 1H), 3.70 (d, J = 17.4 Hz, 1H), 2.48 (s, 3H). |
| 5-009 | (A) δ 8.51 (d, J = 4.5 Hz, 1H), 7.89 (bs, 1H), 7.82 (d, J = 7.8 Hz, 1H), 7.65-7.75 (m, 2H), 7.60 (t, J = 7.8 Hz, 1H), 7.5-7.55 (m, 3H), 7.33 (bs, 1H), 7.32 (d, J = 7.8 Hz, 1H), 7.21 (dd, J = 7.2, 1.5 Hz, 1H), 4.73 (d, J = 5.1 Hz, 2H), 4.15 (d, J = 17.4 Hz, 1H), 3.77 (d, J = 17.4 Hz, 1H), 2.49 (s, 3H). |
| 5-010 | (A) δ 7.25-7.6 (m, 7H), 6.37 (bs, 1H), 4.0-4.15 (m, 2H), 4.11 (d, J = 17.4 Hz, 1H), 3.77 and 3.75 (d, J = 17.4 Hz, 1H), 2.95 (dd, J = 10.2, 8.7 Hz, 1H), 2.41 (s, 3H), 2.03 (dd, J = 10.2, 3.3 Hz, 1H), 1.90 (dd, J = 8.7, 3.3 Hz, 1H). |
| 5-011 | (A) δ 8.51 (d, J = 4.2 Hz, 1H), 7.69 (t, J = 4.8 Hz, 1H), 7.15-7.6 (m, 10H), 4.72 (d, J = 4.8 Hz, 2H), 4.10 (d, J = 17.1 Hz, 1H), 3.77 (dd, J = 17.1, 3.0 Hz, 1H), 2.95 (dd, J = 10.2, 8.4 Hz, 1H), 2.48 (s, 3H), 2.02 (dd, J = 10.2, 3.0 Hz, 1H), 1.89 (dd, J = 8.4, 3.0 Hz, 1H). |
| 5-012 | (A) δ 7.25-7.5 (m, 7H), 7.16 (bs, 1H), 4.0-4.2 (m, 3H), 3.75 (d, J = 17.2 Hz, 1H), 2.42 (s, 3H). |
| 5-013 | (A) δ 8.5-8.6 (m, 1H), 7.65-7.8 (m, 1H), 7.15-7.6 (m, 10H), 4.72 (d, J = 5.2 Hz, 2H), 4.12 (d, J = 17.3 Hz, 1H), 3.74 (d, J = 17.3 Hz, 1H), 2.46 (s, 3H). |
| 5-015 | (B) δ 8.5-8.55 (m, 1H), 7.72 (td, J = 6.8, 4.8 Hz, 1H), 7.45-7.6 (m, 5H), 7.2-7.4 (m, 5H), 4.75 (d, J = 4.8 Hz, 2H), 4.11 (d, J = 17.2 Hz, 1H), 3.74 (d, J = 17.2 Hz, 1H), 2.50 (s, 3H). |
| 5-016 | (A) δ 7.35-7.6 (m, 6H), 7.2-7.3 (m, 1H), 6.10 (d, J = 53.4 Hz, 1H), 6.06 (bs, 1H), 4.0-4.2 (m, 3H), 3.72 (d, J = 16.8 Hz, 1H), 2.47 (s, 3H). |
| 5-017 | (A) δ 8.54 (d, J = 4.8 Hz, 1H), 7.65-7.75 (m, 1H), 7.35-7.6 (m, 6H), 7.2-7.35 (m, 4H), 6.10 (d, J = 53.1 Hz, 1H), 4.75 (d, J = 5.1 Hz, 2H), 4.11 (d, J = 17.4 Hz, 1H), 3.73 (d, J = 17.4 Hz, 1H), 2.50 (s, 3H). |
| 5-018 | (A) δ 8.45-8.55 (m, 1H), 7.15-7.75 (m, 14H), 6.95-7.05 (m, 1H), 5.19 (s, 2H), 4.74 (d, J = 4.4 Hz, 2H), 4.07 (d, J = 16.8 Hz, 1H), 3.75 (d, J = 16.8 Hz, 1H), 2.49 (s, 3H). |
| 5-019 | (A) δ 8.24 (s, 1H), 8.00 (s, 1H), 7.2-7.6 (m, 6H), 7.2-7.3 (m, 1H), 6.44 (t, J = 6.5 Hz, 1H), 3.95-4.15 (m, 2H), 4.09 (d, J = 17.1 Hz, 1H), 3.78 (d, J = 17.1 Hz, 1H), 2.40 (s, 3H). |
| 5-020 | (A) δ 8.52 (d, J = 4.8 Hz, 1H), 8.25 (s, 1H), 8.00 (s, 1H), 7.45-7.75 (m, 7H), 7.15-7.35 (m, 4H), 4.74 (d, J = 4.8 Hz, 2H), 4.10 (d, J = 17.4 Hz, 1H), 3.78 (d, J = 17.4 Hz, 1H), 2.49 (s, 3H). |
| 5-021 | (A) δ 8.51 (d, J = 4.5 Hz, 1H), 7.69 (t, J = 5.1 Hz, 1H), 7.5-7.6 (m, 4H), 7.25-7.4 (m, 5H), 7.21 (dd, J = 7.2, 1.5 Hz, 1H), 4.73 (d, J = 5.1 Hz, 2H), 4.08 (d, J = 17.4 Hz, 1H), 3.74 (d, J = 17.4 Hz, 1H), 2.98 (q, J = 7.2 Hz, 2H), 2.48 (s, 3H), 1.33 (t, J = 7.2 Hz, 3H). |
| 5-022 | (A) δ 7.89 (s, 1H), 7.7-7.8 (m, 2H), 7.5-7.6 (m, 3H), 7.45 (d, J = 8.0 Hz, 1H), 6.06 (t, J = 6.2 Hz, 1H), 4.0-4.2 (m, 3H), 3.73 (d, J = 16.6 Hz, 1H), 2.47 (s, 3H). |
| 5-023 | (A) δ 8.55 (d, J = 4.7 Hz, 1H), 7.90 (s, 1H), 7.65-7.8 (m, 3H), 7.5-7.6 (m, 4H), 7.3-7.45 (m, 2H), 7.2-7.3 (m, 1H), 4.74 (d, J = 5.0 Hz, 2H), 4.12 (d, J = 17.1 Hz, 1H), 3.73 (d, J = 17.1 Hz, 1H), 2.49 (s, 3H). |
| 5-024 | (B) δ 7.65 (d, J = 8.1 Hz, 1H), 7.45-7.6 (m, 4H), 7.40 (d, J = 7.9 Hz, 1H), 7.34 (d, J = 7.7 Hz, 1H), 6.35 (bs, 1H), 4.0-4.15 (m, 3H), 3.73 (d, J = 17.2 Hz, 1H), 3.37 (s, 3H), 2.43 (s, 3H). |
| 5-025 | (B) δ 8.5-8.55 (m, 1H), 7.71 (td, J = 7.7, 1.6 Hz, 1H), 7.3-7.7 (m, 7H), 7.28 (d, J = 4.6 Hz, 1H), 7.26 (t, J = 4.8 Hz, 1H), 7.23 (dd, J = 7.5, 5.9 Hz, 1H), 4.75 (d, J = 4.8 Hz, 2H), 4.12 (d, J = 17.2 Hz, 1H), 3.73 (d, J = 17.2 Hz, 1H), 3.39 (s, 3H), 2.50 (s, 3H). |

TABLE 21-continued

| No. | ¹H NMR |
|---|---|
| 5-026 | (B) δ 7.4-7.65 (m, 6H), 7.36 (d, J = 7.9 Hz, 1H), 6.34 (t, J = 6.1 Hz, 1H), 4.11 (d, J = 17.2 Hz, 1H), 4.08 (qd, J = 9.6, 6.6 Hz, 2H), 3.73 (d, J = 17.4 Hz, 1H), 3.50 (d, J = 0.9 Hz, 3H), 2.41 (s, 3H). |
| 5-027 | (B) δ 8.53 (ddd, J = 4.9, 1.6, 0.9 Hz, 1H), 7.70 (td, J = 7.7, 1.8 Hz, 1H), 7.6-7.65 (m, 2H), 7.5-7.55 (m, 4H), 7.44 (ddd, J = 7.9, 2.0, 1.3 Hz, 1H), 7.33 (d, J = 7.7 Hz, 1H), 7.26 (t, J = 4.8 Hz, 1H), 7.22 (ddd, J = 7.5, 4.8, 1.1 Hz, 1H), 4.75 (d, J = 4.8 Hz, 2H), 4.12 (d, J = 17.2 Hz, 1H), 3.74 (d, J = 17.2 Hz, 1H), 3.51 (s, 3H), 2.49 (s, 3H). |
| 5-028 | (B) δ 8.5-8.55 (m, 1H), 7.83 (bs, 1H), 7.2-7.75 (m, 15H), 4.76 (d, J = 4.8 Hz, 2H), 4.13 (dd, J = 17.2, 1.8 Hz, 1H), 3.82 (d, J = 17.2 Hz, 1H), 2.51 (s, 3H). |
| 5-029 | (A) δ 8.51 (d, J = 4.5 Hz, 1H), 7.69 (t, J = 5.1 Hz, 1H), 7.51 (bs, 2H), 7.50 (bs, 1H), 7.15-7.4 (m, 5H), 6.8-6.95 (m, 1H), 4.74 (d, J = 4.8 Hz, 2H), 4.07 (d, J = 17.4 Hz, 1H), 3.72 (d, J = 17.4 Hz, 1H), 2.48 (s, 3H). |
| 5-030 | (A) δ 7.2-7.45 (m, 6H), 6.49 (bs, 1H), 4.0-4.15 (m, 2H), 3.46 (s, 2H), 2.40 (s, 3H), 1.79 (s, 3H). |
| 5-031 | (A) δ 7.25-7.5 (m, 6H), 6.50 (bs, 1H), 4.0-4.15 (m, 2H), 3.60 (d, J = 16.8 Hz, 1H), 3.39 (d, J = 16.8 Hz, 1H), 2.38 (s, 3H), 2.15-2.3 (m, 1H), 0.98 (d, J = 6.6 Hz, 3H), 0.90 (d, J = 6.9 Hz, 3H). |
| 5-033 | (A) δ 8.51 (d, J = 4.8 Hz, 1H), 7.69 (t, J = 4.5 Hz, 1H), 7.45-7.5 (m, 3H), 7.41 (bs, 2H), 7.15-7.4 (m, 4H), 4.73 (d, J = 4.5 Hz, 2H), 3.57 (d, J = 16.8 Hz, 1H), 3.47 (d, J = 16.8 Hz, 1H), 2.48 (s, 3H), 1.35-1.5 (m, 1H), 0.45-0.7 (m, 4H). |
| 5-035 | (B) δ 8.5-8.55 (m, 1H), 7.72 (td, J = 7.6, 1.8 Hz, 1H), 7.5-7.55 (m, 4H), 7.43 (d, J = 1.8 Hz, 2H), 7.35-7.4 (m, 2H), 7.2-7.25 (m, 1H), 4.76 (d, J = 4.8 Hz, 2H), 3.93 (d, J = 16.8 Hz, 1H), 3.85 (dd, J = 18.6, 11.8 Hz, 2H), 3.53 (d, J = 16.8 Hz, 1H), 2.50 (s, 3H). |
| 5-037 | (A) δ 8.53 (d, J = 5.0 Hz, 1H), 7.65-7.75 (m, 1H), 7.15-7.6 (m, 9H), 5.89 (t, J = 55.2 Hz, 1H), 4.74 (d, J = 4.7 Hz, 2H), 4.00 (d, J = 17.0 Hz, 1H), 3.55 (d, J = 17.0 Hz, 1H), 2.50 (s, 3H). |
| 5-038 | (B) δ 8.17 (t, J = 7.0 Hz, 1H), 7.45-7.6 (m, 4H), 7.44 (t, J = 1.8 Hz, 1H), 7.0-7.1 (m, 1H), 4.05-4.25 (m, 3H), 3.73 (d, J = 17.4 Hz, 1H). |
| 5-040 | (A) δ 8.82 (s, 1H), 8.19 (t, J = 7.8 Hz, 1H), 7.4-7.6 (m, 6H), 7.31 (s, 1H), 4.84 (d, J = 5.4 Hz, 2H), 4.08 (d, J = 17.4 Hz, 1H), 3.69 (d, J = 17.1 Hz, 1H). |
| 5-042 | (B) δ 8.03 (m, 1H), 7.64 (d, J = 1.1 Hz, 1H), 7.58 (d, J = 0.8 Hz, 1H), 7.50 (s, 2H), 7.43 (bs, 1H), 6.39 (bs, 1H), 4.18 (d, J = 16.0 Hz, 1H), 4.1-4.2 (m, 2H), 3.80 (d, J = 16.0 Hz, 1H). |
| 5-048 | (A) δ 8.22 (d, J = 8.7 Hz, 2H), 7.81 (d, J = 7.8 Hz, 1H), 7.74 (d, J = 1.2 Hz, 1H), 7.63 (dd, J = 8.4, 1.8 Hz, 1H), 7.54 (d, J = 8.7 Hz, 2H), 7.50 (bs, 2H), 7.44 (d, J = 2.1 Hz, 1H), 6.72 (bs, 1H), 4.77 (d, J = 6.3 Hz, 2H), 4.04 (d, J = 17.1 Hz, 1H), 3.66 (d, J = 17.1 Hz, 1H). |
| 5-049 | (A) δ 7.81 (d, J = 8.1 Hz, 1H), 7.7-7.75 (m, 2H), 7.63 (dd, J = 8.1, 1.8 Hz, 1H), 7.50 (bs, 2H), 7.44 (bs, 1H), 7.34 (d, J = 3.3 Hz, 1H), 7.16 (bs, 1H), 5.00 (d, J = 5.4 Hz, 2H), 4.06 (d, J = 17.1 Hz, 1H), 3.69 (d, J = 17.1 Hz, 1H). |
| 5-050 | (A) δ 8.79 (s, 1H), 7.75 (dd, J = 8.4, 3.0 Hz, 1H), 7.70 (bs, 1H), 7.60 (bs, 1H), 7.50 (bs, 2H), 7.44 (bs, 1H), 7.33 (s, 1H), 7.01 (bs, 1H), 4.82 (d, J = 5.1 Hz, 2H), 4.07 (d, J = 17.4 Hz, 1H), 3.69 (d, J = 17.1 Hz, 1H). |
| 5-051 | (A) δ 7.7-7.8 (m, 2H), 7.61 (dd, J = 8.1, 1.5 Hz, 1H), 7.50 (bs, 2H), 7.44 (bs, 1H), 7.19 (s, 1H), 6.84 (bs, 1H), 4.69 (d, J = 5.7 Hz, 2H), 4.07 (d, J = 17.4 Hz, 1H), 3.69 (d, J = 17.4 Hz, 1H). |
| 5-052 | (B) δ 8.63 (s, 1H), 7.25-7.75 (m, 7H), 5.10 (d, J = 5.8 Hz, 2H), 4.07 (d, J = 17.0 Hz, 1H), 3.71 (d, J = 17.0 Hz, 1H). |
| 5-053 | (A) δ 8.54 (d, J = 4.2 Hz, 1H), 7.77 (d, J = 7.8 Hz, 1H), 7.6-7.8 (m, 3H), 7.62 (d, J = 7.8 Hz, 1H), 7.50 (bs, 2H), 7.44 (bs, 1H), 7.34 (d, J = 7.5 Hz, 1H), 7.23 (dd, J = 7.5, 2.4 Hz, 1H), 4.78 (d, J = 4.5 Hz, 2H), 4.08 (d, J = 18.0 Hz, 1H), 3.71 (d, J = 18.0 Hz, 1H). |
| 5-056 | (A) δ 8.55 (d, J = 4.5 Hz, 1H), 8.08 (t, J = 4.5 Hz, 1H), 7.96 (s, 1H), 7.78 (d, J = 8.4 Hz, 1H), 7.72 (d, J = 8.4 Hz, 1H), 7.69 (dd, J = 4.5, 2.4 Hz, 1H), 7.50 (bs, 2H), 7.43 (bs, 1H), 7.33 (d, J = 7.2 Hz, 1H), 7.23 (dd, J = 7.2, 2.4 Hz, 1H), 4.73 (d, J = 4.5 Hz, 2H), 4.28 (d, J = 18.0 Hz, 1H), 3.87 (d, J = 18.0 Hz, 1H). |
| 5-058 | (B) δ 8.54 (d, J = 3.9 Hz, 1H), 7.89 (bs, 1H), 7.74 (td, J = 7.8, 1.8 Hz, 1H), 7.6-7.7 (m, 1H), 7.50 (bs, 3H), 7.44 (t, J = 1.8 Hz, 1H), 7.38 (d, J = 7.8 Hz, 1H), 7.2-7.3 (bs, 1H), 4.79 (d, J = 4.7 Hz, 2H), 4.07 (d, J = 17.2 Hz, 1H), 3.70 (d, J = 17.2 Hz, 1H). |
| 5-060 | (B) δ 8.01 (bs, 1H), 7.65-7.75 (m, 2H), 7.50 (bs, 2H), 7.4-7.45 (m, 1H), 6.25-6.3 (m, 1H), 4.06 (d, J = 17.2 Hz, 1H), 3.55-3.75 (m, 3H), 3.45-3.6 (m, 4H), 1.20 (t, J = 7.0 Hz, 3H). |
| 5-061 | (B) δ 8.10 (bs, 1H), 7.69 (d, J = 8.0 Hz, 1H), 7.50 (bs, 2H), 7.4-7.45 (m, 2H), 6.09 (bs, 1H), 4.54 (t, J = 5.2 Hz, 1H), 4.06 (d, J = 17.2 Hz, 1H), 3.69 (d, J = 17.2 Hz, 1H), 3.60 (t, J = 5.2 Hz, 2H), 3.44 (s, 6H). |
| 5-062 | (B) δ 8.13 (bs, 1H), 7.71 (d, J = 8.0 Hz, 1H), 7.4-7.5 (m, 4H), 6.7-6.9 (br, 1H), 6.05-6.3 (br, 1H), 4.05-4.15 (m, 2H), 4.06 (d, J = 17.2 Hz, 1H), 3.69 (d, J = 17.2 Hz, 1H), 2.88 (bs, 3H). |

TABLE 21-continued

| No. | ¹H NMR |
|---|---|
| 5-065 | (B) δ 8.5-8.55 (m, 1H), 8.13 (d, J = 1.8 Hz, 1H), 7.7-7.5 (m, 2H), 7.50 (d, J = 1.8 Hz, 2H), 7.44 (t, J = 1.8 Hz, 1H), 7.37 (d, J = 8.0 Hz, 1H), 7.2-7.3 (m, 3H), 4.78 (d, J = 4.8 Hz, 2H), 4.06 (d, J = 17.2 Hz, 1H), 3.68 (d, J = 17.2 Hz, 1H). |
| 5-070 | (A) δ 7.35-7.55 (m, 6H), 6.02 (bs, 1H), 4.09 (d, J = 17.4 Hz, 1H), 3.71 (d, J = 17.4 Hz, 1H), 3.25-3.35 (m, 2H), 2.45 (s, 3H), 1.0-1.15 (m, 1H), 0.55-0.65 (m, 2H), 0.25-0.35 (m, 2H). |
| 5-072 | (A) δ 7.35-7.55 (m, 6H), 5.78 (bs, 1H), 4.08 (d, J = 17.0 Hz, 1H), 3.69 (d, J = 17.0 Hz, 1H), 3.47 (t, J = 7.1 Hz, 2H), 2.45-2.65 (m, 1H), 2.44 (s, 3H), 1.65-2.2 (m, 6H). |
| 5-077 | (A) δ 7.4-7.5 (m, 6H), 6.19 (bs, 1H), 4.08 (d, J = 16.8 Hz, 1H), 3.5-3.75 (m, 7H), 2.47 (s, 3H), 1.20 (t, J = 6.9 Hz, 3H). |
| 5-079 | (B) δ 7.45-7.55 (m, 4H), 7.43 (t, J = 1.8 Hz, 1H), 7.39 (d, J = 8.4 Hz, 1H), 6.28 (bs, 1H), 4.27 (t, J = 5.1 Hz, 2H), 4.08 (d, J = 17.2 Hz, 1H), 3.65-3.75 (m, 3H), 2.44 (s, 3H), 2.08 (s, 3H). |
| 5-080 | (B) δ 7.45-7.55 (m, 4H), 7.35-7.45 (m, 2H), 6.48 (bs, 1H), 4.80 (bs, 1H), 4.28 (t, J = 5.0 Hz, 2H), 4.08 (d, J = 17.2 Hz, 1H), 3.70 (d, J = 17.2 Hz, 1H), 3.65-3.7 (m, 2H), 3.15-3.25 (m, 2H), 2.46 (s, 3H), 1.13 (t, J = 7.2 Hz, 3H). |
| 5-083 | (A) δ 7.4-7.55 (m, 6H), 5.95 (bs, 1H), 4.48 (t, J = 5.4 Hz, 1H), 4.05 (d, J = 17.4 Hz, 1H), 3.66 (d, J = 17.4 Hz, 1H), 3.59 (t, J = 5.4 Hz, 2H), 3.44 (s, 6H), 2.48 (s, 3H). |
| 5-084 | (A) δ 7.4-7.55 (m, 6H), 6.02 (bs, 1H), 4.63 (t, J = 5.1 Hz, 1H), 4.08 (d, J = 16.8 Hz, 1H), 3.5-3.8 (m, 7H), 2.48 (s, 3H), 1.22 (t, J = 6.6 Hz, 6H). |
| 5-085 | (B) δ 7.45-7.55 (m, 4H), 7.43 (t, J = 1.8 Hz, 1H), 7.39 (d, J = 8.4 Hz, 1H), 6.31 (d, J = 8.1 Hz, 1H), 4.81 (bs, 1H), 4.35-4.45 (m, 1H), 4.22 (dd, J = 11.5, 6.8 Hz, 1H), 4.10 (dd, J = 11.5, 3.7 Hz, 1H), 4.08 (d, J = 17.2 Hz, 1H), 3.70 (d, J = 17.2 Hz, 1H), 3.15-3.25 (m, 2H), 2.45 (s, 3H), 1.27 (d, J = 7.1 Hz, 3H), 1.13 (t, J = 7.2 Hz, 3H). |
| 5-086 | (A) δ 7.35-7.6 (m, 6H), 6.24 (bs, 1H), 4.0-4.15 (m, 2H), 3.65-3.9 (m, 4H) 3.25-3.35 (m, 1H), 2.46 (s, 3H), 1.85-2.1 (m, 3H), 1.55-1.7 (m, 1H). |
| 5-087 | (A) δ 7.35-7.55 (m, 6H), 5.97 (bs, 1H), 4.08 (d, J = 17.4 Hz, 1H), 3.55-4.0 (m, 4H), 3.69 (d, J = 17.1 Hz, 1H), 3.45-3.5 (m, 2H), 2.55-2.65 (m, 1H), 2.47 (s, 3H), 2.05-2.15 (m, 1H), 1.6-1.75 (m, 1H). |
| 5-090 | (A) δ 7.4-7.55 (m, 6H), 6.14 (bs, 1H), 4.75 (t, J = 4.5 Hz, 1H), 4.1-4.2 (m, 2H), 4.08 (d, J = 17.4 Hz, 1H), 3.75-3.9 (m, 2H), 3.71 (d, J = 17.4 Hz, 1H), 3.5-3.65 (m, 2H), 2.47 (s, 3H), 2.0-2.15 (m, 1H), 1.3-1.45 (m, 1H). |
| 5-092 | (A) δ 7.35-7.6 (m, 6H), 7.05 (bs, 1H), 4.08 (d, J = 17.1 Hz, 1H), 3.9-4.05 (m, 2H), 3.70 (d, J = 17.1 Hz, 1H), 3.1-3.25 (m, 1H), 2.8-2.95 (m, 1H), 2.66 (s, 3H), 2.47 (s, 3H). |
| 5-094 | (A) δ 7.4-7.6 (m, 6H), 6.73 (bs, 1H), 4.08 (d, J = 17.1 Hz, 1H), 3.9-4.05 (m, 2H), 3.70 (d, J = 17.1 Hz, 1H), 3.28 (t, J = 5.7 Hz, 2H), 3.08 (q, J = 7.5 Hz, 2H), 2.47 (s, 3H), 1.43 (t, J = 7.5 Hz, 3H). |
| 5-095 | (A) δ 7.2-7.6 (m, 11H), 6.09 (bs, 1H), 4.08 (d, J = 17.1 Hz, 1H), 3.75 (s, 2H), 3.70 (d, J = 17.1 Hz, 1H), 3.5-3.6 (m, 2H), 2.68 (t, J = 6.3 Hz, 2H), 2.45 (s, 3H). |
| 5-096 | (A) δ 7.35-7.55 (m, 11H), 6.62 (t, J = 6.0 Hz, 1H), 4.30 (s, 2H), 4.07 (d, J = 17.4 Hz, 1H), 3.85-3.95 (m, 2H), 3.69 (d, J = 17.4 Hz, 1H), 3.1-3.2 (m, 2H), 2.41 (s, 3H). |
| 5-097 | (A) δ 7.35-7.55 (m, 6H), 7.32 (s, 1H), 6.30 (bs, 1H), 6.22 (d, J = 2.7 Hz, 1H), 6.13 (bs, 1H), 4.08 (d, J = 17.4 Hz, 1H), 3.77 (s, 2H), 3.70 (d, J = 17.4 Hz, 1H), 3.55-3.65 (m, 2H), 2.78 (t, J = 6.3 Hz, 2H), 2.47 (s, 3H). |
| 5-098 | (A) δ 7.4-7.55 (m, 7H), 6.55-6.6 (m, 2H), 6.45 (dd, J = 3.0, 1.8 Hz, 1H), 4.39 (s, 2H), 4.07 (d, J = 17.4 Hz, 1H), 3.85-3.95 (m, 2H), 3.69 (d, J = 17.4 Hz, 1H), 3.25-3.3 (m, 2H), 2.45 (s, 3H). |
| 5-099 | (A) δ 7.4-7.6 (m, 6H), 6.22 (t, J = 5.4 Hz, 1H), 4.08 (d, J = 17.0 Hz, 1H), 3.6-3.75 (m, 2H), 3.35-3.5 (m, 1H), 2.85-3.05 (m, 1H), 2.49 (s, 3H), 2.11 (s, 3H), 1.35 (d, J = 6.9 Hz, 3H). |
| 5-100 | (A) δ 7.4-7.6 (m, 6H), 7.15-7.25 and 6.9-7.0 (m, 1H), 3.9-4.2 (m, 2H), 3.6-3.85 (m, 2H), 2.85-3.2 (m, 1H), 2.68 and 2.56 (s, 3H), 2.49 (s, 3H), 1.32 (d, J = 6.9 Hz, 3H). |
| 5-101 | (A) δ 7.4-7.6 (m, 6H), 6.65 (t, J = 5.8 Hz, 1H), 4.08 (d, J = 17.3 Hz, 1H), 3.75-4.0 (m, 2H), 3.69 (d, J = 17.3 Hz, 1H), 3.25-3.45 (m, 1H), 2.94 (s, 3H), 2.49 (s, 3H), 1.50 (d, J = 6.9 Hz, 3H). |
| 5-102 | (A) δ 7.35-7.65 (m, 6H), 6.08 (bs, 1H), 4.3-4.45 (m, 1H), 4.09 (d, J = 17.4 Hz, 1H), 3.71 (d, J = 17.4 Hz, 1H), 2.71 (d, J = 5.7 Hz, 2H), 2.44 (s, 3H), 2.17 (s, 3H), 1.34 (d, J = 6.6 Hz, 3H). |
| 5-103 | (A) δ 7.4-7.6 (m, 6H), 6.46 (d, J = 8.1 Hz, 1H), 4.6-4.75 (m, 1H), 4.08 (d, J = 17.1 Hz, 1H), 3.70 (d, J = 17.4 Hz, 1H), 3.42 (dd, J = 14.4, 6.3 Hz, 1H), 3.26 (dd, J = 14.4, 5.1 Hz, 1H), 3.03 (s, 3H), 2.45 (s, 3H), 1.53 (d, J = 6.9 Hz, 3H). |
| 5-104 | (A) δ 7.45-7.55 (m, 4H), 7.4-7.45 (m, 2H), 5.75 (bs, 1H), 4.07 (d, J = 17.4 Hz, 1H), 3.69 (d, J = 17.4 Hz, 1H), 3.07 (s, 2H), 2.48 (s, 3H), 2.18 (s, 3H), 1.51 (s, 6H). |

TABLE 21-continued

| No. | ¹H NMR |
|---|---|
| 5-112 | (A) δ 7.45-7.65 (m, 6H), 7.43 and 6.93 (t, J = 4.8 Hz, 1H), 6.29 (bs, 1H), 4.33 and 4.25 (t, J = 4.7 Hz, 2H), 4.08 (d, J = 17.1 Hz, 1H), 3.70 (d, J = 17.4 Hz, 1H), 2.48 (s, 3H). |
| 5-114 | (A) δ 7.4-7.6 (m, 6H), 7.43 and 6.85 (bs, 1H), 6.30 (bs, 1H), 4.25-4.35 and 4.2-4.25 (m, 2H), 4.08 (d, J = 17.4 Hz, 1H), 3.93 and 3.86 (d, J = 7.2 Hz, 2H), 3.70 (d, J = 17.4 Hz, 1H), 2.49 (s, 3H), 1.1-1.3 (m, 1H), 0.5-0.6 (m, 2H), 0.2-0.3 (m, 2H). |
| 5-115 | (A) δ 7.57 and 6.86 (t, J = 4.4 Hz, 1H), 7.25-7.55 (m, 10H), 6.26 (bs, 1H), 5.10 and 5.02 (s, 2H), 4.28 and 4.20 (t, J = 5.3 Hz, 2H), 4.08 (d, J = 17.1 Hz, 1H), 3.70 (d, J = 17.1 Hz, 1H), 2.44 (s, 3H). |
| 5-116 | (A) δ 7.4-7.5 (m, 6H), 7.39 and 6.79 (t, J = 4.5 Hz, 1H), 6.25 and 6.15 (bs, 1H), 4.0-4.3 (m, 4H), 4.05 (d, J = 17.4 Hz, 1H), 3.67 (d, J = 17.4 Hz, 1H), 2.46 and 2.45 (s, 3H), 0.9-1.25 (m, 2H), 0.01 (s, 9H). |
| 5-118 | (A) δ 7.45-7.55 (m, 4H), 7.35-7.45 (m, 2H), 6.19 (bs, 1H), 4.7-4.85 (m, 1H), 4.08 (d, J = 17.4 Hz, 1H), 3.7-3.8 (m, 1H), 3.70 (d, J = 17.4 Hz, 1H), 3.5-3.6 (m, 1H), 3.0-3.15 (m, 1H), 2.7-2.85 (m, 1H), 2.47 (s, 3H), 2.00 (s, 3H). |
| 5-120 | (A) δ 7.4-7.6 (m, 6H), 7.11 (d, J = 9.6 Hz, 1H), 6.30 (d, J = 9.6 Hz, 1H), 4.0-4.25 (m, 3H), 3.70 (d, J = 17.0 Hz, 1H), 2.50 (s, 3H). |
| 5-122 | (A) δ 7.4-7.6 (m, 7H), 6.61 (d, J = 3.3 Hz, 1H), 6.49 (d, J = 8.4 Hz, 1H), 6.44 (dd, J = 3.3, 2.1 Hz, 1H), 6.33 (d, J = 8.4 Hz, 1H), 4.08 (d, J = 17.3 Hz, 1H), 3.70 (d, J = 17.3 Hz, 1H), 2.48 (s, 3H). |
| 5-123 | (A) δ 7.3-7.6 (m, 8H), 7.0-7.1 (m, 1H), 6.49 (d, J = 8.8 Hz, 1H), 6.42 (d, J = 8.8 Hz, 1H), 4.08 (d, J = 17.0 Hz, 1H), 3.69 (d, J = 17.0 Hz, 1H), 2.50 (s, 3H). |
| 5-126 | (A) δ 8.62 (d, J = 5.0 Hz, 1H), 7.85 (td, J = 8.1, 2.1 Hz, 1H), 7.35-7.65 (m, 9H), 6.15 (d, J = 6.9 Hz, 1H), 4.09 (d, J = 17.0 Hz, 1H), 3.71 (d, J = 17.0 Hz, 1H), 2.52 (s, 3H). |
| 5-128 | (A) δ 7.45-7.65 (m, 6H), 6.33 (bs, 1H), 4.23 (d, J = 5.1 Hz, 2H), 4.09 (d, J = 17.4 Hz, 1H), 3.81 (s, 3H), 3.70 (d, J = 17.4 Hz, 1H), 2.49 (s, 3H). |
| 5-130 | (B) δ 7.4-7.55 (m, 6H), 6.33 (d, J = 6.6 Hz, 1H), 4.75-4.85 (m, 1H), 4.08 (d, J = 17.2 Hz, 1H), 3.81 (s, 3H), 3.70 (d, J = 17.2 Hz, 1H), 2.49 (s, 3H), 1.55 (s, 3H). |
| 5-131 | (B) δ 7.4-7.55 (m, 6H), 6.34 (d, J = 7.6 Hz, 1H), 4.7-4.8 (m, 1H), 4.2-4.3 (m, 2H), 4.08 (d, J = 17.4 Hz, 1H), 3.70 (d, J = 17.4 Hz, 1H), 2.49 (s, 3H), 1.54 (t, J = 7.0 Hz, 3H), 1.32 (t, J = 7.2 Hz, 3H). |
| 5-132 | (A) δ 7.4-7.55 (m, 6H), 6.36 (bs, 1H), 4.75-4.9 (m, 1H), 4.6-4.75 (m, 1H), 4.4-4.55 (m, 1H), 4.18 (d, J = 17.4 Hz, 1H), 3.71 (d, J = 17.4 Hz, 1H), 2.45 (s, 3H), 1.57 (d, J = 7.2 Hz, 3H). |
| 5-133 | (A) δ 7.4-7.6 (m, 6H), 7.06 (d, J = 6.6 Hz, 1H), 5.76 (t, J = 6.6 Hz, 1H), 4.27 (d, J = 6.6 Hz, 1H), 4.08 (d, J = 17.1 Hz, 1H), 3.89 (s, 3H), 3.70 (d, J = 17.1 Hz, 1H), 2.49 (s, 3H). |
| 5-134 | (A) δ 7.4-7.6 (m, 6H), 6.79 (d, J = 9.4 Hz, 1H), 5.72 (d, J = 9.4 Hz, 1H), 4.09 (d, J = 17.3 Hz, 1H), 3.87 (s, 3H), 3.71 (d, J = 17.3 Hz, 1H), 3.59 (s, 3H), 2.51 (s, 3H). |
| 5-136 | (A) δ 7.35-7.55 (m, 6H), 6.44 (bs, 1H), 4.05-4.25 (m, 3H), 3.6-3.8 (m, 3H), 2.66 (t, J = 6.0 Hz, 2H), 2.46 (s, 3H), 1.27 (t, J = 7.2 Hz, 3H). |
| 5-138 | (A) δ 7.45-7.6 (m, 6H), 7.09 (bs, 1H), 6.69 (bs, 1H), 4.05-4.15 (m, 3H), 3.72 (d, J = 17.4 Hz, 1H), 2.83 (d, J = 4.8 Hz, 3H), 2.44 (s, 3H). |
| 5-139 | (A) δ 7.5-7.6 (m, 5H), 7.43 (s, 1H), 6.98 (bs, 1H), 4.23 (d, J = 3.9 Hz, 2H), 4.09 (d, J = 17.1 Hz, 1H), 3.71 (d, J = 17.1 Hz, 1H), 3.04 (s, 3H), 3.02 (s, 3H), 2.50 (s, 3H). |
| 5-141 | (B) δ 7.4-7.55 (m, 6H), 7.05-7.1 (m, 1H), 6.62 (bs, 1H), 4.05-4.15 (m, 3H), 3.72 (d, J = 17.2 Hz, 1H), 3.23 (dd, J = 13.8, 7.2 Hz, 2H), 2.45 (s, 3H), 1.5-1.6 (m, 2H), 0.91 (t, J = 7.4 Hz, 3H). |
| 5-143 | (B) δ 7.4-7.55 (m, 6H), 6.9-7.05 (m, 1H), 6.45-6.55 (m, 1H), 4.05-4.2 (m, 3H), 3.70 (d, J = 17.2 Hz, 1H), 3.1-3.15 (m, 2H), 2.45-2.5 (m, 4H), 0.9-1.0 (m, 6H). |
| 5-145 | (B) δ 7.4-7.55 (m, 6H), 6.78 (bs, 1H), 5.93 (bs, 1H), 4.0-4.15 (m, 3H), 3.70 (d, J = 16.8 Hz, 1H), 2.48 (s, 3H), 1.38 (s, 9H). |
| 5-146 | (B) δ 7.4-7.55 (m, 6H), 7.01 (bs, 1H), 6.53 (bs, 1H), 4.05-4.2 (m, 3H), 3.71 (d, J = 17.4 Hz, 1H), 3.05-3.1 (m, 2H), 2.46 (s, 3H), 0.91 (s, 9H). |
| 5-147 | (B) δ 7.4-7.55 (m, 6H), 6.89 (bs, 2H), 4.56 (t, J = 5.0 Hz, 1H), 4.44 (t, J = 5.0 Hz, 1H), 4.16 (d, J = 5.0 Hz, 2H), 4.19 (d, J = 17.2 Hz, 1H), 3.71 (d, J = 17.2 Hz, 1H), 3.5-3.7 (m, 2H), 2.46 (s, 3H). |
| 5-149 | (A) δ 7.45-7.6 (m, 5H), 7.42 (s, 1H), 7.27 (bs, 1H), 4.25-4.4 (m, 2H), 4.09 (d, J = 17.4 Hz, 1H), 3.6-3.8 (m, 5H), 3.17 (s, 3H), 2.49 (s, 3H). |
| 5-150 | (B) δ 7.4-7.55 (m, 6H), 6.8-7.2 (m, 2H), 4.16 (d, J = 5.0 Hz, 2H), 4.09 (d, J = 17.2 Hz, 1H), 3.5-3.75 (m, 3H), 3.48 (t, J = 5.8 Hz, 2H), 2.48 (s, 3H). |
| 5-152 | (A) δ 7.4-7.55 (m, 6H), 7.05 (bs, 1H), 6.90 (bs, 1H), 4.0-4.2 (m, 3H), 3.71 (d, J = 17.0 Hz, 1H), 3.5-3.6 (m, 2H), 3.4-3.5 (m, 2H), 2.45 (s, 3H), 1.9-2.1 (m, 2H). |
| 5-153 | (B) δ 7.4-7.55 (m, 6H), 6.7-7.05 (m, 2H), 4.15-4.2 (m, 2H), 4.09 (d, J = 17.2 Hz, 1H), 3.75-3.9 (m, 1H), 3.71 (d, J = 17.2 Hz, 1H), |

TABLE 21-continued

| No. | ¹H NMR |
|---|---|
| | 3.05-3.2 (m, 1H), 2.47 (s, 3H), 1.49 (bs, 1H), 1.6-1.7 (m, 1H), 1.2-1.3 (m, 1H). |
| 5-154 | (A) δ 7.45-7.55 (m, 5H), 7.43 (s, 1H), 6.86 (bs, 1H), 6.77 (bs, 1H), 4.05-4.15 (m, 3H), 3.65-3.8 (m, 3H), 3.45-3.55 (m, 2H), 2.46 (s, 3H), 1.69 (bs, 1H). |
| 5-155 | (B) δ 7.5-7.55 (m, 5H), 7.43 (t, J = 1.8 Hz, 1H), 6.9-7.0 (m, 1H), 4.25-4.4 (m, 2H), 4.19 (d, J = 17.4 Hz, 1H), 3.8-3.9 (m, 2H), 3.70 (d, J = 17.4 Hz, 1H), 3.63 (t, J = 5.2 Hz, 1H), 3.49 (t, J = 5.2 Hz, 1H), 3.13 and 3.04 (s, 3H), 2.50 (s, 3H). |
| 5-159 | (B) δ 7.4-7.55 (m, 6H), 7.25-7.35 (m, 1H), 7.0-7.05 (m, 1H), 4.10 (d, J = 17.2 Hz, 1H), 4.06 (bs, 2H), 3.77 (bs, 2H), 3.73 (d, J = 17.2 Hz, 1H), 3.25 (t, J = 5.6 Hz, 2H), 2.96 (s, 3H), 2.42 (s, 3H). |
| 5-161 | (B) δ 7.4-7.55 (m, 6H), 6.96 (bs, 1H), 5.7-5.85 (m, 1H), 5.15-5.35 (m, 2H), 4.2-4.3 (m, 2H), 4.05-4.15 (m, 2H), 3.92 (bs, 1H), 3.71 (d, J = 17.2 Hz, 1H), 3.01 and 2.99 (s, 3H), 2.50 (s, 3H). |
| 5-162 | (B) δ 7.45-7.55 (m, 5H), 7.4-7.45 (m, 1H), 6.97 (bs, 1H), 5.7-5.85 (m, 2H), 5.15-5.3 (m, 4H), 4.27 (d, J = 4.0 Hz, 2H), 4.10 (d, J = 17.2 Hz, 1H), 4.05 (d, J = 5.8 Hz, 2H), 3.91 (d, J = 5.8 Hz, 2H), 3.72 (d, J = 17.2 Hz, 1H), 2.50 (s, 3H). |
| 5-163 | (A) δ 7.4-7.6 (m, 6H), 6.9-7.2 (m, 2H), 5.38 (s, 1H), 5.30 (s, 1H), 4.0-4.3 (m, 5H), 3.70 (d, J = 17.0 Hz, 1H), 2.44 (s, 3H). |
| 5-165 | (B) δ 7.4-7.55 (m, 6H), 7.00 (bs, 2H), 4.05-4.2 (m, 5H), 3.72 (d, J = 17.2 Hz, 1H), 2.54 (s, 3H), 2.22 (s, 1H). |
| 5-167 | (B) δ 8.78 (d, J = 1.8 Hz, 1H), 7.45-7.55 (m, 6H), 7.43 (t, J = 1.8 Hz, 1H), 6.65-6.8 (m, 2H), 4.65 (d, J = 7.4 Hz, 2H), 4.05-4.2 (m, 3H), 3.70 (d, J = 17.2 Hz, 1H), 2.46 (s, 3H). |
| 5-168 | (B) δ 8.52 (d, J = 4.1 Hz, 1H), 7.67 (td, J = 7.8, 1.8 Hz, 1H), 7.4-7.55 (m, 8H), 7.2-7.25 (m, 1H), 6.83 (bs, 1H), 4.59 (d, J = 5.0 Hz, 2H), 4.22 (d, J = 5.0 Hz, 2H), 4.08 (d, J = 17.2 Hz, 1H), 3.70 (d, J = 17.2 Hz, 1H), 2.47 (s, 3H). |
| 5-171 | (B) δ 7.45-7.55 (m, 6H), 6.94 (bs, 1H), 4.25 (d, J = 3.8 Hz, 2H), 4.08 (d, J = 17.2 Hz, 1H), 3.65-3.75 (m, 7H), 3.48 (t, J = 4.4 Hz, 2H), 2.50 (s, 3H). |
| 5-173 | (B) δ 7.2-7.6 (m, 7H), 6.6-7.1 (m, 6H), 4.0-4.6 (m, 3H), 3.70 (d, J = 17.0 Hz, 1H), 3.33 (s, 3H), 2.49 (s, 3H). |
| 5-176 | (B) δ 7.3-7.55 (m, 12H), 6.37 (bs, 1H), 5.71 (d, J = 7.0 Hz, 1H), 4.08 (d, J = 17.2 Hz, 1H), 3.71 (d, J = 17.2 Hz, 1H), 2.75 (d, J = 4.9 Hz, 3H), 2.41 (s, 3H). |
| 5-178 | (A) δ 7.45-7.6 (m, 5H), 7.43 (s, 1H), 6.62 (bs, 1H), 4.37 (t, J = 9.3 Hz, 2H), 4.23 (d, J = 4.5 Hz, 2H), 4.09 (d, J = 17.1 Hz, 1H), 3.86 (t, J = 9.3 Hz, 2H), 3.71 (d, J = 17.1 Hz, 1H), 2.48 (s, 3H). |
| 5-179 | (A) δ 8.10 (bs, 1H), 7.4-7.65 (m, 7H), 7.06 (bs, 1H), 4.43 (d, J = 5.1 Hz, 2H), 4.09 (d, J = 17.1 Hz, 1H), 3.71 (d, J = 17.1 Hz, 1H), 2.49 (s, 3H). |
| 5-180 | (A) δ 7.65-7.8 (m, 2H), 7.1-7.6 (m, 12H), 6.03 (d, J = 7.4 Hz, 1H), 4.08 (d, J = 17.0 Hz, 1H), 3.70 (d, J = 17.0 Hz, 1H), 2.45 (s, 3H). |
| 5-181 | (A) δ 7.51 (bs, 4H), 7.4-7.45 (m, 1H), 7.38 (d, J = 8.5 Hz, 1H), 5.5-5.6 (m, 1H), 4.08 (d, J = 17.1 Hz, 1H), 3.69 (d, J = 17.1 Hz, 1H), 2.97 (d, J = 6.1 Hz, 2H), 2.46 (s, 3H), 0.13 (s, 9H). |
| 5-182 | (A) δ 7.51 (bs, 4H), 7.4-7.45 (m, 2H), 5.85-6.05 (m, 1H), 5.81 (bs, 1H), 5.15-5.35 (m, 2H), 4.05-4.15 (m, 3H), 3.69 (d, J = 17.4 Hz, 1H), 2.49 (s, 3H). |
| 5-183 | (A) δ 7.4-7.75 (m, 5H), 7.33 (d, J = 7.8 Hz, 1H), 4.04 (d, J = 17.1 Hz, 1H), 3.75 (m, 1H), 3.66 (d, J = 17.4 Hz, 1H), 3.37 (m, 1H), 3.08 (m, 2H), 1.25 (t, J = 7.4 Hz, 3H), 1.04 (t, J = 7.2 Hz, 3H). |
| 5-184 | (A) δ 7.51 (bs, 4H), 7.4-7.5 (m, 2H), 6.10 (t, J = 6.9 Hz, 1H), 5.95 (bs, 1H), 4.17 (t, J = 6.6 Hz, 2H), 4.08 (d, J = 17.1 Hz, 1H), 3.69 (d, J = 17.4 Hz, 1H), 2.48 (s, 3H). |
| 5-185 | (A) δ 7.4-7.55 (m, 6H), 6.58 and 6.34 (s, 1H), 6.10 and 5.99 (bs, 1H), 4.49 and 4.30 (d, J = 6.0 Hz, 2H), 4.08 (d, J = 17.1 Hz, 1H), 3.69 (d, J = 17.1 Hz, 1H), 2.50 and 2.48 (s, 3H). |
| 5-186 | (A) δ 7.35-7.55 (m, 6H), 6.03 (bs, 1H), 4.27 (q, J = 2.4 Hz, 2H), 4.08 (d, J = 17.4 Hz, 1H), 3.70 (d, J = 17.4 Hz, 1H), 2.47 (s, 3H), 2.30 (t, J = 2.4 Hz, 1H). |
| 5-189 | (A) δ 7.25-7.55 (m, 11H), 6.0-6.2 (m, 1H), 5.2-5.4 (m, 1H), 4.06 (d, J = 17.3 Hz, 1H), 3.68 (d, J = 17.3 Hz, 1H), 2.41 (s, 3H), 1.60 (d, J = 6.9 Hz, 3H). |
| 5-191 | (A) δ 7.2-7.6 (m, 11H), 6.09 (bs, 1H), 5.06 (q, J = 7.5 Hz, 1H), 4.06 (d, J = 17.1 Hz, 1H), 3.68 (d, J = 17.1 Hz, 1H), 2.40 (s, 3H), 1.85-2.0 (m, 2H), 0.97 (t, J = 7.2 Hz, 3H). |
| 5-194 | (B) δ 7.3-7.6 (m, 11H), 6.42 (d, J = 9.6 Hz, 1H), 6.26 (d, J = 9.6 Hz, 1H), 4.07 (d, J = 17.2 Hz, 1H), 3.85-3.95 (m, 1H), 3.7-3.8 (m, 1H), 3.69 (d, J = 17.2 Hz, 1H), 2.50 (s, 3H), 1.33 (t, J = 7.2 Hz, 3H). |
| 5-205 | (A) δ 7.35-7.55 (m, 7H), 6.25-6.35 (m, 2H), 6.10 (bs, 1H), 4.62 (d, J = 5.4 Hz, 2H), 4.07 (d, J = 17.1 Hz, 1H), 3.69 (d, J = 17.1 Hz, 1H), 2.46 (s, 3H). |

TABLE 21-continued

| No. | ¹H NMR |
|---|---|
| 5-207 | (A) δ 7.3-7.55 (m, 6H), 6.7-6.8 (m, 2H), 6.39 (bs, 1H), 4.64 (d, J = 6.0 Hz, 2H), 4.07 (d, J = 17.4 Hz, 1H), 3.69 (d, J = 17.4 Hz, 1H), 2.43 (s, 3H). |
| 5-208 | (A) δ 7.4-7.6 (m, 6H), 6.37 (bs, 1H), 6.04 (s, 1H), 4.66 (d, J = 5.7 Hz, 2H), 4.08 (d, J = 17.4 Hz, 1H), 3.69 (d, J = 17.4 Hz, 1H), 2.49 (s, 3H), 2.43 (s, 3H). |
| 5-209 | (A) δ 7.35-7.6 (m, 6H), 6.57 (t, J = 6.0 Hz, 1H), 6.31 (s, 1H), 4.70 (d, J = 6.0 Hz, 2H), 4.09 (d, J = 17.4 Hz, 1H), 3.71 (d, J = 17.4 Hz, 1H), 2.43 (s, 3H). |
| 5-212 | (A) δ 7.56 (s, 1H), 7.35-7.55 (m, 6H), 5.90 (bs, 1H), 4.46 (d, J = 5.4 Hz, 2H), 4.07 (d, J = 17.1 Hz, 1H), 3.85 (s, 3H), 3.68 (d, J = 17.1 Hz, 1H), 2.47 (s, 3H). |
| 5-213 | (A) δ 7.3-7.55 (m, 6H), 6.19 (bs, 1H), 4.43 (d, J = 5.4 Hz, 2H), 4.07 (d, J = 17.4 Hz, 1H), 3.78 (s, 3H), 3.72 (d, J = 17.1 Hz, 1H), 2.43 (s, 3H). |
| 5-216 | (A) δ 7.74 (d, J = 3.3 Hz, 1H), 7.45-7.55 (m, 5H), 7.43 (bs, 1H), 7.40 (d, J = 3.3 Hz, 1H), 6.66 (bs, 1H), 4.95 (d, J = 5.4 Hz, 2H), 4.08 (d, J = 16.8 Hz, 1H), 3.70 (d, J = 17.4 Hz, 1H), 2.50 (s, 3H). |
| 5-217 | (A) δ 7.75 (d, J = 3.3 Hz, 1H), 7.3-7.6 (m, 13H), 6.59 (d, J = 7.4 Hz, 1H), 4.08 (d, J = 17.3 Hz, 1H), 3.69 (d, J = 17.3 Hz, 1H), 2.46 (s, 3H). |
| 5-218 | (A) δ 7.76 (s, 1H), 7.4-7.75 (m, 6H), 6.78 (bs, 1H), 4.93 (d, J = 3.6 Hz, 2H), 4.09 (d, J = 17.4 Hz, 1H), 3.70 (d, J = 17.4 Hz, 1H), 2.47 (s, 3H). |
| 5-220 | (A) δ 7.4-7.55 (m, 6H), 7.17 (s, 1H), 6.40 (bs, 1H), 4.64 (d, J = 5.7 Hz, 2H), 4.08 (d, J = 17.1 Hz, 1H), 3.73 (d, J = 17.1 Hz, 1H), 2.46 (s, 3H). |
| 5-221 | (A) δ 7.4-7.55 (m, 6H), 7.07 (s, 1H), 6.42 (bs, 1H), 4.66 (d, J = 5.4 Hz, 2H), 4.05 (d, J = 17.4 Hz, 1H), 3.66 (d, J = 17.4 Hz, 1H), 2.70 (s, 3H), 2.47 (s, 3H). |
| 5-222 | (A) δ 8.76 (s, 1H), 7.81 (s, 1H), 7.50 (bs, 4H), 7.35-7.45 (m, 2H), 6.36 (bs, 1H), 4.83 (d, J = 6.0 Hz, 2H), 4.07 (d, J = 17.4 Hz, 1H), 3.69 (d, J = 17.1 Hz, 1H), 2.46 (s, 3H). |
| 5-223 | (A) δ 7.45-7.55 (m, 4H), 7.35-7.45 (m, 3H), 6.27 (t, J = 6.0 Hz, 1H), 4.71 (d, J = 6.0 Hz, 2H), 4.08 (d, J = 17.4 Hz, 1H), 3.69 (d, J = 17.4 Hz, 1H), 2.48 (s, 3H). |
| 5-224 | (B) δ 7.91 (bs, 1H), 7.4-7.55 (m, 6H), 6.84 (s, 1H), 6.79 (s, 1H), 4.66 (d, J = 4.9 Hz, 2H), 4.07 (d, J = 17.0 Hz, 1H), 3.80 (s, 3H), 3.77 (d, J = 17.0 Hz, 1H), 2.45 (s, 3H). |
| 5-225 | (B) δ 7.25-7.55 (m, 7H), 6.9-7.0 (m, 1H), 6.84 (s, 1H), 4.57 (d, J = 5.5 Hz, 2H), 4.07 (d, J = 17.0 Hz, 1H), 3.70 (d, J = 17.0 Hz, 1H), 3.63 (s, 3H), 2.42 (s, 3H). |
| 5-226 | (B) δ 8.62 (s, 1H), 7.35-7.65 (m, 6H), 6.8-6.9 (m, 1H), 5.07 (d, J = 6.1 Hz, 2H), 4.06 (d, J = 17.0 Hz, 1H), 3.69 (d, J = 17.0 Hz, 1H), 2.42 (s, 3H). |
| 5-227 | (B) δ 7.45-7.55 (m, 5H), 7.35-7.4 (m, 1H), 6.9-6.95 (m, 1H), 4.80 (d, J = 5.8 Hz, 2H), 4.08 (d, J = 17.0 Hz, 1H), 3.71 (d, J = 17.0 Hz, 1H), 2.68 (s, 3H), 2.41 (s, 3H). |
| 5-230 | (A) δ 8.43 (s, 1H), 7.45-7.55 (m, 5H), 7.43 (s, 1H), 6.68 (t, J = 5.7 Hz, 1H), 4.90 (d, J = 5.7 Hz, 2H), 4.09 (d, J = 17.1 Hz, 1H), 3.71 (d, J = 17.1 Hz, 1H), 2.48 (s, 3H). |
| 5-231 | (A) δ 7.45-7.55 (m, 5H), 7.43 (s, 1H), 6.78 (t, J = 5.7 Hz, 1H), 4.80 (d, J = 5.7 Hz, 2H), 4.09 (d, J = 17.1 Hz, 1H), 3.72 (d, J = 17.1 Hz, 1H), 2.54 (s, 3H), 2.47 (s, 3H). |
| 5-232 | (A) δ 9.14 (s, 1H), 7.45-7.55 (m, 6H), 6.85 (t, J = 5.7 Hz, 1H), 5.09 (d, J = 5.7 Hz, 2H), 4.08 (d, J = 17.4 Hz, 1H), 3.70 (d, J = 17.4 Hz, 1H), 2.48 (s, 3H). |
| 5-233 | (B) δ 8.42 (s, 1H), 8.05-8.15 (m, 1H), 7.87 (s, 1H), 7.35-7.55 (m, 6H), 5.70 (d, J = 6.4 Hz, 2H), 4.08 (d, J = 17.0 Hz, 1H), 3.72 (d, J = 17.0 Hz, 1H), 2.32 (s, 3H). |
| 5-235 | (A) δ 8.52 (d, J = 4.8 Hz, 1H), 7.65-7.75 (m, 1H), 7.15-7.55 (m, 9H), 5.32 (dq, J = 6.9 Hz, 1H), 4.09 (d, J = 16.8 Hz, 1H), 3.70 (d, J = 16.8 Hz, 1H), 2.48 (s, 3H), 1.59 (d, J = 6.9 Hz, 3H). |
| 5-238 | (B) δ 7.66 (t, J = 7.7 Hz, 1H), 7.45-7.55 (m, 5H), 7.43 (t, J = 1.8 Hz, 1H), 7.25-7.35 (m, 2H), 7.02 (t, J = 5.3 Hz, 1H), 4.69 (d, J = 5.3 Hz, 2H), 4.10 (d, J = 17.2 Hz, 1H), 3.72 (d, J = 17.4 Hz, 1H), 2.47 (s, 3H). |
| 5-239 | (B) δ 8.2-8.3 (m, 1H), 7.55-7.65 (m, 2H), 7.45-7.55 (m, 3H), 7.4-7.5 (m, 3H), 7.25-7.4 (m, 2H), 4.79 (d, J = 6.2 Hz, 2H), 4.07 (d, J = 17.2 Hz, 1H), 3.69 (d, J = 17.2 Hz, 1H), 2.41 (s, 3H). |
| 5-240 | (A) δ 8.58 (d, J = 1.8 Hz, 1H), 8.53 (dd, J = 4.8, 1.8 Hz, 1H), 7.72 (d, J = 7.8 Hz, 1H), 7.4-7.55 (m, 6H), 7.30 (dd, J = 7.8, 4.8 Hz, 1H), 6.40 (t, J = 6.0 Hz, 1H), 4.63 (d, J = 6.0 Hz, 2H), 4.08 (d, J = 17.4 Hz, 1H), 3.70 (d, J = 17.4 Hz, 1H), 2.46 (s, 3H). |
| 5-242 | (A) δ 8.57 (d, J = 6.0 Hz, 2H), 7.4-7.55 (m, 6H), 7.26 (d, J = 6.0 Hz, 2H), 6.42 (t, J = 6.0 Hz, 1H), 4.64 (d, J = 6.0 Hz, 2H), 4.08 (d, J = 17.4 Hz, 1H), 3.70 (d, J = 17.4 Hz, 1H), 2.48 (s, 3H). |
| 5-243 | (A) δ 8.73 (d, J = 5.4 Hz, 2H), 7.5-7.6 (m, 5H), 7.43 (s, 1H), 7.24 (t, J = 5.4 Hz, 1H), 7.19 (bs, 1H), 4.89 (d, J = 5.2 Hz, 2H), 4.10 (d, J = 17.0 Hz, 1H), 3.72 (d, J = 17.0 Hz, 1H), 2.53 (s, 3H). |

TABLE 21-continued

| No. | ¹H NMR |
|---|---|
| 5-245 | (A) δ 9.18 (bs, 1H), 8.73 (d, J = 5.2 Hz, 1H), 7.56 (s, 3H), 7.52 (bs, 2H), 7.4-7.45 (m, 1H), 7.35-7.4 (m, 1H), 7.04 (bs, 1H), 4.77 (d, J = 4.8 Hz, 2H), 4.10 (d, J = 17.2 Hz, 1H), 3.72 (d, J = 17.2 Hz, 1H), 2.52 (s, 3H). |
| 5-246 | (B) δ 8.69 (s, 1H), 8.53 (s, 2H), 7.5-7.55 (m, 5H), 7.4-7.45 (m, 1H), 6.95-7.0 (m, 1H), 4.81 (d, J = 5.3 Hz, 2H), 4.09 (d, J = 17.0 Hz, 1H), 3.71 (d, J = 17.0 Hz, 1H), 2.49 (s, 3H). |
| 5-247 | (B) δ 8.55-8.6 (m, 1H), 8.35-8.4 (m, 1H), 7.4-7.55 (m, 6H), 6.95-7.05 (m, 1H), 4.75-4.8 (m, 2H), 4.08 (d, J = 17.0 Hz, 1H), 3.72 (d, J = 17.0 Hz, 1H), 2.57 (s, 3H), 2.46 (s, 3H). |
| 5-265 | (B) δ 7.5-7.55 (m, 5H), 7.4-7.45 (m, 1H), 6.70 (bs, 1H), 4.08 (d, J = 19.0 Hz, 1H), 3.70 (d, J = 19.0 Hz, 1H), 2.51 (s, 3H), 1.51 (s, 9H). |
| 5-277 | (C) δ 7.45-7.65 (m, 6H), 7.44 (s, 1H), 7.33 (d, J = 7.8 Hz, 1H), 7.21 (t, J = 7.8 Hz, 1H), 7.00 (d, J = 7.8 Hz, 1H), 6.89 (t, J = 7.8 Hz, 1H), 6.69 (s, 1H), 4.08 (d, J = 17.4 Hz, 1H), 3.61 (d, J = 17.4 Hz, 1H), 2.53 (s, 3H). |
| 5-278 | (C) δ 7.45-7.65 (m, 6H), 7.44 (s, 1H), 7.20 (t, J = 8.4 Hz, 1H), 6.85-6.95 (m, 2H), 6.81 (d, J = 8.4 Hz, 1H), 6.33 (s, 1H), 4.10 (d, J = 17.1 Hz, 1H), 3.71 (d, J = 17.1 Hz, 1H), 2.52 (s, 3H). |
| 5-279 | (A) δ 7.95 (s, 1H), 7.35-7.55 (m, 6H), 7.17 (d, J = 8.4 Hz, 2H), 6.79 (d, J = 8.4 Hz, 2H), 6.42 (bs, 1H), 4.09 (d, J = 17.4 Hz, 1H), 3.71 (d, J = 17.4 Hz, 1H), 2.43 (s, 3H). |
| 5-280 | (A) δ 7.4-7.65 (m, 10H), 6.98 (d, J = 8.4 Hz, 2H), 4.10 (d, J = 17.3 Hz, 1H), 3.72 (d, J = 17.3 Hz, 1H), 2.52 (s, 3H). |
| 5-296 | (A) δ 8.76 (bs, 1H), 8.12 (bs, 1H), 8.02 (d, J = 5.4 Hz, 1H), 7.35-7.5 (m, 6H), 6.26 (d, J = 5.4 Hz, 1H), 4.10 (d, J = 17.4 Hz, 1H), 3.73 (d, J = 17.4 Hz, 1H), 2.45 (s, 3H), 2.43 (s, 3H). |
| 5-299 | (C) δ 10.15 (bs, 1H), 9.37 (bs, 1H), 8.40 (s, 1H), 7.5-7.6 (m, 5H), 7.46 (s, 1H), 6.69 (s, 1H), 4.17 (d, J = 17.4 Hz, 1H), 3.86 (d, J = 17.4 Hz, 1H), 2.59 (s, 3H). |
| 5-301 | (A) δ 7.4-7.65 (m, 7H), 7.34 (d, J = 9.3 Hz, 1H), 7.01 (d, J = 9.3 Hz, 1H), 4.10 (d, J = 17.4 Hz, 1H), 4.13 (d, J = 17.4 Hz, 1H), 3.71 (d, J = 17.4 Hz, 1H), 2.52 (s, 3H). |
| 5-303 | (B) δ 10.38 (bs, 1H), 7.2-8.65 (m, 11H), 4.05-4.2 (m, 1H), 3.7-3.85 (m, 1H), 2.44 and 2.37 (s, 3H). |
| 5-311 | (A) δ 7.3-7.75 (m, 6H), 6.52 (t, J = 6.3 Hz, 1H), 4.05-4.2 (m, 3H), 3.77 (d, J = 17.4 Hz, 1H), 2.60 (s, 3H). |
| 5-312 | (A) δ 7.25-7.65 (m, 6H), 6.54 (t, J = 6.3 Hz, 1H), 3.9-4.15 (m, 2H), 4.10 (d, J = 17.7 Hz, 1H), 3.73 (d, J = 17.7 Hz, 1H), 2.74 (q, J = 7.2 Hz, 2H), 1.19 (t, J = 7.2 Hz, 3H). |
| 5-313 | (A) δ 8.50 (d, J = 4.8 Hz, 1H), 7.70 (t, J = 4.5 Hz, 1H), 7.5-7.6 (m, 3H), 7.49 (bs, 2H), 7.42 (bs, 1H), 7.15-7.35 (m, 3H), 4.73 (d, J = 4.5 Hz, 2H), 4.11 (d, J = 17.4 Hz, 1H), 3.73 (d, J = 17.4 Hz, 1H), 2.84 (q, J = 7.5 Hz, 2H), 1.23 (t, J = 7.5 Hz, 3H). |
| 5-316 | (B) δ 7.72 (bs, 3H), 7.51 (bs, 2H), 7.45 (t, J = 1.8 Hz, 1H), 7.15-7.25 (m, 1H), 4.71 (d, J = 6.0 Hz, 2H), 4.15-4.2 (m, 3H), 3.73 (d, J = 17.2 Hz, 1H), 3.34 (t, J = 6.0 Hz, 1H). |
| 5-318 | (A) δ 8.30 (d, J = 8.4 Hz, 1H), 8.18 (bs, 1H), 7.51 (s, 2H), 7.48 (s, 1H), 7.25-7.45 (m, 6H), 7.16 (d, J = 8.4 Hz, 1H), 4.68 (d, J = 5.7 Hz, 2H), 4.11 (d, J = 17.4 Hz, 1H), 3.97 (s, 3H), 3.73 (d, J = 17.4 Hz, 1H). |
| 5-320 | (B) δ 8.11 (d, J = 8.0 Hz, 1H), 7.70 (s, 1H), 7.64 (d, J = 8.0 Hz, 1H), 7.51 (s, 2H), 7.45 (s, 1H), 6.86 (t, J = 6.0 Hz, 1H), 4.0-4.25 (m, 3H), 3.71 (d, J = 17.6 Hz, 1H). |
| 5-322 | (A) δ 8.14 (t, J = 7.8 Hz, 1H), 7.54 (d, J = 7.8 Hz, 1H), 7.50 (d, J = 7.8 Hz, 1H), 7.34 (s, 1H), 7.31 (s, 1H), 7.23 (s, 1H), 7.09 and 7.05 (t, J = 6.3 Hz, 1H), 4.18 (qd, J = 18.5, 6.3 Hz, 2H), 4.08 (d, J = 17.4 Hz, 1H), 3.74 (d, J = 17.4 Hz, 1H), 2.52 (s, 3H). |
| 5-325 | (A) δ 8.59 (bs, 1H), 8.32 (s, 1H), 8.11 (bs, 1H), 8.03 (d, J = 8.1 Hz, 1H), 7.85 (d, J = 8.1 Hz, 1H), 7.73 (t, J = 8.1 Hz, 1H), 7.51 (bs, 2H), 7.43 (bs, 1H), 7.2-7.4 (m, 2H), 4.73 (bs, 2H), 4.23 and 4.21 (d, J = 17.4 Hz, 1H), 3.86 and 3.85 (d, J = 17.4 Hz, 1H), 2.96 and 2.93 (s, 3H). |
| 5-328 | (A) δ 8.16 (t, J = 8.0 Hz, 1H), 7.6-7.8 (m, 3H), 7.56 (d, J = 8.0 Hz, 1H), 7.52 (d, J = 8.1 Hz, 1H), 7.08 and 7.03 (t, J = 6.5 Hz, 1H), 4.35-4.55 (m, 2H), 4.05-4.25 (m, 2H), 4.14 (d, J = 17.4 Hz, 1H), 3.79 (d, J = 17.4 Hz, 1H). |
| 5-330 | (B) δ 8.57 (d, J = 4.8 Hz, 1H), 7.71 (td, J = 7.7, 1.8 Hz, 1H), 7.62 (t, J = 4.6 Hz, 1H), 7.54 (d, J = 8.6 Hz, 1H), 7.50 (d, J = 1.6 Hz, 2H), 7.42 (t, J = 1.8 Hz, 1H), 7.33 (d, J = 7.9 Hz, 1H), 7.24 (dd, J = 7.5, 5.0 Hz, 1H), 6.9-7.0 (m, 2H), 5.73 (bs, 2H), 4.72 (d, J = 4.8 Hz, 2H), 4.04 (d, J = 17.2 Hz, 1H), 3.66 (d, J = 17.4 Hz, 1H). |
| 5-332 | (A) δ 8.57 (d, J = 4.2 Hz, 1H), 7.65-7.75 (m, 2H), 7.45-7.6 (m, 4H), 7.43 (bs, 1H), 7.33 (d, J = 7.8 Hz, 1H), 7.2-7.3 (m, 1H), 6.93 (bs, 1H), 6.85 (d, J = 7.8 Hz, 1H), 4.71 (d, J = 4.8 Hz, 2H), 4.09 (d, J = 17.1 Hz, 1H), 3.69 (d, J = 17.1 Hz, 1H), 2.90 (d, J = 3.6 Hz, 3H). |
| 5-335 | (A) δ 10.29 (bs, 1H), 8.56 (d, J = 6.0 Hz, 1H), 8.18 (d, J = 8.1 Hz, 1H), 7.15-7.75 (m, 8H), 4.79 (d, J = 5.4 Hz, 2H), 4.10 (d, J = 17.1 Hz, 1H), 3.71 (d, J = 17.1 Hz, 1H), 2.75 (s, 6H). |

TABLE 21-continued

| No. | ¹H NMR |
|---|---|
| 5-336 | (A) δ 8.45-8.6 (m, 1H), 8.23 and 8.29 (s, 1H), 7.15-7.9 (m, 10H), 4.65-4.75 (m, 2H), 4.0-4.2 (m, 1H), 3.6-3.8 (m, 1H), 3.25 and 3.34 (s, 3H). |
| 5-337 | (A) δ 8.45-8.6 (m, 1H), 7.15-8.05 (m, 10H), 4.65-4.75 (m, 2H), 4.0-4.2 (m, 1H), 3.65-3.8 (m, 1H), 3.33 and 3.22 (s, 3H), 2.19 and 1.87 (s, 3H). |
| 5-340 | (B) δ 7.95-8.0 (m, 1H), 7.89 (dd, J = 8.0, 2.6 Hz, 1H), 7.79 (dd, J = 7.8, 1.6 Hz, 1H), 7.52 (bs, 2H), 7.44 (t, J = 1.8 Hz, 1H), 5.51 (s, 1H), 4.45-4.55 (m, 1H), 4.14 (dd, J = 20.2, 7.6 Hz, 1H), 3.9-4.05 (m, 1H), 3.77 (dd, J = 17.4, 5.2 Hz, 1H). |
| 5-342 | (B) δ 7.9-7.95 (bs, 2H), 7.53 (d, J = 1.8 Hz, 1H), 7.44 (dd, J = 8.2, 1.8 Hz, 1H), 7.21 (bs, 2H), 7.14 (t, J = 1.8 Hz, 1H), 3.75-3.9 (m, 3H), 0.30 (s, 9H). |
| 5-343 | (B) δ 7.25-7.8 (m, 11H), 5.65 (t, J = 6.0 Hz, 1H), 4.10 (d, J = 17.2 Hz, 1H), 3.7-3.85 (m, 3H). |
| 5-345 | (A) δ 8.47 (s, 1H), 8.43 (d, J = 4.8 Hz, 1H), 7.95 (s, 1H), 7.6-7.85 (m, 5H), 7.50 (bs, 2H), 7.43 (bs, 1H), 7.15-7.25 (m, 2H), 4.55 (d, J = 5.4 Hz, 2H), 4.13 (d, J = 17.7 Hz, 1H), 3.77 (d, J = 17.7 Hz, 1H). |
| 5-346 | (B) δ 7.91 (ddd, J = 8.6, 6.8, 1.8 Hz, 1H), 7.78 (ddd, J = 8.6, 6.8, 1.8 Hz, 1H), 7.49 (d, J = 1.6 Hz, 2H), 7.45 (t, J = 2.0 Hz, 1H), 6.84 (bs, 1H), 4.15-4.25 (m, 3H), 3.80 (bs, 1H). |
| 5-347 | (B) δ 7.85-7.95 (m, 1H), 7.7-7.8 (m, 1H), 7.25-7.5 (m, 8H), 6.90 (bs, 1H), 4.68 (d, J = 5.4 Hz, 2H), 4.16 (bs, 1H), 3.78 (bs, 1H). |
| 5-348 | (B) δ 8.59 (bs, 1H), 8.11 (bs, 1H), 7.89 (bs, 1H), 7.71 (bs, 2H), 7.2-7.5 (m, 5H), 4.80 (bs, 2H), 4.18 (d, J = 17.8 Hz, 1H), 3.80 (d, J = 17.8 Hz, 1H). |
| 5-352 | (A) δ 8.49 (d, J = 4.5 Hz, 1H), 7.65-7.75 (m, 1H), 7.51 (s, 2H), 7.42 (s, 1H), 7.3-7.4 (m, 3H), 7.22 (dd, J = 7.5, 4.5 Hz, 1H), 7.10 (bs, 1H), 4.76 (d, J = 4.5 Hz, 2H), 4.07 (d, J = 17.4 Hz, 1H), 3.69 (d, J = 17.4 Hz, 1H), 2.33 (s, 6H). |
| 5-353 | (A) δ 8.77 (d, J = 2.4 Hz, 1H), 7.73 (d, J = 8.1 Hz, 1H), 7.70 (s, 1H), 7.60 (d, J = 8.1 Hz, 1H), 7.52 (bs, 2H), 7.43 (bs, 1H), 7.33 (d, J = 2.4 Hz, 1H), 7.10 (t, J = 5.4 Hz, 1H), 4.81 (d, J = 5.4 Hz, 2H), 4.12 (d, J = 17.4 Hz, 1H), 3.72 (d, J = 17.4 Hz, 1H). |
| 5-354 | (A) δ 8.53 (d, J = 4.5 Hz, 1H), 7.55-7.8 (m, 5H), 7.53 (bs, 2H), 7.43 (bs, 1H), 7.2-7.4 (m, 2H), 4.77 (d, J = 4.8 Hz, 2H), 4.13 (d, J = 17.4 Hz, 1H), 3.74 (d, J = 17.4 Hz, 1H). |
| 5-356 | (A) δ 7.4-7.6 (m, 6H), 6.17 (bs, 1H), 4.12 (d, J = 17.6 Hz, 1H), 3.72 (d, J = 17.6 Hz, 1H), 3.55-3.7 (m, 4H), 3.53 (q, J = 7.1 Hz, 2H), 2.47 (s, 3H), 1.20 (t, J = 7.1 Hz, 3H). |
| 5-357 | (A) δ 7.4-7.6 (m, 6H), 5.97 (t, J = 5.6 Hz, 1H), 4.50 (t, J = 5.6 Hz, 1H), 4.12 (d, J = 17.6 Hz, 1H), 3.72 (d, J = 17.6 Hz, 1H), 3.60 (t, J = 5.6 Hz, 2H), 3.43 (s, 6H), 2.48 (s, 3H). |
| 5-358 | (A) δ 7.4-7.6 (m, 6H), 5.75-6.0 (m, 2H), 5.27 (d, J = 17.1 Hz, 1H), 5.21 (d, J = 10.2 Hz, 1H), 4.0-4.2 (m, 3H), 3.72 (d, J = 17.3 Hz, 1H), 2.48 (s, 3H). |
| 5-359 | (A) δ 8.79 (d, J = 2.1 Hz, 1H), 7.3-7.6 (m, 7H), 6.54 (t, J = 5.4 Hz, 1H), 4.77 (d, J = 5.4 Hz, 2H), 4.12 (d, J = 17.6 Hz, 1H), 3.72 (d, J = 17.6 Hz, 1H), 2.47 (s, 3H). |
| 5-360 | (A) δ 8.54 (d, J = 5.0 Hz, 1H), 7.65-7.8 (m, 1H), 7.15-7.6 (m, 9H), 4.74 (d, J = 5.0 Hz, 2H), 4.08 (d, J = 17.6 Hz, 1H), 3.72 (d, J = 17.6 Hz, 1H), 2.50 (s, 3H). |
| 5-361 | (B) δ 7.5-7.55 (m, 4H), 7.43 (d, J = 5.0 Hz, 1H), 7.42 (d, J = 1.8 Hz, 1H), 6.07 (t, J = 6.4 Hz, 1H), 4.27 (d, J = 17.4 Hz, 1H), 4.05-4.15 (m, 2H), 3.68 (dd, J = 17.4, 1.8 Hz, 1H), 2.46 (s, 3H). |
| 5-362 | (B) δ 8.5-8.55 (m, 1H), 7.71 (td, J = 7.6, 1.6 Hz, 1H), 7.5-7.55 (m, 4H), 7.42 (t, J = 1.6 Hz, 1H), 7.34 (d, J = 7.8 Hz, 1H), 7.2-7.3 (m, 3H), 4.75 (d, J = 4.8 Hz, 2H), 4.27 (d, J = 17.2 Hz, 1H), 3.68 (d, J = 17.2 Hz, 1H), 2.50 (s, 3H). |
| 5-364 | (A) δ 7.3-7.6 (m, 6H), 6.07 (t, J = 6.3 Hz, 1H), 3.8-4.25 (m, 7H), 3.41 (d, J = 16.8 Hz, 1H), 2.46 (s, 3H). |
| 5-365 | (A) δ 8.52 (d, J = 3.8 Hz, 1H), 7.65-7.75 (m, 1H), 7.15-7.6 (m, 9H), 4.75 (d, J = 4.6 Hz, 2H), 3.8-4.2 (m, 5H), 3.41 (d, J = 16.8 Hz, 1H), 2.50 (s, 3H). |
| 5-366 | (A) δ 7.3-7.55 (m, 6H), 6.83 (t, J = 6.5 Hz, 1H), 4.20 (d, J = 17.4 Hz, 1H), 4.0-4.15 (m, 2H), 3.62 (d, J = 17.4 Hz, 1H), 2.40 (s, 3H), 2.30 (s, 3H). |
| 5-368 | (B) δ 7.5-7.6 (m, 2H), 7.4-7.5 (m, 4H), 6.0-6.5 (m, 1H), 4.1-4.2 (m, 2H), 3.53 (d, J = 3.2 Hz, 2H), 2.50 (s, 3H), 1.64 (d, J = 3.2 Hz, 2H), 0.04 (s, 9H). |
| 5-369 | (B) δ 8.55-8.6 (m, 1H), 7.7-7.8 (m, 1H), 7.5-7.55 (m, 3H), 7.35-7.45 (m, 3H), 7.2-7.3 (m, 3H), 4.79 (d, J = 4.8 Hz, 2H), 3.53 (d, J = 3.2 Hz, 2H), 2.55 (s, 3H), 1.64 (d, J = 5.8 Hz, 2H), 0.04 (s, 9H). |
| 5-370 | (A) δ 7.47 (s, 1H), 7.45 (d, J = 7.8 Hz, 1H), 7.34 (d, J = 7.8 Hz, 1H), 7.15-7.3 (m, 3H), 6.28 (t, J = 6.5 Hz, 1H), 4.07 (qd, J = 18.5, 6.5 Hz, 2H), 3.61 (d, J = 16.2 Hz, 1H), 3.53 (d, J = 16.2 Hz, 1H), 2.40 (s, 3H), 0.11 (s, 9H). |

TABLE 21-continued

| No. | $^1$H NMR |
|---|---|
| 5-371 | (A) δ 8.50 (d, J = 5.1 Hz, 1H), 7.45-7.75 (m, 4H), 7.15-7.35 (m, 6H), 4.72 (d, J = 5.1 Hz, 2H), 3.63 (d, J = 16.2 Hz, 1H), 3.54 (d, J = 16.2 Hz, 1H), 2.48 (s, 3H), 0.11 (s, 9H). |
| 5-372 | (A) δ 8.60 (d, J = 4.7 Hz, 1H), 7.15-7.75 (m, 9H), 6.05 (t, J = 6.0 Hz, 1H), 4.77 (d, J = 16.8 Hz, 1H), 4.0-4.2 (m, 2H), 3.69 (d, J = 16.8 Hz, 1H), 2.45 (s, 3H). |
| 5-373 | (A) δ 8.60 (d, J = 4.9 Hz, 1H), 8.53 (d, J = 5.1 Hz, 1H), 7.15-7.8 (m, 13H), 4.7-4.85 (m, 3H), 3.69 (d, J = 16.7 Hz, 1H), 2.48 (s, 3H). |
| 5-374 | (A) δ 7.3-7.75 (m, 6H), 6.0-6.5 (br, 1H), 3.95-4.25 (m, 3H), 3.70 (d, J = 17.1 Hz, 1H), 2.42 (s, 3H). |
| 5-375 | (A) δ 8.55 (d, J = 4.8 Hz, 1H), 7.45-7.75 (m, 7H), 7.3-7.45 (m, 2H), 7.15-7.3 (m, 1H), 4.74 (d, J = 5.1 Hz, 2H), 4.09 (d, J = 17.4 Hz, 1H), 3.70 (d, J = 17.4 Hz, 1H), 2.49 (s, 3H). |
| 5-377 | (A) δ 8.53 (d, J = 4.5 Hz, 1H), 7.55-7.8 (m, 8H), 7.15-7.4 (m, 2H), 4.77 (d, J = 4.5 Hz, 2H), 4.08 (d, J = 17.4 Hz, 1H), 3.71 (d, J = 17.4 Hz, 1H). |
| 5-378 | (A) δ 7.65-7.8 (m, 3H), 7.4-7.6 (m, 3H), 6.04 (t, J = 6.3 Hz, 1H), 4.0-4.2 (m, 3H), 3.70 (d, J = 17.0 Hz, 1H), 2.47 (s, 3H). |
| 5-379 | (A) δ 7.73 (bs, 1H), 7.71 (bs, 2H), 7.51 (s, 1H), 7.49 (d, J = 8.7 Hz, 1H), 7.42 (d, J = 8.7 Hz, 1H), 6.2-6.3 (m, 1H), 4.08 (d, J = 17.4 Hz, 1H), 3.71 (d, J = 17.4 Hz, 1H), 3.5-3.65 (m, 4H), 3.38 (s, 3H), 2.45 (s, 3H). |
| 5-380 | (A) δ 7.74 (bs, 1H), 7.71 (bs, 2H), 7.51 (s, 1H), 7.50 (d, J = 8.4 Hz, 1H), 7.42 (d, J = 8.4 Hz, 1H), 6.2-6.3 (m, 1H), 4.08 (d, J = 17.4 Hz, 1H), 3.71 (d, J = 17.4 Hz, 1H), 3.55-3.65 (m, 4H), 3.53 (q, J = 7.2 Hz, 2H), 2.46 (s, 3H), 1.20 (t, J = 7.2 Hz, 3H). |
| 5-381 | (A) δ 7.73 (bs, 1H), 7.70 (bs, 2H), 7.51 (s, 1H), 7.50 (d, J = 8.4 Hz, 1H), 7.41 (d, J = 8.4 Hz, 1H), 6.06 (t, J = 5.4 Hz, 1H), 4.50 (t, J = 5.4 Hz, 1H), 4.08 (d, J = 16.8 Hz, 1H), 3.70 (d, J = 16.8 Hz, 1H), 3.59 (t, J = 5.4 Hz, 2H), 3.43 (s, 6H), 2.46 (s, 3H). |
| 5-382 | (A) δ 7.73 (bs, 1H), 7.71 (bs, 2H), 7.50 (s, 1H), 7.49 (d, J = 8.7 Hz, 1H), 7.45 (d, J = 8.7 Hz, 1H), 6.47 (t, J = 5.4 Hz, 1H), 4.20 (d, J = 5.4 Hz, 2H), 4.09 (d, J = 17.4 Hz, 1H), 3.80 (s, 3H), 3.72 (d, J = 17.4 Hz, 1H), 2.46 (s, 3H). |
| 5-385 | (A) δ 7.74 (bs, 1H), 7.70 (bs, 2H), 7.49 (s, 1H), 7.48 (d, J = 8.7 Hz, 1H), 7.39 (d, J = 8.7 Hz, 1H), 6.06 (t, J = 5.4 Hz, 1H), 5.92 (ddd, J = 15.9, 10.2, 5.4 Hz, 1H), 5.26 (d, J = 15.9 Hz, 1H), 5.19 (d, J = 10.2 Hz, 1H), 4.08 (d, J = 17.4 Hz, 1H), 4.05 (t, J = 5.4 Hz, 2H), 3.71 (d, J = 17.4 Hz, 1H), 2.45 (s, 3H). |
| 5-386 | (A) δ 8.76 (d, J = 2.1 Hz, 1H), 7.73 (bs, 1H), 7.70 (bs, 2H), 7.49 (s, 1H), 7.48 (d, J = 8.1 Hz, 1H), 7.42 (d, J = 8.1 Hz, 1H), 7.29 (d, J = 2.1 Hz, 1H), 6.75 (t, J = 5.4 Hz, 1H), 4.76 (d, J = 5.4 Hz, 2H), 4.08 (d, J = 17.4 Hz, 1H), 3.70 (d, J = 17.4 Hz, 1H), 2.44 (s, 3H). |
| 5-387 | (A) δ 8.53 (d, J = 5.1 Hz, 1H), 7.65-7.8 (m, 4H), 7.53 (s, 3H), 7.33 (d, J = 8.1 Hz, 1H), 7.15-7.3 (m, 2H), 4.75 (d, J = 4.8 Hz, 2H), 4.08 (d, J = 17.1 Hz, 1H), 3.70 (d, J = 17.1 Hz, 1H), 2.51 (s, 3H). |
| 5-388 | (A) δ 8.5-8.55 (m, 1H), 7.65-7.75 (m, 1H), 7.5-7.6 (m, 3H), 7.2-7.45 (m, 6H), 4.75 (d, J = 4.8 Hz, 2H), 4.07 (d, J = 17.2 Hz, 1H), 3.72 (d, J = 17.2 Hz, 1H), 2.51 (s, 3H), 2.39 (s, 3H). |
| 5-389 | (A) δ 8.09 (s, 2H), 7.98 (s, 1H), 7.45-7.55 (m, 2H), 7.38 (d, J = 8.4 Hz, 1H), 6.35 (bs, 1H), 4.21 (d, J = 17.4 Hz, 1H), 4.0-4.15 (m, 2H), 3.77 (d, J = 17.4 Hz, 1H), 2.42 (s, 3H). |
| 5-390 | (A) δ 8.53 (d, J = 4.2 Hz, 1H), 8.10 (s, 2H), 7.97 (s, 1H), 7.65-7.8 (m, 1H) 7.54 (bs, 3H), 7.2-7.35 (m, 3H), 4.75 (d, J = 4.5 Hz, 2H), 4.22 (d, J = 17.1 Hz, 1H), 3.77 (d, J = 17.1 Hz, 1H), 2.50 (s, 3H). |
| 5-391 | (A) δ 8.52 (d, J = 5.1 Hz, 1H), 7.72 (t, J = 4.8 Hz, 1H), 7.52 (bs, 3H), 7.15-7.35 (m, 4H), 7.07 (d, J = 9.3 Hz, 1H), 6.96 (d, J = 9.3 Hz, 1H), 4.73 (d, J = 4.8 Hz, 2H), 4.10 (d, J = 17.4 Hz, 1H), 3.72 (d, J = 17.4 Hz, 1H), 2.51 (s, 3H), 2.50 (s, 3H). |
| 5-392 | (A) δ 8.53 (d, J = 4.8 Hz, 1H), 7.6-7.75 (m, 4H), 7.3-7.4 (m, 4H), 7.15-7.35 (m, 2H), 4.77 (d, J = 5.1 Hz, 2H), 4.08 (d, J = 17.1 Hz, 1H), 3.72 (d, J = 17.1 Hz, 1H), 2.52 (s, 3H), 2.50 (s, 3H). |
| 5-393 | (A) δ 8.52 (d, J = 4.5 Hz, 1H), 7.70 (t, J = 4.8 Hz, 1H), 7.53 (bs, 1H), 7.52 (bs, 2H), 7.15-7.45 (m, 6H), 4.74 (d, J = 4.8 Hz, 2H), 4.12 (d, J = 17.4 Hz, 1H), 3.89 (s, 3H), 3.75 (d, J = 17.4 Hz, 1H), 2.50 (s, 3H). |
| 5-394 | (A) δ 8.52 (d, J = 5.1 Hz, 1H), 7.70 (t, J = 4.8 Hz, 1H), 7.52 (bs, 3H), 7.15-7.35 (m, 5H), 7.13 (bs, 1H), 4.74 (d, J = 4.8 Hz, 2H), 4.07 (d, J = 17.4 Hz, 1H), 3.73 (d, J = 17.4 Hz, 1H), 2.51 (s, 6H), 2.50 (s, 3H). |
| 5-398 | (A) δ 8.56 (d, J = 4.5 Hz, 1H), 7.72 (td, J = 7.5, 1.5 Hz, 1H), 7.65 (s, 2H), 7.45-7.6 (m, 4H), 7.39 (d, J = 7.8 Hz, 1H), 7.15-7.3 (m, 1H), 4.72 (d, J = 5.1 Hz, 2H), 4.10 (d, J = 17.4 Hz, 1H), 3.71 (d, J = 17.4 Hz, 1H), 2.46 (s, 3H). |
| 5-399 | (B) δ 7.35-7.55 (m, 6H), 6.12 (bs, 1H), 4.18 (d, J = 17.2 Hz, 1H), 3.65-3.75 (m, 3H), 2.4-2.55 (m, 5H). |
| 5-400 | (B) δ 7.4-7.6 (m, 6H), 6.87 (d, J = 9.2 Hz, 1H), 5.9-6.0 (m, 1H), 4.08 (dd, J = 17.2 Hz, 1H), 3.71 (d, J = 17.2 Hz, 1H), 2.48 (s, 3H). |

TABLE 21-continued

| No. | ¹H NMR |
|---|---|
| 5-401 | (B) δ 7.4-7.6 (m, 6H), 6.27 (d, J = 10.4 Hz, 1H), 5.6-5.8 (m, 1H), 4.08 (d, J = 17.6 Hz, 1H), 3.71 (d, J = 17.6 Hz, 1H), 3.61 (s, 3H), 2.50 (s, 3H). |
| 5-403 | (A) δ 7.35-7.7 (m, 6H), 6.8 (s, 1H), 4.09 (d, J = 17.4 Hz, 1H), 3.73 (d, J = 17.4 Hz, 1H), 3.55 (q, J = 5.4 Hz, 2H), 2.74 (t, J = 5.7 Hz, 2H), 2.60 (bs, 4H), 2.45 (s, 3H), 1.79 (bs, 4H). |
| 5-404 | (A) δ 7.35-7.6 (m, 6H), 6.77 (s, 1H), 4.10 (d, J = 17.4 Hz, 1H), 3.73 (d, J = 17.4 Hz, 1H), 3.53 (q, J = 5.7 Hz, 2H), 2.57 (t, J = 6.0 Hz, 2H), 2.47 (bs, 7H), 1.55-1.65 (m, 4H), 1.35-1.5 (m, 2H). |
| 5-405 | (B) δ 7.45-7.55 (m, 5H), 7.43 (t, J = 1.8 Hz, 1H), 6.56 (d, J = 5.7 Hz, 1H), 4.58 (ddd, J = 10.6, 8.4, 5.7 Hz, 1H), 4.09 (d, J = 17.2 Hz, 1H), 3.95-4.05 (m, 1H), 3.8-3.9 (m, 1H), 3.71 (d, J = 17.2 Hz, 1H), 3.5-3.65 (m, 2H), 2.85-2.9 (m, 1H), 2.48 (s, 3H), 2.0-2.15 (m, 1H). |
| 5-406 | (B) δ 7.4-7.55 (m, 6H), 6.52 (t, J = 6.0 Hz, 1H), 5.35 (bs, 1H), 4.8-4.95 (m, 1H), 4.09 (d, J = 17.4 Hz, 1H), 3.6-3.95 (m, 3H), 3.75 (d, J = 17.4 Hz, 1H), 3.4-3.5 (m, 1H), 2.45 (s, 3H). |
| 5-407 | (B) δ 7.5-7.55 (m, 5H), 7.43 (t, J = 1.8 Hz, 1H), 6.84 (d, J = 7.0 Hz, 1H), 5.37 (d, J = 7.1 Hz, 1H), 4.09 (d, J = 17.2 Hz, 1H), 3.87 (s, 6H), 3.72 (d, J = 17.2 Hz, 1H), 2.49 (s, 3H). |
| 5-409 | (A) δ 9.80 and 8.65 (bs, 1H), 7.4-7.6 (m, 6H), 7.1 and 6.64 (bs, 1H), 5.94 (bs, 1H), 5.2-5.5 (m, 2H), 3.95-4.45 (m, 5H), 3.73 (d, J = 17.0 Hz, 1H), 2.42 (s, 3H). |
| 5-410 | (B) δ 7.4-7.55 (m, 6H), 6.72 (bs, 1H), 6.37 (bs, 1H), 4.65 (q, J = 7.4 Hz, 1H), 4.08 (d, J = 17.4 Hz, 1H), 3.70 (d, J = 17.4 Hz, 1H), 3.25-3.35 (m, 2H), 2.45 (s, 3H), 1.47 (d, J = 7.4 Hz, 3H), 1.16 (t, J = 7.4 Hz, 3H). |
| 5-414 | (B) δ 8.19 (t, J = 6.0 Hz, 1H), 7.45-7.55 (m, 5H), 7.43 (t, J = 1.8 Hz, 1H), 7.21 (d, J = 7.5 Hz, 1H), 4.93 (ddd, J = 11.9, 7.5, 4.2 Hz, 1H), 4.31 (bs, 1H), 4.09 (d, J = 17.2 Hz, 1H), 4.0-4.1 (m, 1H), 3.65-3.9 (m, 3H), 3.72 (d, J = 17.2 Hz, 1H), 2.47 (s, 3H), 2.15-2.25 (m, 1H), 1.8-1.9 (m, 1H). |
| 5-415 | (B) δ 7.67 (t, J = 6.6 Hz, 1H), 7.3-7.55 (m, 6H), 7.11 (d, J = 8.1 Hz, 1H), 4.9-5.0 (m, 1H), 4.3-4.45 (m, 2H), 4.09 (d, J = 17.2 Hz, 1H), 3.8-3.9 (m, 2H), 3.73 (d, J = 17.2 Hz, 1H), 3.03 (s, 3H), 2.33 (s, 3H), 2.2-2.4 (m, 2H). |
| 5-417 | (B) δ 7.3-7.6 (m, 11H), 6.32 (d, J = 9.6 Hz, 1H), 6.24 (d, J = 9.6 Hz, 1H), 4.07 (d, J = 17.2 Hz, 1H), 3.69 (d, J = 17.2 Hz, 1H), 3.59 (s, 3H), 2.51 (s, 3H). |
| 5-420 | (A) δ 8.77 (bs, 1H), 7.35-7.55 (m, 6H), 6.81 (s, 1H), 6.37 (d, J = 9.3 Hz, 1H), 6.31 (s, 1H), 6.15-6.25 (m, 1H), 5.9-6.05 (m, 1H), 4.07 (d, J = 17.3 Hz, 1H), 3.69 (d, J = 17.3 Hz, 1H), 2.43 (s, 3H). |
| 5-421 | (A) δ 8.69 (d, J = 4.8 Hz, 1H), 7.51 (s, 5H), 7.43 (s, 1H), 7.25 (d, J = 4.8 Hz, 1H), 6.86 (t, J = 5.7 Hz, 1H), 4.82 (d, J = 5.7 Hz, 2H), 4.09 (d, J = 17.1 Hz, 1H), 3.70 (d, J = 17.1 Hz, 1H), 2.50 (s, 3H). |
| 5-423 | (B) δ 7.72 (d, J = 3.3 Hz, 1H), 7.45-7.55 (m, 5H), 7.43 (t, J = 1.8 Hz, 1H), 7.31 (d, J = 3.3 Hz, 1H), 6.78 (d, J = 7.7 Hz, 1H), 5.55-5.65 (m, 1H), 4.08 (d, J = 17.2 Hz, 1H), 3.71 (d, J = 17.2 Hz, 1H), 2.47 (s, 3H), 1.72 (d, J = 6.8 Hz, 3H). |
| 5-424 | (A) δ 8.29 (d, J = 9.6 Hz, 1H), 7.4-7.6 (m, 7H), 7.12 (s, 1H), 7.01 (s, 1H), 6.7-6.85 (m, 1H), 4.08 (d, J = 17.3 Hz, 1H), 3.70 (d, J = 17.3 Hz, 1H), 2.38 (s, 3H). |
| 5-425 | (B) δ 7.45-7.55 (m, 6H), 7.34 (bs, 1H), 6.89 (bs, 1H), 6.58 (t, J = 4.8 Hz, 1H), 4.52 (d, J = 15.8 Hz, 2H), 4.07 (d, J = 17.2 Hz, 1H), 3.69 (d, J = 17.2 Hz, 1H), 3.67 (s, 3H), 2.46 (s, 3H). |
| 5-426 | (B) δ 8.33 (s, 1H), 7.92 (s, 1H), 7.45-7.55 (m, 4H), 7.42 (t, J = 1.8 Hz, 1H), 7.25-7.35 (m, 2H), 6.45-6.55 (m, 1H), 4.07 (d, J = 17.2 Hz, 1H), 3.71 (d, J = 17.2 Hz, 1H), 2.29 (s, 3H), 1.87 (d, J = 6.6 Hz, 3H). |
| 5-427 | (A) δ 8.40 (s, 1H), 8.07 (s, 1H), 7.2-7.6 (m, 7H), 6.9-7.1 (m, 1H), 4.08 (d, J = 16.5 Hz, 1H), 3.70 (d, J = 16.5 Hz, 1H), 2.44 (s, 3H). |
| 5-428 | (A) δ 7.97 (s, 1H), 7.4-7.65 (m, 6H), 4.54 (q, J = 8.3 Hz, 1H), 4.08 (d, J = 17.3 Hz, 1H), 3.70 (d, J = 17.3 Hz, 1H), 2.49 (s, 3H). |
| 5-434 | (A) δ 7.4-7.85 (m, 11H), 4.09 (d, J = 17.2 Hz, 1H), 3.72 (d, J = 17.2 Hz, 1H), 2.53 (s, 3H). |
| 5-450 | (A) δ 8.52 (d, J = 4.5 Hz, 1H), 7.69 (t, J = 7.8 Hz, 1H), 7.4-7.6 (m, 5H), 7.15-7.35 (m, 4H), 4.73 (d, J = 4.8 Hz, 2H), 4.49 (s, 1H), 3.99 (d, J = 16.8 Hz, 1H), 3.65-3.85 (m, 3H), 3.3-3.65 (m, 1H), 3.33 (d, J = 16.8 Hz, 1H), 2.48 (s, 3H), 1.20 (t, J = 6.9 Hz, 3H), 1.16 (t, J = 6.9 Hz, 3H). |
| 5-452 | (A) δ 8.68 (s, 1H), 8.59 (s, 1H), 8.25 (s, 1H), 7.4-7.6 (m, 3H), 6.06 (t, J = 6.2 Hz, 1H), 4.24 (d, J = 17.1 Hz, 1H), 4.0-4.2 (m, 2H), 3.79 (d, J = 17.1 Hz, 1H), 2.47 (s, 3H). |
| 5-453 | (A) δ 8.69 (s, 1H), 8.58 (s, 1H), 8.55 (d, J = 4.9 Hz, 1H), 8.26 (s, 1H), 7.71 (td, J = 7.5, 1.5 Hz, 1H), 7.2-7.55 (m, 6H), 4.74 (d, J = 4.9 Hz, 2H), 4.25 (d, J = 17.3 Hz, 1H), 3.79 (d, J = 17.3 Hz, 1H), 2.50 (s, 3H). |
| 5-455 | (B) δ 8.54 (ddd, J = 4.9, 1.6, 0.9 Hz, 1H), 7.70 (td, J = 7.7, 1.8 Hz, 1H), 7.5-7.55 (m, 3H), 7.43 (s, 2H), 7.33 (d, J = 7.7 Hz, 1H), 7.2-7.3 (m, 2H), 4.74 (d, J = 4.9 Hz, 2H), 4.63 (bs, 2H), 4.02 (d, J = 17.2 Hz, 1H), 3.69 (d, J = 17.2 Hz, 1H), 2.49 (s, 3H). |

TABLE 21-continued

| No. | ¹H NMR |
|---|---|
| 5-456 | (B) δ 7.61 (s, 2H), 7.45-7.55 (m, 2H), 7.39 (d, J = 7.9 Hz, 1H), 6.28 (t, J = 6.6 Hz, 1H), 6.24 (bs, 1H), 4.0-4.15 (m, 2H), 4.07 (d, J = 17.2 Hz, 1H), 3.69 (d, J = 17.2 Hz, 1H), 2.43 (s, 3H), 1.50 (s, 9H). |
| 5-457 | (B) δ 8.5-8.55 (m, 1H), 7.71 (td, J = 7.7, 1.7 Hz, 1H), 7.62 (s, 2H), 7.45-7.55 (m, 3H), 7.34 (d, J = 7.9 Hz, 1H), 7.29 (t, J = 4.8 Hz, 1H), 7.2-7.25 (m, 1H), 6.37 (bs, 1H), 4.75 (d, J = 5.0 Hz, 2H), 4.07 (d, J = 17.2 Hz, 1H), 3.70 (d, J = 17.2 Hz, 1H), 2.50 (s, 3H), 1.50 (s, 9H). |
| 5-460 | (B) δ 8.77 (d, J = 2.0 Hz, 1H), 7.71 (d, J = 2.2 Hz, 1H), 7.3-7.55 (m, 6H), 6.67 (t, J = 5.5 Hz, 1H), 4.76 (d, J = 5.7 Hz, 2H), 4.07 (d, J = 17.2 Hz, 1H), 3.69 (d, J = 17.2 Hz, 1H), 2.44 (s, 3H). |
| 5-461 | (B) δ 8.5-8.55 (m, 1H), 7.5-7.75 (m, 6H), 7.45 (dd, J = 8.6, 2.0 Hz, 1H), 7.35 (d, J = 7.9 Hz, 1H), 7.29 (t, J = 4.8 Hz, 1H), 7.15-7.3 (m, 1H), 4.75 (d, J = 4.8 Hz, 2H), 4.09 (d, J = 17.2 Hz, 1H), 3.71 (d, J = 17.2 Hz, 1H), 2.72 (s, 3H). |
| 5-462 | (B) δ 7.83 (d, J = 8.1 Hz, 1H), 7.74 (d, J = 1.7 Hz, 1H), 7.62 (dd, J = 8.1, 1.7 Hz, 1H), 7.5-7.55 (m, 2H), 7.44 (t, J = 1.8 Hz, 1H), 6.48 (bs, 2H), 4.08 (d, J = 17.2 Hz, 1H), 3.71 (d, J = 17.2 Hz, 1H). |
| 5-463 | (B) δ 7.45-7.55 (m, 5H), 7.43 (t, J = 1.8 Hz, 1H), 7.27 (t, J = 5.1 Hz, 1H), 7.21 (bs, 1H), 4.27 (d, J = 5.1 Hz, 2H), 4.07 (d, J = 17.2 Hz, 1H), 3.9-4.0 (m, 2H), 3.70 (d, J = 17.2 Hz, 1H). |
| 5-468 | (B) δ 8.16 (d, J = 1.7 Hz, 1H), 7.69 (dd, J = 8.1, 1.7 Hz, 1H), 7.5-7.55 (m, 2H), 7.43 (t, J = 1.8 Hz, 1H), 7.42 (d, J = 8.1 Hz, 1H), 7.21 (t, J = 5.3 Hz, 1H), 7.03 (bs, 1H), 4.24 (d, J = 5.3 Hz, 2H), 4.07 (d, J = 17.2 Hz, 1H), 3.9-4.0 (m, 2H), 3.70 (d, J = 17.2 Hz, 1H). |
| 5-470 | (B) δ 9.22 (bs, 1H), 8.40 (s, 2H), 8.11 (d, J = 1.6 Hz, 1H), 7.74 (dd, J = 8.1, 1.6 Hz, 1H), 7.45-7.55 (m, 3H), 7.44 (t, J = 1.8 Hz, 1H), 4.08 (d, J = 17.2 Hz, 1H), 3.71 (d, J = 17.2 Hz, 1H). |
| 5-471 | (A) δ 7.35-7.6 (m, 6H), 5.87 (bs, 1H), 4.08 (d, J = 17.1 Hz, 1H), 3.69 (d, J = 17.1 Hz, 1H), 3.01 (d, J = 4.8 Hz, 3H), 2.47 (s, 3H). |
| 5-472 | (B) δ 7.5-7.55 (m, 4H), 7.4-7.5 (m, 2H), 5.8-6.15 (m, 1H), 4.08 (d, J = 17.2 Hz, 1H), 3.84 (tdd, J = 15.0, 6.0, 4.2 Hz, 2H), 3.70 (d, J = 17.2 Hz, 1H), 2.48 (s, 3H). |
| 5-473 | (B) δ 7.4-7.55 (m, 6H), 6.42 (bs, 1H), 4.87 (d, J = 6.8 Hz, 2H), 4.09 (d, J = 17.4 Hz, 1H), 3.70 (d, J = 17.4 Hz, 1H), 3.45 (s, 3H), 2.50 (s, 3H). |
| 5-474 | (B) δ 7.4-7.55 (m, 6H), 6.46 (bs, 1H), 4.92 (d, J = 6.8 Hz, 2H), 4.08 (d, J = 17.4 Hz, 1H), 3.6-3.75 (m, 3H), 2.49 (s, 3H), 1.25 (t, J = 6.8 Hz, 3H). |
| 5-475 | (B) δ 7.5-7.55 (m, 4H), 7.4-7.5 (m, 2H), 6.40 (bs, 1H), 4.92 (d, J = 6.8 Hz, 2H), 4.09 (d, J = 17.4 Hz, 1H), 3.70 (d, J = 17.4 Hz, 1H), 3.57 (t, J = 6.6 Hz, 2H), 2.50 (s, 3H), 1.55-1.7 (m, 2H), 0.95 (t, J = 7.4 Hz, 3H). |
| 5-476 | (B) δ 7.4-7.55 (m, 6H), 6.51 (bs, 1H), 4.92 (d, J = 6.6 Hz, 2H), 4.09 (d, J = 17.4 Hz, 1H), 3.90 (sep, J = 6.0 Hz, 1H), 3.71 (d, J = 17.4 Hz, 1H), 2.47 (s, 3H), 1.22 (d, J = 6.0 Hz, 6H). |
| 5-477 | (B) δ 7.4-7.55 (m, 6H), 6.50 (t, J = 7.2 Hz, 1H), 4.98 (d, J = 6.8 Hz, 2H), 4.09 (d, J = 17.4 Hz, 1H), 3.85-3.95 (m, 2H), 3.70 (d, J = 17.4 Hz, 1H), 2.50 (s, 3H), 1.95-2.05 (m, 2H). |
| 5-478 | (B) δ 7.4-7.6 (m, 6H), 6.35-6.55 (m, 1H), 5.75-6.05 (m, 1H), 4.96 (dd, J = 28.0, 7.2 Hz, 2H), 4.09 (d, J = 17.4 Hz, 1H), 3.65-4.2 (m, 3H), 2.50 (s, 3H). |
| 5-479 | (B) δ 7.45-7.55 (m, 6H), 6.56 (t, J = 7.2 Hz, 1H), 5.82 (t, J = 5.6 Hz, 1H), 5.34 (t, J = 5.6 Hz, 1H), 5.03 (d, J = 5.6 Hz, 2H), 4.09 (d, J = 17.4 Hz, 1H), 3.70 (d, J = 17.4 Hz, 1H), 2.51 (s, 3H), 2.30 (t, J = 7.4 Hz, 1H). |
| 5-481 | (B) δ 7.4-7.6 (m, 6H), 6.65 (t, J = 7.2 Hz, 1H), 5.17 (d, J = 5.6 Hz, 2H), 4.37 (s, 2H), 4.09 (d, J = 17.4 Hz, 1H), 3.70 (d, J = 17.4 Hz, 1H), 2.51 (s, 3H). |
| 5-482 | (B) δ 7.4-7.6 (m, 6H), 6.63 (bs, 1H), 4.97 (d, J = 6.4 Hz, 2H), 4.09 (d, J = 17.4 Hz, 1H), 3.25-3.8 (m, 8H), 2.50 (s, 3H). |
| 5-483 | (B) δ 7.4-7.6 (m, 6H), 6.41 (t, J = 7.2 Hz, 1H), 5.85-6.0 (m, 2H), 5.2-5.5 (m, 3H), 4.95 (d, J = 7.2 Hz, 1H), 4.05-4.2 (m, 2H), 3.70 (d, J = 17.4 Hz, 1H), 2.50 (s, 3H). |
| 5-484 | (B) δ 7.4-7.55 (m, 6H), 6.51 (t, J = 7.2 Hz, 1H), 5.01 (d, J = 7.2 Hz, 2H), 4.32 (d, J = 2.4 Hz, 2H), 4.09 (d, J = 17.4 Hz, 1H), 3.70 (t, J = 17.4 Hz, 1H), 2.51 (s, 3H), 2.47 (t, J = 2.4 Hz, 1H). |
| 5-485 | (B) δ 7.25-7.55 (m, 11H), 6.43 (bs, 1H), 5.01 (d, J = 6.8 Hz, 2H), 4.65-4.75 (m, 2H), 4.08 (d, J = 17.4 Hz, 1H), 3.70 (d, J = 17.4 Hz, 1H), 2.50 (s, 3H). |
| 5-486 | (B) δ 7.5-7.55 (m, 4H), 7.4-7.45 (m, 2H), 6.95 (t, J = 7.2 Hz, 1H), 5.41 (d, J = 7.2 Hz, 2H), 4.08 (d, J = 17.4 Hz, 1H), 3.70 (d, J = 17.4 Hz, 1H), 2.48 (s, 3H), 2.12 (s, 3H). |
| 5-487 | (A) δ 7.45-7.55 (m, 4H), 7.4-7.45 (m, 2H), 6.44 (bs, 1H), 5.6-5.7 (m, 1H), 4.0-4.15 (m, 2H), 3.70 (d, J = 17.4 Hz, 1H), 2.48 (s, 3H), 1.45 (d, J = 6.0 Hz, 3H). |

TABLE 21-continued

| No. | ¹H NMR |
|---|---|
| 5-488 | (A) δ 7.4-7.6 (m, 6H), 6.18 (d, J = 9.4 Hz, 1H), 5.6-5.7 (m, 1H), 4.0-4.2 (m, 3H), 3.71 (d, J = 17.4 Hz, 1H), 2.48 (s, 3H), 1.51 (d, J = 6.0 Hz, 3H). |
| 5-490 | (B) δ 7.45-7.55 (m, 5H), 7.43 (t, J = 1.8 Hz, 1H), 6.57 (t, J = 4.8 Hz, 1H), 4.09 (d, J = 17.2 Hz, 1H), 3.71 (d, J = 17.2 Hz, 1H), 3.55-3.7 (m, 10H), 3.45-3.5 (m, 2H), 3.25 (s, 3H), 2.47 (s, 3H). |
| 5-492 | (A) δ 7.45-7.65 (m, 6H), 5.87 (d, J = 8.4 Hz, 1H), 4.4-4.55 (m, 1H), 4.18 (d, J = 6.9 Hz, 2H), 4.08 (d, J = 17.4 Hz, 1H), 3.69 (d, J = 17.4 Hz, 1H), 2.47 (s, 3H), 2.10 (s, 3H), 1.29 (d, J = 6.9 Hz, 3H). |
| 5-493 | (B) δ 7.35-7.55 (m, 6H), 6.21 (d, J = 5.8 Hz, 1H), 5.27 (bs, 1H), 5.10 (bs, 1H), 4.44 (bs, 1H), 4.0-4.25 (m, 3H), 3.5-3.75 (m, 4H), 2.46 (s, 3H), 1.25-1.3 (m, 3H). |
| 5-495 | (A) δ 7.3-7.55 (m, 6H), 6.4-6.5 (m, 1H), 4.55-4.7 (m, 1H), 3.65-4.15 (m, 6H), 2.39 (s, 3H), 2.2-2.45 (m, 1H), 1.8-2.0 (m, 1H). |
| 5-496 | (A) δ 7.4-7.6 (m, 6H), 6.38 (d, J = 9.0 Hz, 1H), 5.2-5.35 (m, 1H), 4.09 (d, J = 17.4 Hz, 1H), 3.95-4.15 (m, 1H), 3.71 (d, J = 17.4 Hz, 1H), 3.6-3.75 (m, 1H), 2.46 (s, 3H), 1.85-2.0 (m, 2H), 1.4-1.75 (m, 4H). |
| 5-497 | (A) δ 7.5-7.6 (m, 4H), 7.4-7.45 (m, 2H), 6.10 (bs, 1H), 4.55 (d, J = 6.8 Hz, 2H), 4.08 (d, J = 17.4 Hz, 1H), 3.70 (d, J = 17.4 Hz, 1H), 2.49 (s, 3H), 2.26 (s, 3H). |
| 5-500 | (B) δ 7.5-7.6 (m, 4H), 7.43 (t, J = 1.8 Hz, 1H), 7.39 (d, J = 7.7 Hz, 1H), 6.70 (t, J = 6.8 Hz, 1H), 4.83 (d, J = 6.8 Hz, 2H), 4.07 (d, J = 17.2 Hz, 1H), 3.69 (d, J = 17.2 Hz, 1H), 2.46 (s, 3H), 2.40 (s, 3H). |
| 5-501 | (B) δ 7.5-7.55 (m, 4H), 7.42 (t, J = 1.8 Hz, 1H), 7.41 (d, J = 8.8 Hz, 1H), 7.20 (t, J = 6.8 Hz, 1H), 5.11 (d, J = 6.8 Hz, 2H), 4.67 (q, J = 7.2 Hz, 2H), 4.09 (d, J = 17.2 Hz, 1H), 3.73 (d, J = 17.2 Hz, 1H), 2.46 (s, 3H), 1.44 (t, J = 7.2 Hz, 3H). |
| 5-502 | (B) δ 7.4-7.55 (m, 6H), 6.6-6.65 (m, 1H), 4.56 (d, J = 6.4 Hz, 2H), 4.08 (d, J = 17.4 Hz, 1H), 3.70 (d, J = 17.4 Hz, 1H), 3.15 (q, J = 7.2 Hz, 6H), 2.51 (s, 3H), 1.37 (t, J = 7.2 Hz, 9H). |
| 5-504 | (B) δ 7.80 (bs, 1H), 7.45-7.55 (m, 3H), 7.43 (t, J = 1.8 Hz, 1H), 7.3-7.4 (m, 4H), 6.95-7.05 (m, 2H), 6.59 (t, J = 5.3 Hz, 1H), 4.05 (d, J = 17.2 Hz, 1H), 3.65-3.75 (m, 2H), 3.68 (d, J = 17.2 Hz, 1H), 3.22 (t, J = 6.4 Hz, 2H), 2.44 (s, 3H). |
| 5-505 | (B) δ 8.47 (d, J = 4.8 Hz, 2H), 7.45-7.55 (m, 4H), 7.43 (t, J = 1.8 Hz, 1H), 7.34 (d, J = 8.4 Hz, 1H), 7.00 (t, J = 4.8 Hz, 1H), 6.85 (t, J = 5.3 Hz, 1H), 4.08 (d, J = 17.2 Hz, 1H), 3.81 (td, J = 6.2, 5.3 Hz, 2H), 3.71 (d, J = 17.2 Hz, 1H), 3.43 (t, J = 6.2 Hz, 2H), 2.44 (s, 3H). |
| 5-506 | (B) δ 8.96 (d, J = 5.0 Hz, 2H), 7.61 (t, J = 5.0 Hz, 1H), 7.45-7.55 (m, 5H), 7.43 (t, J = 1.8 Hz, 1H), 6.75 (t, J = 5.7 Hz, 1H), 4.08 (d, J = 17.2 Hz, 1H), 3.95-4.1 (m, 2H), 3.85-3.95 (m, 2H), 3.70 (d, J = 17.2 Hz, 1H), 2.48 (s, 3H). |
| 5-508 | (B) δ 7.5-7.55 (m, 4H), 7.4-7.45 (m, 2H), 6.24 (bs, 1H), 4.39 (d, J = 6.8 Hz, 2H), 4.08 (d, J = 17.4 Hz, 1H), 3.70 (d, J = 17.4 Hz, 1H), 2.76 (q, J = 7.2 Hz, 2H), 2.49 (s, 3H), 1.15 (t, J = 7.2 Hz, 3H). |
| 5-509 | (A) δ 7.5-7.55 (m, 5H), 7.35-7.5 (m, 2H), 6.37 (bs, 1H), 4.44 (t, J = 6.6 Hz, 2H), 4.09 (d, J = 17.4 Hz, 1H), 3.70 (d, J = 17.4 Hz, 1H), 3.2-3.4 (m, 2H), 2.48 (s, 3H). |
| 5-510 | (B) δ 7.45-7.55 (m, 4H), 7.35-7.45 (m, 2H), 7.04 (bs, 1H), 4.92 (d, J = 6.8 Hz, 2H), 4.44 (q, J = 8.8 Hz, 2H), 4.08 (d, J = 17.4 Hz, 1H), 3.69 (d, J = 17.4 Hz, 1H), 2.46 (s, 3H), 2.18 (s, 3H). |
| 5-511 | (B) δ 7.5-7.55 (m, 4H), 7.35-7.45 (m, 2H), 6.89 (bs, 1H), 4.91 (d, J = 6.8 Hz, 2H), 4.15-4.3 (m, 2H), 4.08 (d, J = 17.4 Hz, 1H), 3.78 (s, 3H), 3.70 (d, J = 17.4 Hz, 1H), 2.18 (s, 3H). |
| 5-521 | (B) δ 7.4-7.55 (m, 6H), 6.70 (bs, 1H), 5.2-5.3 (m, 1H), 4.03 (d, J = 17.4 Hz, 1H), 3.72 (d, J = 17.4 Hz, 1H), 3.5-3.6 (m, 2H), 3.3-3.4 (m, 2H), 3.03 (q, J = 7.4 Hz, 2H), 2.41 (s, 3H), 1.34 (t, J = 7.2 Hz, 3H). |
| 5-522 | (B) δ 7.65 (t, J = 4.0 Hz, 1H), 7.4-7.6 (m, 6H), 6.23 (bs, 1H), 4.40 (q, J = 8.4 Hz, 2H), 4.25-4.3 (m, 2H), 4.09 (d, J = 17.4 Hz, 1H), 3.71 (d, J = 17.4 Hz, 1H), 2.50 (s, 3H). |
| 5-523 | (A) δ 7.3-7.7 (m, 7H), 6.44 (d, J = 7.5 Hz, 1H), 4.75-4.9 (m, 1H), 4.09 (d, J = 17.4 Hz, 1H), 3.84 (s, 3H), 3.71 (d, J = 17.4 Hz, 1H), 2.47 (s, 3H), 1.44 (d, J = 6.9 Hz, 3H). |
| 5-524 | (A) δ 7.4-7.65 (m, 7H), 6.79 (d, J = 7.3 Hz, 1H), 4.8-4.9 (m, 1H), 4.05-4.2 (m, 3H), 3.83 (s, 3H), 3.69 (d, J = 17.4 Hz, 1H), 2.49 (s, 3H). |
| 5-525 | (B) δ 7.35-7.55 (m, 6H), 6.15 (bs, 1H), 4.05-4.2 (m, 3H), 3.70 (d, J = 17.2 Hz, 1H), 3.49 (q, J = 6.4 Hz, 2H), 2.4-2.5 (m, 5H), 1.9-2.0 (m, 2H), 1.2-1.3 (m, 3H). |
| 5-527 | (B) δ 7.45-7.6 (m, 5H), 7.4-7.45 (m, 1H), 7.07 (bs, 1H), 4.05-4.3 (m, 3H), 3.74 (d, J = 17.4 Hz, 1H), 3.35 and 3.47 (q, J = 6.8 Hz, 2H), 2.98 and 3.00 (s, 3H), 2.49 (s, 3H), 1.1-1.3 (m, 3H). |
| 5-528 | (B) δ 7.4-7.6 (m, 6H), 7.04 (bs, 1H), 4.24 (d, J = 4.0 Hz, 2H), 4.10 (d, J = 17.4 Hz, 1H), 3.72 (d, J = 17.4 Hz, 1H), 3.44 (q, J = 6.8 Hz, 2H), 3.33 (q, J = 6.8 Hz, 2H), 2.50 (s, 3H), 1.24 (t, J = 6.8 Hz, 3H), 1.18 (t, J = 6.8 Hz, 3H). |

TABLE 21-continued

| No. | $^1$H NMR |
|---|---|
| 5-532 | (A) δ 7.4-7.55 (m, 5H), 7.2-7.25 (m, 1H), 6.66 (bs, 1H), 6.16 (bs, 1H), 4.53 (t, J = 5.0 Hz, 1H), 4.1-4.15 (m, 3H), 3.65-3.75 (m, 3H), 3.5-3.6 (m, 2H), 3.46 (t, J = 5.0 Hz, 2H), 2.48 (s, 3H), 1.22 (t, J = 6.8 Hz, 6H). |
| 5-538 | (B) δ 7.4-7.55 (m, 6H), 6.63 (d, J = 7.8 Hz, 1H), 6.29 (bs, 1H), 5.62 (bs, 1H), 4.6-4.8 (m, 1H), 4.08 (d, J = 17.4 Hz, 1H), 3.70 (d, J = 17.4 Hz, 1H), 2.46 (s, 3H), 1.51 (d, J = 7.0 Hz, 3H). |
| 5-546 | (A) δ 7.35-7.6 (m, 5H), 7.15-7.3 (m, 1H), 6.95-7.1 (m, 1H), 6.6-6.8 (m, 2H), 5.52 (bs, 1H), 4.44 (bs, 1H), 4.05 (d, J = 17.3 Hz, 1H), 3.75 (s, 3H), 3.65 (d, J = 17.3 Hz, 1H), 2.65-3.2 (m, 4H), 2.39 (s, 3H), 1.2-2.2 (m, 4H). |
| 5-548 | (A) δ 7.85 (bs, 1H), 7.45-7.55 (m, 6H), 7.03 (t, J = 6.6 Hz, 1H), 6.56 (s, 1H), 5.72 (d, J = 6.6 Hz, 2H), 4.07 (d, J = 17.3 Hz, 1H), 3.68 (d, J = 17.3 Hz, 1H), 2.39 (s, 3H). |
| 5-555 | (B) δ 7.4-7.6 (m, 6H), 7.14 (s, 1H), 6.45 (bs, 1H), 4.6-4.7 (m, 2H), 4.08 (d, J = 19.0 Hz, 1H), 3.70 (d, J = 19.0 Hz, 1H), 2.67 (s, 3H), 2.45 (s, 3H). |
| 5-556 | (B) δ 7.67 (s, 1H), 7.4-7.5 (m, 6H), 6.70 (bs, 1H), 4.75-4.8 (m, 2H), 4.08 (d, J = 19.0 Hz, 1H), 3.70 (d, J = 19.0 Hz, 1H), 3.29 (s, 3H), 2.44 (s, 3H). |
| 5-557 | (A) δ 7.4-7.6 (m, 7H), 6.51 (t, J = 6.0 Hz, 1H), 4.77 (dd, J = 6.0, 0.6 Hz, 2H), 4.08 (d, J = 17.2 Hz, 1H), 3.69 (d, J = 17.2 Hz, 1H), 2.45 (s, 3H). |
| 5-558 | (B) δ 8.59 (s, 1H), 7.45-7.55 (m, 5H), 7.43 (t, J = 1.8 Hz, 1H), 6.81 (t, J = 5.5 Hz, 1H), 4.90 (d, J = 5.7 Hz, 2H), 4.09 (d, J = 17.2 Hz, 1H), 3.72 (d, J = 17.2 Hz, 1H), 2.45 (s, 3H). |
| 5-559 | (B) δ 8.0-8.05 (m, 2H), 7.35-7.6 (m, 9H), 6.29 (d, J = 6.8 Hz, 2H), 4.05 (d, J = 17.4 Hz, 1H), 3.67 (d, J = 17.4 Hz, 1H), 2.38 (s, 3H). |
| 5-560 | (A) δ 7.25-7.7 (m, 8H), 6.99 (d, J = 8.6 Hz, 1H), 6.35-6.5 (m, 1H), 6.25 (bs, 1H), 4.06 (d, J = 17.4 Hz, 1H), 3.68 (d, J = 17.4 Hz, 1H), 2.33 (s, 3H), 1.84 (s, 3H). |
| 5-561 | (B) δ 8.75 (bs, 1H), 7.45-7.55 (m, 4H), 7.43 (t, J = 1.8 Hz, 1H), 7.36 (d, J = 8.1 Hz, 1H), 4.08 (d, J = 17.2 Hz, 1H), 3.89 (s, 3H), 3.70 (d, J = 17.2 Hz, 1H), 2.43 (s, 3H). |
| 5-563 | (B) δ 7.5-7.6 (m, 5H), 7.44 (t, J = 1.8 Hz, 1H), 4.09 (d, J = 17.4 Hz, 1H), 3.71 (d, J = 17.4 Hz, 1H), 3.41 (s, 3H), 2.52 (s, 3H). |
| 5-564 | (B) δ 8.74 (s, 1H), 7.45-7.6 (m, 5H), 7.43 (t, J = 1.8 Hz, 1H), 4.09 (d, J = 17.2 Hz, 1H), 3.72 (d, J = 17.2 Hz, 1H), 3.04 (s, 6H), 2.51 (s, 3H). |
| 5-565 | (A) δ 8.23 (bs, 1H), 7.35-7.65 (m, 11H), 4.10 (s, 2H), 4.07 (d, J = 17.4 Hz, 1H), 3.70 (d, J = 17.4 Hz, 1H), 2.46 (s, 3H). |
| 5-572 | (B) δ 8.10 (s, 1H), 7.45-7.6 (m, 5H), 7.43 (d, J = 8.1 Hz, 1H), 5.20 (tqui, J = 20.1, 4.4 Hz, 1H), 4.5-4.75 (m, 4H), 4.09 (d, J = 17.2 Hz, 1H), 3.71 (d, J = 17.2 Hz, 1H), 2.48 (s, 3H). |
| 5-573 | (B) δ 8.15 (bs, 1H), 7.45-7.6 (m, 4H), 7.46 (d, J = 8.4 Hz, 1H), 7.43 (t, J = 1.8 Hz, 1H), 5.05-5.25 (m, 1H), 4.55-4.75 (m, 2H), 4.09 (d, J = 17.2 Hz, 1H), 3.65-3.8 (m, 3H), 2.47 (s, 3H). |
| 5-575 | (B) δ 8.87 (bs, 1H), 7.4-7.55 (m, 6H), 4.08 (d, J = 17.2 Hz, 1H), 3.70 (d, J = 17.2 Hz, 1H), 3.04 (bs, 6H), 2.44 (s, 3H). |
| 5-581 | (A) δ 9.27 (t, J = 5.5 Hz, 1H), 8.74 (s, 1H), 8.59 (d, J = 5.0 Hz, 1H), 7.4-7.7 (m, 7H), 7.15-7.3 (m, 2H), 4.65 (d, J = 5.5 Hz, 2H), 4.08 (d, J = 17.3 Hz, 1H), 3.70 (d, J = 17.3 Hz, 1H), 2.53 (s, 3H). |
| 5-583 | (B) δ 8.47 (bs, 1H), 7.4-7.55 (m, 6H), 4.08 (d, J = 17.2 Hz, 1H), 3.70 (d, J = 17.2 Hz, 1H), 3.4-3.55 (m, 4H), 2.44 (s, 3H), 1.9-2.05 (m, 4H). |
| 5-585 | (A) δ 7.3-7.7 (m, 11H), 7.18 (t, J = 7.2 Hz, 1H), 4.10 (d, J = 17.4 Hz, 1H), 3.72 (d, J = 17.4 Hz, 1H), 2.54 (s, 3H). |
| 5-588 | (A) δ 7.5-7.65 (m, 7H), 7.4-7.45 (m, 2H), 7.08 (t, J = 8.4 Hz, 2H), 4.10 (d, J = 17.3 Hz, 1H), 3.72 (d, J = 17.3 Hz, 1H), 2.53 (s, 3H). |
| 5-591 | (A) δ 8.20 (bs, 1H), 7.85 (s, 1H), 7.4-7.6 (m, 6H), 6.9-7.25 (m, 4H), 4.10 (d, J = 17.0 Hz, 1H), 3.72 (d, J = 17.0 Hz, 1H), 2.55 (s, 3H). |
| 5-601 | (A) δ 8.04 (s, 1H), 7.81 (d, J = 6.9 Hz, 1H), 7.4-7.65 (m, 9H), 4.10 (d, J = 17.1 Hz, 1H), 3.72 (d, J = 17.1 Hz, 1H), 2.54 (s, 3H). |
| 5-603 | (A) δ 8.77 (d, J = 7.4 Hz, 1H), 7.4-7.7 (m, 9H), 7.14 (t, J = 7.4 Hz, 1H), 6.05 (d, J = 6.9 Hz, 1H), 4.15-4.3 (m, 1H), 4.10 (d, J = 17.3 Hz, 1H), 3.71 (d, J = 17.3 Hz, 1H), 2.58 (s, 3H), 1.25 (d, J = 6.9 Hz, 6H). |
| 5-604 | (A) δ 7.4-7.6 (m, 7H), 6.85-7.0 (m, 2H), 6.65-6.85 (m, 1H), 4.11 (d, J = 17.1 Hz, 1H), 3.72 (d, J = 17.1 Hz, 1H), 2.55 (s, 3H). |
| 5-605 | (A) δ 8.25-8.4 (m, 1H), 7.7-7.75 (m, 1H), 7.55-7.6 (m, 3H), 7.5-7.55 (m, 2H), 7.4-7.45 (m, 1H), 7.05-7.15 (m, 1H), 6.7-6.85 (m, 1H), 4.10 (d, J = 17.4 Hz, 1H), 3.72 (d, J = 17.4 Hz, 1H), 2.55 (s, 3H). |
| 5-609 | (A) δ 7.89 (s, 1H), 7.2-7.7 (m, 9H), 4.10 (d, J = 17.1 Hz, 1H), 3.71 (d, J = 17.1 Hz, 1H), 2.53 (s, 3H). |
| 5-610 | (A) δ 7.45-7.65 (m, 8H), 7.44 (s, 1H), 7.17 (s, 1H), 4.10 (d, J = 17.4 Hz, 1H), 3.72 (d, J = 17.4 Hz, 1H), 2.52 (s, 3H). |
| 5-611 | (A) δ 8.36 (dd, J = 6.3, 2.7 Hz, 1H), 7.9-8.05 (m, 1H), 7.80 (s, 1H), 7.4-7.6 (m, 6H), 7.32 (t, J = 9.0 Hz, 1H), 4.11 (d, J = 17.3 Hz, 1H), 3.73 (d, J = 17.3 Hz, 1H), 2.52 (s, 3H). |

TABLE 21-continued

| No. | ¹H NMR |
|---|---|
| 5-612 | (A) δ 7.5-7.7 (m, 5H), 7.44 (t, J = 2.0 Hz, 1H), 7.03 (bs, 1H), 6.80 (t, J = 7.2 Hz, 2H), 4.11 (d, J = 17.4 Hz, 1H), 3.72 (d, J = 17.4 Hz, 1H), 2.54 (s, 3H). |
| 5-615 | (A) δ 8.41 (bs, 1H), 7.4-7.65 (m, 6H), 6.74 (bs, 2H), 6.23 (bs, 2H), 4.09 (d, J = 17.0 Hz, 1H), 3.73 (d, J = 17.0 Hz, 1H), 2.53 (s, 3H). |
| 5-617 | (A) δ 7.4-7.75 (m, 9H), 6.38 (bs, 1H), 4.08 (d, J = 17.3 Hz, 1H), 3.70 (d, J = 17.3 Hz, 1H), 2.53 (s, 3H). |
| 5-618 | (A) δ 9.23 (bs, 1H), 7.4-7.7 (m, 8H), 4.10 (d, J = 17.3 Hz, 1H), 3.72 (d, J = 17.4 Hz, 1H), 2.53 (s, 3H). |
| 5-619 | (B) δ 9.32 (bs, 1H), 7.45-7.7 (m, 7H), 4.11 (d, J = 17.2 Hz, 1H), 3.73 (d, J = 17.2 Hz, 1H), 2.60 (s, 3H). |
| 5-621 | (B) δ 7.4-7.55 (m, 6H), 6.80 (bs, 1H), 4.56 (d, J = 6.4 Hz, 2H), 4.09 (d, J = 17.0 Hz, 1H), 3.71 (d, J = 17.0 Hz, 1H), 3.16 (q, J = 7.2 Hz, 6H), 2.51 (s, 3H), 1.37 (t, J = 7.2 Hz, 9H). |
| 5-629 | (A) δ 8.4-8.6 (m, 3H), 7.95-8.1 (m, 1H), 7.61 (s, 3H), 7.4-7.55 (m, 3H), 4.12 (d, J = 17.1 Hz, 1H), 3.73 (d, J = 17.1 Hz, 1H), 2.56 (s, 3H). |
| 5-630 | (A) δ 8.29 (d, J = 7.8 Hz, 1H), 8.23 (s, 1H), 7.74 (t, J = 7.8 Hz, 1H), 7.5-7.6 (m, 6H), 7.13 (d, J = 7.2 Hz, 1H), 4.11 (d, J = 17.1 Hz, 1H), 3.73 (d, J = 17.1 Hz, 1H), 2.55 (s, 3H). |
| 5-631 | (A) δ 8.32 (d, J = 8.1 Hz, 1H), 8.21 (s, 1H), 7.2-7.7 (m, 8H), 4.11 (d, J = 17.4 Hz, 1H), 3.73 (d, J = 17.4 Hz, 1H), 2.55 (s, 3H). |
| 5-633 | (A) δ 8.46 (s, 1H), 8.27 (d, J = 7.1 Hz, 1H), 7.76 (s, 1H), 7.3-7.6 (m, 7H), 4.10 (d, J = 17.0 Hz, 1H), 3.72 (d, J = 17.0 Hz, 1H), 2.52 (s, 3H). |
| 5-634 | (A) δ 8.72 (d, J = 2.4 Hz, 1H), 8.52 (dd, J = 8.4, 2.4 Hz, 1H), 7.99 (s, 1H), 7.73 (d, J = 8.4 Hz, 1H), 7.4-7.65 (m, 6H), 4.11 (d, J = 17.3 Hz, 1H), 3.73 (d, J = 17.3 Hz, 1H), 2.54 (s, 3H). |
| 5-635 | (A) δ 8.31 (d, J = 5.4 Hz, 1H), 7.81 (s, 1H), 7.75-7.8 (m, 1H), 7.4-7.6 (m, 7H), 4.10 (d, J = 17.4 Hz, 1H), 3.72 (d, J = 17.4 Hz, 1H), 2.53 (s, 3H). |
| 5-637 | (A) δ 8.82 (s, 1H), 8.41 (d, J = 4.8 Hz, 1H), 7.4-7.6 (m, 6H), 6.90 (d, J = 4.8 Hz, 1H), 4.11 (d, J = 17.4 Hz, 1H), 3.73 (d, J = 17.4 Hz, 1H), 2.53 (s, 3H), 2.45 (s, 3H). |
| 5-647 | (B) δ 7.4-7.55 (m, 4H), 7.37 (d, J = 7.9 Hz, 1H), 6.37 (t, J = 6.0 Hz, 1H), 4.0-4.15 (m, 2H), 4.06 (d, J = 17.2 Hz, 1H), 3.70 (d, J = 17.2 Hz, 1H), 2.48 (s, 3H), 2.41 (s, 3H). |
| 5-648 | (B) δ 8.5-8.6 (m, 1H), 7.71 (td, J = 7.7, 1.8 Hz, 1H), 7.45-7.6 (m, 6H), 7.38 (d, J = 7.9 Hz, 1H), 7.2-7.3 (m, 1H), 4.73 (d, J = 5.1 Hz, 2H), 4.07 (d, J = 17.2 Hz, 1H), 3.71 (d, J = 17.2 Hz, 1H), 2.71 (s, 3H), 2.47 (s, 3H). |
| 5-649 | (B) δ 8.55-8.65 (m, 1H), 7.84 (td, J = 7.7, 1.7 Hz, 1H), 7.3-7.8 (m, 8H), 4.78 (d, J = 5.1 Hz, 2H), 4.05 (d, J = 17.2 Hz, 1H), 3.71 (d, J = 17.2 Hz, 1H), 3.56 (bs, 1H), 2.49 (s, 3H). |
| 5-651 | (B) δ 8.5-8.55 (m, 1H), 7.71 (td, J = 7.8, 1.8 Hz, 1H), 7.5-7.6 (m, 5H), 7.34 (d, J = 7.9 Hz, 1H), 7.2-7.3 (m, 2H), 4.75 (d, J = 4.8 Hz, 2H), 4.05 (d, J = 17.2 Hz, 1H), 3.92 (s, 3H), 3.71 (d, J = 17.2 Hz, 1H), 2.49 (s, 3H). |
| 5-652 | (B) δ 8.5-8.6 (m, 1H), 7.92 (td, J = 7.7, 1.8 Hz, 1H), 7.45-7.7 (m, 6H), 7.39 (d, J = 7.7 Hz, 1H), 7.15-7.3 (m, 1H), 4.71 (d, J = 5.3 Hz, 2H), 4.08 (d, J = 17.2 Hz, 1H), 3.73 (d, J = 17.2 Hz, 1H), 2.46 (s, 3H), 1.57 (s, 9H). |
| 5-653 | (B) δ 7.4-7.55 (m, 4H), 7.39 (d, J = 7.9 Hz, 1H), 6.37 (t, J = 5.9 Hz, 1H), 4.0-4.15 (m, 2H), 4.05 (d, J = 17.2 Hz, 1H), 3.69 (d, J = 17.2 Hz, 1H), 2.90 (s, 6H), 2.42 (s, 3H). |
| 5-654 | (B) δ 8.5-8.6 (m, 1H), 7.71 (td, J = 7.7, 1.8 Hz, 1H), 7.45-7.55 (m, 5H), 7.41 (t, J = 4.8 Hz, 1H), 7.36 (d, J = 7.7 Hz, 1H), 7.2-7.3 (m, 1H), 4.73 (d, J = 5.0 Hz, 2H), 4.05 (d, J = 17.2 Hz, 1H), 3.70 (d, J = 17.2 Hz, 1H), 2.90 (s, 6H), 2.48 (s, 3H). |
| 5-655 | (A) δ 8.12 (s, 1H), 7.7-7.75 (m, 1H), 7.4-7.5 (m, 4H), 6.73 (bs, 1H), 5.03 (d, J = 6.8 Hz, 2H), 4.13 (q, J = 8.4 Hz, 2H), 4.07 (d, J = 17.4 Hz, 1H), 3.69 (d, J = 17.4 Hz, 1H). |
| 5-656 | (A) δ 8.09 (bs, 1H), 7.35-7.75 (m, 5H), 6.27 (bs, 1H), 5.8-5.9 (m, 1H), 3.8-4.2 (m, 3H), 3.69 (d, J = 17.4 Hz, 1H), 2.2-2.35 (m, 1H), 1.9-2.1 (m, 3H). |
| 5-657 | (B) δ 8.37 (d, J = 1.7 Hz, 1H), 7.83 (dd, J = 8.1, 1.8 Hz, 1H), 7.51 (bs, 2H), 7.45 (t, J = 1.8 Hz, 1H), 7.43 (d, J = 8.1 Hz, 1H), 7.35 (bs, 1H), 6.99 (bs, 1H), 4.23 (d, J = 17.8 Hz, 1H), 4.22 (d, J = 5.1 Hz, 2H), 3.9-4.05 (m, 2H), 3.84 (d, J = 17.8 Hz, 1H). |
| 5-658 | (A) δ 7.4-7.6 (m, 6H), 5.9-6.0 (m, 2H), 4.9-5.0 (m, 1H), 4.11 (d, J = 17.4 Hz, 1H), 3.73 (d, J = 17.4 Hz, 1H), 3.53 (s, 3H), 2.33 (s, 3H), 2.1-2.45 (m, 3H), 1.95-2.05 (m, 1H), 1.6-1.8 (m, 2H). |
| 5-662 | (A) δ 8.41 (s, 1H), 7.4-7.55 (m, 6H), 5.67 (t, J = 6.3 Hz, 1H), 4.12 (d, J = 17.4 Hz, 1H), 3.7-3.9 (m, 2H), 3.72 (d, J = 17.4 Hz, 1H), 3.19 (s, 3H), 2.47 (s, 3H). |
| 5-667 | (A) δ 8.78 (bs, 1H), 7.75 (s, 1H), 7.45-7.6 (m, 5H), 7.43 (t, J = 1.5 Hz, 1H), 4.10 (d, J = 17.4 Hz, 1H), 3.73 (d, J = 17.4 Hz, 1H), 2.51 (s, 3H). |

TABLE 21-continued

| No. | $^1$H NMR |
|---|---|
| 5-668 | (A) δ 8.38 (dd, J = 4.8, 1.5 Hz, 1H), 8.04 (s, 1H), 7.77 (dd, J = 7.8, 1.5 Hz, 1H), 7.65-7.65 (m, 5H), 7.57 (t, J = 1.8 Hz, 1H), 7.12 (dd, J = 7.8, 4.8 Hz, 1H), 4.10 (d, J = 17.1 Hz, 1H), 3.71 (d, J = 17.1 Hz, 1H), 2.58 (s, 3H). |
| 5-669 | (A) δ 7.88 (d, J = 8.0 Hz, 1H), 7.74 (s, 1H), 7.64 (d, J = 8.0 Hz, 1H), 7.52 (d, J = 1.5 Hz, 2H), 7.44 (t, J = 1.5 Hz, 1H), 6.38 (bs, 1H), 6.02 (bs, 1H), 4.09 (d, J = 17.4 Hz, 1H), 3.67 (d, J = 17.4 Hz, 1H). |
| 5-670 | (A) δ 7.66 (bs, 1H), 7.5-7.6 (m, 5H), 5.74 (bs, 2H), 4.08 (d, J = 17.4 Hz, 1H), 3.68 (d, J = 17.4 Hz, 1H), 2.53 (s, 3H). |
| 5-672 | (A) δ 8.09 (s, 2H), 7.97 (s, 1H), 7.5-7.6 (m, 3H), 5.79 (bs, 2H), 4.21 (d, J = 17.4 Hz, 1H), 3.76 (d, J = 17.4 Hz, 1H), 2.53 (s, 3H). |
| 5-677 | (A) δ 7.4-7.6 (m, 6H), 5.70 (bs, 2H), 4.09 (d, J = 17.4 Hz, 1H), 3.70 (d, J = 17.4 Hz, 1H), 2.88 (q, J = 7.8 Hz, 2H), 1.26 (t, J = 7.8 Hz, 3H). |
| 5-679 | (A) δ 7.35-8.25 (m, 6H), 6.97 (bs, 1H), 6.70 (t, J = 72.3 Hz, 1H), 6.27 (bs, 1H), 4.10 (d, J = 17.1 Hz, 1H), 3.72 (d, J = 17.1 Hz, 1H). |
| 5-680 | (A) δ 7.45-8.0 (m, 6H), 6.80 (bs, 2H), 4.10 (d, J = 17.4 Hz, 1H), 3.20 (d, J = 17.4 Hz, 1H). |
| 5-682 | (A) δ 11.3 (s, 1H), 7.4-8.85 (m, 8H), 4.15 (d, J = 17.4 Hz, 1H), 3.75 (d, J = 17.4 Hz, 1H), 2.05 (s, 3H). |
| 5-684 | (A) δ 7.81 (s, 1H), 7.75 (s, 1H), 7.69 (s, 1H), 7.5-7.55 (m, 2H), 7.43 (d, J = 8.1 Hz, 1H), 6.06 (t, J = 6.6 Hz, 1H), 4.05-4.2 (m, 3H), 3.72 (d, J = 17.4 Hz, 1H), 2.46 (s, 3H). |
| 5-685 | (A) δ 6.58 (d, J = 6.3 Hz, 2H), 7.5-7.55 (m, 2H), 7.43 (d, J = 8.1 Hz, 1H), 6.05 (t, J = 6.6 Hz, 1H), 4.05-4.2 (m, 3H), 3.68 (d, J = 17.4 Hz, 1H), 2.45 (s, 3H). |
| 5-686 | (A) δ 7.90 (dd, J = 6.3, 2.1 Hz, 1H), 7.75 (d, J = 5.7 Hz, 1H), 7.5-7.55 (m, 2H), 7.43 (d, J = 8.1 Hz, 1H), 6.06 (t, J = 6.6 Hz, 1H), 4.05-4.2 (m, 3H), 3.70 (d, J = 17.4 Hz, 1H), 2.44 (s, 3H). |
| 6-001 | (A) δ 7.4-7.55 (m, 6H), 6.06 (bs, 1H), 5.39 (d, J = 28.6 Hz, 2H), 4.24 (d, J = 6.0 Hz, 2H), 4.05 (d, J = 17.0 Hz, 1H), 3.67 (d, J = 17.3 Hz, 1H), 2.49 (s, 3H). |
| 6-003 | (A) δ 7.45-7.55 (m, 4H), 7.43 (s, 1H), 7.23 (d, J = 7.8 Hz, 1H), 4.09 (d, J = 17.1 Hz, 1H), 3.71 (d, J = 17.1 Hz, 1H), 3.43 (bs, 2H), 3.10 (bs, 2H), 2.32 (s, 3H), 1.26 (t, J = 6.9 Hz, 3H), 1.03 (t, J = 6.9 Hz, 3H). |
| 6-005 | (B) δ 7.98 (m, 1H), 7.2-7.6 (m, 6H), 4.09 (d, J = 17.0 Hz, 1H), 3.18 (bs, 1H), 3.71 (d, J = 17.0 Hz, 1H), 3.40 (bs, 1H), 2.43 and 2.33 (s, 3H), 2.12 and 1.66 (s, 3H), 1.23 and 1.08 (bs, 3H). |
| 6-006 | (B) δ 7.2-7.6 (m, 6H), 4.05-4.15 (m, 1H), 3.75-3.9 and 3.35-3.5 (m, 2H), 3.7 and 3.8 (m, 1H), 2.41 and 2.38 (s, 3H), 2.23 and 1.80 (s, 3H), 2.00 and 1.77 (s, 3H), 1.25-1.3 and 1.05-1.1 (m, 3H). |
| 6-007 | (B) δ 7.5-7.6 (m, 4H), 7.4-7.45 (m, 1H), 7.2-7.25 (m, 1H), 3.2-4.7 (m, 4H), 4.10 (d, J = 17.0 Hz, 1H), 3.72 (d, J = 17.0 Hz, 1H), 2.35 and 2.33 (s, 3H), 1.65-1.8 and 1.5-1.6 (m, 2H), 1.4-1.5 and 1.1-1.25 (m, 2H), 1.0-1.05 and 0.75-0.85 (m, 3H). |
| 6-008 | (B) δ 7.6-7.65 (m, 2H), 7.5-7.55 (m, 2H), 7.4-7.45 (m, 1H), 7.3-7.35 (m, 1H), 4.65 (bs, 2H), 4.19 (bs, 2H), 4.09 (d, J = 17.0 Hz, 1H), 3.71 (d, J = 17.0 Hz, 1H), 2.37 (s, 3H). |
| 6-010 | (B) δ 7.5-7.55 (m, 4H), 7.3-7.5 (m, 7H), 4.85 (bs, 2H), 4.08 (d, J = 17.0 Hz, 1H), 3.69 (d, J = 17.0 Hz, 1H), 3.35 (bs, 3H), 2.27 (s, 3H). |
| 6-011 | (B) δ 7.4-7.55 (m, 5H), 7.25-7.4 (m, 6H), 4.90 (bs, 2H), 4.07 (d, J = 17.0 Hz, 1H), 3.68 (d, J = 17.0 Hz, 1H), 2.40 (s, 3H), 1.88 (bs, 3H). |
| 6-012 | (B) δ 7.4-7.55 (m, 5H), 7.25-7.4 (m, 6H), 4.43 (bs, 2H), 4.07 (d, J = 17.0 Hz, 1H), 3.78 (bs, 3H), 3.68 (d, J = 17.0 Hz, 1H), 2.38 (s, 3H). |
| 6-013 | (B) δ 7.5-7.6 (m, 4H), 7.4-7.45 (m, 1H), 7.3-7.4 (m, 4H), 7.15-7.25 (m, 2H), 4.93 (bs, 2H), 4.08 (d, J = 17.0 Hz, 1H), 3.69 (d, J = 17.0 Hz, 1H), 3.05 (bs, 3H), 2.28 (s, 3H). |
| 6-015 | (A) δ 8.82 (s, 1H), 7.35-7.6 (m, 6H), 7.08 (s, 1H), 4.75-5.2 (m, 2H), 4.56 (bs, 2H), 4.08 (d, J = 17.4 Hz, 1H), 3.79 (d, J = 17.4 Hz, 1H), 2.36 and 2.29 (s, 3H). |
| 6-016 | (A) δ 8.80 and 8.77 (d, J = 7.8 Hz, 1H), 7.45-7.55 (m, 4H), 7.3-7.45 (m, 3H), 4.85-5.2 (m, 1H), 4.2-4.7 (m, 2H), 4.07 and 4.08 (d, J = 17.4 Hz, 1H), 3.75-4.0 (m, 1H), 3.69 (d, J = 17.4 Hz, 1H), 2.31 and 2.36 (s, 3H), 2.25-2.3 (m, 1H). |
| 6-017 | (B) δ 8.72 (s, 1H), 7.5-7.6 (m, 4H), 7.48 (s, 1H), 7.4-7.45 (m, 1H), 7.18 (s, 1H), 5.03 (s, 2H), 4.07 (d, J = 17.0 Hz, 1H), 3.68 (d, J = 17.0 Hz, 1H), 2.41 (s, 3H), 2.35 (s, 3H). |
| 6-018 | (A) δ 8.72 (s, 1H), 7.45-7.55 (m, 4H), 7.4-7.45 (m, 1H), 7.31 (d, J = 7.8 Hz, 1H), 7.20 (s, 1H), 5.04 (s, 2H), 4.07 (d, J = 17.4 Hz, 1H), 3.68 (d, J = 17.4 Hz, 1H), 2.75 (q, J = 7.2 Hz, 2H), 2.34 (s, 3H), 1.12 (t, J = 7.2 Hz, 3H). |
| 6-019 | (B) δ 8.80 (s, 1H), 7.55-7.6 (m, 4H), 7.42 (s, 1H), 7.25-7.3 (m, 2H), 5.26 (s, 2H), 4.07 (d, J = 17.0 Hz, 1H), 3.68 (d, J = 17.0 Hz, 1H), 3.62 (s, 3H), 2.33 (s, 3H). |

TABLE 21-continued

| No. | ¹H NMR |
|---|---|
| 6-021 | (B) δ 8.5-8.6 (m, 1H), 7.65-7.75 (m, 1H), 7.4-7.6 (m, 5H), 7.1-7.35 (m, 3H), 3.0-5.3 (m, 4H), 4.0-4.15 (m, 1H), 3.65-3.8 (m, 1H), 2.37 and 2.34 (s, 3H), 1.25-1.35 and 1.0-1.1 (m, 3H). |
| 6-022 | (B) δ 8.55-8.6 (m, 1H), 7.65-7.75 (m, 1H), 7.05-7.55 (m, 8H), 4.3-5.3 (m, 2H), 4.0-4.15 (m, 1H), 2.9-4.1 (m, 2H), 3.65-3.75 (m, 1H), 2.37 and 2.32 (s, 3H), 1.65-1.75 and 1.45-1.55 (m, 2H), 0.95-1.0 and 0.65-0.75 (m, 3H). |
| 6-023 | (B) δ 8.55-8.6 and 8.45-8.5 (m, 1H), 7.4-7.7 (m, 7H), 7.25-7.35 (m, 1H), 7.1-7.2 (m, 1H), 4.90 (d, J = 16.0 Hz, 1H), 4.76 (d, J = 16.0 Hz, 1H), 4.0-4.15 (m, 1H), 3.6-3.85 (m, 2H), 2.42 and 2.34 (s, 3H), 1.23 and 1.06 (bs, 6H). |
| 6-024 | (B) δ 8.5-8.6 (m, 1H), 7.05-7.7 (m, 9H), 4.83 and 4.39 (s, 2H), 4.0-4.15 (m, 1H), 3.65-3.8 (m, 1H), 2.75-2.85 and 2.65-2.7 (m, 1H), 2.36 and 2.33 (s, 3H), 0.75-0.9 and 0.45-0.6 (m, 4H). |
| 6-025 | (B) δ 8.5-8.55 (m, 1H), 7.65-7.7 (m, 1H), 7.15-7.5 (m, 8H), 4.45 and 4.16 (bs, 2H), 4.02 (d, J = 17.0 Hz, 1H), 3.63 (d, J = 17.0 Hz, 1H), 2.38 (s, 3H), 1.54 (s, 9H). |
| 6-026 | (B) δ 8.55-8.6 (m, 1H), 7.2-7.75 (m, 8H), 6.92 (d, J = 7.7 Hz, 1H), 3.7-5.25 (br, 4H), 4.1-4.15 (m, 1H), 3.65-3.7 (m, 1H), 2.04 and 2.26 (s, 3H). |
| 6-027 | (A) δ 8.55 (bs, 1H), 6.95-7.75 (m, 9H), 5.07 and 4.93 (bs, 2H), 4.53 and 4.48 (bs, 2H), 4.09 and 4.05 (d, J = 17.1 Hz, 1H), 3.70 and 3.66 (d, J = 17.4 Hz, 1H), 3.47 and 3.14 (s, 3H), 2.38 and 2.33 (s, 3H). |
| 6-028 | (B) δ 8.5-8.6 (m, 1H), 7.6-7.75 (m, 1H), 7.05-7.55 (m, 8H), 3.25-5.2 (m, 8H), 3.37 and 3.17 (s, 3H), 2.28 and 2.34 (s, 3H). |
| 6-029 | (A) δ 8.5-8.6 (m, 1H), 6.95-7.75 (m, 9H), 4.98 (bs, 2H), 4.58 and 4.37 (bs, 2H), 4.09 and 4.05 (d, J = 17.2 Hz, 1H), 3.70 and 3.67 (d, J = 17.2 Hz, 1H), 2.38 and 2.31 (s, 3H), 2.29 and 1.99 (s, 3H). |
| 6-030 | (B) δ 8.5-8.65 (m, 1H), 7.15-7.8 (m, 8H), 7.0-7.05 (m, 1H), 3.5-5.3 (m, 6H), 3.77 and 3.65 (s, 3H), 2.45 and 2.32 (s, 3H). |
| 6-031 | (B) δ 8.5-8.65 (m, 1H), 7.2-7.8 (m, 8H), 6.9-7.0 (m, 1H), 4.0-5.2 (m, 5H), 3.6-3.8 (m, 1H), 2.35 (s, 3H). |
| 6-032 | (B) δ 8.5-8.65 (m, 1H), 7.0-7.8 (m, 9H), 5.8-6.0 and 5.55-5.75 (m, 1H), 3.6-5.55 (m, 8H), 2.37 and 2.34 (s, 3H). |
| 6-033 | (B) δ 8.5-8.65 (m, 1H), 7.05-7.75 (m, 9H), 3.5-5.3 (m, 6H), 2.37 (s, 3H), 2.28 (s, 1H). |
| 6-034 | (B) δ 8.45-8.5 (m, 1H), 7.6-7.65 (m, 1H), 7.4-7.55 (m, 6H), 7.15-7.2 (m, 2H), 4.98 (s, 2H), 4.06 (d, J = 17.0 Hz, 1H), 3.68 (d, J = 17.0 Hz, 1H), 2.41 (s, 3H), 2.39 (s, 3H). |
| 6-035 | (A) δ 8.45-8.55 (m, 1H), 7.6-7.7 (m, 1H), 7.35-7.55 (m, 6H), 7.1-7.25 (m, 2H), 4.99 (s, 2H), 4.06 (d, J = 19.0 Hz, 1H), 3.67 (d, J = 19.0 Hz, 1H), 2.74 (q, J = 8.2 Hz, 2H), 2.39 (s, 3H), 1.11 (t, J = 8.2 Hz, 3H). |
| 6-036 | (A) δ 8.49 (d, J = 4.8 Hz, 1H), 7.63 (td, J = 7.8, 1.8 Hz, 1H), 7.35-7.55 (m, 6H), 7.1-7.2 (m, 2H), 4.98 (s, 2H), 4.06 (d, J = 17.4 Hz, 1H), 3.67 (d, J = 17.4 Hz, 1H), 2.70 (t, J = 7.2 Hz, 2H), 1.64 (hex, J = 7.2 Hz, 2H), 1.55 (s, 3H), 0.89 (t, J = 7.2 Hz, 3H). |
| 6-037 | (A) δ 8.49 (d, J = 5.1 Hz, 1H), 7.63 (td, J = 7.8, 1.8 Hz, 1H), 7.35-7.55 (m, 6H), 7.1-7.25 (m, 2H), 4.99 (s, 2H), 4.06 (d, J = 17.4 Hz, 1H), 3.77 (d, J = 17.4 Hz, 1H), 3.1-3.3 (m, 1H), 2.42 (s, 3H), 1.13 (d, J = 6.6 Hz, 6H). |
| 6-038 | (A) δ 8.53 (d, J = 4.8 Hz, 1H), 7.64 (td, J = 7.8, 1.8 Hz, 1H), 7.45-7.55 (m, 5H), 7.4-7.45 (m, 1H), 7.15-7.3 (m, 2H), 5.16 (s, 2H), 4.08 (d, J = 17.4 Hz, 1H), 3.68 (d, J = 17.4 Hz, 1H), 2.45 (s, 3H), 1.9-2.0 (m, 1H), 0.95-1.05 (m, 2H), 0.7-0.8 (m, 2H). |
| 6-039 | (A) δ 8.50 (d, J = 5.2 Hz, 1H), 7.55-7.65 (m, 1H), 7.4-7.55 (m, 6H), 7.1-7.2 (m, 2H), 4.86 (s, 2H), 4.06 (d, J = 19.0 Hz, 1H), 3.68 (d, J = 19.0 Hz, 1H), 2.44 (s, 3H), 1.34 (s, 9H). |
| 6-041 | (B) δ 8.5-8.55 (m, 1H), 7.6-7.7 (m, 1H), 7.4-7.55 (m, 6H), 7.27 (s, 1H), 7.15-7.2 (m, 1H), 6.47 (dd, J = 16.0, 10.0 Hz, 1H), 6.30 (d, J = 16.0 Hz, 1H), 5.62 (d, J = 10.0 Hz, 1H), 5.10 (s, 2H), 4.07 (d, J = 17.0 Hz, 1H), 3.69 (d, J = 17.0 Hz, 1H), 2.44 (s, 3H). |
| 6-042 | (A) δ 8.54 (d, J = 0.9 Hz, 1H), 8.09 (d, J = 7.6 Hz, 1H), 7.15-7.75 (m, 13H), 5.32 (s, 2H), 3.95 (d, J = 19.0 Hz, 1H), 3.58 (d, J = 19.0 Hz, 1H), 2.34 (s, 3H). |
| 6-043 | (A) δ 8.56 (d, J = 4.8 Hz, 1H), 7.65-7.7 (m, 1H), 7.5-7.55 (m, 4H), 7.35-7.45 (m, 2H), 7.15-7.3 (m, 2H), 5.21 (s, 2H), 4.09 (d, J = 17.4 Hz, 1H), 3.70 (d, J = 17.4 Hz, 1H), 3.58 (s, 3H), 2.40 (s, 3H). |
| 6-044 | (A) δ 8.56 (d, J = 3.9 Hz, 1H), 7.65 (td, J = 7.8, 1.8 Hz, 1H), 7.35-7.55 (m, 6H), 7.15-7.3 (m, 2H), 5.21 (s, 2H), 4.09 (d, J = 17.4 Hz, 1H), 4.00 (q, J = 7.2 Hz, 2H), 3.69 (d, J = 17.4 Hz, 1H), 2.41 (s, 3H), 0.92 (t, J = 7.2 Hz, 3H). |

TABLE 21-continued

| No. | ¹H NMR |
|---|---|
| 6-045 | (A) δ 8.55 (d, J = 4.8 Hz, 1H), 7.67 (td, J = 7.8, 1.8 Hz, 1H), 7.45-7.55 (m, 4H), 7.35-7.45 (m, 2H), 7.15-7.3 (m, 2H), 5.20 (s, 2H), 4.7-4.85 (m, 1H), 4.08 (d, J = 17.4 Hz, 1H), 3.69 (d, J = 17.4 Hz, 1H), 2.54 (s, 3H), 0.91 (d, J = 6.3 Hz, 6H). |
| 6-046 | (B) δ 8.5-8.6 (m, 1H), 7.65-7.7 (m, 1H), 7.5-7.55 (m, 4H), 7.4-7.45 (m, 2H), 7.25-7.3 (m, 1H), 7.15-7.2 (m, 1H), 5.23 (s, 2H), 4.17 (d, J = 17.0 Hz, 1H), 3.75 (d, J = 6.8 Hz, 1H), 3.69 (d, J = 17.0 Hz, 1H), 2.42 (s, 3H), 1.55-1.65 (m, 1H), 0.64 (d, J = 6.8 Hz, 6H). |
| 6-047 | (B) δ 8.5-8.6 (m, 1H), 7.65-7.7 (m, 1H), 7.5-7.55 (m, 4H), 7.4-7.45 (m, 2H), 7.25-7.3 (m, 1H), 7.15-7.25 (m, 1H), 5.23 (s, 2H), 4.15-4.25 (m, 2H), 4.08 (d, J = 17.0 Hz, 1H), 3.70 (d, J = 17.0 Hz, 1H), 3.3-3.4 (m, 2H), 2.42 (s, 3H). |
| 6-048 | (B) δ 8.55-8.6 (m, 1H), 7.65-7.7 (m, 1H), 7.5-7.55 (m, 4H), 7.4-7.5 (m, 2H), 7.25-7.3 (m, 1H), 7.15-7.25 (m, 1H), 5.23 (s, 2H), 4.05-4.15 (m, 3H), 3.69 (d, J = 17.0 Hz, 1H), 3.2-3.25 (m, 2H), 3.15 (s, 3H), 2.49 (s, 3H). |
| 6-049 | (B) δ 8.5-8.6 (m, 1H), 7.65-7.7 (m, 1H), 7.45-7.55 (m, 4H), 7.4-7.45 (m, 2H), 7.25-7.3 (m, 1H), 7.15-7.2 (m, 1H), 5.45-5.6 (m, 1H), 5.23 (s, 2H), 5.0-5.1 (m, 2H), 4.4-4.45 (m, 2H), 4.18 (d, J = 17.0 Hz, 1H), 3.69 (d, J = 17.0 Hz, 1H), 2.40 (s, 3H). |
| 6-050 | (B) δ 8.54 (d, J = 4.8 Hz, 1H), 7.6-7.7 (m, 1H), 7.35-7.55 (m, 6H), 7.15-7.25 (m, 2H), 5.13 (s, 2H), 4.07 (d, J = 17.0 Hz, 1H), 3.68 (d, J = 17.0 Hz, 1H), 2.40 (s, 3H), 2.27 (s, 3H). |
| 6-051 | (B) δ 8.55-8.6 (m, 1H), 7.6-7.65 (m, 1H), 7.45-7.5 (m, 5H), 7.35-7.4 (m, 1H), 7.2-7.25 (m, 1H), 7.0-7.05 (m, 1H), 4.96 (s, 2H), 4.05 (d, J = 17.0 Hz, 1H), 3.67 (d, J = 17.0 Hz, 1H), 3.43 (s, 3H), 2.37 (s, 3H). |
| 6-053 | (B) δ 8.65-8.7 (m, 1H), 7.65-7.8 (m, 2H), 7.5-7.55 (m, 2H), 7.3-7.45 (m, 5H), 5.17 (s, 2H), 4.05 (d, J = 17.0 Hz, 1H), 3.67 (d, J = 17.0 Hz, 1H), 3.50 (s, 6H), 2.46 (s, 3H). |
| 6-054 | (B) δ 8.4-8.45 (m, 1H), 7.8-7.85 (m, 1H), 7.2-7.6 (m, 7H), 4.2-5.3 (m, 2H), 4.05-4.15 (m, 1H), 3.65-3.75 (m, 1H), 3.05-3.15 (m, 2H), 2.34 and 2.29 (s, 3H), 1.25-1.3 and 1.0-1.1 (m, 3H). |
| 6-055 | (A) δ 8.6-8.65 (m, 2H), 7.5-7.55 (m, 4H), 7.43 (s, 1H), 7.25-7.3 (m, 3H), 4.76 (s, 2H), 4.11 (d, J = 19.0 Hz, 1H), 3.71 (d, J = 19.0 Hz, 1H), 2.45-2.5 (m, 1H), 2.34 (s, 3H), 1.2-1.3 (m, 3H). |
| 6-056 | (A) δ 8.6-8.75 (m, 2H), 7.4-7.6 (m, 6H), 7.15-7.25 (m, 1H), 5.12 (s, 2H), 4.06 (d, J = 17.0 Hz, 1H), 3.68 (d, J = 17.0 Hz, 1H), 2.69 (q, J = 7.9 Hz, 2H), 2.43 (s, 3H), 1.11 (t, J = 7.9 Hz, 3H). |
| 6-069 | (B) δ 7.8-7.9 (m, 2H), 7.67 (d, J = 7.6 Hz, 1H), 7.51 (bs, 2H), 7.4-7.45 (m, 1H), 4.42 (s, 2H), 4.13 (d, J = 17.4 Hz, 1H), 3.77 (d, J = 17.4 Hz, 1H), 3.22 (s, 3H). |
| 6-070 | (A) δ 8.55 (d, J = 4.4 Hz, 1H), 7.92 (d, J = 7.8 Hz, 1H), 7.81 (s, 1H), 7.15-7.7 (m, 7H), 4.93 (s, 2H), 4.52 (s, 2H), 4.13 (d, J = 17.0 Hz, 1H), 3.76 (d, J = 17.0 Hz, 1H). |
| 6-073 | (A) δ 8.55 (d, J = 4.7 Hz, 1H), 8.37 (bs, 1H), 8.02 (d, J = 8.5 Hz, 1H), 7.91 (d, J = 8.5 Hz, 1H), 7.83 (bs, 1H), 7.69 (t, J = 7.7 Hz, 1H), 7.52 (bs, 2H), 7.4-7.5 (m, 2H), 7.15-7.3 (m, 1H), 5.27 (s, 2H), 4.15 (d, J = 17.3 Hz, 1H), 3.77 (d, J = 17.3 Hz, 1H). |
| 6-074 | (B) δ 7.5-7.7 (m, 4H), 7.43 (s, 1H), 7.35-7.4 (m, 1H), 4.50 (q, J = 8.4 Hz, 2H), 4.16 (d, J = 17.0 Hz, 1H), 3.75 (d, J = 17.0 Hz, 1H), 2.44 (s, 3H), 2.15 (s, 3H). |
| 6-075 | (B) δ 7.7-7.8 (m, 3H), 7.55-7.65 (m, 2H), 7.35-7.4 (m, 1H), 4.50 (q, J = 8.6 Hz, 2H), 4.10 (d, J = 17.0 Hz, 1H), 3.71 (d, J = 17.0 Hz, 1H), 2.44 (s, 3H), 2.16 (s, 3H). |
| 6-076 | (B) δ 8.45-8.5 (m, 2H), 7.7-7.75 (m, 2H), 7.6-7.65 (m, 1H), 7.69 (s, 1H), 7.4-7.45 (m, 2H), 7.15-7.2 (m, 2H), 4.97 (s, 2H), 4.06 (d, J = 17.0 Hz, 1H), 3.68 (d, J = 17.0 Hz, 1H), 2.41 (s, 3H), 2.40 (s, 3H). |
| 6-077 | (B) δ 7.5-7.6 (m, 4H), 7.43 (t, J = 1.8 Hz, 1H), 7.23 (d, J = 7.9 Hz, 1H), 4.62 (q, J = 8.4 Hz, 2H), 4.08 (d, J = 17.2 Hz, 1H), 3.70 (d, J = 17.2 Hz, 1H), 3.67 (s, 3H), 2.36 (s, 3H). |
| 6-078 | (A) δ 8.79 and 8.75 (d, J = 1.8 Hz, 1H), 7.3-7.55 (m, 7H), 4.85-5.2 (m, 2H), 4.53 and 4.50 (bs, 2H), 4.08 (d, J = 17.1 Hz, 1H), 3.69 (d, J = 17.1 Hz, 1H), 3.47 and 3.14 (s, 3H), 2.36 and 2.25 (s, 3H). |
| 6-079 | (A) δ 8.55 and 8.53 (d, J = 4.8 Hz, 1H), 7.69 and 7.59 (td, J = 7.8, 1.8 Hz, 1H), 7.25-7.55 (m, 8H), 4.8-5.25 (m, 2H), 4.57 and 4.49 (bs, 2H), 4.09 (d, J = 17.1 Hz, 1H), 3.70 (d, J = 17.1 Hz, 1H), 3.65 and 3.27 (q, J = 6.9 Hz, 2H), 2.37 and 2.34 (s, 3H), 1.26 and 1.08 (t, J = 6.9 Hz, 3H). |
| 6-080 | (B) δ 8.58 (ddd, J = 4.9, 1.8, 0.9 Hz, 1H), 7.70 (td, J = 7.7, 1.8 Hz, 1H), 7.35-7.55 (m, 7H), 7.18 (dd, J = 7.5, 4.9 Hz, 1H), 5.98 (q, J = 7.1 Hz, 1H), 4.08 (d, J = 17.2 Hz, 1H), 3.70 (d, J = 17.2 Hz, 1H), 3.42 (s, 3H), 2.43 (s, 3H), 1.90 (d, J = 7.0 Hz, 3H). |
| 6-081 | (A) δ 8.21 (d, J = 4.2 Hz, 1H), 7.3-7.6 (m, 7H), 6.80 (dd, J = 8.1, 4.2 Hz, 1H), 6.60 (d, J = 8.7 Hz, 1H), 4.05 (d, J = 17.1 Hz, 1H), 3.66 (d, J = 17.1 Hz, 1H), 3.34 (s, 3H), 2.45 (s, 3H), 2.42 (s, 3H). |
| 6-082 | (A) δ 8.22 (d, J = 4.8 Hz, 1H), 7.4-7.65 (m, 7H), 6.78 (dd, J = 7.2, 4.8 Hz, 1H), 6.63 (d, J = 8.4 Hz, 1H), |

TABLE 21-continued

| No. | $^1$H NMR |
|---|---|
| | 4.08 (d, J = 16.8 Hz, 1H), 3.70 (s, 3H), 3.69 (d, J = 16.8 Hz, 1H), 3.40 (s, 3H), 2.46 (s, 3H). |
| 6-083 | (A) δ 8.42 (s, 2H), 7.35-7.55 (m, 6H), 6.77 (t, J = 5.1 Hz, 1H), 4.06 (d, J = 18.1 Hz, 1H), 3.67 (d, J = 18.1 Hz, 1H), 3.43 (s, 3H), 2.44 (s, 3H), 2.43 (s, 3H). |
| 6-084 | (A) δ 8.46 (bs, 1H), 8.40 (bs, 1H), 7.45-7.6 (m, 5H), 7.43 (s, 1H), 6.74 (t, J = 4.8 Hz, 1H), 4.09 (d, J = 17.4 Hz, 1H), 3.70 (d, J = 17.4 Hz, 1H), 3.69 (s, 3H), 3.53 (s, 3H), 2.46 (s, 3H). |
| 6-085 | (B) δ 7.4-7.55 (m, 5H), 7.2-7.3 (m, 1H), 3.85-4.2 (m, 3H), 3.6-3.8 (m, 1H), 2.5-2.65 (m, 2H), 2.32 and 2.30 (s, 3H), 2.1-2.2 (m, 2H). |
| 6-086 | (A) δ 7.4-7.6 (m, 6H), 4.09 (d, J = 17.2 Hz, 1H), 3.71 (d, J = 17.2 Hz, 1H), 2.89 (s, 4H), 2.57 (s, 3H). |
| 6-089 | (B) δ 7.45-7.6 (m, 4H), 7.4-7.45 (m, 1H), 7.2-7.3 (m, 1H), 4.09 (d, J = 17.4 Hz, 1H), 3.71 (d, J = 17.4 Hz, 1H), 3.13 (bs, 3H), 2.7-2.8 (m, 2H), 2.37 (bs, 3H), 1.15 (m, 3H). |
| 6-092 | (B) δ 7.45-7.55 (m, 4H), 7.4-7.45 (m, 1H), 7.33 (d, J = 8.0 Hz, 1H), 5.10 (s, 2H), 4.50 (s, 2H), 4.09 (d, J = 17.2 Hz, 1H), 3.6-3.75 (m, 3H), 3.27 (q, J = 6.8 Hz, 2H), 2.36 (s, 3H), 1.25 (t, J = 7.0 Hz, 3H), 1.10 (t, J = 7.0 Hz, 3H). |
| 6-093 | (A) δ 7.5-7.7 (m, 4H), 7.44 (t, J = 2.0 Hz, 1H), 7.35 (d, J = 7.6 Hz, 1H), 5.03 (s, 2H), 4.11 (d, J = 17.4 Hz, 1H), 3.70 (d, J = 17.4 Hz, 1H), 3.50 (q, J = 7.0 Hz, 2H), 2.48 (s, 3H), 2.40 (s, 3H), 1.15 (t, J = 7.0 Hz, 3H). |
| 6-094 | (A) δ 7.5-7.6 (m, 4H), 7.44 (t, J = 1.8 Hz, 1H), 7.2-7.3 (m, 1H), 5.14 and 4.62 (s, 2H), 4.05-4.15 (m, 2H), 3.6-3.75 (m, 2H), 3.20 and 2.87 (s, 3H), 2.33 and 2.35 (s, 3H). |
| 6-095 | (B) δ 7.3-7.6 (m, 6H), 5.15 (s, 2H), 3.95-4.2 (m, 3H), 3.71 (d, J = 17.4 Hz, 1H), 2.48 (s, 3H), 2.40 (s, 3H). |
| 6-096 | (B) δ 7.45-7.55 (m, 4H), 7.43 (t, J = 1.8 Hz, 1H), 7.24 (d, J = 8.1 Hz, 1H), 4.12 (t, J = 5.5 Hz, 2H), 4.09 (d, J = 17.2 Hz, 1H), 3.71 (d, J = 17.2 Hz, 1H), 3.66 (t, J = 5.5 Hz, 2H), 3.61 (s, 3H), 3.37 (s, 3H), 2.36 (s, 3H). |
| 6-097 | (A) δ 7.4-7.55 (m, 5H), 7.2-7.3 (m, 1H), 5.18 and 4.87 (t, J = 4.6 Hz, 1H), 3.65-4.2 (m, 8H), 3.20 and 2.89 (s, 3H), 2.34 and 2.32 (s, 3H). |
| 6-098 | (A) δ 7.5-7.6 (m, 4H), 7.44 (t, J = 1.8 Hz, 1H), 7.37 (d, J = 7.8 Hz, 1H), 5.12 (t, J = 4.6 Hz, 1H), 4.09 (d, J = 17.4 Hz, 1H), 3.8-3.95 (m, 6H), 3.70 (d, J = 17.4 Hz, 1H), 2.43 (s, 3H), 2.33 (s, 3H). |
| 6-099 | (A) δ 7.45-7.55 (m, 4H), 7.43 (t, J = 1.8 Hz, 1H), 7.25-7.3 (m, 1H), 5.32 (t, J = 4.6 Hz, 1H), 3.9-4.15 (m, 7H), 3.69 (d, J = 17.4 Hz, 1H), 3.62 (s, 3H), 2.38 (s, 3H). |
| 6-100 | (A) δ 7.4-7.65 (m, 6H), 5.72 (dd, J = 7.2, 5.7 Hz, 1H), 4.10 (d, J = 17.1 Hz, 1H), 4.0-4.15 (m, 1H), 3.75-3.85 (m, 1H), 3.71 (d, J = 17.1 Hz, 1H), 2.49 (s, 3H), 2.3-2.45 (m, 1H), 2.22 (s, 3H), 2.1-2.25 (m, 2H), 1.8-1.95 (m, 1H). |
| 6-101 | (A) δ 7.35-7.6 (m, 5H), 6.6-7.3 (m, 2H), 3.65-4.45 (m, 7H), 3.13 and 2.82 (d, J = 7.8 Hz, 3H), 2.3-2.35 (m, 3H). |
| 6-102 | (A) δ 6.6-7.6 (m, 7H), 4.35-4.45 (m, 2H), 3.65-4.15 (m, 5H), 2.3-2.45 (m, 6H). |
| 6-103 | (A) δ 6.65-7.55 (m, 7H), 4.6-4.75 (m, 2H), 3.6-4.15 (m, 8H), 2.37 and 2.35 (s, 3H). |
| 6-105 | (B) δ 7.45-7.55 (m, 4H), 7.43 (t, J = 1.8 Hz, 1H), 7.37 (d, J = 8.8 Hz, 2H), 7.14 (d, J = 8.1 Hz, 1H), 6.87 (d, J = 8.8 Hz, 2H), 5.00 (s, 2H), 4.08 (d, J = 17.2 Hz, 1H), 3.81 (s, 3H), 3.68 (d, J = 17.2 Hz, 1H), 3.58 (s, 3H), 2.29 (s, 3H). |
| 6-106 | (B) δ 8.22 (d, J = 8.7 Hz, 2H), 7.59 (d, J = 8.7 Hz, 2H), 7.45-7.55 (m, 4H), 7.43 (t, J = 1.8 Hz, 1H), 7.18 (d, J = 7.9 Hz, 1H), 5.15 (s, 2H), 4.08 (d, J = 17.2 Hz, 1H), 3.70 (d, J = 17.2 Hz, 1H), 3.58 (s, 3H), 2.16 (s, 3H). |
| 6-107 | (B) δ 7.3-7.6 (m, 14H), 7.19 (d, J = 8.1 Hz, 1H), 5.11 (s, 2H), 4.07 (d, J = 17.2 Hz, 1H), 3.68 (d, J = 17.2 Hz, 1H), 3.60 (s, 3H), 2.37 (s, 3H). |
| 6-108 | (A) δ 7.81 (bs, 1H), 7.4-7.55 (m, 5H), 7.2-7.3 (m, 1H), 6.56 (s, 1H), 6.13 (s, 2H), 4.07 (d, J = 17.3 Hz, 1H), 3.68 (d, J = 17.3 Hz, 1H), 2.28 (s, 3H), 1.23 (s, 9H). |
| 6-109 | (B) δ 8.08 (dt, J = 7.5, 0.9 Hz, 1H), 7.89 (dt, J = 8.4, 0.9 Hz, 1H), 7.4-7.6 (m, 7H), 7.14 (d, J = 8.1 Hz, 1H), 6.72 (s, 2H), 4.06 (d, J = 17.2 Hz, 1H), 3.69 (s, 3H), 3.68 (d, J = 17.2 Hz, 1H), 2.25 (s, 3H). |
| 6-111 | (A) δ 8.56 (d, J = 4.2 Hz, 1H), 6.7-7.85 (m, 13H), 5.21 (s, 2H), 4.00 (d, J = 17.4 Hz, 1H), 3.60 (d, J = 17.4 Hz, 1H), 2.40 (s, 3H). |
| 6-112 | (A) δ 8.72 (d, J = 4.8 Hz, 2H), 7.4-7.6 (m, 6H), 7.22 (t, J = 4.8 Hz, 1H), 5.33 (s, 2H), 4.10 (d, J = 17.1 Hz, 1H), 3.71 (d, J = 17.1 Hz, 1H), 3.58 (s, 3H), 2.44 (s, 3H). |
| 6-113 | (B) δ 7.82 (t, J = 6.0 Hz, 1H), 7.5-7.6 (m, 4H), 7.43 (bs, 1H), 7.2-7.3 (m, 1H), 4.8-4.85 (m, 1H), 3.65-4.15 (m, 4H), 3.15-3.25 (m, 2H), 2.5-2.6 (m, 1H), 2.34 (s, 3H), 1.85-2.1 (m, 3H). |

TABLE 21-continued

| No. | ¹H NMR |
|---|---|
| 6-114 | (A) δ 7.5-7.6 (m, 4H), 7.43 (t, J = 2.0 Hz, 1H), 7.25-7.35 (m, 1H), 5.19 (s, 1H), 4.59 (s, 1H), 4.0-4.2 (m, 3H), 3.65-3.8 (m, 2H), 3.27 (t, J = 6.4 Hz, 1H), 2.39 (bs, 3H). |
| 6-115 | (A) δ 7.4-7.6 (m, 5H), 7.25-7.35 (m, 1H), 4.77 (s, 1H), 4.0-4.2 (m, 3H), 3.70 (d, J = 17.4 Hz, 1H), 3.45 (t, J = 6.4 Hz, 1H), 3.13 (t, J = 6.4 Hz, 1H), 2.97 (t, J = 6.4 Hz, 1H), 2.36 (m, 3H). |
| 6-119 | (A) δ 7.4-7.55 (m, 6H), 4.08 (d, J = 17.4 Hz, 1H), 3.8-3.85 (m, 2H), 3.69 (d, J = 17.4 Hz, 1H), 3.2-3.25 (m, 2H), 2.45-2.5 (m, 2H), 2.2-2.35 (m, 8H). |
| 6-120 | (B) δ 7.45-7.55 (m, 4H), 7.43 (t, J = 1.8 Hz, 1H), 7.30 (d, J = 7.9 Hz, 1H), 4.08 (d, J = 17.2 Hz, 1H), 3.89 (s, 3H), 3.82 (s, 3H), 3.69 (d, J = 17.2 Hz, 1H), 2.38 (s, 3H). |
| 6-121 | (B) δ 7.45-7.55 (m, 4H), 7.43 (t, J = 1.8 Hz, 1H), 7.21 (d, J = 7.9 Hz, 1H), 4.09 (d, J = 17.2 Hz, 1H), 3.77 (s, 3H), 3.70 (d, J = 17.2 Hz, 1H), 2.84 (s, 6H), 2.40 (s, 3H). |
| 6-122 | (B) δ 8.0-8.15 (m, 1H), 7.4-7.6 (m, 5H), 4.11 (d, J = 17.4 Hz, 1H), 3.72 (d, J = 17.4 Hz, 1H), 2.68 (s, 3H), 2.33 (s, 6H). |
| 6-123 | (B) δ 7.45-7.55 (m, 4H), 7.43 (t, J = 1.8 Hz, 1H), 7.31 (d, J = 7.9 Hz, 1H), 4.8-4.9 (m, 1H), 4.76 (ddd, J = 47.6, 11.0, 2.4 Hz, 1H), 4.58 (ddd, J = 46.0, 11.0, 2.7 Hz, 1H), 4.28 (dd, J = 11.2, 10.0 Hz, 1H), 4.18 (dd, J = 11.2, 5.5 Hz, 1H), 4.08 (d, J = 17.2 Hz, 1H), 3.70 (d, J = 17.2 Hz, 1H), 2.35 (s, 3H). |
| 6-124 | (B) δ 7.5-7.6 (m, 4H), 7.43 (t, J = 1.8 Hz, 1H), 7.34 (d, J = 8.6 Hz, 1H), 4.09 (d, J = 17.2 Hz, 1H), 3.75 (s, 3H), 3.70 (d, J = 17.2 Hz, 1H), 3.14 (bs, 3H), 3.07 (bs, 3H), 2.44 (s, 3H). |
| 6-125 | (B) δ 9.12 (t, J = 7.3 Hz, 1H), 7.5-7.6 (m, 4H), 7.43 (t, J = 1.8 Hz, 1H), 7.23 (d, J = 8.2 Hz, 1H), 4.07 (d, J = 17.2 Hz, 1H), 3.68 (d, J = 17.2 Hz, 1H), 3.39 (tq, J = 7.3, 7.1 Hz, 2H), 3.01 (s, 3H), 2.37 (s, 3H), 1.24 (t, J = 7.1 Hz, 3H). |
| 6-126 | (B) δ 9.65 (t, J = 6.2 Hz, 1H), 7.15-7.65 (m, 4H), 7.44 (t, J = 1.8 Hz, 1H), 7.29 (d, J = 7.9 Hz, 1H), 4.09 (d, J = 17.2 Hz, 1H), 3.95-4.1 (m, 2H), 3.71 (d, J = 17.2 Hz, 1H), 3.07 (s, 3H), 2.36 (s, 3H). |
| 6-130 | (A) δ 7.2-7.7 (m, 6H), 6.15 (s, 1H), 5.15-5.35 (m, 1H), 4.5-4.8 (m, 1H), 4.09 (d, J = 17.4 Hz, 1H), 3.6-4.3 (m, 3H), 3.48 and 3.03 (s, 3H), 2.36 and 2.34 (s, 3H), 1.7-2.45 (m, 4H). |
| 6-131 | (A) δ 7.35-7.6 (m, 6H), 5.65-5.75 (m, 1H), 4.05-4.2 (m, 1H), 4.08 (d, J = 17.4 Hz, 1H), 3.7-3.85 (m, 1H), 3.70 (d, J = 17.4 Hz, 1H), 2.51 (q, J = 6.0 Hz, 2H), 2.49 (s, 3H), 1.6-2.6 (m, 4H), 1.08 (t, J = 6.0 Hz, 3H). |
| 6-132 | (A) δ 7.5-7.6 (m, 4H), 7.4-7.45 (m, 2H), 5.78 (t, J = 6.3 Hz, 1H), 4.05-4.15 (m, 2H), 3.75-3.85 (m, 1H), 3.71 (d, J = 17.4 Hz, 1H), 2.7-2.9 (m, 1H), 2.50 (s, 3H), 2.25-2.4 (m, 1H), 2.1-2.25 (m, 2H), 1.8-1.95 (m, 1H), 1.06 and 1.08 (d, J = 6.0 Hz, 6H). |
| 7-002 | (A) δ 7.87 (bs, 1H), 7.78 (d, J = 8.1 Hz, 2H), 7.65 (d, J = 8.1 Hz, 2H), 7.50 (bs, 2H), 7.43 (bs, 1H), 4.55-4.7 (m, 2H), 4.09 (d, J = 17.4 Hz, 1H), 3.71 (d, J = 17.4 Hz, 1H). |
| 7-003 | (A) δ 8.85 (s, 1H), 8.49 (bs, 1H), 7.86 (d, J = 8.4 Hz, 2H), 7.67 (d, J = 8.7 Hz, 2H), 7.51 (bs, 2H), 7.43 (t, J = 1.8 Hz, 1H), 7.40 (s, 1H), 5.13 (d, J = 4.8 Hz, 2H), 4.06 (d, J = 17.4 Hz, 1H), 3.67 (d, J = 17.1 Hz, 1H). |
| 7-008 | (A) δ 8.79 (s, 1H), 8.14 (bs, 1H), 7.35-7.5 (m, 7H), 5.11 (d, J = 5.0 Hz, 2H), 4.06 (d, J = 17.4 Hz, 1H), 3.67 (d, J = 17.1 Hz, 1H), 2.37 (s, 3H). |
| 7-009 | (A) δ 9.06 (bs, 1H), 8.50 (d, J = 4.5 Hz, 1H), 7.75 (t, J = 7.2 Hz, 1H), 7.2-7.6 (m, 8H), 5.04 (d, J = 4.2 Hz, 2H), 4.08 (d, J = 17.4 Hz, 1H), 3.70 (d, J = 17.4 Hz, 1H), 2.44 (s, 3H). |
| 8-001 | (A) δ 8.40 (d, J = 8.2 Hz, 2H), 7.74 (d, J = 8.2 Hz, 2H), 7.53 (s, 2H), 7.43 (s, 1H), 7.04 (d, J = 4.7 Hz, 1H), 6.74 (d, J = 4.7 Hz, 1H), 4.13 (d, J = 17.3 Hz, 1H), 3.89 (s, 3H), 3.74 (d, J = 17.3 Hz, 1H). |
| 8-002 | (A) δ 8.22 (d, J = 8.0 Hz, 2H), 7.56 (s, 1H), 7.53 (s, 2H), 7.43 (s, 1H), 7.03 (d, J = 4.7 Hz, 1H), 6.72 (d, J = 4.7 Hz, 1H), 4.12 (d, J = 17.3 Hz, 1H), 3.84 (s, 3H), 3.72 (d, J = 17.3 Hz, 1H), 2.74 (s, 3H). |
| 8-003 | (A) δ 8.19 (d, J = 8.1 Hz, 1H), 7.5-7.6 (m, 4H), 7.43 (s, 1H), 7.04 (d, J = 4.8 Hz, 1H), 6.71 (d, J = 4.8 Hz, 1H), 4.23 (t, J = 7.2 Hz, 2H), 4.12 (d, J = 17.1 Hz, 1H), 3.72 (d, J = 17.1 Hz, 1H), 2.73 (s, 3H), 1.91 (hex, J = 7.2 Hz, 2H), 0.99 (t, J = 7.2 Hz, 3H). |
| 8-004 | (A) δ 8.17 (d, J = 8.1 Hz, 1H), 7.45-7.65 (m, 4H), 7.41 (s, 1H), 7.36 (t, J = 4.2 Hz, 1H), 4.12 (d, J = 17.4 Hz, 1H), 3.79 (s, 3H), 3.74 (d, J = 17.4 Hz, 1H), 3.17 (d, J = 4.2 Hz, 2H), 2.69 (s, 3H). |
| 8-005 | (A) δ 8.50 (s, 1H), 7.95 (d, J = 7.8 Hz, 1H), 7.68 (d, J = 6.6 Hz, 1H), 7.4-7.6 (m, 5H), 6.32 (dd, J = 6.6, 4.2 Hz, 1H), 4.10 (d, J = 17.4 Hz, 1H), 3.71 (d, J = 17.4 Hz, 1H), 3.67 (s, 3H), 2.68 (s, 3H). |
| 8-006 | (A) δ 8.97 (s, 1H), 7.3-7.7 (m, 6H), 4.12 (d, J = 17.4 Hz, 1H), 3.73 (d, J = 17.4 Hz, 1H), 3.62 (s, 3H), 2.36 (s, 3H). |
| 8-007 | (A) δ 8.58 (d, J = 9.9 Hz, 1H), 8.08 (d, J = 7.8 Hz, 1H), 7.4-7.6 (m, 5H), 7.30 (d, J = 9.9 Hz, 1H), 4.11 (d, J = 17.1 Hz, 1H), 4.00 (s, 3H), 3.72 (d, J = 17.1 Hz, 1H), 2.67 (s, 3H). |

TABLE 21-continued

| No. | ¹H NMR |
|---|---|
| 9-003 | (B) δ 8.75 (d, J = 1.2 Hz, 1H), 8.7-8.75 (m, 1H), 8.14 (t, J = 1.8 Hz, 1H), 7.5-7.6 (m, 2H), 7.45 (d, J = 8.6 Hz, 1H), 6.0-6.05 (m, 1H), 4.05-4.2 (m, 3H), 3.74 (d, J = 17.2 Hz, 1H), 2.48 (s, 3H). |
| 9-008 | (A) δ 7.97 (s, 1H), 7.45-7.55 (m, 2H), 7.35-7.4 (m, 1H), 6.44 (t, J = 6.3 Hz, 1H), 4.40 (d, J = 17.6 Hz, 1H), 4.0-4.15 (m, 3H), 2.42 (s, 3H). |
| 9-009 | (A) δ 8.51 (dd, J = 5.1, 0.9 Hz, 1H), 7.96 (s, 1H), 7.70 (td, J = 7.5, 1.5 Hz, 1H), 7.5-7.6 (m, 3H), 7.3-7.4 (m, 2H), 7.15-7.25 (m, 1H), 4.74 (d, J = 4.8 Hz, 2H), 4.40 (d, J = 17.6 Hz, 1H), 4.09 (d, J = 17.6 Hz, 1H), 2.50 (s, 3H). |
| 9-010 | (B) δ 7.45-7.55 (m, 2H), 7.40 (d, J = 7.9 Hz, 1H), 7.04 (d, J = 4.0 Hz, 1H), 6.89 (d, J = 4.0 Hz, 1H), 6.25 (bs, 1H), 4.05-4.15 (m, 2H), 4.03 (d, J = 17.2 Hz, 1H), 3.74 (d, J = 17.2 Hz, 1H), 2.43 (s, 3H). |
| 9-011 | (B) δ 8.5-8.55 (m, 1H), 7.70 (td, J = 7.5, 1.8 Hz, 1H), 7.45-7.65 (m, 3H), 7.43 (t, J = 5.1 Hz, 1H), 7.34 (d, J = 7.9 Hz, 1H), 7.15-7.25 (m, 1H), 7.04 (d, J = 3.8 Hz, 1H), 6.88 (d, J = 4.0 Hz, 1H), 4.73 (d, J = 5.0 Hz, 2H), 4.04 (d, J = 17.2 Hz, 1H), 3.74 (d, J = 17.2 Hz, 1H), 2.48 (s, 3H). |
| 10-001 | (A) δ 8.87 (d, J = 2.1 Hz, 1H), 8.25-8.3 (m, 2H), 8.14 (dd, J = 8.1, 2.1 Hz, 1H), 7.51 (bs, 2H), 7.45 (d, J = 1.8 Hz, 1H), 4.05-4.2 (m, 3H), 3.75 (d, J = 17.4 Hz, 1H). |
| 10-002 | (A) δ 8.94 (bs, 1H), 8.88 (bs, 1H), 8.61 (d, J = 5.1 Hz, 1H), 8.30 (d, J = 7.8 Hz, 1H), 8.12 (dd, J = 8.1, 2.1 Hz, 1H), 7.68 (td, J = 7.8, 1.8 Hz, 1H), 7.51 (bs, 2H), 7.45 (t, J = 1.8 Hz, 1H), 7.34 (d, J = 7.8 Hz, 1H), 7.2-7.25 (m, 1H), 4.80 (d, J = 5.4 Hz, 2H), 4.12 (d, J = 17.4 Hz, 1H), 3.74 (d, J = 17.4 Hz, 1H). |
| 10-003 | (A) δ 8.53 (d, J = 1.8 Hz, 1H), 8.48 (d, J = 8.4 Hz, 1H), 7.74 (dd, J = 8.4, 1.8 Hz, 1H), 7.47 (bs, 3H), 4.0-4.2 (m, 2H), 4.05 (d, J = 17.4 Hz, 1H), 3.68 (d, J = 17.4 Hz, 1H). |
| 10-004 | (A) δ 9.01 (s, 1H), 8.17 (d, J = 8.4 Hz, 1H), 8.10 (d, J = 8.4 Hz, 1H), 7.51 (s, 2H), 7.43 (s, 1H), 6.77 (t, J = 6.3 Hz, 1H), 4.26 (d, J = 18.3 Hz, 1H), 4.05-4.25 (m, 2H), 3.89 (d, J = 18.3 Hz, 1H). |
| 10-005 | (A) δ 9.09 (s, 1H), 8.57 (d, J = 5.1 Hz, 1H), 8.24 (d, J = 8.4 Hz, 1H), 8.12 (d, J = 8.4 Hz, 1H), 7.86 (bs, 1H), 7.65-7.75 (m, 1H), 7.52 (s, 2H), 7.43 (s, 1H), 7.2-7.35 (m, 2H), 4.78 (d, J = 4.2 Hz, 2H), 4.28 (d, J = 18.3 Hz, 1H), 3.90 (d, J = 18.3 Hz, 1H). |
| 11-034 | (A) δ 7.96 (t, J = 7.0 Hz, 1H), 7.88 (dd, J = 8.2, 1.6 Hz, 1H), 7.81 (dd, J = 11.8, 1.4 Hz, 1H), 7.51 (bs, 2H), 7.4-7.45 (m, 1H), 4.20 (dd, J = 18.2, 1.4 Hz, 1H), 3.82 (d, J = 18.2 Hz, 1H). |
| 11-038 | (A) δ 7.89 (d, J = 8.1 Hz, 1H), 7.72 (s, 1H), 7.64 (d, J = 8.1 Hz, 1H), 7.50 (s, 2H), 7.43 (s, 1H), 4.09 (d, J = 17.1 Hz, 1H), 3.95 (s, 3H), 3.71 (d, J = 17.1 Hz, 1H). |
| 11-056 | (A) δ 8.64 (d, J = 4.5 Hz, 1H), 8.06 (d, J = 8.4 Hz, 1H), 7.75 (td, J = 7.7, 1.1 Hz, 1H), 7.5-7.6 (m, 4H), 7.35-7.45 (m, 2H), 7.28 (t, J = 6.2 Hz, 1H), 5.48 (s, 2H), 4.11 (d, J = 17.1 Hz, 1H), 3.72 (d, J = 17.1 Hz, 1H), 2.65 (s, 3H). |
| 11-057 | (B) δ 8.4-8.45 (m, 1H), 7.75 (s, 1H), 7.5-7.65 (m, 5H), 7.44 (s, 1H), 6.55 (s, 1H), 4.12 (d, J = 17.0 Hz, 1H), 3.73 (d, J = 17.0 Hz, 1H), 2.37 (s, 3H). |
| 11-059 | (A) δ 7.90 (d, J = 8.4 Hz, 1H), 7.4-7.7 (m, 5H), 4.11 (d, J = 17.4 Hz, 1H), 3.91 (s, 3H), 3.72 (d, J = 17.4 Hz, 1H), 3.50 (q, J = 7.5 Hz, 2H), 1.25 (t, J = 7.5 Hz, 3H). |
| 11-060 | (A) δ 8.02 (d, J = 6.3 Hz, 1H), 7.75 (s, 1H), 7.67 (d, J = 6.3 Hz, 1H), 7.51 (s, 2H), 7.43 (s, 1H), 4.95 (s, 2H), 4.12 (d, J = 17.4 Hz, 1H), 3.97 (s, 3H), 3.74 (d, J = 17.4 Hz, 1H). |
| 11-062 | (B) δ 8.07 (t, J = 0.8 Hz, 1H), 7.99 (ddd, J = 8.0, 1.6, 0.4 Hz, 1H), 7.93 (dd, J = 7.4, 0.6 Hz, 1H), 7.48-7.52 (m, 2H), 7.46 (t, J = 1.4 Hz, 1H), 4.11 (d, J = 16.8 Hz, 1H), 3.74 (dd, J = 17.4, 1.0 Hz, 1H). |
| 11-063 | (B) δ 8.00 (s, 1H), 7.93 (d, J = 8.1 Hz, 1H), 7.87 (d, J = 8.1 Hz, 1H), 7.51 (s, 2H), 7.4-7.5 (m, 1H), 4.12 (d, J = 16.7 Hz, 1H), 3.96 (s, 3H), 3.74 (d, J = 16.7 Hz, 1H). |
| 11-071 | (B) δ 8.03 (d, J = 8.0 Hz, 1H), 7.6-7.7 (m, 2H), 7.51 (s, 2H), 7.4-7.5 (m, 1H), 4.09 (d, J = 17.2 Hz, 1H), 3.95 (s, 3H), 3.70 (d, J = 17.2z, 1H). |
| 11-073 | (A) δ 7.95-8.05 (m, 1H), 7.4-7.5 (m, 2H), 7.2-7.35 (m, 3H), 4.06 (d, J = 17.1 Hz, 1H), 3.95 (s, 3H), 3.70 (d, J = 17.1 Hz, 1H), 2.52 (s, 3H). |
| 11-092 | (A) δ 7.94 (d, J = 8.8 Hz, 1H), 7.4-7.6 (m, 5H), 4.37 (q, J = 7.1 Hz, 2H), 4.15 (d, J = 17.3 Hz, 1H), 3.73 (d, J = 17.3 Hz, 1H), 2.62 (s, 3H), 1.40 (t, J = 7.1 Hz, 3H). |
| 11-095 | (A) δ 7.94 (d, J = 8.8 Hz, 1H), 7.5-7.8 (m, 5H), 4.37 (q, J = 7.1 Hz, 2H), 4.09 (d, J = 17.3 Hz, 1H), 3.70 (d, J = 17.3 Hz, 1H), 2.62 (s, 3H), 1.40 (t, J = 7.1 Hz, 3H). |
| 11-102 | (A) δ 7.85-7.95 (m, 1H), 7.35-7.6 (m, 5H), 6.91 (s, 1H), 4.05 (d, J = 17.4 Hz, 1H), 3.67 (d, J = 17.4 Hz, 1H). |
| 11-105 | (A) δ 8.06 (d, J = 8.4 Hz, 1H), 7.68 (dd, J = 8.4, 1.8 Hz, 1H), 7.62 (d, J = 1.8 Hz, 1H), 7.50 (d, J = 1.5 Hz, 2H), 7.43 (t, J = 1.5 Hz, 1H), 7.08 (s, 1H), 4.05 (d, J = 17.4 Hz, 1H), 3.67 (d, J = 17.4 Hz, 1H). |

TABLE 21-continued

| No. | $^1$H NMR |
|---|---|
| 11-107 | (A) δ 7.68 (d, J = 1.8 Hz, 1H), 7.58 (dd, J = 8.1, 1.8 Hz, 1H), 7.45-7.55 (m, 3H), 7.43 (t, J = 1.8 Hz, 1H), 5.22 (s, 2H), 4.06 (d, J = 17.4 Hz, 1H), 3.68 (d, J = 17.4 Hz, 1H), 2.15 (s, 3H). |
| 11-112 | (A) δ 8.08 (d, J = 8.4 Hz, 1H), 7.79 (d, J = 1.8 Hz, 1H), 7.73 (d, J = 8.4 Hz, 1H), 7.49 (d, J = 1.5 Hz, 2H), 7.44 (t, J = 1.5 Hz, 1H), 7.04 (s, 1H), 4.06 (d, J = 17.4 Hz, 1H), 3.67 (d, J = 17.4 Hz, 1H). |
| 11-113 | (A) δ 7.84 (s, 1H), 7.55-7.7 (m, 2H), 7.50 (d, J = 1.5 Hz, 2H), 7.43 (t, J = 1.5 Hz, 1H), 4.77 (s, 2H), 4.07 (d, J = 17.4 Hz, 1H), 3.67 (d, J = 17.4 Hz, 1H). |
| 11-114 | (A) δ 7.86 (s, 1H), 7.63 (d, J = 8.1 Hz, 1H), 7.4-7.55 (m, 4H), 4.20 (s, 2H), 4.07 (d, J = 17.4 Hz, 1H), 3.67 (d, J = 17.4 Hz, 1H), 2.17 (s, 3H). |
| 11-116 | (A) δ 10.07 (s, 1H), 8.23 (s, 1H), 7.91 (d, J = 8.4 Hz, 1H), 7.77 (d, J = 8.4 Hz, 1H), 7.50 (s, 2H), 7.44 (s, 1H), 4.09 (d, J = 17.4 Hz, 1H), 3.70 (d, J = 17.4 Hz, 1H). |
| 11-118 | (A) δ 7.5-7.55 (m, 3H), 7.48 (dd, J = 8.1, 1.8 Hz, 1H), 7.42 (t, J = 1.8 Hz, 1H), 7.38 (d, J = 8.1 Hz, 1H), 4.60 (s, 2H), 4.07 (d, J = 17.4 Hz, 1H), 3.67 (d, J = 17.4 Hz, 1H), 2.45 (s, 3H). |
| 11-119 | (A) δ 7.45-7.55 (m, 3H), 7.47 (s, 2H), 7.42 (s, 1H), 4.74 (s, 2H), 4.09 (d, J = 17.4 Hz, 1H), 3.70 (d, J = 17.4 Hz, 1H), 2.36 (s, 3H). |
| 11-122 | (A) δ 9.35 (s, 1H), 7.4-7.45 (m, 5H), 7.2-7.3 (m, 1H), 4.39 (q, J = 7.1 Hz, 2H), 4.21 (d, J = 17.3 Hz, 1H), 3.83 (d, J = 17.3 Hz, 1H), 1.40 (t, J = 7.1 Hz, 3H). |
| 11-125 | (A) δ 7.45-8.05 (m, 6H), 6.66 (t, J = 72.3 Hz, 1H), 4.08 (d, J = 17.4 Hz, 1H), 3.71 (d, J = 17.4 Hz, 1H). |
| 11-126 | (A) δ 6.7-7.5 (m, 6H), 6.50 (t, J = 74.1 Hz, 1H), 4.23 (bs, 2H), 4.02 (d, J = 17.4 Hz, 1H), 3.63 (d, J = 17.4 Hz, 1H). |
| 11-127 | (A) δ 7.2-7.95 (m, 6H), 6.57 (t, J = 73.2 Hz, 1H), 4.05 (d, J = 17.4 Hz, 1H), 3.66 (d, J = 17.4 Hz, 1H). |
| 11-129 | (A) δ 7.95 (q, J = 8.7 Hz, 1H), 7.66 (s, 1H), 7.5-7.6 (m, 4H), 4.37 (q, J = 7.2 Hz, 2H), 4.10 (d, J = 17.4 Hz, 1H), 3.71 (d, J = 17.4 Hz, 1H), 2.62 (s, 3H), 1.40 (t, J = 7.2 Hz, 3H). |
| 11-130 | (A) δ 8.09 (s, 2H), 7.95-8.0 (m, 2H), 7.5-7.6 (m, 2H), 4.38 (q, J = 7.2 Hz, 2H), 4.21 (d, J = 17.4 Hz, 1H), 3.76 (d, J = 17.4 Hz, 1H), 2.63 (s, 3H), 1.41 (t, J = 7.2 Hz, 3H). |
| 14-004 | (A) δ 7.40 (s, 1H), 7.35 (s, 2H), 5.99 (s, 1H), 5.65 (s, 1H). |
| 14-005 | (B) δ 7.2-7.45 (m, 3H), 6.10 (s, 1H), 5.92 (s, 1H). |
| 14-006 | (A) δ 7.40 (s, 2H), 7.33 (s, 1H), 5.63 (s, 1H), 5.45 (s, 1H), 4.47 (s, 2H), 3.84 (q, J = 8.8 Hz, 2H). |
| 14-007 | (B) δ 7.3-7.4 (m, 3H), 5.22 (s, 1H), 5.02 (s, 1H), 2.07 (s, 2H), 0.04 (s, 9H). |
| 14-008 | (A) δ 8.63 (d, J = 5.1 Hz, 1H), 7.69 (t, J = 8.0 Hz, 1H), 7.2-7.4 (m, 5H), 5.99 (s, 1H), 5.64 (s, 1H). |
| 14-009 | (A) δ 7.25-7.6 (m, 3H), 6.04 (s, 1H), 5.80 (s, 1H). |
| 14-010 | (B) δ 7.24 (s, 1H), 7.20 (s, 1H), 7.14 (s, 1H), 5.97 (s, 1H), 5.77 (s, 1H), 2.36 (s, 3H). |
| 14-012 | (A) δ 7.40 (d, J = 6.3 Hz, 2H), 6.04 (s, 1H), 5.79 (s, 1H). |
| 14-013 | (B) δ 7.54 (s, 2H), 6.06 (s, 1H), 5.83 (s, 1H). |
| 14-016 | (A) δ 7.70 (s, 1H), 7.52 (s, 2H), 6.04 (s, 1H), 5.80 (s, 1H). |
| 14-018 | (A) δ 7.65 (s, 1H), 7.62 (s, 1H), 7.58 (s, 1H), 6.11 (s, 1H), 5.87 (s, 1H). |
| 14-020 | (A) δ 7.69 (d, J = 6.3 Hz, 1H), 7.58 (d, J = 5.7 Hz, 1H), 6.10 (s, 1H), 5.83 (s, 1H). |
| 14-021 | (A) δ 7.2-7.45 (m, 4H), 5.98 (s, 1H), 5.78 (s, 1H), 2.93 (dd, J = 10.8, 7.8 Hz, 1H), 2.01 (dd, J = 10.8, 7.8 Hz, 1H), 1.87 (t, J = 7.8 Hz, 1H). |
| 14-022 | (B) δ 7.35-7.45 (m, 2H), 7.2-7.3 (m, 2H), 6.09 (d, J = 53.2 Hz, 1H), 6.03 (s, 1H), 5.82 (s, 1H). |
| 14-023 | (B) δ 7.2-7.5 (m, 6H), 6.95-7.1 (m, 3H), 5.93 (s, 1H), 5.77 (s, 1H), 5.17 (s, 2H). |
| 14-024 | (A) δ 7.57 (d, J = 2.7 Hz, 1H), 7.2-7.55 (m, 4H), 6.9-7.15 (m, 3H), 5.96 (s, 1H), 5.78 (s, 1H), 5.19 (s, 2H). |
| 14-025 | (A) δ 8.27 (s, 1H), 7.99 (s, 1H), 7.15-7.6 (m, 4H), 6.00 (s, 1H), 5.83 (s, 1H). |
| 14-026 | (A) δ 7.74 (s, 1H), 7.69 (d, J = 7.7 Hz, 1H), 7.58 (d, J = 7.7 Hz, 1H), 7.46 (t, J = 7.7 Hz, 1H), 6.04 (s, 1H), 5.82 (s, 1H). |
| 14-027 | (A) δ 8.34 (s, 1H), 8.25 (d, J = 8.0 Hz, 1H), 7.79 (d, J = 8.0 Hz, 1H), 7.60 (t, J = 8.0 Hz, 1H), 6.14 (s, 1H), 5.93 (s, 1H). |

Test Examples

Next, usefulness of the compound of the present invention as a pesticide is specifically explained in the following Test Examples to which the present invention is not limited.

Test Example 1

Insecticidal Test Against Cabbage Moth

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of cabbage for about 10 seconds, and after air-drying, they were placed in a laboratory dish, then 5-cabbage moth (*Plutella xylostella*) in the stage of second instar larva per the dish were released therein, and the dish was covered with a lid and contained at a thermostat chamber at 25° C. A number of dead insect(s) after 6 days was counted and a rate of dead insects was calculated by the following calculation equation. Incidentally, the test was carried out with two districts.

Rate of dead insects (%)=(Number of dead insects/ Number of released insects)×100

As a result, the following compounds showed an insecticidal rate of 80% or more among the compounds tested.

The compounds of the present invention:

No. 1-005, 1-006, 1-015, 1-016, 1-025, 1-031, 1-040, 1-041, 1-053, 1-055~1-058, 1-062-1-074, 1-076, 1-077, 1-079~1-096, 1-098, 1-101, 1-102, 1-104~1-110, 1-113, 1-114, 1-116~1-140, 1-145~147, 1-149~1-157, 1-159~1-161, 1-166~1-168, 1-171, 1-172, 1-174, 1-175, 1-176*, 1-177*, 1-178~1-184, 1-185*, 1-187, 1-188*, 189*, 1-190, 1-194, 1-196, 1-199, 1-206*, 1-207, 1-209, 1-212, 1-214, 1-215, 1-225, 1-226, 2-001~2-005, 2-011~2-021, 2-022*, 2-024~2-027, 2-028, 2-029, 2-030, 2-031, 2-032*, 2-033, 2-034, 2-035, 2-036~2-041, 2-042, 2-043, 2-044, 2-045, 2-046, 2-047*, 2-048, 2-049, 2-050*, 2-051*, 2-052, 2-053, 2-054, 2-055, 2-057*, 2-058*, 2-059*, 2-060*, 2-061*, 2-062*, 2-063*, 2-064, 2-065*, 2-066, 2-067*, 2-068*, 2-069, 3-002~3-004, 3-006, 3-007, 3-012, 3-018, 3-023, 3-025~3-028, 3-030~3-035, 3-037, 3-038, 3-040, 3-043, 3-044, 3-046, 3-047, 3-050, 3-055, 3-058*, 3-060, 3-061*, 3-062~3-067, 3-068*, 3-069, 3-070*, 3-071*, 3-073~3-075, 3-077~3-081, 3-084, 3-085*, 3-086*, 3-087~3-089, 3-090*, 3-091*, 3-092*, 3-093*, 3-094~3-098, 3-100*, 3-102~3-104, 3-105*, 3-106~3-108, 3-109*, 3-110*, 3-111*, 3-112*, 3-113*, 3-114, 3-115, 3-116*, 3-117, 3-119~3-127, 3-129, 3-131, 3-132*, 3-133~3-136, 3-138~3-141, 3-143, 3-146, 3-148, 3-150, 3-151**, 4-002, 4-003*, 4-004*, 4-005, 4-006*, 4-008~4-010, 5-001*, 5-002*, 5-003*, 5-004*, 5-005*, 5-006, 5-007, 5-008*, 5-009*, 5-010*, 5-011*, 5-012*, 5-013*, 5-014*, 5-015*, 5-016, 5-017, 5-019, 5-022*, 5-023*, 5-029*, 5-030~5-035, 5-036*, 5-037*, 5-038*, 5-039*, 5-040*, 5-041*, 5-042, 5-043, 5-044*, 5-045*, 5-046*, 5-047*, 5-048*, 5-049*, 5-050*, 5-051*, 5-052*, 5-053*, 5-054~5-056, 5-057*, 5-058*, 5-059*, 5-060*, 5-061*, 5-062*, 5-063*, 5-064*, 5-065*, 5-066, 5-067*, 5-068*, 5-069*, 5-070*, 5-071*, 5-072*, 5-073*, 5-074*, 5-075, 5-075(+)*, 5-075(−), 5-076*, 5-077*, 5-078*, 5-079~5-082, 5-083*, 5-084, 5-085*, 5-086*, 5-087*, 5-088*, 5-089*, 5-090**, 5-091*, 5-092*, 5-093*, 5-094*, 5-095, 5-097, 5-098, 5-099, 5-100*, 5-101*, 5-102*, 5-103*, 5-104*, 5-105*, 5-106~5-108, 5-109*, 5-110, 5-111*, 5-112*, 5-113*, 5-114*, 5-115, 5-116, 5-117*, 5-118*, 5-119*, 5-120**, 5-121*, 5-122*, 5-123*, 5-124**, 5-125, 5-126*, 5-127, 5-128*, 5-129, 5-130*, 5-131~5-133, 5-134*, 5-135~5-137, 5-138*, 5-139*, 5-140*, 5-141*, 5-142*, 5-143, 5-144*, 5-145*, 5-146, 5-147*, 5-148*, 5-149, 5-150, 5-151*, 5-151(+)*, 5-151(−), 5-152~5-155, 5-156*, 5-158, 5-159, 5-160*, 5-161**, 5-162*, 5-163, 5-164, 5-165*, 5-166*, 5-167, 5-168*, 5-169*, 5-170~5-172, 5-173, 5-174, 5-175, 5-176*, 5-177, 5-178, 5-179*, 5-180*, 5-181*, 5-182*, 5-183*, 5-184, 5-185*, 5-186*, 5-187*, 5-188*, 5-189**, 5-189(+)*, 5-189(−), 5-190(+)*, 5-190(−), 5-191*, 5-192*, 5-193*, 5-194*, 5-195**, 5-196*, 5-197**, 5-198~5-200, 5-201*, 5-202*, 5-203**, 5-204, 5-205*, 5-206*, 5-207, 5-208**, 5-209, 5-210*, 5-211*, 5-212*, 5-213*, 5-214*, 5-215*, 5-216*, 5-217**, 5-218*, 5-219*, 5-219(+)*, 5-219(−)*, 5-220*, 5-221, 5-222*, 5-223*, 5-224*, 5-225*, 5-226*, 5-227*, 5-228*, 5-229*, 5-230*, 5-231*, 5-232*, 5-233*, 5-234*, 5-235**, 5-236*, 5-237, 5-238*, 5-239*, 5-240*, 5-241*, 5-242*, 5-243*, 5-244, 5-245*, 5-246*, 5-247*, 5-248, 5-249*, 5-250, 5-251*, 5-252, 5-253, 5-254*, 5-255, 5-256*, 5-257*, 5-258**, 5-259*, 5-260, 5-261*, 5-262, 5-263, 5-264*, 5-265*, 5-266, 5-267*, 5-268*, 5-270, 5-271, 5-272*, 5-273*, 5-274*, 5-275*, 5-276*, 5-277*, 5-278*, 5-279*, 5-280, 5-281, 5-282*, 5-283*, 5-284*, 5-285*, 5-286*, 5-287, 5-288*, 5-289*, 5-290, 5-291*, 5-292, 5-293, 5-294*, 5-295*, 5-296, 5-298, 5-299*, 5-300*, 5-301*, 5-302, 5-303*, 5-304, 5-305**, 5-306*, 5-307*, 5-308**, 5-309*, 5-310**, 5-311, 5-312*, 5-313*, 5-314*, 5-315*, 5-316, 5-317*, 5-318*, 5-319*, 5-320*, 5-321, 5-322, 5-323*, 5-324~5-326, 5-328, 5-329*, 5-330*, 5-331*, 5-332*, 5-333*, 5-334*, 5-335*, 5-336*, 5-337*, 5-338*, 5-339*, 5-340, 5-341, 5-342*, 5-343*, 5-344*, 5-345, 5-346*, 5-347, 5-349*, 5-350~5-352, 5-353*, 5-354*, 5-355*, 5-356*, 5-357*, 5-358*, 5-359**, 5-360*, 5-361*, 5-362*, 5-363, 5-366, 5-372, 5-374*, 5-375*, 5-376, 5-377, 5-378*, 5-379*, 5-380**, 5-381*, 5-383*, 5-384*, 5-385, 5-386, 5-387*, 5-389*, 5-390*, 5-391, 5-392*, 5-393*, 5-395*, 5-396**, 5-397*, 5-398*, 5-399*, 5-400*, 5-401*, 5-402*, 5-403~5-407, 5-408*, 5-409, 5-410*, 5-411*, 5-412*, 5-413*, 5-414, 5-415*, 5-416, 5-417*, 5-418*, 5-419*, 5-420*, 5-421*, 5-422*, 5-423*, 5-424*, 5-425*, 5-426*, 5-427*, 5-428*, 5-429*, 5-430*, 5-431, 5-432*, 5-433*, 5-434*, 5-436~5-438, 5-439*, 5-440*, 5-441*, 5-442*, 5-443*, 5-444*, 5-445*, 5-446*, 5-447~5-450, 5-452*, 5-453*, 5-454*, 5-455*, 5-456, 5-457, 5-458*, 5-459*, 5-460*, 5-461*, 5-462*, 5-463, 5-464, 5-465, 5-466, 5-467*, 5-468, 5-469, 5-470**, 5-471*, 5-472*, 5-473*, 5-474*, 5-475**, 5-476*, 5-477, 5-478, 5-479, 5-480*, 5-481~5-486, 5-487, 5-488, 5-489*, 5-490~5-493, 5-494, 5-495, 5-496, 5-497, 5-498, 5-499, 5-500*, 5-501~5-505, 5-507, 5-508, 5-509*, 5-510, 5-511, 5-512*, 5-513*, 5-514*, 5-515*, 5-516*, 5-517, 5-518, 5-519*, 5-520*, 5-521*, 5-522*, 5-523*, 5-524, 5-525, 5-526*, 5-527*, 5-528*, 5-529*, 5-530*, 5-531*, 5-532, 5-533*, 5-534, 5-535, 5-536*, 5-537*, 5-538*, 5-539*, 5-540, 5-540(+)*, 5-541*, 5-541(R), 5-541(S)*, 5-542, 5-543*, 5-544*, 5-545, 5-546*, 5-547*, 5-548*, 5-549*, 5-550, 5-551*, 5-552*, 5-553*, 5-554*, 5-555*, 5-556, 5-557*, 5-558*, 5-559~5-565, 5-566*, 5-567, 5-568*, 5-569*, 5-570*, 5-571, 5-572*, 5-573*, 5-574*, 5-575*, 5-576*, 5-577*, 5-578*, 5-579*, 5-580*, 5-581*, 5-582*, 5-583*, 5-584*, 5-585*, 5-586*, 5-587*, 5-588*, 5-589*, 5-590*, 5-591, 5-592, 5-593*, 5-594*, 5-595*, 5-596*, 5-597*, 5-598*, 5-599*, 5-600*, 5-601, 5-602, 5-603, 5-604*, 5-605, 5-606, 5-607*, 5-608**, 5-609, 5-610, 5-611*, 5-612, 5-6138, 5-614*, 5-615*, 5-616*, 5-617*, 5-618, 5-619*, 5-620~5-622, 5-623*, 5-624*, 5-625*, 5-626, 5-627, 5-628, 5-629*, 5-630*, 5-631*, 5-632*, 5-633*, 5-634*, 5-635*, 5-636, 5-637*, 5-638*, 5-639*, 5-640, 5-641*, 5-642**, 5-643*, 5-644**, 5-645*, 5-646*, 5-648*, 5-651, 5-653*, 5-654*, 5-655, 5-656, 5-657**, 5-658*, 5-659*, 5-660, 5-661, 5-662, 5-663, 5-664, 5-665, 5-666**, 5-667*, 5-668**, 5-669*, 5-670*, 5-671, 5-672, 5-674**, 5-676*, 5-678, 5-684*, 5-685*, 5-686**, 6-001*, 6-002, 6-003*, 6-004, 6-005, 6-006, 6-007*, 6-008*, 6-009, 6-010, 6-011*, 6-012, 6-013*, 6-015**, 6-016*, 6-017*, 6-018*, 6-019*, 6-020*, 6-021, 6-022, 6-023*, 6-024*, 6-025, 6-026*, 6-027*, 6-028*, 6-029*, 6-030, 6-031*, 6-032*, 6-033*, 6-034*, 6-035*, 6-036*, 6-037*, 6-038*, 6-039*, 6-040*, 6-041*, 6-042*, 6-043*, 6-044*, 6-045*, 6-046*, 6-047*, 6-048*, 6-049*, 6-050*, 6-051*, 6-052, 6-053, 6-054*, 6-055*, 6-056*, 6-057, 6-058*, 6-059*, 6-060**, 6-061, 6-062*, 6-063*, 6-064, 6-065, 6-066, 6-067, 6-071*, 6-074*, 6-075*, 6-076*, 6-077*, 6-078*, 6-079*, 6-080*, 6-080(+)*, 6-080(−)*, 6-082*, 6-083*, 6-084*, 6-085~6-088, 6-089, 6-090*, 6-091*, 6-092, 6-093, 6-094, 6-095, 6-096*, 6-097, 6-099, 6-100, 6-101, 6-102, 6-103, 6-104*, 6-105, 6-106, 6-108, 6-109, 6-110, 6-111, 6-112, 6-113, 6-114, 6-115*, 6-116, 6-117~6-120, 6-121*, 6-122, 6-123*, 6-124*, 6-125**, 6-126*, 6-127, 6-129*, 6-130, 6-131, 6-132, 6-133, 7-001, 7-002*, 7-003*, 7-004*, 7-005*, 7-006*, 7-007*, 7-008*, 7-009*, 7-010*, 8-002*, 8-003*, 8-004, 8-005, 8-006*, 8-007*, 9-003, 9-008~9-011, 10-001, 10-002*, 10-003~10-005, 10-006*, 11-006, 11-018, 11-024, 11-025*, 11-026*, 11-038, 11-043, 11-045, 11-046, 11-049*, 11-050-11-052, 11-054, 11-056, 11-058~11-062, 11-066, 11-075, 11-088, 11-089, 11-098*, 11-099*, 11-101~11-107, 11-108*, 11-109*, 11-110-11-117, 11-119, 11-120*, 11-122, 11-124*, 11-125*, 11-128, 11-129, 11-132, 12-001, 12-002, 12-008.

In the interim, the indication of "*" shows that the insecticidal test was carried out by use of a chemical solution of a concentration of 100 ppm, and the indication "**" shows that the insecticidal test was carried out by use of a chemical solution of a concentration of 10 ppm.

Test Example 2

Insecticidal Test Against Common Cutworm

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of cabbage for about 10 seconds, and after air-drying, they were placed in a laboratory dish, then 5-common cutworm (Spodoptera litura) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention:
No. 1-005, 1-015, 1-016, 1-057, 1-058, 1-062, 1-066, 1-069, 1-080, 1-081, 1-088, 1-101, 1-102, 1-105~1-109, 1-118, 1-122, 1-123, 1-125, 1-127, 1-129, 1-130, 1-132, 1-153, 1-156, 1-157, 1-166~1-168, 1-175, 1-176, 1-177*, 1-182~1-184, 1-185*, 1-188*, 1-189*, 1-194, 1-206*, 1-207, 1-212, 1-214, 1-215, 1-225, 2-002, 2-003, 2-013, 2-019~2-021, 2-022*, 2-024~2-026, 2-028, 2-029, 2-031, 2-032, 2-034~2-039, 2-041, 2-042, 2-044~2-046, 2-047*, 2-048, 2-049, 2-050*, 2-051*, 2-052*, 2-054~2-056, 2-057*, 2-058*, 2-059*, 2-061*, 2-062*, 2-064, 2-065*, 2-067*, 2-068*, 3-006, 3-018, 3-026, 3-030, 3-032~3-035, 3-037, 3-043, 3-044, 3-047, 3-058, 3-060~3-064, 3-068*, 3-069, 3-070*, 3-071*, 3-072, 3-078, 3-079, 3-081, 3-083~3-086, 3-089, 3-090*, 3-091*, 3-093*, 3-094, 3-095, 3-098, 3-100*, 3-102, 3-103, 3-105*, 3-106, 3-107, 3-109, 3-110*, 3-111*, 3-112*, 3-113*, 3-114, 3-115, 3-116*, 3-117, 3-121, 3-123~3-126, 3-129, 3-131, 3-132*, 3-135, 3-136, 3-139, 3-140, 3-145, 3-148, 3-150, 3-151**, 4-003*, 4-004, 4-006*, 4-010,
5-001*, 5-002*, 5-003*, 5-004*, 5-005*, 5-006, 5-007, 5-008*, 5-009*, 5-010, 5-011, 5-012*, 5-013*, 5-014*, 5-015*, 5-016, 5-017, 5-019, 5-022*, 5-023*, 5-029*, 5-032, 5-034, 5-035, 5-036*, 5-037*, 5-038*, 5-039*, 5-040*, 5-041*, 5-042, 5-045*, 5-046*, 5-047*, 5-048*, 5-049*, 5-050*, 5-051*, 5-052*, 5-053*, 5-054, 5-057*, 5-058*, 5-059*, 5-060~5-064, 5-065*, 5-066~5-068, 5-069*, 5-070*, 5-071*, 5-072*, 5-073~5-075, 5-075(+)*, 5-076*, 5-077*, 5-078~5-081, 5-083*, 5-084, 5-085, 5-086*, 5-087*, 5-088*, 5-089*, 5-090, 5-091*, 5-092*, 5-093*, 5-094*, 5-099~5-101, 5-102*, 5-103*, 5-104*, 5-105*, 5-106, 5-109, 5-111*, 5-112, 5-113*, 5-114*, 5-115, 5-116, 5-117*, 5-118, 5-119*, 5-120, 5-121*, 5-122~5-126, 5-128*, 5-130, 5-132~5-134, 5-136, 5-137, 5-138*, 5-139*, 5-140~5-147, 5-148*, 5-149, 5-151, 5-151(+)*, 5-152~5-156, 5-159~5-169, 5-171~5-178, 5-179*, 5-180, 5-181, 5-182*, 5-183*, 5-184, 5-185*, 5-186*, 5-187*, 5-188*, 5-189, 5-189(+), 5-191*, 5-192*, 5-193~5-201, 5-202*, 5-203, 5-204, 5-205*, 5-206*, 5-207~5-209, 5-210*, 5-211*, 5-212*, 5-213*, 5-214*, 5-215*, 5-216*, 5-217, 5-218*, 5-219*, 5-219(+)*, 5-219(−), 5-220*, 5-221, 5-222*, 5-223*, 5-224*, 5-225, 5-226*, 5-227*, 5-228, 5-229, 5-230*, 5-231, 5-232*, 5-233*, 5-234*, 5-235, 5-236*, 5-237*, 5-239, 5-240*, 5-241*, 5-242*, 5-243~5-245, 5-246*, 5-247*, 5-249*, 5-250, 5-251, 5-254*, 5-256*, 5-257~5-259, 5-261*, 5-262, 5-263, 5-264*, 5-265*, 5-267, 5-268*, 5-269, 5-271, 5-272*, 5-273*, 5-274*, 5-275~5-277, 5-278*, 5-279*, 5-280, 5-282*, 5-283*, 5-284, 5-285*, 5-286*, 5-288*, 5-289*, 5-291*, 5-292, 5-294*, 5-295*, 5-296, 5-298, 5-299*, 5-300, 5-301*, 5-302, 5-303, 5-305, 5-306*, 5-307*, 5-308~5-311, 5-312*, 5-313*, 5-314*, 5-315*, 5-316, 5-317*, 5-318*, 5-319*, 5-320~5-322, 5-323*, 5-329*, 5-330*, 5-331*, 5-332, 5-333*, 5-334*, 5-335~5-337, 5-338*, 5-339*, 5-341, 5-342, 5-343*, 5-344*, 5-345, 5-346, 5-349*, 5-351, 5-353, 5-354, 5-355*, 5-356~5-359, 5-360*, 5-361*, 5-362*, 5-363, 5-374*, 5-375*, 5-376, 5-377, 5-378*, 5-379~5-386, 5-387*, 5-389*, 5-390*, 5-392*, 5-393*, 5-395, 5-396, 5-397*, 5-398*, 5-399*, 5-400*, 5-401*, 5-402*, 5-405~5-407, 5-408*, 5-409, 5-410*, 5-411*, 5-412*, 5-413*, 5-415*, 5-417*, 5-418*, 5-419*, 5-420*, 5-421*, 5-422*, 5-423*, 5-424*, 5-425*, 5-426*, 5-427*, 5-428*, 5-429*, 5-430*, 5-432*, 5-433*, 5-434*, 5-437, 5-438, 5-439*, 5-440*, 5-441*, 5-442*, 5-443*, 5-444*, 5-446*, 5-447, 5-452*, 5-453*, 5-454*, 5-455*, 5-458*, 5-459*, 5-460*, 5-461*, 5-462*, 5-463, 5-464, 5-465, 5-466, 5-467*, 5-468, 5-469, 5-470**, 5-471*, 5-472*, 5-473*, 5-474*, 5-475**, 5-476*, 5-477, 5-478, 5-479, 5-480*, 5-481~5-486, 5-487, 5-488, 5-489*, 5-490~5-493, 5-494, 5-495, 5-496, 5-497, 5-498, 5-499, 5-500*, 5-501, 5-503, 5-505, 5-507, 5-508, 5-509, 5-511, 5-513*, 5-514*, 5-515*, 5-516*, 5-517*, 5-518, 5-519*, 5-520*, 5-521, 5-522*, 5-523*, 5-526*, 5-527*, 5-528*, 5-529*, 5-530*, 5-531*, 5-532, 5-533*, 5-535, 5-536*, 5-537*, 5-538*, 5-539*, 5-540(+), 5-541*, 5-541 (R), 5-541(S)*, 5-542, 5-543*, 5-545, 5-546, 5-548*, 5-549*, 5-551*, 5-552*, 5-553*, 5-554*, 5-555*, 5-556, 5-557*, 5-558*, 5-559, 5-560, 5-562, 5-565, 5-566*, 5-568*, 5-569*, 5-570*, 5-571, 5-572*, 5-573*, 5-574*, 5-575*, 5-576*, 5-577*, 5-578*, 5-579*, 5-580*, 5-581*, 5-582*, 5-583*, 5-584*, 5-585*, 5-586*, 5-587*, 5-588*, 5-589*, 5-590*, 5-592, 5-593*, 5-594*, 5-595*, 5-596*, 5-598*, 5-599*, 5-600*, 5-601*, 5-602, 5-603, 5-604*, 5-605, 5-606, 5-607*, 5-608**, 5-609, 5-610, 5-611*, 5-612, 5-613, 5-614*, 5-615*, 5-616*, 5-617*, 5-618, 5-619*, 5-621, 5-623*, 5-624*, 5-625*, 5-626, 5-627, 5-628, 5-629*, 5-630*, 5-631*, 5-632*, 5-633*, 5-634*, 5-635*, 5-636, 5-637*, 5-638*, 5-639*, 5-641*, 5-642**, 5-643*, 5-644**, 5-645*, 5-646, 5-647, 5-648*, 5-650, 5-651, 5-653*, 5-654*, 5-655, 5-656, 5-657**, 5-659*, 5-660**, 5-661*, 5-662, 5-664, 5-665*, 5-666**, 5-667*, 5-668*, 5-669*, 5-670*, 5-671, 5-672, 5-674, 5-676, 5-678, 5-684, 5-685, 5-686**, 6-001*, 6-002, 6-003*, 6-004~6-006, 6-007*, 6-008*, 6-010, 6-012, 6-013, 6-015, 6-016, 6-017*, 6-018, 6-019*, 6-020*, 6-021*, 6-022~6-025, 6-026*, 6-027*, 6-028~6-030, 6-031*, 6-032*, 6-033*, 6-034*, 6-035*, 6-036~6-038, 6-039*, 6-040, 6-041, 6-042*, 6-043*, 6-044, 6-045, 6-046*, 6-047*, 6-048*, 6-049*, 6-050*, 6-051*, 6-053, 6-054*, 6-055*, 6-056, 6-058~6-067, 6-071, 6-074*, 6-075*, 6-076*, 6-077*, 6-078*, 6-079*, 6-080*, 6-080(+)*, 6-080(−)*, 6-082*, 6-083*, 6-084*, 6-086, 6-087, 6-089*, 6-090*, 6-091*, 6-092, 6-093, 6-094, 6-095, 6-096*, 6-098*, 6-099, 6-100, 6-101, 6-102, 6-103, 6-104*, 6-105, 6-106*, 6-110*, 6-111*, 6-112*, 6-114*, 6-120, 6-121*, 6-123*, 6-124*, 6-125**, 6-126*, 6-129*, 6-130, 6-131, 6-132, 6-133, 7-001, 7-002*, 7-003*, 7-004*, 7-005*, 7-006*, 7-007*, 7-008*, 7-009*, 7-010*, 8-002*, 8-003*, 8-004, 8-005, 8-006*, 8-007*, 9-009, 10-001~10-005, 10-006*, 11-024, 11-025*, 11-026*, 11-038, 11-049*, 11-052, 11-055, 11-056, 11-061, 11-062, 11-066, 11-070, 11-098*, 11-099*, 11-108*, 11-109*, 11-119, 11-120*, 1-124*, 1125*, 1129, 12-001, 12-002, 12-008.
In the interim, the indication of "*" shows that the insecticidal test was carried out by use of a chemical solution of a concentration of 100 ppm.

Test Example 3

Insecticidal Test Against Beet Armyworm

A 10% emulsifiable concentrate (depending on the compounds, 10% wettable powder was applied for the test) of the compound of the present invention was diluted with water containing a spreading agent to prepare a chemical solution with a concentration of 100 ppm. To the chemical solution was dipped leaves of cabbage for about 10 seconds, and after air-drying, they were placed in a laboratory dish, then 5-beet armyworm (*Spodoptera exigua*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention: No. 1-015, 1-016, 1-057, 1-058, 1-062~1-064, 1-066, 1-080, 1-081, 1-088, 1-102, 1-105, 1-106, 1-109, 1-118, 1-122, 1-123, 1-125, 1-127, 1-151, 1-153, 1-155~1-157, 1-166, 1-175, 1-189, 1-207, 1-214, 1-215, 2-003, 2-019, 2-020, 3-026, 3-027, 3-030, 3-032, 3-037, 3-060, 3-091, 3-093, 3-095, 3-109, 3-110, 3-112, 3-125, 5-001~5-005, 5-008, 5-009, 5-029, 5-036, 5-037, 5-040, 5-041, 5-045, 5-046, 5-048, 5-049, 5-050, 5-052, 5-053, 5-057~5-059, 5-061~5-065, 5-067~5-069, 5-071, 5-073~5-075, 5-075(+), 5-076, 5-083, 5-086~5-089, 5-091, 5-092, 5-094, 5-111, 5-113, 5-117~5-119, 5-122, 5-138~5-142, 5-147, 5-148, 5-151, 5-160, 5-165, 5-174, 5-182, 5-183, 5-185~5-188, 5-189(+), 5-202, 5-205, 5-210~5-212, 5-214~5-216, 5-218, 5-219, 5-219(+), 5-220, 5-223, 5-226, 5-227, 5-230, 5-232~5-234, 5-236, 5-239, 5-241, 5-247, 5-251, 5-257, 5-261, 5-264, 5-268, 5-273~5-275, 5-279, 5-282, 5-283, 5-285, 5-286, 5-288, 5-291, 5-294, 5-295, 5-301, 5-306, 5-307, 5-309, 5-310, 5-312~5-315, 5-320, 5-321, 5-323, 5-331~5-334, 5-339, 5-341, 5-355~5-357, 5-360~5-362, 5-374, 5-375, 5-378, 5-387, 5-389, 5-390, 5-397, 5-398, 5-412, 5-429, 5-433, 5-440, 5-474, 5-476, 5-478, 5-480, 5-488, 5-494, 5-495, 5-588, 5-604, 5-638, 5-642, 6-017~6-021, 6-026, 6-027, 6-031, 6-033~6-041, 6-043~6-045, 6-048, 6-049, 6-058, 6-059, 6-063~6-066, 6-074~6-076, 6-095, 6-131, 7-002, 7-003, 7-005~7-009, 8-002, 11-024, 11-025, 11-026.

Test Example 4

Insecticidal Test Against Oriental Tea Tortix

A 10% emulsifiable concentrate (depending on the compounds, 10% wettable powder was applied for the test) of the compound of the present invention was diluted with water containing a spreading agent to prepare a chemical solution with a concentration of 100 ppm. To the chemical solution was dipped leaves of cabbage for about 10 seconds, and after air-drying, they were placed in a laboratory dish, then 5-oriental tea tortix (*Homona magnanima*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention: No. 1-015, 1-016, 1-057, 1-058, 1-062, 1-080, 1-105, 1-107, 1-0122, 1-123, 1-125, 1-127, 1-153, 1-156, 1-189, 1-207, 1-214, 1-215, 2-003, 2-034, 2-035, 2-051, 2-052, 3-037, 3-060, 3-095, 3-110, 3-112, 3-125, 3-129, 4-003, 5-001, 5-003~5-005, 5-008, 5-009, 5-012, 5-013, 5-022, 5-029, 5-037, 5-040, 5-041, 5-045~5-050, 5-052, 5-053, 5-057~5-059, 5-061~5-065, 5-069~5-071, 5-073, 5-075, 5-075(+), 5-076, 5-077, 5-083, 5-086~5-090, 5-092~5-094, 5-102, 5-103, 5-111, 5-113, 5-114, 5-117, 5-119, 5-121, 5-122, 5-138~5-142, 5-147, 5-148, 5-151, 5-151(+), 5-156, 5-160, 5-161, 5-165, 5-166, 5-180, 5-182, 5-183, 5-185, 5-187, 5-188, 5-189(+), 5-202, 5-205, 5-208, 5-210~5-212, 5-214~5-216, 5-218, 5-219, 5-219(+), 5-220, 5-221, 5-223, 5-226~5-228, 5-230, 5-232~5-234, 5-236, 5-240~5-242, 5-246, 5-247, 5-251, 5-254, 5-273~5-275, 5-279, 5-282, 5-283, 5-285, 5-286, 5-288, 5-289, 5-291, 5-294, 5-295, 5-301, 5-306, 5-307, 5-310, 5-312, 5-313, 5-315, 5-319, 5-321, 5-323, 5-329, 5-330, 5-338, 5-339, 5-341, 5-356, 5-357, 5-359, 5-360, 5-362, 5-374, 5-375, 5-378, 5-379, 5-381, 5-387~5-390, 5-392, 5-393, 5-395~5-399, 5-401, 5-412, 5-418, 5-419, 5-426, 5-429, 5-430, 5-433, 5-434, 5-441, 5-458~5-461, 5-463~5-465, 5-468, 5-470, 5-472, 5-474, 5-476~5-478, 5-480, 5-488, 5-494, 5-515, 5-519, 5-523, 5-539, 5-541, 5-541(S), 5-553, 5-554, 5-576, 5-579, 5-585, 5-588, 5-594, 5-601, 5-604, 5-606, 5-612, 5-617, 5-638, 5-642, 5-655, 5-656, 6-001, 6-003, 6-017, 6-018, 6-020, 6-021, 6-027, 6-031, 6-033~6-035, 6-038~6-041, 6-043, 6-066, 6-075, 6-076, 6-081, 6-093, 6-095, 6-124, 6-131, 7-002~7-009, 8-002, 11-024, 11-026.

Test Example 5

Insecticidal Test Against Corn Earworm

A 10% emulsifiable concentrate (depending on the compounds, 10% wettable powder was applied for the test) of the compound of the present invention was diluted with water containing a spreading agent to prepare a chemical solution with a concentration of 100 ppm. To the chemical solution was dipped leaves of cabbage for about 10 seconds, and after air-drying, they were placed in a laboratory dish, then 1-corn earworm (*Helicoverpa armigera*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with twelve districts.

As a result, the following compounds showed an insecticidal rate of 80% or more among the compounds tested.

The compounds of the present invention: No. 1-066, 1-153, 1-156, 1-207, 1-214, 1-215, 2-034, 2-035, 2-042, 2-055, 2-057, 2-059, 2-062, 2-063, 2-067, 2-068, 3-027, 3-030, 3-032, 3-086, 3-095, 3-109, 3-110, 3-112, 3-151, 5-008, 5-009, 5-022, 5-040, 5-046, 5-047, 5-049, 5-050, 5-052, 5-053, 5-057~5-059, 5-061~5-063, 5-065, 5-068, 5-070, 5-071, 5-075, 5-075(+), 5-076, 5-077, 5-083, 5-086~5-089, 5-099~5-101, 5-109, 5-113, 5-117, 5-120~5-122, 5-126, 5-138, 5-139, 5-141, 5-142, 5-147, 5-148, 5-151, 5-151(+), 5-156, 5-160, 5-165, 5-169, 5-177, 5-180, 5-185, 5-189(+), 5-193, 5-208, 5-210~5-212, 5-214~5-219, 5-219(+), 5-223, 5-227, 5-228, 5-230, 5-231, 5-233, 5-234, 5-236, 5-241, 5-245, 5-246, 5-249, 5-251, 5-254, 5-261, 5-264, 5-269, 5-273~5-275, 5-279, 5-284, 5-286, 5-291, 5-294, 5-295, 5-306, 5-307, 5-309, 5-310, 5-312~5-315, 5-319, 5-323, 5-331~5-336, 5-338, 5-339, 5-341, 5-353~5-355, 5-357, 5-359, 5-360, 5-374, 5-375, 5-378~5-381, 5-383, 5-384, 5-387, 5-389, 5-390, 5-393, 5-395, 5-397~5-400, 5-408~5-413, 5-415, 5-420~5-424, 5-426, 5-427, 5-429, 5-433, 5-434, 5-440, 5-443, 5-446, 5-452~5-454, 5-458~5-470, 5-473~5-481, 5-483, 5-484, 5-487~5-489, 5-494~5-499, 5-508~5-511, 5-513, 5-515~5-517, 5-519, 5-522, 5-523, 5-526~5-529, 5-531~5-533, 5-538, 5-539, 5-541, 5-541(S), 5-543, 5-548, 5-549, 5-558~5-560, 5-566, 5-568, 5-570, 5-572~5-577, 5-579~5-589, 5-595, 5-599~5-601, 5-604, 5-606~5-608, 5-611, 5-612, 5-614~5-619, 5-623~5-625, 5-627~5-639, 5-641~5-646, 5-654~5-657, 5-660~5-662, 5-664~5-668, 5-671, 5-672, 5-674, 5-676, 5-684, 5-685, 6-003, 6-004, 6-016~6-019, 6-021, 6-023, 6-024, 6-026, 6-027, 6-031, 6-033~6-041, 6-043~6-045, 6-048, 6-049, 6-056, 6-066, 6-074~6-080, 6-080(+), 6-080(−), 6-081~6-084, 6-091~6-095, 6-098, 6-100, 6-102~6-106, 6-110, 6-111, 6-124, 6-126, 6-130~6-132, 7-002~7-009, 8-002, 8-005~8-007, 10-006, 11-024, 11-125, 11-130.

Test Example 6

Insecticidal Test Against Peach Fruit Moth

A 10% emulsifiable concentrate (depending on the compounds, 10% wettable powder was applied for the test) of the compound of the present invention was diluted with water containing a spreading agent to prepare a chemical solution with a concentration of 100 ppm. To the chemical solution was dipped apple young fruits on which peach fruit moth (*Carpocina sasakii*) laid eggs (20-egg/fruit) for about 10 seconds, and after air-drying, they were placed in a laboratory dish, and the dish was covered with a lid and contained at a thermostat chamber at 25° C. A number of dead insect(s) after 20 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 5-049, 5-050, 5-070, 5-076, 5-083, 5-088, 5-111, 5-148, 5-219, 5-219(+), 5-221, 5-234, 5-286, 5-291, 5-323, 5-360, 5-387, 5-390, 5-398, 5-480, 5-494, 6-027, 6-039, 7-008.

Test Example 7

Insecticidal Test Against *Frankliniella occidentalis*

A wet filter paper was laid in a styrol cup having an inner diameter of 7 cm, a leaf of a common bean cut out so as to have the same diameter was laid theron, and 10-*Frankliniella occidentalis* with first instar larva per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 2 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-175, 1-177~1-179, 1-182, 2-020, 2-022, 2-028*, 2-029*, 2-032, 2-033, 2-034*, 2-035*, 2-037*, 2-038*, 2-039*, 2-040*, 2-041*, 2-042*, 2-043*, 2-044*, 2-045*, 2-046*, 2-047, 2-048*, 2-049*, 2-050~2-052, 2-057~2-068, 3-068, 3-072*, 3-080, 3-084~3-086, 3-090, 3-093, 3-105, 3-107, 3-109, 3-110, 3-1,2,3-114, 3-122~3-125, 3-132, 3-135, 3-136, 3-151, 4-004, 4-006, 5-001, 5-003, 5-009, 5-013, 5-022, 5-023, 5-029, 5-037~5-041, 5-044~5-053, 5-057~5-075, 5-075(+), 5-076~5-078, 5-081~5-089, 5-090*, 5-091~5-094, 5-099~5-105, 5-109, 5-111~5-119, 5-120*, 5-121~5-123, 5-124*, 5-126~5-128, 5-129*, 5-130, 5-131*, 5-134, 5-137~5-142, 5-143*, 5-144, 5-145, 5-146*, 5-147, 5-148, 5-150, 5-151, 5-151(+), 5-153*, 5-154, 5-156, 5-158~5-160, 5-161*, 5-162, 5-164~5-166, 5-167*, 5-168*, 5-169, 5-171, 5-172*, 5-178~5-188, 5-189(+), 5-190(+), 5-191~5-194, 5-201, 5-202, 5-205~5-207, 5-208*, 5-210~5-216, 5-217*, 5-218, 5-219, 5-219(+), 5-219(−), 5-220~5-234, 5-236~5-242, 5-244~5-247, 5-249, 5-251~5-254, 5-255*, 5-256, 5-257, 5-258*, 5-259~5-261, 5-264, 5-265, 5-269*, 5-270, 5-271*, 5-272~5-283, 5-284~5-289, 5-291, 5-292, 5-294, 5-295, 5-297, 5-299, 5-300, 5-301, 5-302*, 5-303, 5-306, 5-307, 5-309, 5-310*, 5-311~5-315, 5-318, 5-319, 5-321~5-323, 5-329~5-336, 5-338, 5-339, 5-341~5-346, 5-348, 5-349, 5-353~5-358, 5-360~5-362, 5-374, 5-375, 5-378, 5-379*, 5-380*, 5-381*, 5-383, 5-384, 5-385*, 5-387~5-393, 5-395, 5-396*, 5-397~5-401, 5-403~5-406, 5-408~5-413, 5-415, 5-417~5-430, 5-432~5-434, 5-439~5-443, 5-445, 5-446, 5-449, 5-452, 5-453, 5-455, 5-458~5-503, 5-507~5-512, 5-514~5-516, 5-518, 5-519, 5-521~5-525, 5-527~5-534, 5-537~5-539, 5-541, 5-541(S), 5-542, 5-543, 5-545~5-549, 5-550~5-562, 5-564, 5-565, 5-567~5-576, 5-579~5-590, 5-592, 5-599~5-601, 5-604~5-609, 5-611, 5-612, 5-614~5-619, 5-621, 5-623, 5-624, 5-626~5-639, 5-641~5-648, 5-650, 5-651, 5-653~5-672, 5-674, 5-676, 5-678, 5-684~5-686, 6-001~6-003, 6-004*, 6-005*, 6-006*, 6-007~6-013, 6-015*, 6-016~6-021, 6-022*, 6-023, 6-024*, 6-025*, 6-026~6-050, 6-054~6-056, 6-058, 6-059, 6-063, 6-066, 6-070, 6-071*, 6-074~6-080, 6-080(+), 6-080(−), 6-081~6-086, 6-089~6-111, 6-113~6-115, 6-117, 6-119~6-124, 6-126, 6-127, 6-129~6-133, 7-001, 7-003~7-010, 8-002, 8-003, 8-005, 8-006, 10-002, 10-005, 10-006, 11-024~11-026, 11-043, 11-045, 11-054~11-056, 11-059, 11-070, 11-089, 11-099, 11-107, 11-114, 11-120, 11-125, 11-128~11-130, 11-132, 12-002, 12-007, 12-008.
In the interim, the indication of "*" shows that the insecticidal test was carried out by use of a chemical solution of a concentration of 100 ppm.

Test Example 8

Insecticidal Test Against *Thrips palmi*

A wet filter paper was laid in a styrol cup having an inner diameter of 7 cm, a leaf of a common bean cut out so as to have the same diameter was laid thereon, and 10-*Thrips palmi* in the stage of adult per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 100 ppm. The chemical solution was sprayed with a rotating spray tower in an amount of 2.5 ml per styrol cup, and the styrol cups were covered with lids and contained at a thermostat chamber at 25° C. A number of dead insect(s) after 2 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention: No. 1-179, 1-196, 2-022, 2-024~2-026, 2-028, 2-029, 2-033, 2-035, 2-039, 2-044~2-048, 2-050~2-052, 2-057~2-059, 2-061, 2-063, 2-065, 2-067, 3-079, 3-085, 3-086, 3-091, 3-110, 3-112, 3-124, 3-131, 3-148, 3-151, 4-003~4-005, 4-010, 5-001, 5-003, 5-006, 5-008, 5-012~5-015, 5-022, 5-023, 5-029, 5-036, 5-037, 5-040, 5-045~5-053, 5-057~5-063, 5-065, 5-067, 5-068, 5-070~5-075, 5-075(+), 5-076~5-079, 5-081~5-084, 5-086~5-093, 5-099, 5-102~5-104, 5-111~5-114, 5-117~5-121, 5-124, 5-128~5-130, 5-137~5-148, 5-151, 5-151(+), 5-153, 5-156, 5-160~5-162, 5-165, 5-166, 5-179, 5-180, 5-182~5-186, 5-188, 5-189(+), 5-193, 5-202, 5-205, 5-206, 5-208~5-210, 5-214~5-216, 5-218, 5-219, 5-219(+), 5-220, 5-224~5-226, 5-228~5-230, 5-232~5-234, 5-236, 5-238, 5-239, 5-242, 5-246, 5-247, 5-251, 5-256~5-258, 5-261, 5-264, 5-269, 5-273~5-276, 5-278, 5-279, 5-280, 5-282, 5-283, 5-285, 5-286, 5-288, 5-289, 5-291, 5-294, 5-295, 5-299, 5-303, 5-306, 5-309, 5-310, 5-312~5-314, 5-319, 5-322, 5-323, 5-329, 5-330, 5-332, 5-334, 5-335, 5-338, 5-339, 5-346, 5-349, 5-353~5-362, 5-374, 5-375, 5-378~5-381, 5-383~5-385, 5-387, 5-389, 5-390, 5-395~5-401, 5-408~5-413, 5-415, 5-418~5-424, 5-426, 5-427, 5-429, 5-430, 5-432~5-434, 5-439~5-443, 5-446, 5-452~5-455, 5-458~5-470, 5-471~5-492, 5-494~5-501, 5-508~5-513, 5-515, 5-516, 5-519, 5-521~5-523, 5-525, 5-527~5-531, 5-533, 5-536, 5-538, 5-539, 5-541, 5-541(S), 5-543, 5-547, 5-549, 5-553~5-555, 5-560, 5-564, 5-568~5-570, 5-572~5-576, 5-579, 5-581, 5-582, 5-584~5-590, 5-593, 5-598~5-601, 5-604~5-609, 5-611~5-613, 5-616~5-619, 5-621, 5-623~5-625, 5~627~5-639, 5-641~5-648, 5-650, 5-651, 5-655~5-657, 5-659~5-662, 5-664~5-669, 5-672, 5-674, 5-676, 5-684, 5-685, 6-001, 6-003~6-008, 6-015, 6-017~6-024, 6-026~6-035, 6-037~6-041, 6-043~6-045, 6-047~6-049, 6-054~6-056, 6-058, 6-059, 6-063, 6-066, 6-070, 6-073~6-080, 6-080 (+), 6-080(−), 6-081~6-084, 6-089, 6-090, 6-092~6-096, 6-098~6-107, 6-109~6-111, 6-114, 6-115, 6-120, 6-121, 6-123, 6-124, 6-130~6-133, 7-003, 7-005~7-009, 8-002, 8-006, 8-007, 9-011, 10-002, 10-006, 11-025, 11-026, 11-054, 11-056, 11-059, 11-125, 11-129, 12-002, 12-008.

Test Example 9

Insecticidal Test Against *Eysarcoris lewisi*

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leave sheaths of rice for about 10 seconds, and after air-drying, they were placed in a test tube, then 5-*Eysarcoris lewisi* in the stage of first instar larva per the test tube were released therein, and the test tube was covered with a sponge and contained at a thermostat chamber at 25° C. A number of dead insect(s) after 2 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention:
No. 1-015, 1-050, 1-051, 1-175, 1-209, 2-029, 2-034, 2-035, 2-042, 2-044~2-052, 2-054, 2-055, 2-057~2-059, 2-061, 2-062, 2-065, 2-067, 2-068, 3-047, 3-068, 3-070~3-072, 3-086, 3-090, 3-093, 3-106, 3-109~3-112, 3-114, 3-125, 3-131, 3-151, 5-001, 5-003, 5-005, 5-008, 5-009, 5-013~5-015, 5-017, 5-022, 5-023, 5-026, 5-029, 5-037~5-041, 5-045~5-053, 5-058~5-065, 5-067~5-069, 5-071~5-075, 5-075(+), 5-076~5-078, 5-081, 5-083, 5-084~5-094, 5-099~5-105, 5-111~5-114, 5-116~5-122, 5-124, 5-126, 5-128, 5-130, 5-134, 5-137~5-142, 5-144, 5-145, 5-147, 5-148, 5-150, 5-151, 5-151(+), 5-154, 5-156, 5-158~5-162, 5-165, 5-166, 5-168, 5-169, 5-171, 5-173, 5-174, 5-179~5-189, 5-189(+), 5-191, 5-195~5-197, 5-203, 5-205, 5-206, 5-208~5-210, 5-212~5-216, 5-218, 5-219, 5-219(+), 5-220~5-230, 5-232, 5-233, 5-235, 5-236, 5-238~5-247, 5-249, 5-251, 5-254, 5-256~5-262, 5-264, 5-265, 5-273~5-279, 5-283, 5-285, 5-286, 5-288, 5-289, 5-291, 5-294, 5-295, 5-299~5-301, 5-304~5-310, 5-312~5-315, 5-318~5-321, 5-323, 5-329, 5-330, 5-332, 5-334, 5-335, 5-338, 5-339, 5-341~5-344, 5-346, 5-348, 5-353~5-360, 5-362, 5-374~5-387, 5-389, 5-390, 5-392, 5-393, 5-395~5-401, 5-403~5-405, 5-408~5-413, 5-415, 5-417~5-424, 5-426~5-429, 5-431~5-434, 5-440, 5-443, 5-445, 5-446, 5-448, 5-452~5-455, 5-457~5-465, 5-467~5-470, 5-472~5-478, 5-480, 5-487~5-489, 5-491, 5-492, 5-494~5-500, 5-505, 5-509, 5-510, 5-512, 5-515~5-517, 5-519~5-523, 5-526~5-533, 5-537~5-539, 5-541, 5-541(S), 5-543, 5-546, 5-547, 5-549, 5-551~5-558, 5-562, 5-568~5-570, 5-572~5-577, 5-579, 5-582~5-588, 5-593, 5-595, 5-598, 5-600, 5-601, 5-604, 5-606, 5-611, 5-612, 5-614~5-617, 5-619, 5-621, 5-623, 5-627, 5-631, 5-635~5-638, 5-642, 5-643, 5-646, 5-648, 5-654~5-657, 5-660, 5-661, 5-664, 5-668, 5-670, 5-672, 5-674, 5-684~5-686, 6-001, 6-006~6-013, 6-015~6-024, 6-026~6-029, 6-031~6-051, 6-054~6-056, 6-058~6-060, 6-062~6-067, 6-070, 6-071, 6-074~6-080, 6-080(+), 6-080(−), 6-081~6-086, 6-089~6-093, 6-095, 6-098~6-103, 6-110~6-112, 6-114~6-118, 6-121, 6-124, 6-129~6-132, 7-002~7-010, 10-006, 11-060, 11-098, 11-125.

Test Example 10

Insecticidal Test Against Brown Rice Planthopper

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leave sheaths of rice for about 10 seconds, and after air-drying, they were placed in a test tube, then 5-brown rice planthopper (*Nilaparvata lugens*) in the second instar larva per the test tube were released therein, and the test tube was covered with a sponge and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-005~1-007, 1-017, 1-061, 1-154, 1-175, 1-185, 1-188, 1-189, 2-018, 2-020, 2-025~2-027, 2-029, 2-033, 2-034, 2-036, 2-044, 2-046, 2-051, 2-052, 2-054, 2-057~2-059, 2-062, 2-065, 2-068, 3-013, 3-068, 3-070, 3-072, 3-075, 3-109, 3-112, 3-125, 3-151, 5-001, 5-003, 5-009, 5-013, 5-015, 5-023, 5-029, 5-040, 5-041, 5-049, 5-050, 5-053, 5-058, 5-060, 5-061, 5-063, 5-065~5-068, 5-070~5-074, 5-075(+), 5-076, 5-077, 5-080, 5-081, 5-083, 5-084, 5-086~5-088, 5-090~5-094, 5-099, 5-102, 5-106, 5-111, 5-113, 5-117~5-120, 5-130, 5-138~5-148, 5-151, 5-151(+), 5-152~5-156, 5-160, 5-161, 5-163, 5-170, 5-173, 5-174, 5-182, 5-186, 5-189, 5-189(+), 5-195, 5-197, 5-203, 5-205, 5-208, 5-210, 5-212, 5-214, 5-216, 5-219, 5-219(+), 5-220, 5-226, 5-230~5-232, 5-234~5-236, 5-239, 5-240, 5-242, 5-243, 5-245, 5-246, 5-251, 5-254, 5-257, 5-258, 5-261, 5-262, 5-264, 5-265, 5-273~5-275, 5-279, 5-280, 5-285, 5-286, 5-288, 5-294, 5-295, 5-305~5-310, 5-313, 5-315, 5-323, 5-330, 5-335, 5-339, 5-341, 5-344, 5-353~5-360, 5-374~5-377, 5-379~5-388, 5-390, 5-392, 5-393, 5-396, 5-398~5-401, 5-405, 5-410, 5-412, 5-413, 5-419, 5-421~5-423, 5-426, 5-427, 5-429, 5-432, 5-433, 5-440, 5-453, 5-455, 5-460, 5-461, 5-463~5-465, 5-467, 5-470, 5-472~5-476, 5-482, 5-483, 5-487, 5-490~5-492, 5-494~5-496, 5-498, 5-499, 5-501, 5-510~5-512, 5-515, 5-519, 5-521, 5-523, 5-525, 5-527~5-530, 5-532, 5-537~5-539, 5-541, 5-541(S), 5-546, 5-547, 5-550~5-554, 5-560, 5-568, 5-570, 5-572~5-576, 5-579, 5-583, 5-585, 5-586, 5-588, 5-608, 5-614, 5-617, 5-619, 5-621, 5-627, 5-628, 5-636, 5-637, 5-642, 5-646, 5-648, 5-651, 5-654, 5-656, 5-657, 5-660, 5-662, 5-664, 5-670, 5-672, 5-674, 5-684, 5-686, 6-001, 6-003, 6-007, 6-015~6-023, 6-027~6-045, 6-048~6-050, 6-056, 6-058~6-065, 6-076~6-080, 6-080 (+), 6-080(−), 6-081~6-083, 6-086, 6-090~6-093, 6-096, 6-098, 6-100~6-103, 6-105, 6-114, 6-115, 6-117, 6-124, 6-125, 6-130~6-132, 7-001~7-004, 7-006, 7-008, 7-009, 8-003, 9-009, 11-039, 11-041, 11-054, 11-098, 11-101, 11-132.

Test Example 11

Insecticidal Test Against *Bemisia argentifolii*

A wet filter paper was laid in a styrol cup having an inner diameter of 7 cm, a leaf of a tomato cut out on which *Bemisia argentifolii* laid eggs (10-egg/leaf) was laid thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-011, 1-182, 2-024*, 2-025*, 2-026*, 2-028*, 2-029*, 2-033, 2-034*, 2-035*, 2-037*, 2-044*, 2-047, 2-050, 2-051, 2-058~2-062, 2-065, 2-066, 3-068, 3-079, 3-090, 3-112, 3-125, 3-151, 4-003, 4-006, 5-001, 5-003, 5-005, 5-007, 5-009, 5-011, 5-013~5-015, 5-021~5-023, 5-029, 5-035, 5-037~5-041, 5-045~5-053, 5-057~5-061, 5-063, 5-065, 5-067~5-075, 5-075(+), 5-076~5-078, 5-079*, 5-081, 5-084~5-089, 5-090*, 5-091~5-094, 5-099~5-104, 5-112~5-114, 5-117, 5-118, 5-120*, 5-122, 5-123, 5-126, 5-128, 5-130, 5-137~5-142, 5-143*, 5-144, 5-145, 5-146*, 5-148, 5-151, 5-151(+), 5-153, 5-154, 5-156, 5-158~5-160, 5-161*, 5-162, 5-164, 5-165, 5-167*, 5-171, 5-180, 5-182~5-188, 5-189(+), 5-191, 5-193, 5-201, 5-202, 5-205~5-207, 5-208*, 5-209~5-216, 5-218, 5-219, 5-219(+), 5-220~5-223, 5-225~5-234, 5-236, 5-238~5-242, 5-245~5-247, 5-249, 5-254, 5-258*, 5-261, 5-264, 5-273~5-275, 5-277~5-279, 5-281, 5-285~5-288, 5-291, 5-292, 5-294, 5-295, 5-297, 5-299, 5-301, 5-306, 5-309, 5-310*, 5-312~5-315, 5-318, 5-319, 5-321, 5-323, 5-330, 5-332, 5-335, 5-339, 5-341, 5-344, 5-345, 5-353-5-358, 5-359*, 5-360, 5-362, 5-374, 5-375, 5-378, 5-379*, 5-380*, 5-381*, 5-383, 5-384, 5-385*, 5-387~5-393, 5-396*, 5-397~5-401, 5-405, 5-409, 5-410, 5-412, 5-417, 5-418, 5-421~5-423, 5-426~5-428, 5-430, 5-433, 5-434, 5-440, 5-446, 5-453, 5-455, 5-458, 5-460, 5-461, 5-463~5-465, 5-468~5-488, 5-490~5-498, 5-509, 5-510, 5-515, 5-516, 5-519, 5-521~5-523, 5-525, 5-527~5-532, 5-538, 5-539, 5-541, 5-543, 5-549, 5-551~5-555, 5-557, 5-558, 5-560, 5-562, 5-569~5-576, 5-579, 5-583~5-589, 5-600, 5-604~5-607, 5-611, 5-612, 5-616~5-619, 5-623, 5-628, 5-630, 5-631, 5-637~5-639, 5-642, 5-646~5-648, 5-650~5-657, 5-660~5-662, 5-664, 5-665, 5-667, 5-668, 5-671, 5-672, 5-674, 5-684~5-686, 6-001, 6-003, 6-009, 6-011~6-013, 6-016~6-018, 6-020, 6-021, 6-022*, 6-027, 6-028, 6-031~6-041, 6-043, 6-044, 6-048~6-050, 6-056, 6-074~6-076, 6-078, 6-079, 6-081, 6-083, 6-089, 6-090, 6-093, 6-095, 6-096, 6-098, 6-100, 6-102, 6-110, 6-114, 6-124, 6-130~6-132, 7-001, 7-003~7-006, 7-008~7-010, 11-017, 11-024, 11-026, 11-028, 11-056, 11-099, 11-120, 11-125, 11-132.

In the interim, the indication of "*" shows that the insecticidal test was carried out by use of a chemical solution of a concentration of 100 ppm.

Test Example 12

Insecticidal Test Against Green Peach Aphid

A wet cotton wool was laid in a laboratory dish having an inner diameter of 3 cm, a leaf of a cabbage cut out so as to have the same diameter was laid theron, and 4-green peach aphid (*Myzus persicae*) in the stage of no-wing adult was left. After 1 day, a 10% emulsifiable concentrate (depending on the compounds, 10% wettable powder was applied for the test) of the compound of the present invention was diluted with water containing a spreading agent to prepare a chemical solution with a concentration of 500 ppm, and the chemical solution was sprayed with a rotating spray tower (2.5 mg/cm$^2$), and the laboratory dish was covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention:
No. 1-006, 1-063, 1-067, 1-069, 1-153, 1-158, 1-163, 1-166, 1-167, 1-171, 1-175, 1-207, 1-209, 1-215, 2-005, 2-015, 2-017, 2-024*, 2-025*, 2-026*, 2-027, 2-029*, 2-034*, 2-044*, 2-046*, 2-050, 2-051, 2-057~2-059, 2-062, 2-065, 2-066, 3-006, 3-029, 3-064, 3-068, 3-089, 3-110, 3-114, 3-125, 3-131, 3-139, 3-143, 4-003, 5-001, 5-003, 5-005, 5-009, 5-013, 5-015, 5-022, 5-023, 5-037~5-041, 5-045~5-050, 5-052, 5-053, 5-056, 5-058~5-061, 5-063, 5-065~5-068, 5-070~5-075, 5-075(+), 5-076, 5-077, 5-079*, 5-081, 5-083~5-086, 5-090*, 5-091~5-094, 5-099, 5-100, 5-102, 5-103, 5-113, 5-117, 5-118, 5-128, 5-130, 5-134, 5-138~5-142, 5-143, 5-144, 5-145, 5-146, 5-147, 5-148, 5-151, 5-151(+), 5-153*, 5-154, 5-156, 5-158, 5-160, 5-161*, 5-162, 5-165, 5-180~5-187, 5-189(+), 5-193, 5-202, 5-205, 5-209, 5-210, 5-212, 5-214~5-216, 5-219, 5-219(+), 5-220~5-223, 5-226, 5-228, 5-230, 5-231, 5-233, 5-234, 5-236, 5-238, 5-240, 5-242, 5-243*, 5-245~5-247, 5-251, 5-254, 5-256, 5-258*, 5-259, 5-261, 5-264, 5-272~5-275, 5-277~5-280, 5-282, 5-284~5-288, 5-291, 5-294, 5-295, 5-300, 5-301, 5-306, 5-307, 5-309, 5-310*, 5-313~5-315, 5-320, 5-321, 5-323, 5-330, 5-334, 5-335, 5-339, 5-341, 5-343, 5-344, 5-348, 5-352, 5-353~5-358, 5-359*, 5-360, 5-362, 5-364, 5-374, 5-375, 5-378, 5-379*, 5-380*, 5-383, 5-384, 5-385*, 5-387, 5-389, 5-390, 5-392, 5-393, 5-398, 5-399, 5-401, 5-409, 5-410, 5-415, 5-418, 5-421~5-424, 5-427, 5-428, 5-433, 5-434, 5-440~5-442, 5-446, 5-453, 5-455, 5-458~5-465, 5-468, 5-470~5-484, 5-486, 5-487, 5-490, 5-491, 5-494~5-499, 5-510, 5-512, 5-515, 5-516, 5-519, 5-523, 5-527~5-529, 5-532, 5-538, 5-541, 5-541(S), 5-546, 5-551~5-554, 5-557, 5-558, 5-560, 5-569~5-576, 5-581, 5-583, 5-587, 5-588, 5-608, 5-611, 5-612, 5-617, 5-619, 5-628, 5-630~5-632, 5-637, 5-638, 5-642, 5-644, 5-646, 5-654, 5-655, 5-662, 5-664, 5-669, 5-670, 5-672, 5-674, 5-684, 5-686, 6-001, 6-003, 6-005*, 6-007, 6-009~6-012, 6-015*, 6-016~6-021, 6-022*, 6-027, 6-028, 6-030~6-033, 6-035~6-044, 6-048~6-050, 6-054, 6-056~6-059, 6-063, 6-066, 6-074~6-076, 6-078~6-084, 6-086, 6-089~6-095, 6-097, 6-098, 6-100~6-103, 6-112, 6-114, 6-115, 6-121, 6-124, 6-130~6-132, 7-003~7-007, 7-009, 8-005, 8-006, 9-004, 9-009, 10-002, 10-006, 11-005, 11-006, 11-026, 11-118, 11-125, 11-130, 12-004.
In the interim, the indication of "*" shows that the insecticidal test was carried out by use of a chemical solution of a concentration of 100 ppm.

Test Example 13

Insecticidal Test Against Japanese Mealybug

A wet filter paper was laid in a styrol cup having an inner diameter of 7 cm, a leaf of a common bean cut out so as to have the same diameter was laid theron, and 10-Japanese mealybug (*Planococcus kraunhiae*) in the first instar larva per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention: No. 1-011, 1-177, 1-182, 2-020, 2-028, 2-029*, 2-033, 2-034*, 2-035*, 2-037*, 2-039*, 2-040*, 2-041*, 2-042*, 2-044*, 2-045*, 2-046*, 2-047, 2-048*, 2-049*, 2-050~2-052, 2-055*, 2-057, 2-059, 2-062, 2-065~2-067, 3-065, 3-069, 3-085, 3-086, 3-091~3-093, 3-104, 3-109, 3-125, 3-151, 4-003, 4-004, 4-006, 5-001, 5-003, 5-005, 5-007, 5-009, 5-013~5-015, 5-017, 5-022, 5-023, 5-029, 5-037, 5-039~5-041, 5-045~5-050, 5-052, 5-053, 5-057~5-061, 5-063~5-065, 5-067~5-075, 5-075(+), 5-076~5-078, 5-081, 5-083~5-089, 5-090*, 5-091~5-094, 5-098~5-105, 5-109, 5-111~5-114, 5-116~5-118, 5-121, 5-123, 5-126, 5-128, 5-129*, 5-130, 5-131*, 5-138~5-142, 5-143*, 5-144, 5-145, 5-146*, 5-147, 5-148, 5-151, 5-151(+), 5-153*, 5-154, 5-156, 5-158~5-160, 5-161*, 5-162, 5-164, 5-165, 5-166, 5-167*, 5-168*, 5-171, 5-172*, 5-179~5-188, 5-189(+), 5-190(+), 5-192~5-194, 5-201, 5-202, 5-205, 5-206, 5-208*, 5-210~5-212, 5-214~5-216, 5-219, 5-219(+), 5-221, 5-222, 5-223, 5-226~5-234, 5-236~5-240, 5-242, 5-245~5-247, 5-249, 5-251, 5-253, 5-254, 5-255*, 5-256, 5-257, 5-258*, 5-259, 5-261, 5-264, 5-269*, 5-271*, 5-272~5-288, 5-291, 5-292, 5-295~5-297, 5-299~5-301, 5-302*, 5-303, 5-306, 5-307, 5-309, 5-310*, 5-312~5-315, 5-318, 5-319, 5-321, 5-322, 5-323, 5-331, 5-332, 5-334~5-336, 5-338, 5-339, 5-344, 5-345, 5-348, 5-349, 5-353~5-358, 5-360~5-362, 5-375, 5-378, 5-379*, 5-380*, 5-381*, 5-383, 5-384, 5-385*, 5-387, 5-388, 5-390, 5-392, 5-393, 5-395, 5-396*, 5-397~5-399, 5-401, 5-406, 5-407, 5-410, 5-412, 5-417~5-419, 5-422~5-424, 5-426~5-434, 5-439~5-443, 5-445, 5-446, 5-452, 5-453, 5-457, 5-458, 5-460, 5-461, 5-463~5-465, 5-468, 5-470~5-473, 5-475~5-477, 5-480, 5-482~5-485, 5-487, 5-488, 5-490~5-492, 5-494~5-496, 5-498, 5-500, 5-516, 5-519, 5-521~5-523, 5-525, 5-527, 5-531, 5-532, 5-538, 5-541, 5-543, 5-546, 5-547, 5-549~5-554, 5-558, 5-569, 5-572~5-576, 5-579, 5-581~5-584, 5-587, 5-589, 5-599, 5-605, 5-607, 5-616, 5-623, 5-627, 5-628, 5-637, 5-638, 5-647, 5-651, 5-654~5-656, 5-658~5-662, 5-664~5-666, 5-668~5-672, 5-674, 5-684~5-686, 6-001~6-003, 6-005*, 6-006*, 6-007~6-013, 6-015*, 6-016~6-021, 6-022*, 6-023, 6-024*, 6-025*, 6-026~6-050, 6-054~6-056, 6-058, 6-059, 6-063, 6-066, 6-074~6-076, 6-078~6-080, 6-080(+), 6-082~6-085, 6-089, 6-090~6-096, 6-098~6-102, 6-103, 6-110, 6-114, 6-115, 6-130~6-132, 7-003~7-010, 8-003, 9-003, 9-011, 10-002, 10-006, 11-024~11-026, 11-043, 11-045, 11-056, 11-058, 11-059, 11-089, 11-120, 11-125, 11-132, 12-006, 12-008.
In the interim, the indication of "*" shows that the insecticidal test was carried out by use of a chemical solution of a concentration of 100 ppm.

Test Example 14

Insecticidal Test Against Cucurbit Leaf Beetle

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of cucumber for about 10 seconds, and after air-drying, they were placed in a laboratory dish, then 5-cucurbit leaf beetle (*Aulacophora femoralis*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-005, 1-015, 1-016, 1-040, 1-042, 1-055~1-057, 1-059, 1-061~1-067, 1-069~1-071, 1-073, 1-074, 1-076, 1-077, 1-079~1-081, 1-083~1-085, 1-087, 1-088, 1-090, 1-092~1-095, 1-098, 1-099, 1-102, 1-104~1-110, 1-113, 1-116, 1-118, 1-119, 1-122~1-129, 1-131, 1-135, 1-136, 1-138, 1-146, 1-147, 1-151~1-153, 1-155~1-157, 1-159, 1-166, 1-167, 1-171, 1-172, 1-174~1-177, 1-179~1-185, 1-187~1-189, 1-194, 1-199, 1-206, 1-207, 1-210, 1-212, 1-214, 1-215, 1-220, 1-225, 2-001, 2-004, 2-006, 2-011, 2-013, 2-019~2-022, 2-025~2-029, 2-031, 2-032, 2-034~2-055, 2-057~2-068, 3-002, 3-003, 3-006, 3-011, 3-018, 3-025~3-028, 3-031~3-035, 3-037, 3-044, 3-046, 3-047, 3-050, 3-058, 3-061~3-065, 3-068~3-072, 3-074, 3-076, 3-078~3-081, 3-084~3-087, 3-089~3-095, 3-097~3-116, 3-118~3-125, 3-127~3-132, 3-134~3-136, 3-138~3-143, 3-145~3-151, 4-003~4-007, 4-009~4-011, 5-001~5-015, 5-017, 5-021~5-023, 5-028~5-042, 5-044~5-075, 5-075(+), 5-075(−), 5-076~5-081, 5-083~5-095, 5-097, 5-099~5-107, 5-109~5-130, 5-132~5-135, 5-137~5-151, 5-151(+), 5-151(−), 5-152~5-156, 5-158~5-189, 5-189(+), 5-190(+), 5-191~5-219, 5-219(+), 5-219(−), 5-220~5-236, 5-238~5-296, 5-298~5-326, 5-329~5-339, 5-341~5-350, 5-352~5-363, 5-365, 5-369, 5-371, 5-374~5-403, 5-405~5-413, 5-415~5-447, 5-449, 5-452~5-455, 5-458~5-491, 5-493~5-503, 5-505, 5-507~5-534, 5-536~5-540, 5-540(+), 5-541, 5-541(R), 5-541(S), 5-542~5-560, 5-562~5-570, 5-572~5-590, 5-592~5-602, 5-604~5-609, 5-611~5-619, 5-621~5-648, 5-650, 5-651, 5-653~5-672, 5-674, 5-676, 5-678, 5-684~5-686, 6-001~6-013, 6-015~6-024, 6-026~6-051, 6-053~6-067, 6-070, 6-071, 6-074~6-080, 6-080(+), 6-080(−), 6-081~6-086, 6-089~6-096, 6-098~6-106, 6-108~6-115, 6-117~6-127, 6-129~6-133, 7-001~7-010, 8-001~8-007, 9-003, 9-009, 9-010, 10-002~10-005, 11-005, 11-015, 11-017, 11-020, 11-023~11-026, 11-038, 11-043, 11-045, 11-046, 11-052~11-054, 11-056~11-060, 11-066, 11-067, 11-072, 11-076, 11-098, 11-099, 11-101~11-104, 11-106, 11-108, 11-110, 11-112~11-114, 11-119, 11-120, 11-124, 11-125, 11-129, 11-130, 11-132, 12-006.

Test Example 15

Insecticidal Test Against Serpentine Leaf Miner

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of common bean on which serpentine leaf miner (Liriomyza trifolii) laid eggs (10 eggs/leaf) for about 10 seconds, and after air-drying, they were placed on a wet filter paper laid in a styrol cup having an inner diameter of 7 cm, and the styrol cup was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-175, 1-177, 2-029*, 2-034*, 2-035*, 2-044*, 2-045*, 2-050, 2-051, 2-057, 2-059, 2-062, 2-064, 2-065, 2-067, 3-060, 3-068, 3-069, 3-071, 3-072*, 3-085, 3-086, 3-093, 3-105, 3-109, 3-112, 3-125, 3-148, 3-151, 5-001, 5-003, 5-005, 5-007, 5-009, 5-015, 5-022, 5-023, 5-036, 5-037, 5-040, 5-041, 5-045~5-053, 5-058~5-061, 5-063~5-065, 5-067, 5-068, 5-070~5-075, 5-075(+), 5-076, 5-077, 5-081, 5-083, 5-085~5-089, 5-090*, 5-091~5-094, 5-099~5-105, 5-113, 5-117~5-119, 5-120*, 5-121~5-123, 5-124*, 5-126, 5-129*, 5-131*, 5-133*, 5-138~5-142, 5-144, 5-145, 5-147, 5-148, 5-150, 5-151, 5-151(+), 5-154, 5-156, 5-158, 5-160, 5-161*, 5-162, 5-164~5-166, 5-168*, 5-169, 5-171, 5-172*, 5-178, 5-180, 5-182~5-188, 5-189(+), 5-201, 5-202, 5-208*, 5-209, 5-210, 5-212, 5-214~5-216, 5-217*, 5-219, 5-219(+), 5-221~5-223, 5-226~5-234, 5-236, 5-238, 5-239, 5-241, 5-245~5-247, 5-251, 5-256, 5-257, 5-258*, 5-259, 5-261, 5-264, 5-265, 5-270, 5-274, 5-275, 5-283, 5-284, 5-286, 5-291, 5-294, 5-295, 5-302*, 5-303, 5-306, 5-309, 5-310*, 5-313~5-315, 5-319, 5-323, 5-335, 5-336, 5-338, 5-339, 5-341, 5-344, 5-345, 5-353~5-358, 5-360, 5-362, 5-374, 5-375, 5-378, 5-379*, 5-380*, 5-381*, 5-383, 5-384, 5-385*, 5-387, 5-388, 5-390, 5-392, 5-393, 5-395, 5-396*, 5-397~5-401, 5-408~5-413, 5-415, 5-417~5-423, 5-425~5-430, 5-432, 5-433, 5-439~5-441, 5-443, 5-445, 5-446, 5-452, 5-453, 5-455, 5-458~5-465, 5-467, 5-468, 5-470~5-488, 5-490, 5-491, 5-494~5-499, 5-501, 5-508~5-512, 5-515~5-517, 5-519, 5-520~5-523, 5-527~5-532, 5-538, 5-539, 5-541, 5-541(S), 5-543, 5-549, 5-551~5-554, 5-556~5-560, 5-566, 5-569, 5-570, 5-572~5-576, 5-579, 5-581, 5-584, 5-596, 5-601, 5-606, 5-616, 5-617, 5-630, 5-631, 5-634, 5-635, 5-637, 5-638, 5-642, 5-643, 5-646, 5-651, 5-653~5-657, 5-659, 5-660, 5-662, 5-664~5-672, 5-674, 5-684~5-686, 6-001, 6-004*, 6-005*, 6-006*, 6-007, 6-008, 6-011~6-013, 6-015*, 6-016~6-021, 6-022*, 6-024*, 6-025*, 6-027, 6-031, 6-033~6-041, 6-043, 6-044, 6-048~6-050, 6-054~6-056, 6-066, 6-070, 6-074~6-076, 6-078, 6-079, 6-081, 6-083, 6-085, 6-089, 6-091, 6-092, 6-093, 6-095, 6-098, 6-100, 6-102, 6-103, 6-110, 6-114, 6-123, 6-124, 6-129~6-133, 7-003, 7-005~7-009.

In the interim, the indication of "*" shows that the insecticidal test was carried out by use of a chemical solution of a concentration of 100 ppm.

Test Example 16

Insecticidal Test Against Two-Spotted Spider Mite

A wet filter paper was laid in a styrol cup having an inner diameter of 7 cm, a leaf of a common bean cut out so as to have the same diameter was laid thereon, and 10 larvae of two-spotted spider mite (Tetranychus urticae) per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-177, 1-182, 2-027, 2-028*, 2-029*, 2-034*, 2-035*, 2-036, 2-037*, 2-039*, 2-040*, 2-041*, 2-042*, 2-044*, 2-045*, 2-046*, 2-047, 2-048*, 2-049*, 2-050~2-052, 2-057~2-063, 2-065~2-067, 3-068, 3-084, 3-086, 3-109, 3-110, 3-1,2,3-114, 3-124, 3-131, 3-151, 5-001, 5-003, 5-005, 5-007~5-009, 5-011, 5-013, 5-015, 5-019, 5-021, 5-022, 5-023, 5-028, 5-029, 5-035~5-037, 5-040, 5-041, 5-045~5-053, 5-057~5-075, 5-075(+), 5-076~5-078, 5-080~5-089, 5-090*, 5-091~5-094, 5-098~5-105, 5-109, 5-112~5-114, 5-117~5-119, 5-121~5-123, 5-126, 5-128, 5-129*, 5-130, 5-132, 5-134, 5-136~5-142, 5-143*, 5-144, 5-145, 5-146*, 5-147, 5-148, 5-150, 5-151, 5-151(+), 5-152, 5-153*, 5-154~5-156, 5-158~5-160, 5-161*, 5-162~5-166, 5-167*, 5-168*, 5-171, 5-172*, 5-177~5-180, 5-182~5-188, 5-189*, 5-189(+), 5-190(+), 5-191, 5-192, 5-196*, 5-197*, 5-199~5-202, 5-204~5-207, 5-208*, 5-209~5-212, 5-214~5-216, 5-218, 5-219, 5-219(+), 5-219(−), 5-220~5-234, 5-235*, 5-236, 5-238~5-242, 5-243*, 5-245~5-247, 5-249, 5-251, 5-254, 5-255*, 5-256, 5-257, 5-258*, 5-259, 5-261, 5-264, 5-265, 5-269*, 5-271*, 5-273~5-275, 5-277~5-279, 5-283~5-286, 5-288, 5-291, 5-292, 5-294, 5-295, 5-299~5-301, 5-306, 5-307, 5-312~5-316, 5-321, 5-323, 5-325, 5-330, 5-336, 5-338, 5-339, 5-341, 5-344, 5-345, 5-349, 5-353~5-358, 5-360, 5-362, 5-374, 5-375, 5-376*, 5-377*, 5-378, 5-379*, 5-380*, 5-381*, 5-383, 5-384, 5-385*, 5-386*, 5-387~5-395, 5-396*, 5-397~5-399, 5-401, 5-402, 5-405, 5-406, 5-408~5-413, 5-415, 5-417~5-419, 5-421~5-423, 5-425~5-427, 5-430, 5-432, 5-433, 5-440, 5-441, 5-443, 5-445, 5-452~5-455, 5-457~5-463, 5-465, 5-467, 5-468, 5-470~5-487, 5-489~5-492, 5-494~5-499, 5-503, 5-505, 5-506, 5-509~5-513, 5-515~5-525, 5-527~5-534, 5-538, 5-539, 5-540(+), 5-543~5-545, 5-548~5-554, 5-557~5-560, 5-566, 5-568~5-570, 5-572~5-576, 5-578, 5-579, 5-581, 5-583, 5-584, 5-600, 5-601, 5-604, 5-606, 5-616, 5-617, 5-630, 5-631, 5-635, 5-637, 5-638, 5-642, 5-646, 5-647, 5-650, 5-651, 5-654~5-657, 5-659~5-662, 5-664~5-672, 5-678, 5-684~5-686, 6-001, 6-003, 6-007, 6-008, 6-011~6-013, 6-015*, 6-016~6-021, 6-023, 6-027, 6-030~6-044, 6-046~6-050, 6-054~6-056, 6-066, 6-074~6-076, 6-078, 6-079, 6-082~6-085, 6-089~6-093, 6-095, 6-096, 6-098, 6-100, 6-102, 6-103, 6-110, 6-112, 6-114, 6-115, 6-121, 6-123, 6-124, 6-129~6-133, 7-003~7-010, 8-003, 10-002, 10-006, 11-026, 11-098, 11-108, 12-002.

In the interim, the indication of "*" shows that the insecticidal test was carried out by use of a chemical solution of a concentration of 100 ppm.

Test Example 17

Insecticidal Test Against Pink Citrus Rust Mite

A wet filter paper was laid in a styrol cup having an inner diameter of 7 cm, a leaf of a mandarin orange cut out so as to have the same diameter was laid thereon, and 10 larvae of pink citrus rust mite (*Aculops pelekassi*) per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 100 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-177, 3-093, 3-112, 5-001~5-003, 5-005, 5-008, 5-009, 5-022, 5-023, 5-036, 5-037, 5-040, 5-041, 5-046, 5-047, 5-049, 5-050, 5-053, 5-057~5-059, 5-061, 5-063, 5-065, 5-066, 5-069~5-071, 5-074~5-077, 5-081, 5-083, 5-084, 5-086, 5-088, 5-111~5-113, 5-121, 5-137~5-140, 5-148, 5-151, 5-174, 5-182, 5-183, 5-185, 5-187, 5-188, 5-202, 5-205, 5-206, 5-215, 5-216, 5-219~5-221, 5-225, 5-226, 5-233~5-235, 5-241, 5-247, 5-274, 5-285, 5-291, 5-294, 5-295, 5-301, 5-313, 5-323, 5-331, 5-334, 5-338, 5-339, 5-355, 5-360, 5-374, 5-378, 5-387~5-390, 5-393, 5-397, 5-398, 5-480, 5-494, 5-638, 5-642, 5-645, 6-003, 6-017, 6-020, 6-021, 6-027, 6-031, 6-033~6-035, 6-043, 6-049, 6-054, 6-064, 6-070, 6-076, 6-131, 7-003, 7-007~7-009, 10-002.

Test Example 18

Insecticidal Test Against Broad Mite

A wet filter paper was laid in a styrol cup having an inner diameter of 7 cm, a leaf of a common bean cut out so as to have the same diameter was laid thereon, and 10 adults of broad mite (*Polyphagotarsonemus latus*) per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 100 ppm. The chemical solution was sprayed with a rotating spray tower in an amount of 2.5 ml per styrol cup, and the styrol cups were covered with lids and contained at a thermostat chamber at 25° C. A number of dead insect(s) after 2 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention:
No. 3-093, 5-009, 5-036, 5-037, 5-040, 5-041, 5-050, 5-053, 5-058, 5-063, 5-067, 5-071, 5-075~5-077, 5-083, 5-088, 5-089, 5-113, 5-121, 5-140, 5-147, 5-148, 5-151, 5-174, 5-179, 5-185, 5-188, 5-214, 5-215, 5-219, 5-230, 5-233~5-236, 5-249, 5-251, 5-254, 5-274, 5-288, 5-289, 5-291, 5-294, 5-309, 5-332, 5-339, 5-355, 5-360, 5-374, 5-375, 5-387, 5-398, 5-474, 5-476, 5-480, 5-494, 5-604, 5-642, 6-017, 6-026, 6-031, 6-033~6-035, 6-038, 6-045, 6-064, 6-070, 6-076, 6-131, 7-003, 7-007~7-009.

Test Example 19

Insecticidal Test Against *Ctenocephalides felis*

After 400 μl of acetone solution in which 4 mg of the compound of the present invention was dissolved in 40 ml of acetone (concentration 100 ppm) was coated on the bottom face and side face of a laboratory dish having an inner diameter of 5.3 cm, acetone was vaporized to prepare a thin film of the compound of the present invention on the inner wall of the laboratory dish. As the surface area of the inner wall is 40 cm$^2$, the treated dosage is 1 μg/cm$^2$. 10 adults of *Ctenocephalides felis* (male and female are mixed) were left in the laboratory dish, covered with lid and contained at a thermostat chamber at 25° C. A number of dead insect(s) after 4 days was counted and a rate of dead insects was calculated by the calculation equation similar to that in Test Example 1. Incidentally, the test was carried out with one district.

As a result, the following compounds showed an insecticidal rate of 80% or more among the compounds tested.

The compounds of the present invention: No. 2-029*, 2-052, 3-151, 5-002, 5-003, 5-005, 5-007, 5-008, 5-012, 5-013, 5-023, 5-029, 5-037, 5-058, 5-071*, 5-072, 5-075*, 5-076, 5-077, 5-086, 5-088*, 5-093, 5-100*, 5-101*, 5-111*, 5-117, 5-121, 5-130*, 5-138, 5-139, 5-140*, 5-142*, 5-148*, 5-151*, 5-160*, 5-161*, 5-165*, 5-174*, 5-182*, 5-184, 5-187, 5-188, 5-192, 5-205, 5-206, 5-209, 5-214*, 5-215*, 5-218, 5-219*, 5-223, 5-229, 5-230, 5-232, 5-234*, 5-235*, 5-236, 5-238, 5-240, 5-241*, 5-243*, 5-245*, 5-247, 5-264, 5-274*, 5-287, 5-291, 5-294, 5-310*, 5-312, 5-313, 5-323, 5-354*, 5-356*, 5-359*, 5-360, 5-362, 5-376*, 5-377*, 5-378*, 5-379*, 5-383*, 5-384*, 5-387*, 5-389*, 5-390, 5-393, 5-399*, 5-401, 5-405*, 5-412*, 5-423*, 5-427*, 5-429*, 5-430*, 5-440*, 5-461*, 5-466*, 5-468*, 5-470*, 5-473, 5-474*, 5-475, 5-476, 5-477*, 5-478*, 5-480*, 5-487, 5-494*, 5-495~5-499, 5-579*, 5-587*, 5-623, 5-646*, 5-648*, 5-658, 6-020, 6-026, 6-033, 6-034, 6-035*, 6-043*, 6-046~6-049, 6-054, 6-055, 6-064, 6-065*, 6-074, 6-092, 6-094, 6-095, 6-129, 6-130, 6-133, 7-002*, 7-004, 7-008*, 7-009.

In the interim, the indication of "*" shows that the insecticidal test was carried out with a treated dosage of 0.1 µg/cm².

Test Example 20

Insecticidal Test Against American Dog Tick

After 400 µl of acetone solution in which 4 mg of the compound of the present invention was dissolved in 40 ml of acetone (concentration 100 ppm) was coated on the bottom face and side face of two laboratory dishes having an inner diameter of 5.3 cm, acetone was vaporized to prepare a thin film of the compound of the present invention on the inner wall of the laboratory dish. As the surface area of the inner wall is 40 cm², the treated dosage is 1 µg/cm². 10-American dog tick (Dermacentor variabilis) (male and female are mixed) in the stage of protonymph were left in the laboratory dishes, two laboratory dishes together were sealed with a tape so that ticks do not escape, and contained at a thermostat chamber at 25° C. A number of dead insect(s) after 4 days was counted and a rate of dead insects was calculated by the calculation equation similar to that in Test Example 1. Incidentally, the test was carried out with one district.

As a result, the following compounds showed an insecticidal rate of 80% or more among the compounds tested.

The compounds of the present invention: No. 2-029*, 2-052, 2-054*, 5-003, 5-005, 5-008, 5-023, 5-029, 5-037, 5-058, 5-063*, 5-071*, 5-072, 5-075*, 5-076*, 5-077, 5-086, 5-088*, 5-093*, 5-100*, 5-101*, 5-117, 5-121, 5-128, 5-130*, 5-138, 5-139, 5-140*, 5-142*, 5-148*, 5-151, 5-160*, 5-161*, 5-165*, 5-174*, 5-182*, 5-184, 5-187, 5-188, 5-191, 5-192, 5-205, 5-206, 5-209, 5-214*, 5-215*, 5-219*, 5-223, 5-229, 5-230, 5-232, 5-233*, 5-234*, 5-235*, 5-236, 5-238, 5-240, 5-241*, 5-243*, 5-245*, 5-247, 5-264, 5-274*, 5-287, 5-291, 5-294, 5-308*, 5-309*, 5-310*, 5-312, 5-313, 5-320, 5-321, 5-323, 5-354*, 5-356*, 5-359*, 5-360, 5-362, 5-376*, 5-377*, 5-378*, 5-379*, 5-383*, 5-384*, 5-386*, 5-387*, 5-390, 5-393, 5-399*, 5-401*, 5-405*, 5-412*, 5-418*, 5-423*, 5-427*, 5-429*, 5-430*, 5-432*, 5-440*, 5-461*, 5-466*, 5-468*, 5-469*, 5-470*, 5-473*, 5-474*, 5-475*, 5-476*, 5-477*, 5-478*, 5-480*, 5-487*, 5-494*, 5-495*, 5-496*, 5-497*, 5-498*, 5-499*, 5-500*, 5-555*, 5-579*, 5-581*, 5-585*, 5-587*, 5-588*, 5-589*, 5-593*, 5-601*, 5-607*, 5-610*, 5-623*, 5-638*, 5-646*, 5-648*, 5-654*, 5-658*, 6-020, 6-026, 6-033, 6-034*, 6-035*, 6-043*, 6-046~6-049, 6-054, 6-055, 6-064, 6-065*, 6-074, 6-092*, 6-094*, 6-095*, 6-129*, 6-130*, 6-133*, 7-004, 7-008*, 7-009, 11-056.

In the interim, the indication of "*" shows that the insecticidal test was carried out with a treated dosage of 0.1 µg/cm².

Test Example 21

Insecticidal Test Against German Cockroach

A chemical solution having a concentration of 10 µg/µl was prepared by diluting the compound of the present invention with acetone. The chemical solution was coated on the abdominal region of male adults of German cockroach (Blattella germanica) in an amount of 1 µl per cockroach, and the treated cockroaches were contained at a thermostat chamber at 25° C. A number of dead insect(s) after 2 days was counted and a rate of dead insects was calculated by the calculation equation similar to that in Test Example 1. Incidentally, the test was carried out with five districts.

As a result, the following compounds showed an insecticidal rate of 80% or more among the compounds tested.

The compounds of the present invention: No. 5-075, 5-140*, 5-147*, 5-148*, 5-151*, 5-174*, 5-234*, 5-412*, 5-480*, 5-494*, 5-541, 5-638*, 6-103*.

Test Example 22

Insecticidal Test Against Musca domestica

A chemical solution having a concentration of 1 µg/µl was prepared by diluting the compound of the present invention with acetone. The chemical solution was coated on the abdominal region of female adults of Musca domestica in an amount of 1 µl per fly, and the treated flies were contained at a thermostat chamber at 25° C. A number of dead insect(s) after 2 days was counted and a rate of dead insects was calculated by the calculation equation similar to that in Test Example 1. Incidentally, the test was carried out with ten districts.

As a result, the following compounds showed an insecticidal rate of 80% or more among the compounds tested.

The compounds of the present invention:
No. 5-075, 5-140, 5-147, 5-148, 5-151, 5-174, 5-219, 5-234, 5-412, 5-480, 5-494, 5-541, 5-638, 6-103.

Test Example 23

Insecticidal Test Against Eastern Subterranean Termite

A 10% emulsifiable concentrate (depending on the compounds, 10% wettable powder was applied for the test) of the compound of the present invention was diluted with water containing a spreading agent to prepare a chemical solution with a concentration of 10 ppm. 0.5 ml of the chemical solution was added dropwise in 10 g of sand and mixed. A filter paper and the sand treated with the chemical solution were placed in a laboratory dish in which 1% agar was laid. 10-Eastern subterranean termite (Reticulitermes flavipes) per dish was left and contained at a thermostat chamber at 25° C. A number of dead insect(s) after 2 days was counted and a rate of dead insects was calculated by the calculation equation similar to that in Test Example 1.

As a result, the following compounds showed an insecticidal rate of 80% or more among the compounds tested.

The compounds of the present invention: No. 5-234.

Test Example 24

Insecticidal Test Against Rust-Red Flour Beetle

A chemical solution having a concentration of 0.1 mg/ml was prepared by diluting the compound of the present invention with acetone. After 10 ml of the chemical solution was added dropwise in 10 g of bran, 20 adults of rust-red flour beetle (*Tribolium castaneum*) were left therein, and contained at a thermostat chamber at 25° C. A number of dead insect(s) after 2 months was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 5-234.

INDUSTRIAL APPLICABILITY

The isoxazoline-substituted benzanilide compounds according to the present invention are extremely useful compounds showing an excellent pesticidal activity, particularly an insecticidal and acaricidal activity, and causing little adverse effect against non-targeted beings such as mammals, fishes and useful insects.

The invention claimed is:

1. A method for controlling endo- or ecto-parasites of mammals or birds, the endo- or ecto-parasite being selected from the group consisting of Rust Red Flour Beetle, *Musca domestica*, German Cockroach, Broad Mite, Spide Mite, *Ctenocephalides felis* and American Dog Tick, the method comprising administering to a mammal or bird an effective amount of an endo- or ecto-parasiticide comprising, as an active ingredient, one or more compounds selected from the group consisting of:

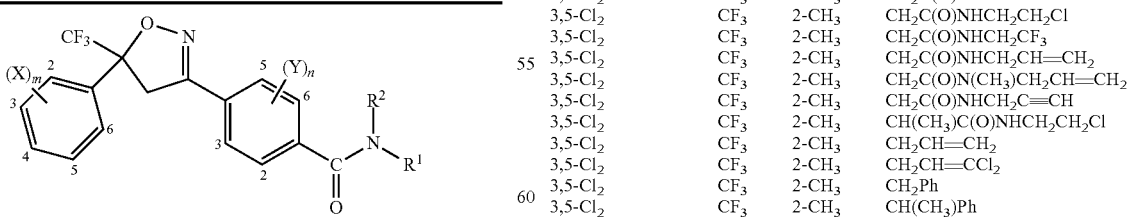

| $(X)_m$ | $(Y)_n$ | $R^2$ | $R^1$ |
|---|---|---|---|
| 3,5-Cl$_2$ | 2-CH$_3$ | H | CH(CH$_3$)CH$_2$OCH$_3$ |
| 3,5-Cl$_2$ | 2-CH$_3$ | H | N(CH$_3$)(D-47d)CF$_3$ |
| 3,5-Cl$_2$ | 2-CH$_3$ | H | D-47a |

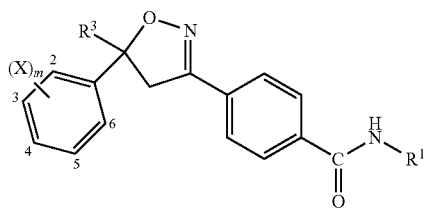

| $(X)_m$ | $R^3$ | $R^1$ |
|---|---|---|
| 3,5-Cl$_2$ | CF$_3$ | E-4a |

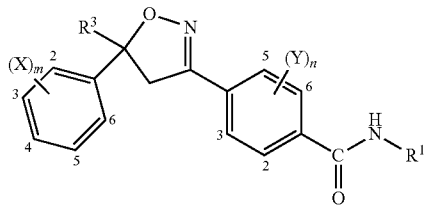

| $(X)_m$ | $R^3$ | $(Y)_n$ | $R^1$ |
|---|---|---|---|
| 3-Br | CF$_3$ | 2-CH$_3$ | CH$_2$CF$_3$ |
| 3-Br | CF$_3$ | 2-CH$_3$ | CH$_2$(D-47a) |
| 3-I | CF$_3$ | 2-CH$_3$ | CH$_2$(D-47a) |
| 4-I | CF$_3$ | 2-CH$_3$ | CH$_2$(D-47a) |
| 3-CF$_3$ | CF$_3$ | 2-CH$_3$ | CH$_2$CF$_3$ |
| 3-OCF$_3$ | CF$_3$ | 2-CH$_3$ | CH$_2$CF$_3$ |
| 3-OCF$_3$ | CF$_3$ | 2-CH$_3$ | CH$_2$(D-47a) |
| 3-SCF$_3$ | CF$_3$ | 2-CH$_3$ | CH$_2$(D-47a) |
| 3,5-F$_2$ | CF$_3$ | 2-CH$_3$ | CH$_2$(D-47a) |
| 3,5-Cl$_2$ | CHF$_2$ | 2-CH$_3$ | CH$_2$(D-47a) |
| 3,5-Cl$_2$ | CF$_3$ | 2-Br | CH$_2$(D-47a) |
| 3,5-Cl$_2$ | CF$_3$ | 2-I | CH$_2$C(O)NHCH$_2$CH$_2$Cl |
| 3,5-Cl$_2$ | CF$_3$ | 2-CH$_3$ | c-Bu |
| 3,5-Cl$_2$ | CF$_3$ | 2-CH$_3$ | CH$_2$Bu-c |
| 3,5-Cl$_2$ | CF$_3$ | 2-CH$_3$ | CH$_2$CF$_3$ |
| 3,5-Cl$_2$ | CF$_3$ | 2-CH$_3$ | CH$_2$CH$_2$OCH$_3$ |
| 3,5-Cl$_2$ | CF$_3$ | 2-CH$_3$ | CH$_2$CH$_2$OEt |
| 3,5-Cl$_2$ | CF$_3$ | 2-CH$_3$ | CH$_2$(E-4a) |
| 3,5-Cl$_2$ | CF$_3$ | 2-CH$_3$ | CH$_2$(E-10a) |
| 3,5-Cl$_2$ | CF$_3$ | 2-CH$_3$ | CH$_2$CH$_2$SEt |
| 3,5-Cl$_2$ | CF$_3$ | 2-CH$_3$ | CH$_2$CH(CH$_3$)S(O)CH$_3$ |
| 3,5-Cl$_2$ | CF$_3$ | 2-CH$_3$ | CH$_2$CH(CH$_3$)SO$_2$CH$_3$ |
| 3,5-Cl$_2$ | CF$_3$ | 2-CH$_3$ | CH$_2$C(O)CH$_3$ |
| 3,5-Cl$_2$ | CF$_3$ | 2-CH$_3$ | CH$_2$C(CH$_3$)=NOCH$_3$ |
| 3,5-Cl$_2$ | CF$_3$ | 2-CH$_3$ | CH(Ph)CN |
| 3,5-Cl$_2$ | CF$_3$ | 2-CH$_3$ | CH$_2$C(O)OCH$_3$ |
| 3,5-Cl$_2$ | CF$_3$ | 2-CH$_3$ | CH(CH$_3$)C(O)OCH$_3$(D) |
| 3,5-Cl$_2$ | CF$_3$ | 2-CH$_3$ | CH$_2$C(O)NHCH$_3$ |
| 3,5-Cl$_2$ | CF$_3$ | 2-CH$_3$ | CH$_2$C(O)N(CH$_3$)$_2$ |
| 3,5-Cl$_2$ | CF$_3$ | 2-CH$_3$ | CH$_2$C(O)NHEt |
| 3,5-Cl$_2$ | CF$_3$ | 2-CH$_3$ | CH$_2$C(O)NHPr-i |
| 3,5-Cl$_2$ | CF$_3$ | 2-CH$_3$ | CH$_2$C(O)NHCH$_2$CH$_2$Cl |
| 3,5-Cl$_2$ | CF$_3$ | 2-CH$_3$ | CH$_2$C(O)NHCH$_2$CF$_3$ |
| 3,5-Cl$_2$ | CF$_3$ | 2-CH$_3$ | CH$_2$C(O)NHCH$_2$CH=CH$_2$ |
| 3,5-Cl$_2$ | CF$_3$ | 2-CH$_3$ | CH$_2$C(O)N(CH$_3$)CH$_2$CH=CH$_2$ |
| 3,5-Cl$_2$ | CF$_3$ | 2-CH$_3$ | CH$_2$C(O)NHCH$_2$C≡CH |
| 3,5-Cl$_2$ | CF$_3$ | 2-CH$_3$ | CH(CH$_3$)C(O)NHCH$_2$CH$_2$Cl |
| 3,5-Cl$_2$ | CF$_3$ | 2-CH$_3$ | CH$_2$CH=CH$_2$ |
| 3,5-Cl$_2$ | CF$_3$ | 2-CH$_3$ | CH$_2$CH=CCl$_2$ |
| 3,5-Cl$_2$ | CF$_3$ | 2-CH$_3$ | CH$_2$Ph |
| 3,5-Cl$_2$ | CF$_3$ | 2-CH$_3$ | CH(CH$_3$)Ph |
| 3,5-Cl$_2$ | CF$_3$ | 2-CH$_3$ | CH(Et)Ph |
| 3,5-Cl$_2$ | CF$_3$ | 2-CH$_3$ | C(CH$_3$)$_2$Ph |
| 3,5-Cl$_2$ | CF$_3$ | 2-CH$_3$ | CH$_2$(D-1a) |
| 3,5-Cl$_2$ | CF$_3$ | 2-CH$_3$ | CH$_2$(D-3a) |
| 3,5-Cl$_2$ | CF$_3$ | 2-CH$_3$ | CH$_2$(D-10b)Cl |
| 3,5-Cl$_2$ | CF$_3$ | 2-CH$_3$ | CH$_2$(D-17a)CH$_3$ |
| 3,5-Cl$_2$ | CF$_3$ | 2-CH$_3$ | CH$_2$(D-17b)Cl |

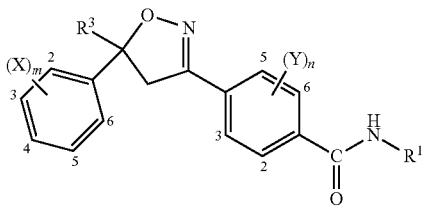

| (X)$_m$ | R$^3$ | (Y)$_n$ | R$^1$ |
|---|---|---|---|
| 3,5-Cl$_2$ | CF$_3$ | 2-CH$_3$ | CH$_2$(D-21b)CF$_3$ |
| 3,5-Cl$_2$ | CF$_3$ | 2-CH$_3$ | CH$_2$(D-22a) |
| 3,5-Cl$_2$ | CF$_3$ | 2-CH$_3$ | CH$_2$(D-23b)Cl |
| 3,5-Cl$_2$ | CF$_3$ | 2-CH$_3$ | CH$_2$(D-31a) |
| 3,5-Cl$_2$ | CF$_3$ | 2-CH$_3$ | CH$_2$(D-34a) |
| 3,5-Cl$_2$ | CF$_3$ | 2-CH$_3$ | CH$_2$(D-35a) |
| 3,5-Cl$_2$ | CF$_3$ | 2-CH$_3$ | CH$_2$(D-38a) |
| 3,5-Cl$_2$ | CF$_3$ | 2-CH$_3$ | CH$_2$(D-47a) |
| 3,5-Cl$_2$ | CF$_3$ | 2-CH$_3$ | CH(CH$_3$)(D-47a) |
| 3,5-Cl$_2$ | CF$_3$ | 2-CH$_3$ | CH$_2$(D-47c)Cl |
| 3,5-Cl$_2$ | CF$_3$ | 2-CH$_3$ | CH$_2$(D-47e)Cl |
| 3,5-Cl$_2$ | CF$_3$ | 2-CH$_3$ | CH$_2$(D-48a) |
| 3,5-Cl$_2$ | CF$_3$ | 2-CH$_3$ | CH$_2$(D-48e)Cl |
| 3,5-Cl$_2$ | CF$_3$ | 2-CH$_3$ | CH$_2$(D-50a) |
| 3,5-Cl$_2$ | CF$_3$ | 2-CH$_3$ | CH$_2$(D-51a) |
| 3,5-Cl$_2$ | CF$_3$ | 2-CH$_3$ | CH$_2$(D-53b)CH$_3$ |
| 3,5-Cl$_2$ | CF$_3$ | 2-CH$_3$ | NHC(O)OEt |
| 3,5-Cl$_2$ | CF$_3$ | 2-CH$_3$ | N(CH$_3$)Ph |
| 3,5-Cl$_2$ | CF$_3$ | 2-CH$_3$ | NH(D-47b)Cl |
| 3,5-Cl$_2$ | CF$_3$ | 2-CH$_3$ | NH(D-50a) |
| 3,5-Cl$_2$ | CF$_3$ | 2-CH$_3$ | N(CH$_3$)(D-50a) |
| 3,5-Cl$_2$ | CF$_3$ | 2-CH$_3$ | D-48a |
| 3,5-Cl$_2$ | CF$_3$ | 2-CH$_3$ | D-50a |
| 3,5-Cl$_2$ | CF$_3$ | 2-CH$_3$ | D-51a |
| 3,5-Cl$_2$ | CF$_3$ | 2-Et | CH$_2$CF$_3$ |
| 3,5-Cl$_2$ | CF$_3$ | 2-Et | CH$_2$(D-47a) |
| 3,5-Cl$_2$ | CF$_3$ | 2-OCF$_3$ | CH$_2$CF$_3$ |
| 3,5-Cl$_2$ | CF$_3$ | 2-OCF$_3$ | CH$_2$(D-47a) |
| 3,5-Cl$_2$ | CF$_3$ | 2-SCH$_3$ | CH$_2$(D-47a) |
| 3,5-Cl$_2$ | CF$_2$Cl | 2-Cl | CH$_2$(D-47a) |
| 3,5-Cl$_2$ | CF$_2$Cl | 2-CH$_3$ | CH$_2$CH$_2$OEt |
| 3,5-Cl$_2$ | CF$_2$Cl | 2-CH$_3$ | CH$_2$(D-22a) |
| 3,5-Cl$_2$ | CF$_2$Cl | 2-CH$_3$ | CH$_2$(D-47a) |
| 3,5-Cl$_2$ | CF$_2$CF$_3$ | 2-CH$_3$ | CH$_2$(D-47a) |
| 3,5-Br$_2$ | CF$_3$ | 2-Cl | CH$_2$(D-22a) |
| 3,5-Br$_2$ | CF$_3$ | 2-Cl | CH$_2$(D-47a) |
| 3,5-Br$_2$ | CF$_3$ | 2-CH$_3$ | CH$_2$CF$_3$ |
| 3,5-Br$_2$ | CF$_3$ | 2-CH$_3$ | CH$_2$CH$_2$OCH$_3$ |
| 3,5-Br$_2$ | CF$_3$ | 2-CH$_3$ | CH$_2$C(O)NHCH$_2$CH$_2$Cl |
| 3,5-Br$_2$ | CF$_3$ | 2-CH$_3$ | CH$_2$C(O)NHCH$_2$CF$_3$ |
| 3,5-Br$_2$ | CF$_3$ | 2-CH$_3$ | CH$_2$(D-22a) |
| 3,5-Br$_2$ | CF$_3$ | 2-CH$_3$ | CH$_2$(D-47a) |
| 3,5-(CF$_3$)$_2$ | CF$_3$ | 2-CH$_3$ | CH$_2$CF$_3$ |
| 3,5-(CF$_3$)$_2$ | CF$_3$ | 2-CH$_3$ | CH$_2$(D-47a) |
| 3-CF$_3$-5-OCH$_3$ | CF$_3$ | 2-CH$_3$ | CH$_2$(D-47a) |
| 3,5-Cl$_2$ | CF$_3$ | 2-CH$_3$ | CH$_2$CH$_2$CF$_3$ |
| 3,5-Cl$_2$ | CF$_3$ | 2-CH$_3$ | CH(CF$_3$)OCH$_3$ |
| 3,5-Cl$_2$ | CF$_3$ | 2-CH$_3$ | (E-9b)CH$_2$CF$_3$ |
| 3,5-Cl$_2$ | CF$_3$ | 2-CH$_3$ | CH(CH$_3$)C(O)NHCH$_2$CF$_3$ |
| 3,5-Cl$_2$ | CF$_3$ | 2-CH$_3$ | CH(CH$_3$)(D-1a) |
| 3,5-Cl$_2$ | CF$_3$ | 2-CH$_3$ | CH(CH$_3$)(D-21a) |
| 3,5-Cl$_2$ | CF$_3$ | 2-CH | CH(CF$_3$)(D-38a) |
| 3,5-Cl$_2$ | CF$_3$ | 2-CH$_3$ | C(O)NHCH$_2$CF$_3$ |
| 3,5-Cl$_2$ | CF$_3$ | 2-CH$_3$ | C(S)NHCH$_2$CF$_3$ |
| 3,5-Cl$_2$ | CF$_3$ | 2-CH$_3$ | NHC(O)NHCH$_2$CH$_2$Cl |
| 3,5-Cl$_2$ | CF$_3$ | 2-CH$_3$ | (D-15a)CH$_3$ |
| 3,4-Cl$_2$ | CF$_3$ | 2-CH$_3$ | CH$_2$(D-47a) |
| 3,5-Cl$_2$ | CF$_3$ | 2-I | CH$_2$C(O)NHCH$_2$CF$_3$ |
| 3,5-Cl$_2$ | CF$_3$ | 2-I | (D-47d)Cl |
| 3,5-Cl$_2$ | CF$_3$ | 2-I | (D-50c)Cl |
| 3,5-Cl$_2$ | CF$_3$ | 2-CH$_3$ | CH$_2$OCH$_3$ |
| 3,5-Cl$_2$ | CF$_3$ | 2-CH$_3$ | CH$_2$OEt |
| 3,5-Cl$_2$ | CF$_3$ | 2-CH$_3$ | CH$_2$OPr-n |
| 3,5-Cl$_2$ | CF$_3$ | 2-CH$_3$ | CH$_2$OPr-i |
| 3,5-Cl$_2$ | CF$_3$ | 2-CH$_3$ | CH$_2$OCH$_2$CH$_2$Cl |
| 3,5-Cl$_2$ | CF$_3$ | 2-CH$_3$ | CH$_2$OCH$_2$CHF$_2$ |
| 3,5-Cl$_2$ | CF$_3$ | 2-CH$_3$ | CH$_2$OCH$_2$CF$_3$ |

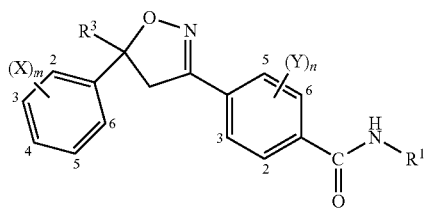

| (X)$_m$ | R$^3$ | (Y)$_n$ | R$^1$ |
|---|---|---|---|
| 3,5-Cl$_2$ | CF$_3$ | 2-CH$_3$ | CH(CH$_3$)OH |
| 3,5-Cl$_2$ | CF$_3$ | 2-CH$_3$ | E-4a |
| 3,5-Cl$_2$ | CF$_3$ | 2-CH$_3$ | E-5a(R) |
| 3,5-Cl$_2$ | CF$_3$ | 2-CH$_3$ | E-23a |
| 3,5-Cl$_2$ | CF$_3$ | 2-CH$_3$ | CH$_2$SCH$_3$ |
| 3,5-Cl$_2$ | CF$_3$ | 2-CH$_3$ | CH$_2$S(O)CH$_3$ |
| 3,5-Cl$_2$ | CF$_3$ | 2-CH$_3$ | CH$_2$SO$_2$CH$_3$ |
| 3,5-Cl$_2$ | CF$_3$ | 2-CH$_3$ | CH$_2$SC(O)CH$_3$ |
| 3,5-Cl$_2$ | CF$_3$ | 2-CH$_3$ | CH$_2$(D-22b)SCH$_3$ |
| 3,5-Cl$_2$ | CF$_3$ | 2-CH$_3$ | C(O)NHCH$_2$CH=CH$_2$ |
| 3,5-Cl$_2$ | CF$_3$ | 2-CH$_3$ | C(O)NHCH$_2$(D-47a) |
| 3,5-Cl$_2$ | CF$_3$ | 2-CH$_3$ | Ph |
| 3,5-Cl$_2$ | CF$_3$ | 2-CH$_3$ | Ph-3-F |
| 3,5-Cl$_2$ | CF$_3$ | 2-CH$_3$ | Ph-4-F |
| 3,5-Cl$_2$ | CF$_3$ | 2-CH$_3$ | Ph-4-Cl |
| 3,5-Cl$_2$ | CF$_3$ | 2-CH$_3$ | Ph-4-OCF$_3$ |
| 3,5-Cl$_2$ | CF$_3$ | 2-CH$_3$ | Ph-3-CN |
| 3,5-Cl$_2$ | CF$_3$ | 2-CH$_3$ | Ph-3,4-F$_2$ |
| 3,5-Cl$_2$ | CF$_3$ | 2-CH$_3$ | Ph-3,5-Cl$_2$ |
| 3,5-Cl$_2$ | CF$_3$ | 2-CH$_3$ | (D-47d)Cl |
| 3,5-Cl$_2$ | CF$_3$ | 2-CH$_3$ | (D-50c)Cl |
| 3,5-Cl$_2$ | CF$_2$Cl | 2-CH$_3$ | CH$_2$C(O)NHCH$_2$CF$_3$ |
| 3,5-Cl$_2$-4-CH$_3$ | CF$_3$ | 2-CH$_3$ | CH$_2$(D-47a) |
| 3,5-Cl$_2$-4-N(CH$_3$)$_2$ | CF$_3$ | 2-CH$_3$ | CH$_2$(D-47a) |
| 3,5-Cl$_2$ | CF$_3$ | 2-CH$_3$ | (E-23b)OCH$_3$ |

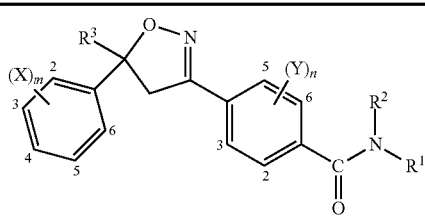

| (X)$_m$ | R$^3$ | (Y)$_n$ | R$^2$ | R$^1$ |
|---|---|---|---|---|
| 3,5-Cl$_2$ | CF$_3$ | 2-CH$_3$ | CH$_3$ | CH$_2$(D-47a) |
| 3,5-Cl$_2$ | CF$_3$ | 2-CH$_3$ | CH$_2$CF$_3$ | CH$_2$(D-47a) |
| 3,5-Cl$_2$ | CF$_3$ | 2-CH$_3$ | CH$_2$C≡CH | CH$_2$(D-47a) |
| 3,5-Cl$_2$ | CF$_3$ | 2-CH$_3$ | C(O)CH$_3$ | CH$_2$(D-47a) |
| 3,5-Cl$_2$ | CF$_3$ | 2-CH$_3$ | C(O)Et | CH$_2$(D-47a) |
| 3,5-Cl$_2$ | CF$_3$ | 2-CH$_3$ | C(O)OCH$_3$ | CH$_2$(D-47a) |
| 3,5-Cl$_2$ | CF$_3$ | 2-CH$_3$ | C(O)OBu-i | CH$_2$(D-47a) |
| 3,5-Cl$_2$ | CF$_3$ | 2-CH$_3$ | C(O)OCH$_2$CH$_2$Cl | CH$_2$(D-47a) |
| 3,5-Cl$_2$ | CF$_3$ | 2-CH$_3$ | C(O)OCH$_2$CH$_2$OCH$_3$ | CH$_2$(D-47a) |
| 3,5-Cl$_2$ | CF$_3$ | 2-CH$_3$ | C(O)OCH$_2$CH=CH$_2$ | CH$_2$(D-47a) |
| 3,5-Cl$_2$ | CF$_3$ | 2-CH$_3$ | Et | CH$_2$(D-48e)Cl |
| 3,5-Cl$_2$ | CF$_3$ | 2-CH$_3$ | c-Pr | CH$_2$(D-49a) |
| 3,5-Cl$_2$ | CF$_3$ | 2-CH$_3$ | C(O)CH$_3$ | N(CH$_3$)$_2$ |
| 3,5-Cl$_2$ | CF$_3$ | 2-CH$_3$ | C(O)OCH$_3$ | N(CH$_3$)Ph |
| 3,5-Cl$_2$ | CF$_2$Cl | 2-CH$_3$ | C(O)CH$_3$ | CH$_2$CF$_3$ |
| 3,5-Cl$_2$ | CF$_3$ | 2-CH$_3$ | CH$_2$OEt | CH$_2$OEt |
| 3,5-Cl$_2$ | CF$_3$ | 2-CH$_3$ | CH$_3$ | CH$_2$OCH$_2$CF$_3$ |
| 3,5-Cl$_2$ | CF$_3$ | 2-CH$_3$ | C(O)CH$_3$ | CH$_2$OCH$_2$CF$_3$ |
| 3,5-Cl$_2$ | CF$_3$ | 2-CH$_3$ | CH$_3$ | E-4a |
| 3,5-Cl$_2$ | CF$_3$ | 2-CH$_3$ | CH$_2$OCH$_3$ | E-4a |

| (X)$_m$ | R$^3$ | (Y)$_n$ | R$^2$ | R$^1$ |
|---|---|---|---|---|
| 3,5-Cl$_2$ | CF$_3$ | — | H | CH$_2$CF$_3$ |
| 3,5-Cl$_2$ | CF$_3$ | — | H | CH$_2$(D-47a) |
| 3,5-Cl$_2$ | CF$_3$ | 2-CH$_3$ | H | CH$_2$(D-22a) |
| 3,5-Cl$_2$ | CF$_3$ | 2-CH$_3$ | H | CH$_2$(D-47a) |
and
| (X)$_m$ | R$^3$ | (Y)$_n$ | R |
|---|---|---|---|
| 3,5-Cl2 | CF3 | 2-CH3 | C(O)OCH 2(D-47a) |
wherein
D-1a:
D-3a:
(D-10b)Cl:
(D-15a)CH$_3$:
(D-17a)CH$_3$:
(D-17b)Cl:
D-21a:
(D-21b)CF$_3$:
D-22a:
(D-22b)SCH$_3$:
(D-23b)Cl:
D-31a:
D-34a:
D-35a:
D-38a:
D-47a: 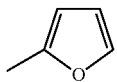
(D-47b)Cl: 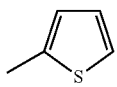
(D-47c)Cl: 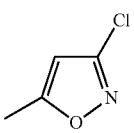
(D-47d)Cl: 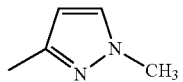

-continued (D-47d)CF₃: 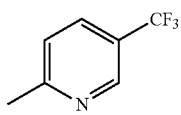

(D-47c)Cl: 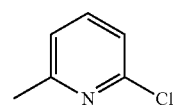

D-48a: 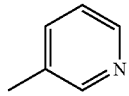

(D-48c)Cl: 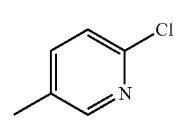

D-49a: 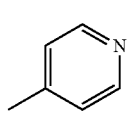

D-50a: 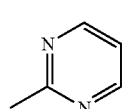

(D-50c)Cl: 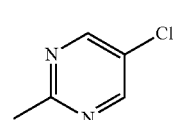

D-51a: 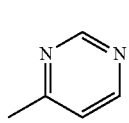

(D-53b)CH₃: 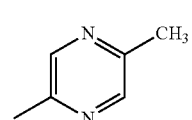

E-4a: 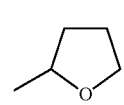

(E-9b)CH₂CF₃: 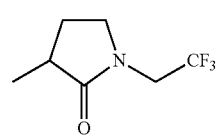

E-5a(R): 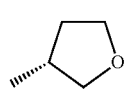

E-10a: 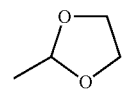

-continued

E-23a: 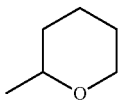

(E-23b)OCH₃: 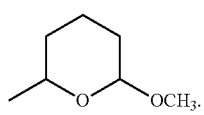

2. The method of claim 1 wherein said administration is oral administration.

3. The method of claim 1 wherein said administration is parenteral administration.

4. The method of claim 1 wherein said administration is injection.

5. The method of claim 1 wherein said administration is intramuscular, subcutaneous, intravenous or intraperitoneal injection.

6. The method of claim 1 wherein said administration is transdermal administration.

7. The method of claim 1 wherein said administration is transnasal administration.

8. The method of claim 1 wherein said administration is dipping, spray, bathing, washing, pouring-on, spotting-on or dusting.

9. A method for controlling endo- or ecto-parasites of mammals or birds, the endo- or ecto-parasite being selected from the group consisting of Rust Red Flour Beetle, *Musca domestica*, German Cockroach, Broad Mite, Spide Mite, *Ctenocephalides felis* and American Dog Tick, the method comprising administering to a mammal or bird an effective amount of an endo- or ecto-parasiticide comprising as an active ingredient, 4-[5-(3,5-dichlorophenyl)-4,5-dihydro-5-(trifluoromethyl)-3-isoxazolyl]-2-methyl-N-[2-oxo-2-[(2,2,2-trifluoroethyl)amino]ethyl)benzamide, an optically active form, or a salt thereof.

10. The method of claim 9 wherein said administration is oral administration.

11. The method of claim 9 wherein said administration is parenteral administration.

12. The method of claim 9 wherein said administration is injection.

13. The method of claim 9 wherein said administration is intramuscular, subcutaneous, intravenous or intraperitoneal injection.

14. The method of claim 9 wherein said administration is transdermal administration.

15. The method of claim 9 wherein said administration is transnasal administration.

16. The method of claim 9 wherein said administration is dipping, spray, bathing, washing, pouring-on, spotting-on or dusting.

17. A method for controlling endo- or ecto-parasites of mammals or birds, the endo- or ecto-parasite being selected from the group consisting of Rust Red Flour Beetle, *Musca domestica*, German Cockroach, Broad Mite, Spide Mite, *Ctenocephalides felis* and American Dog Tick, the method comprising administering to a mammal or bird an effective amount of an endo- or ecto-parasiticide comprising, as an active ingredient, one or more compounds selected from the group consisting of:

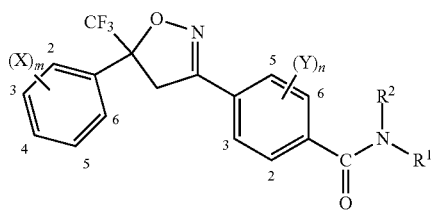

wherein
(X)$_m$ is 3,5-Cl$_2$;
Y is 2-CH$_3$;
R$^1$ is CH(CH$_3$)CH2OCH$_3$, N(CH$_3$)(D-47d)CF$_3$, or D-47a; and
R$^2$ is H;

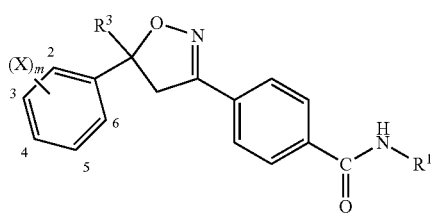

wherein
(X)$_m$ is 3,5-Cl$_2$;
R$^1$ is E-4a; and
R$^3$ is CF$_3$;

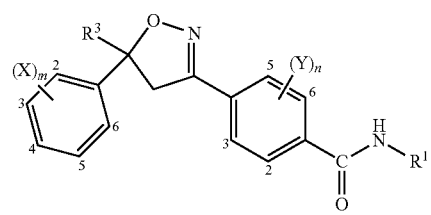

wherein
(X)$_m$ is 3-Br, 3-I, 4-I, 3-CF$_3$, 3-OCF$_3$, 3-SCF$_3$, 3,5-F$_2$, 3,5-Br$_2$, 3,5-(CF$_3$)$_2$, 3-CF$_3$-5-OCH$_3$, 3,5-Cl$_2$, 3,4-Cl$_2$, or 3,5-Cl$_2$-4-CH$_3$, or 3,5-Cl$_2$-4-N(CH$_3$)$_2$;
Y is 2-CH$_3$, 2-Br, 2-Et, 2-SCH$_3$, 2-Cl, 2-I, or 2-OCF$_3$;
R$^1$ is CH$_2$CF$_3$, CH$_2$(D-47a), c-Bu, CH$_2$Bu-c, CH$_2$CH$_2$OCH$_3$, CH$_2$CH$_2$OEt, CH$_2$(E-4a), CH$_2$(E-10a), CH$_2$CH$_2$OEt, CH$_2$CH(CH$_3$)S(O)CH$_3$, CH$_2$CH(CH$_3$)SO$_2$CH$_3$, CH$_2$C(O)CH$_3$, CH$_2$C(CH$_3$)=NOCH$_3$, CH(Ph)CN, CH(CH$_3$)C(O)OCH$_3$(D), CH$_2$C(O)NHCH$_3$, CH$_2$C(O)N(CH$_3$)$_2$, CH$_2$C(O)NHEt, CH$_2$C(O)NHPr-i, CH$_2$C(O)NHCH$_2$CH$_2$Cl, CH$_2$C(O)NHCH$_2$CF$_3$, CH$_2$C(O)NHCH$_2$CH=CH$_2$, CH$_2$C(O)N(CH$_3$)CH$_2$CH=CH$_2$, CH$_2$C(O)NHCH$_2$C≡CH, CH(CH$_3$)C(O)NHCH$_2$CH$_2$Cl, CH$_2$CH=CH$_2$, CH$_2$CH=CCl$_2$, CH$_2$Ph, CH(CH$_3$)Ph, C(CH$_3$)$_2$Ph, CH$_2$(D-1a), CH$_2$(D-3a), CH$_2$(D-10b)Cl, CH$_2$(D-17a)CH$_3$, CH$_2$(D-17b)Cl, CH$_2$(D-21b)CF$_3$, CH$_2$(D-22a), CH$_2$(D-23b)Cl, CH$_2$(D-31a), CH$_2$(D-34a), CH$_2$(D-35a), CH(CH$_3$)(D-47a), CH$_2$(D-47c)Cl, CH$_2$(D-47e)Cl, CH$_2$(D-48a), CH$_2$(D-48e)Cl, CH$_2$(D-50a), CH$_2$(D-51a), CH$_2$(D-53b)CH$_3$, NHC(O)OEt, N(CH$_3$)Ph, NH(D-47b)Cl, NH(D-50a), N(CH$_3$)(D-50a), D-51a, CH(CF$_3$)OCH$_3$, (E-9b)CH$_2$CF$_3$, CH(CH$_3$)C(O)NHCH$_2$CF$_3$, CH(CH$_3$)(D-21a), CH(CF$_3$)(D-38a), C(O)NHCH$_2$CF$_3$, C(S)NHCH$_2$CF$_3$, (D-15a)CH$_3$, CH$_2$(D-47a), CH$_2$C(O)NHCH$_2$CF$_3$, (D-50c)Cl, CH$_2$OCH$_3$, CH$_2$OEt, CH$_2$OPr-n, CH$_2$OPr-i, CH$_2$OCH$_2$CH$_2$Cl, CH$_2$OCH$_2$CHF$_2$, CH$_2$OCH$_2$CF$_3$, CH(CH$_3$)OH, E-4a, E-5a(R), E-23a, CH$_2$SCH$_3$, CH$_2$S(O)CH$_3$, CH$_2$SO$_2$CH$_3$, C(O)NHCH$_2$CH=CH$_2$, Ph-3-F, (D-47d)Cl, (E-23b)OCH$_3$, CH$_2$C(O)NHCH$_2$CH$_2$Cl, CH$_2$C(O)OCH$_3$, CH(Et)Ph, CH$_2$(D-38a), D-48a, D-50a, CH(CH$_3$)(D-1a), NHC(O)NHCH$_2$CH$_2$Cl, CH$_2$SC(O)CH$_3$, CH$_2$(D-22b)SCH$_3$, C(O)NHCH$_2$(D-47a), Ph, Ph-4-F, Ph-4-Cl, Ph-4-OCF$_3$, Ph-3-CN, Ph-3,4-F$_2$, Ph-3,5-Cl$_2$, or (D-50c)Cl; and
R$^3$ is CHF$_2$, CF$_2$Cl, CF$_2$CF$_3$, or CF$_3$;

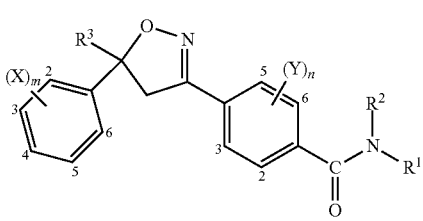

wherein
(X)$_m$ is 3,5-Cl$_2$;
Y is 2-CH$_3$;
R$^1$ is CH$_2$(D-47a), CH$_2$(D-48e)Cl, CH$_2$(D-49a), N(CH$_3$)Ph, CH$_2$CF$_3$, CH$_2$OEt, CH$_2$OCH$_2$CF$_3$, or E-4a;
R$^2$ is CH$_3$, CH$_2$CF$_3$, CH$_2$C≡CH, C(O)CH$_3$, C(O)Et, C(O)OCH$_3$, C(O)OBu-i, C(O)OCH$_2$CH$_2$Cl, C(O)OCH$_2$CH$_2$OCH$_3$, C(O)OCH$_2$CH=CH$_2$, Et, c-Pr, CH$_2$OEt, or CH$_2$OCH$_3$; and
R$^3$ is CF$_3$ or CF$_2$Cl;

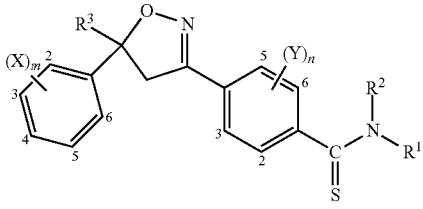

wherein
(X)$_m$ is 3,5-Cl$_2$;
Y is 2-CH$_3$;
R$^1$ is CH$_2$CF$_3$, CH$_2$(D-47a), CH$_2$(D-22a), or CH$_2$(D-47a);
R$^2$ is H; and
R$^3$ is CF$_3$; and

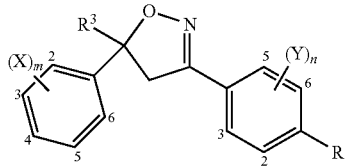

wherein
(X)$_m$ is 3,5-Cl$_2$;
Y is 2-CH$_3$;
R is C(O)OCH$_2$(D-47a); and
R$^3$ is CF$_3$;

wherein
D-1a: 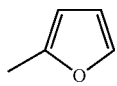
D-3a: 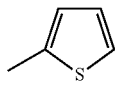
(D-10b)Cl: 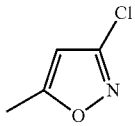
(D-15a)CH₃: 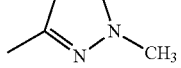
(D-17a)CH₃: 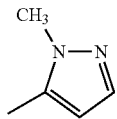
(D-17b)Cl: 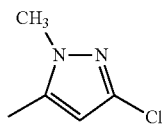
D-21a: 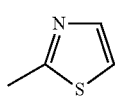
(D-21b)CF₃: 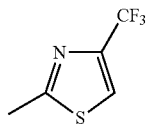
D-22a: 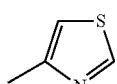
(D-22b)SCH₃: 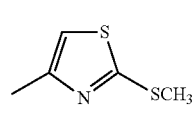
(D-23b)Cl: 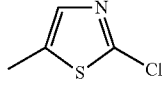
D-31a: 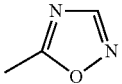
D-34a: 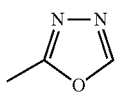
D-35a: 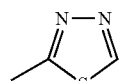
D-38a: 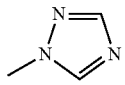
D-47a: 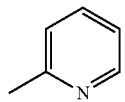
(D-47b)Cl: 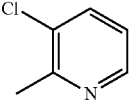
(D-47c)Cl: 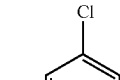
(D-47d)Cl: 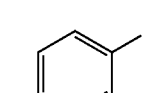
(D-47d)CF₃: 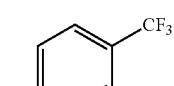
(D-47e)Cl: 
D-48a: 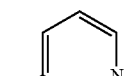
(D-48c)Cl: 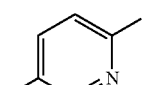
D-49a: 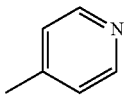
D-50a: 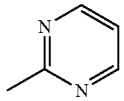
(D-50c)Cl: 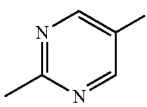

D-51a: 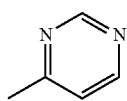
(D-53b)CH₃: 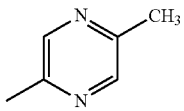
E-4a: 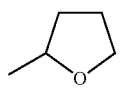
(E-9b)CH₂CF₃: 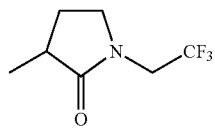
E-5a(R): 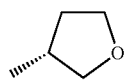
E-10a: 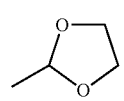
E-23a: 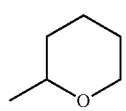
(E-23b)OCH₃: 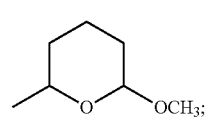
wherein
Et is ethyl, c-Bu and Bu-c is cyclic butyl, Bu-I is iso-butyl, ph is phenyl, Pr-I is isopropyl, Pr-n is N-propyl, and c-Pr is cyclic-propyl.
* * * * *

UNITED STATES PATENT AND TRADEMARK OFFICE
CERTIFICATE OF CORRECTION

PATENT NO. : 8,022,089 B2
APPLICATION NO. : 12/509859
DATED : September 20, 2011
INVENTOR(S) : Mita et al.

Page 1 of 1

It is certified that error appears in the above-identified patent and that said Letters Patent is hereby corrected as shown below:

In column 565, line 45 (claim 1), change "Spide Mite" to --Spider Mite--;

In column 572, line 10 (claim 1), change "  " to -- ' wherein Et is ethyl, c-Bu and Bu-c is cyclic butyl, Bu-i is iso-butyl, ph is phenyl, Pr-i is isopropyl, Pr-n is n-propyl, and c-Pr is cyclic propyl.--;
In column 572, line 33 (claim 9), change "Spide Mite" to --Spider Mite--;
In column 572, line 62 (claim 17), change "Spide Mite" to --Spider Mite--;
In column 573, line 14 (claim 17), change "CH(CH$_3$)CH2OCH$_3$" to --CH(CH$_3$)CH$_2$OCH$_3$--;
In column 573, line 46 (claim 17), change "3,4-Cl$_2$, or" to --3,4-Cl$_2$,--;
In column 578, line 20 (claim 17), change "Bu-I" to --Bu-i--;
In column 578, line 21 (claim 17), change "Pr-I" to --Pr-i--;
In column 578, line 21 (claim 17), change "N-propyl" to --n-propyl--.

Signed and Sealed this
Twentieth Day of December, 2011

David J. Kappos
*Director of the United States Patent and Trademark Office*